US012227523B2

(12) United States Patent
Jin

(10) Patent No.: US 12,227,523 B2
(45) Date of Patent: Feb. 18, 2025

(54) LUMINESCENCE DEVICE AND POLYCYCLIC COMPOUND FOR LUMINESCENCE DEVICE

(71) Applicant: Samsung Display Co., Ltd., Yongin-si (KR)

(72) Inventor: XiuLan Jin, Yokohama (JP)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 632 days.

(21) Appl. No.: 17/512,185

(22) Filed: Oct. 27, 2021

(65) Prior Publication Data

US 2022/0235071 A1 Jul. 28, 2022

(30) Foreign Application Priority Data

Jan. 14, 2021 (KR) ........................ 10-2021-0005555

(51) Int. Cl.

| | |
|---|---|
| ***C07D 519/00*** | (2006.01) |
| ***H10K 85/60*** | (2023.01) |
| *H10K 50/11* | (2023.01) |
| *H10K 50/15* | (2023.01) |
| *H10K 71/00* | (2023.01) |
| *H10K 101/10* | (2023.01) |

(52) U.S. Cl.

CPC ....... *C07D 519/00* (2013.01); *H10K 85/6572* (2023.02); *H10K 85/6574* (2023.02); *H10K 85/6576* (2023.02); *H10K 50/11* (2023.02); *H10K 50/15* (2023.02); *H10K 71/00* (2023.02); *H10K 2101/10* (2023.02)

(58) Field of Classification Search

None

See application file for complete search history.

(56) References Cited

U.S. PATENT DOCUMENTS

| | | | | |
|---|---|---|---|---|
| 9,118,028 | B2 | 8/2015 | Sawada et al. | |
| 10,892,422 | B2 | 1/2021 | Hwang et al. | |
| 2014/0197386 | A1 * | 7/2014 | Kim .................. | H10K 85/6572 252/500 |
| 2014/0203257 | A1 * | 7/2014 | Hwang .................. | H10K 85/40 544/333 |
| 2015/0171339 | A1 * | 6/2015 | Sakamoto ............ | C07D 407/12 548/440 |
| 2015/0340625 | A1 | 11/2015 | Takaku et al. | |

FOREIGN PATENT DOCUMENTS

| | | | |
|---|---|---|---|
| CN | 106632360 A * | 5/2017 | ......... C07D 491/048 |
| CN | 108774233 | 11/2018 | |
| CN | 109111453 | 1/2019 | |
| JP | 2009-182034 | 8/2009 | |
| JP | 5436875 | 3/2014 | |
| JP | 5556916 | 7/2014 | |
| JP | 2014-170928 | 9/2014 | |
| KR | 10-2011-0116635 | 10/2011 | |
| KR | 10-2015-0145131 | 12/2015 | |
| KR | 10-1771020 | 8/2017 | |
| KR | 10-1789254 | 10/2017 | |
| WO | 00/34285 | 6/2000 | |
| WO | 2011/132866 | 10/2011 | |
| WO | 2012/035934 | 3/2012 | |
| WO | 2014/038417 | 3/2014 | |
| WO | 2014/058183 | 4/2014 | |
| WO | 2019/022435 | 1/2019 | |

* cited by examiner

*Primary Examiner* — Robert S Loewe

(74) *Attorney, Agent, or Firm* — KILE PARK REED & HOUTTEMAN PLLC

(57) ABSTRACT

Provided is a luminescence device including a first electrode, a hole transport region disposed on the first electrode, an emission layer disposed on the hole transport region, an electron transport region disposed on the emission layer, and a second electrode disposed on the electron transport region, wherein the hole transport region may include a polycyclic compound represented by Formula 1, thereby exhibiting a long service life and high efficiency.

20 Claims, 6 Drawing Sheets

LUMINESCENCE DEVICE AND POLYCYCLIC COMPOUND FOR LUMINESCENCE DEVICE

CROSS-REFERENCE TO RELATED APPLICATION(S)

This application claims priority to and benefits of Korean Patent Application No. 10-2021-0005555 under 35 U.S.C. § 119, filed on Jan. 14, 2021 in the Korean Intellectual Property Office, the entire contents of which are incorporated herein by reference.

BACKGROUND

1. Technical Field

The disclosure relates to a luminescence device and a polycyclic compound for the luminescence device.

2. Description of the Related Art

Active development continues for a luminescence device as an image display apparatus. In contrast to a liquid crystal display apparatus, etc., the luminescence device is a so-called self-luminescent display in which holes and electrons respectively injected from a first electrode and a second electrode recombine in an emission layer, so that a luminescent material including an organic compound in the emission layer emits light to achieve display.

In the application of a luminescence device to an image display apparatus, there is a demand for a luminescence device having low driving voltage, high luminous efficiency, and a long service life, and continuous development is required on materials for a luminescence device which is capable of stably achieving such characteristics.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a luminescence device having high efficiency and a polycyclic compound included in a hole transport region of the luminescence device.

An embodiment provides a polycyclic compound which may be represented by Formula 1 below:

[Formula 1]

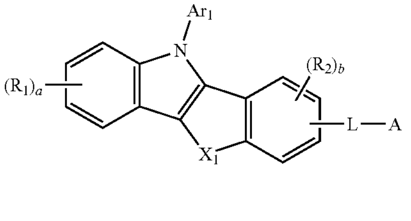

In Formula 1 above, $X_1$ may be O or S, $Ar_1$ may be a substituted or unsubstituted aryl group having 6 to 30 ring-forming carbon atoms, or a substituted or unsubstituted heteroaryl group having 2 to 30 ring-forming carbon atoms, except that $Ar_1$ is not a heteroaryl group containing two or more nitrogen (N) atoms, $R_1$ may be a hydrogen atom, a deuterium atom, a halogen atom, or a substituted or unsubstituted alkyl group having 1 to 20 carbon atoms, $R_2$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, a may be an integer from 0 to 4, b may be an integer from 0 to 3, L may be a direct linkage, a substituted or unsubstituted arylene group having 6 to 30 ring-forming carbon atoms, or a substituted or unsubstituted heteroaryl group having 2 to 30 ring-forming carbon atoms, except that L does not include a carbazole group, and A may be a group represented by Formula 2-1 or Formula 2-2 below, except that L is not a direct linkage when A is a group represented by Formula 2-2 below:

[Formula 2-1]

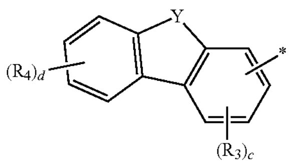

[Formula 2-2]

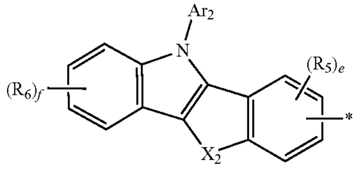

In Formula 2-1 and Formula 2-2 above, Y may be $N(Ar_3)$, O, or S, $X_2$ may be O or S, $Ar_2$ and $Ar_3$ may each independently be a substituted or unsubstituted aryl group having 6 to 30 ring-forming carbon atoms, or a substituted or unsubstituted heteroaryl group having 2 to 30 ring-forming carbon atoms, except that $Ar_2$ and $Ar_3$ are each not a heteroaryl group containing two or more nitrogen (N) atoms, $R_3$ to $R_5$ may each independently be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, $R_6$ may be a hydrogen atom, a deuterium atom, a halogen atom, or a substituted or unsubstituted alkyl group having 1 to 20 carbon atoms, c and e may each independently be an integer from 0 to 3, and d and f may each independently be an integer from 0 to 4. In Formula 2-1 and Formula 2-2, —* represents a binding site to a neighboring atom.

In an embodiment, the polycyclic compound represented by Formula 1 above may be represented by any one of Formula 3-1 to Formula 3-3 below:

[Formula 3-1]

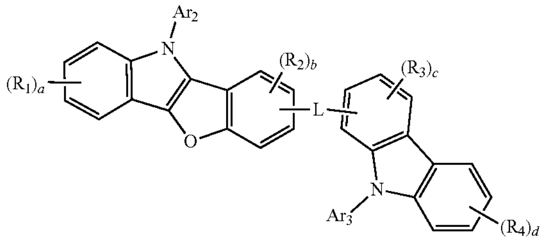

[Formula 3-2]

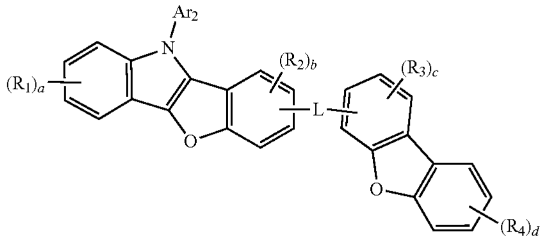

[Formula 3-3]

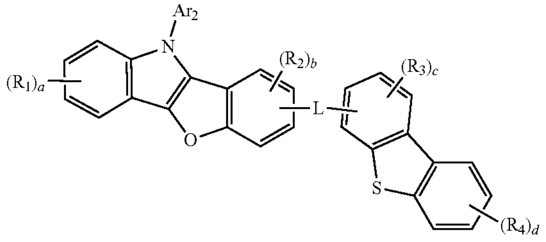

In Formula 3-1 and Formula 3-3 above, $R_1$ to $R_4$, L, $Ar_1$, $Ar_3$, and a to d may be the same as defined in connection with Formula 1, Formula 2-1, and Formula 2-2.

In an embodiment, the polycyclic compound represented by Formula 1 above may be represented by any one of Formula 4-1 to Formula 4-3 below.

[Formula 4-1]

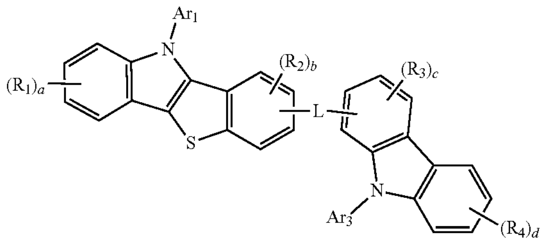

-continued

[Formula 4-2]

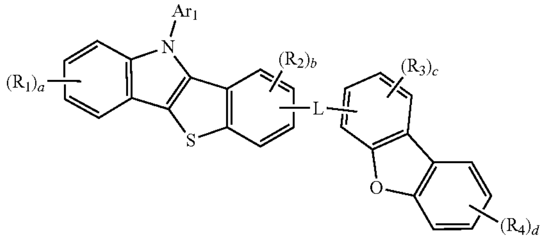

[Formula 4-3]

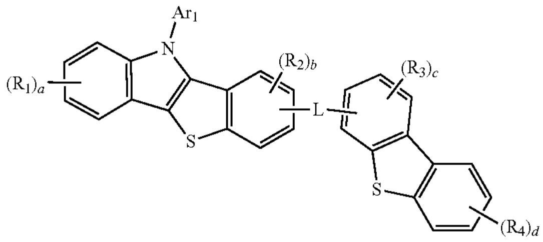

In Formula 4-1 and Formula 4-3 above, $R_1$ to $R_4$, L, $Ar_1$, $Ar_3$, and a to d may be the same as defined in connection with Formula 1, Formula 2-1, and Formula 2-2.

In an embodiment, the polycyclic compound represented by Formula 1 above may be represented by any one of Formula 5-1 to Formula 5-3 below.

[Formula 5-1]

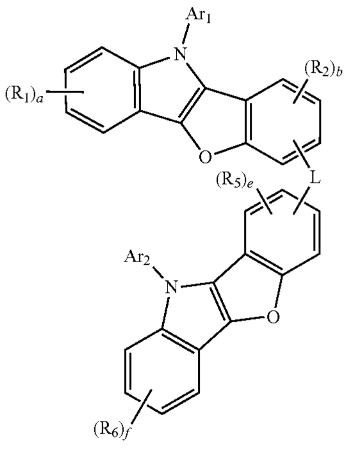

-continued

[Formula 5-2]

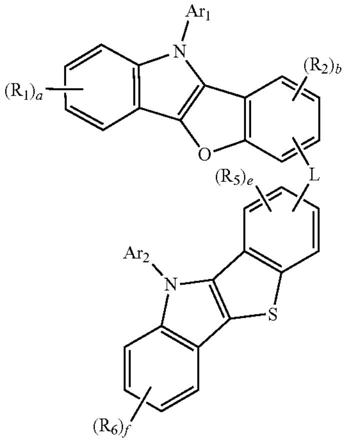

[Formula 5-3]

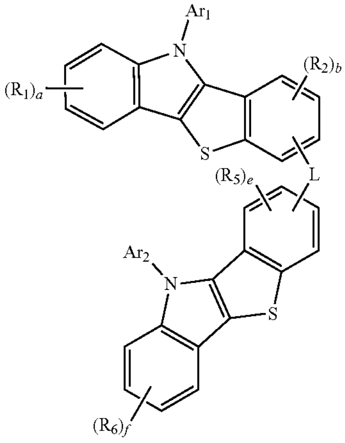

In Formula 5-1 to Formula 5-3 above, $R_1$, $R_2$, $R_5$, $R_6$, L, $Ar_1$, $Ar_2$, a, b, e, and f may be the same as defined in connection with Formula 1, Formula 2-1, and Formula 2-2.

In an embodiment, the polycyclic compound represented by Formula 1 above may be represented by Formula 6 below:

[Formula 6]

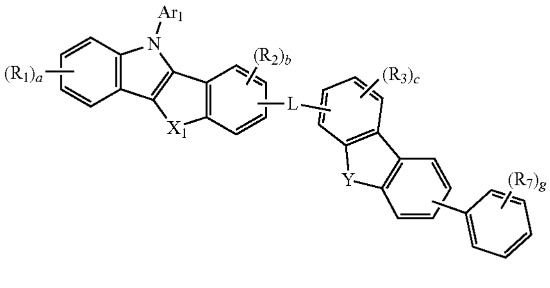

In Formula 6 above, $R_7$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, g may be an integer from 0 to 5, and $R_1$ to $R_3$, L, $Ar_1$, Y, $X_1$, and a to c may be the same as defined in connection with Formula 1, Formula 2-1, and Formula 2-2.

In an embodiment, the polycyclic compound represented by Formula 1 above may be represented by any one of Formula 7-1 to Formula 7-3 below:

[Formula 7-1]

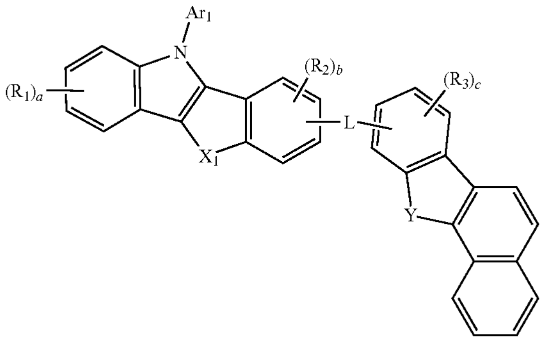

[Formula 7-2]

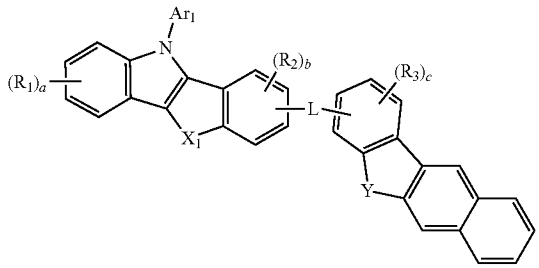

[Formula 7-3]

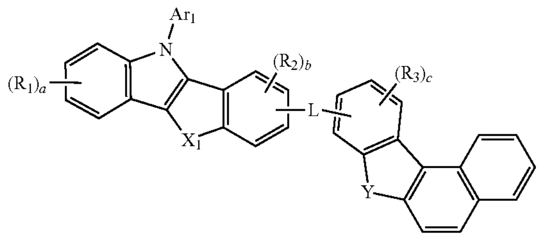

In Formula 7-1 and Formula 7-3 above, $R_1$ to $R_3$, L, $Ar_1$, Y, $X_1$, and a to c may be the same as defined in connection with Formula 1, Formula 2-1, and Formula 2-2.

In an embodiment, $R_1$ above may be a hydrogen atom or a deuterium atom.

In an embodiment, $Ar_1$, $Ar_2$, and $Ar_3$ above may be each independently a substituted or unsubstituted phenyl group.

In an embodiment, L above may be a direct linkage, a substituted or unsubstituted arylene group having 6 to 18 ring-forming carbon atoms, or a substituted or unsubstituted heteroaryl group having 6 to 12 ring-forming carbon atoms, except that L may not include a carbazole group.

In an embodiment, L above may be a direct linkage, or may be a group represented by any one of L-1 to L-4 below:

L-1

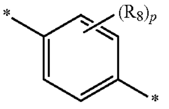

-continued

L-2

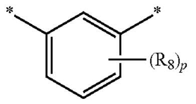

L-3

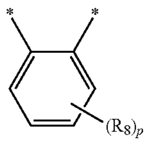

L-4

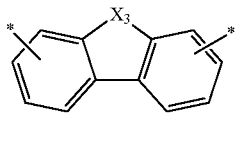

In L-1 to L-4 above, $X_3$ may be O or S, $R_8$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, p may be an integer from 0 to 4, and —* represents a binding site to a neighboring atom.

In an embodiment, the polycyclic compound represented by Formula 1 above may be at least one selected from Compound Group 1.

In an embodiment, a luminescence device may include a first electrode, a hole transport region disposed on the first electrode, an emission layer disposed on the hole transport region, an electron transport region disposed on the emission layer, and a second electrode disposed on the electron transport region, wherein the hole transport region may include a polycyclic compound represented by Formula 1 above.

In an embodiment, the hole transport region may include a hole injection layer disposed on the first electrode, and a hole transport layer disposed on the hole injection layer, wherein the hole transport layer may include the polycyclic compound represented by Formula 1 above.

In an embodiment, the hole transport region may include a hole transport layer disposed on the first electrode, and an electron blocking layer disposed on the hole transport layer, wherein the electron blocking layer may include the polycyclic compound represented by Formula 1 above.

BRIEF DESCRIPTION OF THE DRAWINGS

The accompanying drawings are included to provide a further understanding of the embodiments, and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
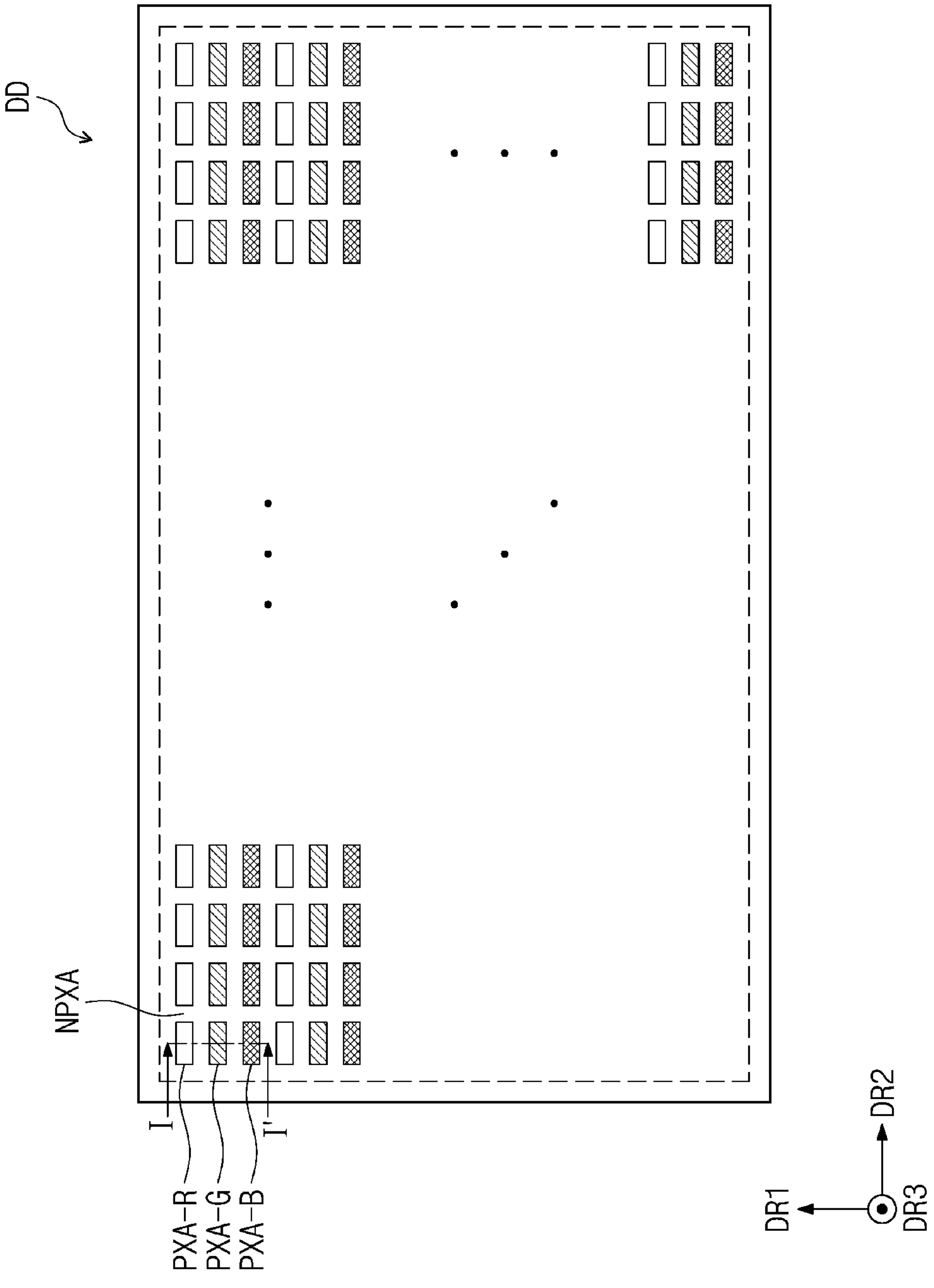
FIG. 1 is a plan view illustrating a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

Hereinafter, embodiments of the disclosure will be described with reference to the accompanying drawings.

Figure 2:
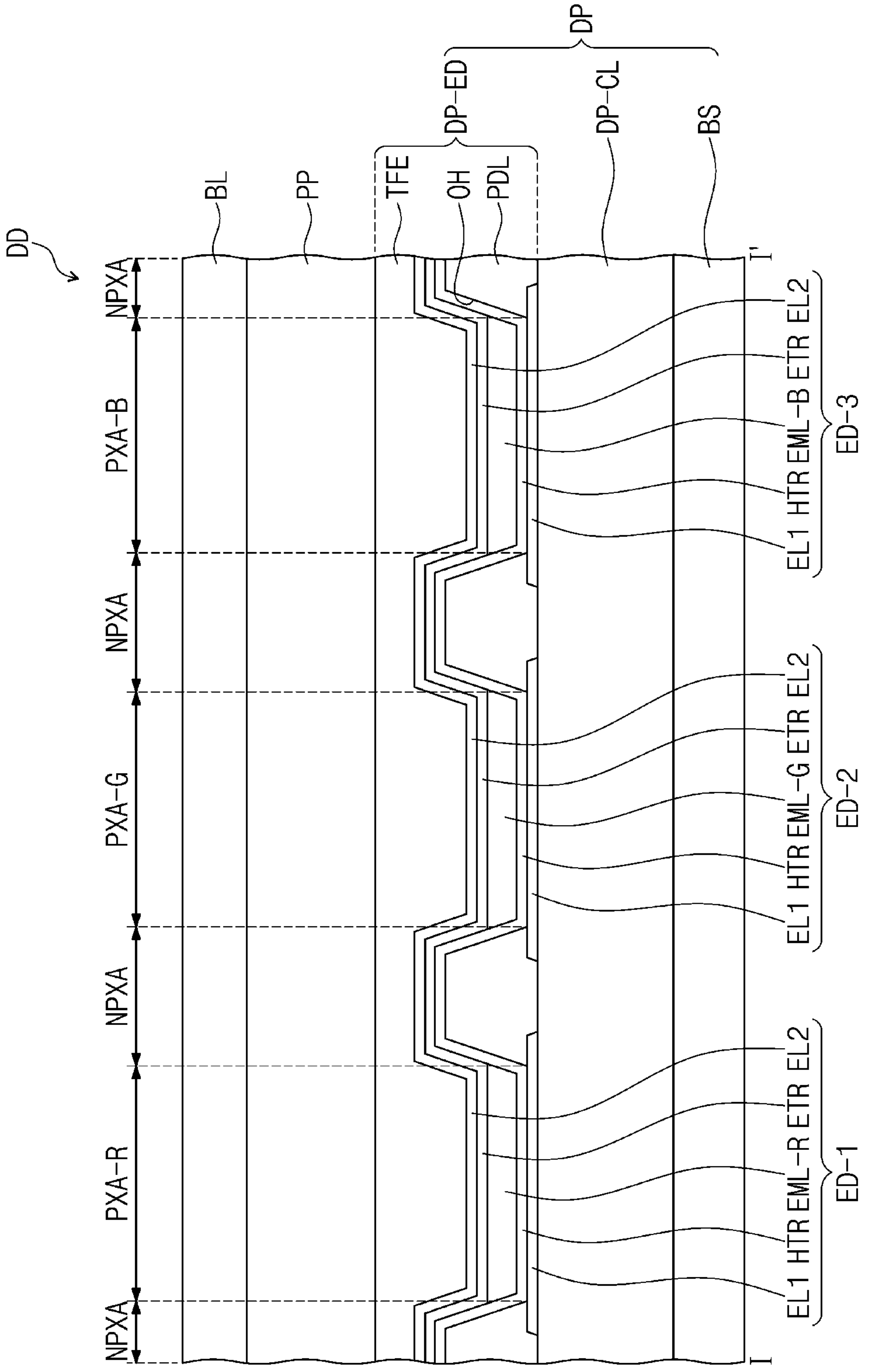
FIG. 2 is a schematic cross-sectional view illustrating a display apparatus according to an embodiment.

FIG. 1 is a plan view illustrating an embodiment of a display apparatus DD. FIG. 2 is a schematic cross-sectional view of a display apparatus DD according to an embodiment. FIG. 2 is a schematic cross-sectional view illustrating a part taken along line I-I' of FIG. 1.

The display apparatus DD may include a display panel DP and an optical layer PP disposed on the display panel DP. The display panel DP may include luminescence devices ED-1, ED-2, and ED-3. The display apparatus DD may include multiples of each of the luminescence devices ED-1, ED-2, and ED-3. The optical layer PP may be disposed on the display panel DP and may control light reflected at the display panel DP from an external light. The optical layer PP may include, for example, a polarization layer or a color filter layer. Although not shown in the drawing, in an embodiment, the optical layer PP may be omitted from the display apparatus DD.

The display panel DP may include a base layer BS, a circuit layer DP-CL provided on the base layer BS, and a display device layer DP-ED. The display device layer DP-ED may include a pixel defining film PDL, the luminescence devices ED-1, ED-2, and ED-3 disposed in the pixel defining film PDL, and an encapsulation layer TFE disposed on the luminescence devices ED-1, ED-2, and ED-3.

The base layer BS may provide a base surface on which the display device layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL may be disposed on the base layer BS, and the circuit layer DP-CL may include transistors (not shown). Each of the transistors (not shown) may include a control electrode, an input electrode, and an output electrode. For example, the circuit layer DP-CL may include a switching transistor and a driving transistor in order to drive the luminescence devices ED-1, ED-2, and ED-3 of the display device layer DP-ED.

Each of the luminescence devices ED-1, ED-2, and ED-3 may have a structure of a luminescence device ED of an embodiment according to FIGS. 3 to 6, which will be described later. Each of the luminescence devices ED-1, ED-2 and ED-3 may include a first electrode EL1, a hole transport region HTR, emission layers EML-R, EML-G and EML-B, an electron transport region ETR, and a second electrode EL2.

FIG. 2 illustrates an embodiment in which the emission layers EML-R, EML-G, and EML-B of the luminescence devices ED-1, ED-2, and ED-3 are disposed in the openings OH defined in the pixel defining film PDL, and the hole transport region HTR, the electron transport region ETR, and the second electrode EL2 are each provided as a common layer for the entire luminescence devices ED-1, ED-2, and ED-3. However, embodiments are not limited thereto. Although not shown in FIG. 2, in an embodiment, the hole transport region HTR and the electron transport region ETR may each be patterned and provided inside the opening OH defined in the pixel defining film PDL. For example, in an embodiment, the hole transport region HTR, the emission layers EML-R, EML-G, and EML-B, and the electron transport region ETR of the luminescence devices ED-1, ED-2, and ED-3 may each be patterned by an inkjet printing method and provided.

The encapsulation layer TFE may cover the luminescence devices ED-1, ED-2, and ED-3. The encapsulation layer TFE may seal the display device layer DP-ED. The encapsulation layer TFE may be a thin film encapsulation layer. The encapsulation layer TFE may a single layer or a stack of multiple layers. The encapsulation layer TFE may include at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film may protect the display device layer DP-ED from moisture and/or oxygen, and the encapsulation-organic film may protect the display device layer DP-ED from foreign substances such as dust particles. The encapsulation-inorganic film may include silicon nitride, silicon oxynitride, silicon oxide, titanium oxide, aluminum oxide, or the like, but embodiments are not limited thereto. The encapsulation-organic film may include an acrylic-based compound, an epoxy-based compound, or the like. The encapsulation-organic film may include a photopolymerizable organic material, but embodiments are not limited thereto.

The encapsulation layer TFE may be disposed on the second electrode EL2 and may be disposed to fill the opening OH.

Referring to FIGS. 1 and 2, the display apparatus DD may include a non-light emitting region NPXA and light emitting regions PXA-R, PXA-G, and PXA-B. The light emitting regions PXA-R, PXA-G, and PXA-B each may be a region which emits light generated from the luminescence devices ED-1, ED-2, and ED-3, respectively. The light emitting regions PXA-R, PXA-G, and PXA-B may be spaced apart from each other in a plane.

Each of the light emitting regions PXA-R, PXA-G, and PXA-B may be a region divided by the pixel defining film PDL. The non-light emitting regions NPXA may be regions between the adjacent light emitting regions PXA-R, PXA-G, and PXA-B, which may correspond to portions of the pixel defining film PDL. In the specification, each of the light emitting regions PXA-R, PXA-G, and PXA-B may correspond to a pixel. The pixel defining film PDL may separate the luminescence devices ED-1, ED-2, and ED-3. The emission layers EML-R, EML-G and EML-B of the luminescence devices ED-1, ED-2, and ED-3 may be disposed in openings OH defined by the pixel defining film PDL and separated from each other.

The light emitting regions PXA-R, PXA-G, and PXA-B may be divided into groups according to a color of light generated from each of the luminescence devices ED-1, ED-2, and ED-3. In the display apparatus DD of an embodiment shown in FIGS. 1 and 2, three light emitting regions PXA-R, PXA-G, and PXA-B which respectively emit red light, green light, and blue light, are illustrated. For example, the display apparatus DD of an embodiment may include the red light emitting region PXA-R, the green light emitting region PXA-G, and the blue light emitting region PXA-B, which are separated from one another.

In the display apparatus DD according to an embodiment, the luminescence devices ED-1, ED-2 and ED-3 may each emit light having wavelengths different from one another. For example, in an embodiment, the display apparatus DD may include a first luminescence device ED-1 that emits red light, a second luminescence device ED-2 that emits green light, and a third luminescence device ED-3 that emits blue light. For example, the red light emitting region PXA-R, the green light emitting region PXA-G, and the blue light emitting region PXA-B of the display apparatus DD may correspond to the first luminescence device ED-1, the second luminescence device ED-2, and the third luminescence device ED-3, respectively.

However, embodiments are not limited thereto, and the first to third luminescence devices ED-1, ED-2, and ED-3 may emit light in a same wavelength range or at least one luminescence device may emit light in a wavelength range different from the others. For example, the first to third luminescence devices ED-1, ED-2, and ED-3 may all emit blue light.

The light emitting regions PXA-R, PXA-G, and PXA-B in the display apparatus DD according to an embodiment may be arranged in a stripe form. Referring to FIG. 1, the red light emitting regions PXA-R, the green light emitting regions PXA-G, and the blue light emitting regions PXA-B each may be arranged along a second directional axis DR2. The red light emitting region PXA-R, the green light emitting region PXA-G, and the blue light emitting region PXA-B may be alternately arranged in this order along a first directional axis DR1.

FIGS. 1 and 2 illustrate that all the light emitting regions PXA-R, PXA-G, and PXA-B have a similar area, but embodiments are not limited thereto, and the light emitting regions PXA-R, PXA-G, and PXA-B may have different areas from each other according to a wavelength range of emitted light. The areas of the light emitting regions PXA-R, PXA-G, and PXA-B may be areas in a plan view that are defined by the first directional axis DR1 and the second directional axis DR2.

The arrangement form of the light emitting regions PXA-R, PXA-G, and PXA-B is not limited to the feature illustrated in FIG. 1, and the order in which the red light emitting region PXA-R, the green light emitting region PXA-G, and the blue light emitting region PXA-B are arranged may be variously combined and provided according to display quality characteristics required in the display apparatus DD. For example, the arrangement form of the light emitting regions PXA-R, PXA-G, and PXA-B may be a PenTile® arrangement form or a diamond arrangement form.

In an embodiment, the areas of the light emitting regions PXA-R, PXA-G, and PXA-B may be different in size from each other. For example, in an embodiment, an area of the green light emitting region PXA-G may be smaller than that of the blue light emitting region PXA-B, but embodiments are not limited thereto.

Hereinafter, FIGS. 3 to 6 are each a schematic cross-sectional view illustrating a luminescence device according to embodiments. Each of the luminescence devices ED according to embodiments may include a first electrode EL1, a hole transport region HTR, an emission layer EML, an electron transport region ETR, and a second electrode EL2 that are sequentially stacked.

The luminescence device ED of an embodiment includes a polycyclic compound of an embodiment, which will be described later, in the hole transport region HTR disposed between the first electrode EL1 and the second electrode EL2. However, embodiments are not limited thereto, and the luminescence device ED of an embodiment may include a compound according to an embodiment, which will be described later, not only in the hole transport region HTR but also in the emission layer EML or electron transport region ETR, which may be among the functional layers disposed between the first electrode EL1 and the second electrode EL2, or in the capping layer CPL disposed on the second electrode EL2.

Figure 3:
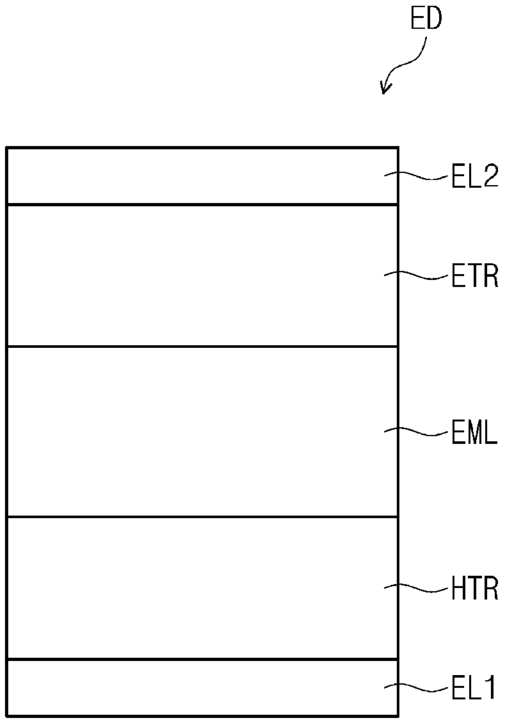
FIG. 3 is a schematic cross-sectional view illustrating a luminescence device according to an embodiment.
Figure 4:
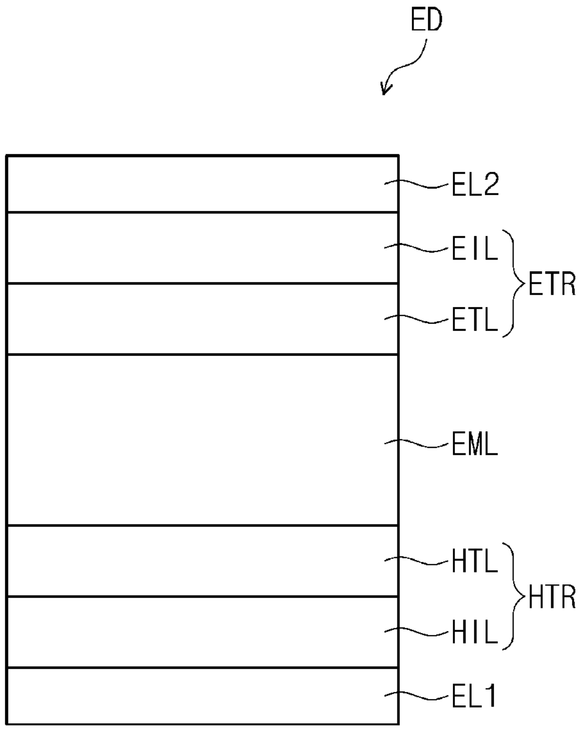
FIG. 4 is a schematic cross-sectional view illustrating a luminescence device according to an embodiment.
Figure 5:
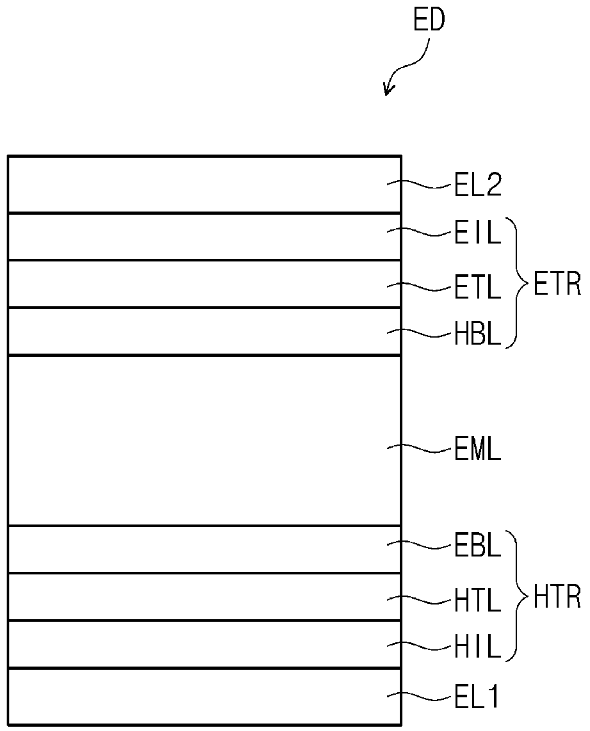
FIG. 5 is a schematic cross-sectional view illustrating a luminescence device according to an embodiment.
Figure 6:
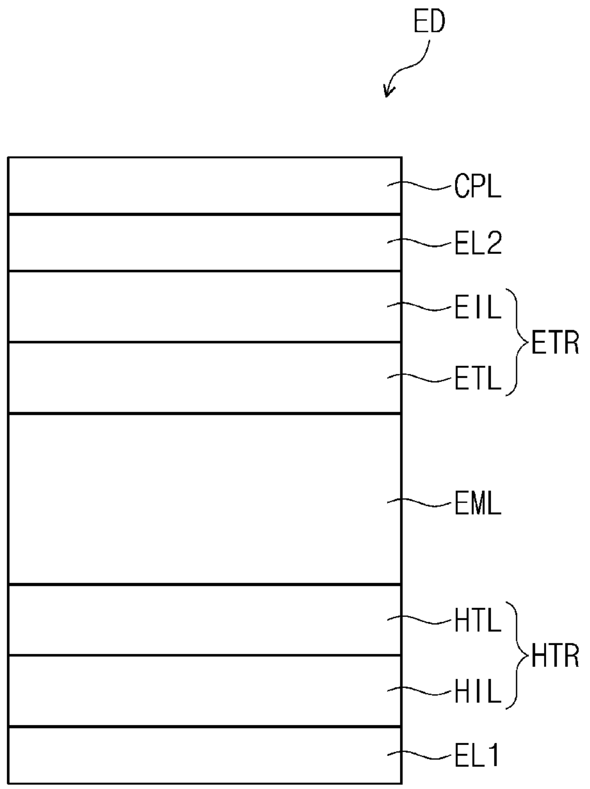
FIG. 6 is a schematic cross-sectional view illustrating a luminescence device according to an embodiment.

In comparison to FIG. 3, FIG. 4 illustrates a schematic cross-sectional view of a luminescence device ED of an embodiment, in which a hole transport region HTR includes a hole injection layer HIL and a hole transport layer HTL, and an electron transport region ETR includes an electron injection layer EIL and an electron transport layer ETL. In comparison to FIG. 3, FIG. 5 illustrates a schematic cross-sectional view of a luminescence device ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 illustrates a schematic cross-sectional view of a luminescence device ED of an embodiment including a capping layer CPL disposed on a second electrode EL2.

The first electrode EL1 has conductivity. The first electrode EL1 may be formed of a metal alloy or a conductive compound. The first electrode EL1 may be an anode or a cathode. However, embodiments are not limited thereto. In an embodiment, the first electrode EL1 may be a pixel electrode. The first electrode EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an embodiment, the second electrode EL2 may have a multilayer structure including a reflective layer or a transflective layer formed of the above-described materials, and a transparent conductive layer formed of ITO, IZO, ZnO, ITZO, etc. For example, the first electrode EL1 may have a three-layer structure of ITO/Ag/ITO, but embodiments are not limited thereto. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. The hole transport region HTR may include at least one of a hole injection layer HIL, a hole transport layer HTL, a hole buffer layer (not shown), and an electron blocking layer EBL. A thickness of the hole transport region HTR may be, for example, in a range of about 50 Å to about 15,000 Å.

The hole transport region HTR may have a layer formed of a single material, a layer formed of different materials, or a multilayer structure including layers formed of different materials.

For example, the hole transport region HTR may have a single layer structure of the hole injection layer HIL or the hole transport layer HTL, or may have a single layer structure formed of a hole injection material and a hole transport material. In embodiments, the hole transport region HTR may have a single layer structure formed of different materials, or a structure in which a hole injection layer HIL/a hole transport layer HTL, a hole injection layer HIL/a hole transport layer HTL/a hole buffer layer (not shown), a hole injection layer HIL/a hole buffer layer (not shown), a hole transport layer HTL/a hole buffer layer, or a hole injection layer HIL/a hole transport layer HTL/an electron blocking layer EBL are stacked in order from the first electrode EL1, but embodiments are not limited thereto.

The hole transport region HTR in the luminescence device ED of an embodiment includes a polycyclic compound according to an embodiment.

In the specification, the term "substituted or unsubstituted" as used herein may mean a group that is substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. Each of the substituents listed above may themselves be substituted or unsubstituted. For example, a biphenyl group may be interpreted as an aryl group or as a phenyl group substituted with a phenyl group.

In the specification, the term "bonded to an adjacent group to form a ring" may mean a group that is bonded to an adjacent group to form a substituted or unsubstituted hydrocarbon ring, or a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may each be monocyclic or polycyclic. A ring formed by groups being bonded to each other may be connected to another ring to form a spiro structure.

In the specification, the term "adjacent group" may mean a substituent substituted for an atom which is directly bonded to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as "adjacent groups" to each other, and two ethyl groups in 1,1-diethylcyclopentane may be interpreted as "adjacent groups" to each other. For example, two methyl groups in 4,5-dimethylphenanthrene may be interpreted as "adjacent groups" to each other.

In the specification, examples of a halogen atom may include a fluorine atom, a chlorine atom, a bromine atom, and an iodine atom.

In the specification, an alkyl group may be a linear, a branched, or a cyclic type. The number of carbon atoms in the alkyl group may be 1 to 50, 1 to 30, 1 to 20, 1 to 10, or 1 to 6. Examples of the alkyl group may include a methyl group, an ethyl group, an n-propyl group, an isopropyl group, an n-butyl group, a s-butyl group, a t-butyl group, an i-butyl group, a 2-ethylbutyl group, a 3,3-a dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but are not limited thereto.

In the specification, an alkenyl group may be a hydrocarbon group that includes at least one carbon double bond in the middle or end of an alkyl group having 2 or more carbon atoms. The alkenyl group may be a linear chain or a branched chain. The number of carbon atoms is not specifically limited, but may be 2 to 30, 2 to 20 or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the specification, an alkynyl group may be a hydrocarbon group including at least one carbon triple bond in the middle or end of an alkyl group having 2 or more carbon atoms. The alkynyl group may be a linear chain or a branched chain. The number of carbon atoms is not specifically limited, but may be 2 to 30, 2 to 20 or 2 to 10. Examples of the alkynyl group may include an ethynyl group, a propynyl group, etc., without limitation.

In the specification, a hydrocarbon ring group may be any functional group or substituent derived from an aliphatic hydrocarbon ring, or an any functional group or substituent derived from an aromatic hydrocarbon ring. The number of ring-forming carbon atoms in the hydrocarbon ring group may be 5 to 60, 5 to 30, or 5 to 20.

In the specification, an aryl group may be any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinqphenyl group, a sexiphenyl group, a triphenylenyl group, a pyrenyl group, a benzofluoranthenyl group, a chrysenyl group, etc., but embodiments are not limited thereto.

In the specification, a fluorenyl group may be substituted, and two substituents may be combined with each other to form a spiro structure. Examples of substituted fluorenyl groups are as follows. However, embodiments are not limited thereto.

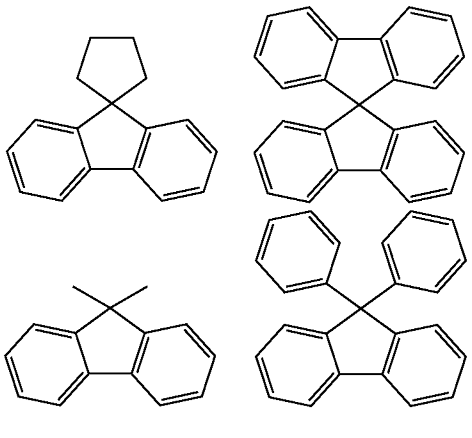

In the specification, a heterocyclic group may be any functional group or substituent derived from a ring containing at least one of B, O, N, P, Si, and S as a heteroatom. The heterocyclic group may be an aliphatic heterocyclic group or an aromatic heterocyclic group. The aromatic heterocyclic group may be a heteroaryl group. The aliphatic heterocyclic group and the aromatic heterocyclic group may each be monocyclic or polycyclic.

In the specification, a heterocyclic group may include at least one of B, O, N, P, Si, and S as a heteroatom. If the heterocyclic group includes two or more heteroatoms, the two or more heteroatoms may be the same as or different from each other. The heterocyclic group may be a monocyclic heterocyclic group or a polycyclic heterocyclic group and the heterocyclic group may be a heteroaryl group. The number of ring-forming carbon atoms in the heterocyclic group may be 2 to 30, 2 to 20, or 2 to 10.

In the specification, an aliphatic heterocyclic group may include at least one of B, O, N, P, Si, and S as a heteroatom. The number of ring-forming carbon atoms in the aliphatic heterocyclic group may be 2 to 30, 2 to 20, or 2 to 10. Examples of the aliphatic heterocyclic group may include an oxirane group, a tyran group, a pyrrolidine group, a piperidine group, a tetrahydrofuran group, a tetrahydrothiophene group, a thian group, a tetrahydropyran group, a 1,4-dioxane group, etc., but embodiments are not limited thereto.

In the specification, a heteroaryl group may include at least one of B, O, N, P, Si, and S as a heteroatom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but embodiments are not limited thereto.

In the specification, the number of carbon atoms in an amine group is not specifically limited, but may be 1 to 30. The amine group may include an alkyl amine group, an aryl amine group, or a heteroaryl amine group. Examples of the amine group may include a methylamine group, a dimethylamine group, a phenylamine group, a diphenylamine group, a naphthylamine group, a 9-methyl-anthracenylamine group, a triphenylamine group, etc., but embodiments are not limited thereto.

In the specification, the above description with respect to the aryl group may be applied to an arylene group, except that the arylene group is a divalent group.

In the specification, the above description with respect to the heteroaryl group may be applied to a heteroarylene group, except that the heteroarylene group is a divalent group.

In the specification, ——* and ——* as used herein each represents a binding site to a neighboring atom.

The polycyclic compound according to an embodiment may be represented by Formula 1 below:

[Formula 1]

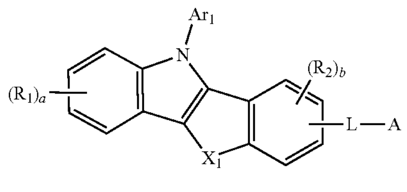

In Formula 1, $X_1$ may be O or S.

In Formula 1, $Ar_1$ may be a substituted or unsubstituted aryl group having 6 to 30 ring-forming carbon atoms, or a substituted or unsubstituted heteroaryl group having 2 to 30 ring-forming carbon atoms, except that $Ar_1$ is not a heteroaryl group containing two or more nitrogen (N) atoms.

In Formula 1, $R_1$ may be a hydrogen atom, a deuterium atom, a halogen atom, or a substituted or unsubstituted alkyl group having 1 to 20 carbon atoms.

In Formula 1, $R_2$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 1, a may be an integer from 0 to 4, and b may be an integer from 0 to 3. When a is 2 or more, multiple $R_1$ groups may be the same as or different from each other, and when b is 2 or more, multiple $R_2$ groups may be the same as or different from each other.

In Formula 1, L may be a direct linkage, a substituted or unsubstituted arylene group having 6 to 30 ring-forming carbon atoms, or a substituted or unsubstituted heteroaryl group having 2 to 30 ring-forming carbon atoms, except that L does not include a carbazole group.

In Formula 1, A may be a group represented by Formula 2-1 or Formula 2-2 below. However, L in Formula 1 may not be a direct linkage when A is a group represented by Formula 2-2.

[Formula 2-1]

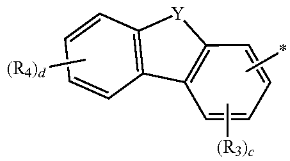

[Formula 2-2]

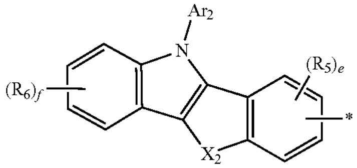

In Formula 2-1 and Formula 2-2, Y may be $N(Ar_3)$, O, or S, and $X_2$ may be O or S.

In Formula 2-1 and Formula 2-2, $Ar_2$ and $Ar_3$ may each independently be a substituted or unsubstituted aryl group having 6 to 30 ring-forming carbon atoms, or a substituted or unsubstituted heteroaryl group having 2 to 30 ring-forming carbon atoms, except that $Ar_2$ and $Ar_3$ are each not a heteroaryl group containing two or more nitrogen (N) atoms.

In Formula 2-1 and Formula 2-2, $R_3$ to $R_5$ may each independently be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula 2-2, $R_6$ may be a hydrogen atom, a deuterium atom, a halogen atom, or a substituted or unsubstituted alkyl group having 1 to 20 carbon atoms.

In Formula 2-1 and Formula 2-2, c and e may each independently be an integer from 0 to 3. When c is 2 or more, multiple $R_3$ groups may be the same as or different from each other, and when e is 2 or more, multiple $R_5$ groups may be the same as or different from each other.

In Formula 2-1 and Formula 2-2, d and f may each independently be an integer from 0 to 4. When d is 2 or more, multiple $R_4$ groups may be the same as or different from each other, and when f is 2 or more, multiple $R_6$ groups may be the same as or different from each other.

In an embodiment, $R_1$ in Formula 1 may be a hydrogen atom or a deuterium atom.

In an embodiment, $Ar_1$, $Ar_2$, and $Ar_3$ in Formula 1 may each independently be a substituted or unsubstituted phenyl group.

In an embodiment, L in Formula 1 may be a direct linkage, a substituted or unsubstituted arylene group having 6 to 18 ring-forming carbon atoms, or a substituted or unsubstituted heteroaryl group having 6 to 12 ring-forming carbon atoms. However, L may not include a carbazole group.

In an embodiment, $X_1$ in Formula 1 may be O, and A in Formula 1 may be a group represented by Formula 2-1. In an embodiment, the polycyclic compound represented by Formula 1 may be represented by any one of Formula 3-1 to Formula 3-3 below:

[Formula 3-1]

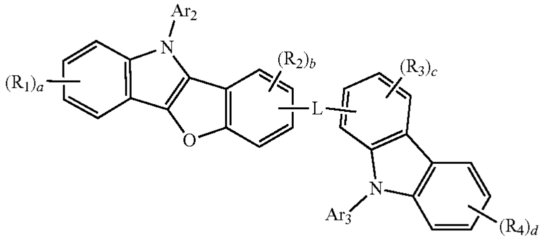

[Formula 3-2]

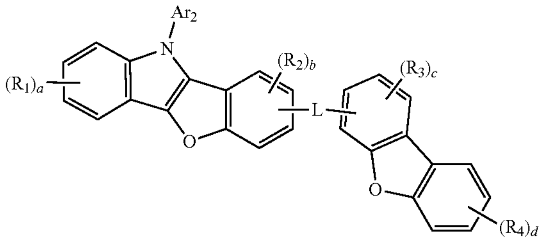

[Formula 3-3]

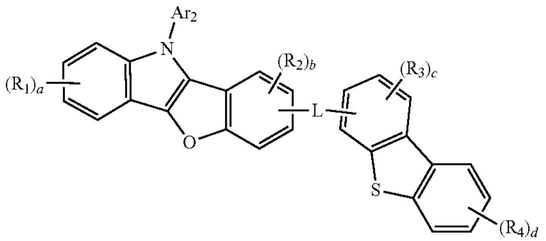

In Formula 3-1 to Formula 3-3, $R_1$ to $R_4$, L, $Ar_1$, $Ar_3$, and a to d may be the same as defined in connection with Formula 1 and Formula 2-1.

In an embodiment, $X_1$ in Formula 1 may be S, and A in Formula 1 may be a group represented by Formula 2-1. In an embodiment, the polycyclic compound represented by Formula 1 may be represented by any one of Formula 4-1 to Formula 4-3 below:

[Formula 4-1]

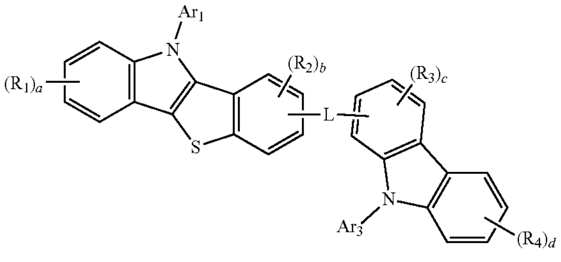

[Formula 4-2]

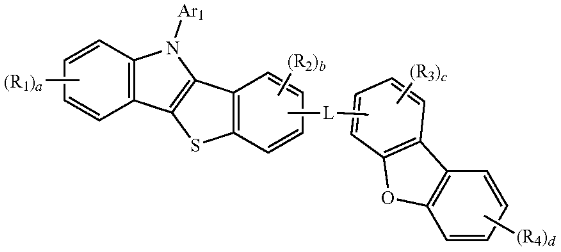

[Formula 4-3]

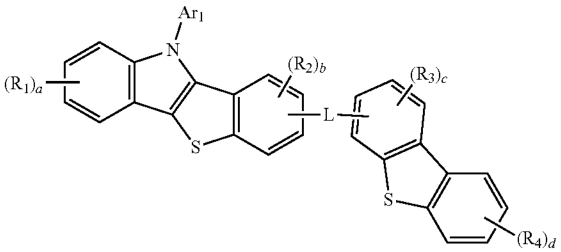

In Formula 4-1 to Formula 4-3, $R_1$ to $R_4$, L, $Ar_1$, $Ar_3$, and a to d may be the same as defined in connection with Formula 1 and Formula 2-1.

In an embodiment, in any one Formula among Formula 3-1 to Formula 3-3 and Formula 4-1 to Formula 4-3, L may be a direct linkage, or L may be a group represented by any one of L-1 to L-4 below:

L-1

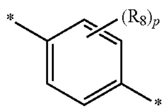

L-2

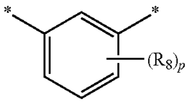

L-3

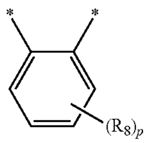

-continued

L-4

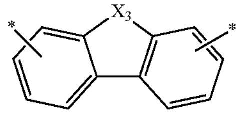

In L-1 to L-3, $R_8$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In L-1 to L-3, p may be an integer from 0 to 4. When p is 2 or more, multiple $R_8$ groups may be the same as or different from each other.

In L-4, $X_3$ may be O or S.

In an embodiment, A in Formula 1 may be a group represented by Formula 2-2. In an embodiment, the polycyclic compound represented by Formula 1 may be represented by any one of Formula 5-1 to Formula 5-3 below:

[Formula 5-1]

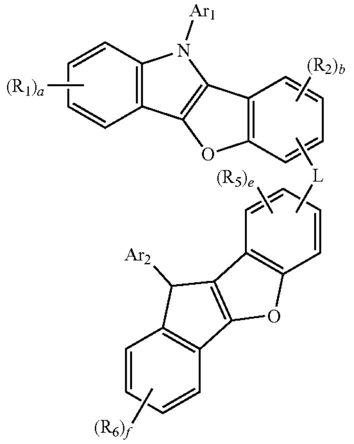

[Formula 5-2]

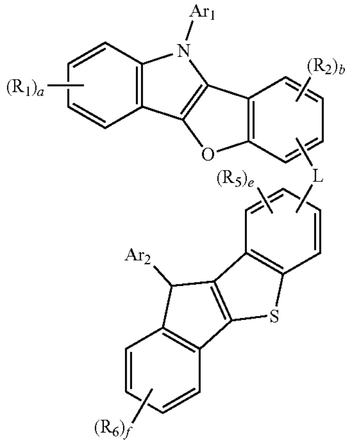

-continued

[Formula 5-3]

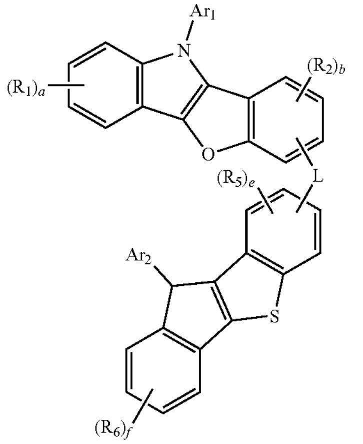

In Formula 5-1 to Formula 5-3, in an embodiment, L may be a substituted or unsubstituted arylene group having 6 to 30 ring-forming carbon atoms, or a substituted or unsubstituted heteroaryl group having 2 to 30 ring-forming carbon atoms, except that L may not include a carbazole group.

In Formula 5-1 to Formula 5-3, $R_1$, $R_2$, $R_5$, $R_6$, L, $Ar_1$, $Ar_2$, a, b, e, and f may be the same as defined in connection with Formula 1 and Formula 2-2.

In an embodiment, in any one Formula among Formula 5-1 to Formula 5-3, L may be a group represented by any one of L-1 to L-4 below:

L-1

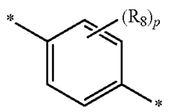

L-2

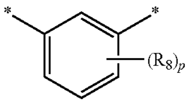

L-3

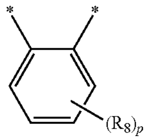

L-4

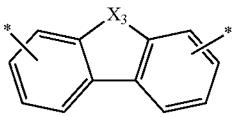

In L-1 to L-3, $R_8$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In L-1 to L-3, p may be an integer of 0 to 4. When p is 2 or more, multiple $R_8$ groups may be the same as or different from each other.

In L-4, $X_3$ may be O or S.

In an embodiment, the polycyclic compound represented by Formula 1 may be represented by Formula 6 below:

[Formula 6]

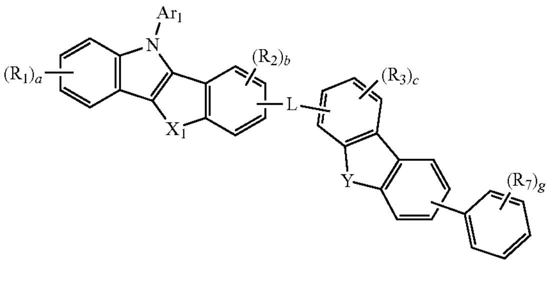

In Formula 6, $R_7$ may be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 6, g may be an integer from 0 to 5. When g is 2 or more, multiple $R_7$ groups may be the same as or different from each other.

In Formula 6, $R_1$ to $R_3$, L, $Ar_1$, Y, $X_1$, and a to c may be the same as defined in connection with Formula 1 and Formula 2-1.

In an embodiment, the polycyclic compound represented by Formula 1 may be represented by any one of Formula 7-1 to Formula 7-3 below:

[Formula 7-1]

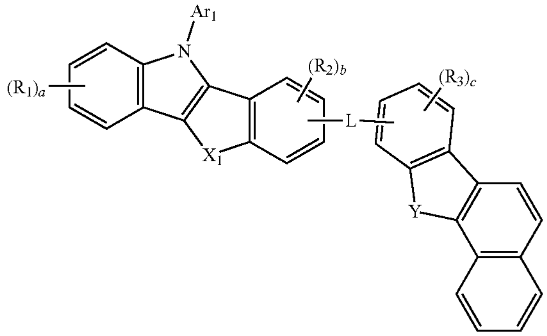

[Formula 7-2]

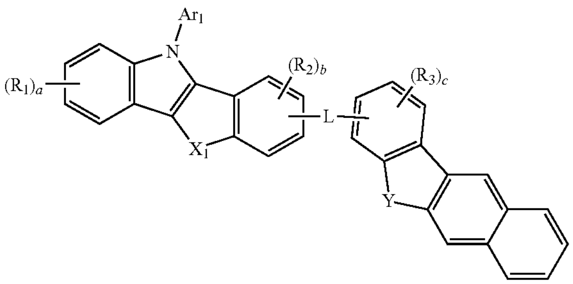

-continued
[Formula 7-3]
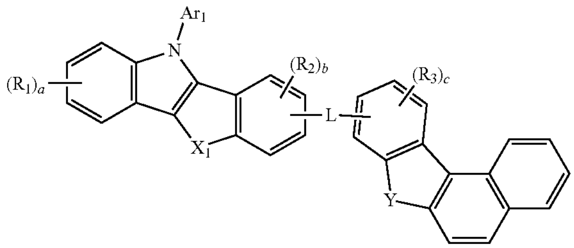
In Formula 7-1 and Formula 7-3, $R_1$ to $R_3$, L, $Ar_1$, Y, $X_1$, and a to c may be the same as defined in connection with Formula 1 and Formula 2-1.
The polycyclic compound represented by Formula 1 according to an embodiment may be any one selected from Compound Group 1 below. However, embodiments are not limited thereto.
[Compound Group 1]
1
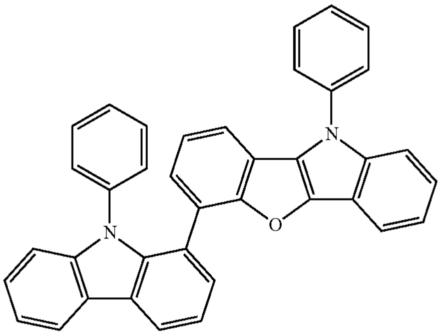
2
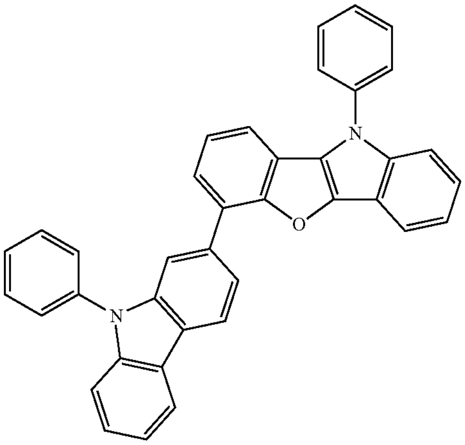
-continued
3
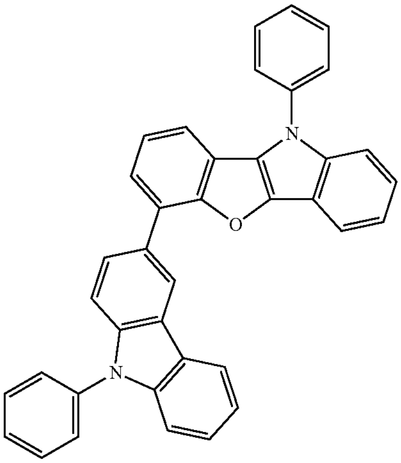
4
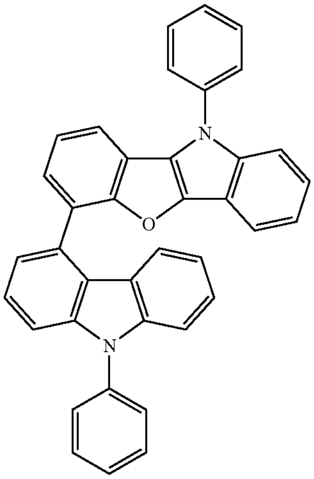
5
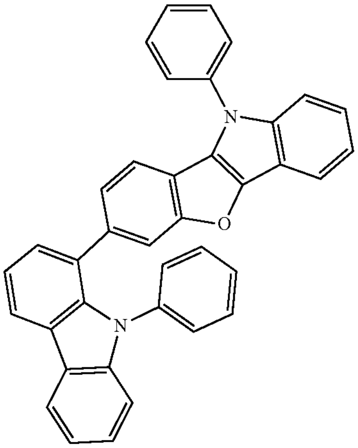

-continued
6
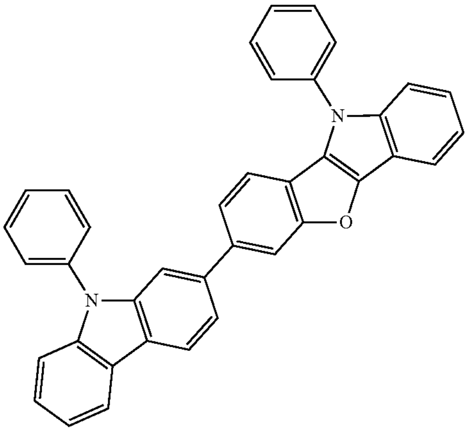
7
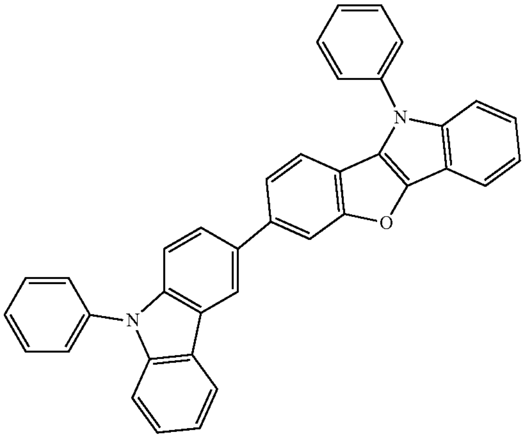
8
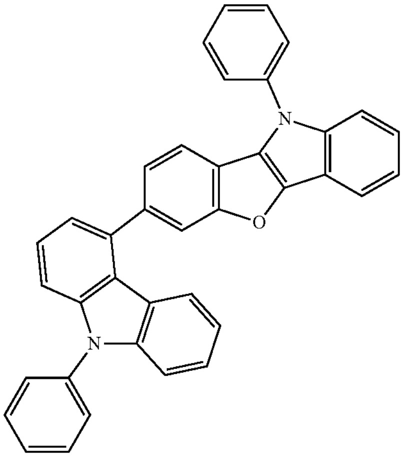
9
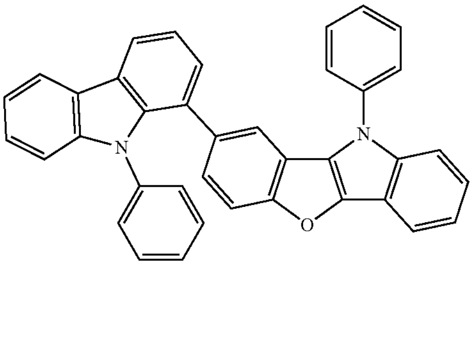
-continued
10
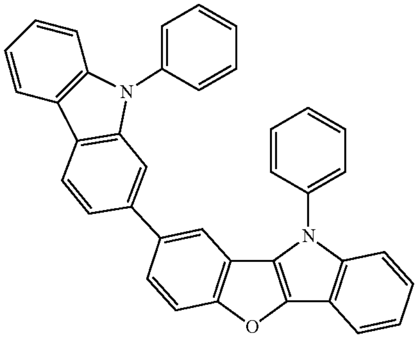
11
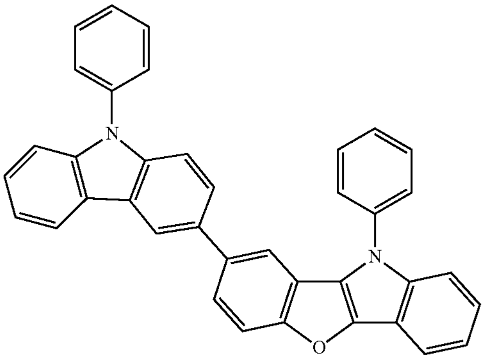
12
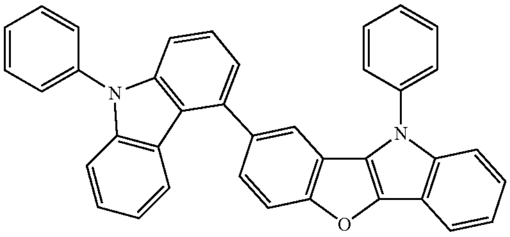
13
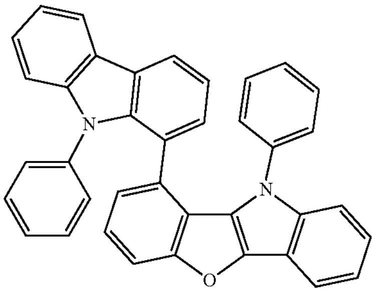
14
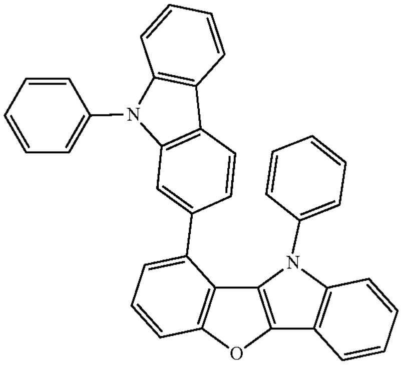

-continued
15
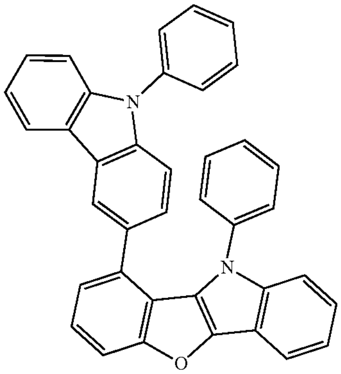
16
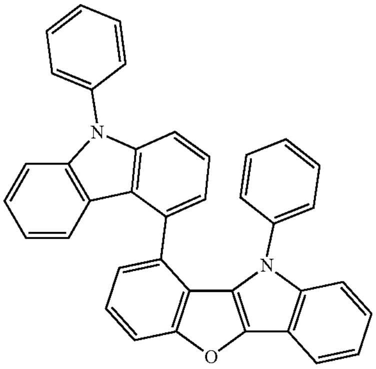
17
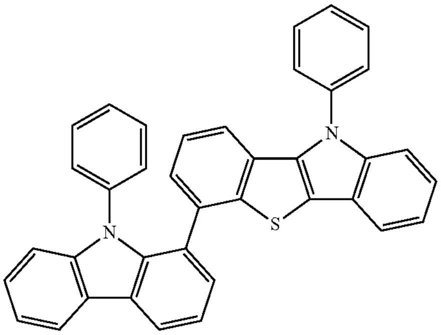
18
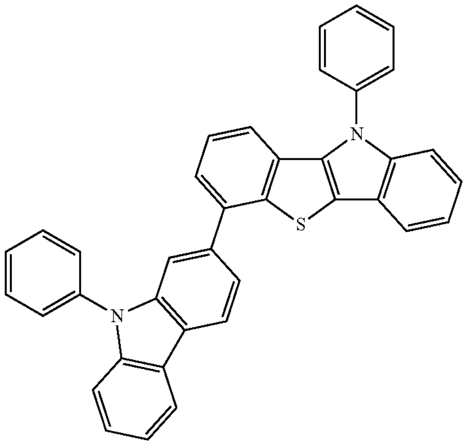
-continued
19
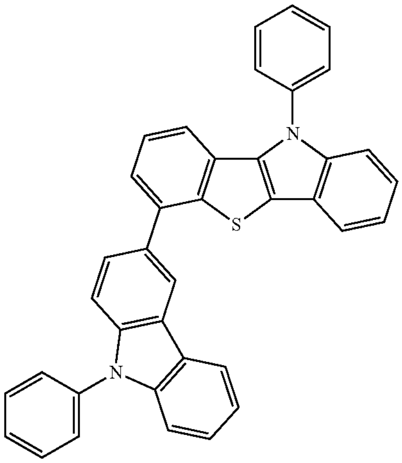
20
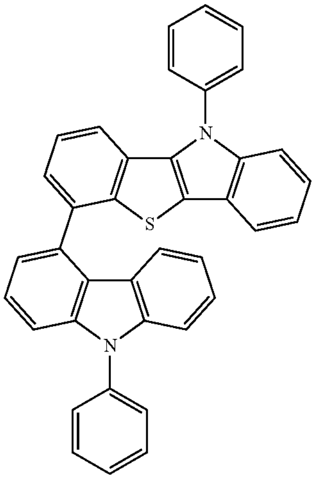
21
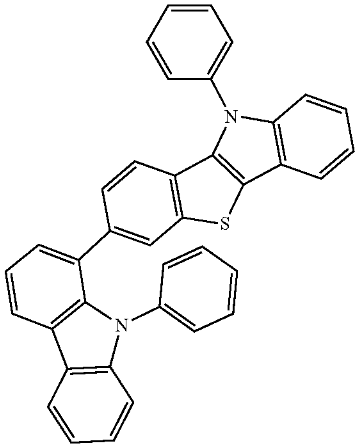

-continued
22
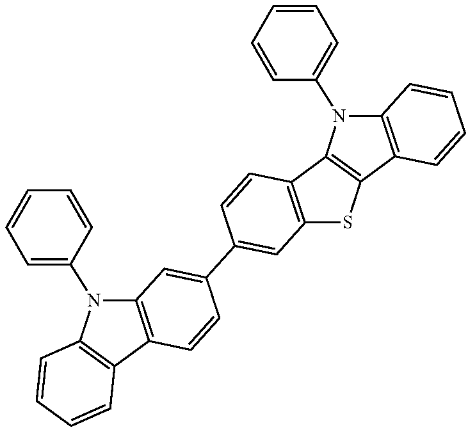
23
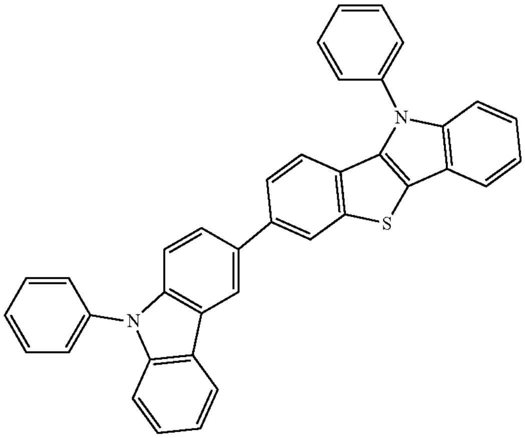
24
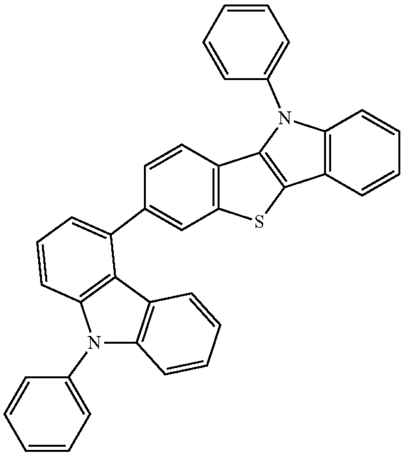
25
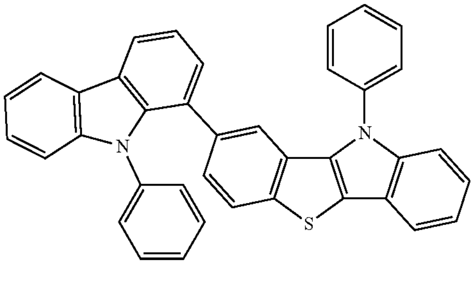
-continued
26
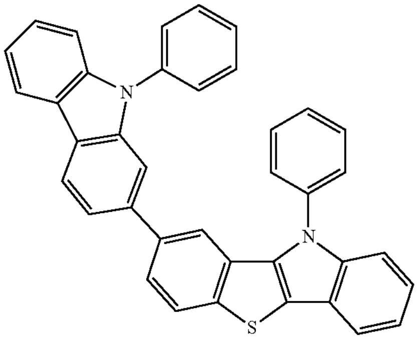
27
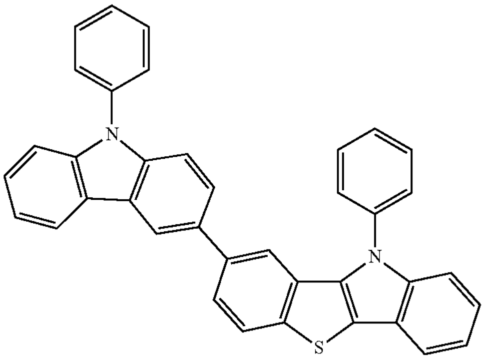
28
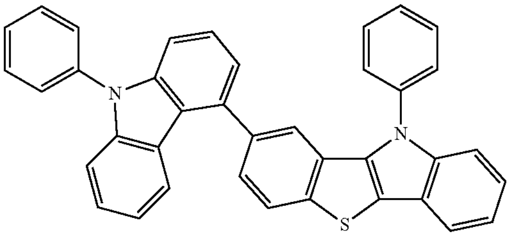
29
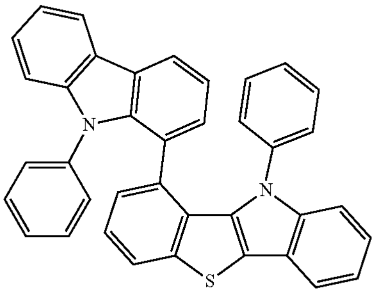
30
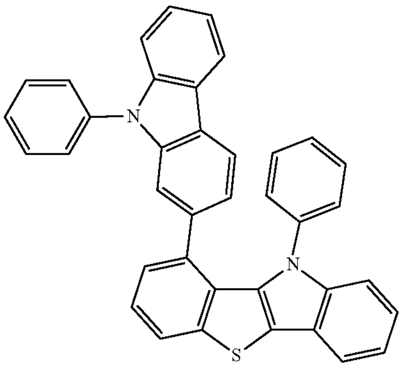

-continued
31
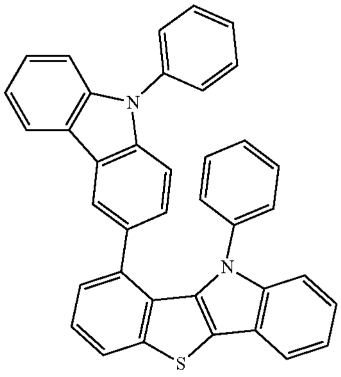
32
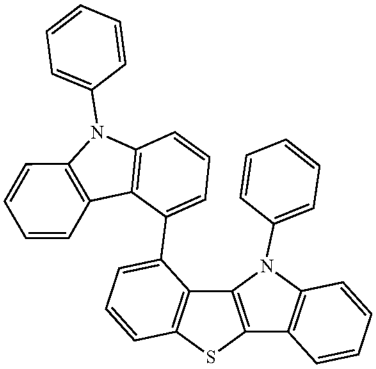
33
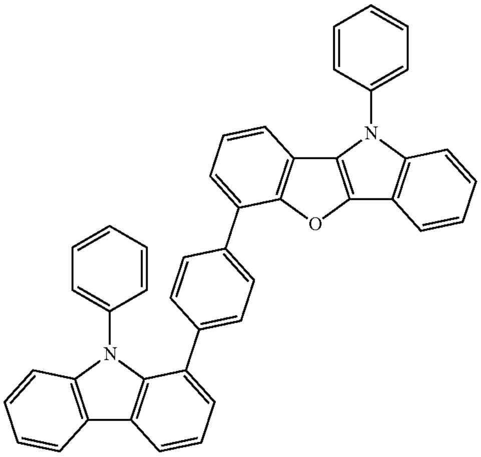
-continued
34
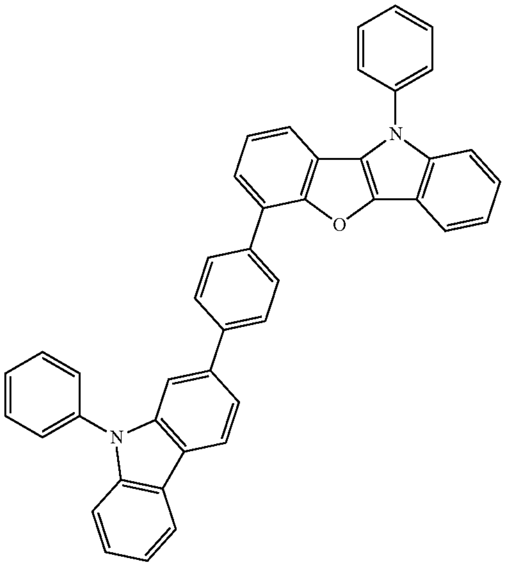
35
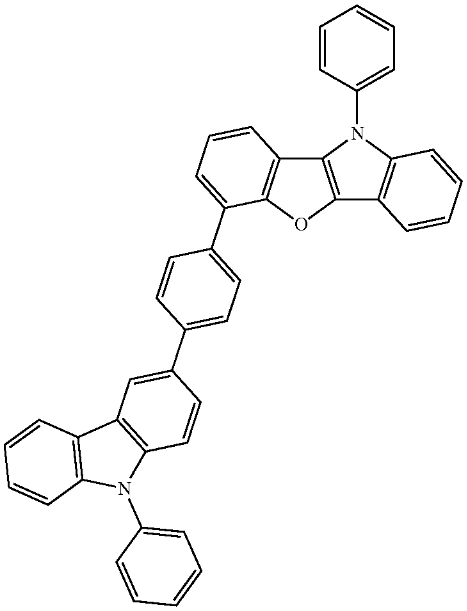

-continued
36
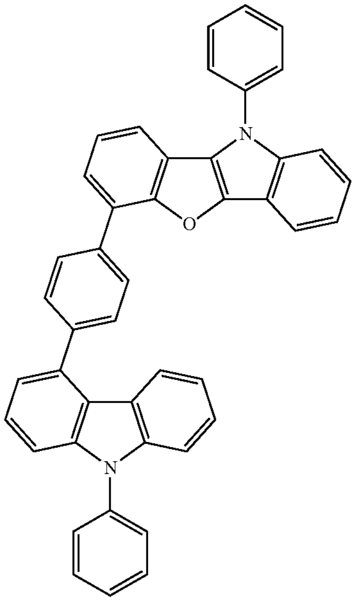
37
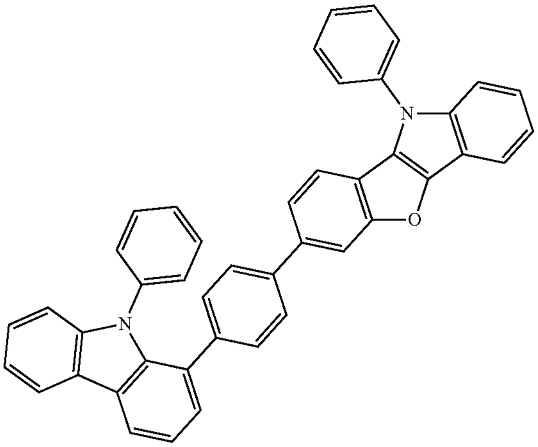
38
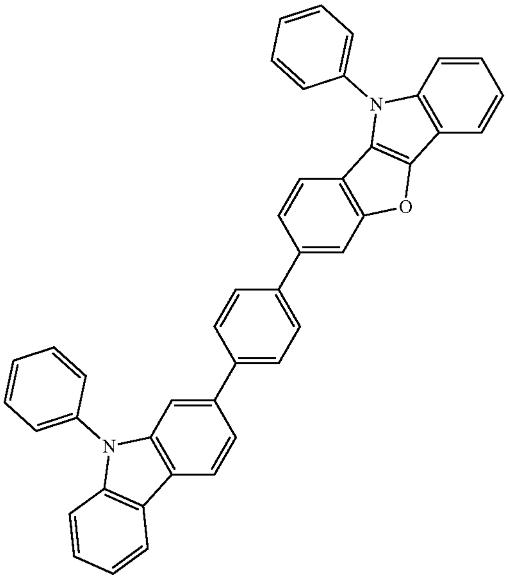
-continued
39
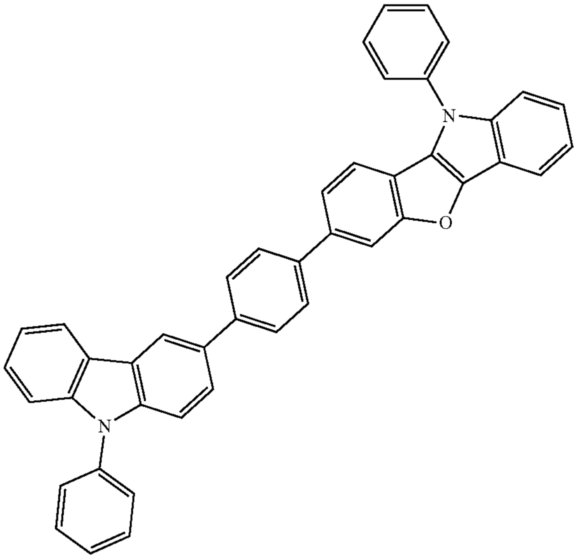
40
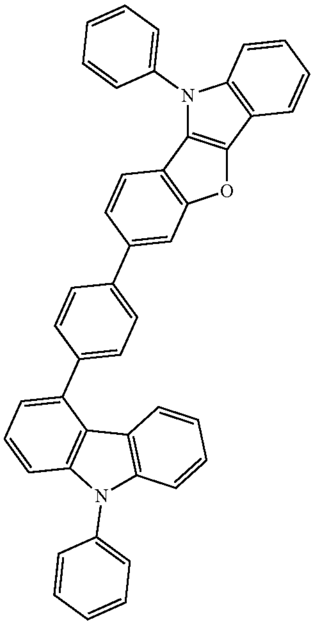

41
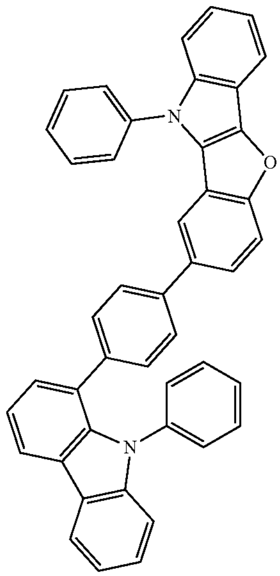
42
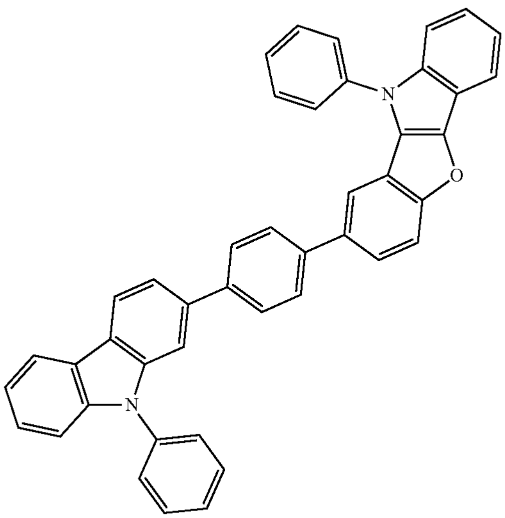
43
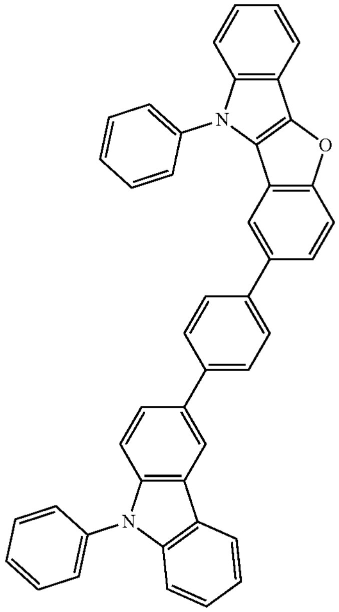
44
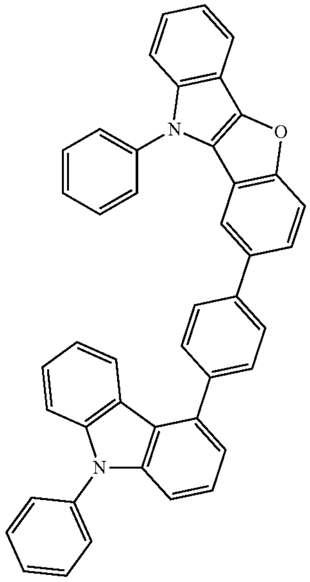

-continued
45
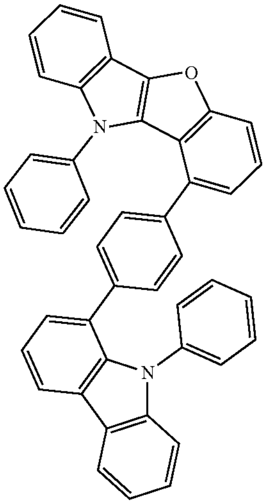
46
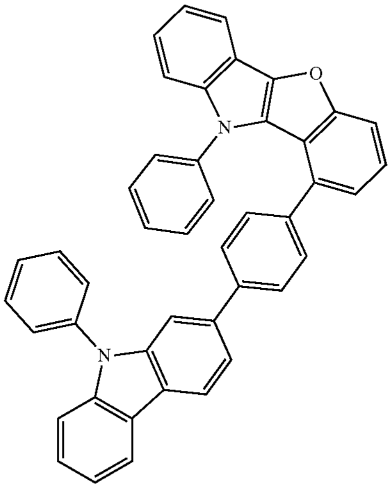
47
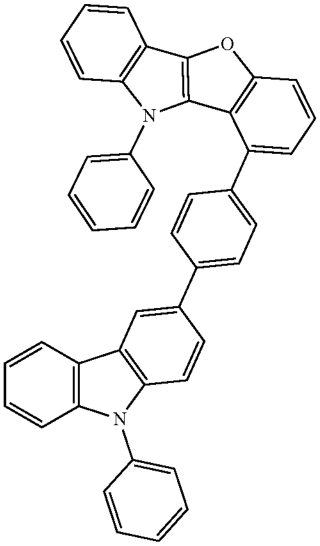
-continued
48
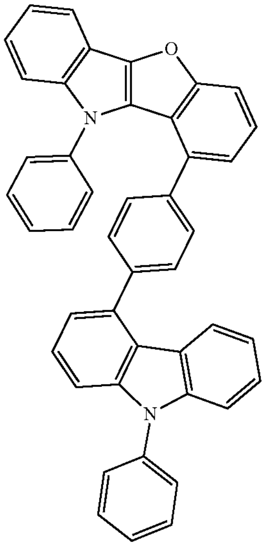
49
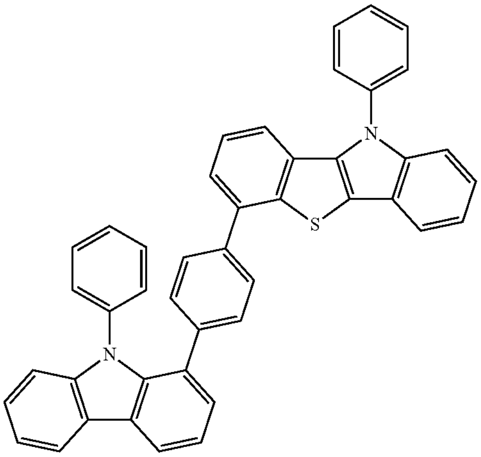
50
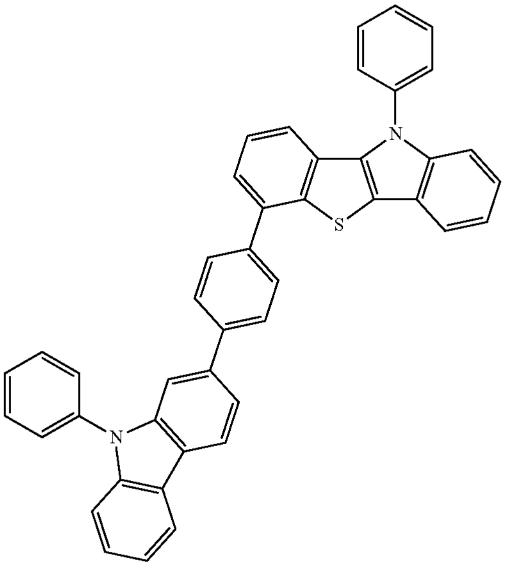

-continued
51
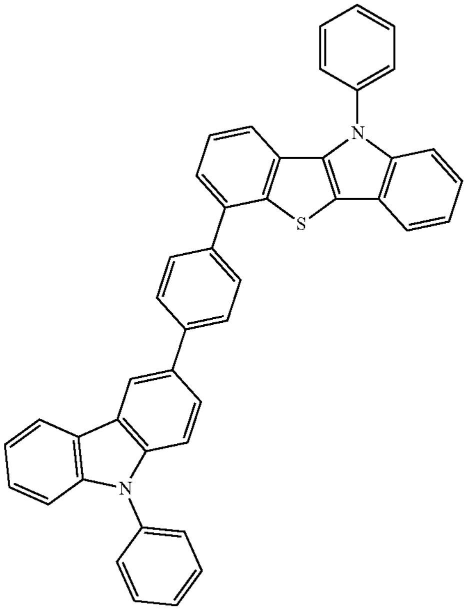
52
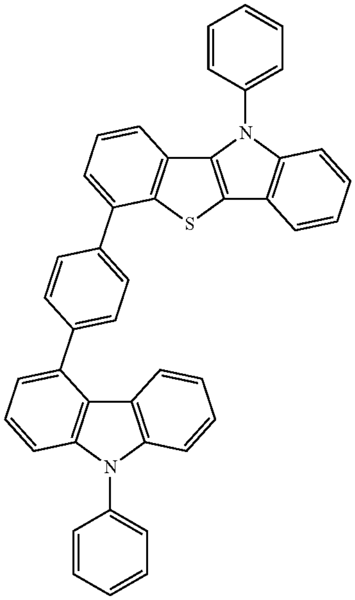
-continued
53
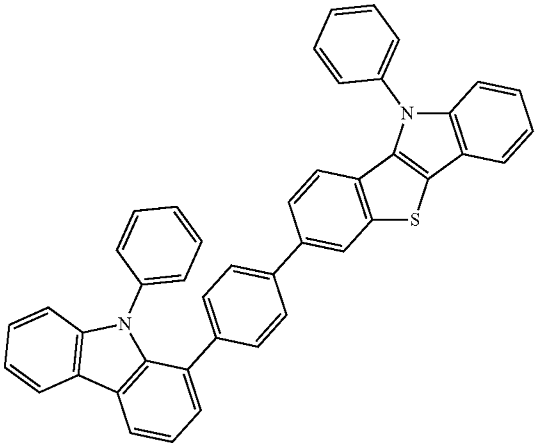
54
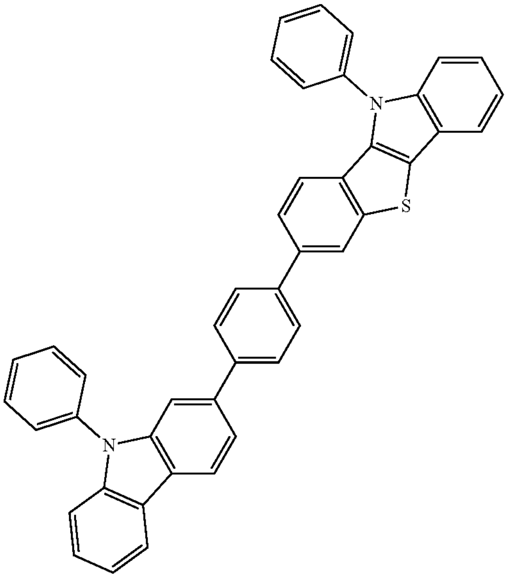
55
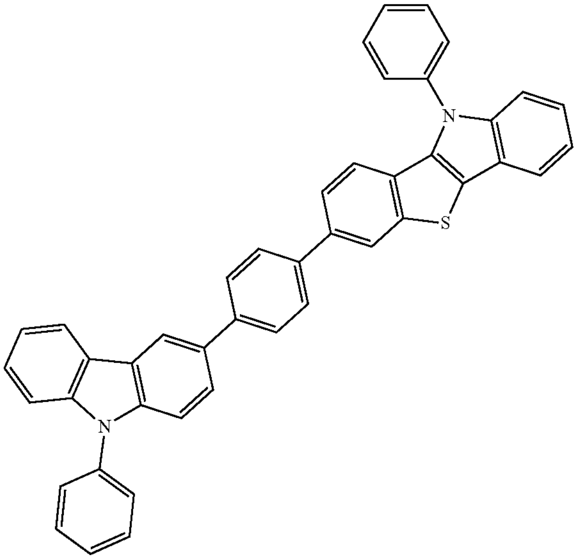

-continued
56
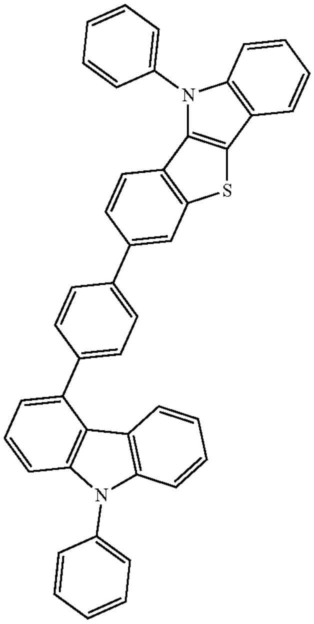
57
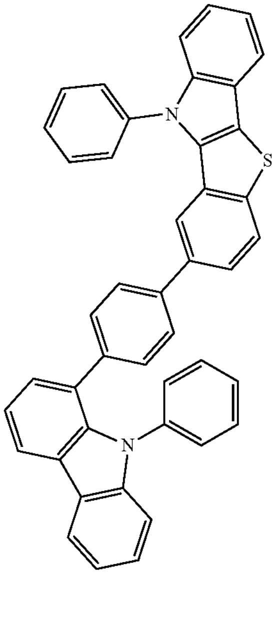
-continued
58
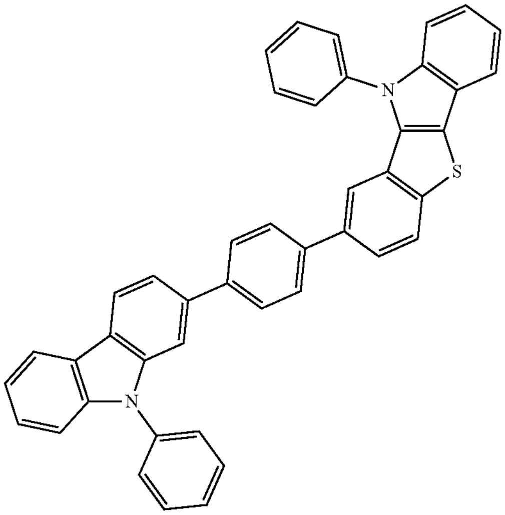
59
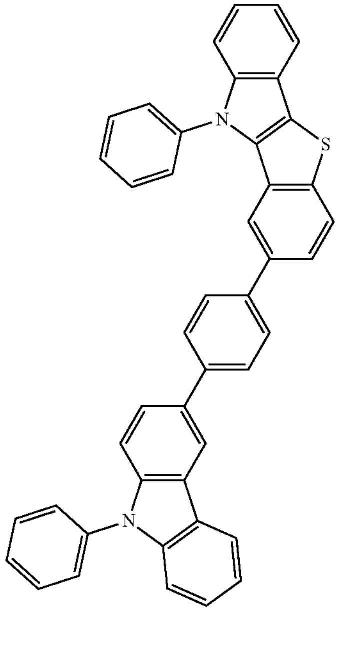

-continued
60
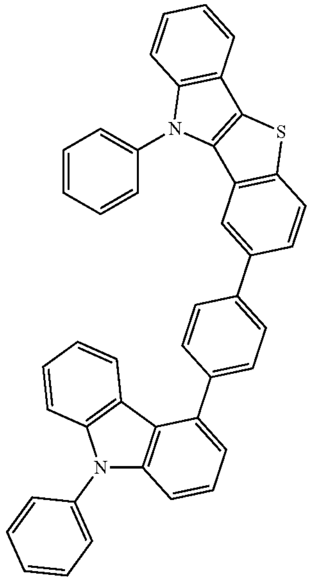
61
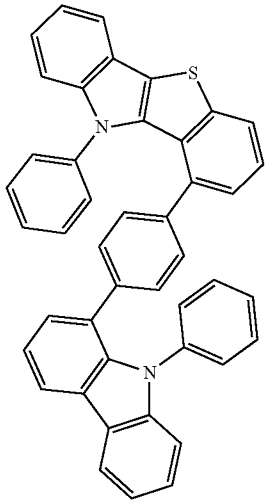
62
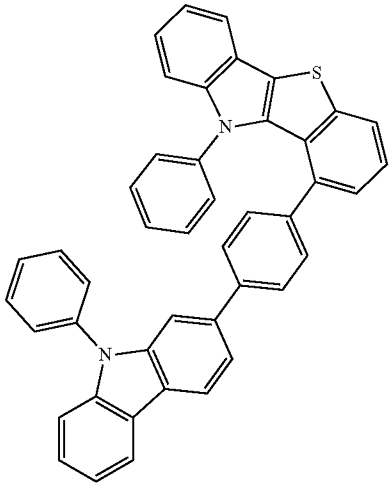
-continued
63
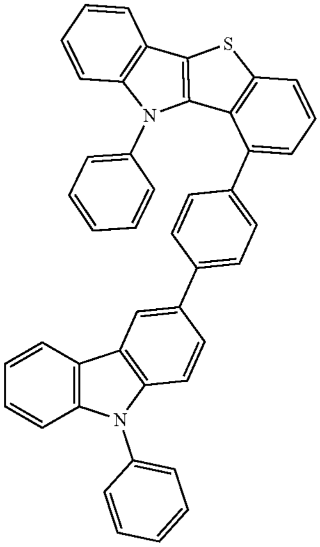
64
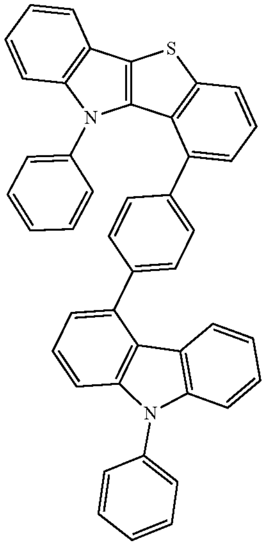
65
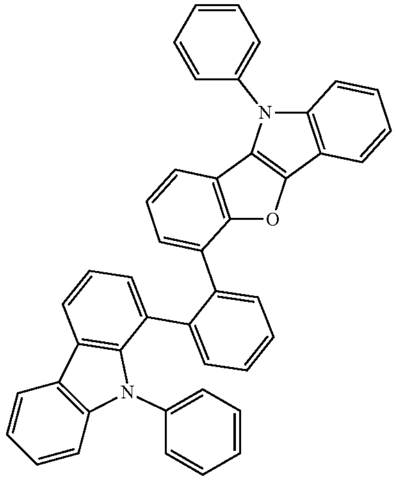

-continued
66
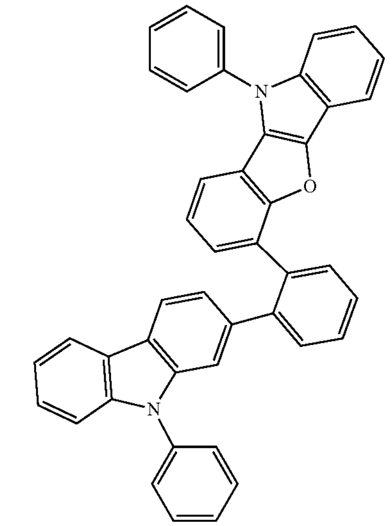
67
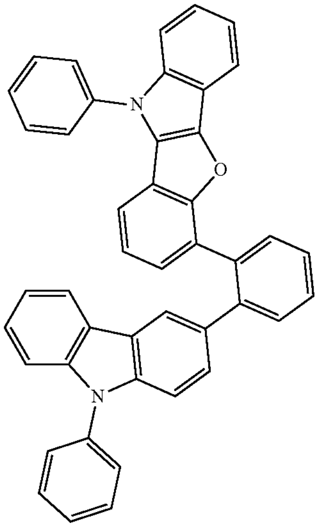
68
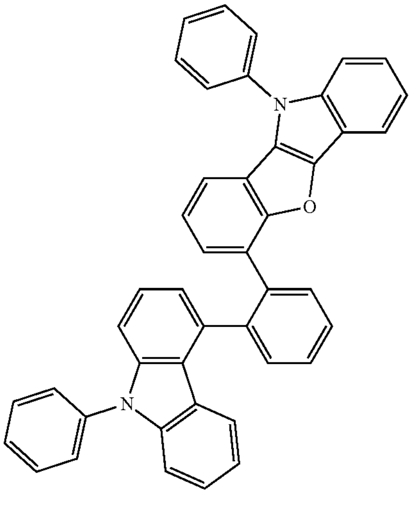
-continued
69
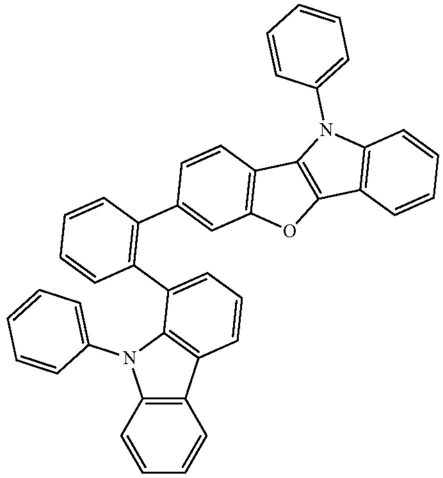
70
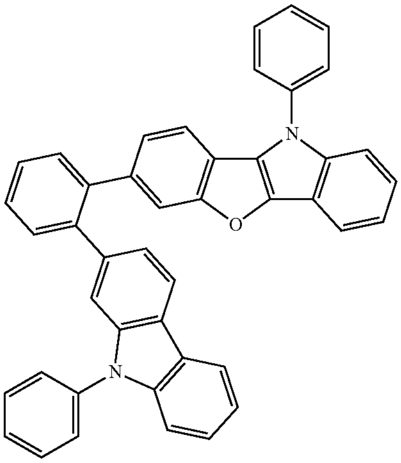
71
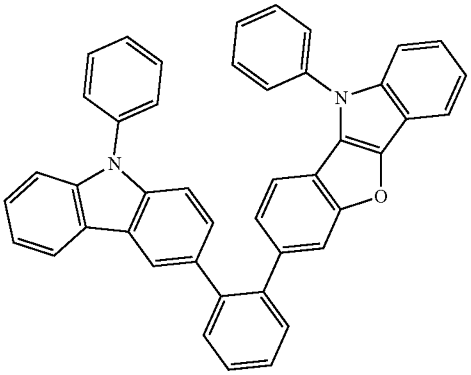

-continued
72
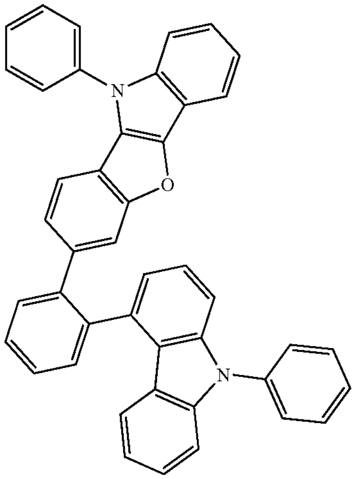
73
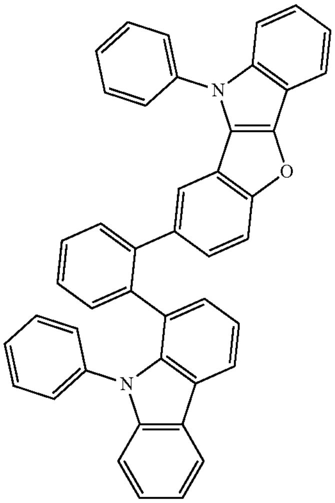
74
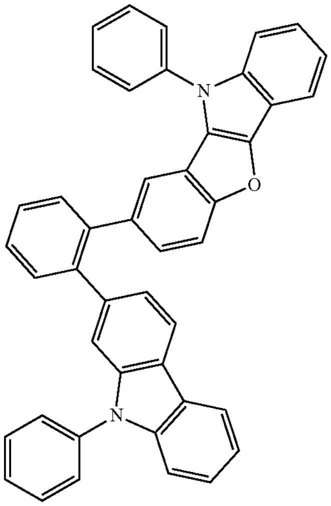
-continued
75
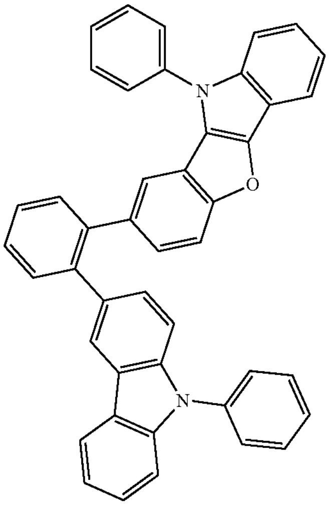
76
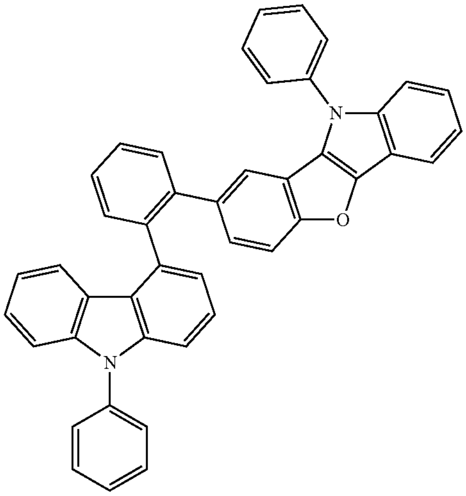
77
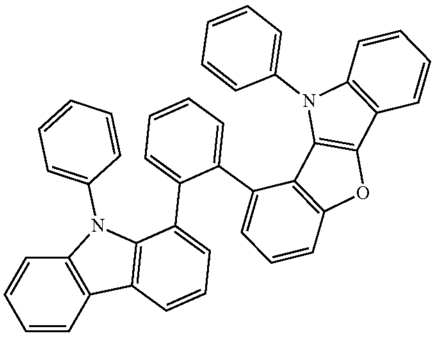

-continued
78
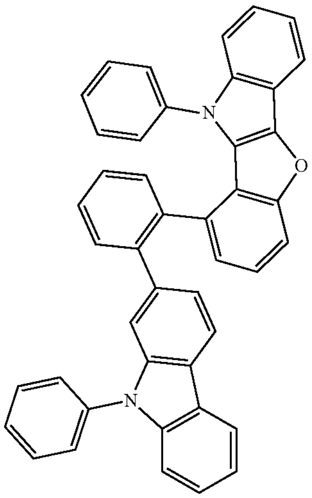
79
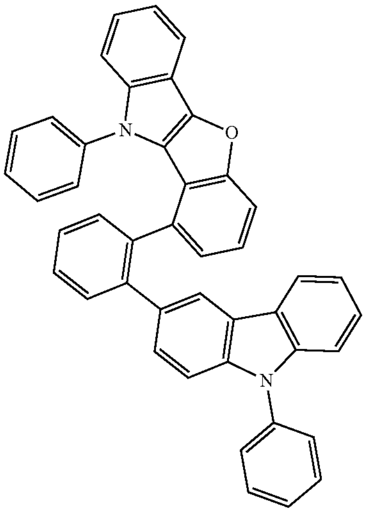
80
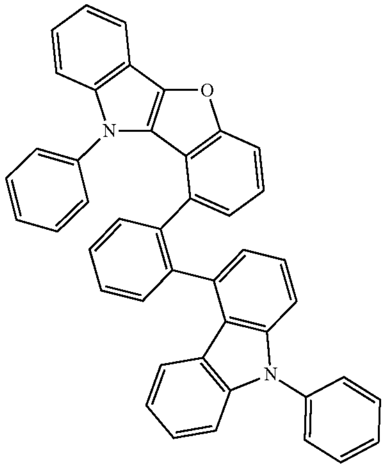
-continued
81
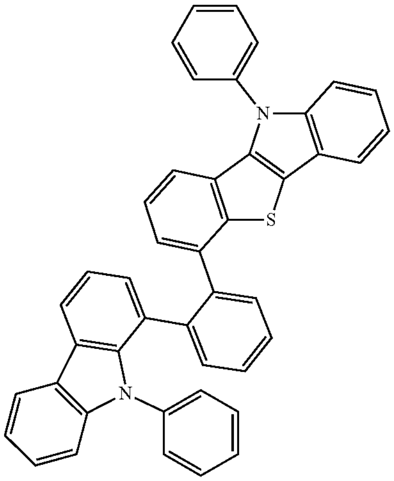
82
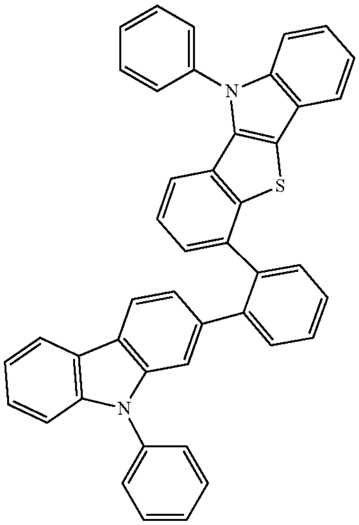
83
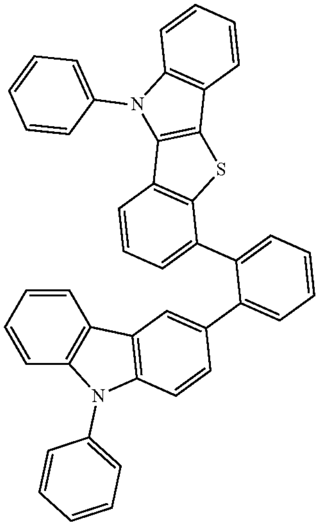

-continued
84
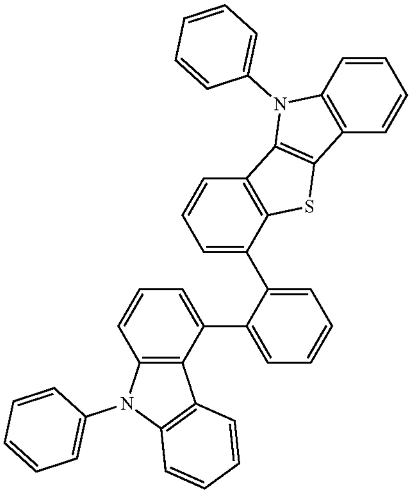
85
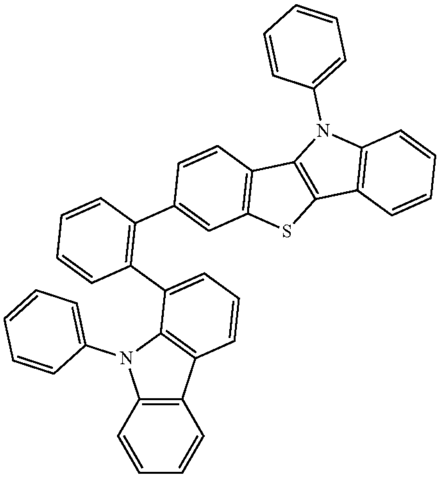
86
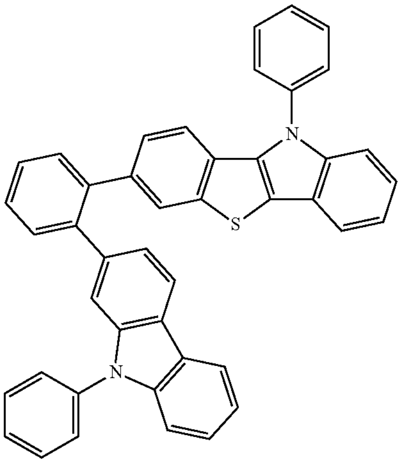
-continued
87
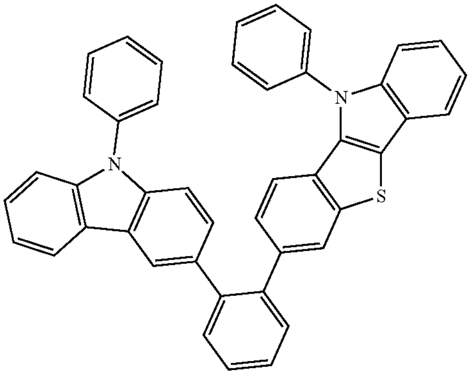
88
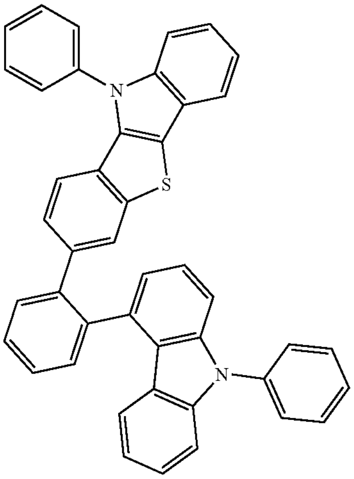
89
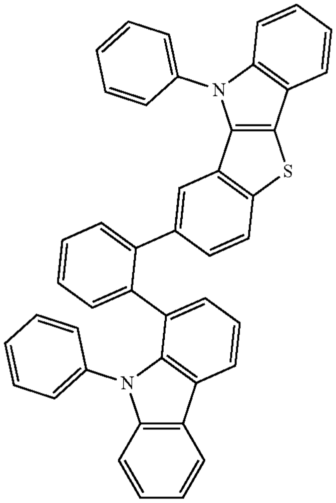

-continued
90
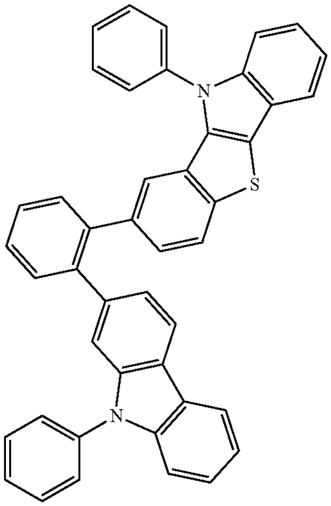
91
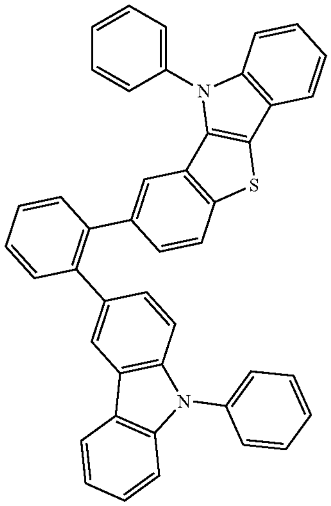
92
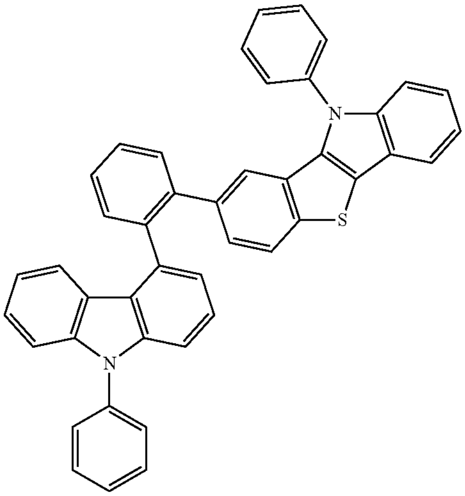
-continued
93
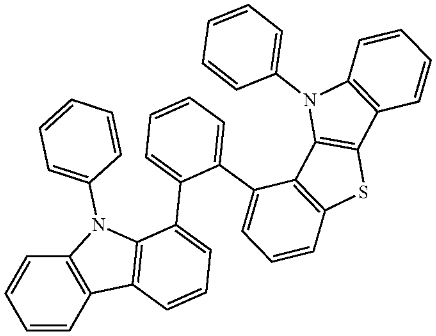
94
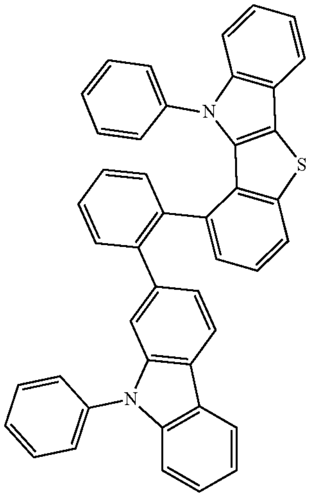
95
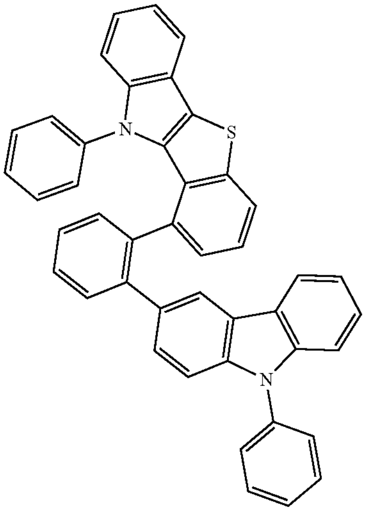

-continued
96
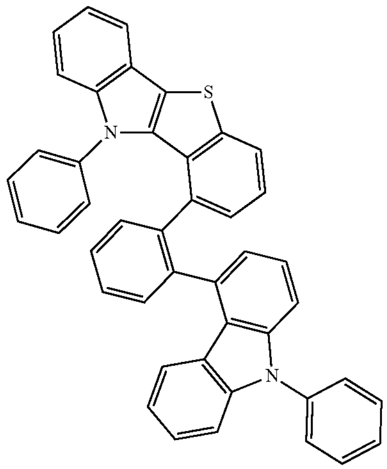
97
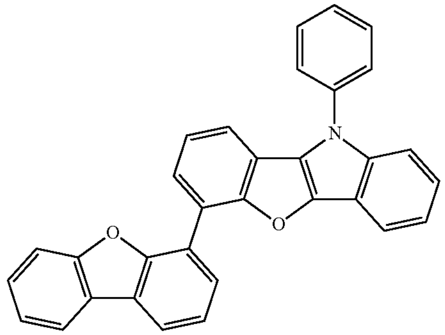
98
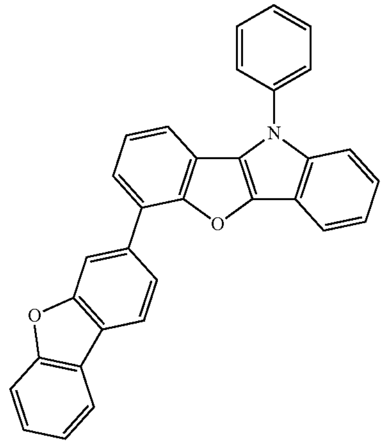
-continued
99
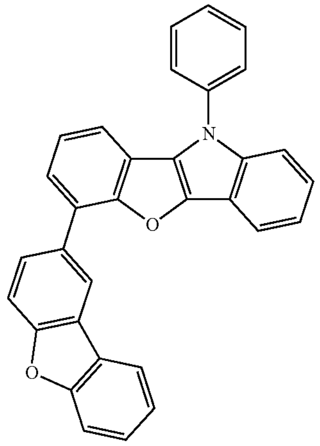
100
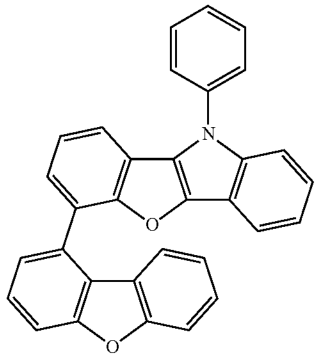
101
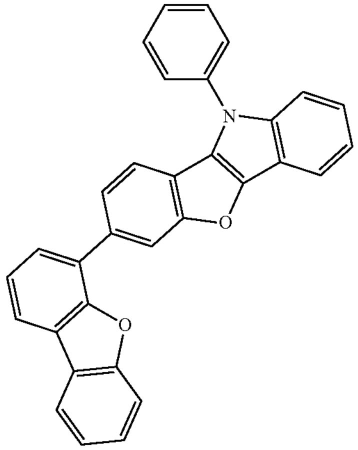

-continued
102
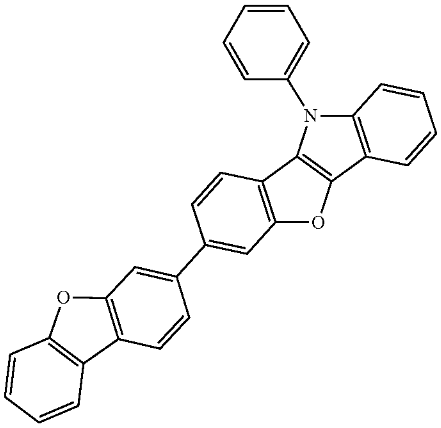
103
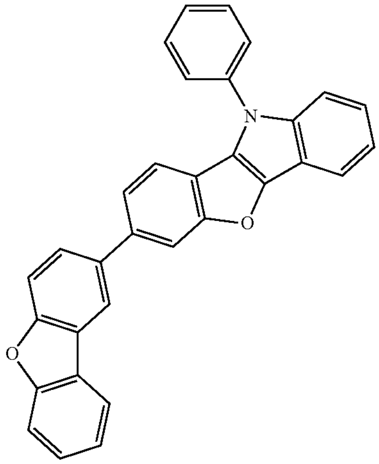
104
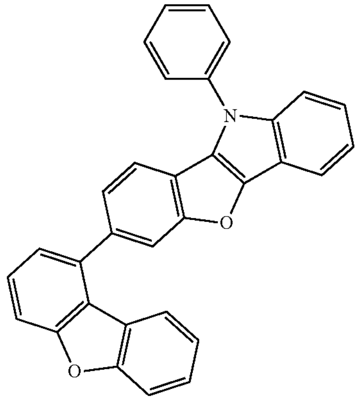
105
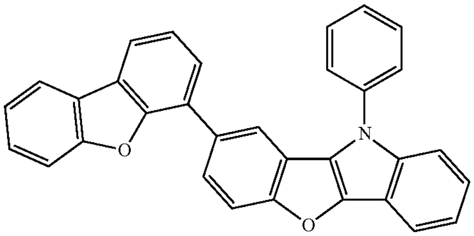
-continued
106
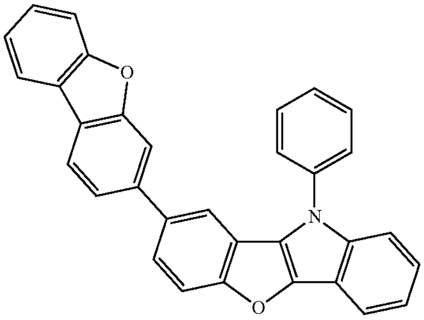
107
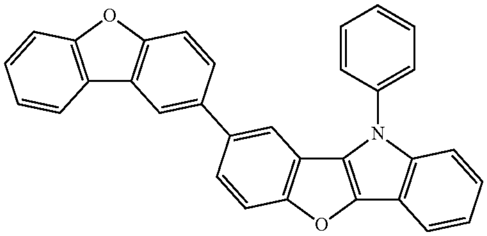
108
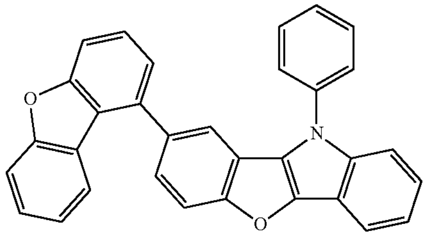
109
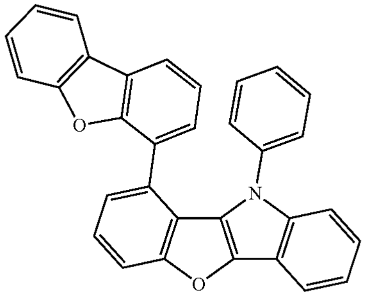
110
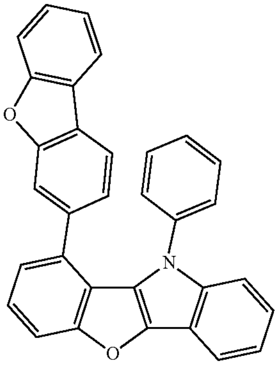

-continued
111
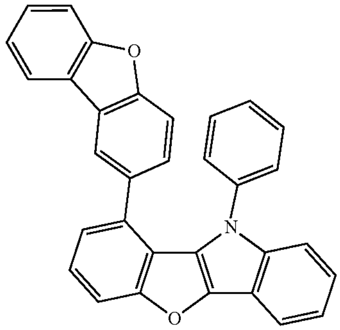
112
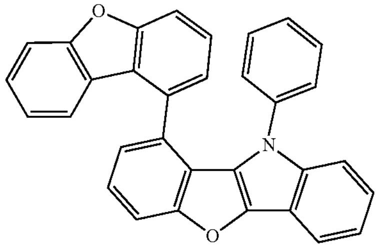
113
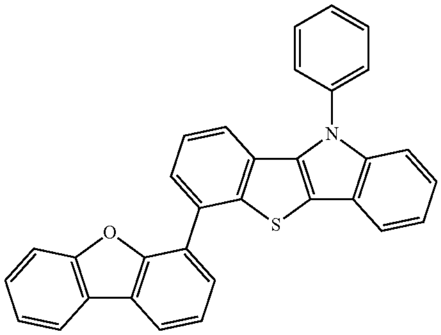
114
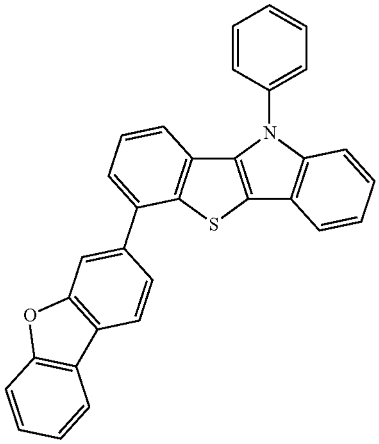
-continued
115
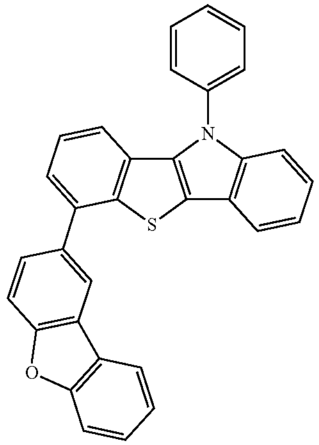
116
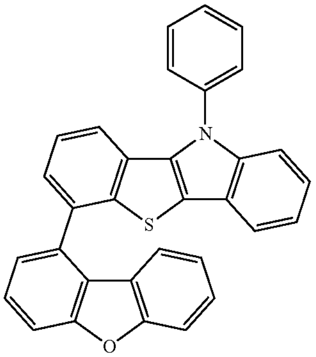
117
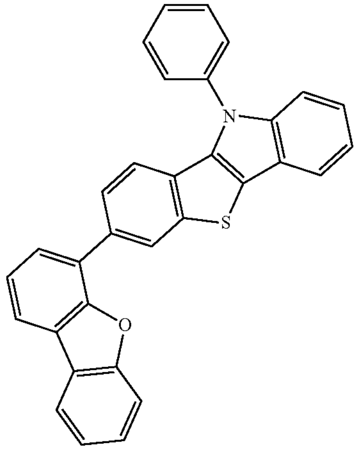

-continued
118
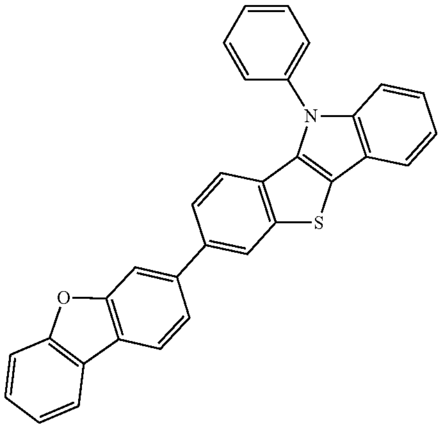
119
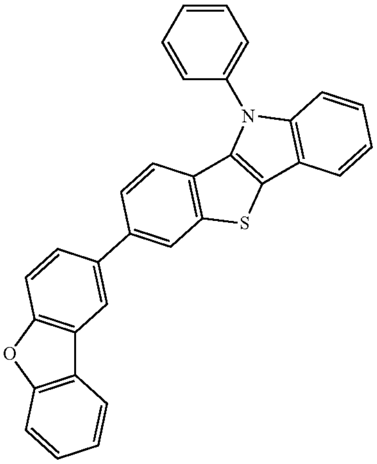
120
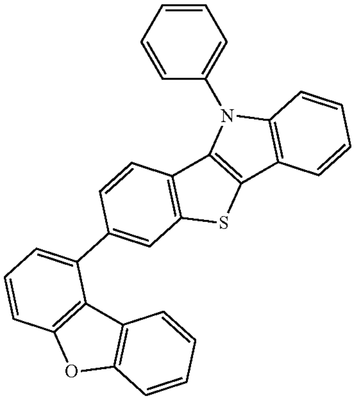
121
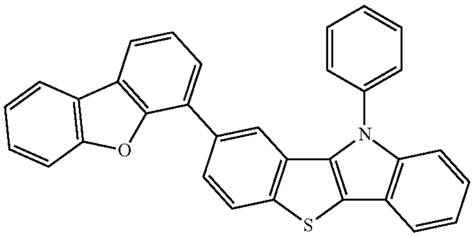
-continued
122
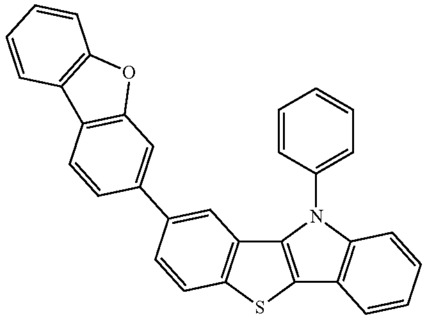
123
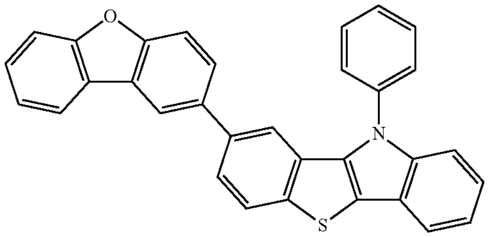
124
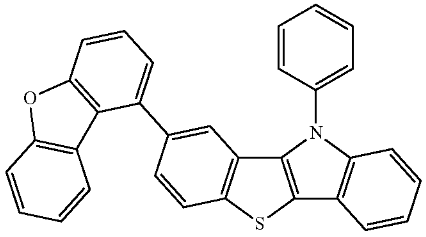
125
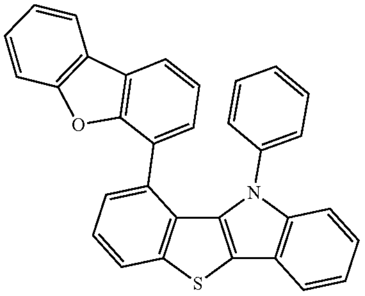
126
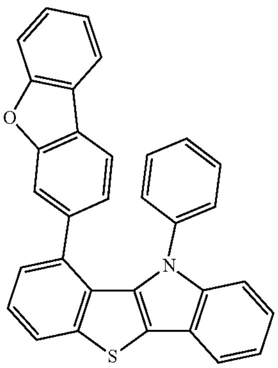

-continued
127
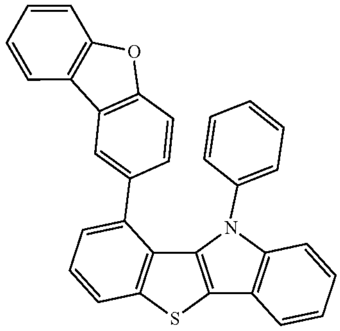
128
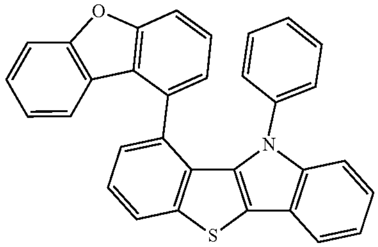
129
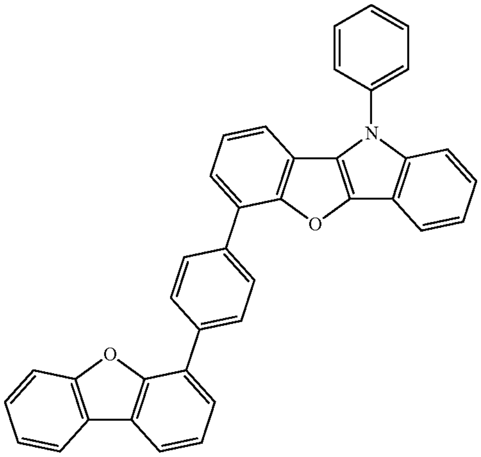
130
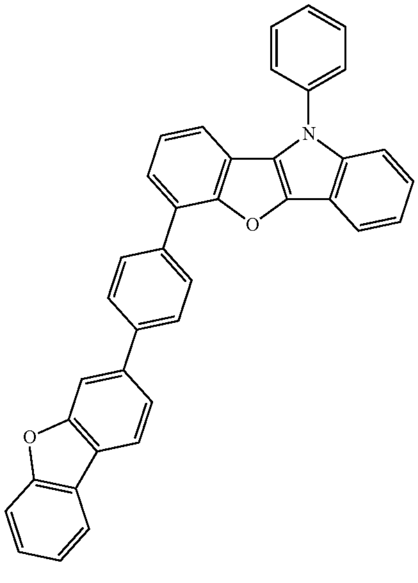
-continued
131
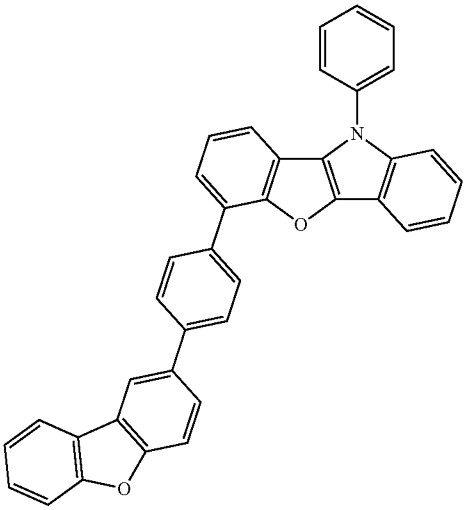
132
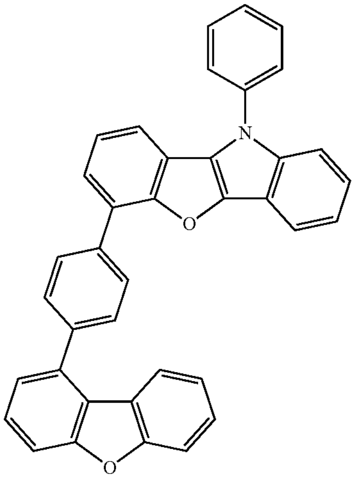
133
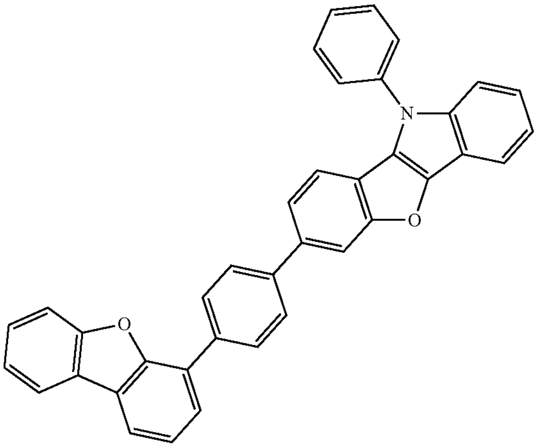

-continued
134
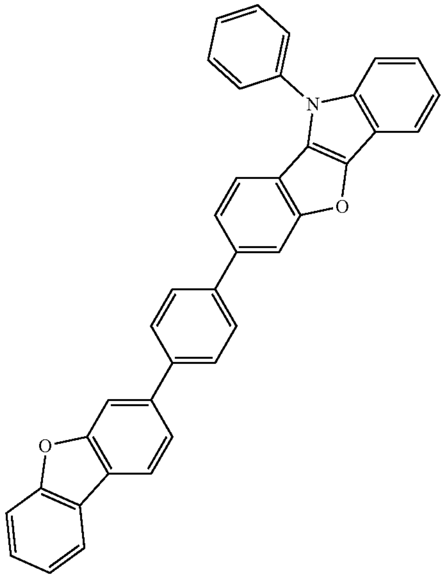
135
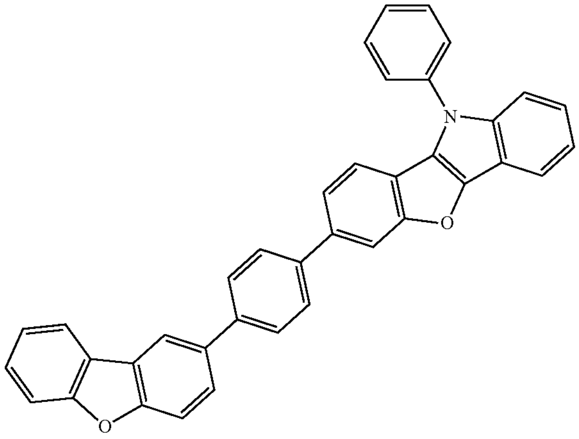
136
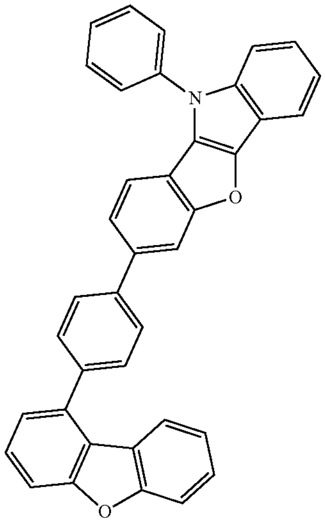
-continued
137
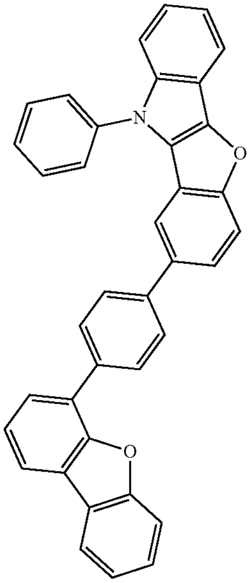
138
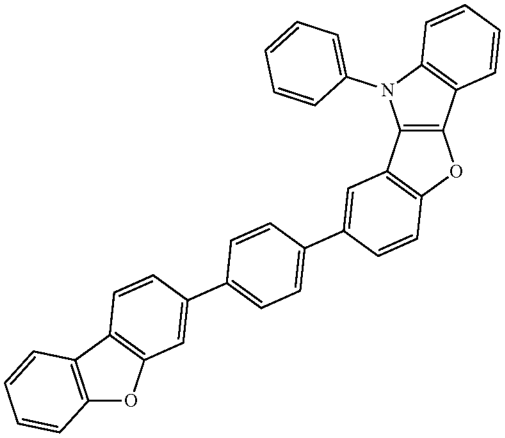
139
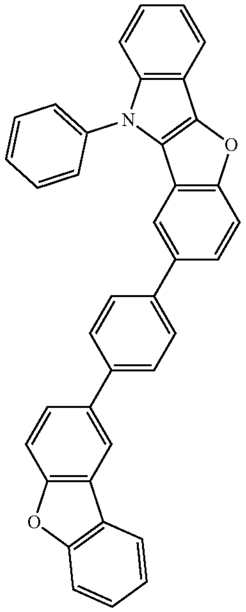

-continued
140
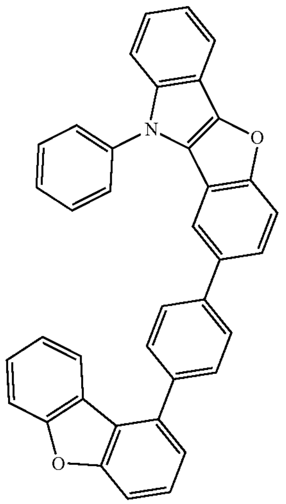
141
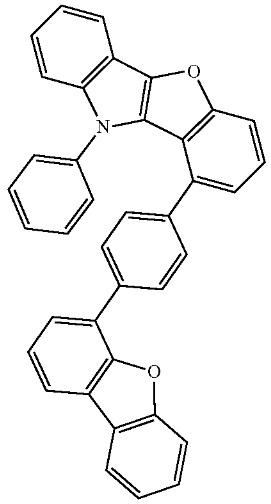
142
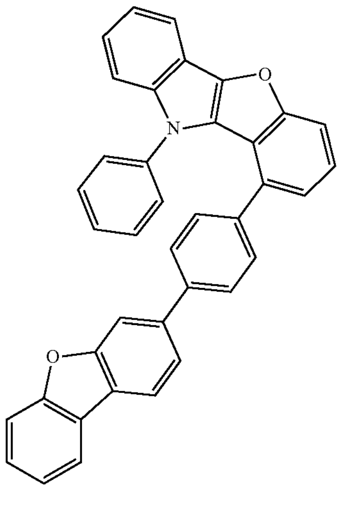
-continued
143
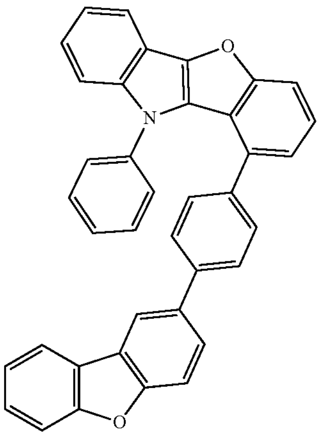
144
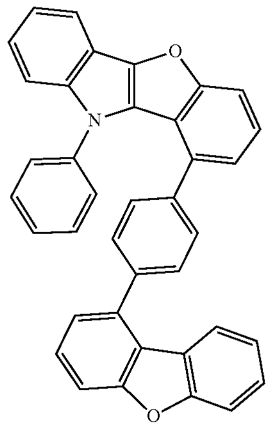
145
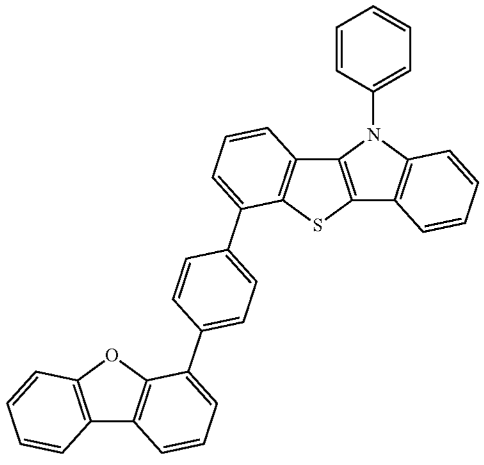

-continued
146
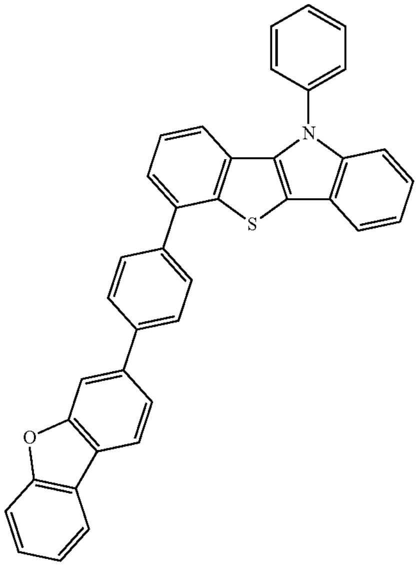
147
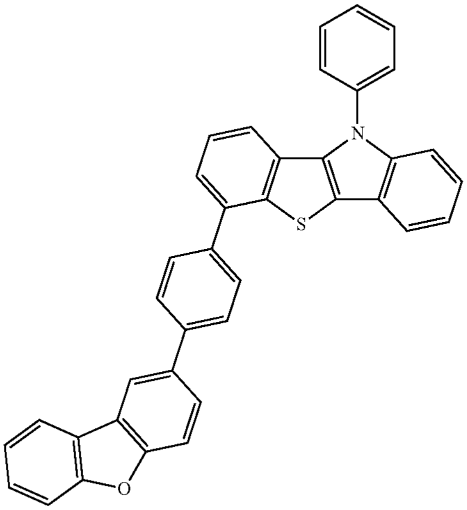
148
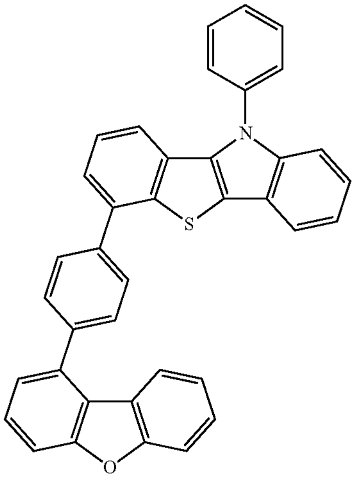
-continued
149
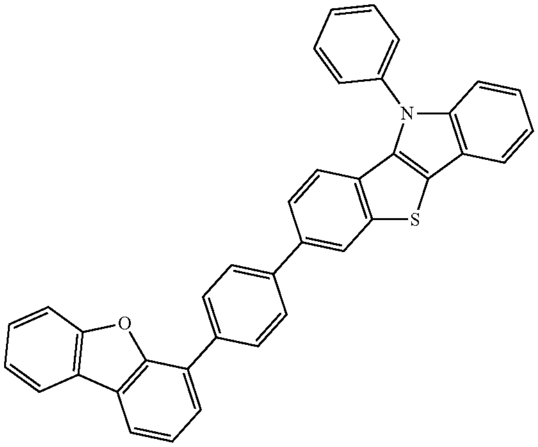
150
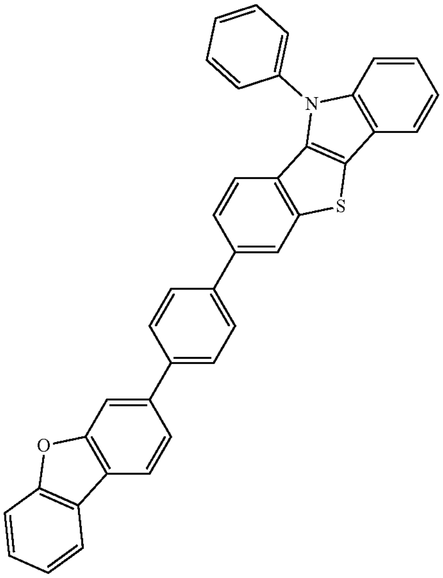
151
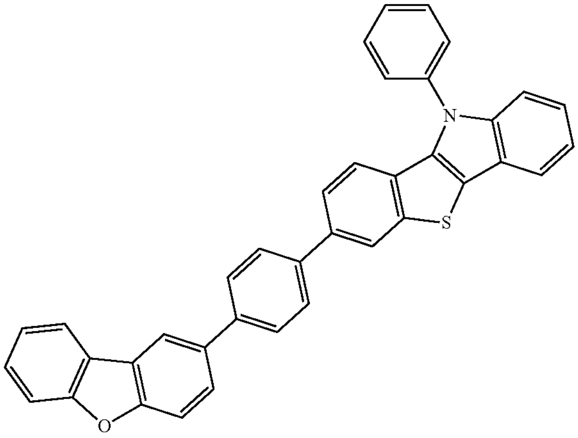

-continued
152
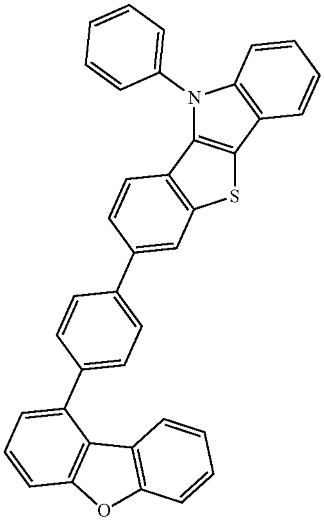
153
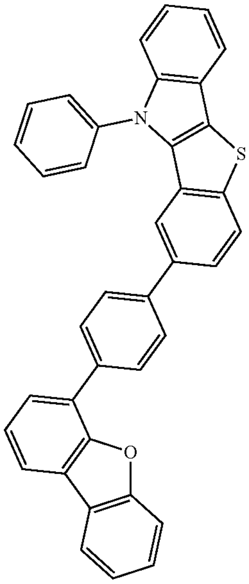
154
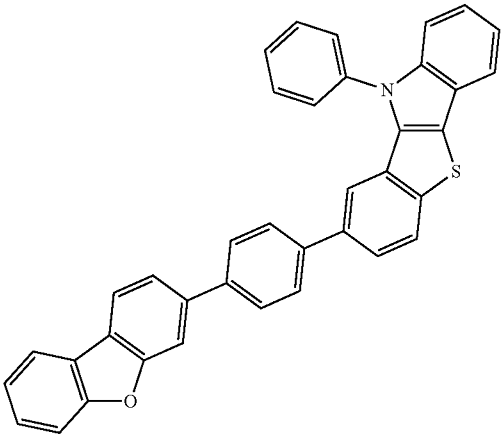
-continued
155
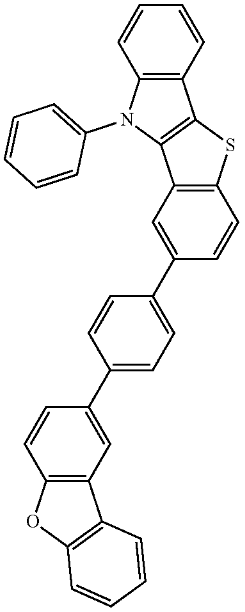
156
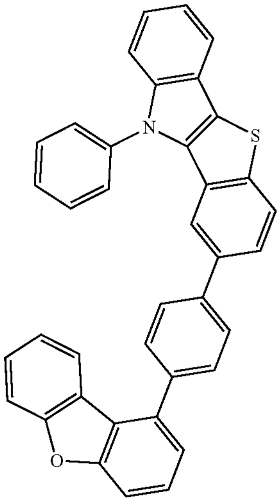
157
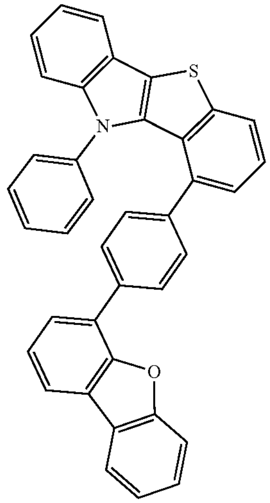

-continued
158
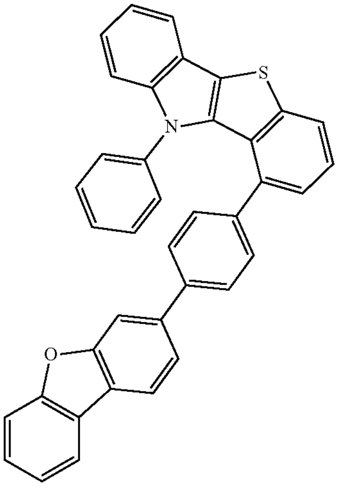
159
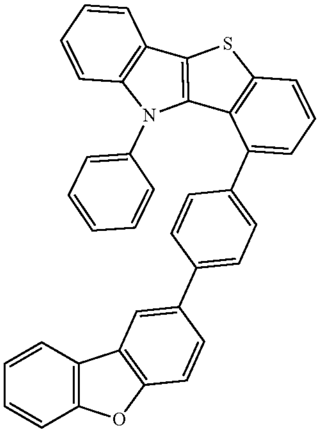
160
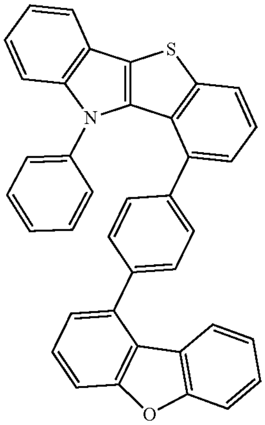
-continued
161
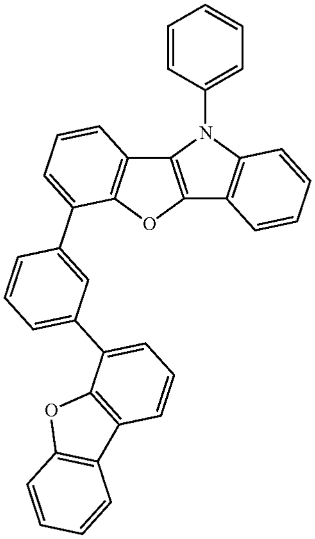
162
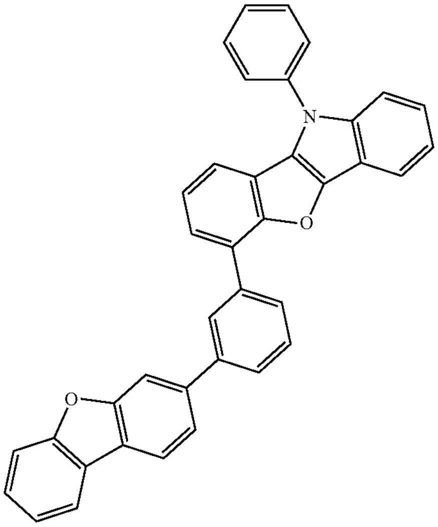
163
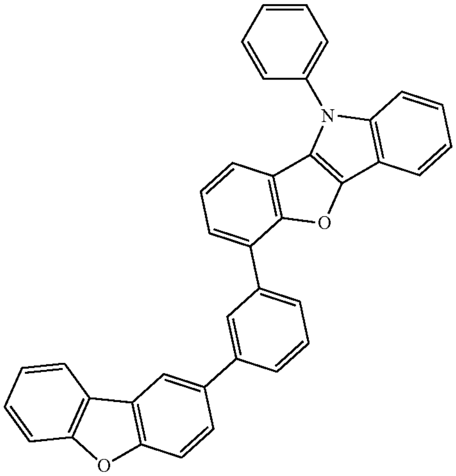

-continued
164
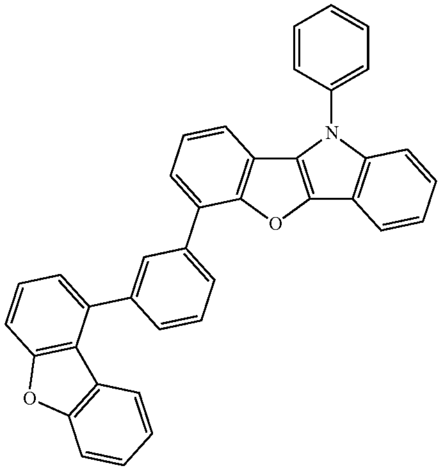
165
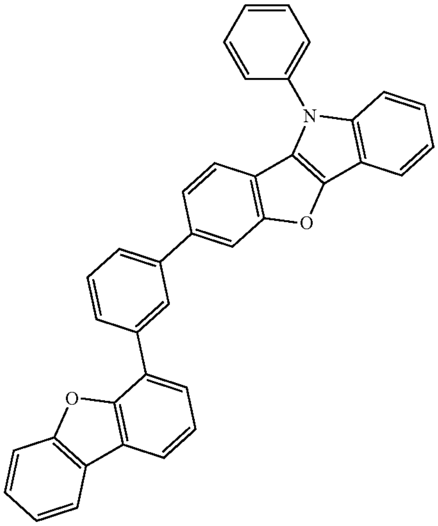
166
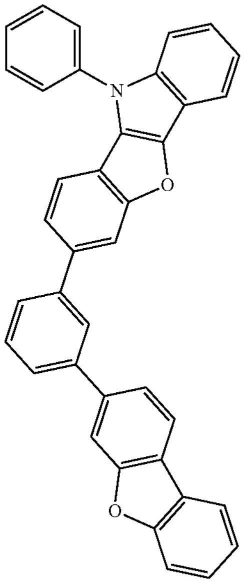
-continued
167
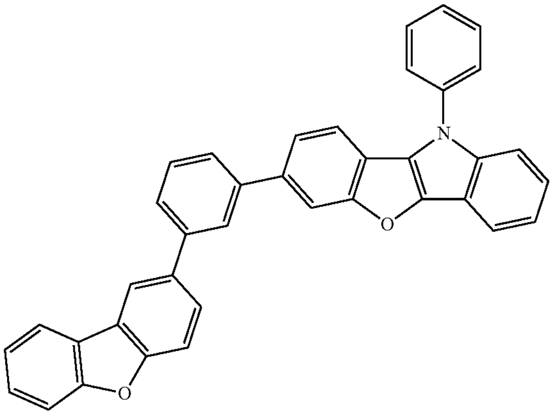
168
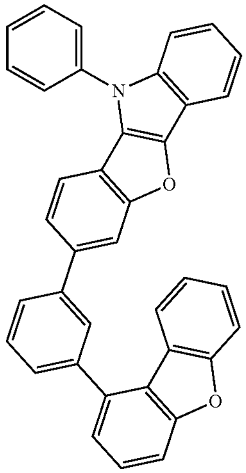
169
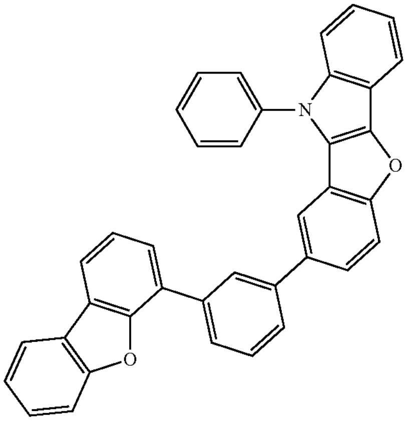

-continued
170
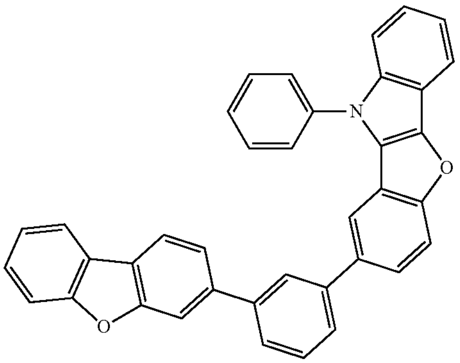
171
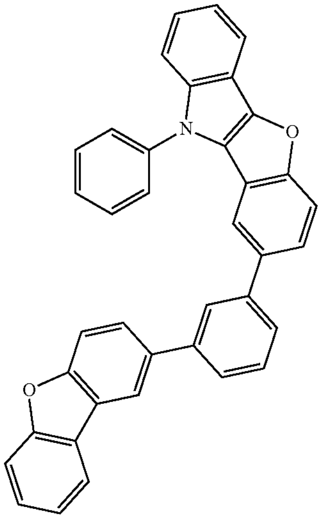
172
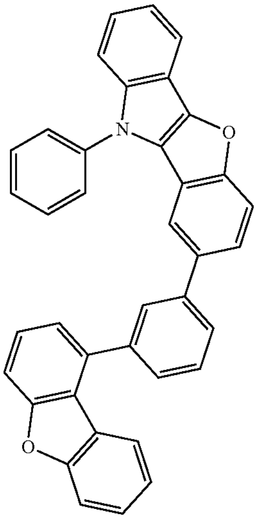
-continued
173
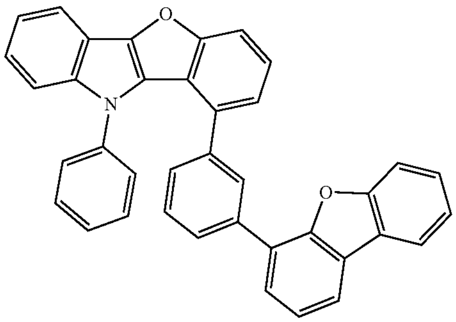
174
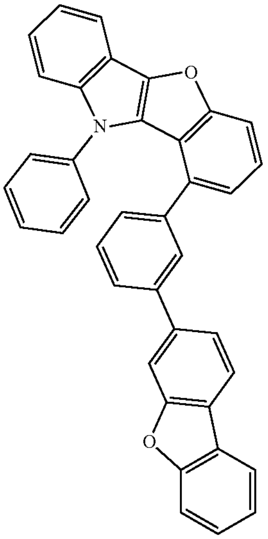
175
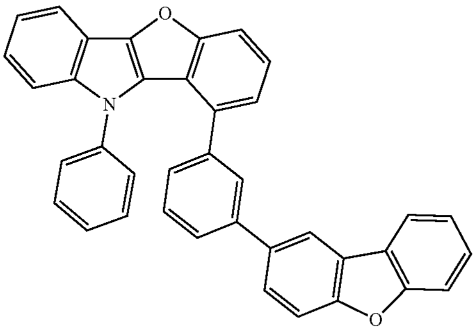
176
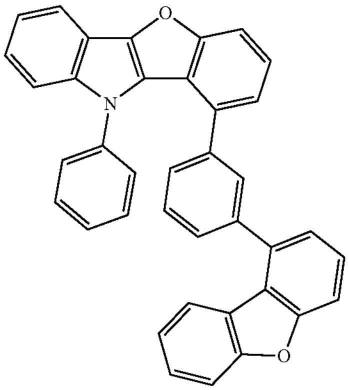

-continued
177
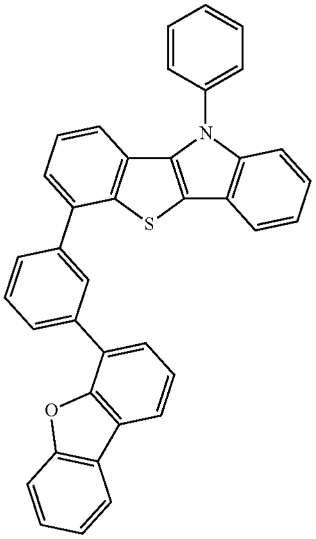
178
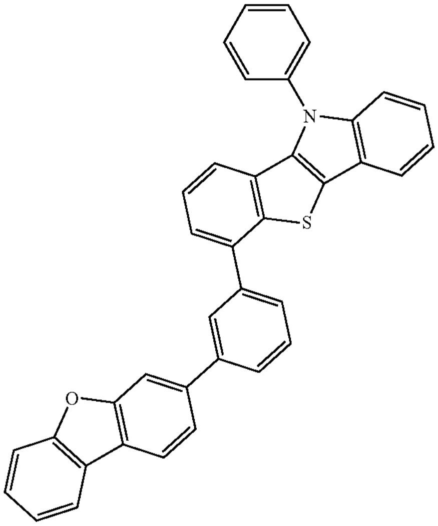
179
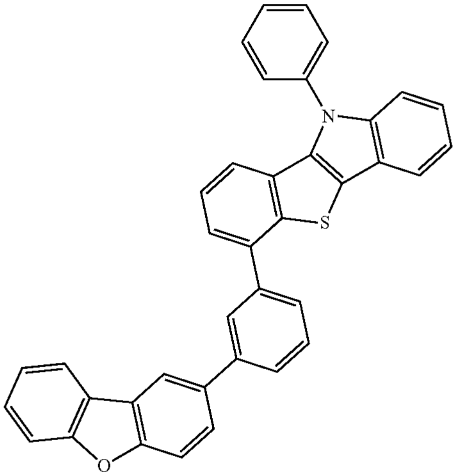
-continued
180
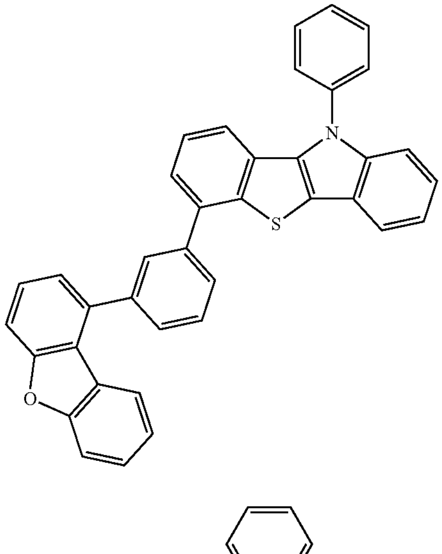
181
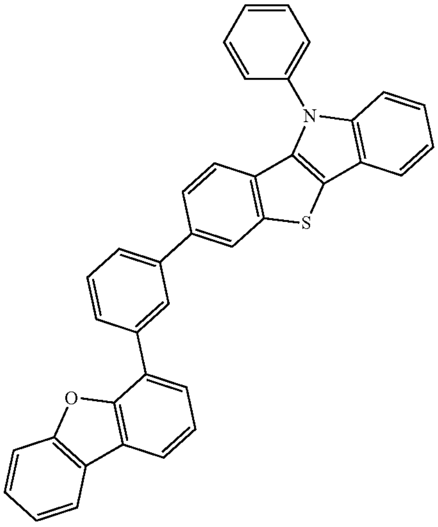
182
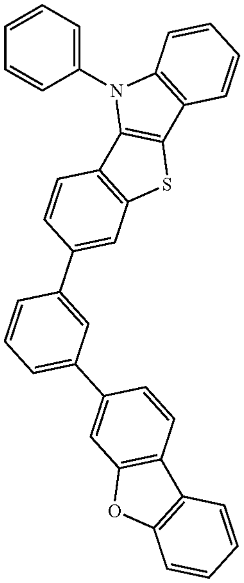

-continued
183
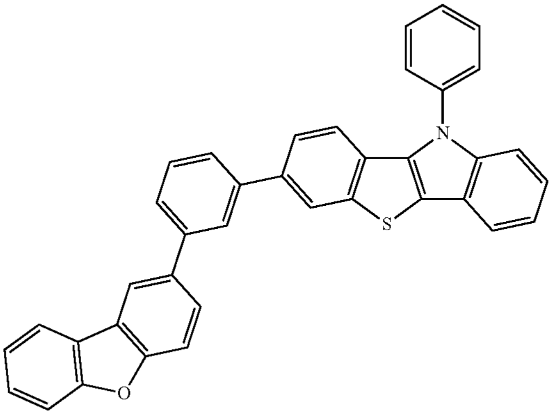
184
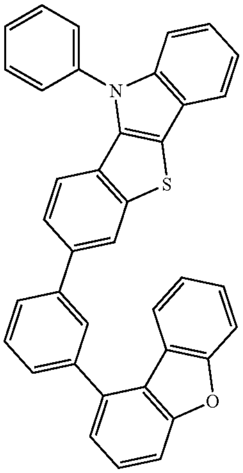
185
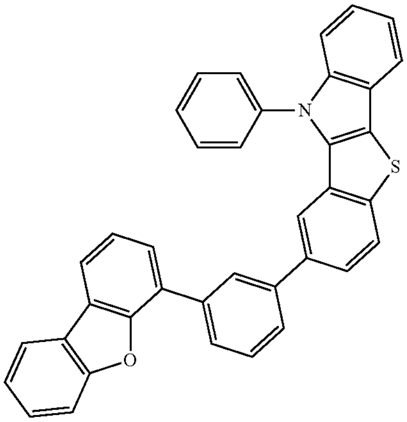
-continued
186
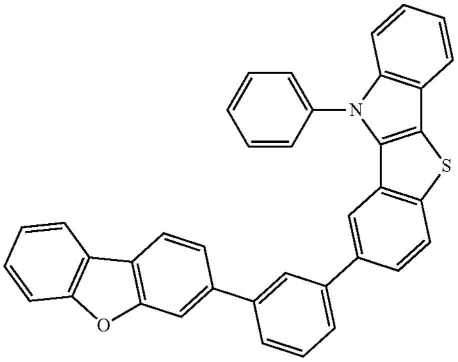
187
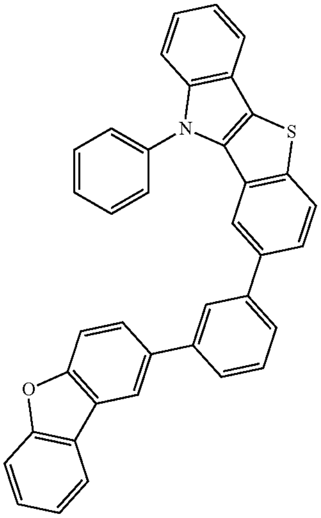
188
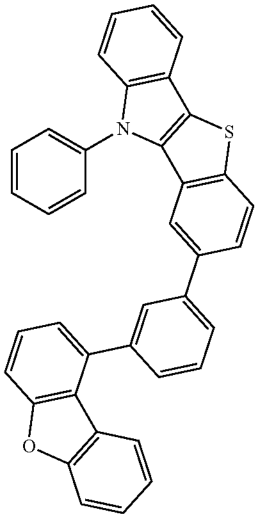

-continued
189
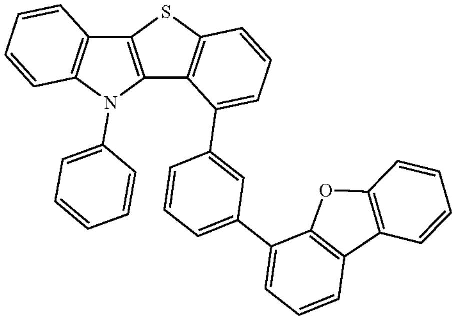
190
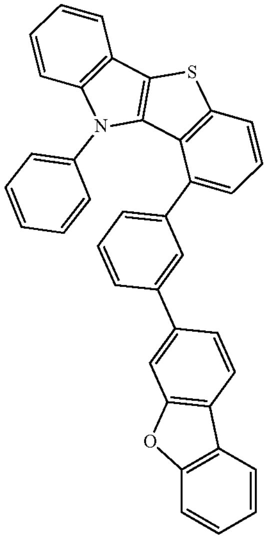
191
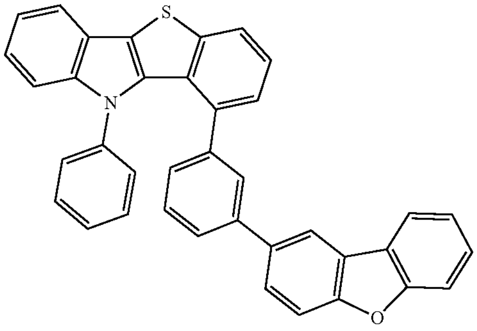
192
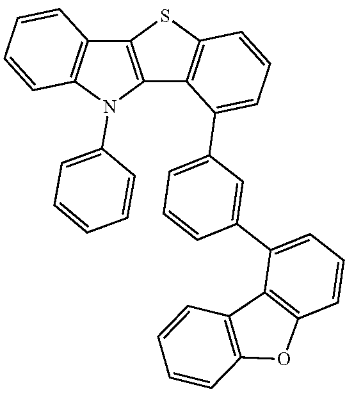
-continued
193
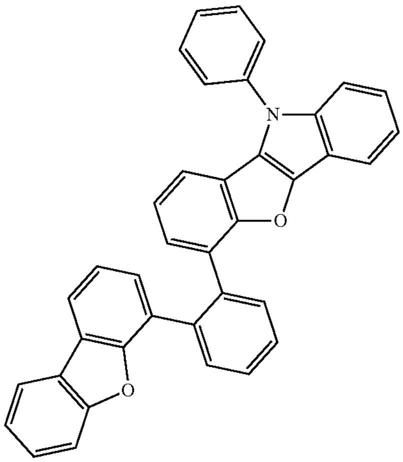
194
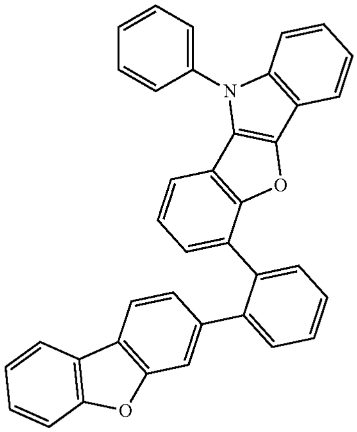
195
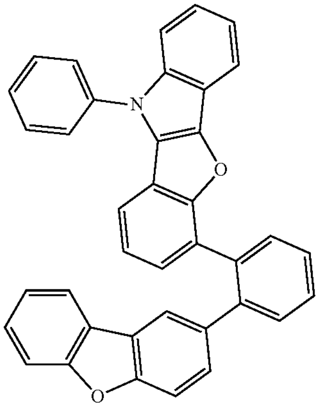

-continued
196
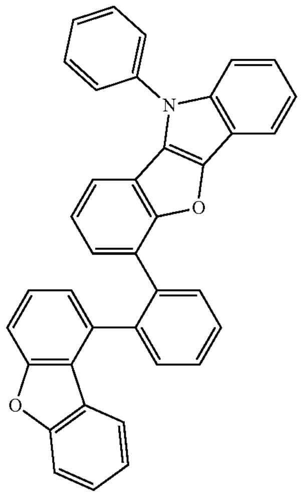
197
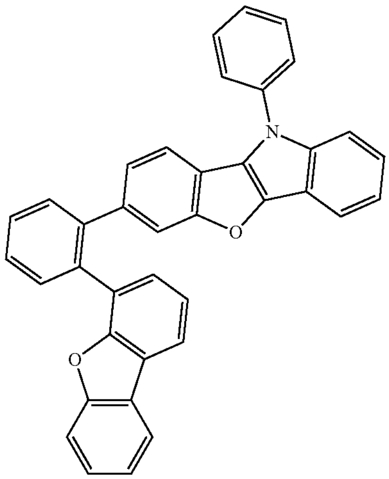
198
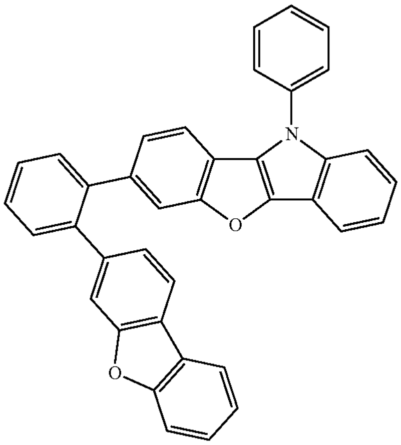
-continued
199
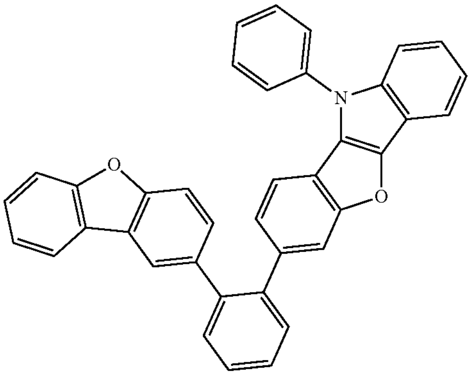
200
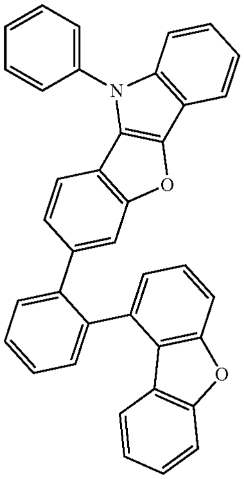
201
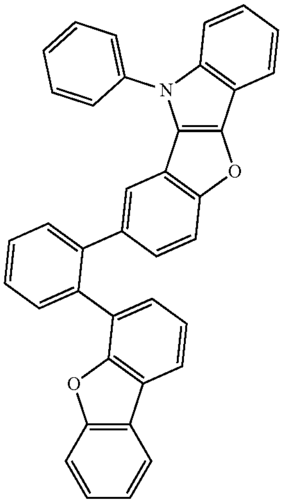

-continued
202
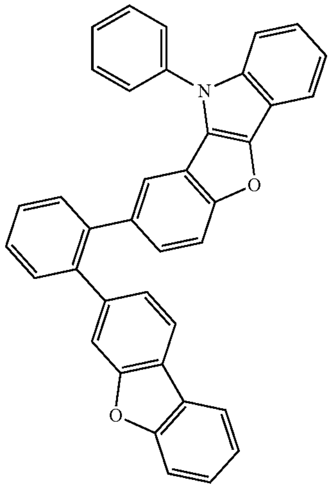
203
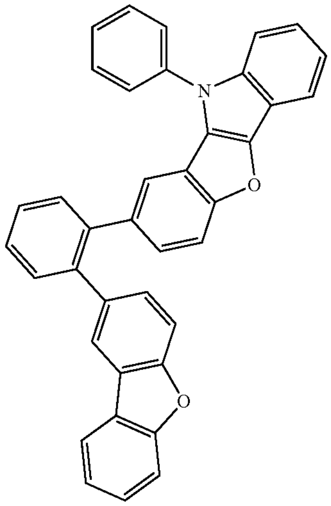
204
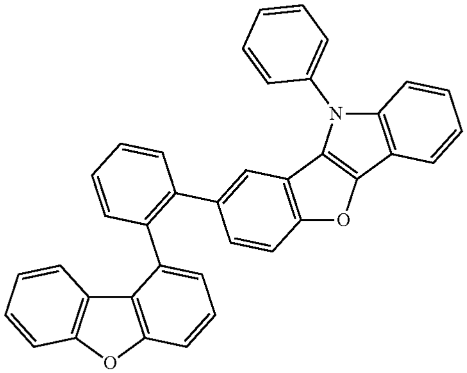
-continued
205
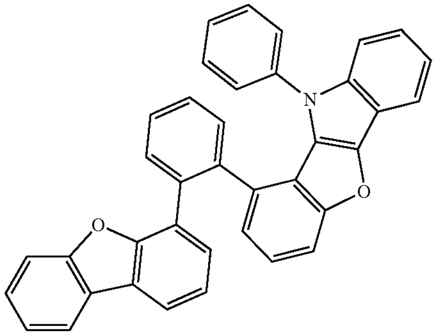
206
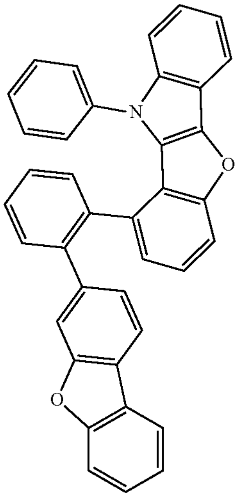
207
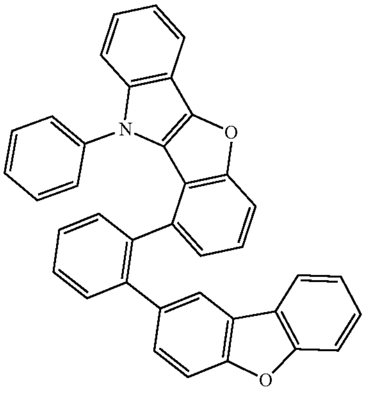

-continued
208
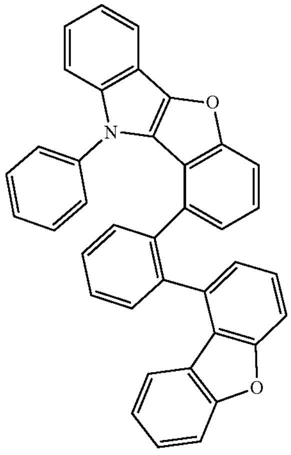
209
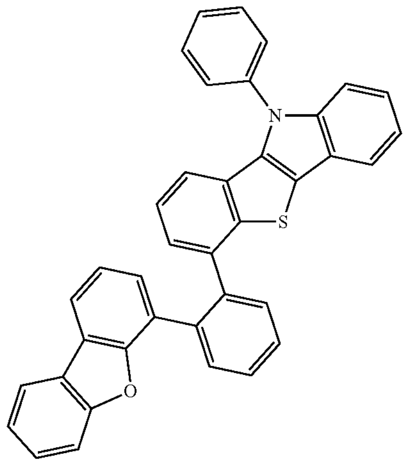
210
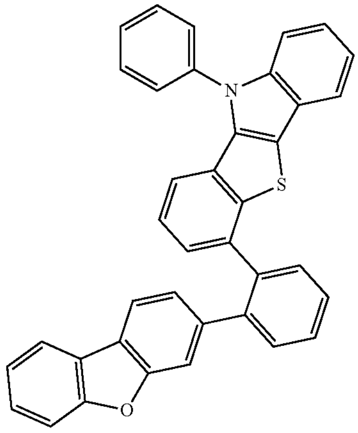
-continued
211
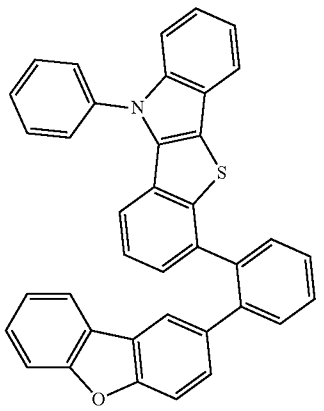
212
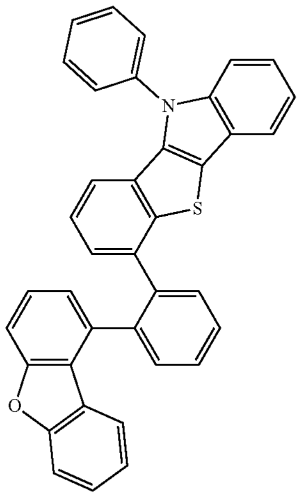
213
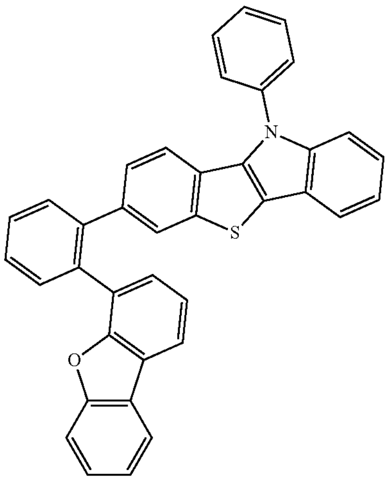

-continued
214
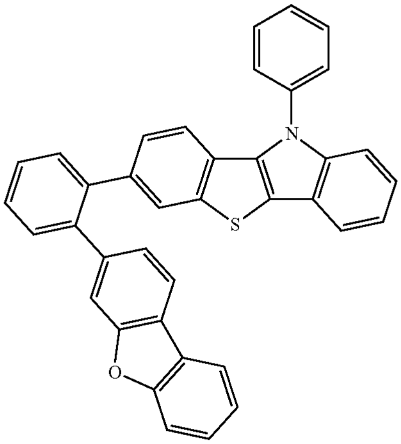
215
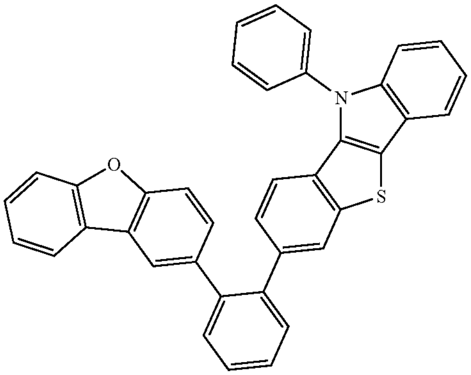
216
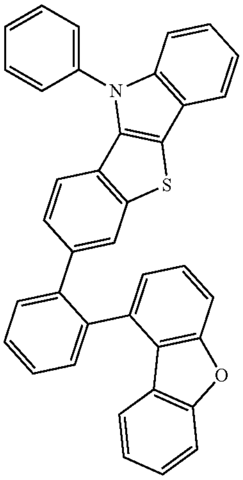
-continued
217
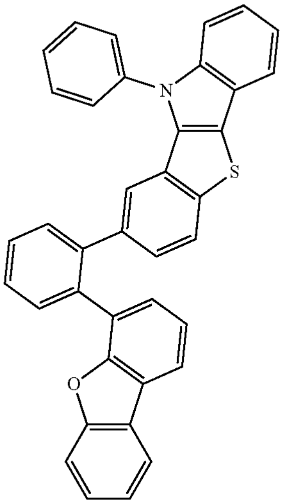
218
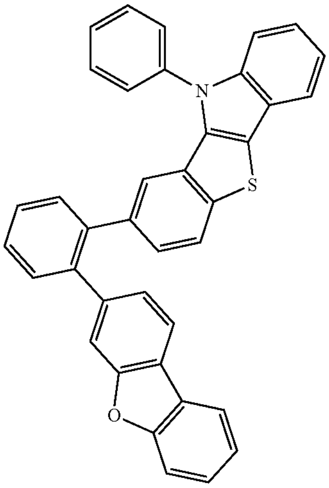
219
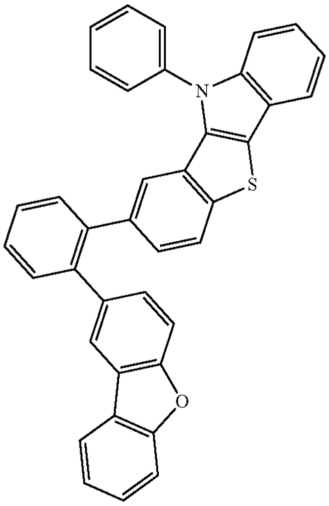

-continued
220
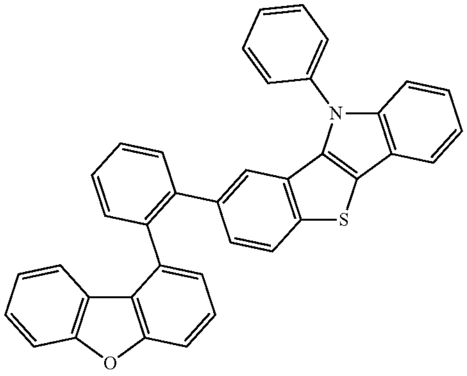
221
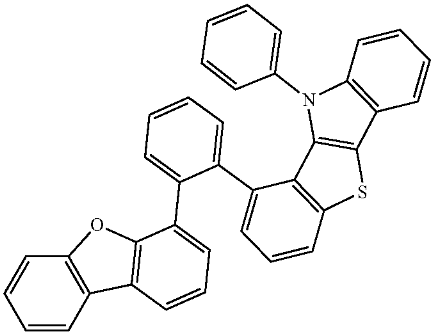
222
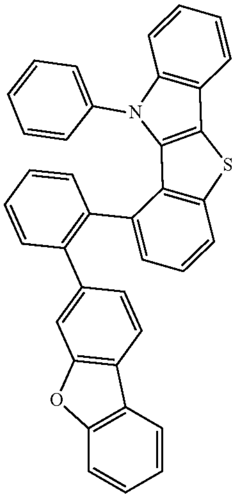
223
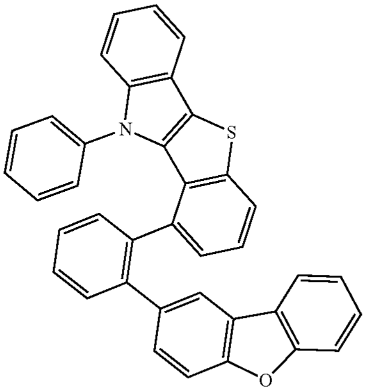
-continued
224
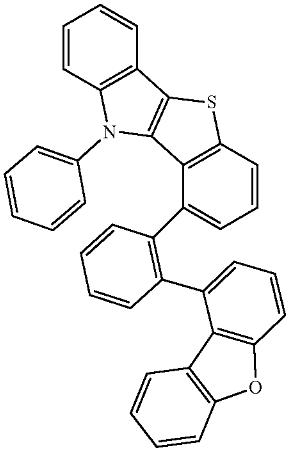
225
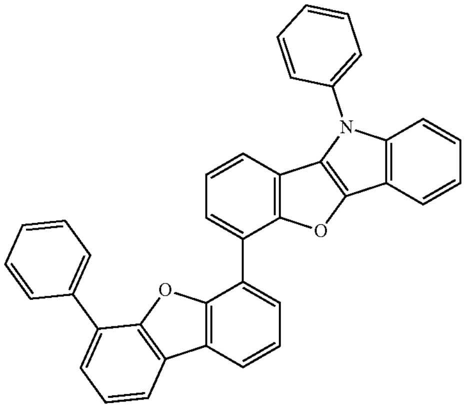
226
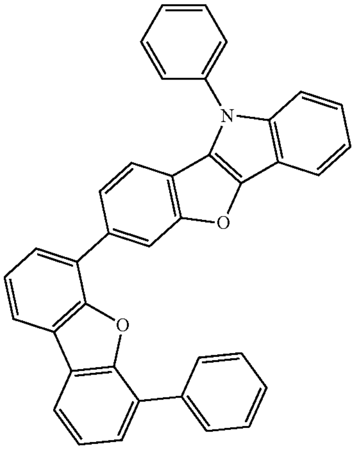

-continued
227
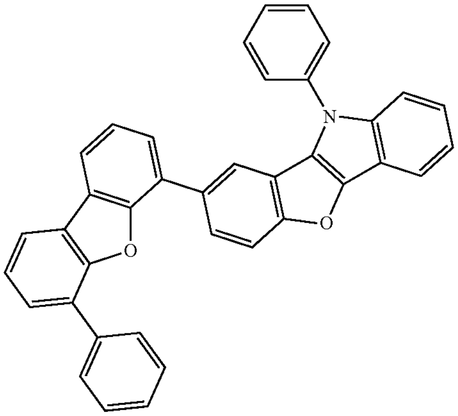
228
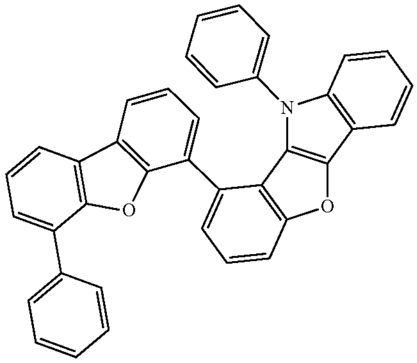
229
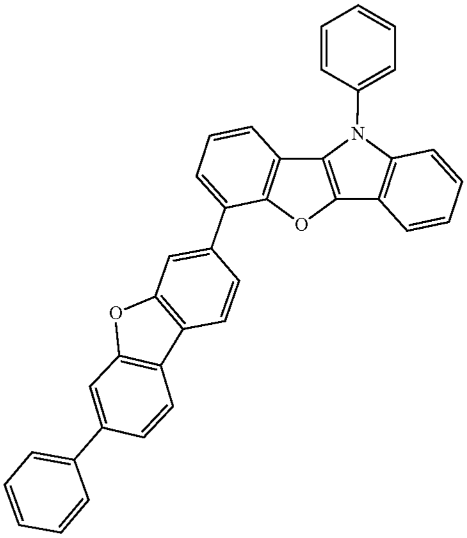
-continued
230
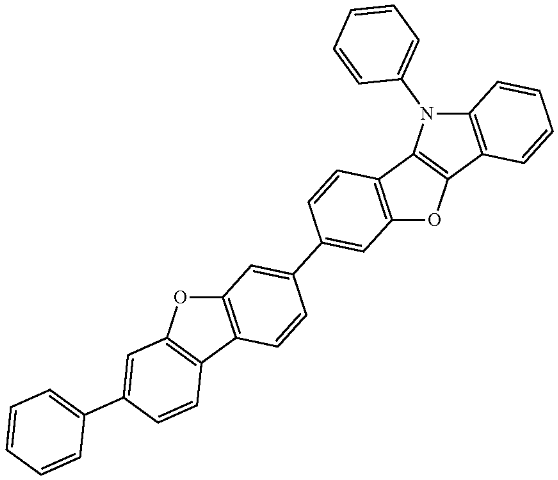
231
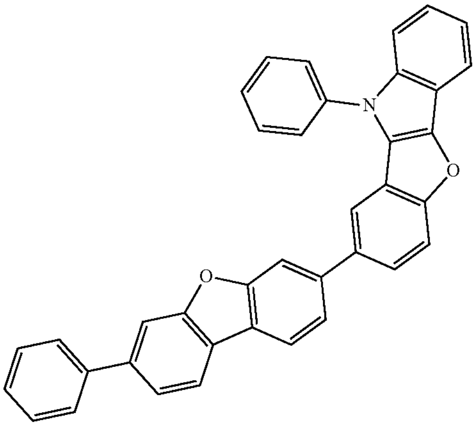
232
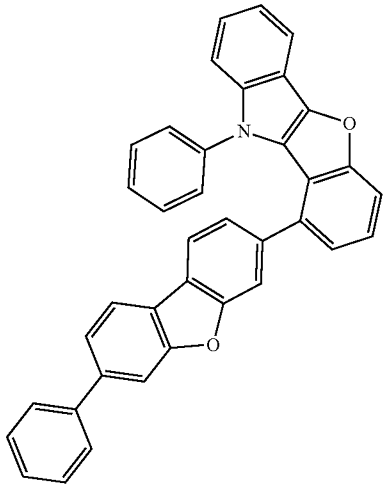

-continued
233
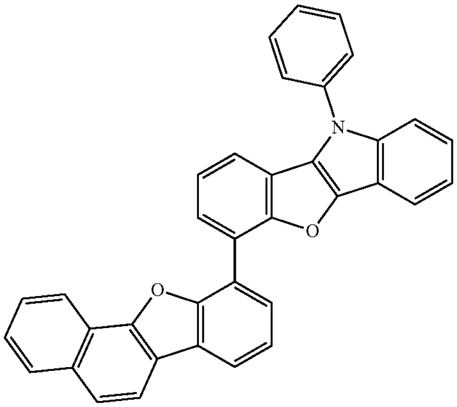
234
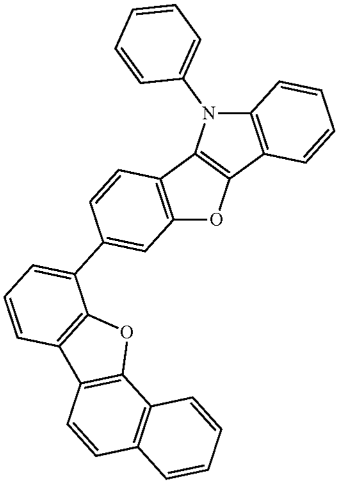
235
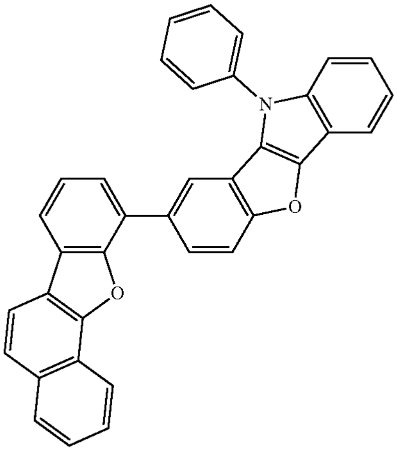
-continued
236
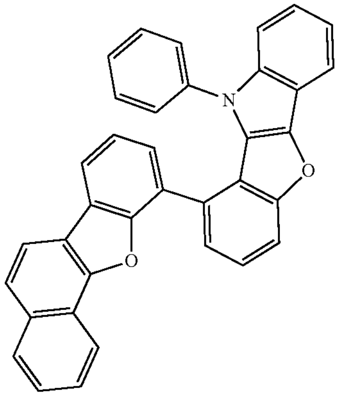
237
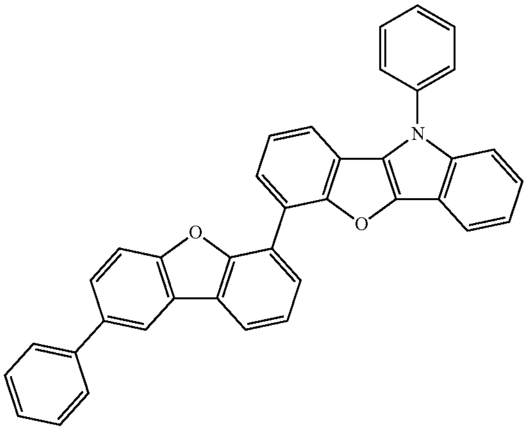
238
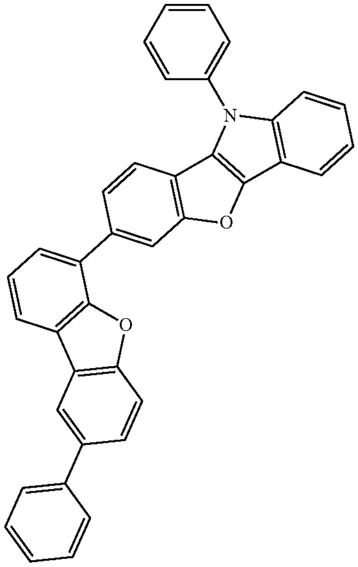

-continued
239
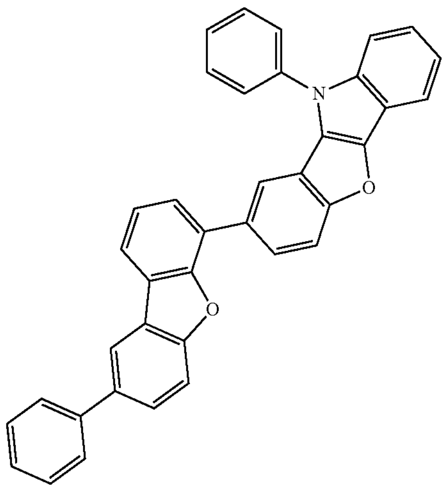
240
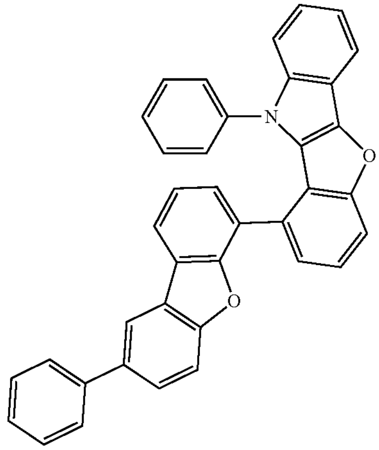
241
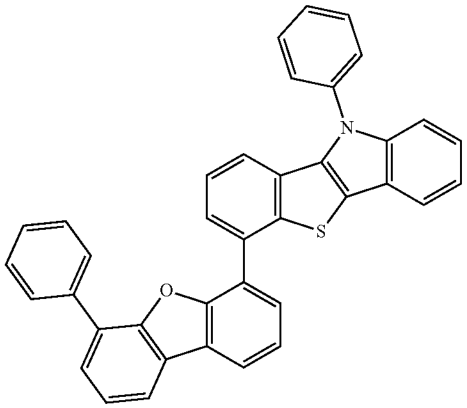
-continued
242
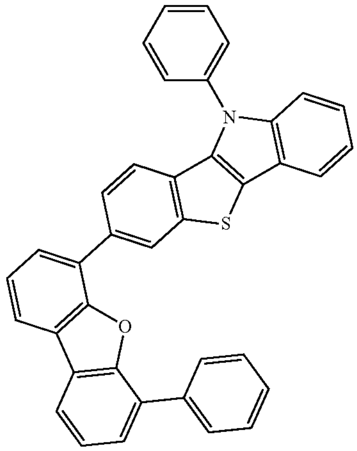
243
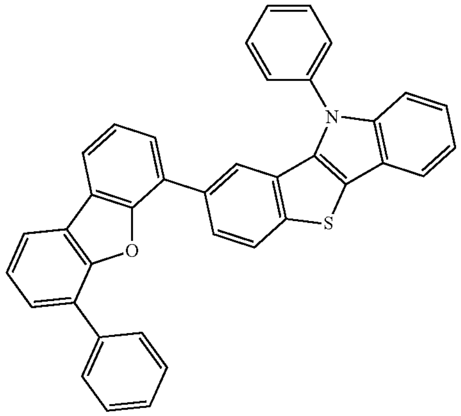
244
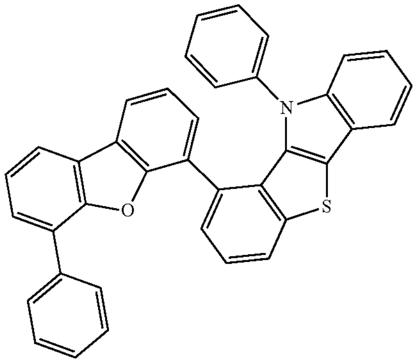

-continued
245
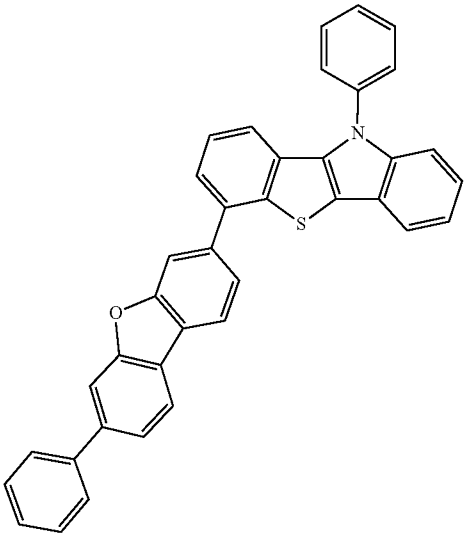
246
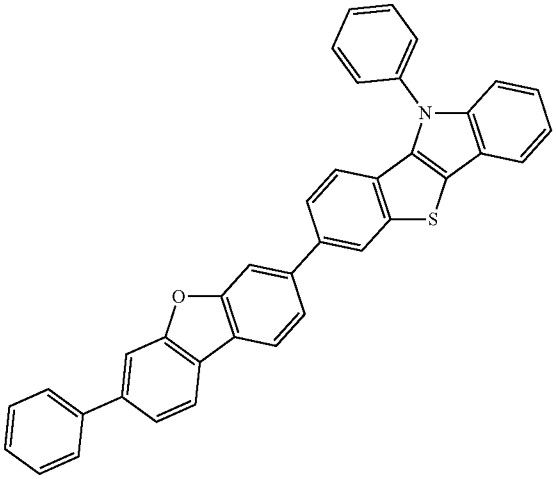
247
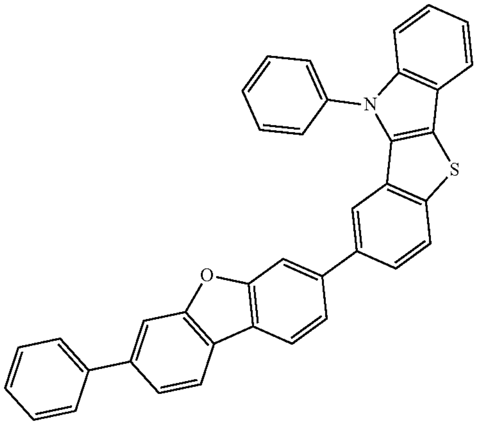
-continued
248
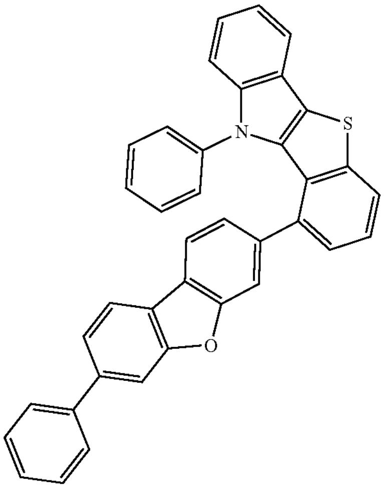
249
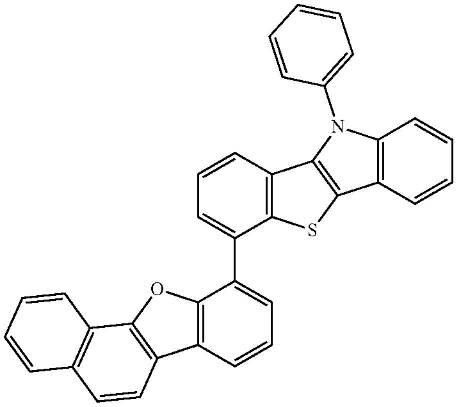
250
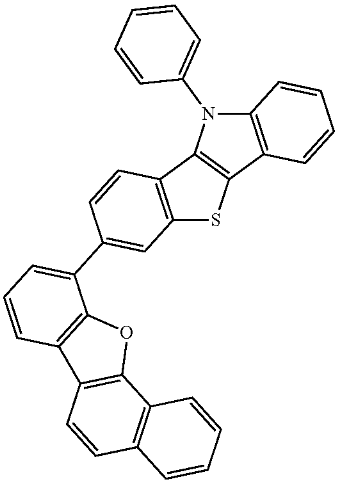

-continued
251
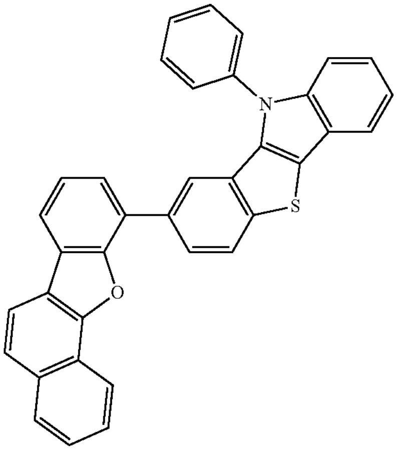
252
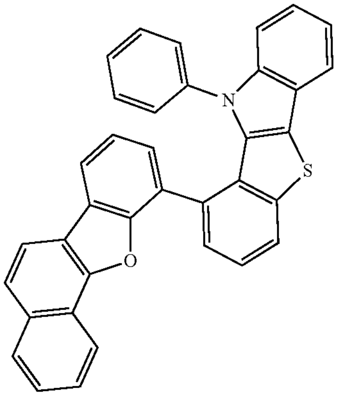
253
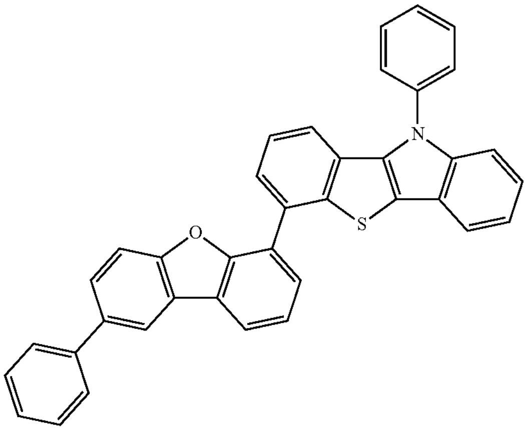
-continued
254
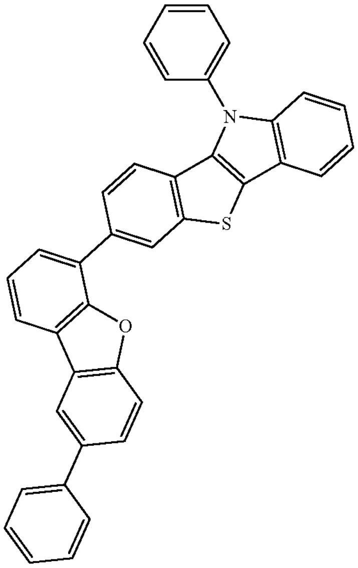
255
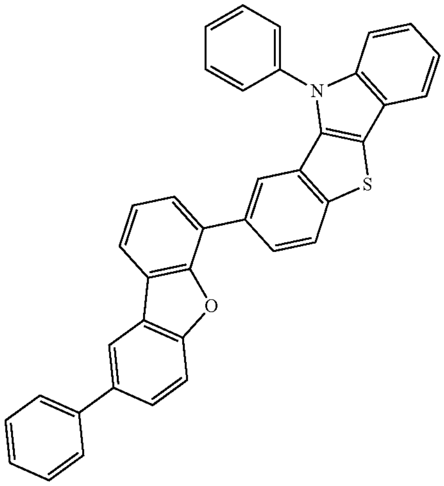
256
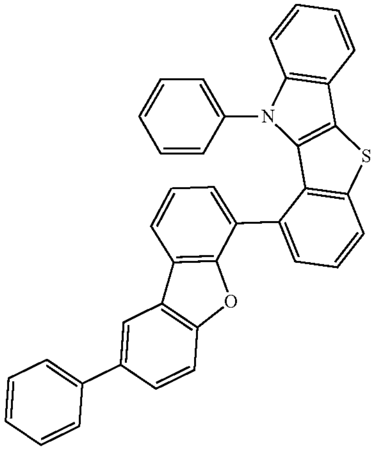

-continued
257
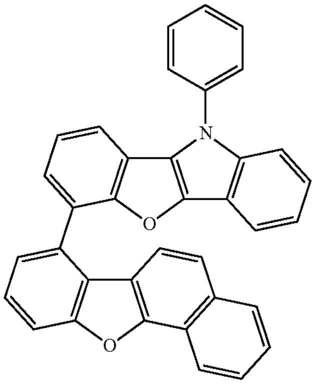
258
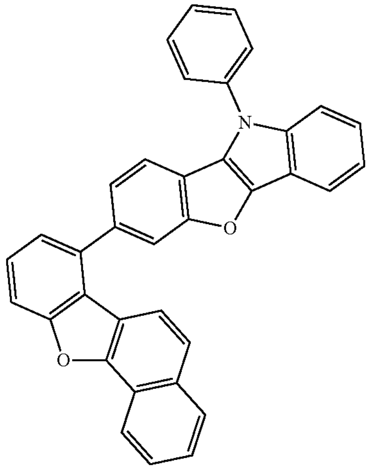
259
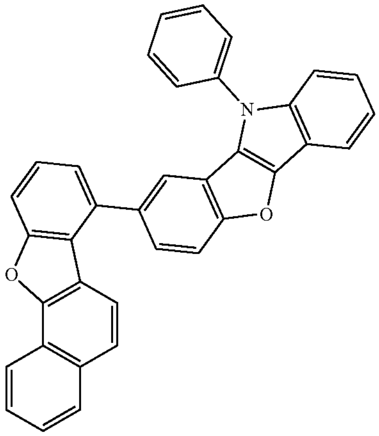
260
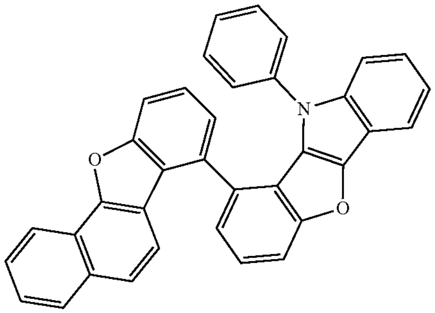
-continued
261
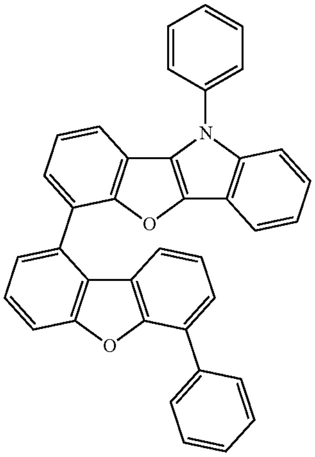
262
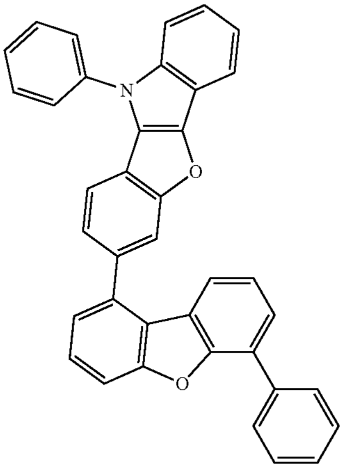
263
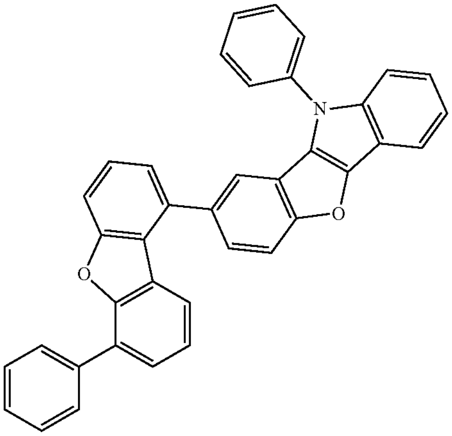

-continued
264
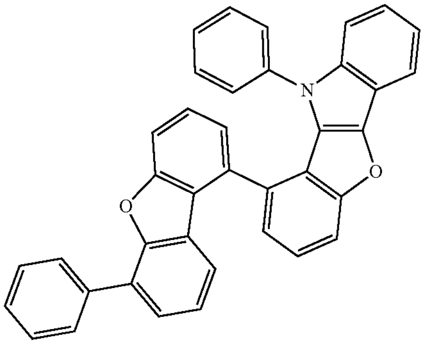
265
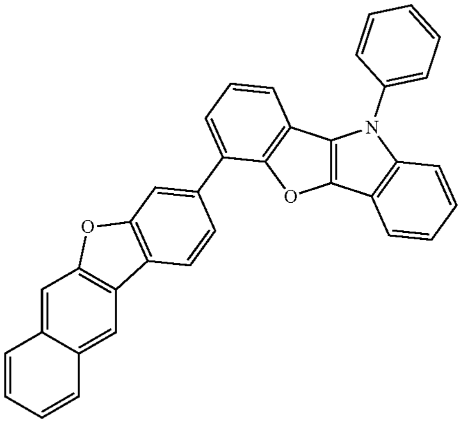
266
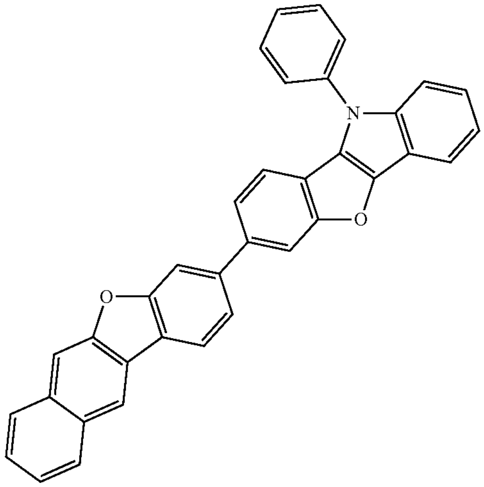
-continued
267
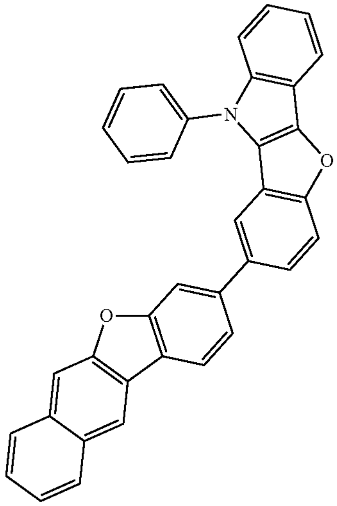
268
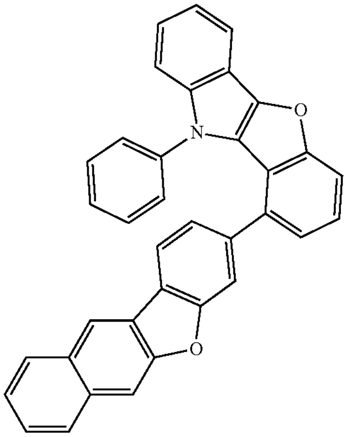
269
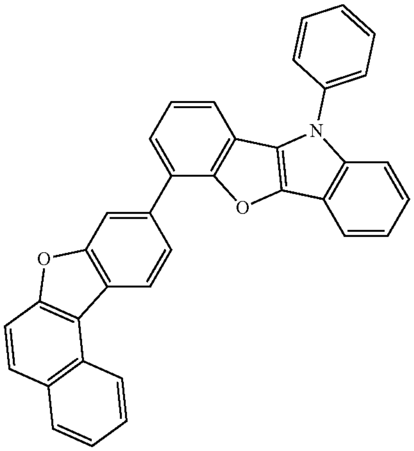

-continued
270
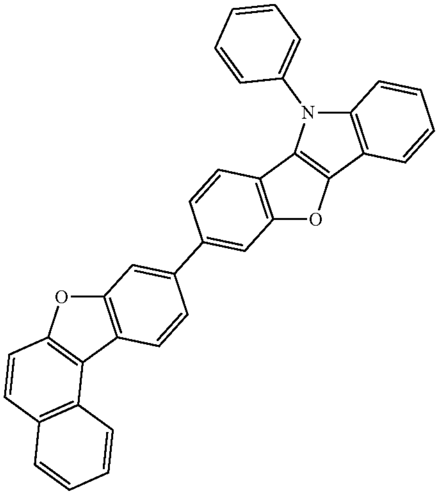
271
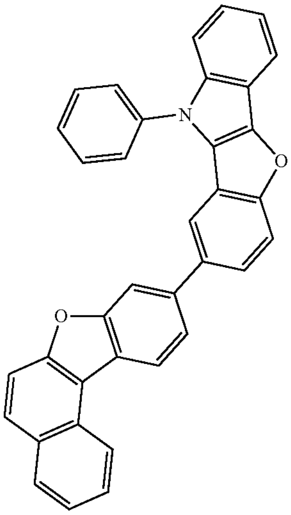
272
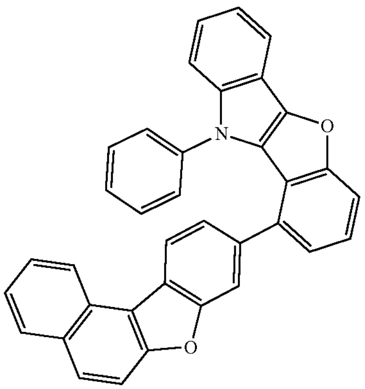
-continued
273
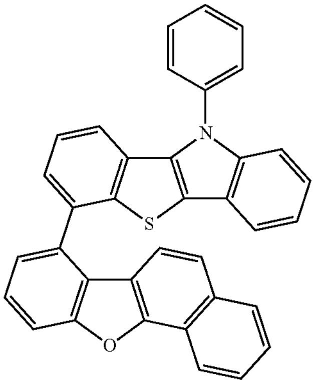
274
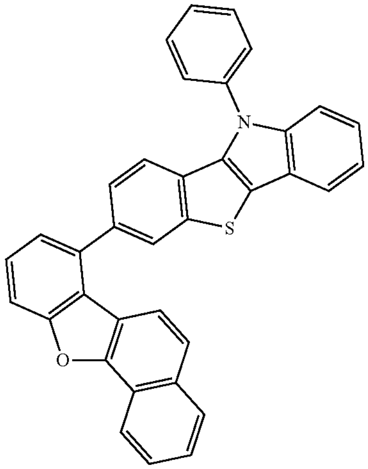
275
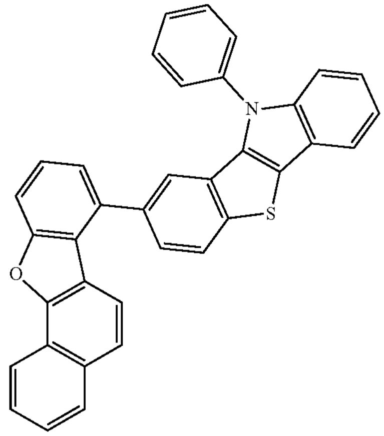
276
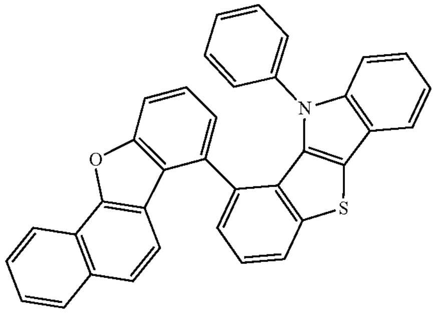

-continued
277
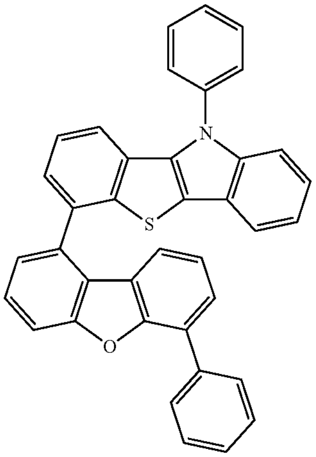
278
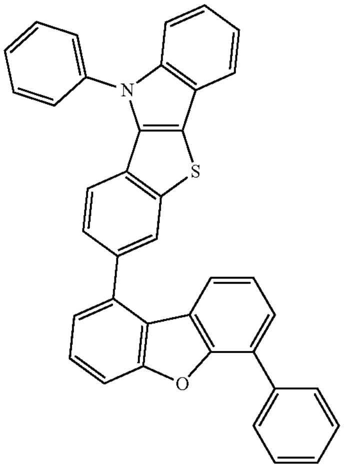
279
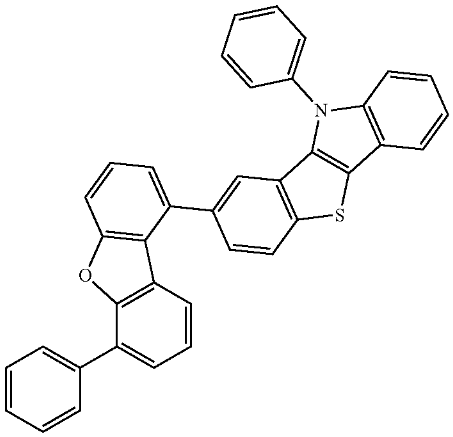
-continued
280
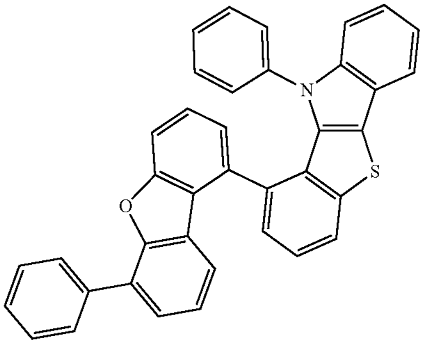
281
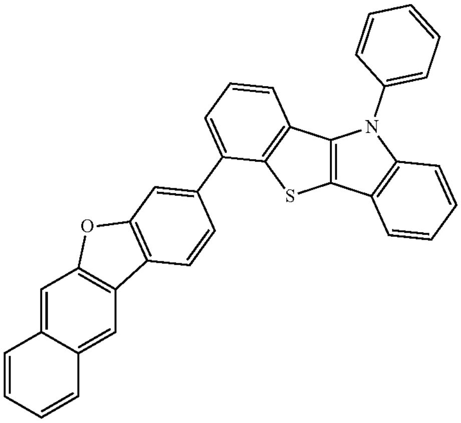
282
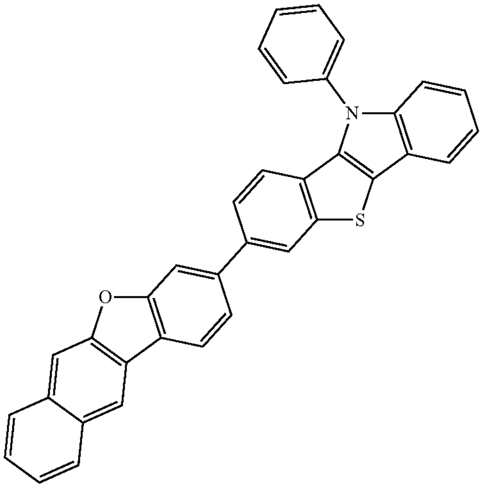

283
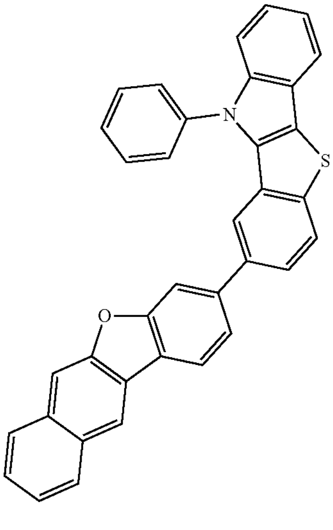
284
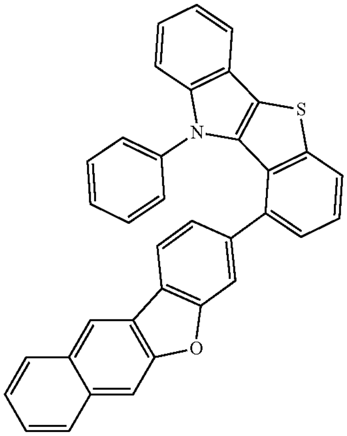
285
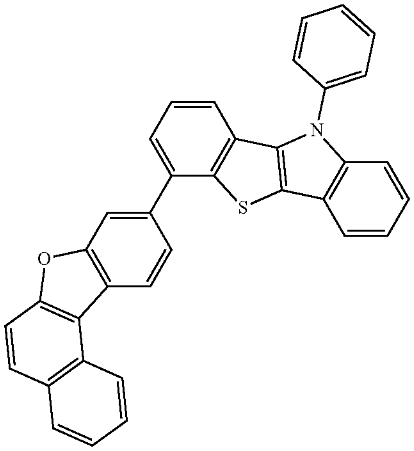
286
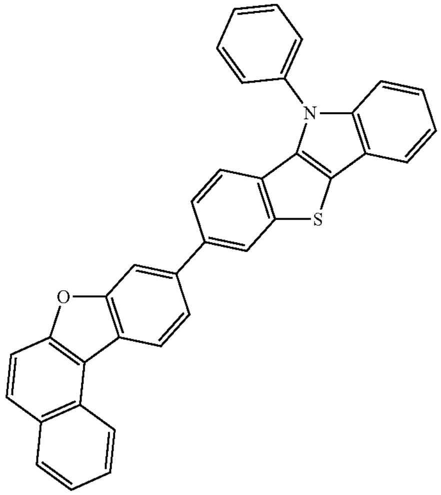
287
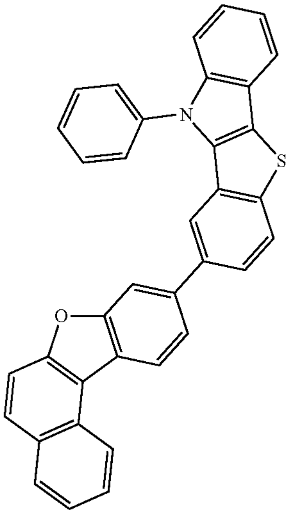
288
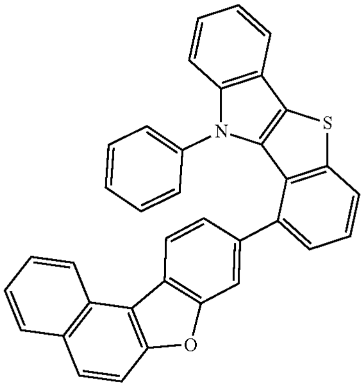

-continued
289
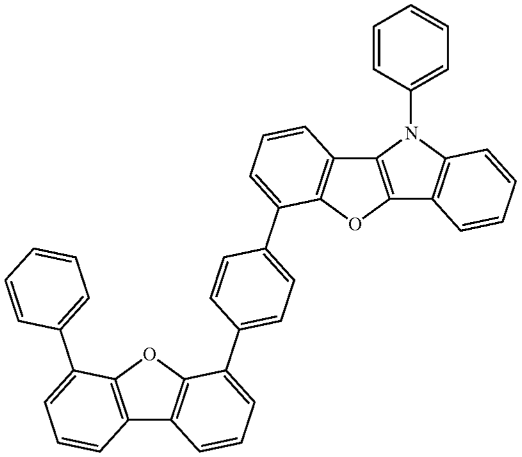
290
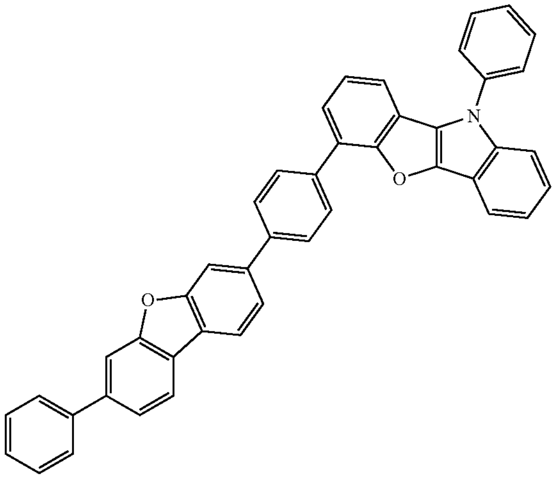
291
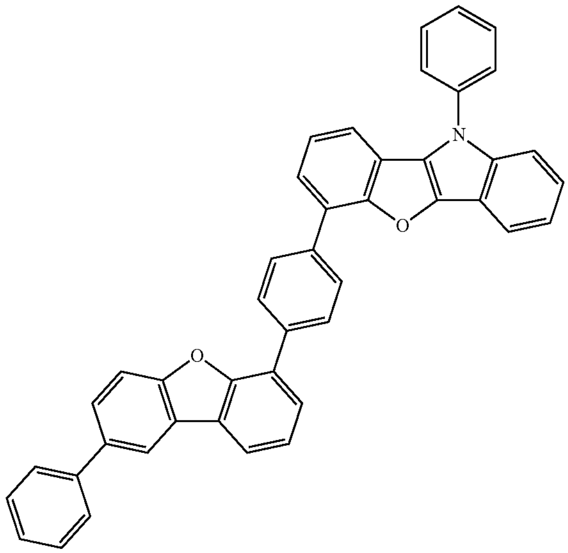
292
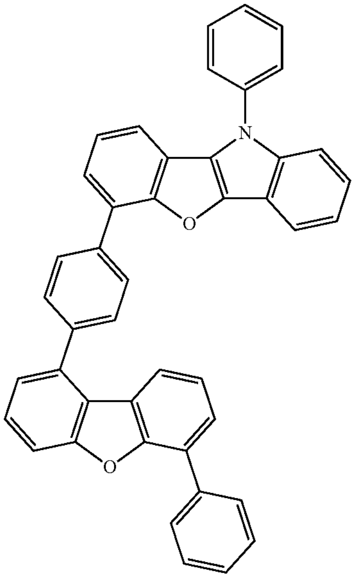
293
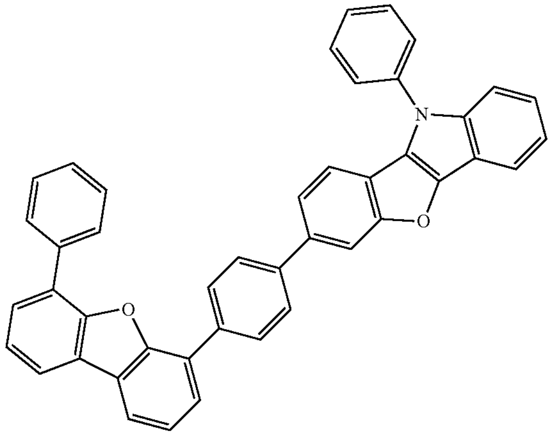
294
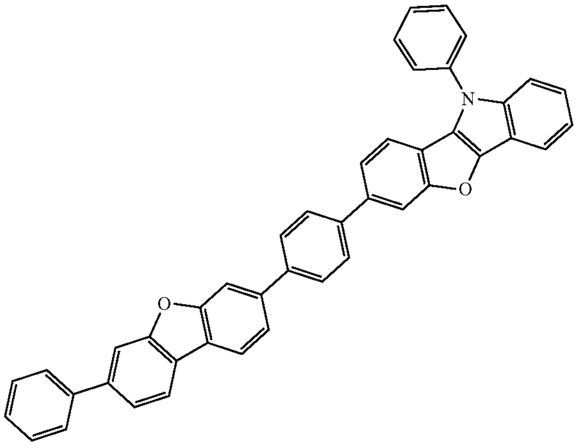

-continued
295
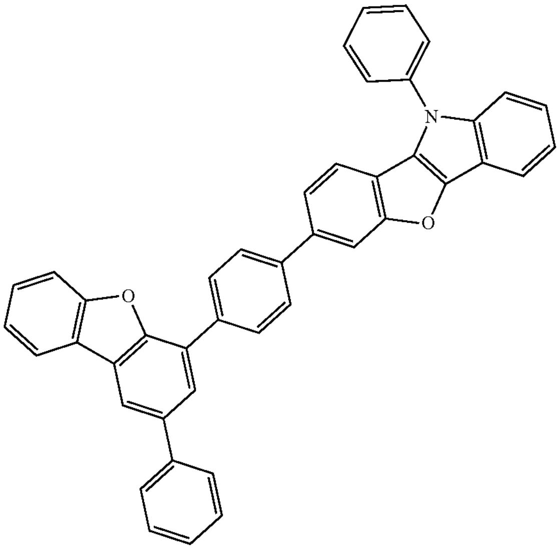
296
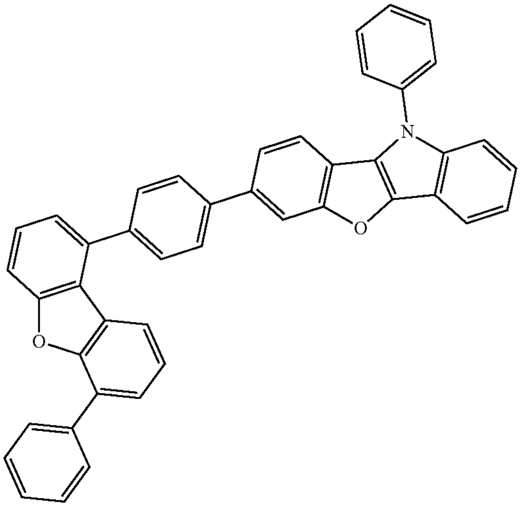
297
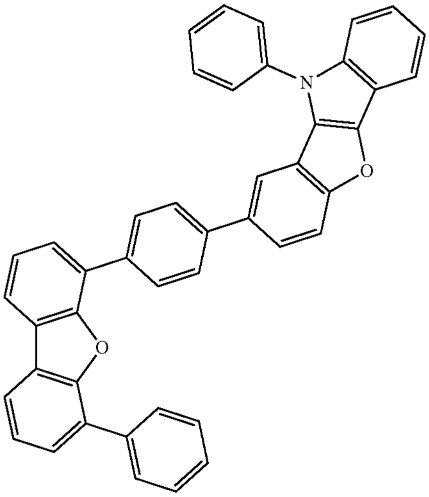
-continued
298
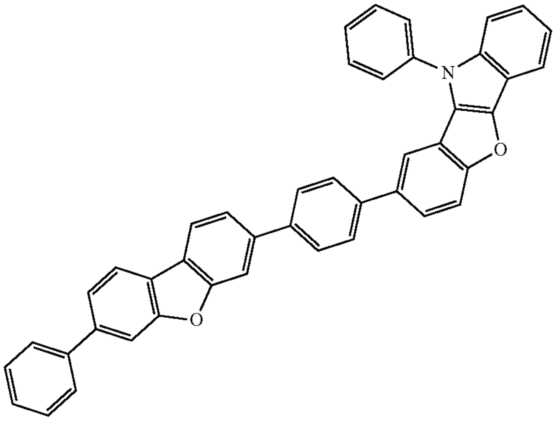
299
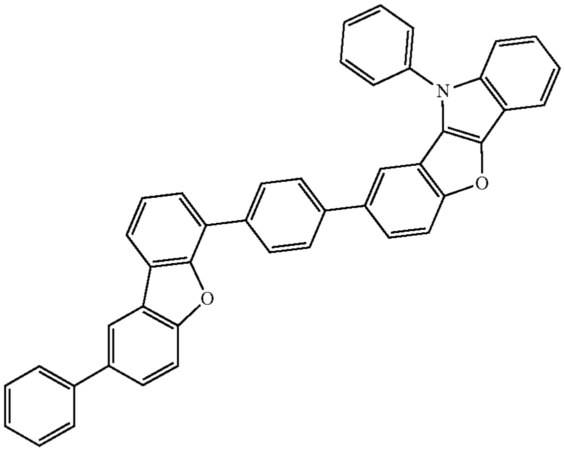
300
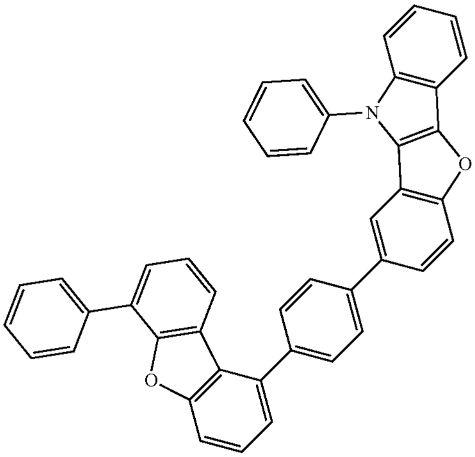

-continued
301
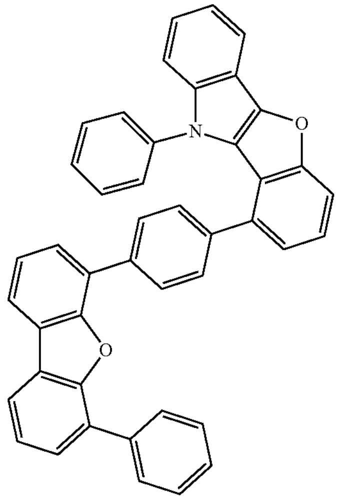
302
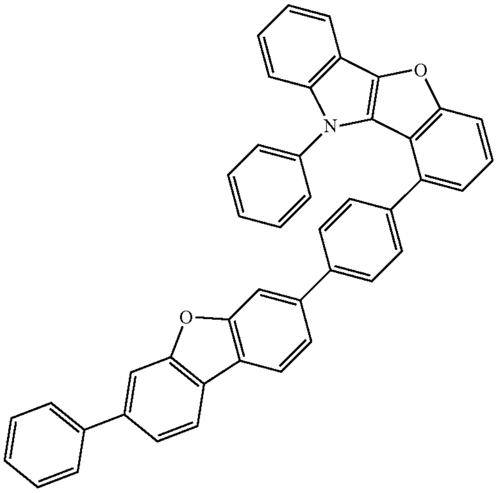
303
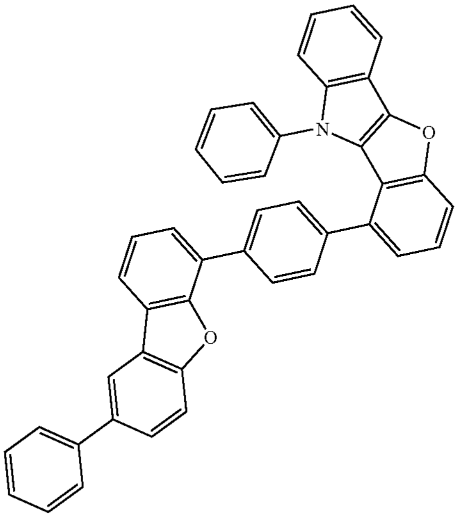
-continued
304
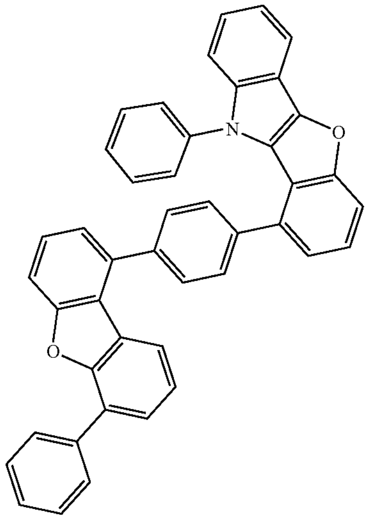
305
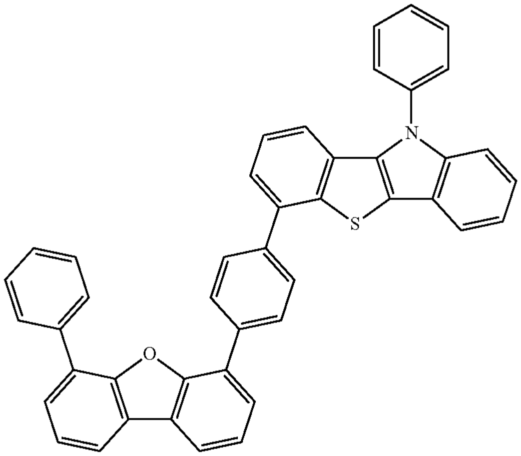
306
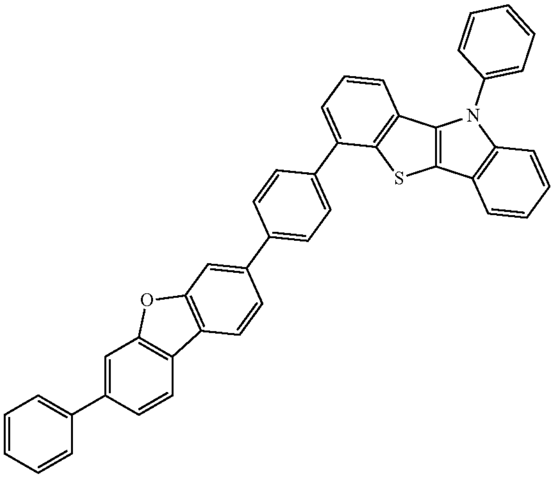

-continued
307
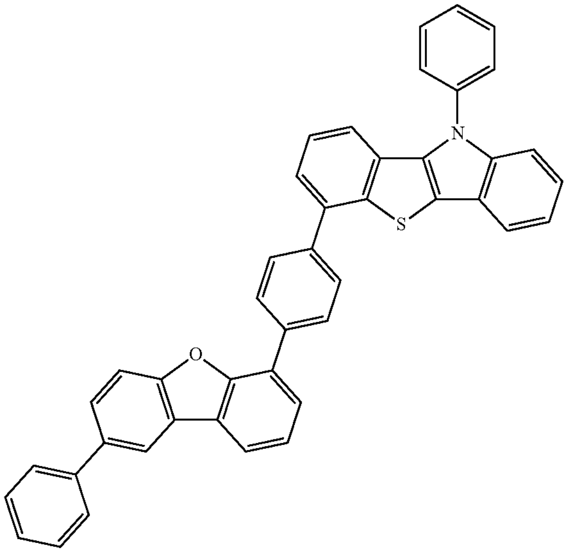
308
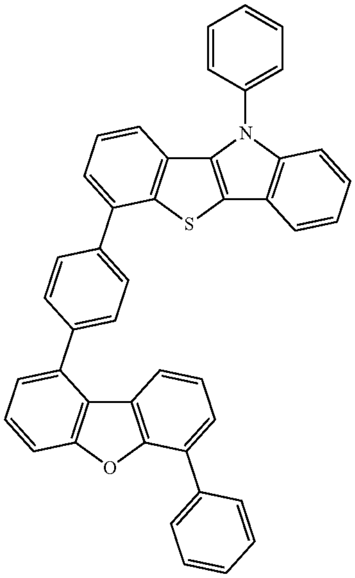
309
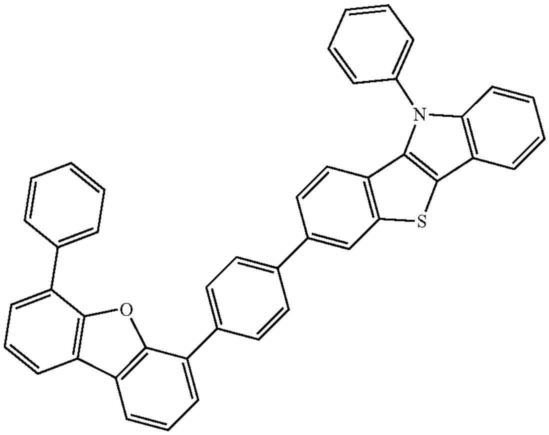
-continued
310
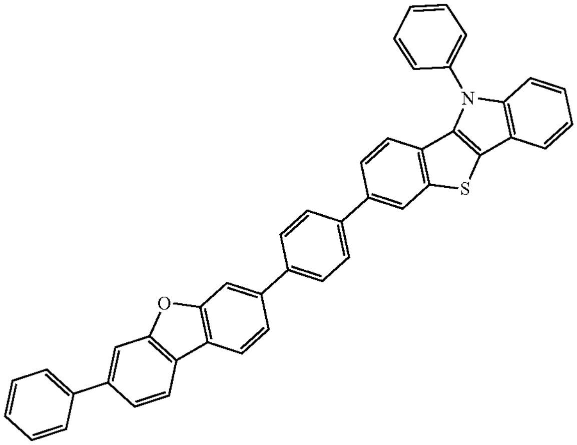
311
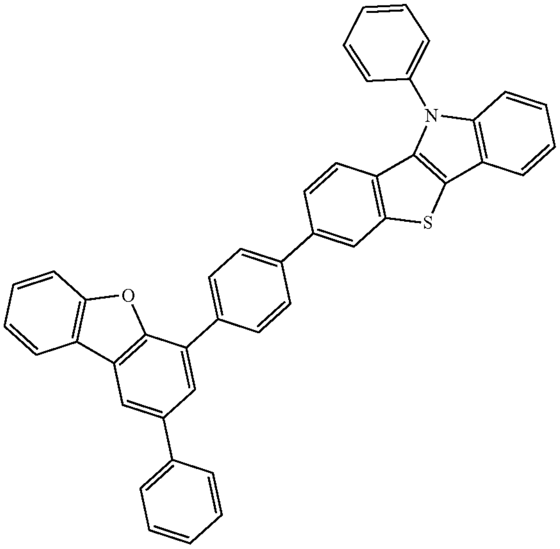
312
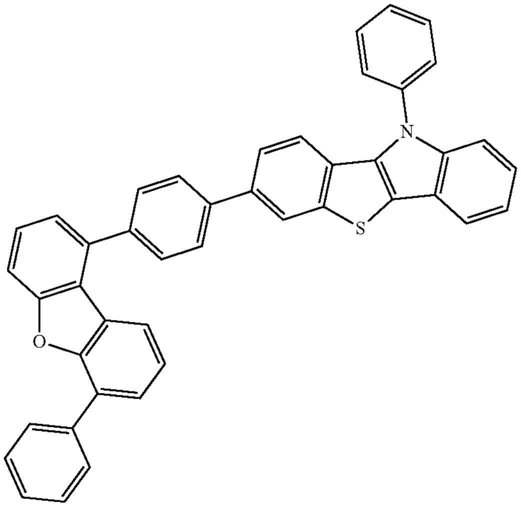

-continued
313
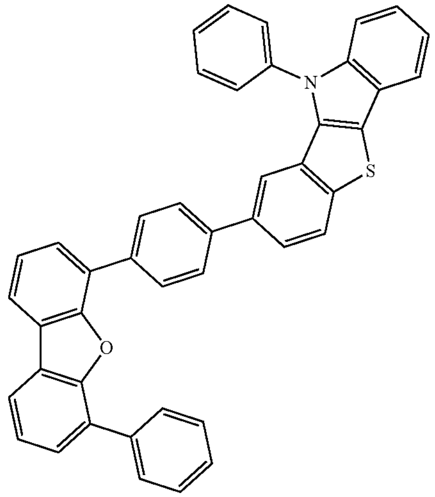
314
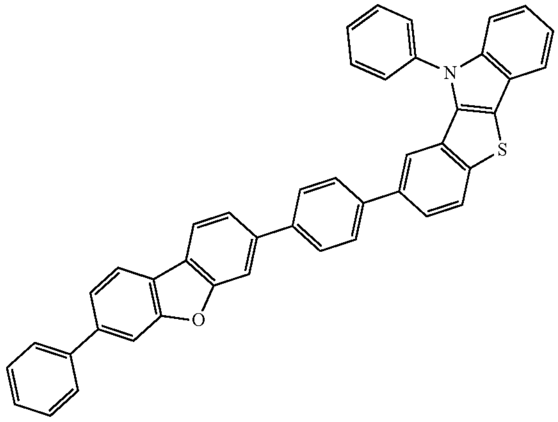
315
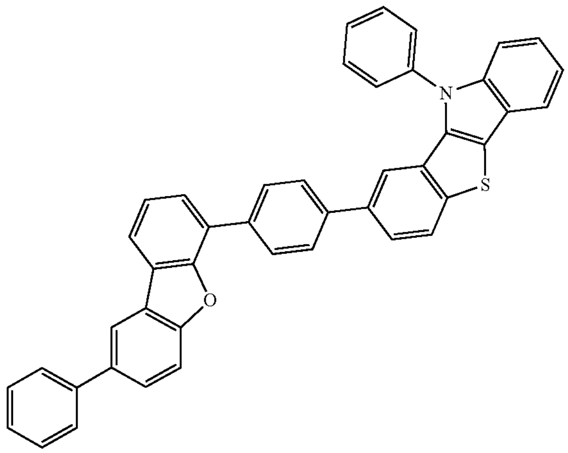
-continued
316
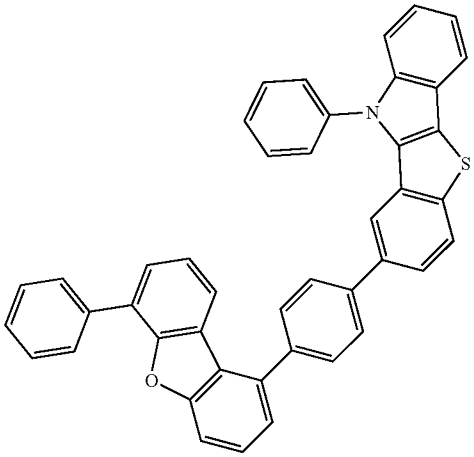
317
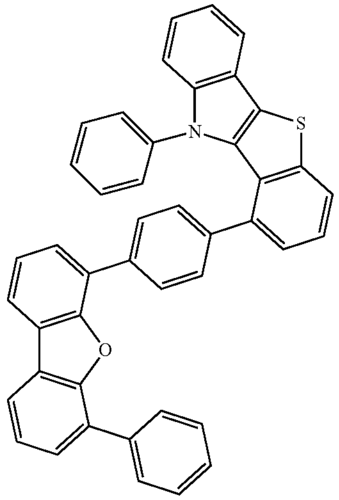
318
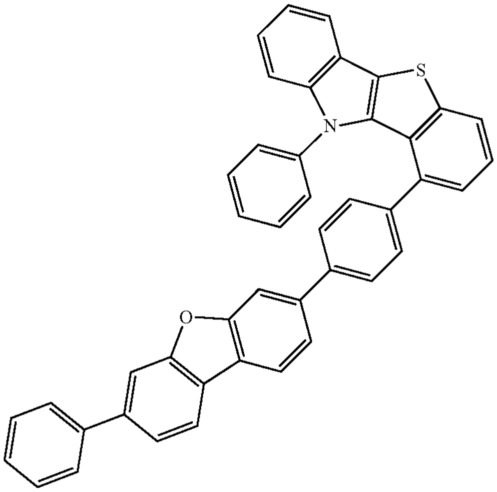

-continued
319
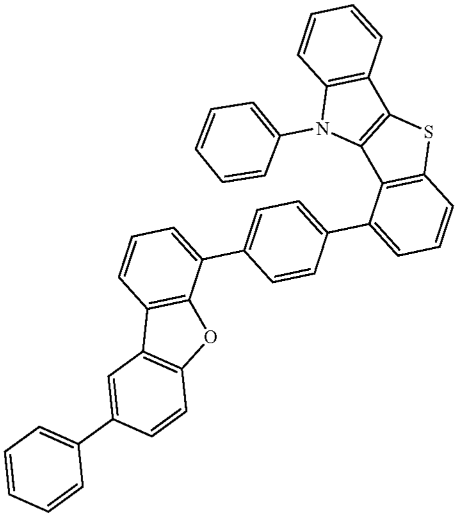
320
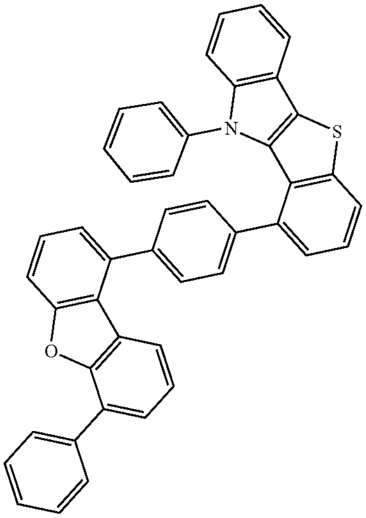
321
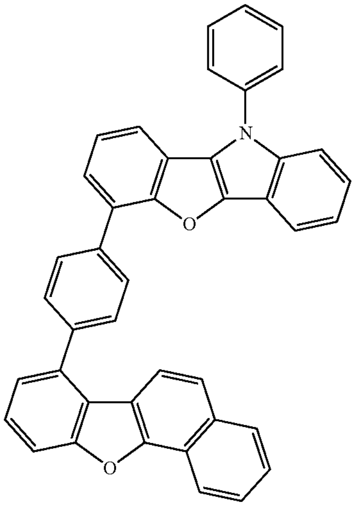
-continued
322
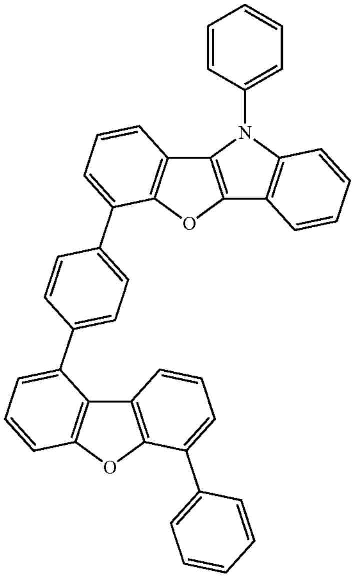
323
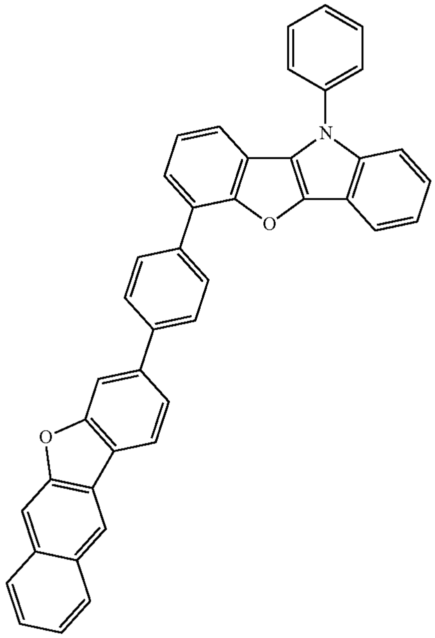

-continued
324
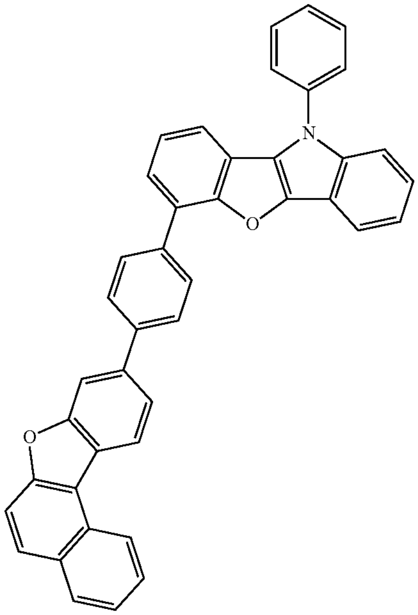
325
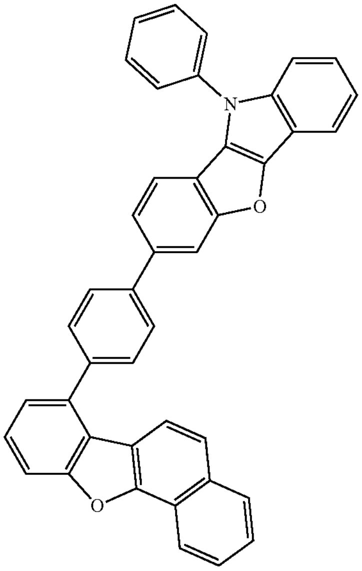
-continued
326
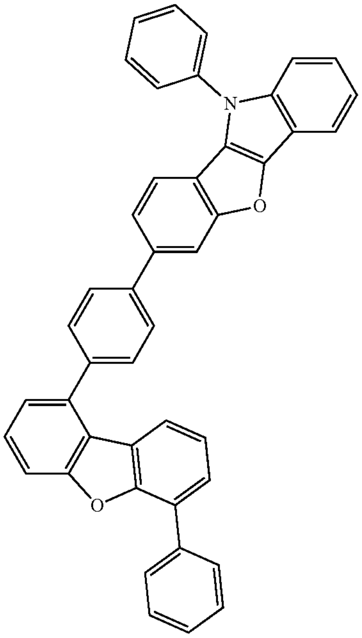
327
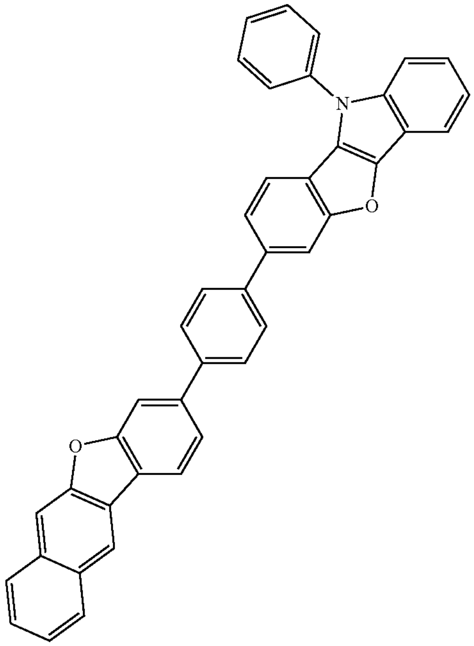

-continued
328
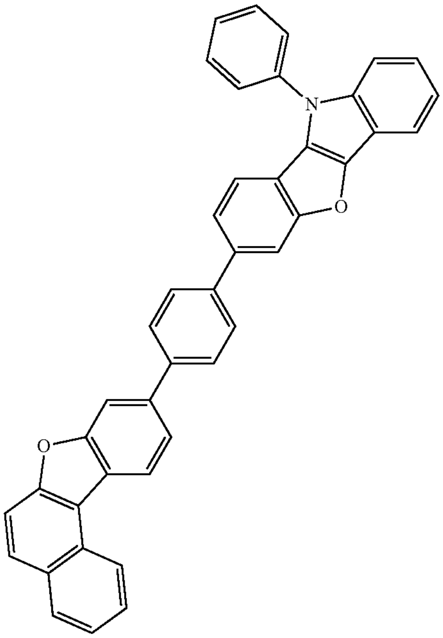
329
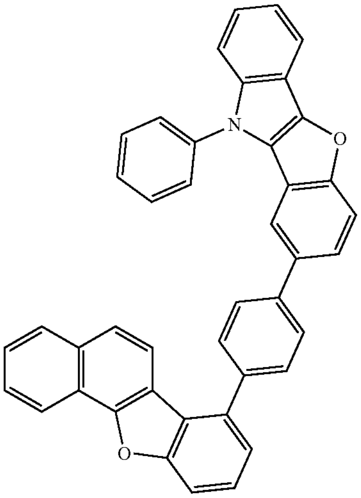
330
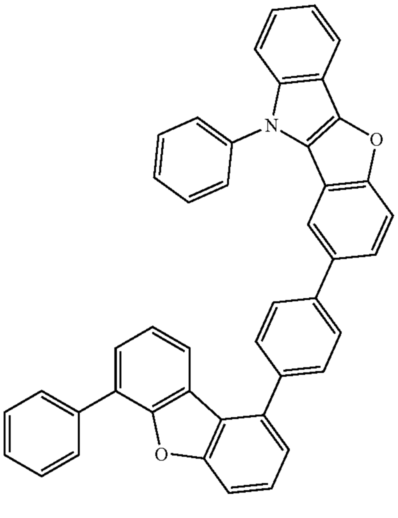
-continued
331
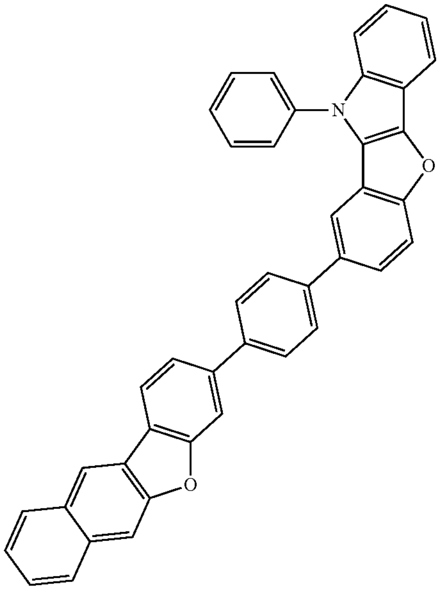
332
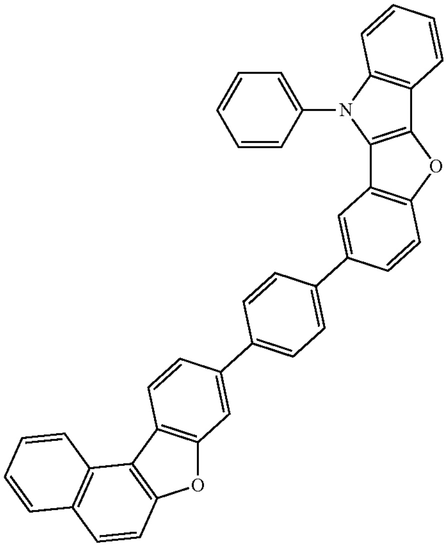
333
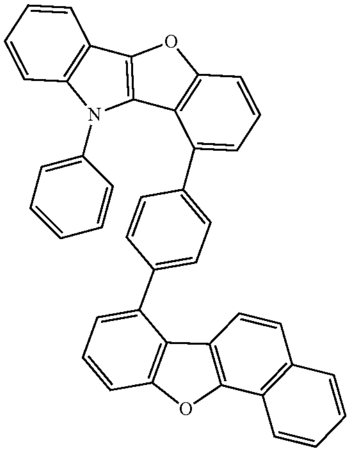

-continued
334
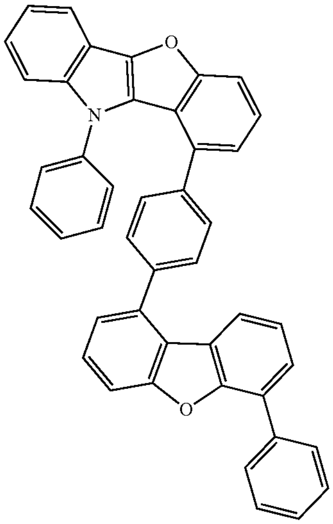
335
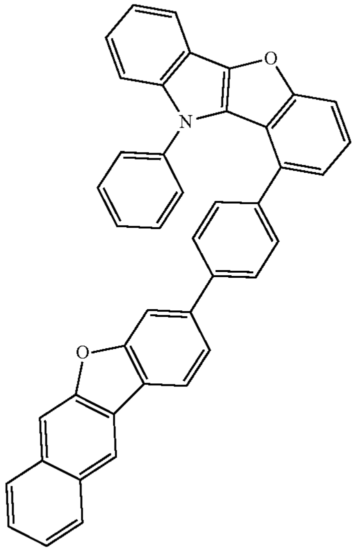
336
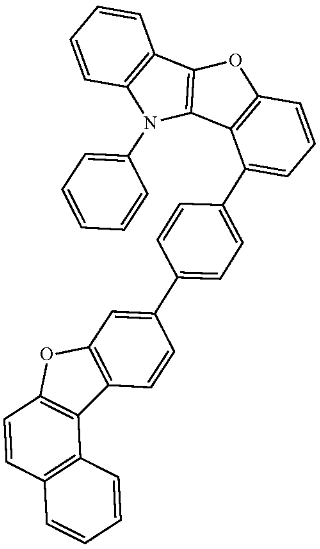
-continued
337
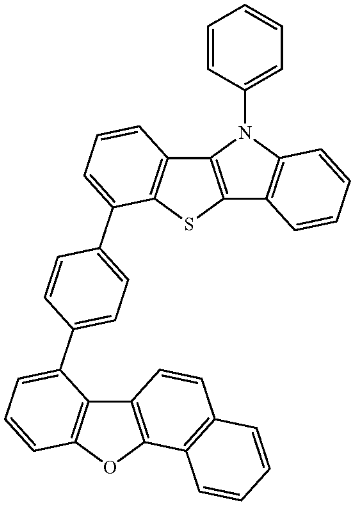
338
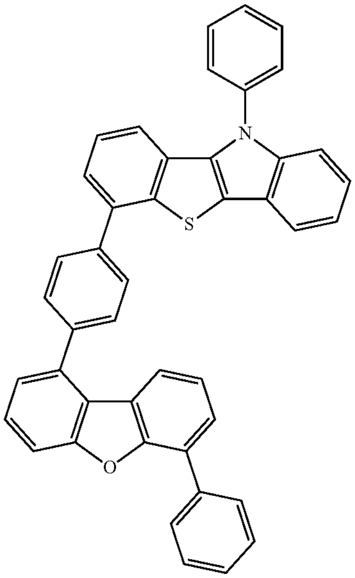

-continued
339
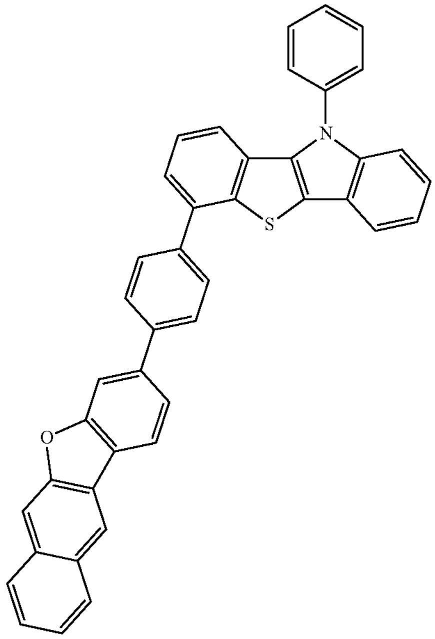
340
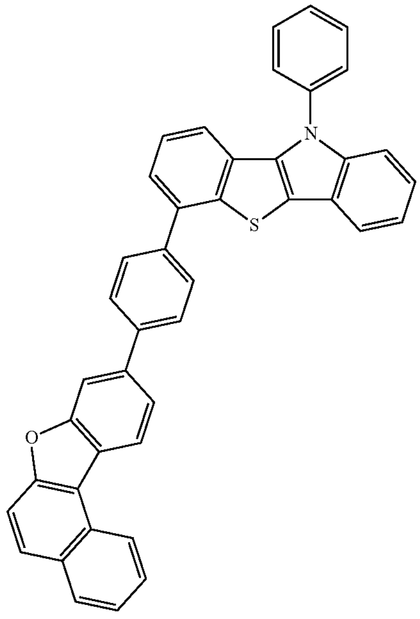
-continued
341
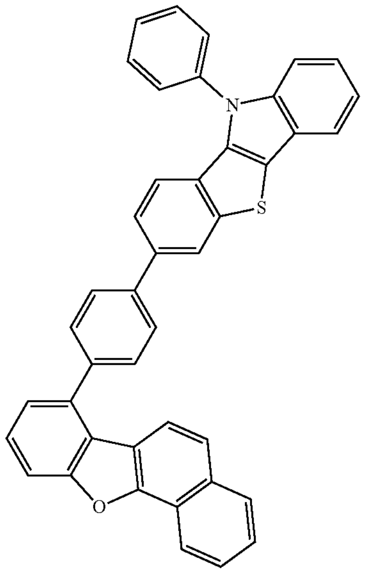
342
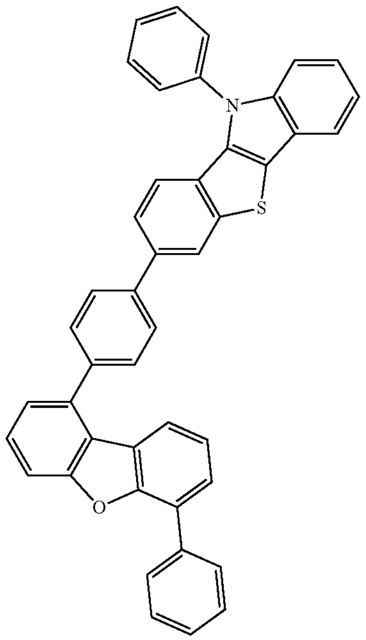

343
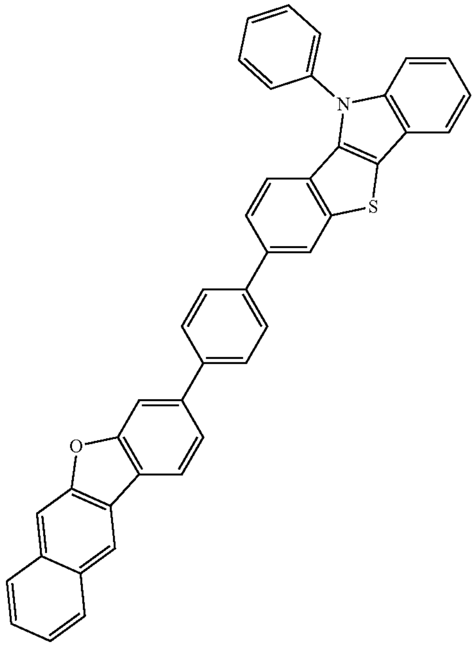
344
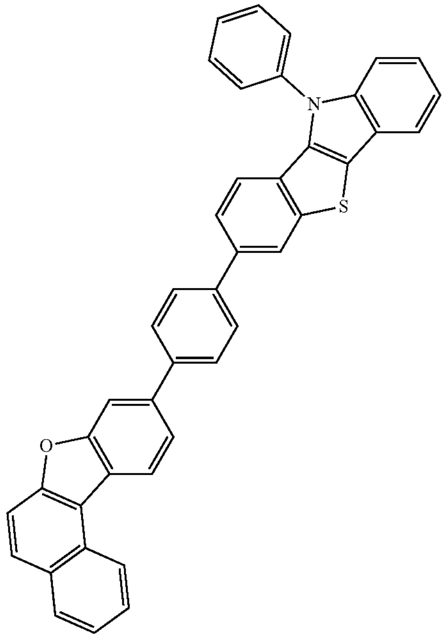
345
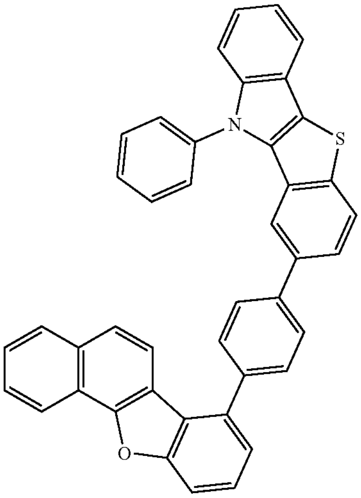
346
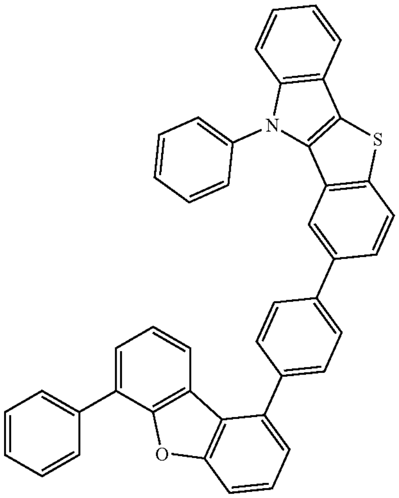
347
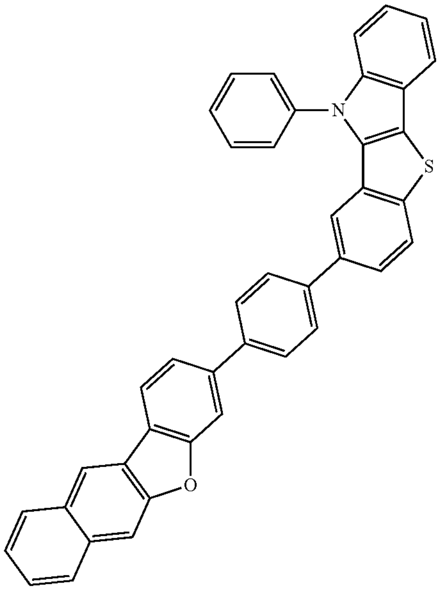

-continued
348
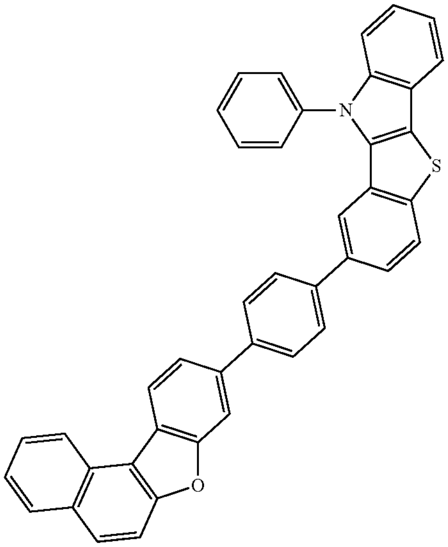
349
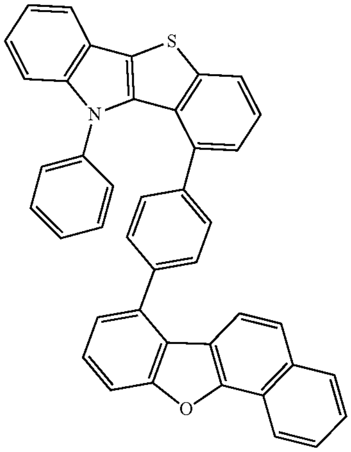
350
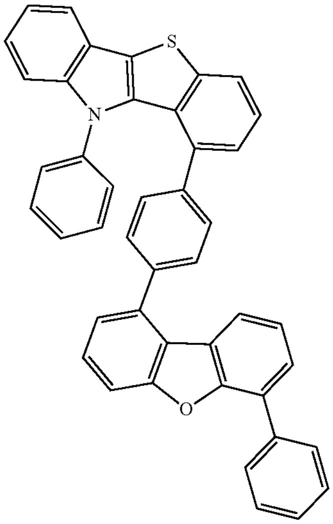
-continued
351
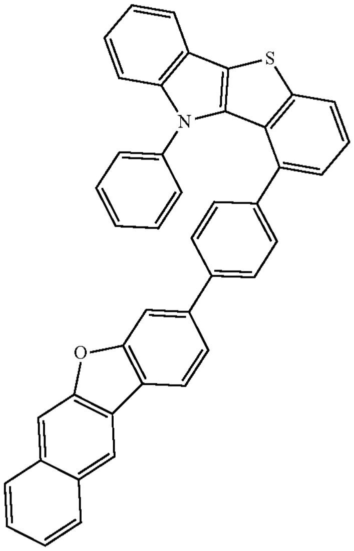
352
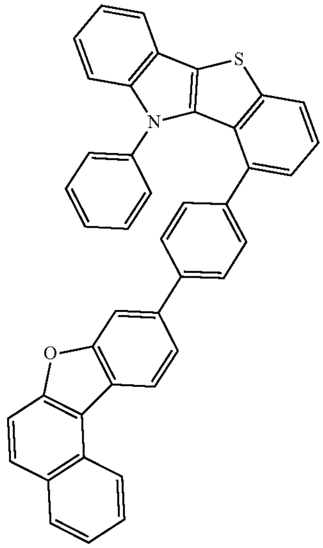
353
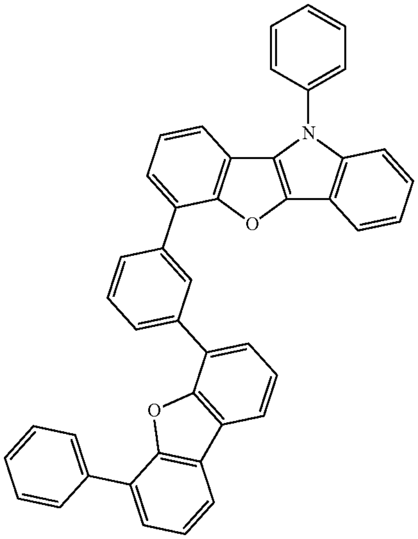

-continued
354
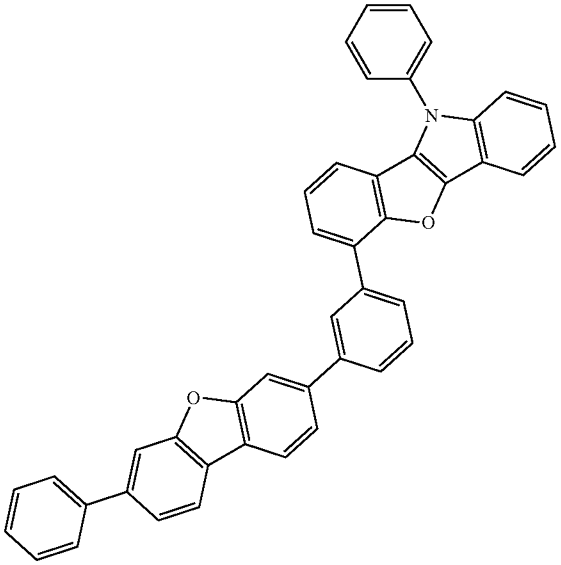
355
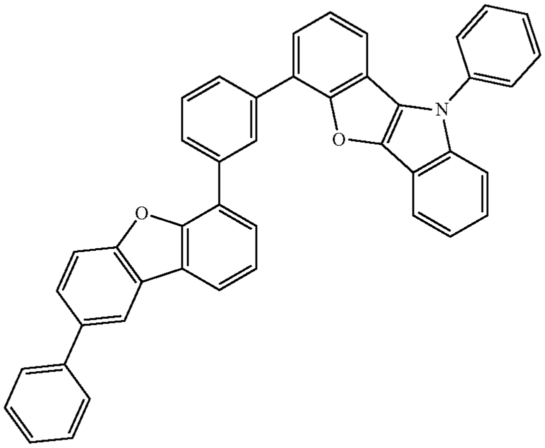
356
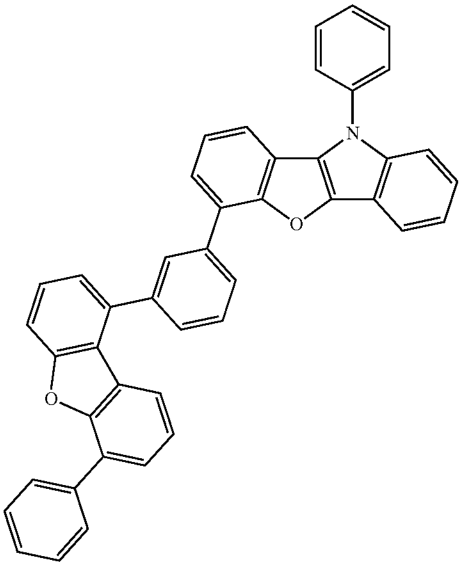
-continued
357
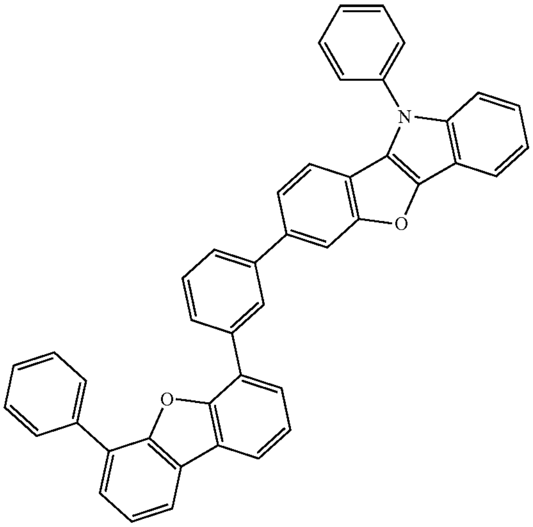
358
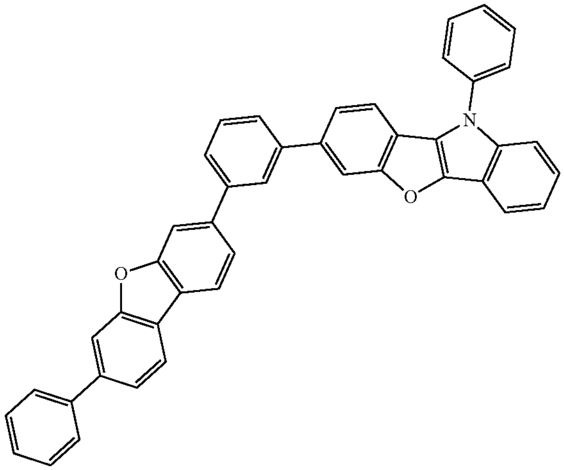
359
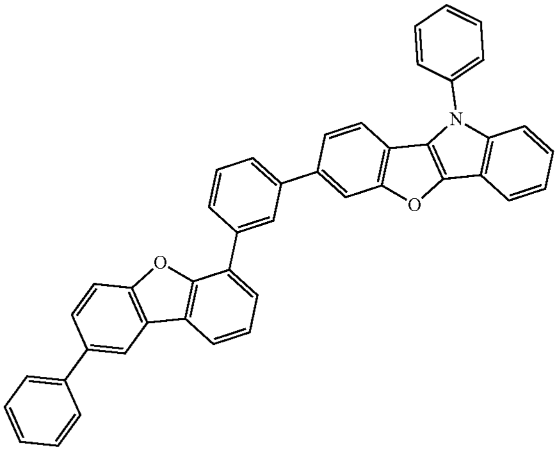

-continued
360
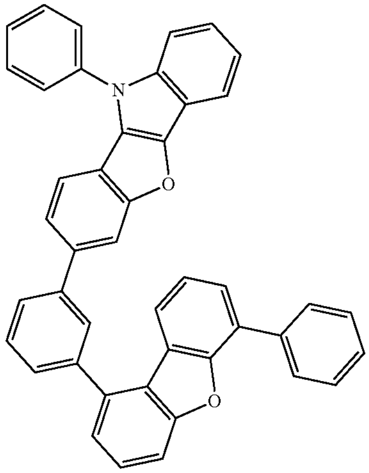
361
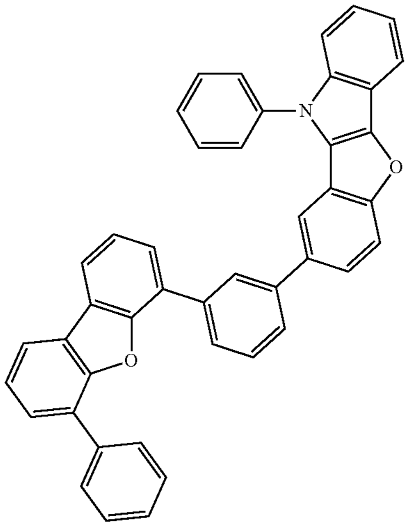
362
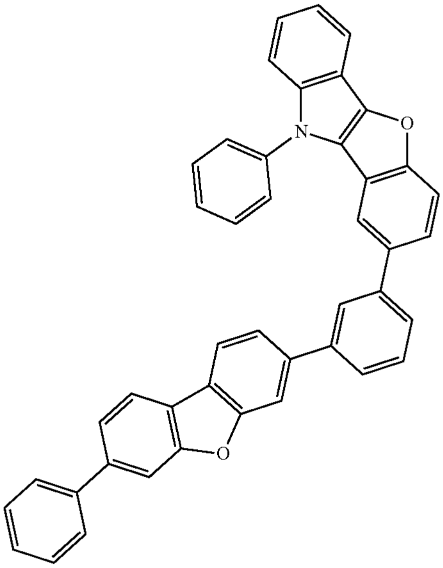
-continued
363
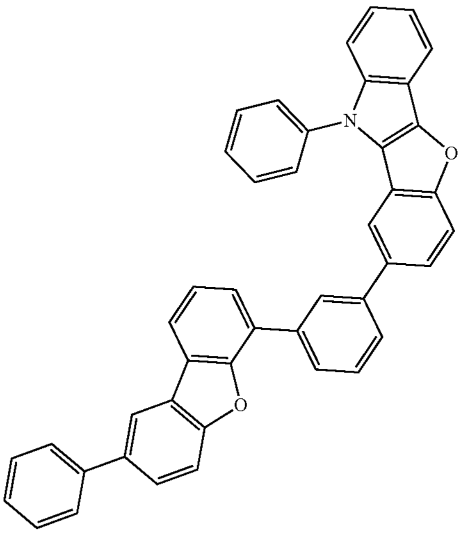
364
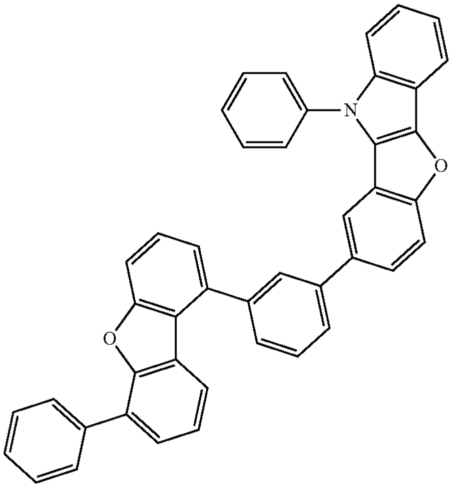
365
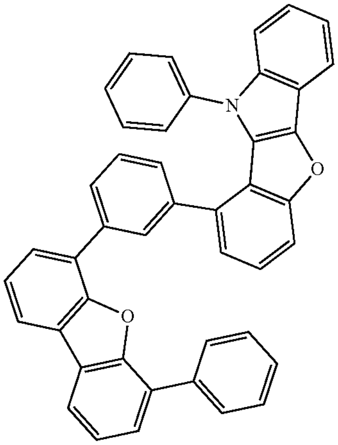

-continued
366
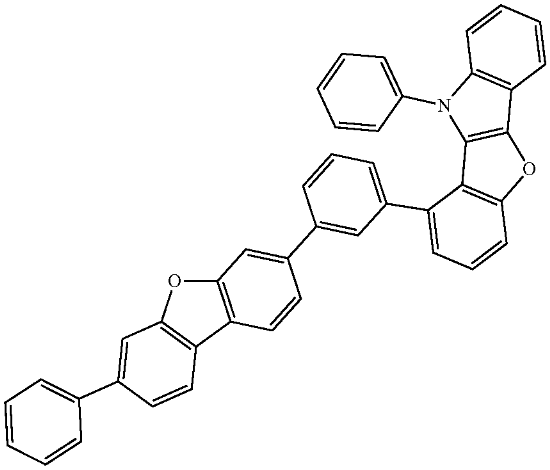
367
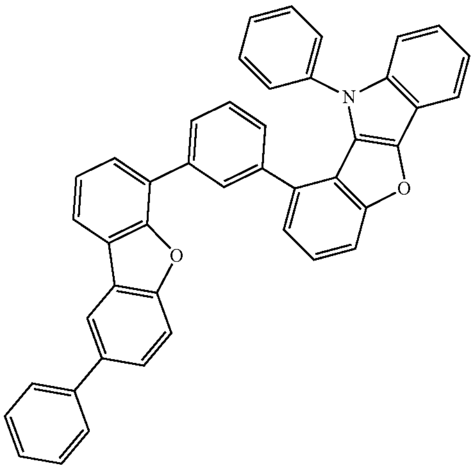
368
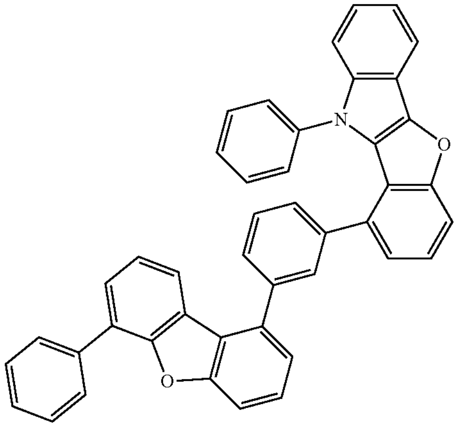
-continued
369
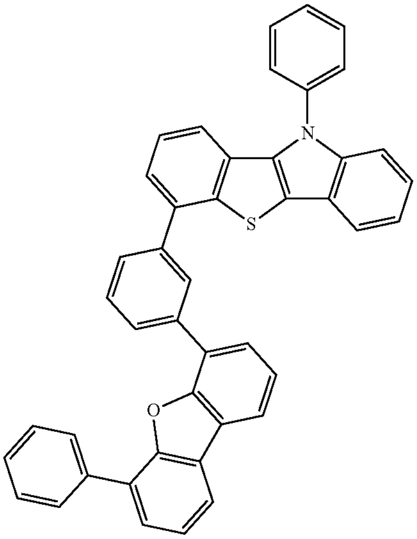
370
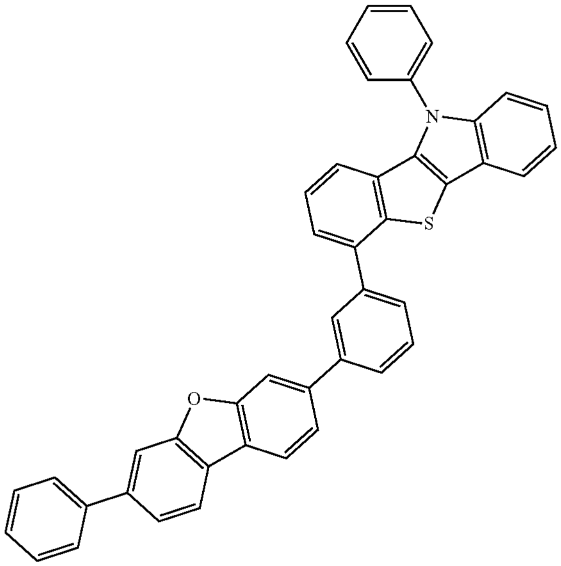
371
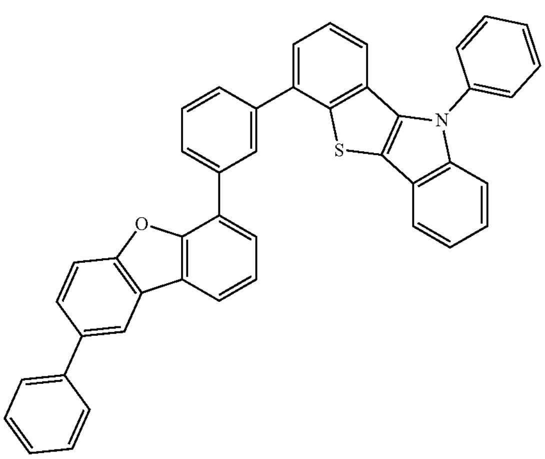

-continued
372
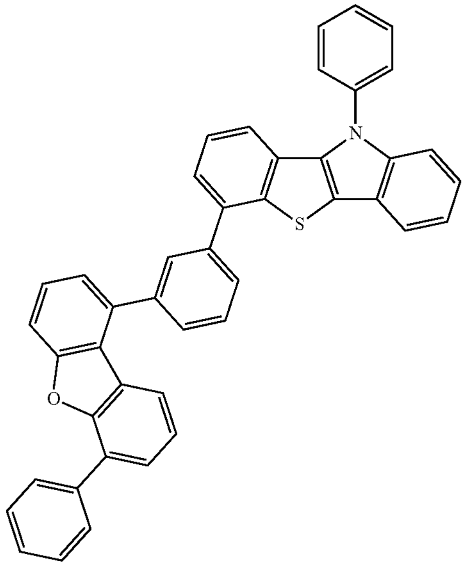
373
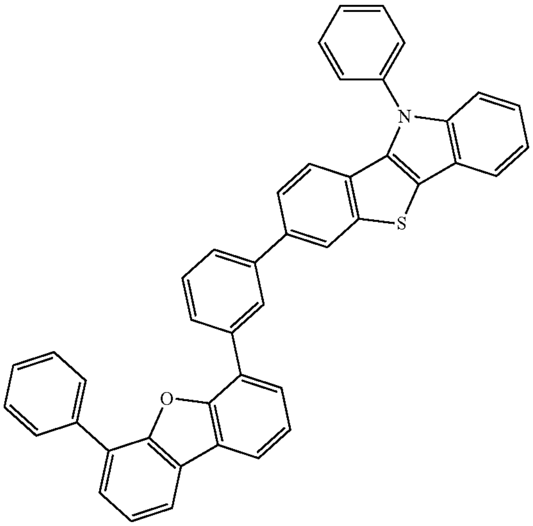
374
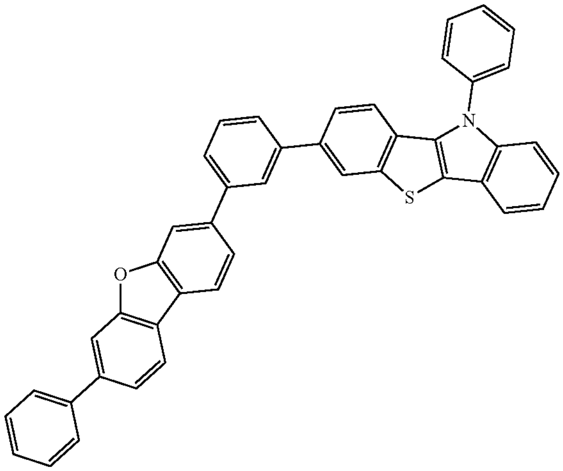
-continued
375
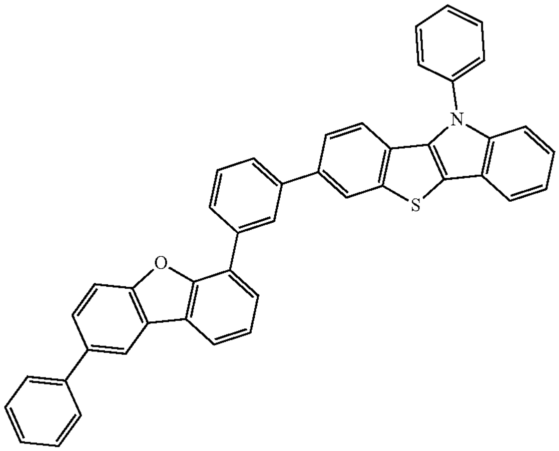
376
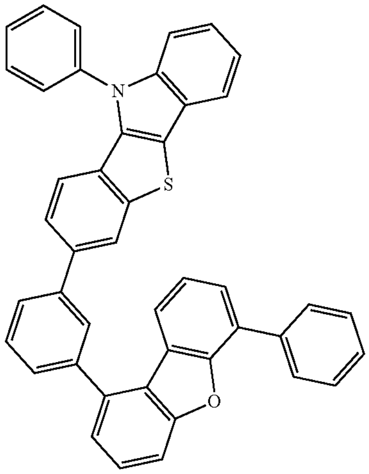
377
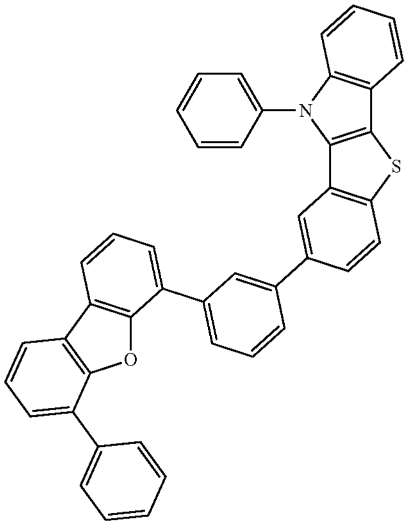

-continued
378
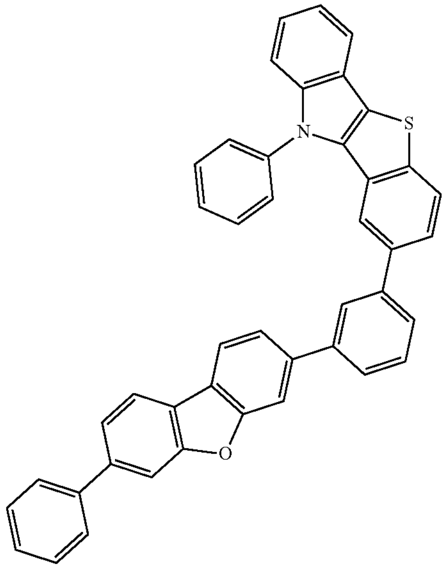
379
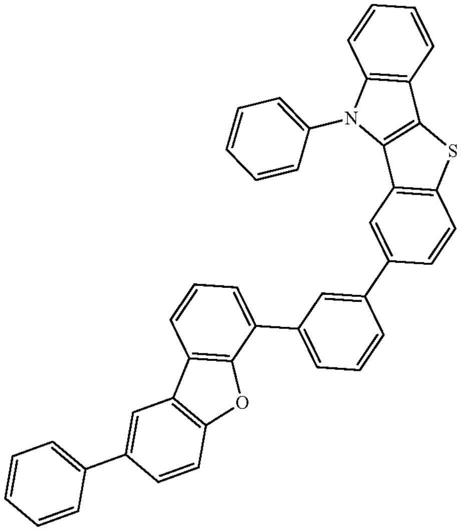
380
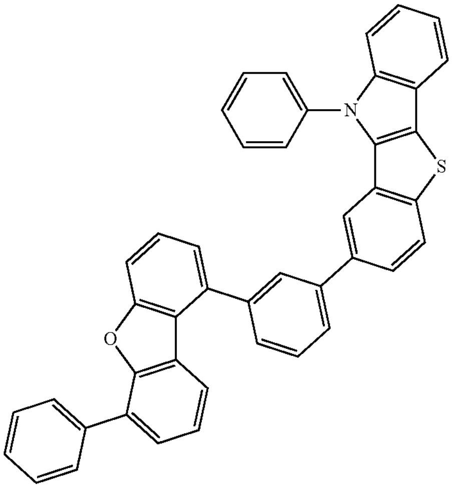
-continued
381
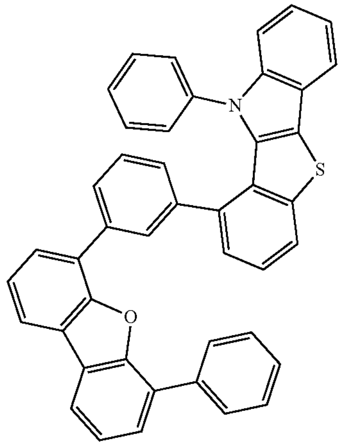
382
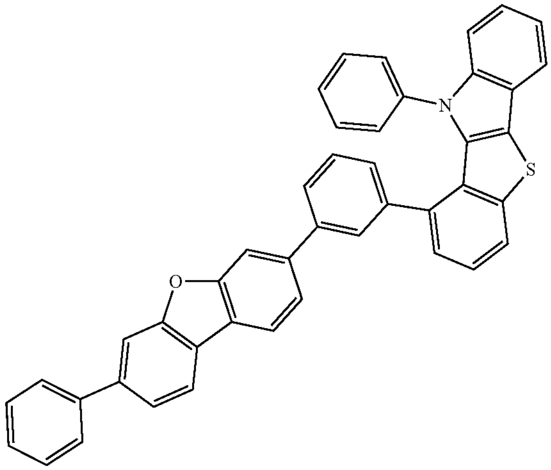
383
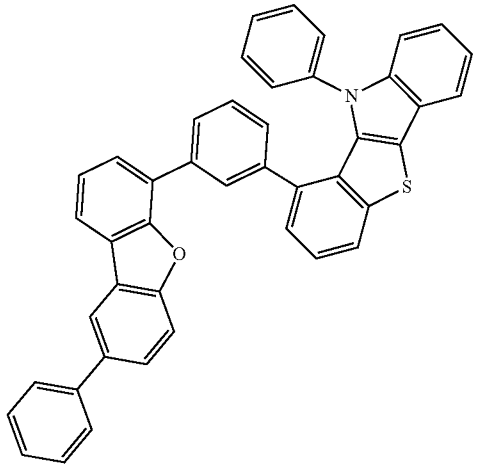

-continued
384
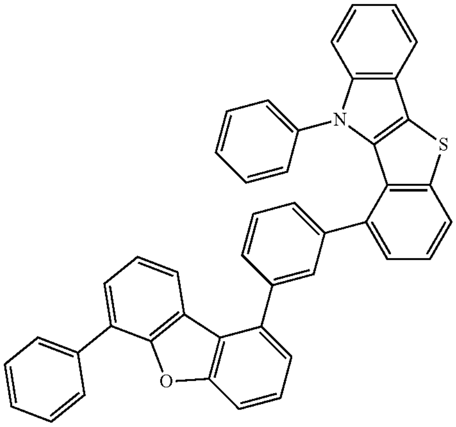
385
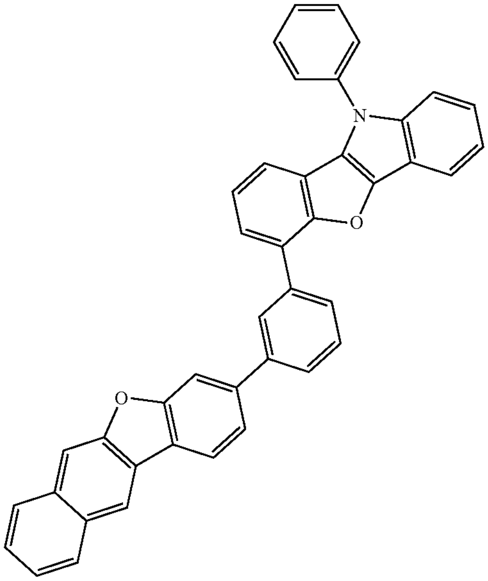
386
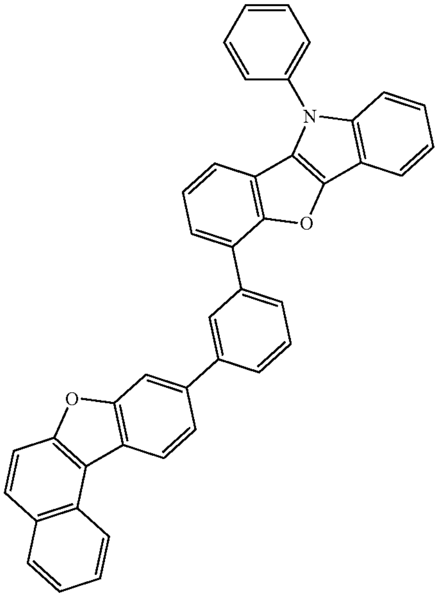
-continued
387
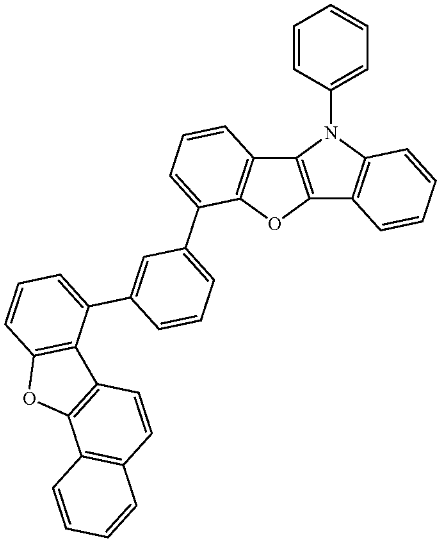
388
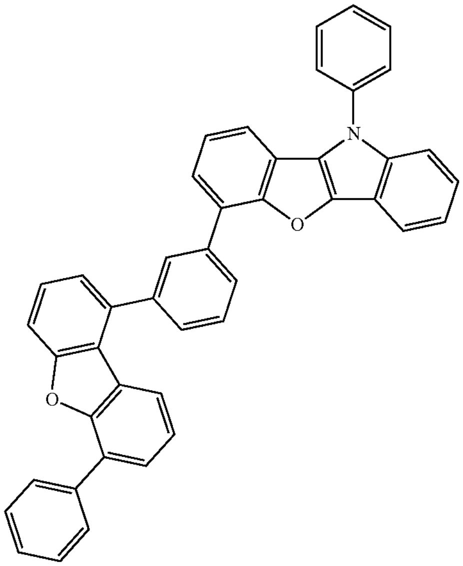

-continued
389
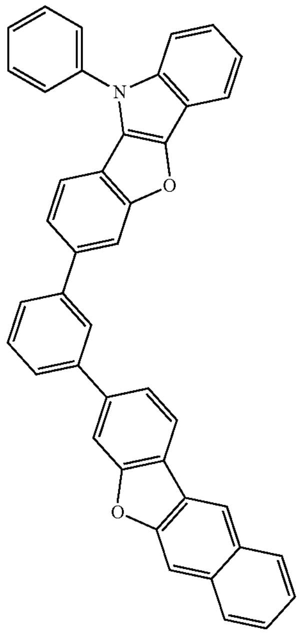
390
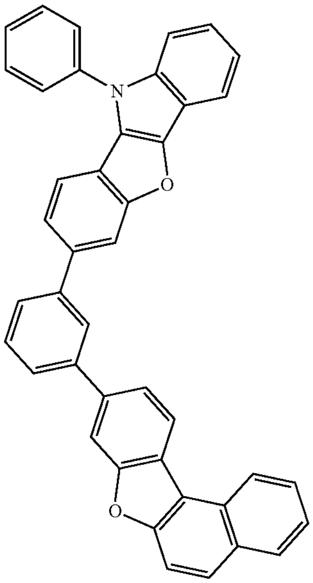
-continued
391
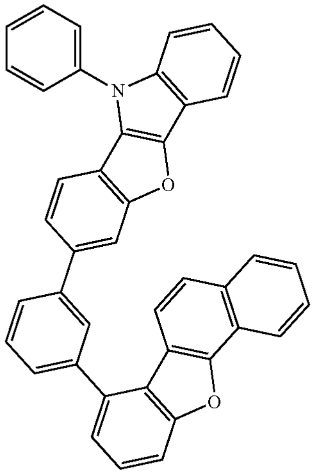
392
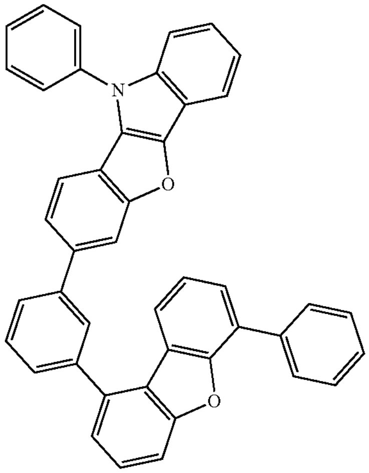
393
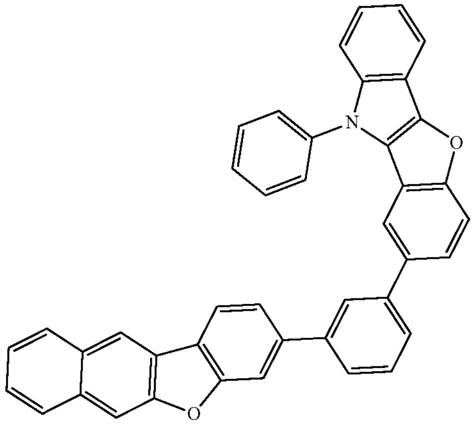

-continued
394
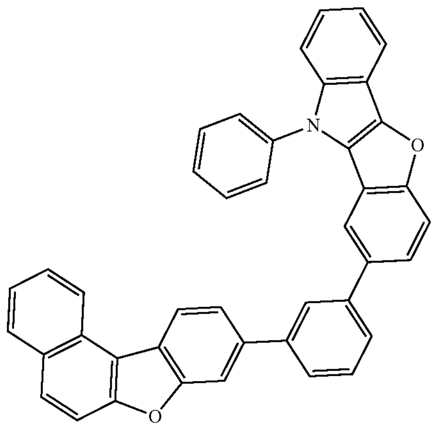
395
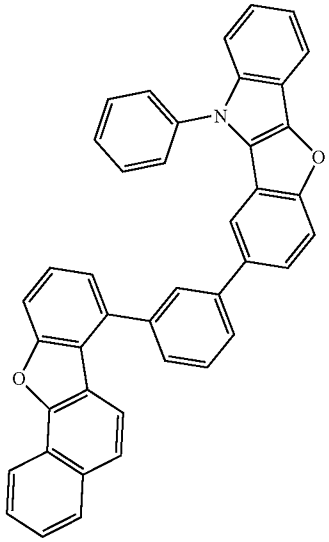
396
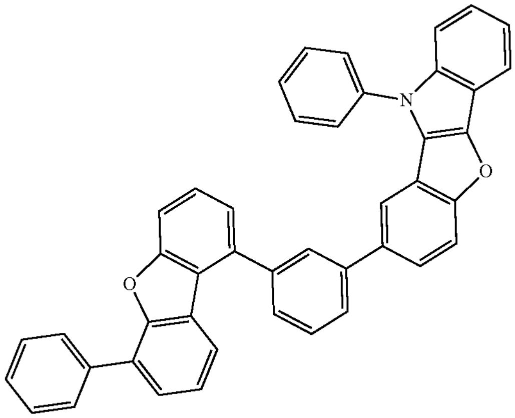
-continued
397
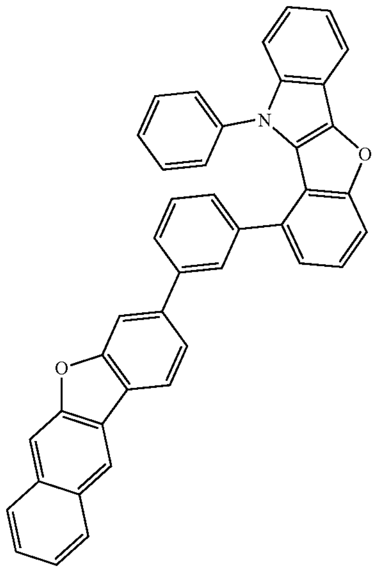
398
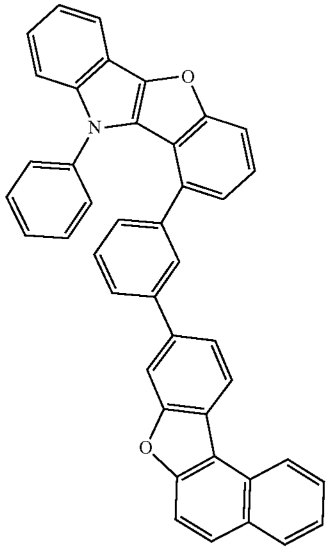
399
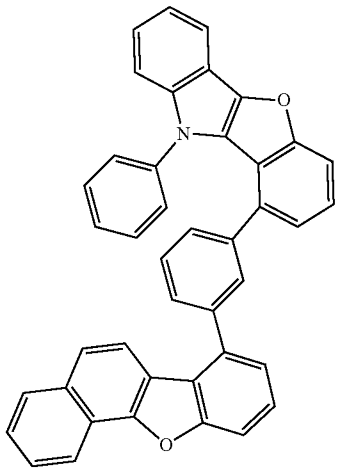

-continued
400
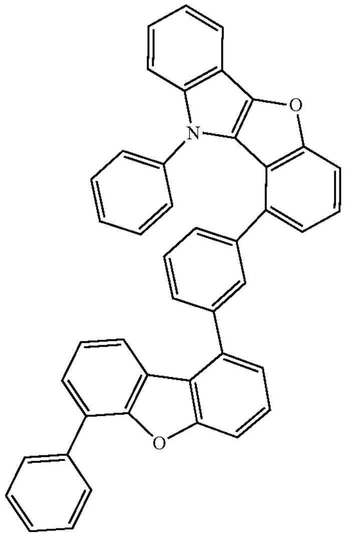
401
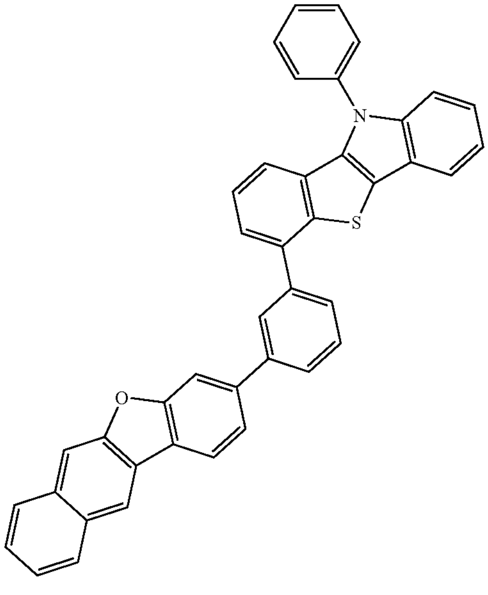
-continued
402
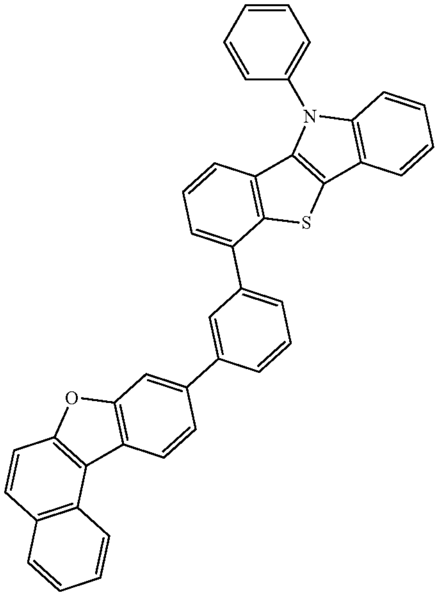
403
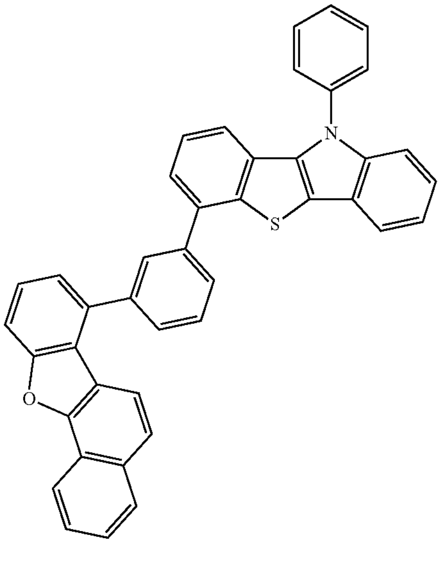

-continued
404
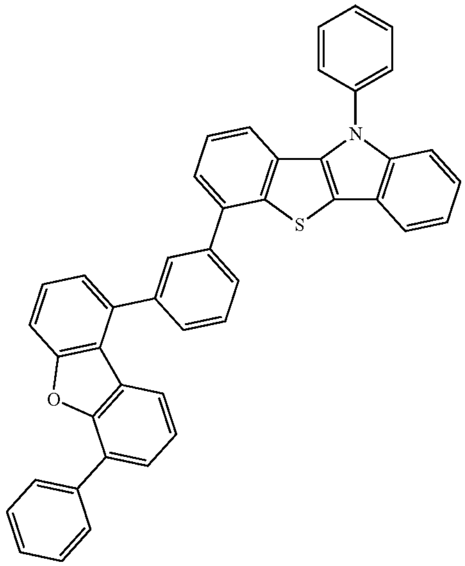
405
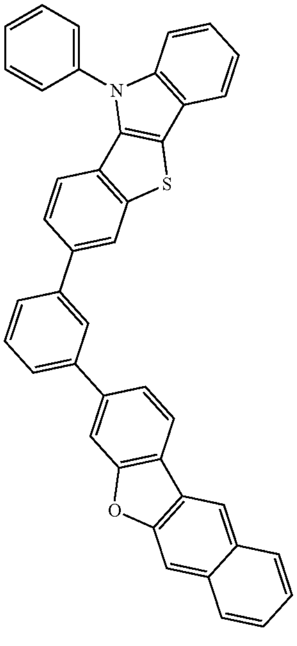
-continued
406
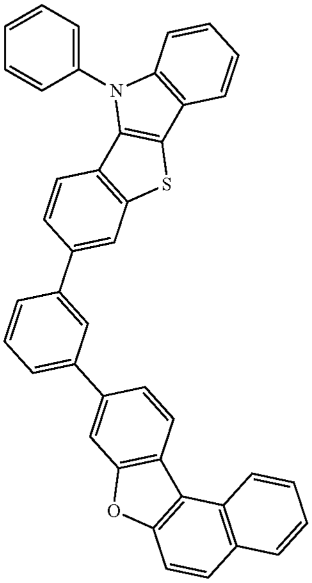
407
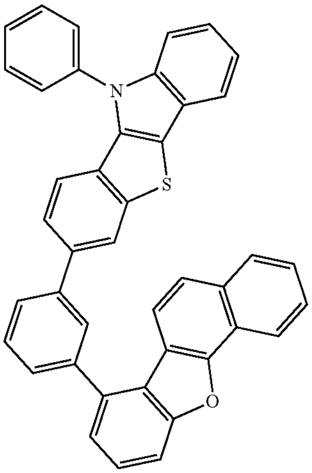
408
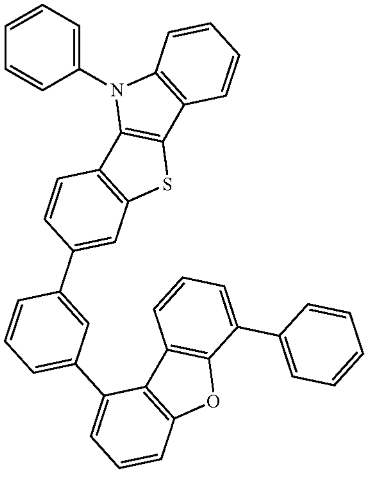

-continued
409
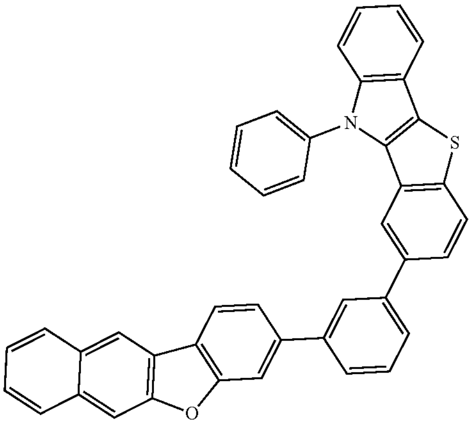
410
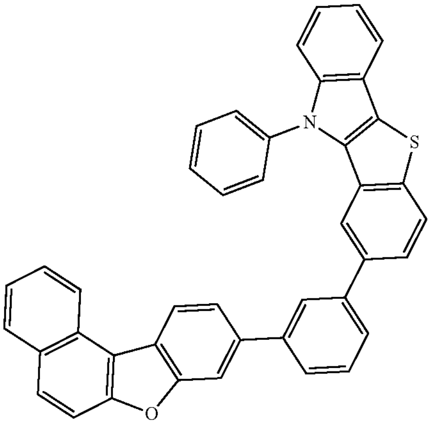
411
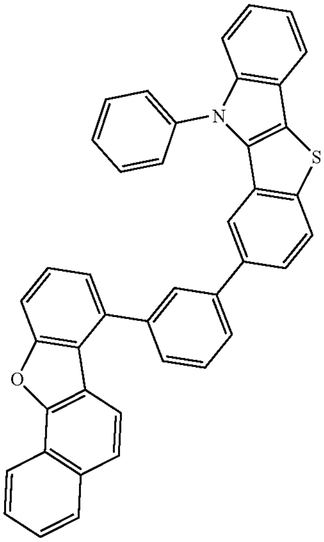
-continued
412
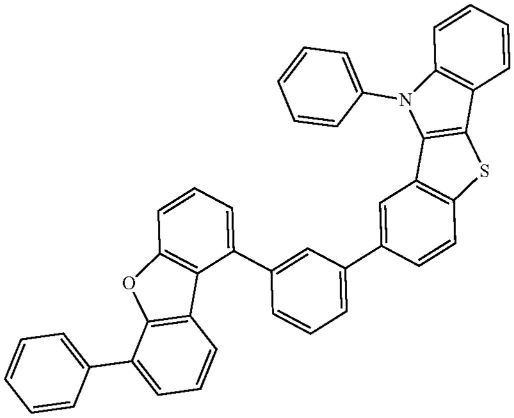
413
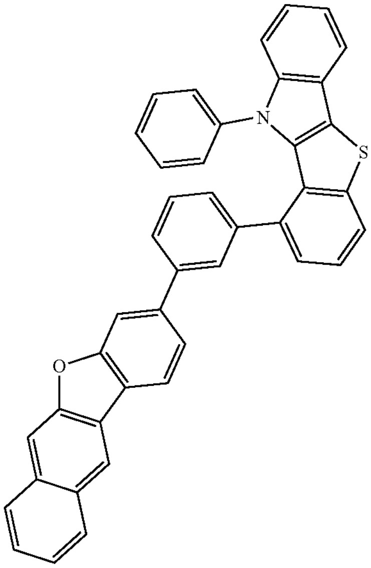
414
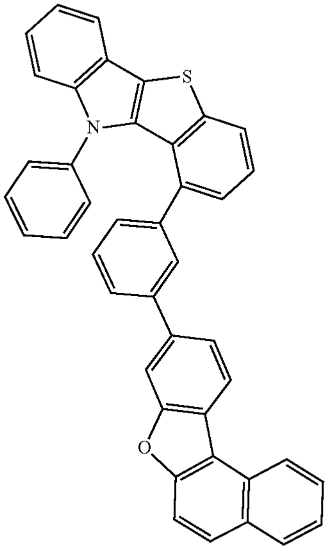

-continued
415
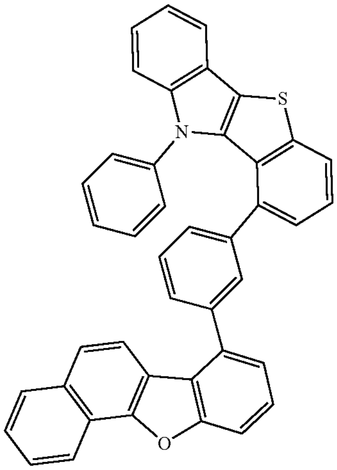
416
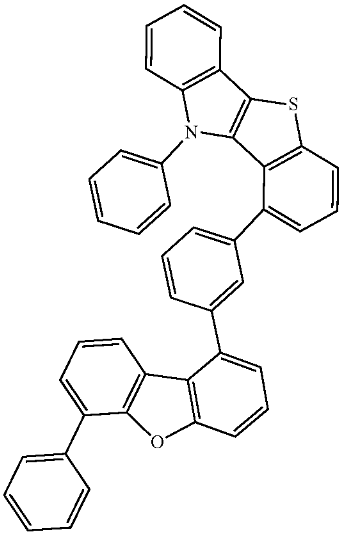
417
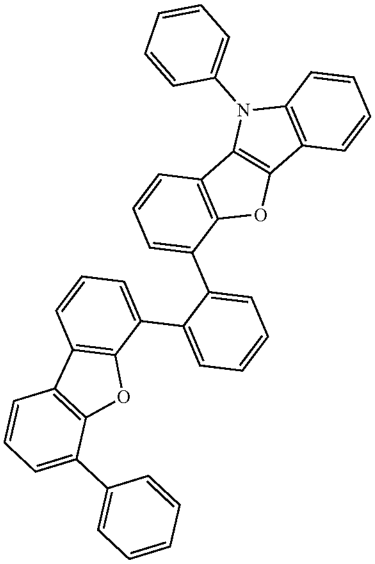
-continued
418
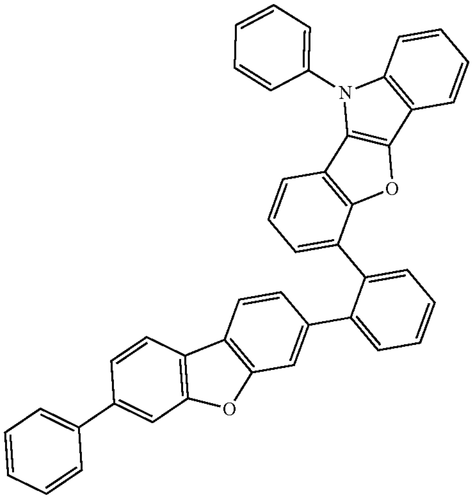
419
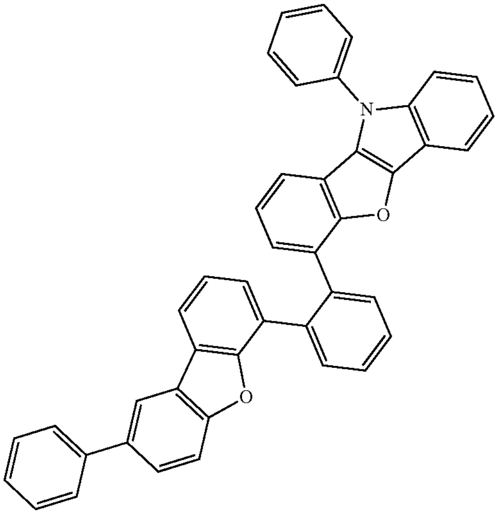
420
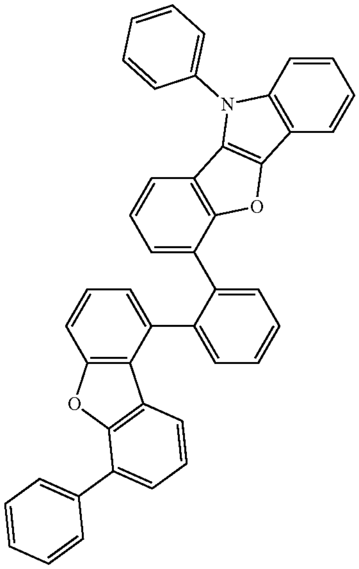

-continued
421
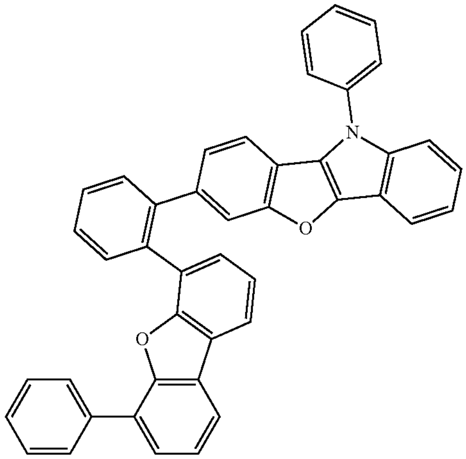
422
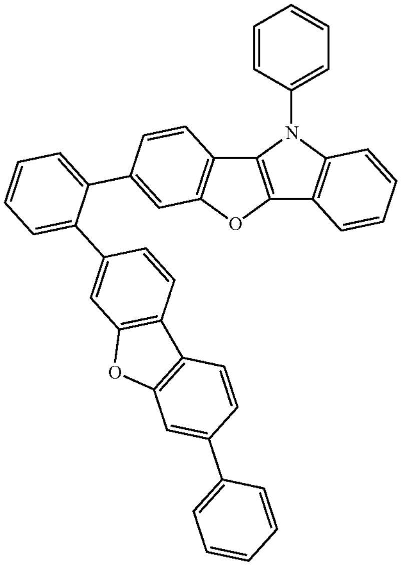
423
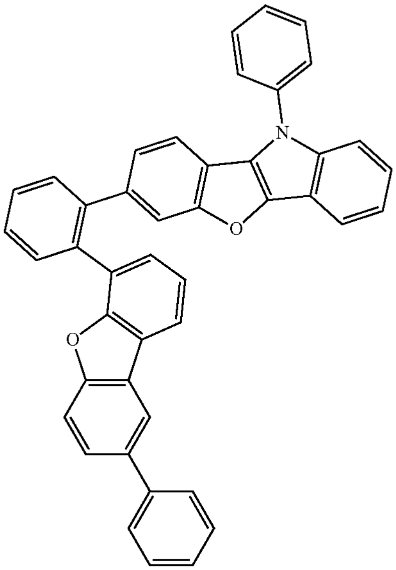
-continued
424
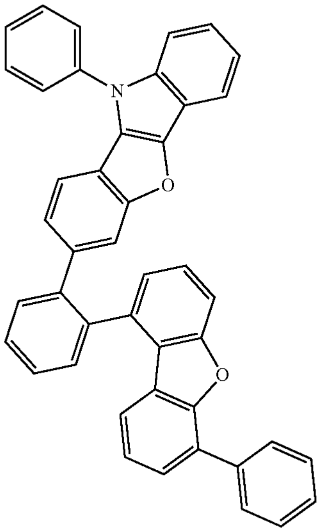
425
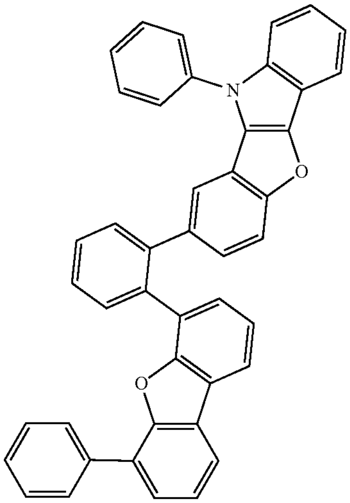
426
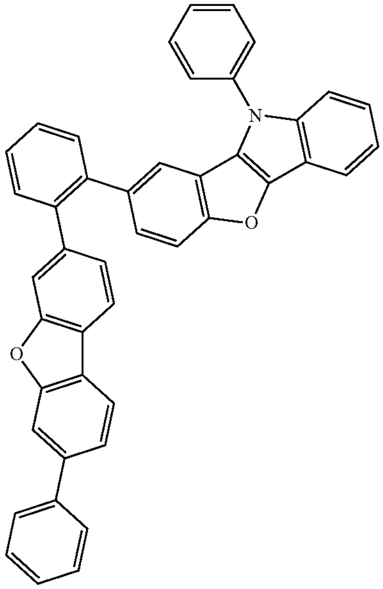

427
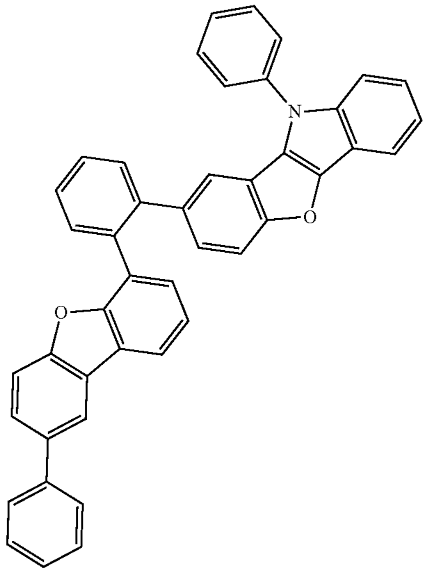
428
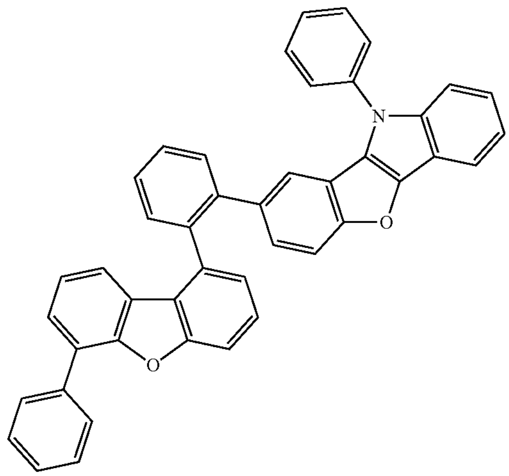
429
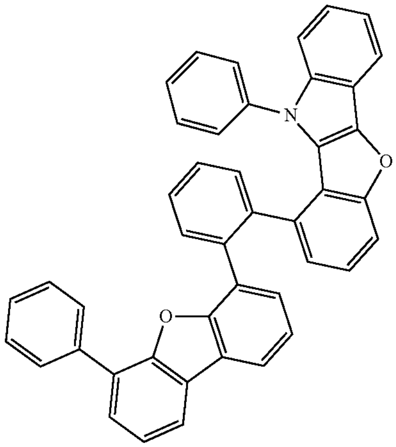
430
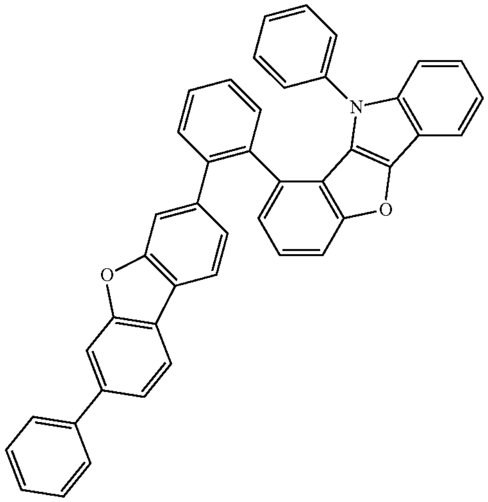
431
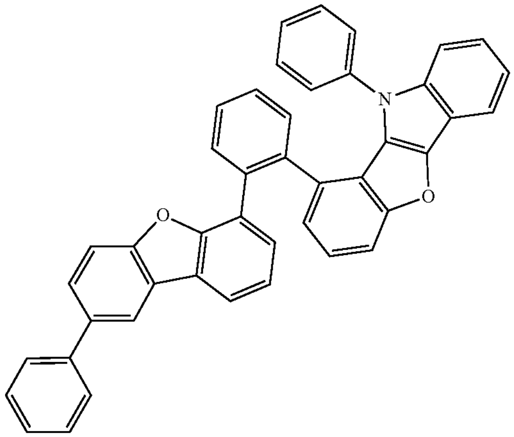
432
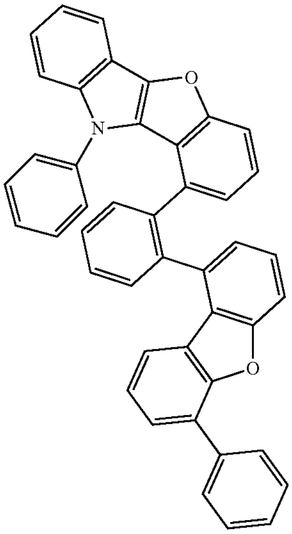

-continued
433
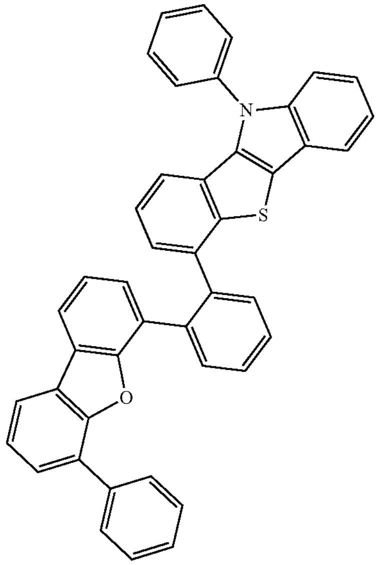
434
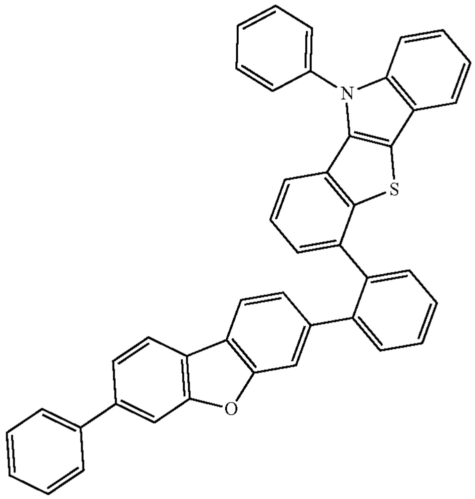
435
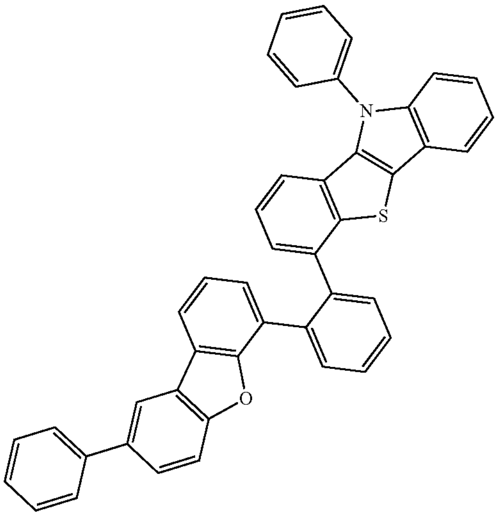
-continued
436
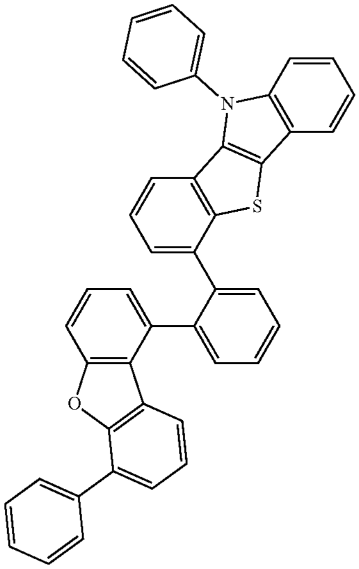
437
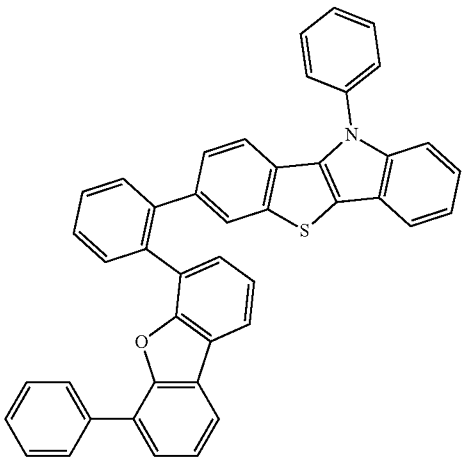
438
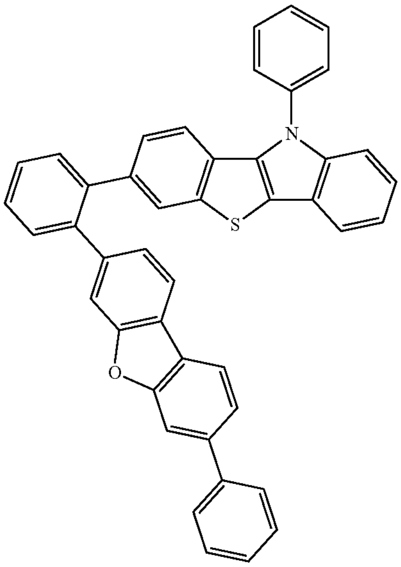

-continued
439
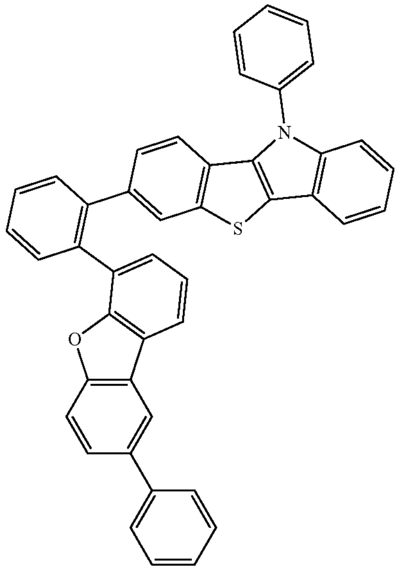
440
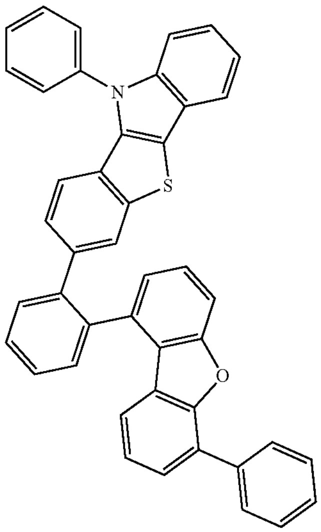
441
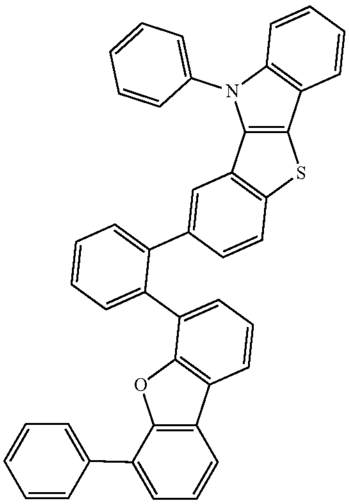
-continued
442
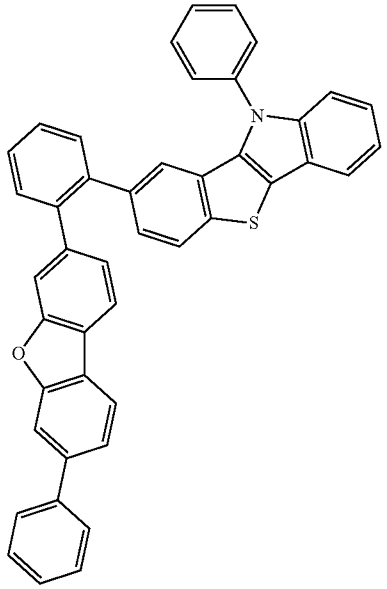
443
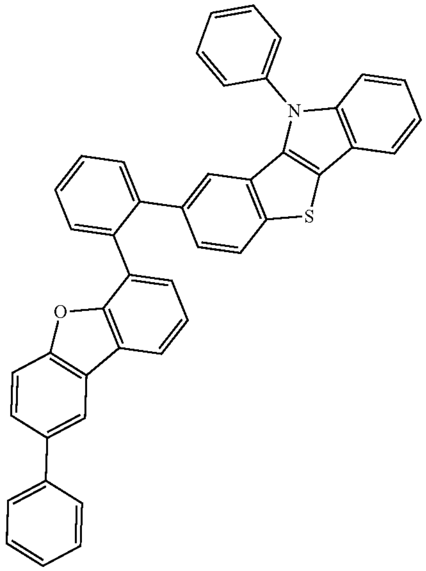
444
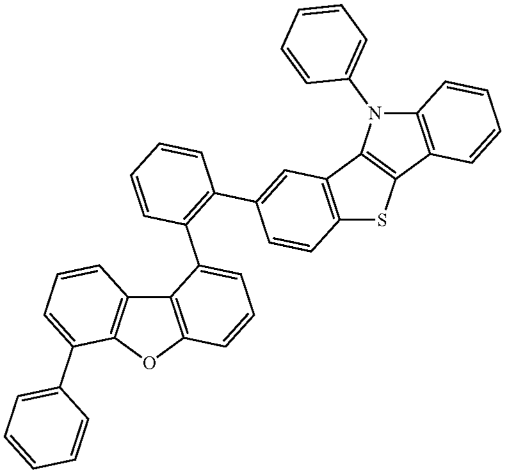

-continued
445
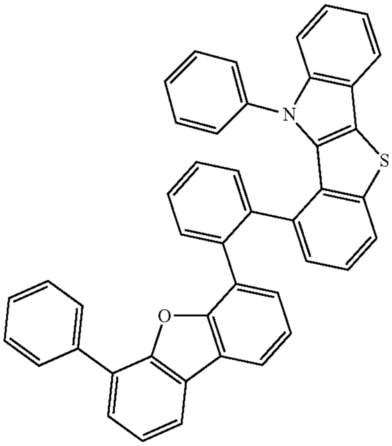
446
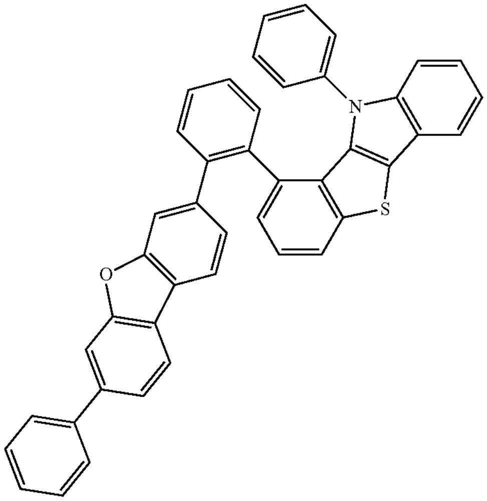
447
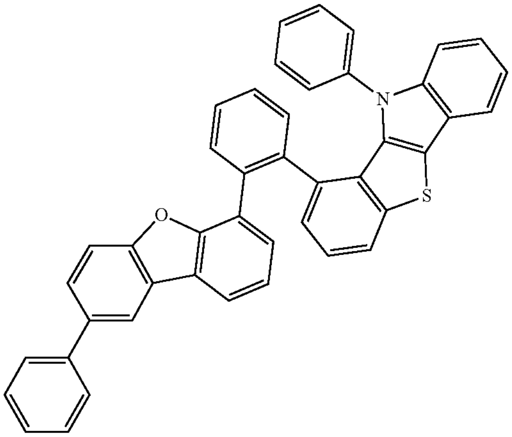
-continued
448
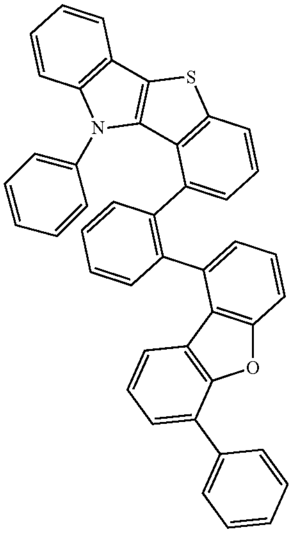
449
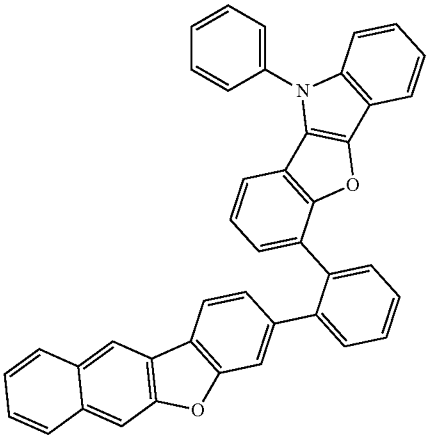
450
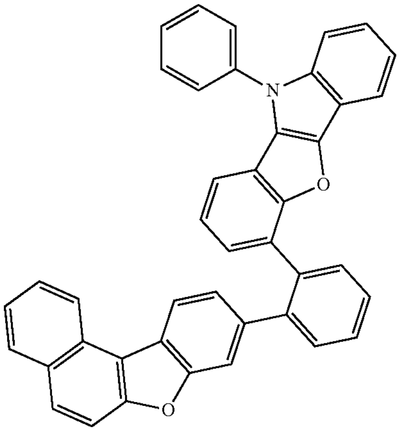

-continued
451
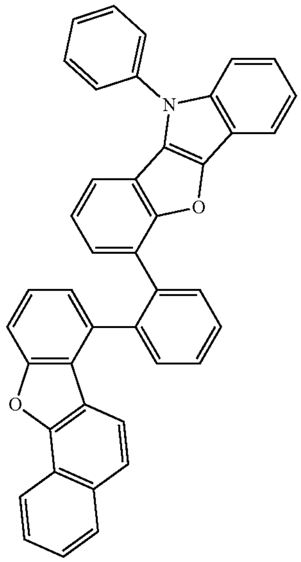
452
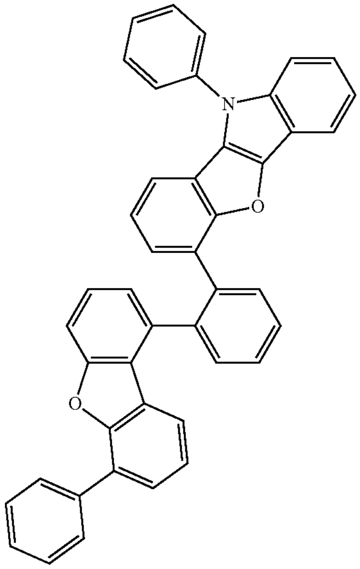
453
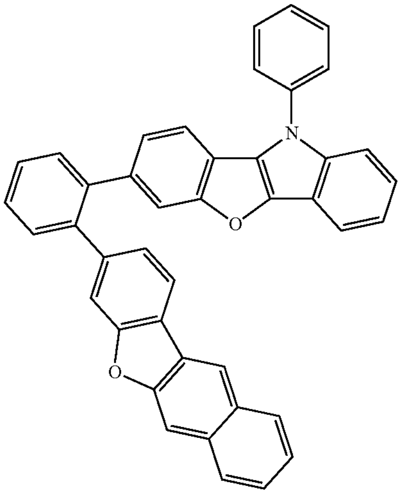
-continued
454
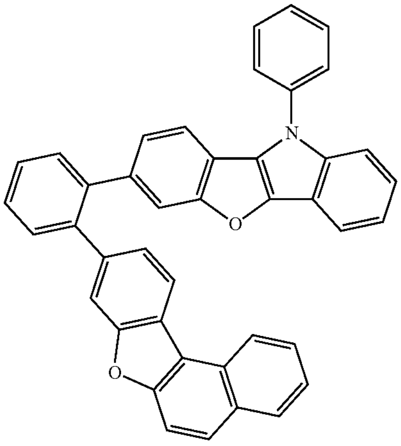
455
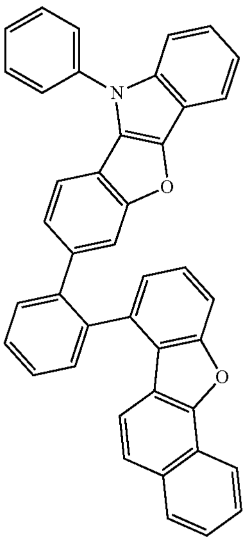
456
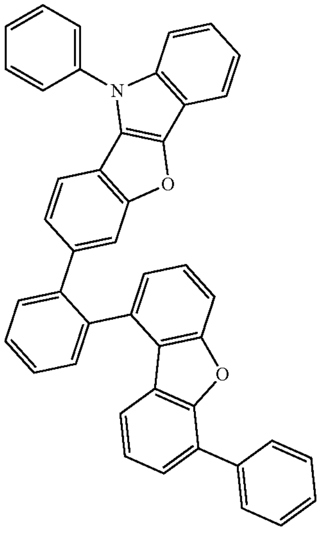

-continued
457
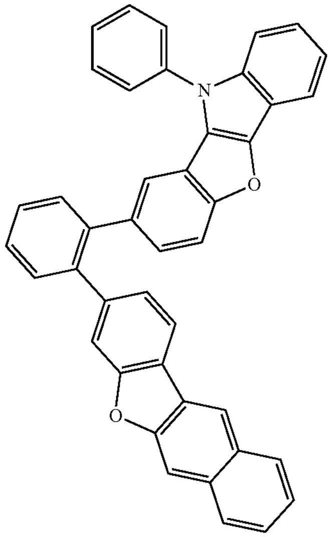
458
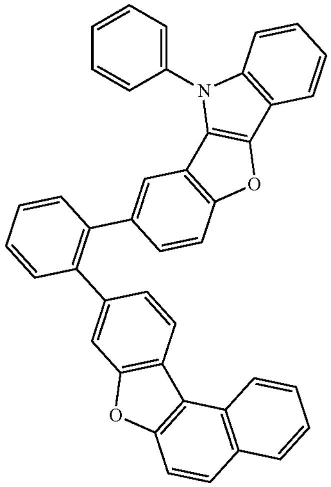
459
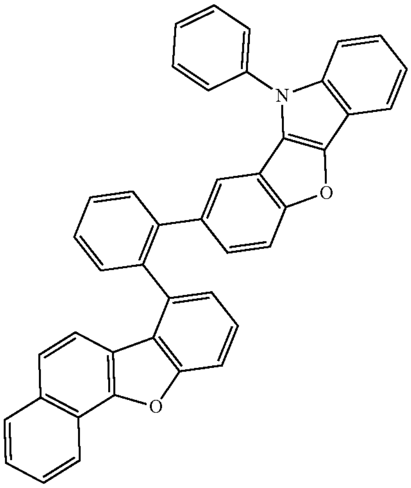
-continued
460
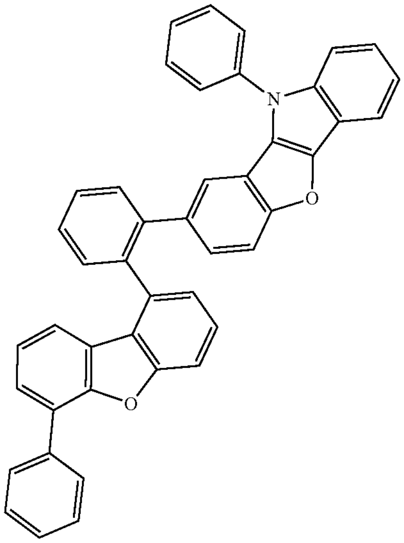
461
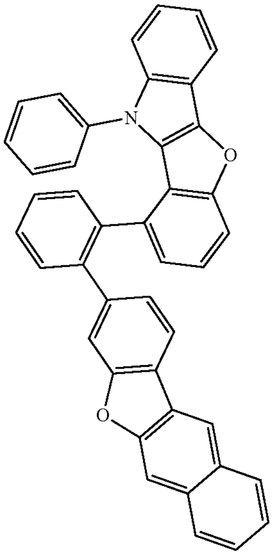
462
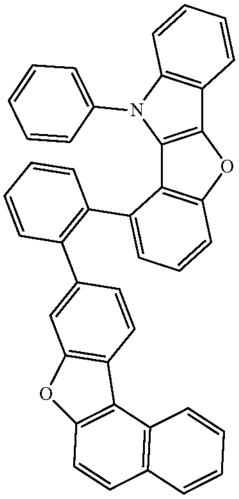

-continued
463
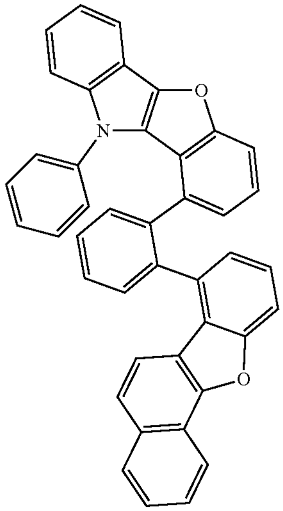
464
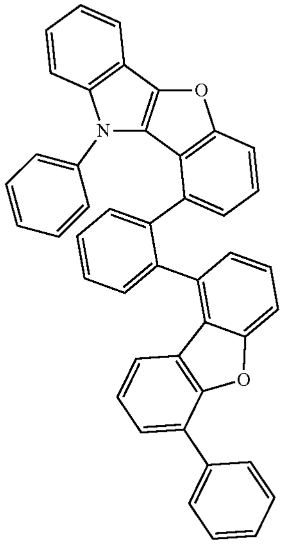
465
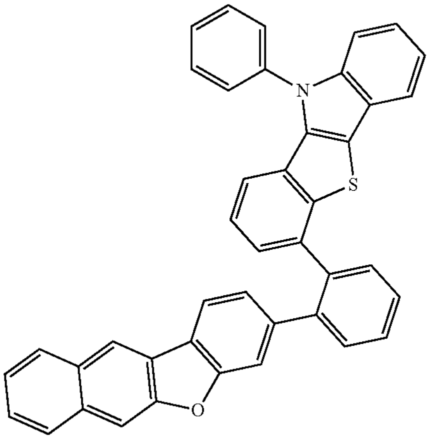
-continued
466
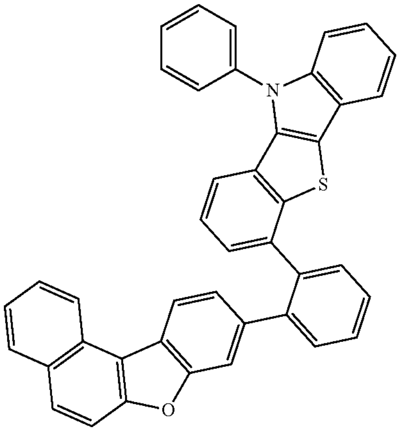
467
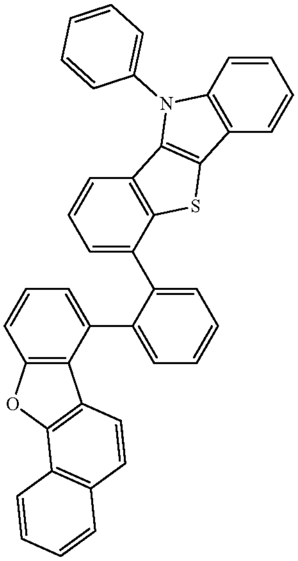
468
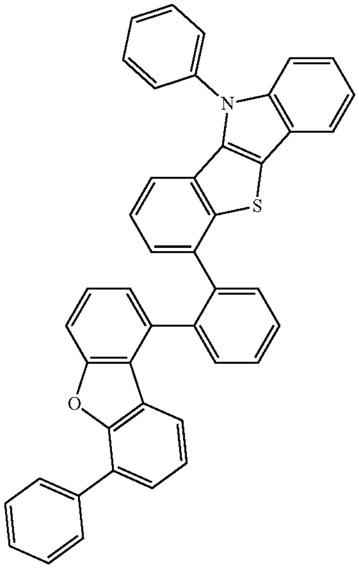

-continued
469
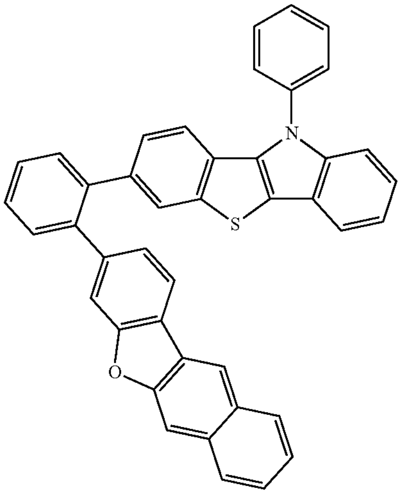
470
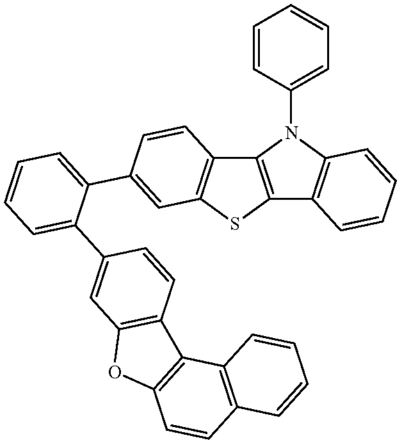
471
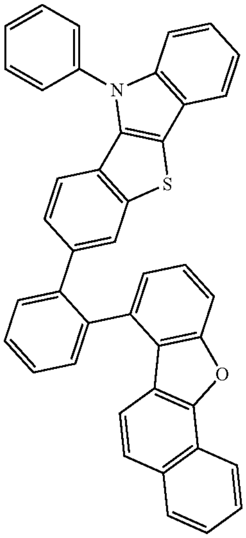
-continued
472
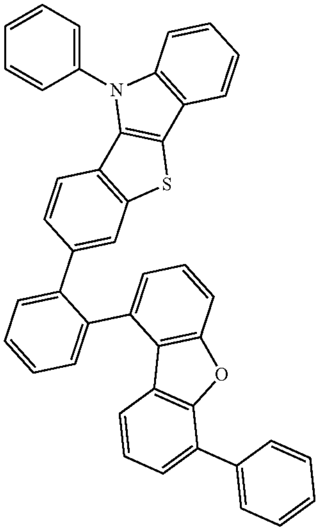
473
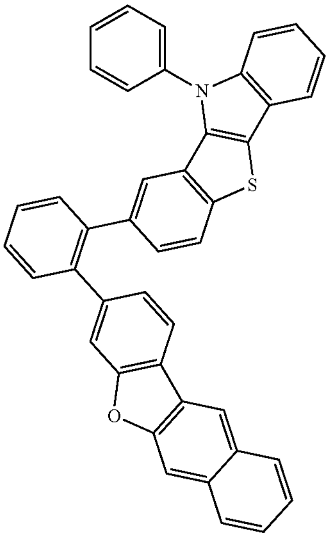
474
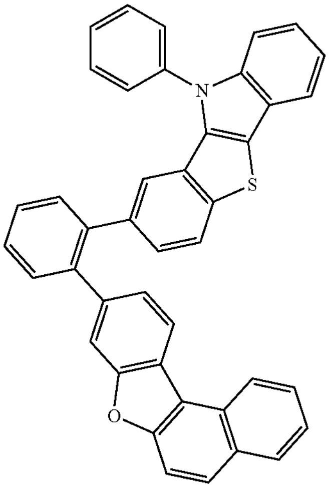

-continued
475
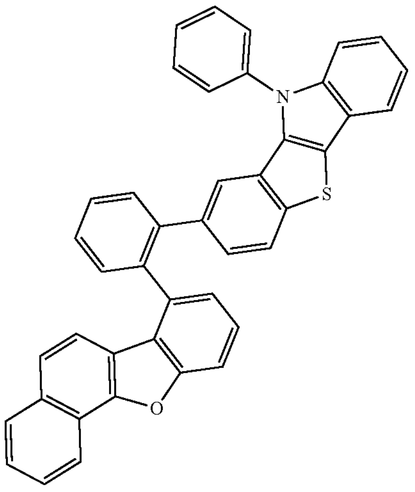
476
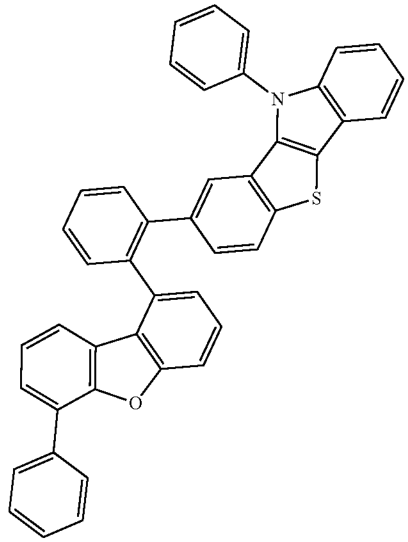
477
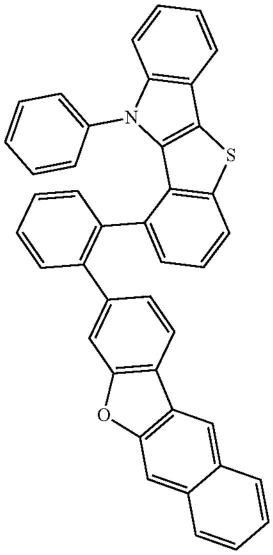
-continued
478
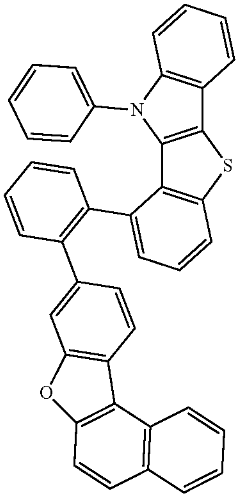
479
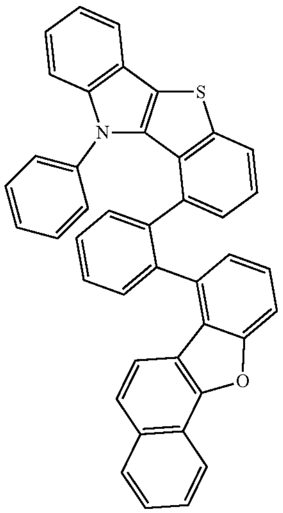
480
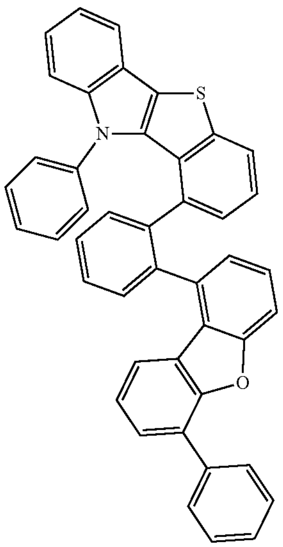

-continued
481
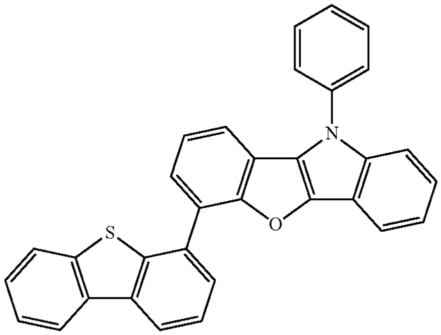
482
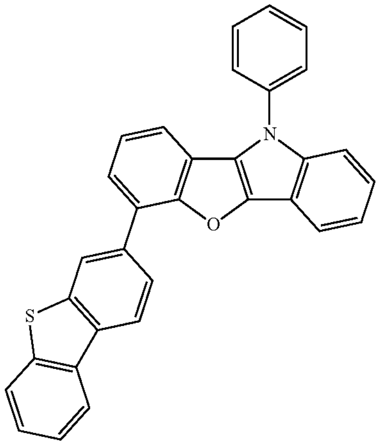
483
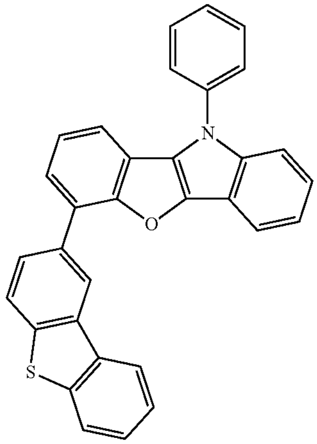
484
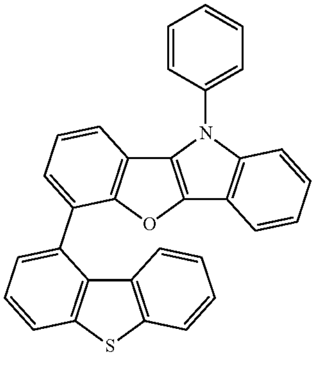
-continued
485
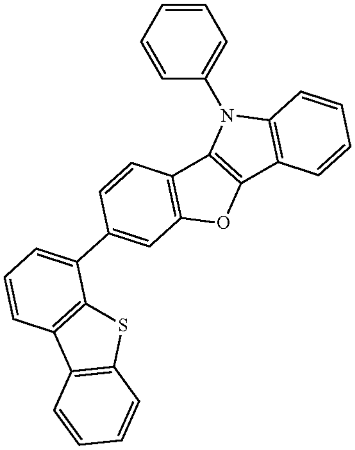
486
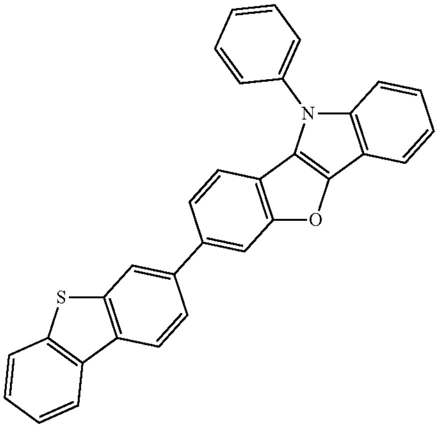
487
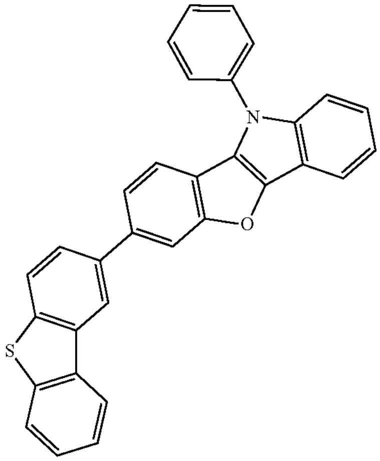

-continued
488
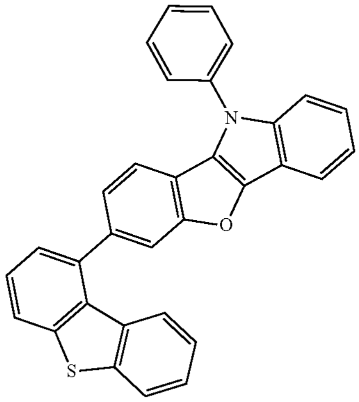
489
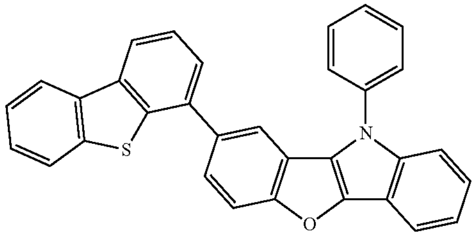
490
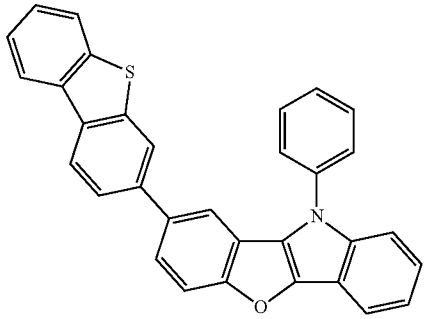
491
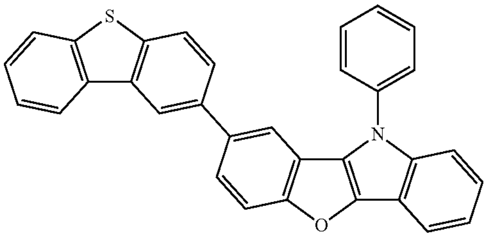
492
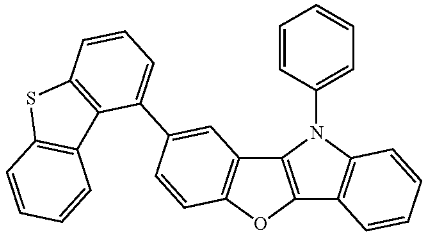
-continued
493
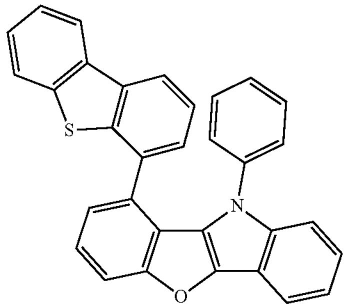
494
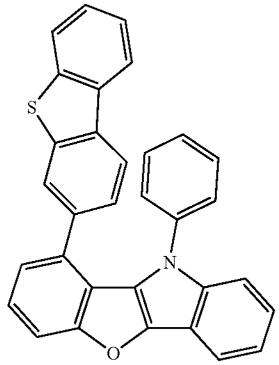
495
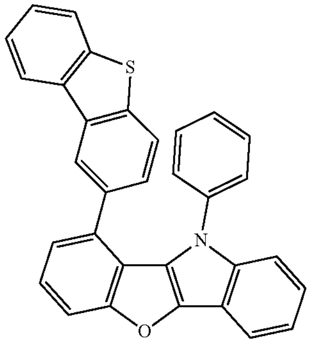
496
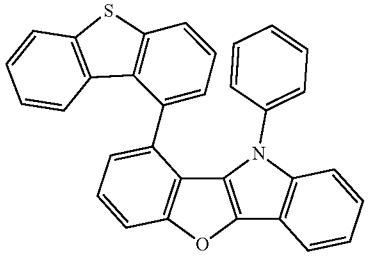
497
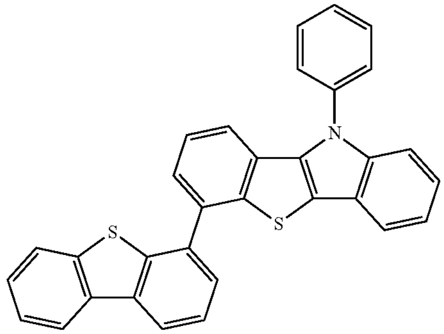

-continued
498
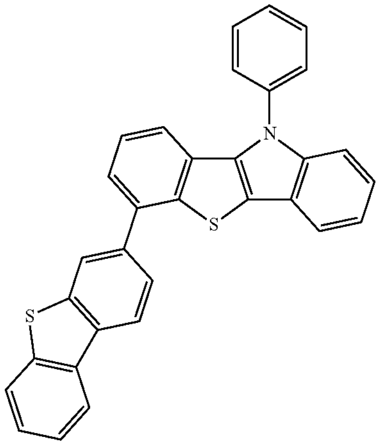
499
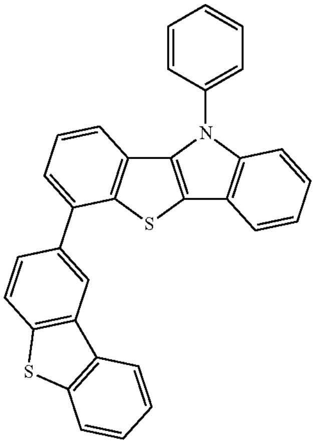
500
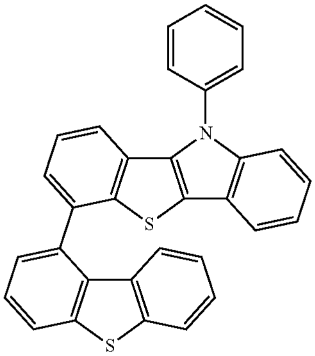
-continued
501
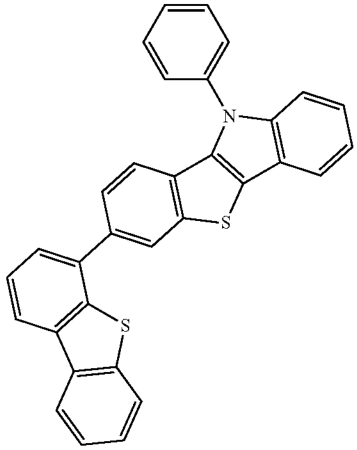
502
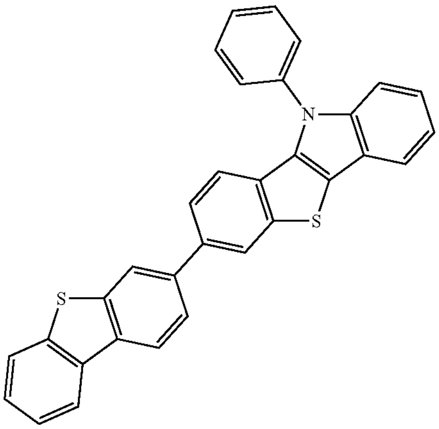
503
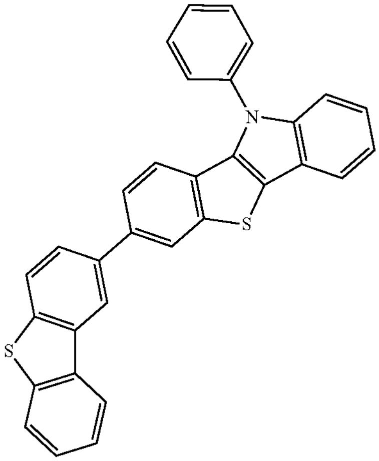

-continued
504
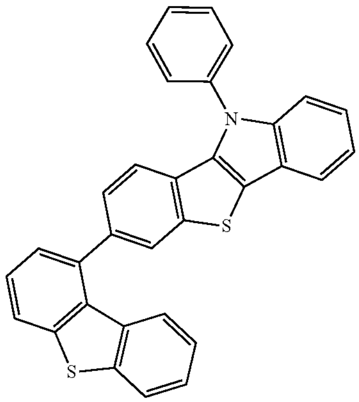
505
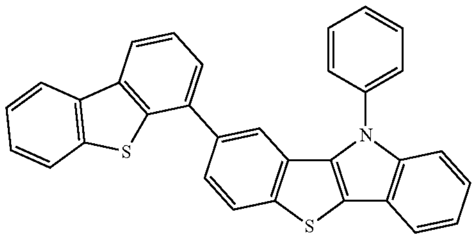
506
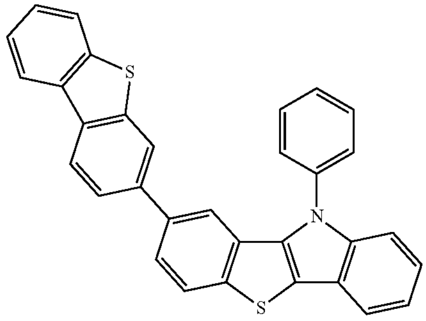
507
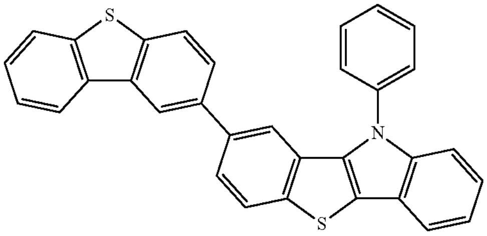
508
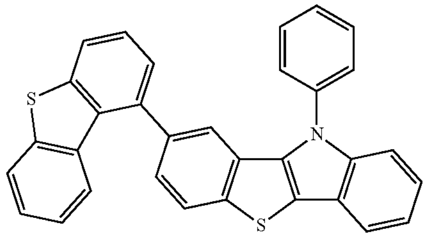
-continued
509
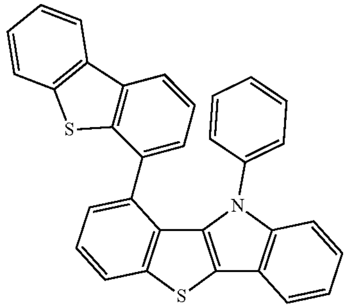
510
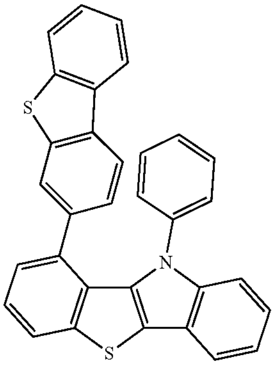
511
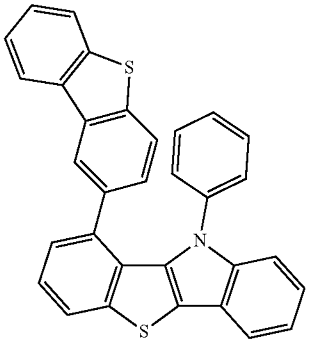
512
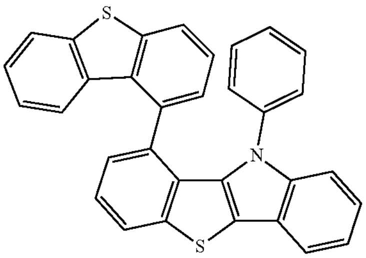

-continued
513
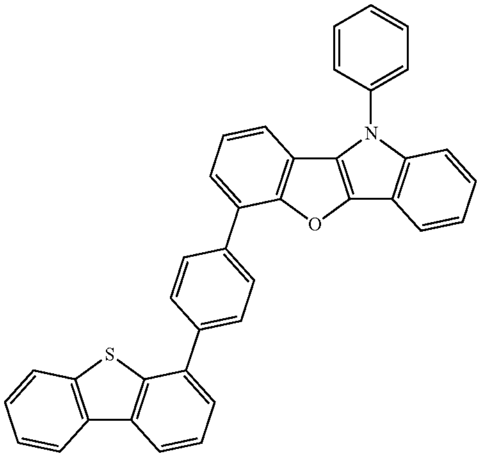
514
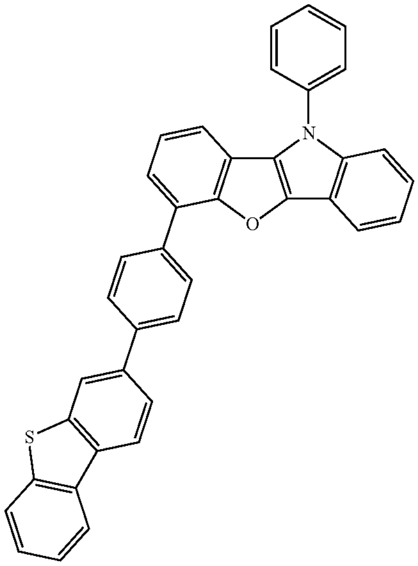
515
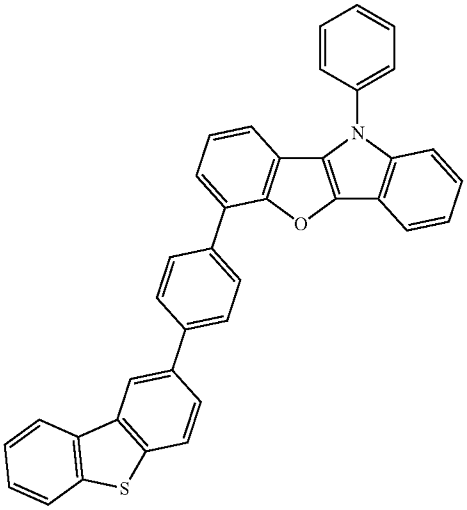
-continued
516
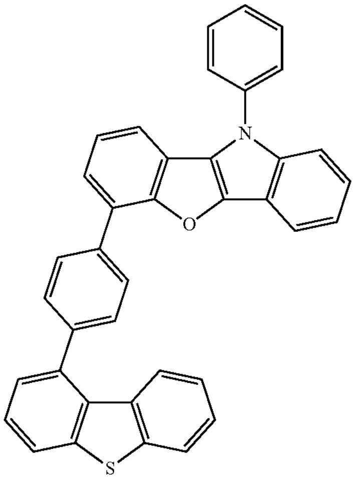
517
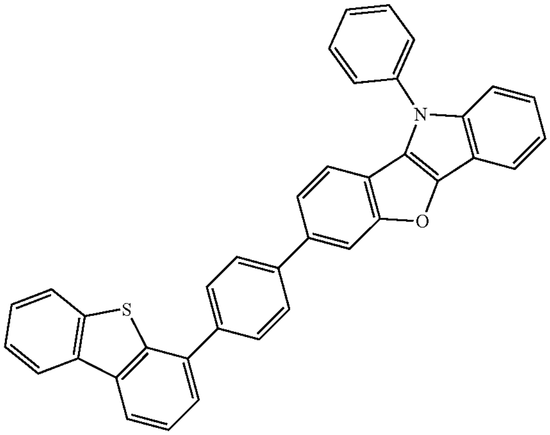
518
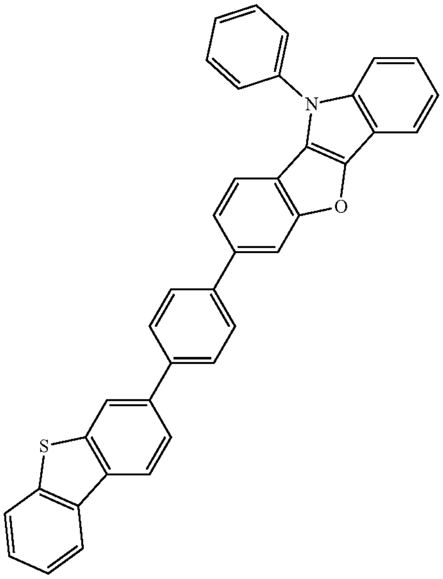

-continued
519
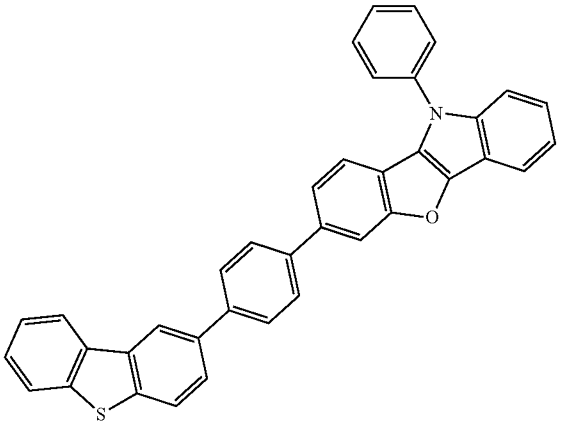
520
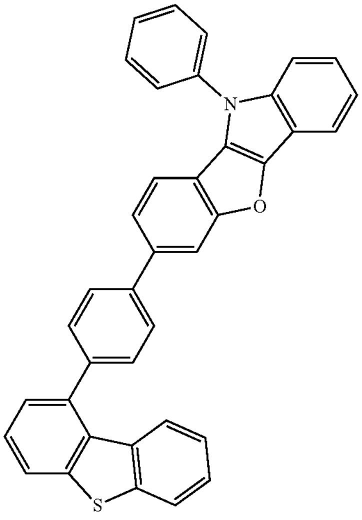
521
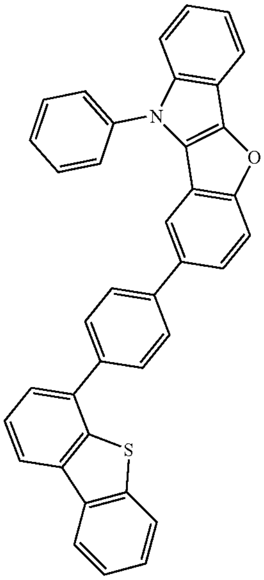
-continued
522
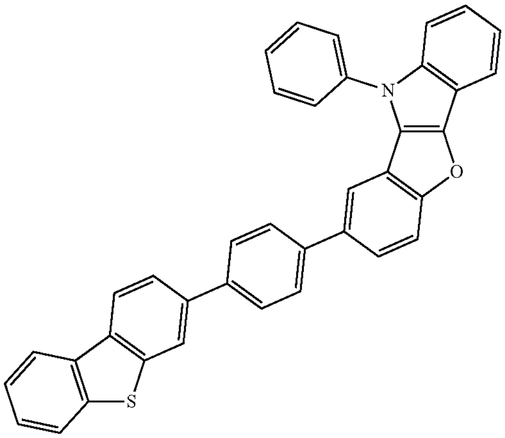
523
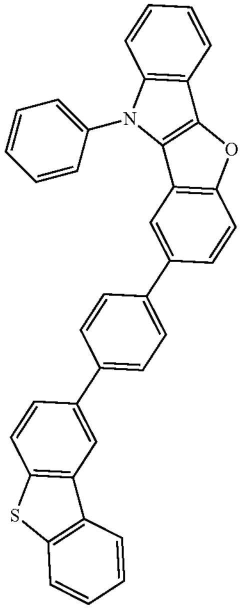
524
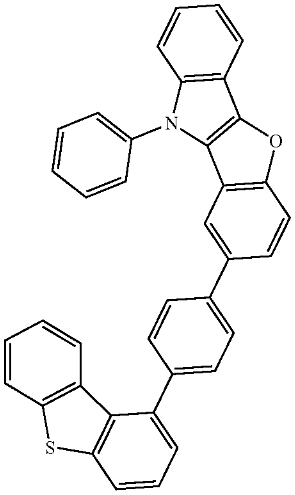

-continued
525
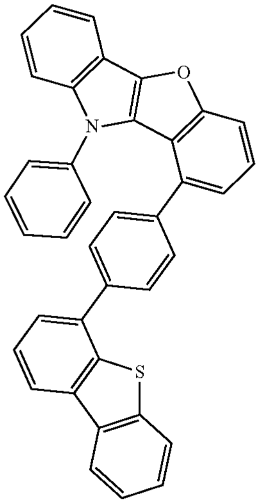
526
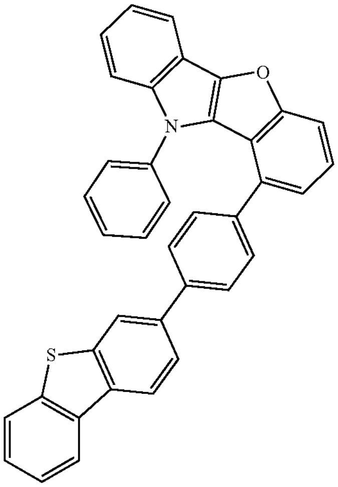
527
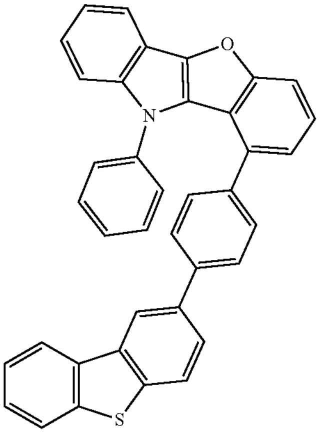
-continued
528
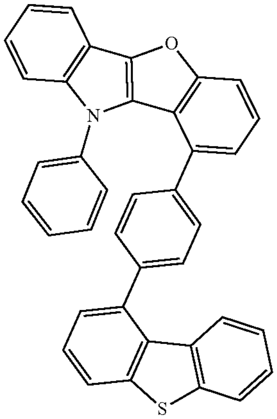
529
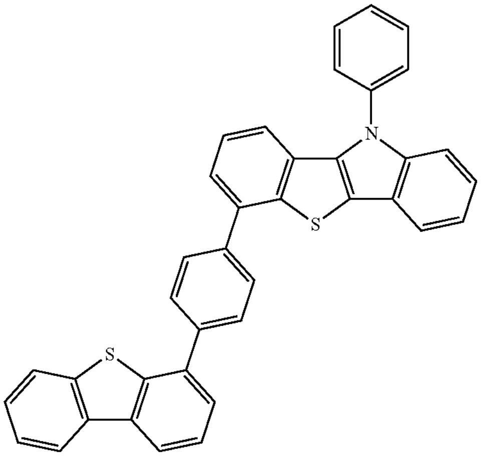
530
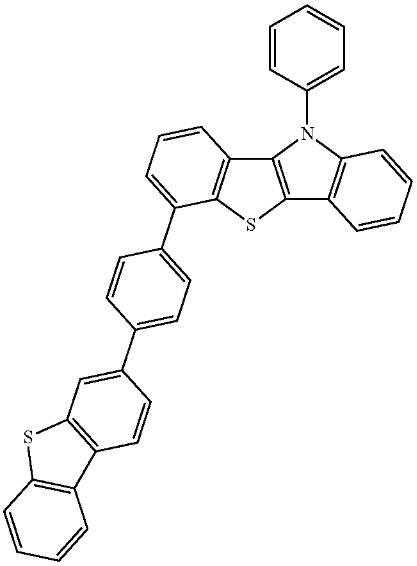

-continued
531
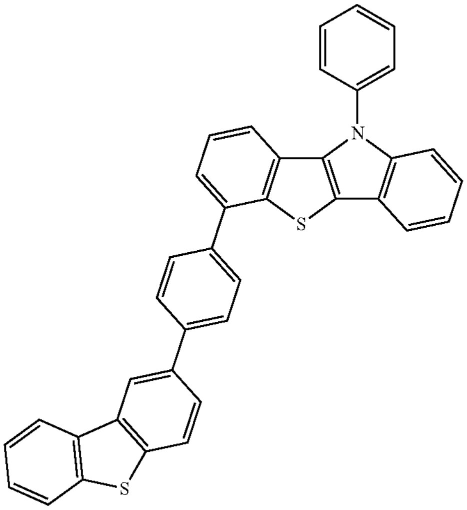
532
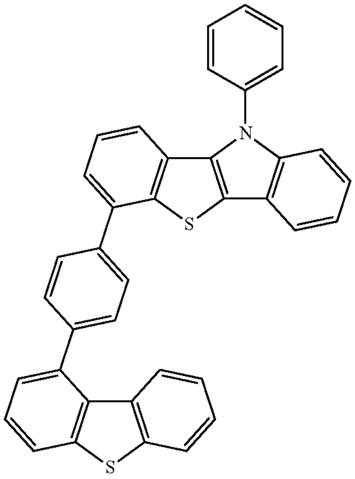
533
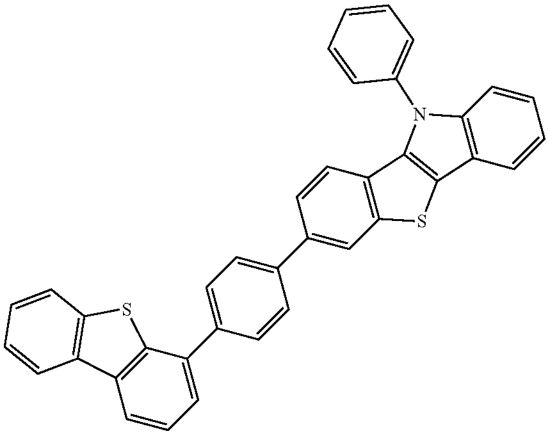
-continued
534
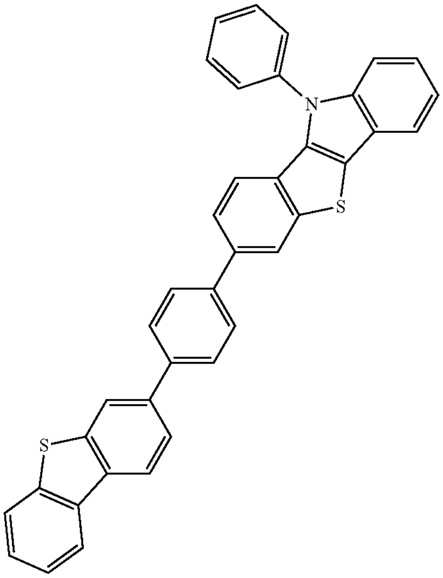
535
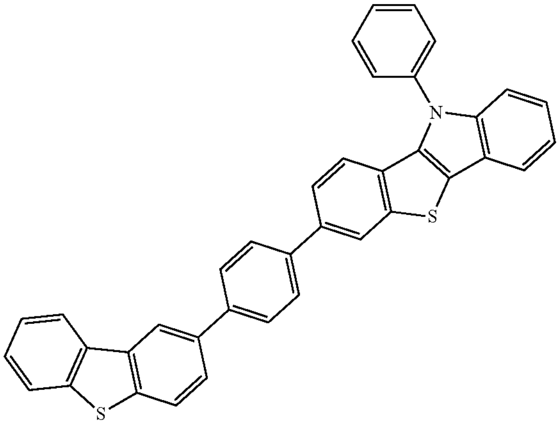
536
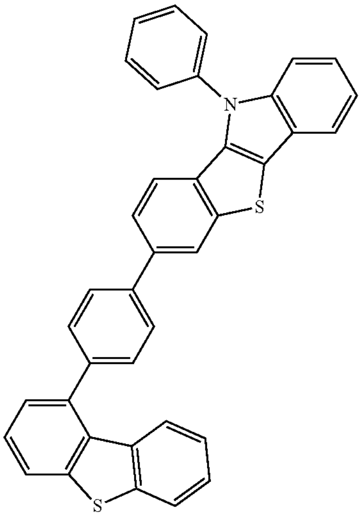

-continued
537
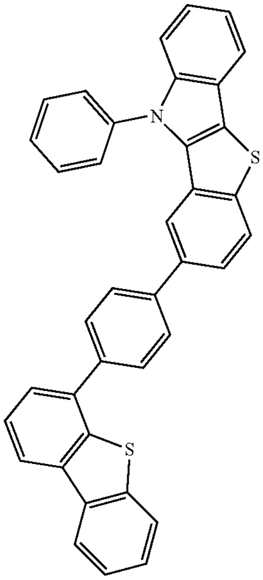
538
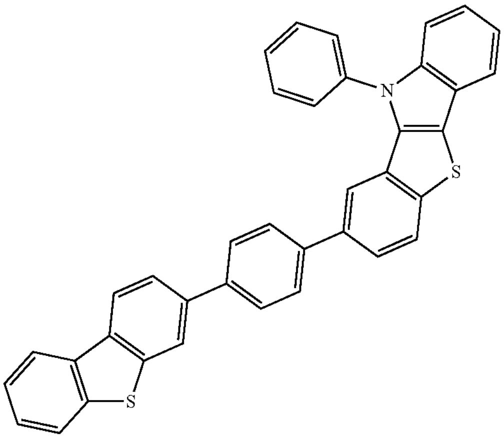
539
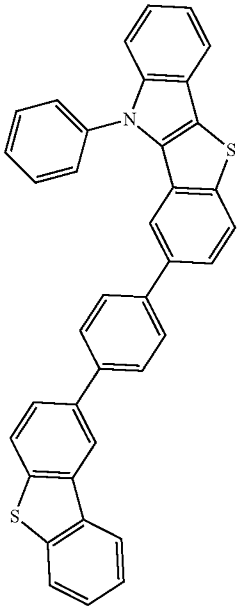
-continued
540
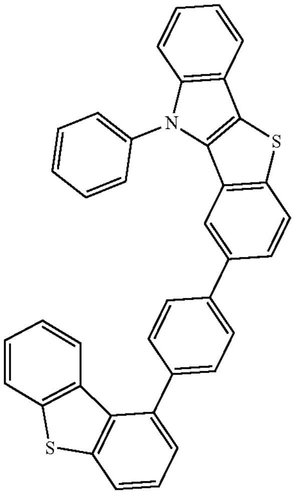
541
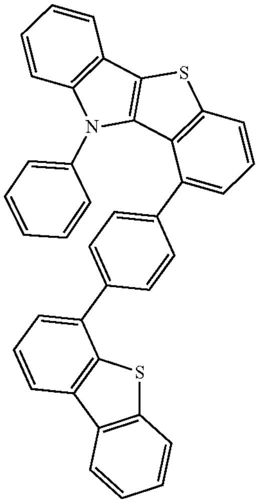
542
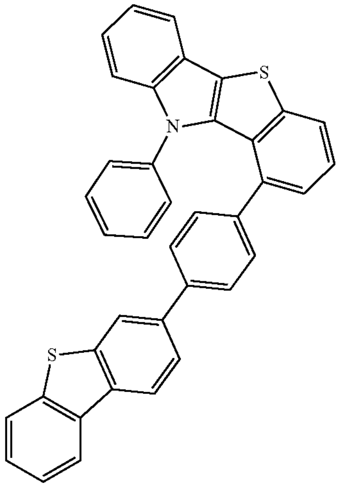

-continued
543
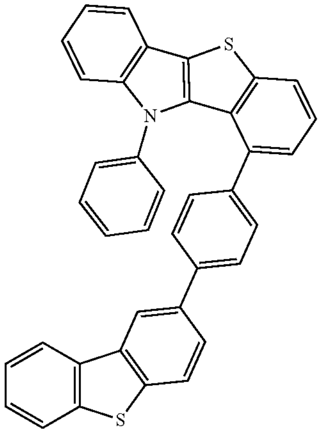
544
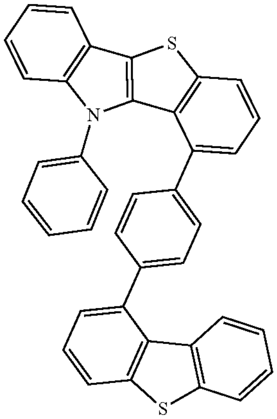
545
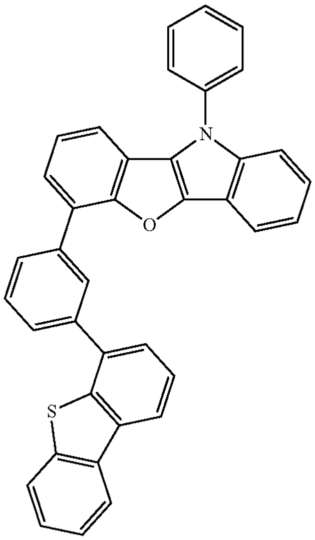
-continued
546
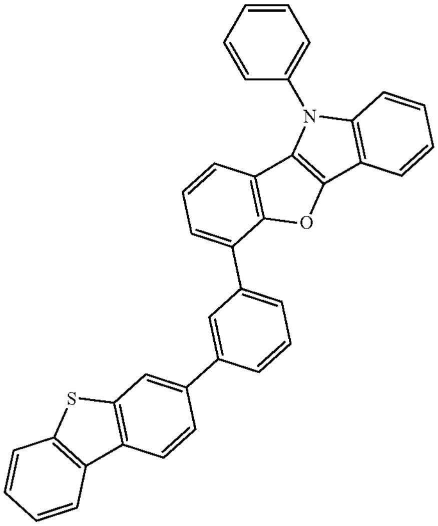
547
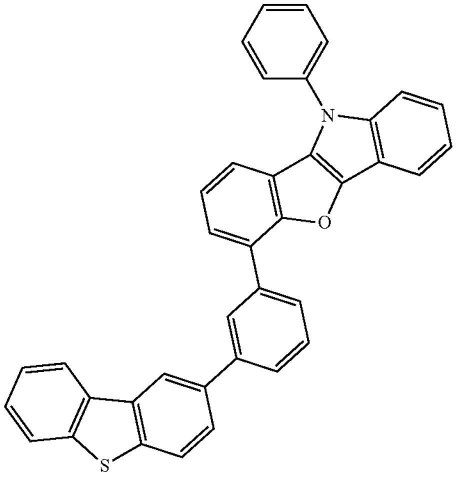
548
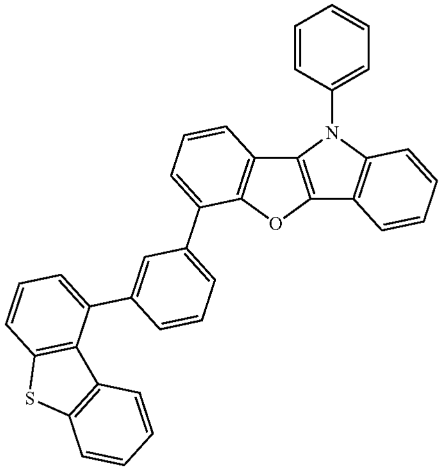

-continued
549
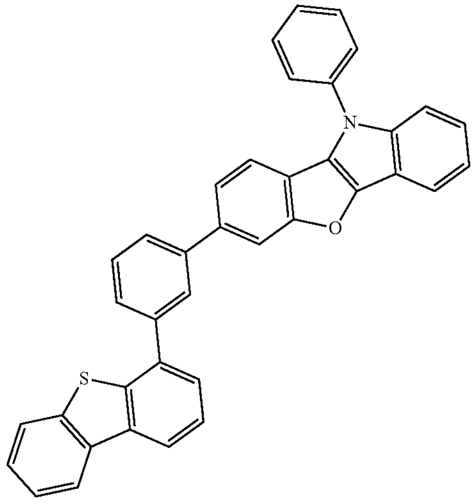
550
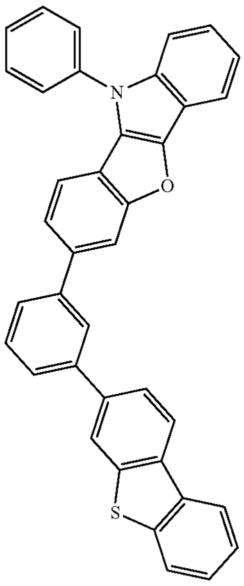
551
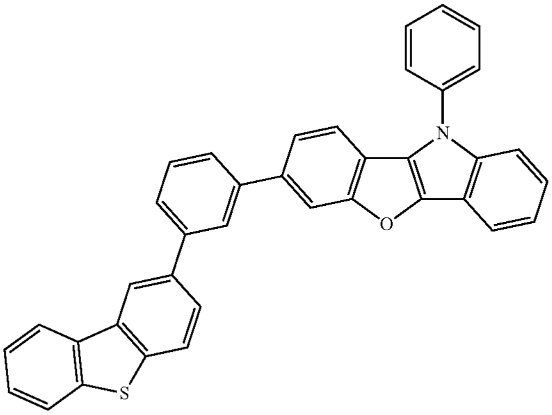
-continued
552
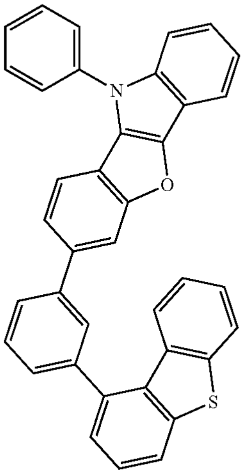
553
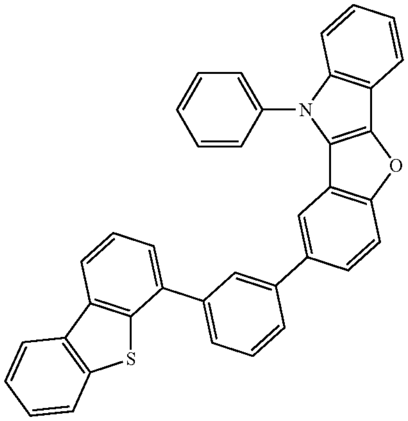
554
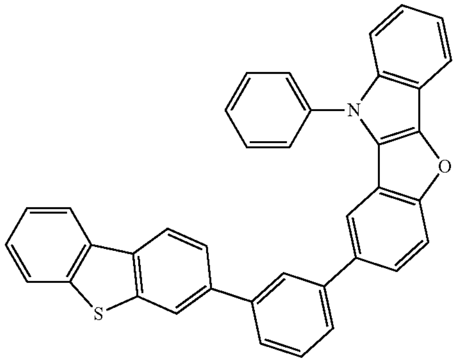

555
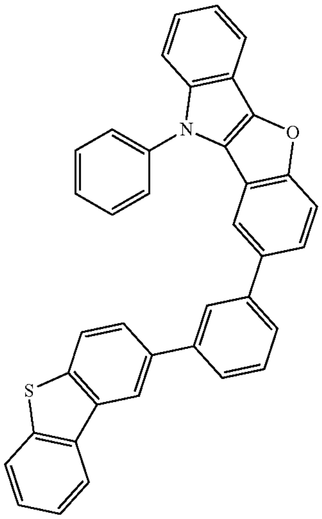
556
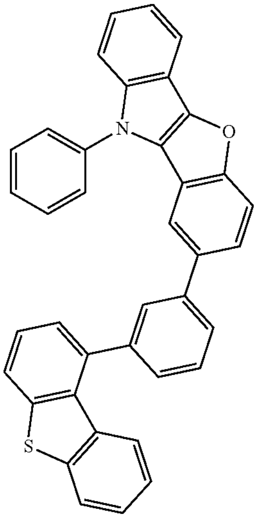
557
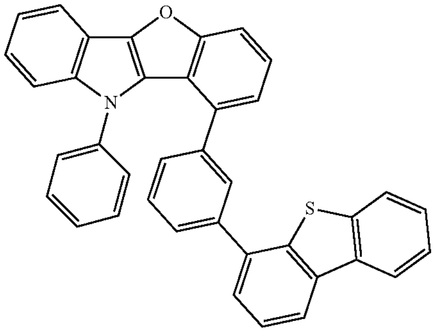
558
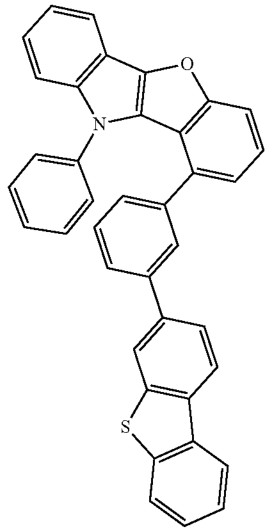
559
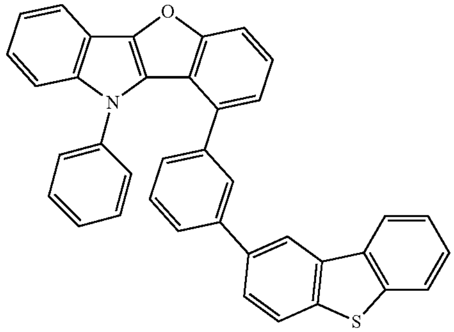
560
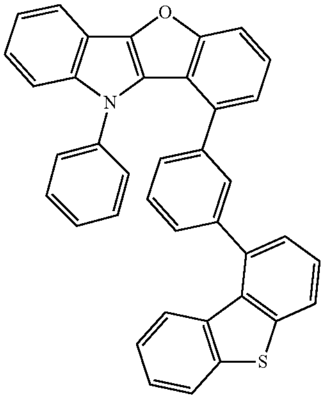

-continued
561
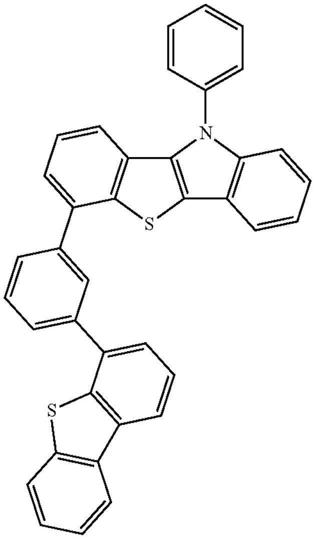
562
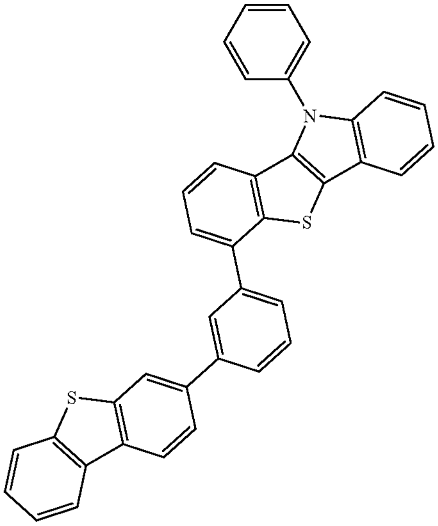
563
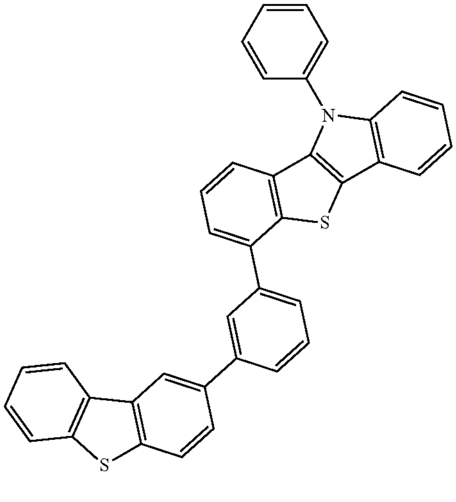
-continued
564
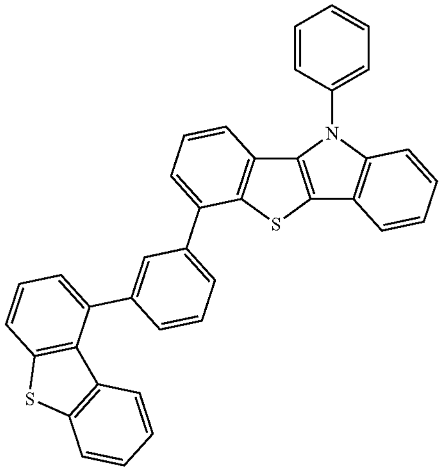
565
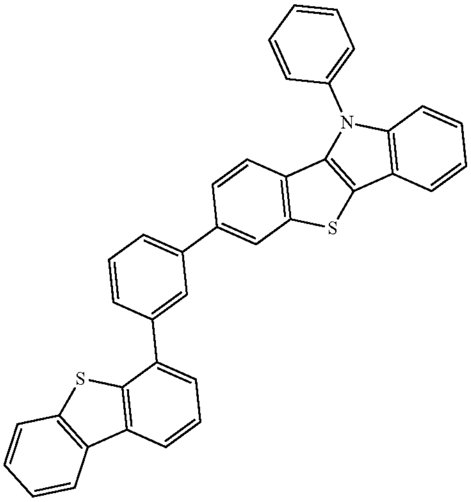
566
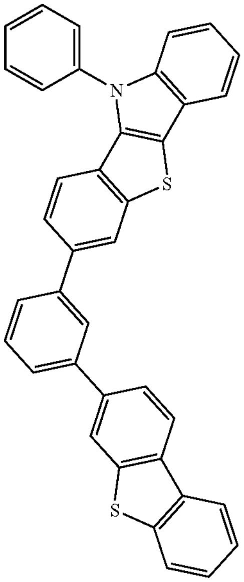

-continued
567
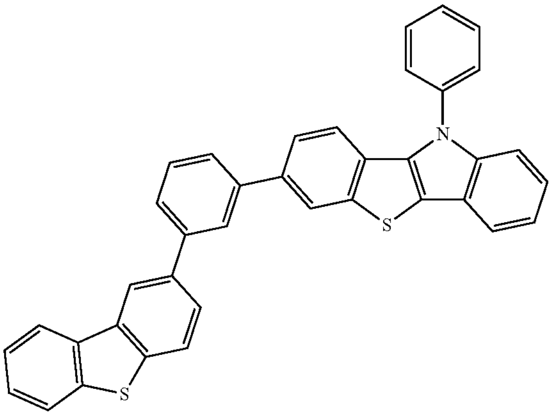
568
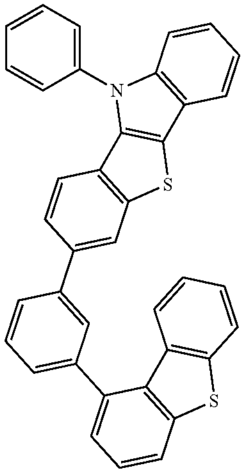
569
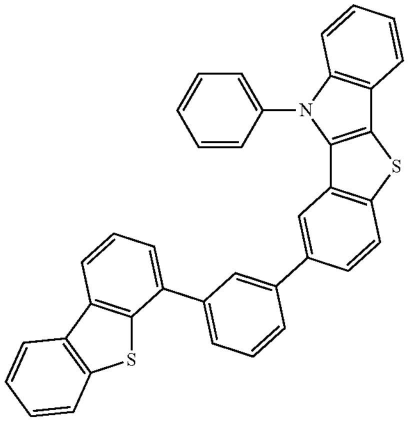
-continued
570
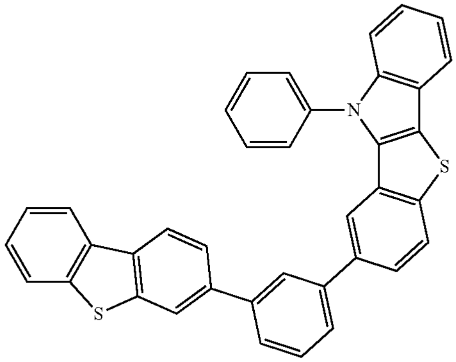
571
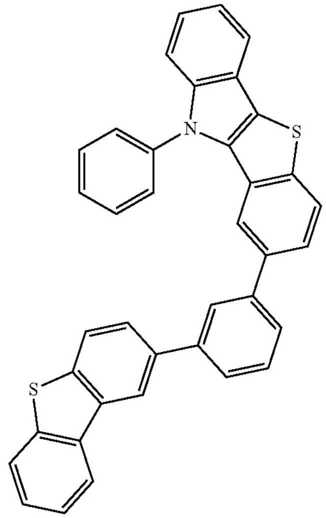
572
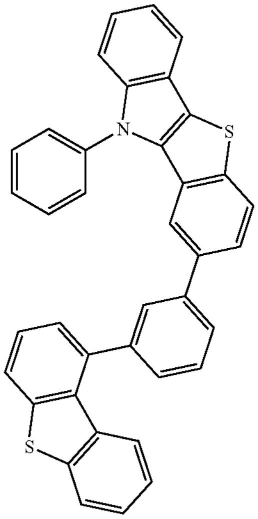

-continued
573
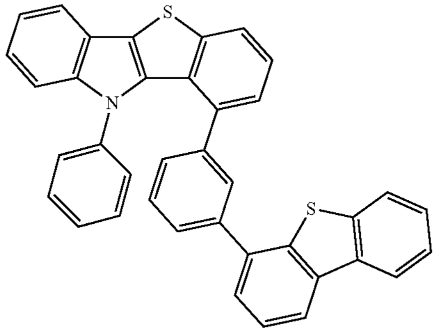
574
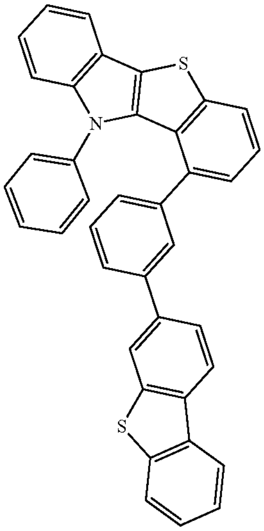
575
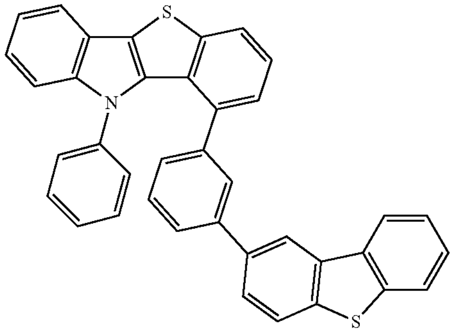
576
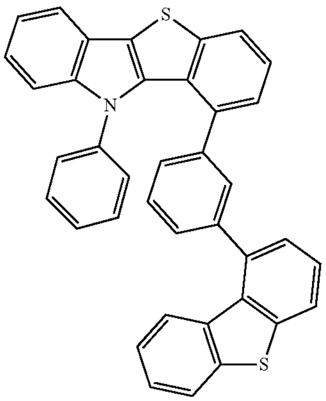
577
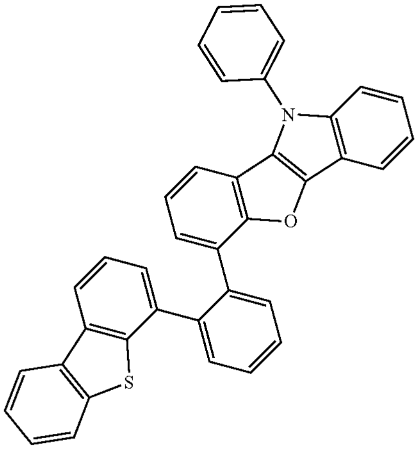
578
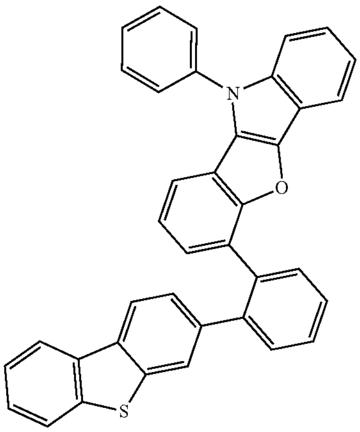
579
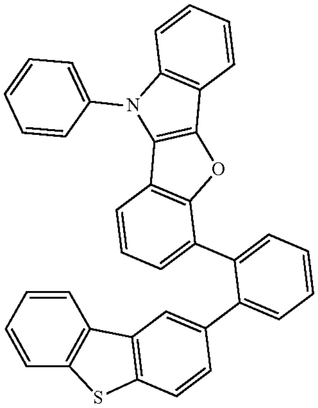

-continued
580
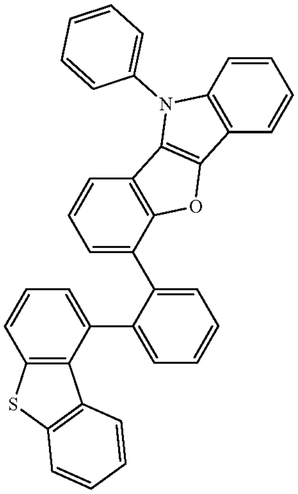
581
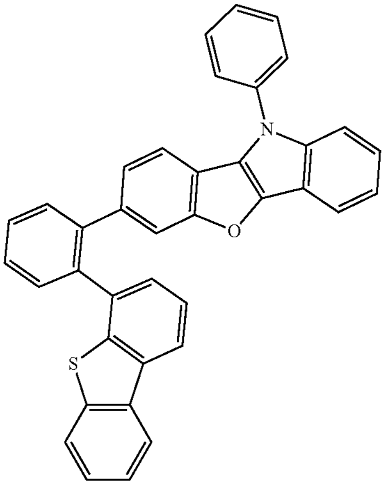
582
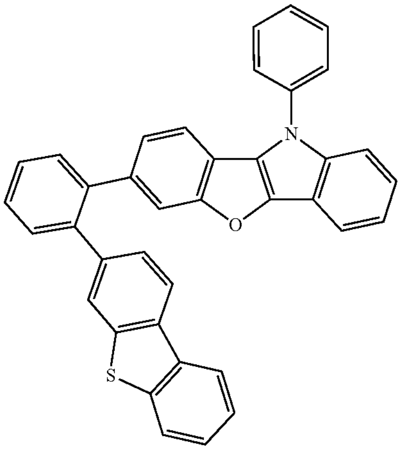
-continued
583
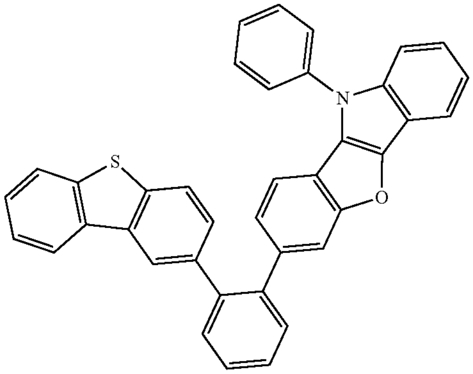
584
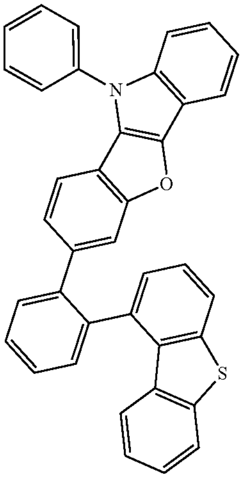
585
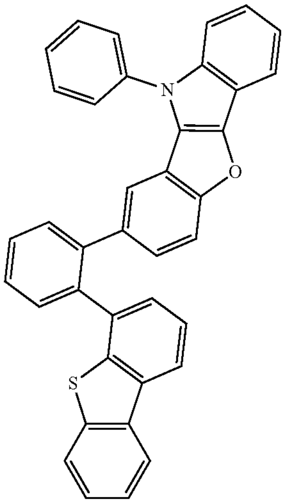

-continued
586
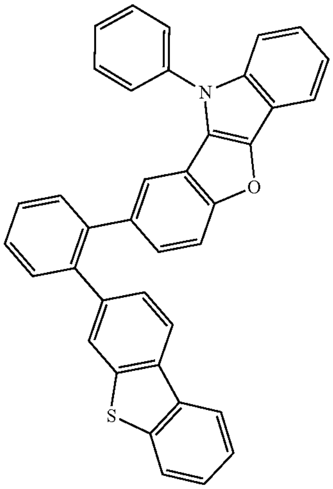
587
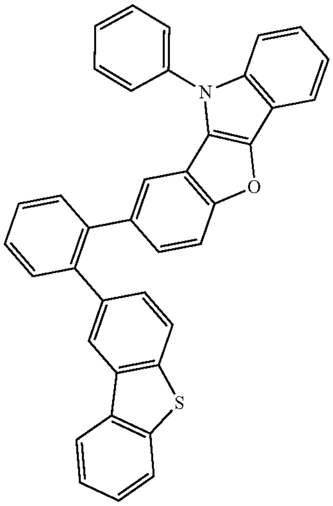
588
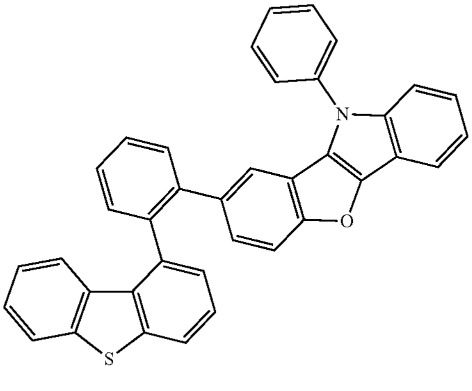
-continued
589
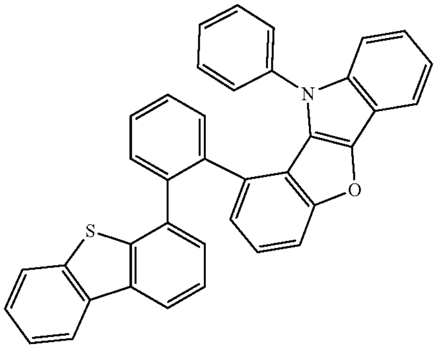
590
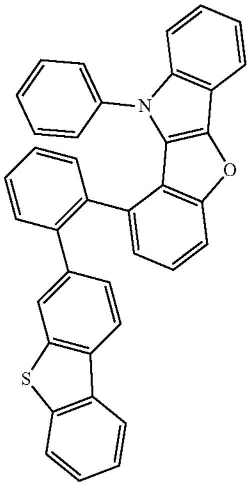
591
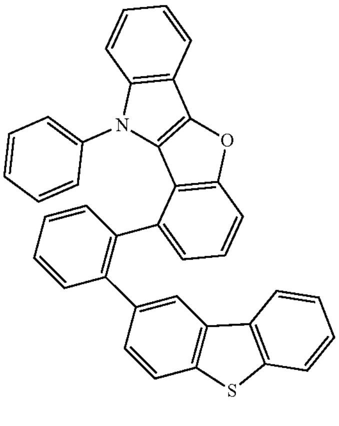

-continued
592
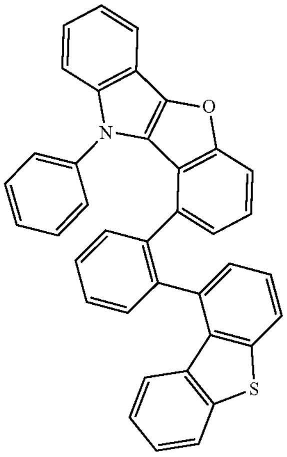
593
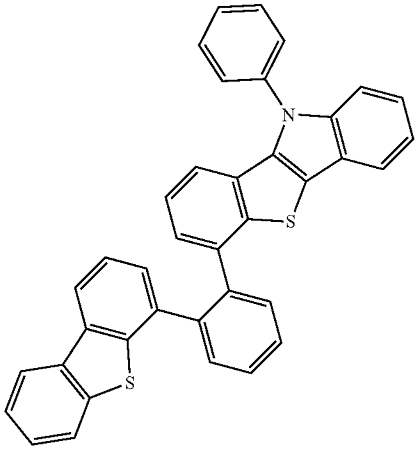
594
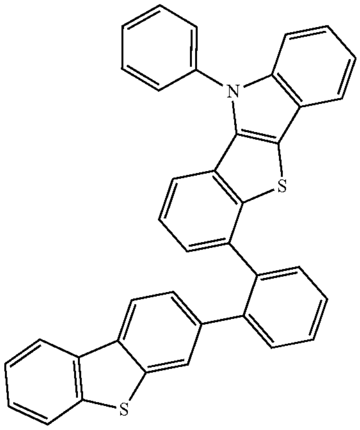
-continued
595
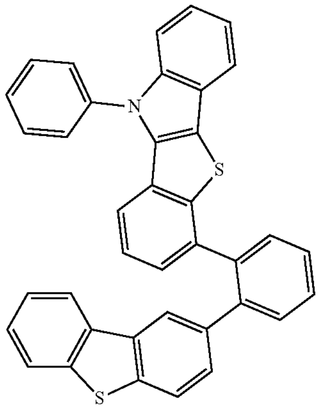
596
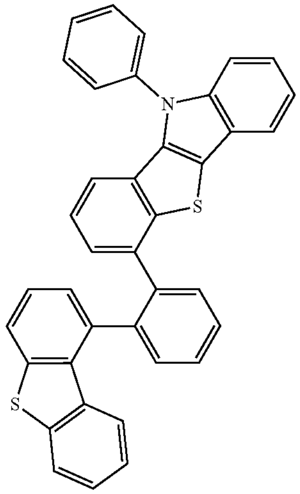
597
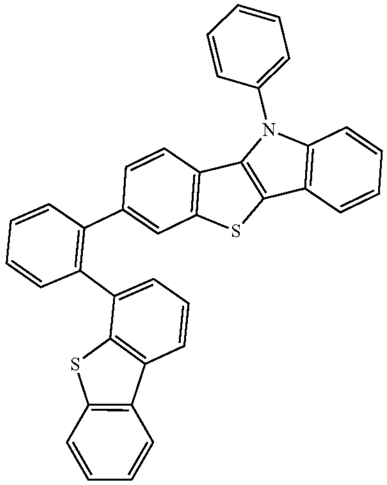

-continued
598
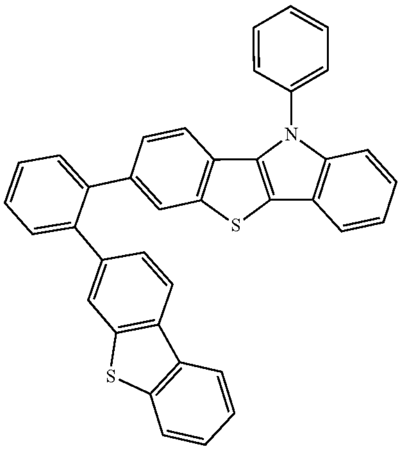
599
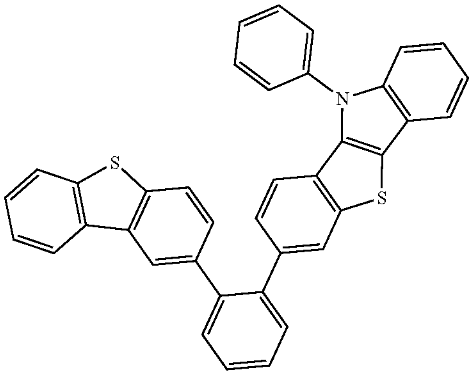
600
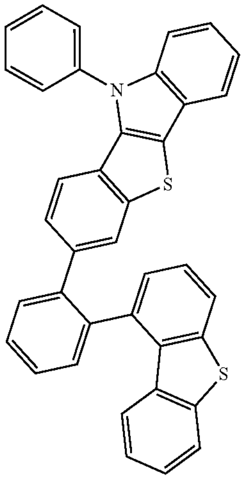
-continued
601
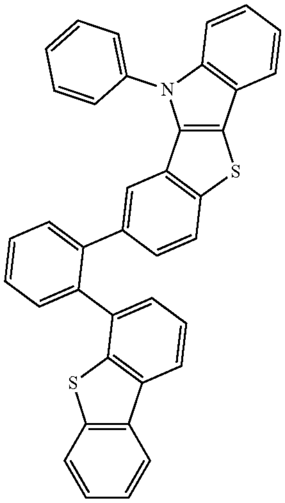
602
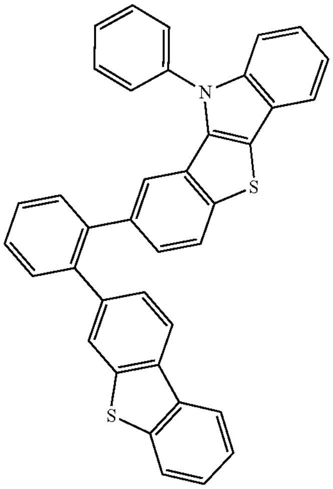
603
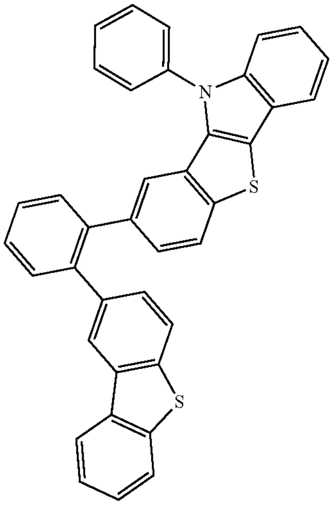

-continued
604
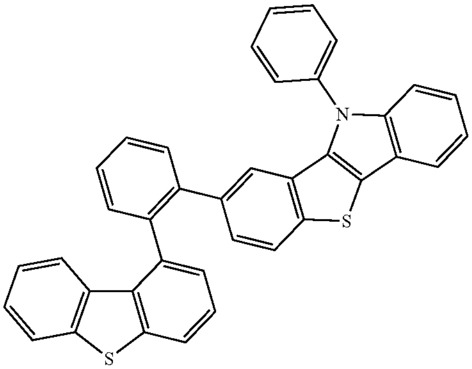
605
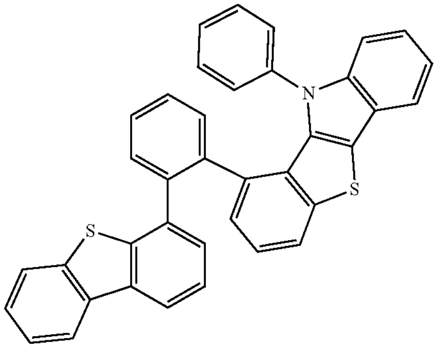
606
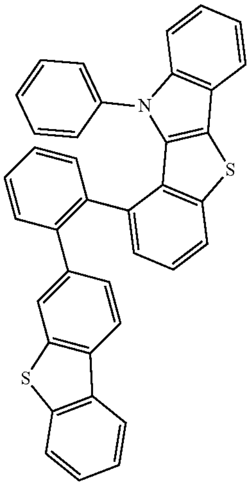
607
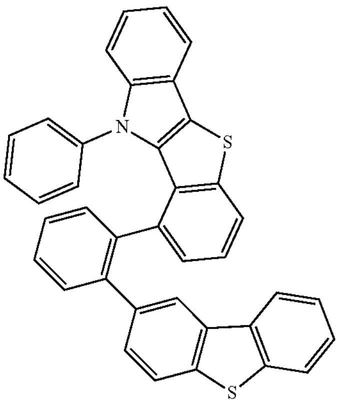
-continued
608
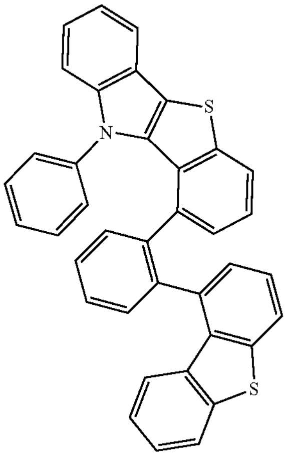
609
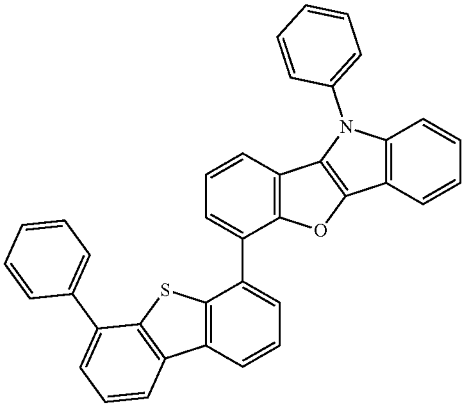
610
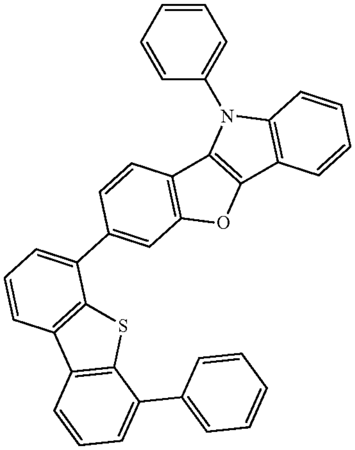

-continued
611
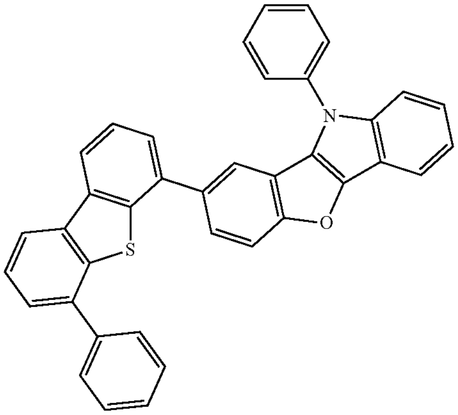
612
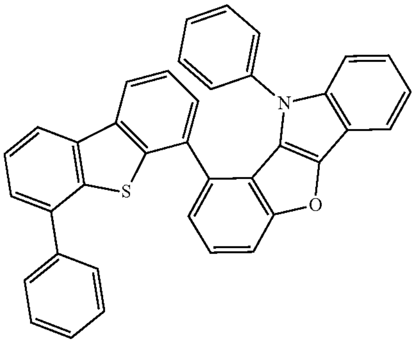
613
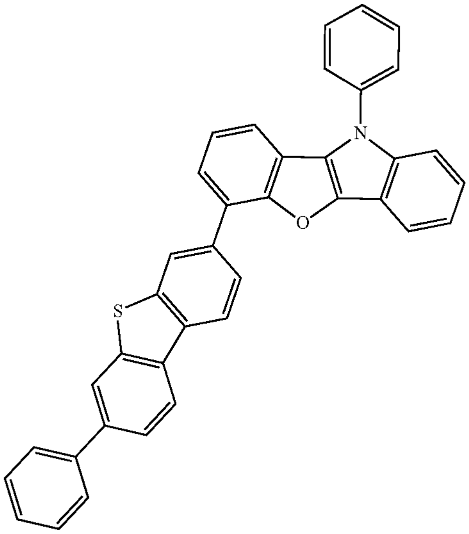
-continued
614
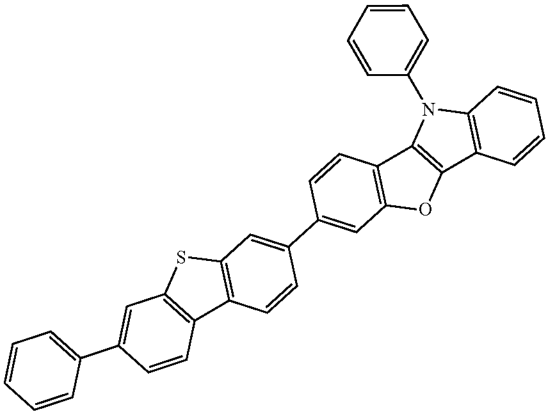
615
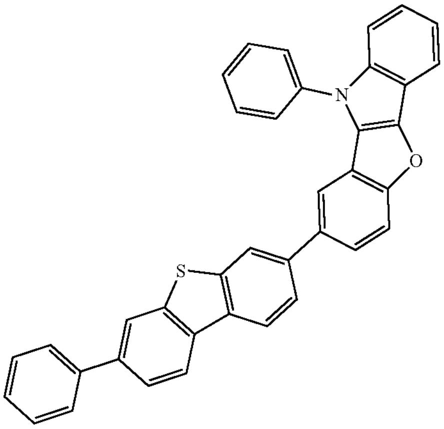
616
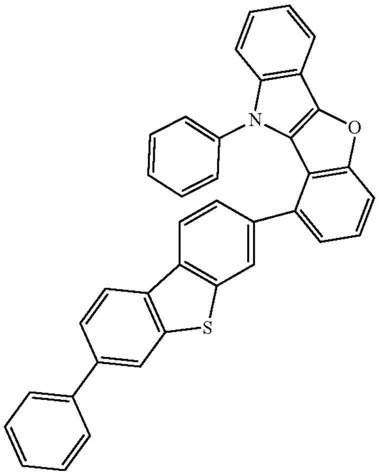

-continued
617
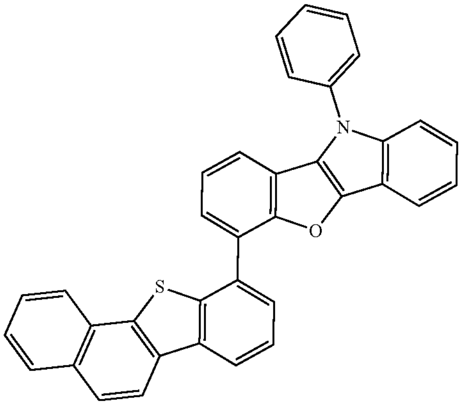
618
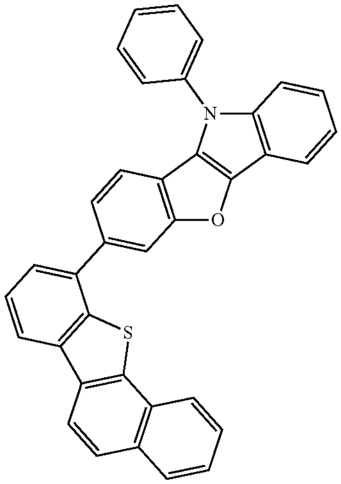
619
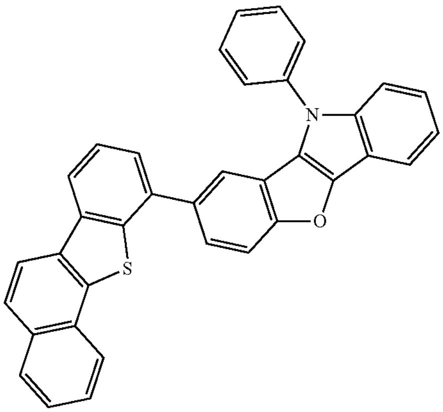
-continued
620
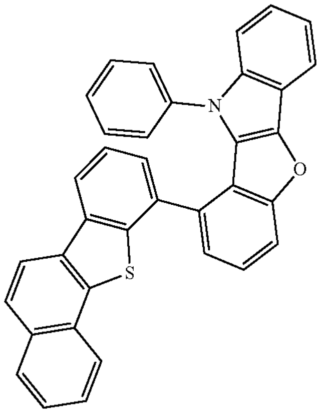
621
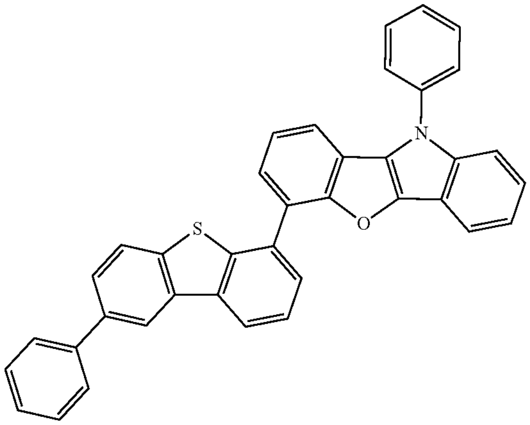
622
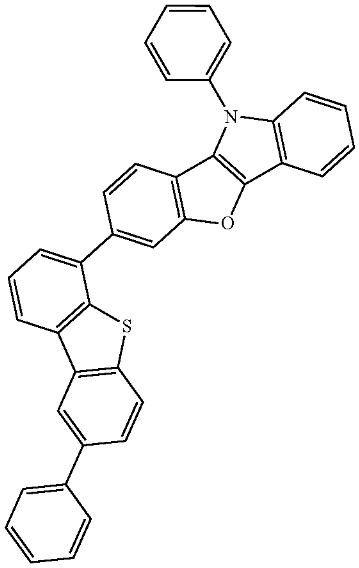

-continued
623
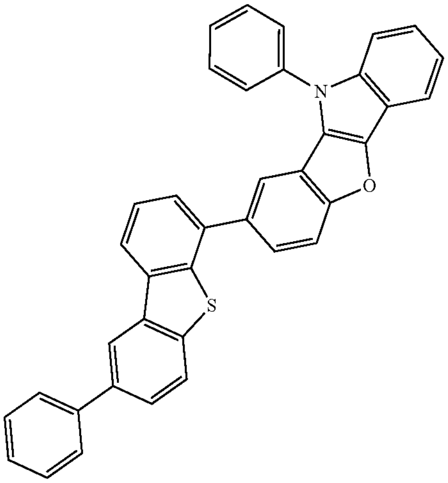
624
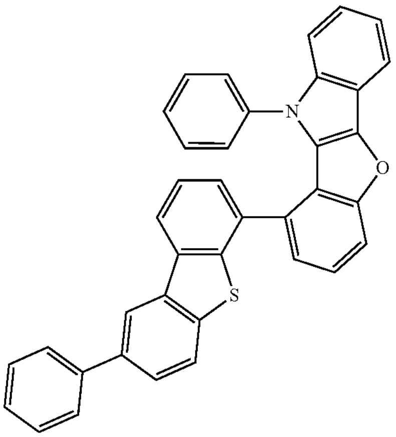
625
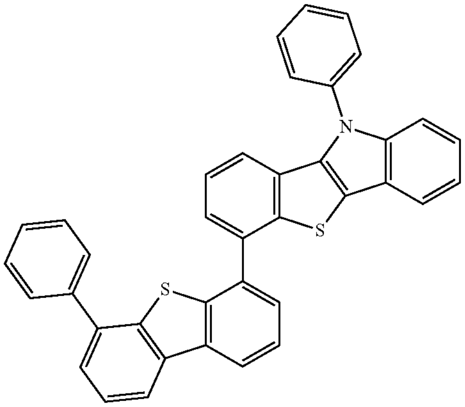
-continued
626
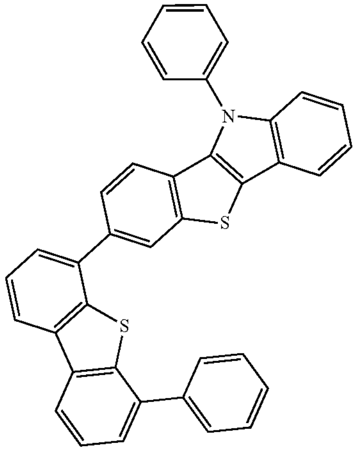
627
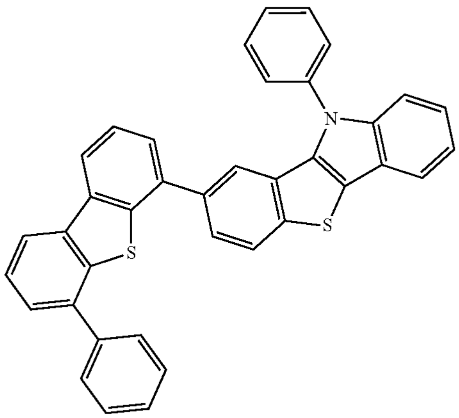
628
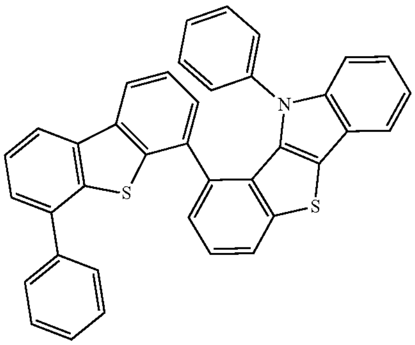

-continued
629
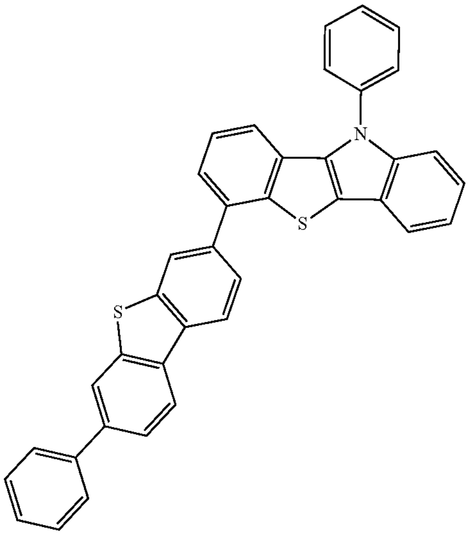
630
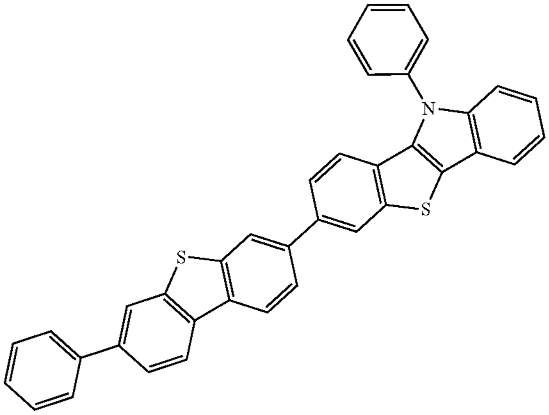
631
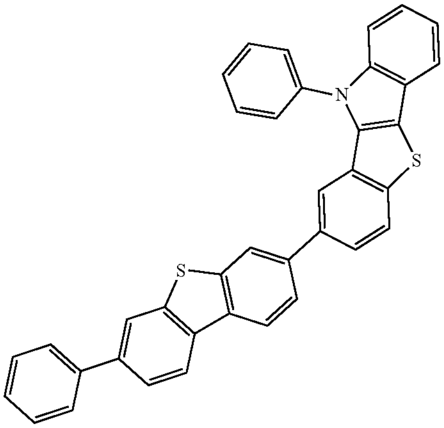
-continued
632
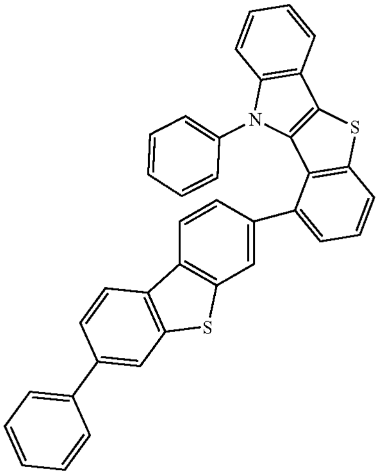
633
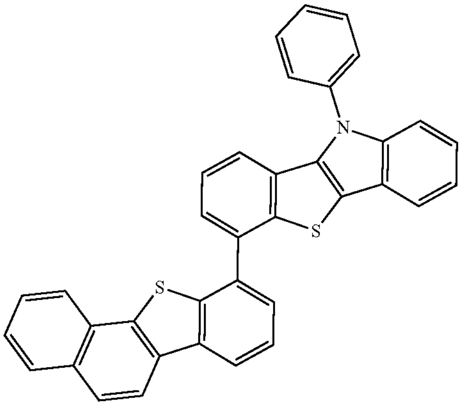
634
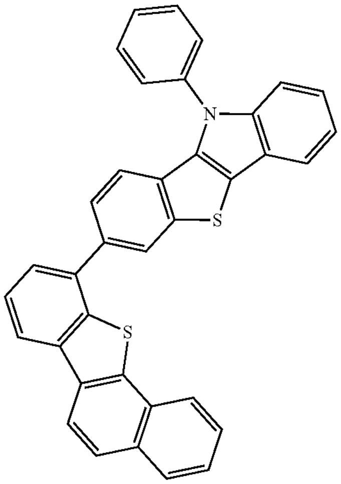

-continued
635
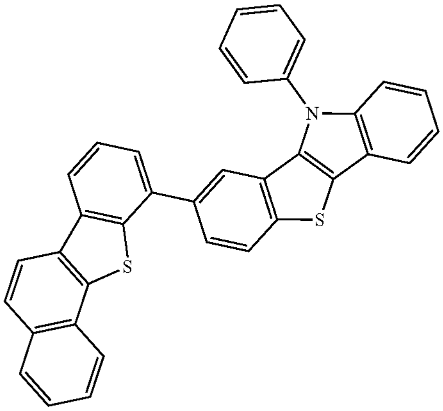
636
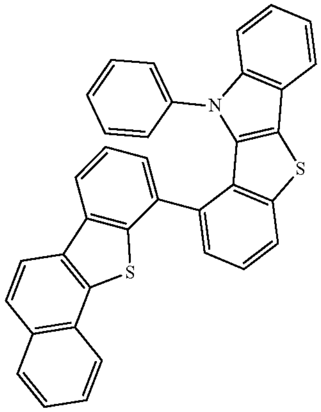
637
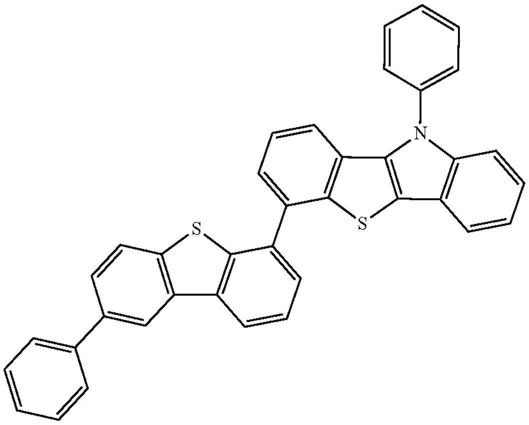
-continued
638
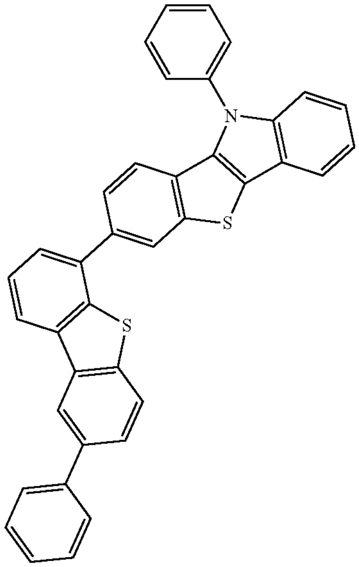
639
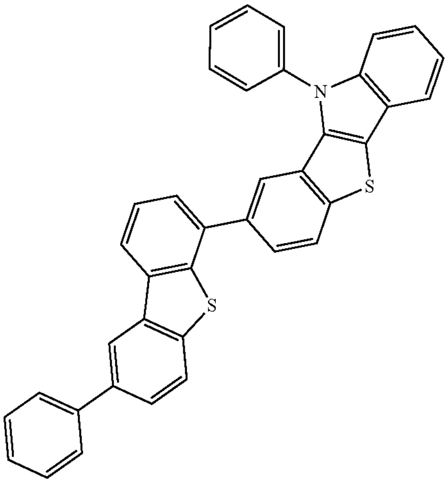
640
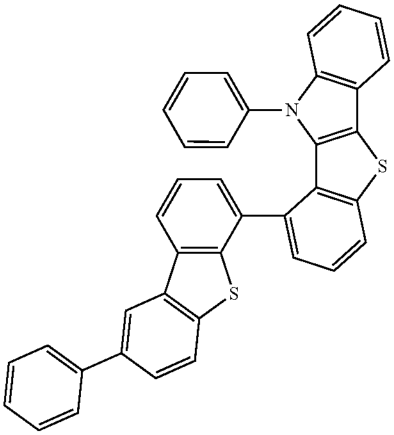

-continued
641
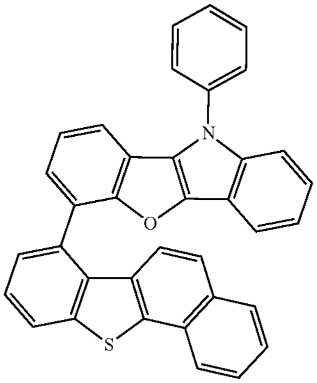
642
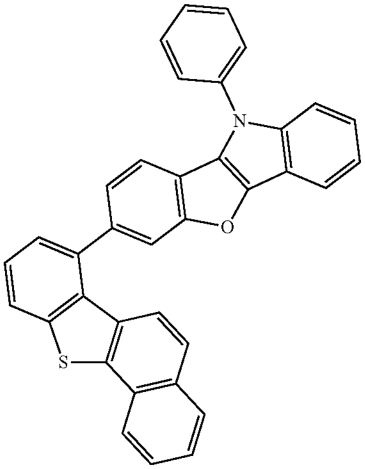
643
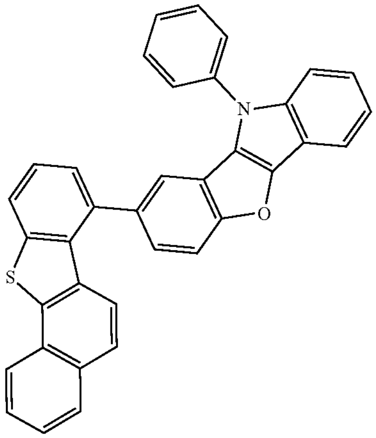
644
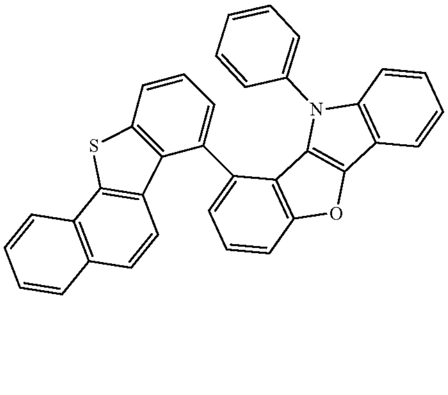
-continued
645
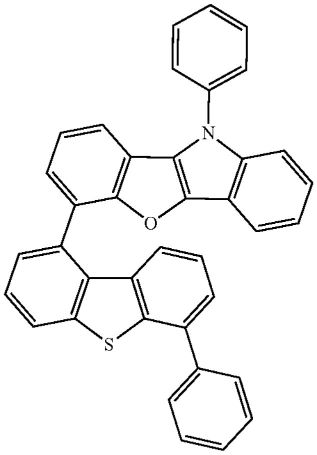
646
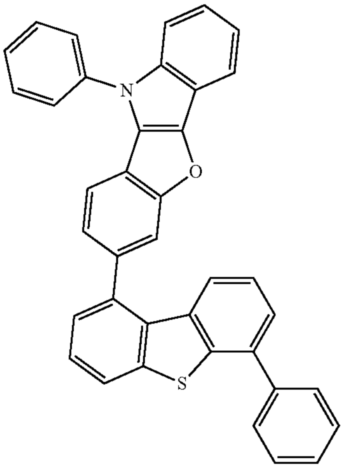
647
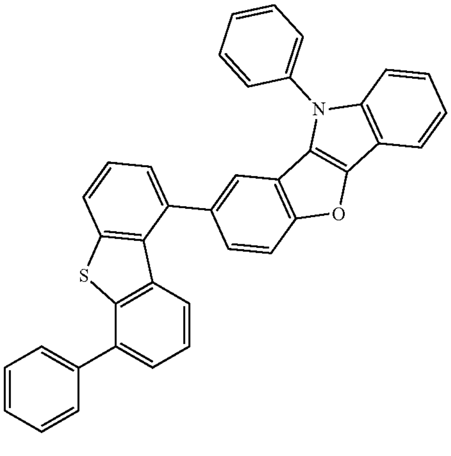

-continued
648
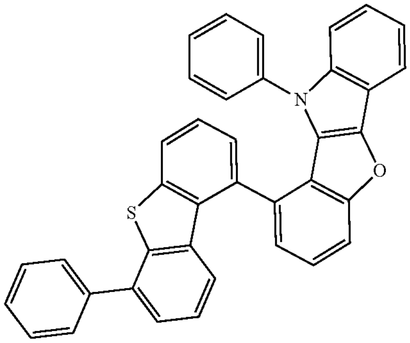
649
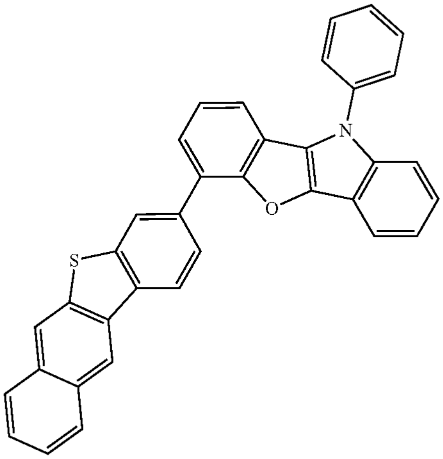
650
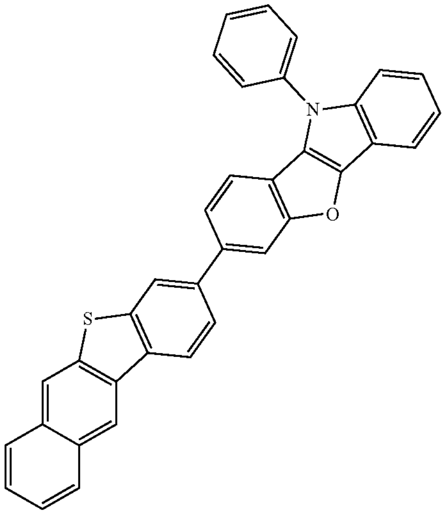
-continued
651
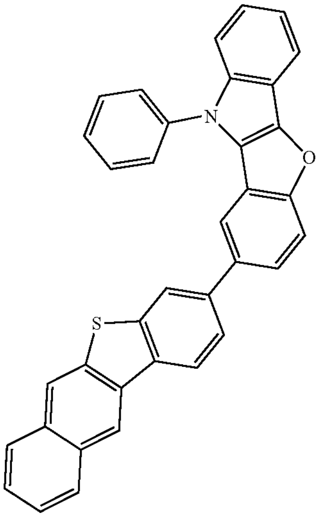
652
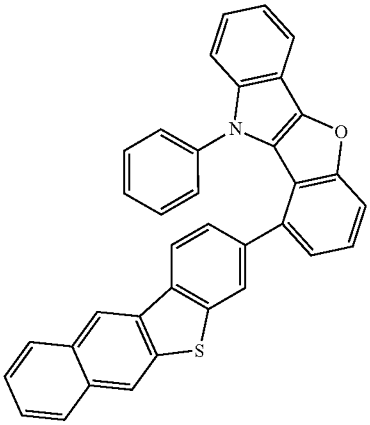
653
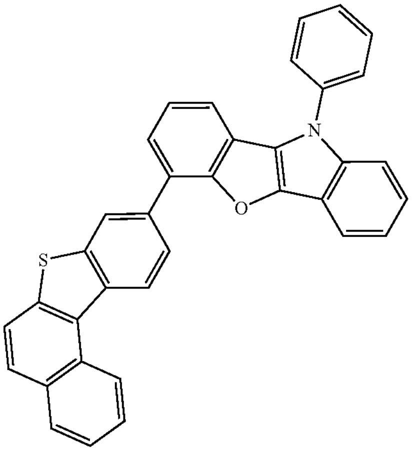

-continued
654
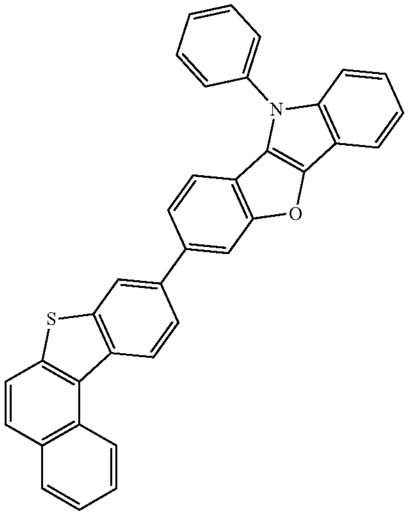
655
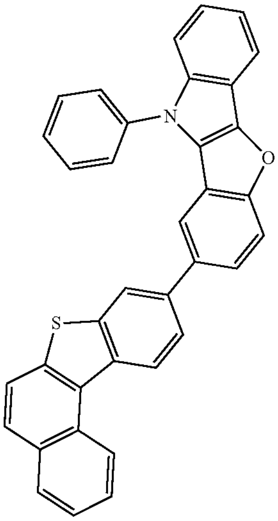
656
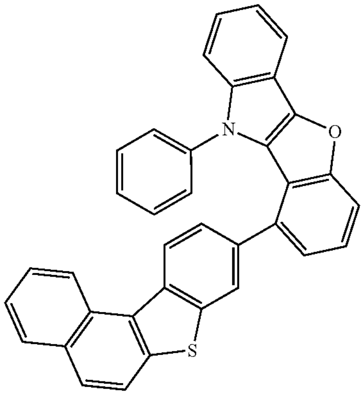
-continued
657
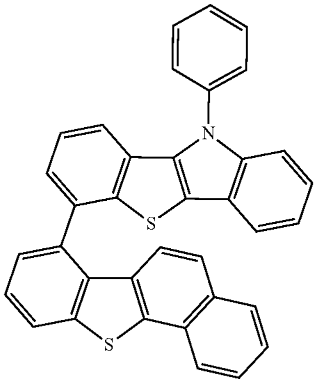
658
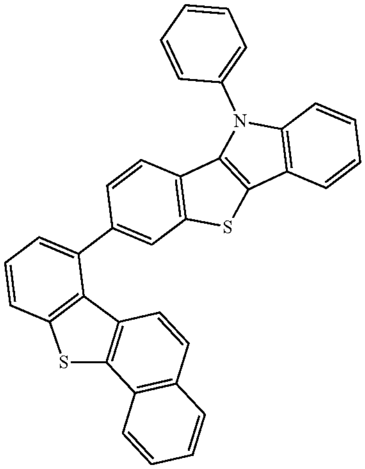
659
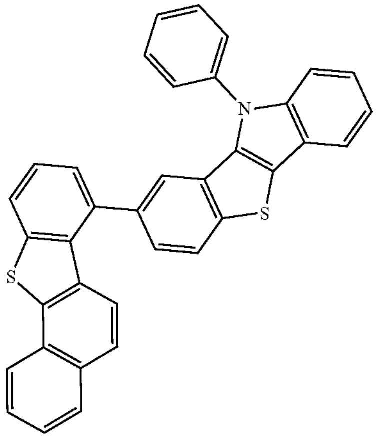
660
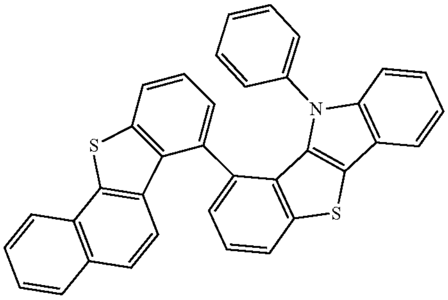

-continued
661
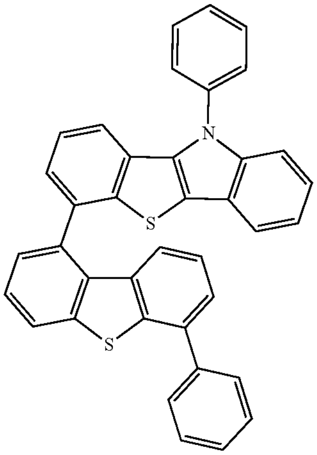
662
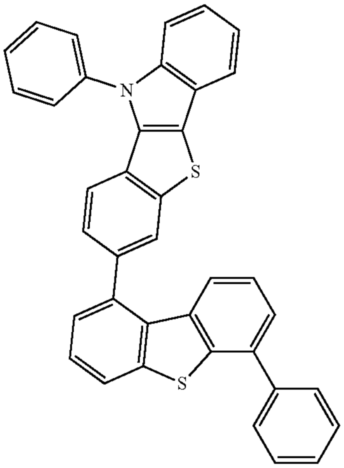
663
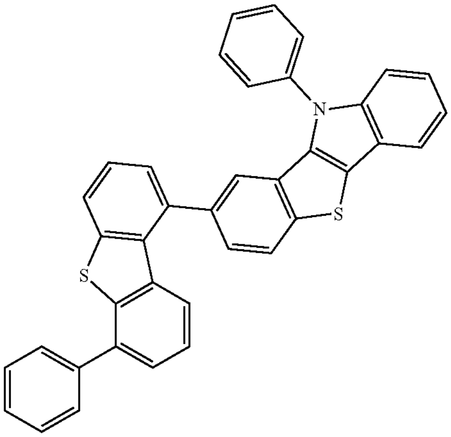
-continued
664
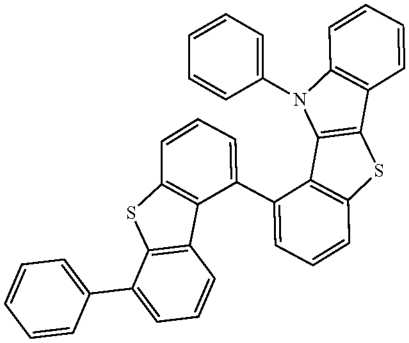
665
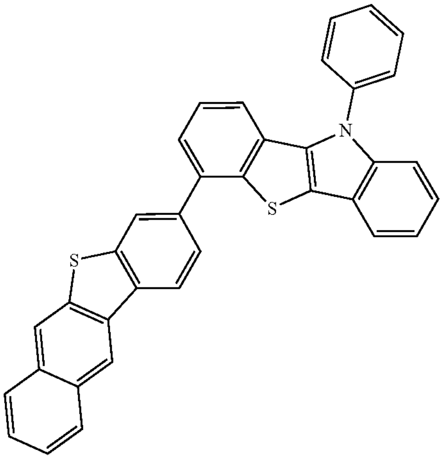
666
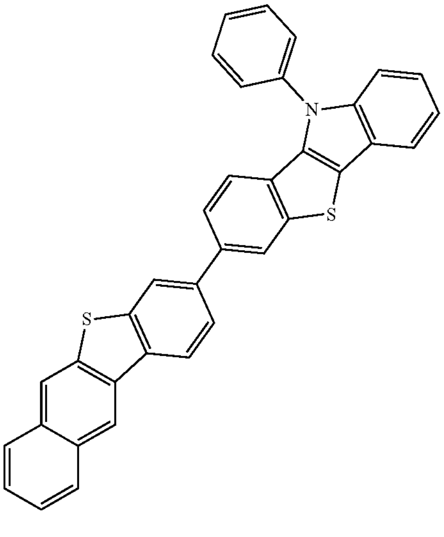

-continued
667
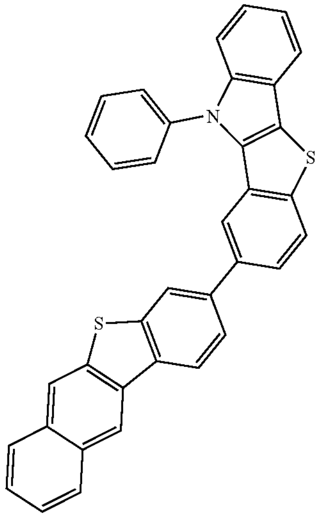
668
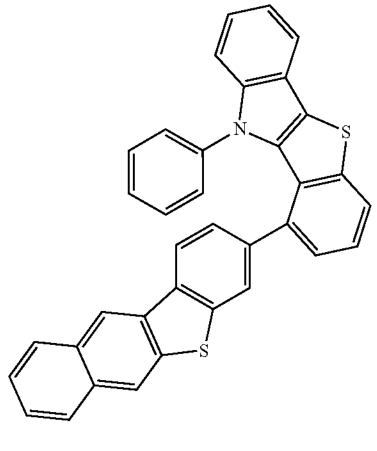
669
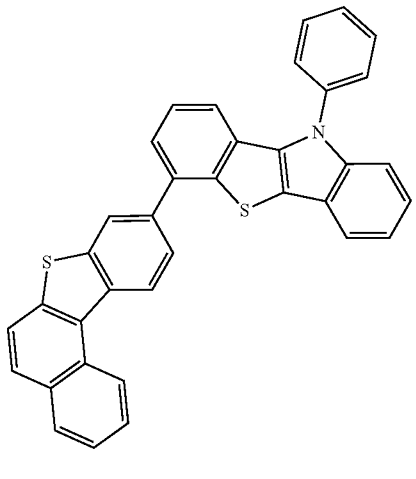
-continued
670
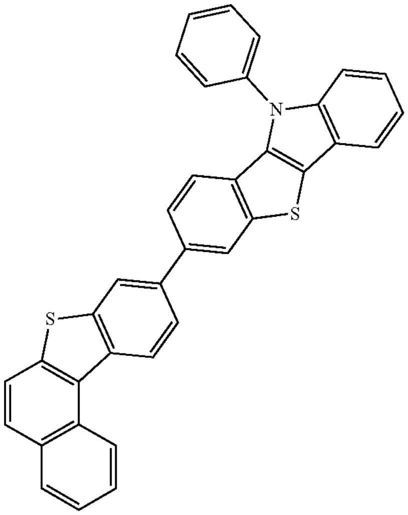
671
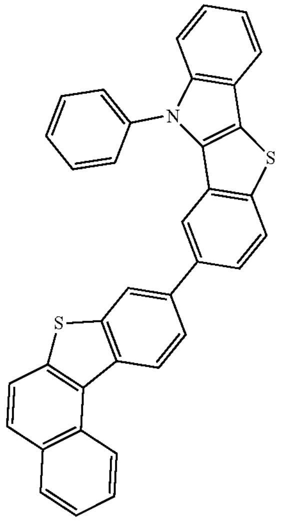
672
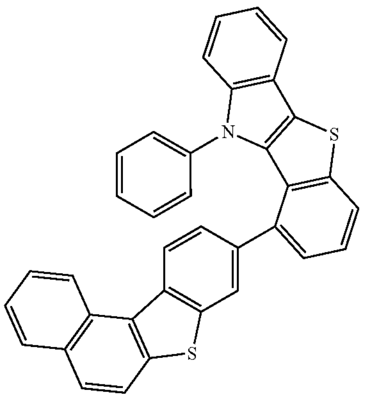

-continued
673
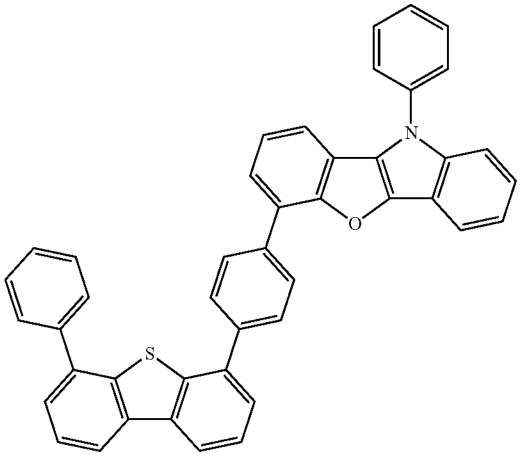
674
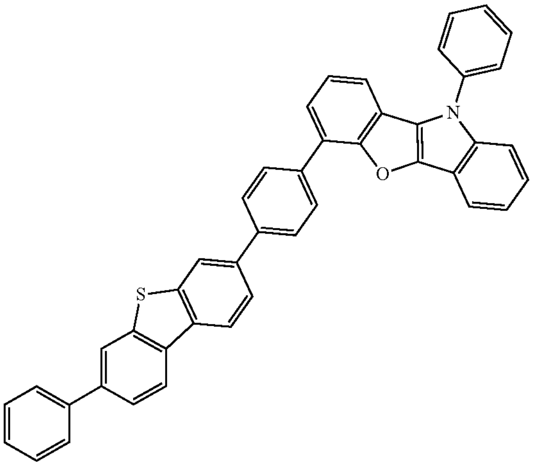
675
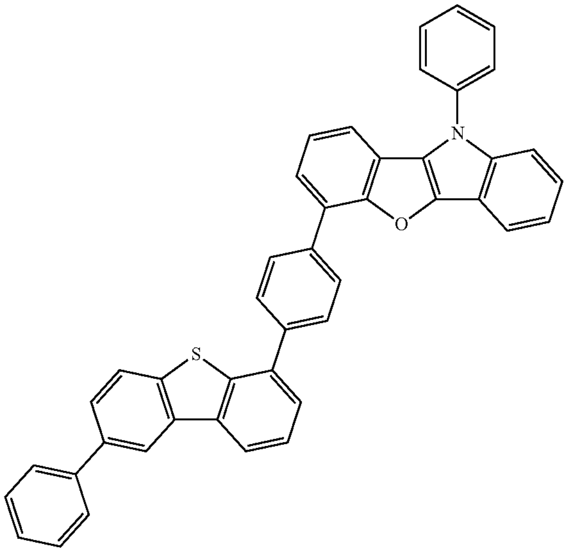
-continued
676
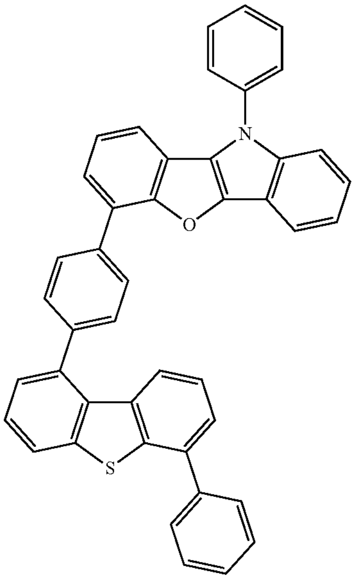
677
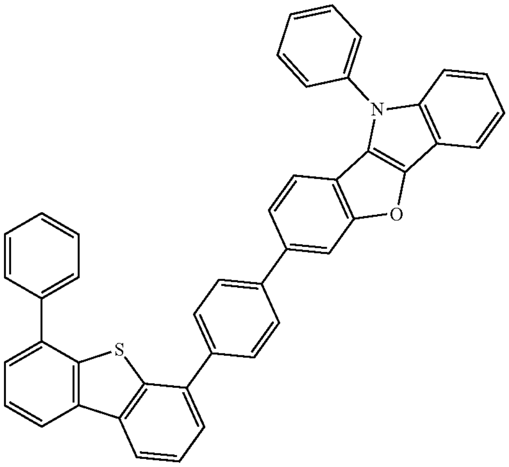
678
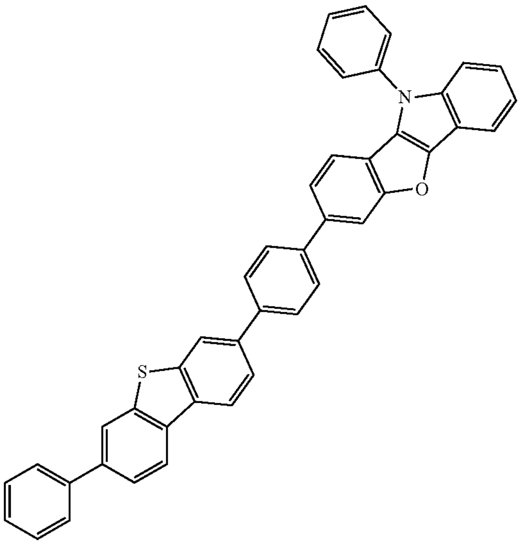

-continued
679
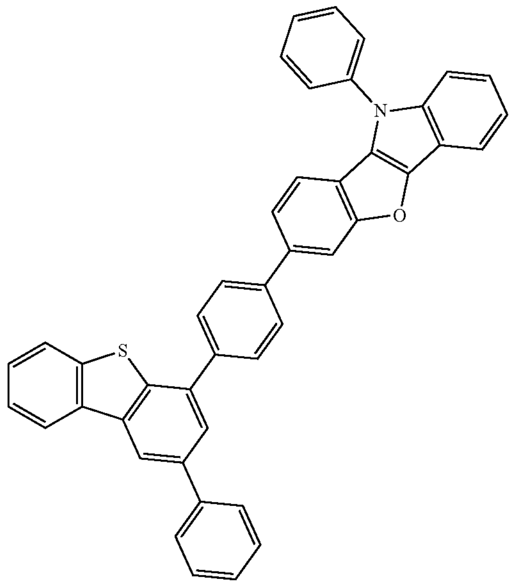
680
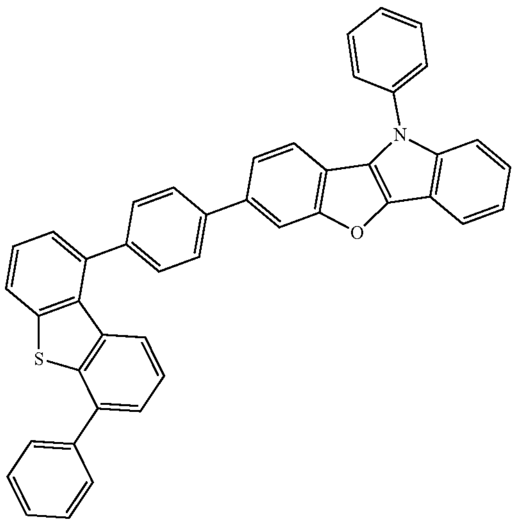
681
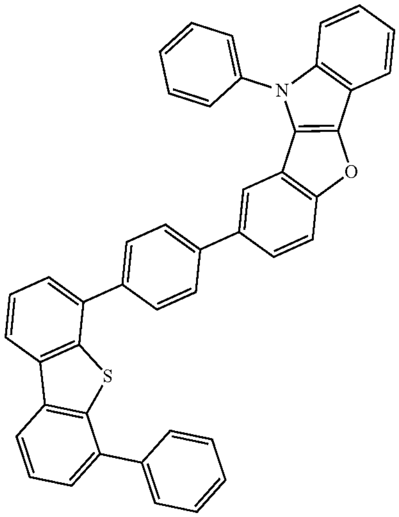
-continued
682
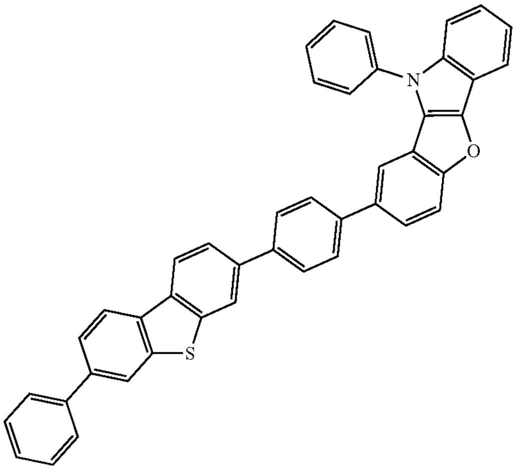
683
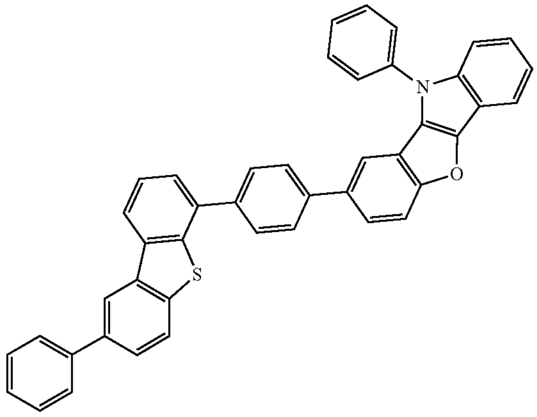
684
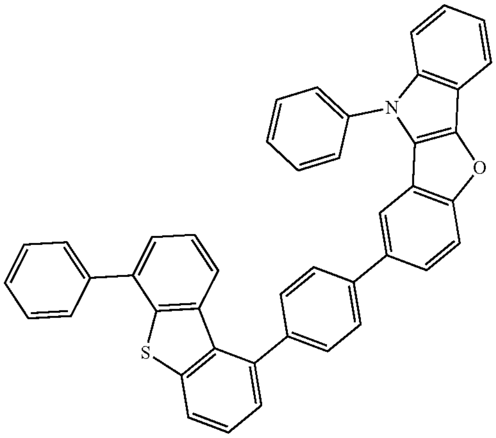

-continued
685
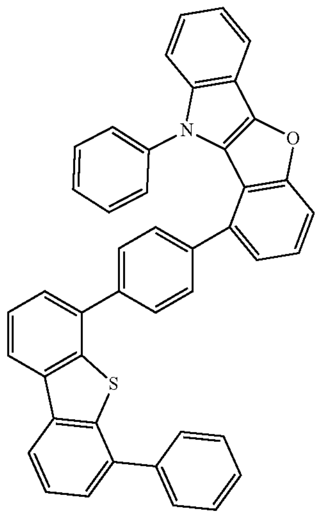
686
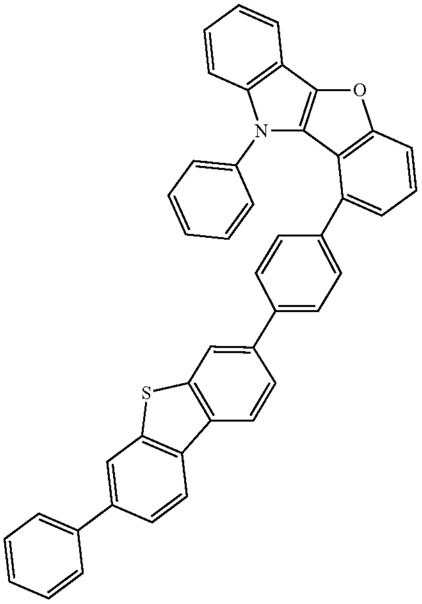
687
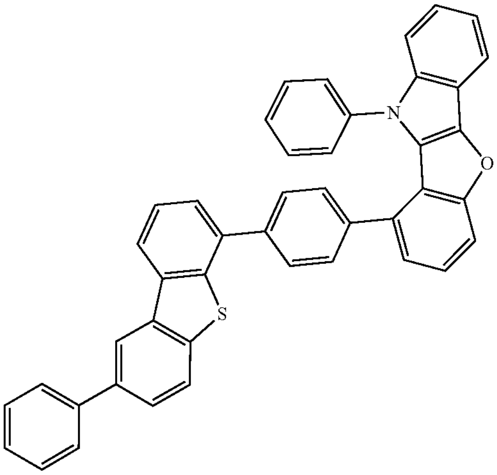
-continued
688
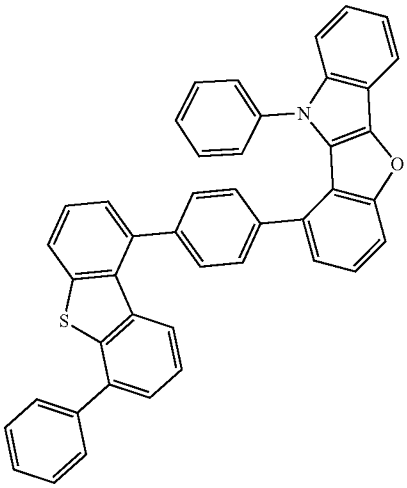
689
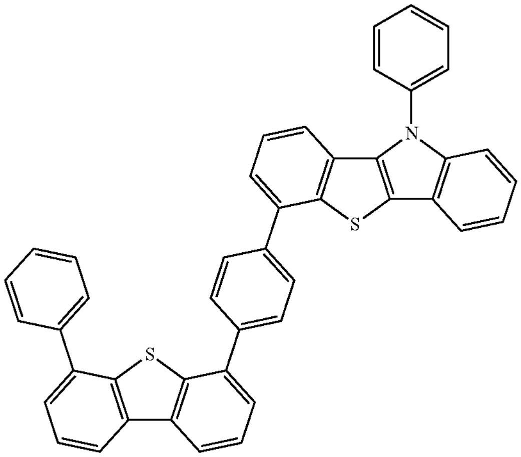
690
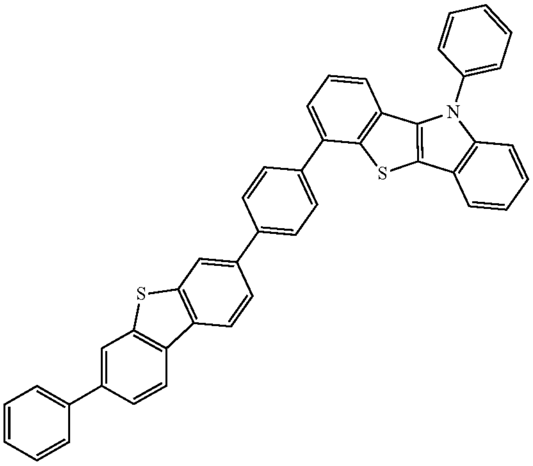

691
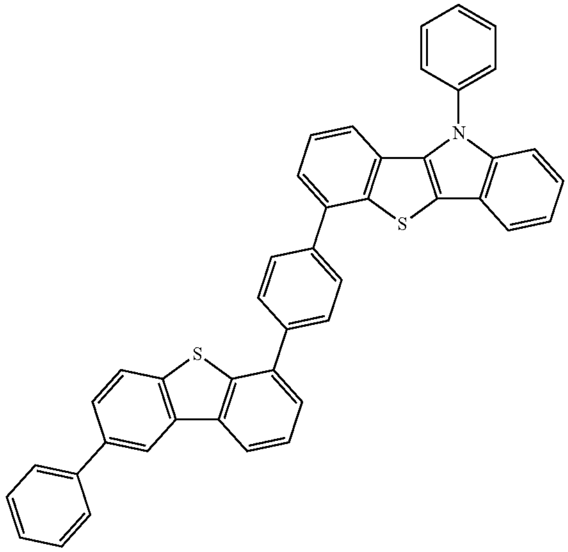
692
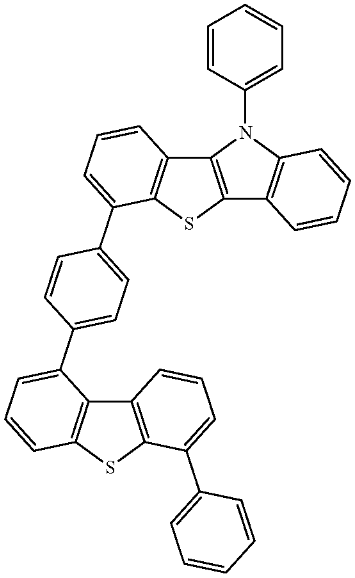
693
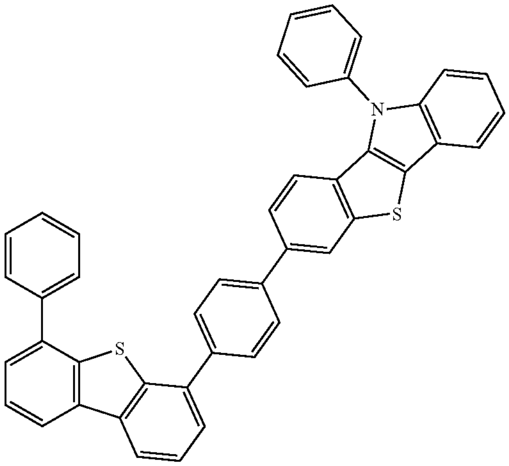
694
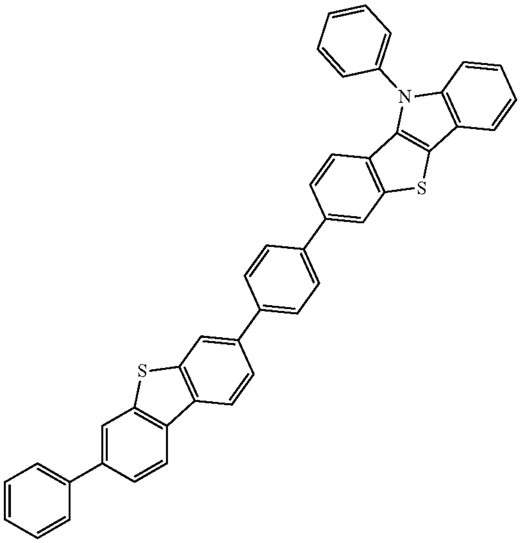
695
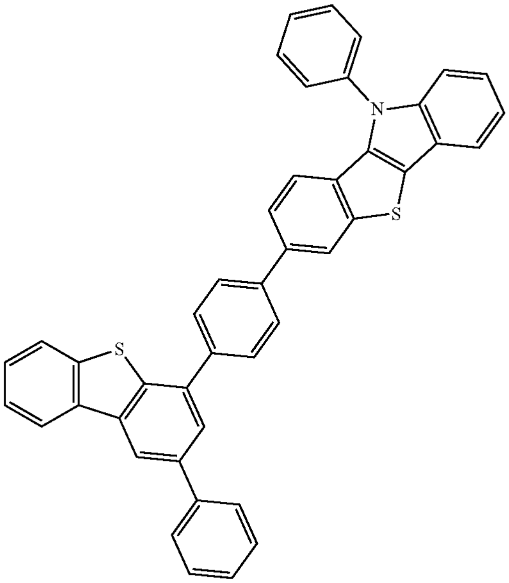
696
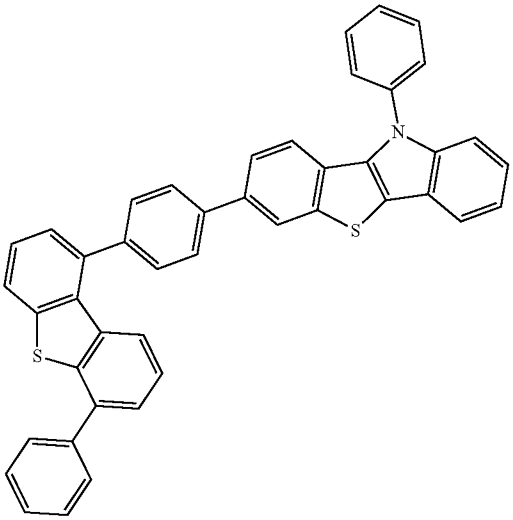

-continued
697
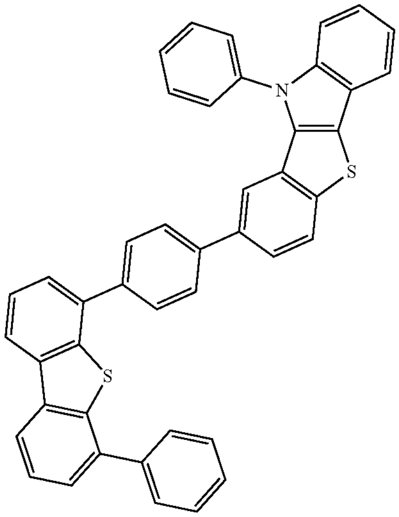
698
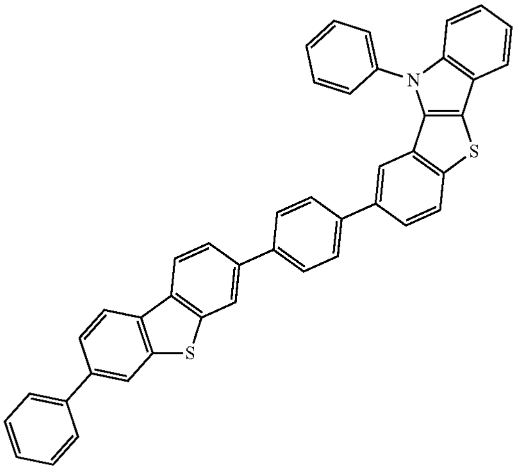
699
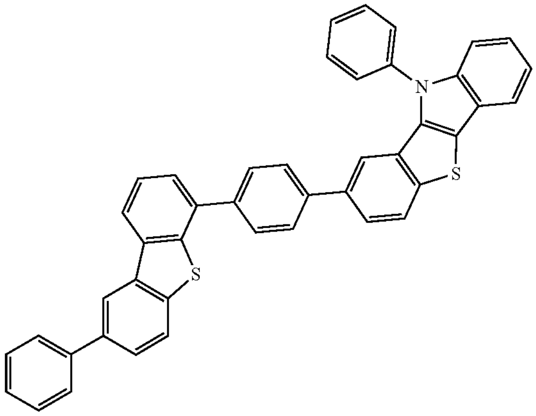
-continued
700
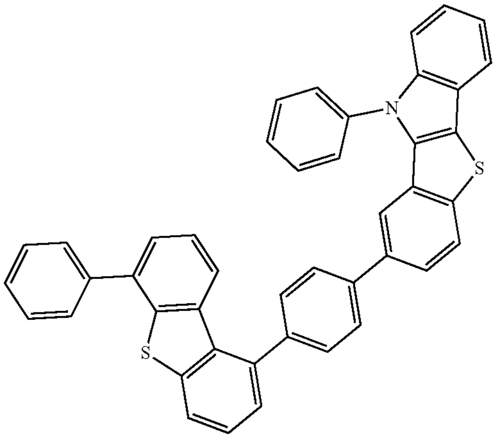
701
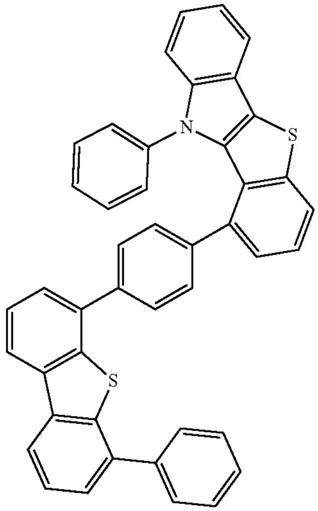
702
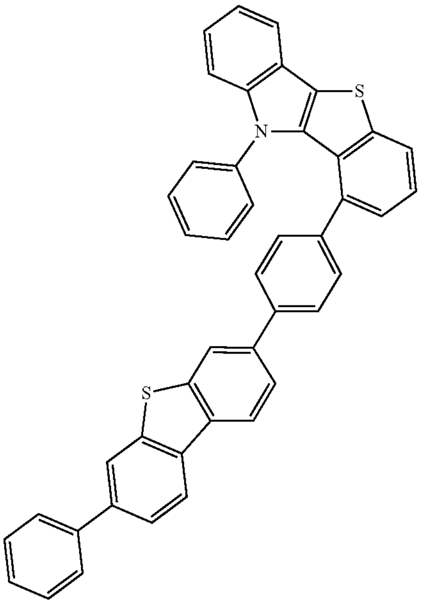

-continued
703
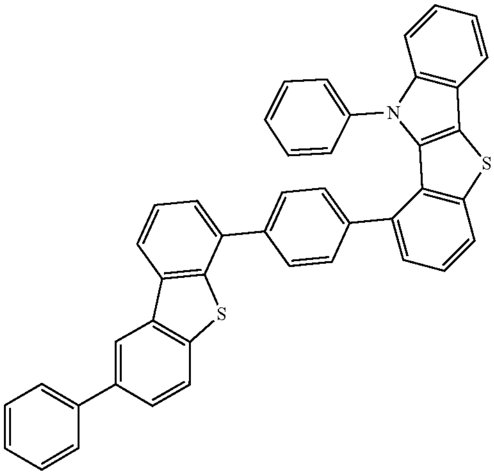
704
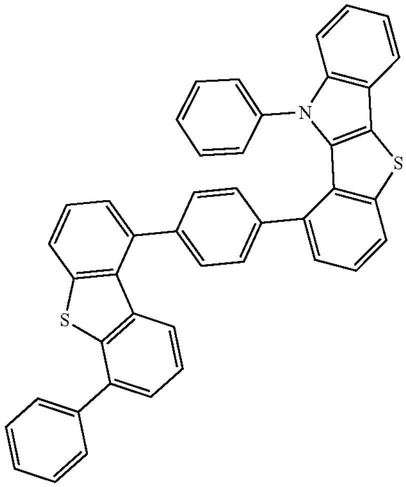
705
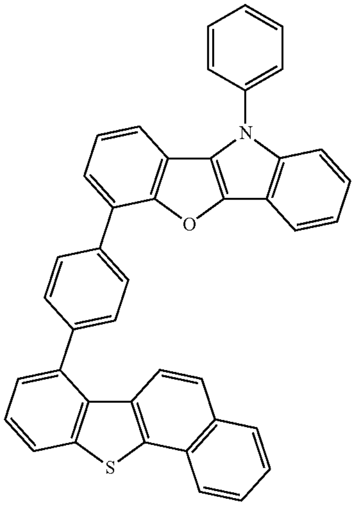
-continued
706
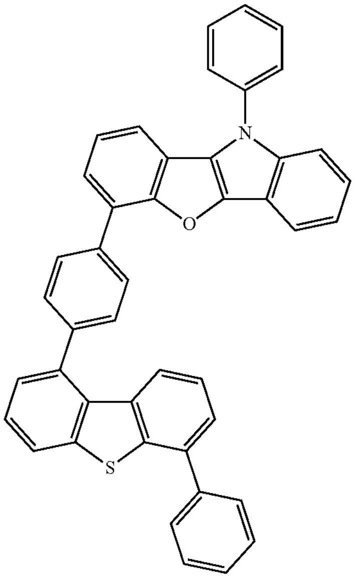
707
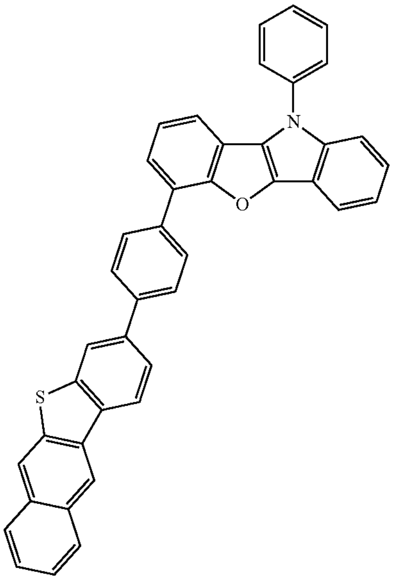

-continued
708
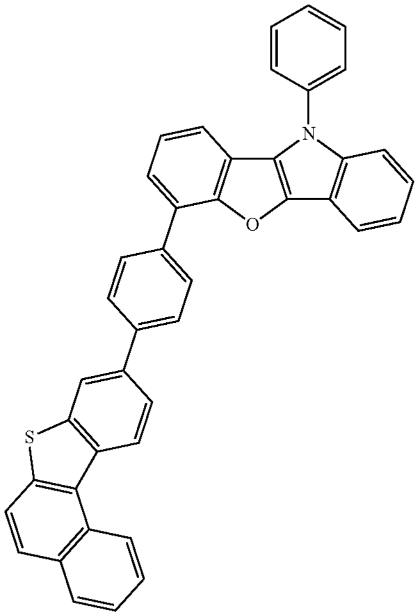
709
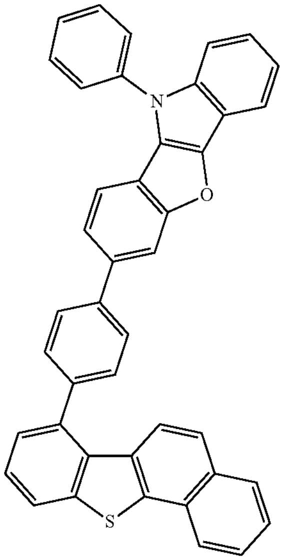
-continued
710
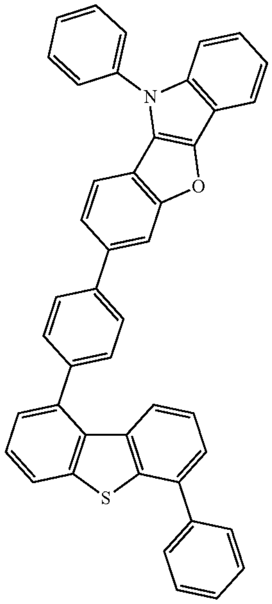
711
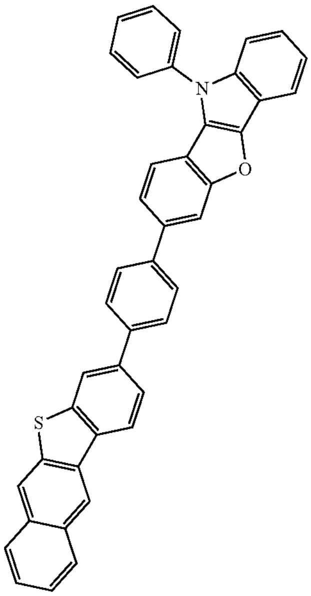

-continued
712
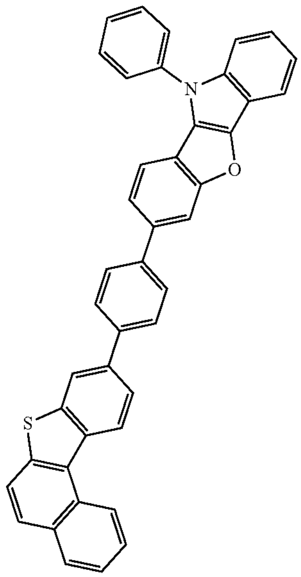
713
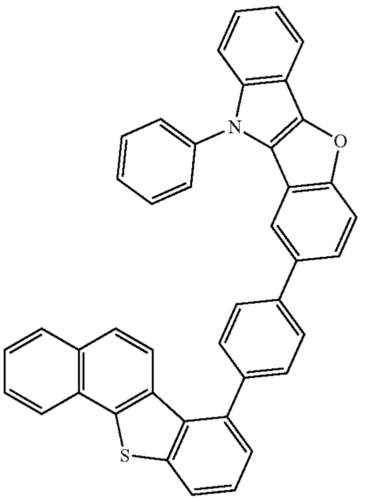
714
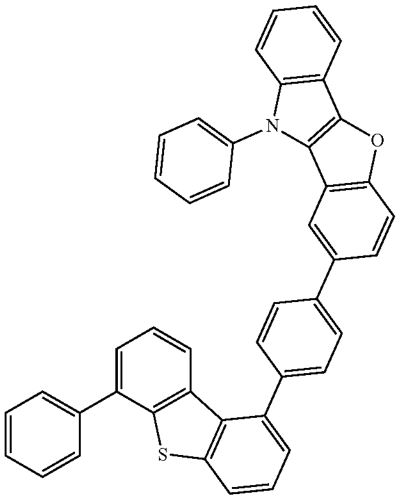
-continued
715
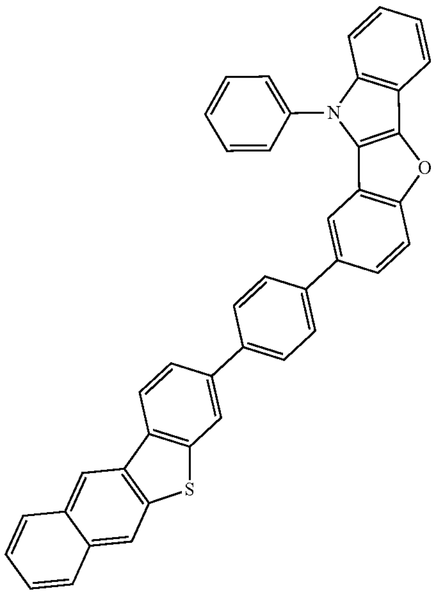
716
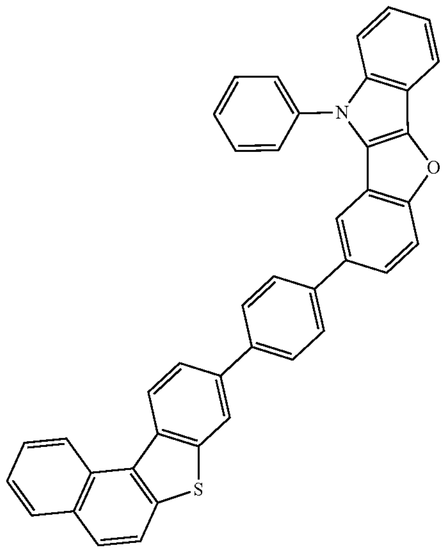
717
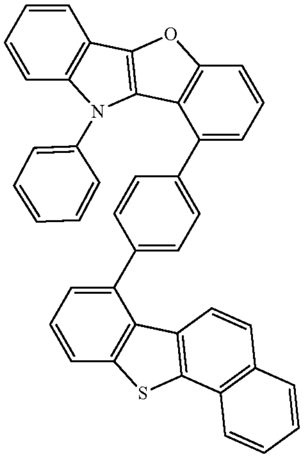

-continued
718
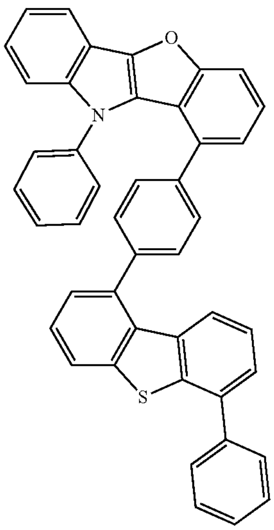
719
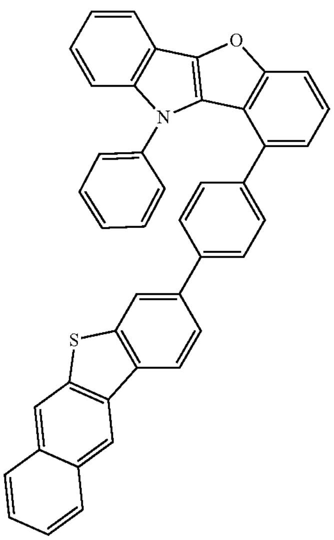
720
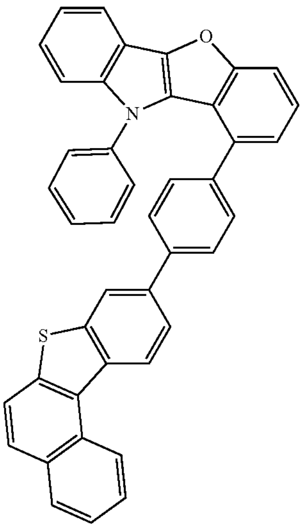
-continued
721
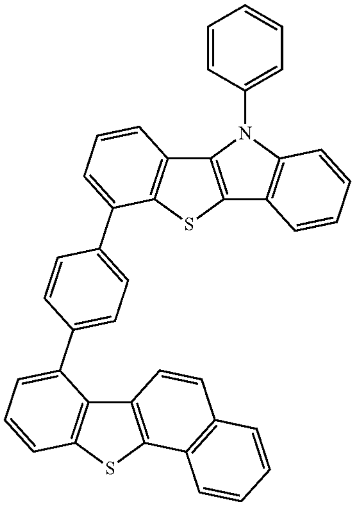
722
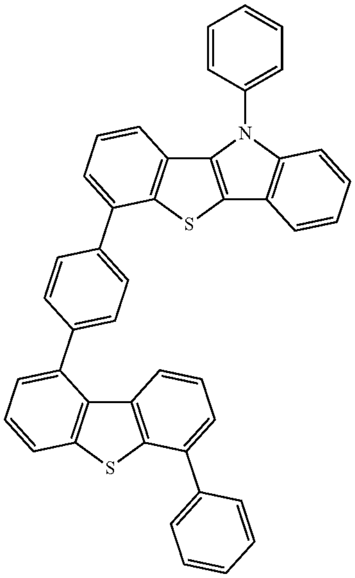
723
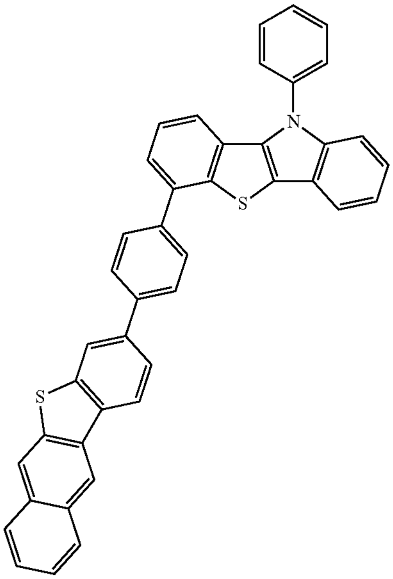

-continued
724
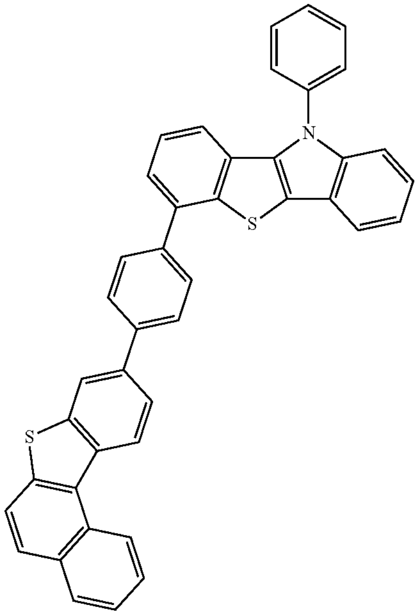
725
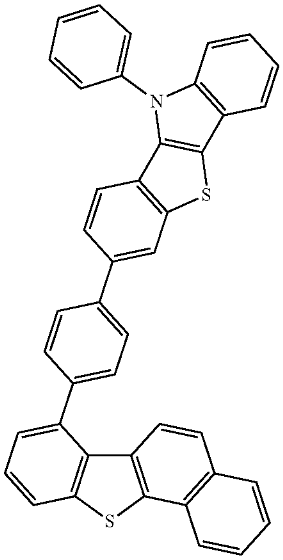
-continued
726
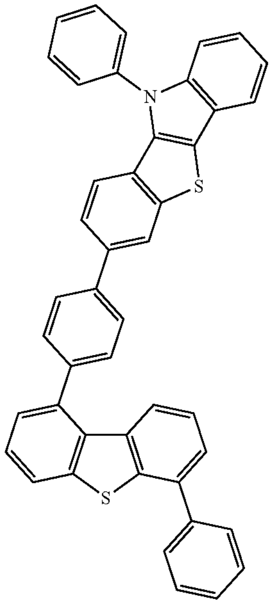
727
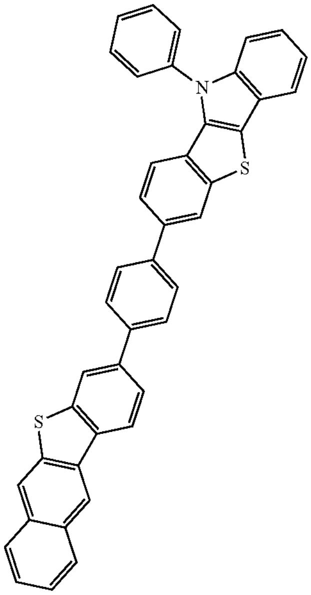

-continued
728
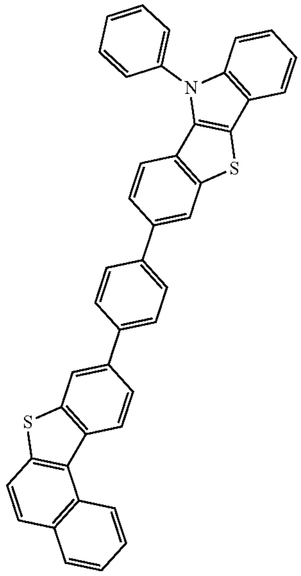
729
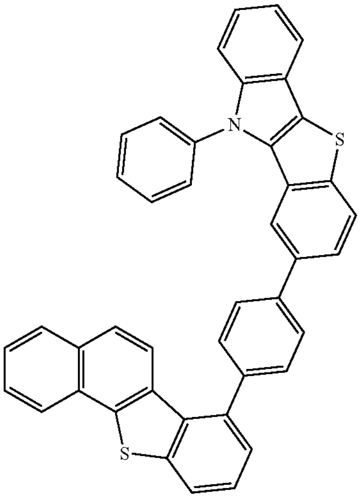
730
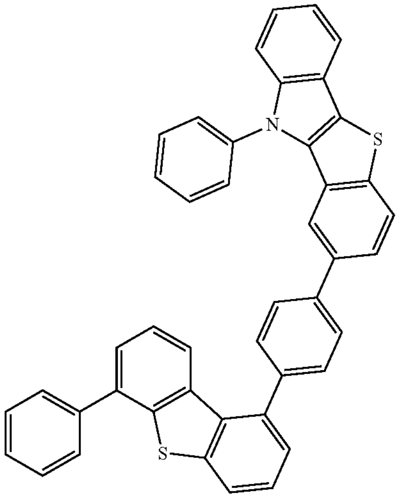
-continued
731
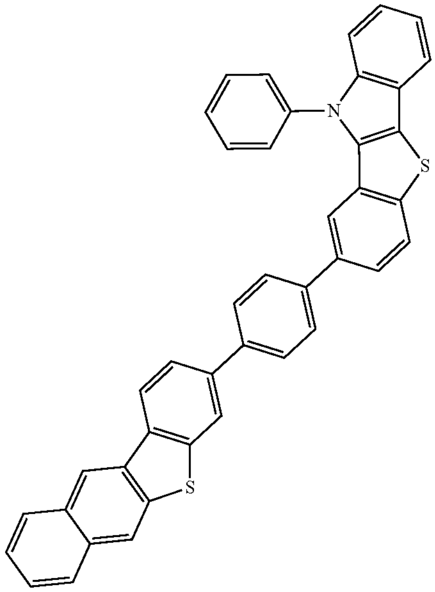
732
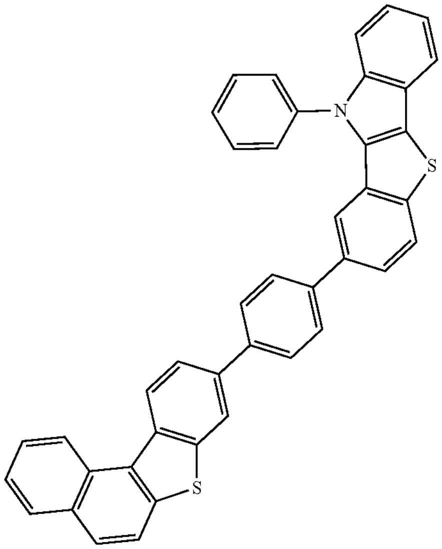
733
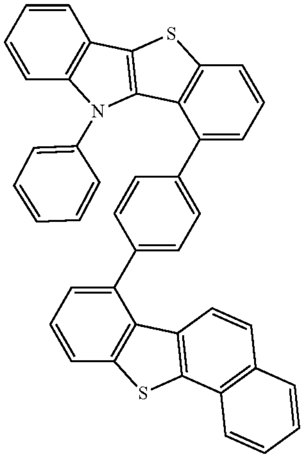

-continued
734
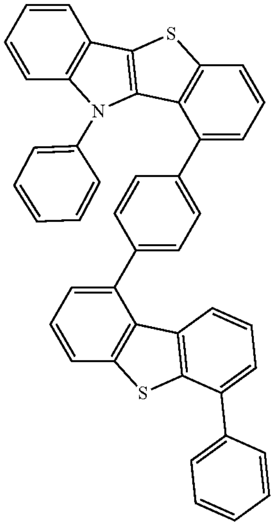
735
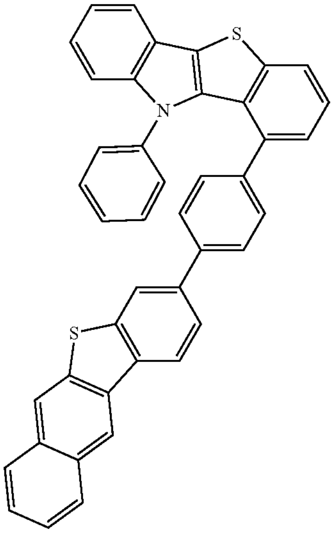
736
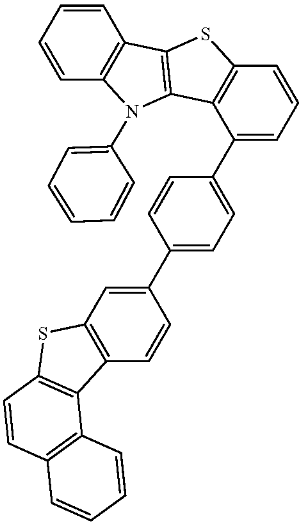
-continued
737
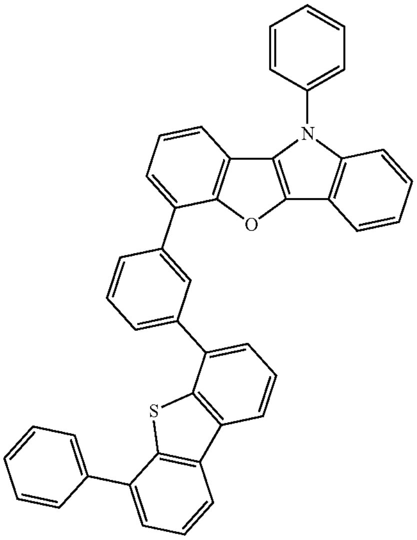
738
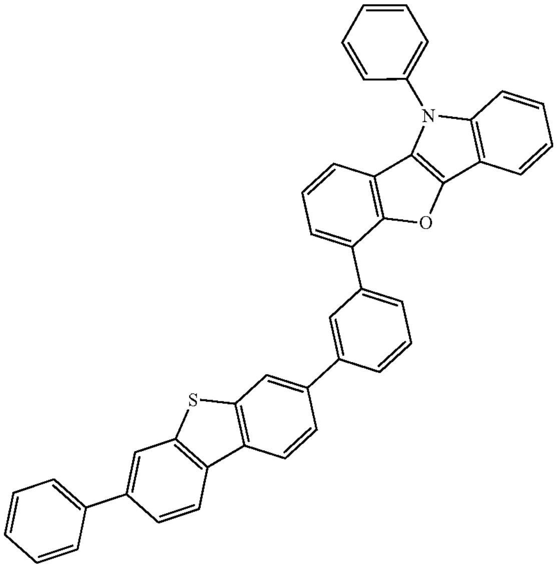
739
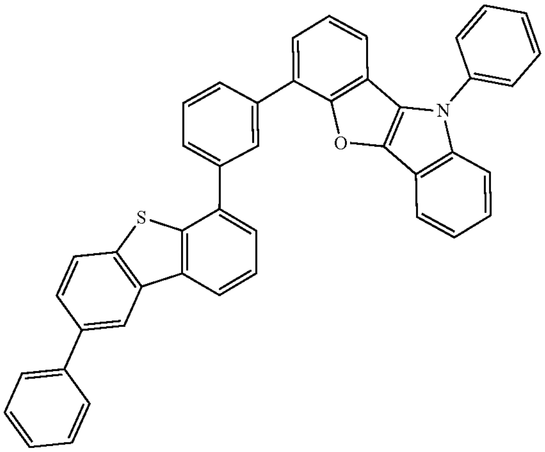

-continued
740
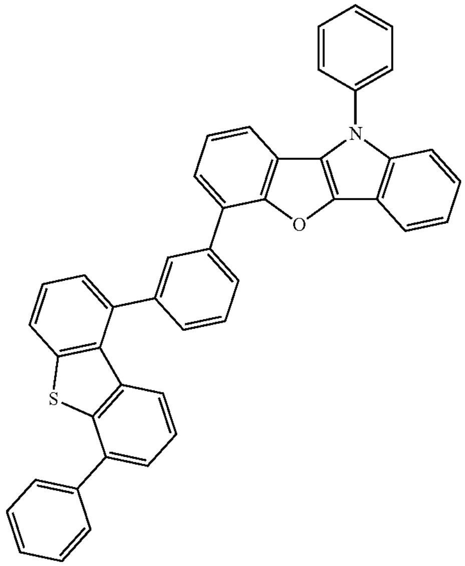
741
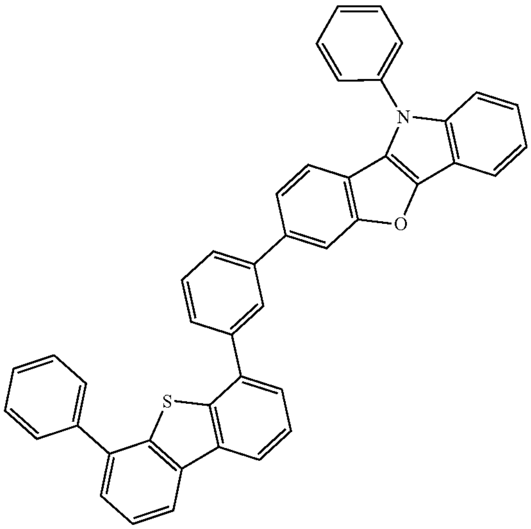
742
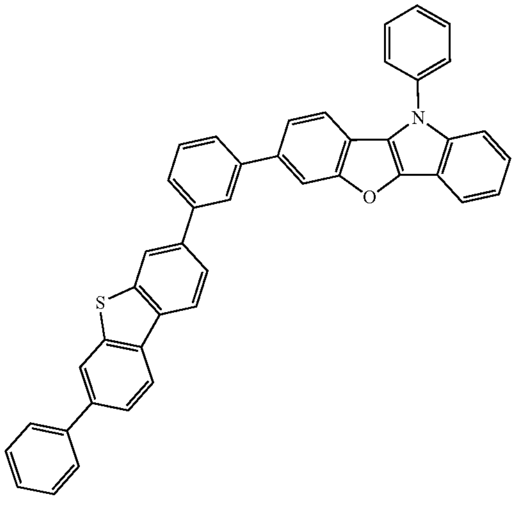
-continued
743
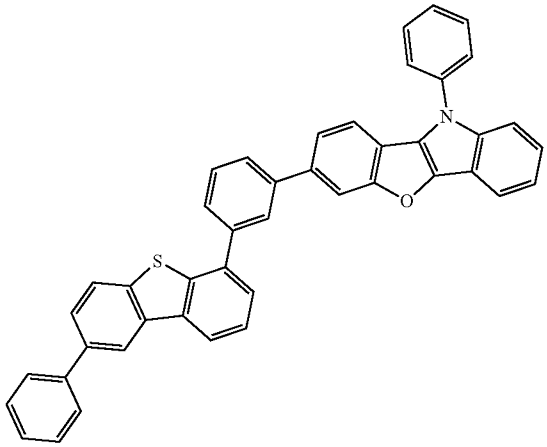
744
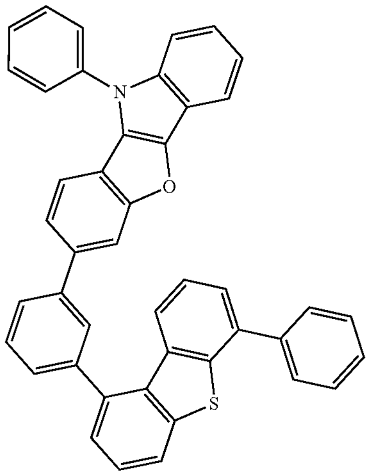
745
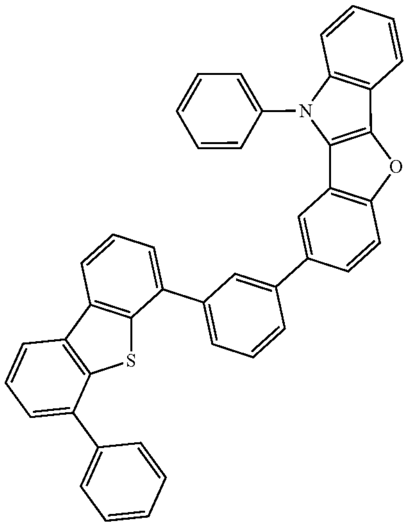

-continued
746
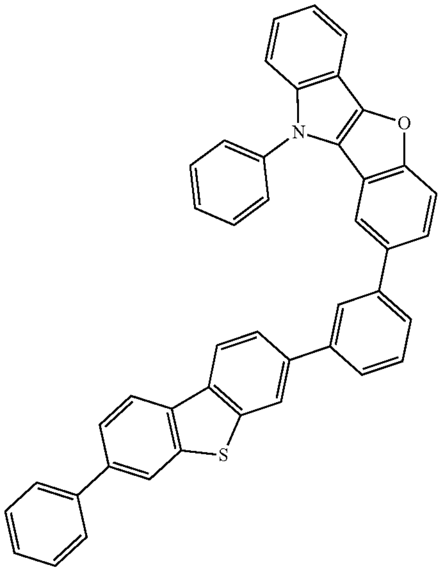
747
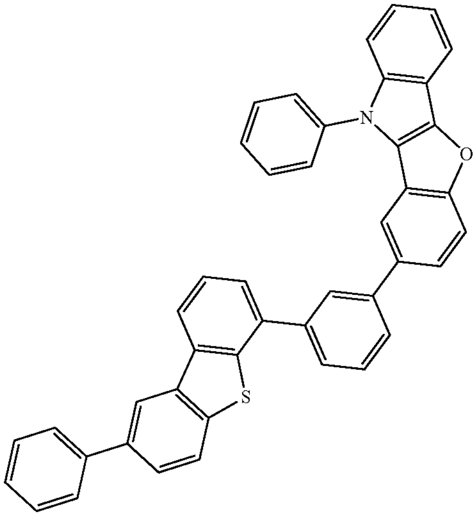
748
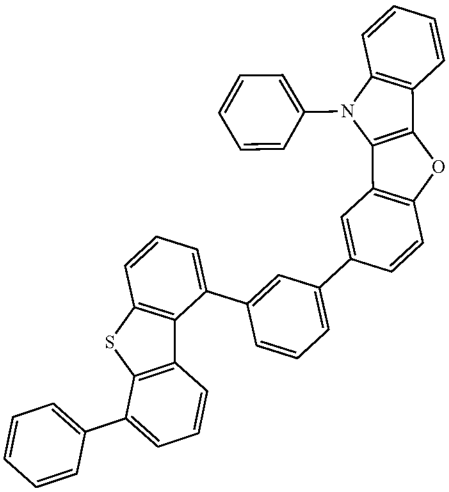
-continued
749
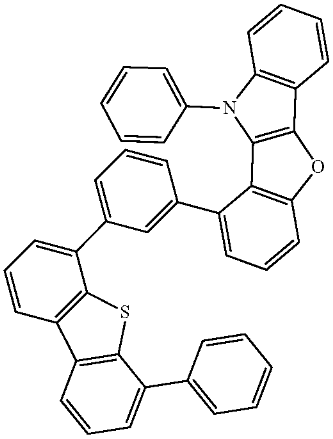
750
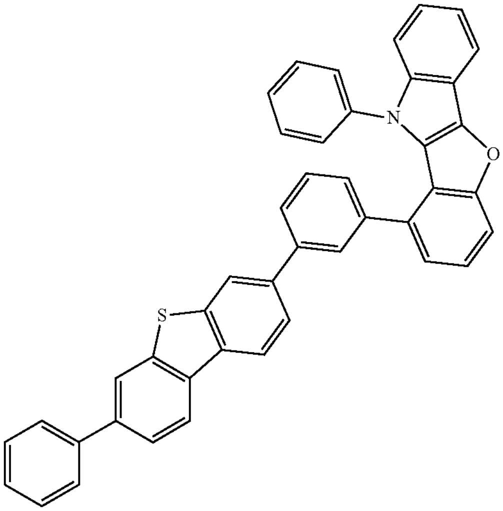
751
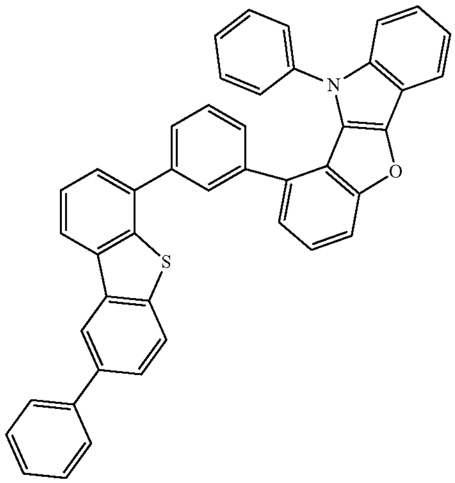

-continued
752
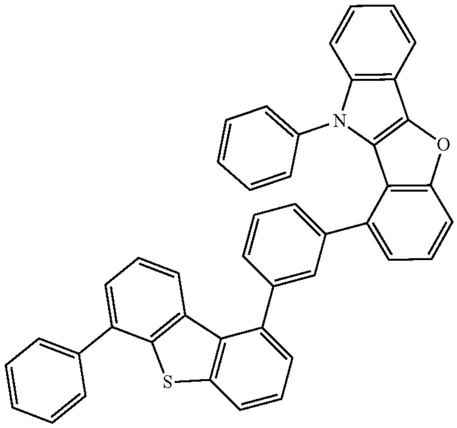
753
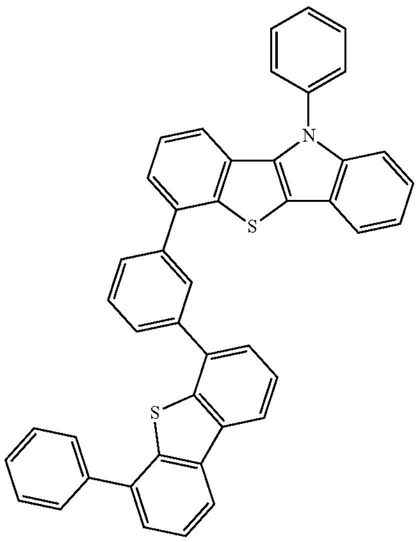
754
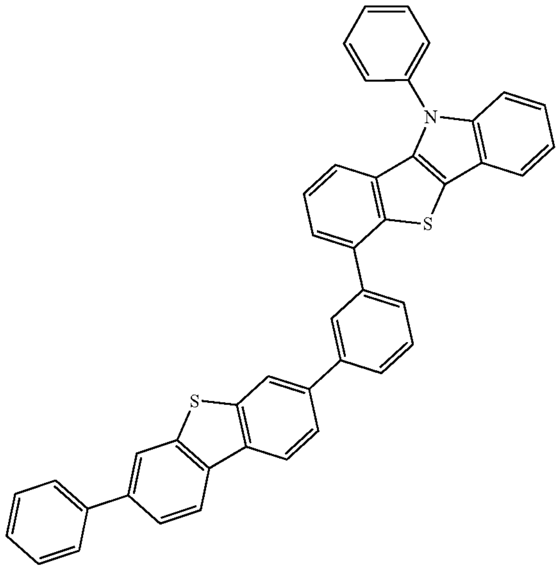
-continued
755
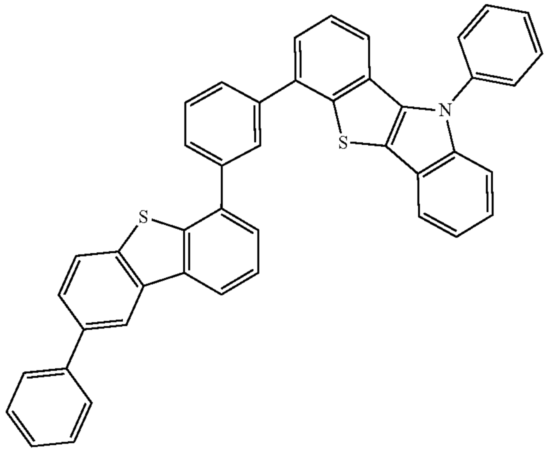
756
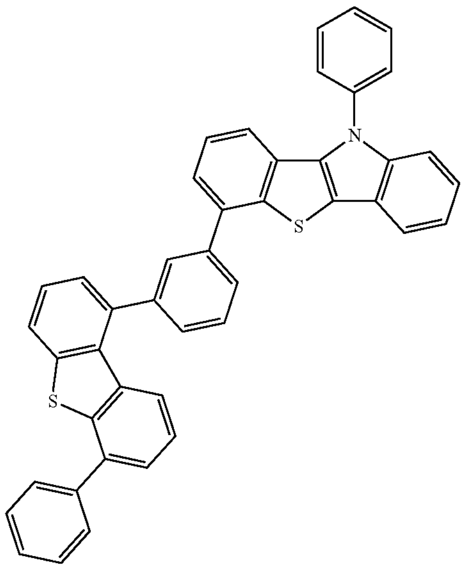
757
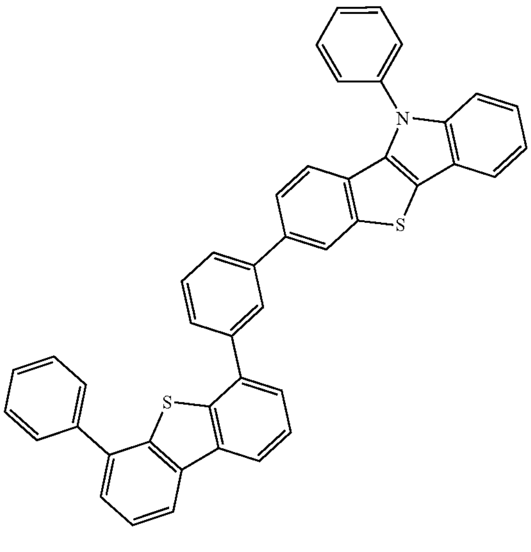

-continued
758
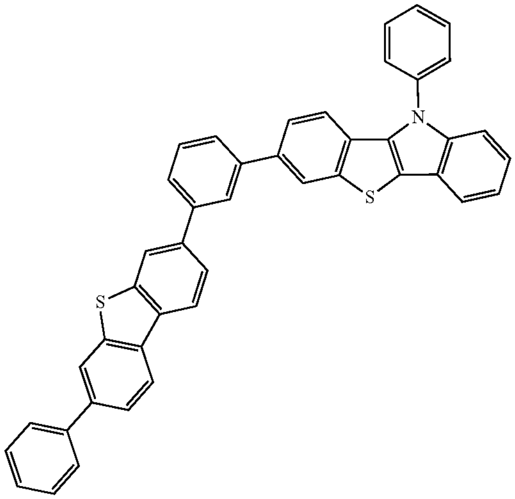
759
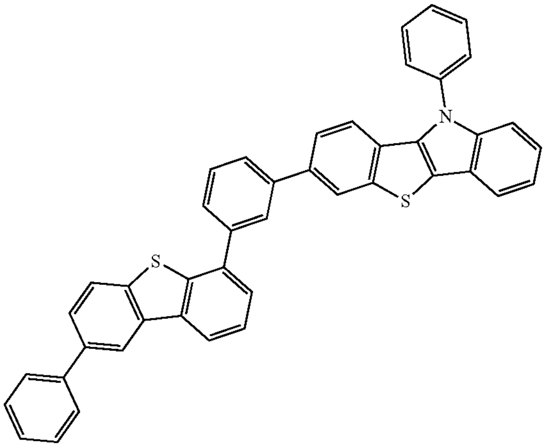
760
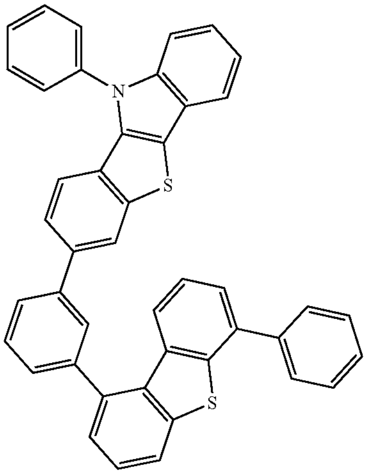
-continued
761
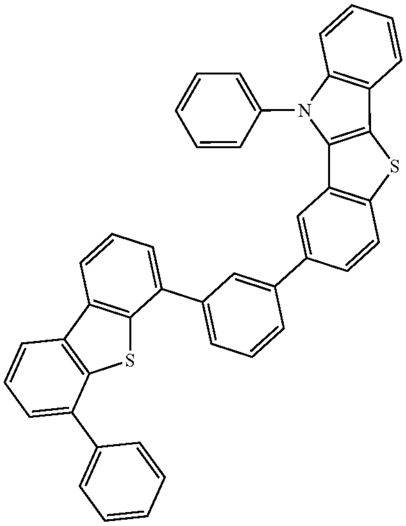
762
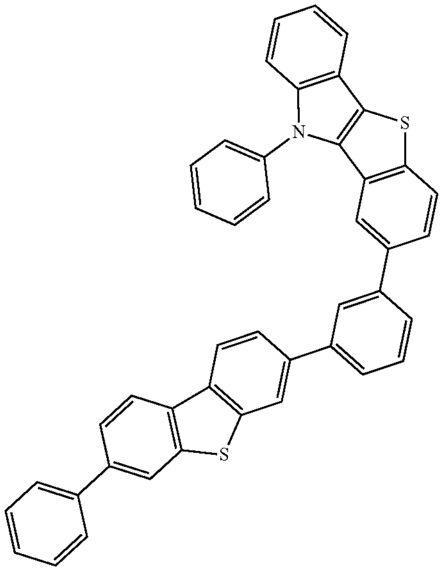
763
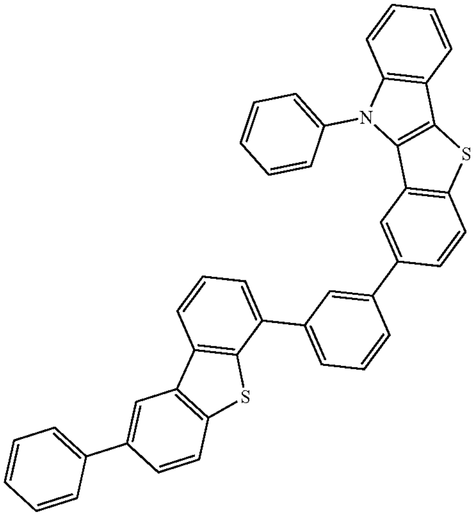

-continued
764
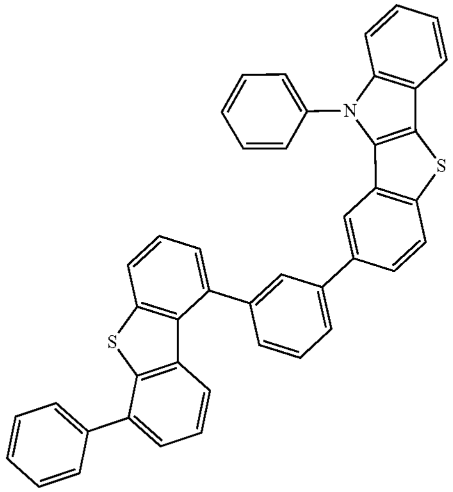
765
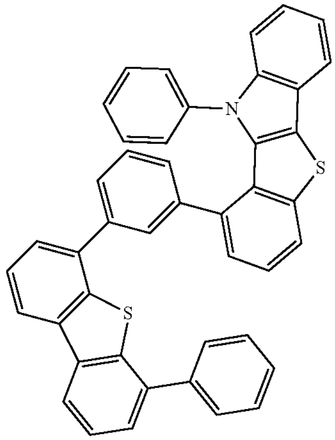
766
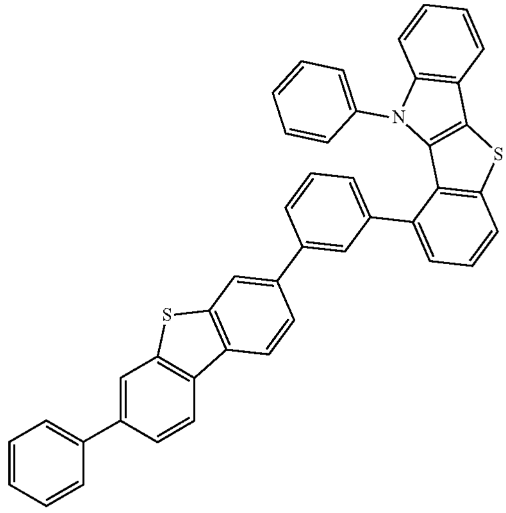
-continued
767
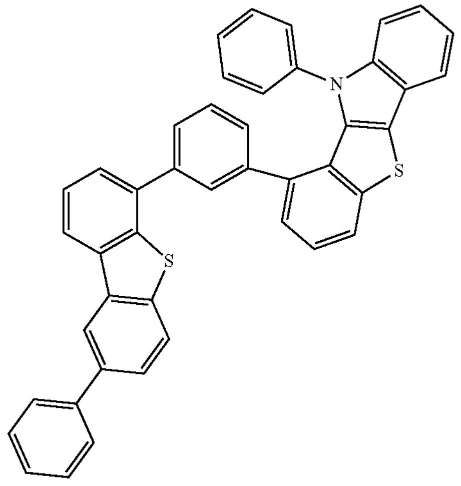
768
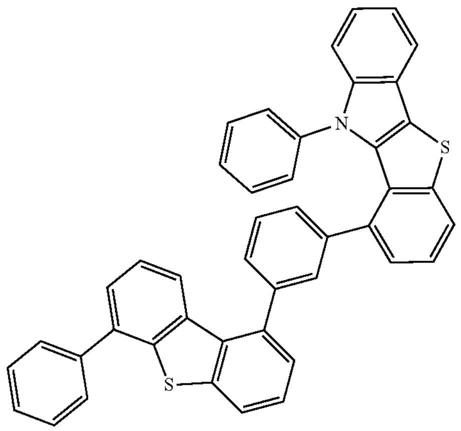
769
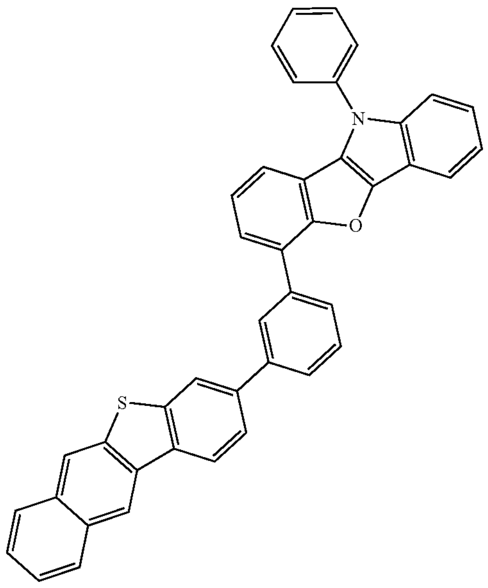

-continued
770
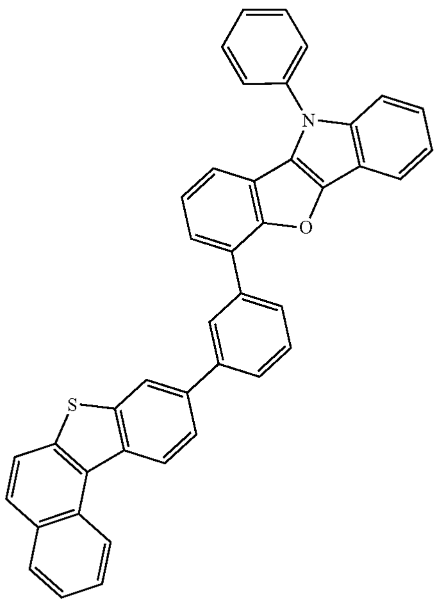
771
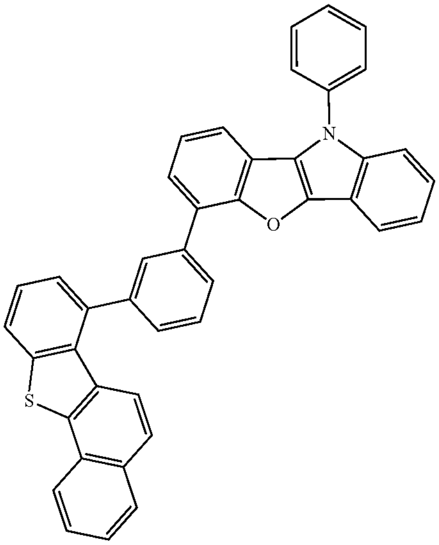
-continued
772
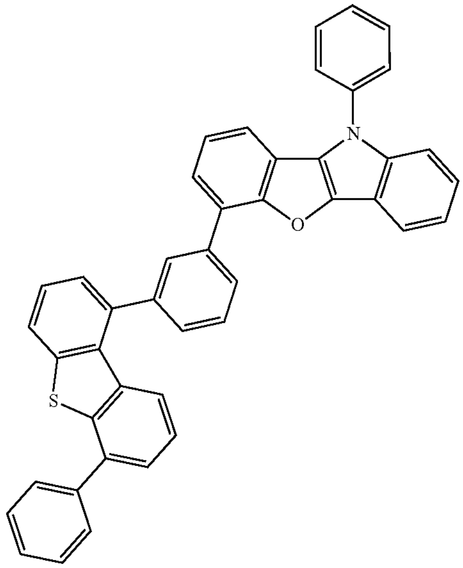
773
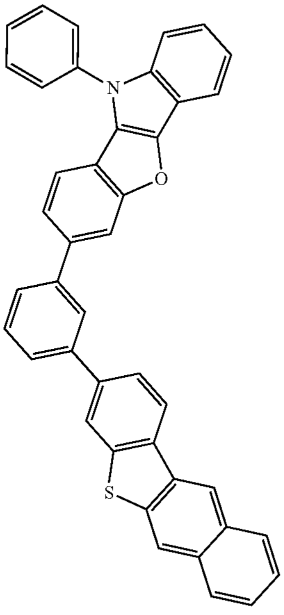

-continued
774
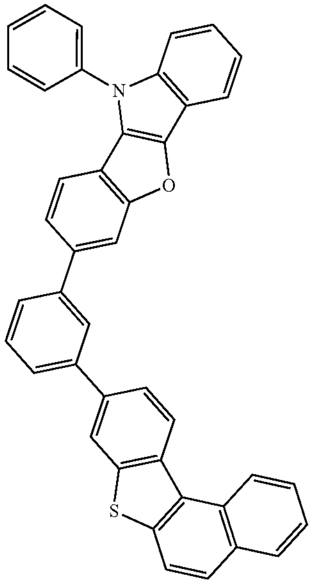
775
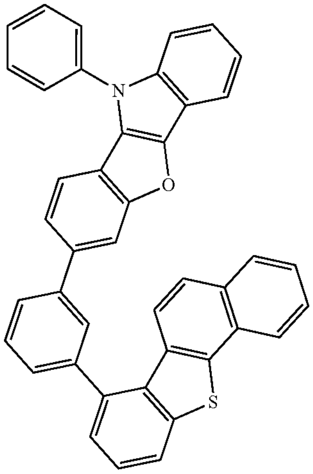
776
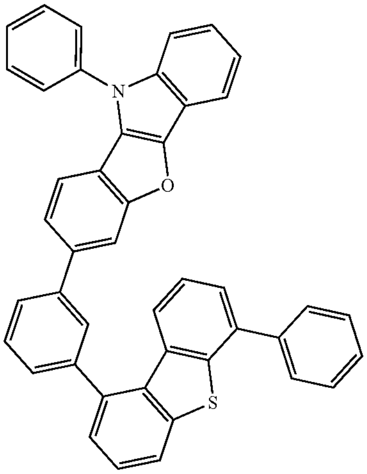
-continued
777
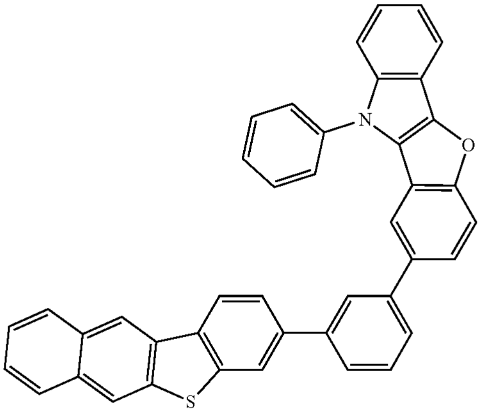
778
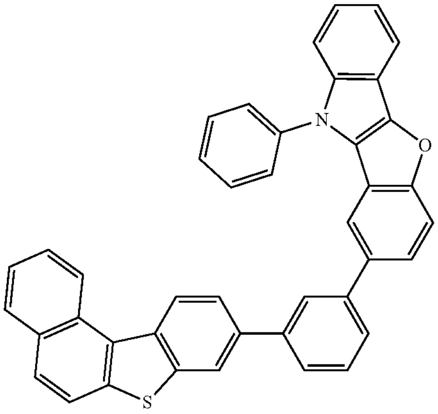
779
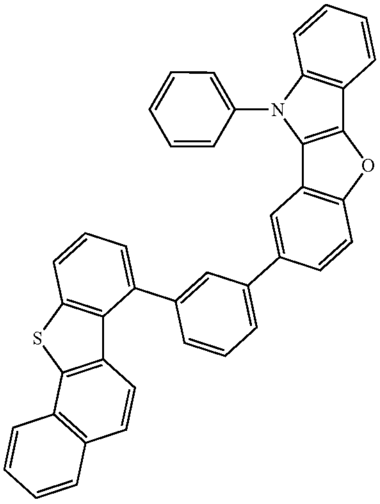

-continued
780
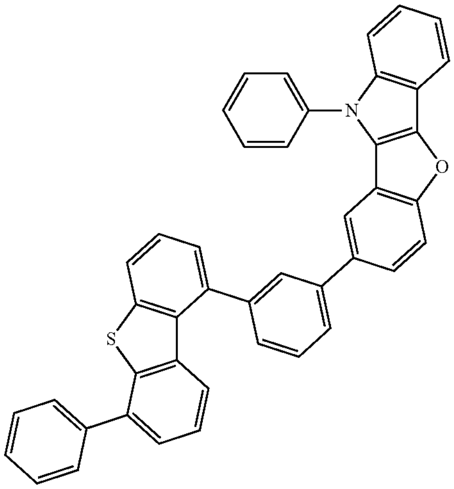
781
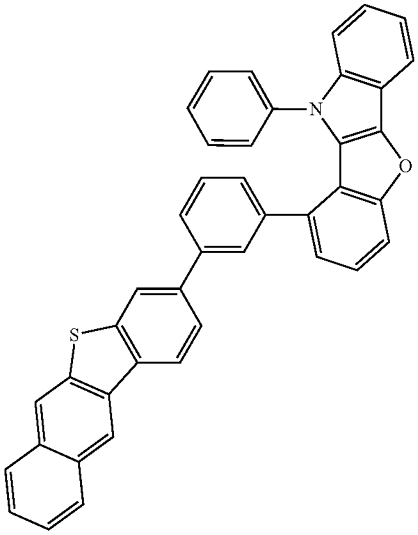
782
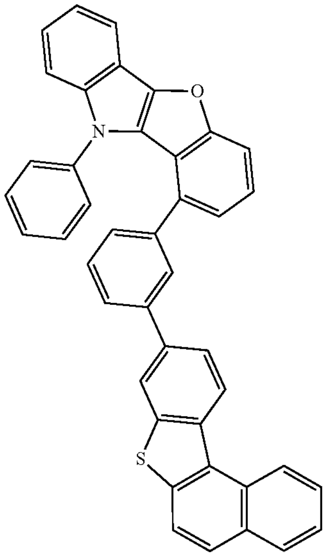
-continued
783
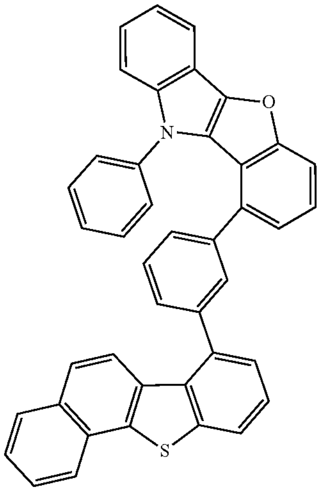
784
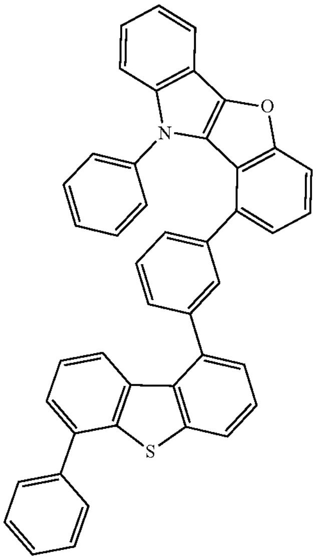
785
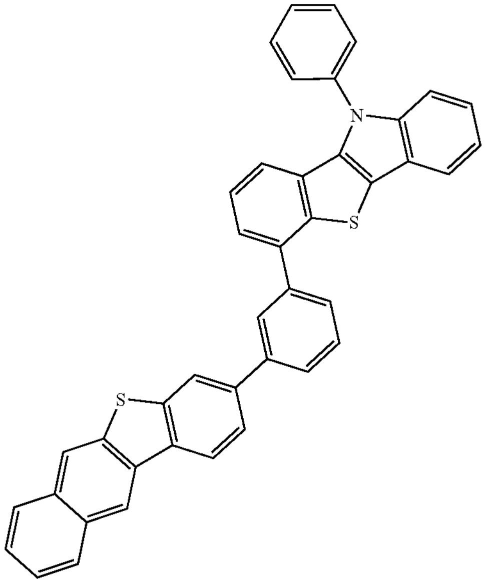

-continued
786
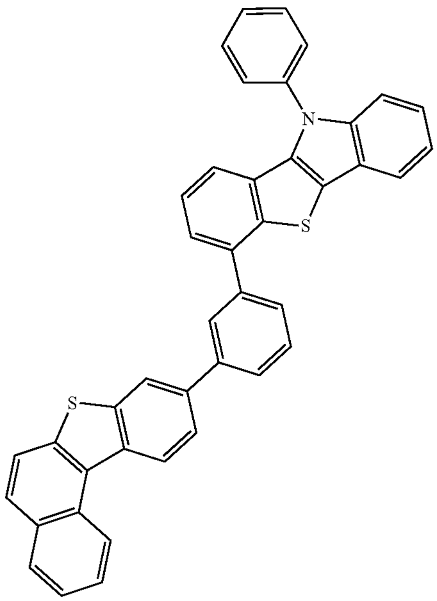
787
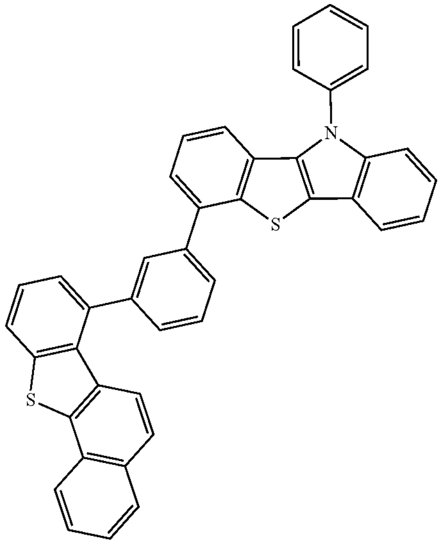
-continued
788
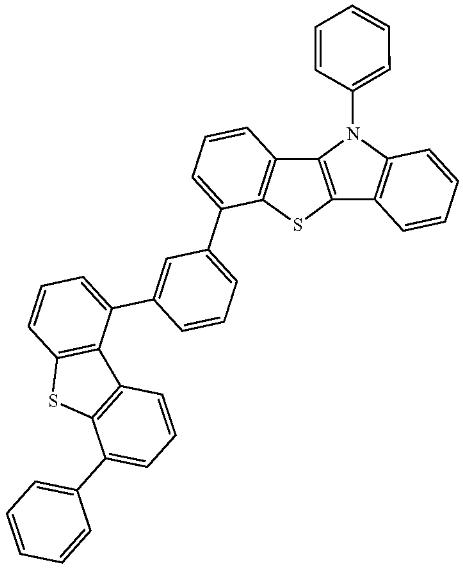
789
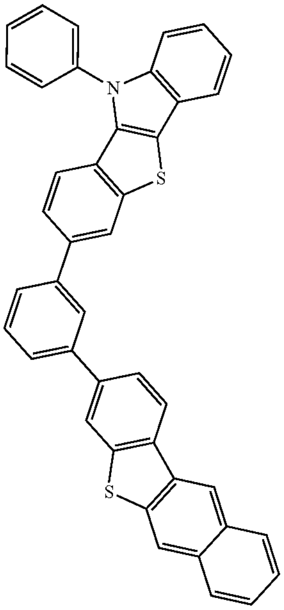

-continued
790
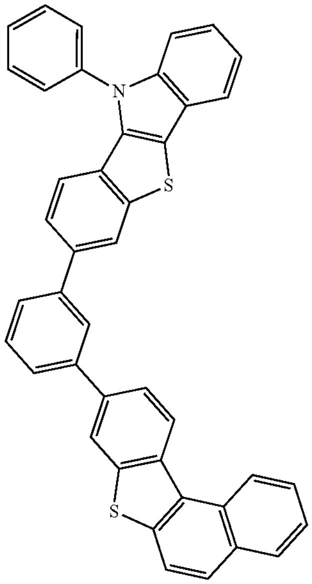
791
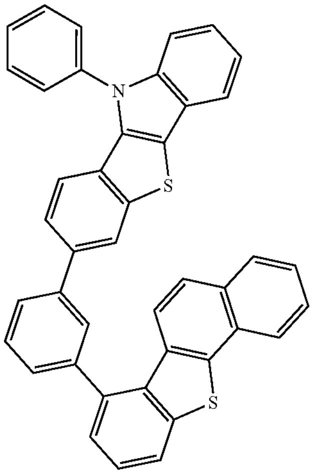
792
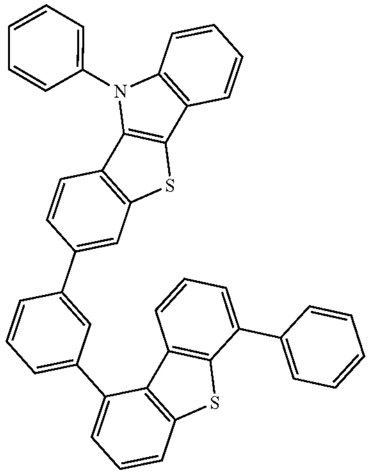
-continued
793
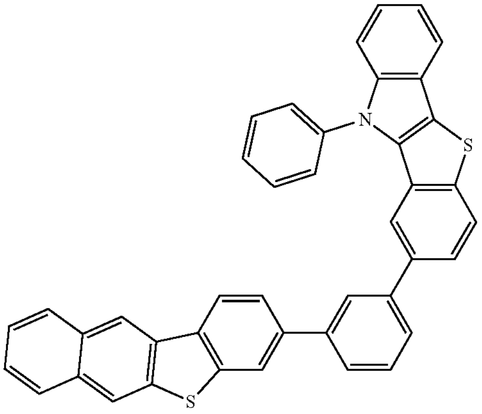
794
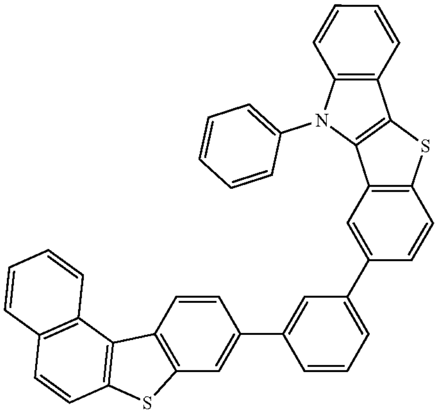
795
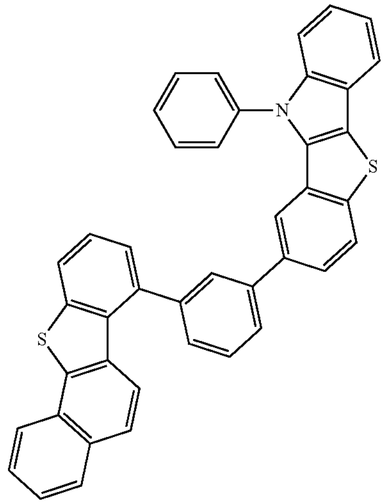

-continued
796
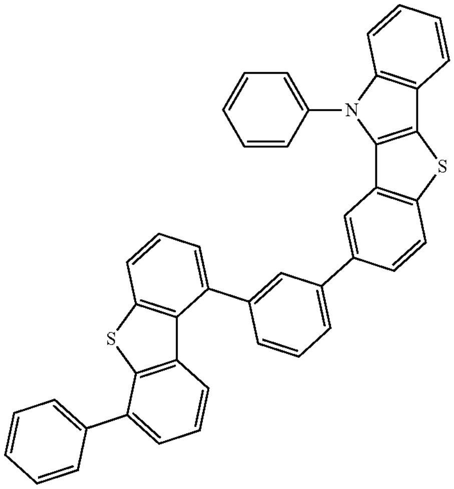
797
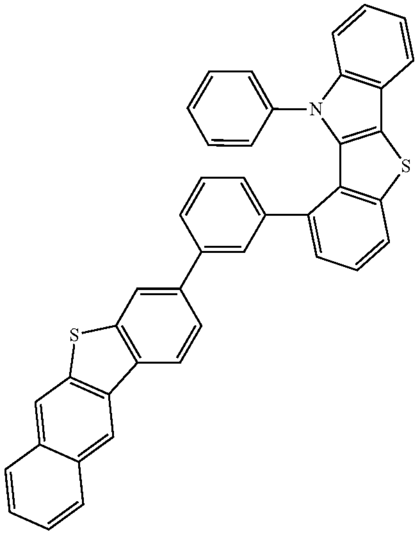
798
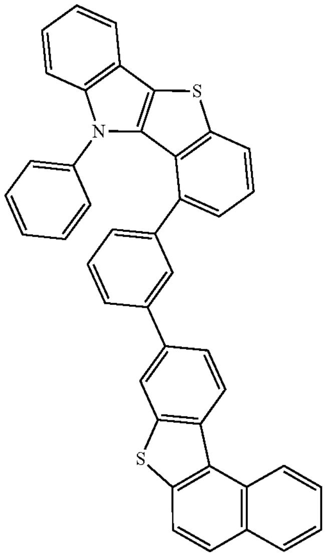
-continued
799
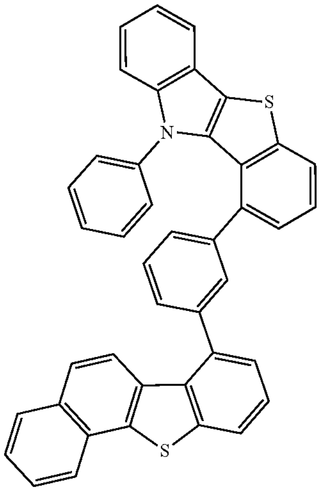
800
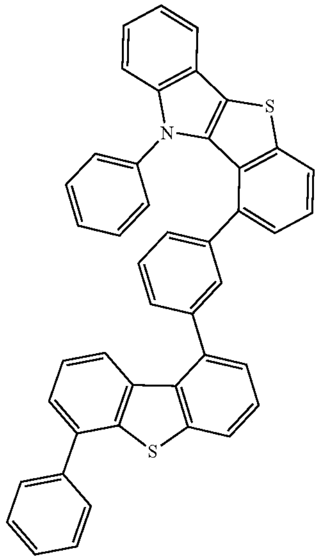
801
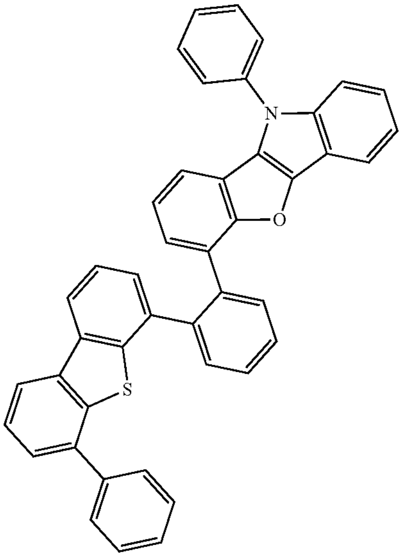

-continued
802
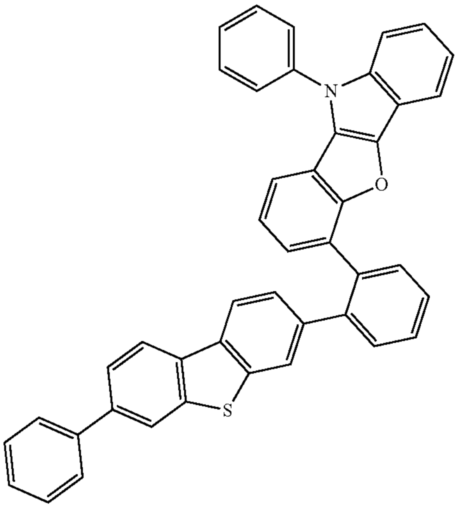
803
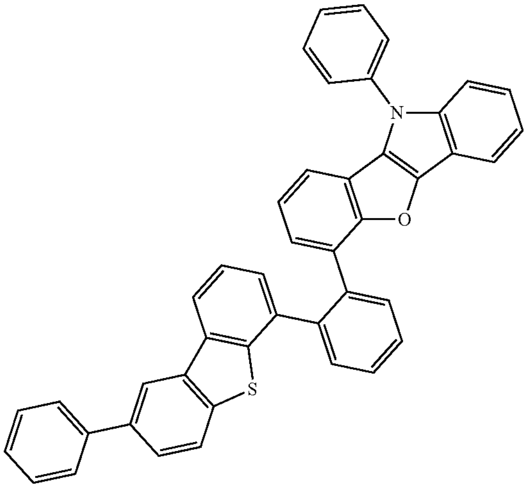
804
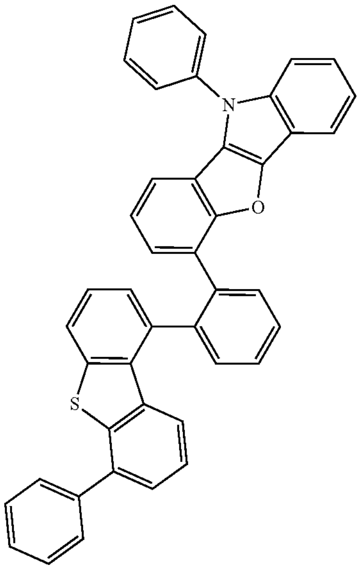
-continued
805
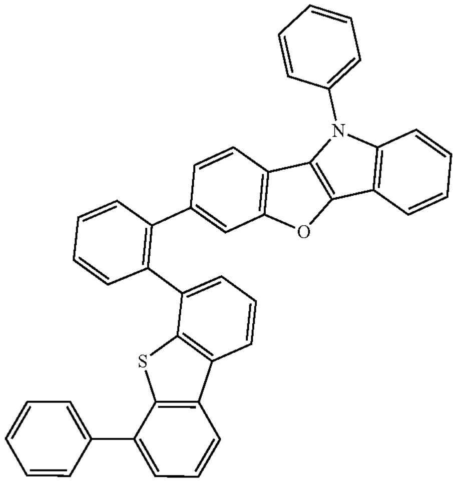
806
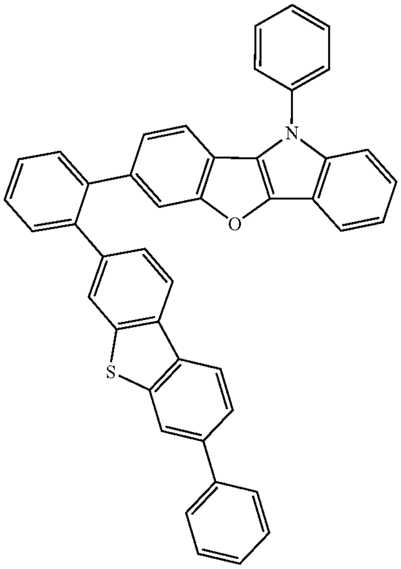
807
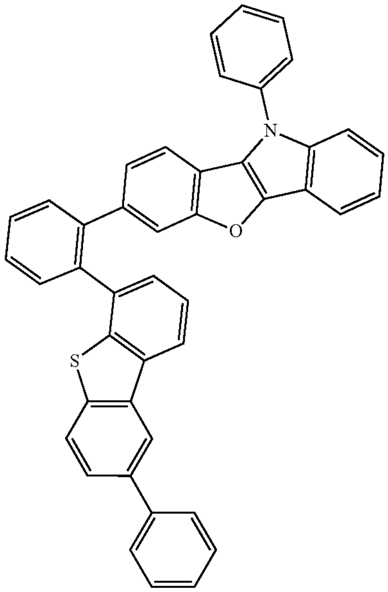

-continued
808
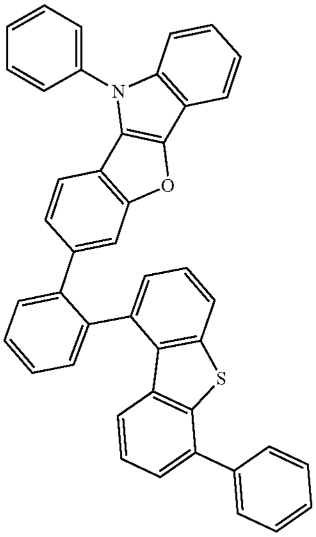
809
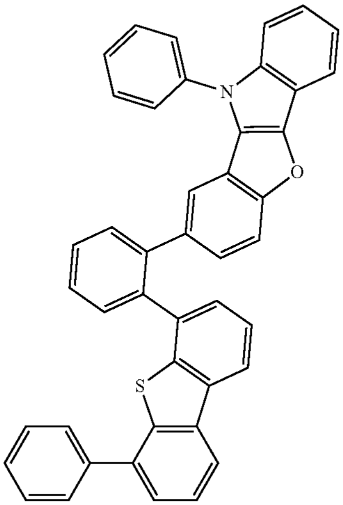
810
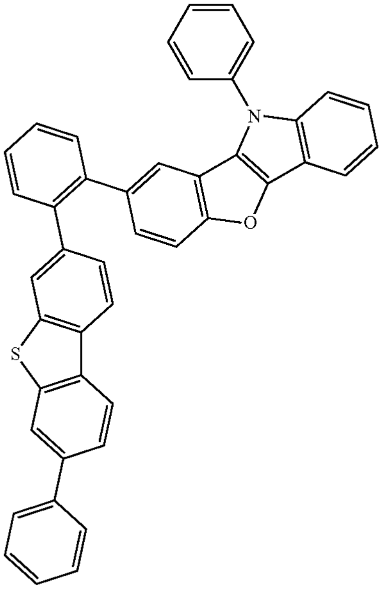
-continued
811
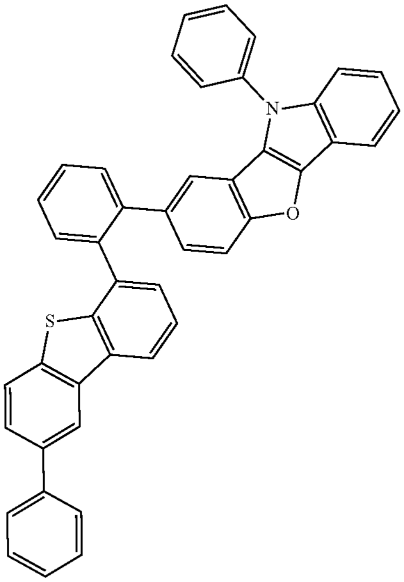
812
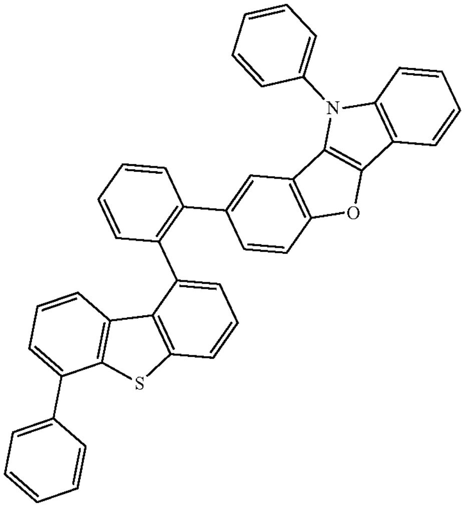
813
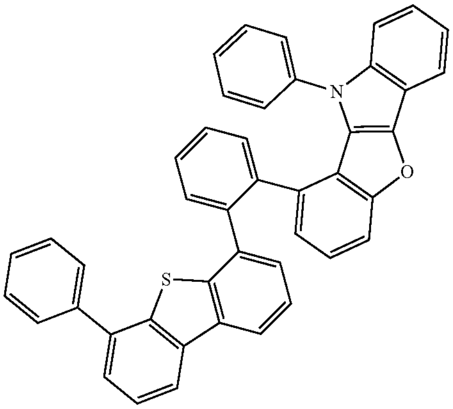

-continued
814
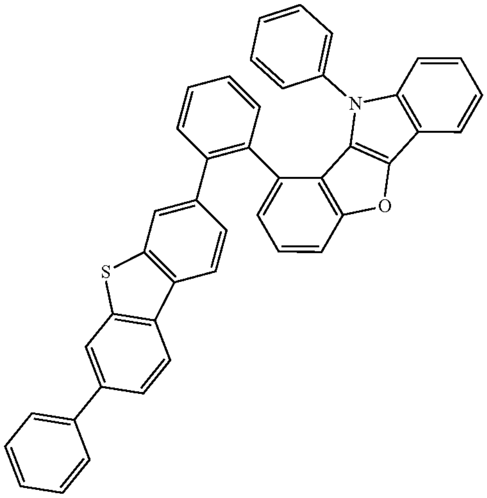
815
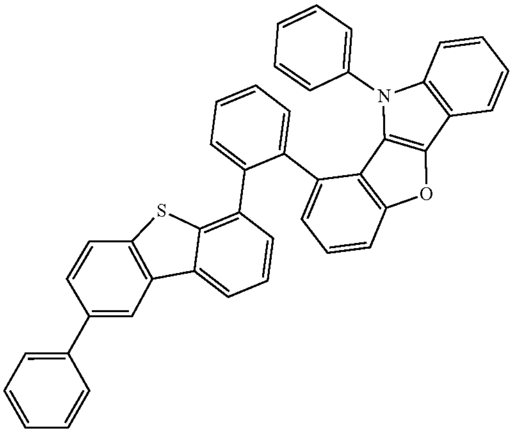
816
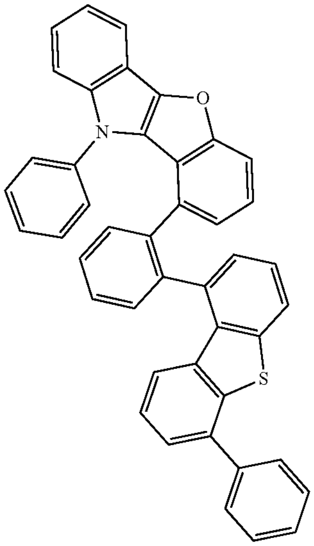
-continued
817
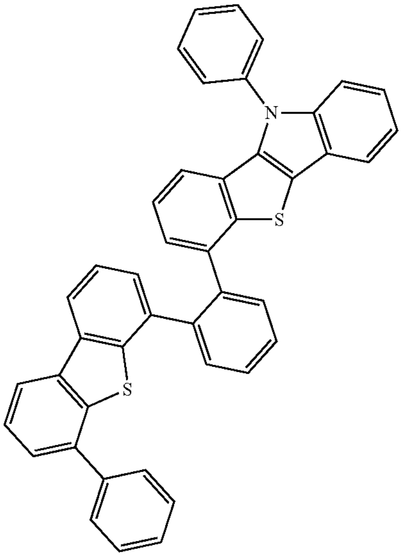
818
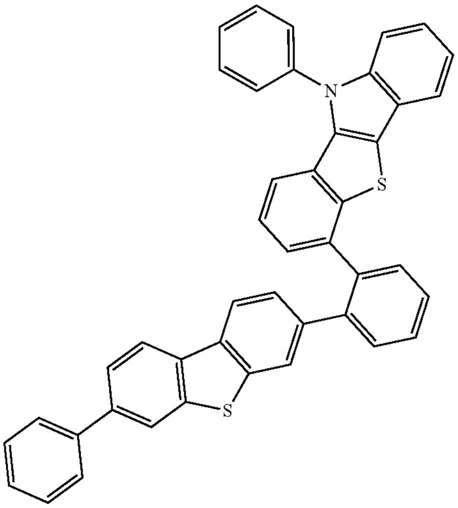
819
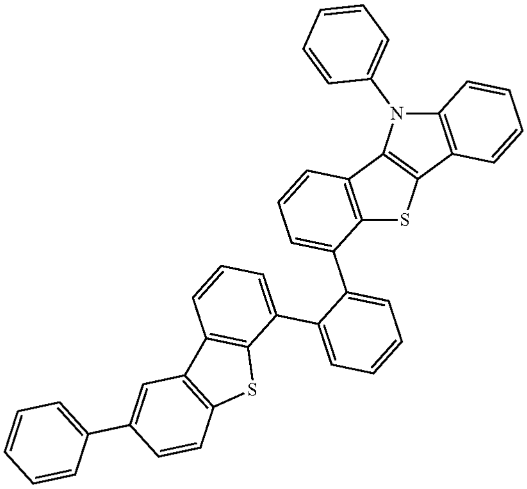

-continued
820
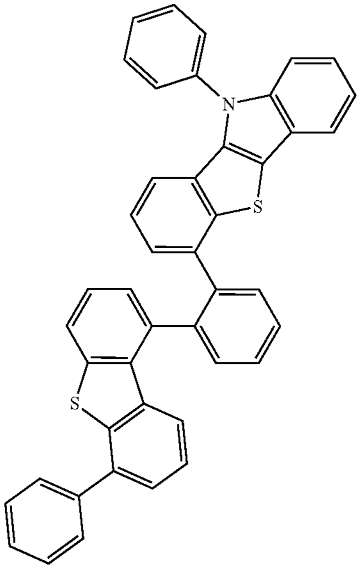
821
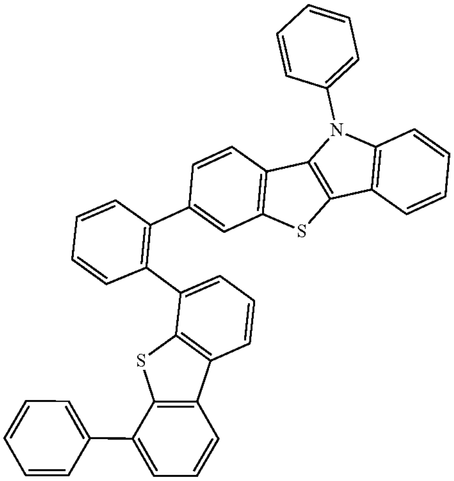
822
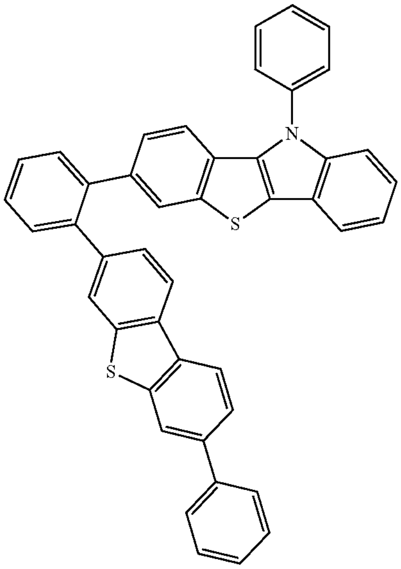
-continued
823
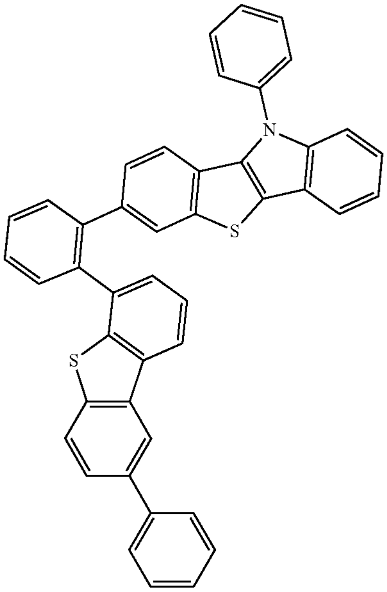
824
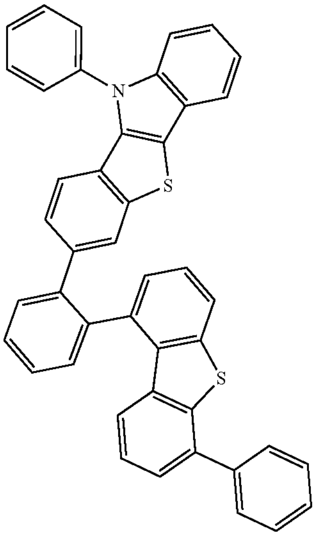
825
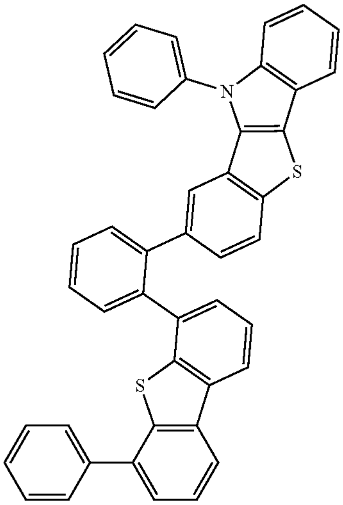

-continued
826
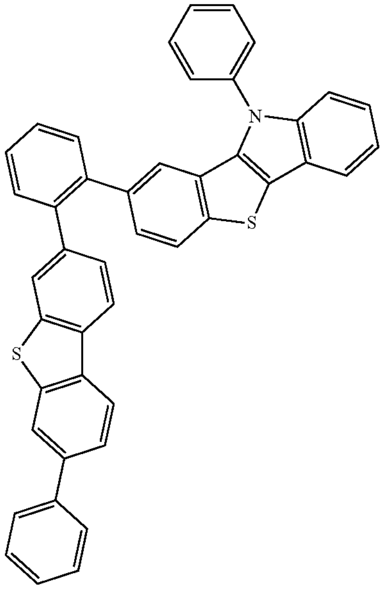
827
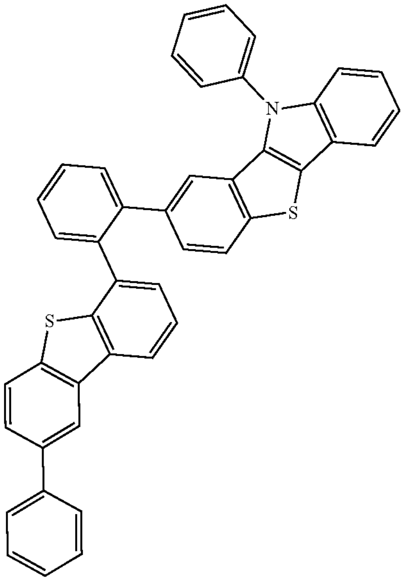
-continued
828
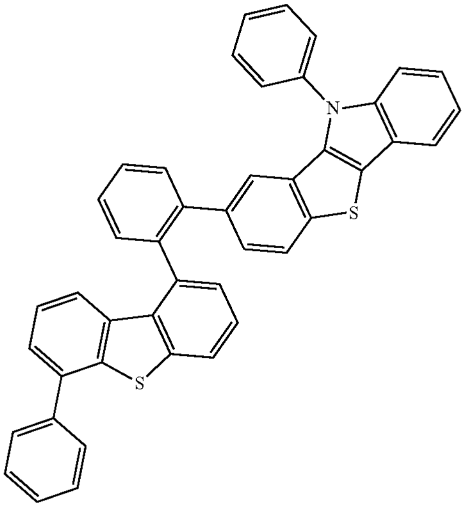
829
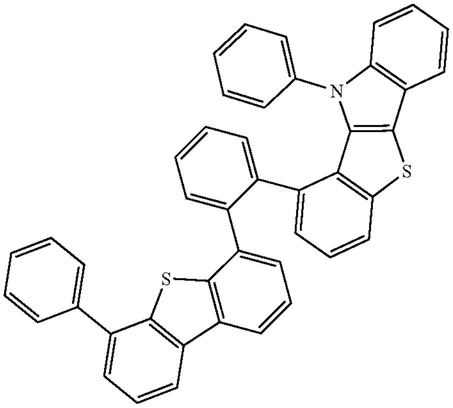
830
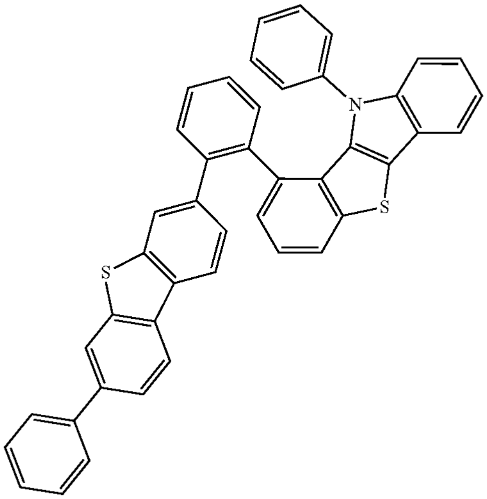

-continued
831
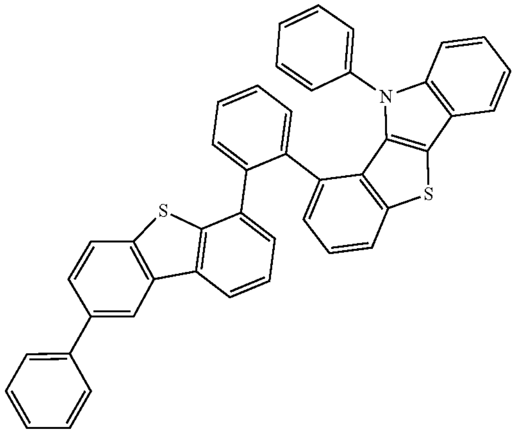
832
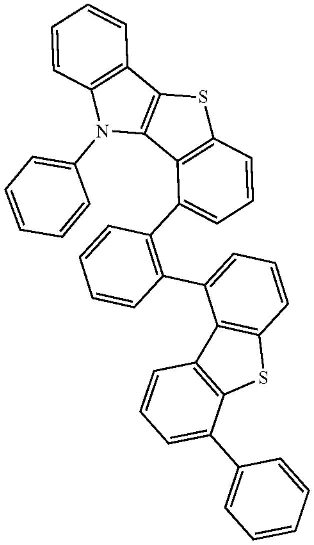
833
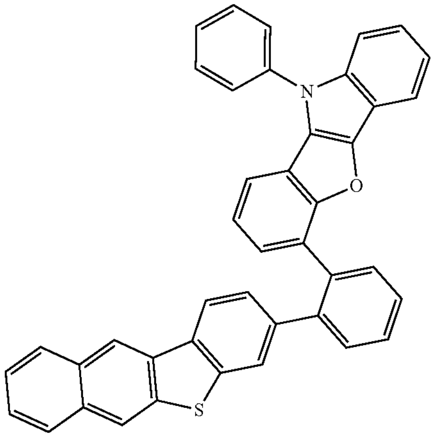
-continued
834
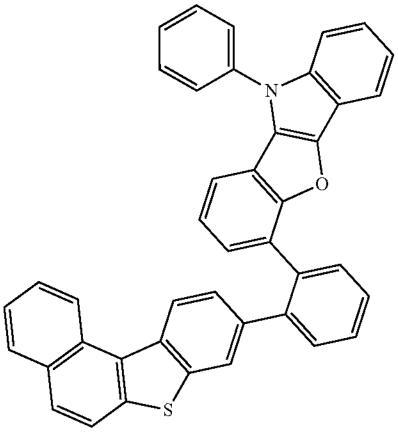
835
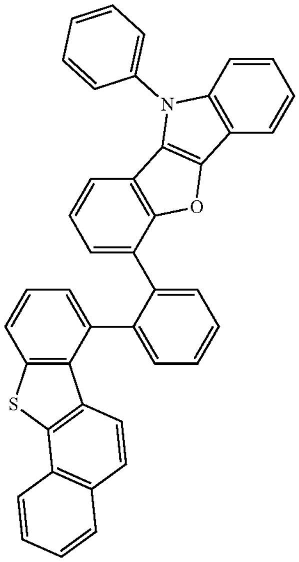
836
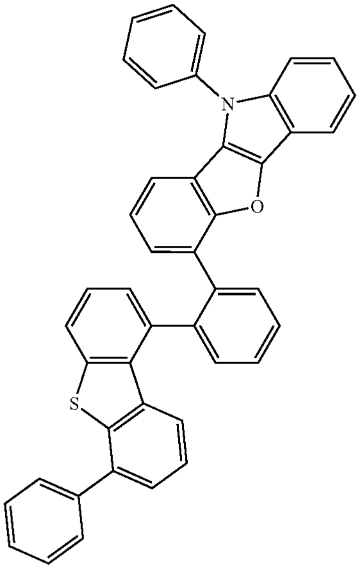

-continued
837
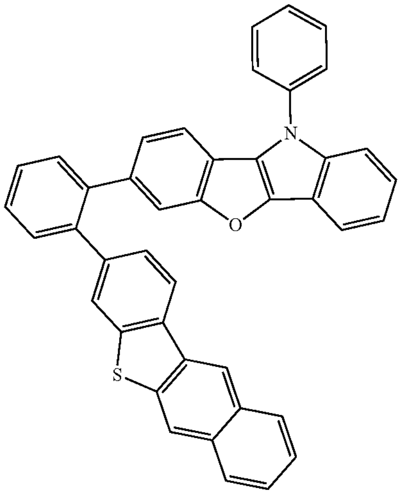
838
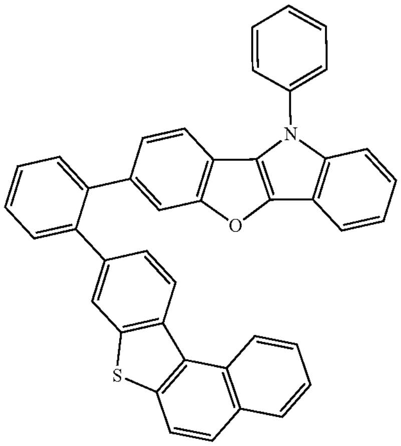
839
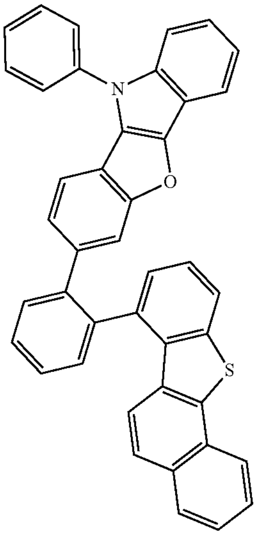
-continued
840
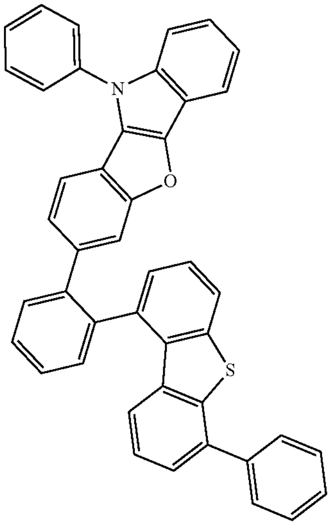
841
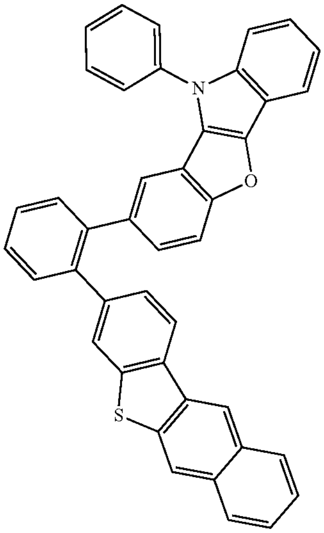
842
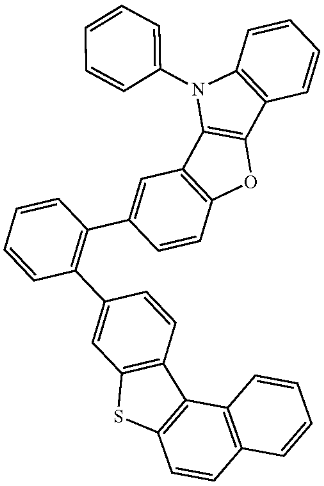

843
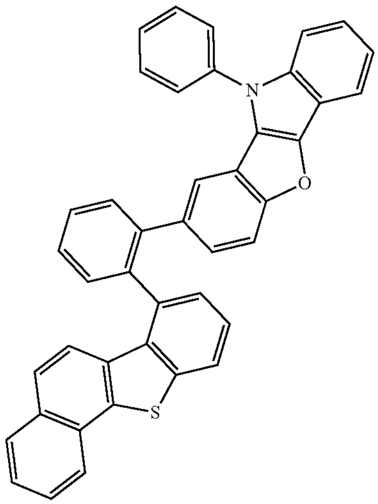
844
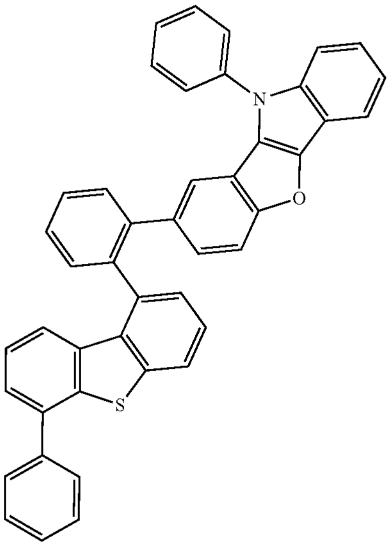
845
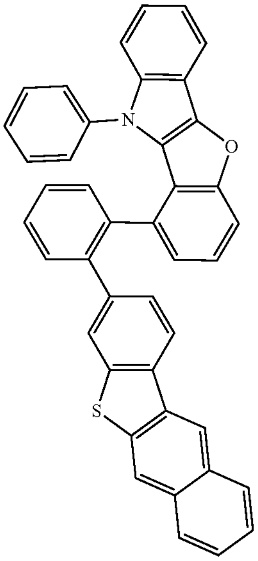
846
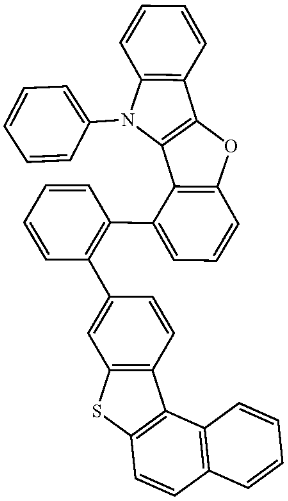
847
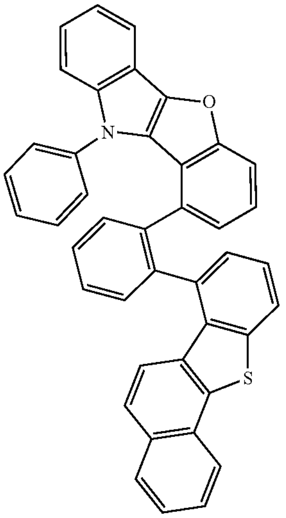
848
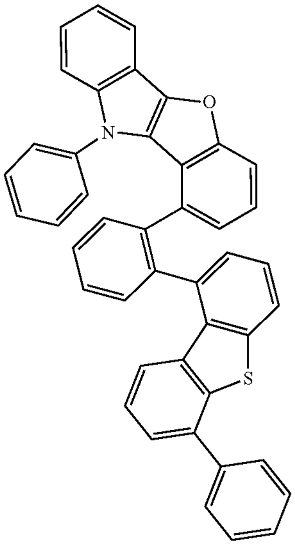

-continued
849
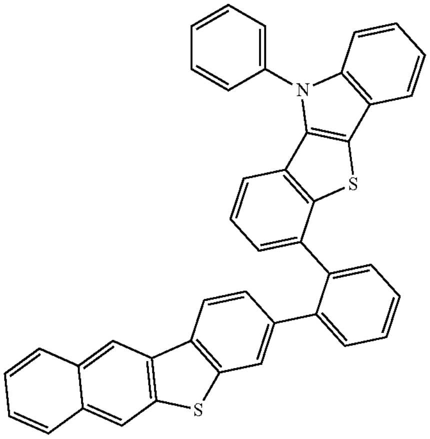
850
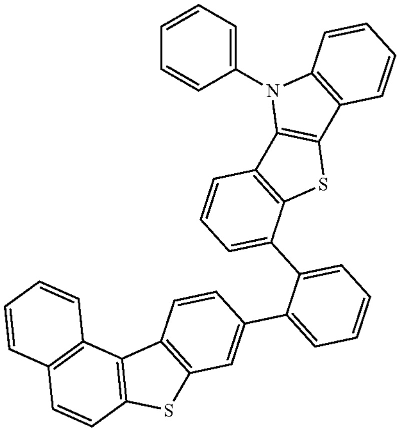
851
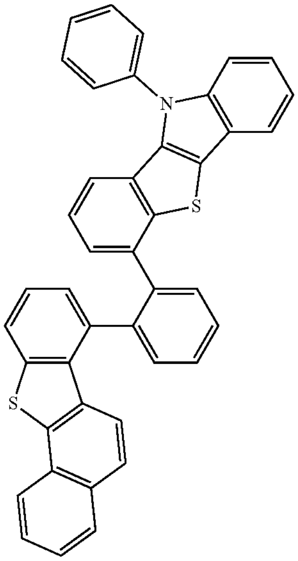
852
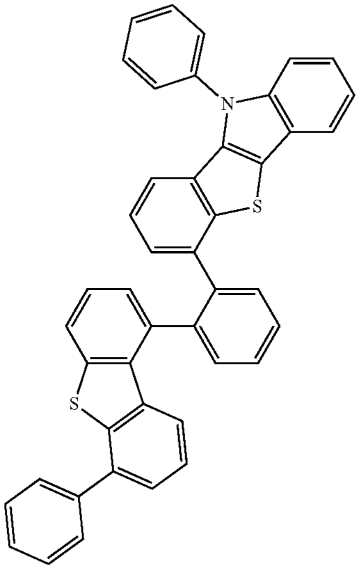
853
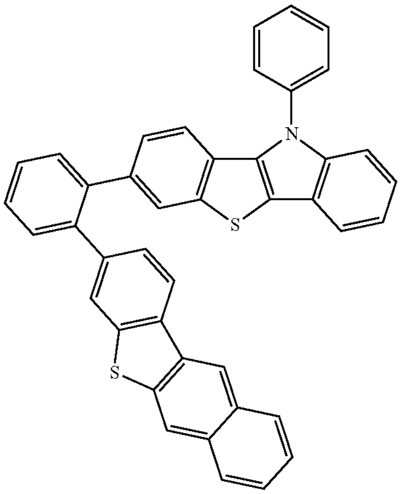
854
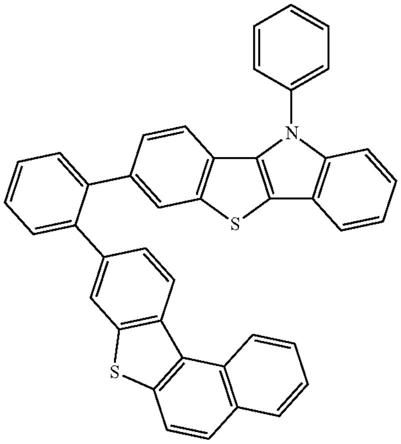

855
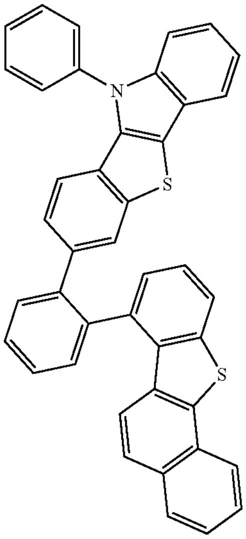
856
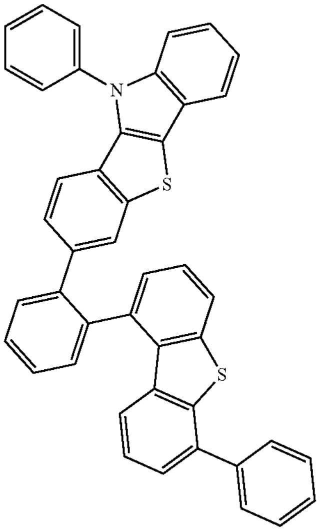
857
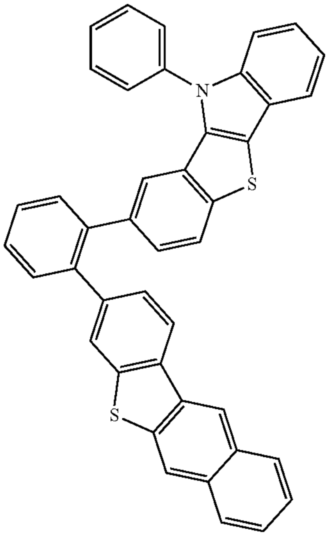
858
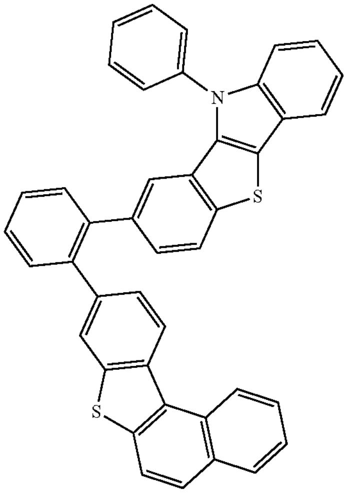
859
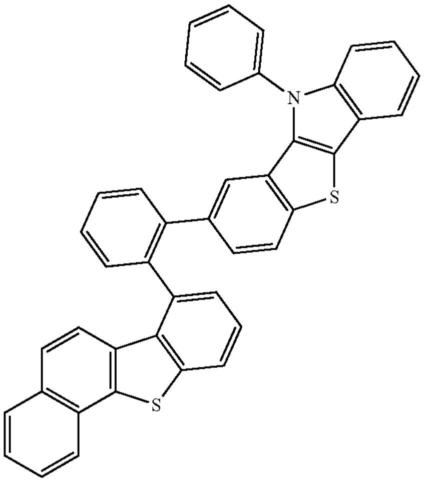
860
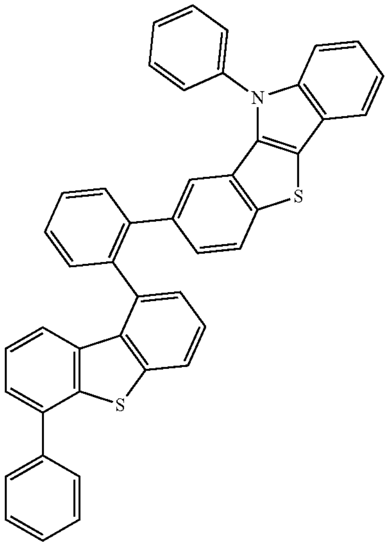

-continued
861
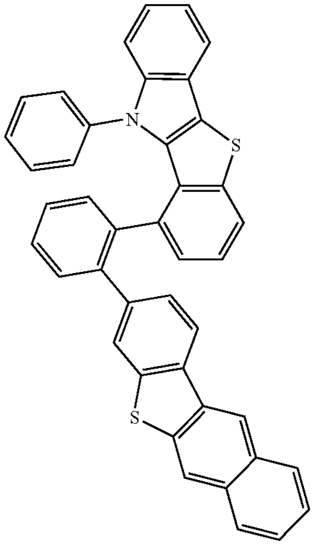
862
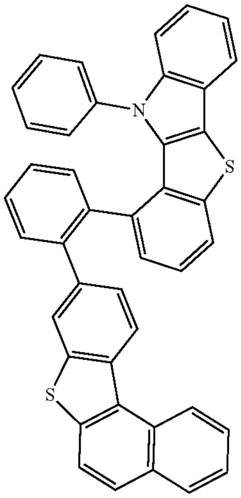
863
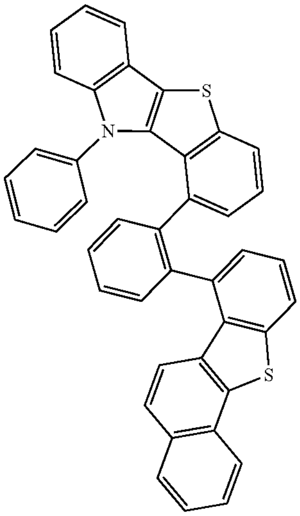
-continued
864
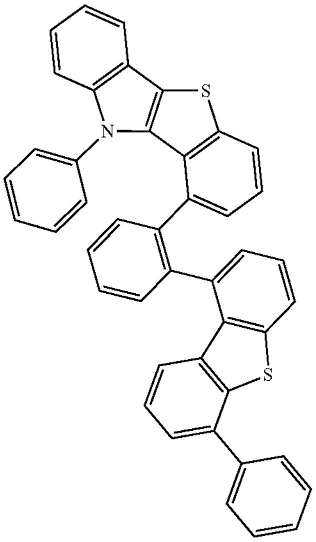
865
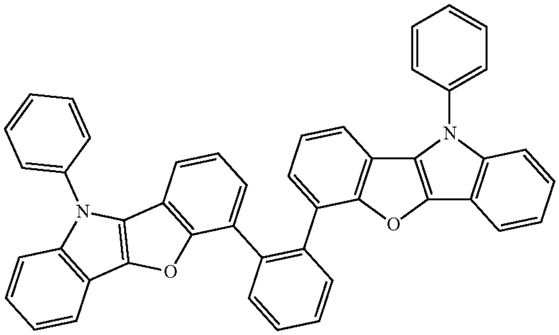
866
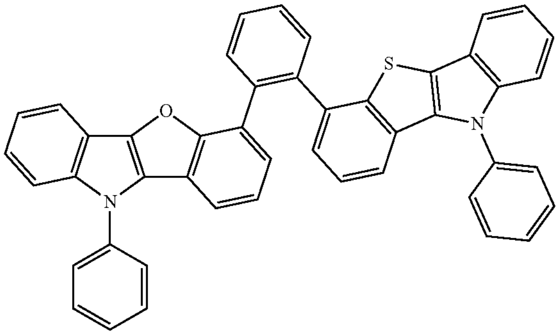
867
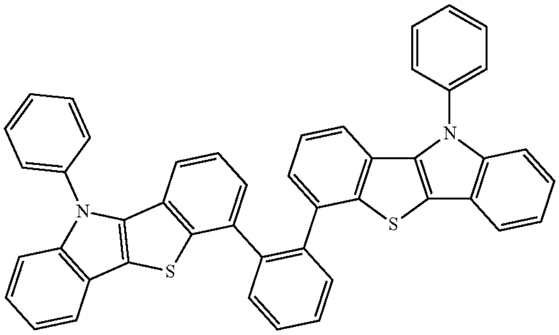

-continued
868
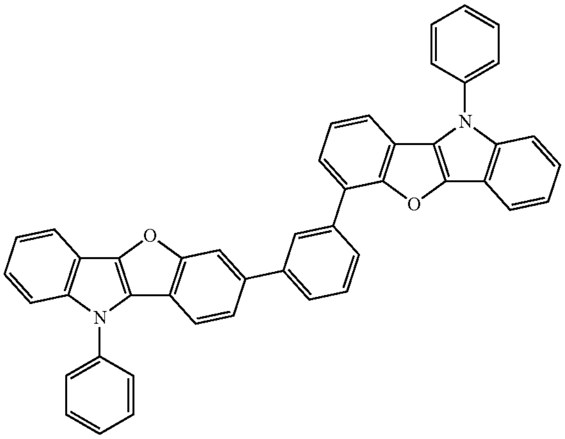
869
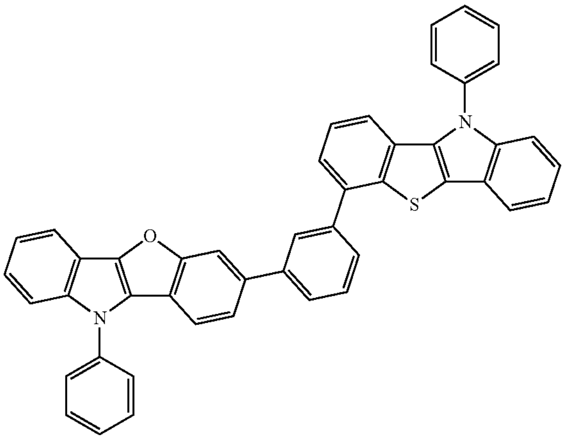
870
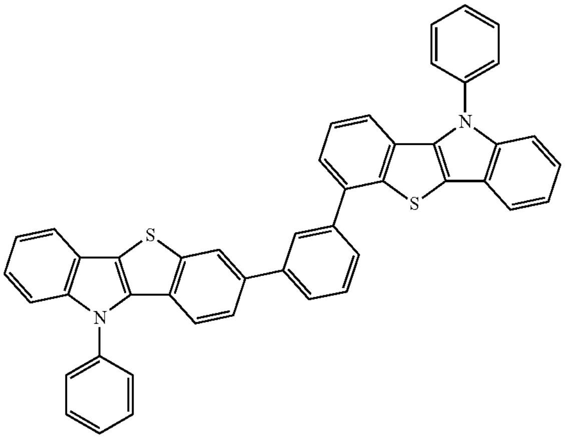
-continued
871
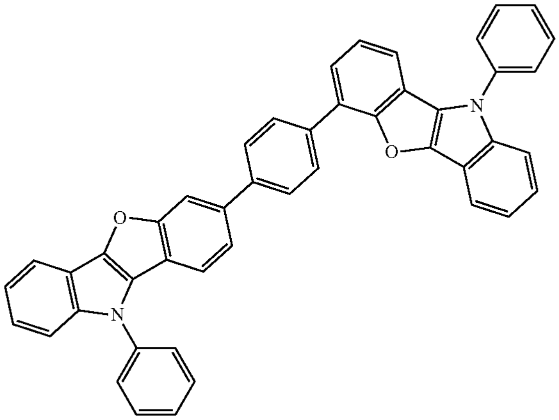
872
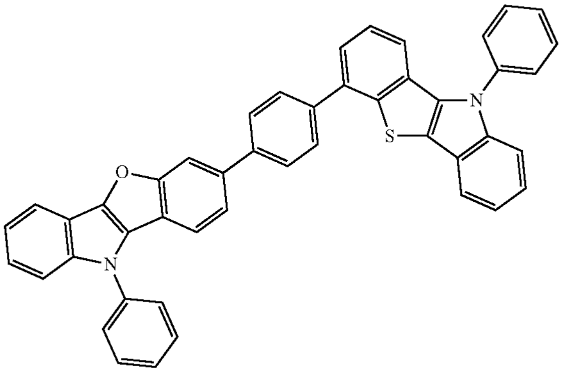
873
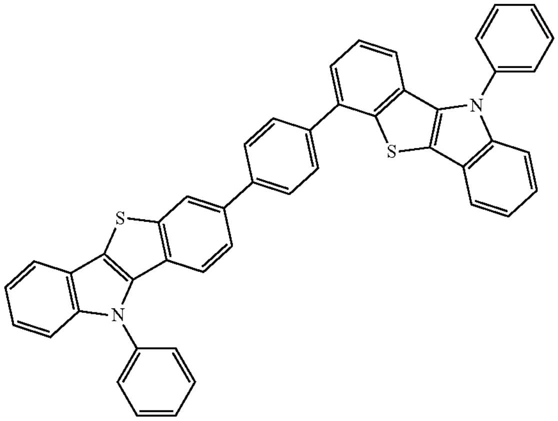

-continued
874
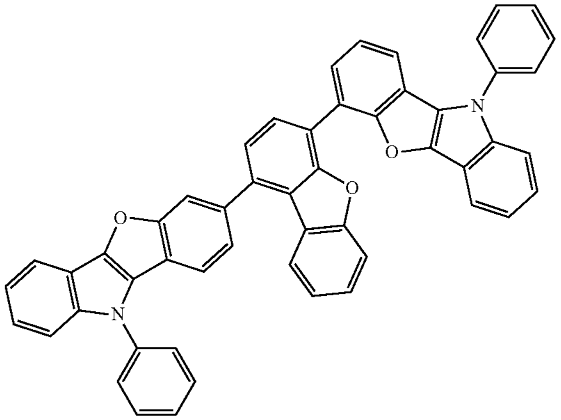
875
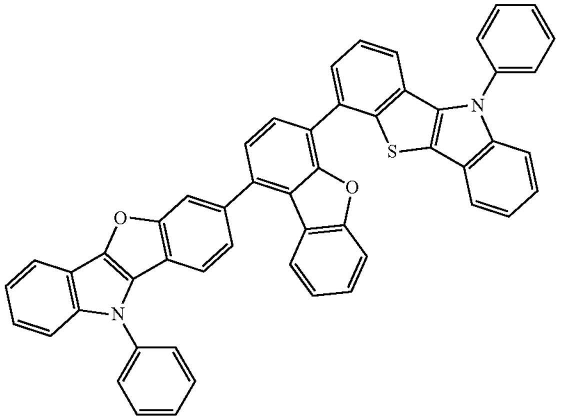
876
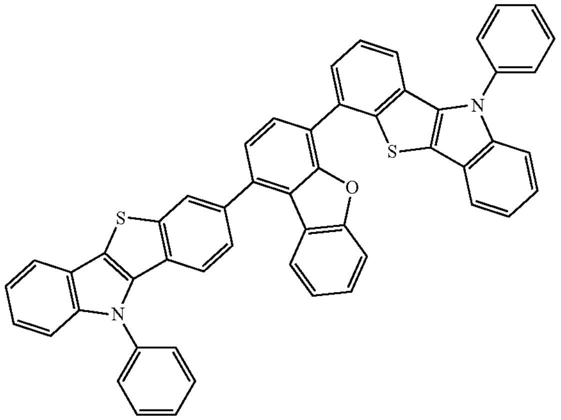
-continued
877
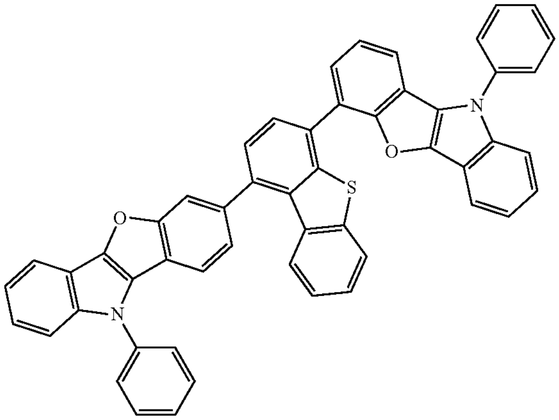
878
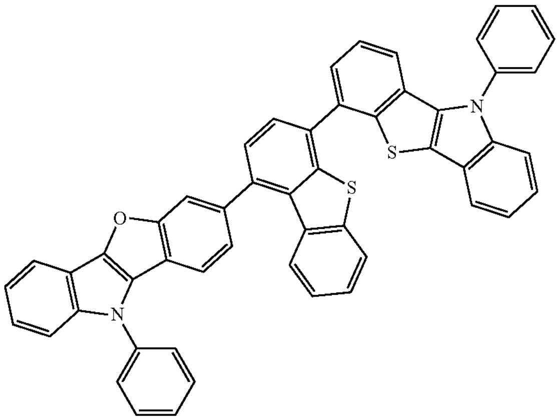
879
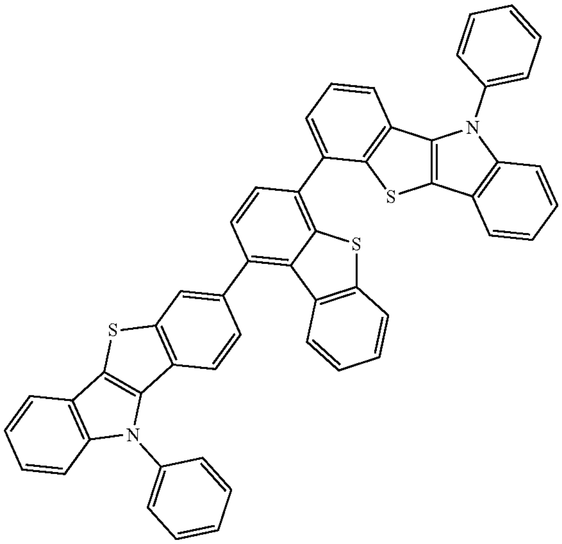

-continued
880
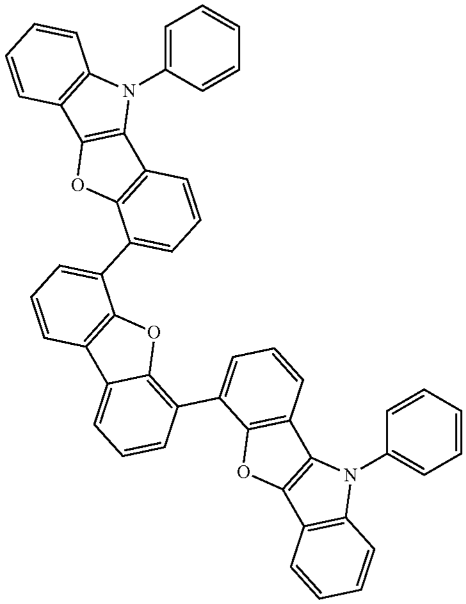
882
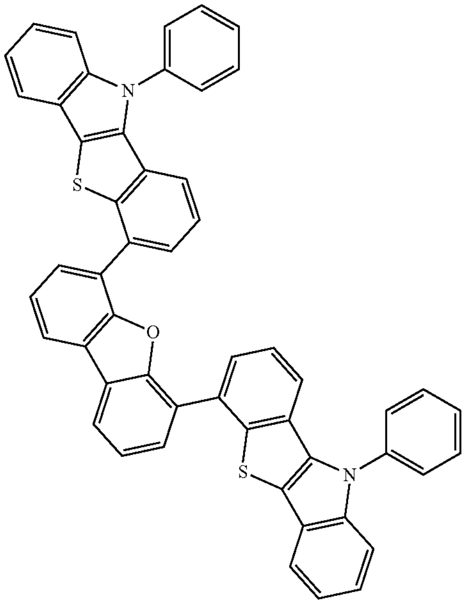
881
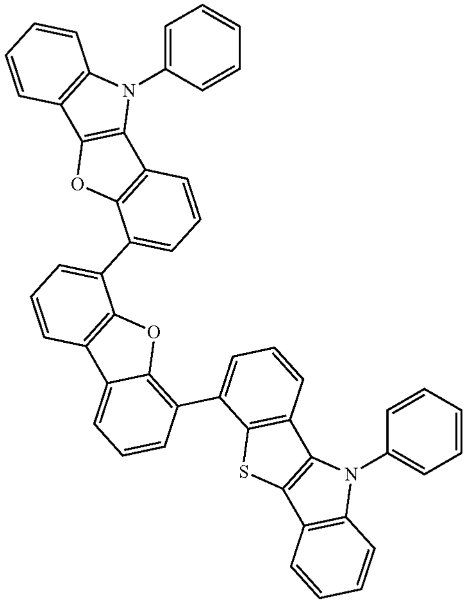
883
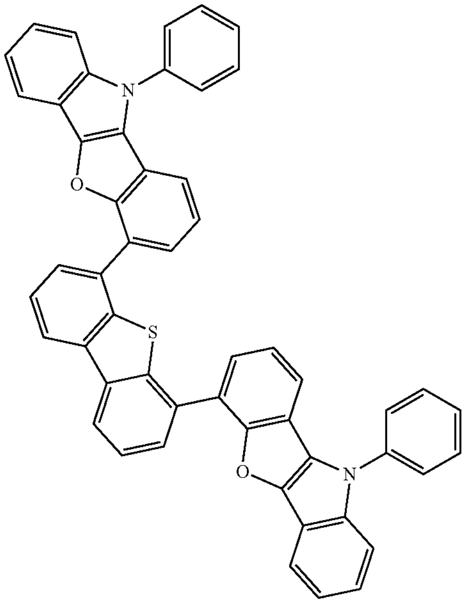

884
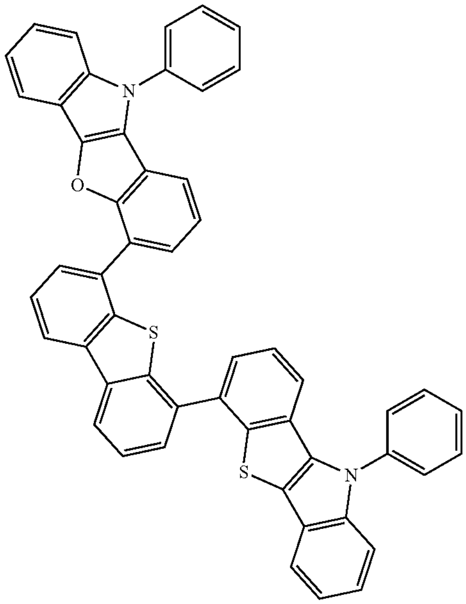
885
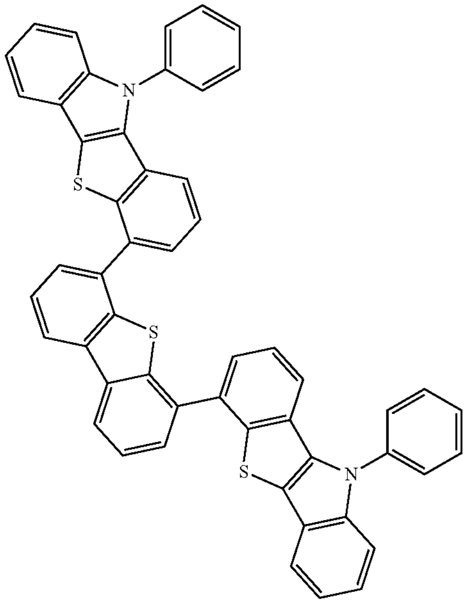
886
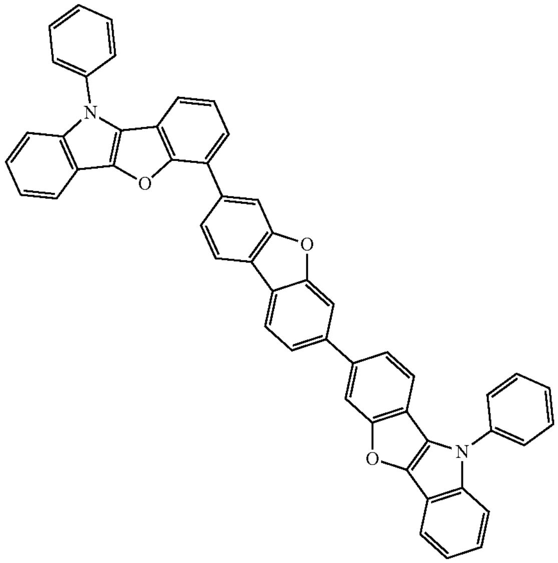
887
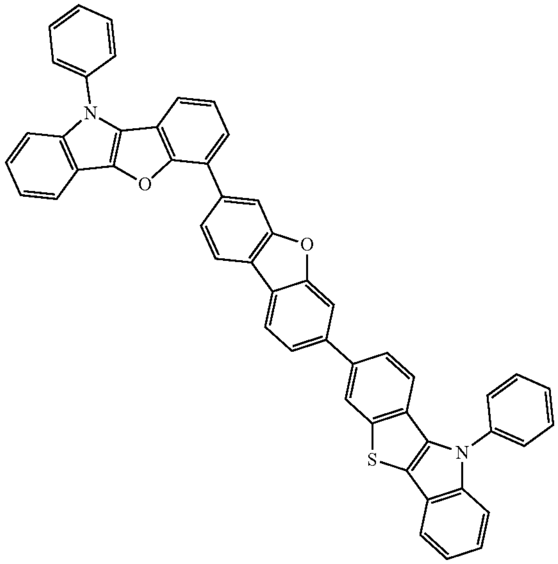

-continued
888
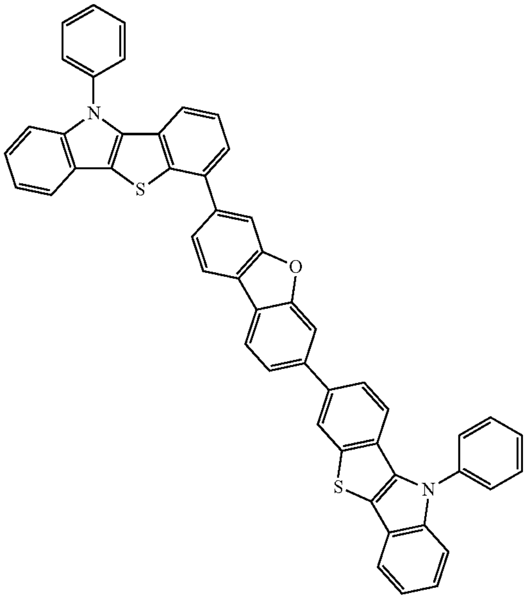
889
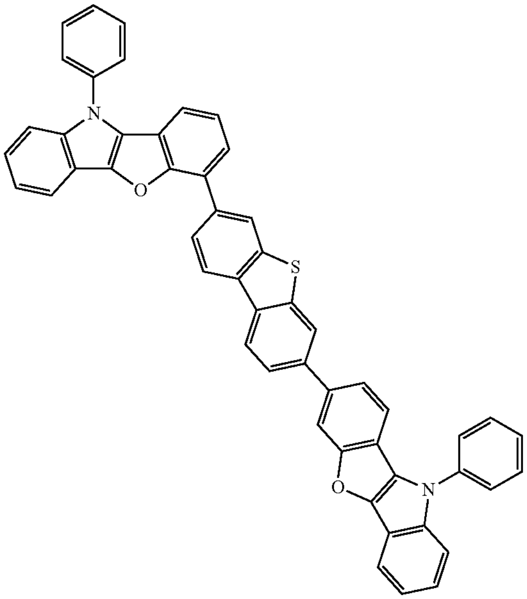
-continued
890
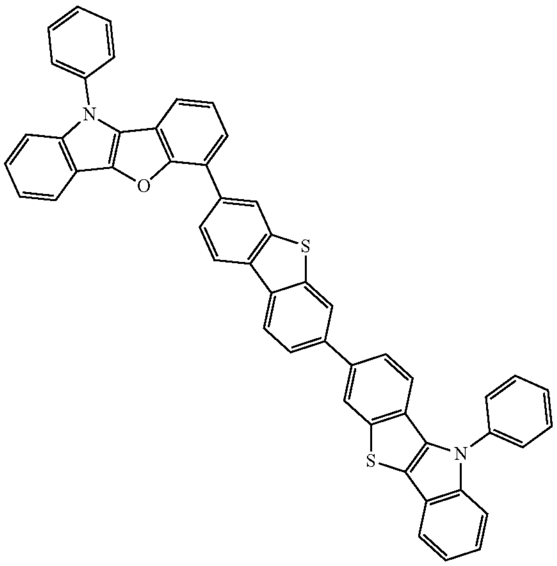
891
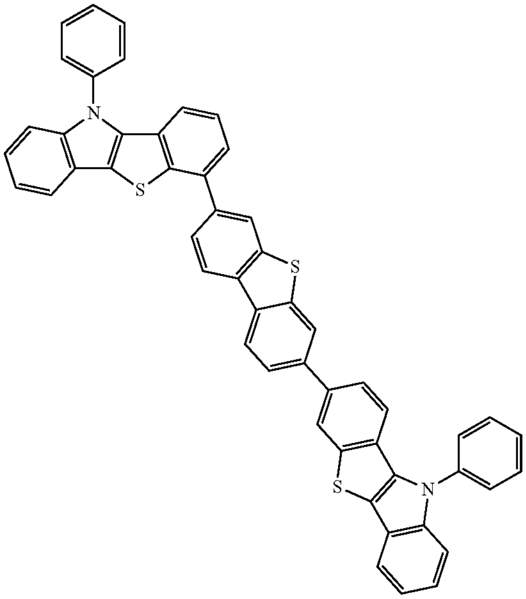
892
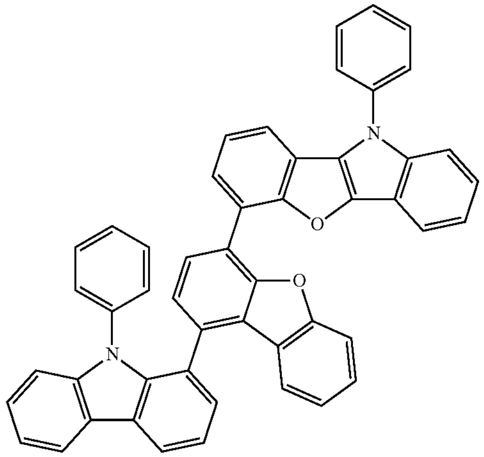

-continued
893
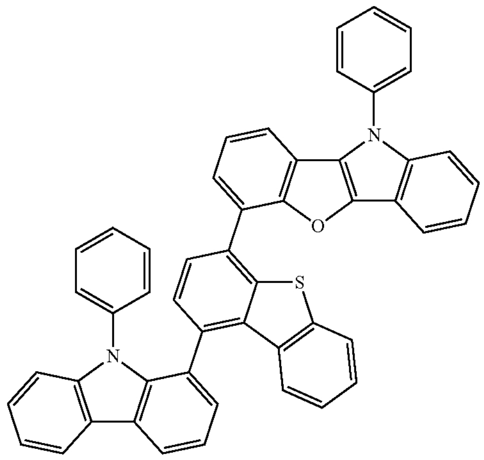
894
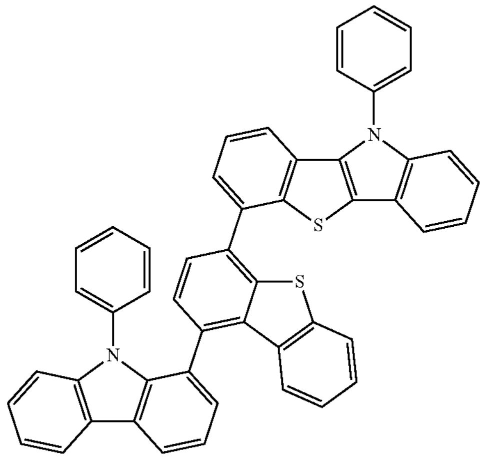
895
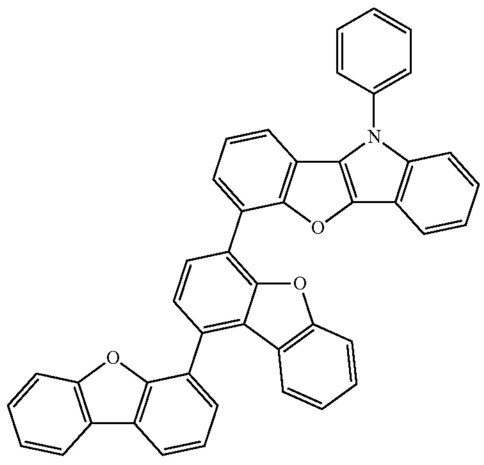
-continued
896
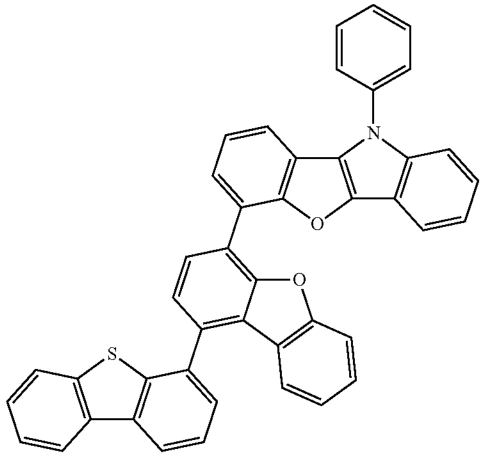
897
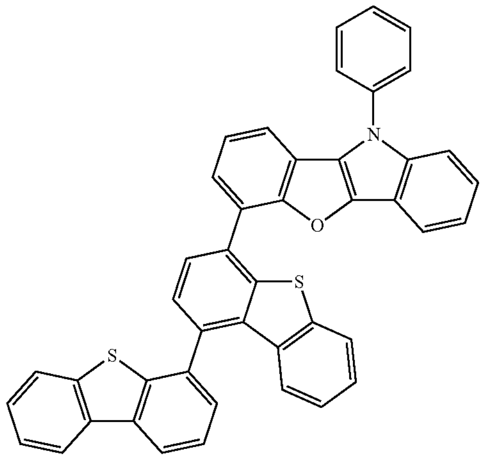
898
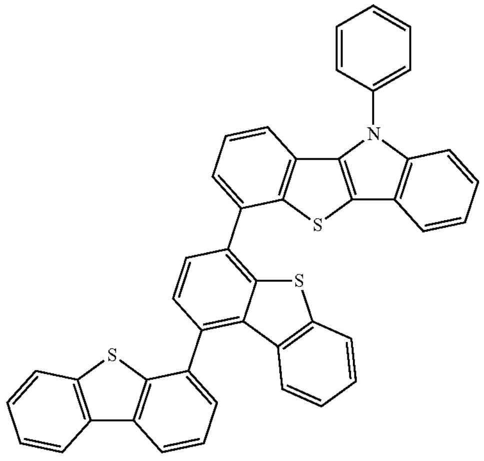

-continued
899
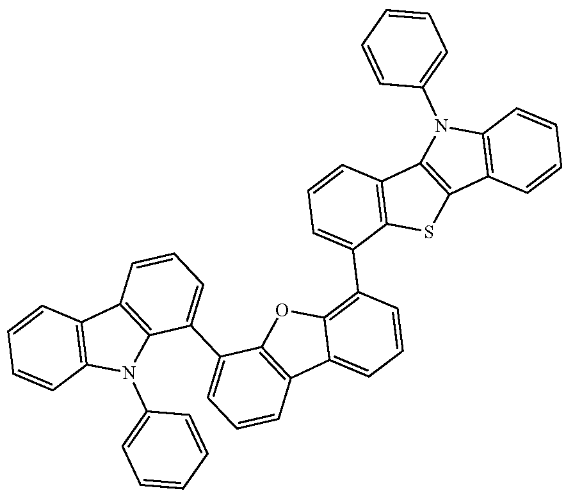
900
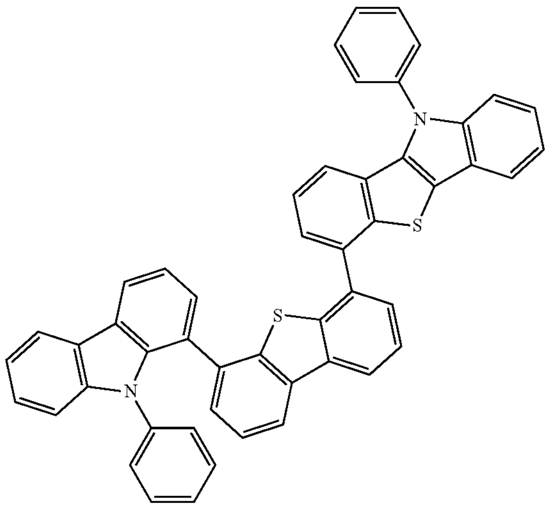
901
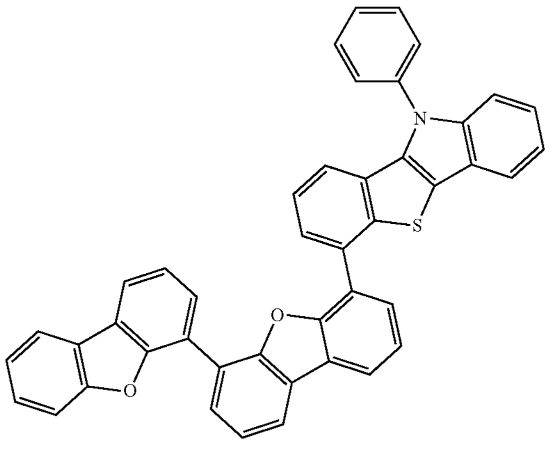
-continued
902
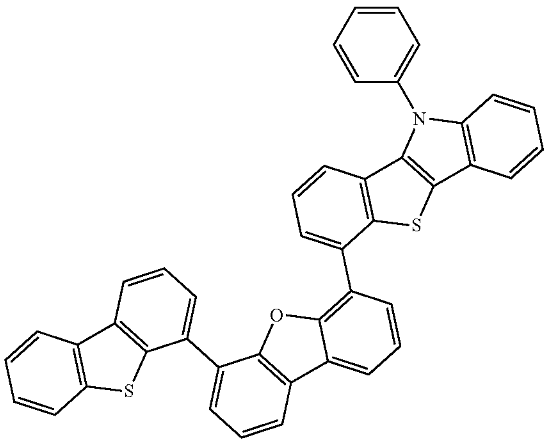
903
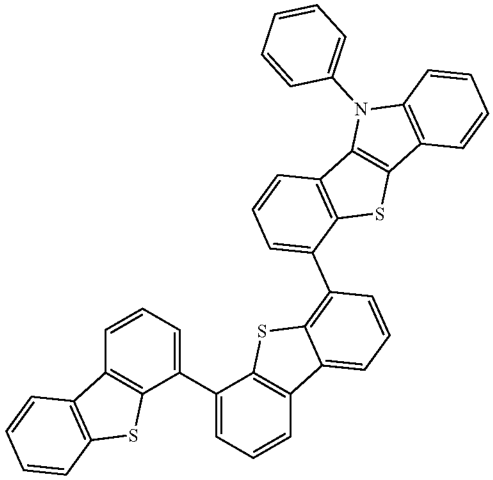
904
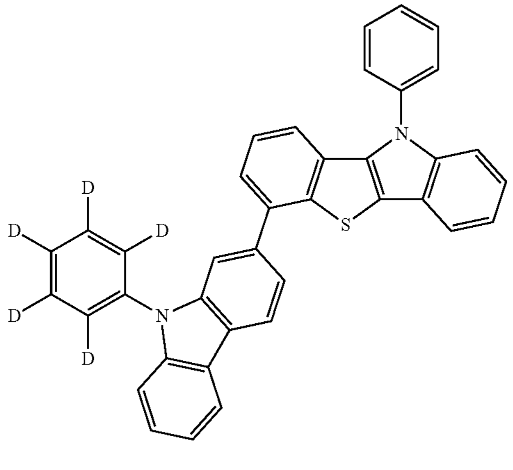

-continued

905

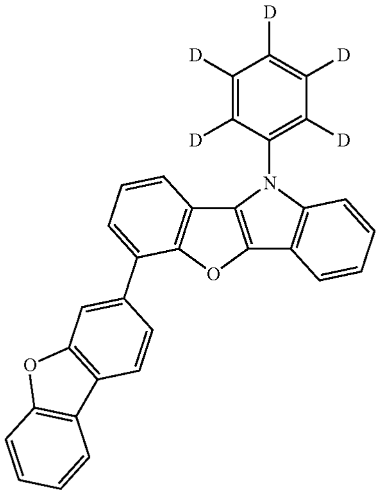

906

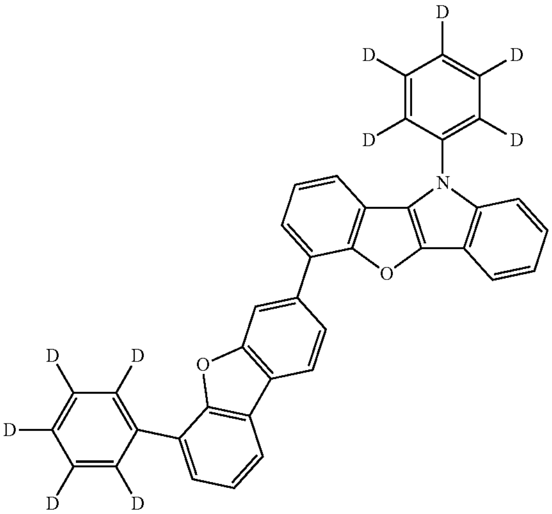

907

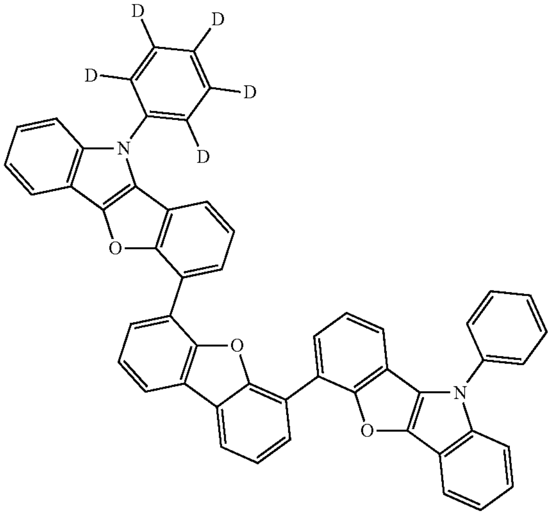

-continued

909

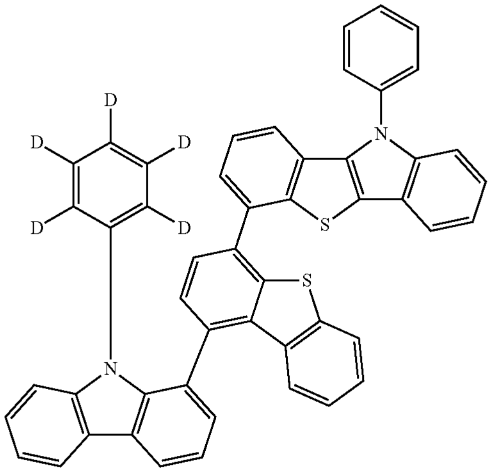

.

A luminescence device ED according to an embodiment will be further described with reference to FIGS. 3 to 6.

As described above, the hole transport region HTR includes a polycyclic compound according to an embodiment as described above. For example, the hole transport region HTR may include the polycyclic compound represented by Formula 1.

When the hole transport region HTR includes multiple layers, any of the layers may include a polycyclic compound represented by Formula 1. For example, in an embodiment, the hole transport region HTR may include a hole injection layer HIL disposed on the first electrode EL1 and a hole transport layer HTL disposed on the hole injection layer, wherein the hole transport layer HTL may include a polycyclic compound represented by Formula 1. However, embodiments are not limited thereto, and, for example, the hole injection layer HIL may include a polycyclic compound represented by Formula 1. For example, in another embodiment, the hole transport region HTR may include a hole transport layer HTL disposed on the first electrode EL1 and an electron blocking layer EBL disposed on the hole transport layer, wherein the electron blocking layer EBL may include a polycyclic compound represented by Formula 1.

The hole transport region HTR may include one or two or more of polycyclic compounds represented by Formula 1. For example, the hole transport region HTR may include at least one selected from Compound Groups 1 as described above.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may further include a compound represented by Formula H-1 below:

[Formula H-1]

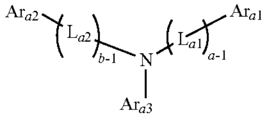

In Formula H-1 above, $L_{a1}$ and $L_{a2}$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula H-1, a-1 and b-1 may each independently be an integer from 0 to 10. In Formula H-1, when a-1 or b-1 is 2 or more, multiple $L_{a1}$ groups and multiple $L_{a2}$ groups may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_{a1}$ to $Ar_{a3}$ may each independently be a substituted or unsubstituted aryl group having 6 to 30 ring-forming carbon atoms, or a substituted or unsubstituted heteroaryl group having 2 to 30 ring-forming carbon atoms.

The compound represented by Formula H-1 above may be a monoamine compound. In another embodiment, the compound represented by Formula H-1 above may be a diamine compound in which at least one of $Ar_{a1}$ to $Ar_{a3}$ includes an amine group as a substituent. For example, the compound represented by Formula H-1 above may be a carbazole-based compound including a substituted or unsubstituted carbazole group in at least one of Arai and $Ar_{a2}$, or a fluorene-based compound including a substituted or unsubstituted fluorene group in at least one of $Ar_{a1}$ and $Ar_{a2}$.

The compound represented by Formula H-1 may be any one selected from the compounds of Compound Group H below. However, the compounds listed in Compound Group H below are examples, and the compounds represented by Formula H-1 are not limited to those listed in Compound Group H below:

[Compound Group H]

H-1-1

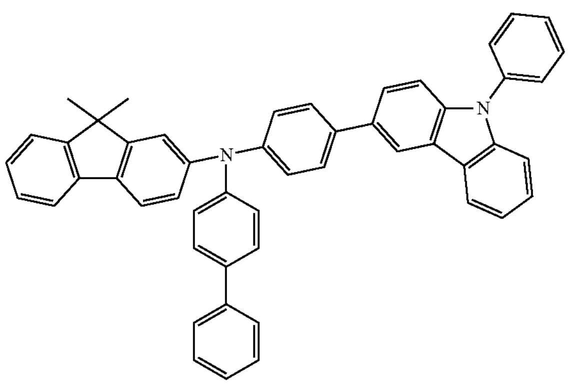

H-1-2

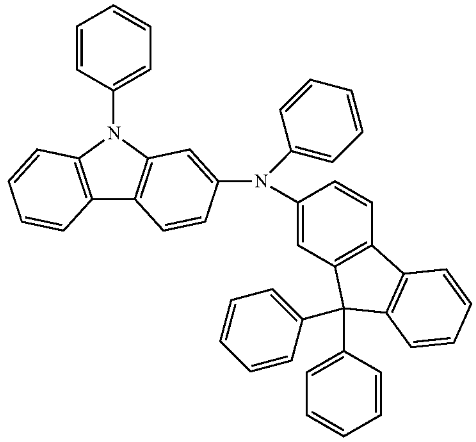

-continued

H-1-3

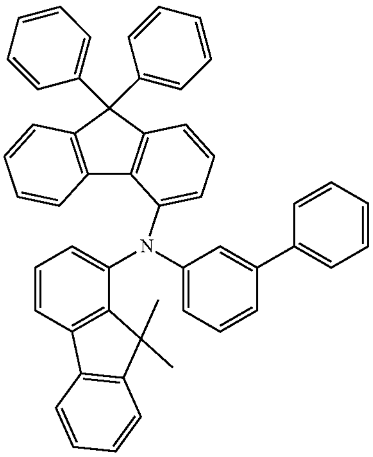

H-1-4

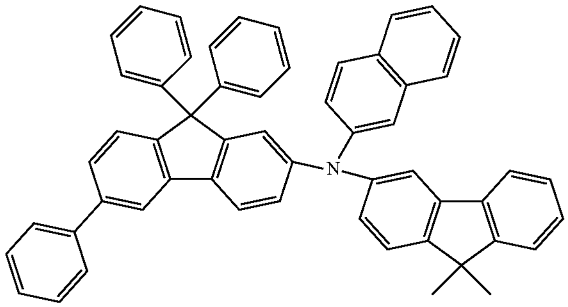

H-1-5

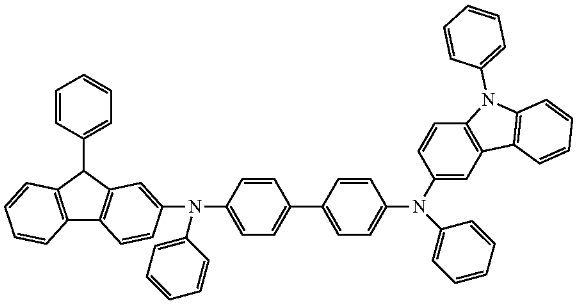

H-1-6

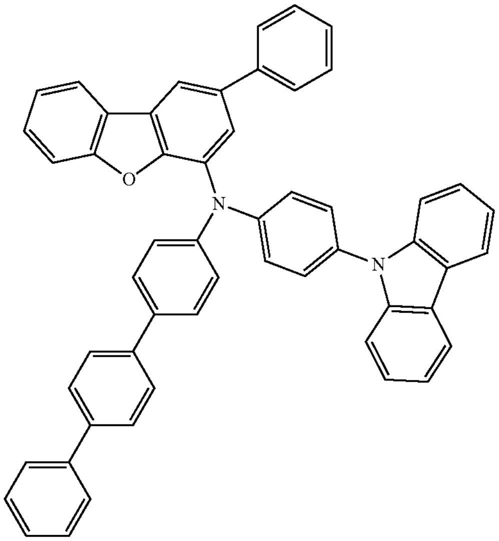

-continued
H-1-7
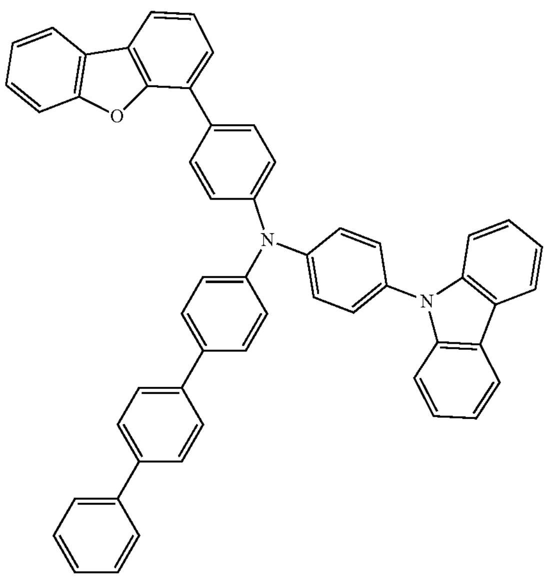
H-1-8
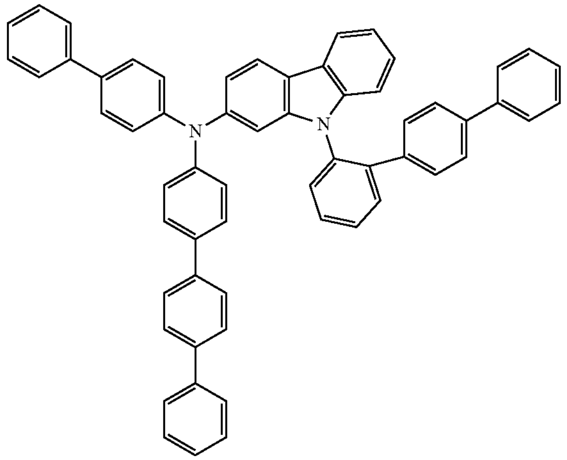
H-1-9
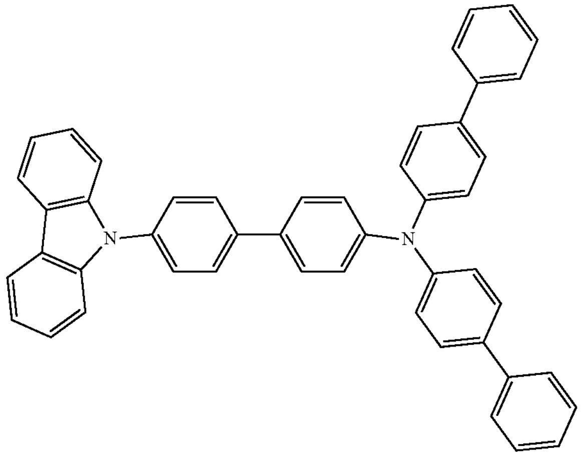
-continued
H-1-10
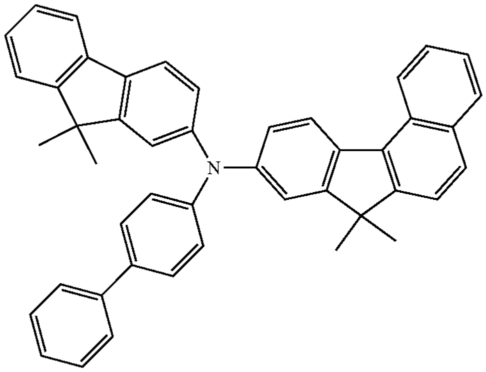
H-1-11
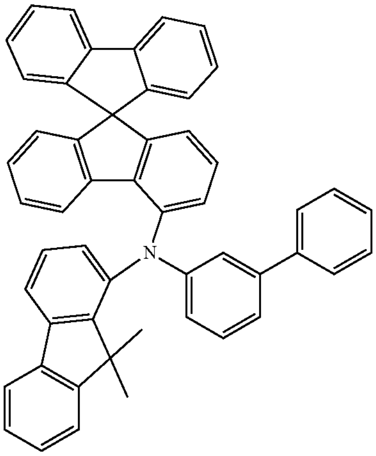
H-1-12
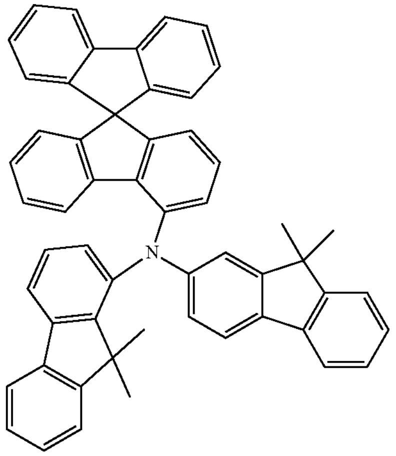
H-1-13
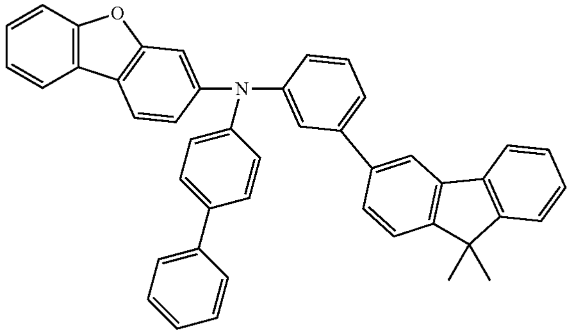

-continued

H-1-14

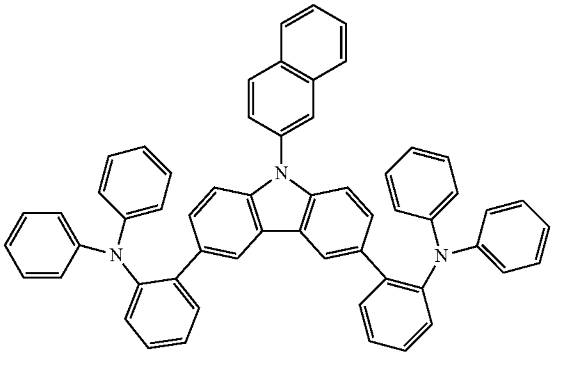

H-1-15

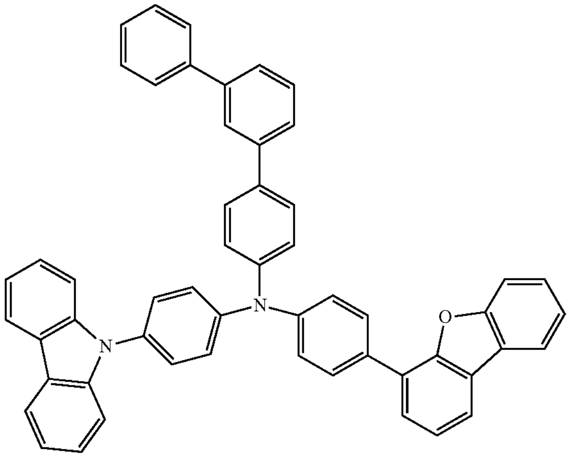

H-1-16

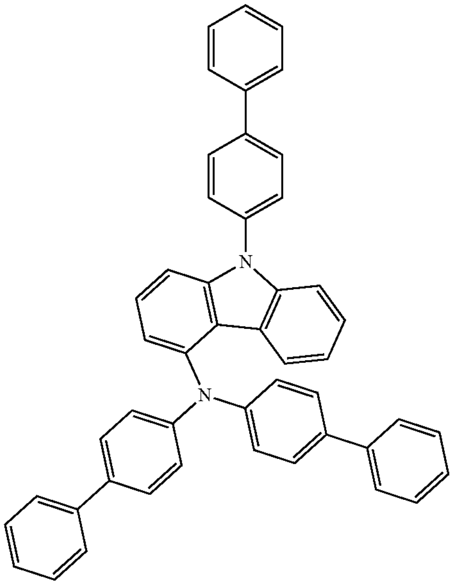

-continued

H-1-17

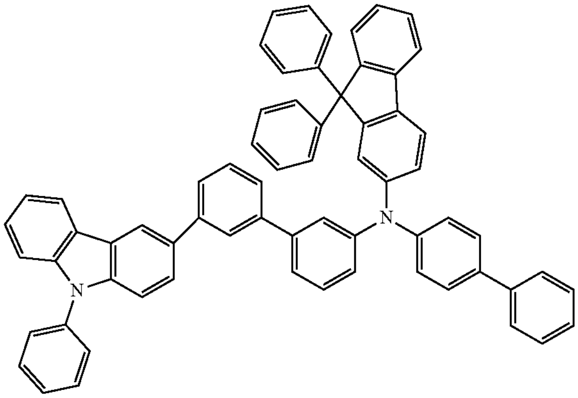

H-1-18

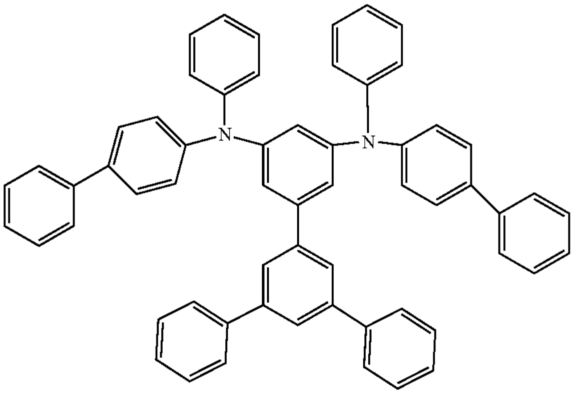

H-1-19

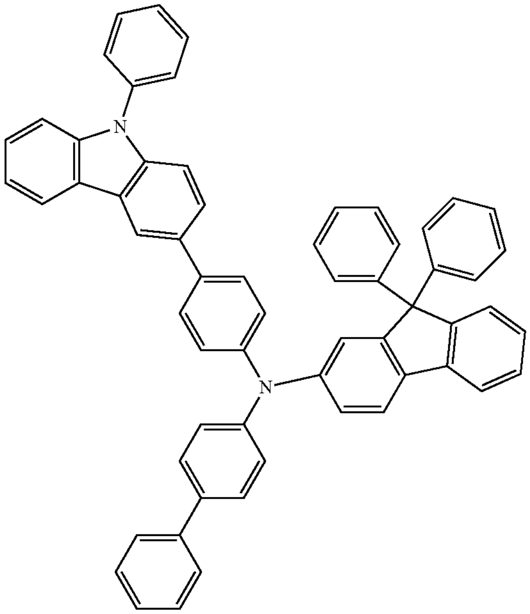

The hole transport region HTR may include a phthalocyanine compound such as copper phthalocyanine; $N^1$,$N^{1'}$-([1,1'-biphenyl]-4,4'-diyl)bis($N^1$-phenyl-$N^4$, $N^4$-di-m-tolyl-benzene-1,4-diamine) (DNTPD), 4,4',4"-[tris(3-methylphenyl)phenylamino]triphenylamine (m-MTDATA), 4,4'4"-tris(N,N-diphenylamino)triphenylamine (TDATA), 4,4',4"-tris[N(1-naphthyl)-N-phenylamino]-triphenylamine (1-TNATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl) borate], dipyrazino[2,3-f: 2',3'-h]quinoxaline-2,3,6,7,10,11-hexacarbonitrile (HATCN), etc.

The hole transport region HTR may include carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl) triphenylamine (TCTA), N,N'-di(naphthalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis (N-carbazolyl)benzene (mCP), etc.

The hole transport region HTR may further include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the above-described compound of the hole transport region in at least one of a hole injection layer HIL, a hole transport layer HTL, and an electron blocking layer EBL.

A thickness of the hole transport region HTR may be in a range of about 100 Å to about 10,000 Å. For example, the thickness of the hole transport region HTR may be in a range of about 100 Å to about 5,000 Å. A thickness of the hole injection layer HIL may be, for example, in a range of about 30 Å to about 1,000 Å, and a thickness of the hole transport layer HTL may be in a range of about 30 Å to about 1,000 Å. For example, a thickness of the electron blocking layer EBL may be in a range of about 10 Å to about 1,000 Å. If the thicknesses of the hole transport region HTR, the hole injection layer HIL, the hole transport layer HTL and the electron blocking layer EBL satisfy the above-described ranges, satisfactory hole transport characteristic may be achieved without a substantial increase in a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of quinone derivatives, metal oxides, and cyano group-containing compounds, but embodiments are not limited thereto. For example, non-limiting examples of the p-dopant may include quinone derivatives such as tetracyanoquinodimethane (TCNQ) and 2,3,5,6-tetrafluoro-7,7'8,8-tetracyanoquinodimethane (F4-TCNQ), metal oxides such as tungsten oxide and molybdenum oxide, etc., but embodiments are not limited thereto.

As described above, the hole transport region HTR may further include at least one of a hole buffer layer (not shown) and an electron blocking layer EBL in addition to the hole injection layer HIL and the hole transport layer HTL. The hole buffer layer (not shown) may compensate for a resonance distance according to a wavelength of light emitted from the emission layer EML, and may thus increase luminous efficiency. Materials which may be included in the hole transport region HTR may be used as materials to be included in the hole buffer layer (not shown). The electron blocking layer EBL may prevent electron injection from the electron transport region ETR to the hole transport region HTR.

The emission layer EML is provided on the hole transport region HTR. The emission layer EML may have a thickness, for example, in a range of about 100 Å to about 1,000 Å. For example, the emission layer EML may have a thickness in a range of about 100 Å to about 300 Å. The emission layer EML may have a layer formed of a single material, a layer formed of different materials, or a multilayer structure having layers formed of different materials.

In the luminescence device ED of an embodiment, the emission layer EML may include anthracene derivatives, pyrene derivatives, fluoranthene derivatives, chrysene derivatives, dihydrobenzanthracene derivatives, or triphenylene derivatives. For example, in an embodiment, the emission layer EML may include anthracene derivatives or pyrene derivatives.

In each luminescence device ED of embodiments illustrated in FIGS. 3 to 6, the emission layer EML may include a host and a dopant, and the emission layer EML may include a compound represented by Formula E-1 below. The compound represented by Formula E-1 below may be used as a fluorescence host material.

[Formula E-1]

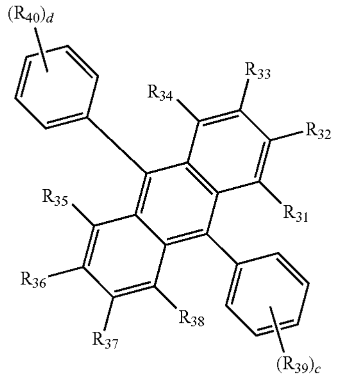

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula E-1, $R_{31}$ to $R_{40}$ may be bonded to an adjacent group to form a saturated hydrocarbon ring or an unsaturated hydrocarbon ring, a saturated heterocycle, or an unsaturated heterocycle.

In Formula E-1, c and d may each independently be an integer from 0 to 5.

The compound represented by Formula E-1 may be any one selected from Compound E1 to Compound E19 below:
E1
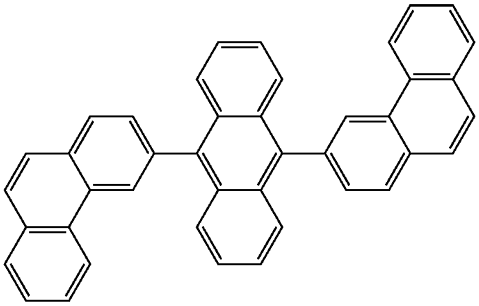
E2
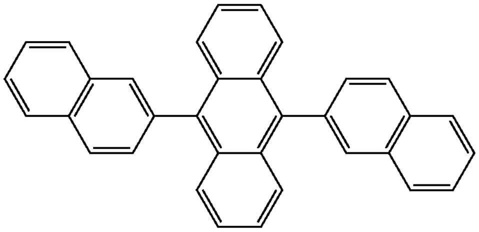
E3
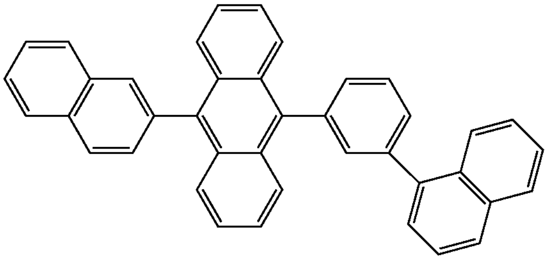
E4
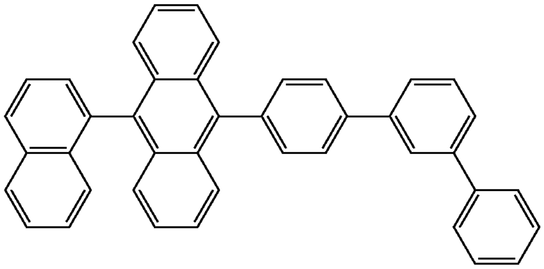
E5
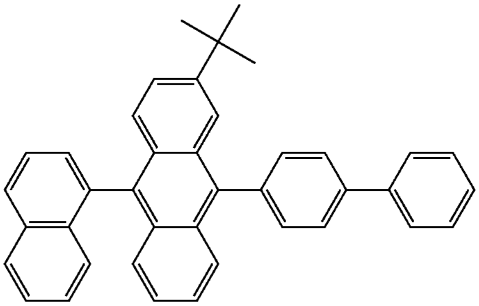
-continued
E6
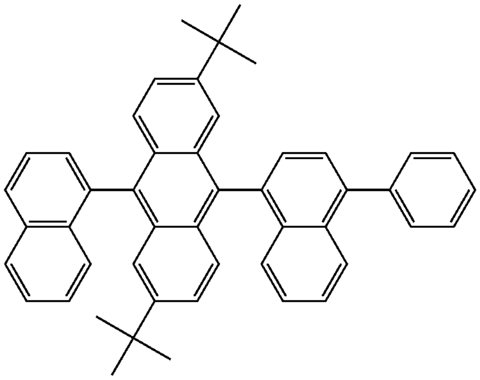
E7
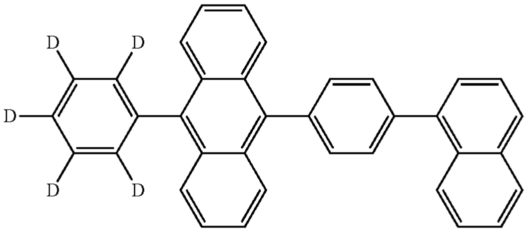
E8
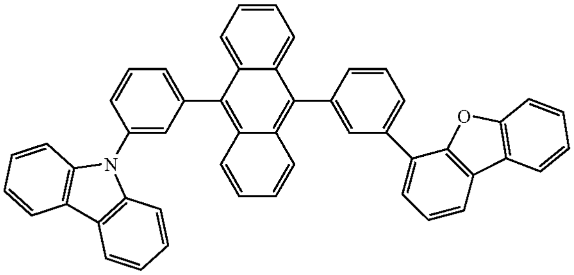
E9
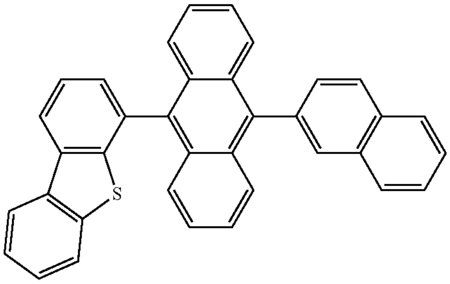
E10
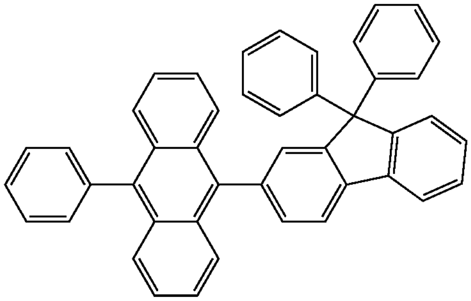

-continued
E11
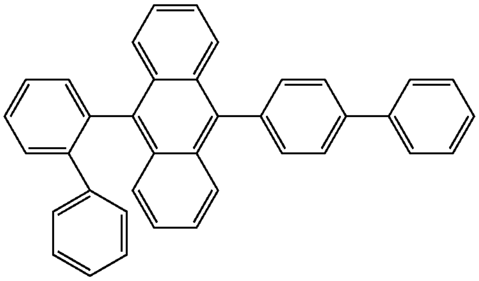
E12
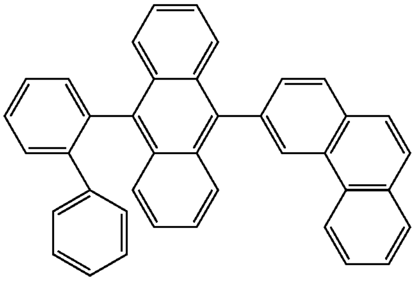
E13
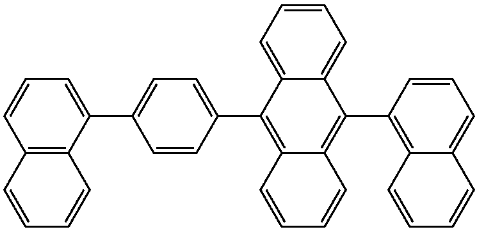
E14
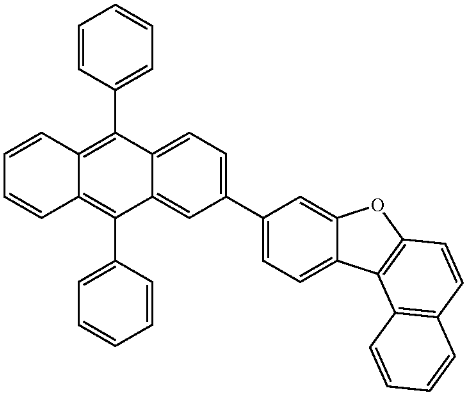
-continued
E15
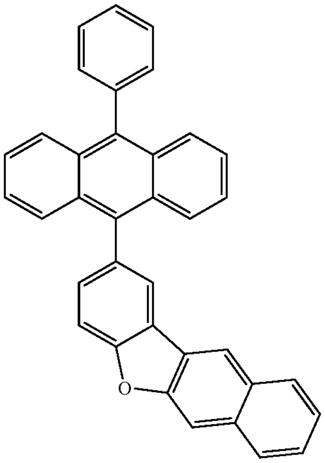
E16
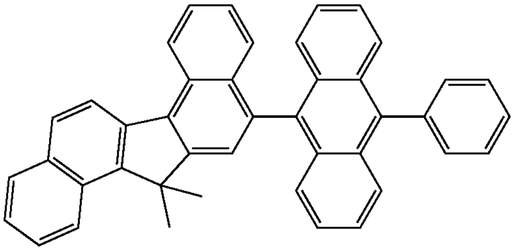
E17
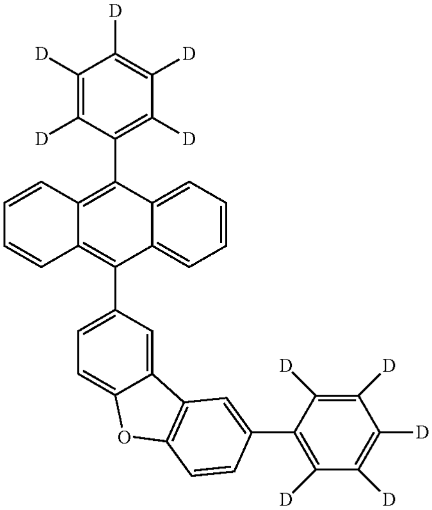
E18
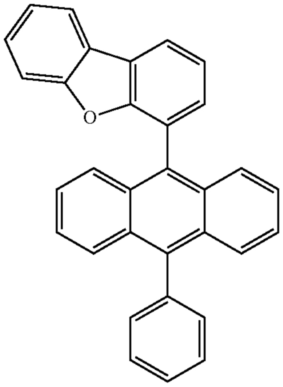

-continued

E19

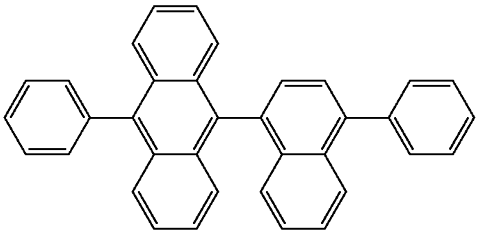

In an embodiment, the emission layer EML may include a compound represented by Formula E-2a or Formula E-2b below. The compound represented by Formula E-2a or Formula E-2b below may be used as a phosphorescence host material.

[Formula E-2a]

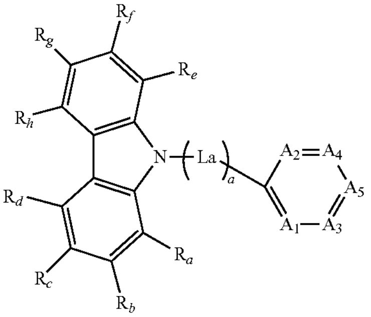

In Formula E-2a, a may be an integer from 0 to 10, $L_a$ may be a direct linkage, a substituted or unsubstituted arylene group having 6 to 30 ring-forming carbon atoms, or a substituted or unsubstituted heteroarylene group having 2 to 30 ring-forming carbon atoms. When a is 2 or more, multiple $L_a$ groups may each independently be a substituted or unsubstituted arylene group having 6 to 30 ring-forming carbon atoms, or a substituted or unsubstituted heteroarylene group having 2 to 30 ring-forming carbon atoms.

In Formula E-2a, $A_1$ to $A_5$ may each independently be N or $C(R_i)$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $R_a$ to $R_i$ may be bonded to an adjacent group to form a hydrocarbon ring or a heterocycle containing N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(Cbz1)\!-\!(L_b)_b\!-\!(Cbz2)$$

In Formula E-2b, Cbz1 and Cbz2 may each independently be an unsubstituted carbazole group, or a carbazole group substituted with an aryl group having 6 to 30 ring-forming carbon atoms. $L_b$ may be a direct linkage, a substituted or unsubstituted arylene group having 6 to 30 ring-forming carbon atoms, or a substituted or unsubstituted heteroarylene group having 2 to 30 ring-forming carbon atoms. In Formula E-2b, b may be an integer from 0 to 10. When b is 2 or more, multiple $L_b$ groups may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be any one selected from Compound Group E-2 below. However, the compounds listed in Compound Group E-2 below are only examples, and the compound represented by Formula E-2a or Formula E-2b is not limited to those listed in Compound Group E-2 below.

[Compound Group E-2]

E-2-1

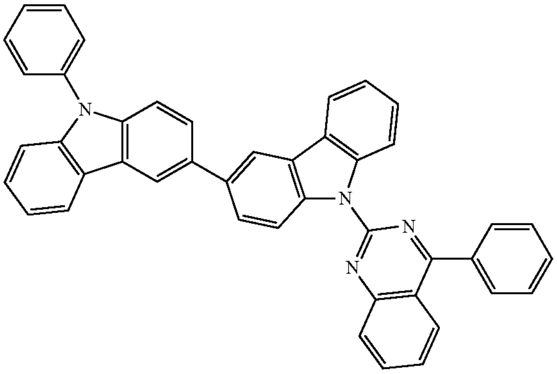

E-2-2

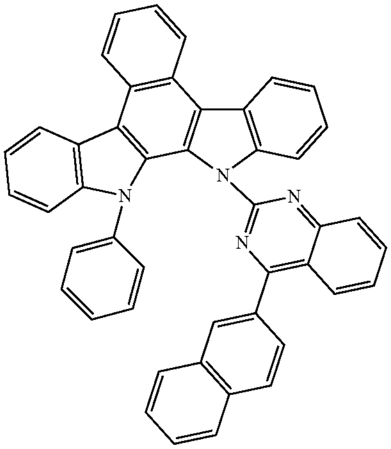

-continued
E-2-3
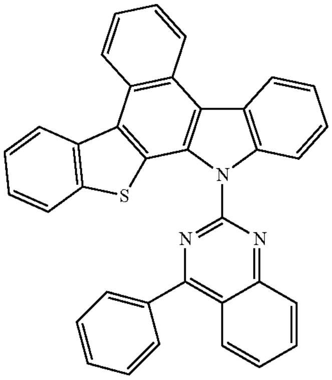
E-2-4
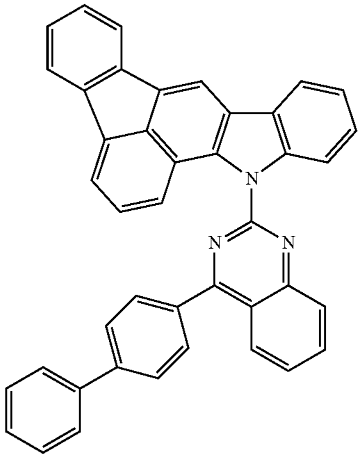
E-2-5
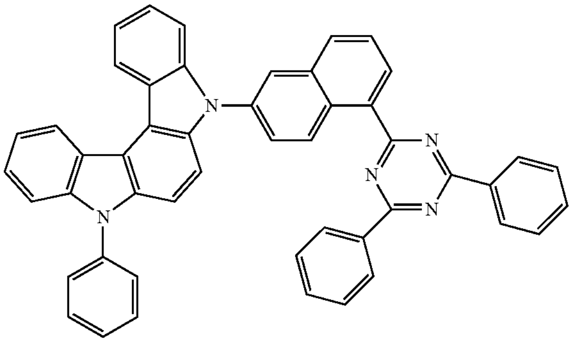
-continued
E-2-6
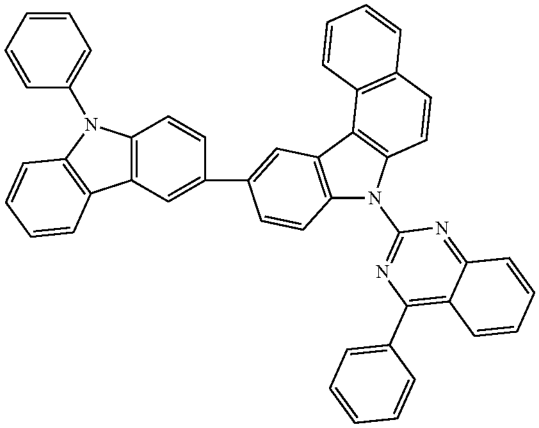
E-2-7
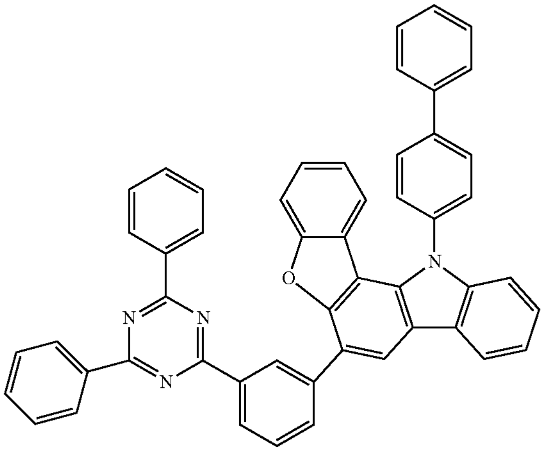
E-2-8
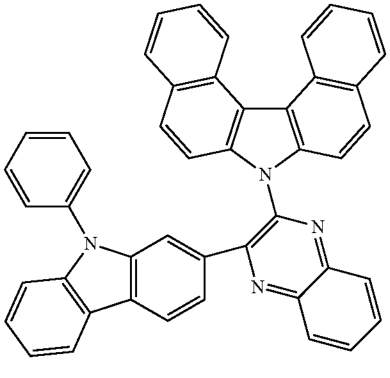

-continued
E-2-9
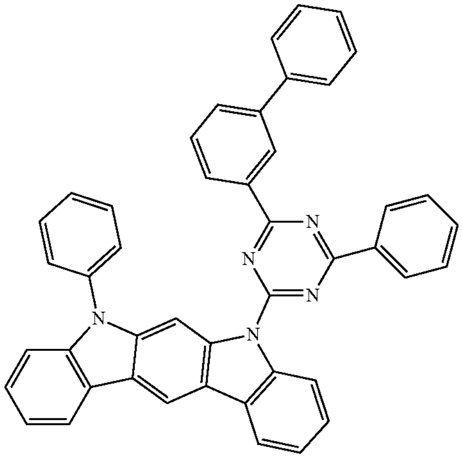
E-2-10
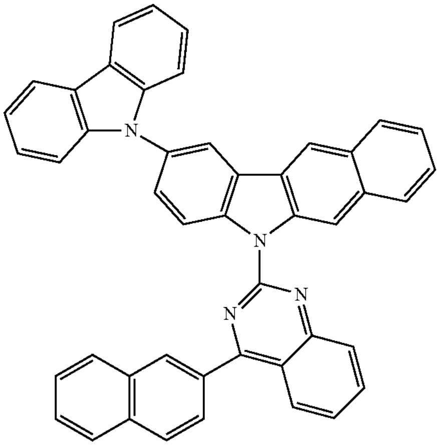
E-2-11
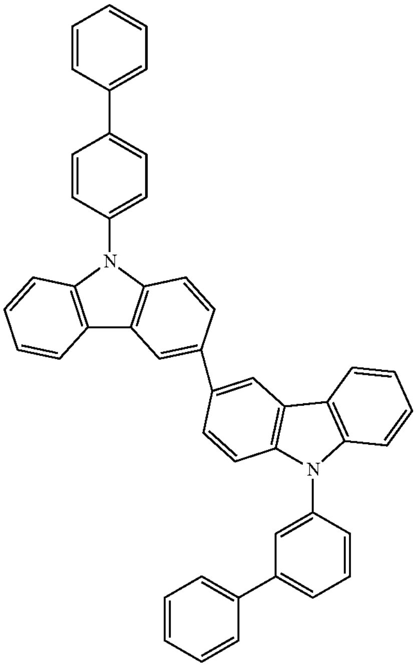
-continued
E-2-12
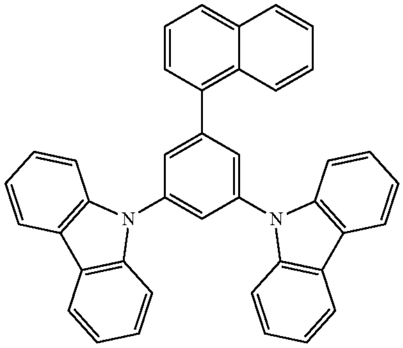
E-2-13
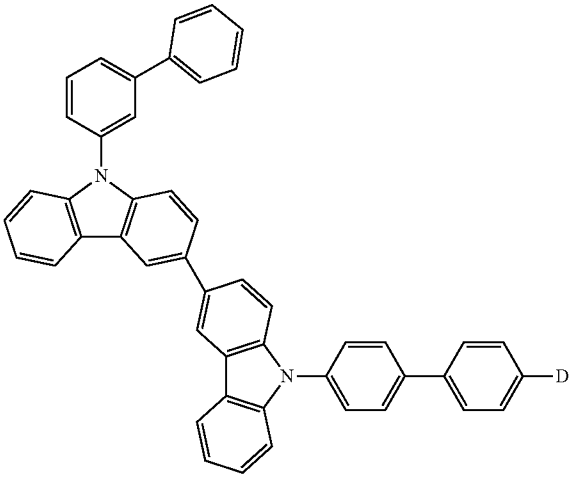
E-2-14
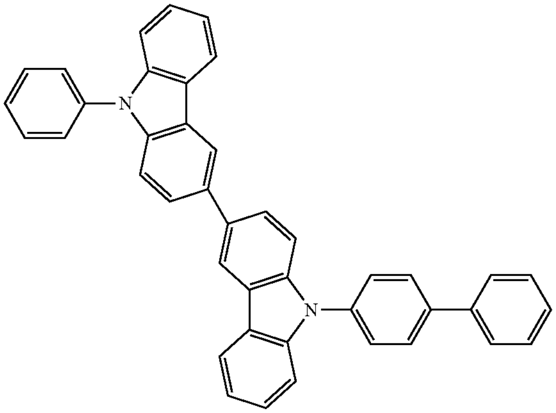
E-2-15
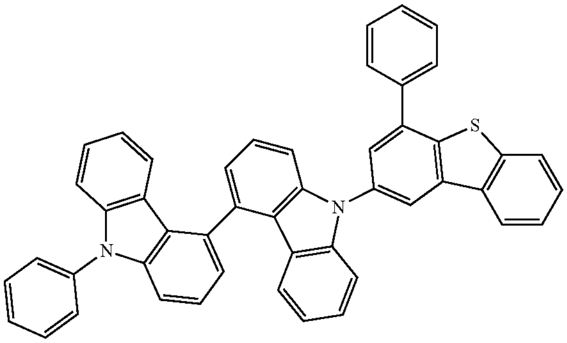

E-2-16
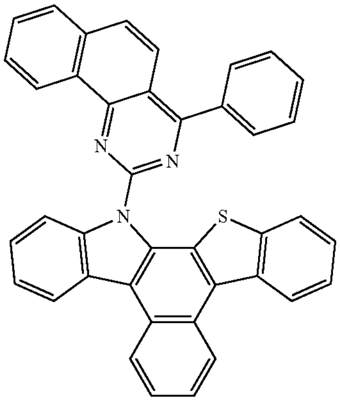
E-2-17
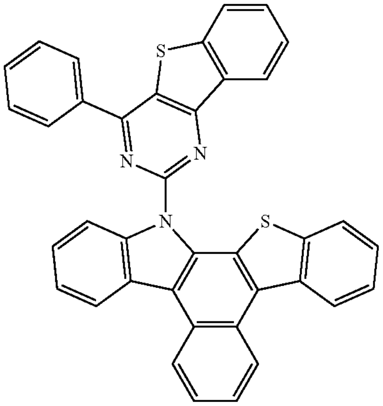
E-2-18
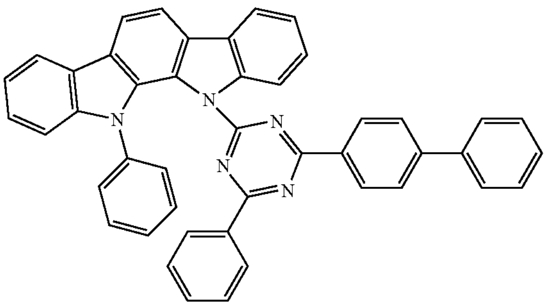
E-2-19
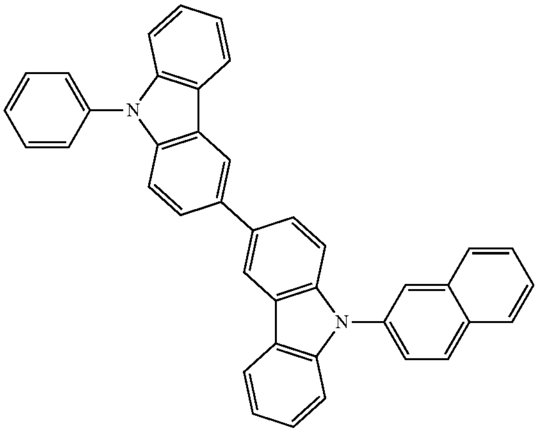
E-2-20
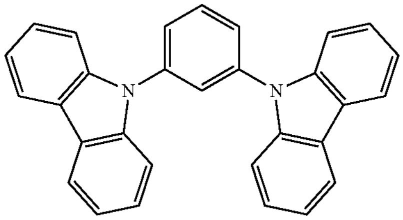
E-2-21
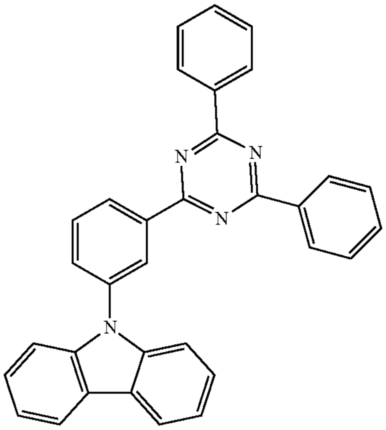
E-2-22
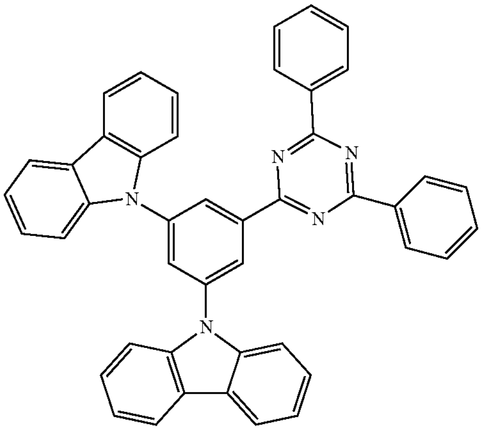
E-2-23
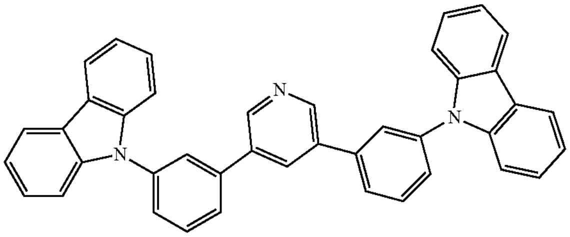

-continued

E-2-24

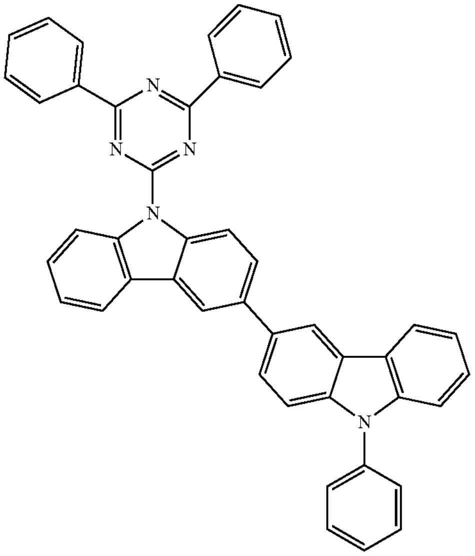

The emission layer EML may further include a general material in the art as a host material. For example, the emission layer EML may include, as a host material, at least one of bis[2-(diphenylphosphino)phenyl] ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), and 1,3,5-tris(1-phenyl-1H-benzo[d]imidazole-2-yl)benzene (TPBi). However, embodiments are not limited thereto, and for example, tris(8-hydroxyquinolino)aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be used as a host material.

The emission layer EML may include a compound represented by Formula M-a or Formula M-b below. The compound represented by Formula M-a or Formula M-b below may be used as a phosphorescence dopant material.

[Formula M-a]

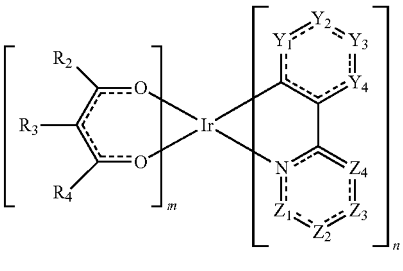

In Formula M-a above, $Y_1$ to $Y_4$ and $Z_1$ to $Z_4$ may each independently be $C(R_1)$ or N, $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a phosphorescence dopant.

The compound represented by Formula M-a may be any one selected from Compound M-a1 to Compound M-a25 below. However, Compounds M-a1 to M-a25 below are examples, and the compound represented by Formula M-a is not limited to Compounds M-a1 to M-a25 below.

M-a1

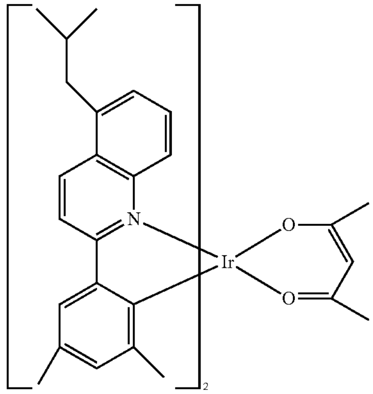

M-a2

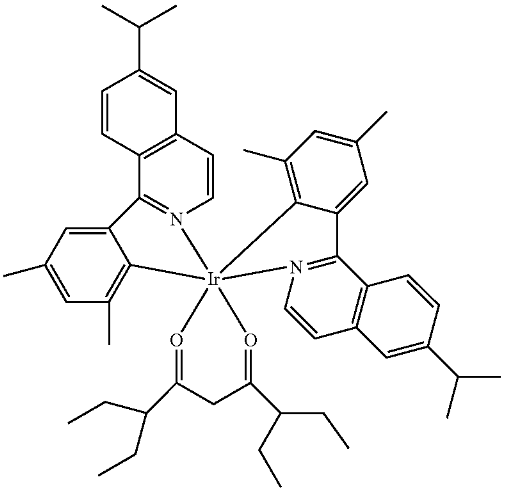

M-a3

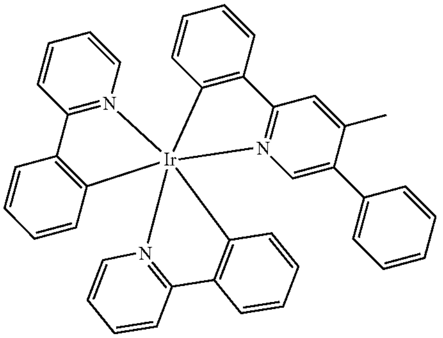

-continued
M-a4
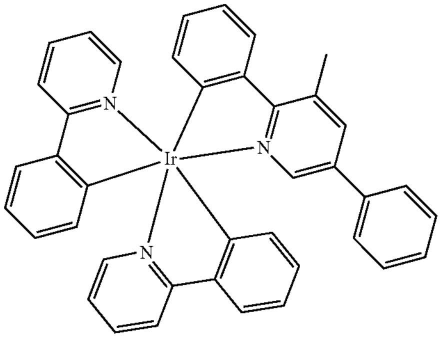
M-a5
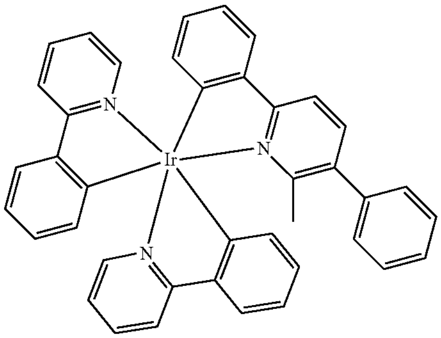
M-a6
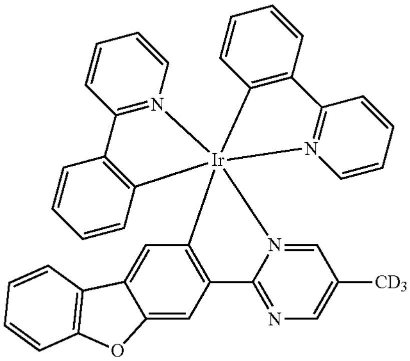
M-a7
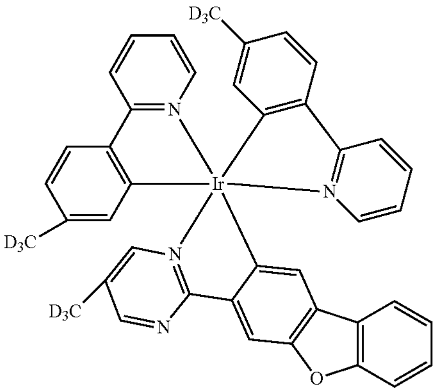
-continued
M-a8
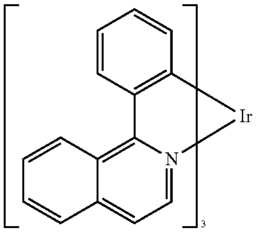
M-a9
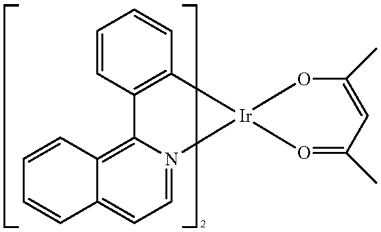
M-a10
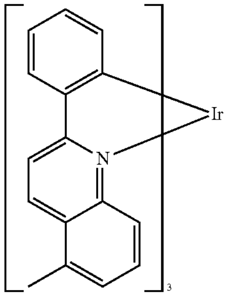
M-a11
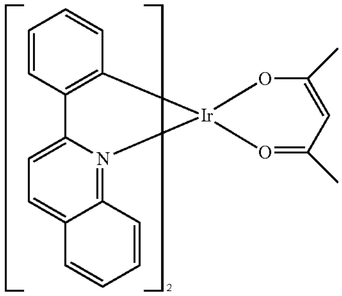
M-a12
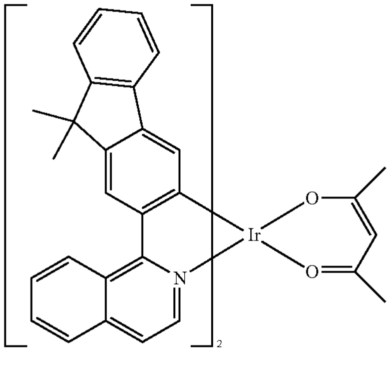

M-a13
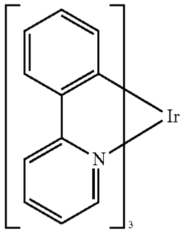
M-a14
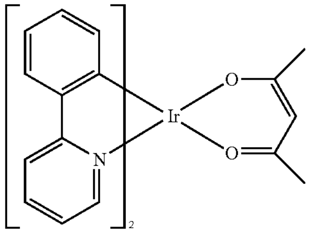
M-a15
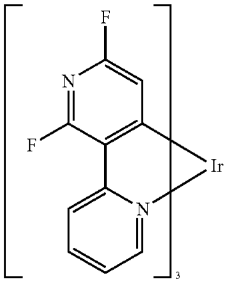
M-a16
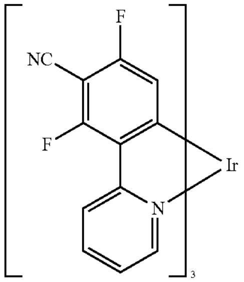
M-a17
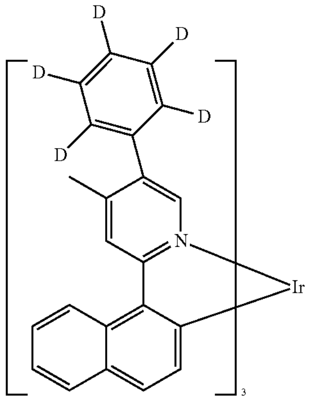
M-a18
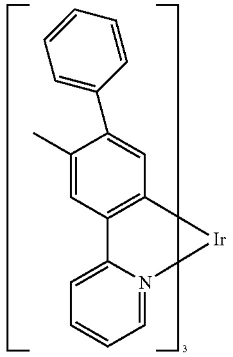
M-a19
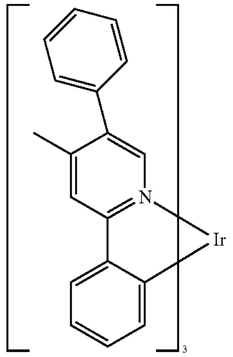
M-a20
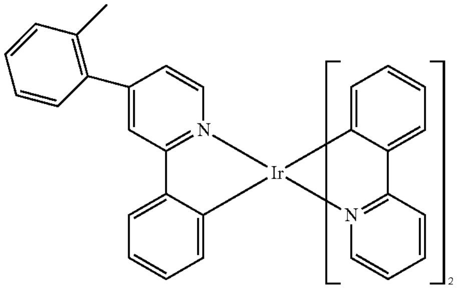
M-a21
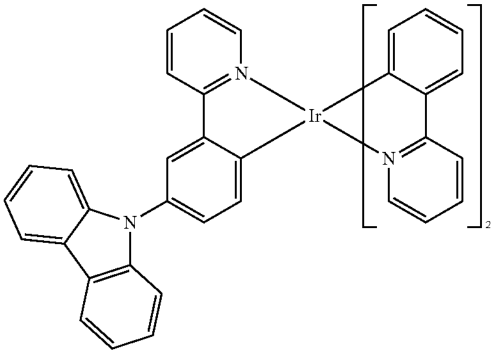

-continued

M-a22

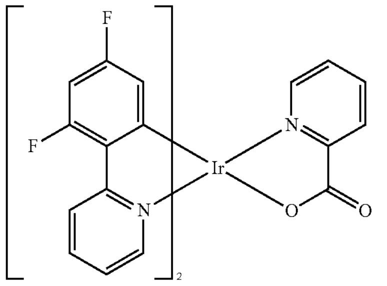

M-a23

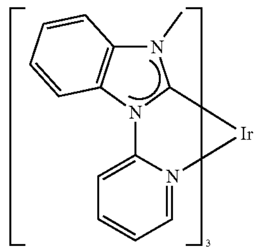

M-a24

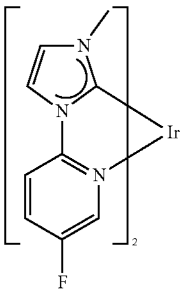

M-a25

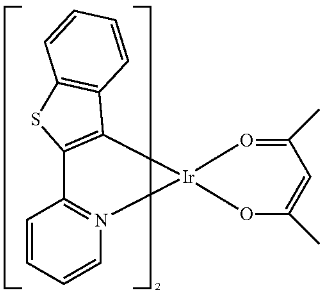

Compound M-a1 and Compound M-a2 may be used as a red dopant material, and Compound M-a3 and Compound M-A4 may be used as a green dopant material.

[Formula M-b]

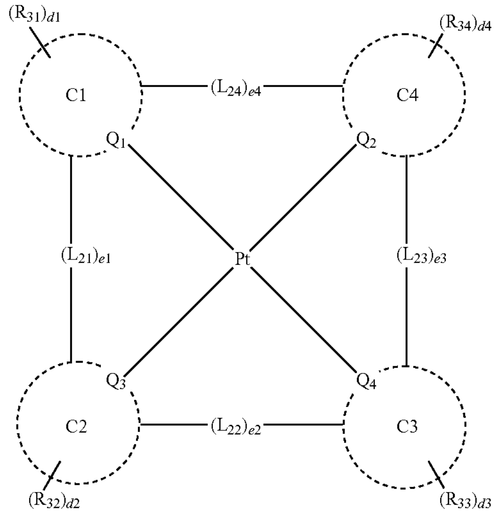

In Formula M-b, $Q_1$ to $Q_4$ may each independently be C or N, and C1 to C4 may each independently be a substituted or unsubstituted hydrocarbon ring having 5 to 30 ring-forming carbon atoms, or a substituted or unsubstituted heterocycle having 2 to 30 ring-forming carbon atoms. In Formula M-b, $L_{21}$ to $L_{24}$ may each independently be a direct linkage,

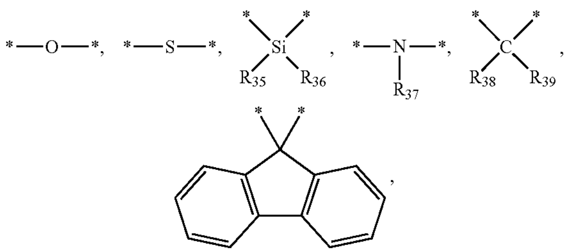

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. In Formula M-b, $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be any one selected from the compounds below. However, the compounds below are examples, and the compound represented by Formula M-b is not limited to the compounds below.

-continued
M-b-1
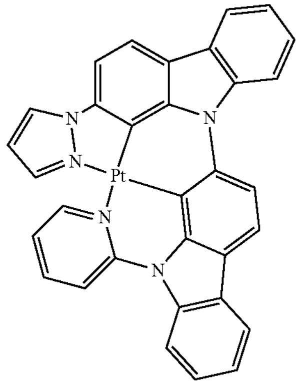
M-b-2
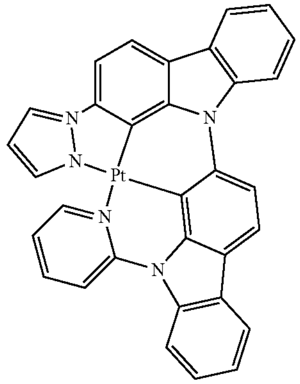
M-b-3
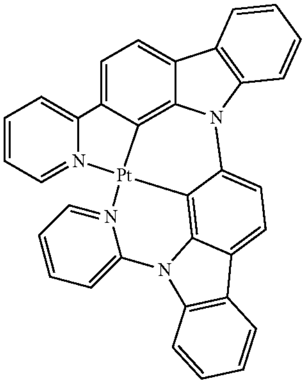
M-b-4
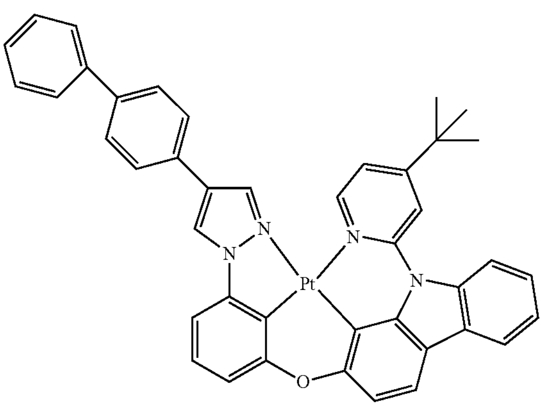
M-b-5
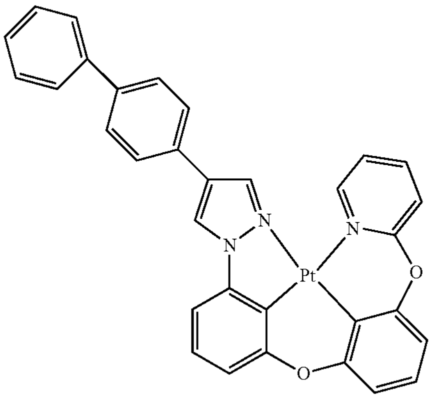
M-b-6
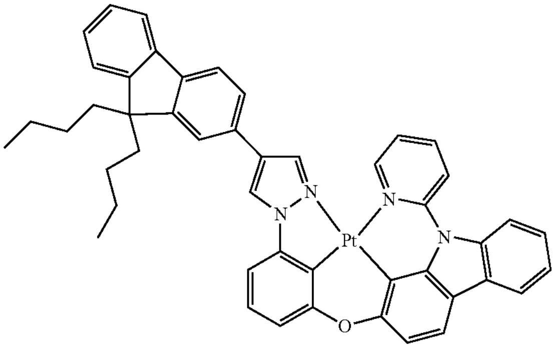
M-b-7
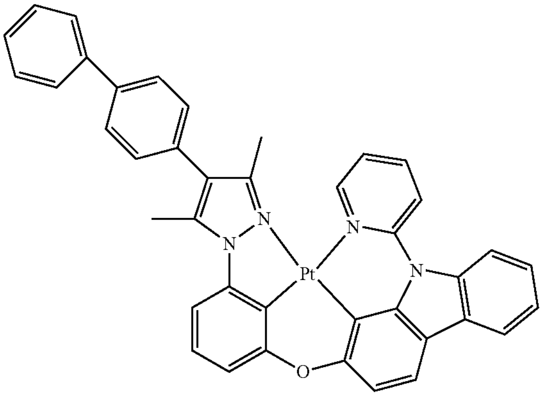
M-b-8
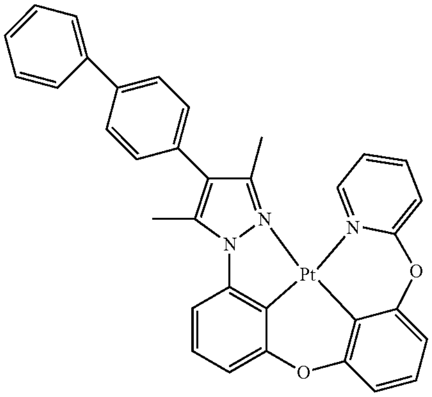

-continued

M-b-9

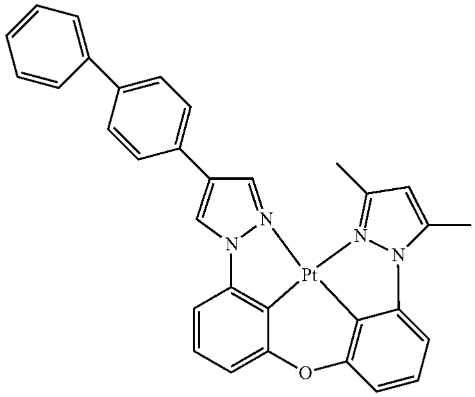

M-b-10

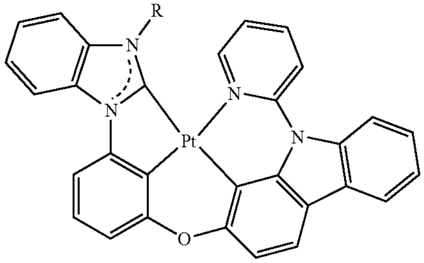

M-b-11

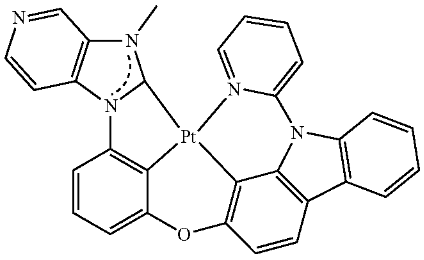

M-b-12

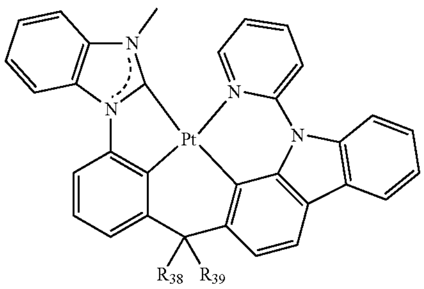

In the compounds, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one of Formula F-a to Formula F-c below. The compound represented by Formula F-a to Formula F-c below may be used as a fluorescence dopant material.

[Formula F-a]

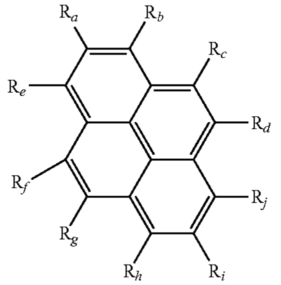

In Formula F-a, two selected from $R_a$ to $R_j$ may each independently be substituted with $$*—NAr_1Ar_2.$$

The remainder of $R_a$ to $R_j$ which are not substituted with $$*—NAr_1Ar_2$$

may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In the group $$*—NAr_1Ar_2,$$

$Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ and $Ar_2$ may be a heteroaryl group containing O or S as a ring-forming atom.

[Formula F-b]

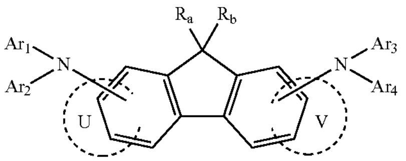

In Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-b, U and V may each independently be 0 or 1. If Formula F-b, U indicates the number of rings fused at the position of U, and V indicates the number of rings fused at the position of V. For example, when U or V is 1, a ring indicated by U or V may form a condensed ring, and when U or V is 0, a ring indicated by U or V may not be present. When U is 0 and V is 1, or when U is 1 and V is 0, the condensed ring having a fluorene core of Formula F-b may be a four-ring cyclic compound. When both U and V are 0, the condensed ring of Formula F-b may be a three-ring cyclic compound. When both U and V are 1, the condensed ring having a fluorene core of Formula F-b may be a five-ring cyclic compound.

In Formula F-b, when U or V is 1, U and V may each independently be a substituted or unsubstituted hydrocarbon ring having 5 to 30 ring-forming carbon atoms, or a substituted or unsubstituted heterocycle having 2 to 30 ring-forming carbon atoms.

[Formula F-c]

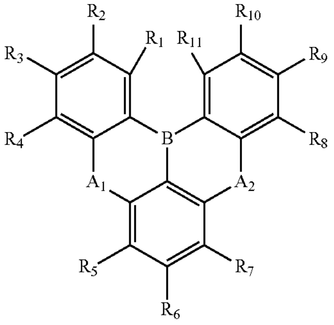

In Formula F-c, $A_1$ and $A_2$ may each independently be O, S, Se, or $N(R_m)$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-c, $A_1$ and $A_2$ may each independently be bonded to substituents of an adjacent ring to form a condensed ring. For example, when $A_1$ and $A_2$ are each independently $N(R_m)$, $A_1$ may be bonded to $R_4$ or $R_5$ to form a ring. For example, $A_2$ may be bonded to $R_7$ or $R_8$ to form a ring.

In an embodiment, the emission layer EML may include, as dopant materials, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), etc.

The emission layer EML may include a phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), or thulium (Tm) may be used as a phosphorescence dopant. For example, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as a phosphorescence dopant. However, embodiments are not limited thereto.

The emission layer EML may include a quantum dot material. The quantum dot may be selected from among a Group II-VI compound, a Group III-VI compound, a Group I-III-VI compound, a Group III-V compound, a Group III-II-V compound, a Group IV-VI compound, a Group IV element, a Group IV compound, and a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and $In_2Se_3$, a ternary compound such as $InGaS_3$ and $InGaSe_3$, or any combination thereof.

A Group I-III-VI compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, or a quaternary compound such as $AgInGaS_2$ and $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, or a quaternary compound may be present in particles at a uniform concentration distribution, or may be present in the same particle at a partially different concentration distribution. In an embodiment, the quantum dot may have a core/shell structure in which one quantum dot surrounds another quantum dot. An interface between the core and the shell may have a concentration gradient in which the concentration of an element that is present in the shell decreases towards the core.

In embodiments, a quantum dot may have the above-described core-shell structure including a core containing nanocrystals and a shell surrounding the core. The shell of the quantum dot may be a protection layer that prevents the chemical deformation of the core so as to maintain semiconductor properties, and/or may be a charging layer to impart electrophoresis properties to the quantum dot. The shell may be a single layer or a multilayer.

An example of the shell of the quantum dot may include a metal or non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $CO_3O_4$, and NiO, or a ternary compound such as $MgAl_2O_4$, $CoFe_2O_4$, $NiFe_2O_4$, and $CoMn_2O_4$, but embodiments are not limited thereto.

The semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of a light emission wavelength spectrum equal to or less than about 45 nm. For example, the quantum dot may have a FWHM of a light emission wavelength spectrum equal to or less than about 40 nm. For example, the quantum dot may have a FWHM of a light emission wavelength spectrum equal to or less than about 30 nm. Color purity and/or color reproducibility may be improved in the above ranges. Light emitted through such a quantum dot may be emitted in all directions, and thus a wide viewing angle may be improved.

The form of a quantum dot is not particularly limited and may be a form commonly used in the art. For example, a quantum dot may have a spherical, a pyramidal, a multi-arm, or a cubic shape, or the quantum dot may be in the form of nanoparticles, nanotubes, nanowires, nanofibers, nanoparticles, etc.

The quantum dot may control the color of emitted light according to the particle size thereof. Accordingly, the quantum dot may have various light emission colors such as blue, red, and green.

In each luminescence device ED of embodiments illustrated in FIGS. 3 to 6, the electron transport region ETR is provided on the emission layer EML. The electron transport region ETR may include at least one of a hole blocking layer HBL, an electron transport layer ETL, or an electron injection layer EIL, but embodiments are not limited thereto.

The electron transport region ETR may have a layer formed of a single material, a layer formed of different materials, or a multilayer structure including layers formed of different materials.

For example, the electron transport region ETR may have a single layer structure of the electron injection layer EIL or the electron transport layer ETL, and may have a single layer structure formed of an electron injection material and an electron transport material. In embodiments, the electron transport region ETR may have a single layer structure formed of different materials, or may have a structure in which an electron transport layer ETL/an electron injection layer EIL, or a hole blocking layer HBL/an electron transport layer ETL/an electron injection layer EIL are stacked in order from the emission layer E-L, but embodiments are not limited thereto. The electron transport region ETR may have a thickness, for example, in a range of about 1,000 Å to about 1,500 Å.

The electron transport region ETR may be formed by using various methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1 below:

[Formula ET-1]

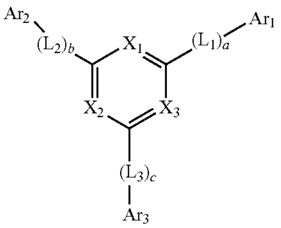

In Formula ET-1, at least one of $X_1$ to $X_3$ may be N, and the remainder of $X_1$ to $X_3$ may be $C(R_a)$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula ET-1, $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula ET-1, when a to c are 2 or more, $L_1$ to $L_3$ may each independently be a substituted or unsubstituted arylene group having 6 to 30 ring-forming carbon atoms, or a substituted or unsubstituted heteroarylene group having 2 to 30 ring-forming carbon atoms.

When the electron transport region ETR includes an electron transport layer ETL, the electron transport region ETR may include an anthracene-based compound. However, embodiments are not limited thereto, and the electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebg_2$), 9,10-di(naphthalene-2-yl)anthracene (ADN), 1,3-bis[3,5-di(pyridin-3-yl)phenyl]benzene (BmPyPhB), or a mixture thereof.
The electron transport region ETR may include at least one selected from Compound ET1 to Compound ET36 below:
ET1
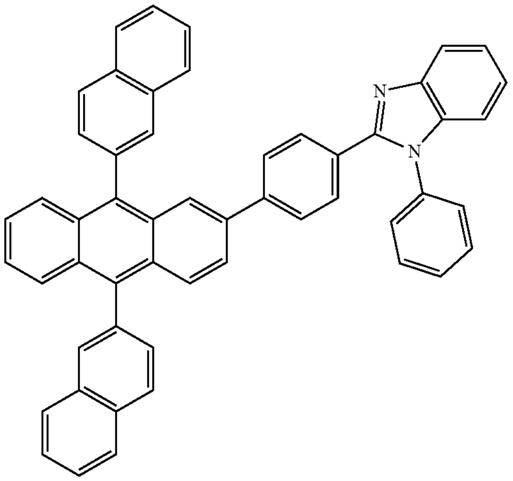
ET2
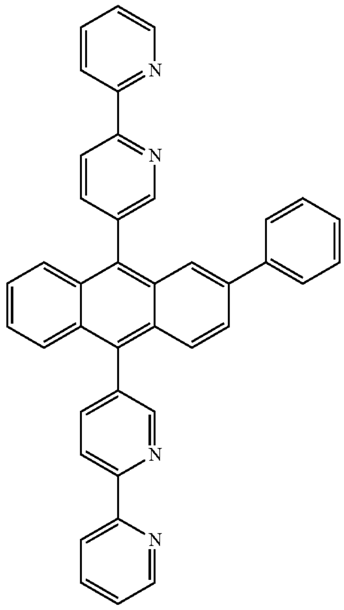
-continued
ET3
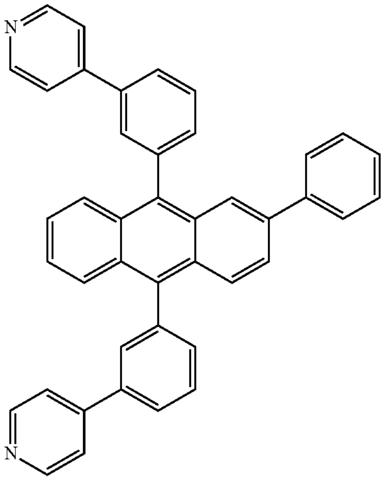
ET4
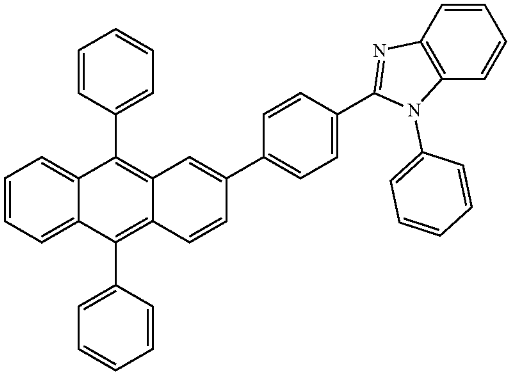
ET5
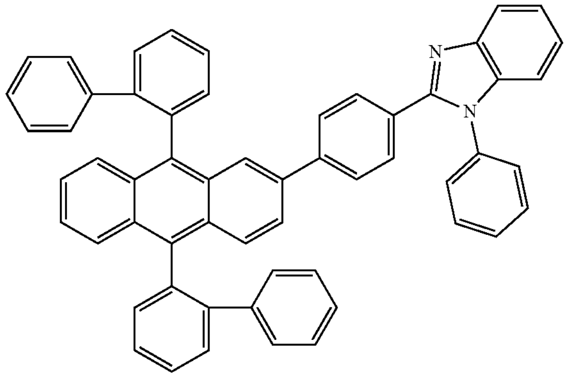
ET6
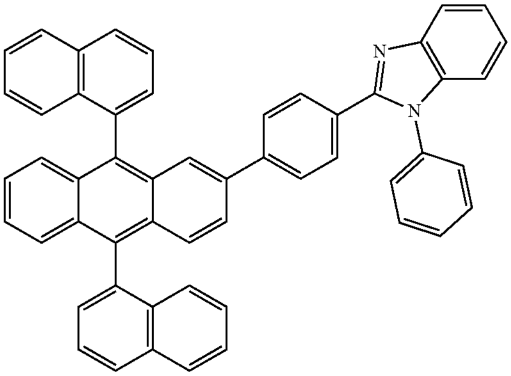

-continued
ET7
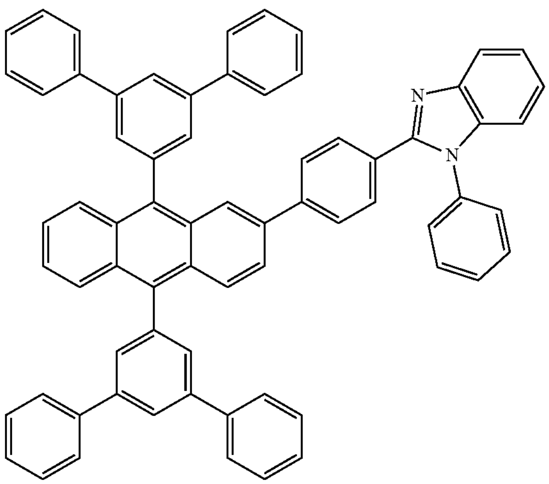
ET8
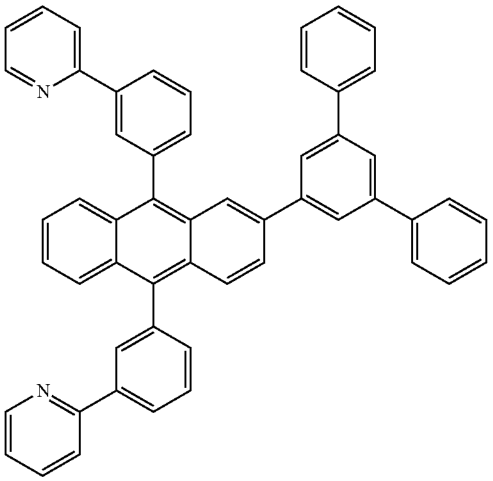
ET9
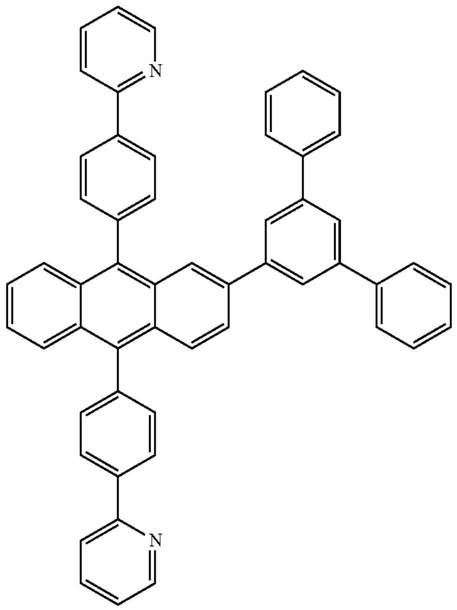
-continued
ET10
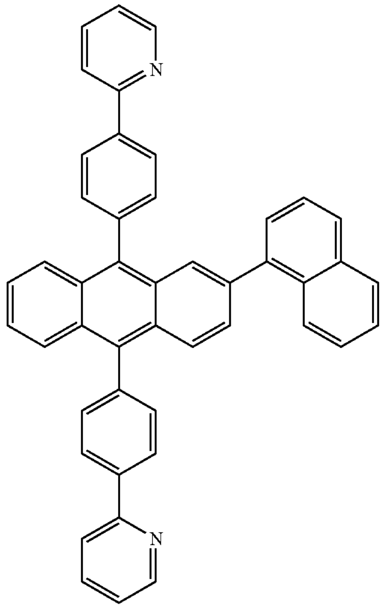
ET11
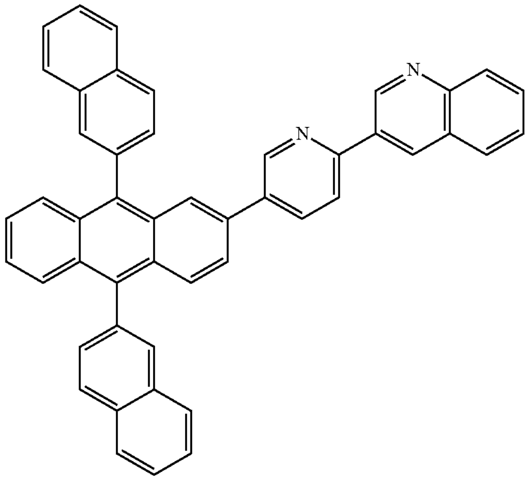
ET12
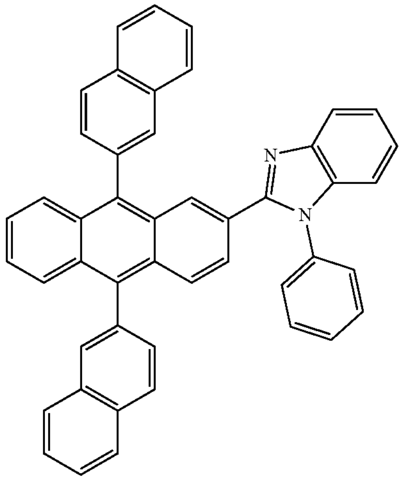

-continued
ET13
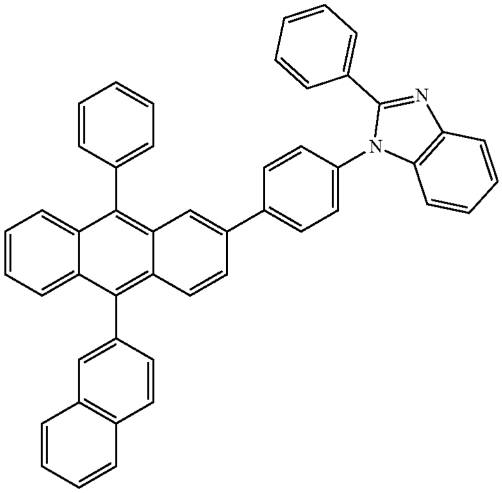
ET14
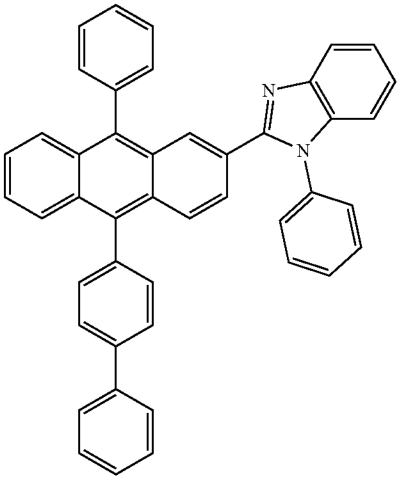
ET15
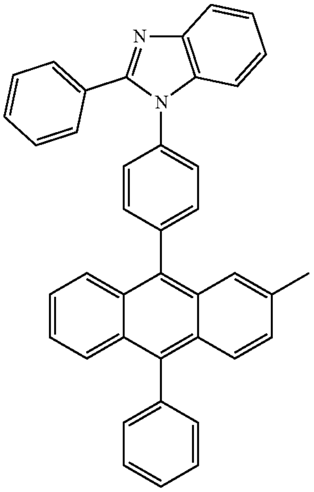
-continued
ET16
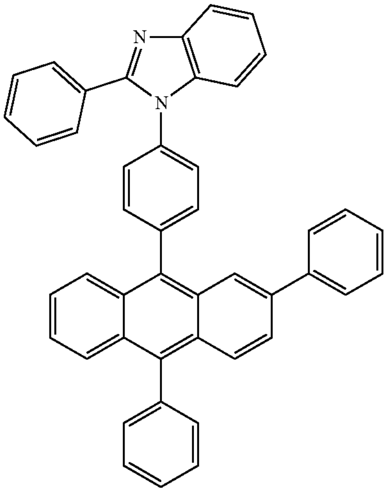
ET17
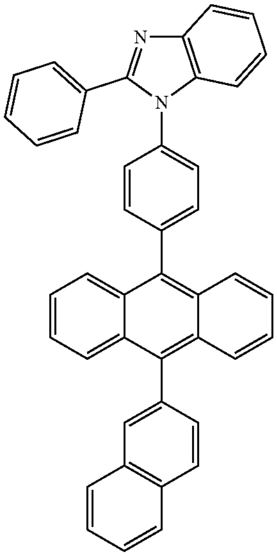
ET18
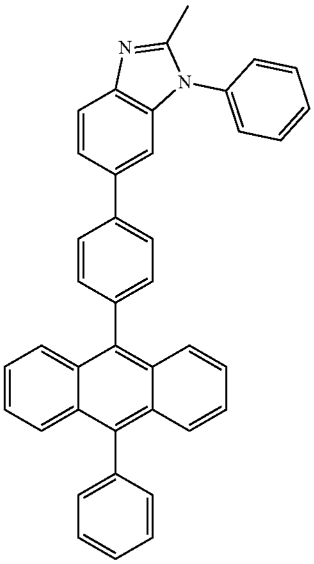

-continued
ET19
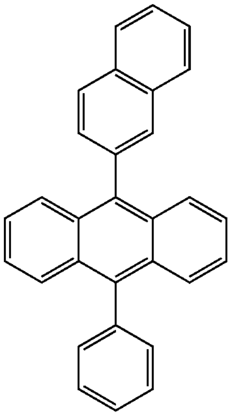
ET20
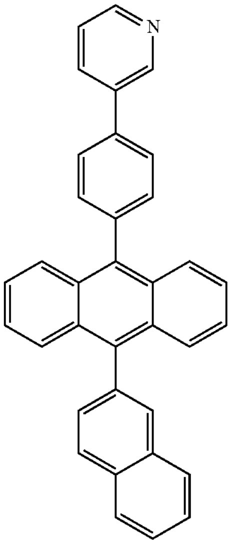
ET21
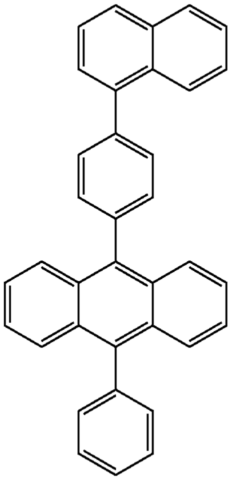
-continued
ET22
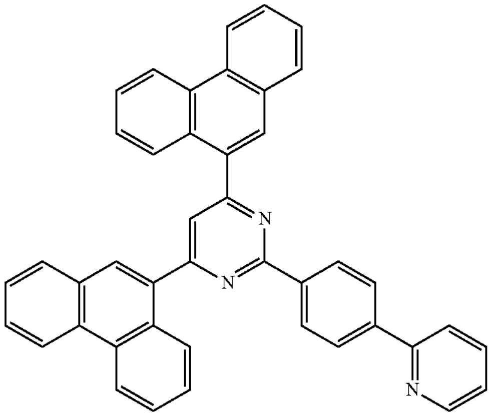
ET23
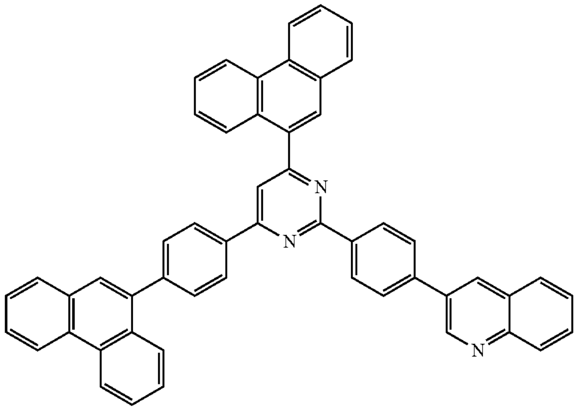
ET24
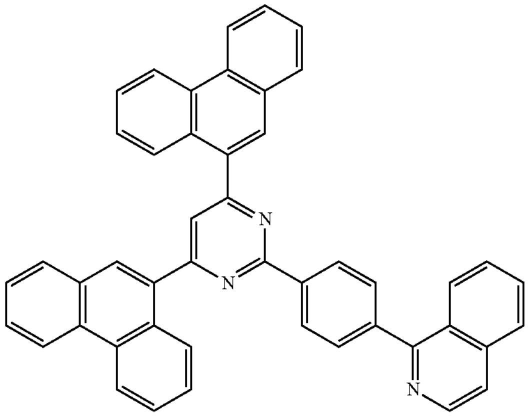

-continued
ET25
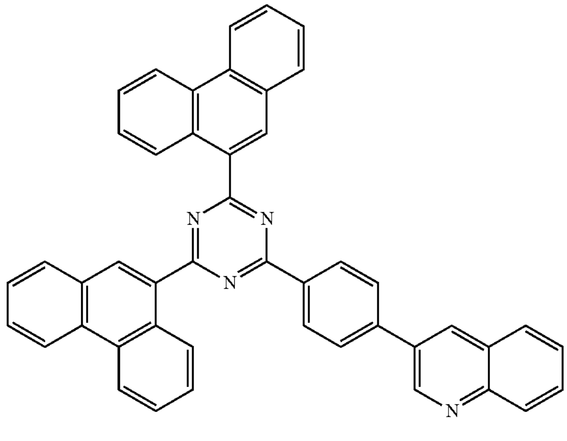
ET26
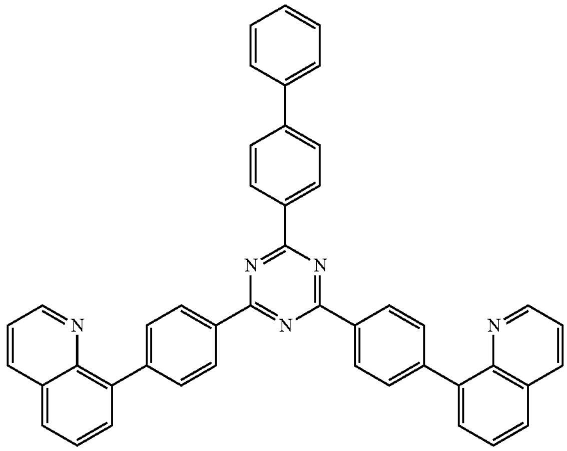
ET27
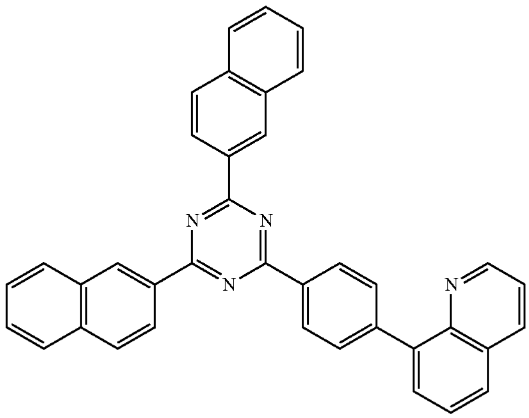
-continued
ET28
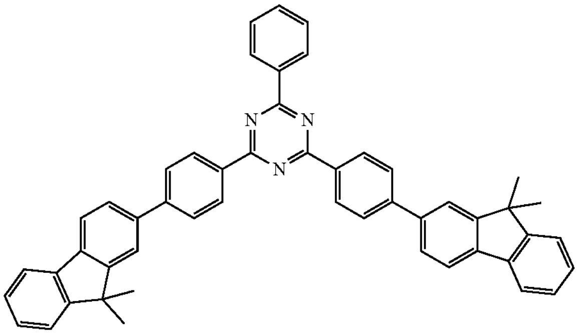
ET29
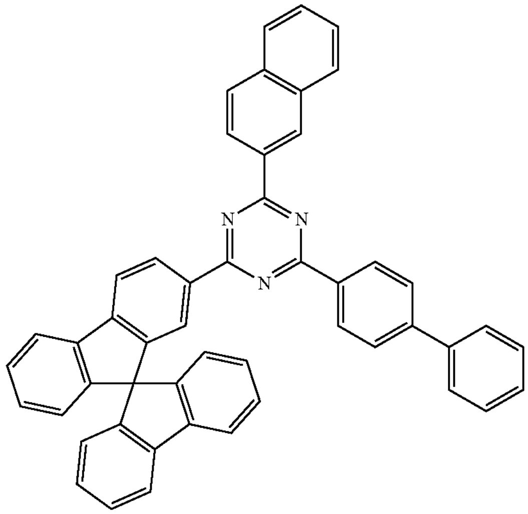
ET30
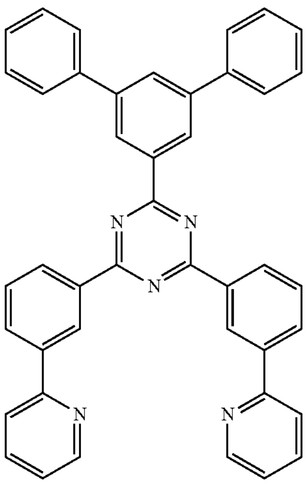

-continued

ET31

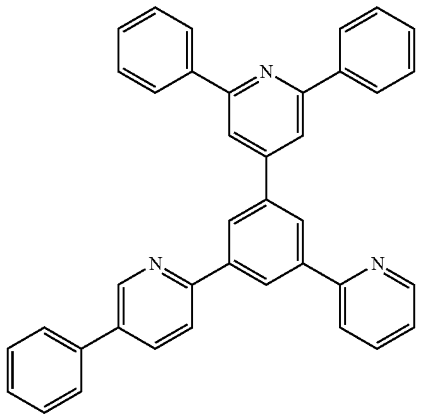

ET32

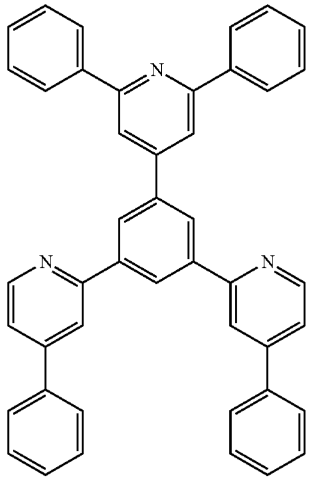

ET33

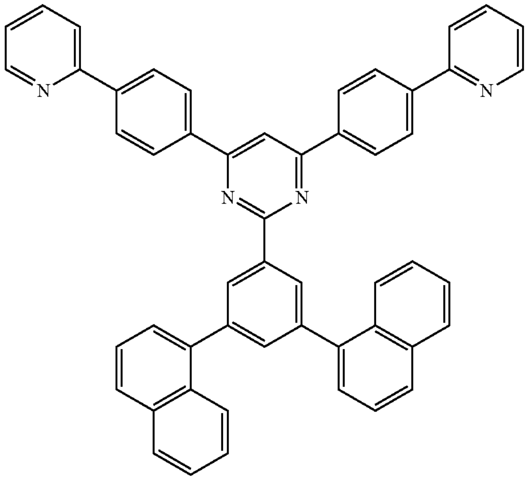

-continued

ET34

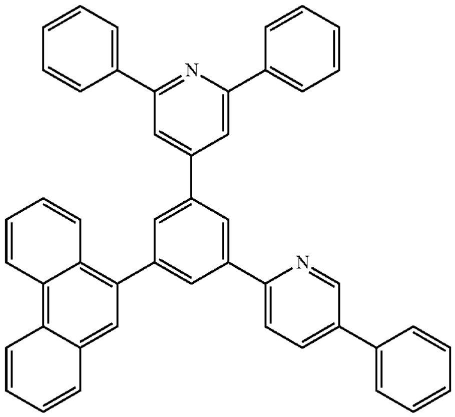

ET35

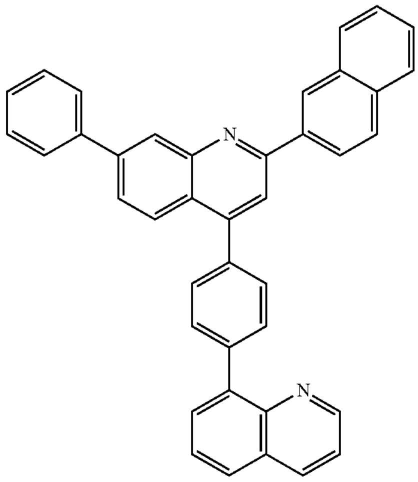

ET36

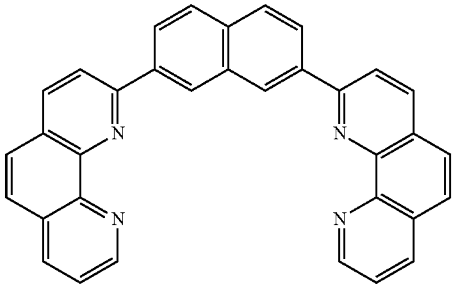

The electron transport regions ETR may include a metal halide such as LiF, NaCl, CsF, RbCl, RbI, CuI, or KI, a lanthanide metal such as Yb, or a co-deposited material of the metal halide and the lanthanide metal. For example, the electron transport region ETR may include KI:Yb, RbI:Yb, etc. as a co-deposited material. The electron transport region ETR may include a metal oxide such as $Li_2O$ or BaO, or 8-hydroxyl-lithium quinolate (Liq), etc., but embodiments are not limited thereto. The electron transport region ETR may also be formed of a mixture material of an electron transport material and an insulating organometallic salt. The organometallic salt may be a material having an energy band gap equal to or greater than about 4 eV. For example, the organometallic salt may include metal acetates, metal benzoates, metal acetoacetates, metal acetylacetonates, or metal stearates, but embodiments are not limited thereto.

The electron transport region ETR may include the above-described compounds of the hole transport region in at least one of the electron injection layer EIL, the electron transport layer ETL, and the hole blocking layer HBL.

When the electron transport region ETR includes an electron transport layer ETL, the electron transport layer ETL may have a thickness in a range of about 100 Å to about 1,000 Å. For example, electron transport layer ETL may have a thickness in a range of about 150 Å to about 500 Å. If the thickness of the electron transport layer ETL satisfies the aforementioned range, satisfactory electron transport characteristics may be obtained without a substantial increase in driving voltage. When the electron transport region ETR includes an electron injection layer EIL, the electron injection layer EIL may have a thickness in a range of about 1 Å to about 100 Å. For example, the electron injection layer EIL may have a thickness in a range of about 3 Å to about 90 Å. If the thickness of the electron injection layer EIL satisfies the above-described range, satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, $L_1$, Ca, LiF/Ca, LiF/Al, Mo, Ti, Yb, W, a compound thereof, or a mixture thereof (e.g., AgMg, AgYb, or MgAg). In an embodiment, the second electrode EL2 may have a multilayer structure including a reflective film or a transflective film formed of the above-described materials, and a transparent conductive film formed of ITO, IZO, ZnO, ITZO, etc. For example, the second electrode EL2 may include the above-described metal materials, combinations of at least two metal materials of the above-described metal materials, oxides of the above-described metal materials, or the like.

Although not shown in the drawings, the second electrode EL2 may be electrically connected to an auxiliary electrode. If the second electrode EL2 is electrically connected to the auxiliary electrode, the resistance of the second electrode EL2 may decrease.

In an embodiment, the luminescence device ED may further include a capping layer CPL disposed on the second electrode EL2. The capping layer CPL may include a multilayer or a single layer.

In an embodiment, the capping layer CPL may include an organic layer or an inorganic layer. For example, when the capping layer CPL includes an inorganic material, the inorganic material may include an alkaline metal compound such as LiF, an alkaline earth metal compound such as $MgF_2$, SiON, $SiN_x$, SiOy, etc.

For example, when the capping layer CPL includes an organic material, the organic material may include α-NPD, NPB, TPD, m-MTDATA, $Alq_3$, CuPc, N4,N4,N4',N4'-tetra (biphenyl-4-yl)biphenyl-4,4'-diamine (TPD15), 4,4',4"-tris (carbazol sol-9-yl)triphenylamine (TCTA), etc., or an epoxy resin, or acrylate such as methacrylate. However, embodiments are not limited thereto, and the organic material may also include Compounds P1 to P5 below.

P1

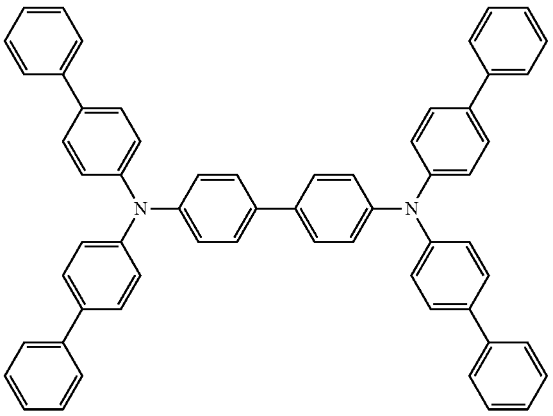

P2

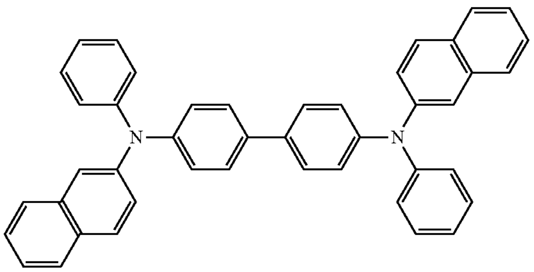

P3

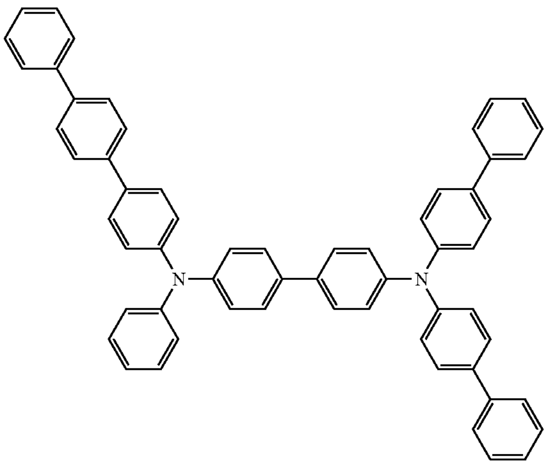

P4

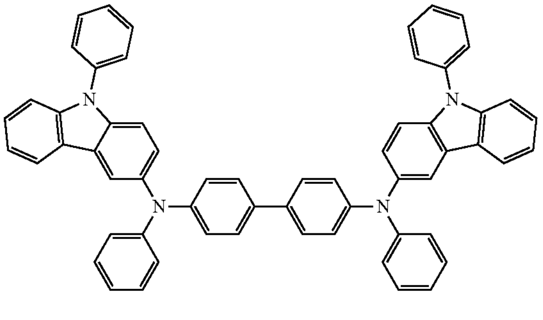

-continued

P5

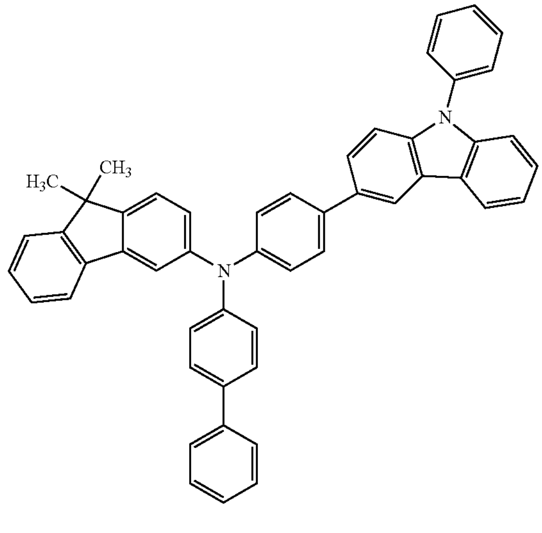

A refractive index of the capping layer CPL may be equal to or greater than about 1.6. For example, the refractive index of the capping layer CPL may be equal to or greater than about 1.6 or more with respect to light in a wavelength range of about 550 nm to about 660 nm.

Figure 7:
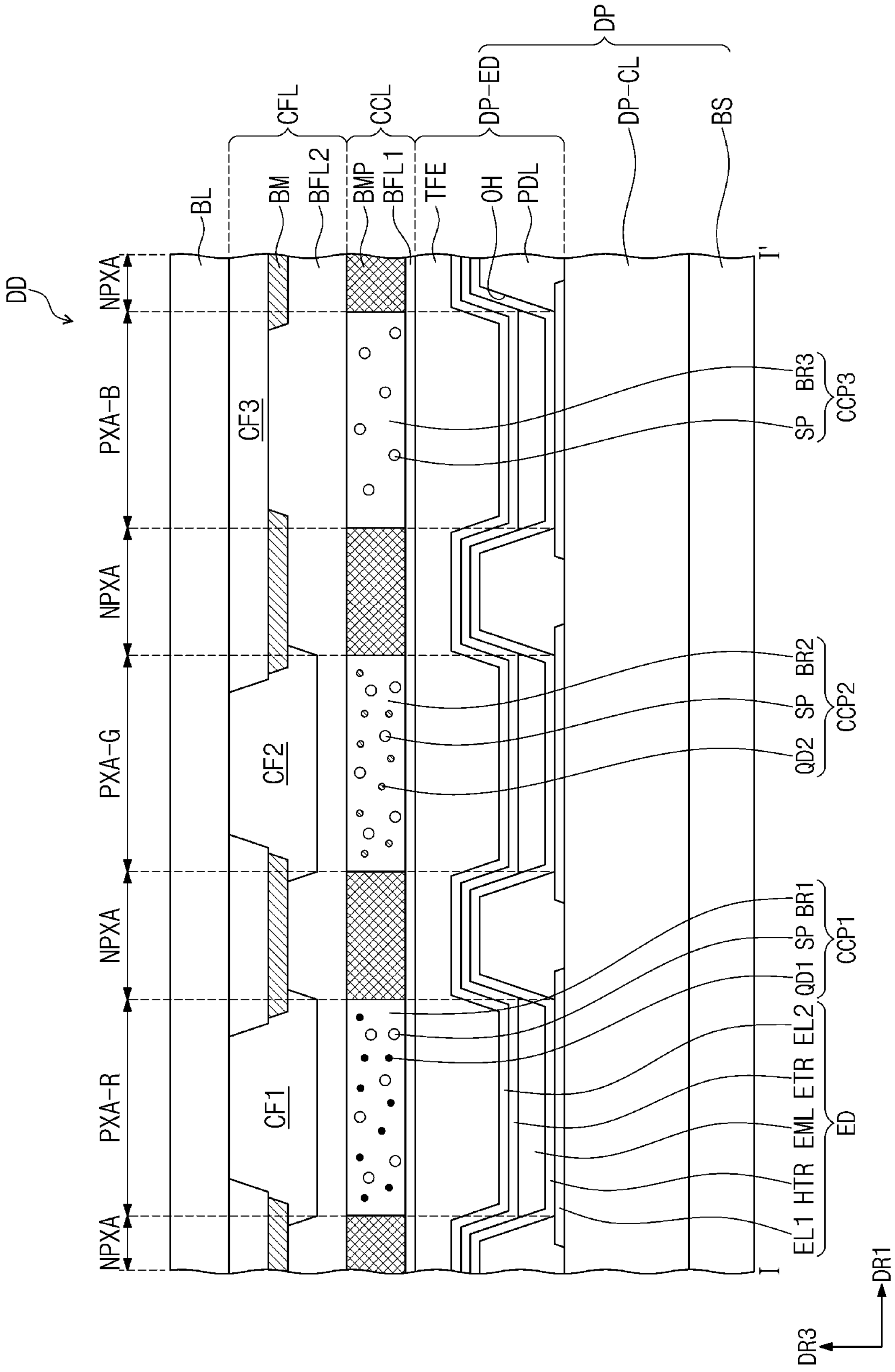
FIG. 7 is a schematic cross-sectional view illustrating a display apparatus according to an embodiment.
Figure 8:
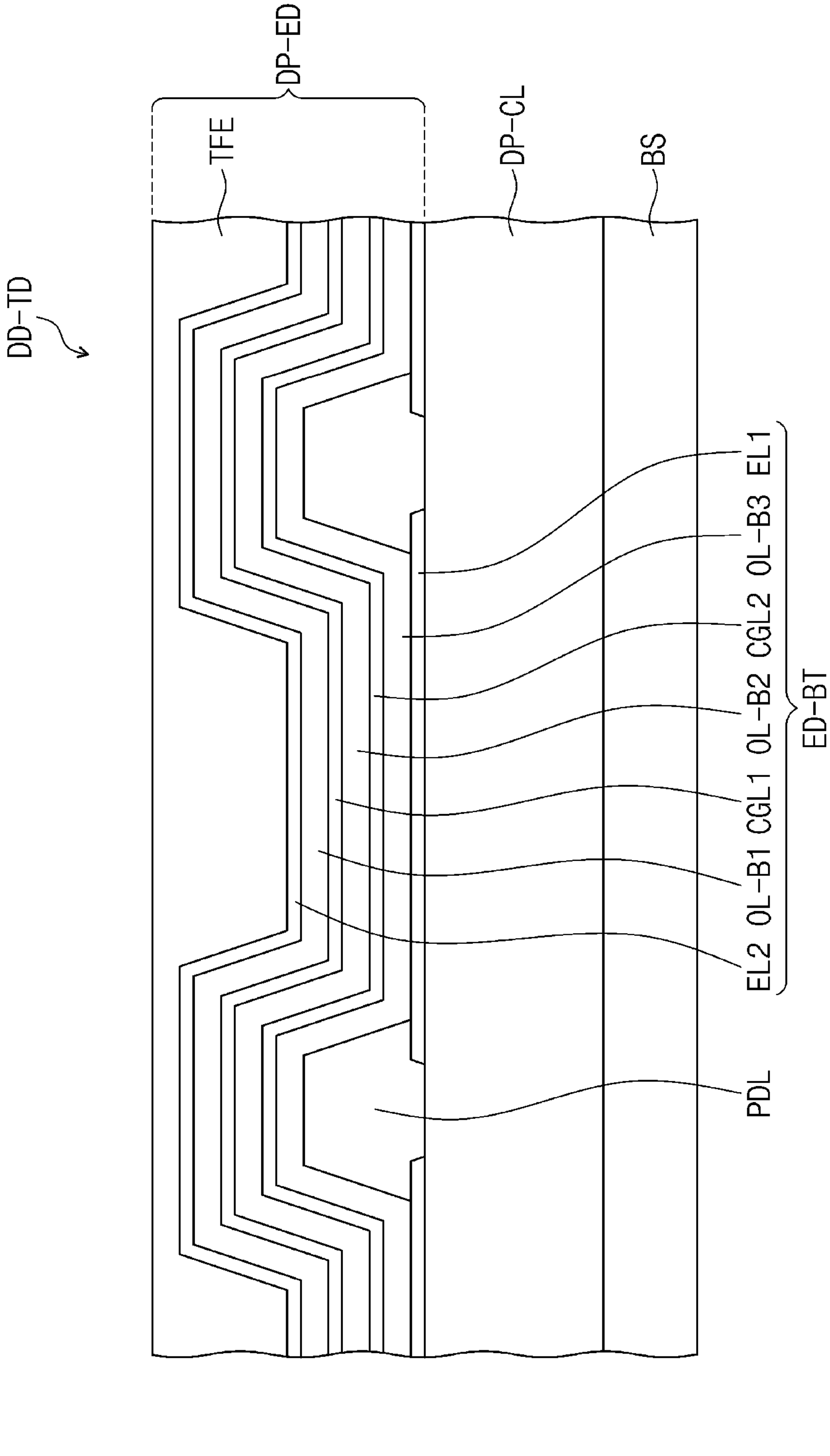
FIG. 8 is a schematic cross-sectional view illustrating a display apparatus according to an embodiment.

FIGS. 7 and 8 each are a schematic cross-sectional view of a display apparatus according to an embodiment. Hereinafter, in describing the display apparatus of an embodiment with reference to FIGS. 7 and 8, the features which have been previously described in FIGS. 1 to 6 will not be described again, but their differences will be described.

Referring to FIG. 7, the display apparatus DD according to an embodiment may include a display panel DP including a display device layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and the display device layer DP-ED, and the display device layer DP-ED may include a luminescence device ED.

The luminescence device ED may include a first electrode EL1, a hole transport region HTR disposed on the first electrode EL1, an emission layer EML disposed on the hole transport region HTR, an electron transport region ETR disposed on the emission layer EIL, and a second electrode EL2 disposed on the electron transport region ETR. The structures of the luminescence devices of FIGS. 3 to 6 as described above may be equally applied to the structure of the luminescence device ED shown in FIG. 7.

Referring to FIG. 7, the emission layer EIL may be disposed in an opening OH defined in a pixel defining film PDL. For example, the emission layer EIL, which is divided by the pixel defining film PDL and provided corresponding to each of the light emitting regions PXA-R, PXA-G, and PXA-B, may emit light in a same wavelength range. In the display apparatus DD of an embodiment, the emission layer EIL may emit blue light. Although not shown in the drawings, in an embodiment, the emission layer EIL may be provided as a common layer for all light emitting regions PXA-R, PXA-G, and PXA-B.

The light control layer CCL may be disposed on the display panel DP. The light control layer CCL may include a light conversion body. The light conversion body may include a quantum dot, a phosphor, or the like. The light conversion body may convert the wavelength of provided and emit the converted light. For example, the light control layer CCL may be a layer containing the quantum dot or a layer containing the phosphor.

The light control layer CCL may include light control parts CCP1, CCP2, and CCP3. The light control parts CCP1, CCP2, and CCP3 may be spaced apart from one another.

Referring to FIG. 7, divided patterns BMP may be disposed between the light control parts CCP1, CCP2, and CCP3 which are spaced apart from each other, but embodiments are not limited thereto. FIG. 7 illustrates that the divided patterns BMP do not overlap the light control parts CCP1, CCP2, and CCP3, but at least a portion of the edges of the light control parts CCP1, CCP2, and CCP3 may overlap the divided patterns BMP.

The light control layer CCL may include a first light control part CCP1 containing a first quantum dot QD1 which converts first color light provided from the luminescence device ED into second color light, a second light control part CCP2 containing a second quantum dot QD2 which converts the first color light into third color light, and a third light control part CCP3 which transmits the first color light.

In an embodiment, the first light control part CCP1 may provide red light that is the second color light, and the second light control part CCP2 may provide green light that is the third color light. The third light control part CCP3 may provide blue light by transmitting the blue light that is the first color light provided by the luminescence device ED. For example, the first quantum dot QD1 may be a red quantum dot, and the second quantum dot QD2 may be a green quantum dot. The same as described above with respect to quantum dots may be applied to the quantum dots QD1 and QD2.

The light control layer CCL may further include a scatterer SP. The first light control part CCP1 may include the first quantum dot QD1 and the scatterer SP, the second light control part CCP2 may include the second quantum dot QD2 and the scatterer SP, and the third light control part CCP3 may not include any quantum dot but include the scatterer SP.

The scatterer SP may be inorganic particles. For example, the scatterer SP may include at least one of $TiO_2$, ZnO, $Al_2O_3$, $SiO_2$, and hollow silica. The scatterer SP may include any one of $TiO_2$, ZnO, $Al_2O_3$, $SiO_2$, or hollow silica, or may be a mixture of at least two materials selected from among $TiO_2$, ZnO, $Al_2O_3$, $SiO_2$, and hollow silica.

The light control layer CCL may include a barrier layer BFL1. The barrier layer BFL1 may prevent the penetration of moisture and/or oxygen (hereinafter, referred to as 'moisture/oxygen'). The barrier layer BFL1 may be disposed on the light control parts CCP1, CCP2, and CCP3 to block the light control parts CCP1, CCP2, and CCP3 from being exposed to moisture/oxygen. The barrier layer BFL1 may cover the light control parts CCP1, CCP2, and CCP3. In an embodiment, barrier layer BFL2 may be provided between the light control parts CCP1, CCP2, and CCP3 and the color filter layer CFL.

The barrier layers BFL1 and BFL2 may include at least one inorganic layer. For example, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. The barrier layers BFL1 and BFL2 may further include an organic film. The barrier layers BFL1 and BFL2 may be formed of a single layer or of multiple layers.

In the display apparatus DD of an embodiment, the color filter layer CFL may be disposed on the light control layer CCL. For example, the color filter layer CFL may be directly disposed on the light control layer CCL. In an embodiment, the barrier layer BFL2 may be omitted.

The color filter layer CFL may include a light shielding unit BM and filters CF1, CF2, and CF3. The color filter layer CFL may include a first filter CF1 that transmits the second color light, a second filter CF2 that transmits the third color light, and a third filter CF3 that transmits the first color light. For example, the first filter CF1 may be a red filter, the second filter CF2 may be a green filter, and the third filter CF3 may be a blue filter. The filters CF1, CF2, and CF3 each may include a polymeric photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

In an embodiment, the first filter CF1 and the second filter CF2 may each be a yellow filter. The first filter CF1 and the second filter CF2 may not be separated but be provided as one filter.

The light shielding unit BM may be a black matrix. The light shielding unit BM may include an organic light shielding material or an inorganic light shielding material containing a black pigment or dye. The light shielding unit BM may prevent light leakage, and may separate boundaries between the adjacent filters CF1, CF2, and CF3. In an embodiment, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

A base substrate BL may be disposed on the color filter layer CFL. The base substrate BL may provide a base surface in which the color filter layer CFL, the light control layer CCL, and the like are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

FIG. 8 is a schematic cross-sectional view illustrating a part of a display apparatus according to an embodiment. FIG. 8 illustrates a schematic cross-sectional view of a part corresponding to the display panel DP of FIG. 7. In the display apparatus DD-TD of an embodiment, the luminescence device ED-BT may include light emitting structures OL-B1, OL-B2, and OL-B3. The luminescence device ED-BT may include a first electrode EL1 and a second electrode EL2 which face each other, and the light emitting structures OL-B1, OL-B2, and OL-B3 sequentially stacked in a thickness direction between the first electrode EL1 and the second electrode EL2. The light emitting structures OL-B1, OL-B2, and OL-B3 each may include an emission layer EML (FIG. 7) and a hole transport region HTR, and an electron transport region ETR, with the emission layer EML (FIG. 7) disposed therebetween.

For example, the luminescence device ED-BT included in the display apparatus DD-TD of an embodiment may be a luminescence device having a tandem structure and including multiple emission layers.

In an embodiment illustrated in FIG. 8, all light respectively emitted from the light emitting structures OL-B1, OL-B2, and OL-B3 may be blue light. However, embodiments are not limited thereto, and the light respectively emitted from the light emitting structures OL-B1, OL-B2, and OL-B3 may have wavelength ranges different from each other. For example, the luminescence device ED-BT including the light emitting structures OL-B1, OL-B2, and OL-B3 which emit light having wavelength ranges different from each other may emit white light.

Charge generation layers CGL1 and CGL2 may be disposed between the neighboring light emitting structures OL-B1, OL-B2, and OL-B3. The charge generation layers CGL1 and CGL2 may each independently include a p-type charge generation layer and/or an n-type charge generation layer.

Hereinafter, embodiments will be described through the Examples and Comparative Examples. The Examples below are only illustrations for assisting the understanding of the disclosure, and the scope thereof is not limited thereto.

Synthesis Examples

The polycyclic compound according to an embodiment of the inventive concept may be synthesized as, for example, the following. However, a synthesis method of the polycyclic compound according to an embodiment of the inventive concept is not limited thereto.

1. Synthesis of Intermediates A-4 and B-4

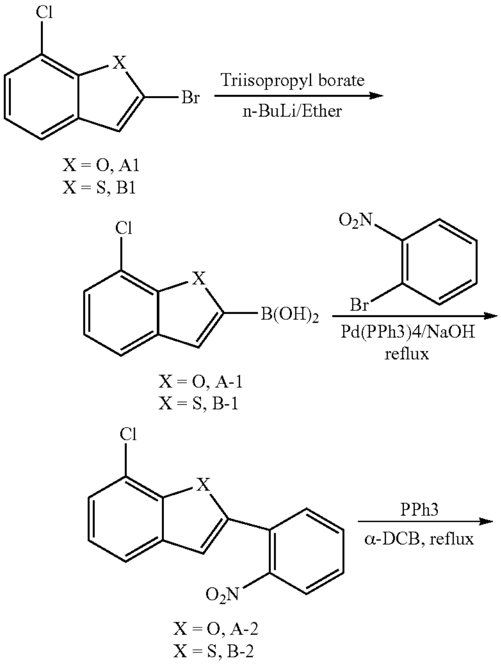

-continued

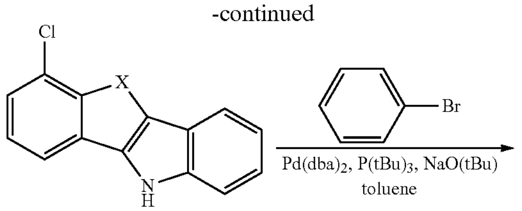

X = O, A-3
X = S, B-3

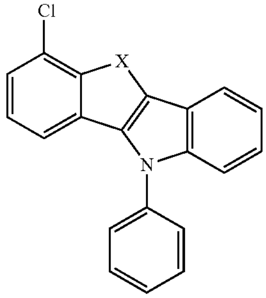

X = O, A-4
X = S, B-4

(1) Synthesis of Intermediates B-1

In an Ar atmosphere, in a 500 mL three-neck, B1 (12.37 g, 50 mmol) and ether (250 mL) were added and cooled to about −78° C., and n-BuLi (74.07 g, 120 mmol) was dropped thereto and stirred for about 1 hour. $B(OMe)_3$ (15.59 g, 150 mmol) was dropped thereto, and the reaction mixture was returned to room temperature and stirred for about 3 hours. After the reaction, the resulting product was neutralized with 1M HCl, extracted with $CH_2Cl_2$, dried over $MgSO_4$, and concentrated. The resulting crude product was purified by silica gel column chromatography to obtain Compound B-1 which is a white solid (7.65 g, yield 72%).

By measuring FAB-MS, a mass number of m/z=212 was observed by molecular ion peak, thereby identifying Intermediate B-1.

(2) Synthesis of Intermediate B-2

In an Ar atmosphere, in a 500 mL three-neck, 2-nitrobromobenzene (7.0 g, 34.6 mmol), Intermediate B-1 (7.36 g, 41.6 mmol), $K_3PO_4$ (14.7 g, 69.3 mmol), toluene (138.6 mL), ethanol (69.3 mL), and $H_2O$ (34.6 mL) were sequentially added and fully bubbled, and at last $Pd(PPh_3)_4$(1.2 g, 1.04 mmol) was added thereto, and the mixture was heated and stirred at about 80° C. for about 4 hours. After the mixture was air-cooled to room temperature, the reaction solvent was removed by distillation to obtain a crude product. The resulting crude product was purified by silica gel column chromatography to obtain Compound B-2 which is a white solid (7.8 g, yield 78%).

By measuring FAB-MS, a mass number of m/z=289 was observed by molecular ion peak, thereby identifying Intermediate B-2.

(3) Synthesis of Intermediate B-3

In an Ar atmosphere, in a 500 mL three-neck flask, B-2 (7.5 g, 25.9 mmol), $PPh_3$ (6.8 g, 25.9 mmol), and o-dichlorobenzene (105 mL) were added and stirred under reflux for about 24 hours. The mixture was air-cooled to room temperature, and filtered. The filtrate was concentrated and purified by silica gel column chromatography to obtain Compound B-3 (5.3 g, yield 79%).

By measuring FAB-MS, a mass number of m/z=257 was observed by molecular ion peak, thereby identifying Intermediate B-3.

(4) Synthesis of Intermediate B-4

In an Ar atmosphere in atmosphere, in a 500 mL three-neck flask, Intermediate B-3 (5.0 g, 19.4 mmol), $Pd(dba)_2$ (0.56 g, 0.05 equiv, 0.97 mmol), NaOtBu (1.86 g, 1 equiv, 19.40 mmol), toluene (194 mL), bromobenzene (3.05 g, 1.1 equiv, 21.34 mmol), and $tBu_3P$ (0.79 g, 0.2 equiv, 3.88 mmol) were sequentially added and heated and stirred under reflux for about 6 hours. After the mixture was air-cooled to room temperature, the organic layer was fractionated by adding water to the reaction solvent. The organic layer was further extracted by adding toluene to a water layer, and the combined organic layers were washed with saline and dried over $MgSO_4$. $MgSO_4$ was filtered off and the organic layer was concentrated, and the resulting crude product was purified by silica gel column chromatography to obtain Compound B-4 which is a white solid (5.6 g, yield 87%).

By measuring FAB-MS, a mass number of m/z=333 was observed by molecular ion peak, thereby identifying Intermediate B-4.

(5) Synthesis of Intermediate A-4

Intermediate A-4 was synthesized by the same method as the synthesis method of Intermediate B-4 except that A1 was used instead of B1.

By measuring FAB-MS, a mass number of m/z=371 was observed by molecular ion peak, thereby identifying Compound A-4.

2. Synthesis of Compound 1

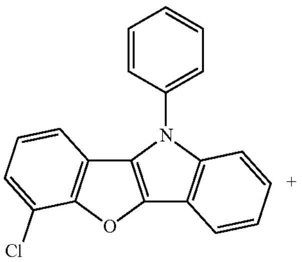

A-4

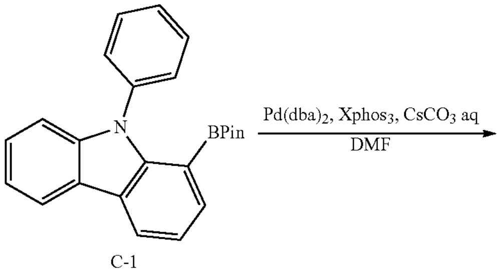

C-1

-continued

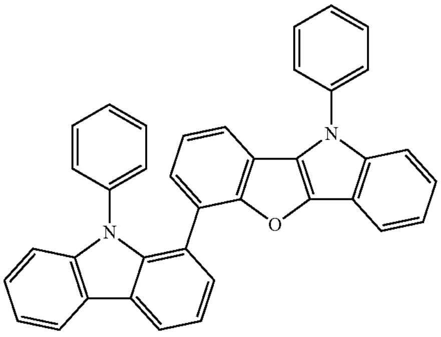

1

In an Ar atmosphere, in a 200 mL three-neck flask, A-4 (5.0 g, 14.98 mmol), C-1 (3.6 g, 14.98 mmol), $Pd(dba)_2$ (0.43 g, 0.05 equiv, 0.75 mmol), $Cs_2CO_3$ (14.64 g, 3 equiv, 14.98 mmol), and DMF (100 mL) were sequentially added and heated and stirred under reflux at about 130° C. for about 6 hours. After the mixture was air-cooled to room temperature, the organic layer was fractionated by adding water to the reaction solvent. The organic layer was further extracted by adding toluene to a water layer, and the combined organic layers were washed with saline and dried over $MgSO_4$. $MgSO_4$ was filtered off and the organic layer was concentrated, and the resulting crude product was purified by silica gel column chromatography to obtain Compound 1 which is a white solid (5.9 g, yield 75%).

By measuring FAB-MS, a mass number of m/z=524 was observed by molecular ion peak, thereby identifying Compound 1.

3. Synthesis of Compound 481

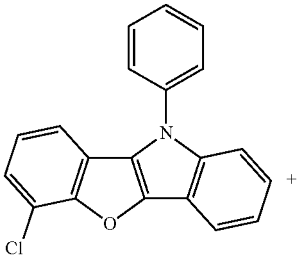

A-4

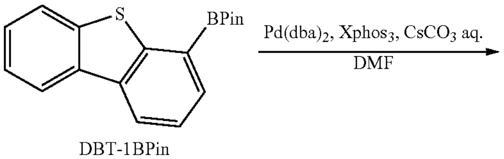

DBT-1BPin

-continued

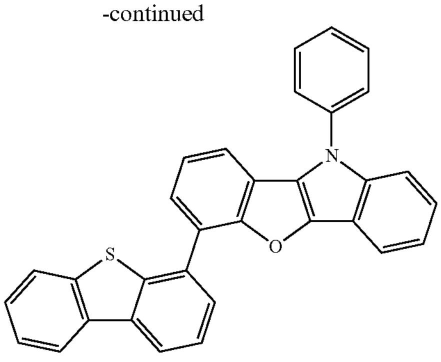

481

Compound 481 was synthesized by the same synthesis method as that of Compound 1 except that DBT-1BPin was used instead of C-1.

By measuring FAB-MS, a mass number of m/z=465 was observed by molecular ion peak, thereby identifying Compound 481.

4. Synthesis of Compound 241

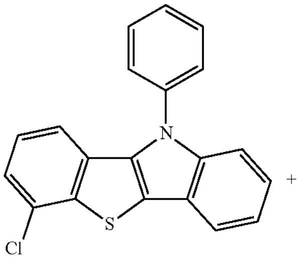

B-4

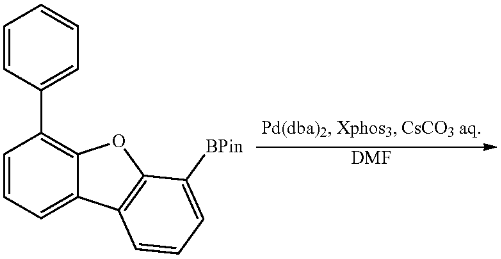

6-Ph-DBF-4BPin

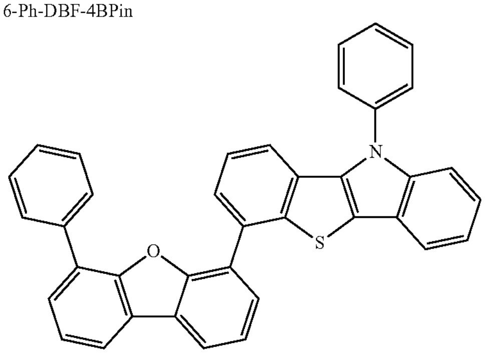

241

Compound 241 was synthesized by the same synthesis method as that of Compound 1 except that 6-Ph-DBF-4BPin was used instead of C-1.

By measuring FAB-MS, a mass number of m/z=541 was observed by molecular ion peak, thereby identifying Compound 241.

5. Synthesis of Compound 249

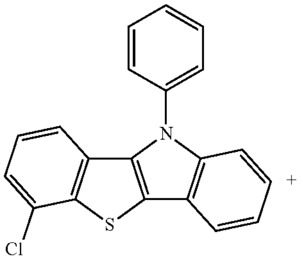

B-4

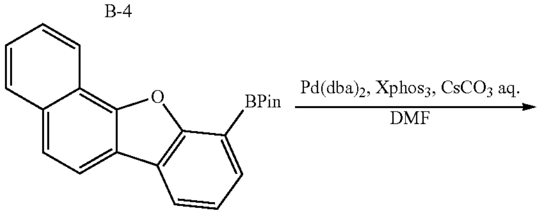

NaP-DBF-4BPin

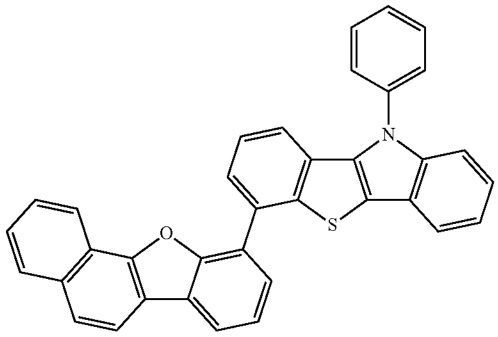

249

Compound 249 was synthesized by the same synthesis method as that of Compound 1 except that NaP-DBF-4BPin was used instead of C-1.

By measuring FAB-MS, a mass number of m/z=515 was observed by molecular ion peak, thereby identifying Compound 249.

6. Synthesis of Compound 551

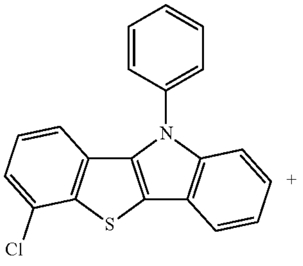

B-4

-continued

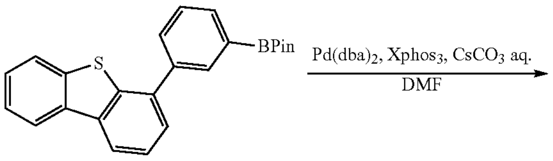

4-Ph-DBT-3'BPin

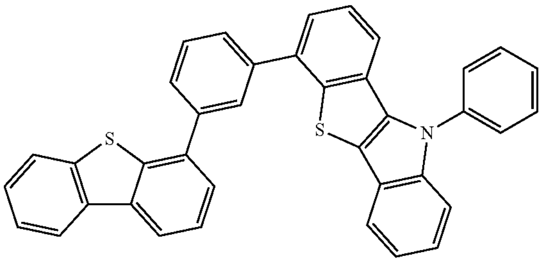

551

Compound 551 was synthesized by the same synthesis method as that of Compound 1 except that 4-Ph-DBT-3'BPin was used instead of C-1.

By measuring FAB-MS, a mass number of m/z=557 was observed by molecular ion peak, thereby identifying Compound 551.

7. Synthesis of Compound 855

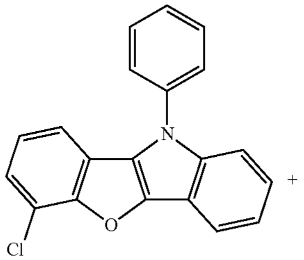

A-4

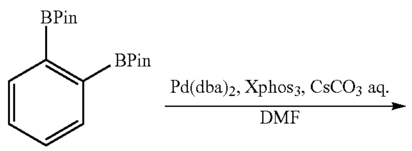

Benzene-1,2-BPin

-continued

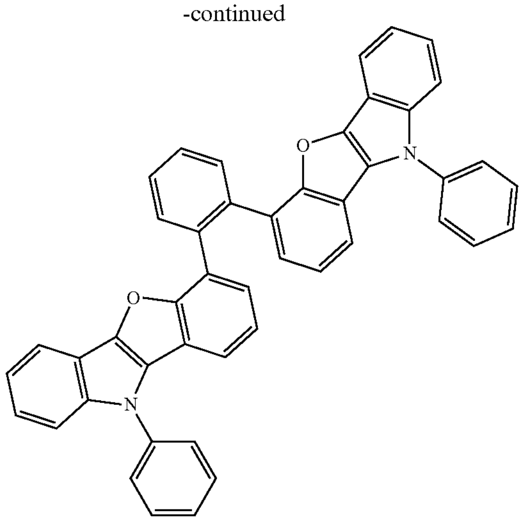

855

Compound 855 was synthesized by the same synthesis method as that of Compound 1 except that Benzene-1,2-BPin was used instead of C-1.

By measuring FAB-MS, a mass number of m/z=640 was observed by molecular ion peak, thereby identifying Compound 855.

8. Synthesis of Compound 873

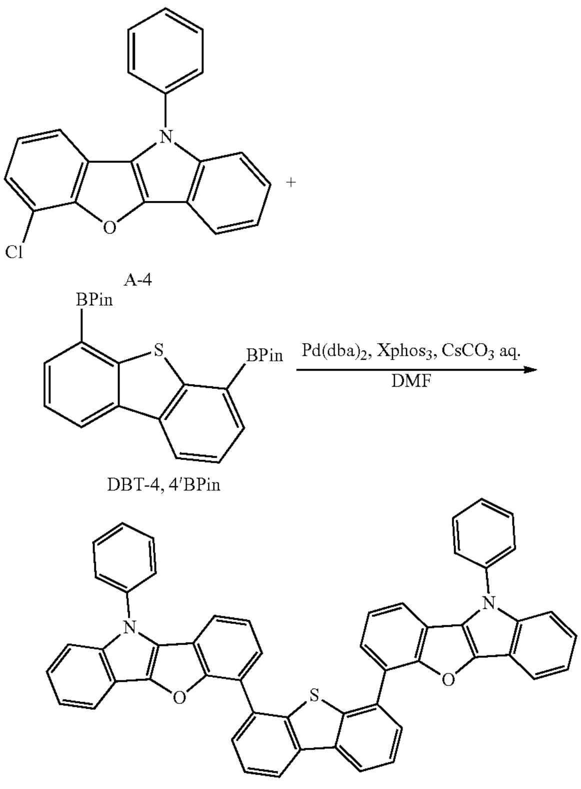

A-4

DBT-4, 4'BPin

873

Compound 873 was synthesized by the same synthesis method as that of Compound 1 except that DBT-4,4'-BPin was used instead of C-1.

By measuring FAB-MS, a mass number of m/z=746 was observed by molecular ion peak, thereby identifying Compound 873.

9. Synthesis of Compound 896

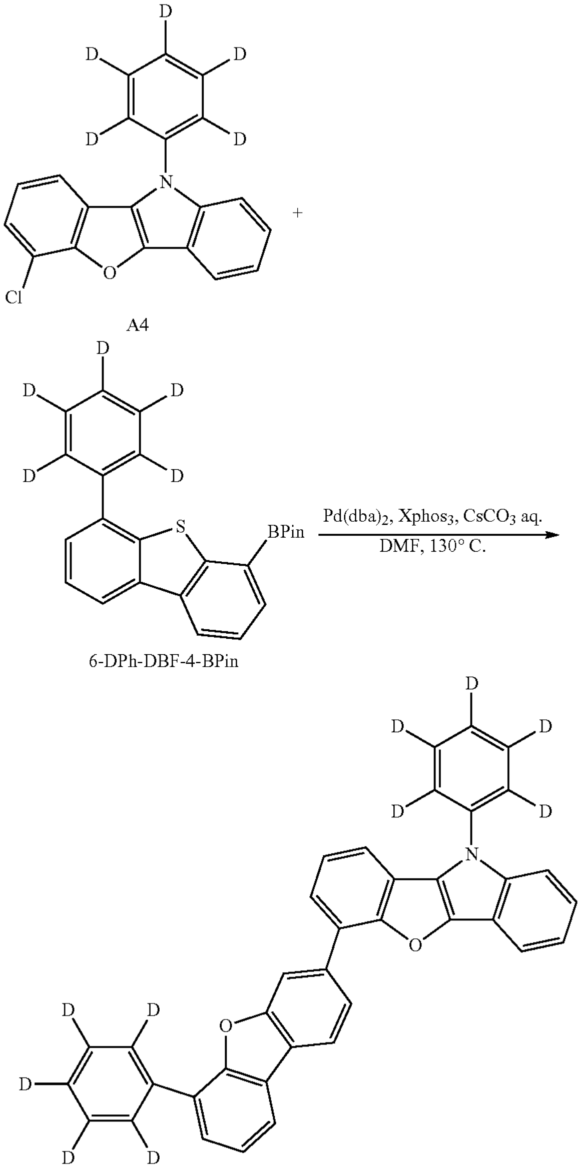

A4

6-DPh-DBF-4-BPin

896

Compound 896 was synthesized by the same synthesis method as that of Compound 1 except that A4 was used instead of A-4 and 6-DPh-DBF-4-BPin was used instead of C-1.

By measuring FAB-MS, a mass number of m/z=535 was observed by molecular ion peak, thereby identifying Compound 896.

Device Manufacturing Examples
Luminescence devices were manufactured using Example Compounds and Comparative Example Compounds below as an emission layer material.
[Example Compounds]
1
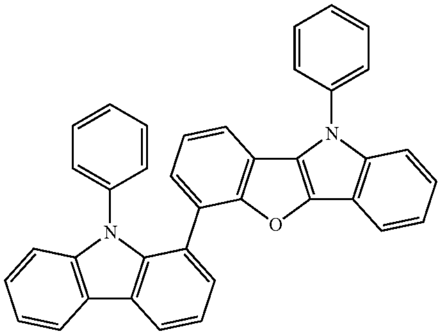
481
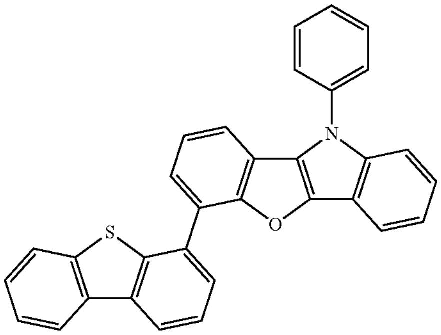
241
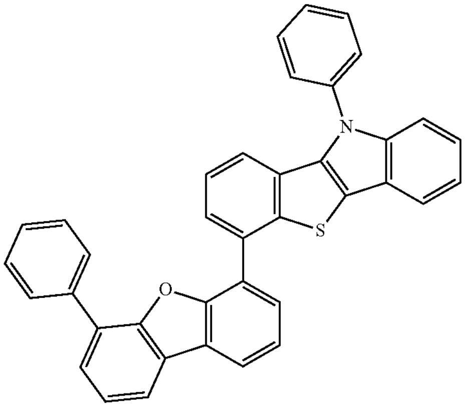
-continued
249
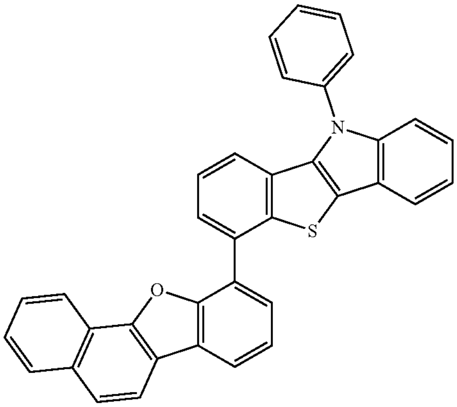
551
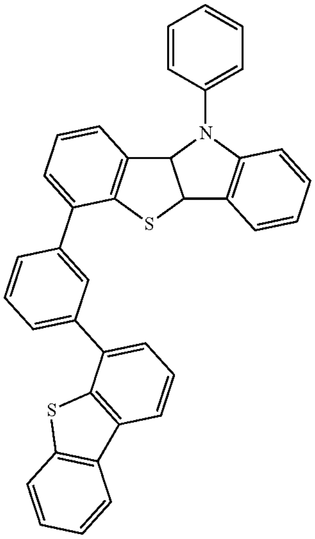
873
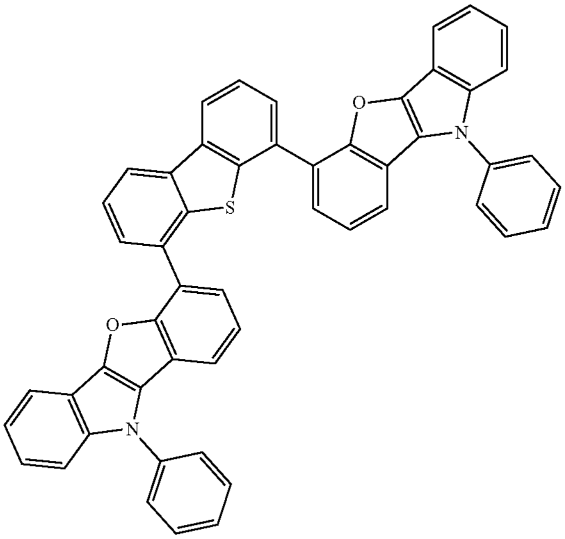

896
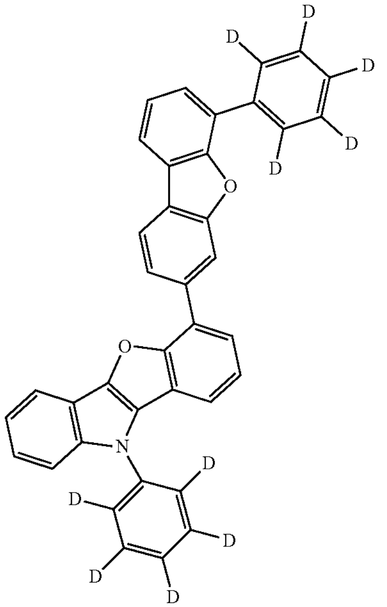
855
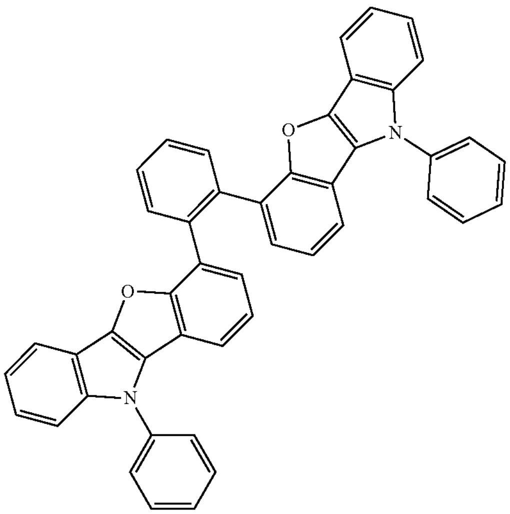
[Comparative Example Compounds]
R-1
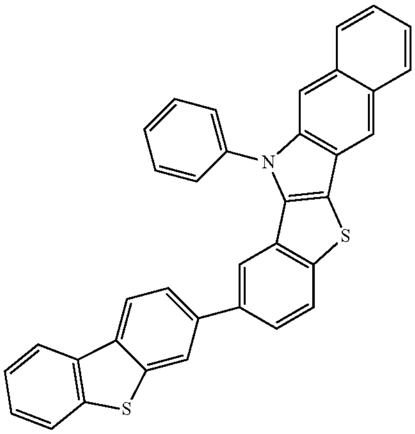
R-2
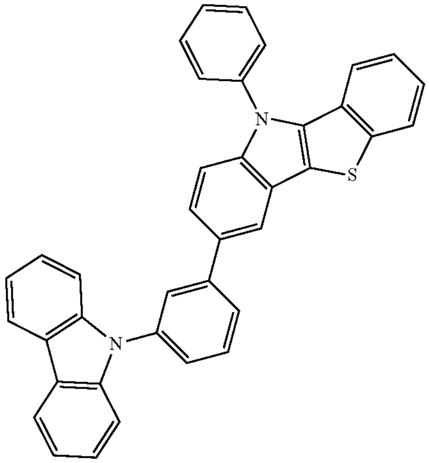
R-3
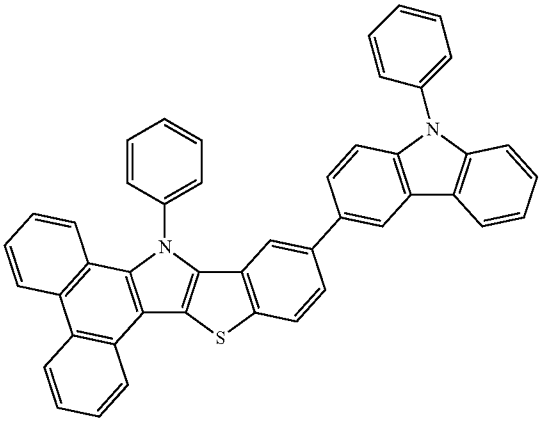
R-4
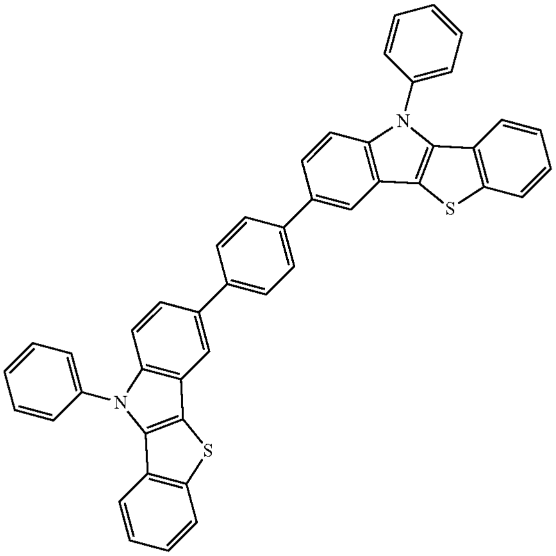

-continued

R-5

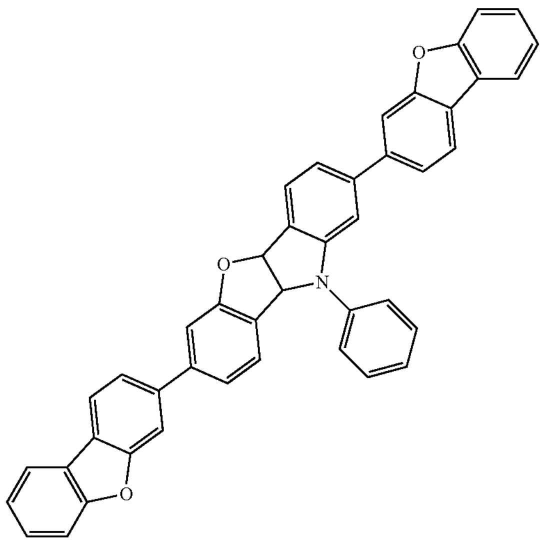

R-6

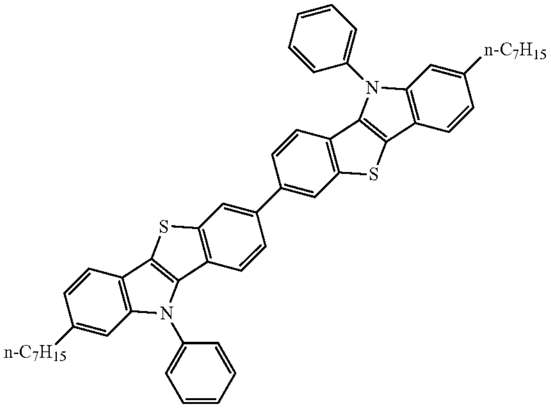

The luminescence devices of Examples and Comparative Examples were manufactured by the following method. A 150 nm-thick ITO was patterned on a glass substrate, and the glass substrate was washed with ultrapure water and treated with UV and ozone for about 10 minutes to form a first electrode. 2-TNATA was deposited thereon to have a thickness of about 60 nm, and Example Compound or Comparative Example Compound was used to form a 30 nm-thick hole transport layer. TBP was doped to ADN by 3% to form a 25 nm-thick emission layer, a 25 nm-thick layer was formed with $Alq_3$ on the emission layer, and a 1 nm-thick layer was formed with LiF to form an electron transport region. A 100 nm-thick second electrode was formed with aluminum (Al). Each layer was formed by a vacuum deposition method.

The measured values according to Examples 1 to 8 and Comparative Examples 1 to 6 are shown in Table 1 below. Current efficiency was measured at 10 mA/cm, and a half service life represents a time taken to reduce the brightness to about 500 with respect to an initial brightness of 1,000 cd/m$^2$.

TABLE 1

| | Hole transport layer | Voltage (V) | Current efficiency (cd/A) | Service life LT50 (h) |
|---|---|---|---|---|
| Example 1 | Example Compound 1 | 5.7 | 8.7 | 2100 |
| Example 2 | Example Compound 481 | 5.8 | 8.5 | 2000 |
| Example 3 | Example Compound 241 | 5.6 | 8.4 | 2250 |
| Example 4 | Example Compound 249 | 5.7 | 8.6 | 2200 |
| Example 5 | Example Compound 551 | 5.6 | 8.9 | 2100 |
| Example 6 | Example Compound 873 | 5.8 | 8.7 | 2300 |
| Example 7 | Example Compound 896 | 5.7 | 8.2 | 2150 |
| Example 8 | Example Compound 855 | 5.6 | 8.8 | 2000 |
| Comparative Example 1 | Comparative Example Compound R-1 | 6.0 | 6.2 | 1700 |
| Comparative Example 2 | Comparative Example Compound R-2 | 6.0 | 6.0 | 1500 |
| Comparative Example 3 | Comparative Example Compound R-3 | 5.9 | 7.4 | 1800 |
| Comparative Example 4 | Comparative Example Compound R-4 | 6.1 | 7.5 | 1900 |
| Comparative Example 5 | Comparative Example Compound R-5 | 6.2 | 5.8 | 1950 |
| Comparative Example 6 | Comparative Example Compound R-6 | 6.3 | 5.9 | 1600 |

Referring to Table 1 above, it may be identified that Examples 1 to 8 have achieved all of low voltage, long service life, and high efficiency compared to Comparative Examples 1 to 6.

A polycyclic compound according to an embodiment is used in the hole transport region to contribute to a low driving voltage, high efficiency, and long service life of organic electroluminescence devices. The polycyclic compound according to an embodiment is a non-amine compound having a linear benzoheterolephene-fused tetracyclic heteroacene skeleton with multiple heteroatoms. The polycyclic compound contains a structural bond of an indole and a benzohetero compound. In general, the indole side is relatively stable and the benzohetero compound side lacks the stability. The polycyclic compound according to an embodiment may become a more stable structure by adding a substituent increasing the stability to the unstable benzohetero compound. Accordingly, the polycyclic compound according to an embodiment may have excellent characteristics in heat resistance and charge resistance and achieve a long service life of the luminescence device. It is believed that N atoms, S atoms, or O atoms contained in the polycyclic compound of an embodiment may improve the hole transport ability of the entire molecule, and thus the recombination probability of holes and electrons in the emission layer is improved, thereby improving luminous efficiency of the luminescence device.

It can be seen that Example 5 achieved high device efficiency. In Example 5, it is believed that the introduction of an asymmetric meta-phenyl(4-dibenzothiophene) group to the benzoheterolephene-fused tetracyclic heteroacene ring breaks the symmetry of the entire molecule, thereby suppressing crystallinity and improving a hole transport property, and thus the recombination probability of holes and electrons in the emission layer is improved.

In Comparative Example 1 and Comparative Example 2, since the benzene ring adjacent to N is further condensed, the planarity is increased, and a sterically large volume structure cannot be taken. Therefore, both efficiency and service life of the luminescence device were reduced compared to Examples.

In Comparative Example 5 and Comparative Example 6, since the symmetry of the molecule is increased and crystallinity is thus good, the formation of film in the device may be suppressed. Thus, the efficiency and service life of the luminescence device were reduced.

The luminescence device according to an embodiment has excellent efficiency.

The polycyclic compound according to an embodiment may be used as a material of the hole transport region of the luminescence device, and thereby the luminescence device may have improved efficiency.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A luminescence device comprising:

a first electrode;

a hole transport region disposed on the first electrode;

an emission layer disposed on the hole transport region;

an electron transport region disposed on the emission layer; and a second electrode disposed on the electron transport region, wherein the hole transport region comprises a polycyclic compound represented by Formula 1:

[Formula 1]

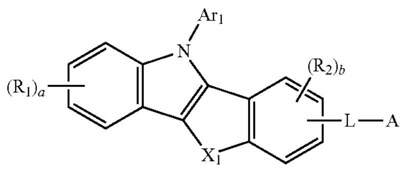

wherein in Formula 1, $X_1$ is O or S, $Ar_1$ is a substituted or unsubstituted aryl group having 6 to 30 ring-forming carbon atoms, or a substituted or unsubstituted heteroaryl group having 2 to 30 ring-forming carbon atoms, except that $Ar_1$ is not a heteroaryl group containing two or more nitrogen (N) atoms, $R_1$ is a hydrogen atom, a deuterium atom, a halogen atom, or a substituted or unsubstituted alkyl group having 1 to 20 carbon atoms, $R_2$ is a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or is bonded to an adjacent group to form a ring, a is an integer from 0 to 4, b is an integer from 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, except that L does not include a carbazole group, and A is a group represented by Formula 2-1 or Formula 2-2, except that L is not a direct linkage when A is a group represented by Formula 2-2:

[Formula 2-1]

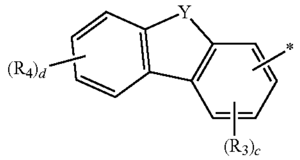

[Formula 2-2]

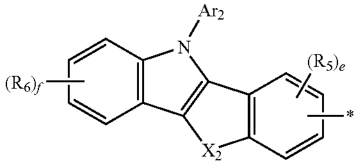

wherein in Formula 2-1 and Formula 2-2,

Y is $N(Ar_3)$, O, or S, $X_2$ is O or S, $Ar_2$ and $Ar_3$ are each independently a substituted or unsubstituted aryl group having 6 to 30 ring-forming carbon atoms, or a substituted or unsubstituted heteroaryl group having 2 to 30 ring-forming carbon atoms, except that $Ar_2$ and $Ar_3$ are each not a heteroaryl group containing two or more nitrogen (N) atoms, $R_3$ to $R_5$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, $R_6$ is a hydrogen atom, a deuterium atom, a halogen atom, or a substituted or unsubstituted alkyl group having 1 to 20 carbon atoms, c and e are each independently an integer from 0 to 3, d and f are each independently an integer from 0 to 4, and —* represents a binding site to a neighboring atom.

2. The luminescence device of claim 1, wherein the hole transport region comprises:

a hole injection layer disposed on the first electrode; and a hole transport layer disposed on the hole injection layer, wherein the hole transport layer comprises the polycyclic compound represented by Formula 1.

3. The luminescence device of claim 1, wherein the hole transport region comprises:

a hole transport layer disposed on the first electrode; and an electron blocking layer disposed on the hole transport layer, wherein the electron blocking layer comprises the polycyclic compound represented by Formula 1.

4. The luminescence device of claim 1, wherein the polycyclic compound represented by Formula 1 is represented by one of Formula 3-1 to Formula 3-3:

[Formula 3-1]

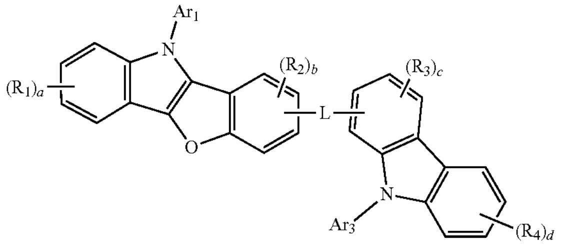

[Formula 3-2]

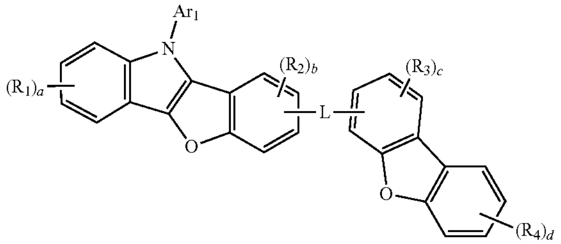

[Formula 3-3]

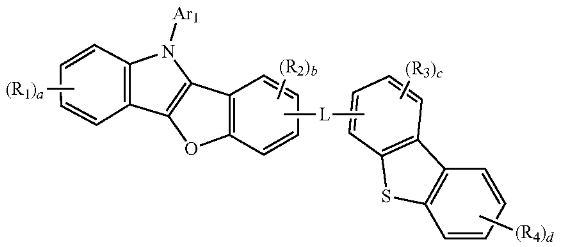

wherein in Formula 3-1 to Formula 3-3, $R_1$ to $R_4$, L, $Ar_1$, $Ar_3$, and a to d are the same as defined in connection with Formulas 1 and 2-1.

5. The luminescence device of claim 1, wherein the polycyclic compound represented by Formula 1 is represented by one of Formula 4-1 to Formula 4-3:

[Formula 4-1]

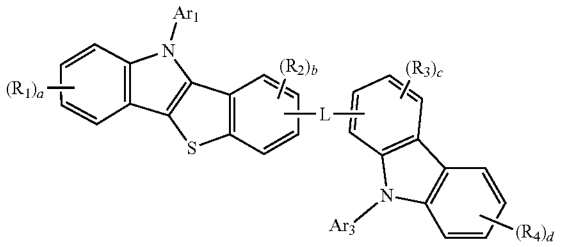

-continued

[Formula 4-2]

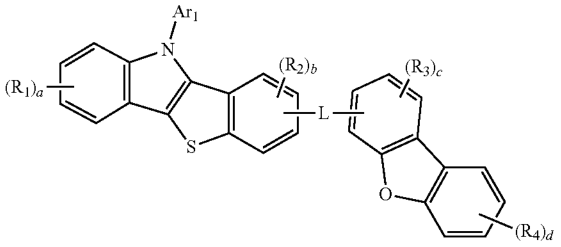

[Formula 4-3]

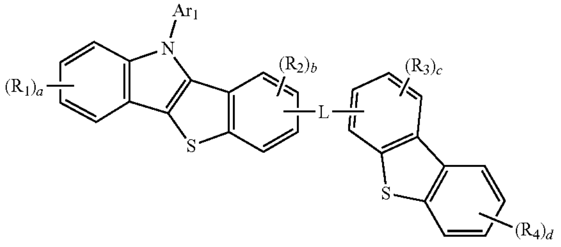

wherein in Formula 4-1 to Formula 4-3, $R_1$ to $R_4$, L, $Ar_1$, $Ar_3$, and a to d are the same as defined in connection with Formulas 1 and 2-1.

6. The luminescence device of claim 1, wherein the polycyclic compound represented by Formula 1 is represented by one of Formula 5-1 to Formula 5-3:

[Formula 5-1]

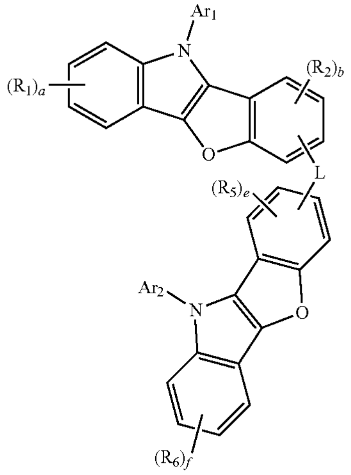

-continued

[Formula 5-2]

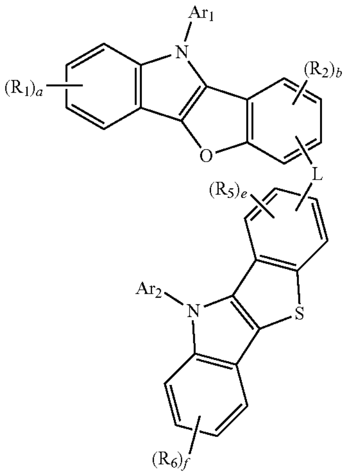

[Formula 5-3]

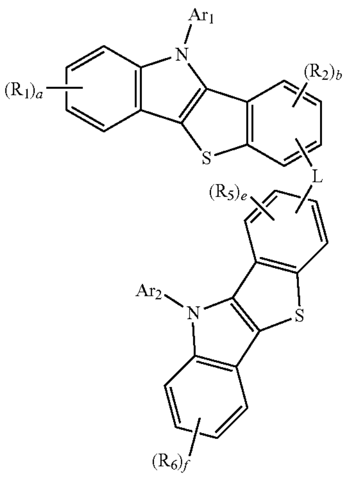

wherein in Formula 5-1 to Formula 5-3, $R_1$, $R_2$, $R_5$, $R_6$, L, $Ar_1$, $Ar_2$, a, b, e, and f are the same as defined in connection with Formulas 1 and 2-2.

7. The luminescence device of claim 1, wherein

L is a direct linkage, a substituted or unsubstituted arylene group having 6 to 18 ring-forming carbon atoms, or a substituted or unsubstituted heteroarylene group having 6 to 12 ring-forming carbon atoms, except that L does not include a carbazole group.

8. The luminescence device of claim 7, wherein L is a direct linkage or is a group represented by one of L-1 to L-4:

L-1

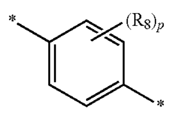

L-2

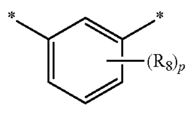

-continued

L-3

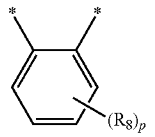

L-4

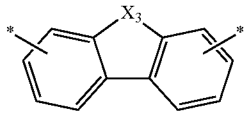

wherein in L-1 to L-4, $X_3$ is O or S, $R_8$ is a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, p is an integer from 0 to 4, and —* represents a binding site to a neighboring atom.

9. The luminescence device of claim 1, wherein the polycyclic compound represented by Formula 1 is represented by Formula 6:

[Formula 6]

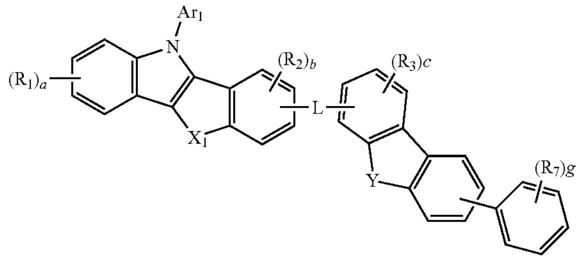

wherein in Formula 6, $R_7$ is a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, g is an integer from 0 to 5, and $R_1$ to $R_3$, L, $Ar_1$, Y, $X_1$, and a to c are the same as defined in connection with Formulas 1 and 2-1.

10. The luminescence device of claim 1, wherein the polycyclic compound represented by Formula 1 is represented by one of Formula 7-1 to Formula 7-3:

[Formula 7-1]

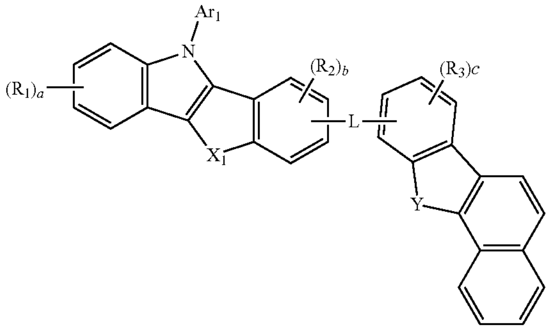

[Formula 7-2]

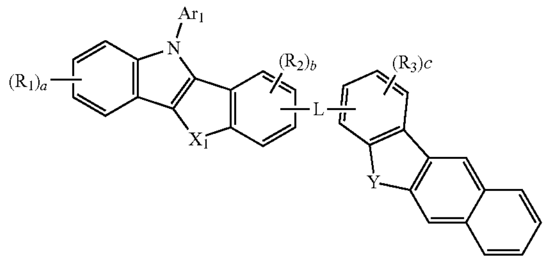

[Formula 7-3]

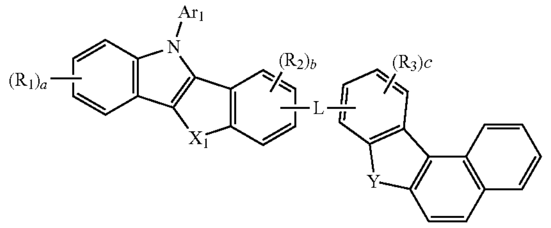

wherein in Formula 7-1 to Formula 7-3, $R_1$ to $R_3$, L, $Ar_1$, Y, $X_1$, and a to c are the same as defined in connection with Formulas 1 and 2-1.

11. The luminescence device of claim 1, wherein $R_1$ is a hydrogen atom or a deuterium atom.

12. The luminescence device of claim 1, wherein $Ar_1$, $Ar_2$, and $Ar_3$ are each independently a substituted or unsubstituted phenyl group.

13. The luminescence device of claim 1, wherein the polycyclic compound represented by Formula 1 is at least one selected from Compound Group 1:

[Compound Group 1]

1

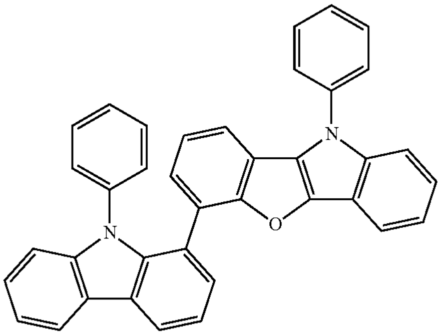

-continued

2

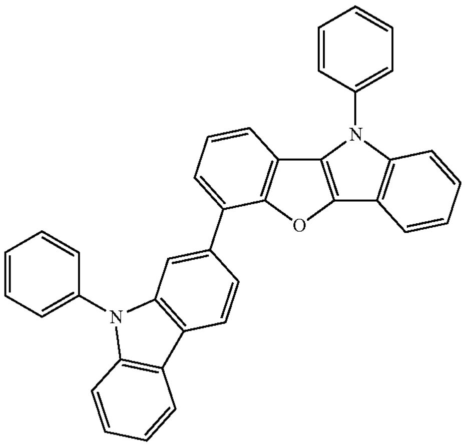

3

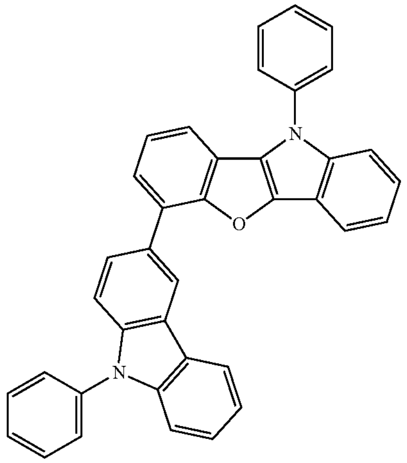

4

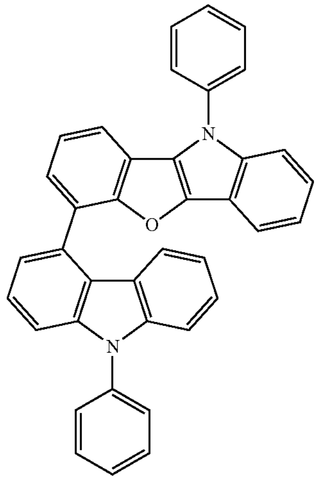

-continued
5
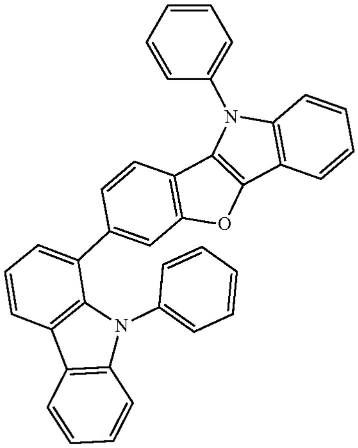
6
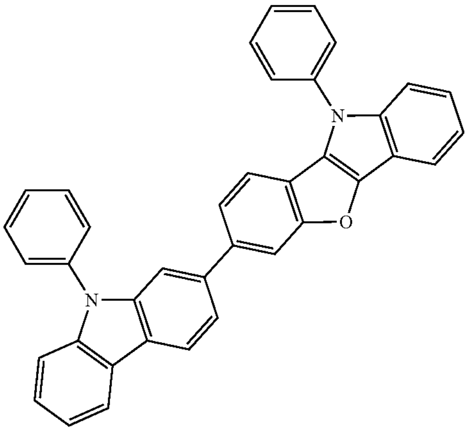
7
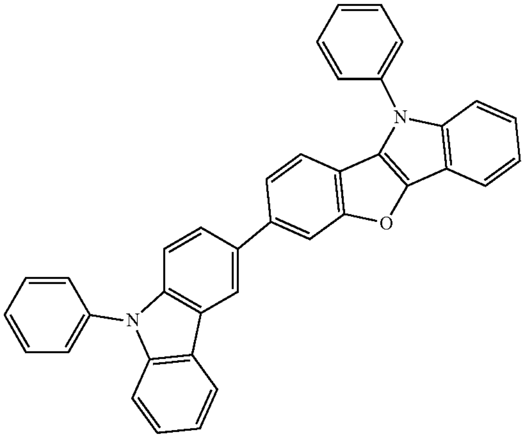
-continued
8
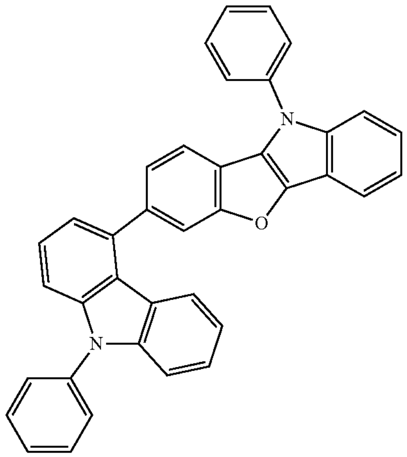
9
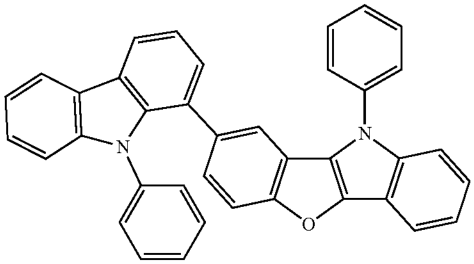
10
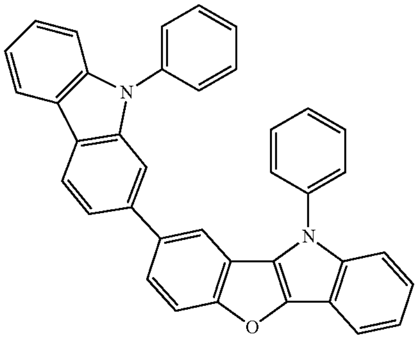
11
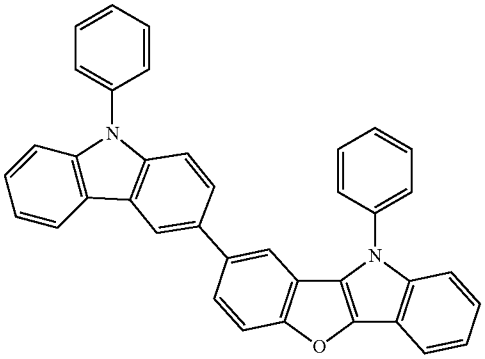

-continued
12
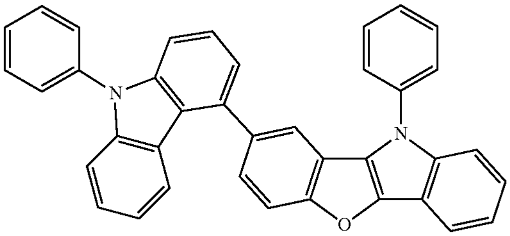
13
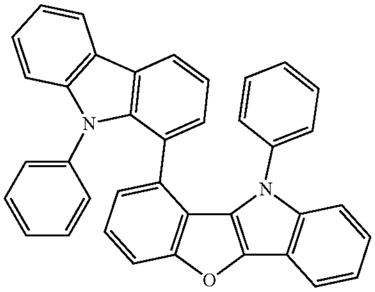
14
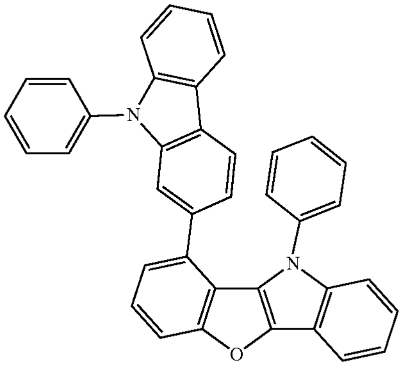
15
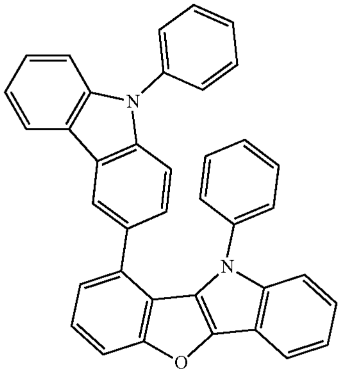
-continued
16
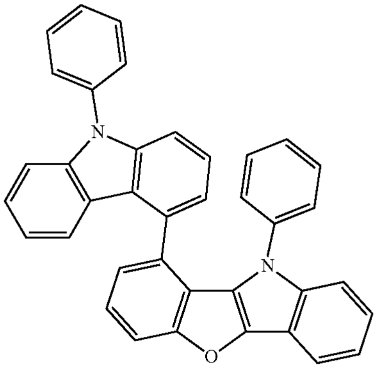
17
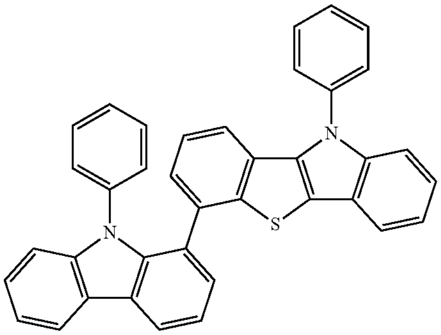
18
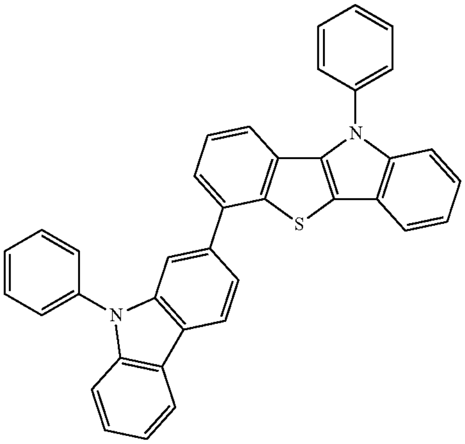
19
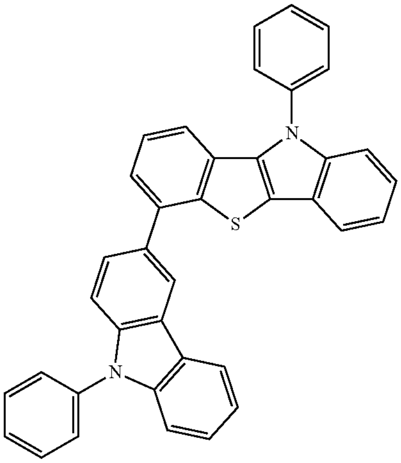

-continued
20
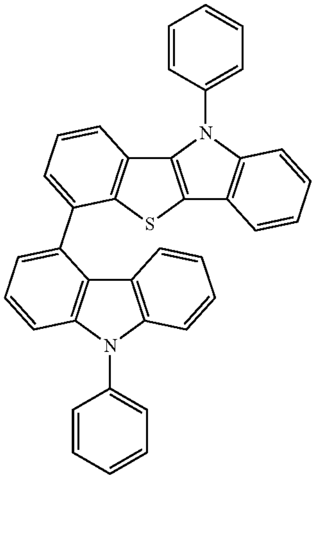
21
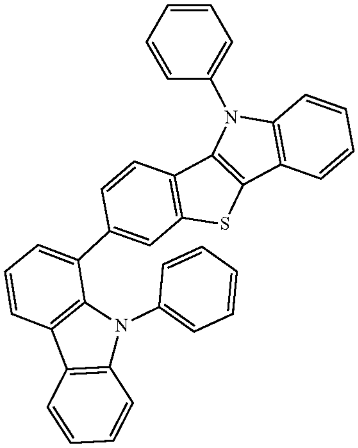
22
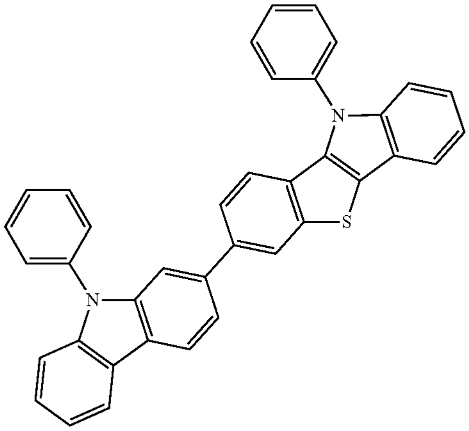
-continued
23
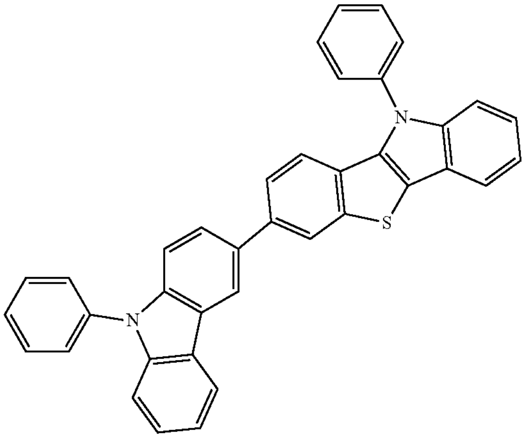
24
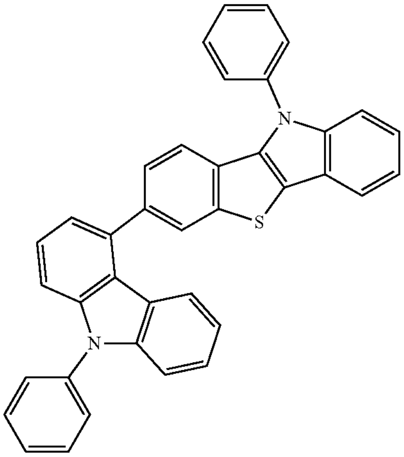
25
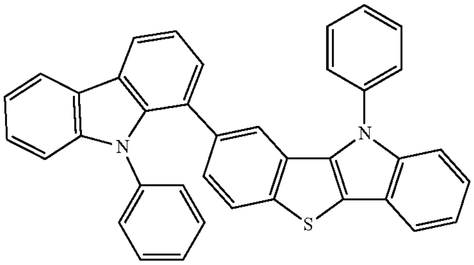
26
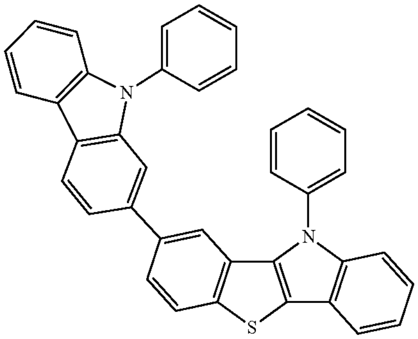

-continued
27
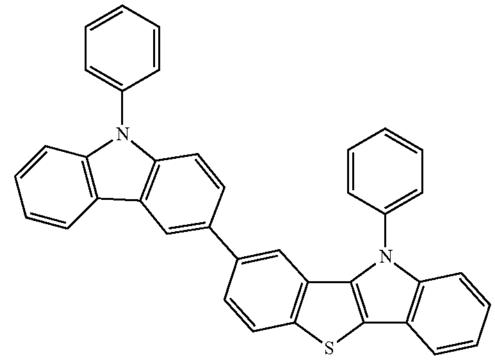
28
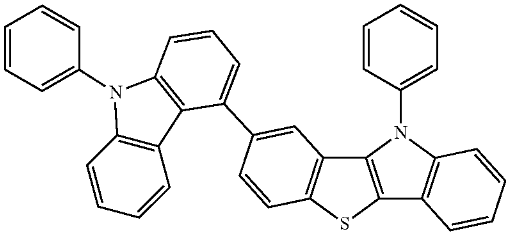
29
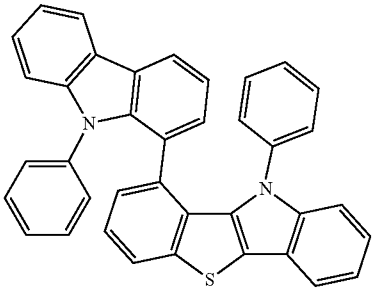
30
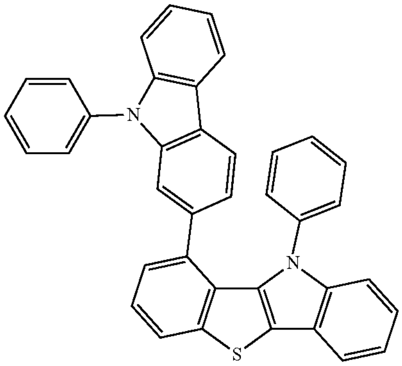
31
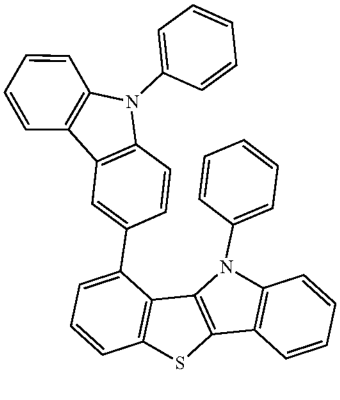
-continued
32
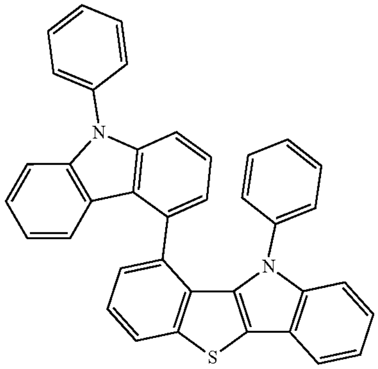
33
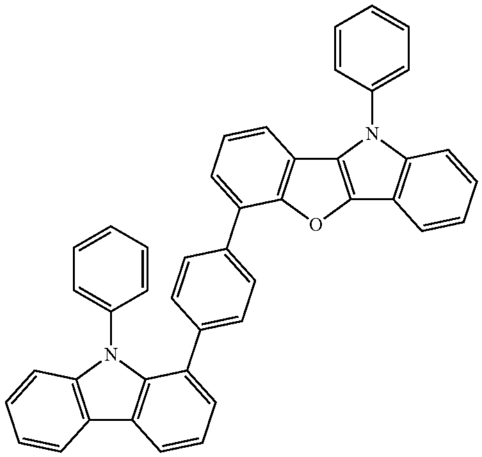
34
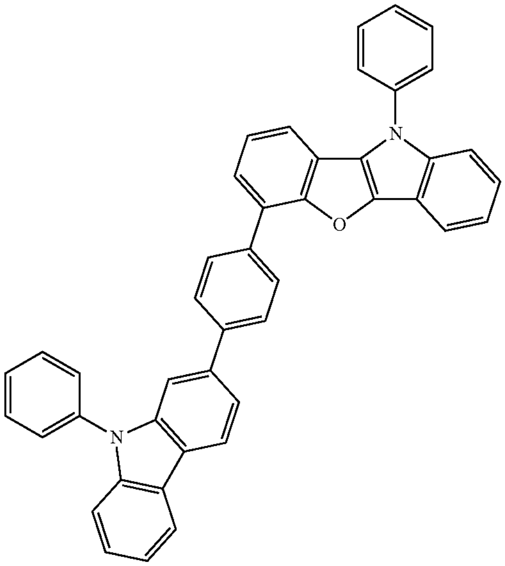

-continued
35
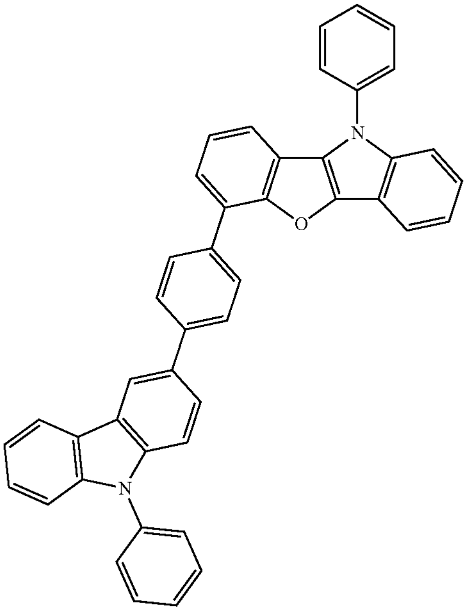
36
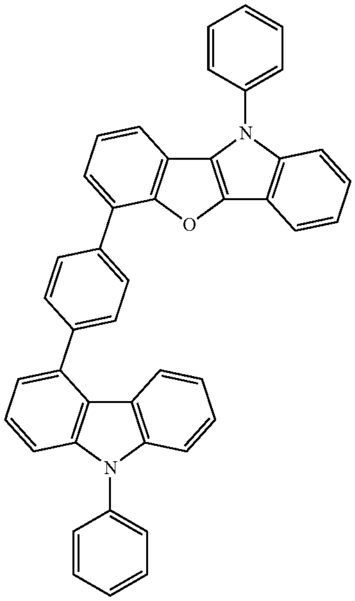
-continued
37
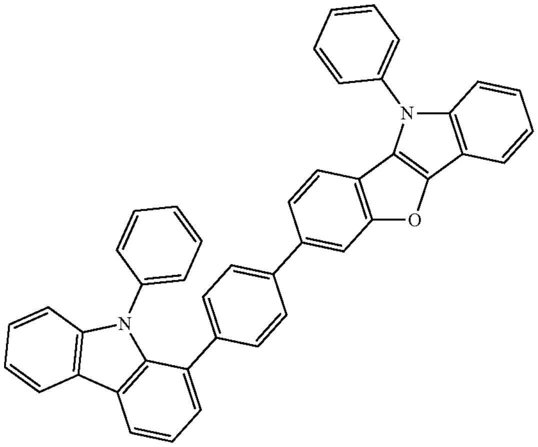
38
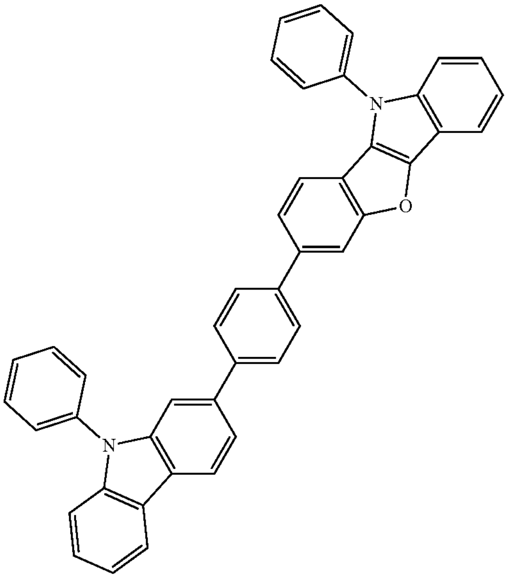
39
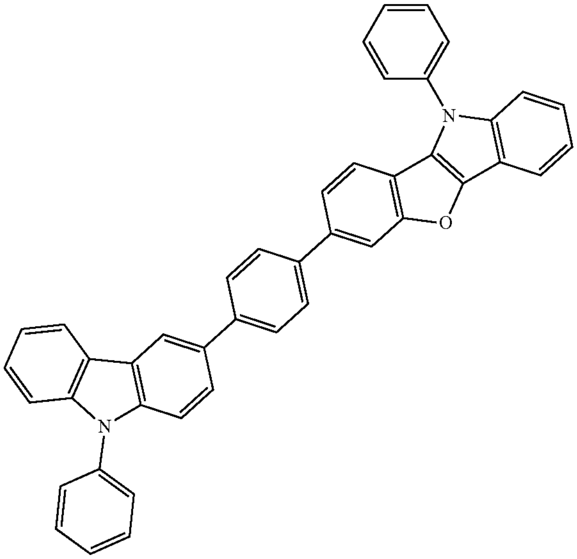

-continued
40
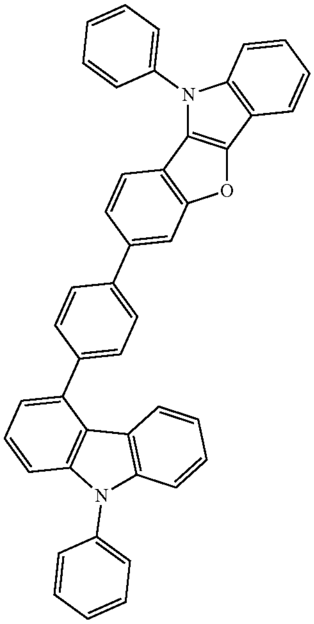
41
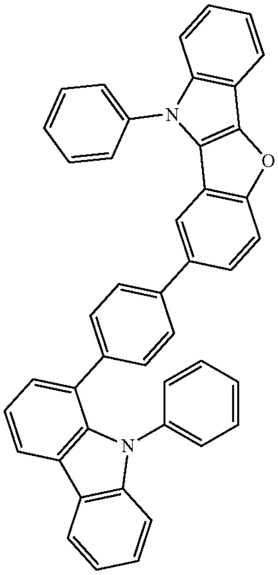
-continued
42
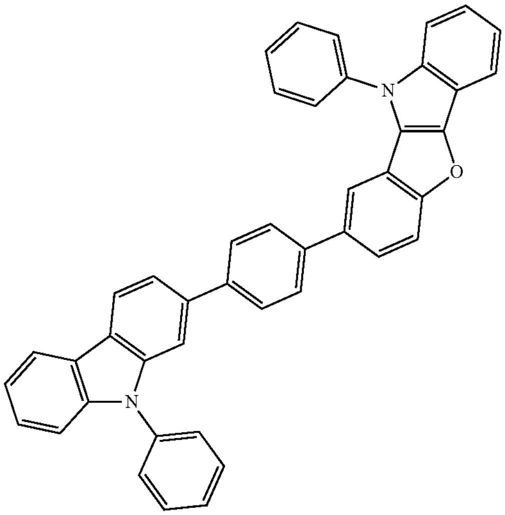
43
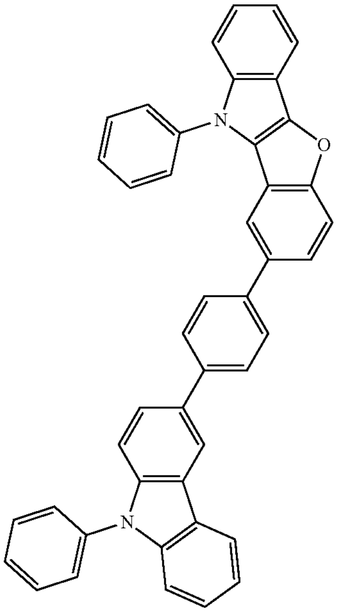

-continued
44
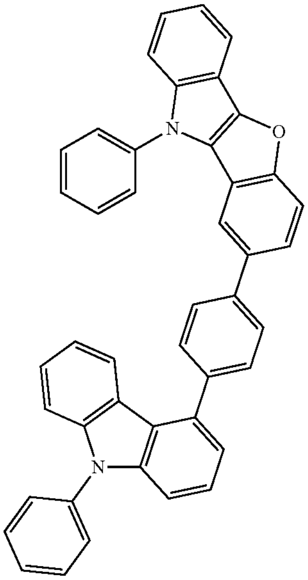
45
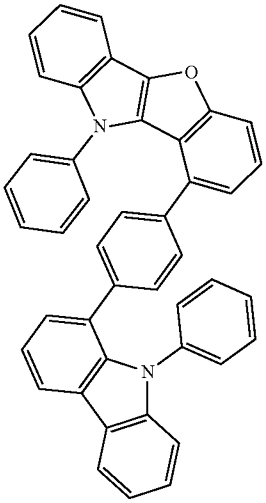
46
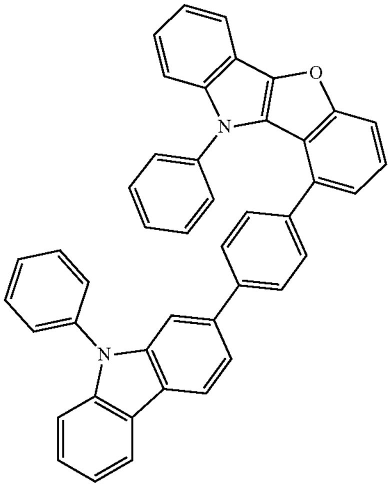
-continued
47
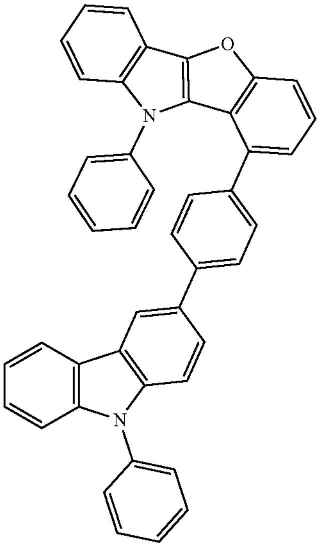
48
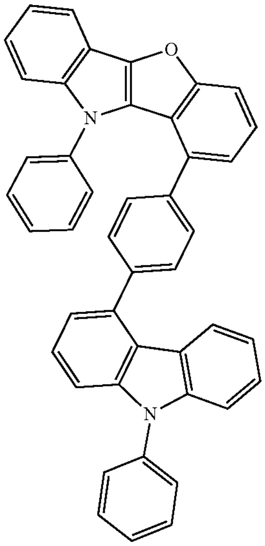
49
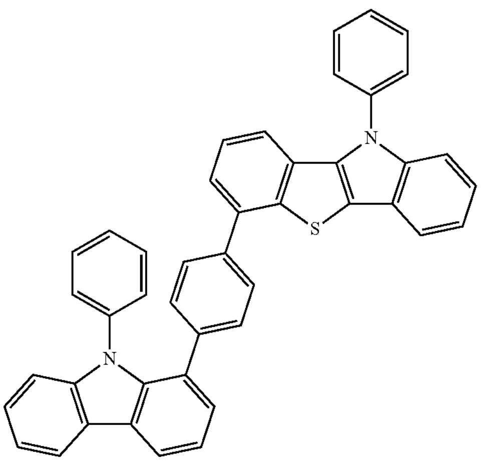

-continued
50
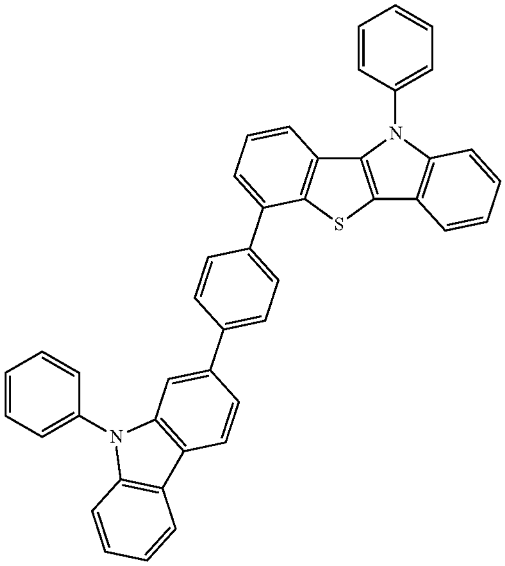
51
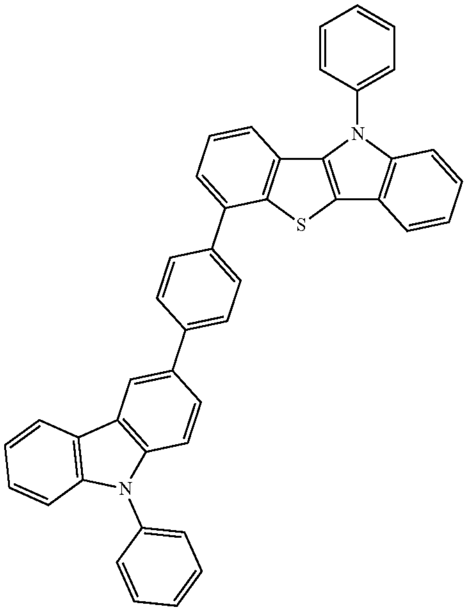
-continued
52
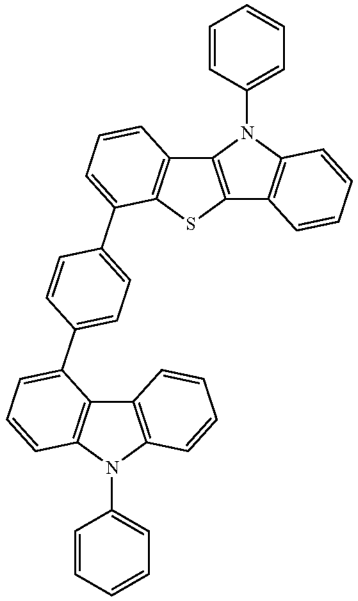
53
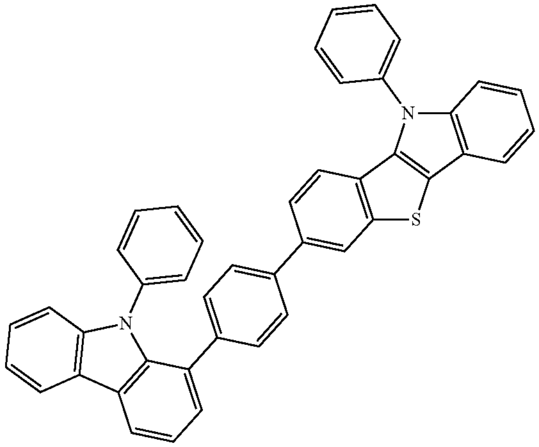
54
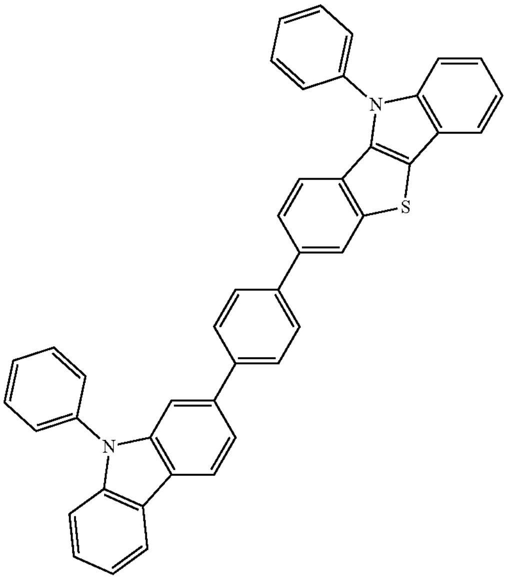

55
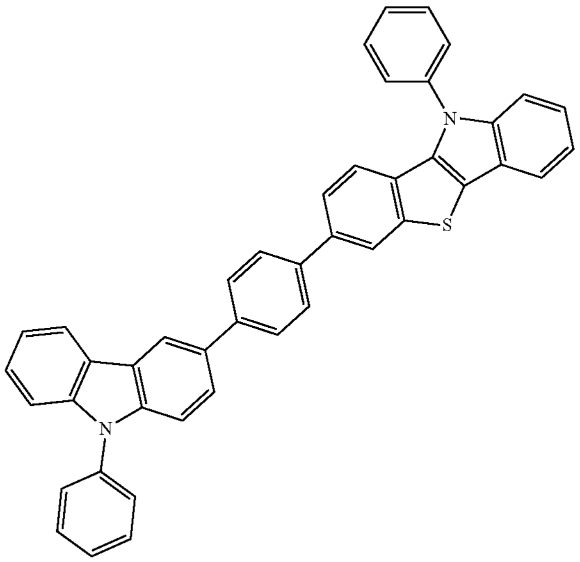
56
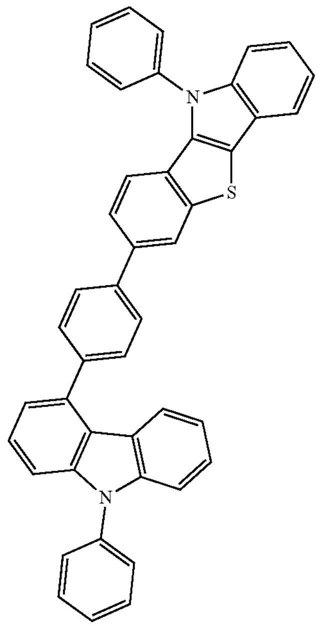
57
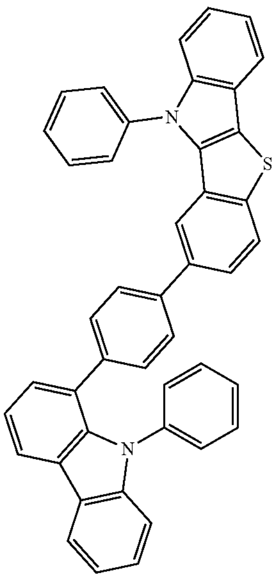
58
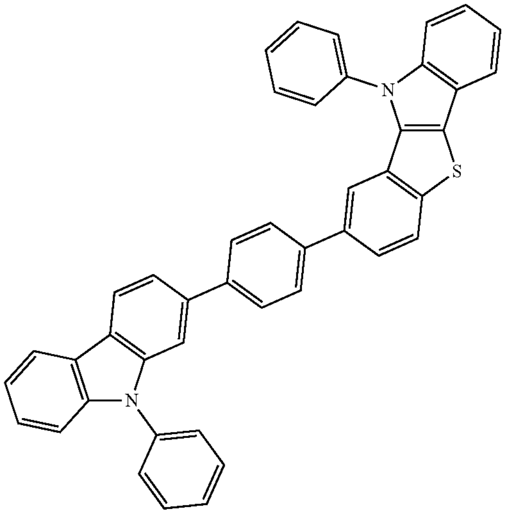

-continued
59
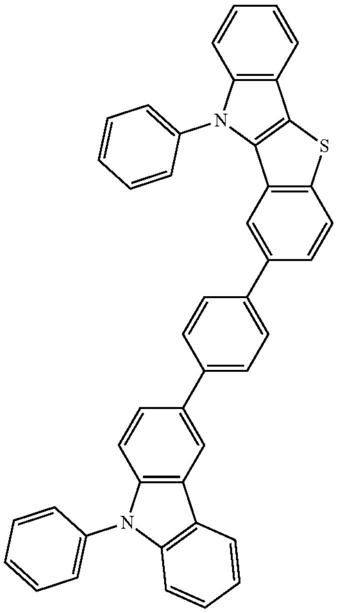
60
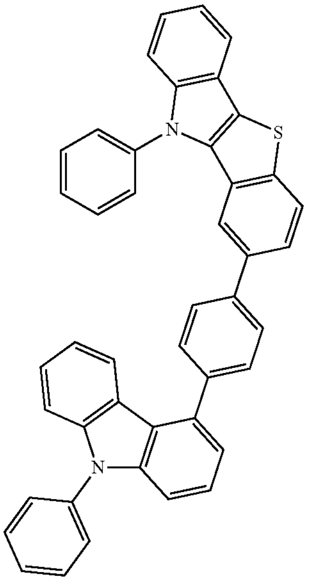
-continued
61
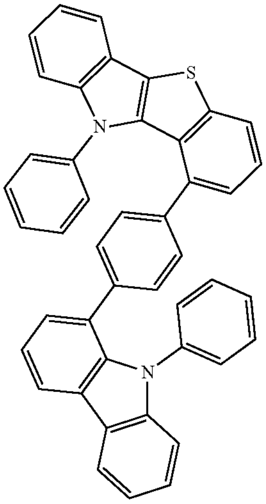
62
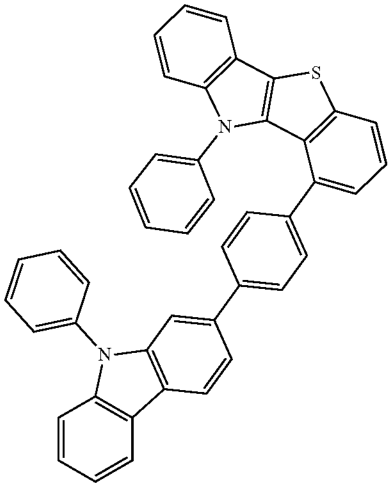
63
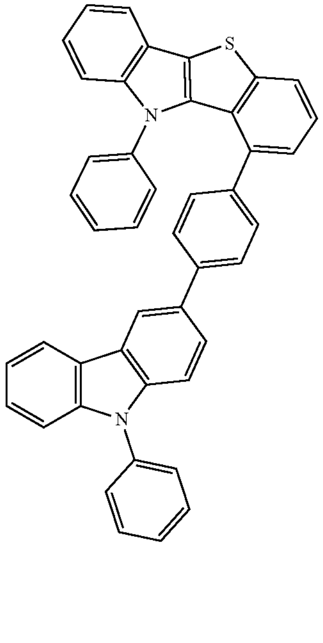

-continued
64
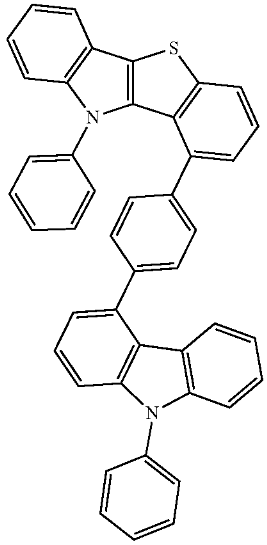
65
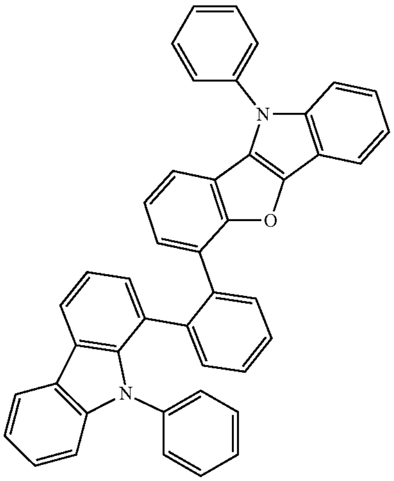
66
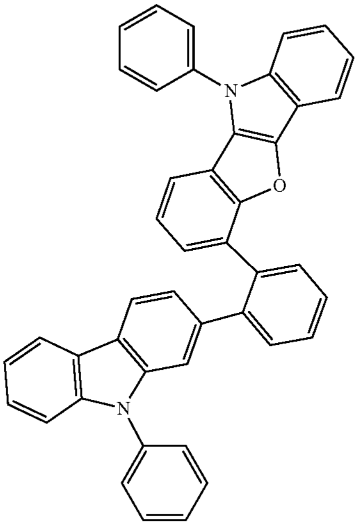
-continued
67
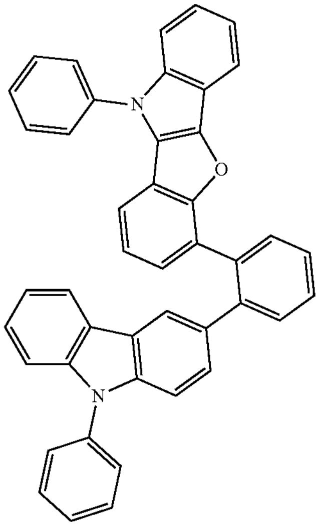
68
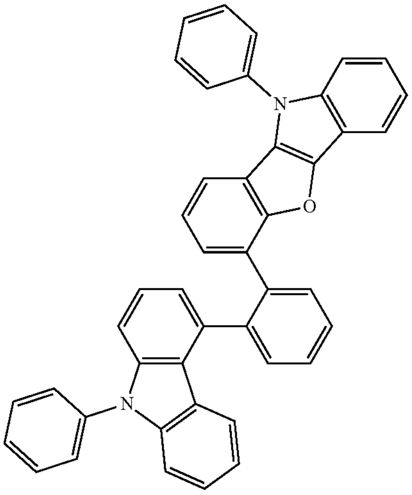
69
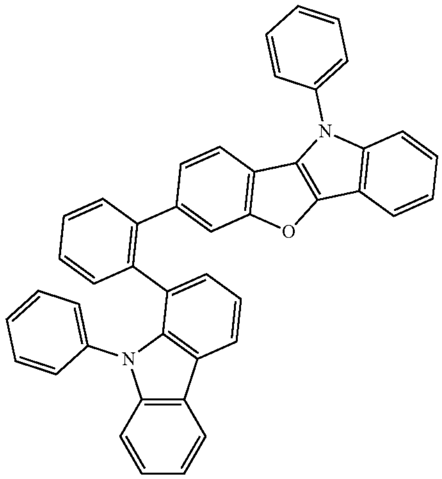

-continued
70
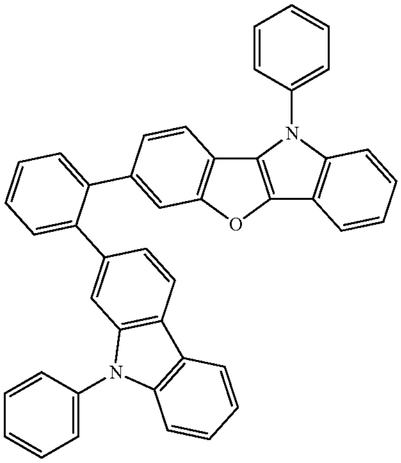
71
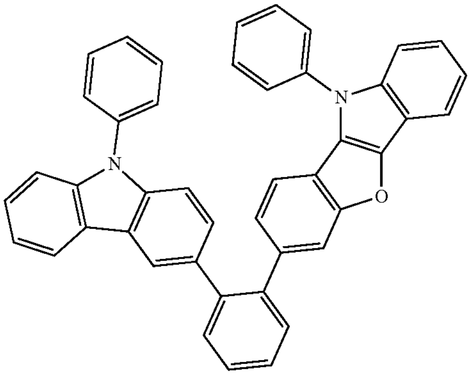
72
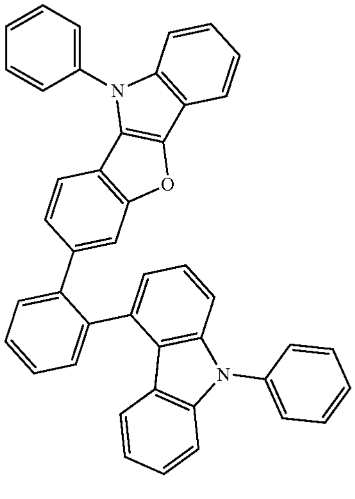
-continued
73
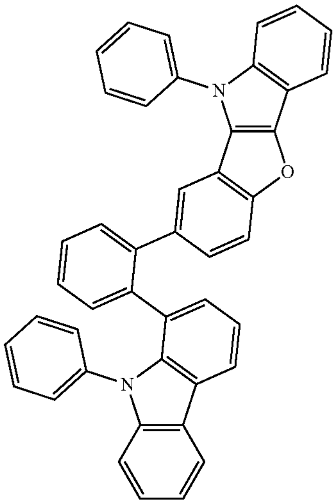
74
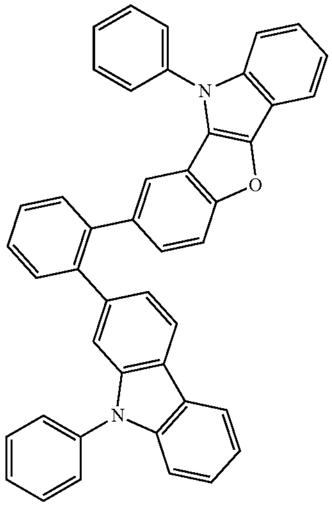
75
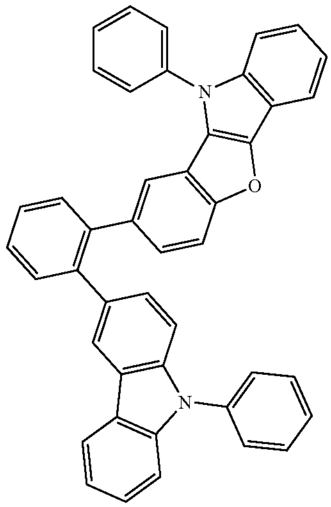

-continued
76
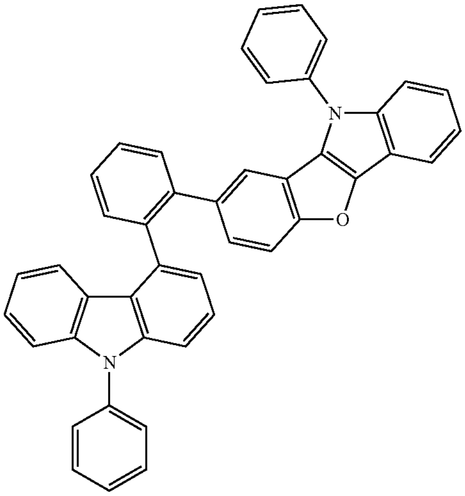
77
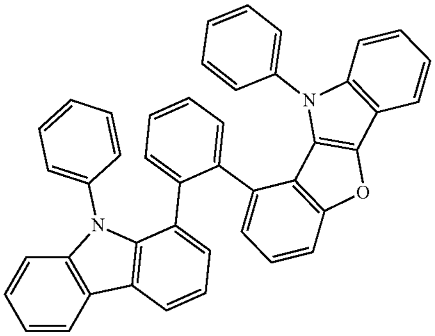
78
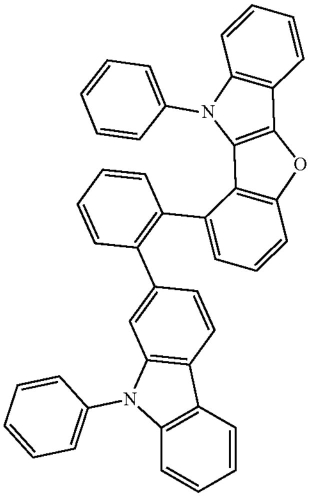
-continued
79
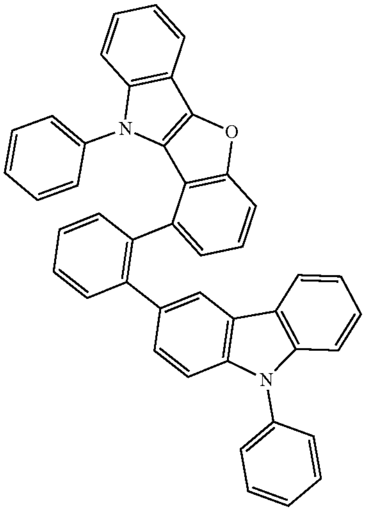
80
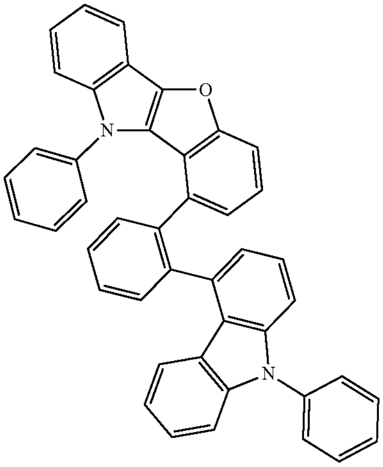
81
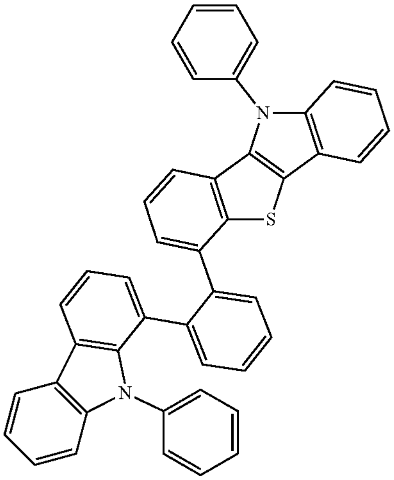

-continued
82
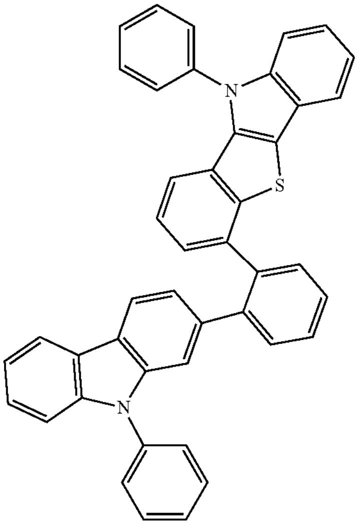
83
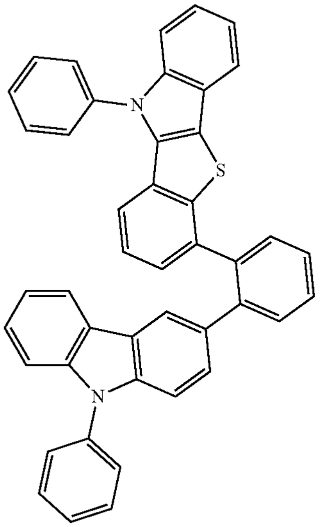
84
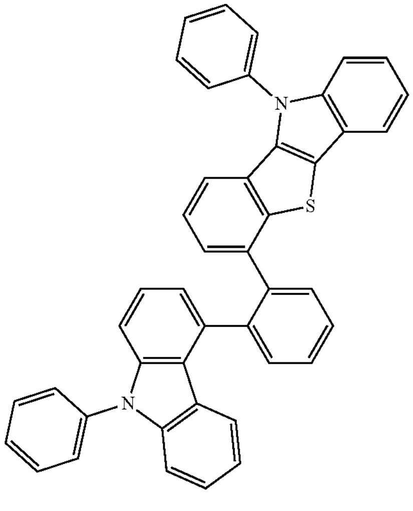
-continued
85
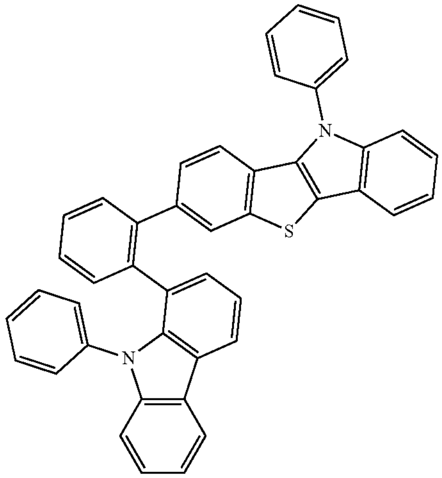
86
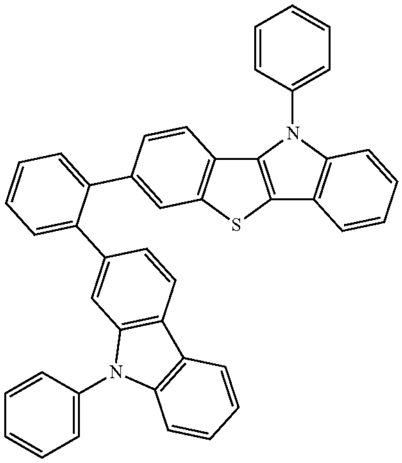
87
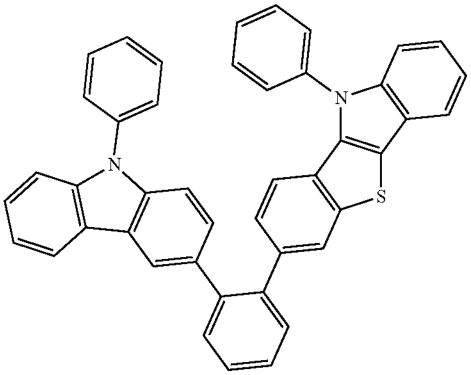

-continued
88
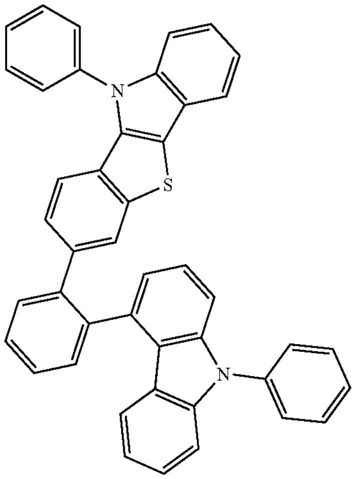
89
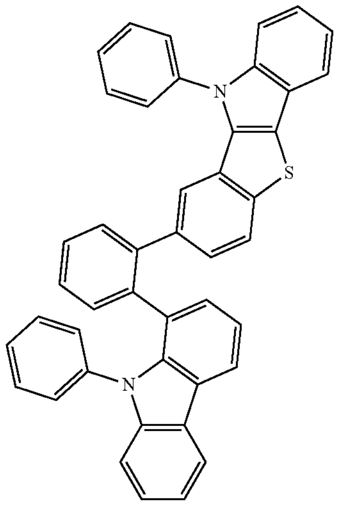
90
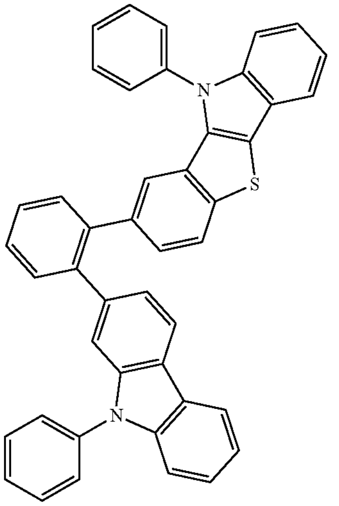
-continued
91
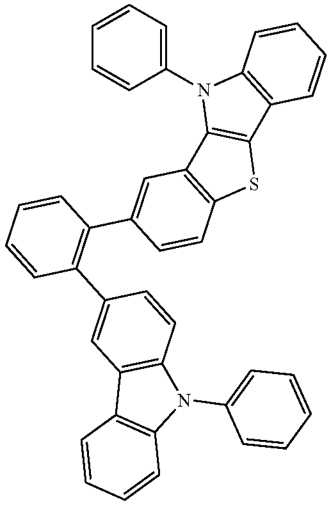
92
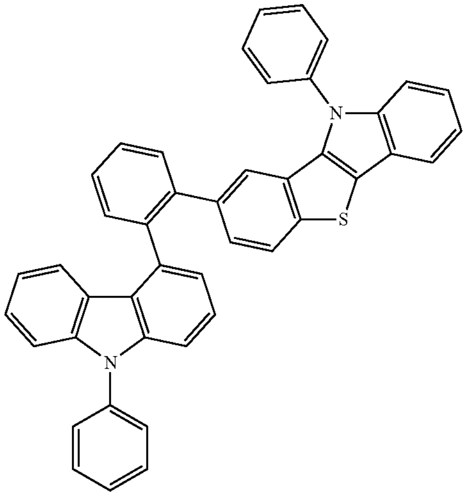
93
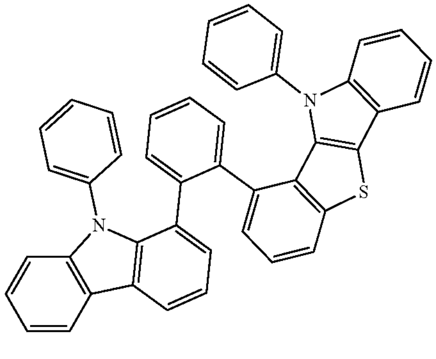

-continued
94
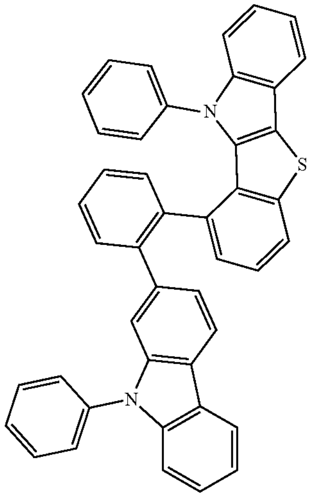
95
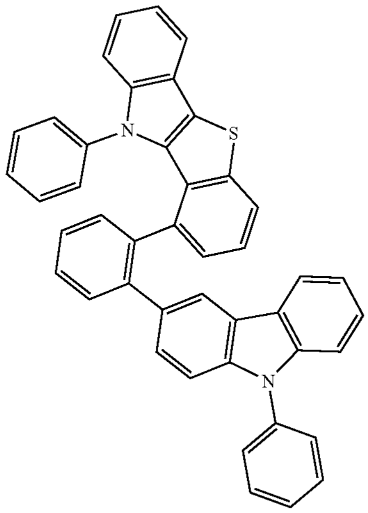
96
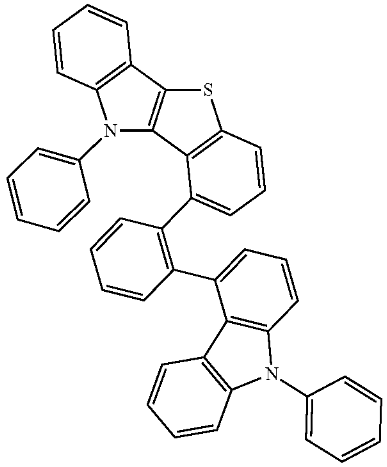
-continued
97
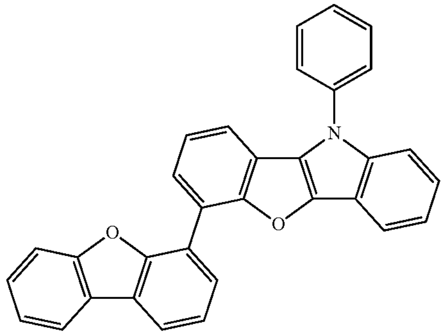
98
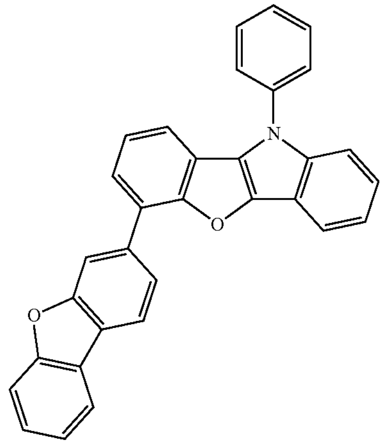
99
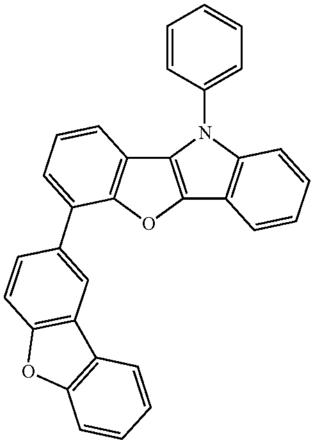
100
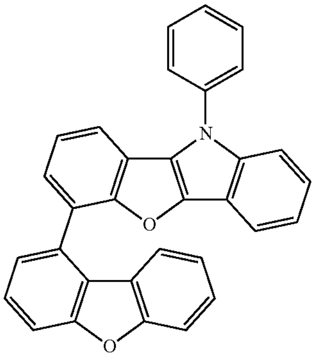

-continued
101
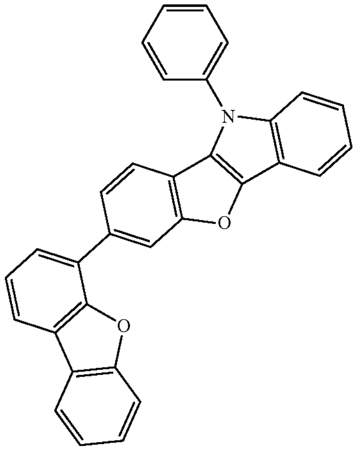
102
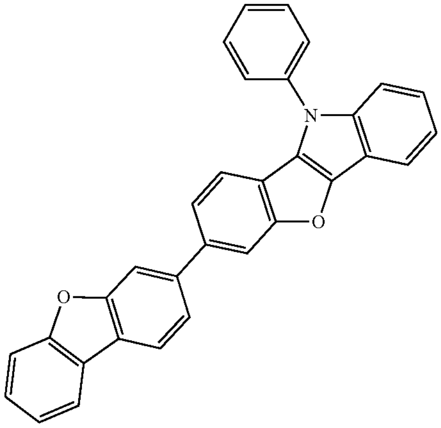
103
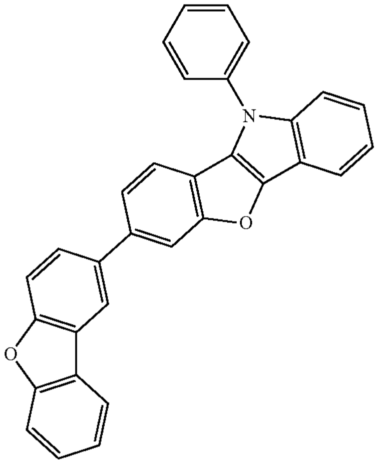
-continued
104
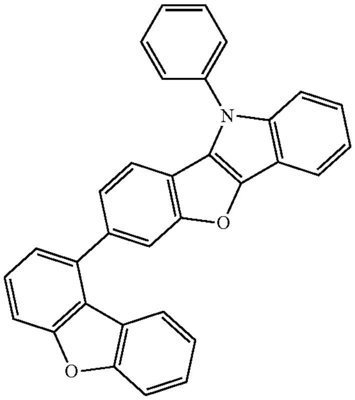
105
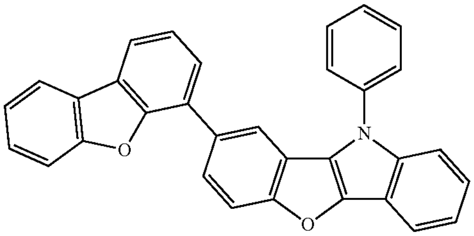
106
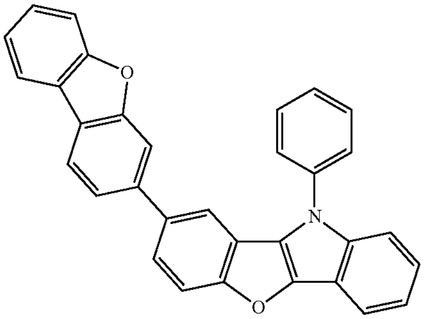
107
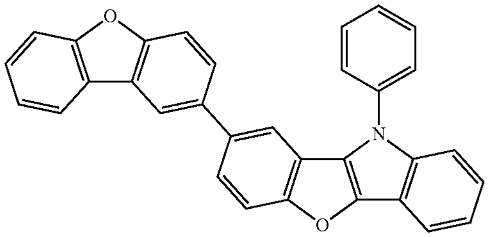
108
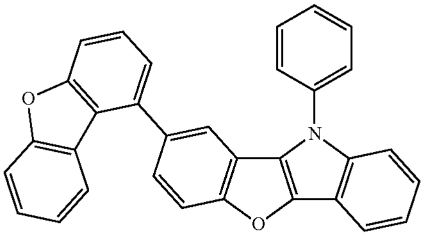

-continued
109
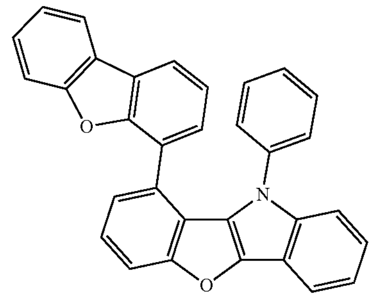
110
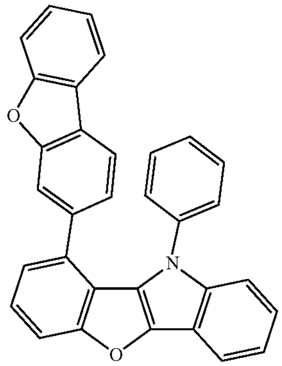
111
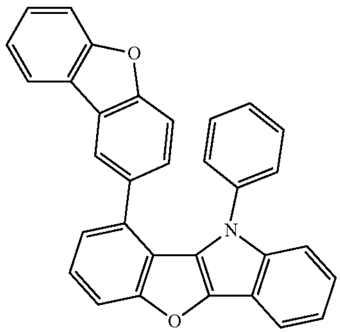
112
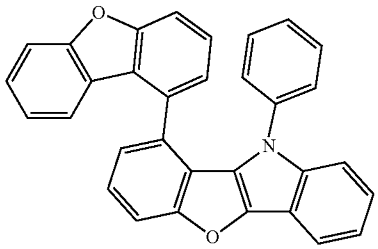
113
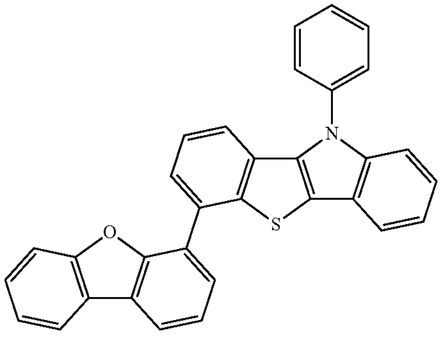
-continued
114
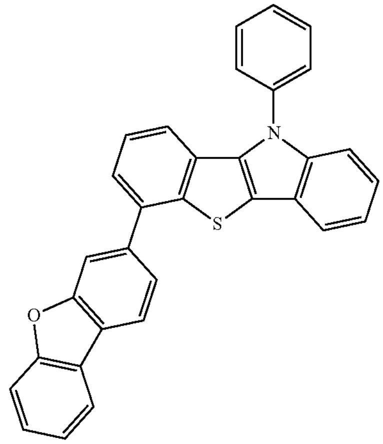
115
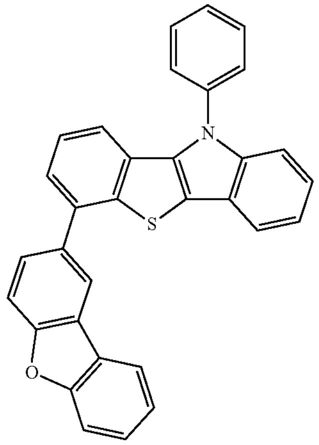
116
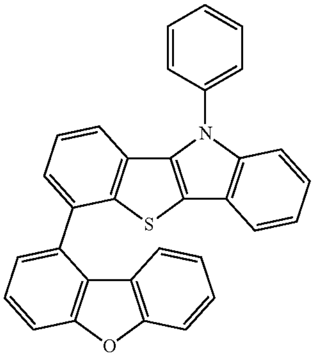

-continued
117
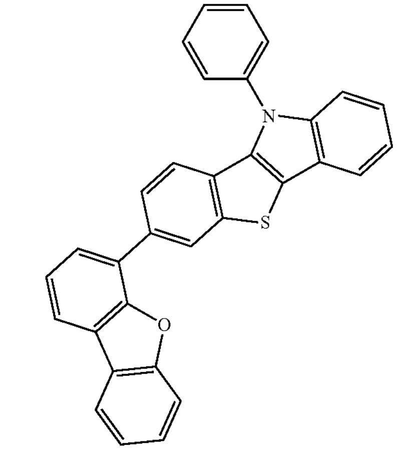
118
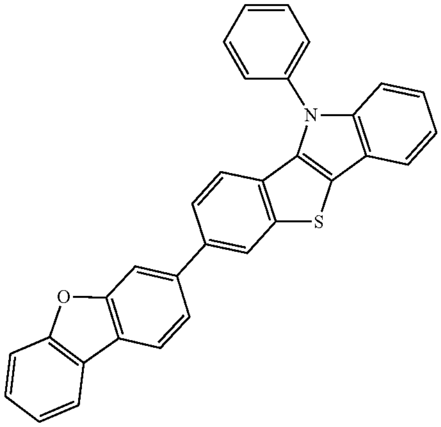
119
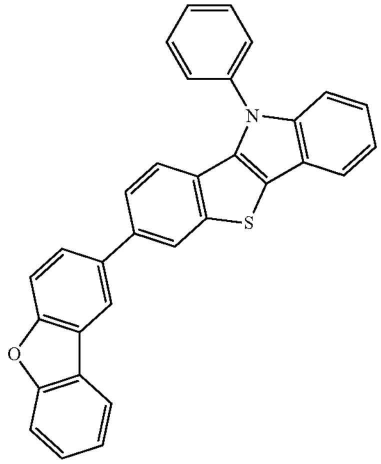
-continued
120
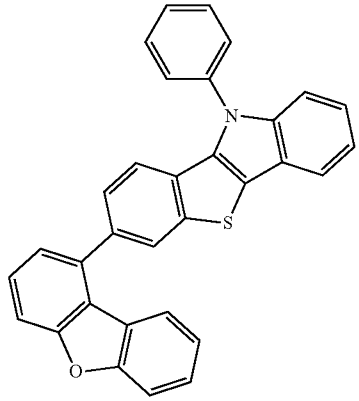
121
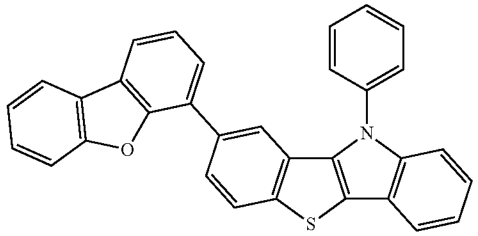
122
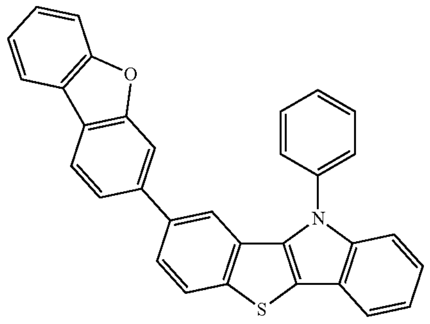
123
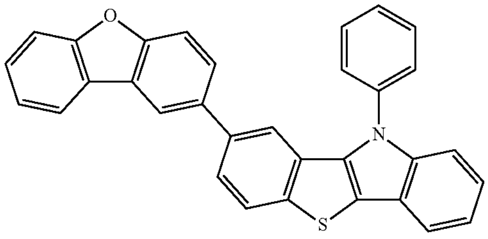
124
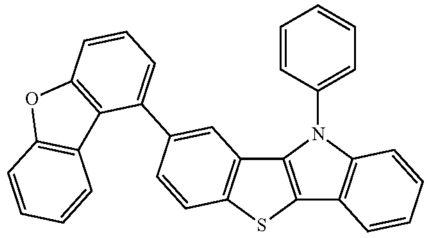

-continued
125
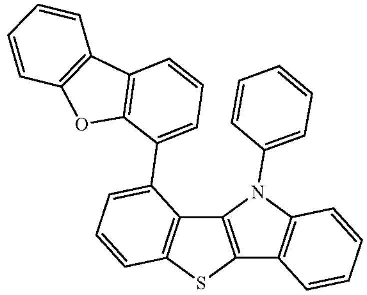
126
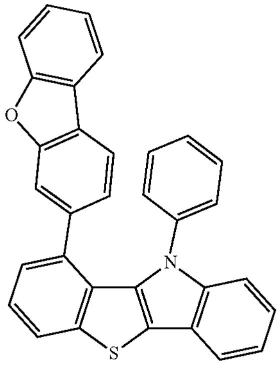
127
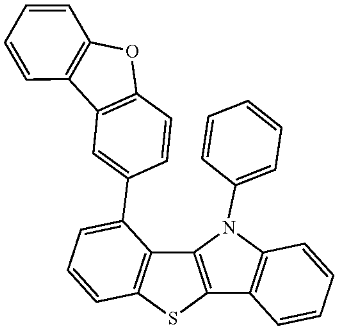
128
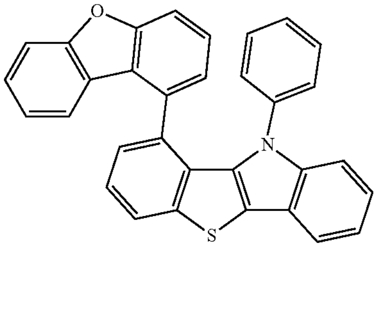
-continued
129
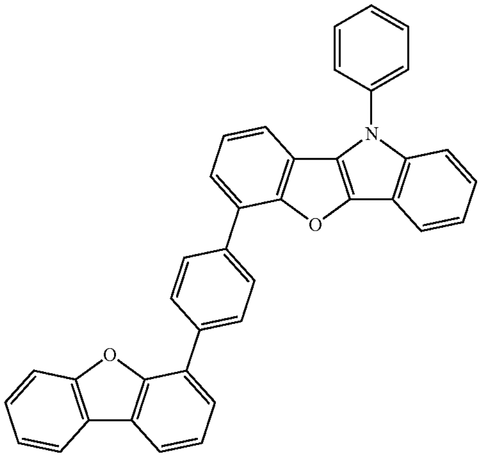
130
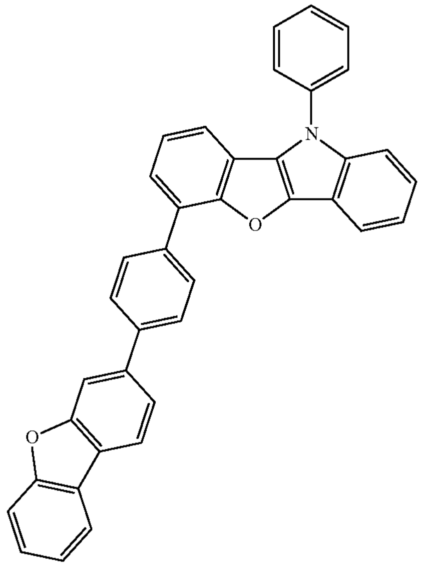
131
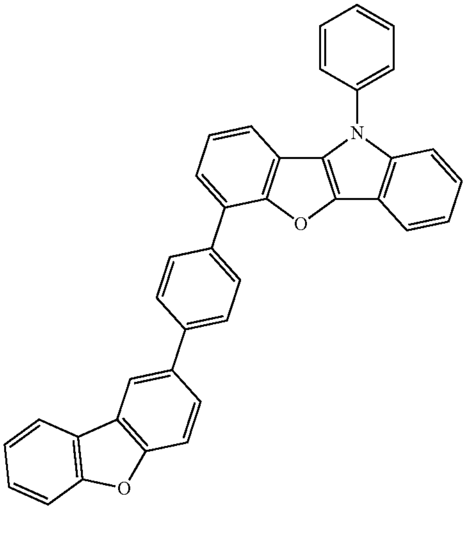

-continued
132
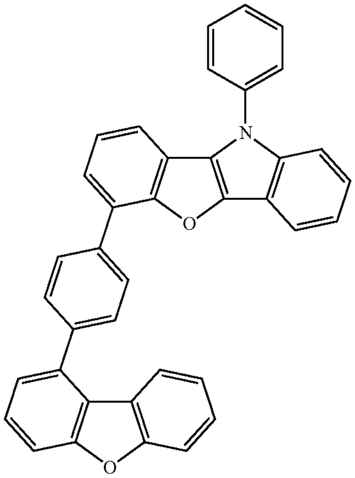
133
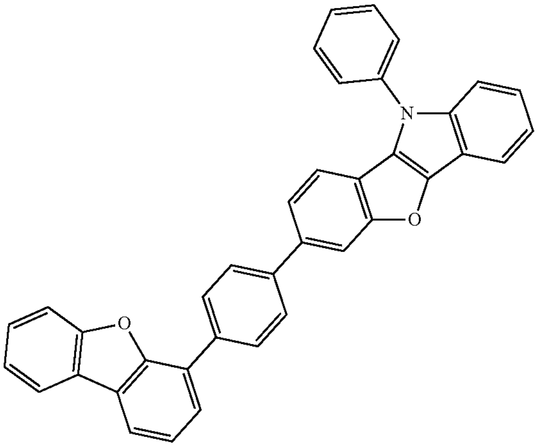
134
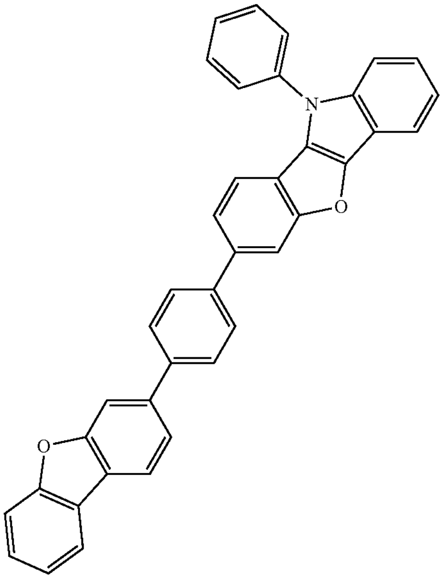
-continued
135
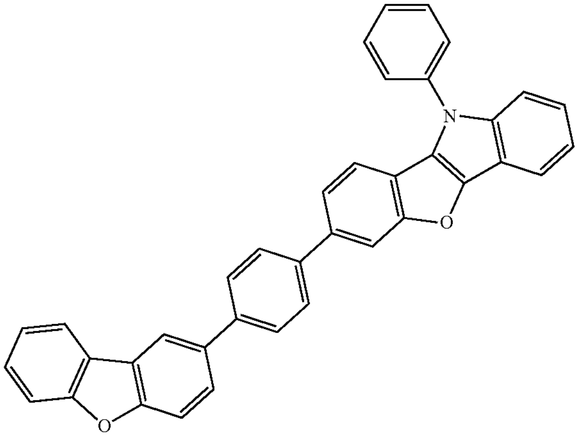
136
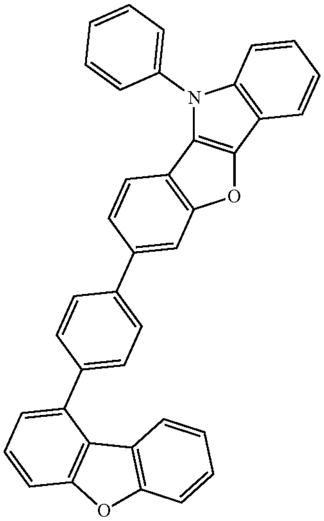
137
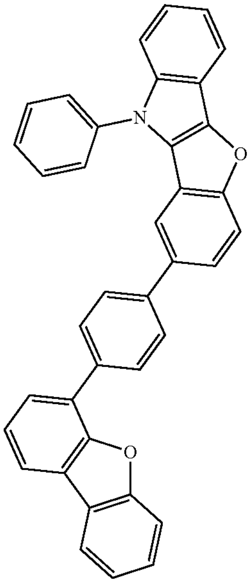

138
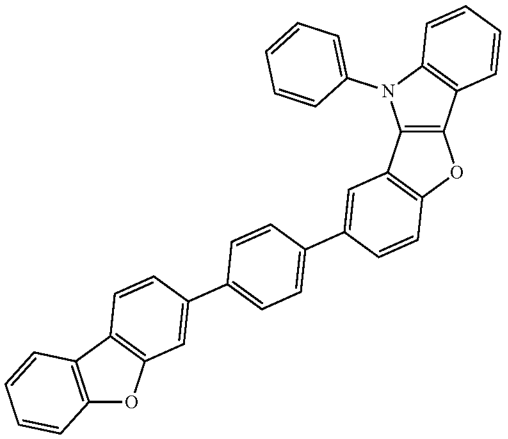
139
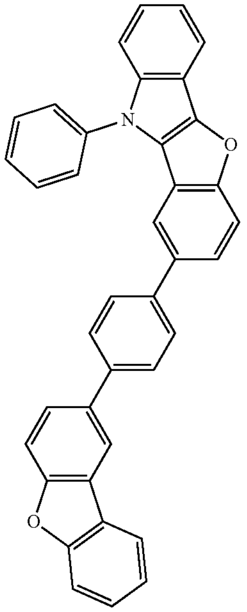
140
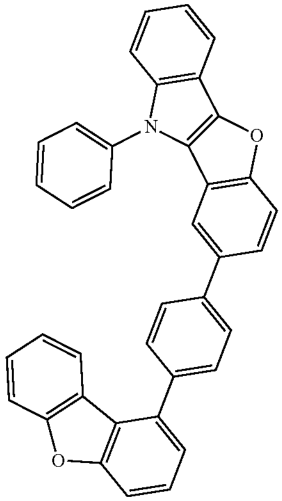
141
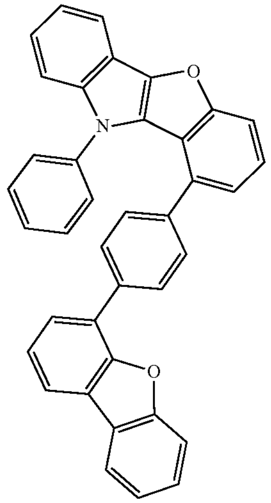
142
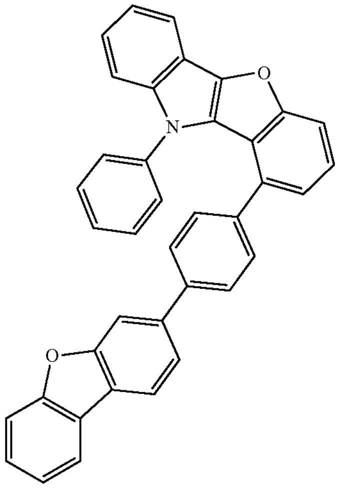
143
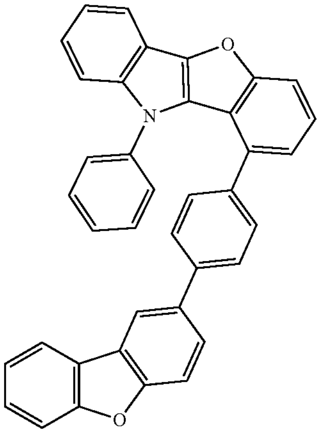

-continued
144
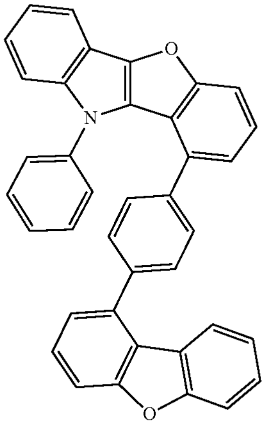
145
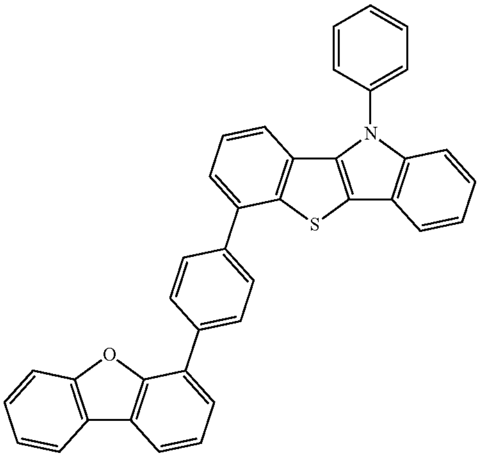
146
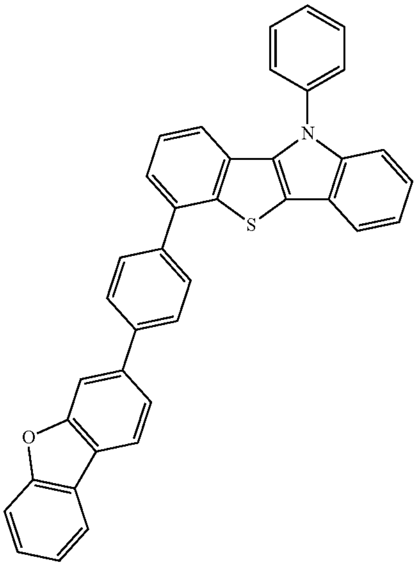
-continued
147
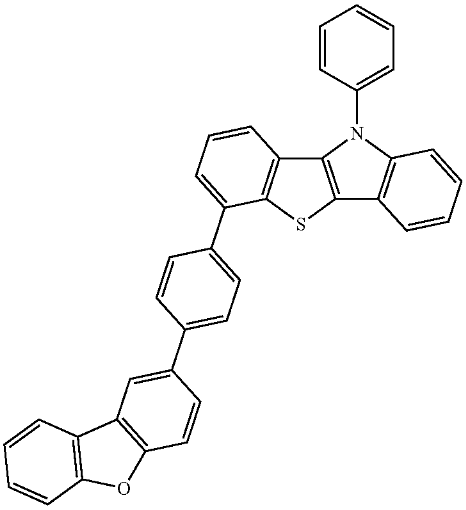
148
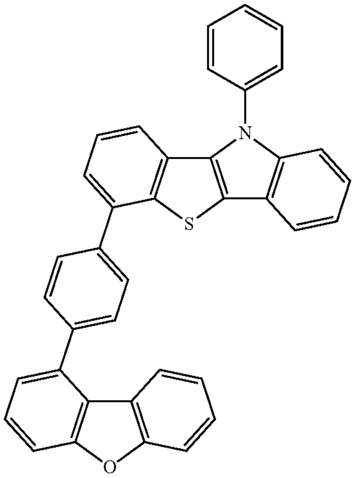
149
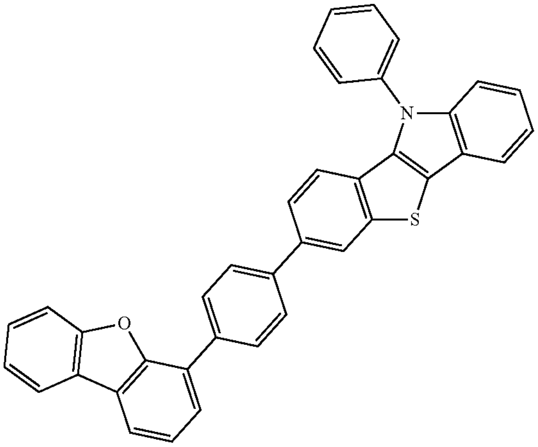

-continued
150
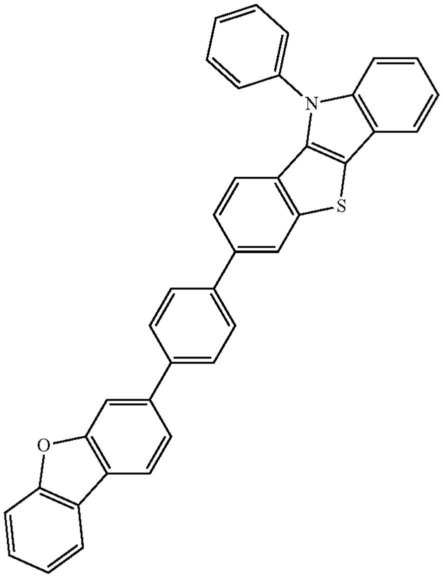
151
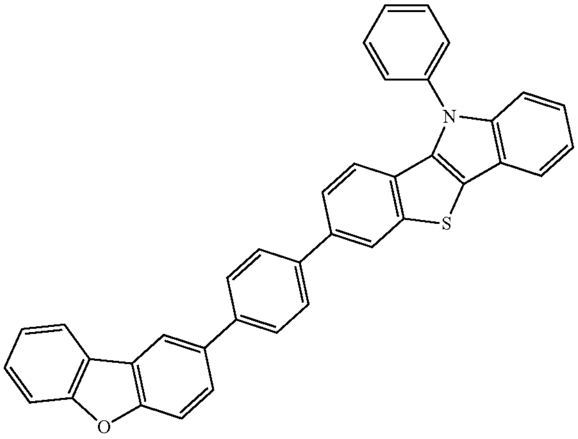
152
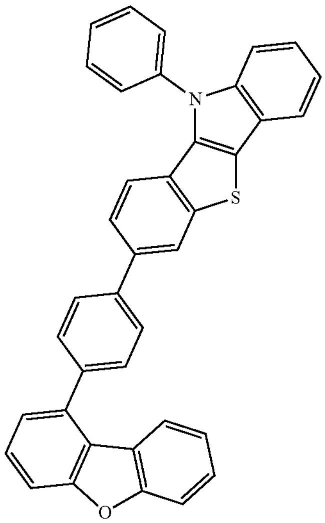
-continued
153
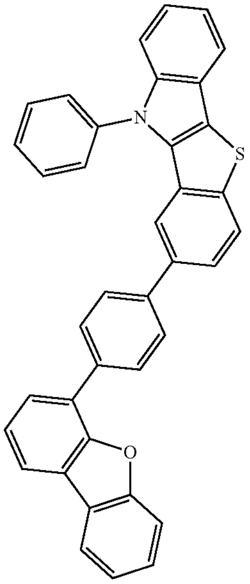
154
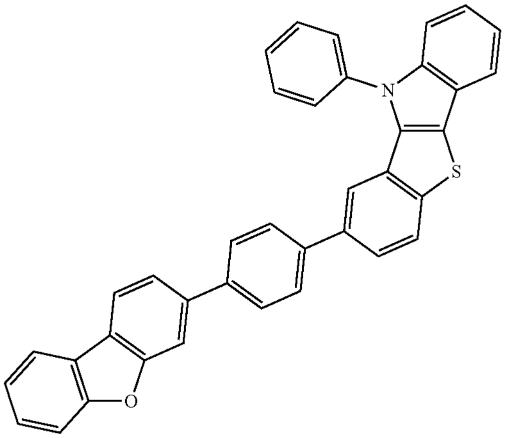
155
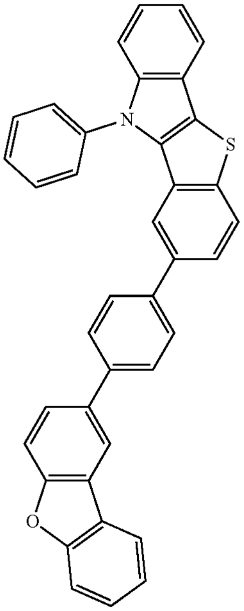

-continued
156
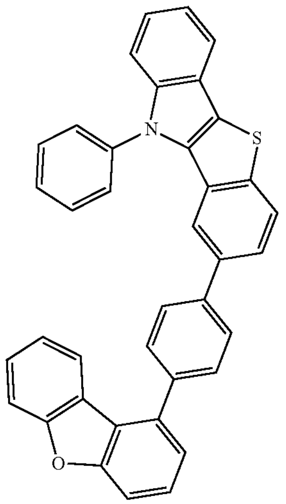
157
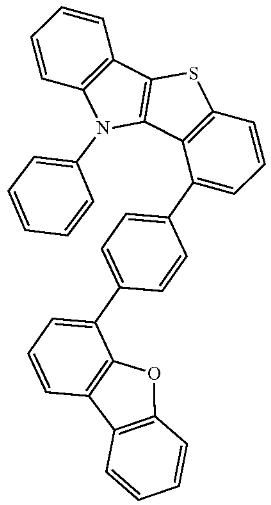
158
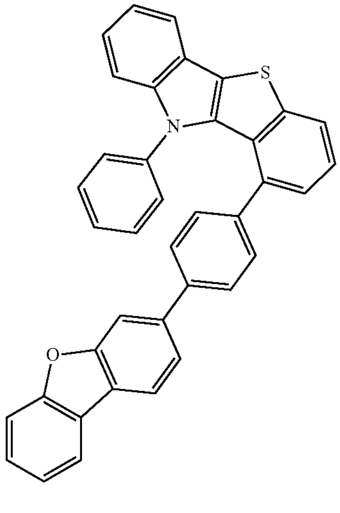
-continued
159
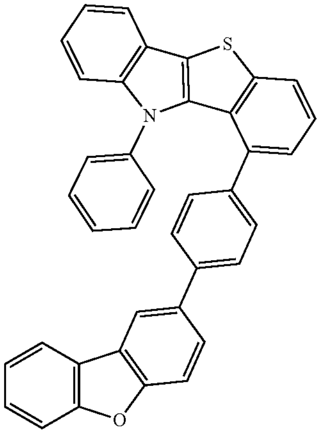
160
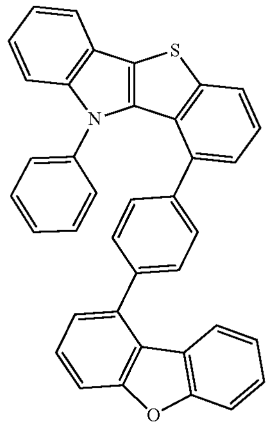
161
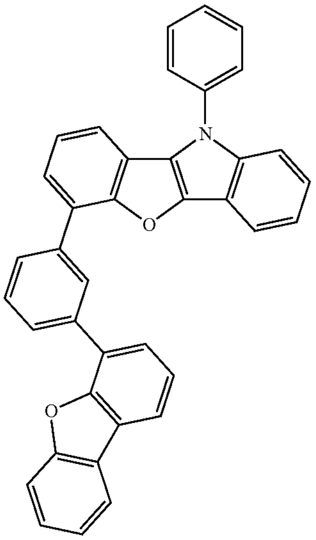

-continued
162
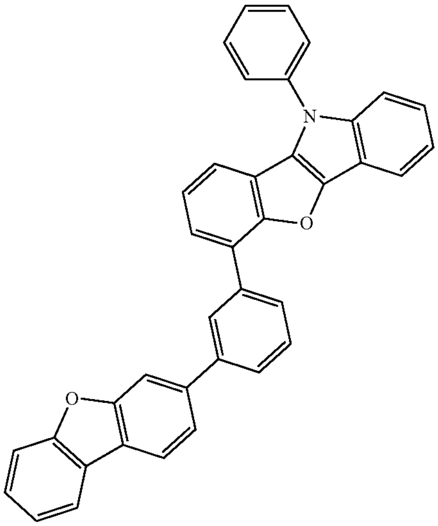
163
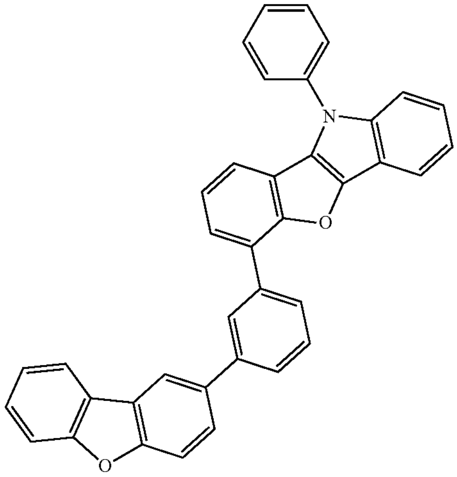
164
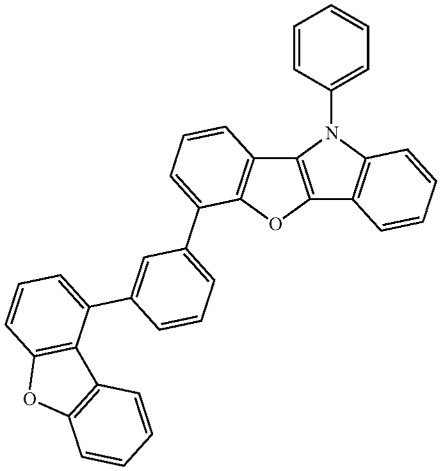
-continued
165
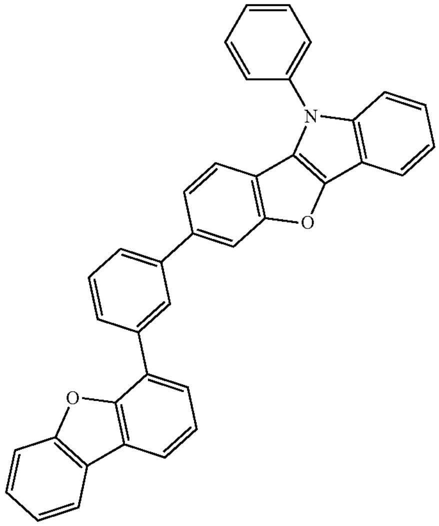
166
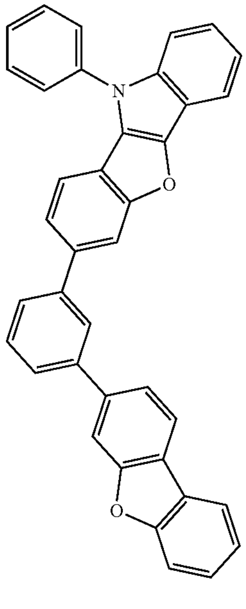
167
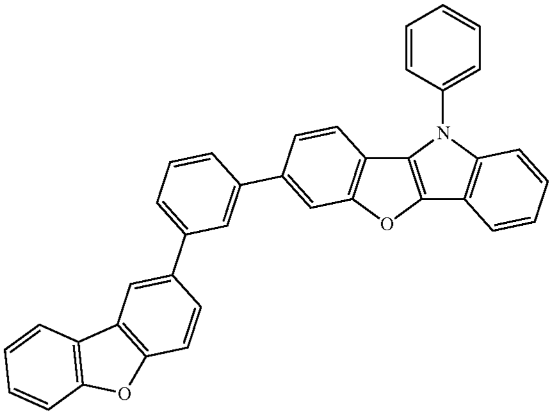

-continued
168
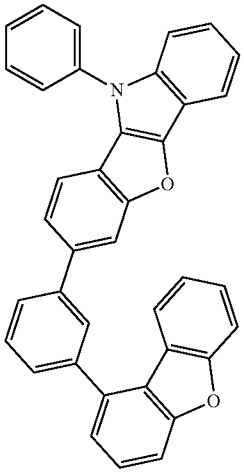
169
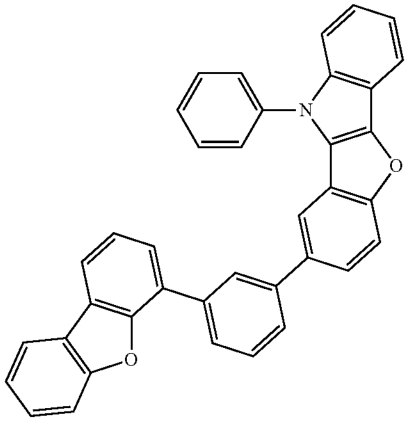
170
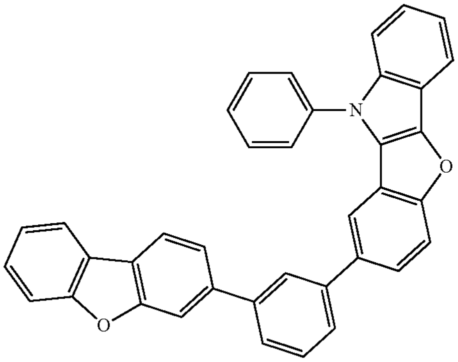
-continued
171
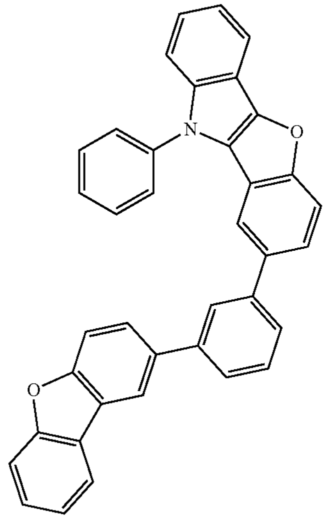
172
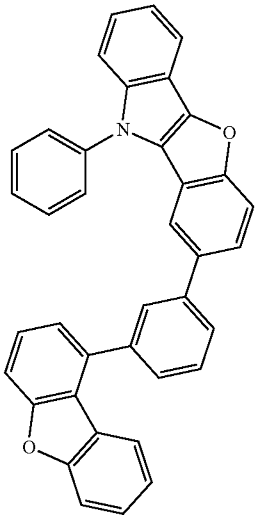
173
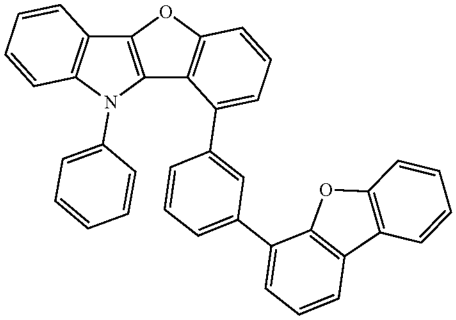

-continued
174
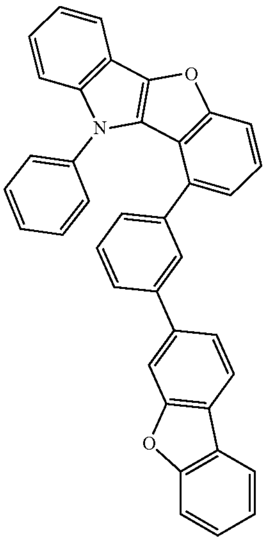
175
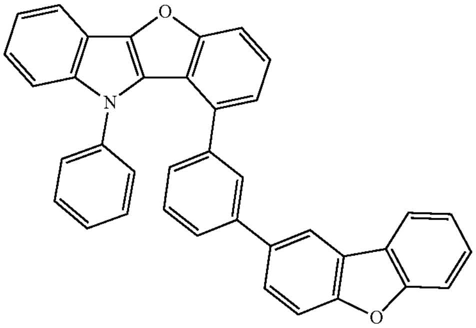
176
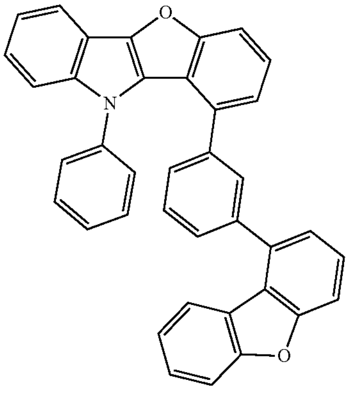
-continued
177
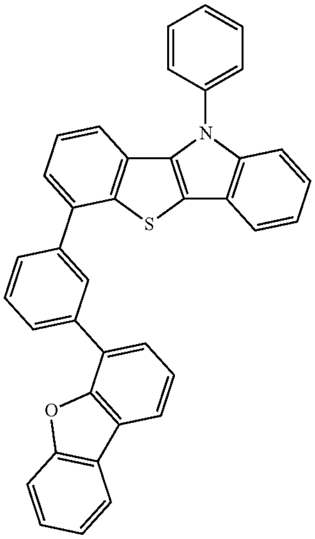
178
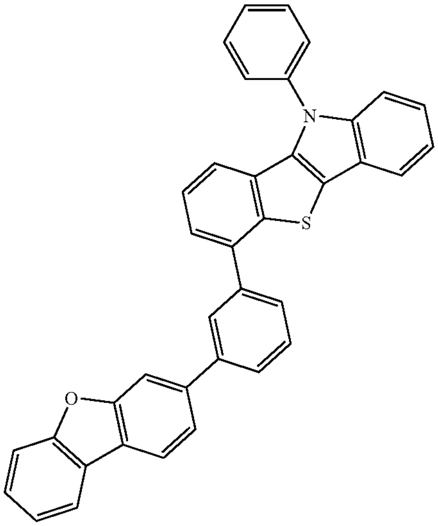
179
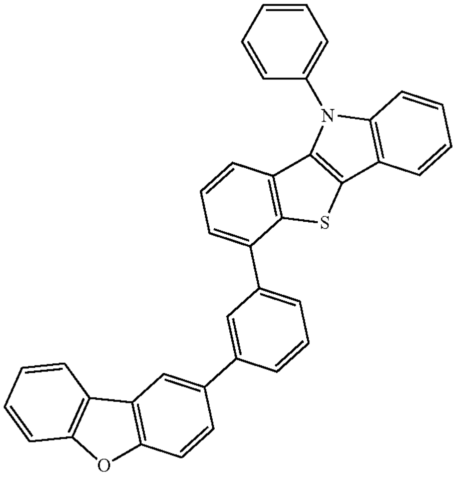

-continued
180
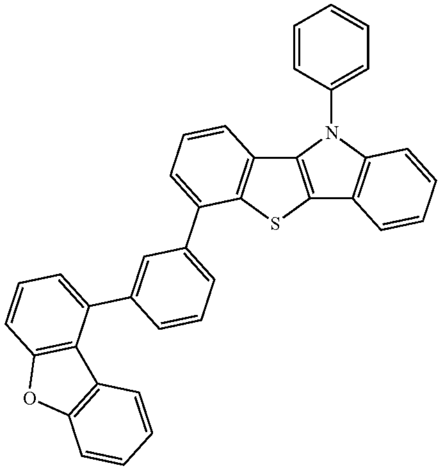
181
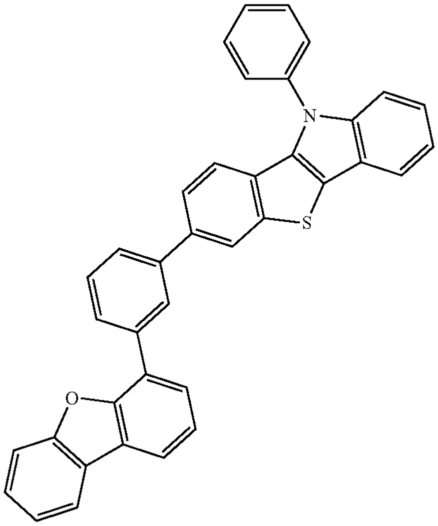
182
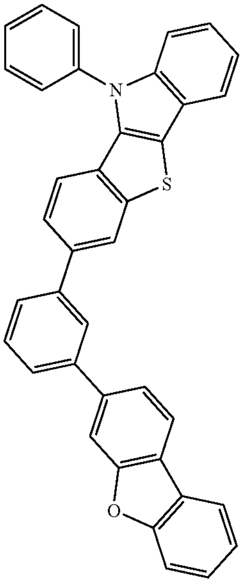
-continued
183
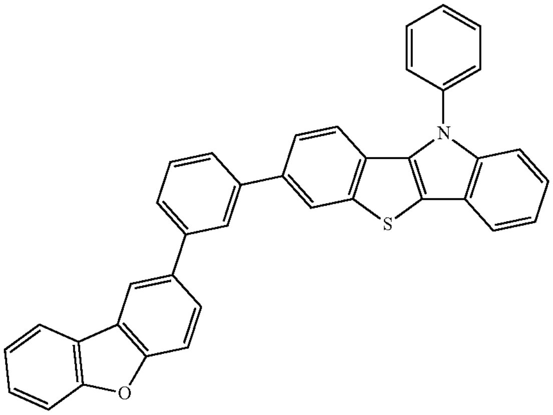
184
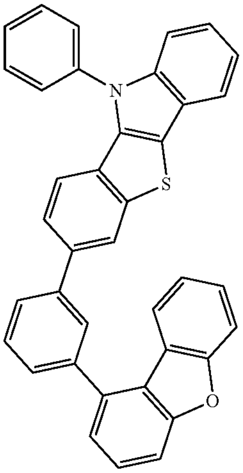
185
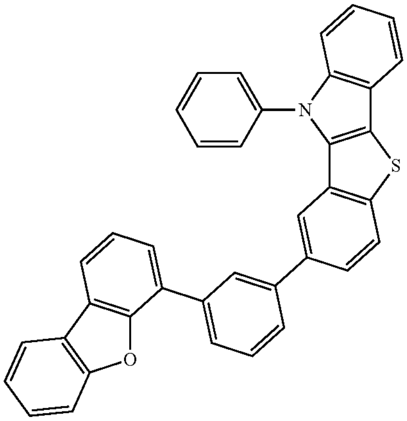

-continued
186
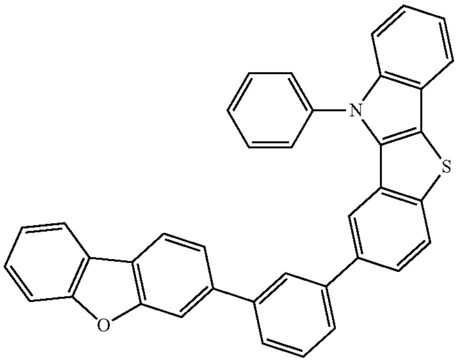
187
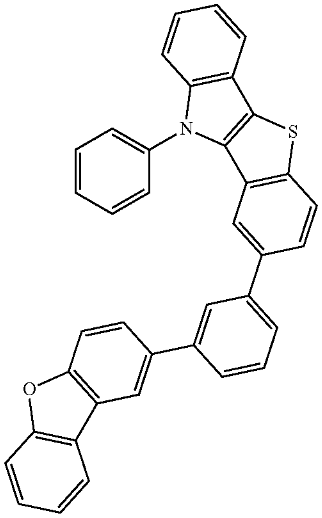
188
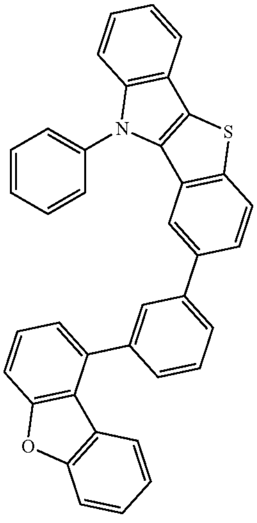
-continued
189
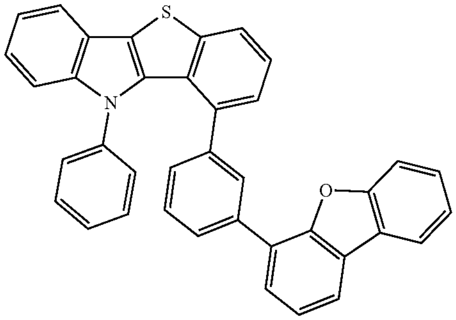
190
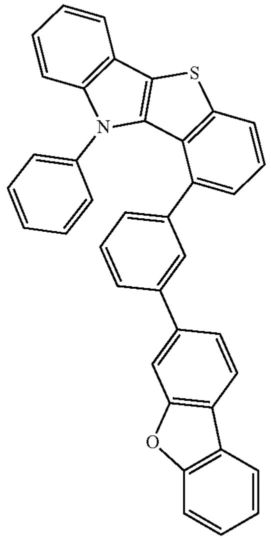
191
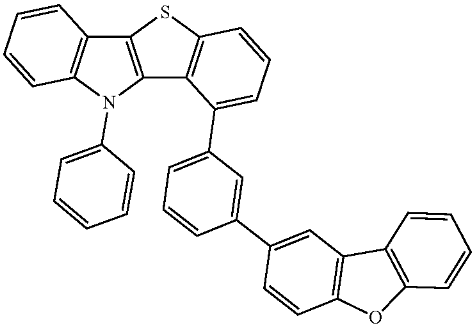
192
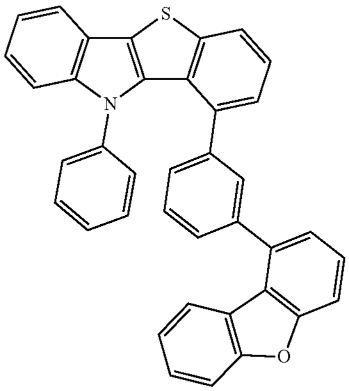

-continued
193
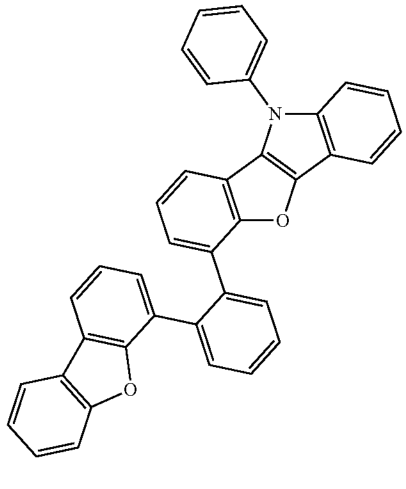
194
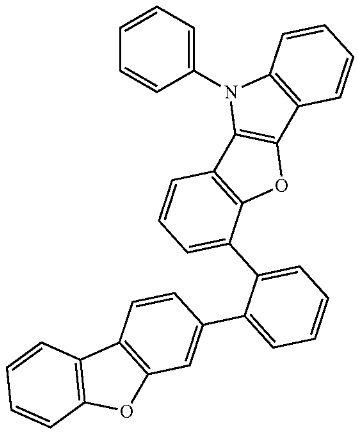
195
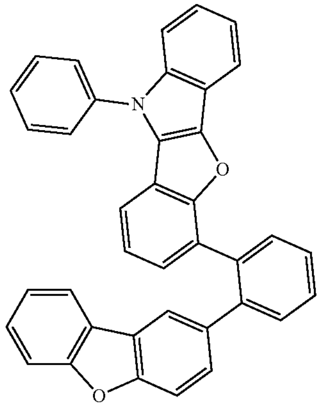
-continued
196
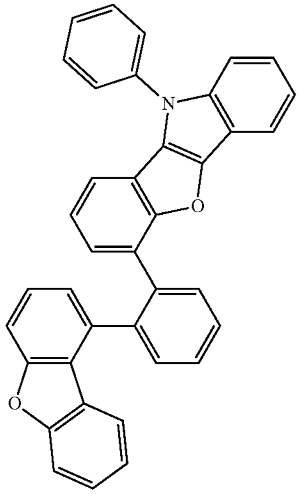
197
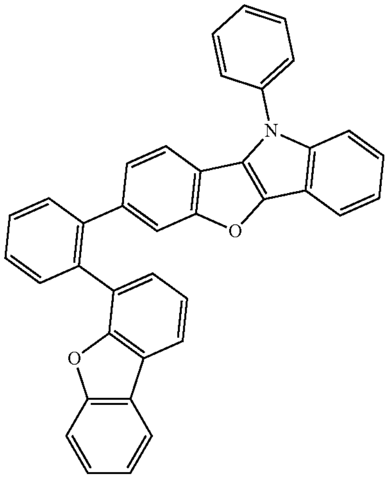
198
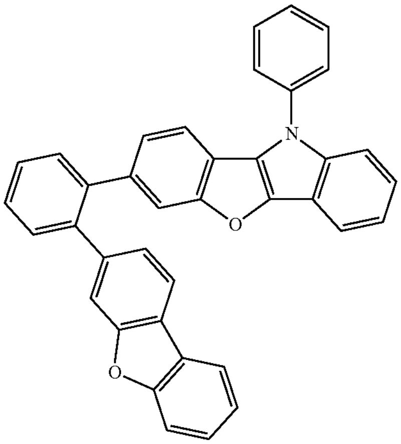

-continued
199
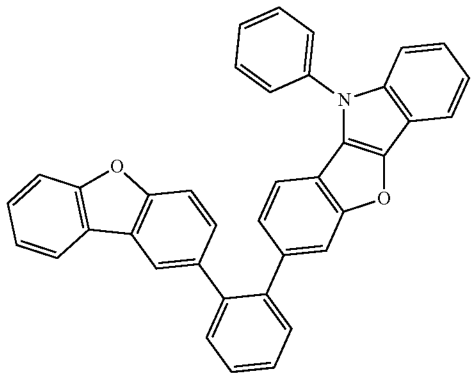
200
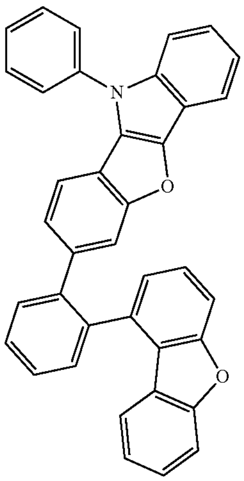
201
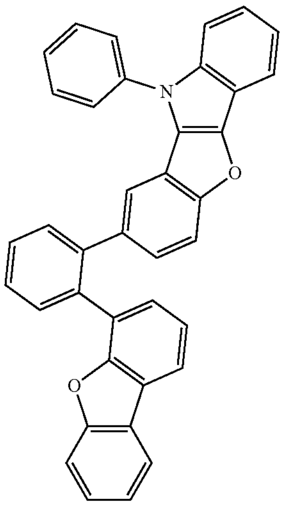
-continued
202
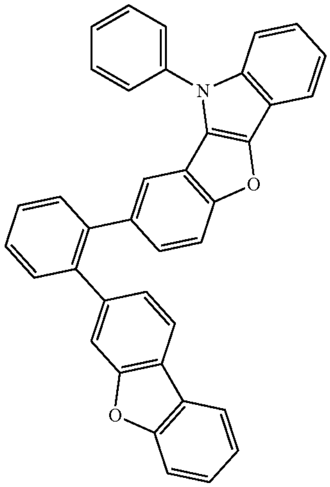
203
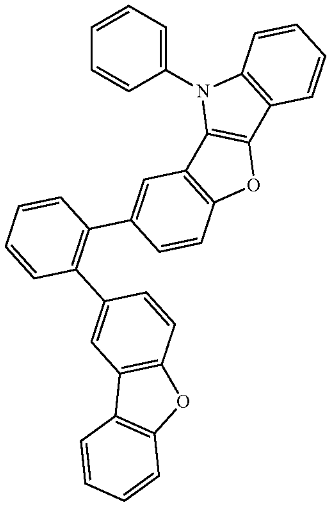
204
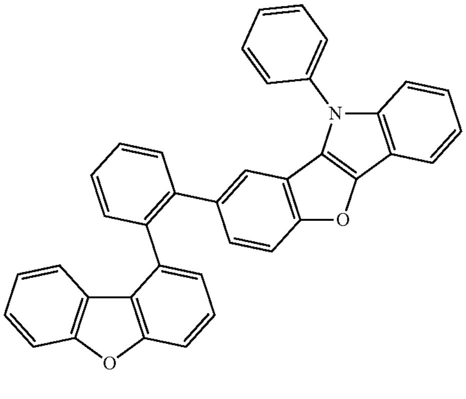

-continued
205
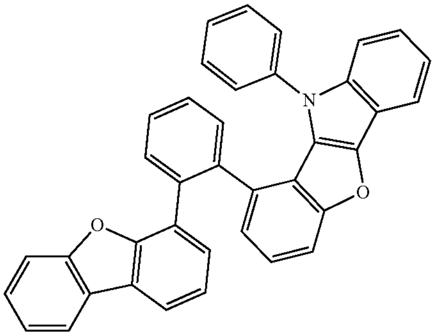
206
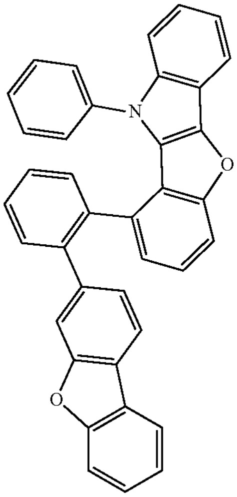
207
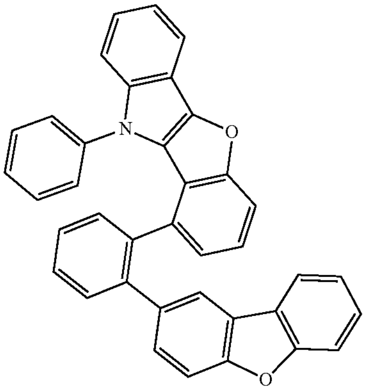
-continued
208
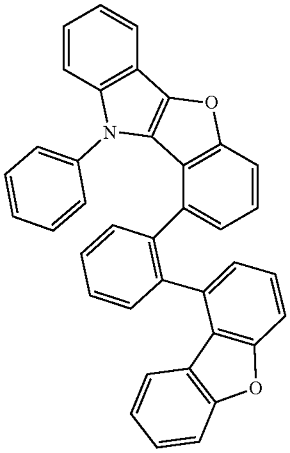
209
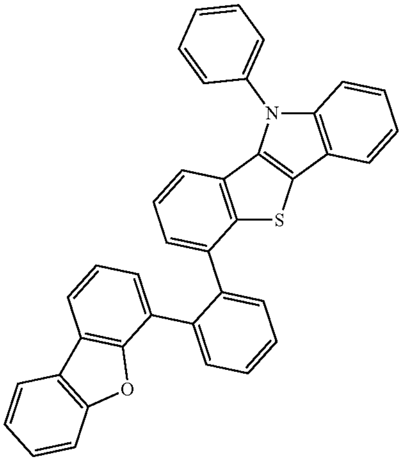
210
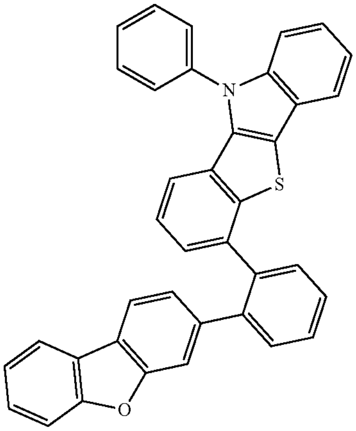

-continued
211
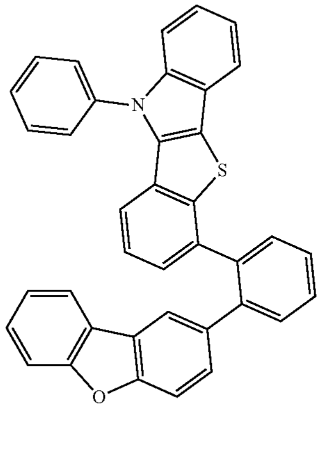
212
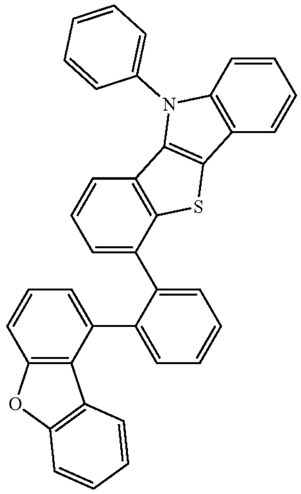
213
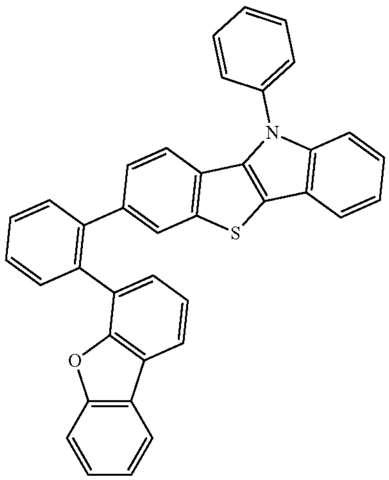
-continued
214
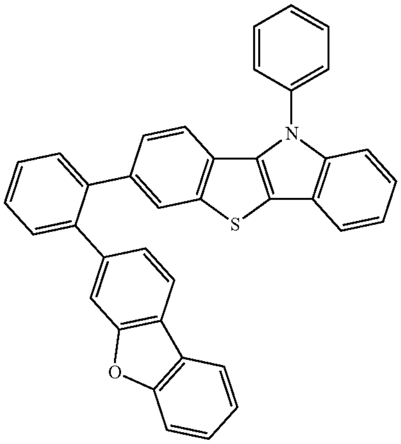
215
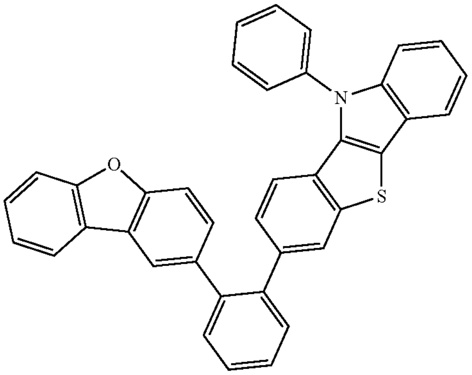
216
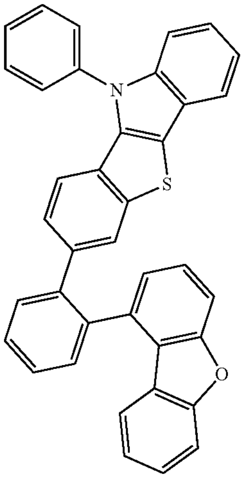

-continued
217
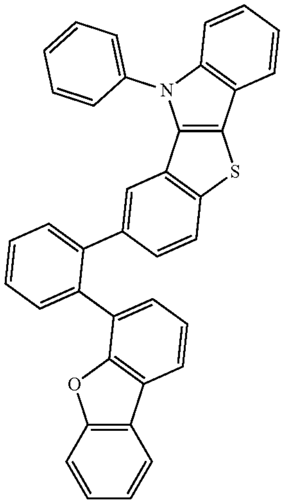
218
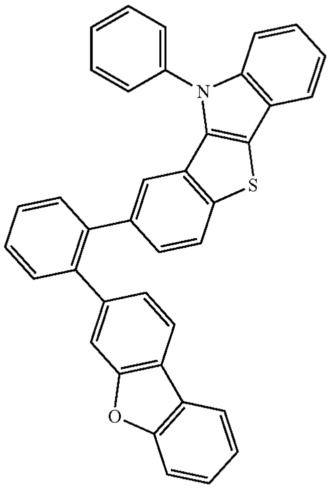
219
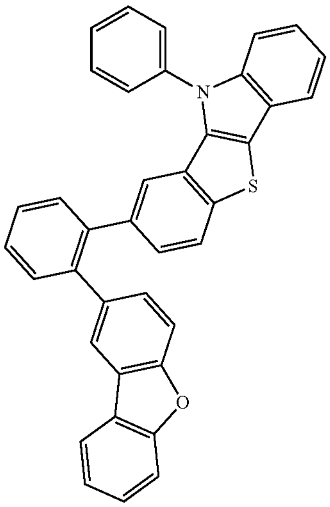
-continued
220
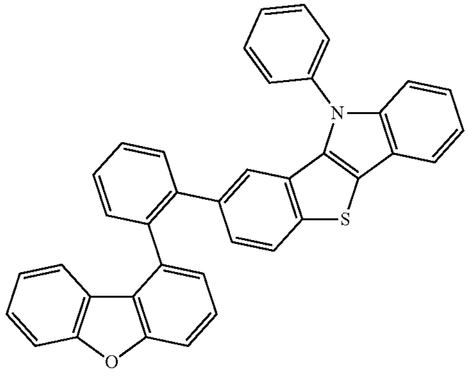
221
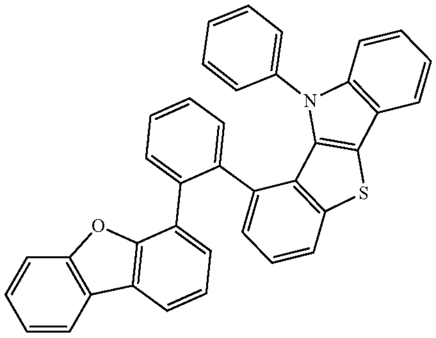
222
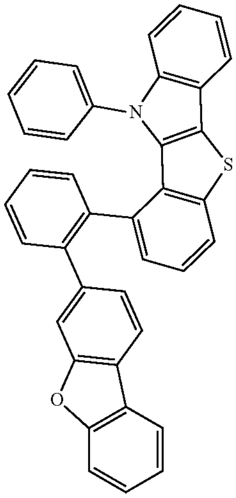
223
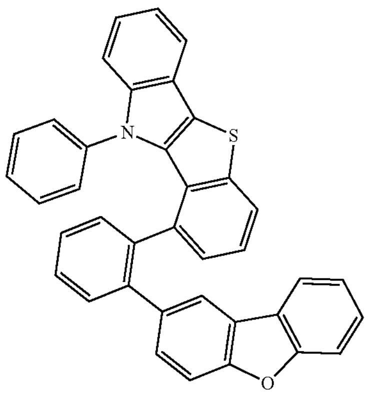

-continued
224
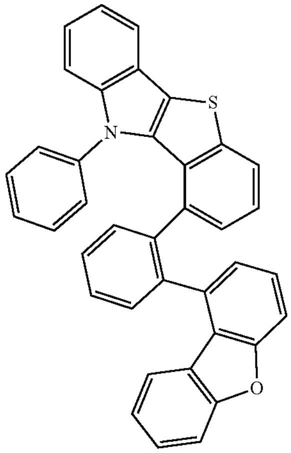
225
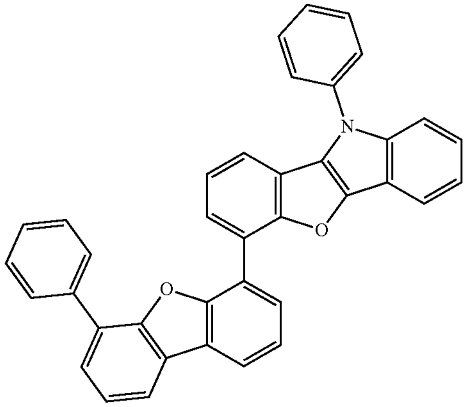
226
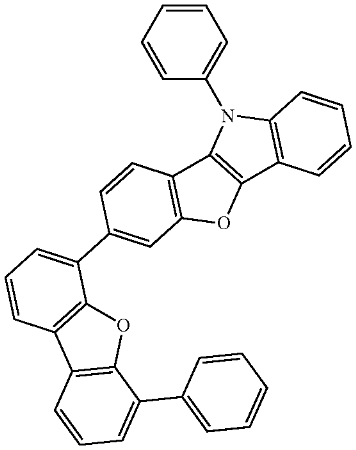
-continued
227
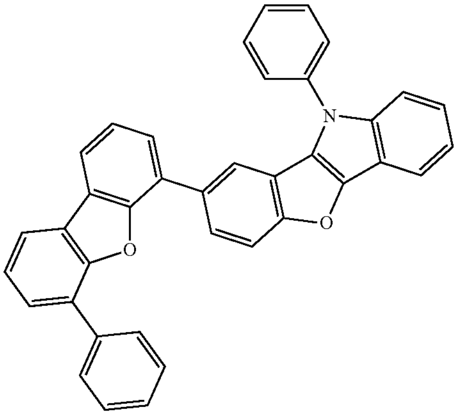
228
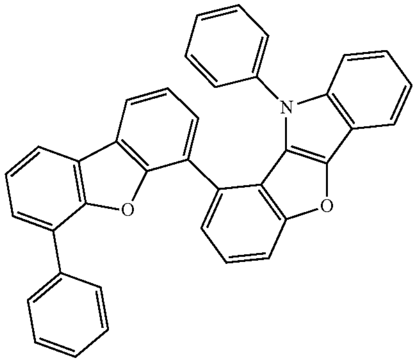
229
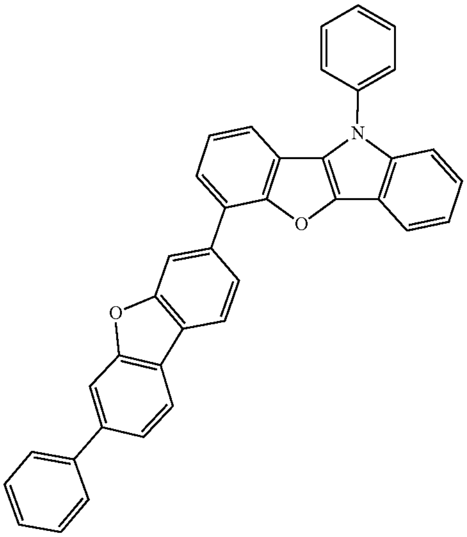

-continued
230
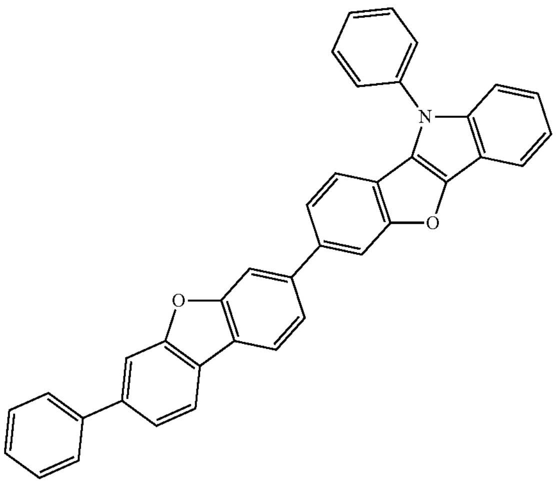
231
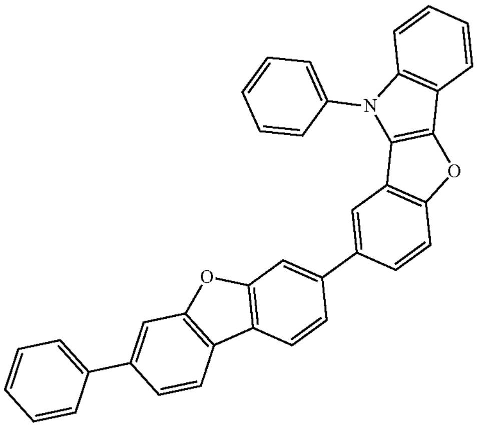
232
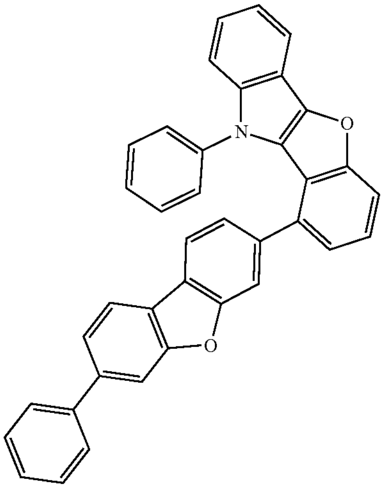
-continued
233
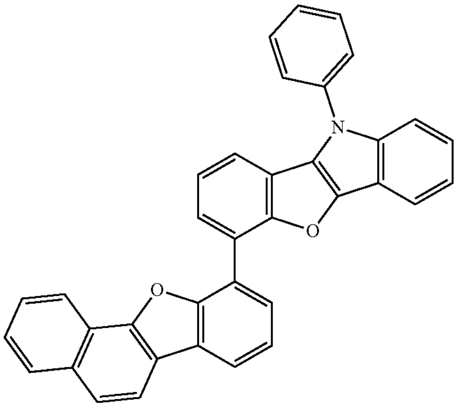
234
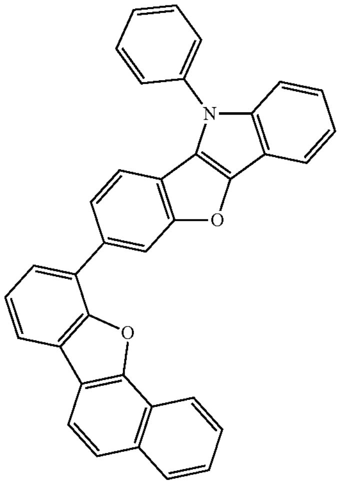
235
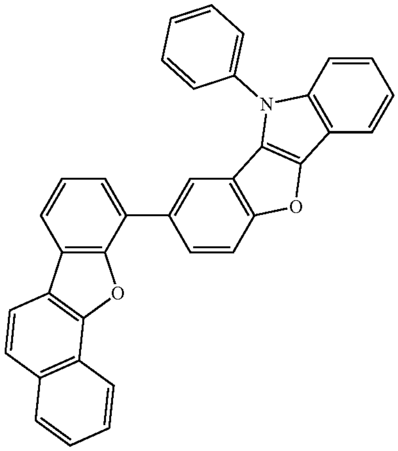

-continued
236
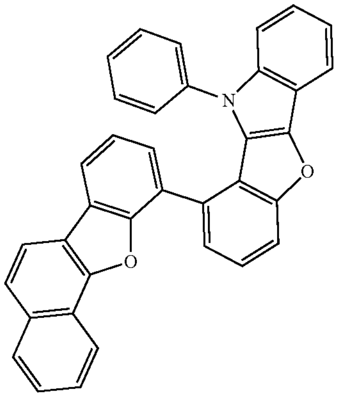
237
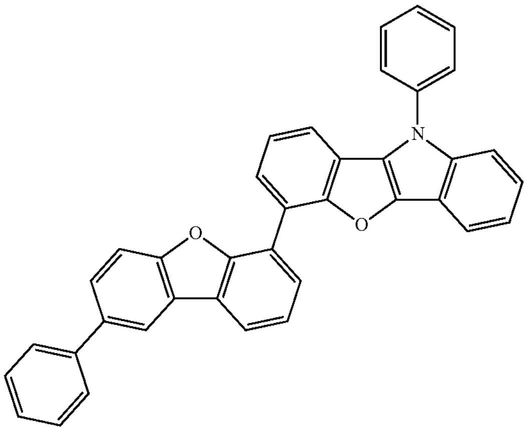
238
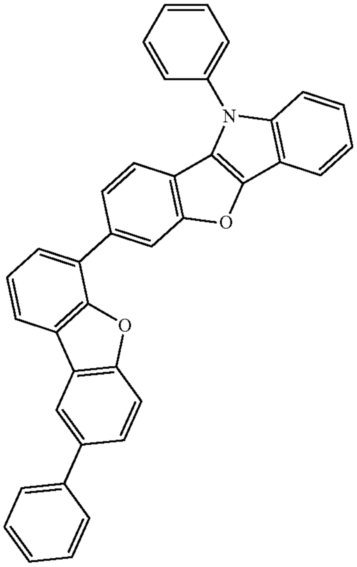
-continued
239
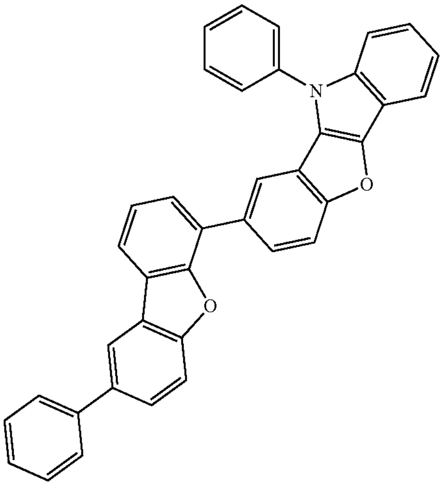
240
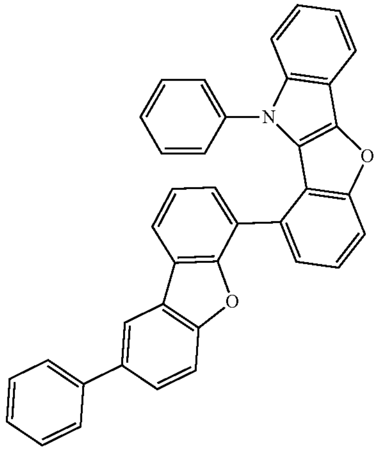
241
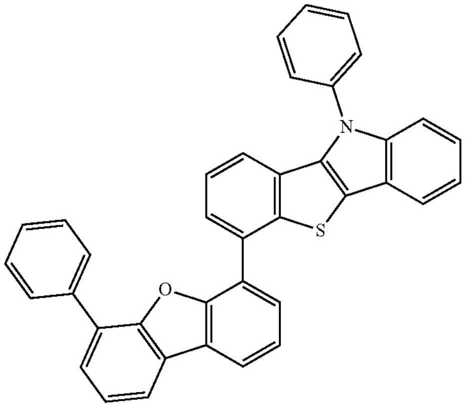

-continued
242
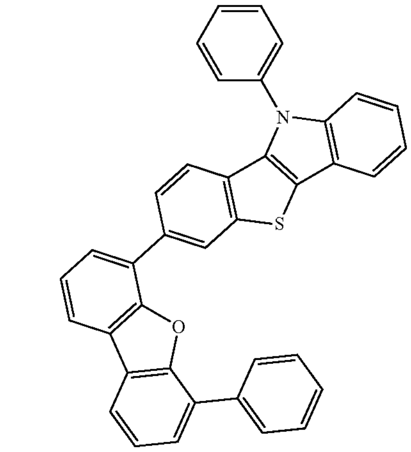
243
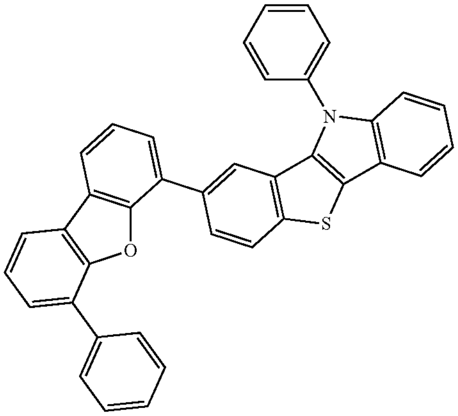
244
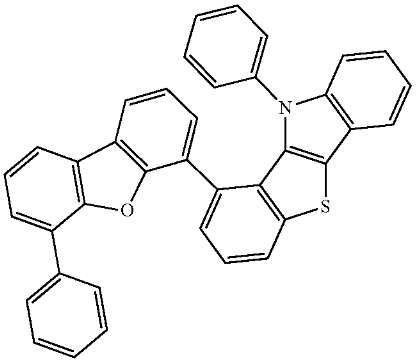
-continued
245
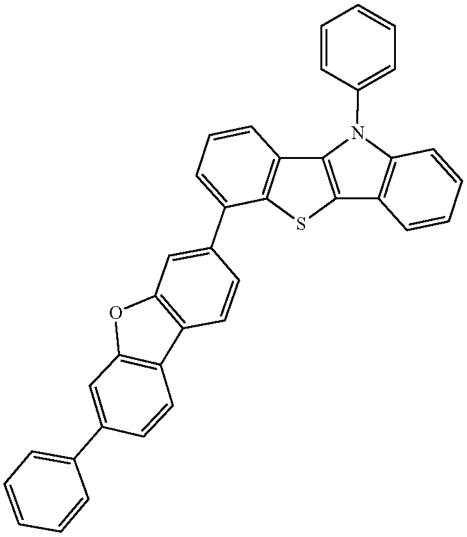
246
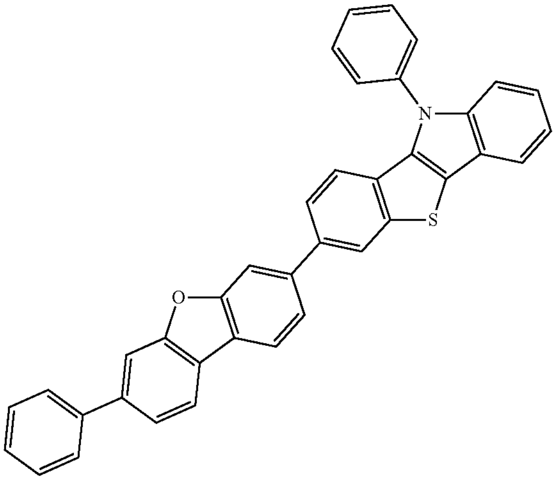
247
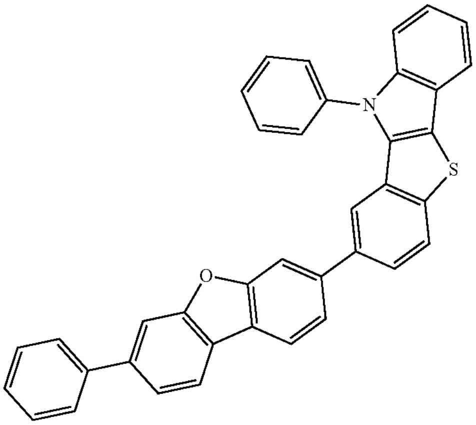

248
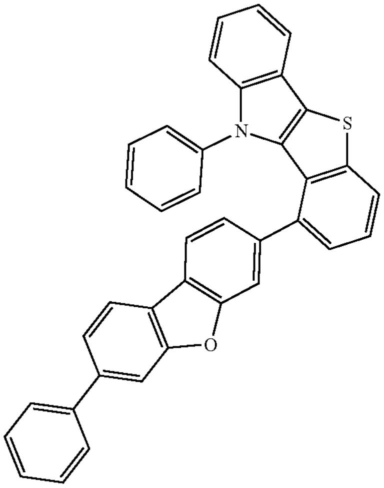
249
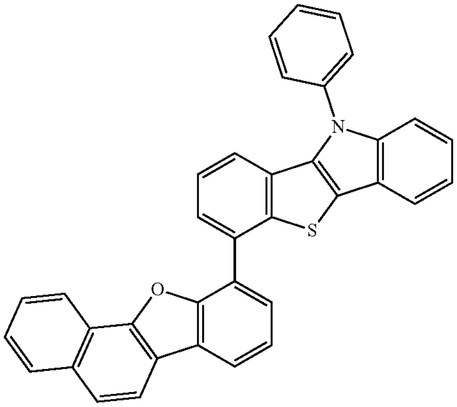
250
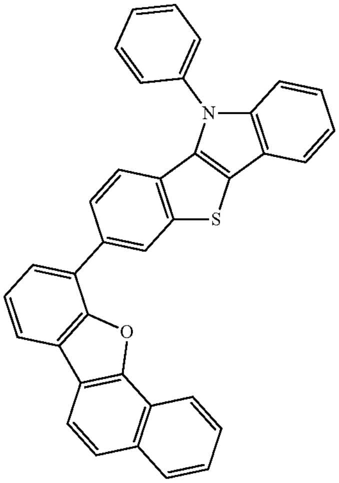
251
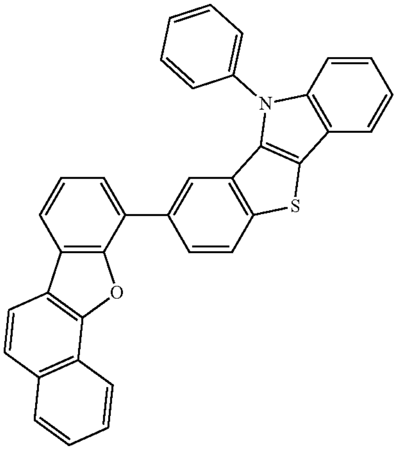
252
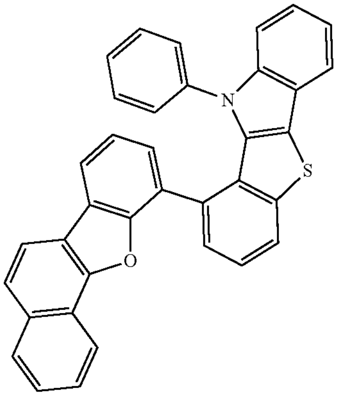
253
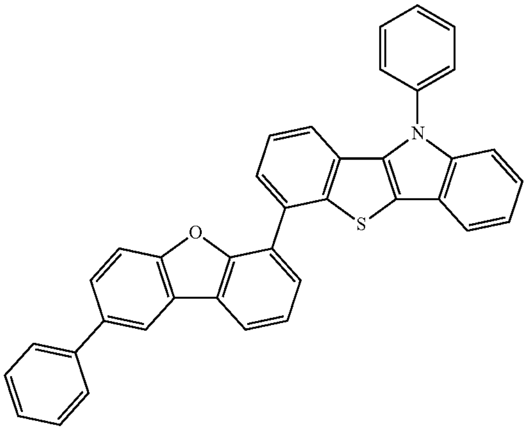

-continued
254
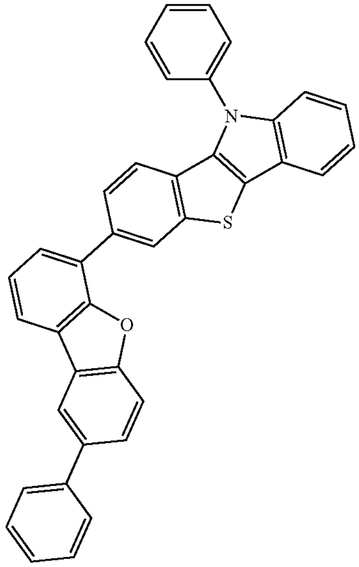
255
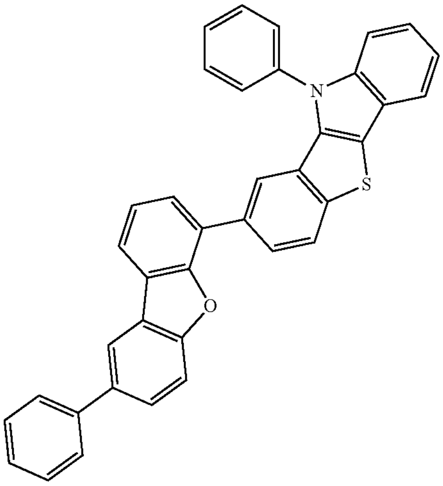
256
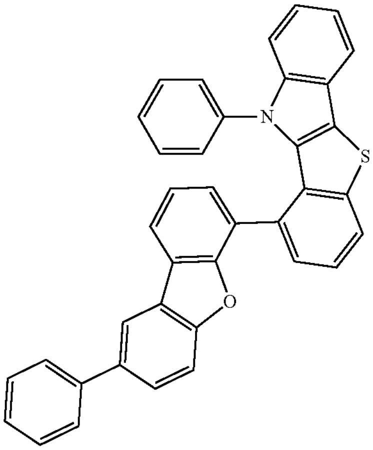
-continued
257
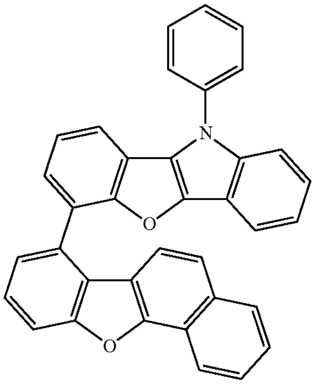
258
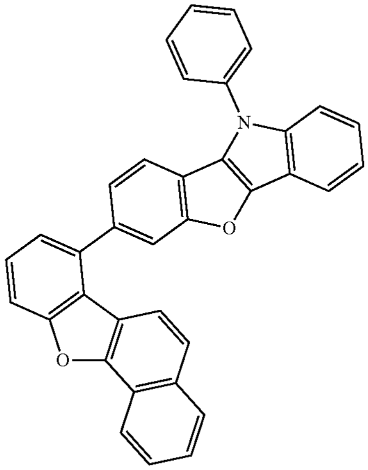
259
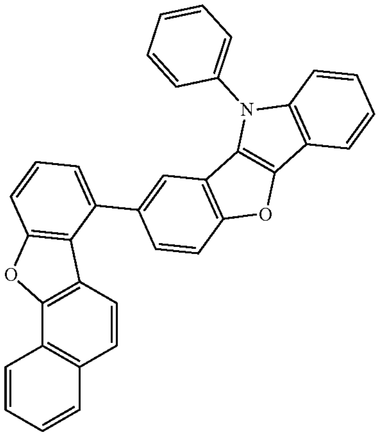
260
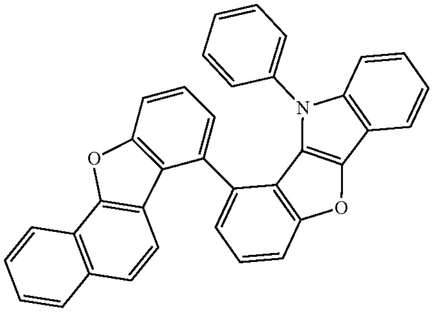

-continued
261
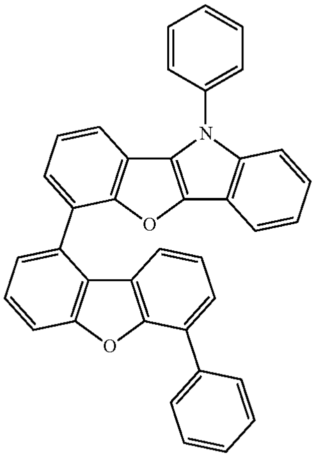
262
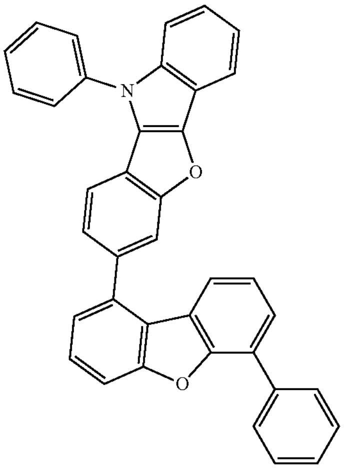
263
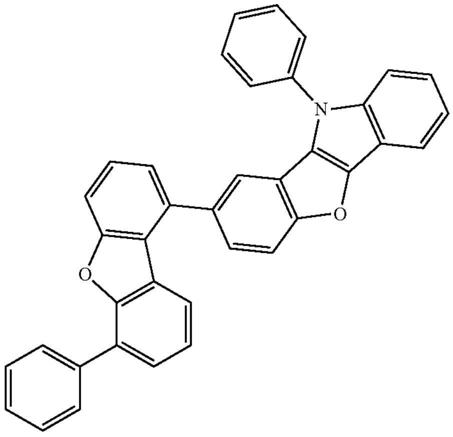
-continued
264
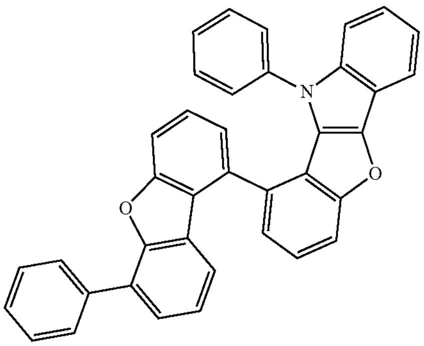
265
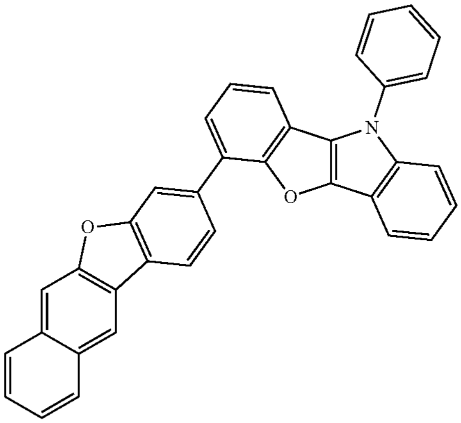
266
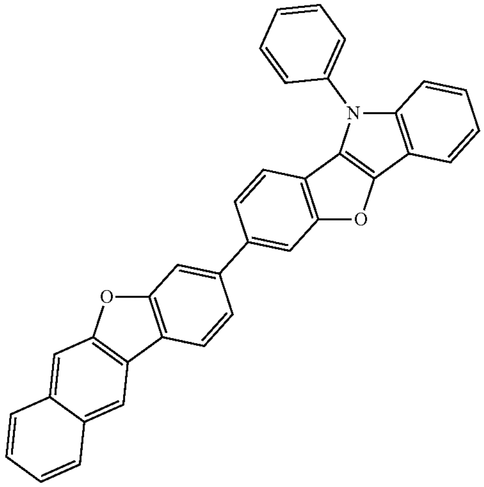

-continued
267
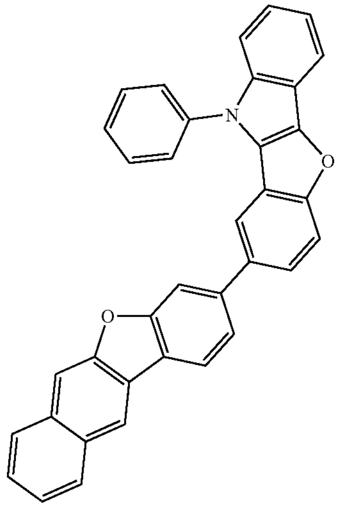
268
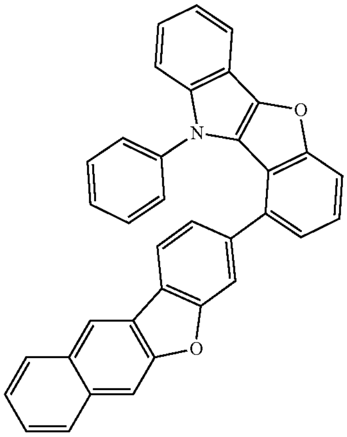
269
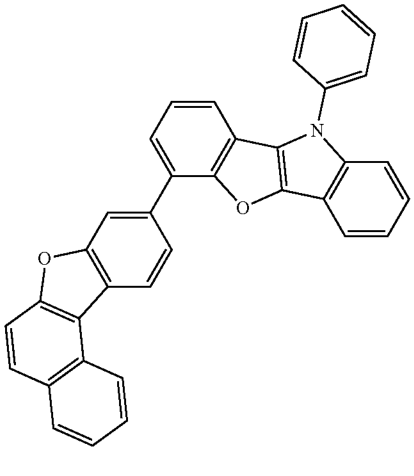
-continued
270
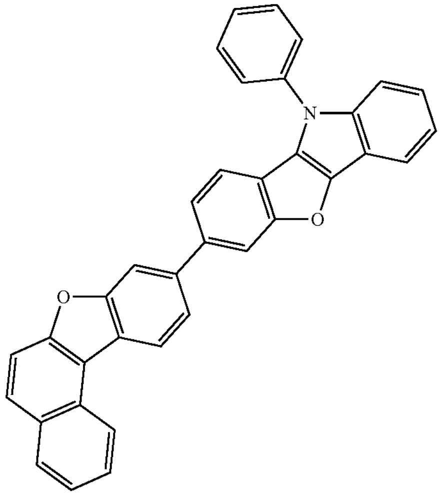
271
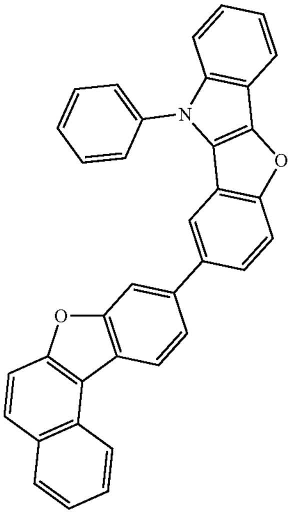
272
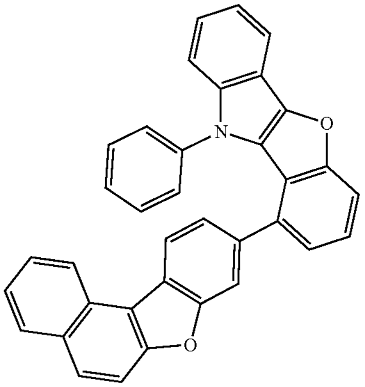

-continued
273
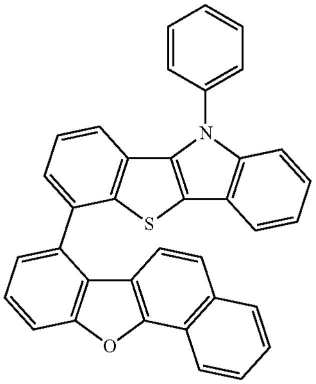
274
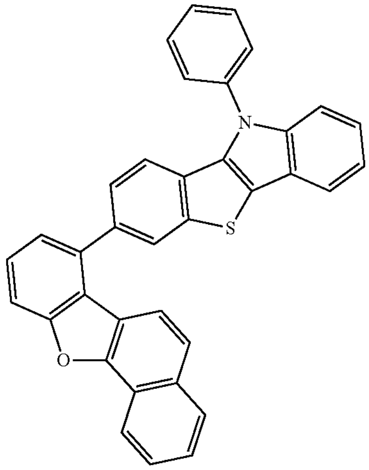
275
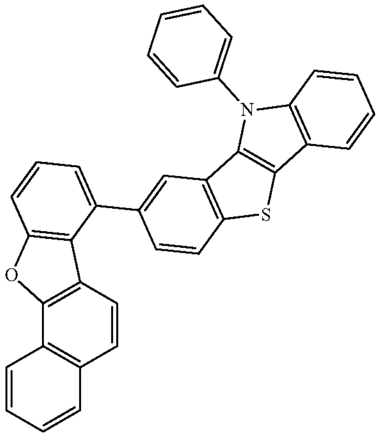
276
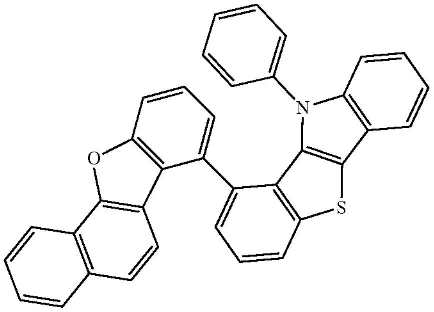
-continued
277
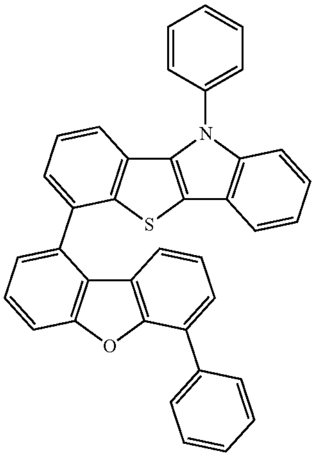
278
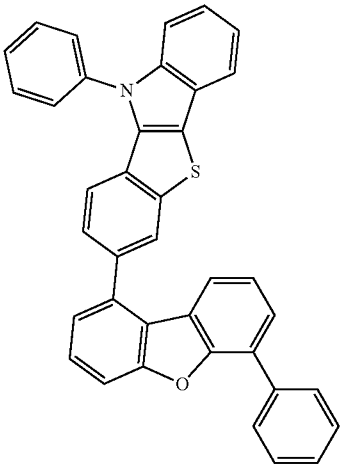
279
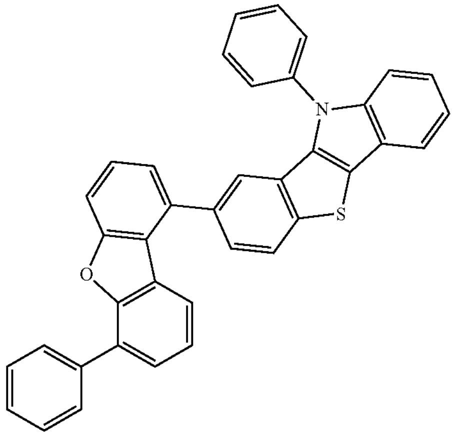

-continued
280
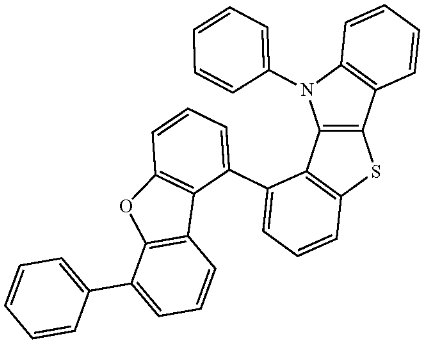
281
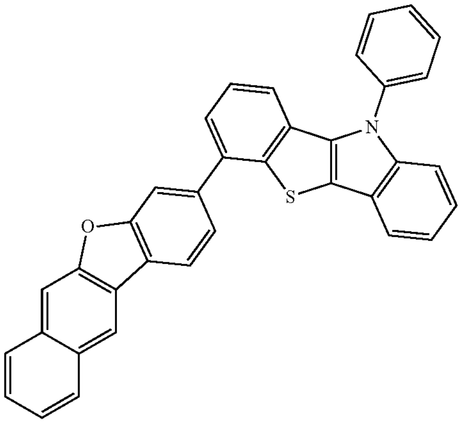
282
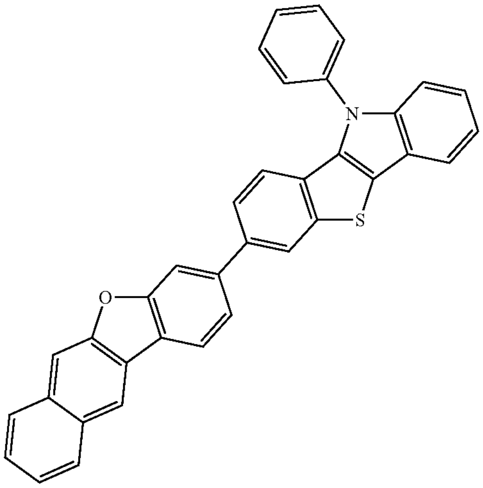
-continued
283
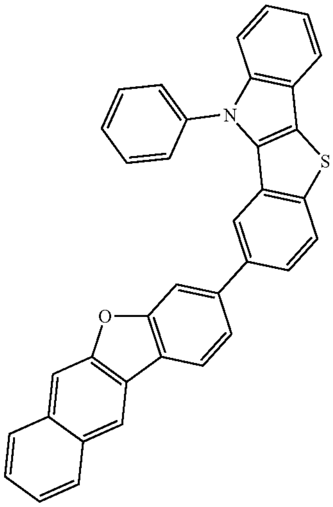
284
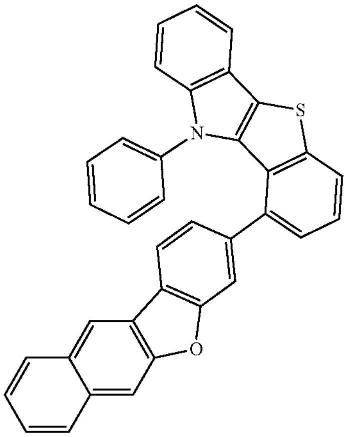
285
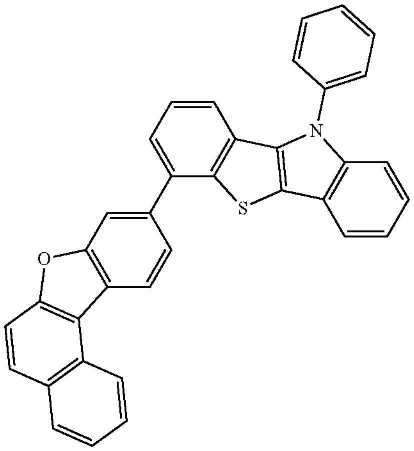

286
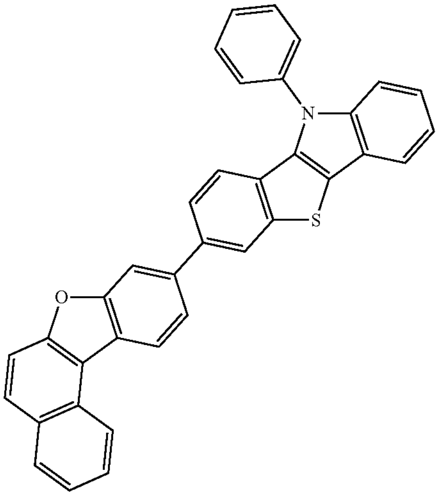
287
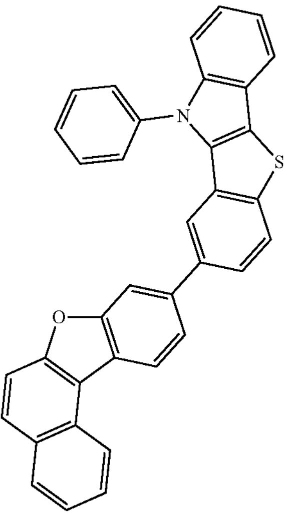
288
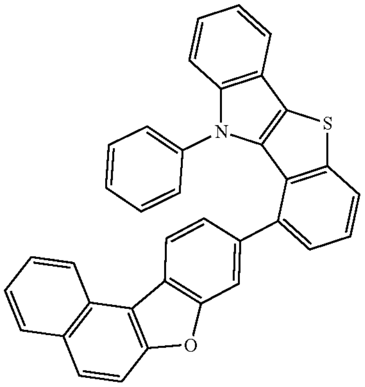
289
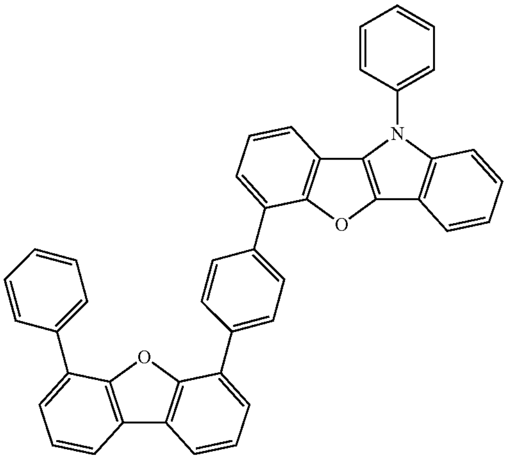
290
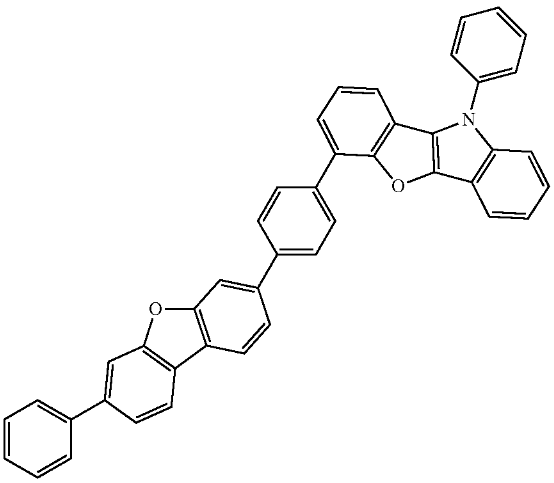
291
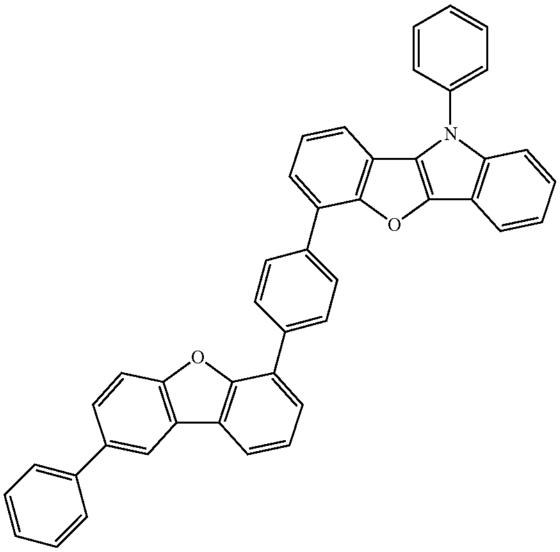

-continued
292
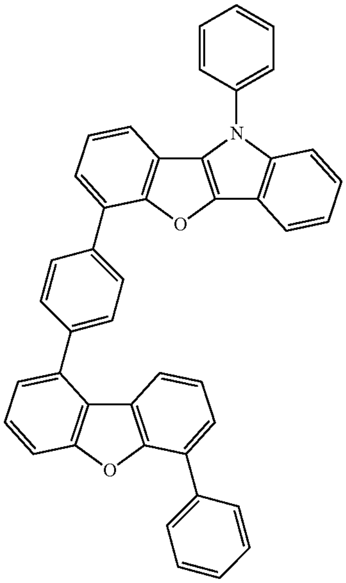
293
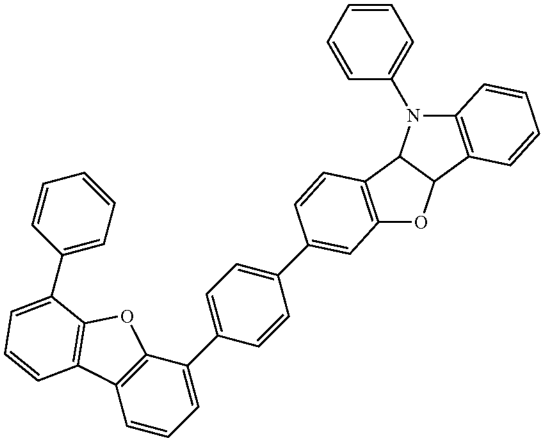
294
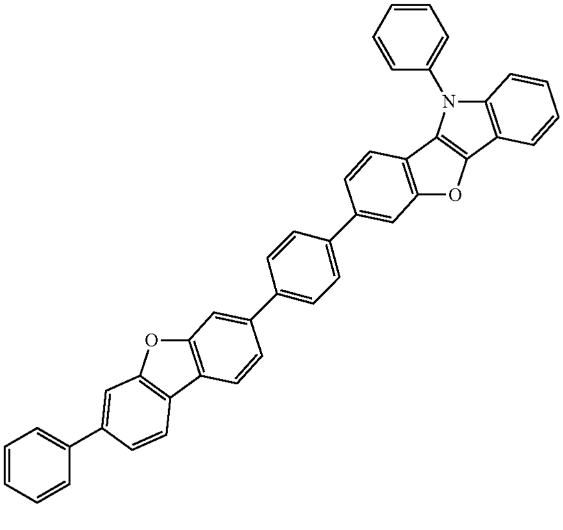
-continued
295
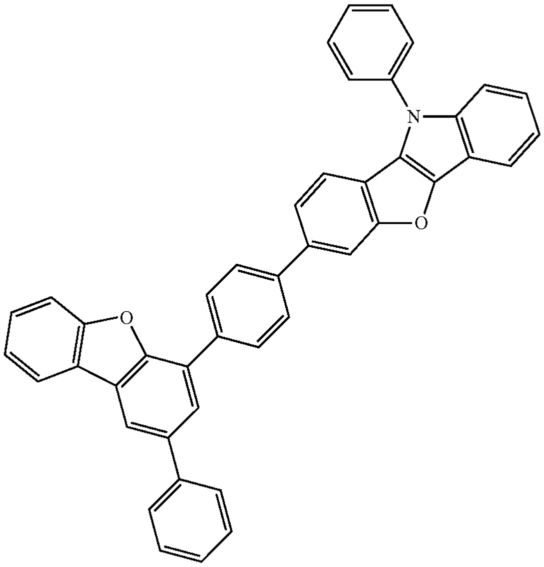
296
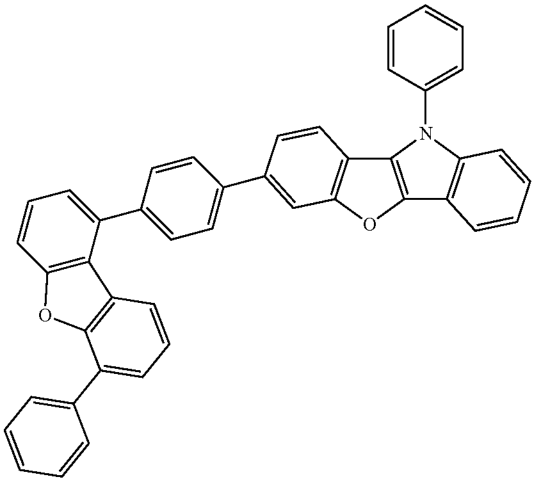
297
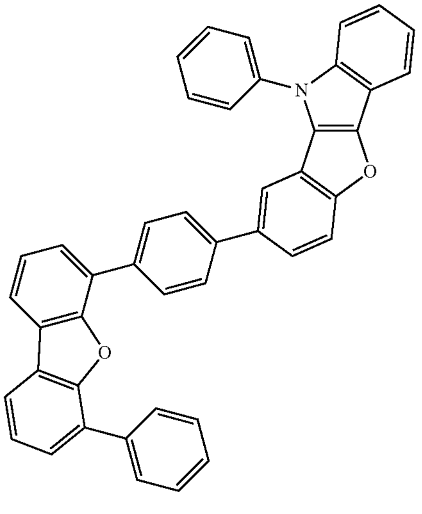

-continued
298
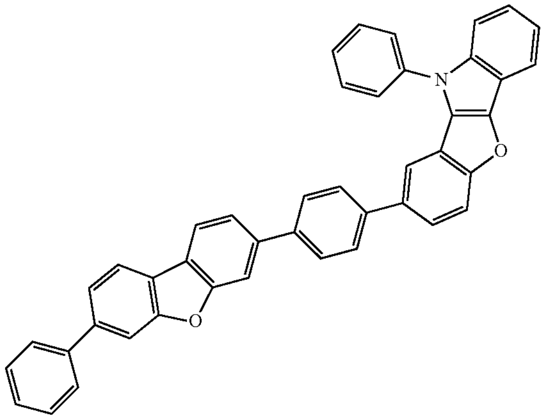
299
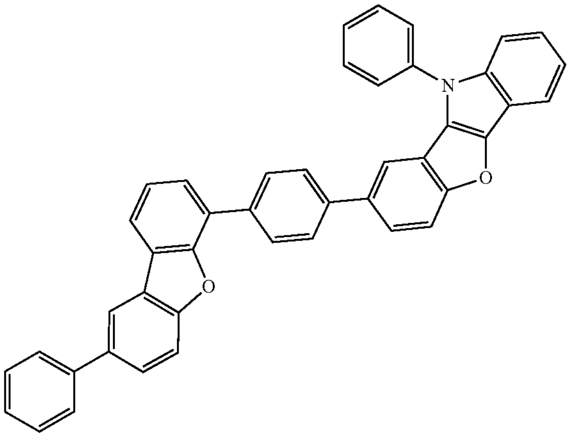
300
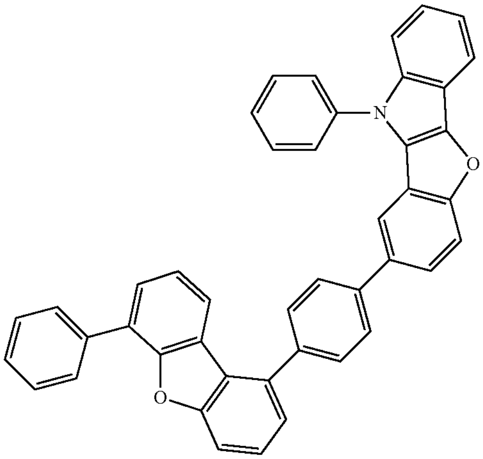
-continued
301
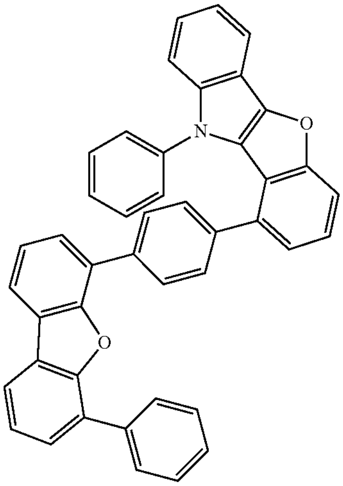
302
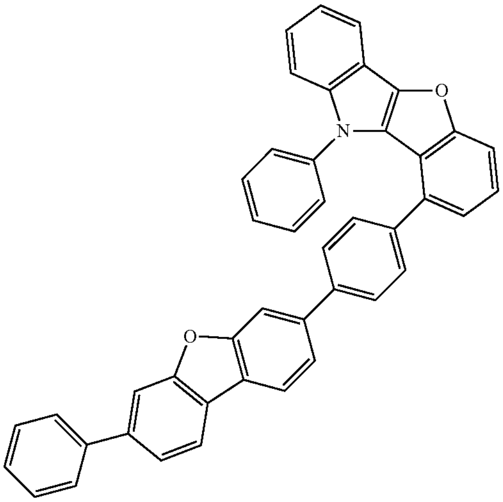
303
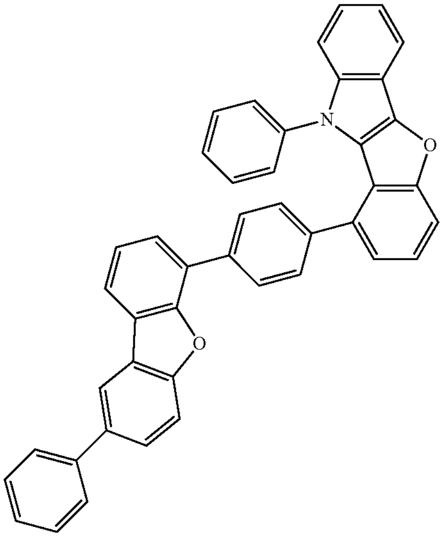

-continued
304
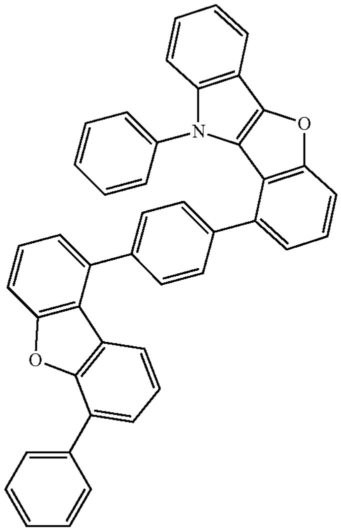
305
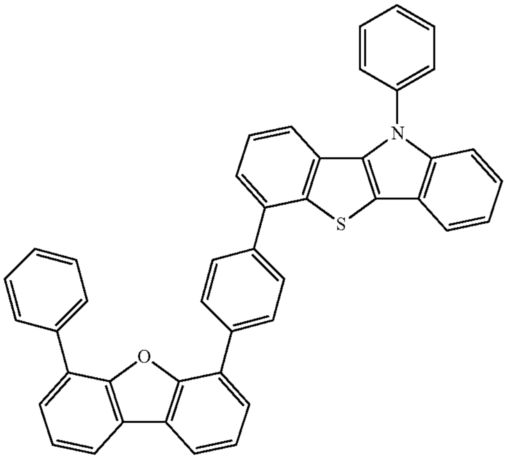
306
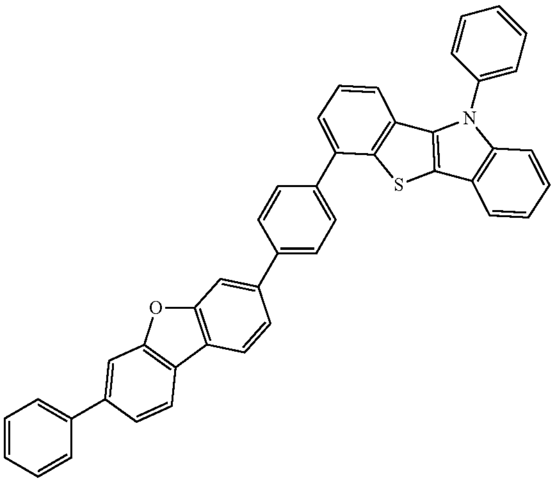
-continued
307
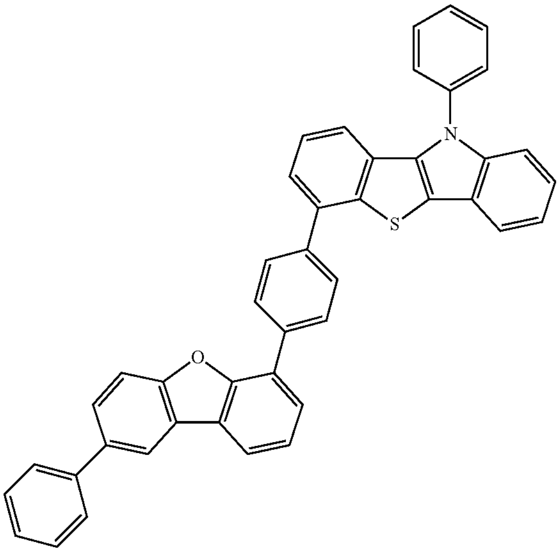
308
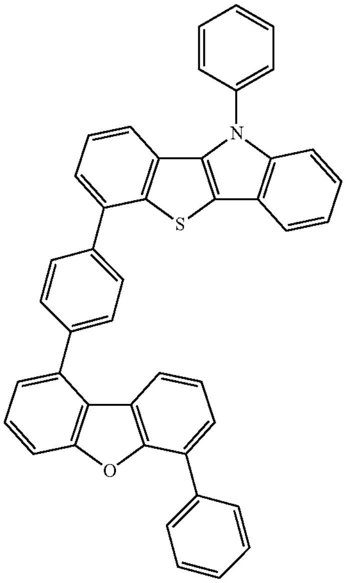
309
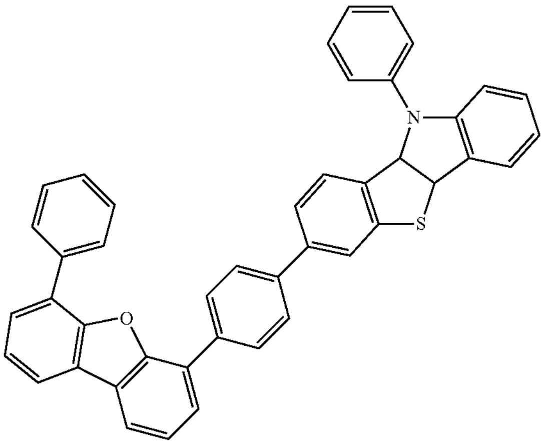

310
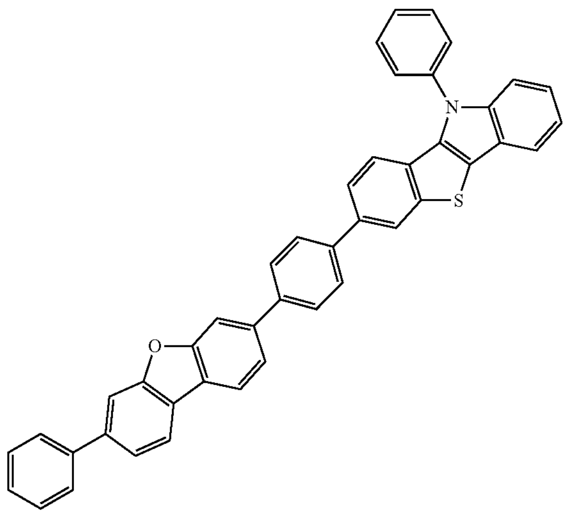
311
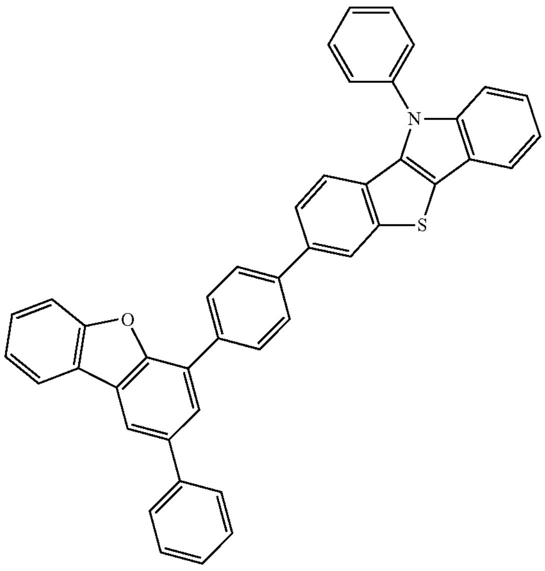
312
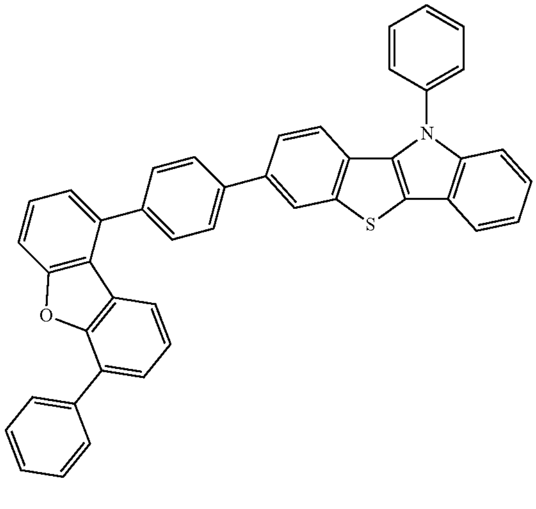
313
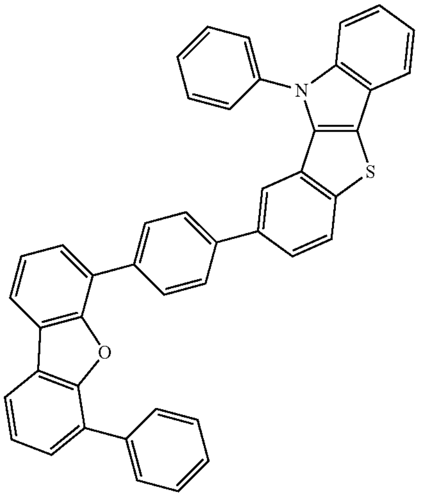
314
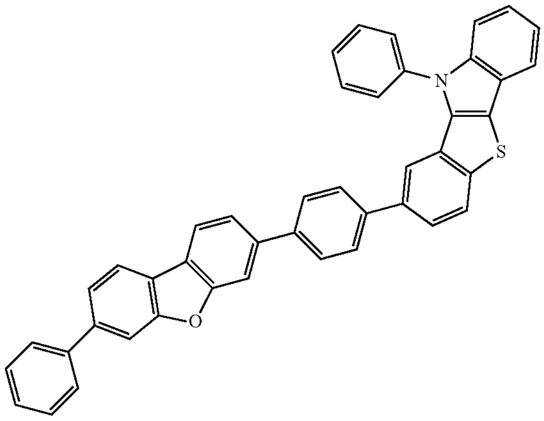
315
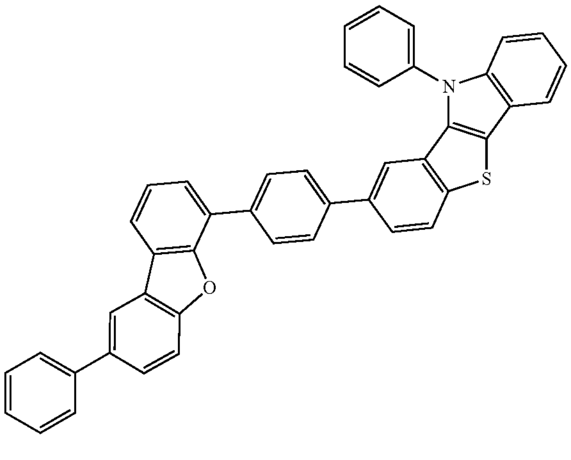

316
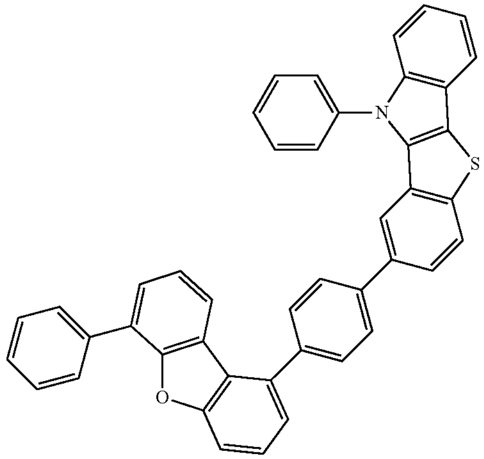
317
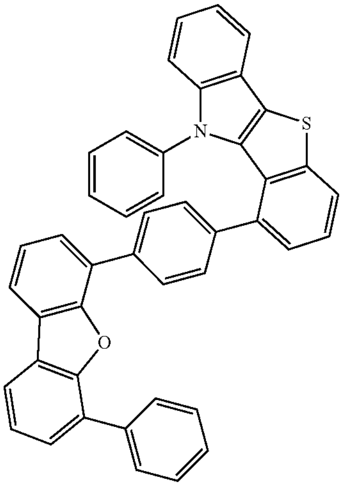
318
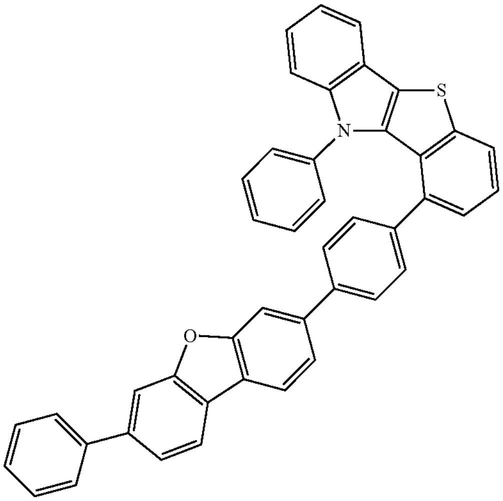
319
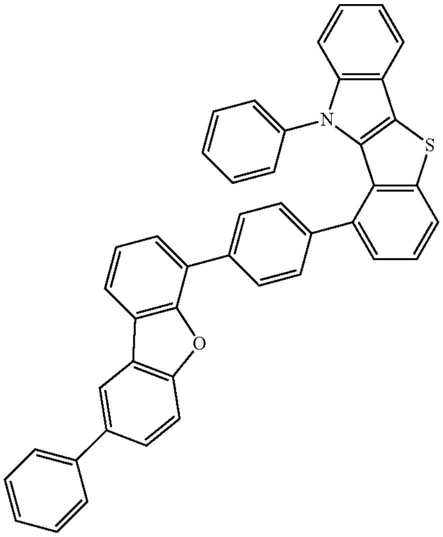
320
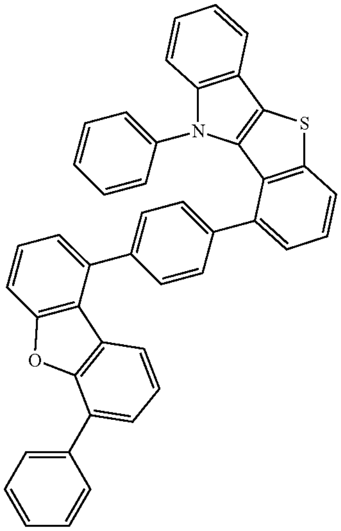
321
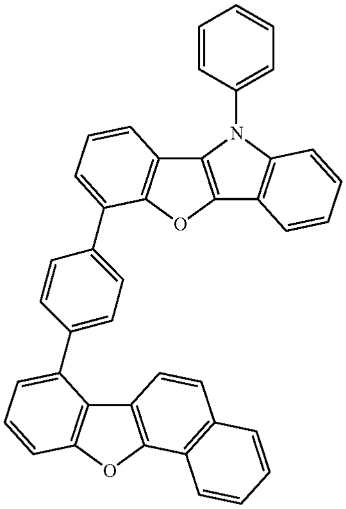

-continued
322
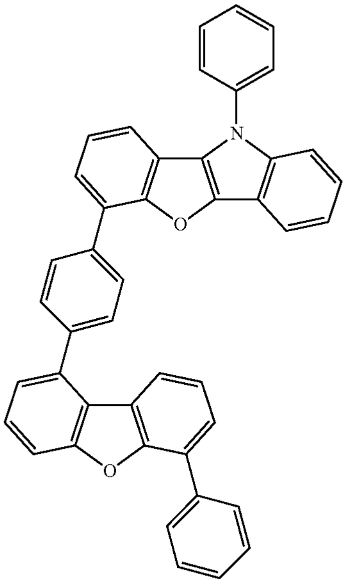
323
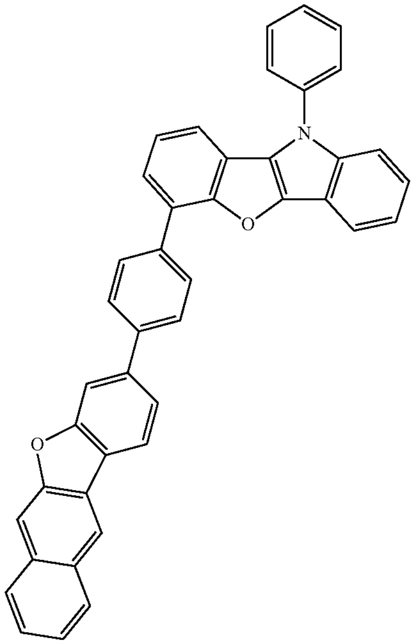
-continued
324
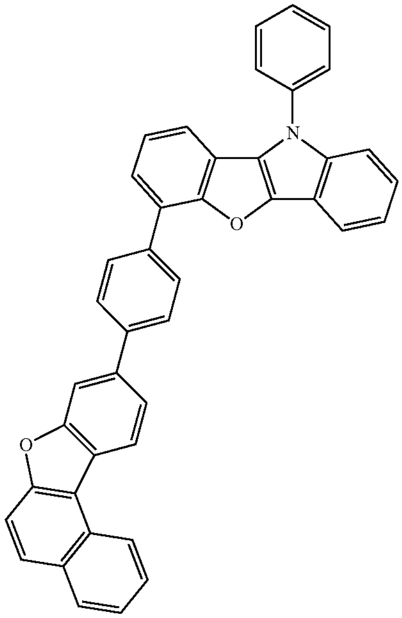
325
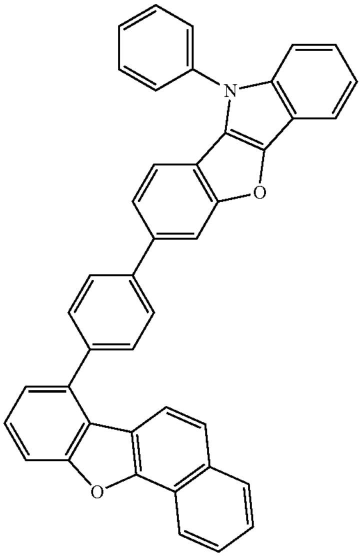

-continued
326
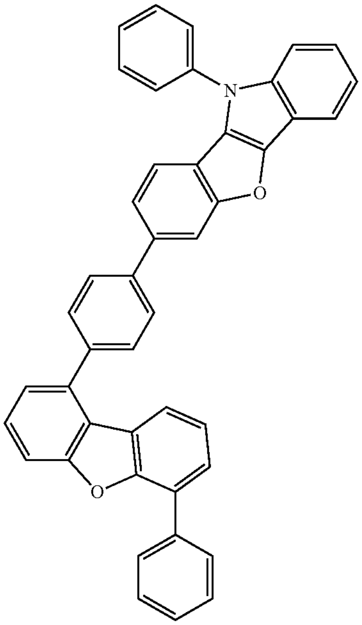
327
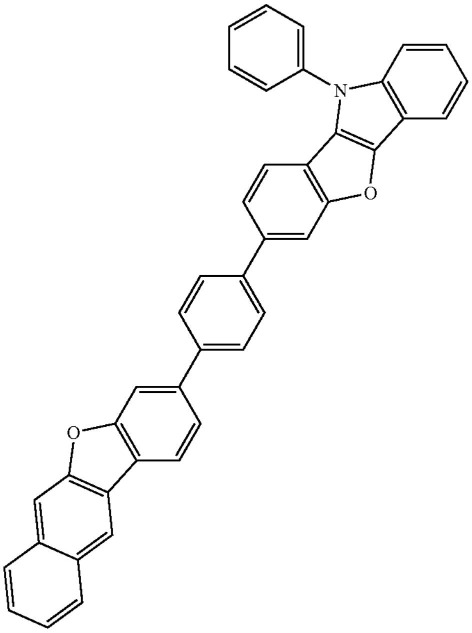
-continued
328
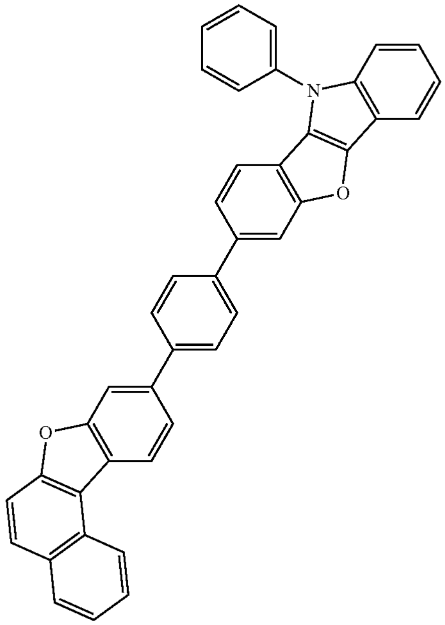
329
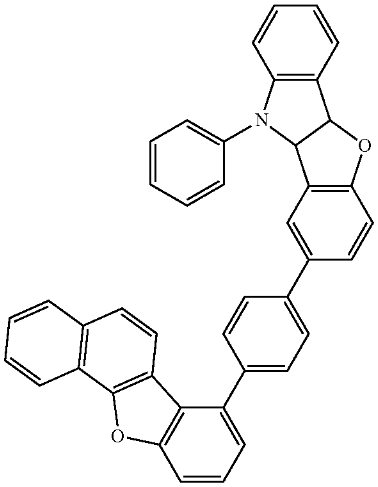
330
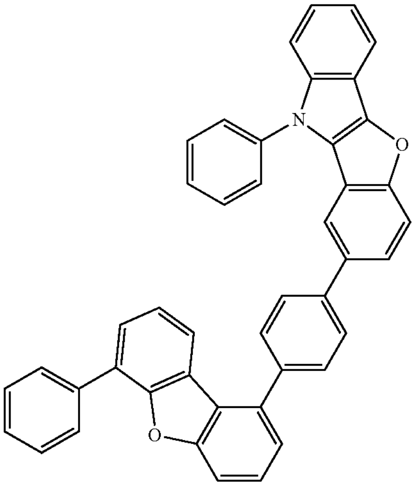

-continued
331
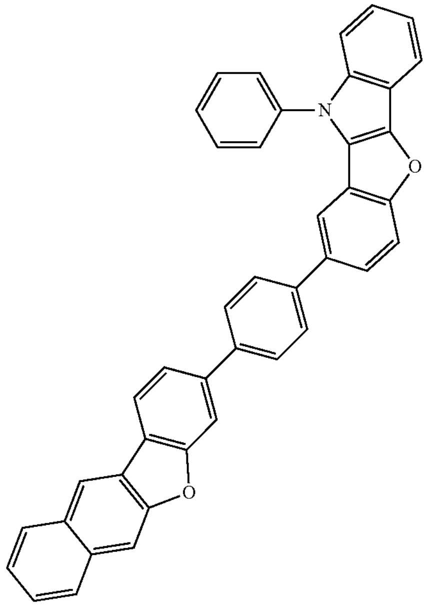
332
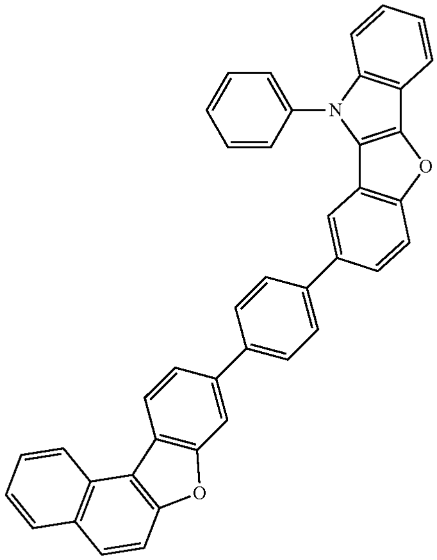
333
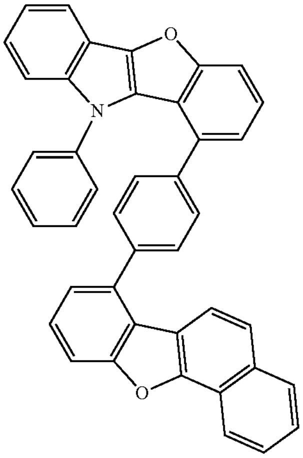
-continued
334
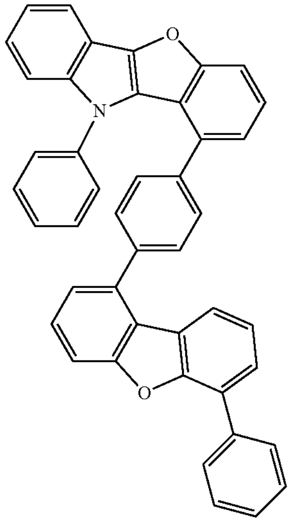
335
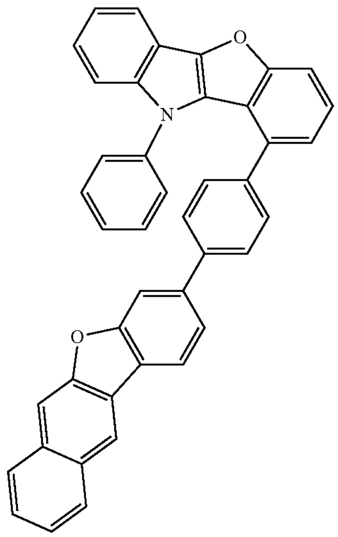
336
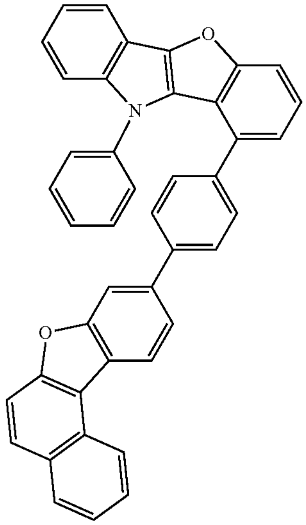

-continued
337
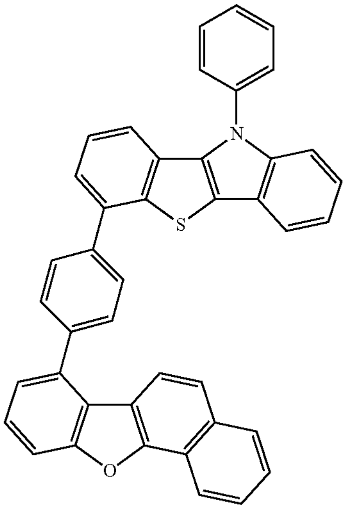
338
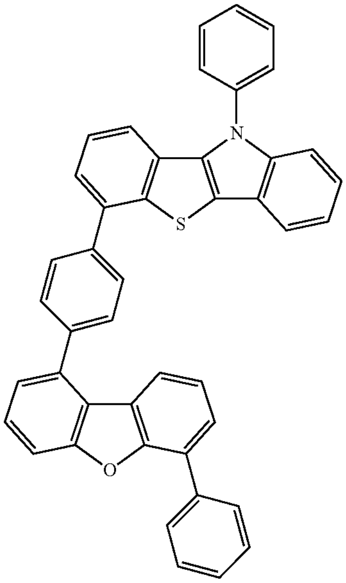
-continued
339
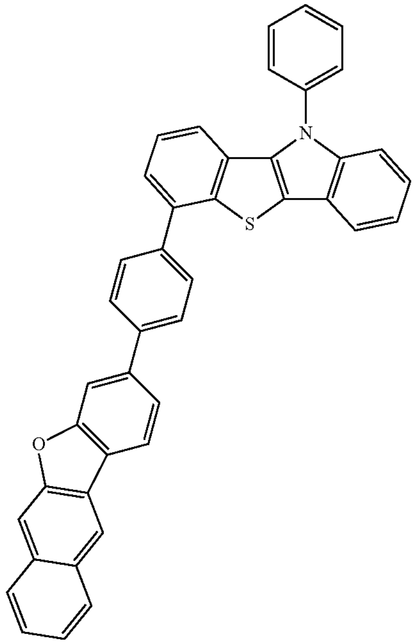
340
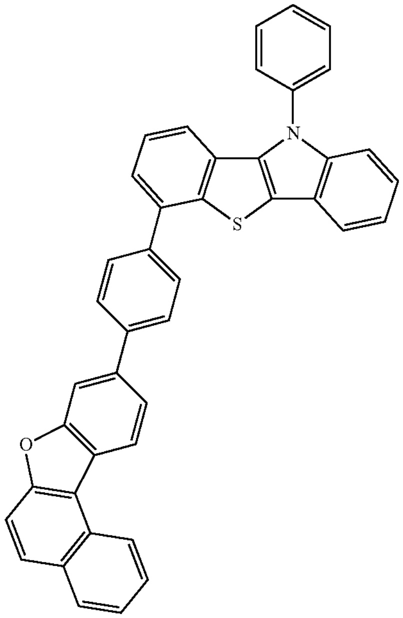

-continued
341
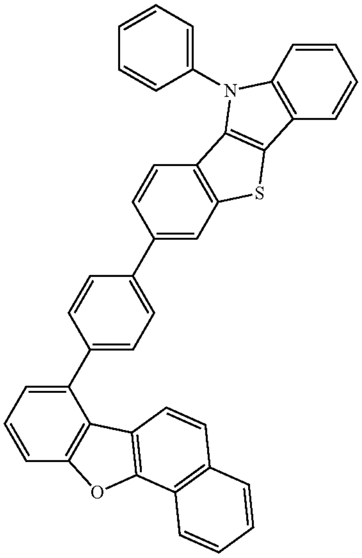
342
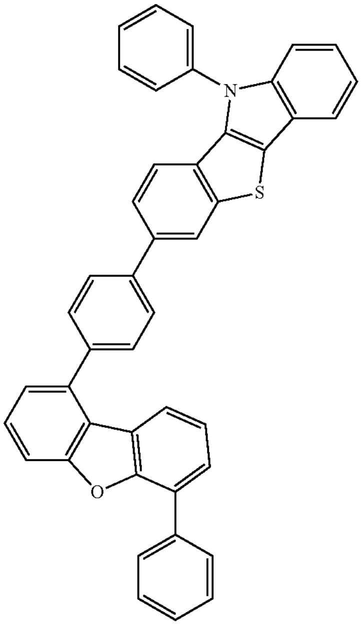
-continued
343
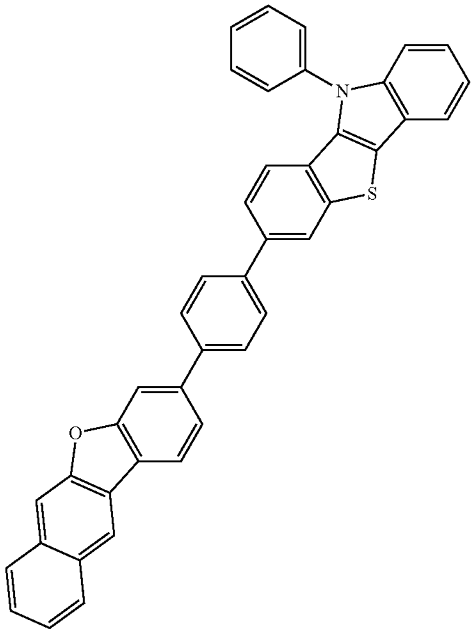
344
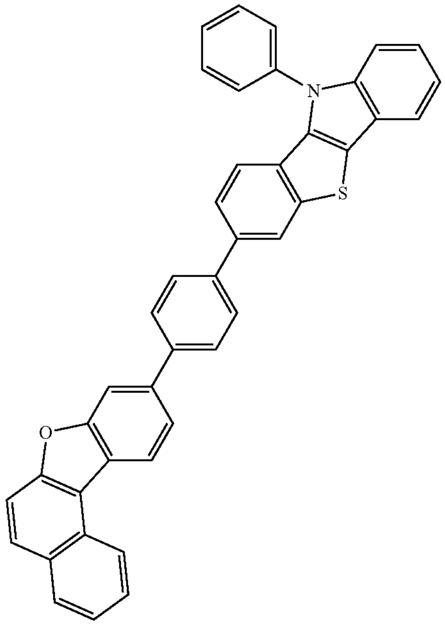

-continued
345
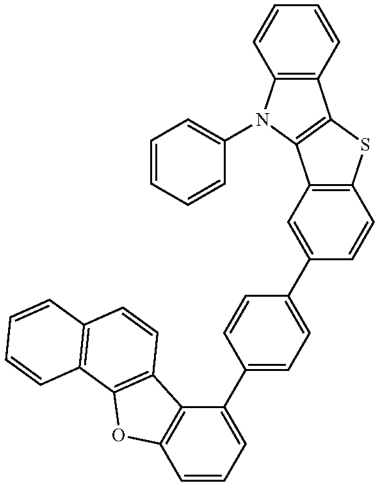
346
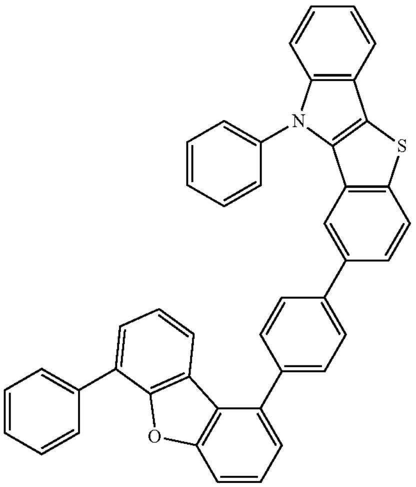
347
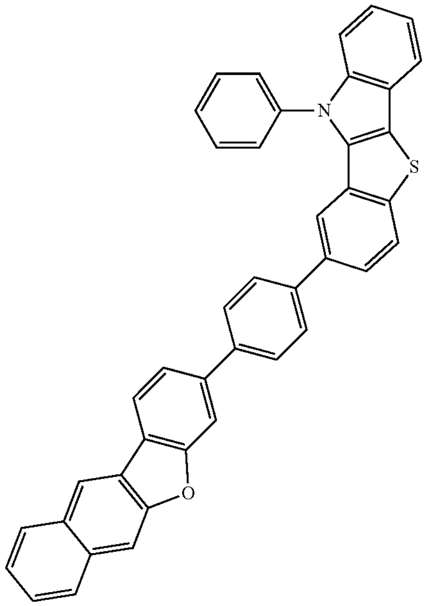
-continued
348
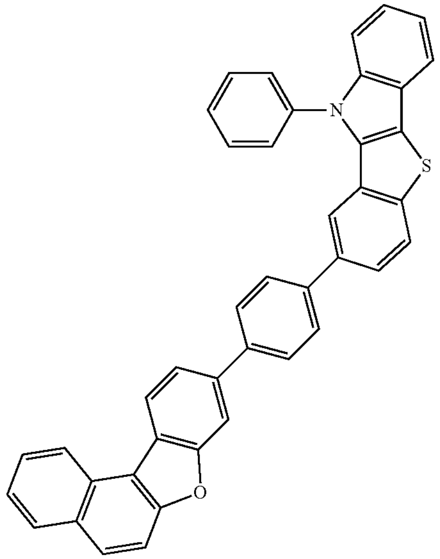
349
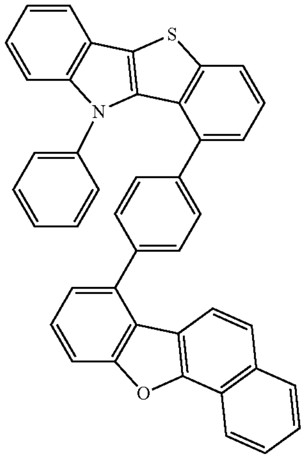
350
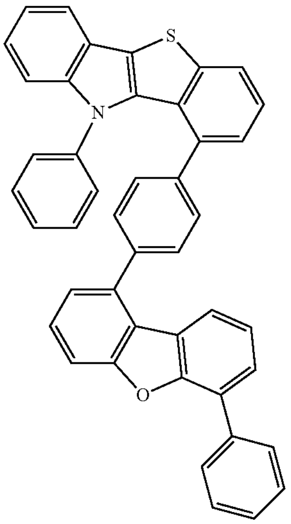

-continued
351
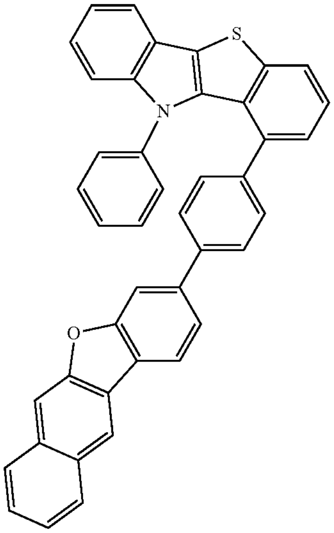
352
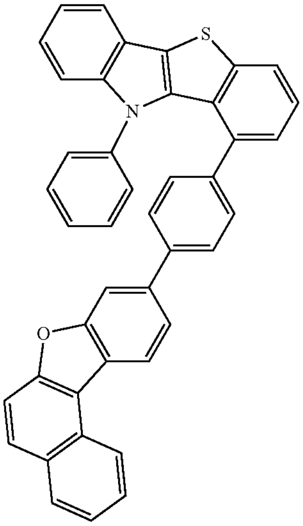
353
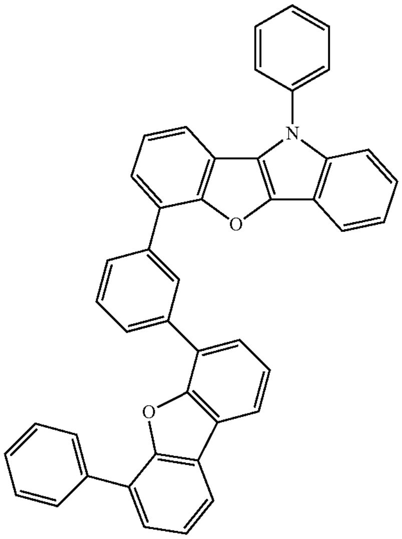
-continued
354
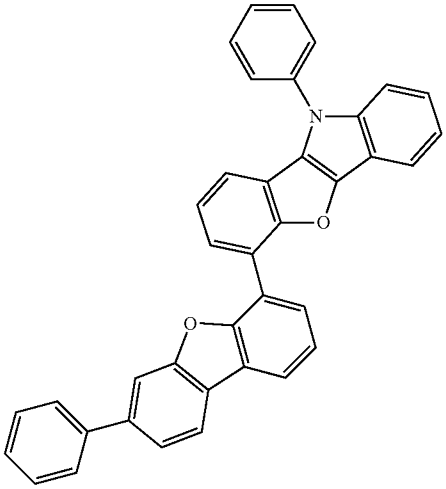
355
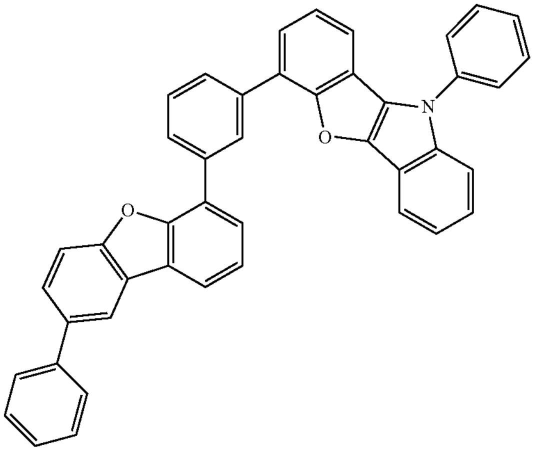
356
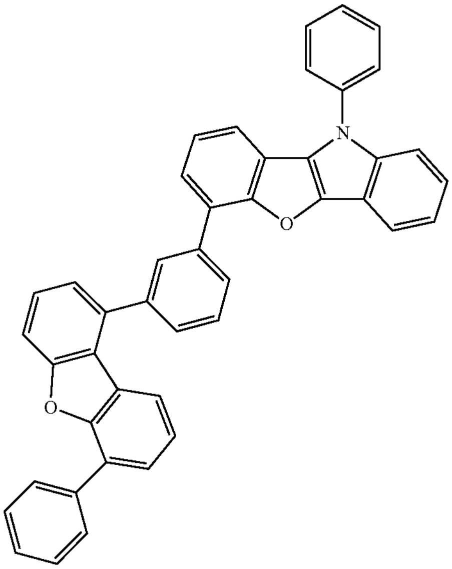

-continued
357
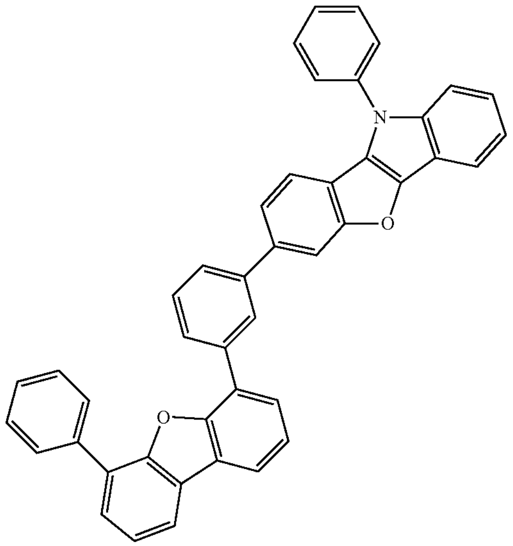
358
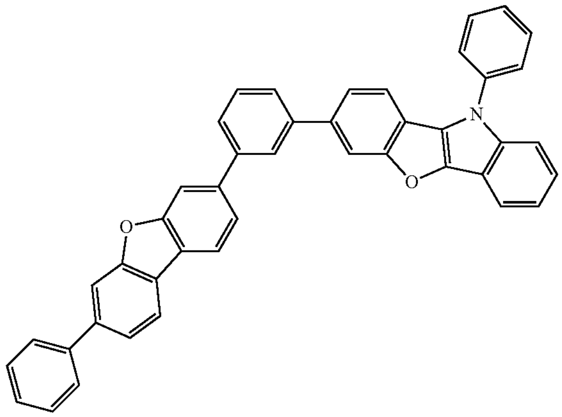
359
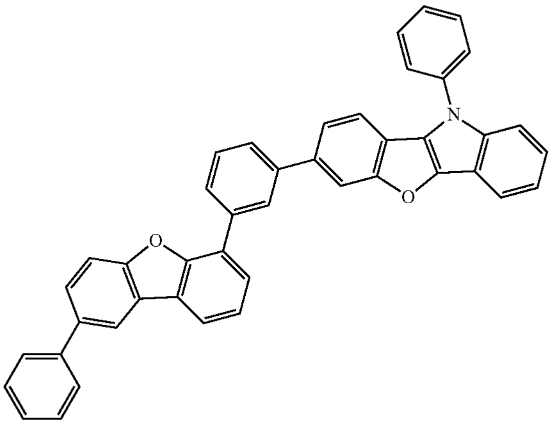
-continued
360
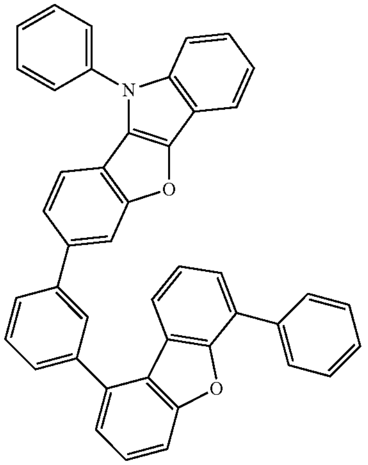
361
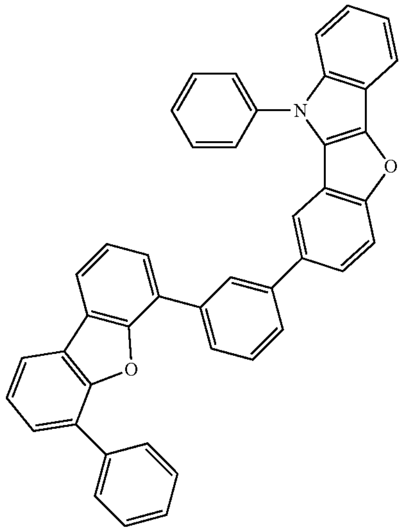
362
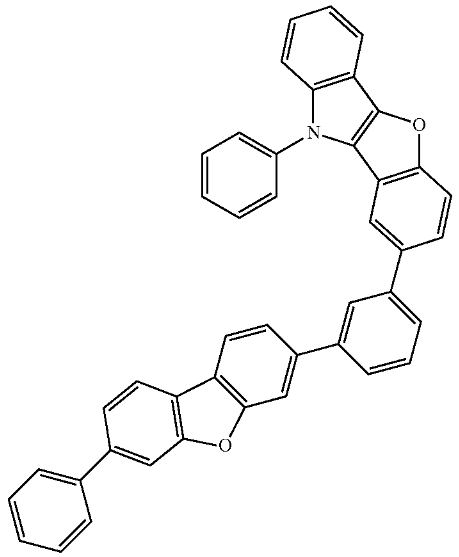

-continued
363
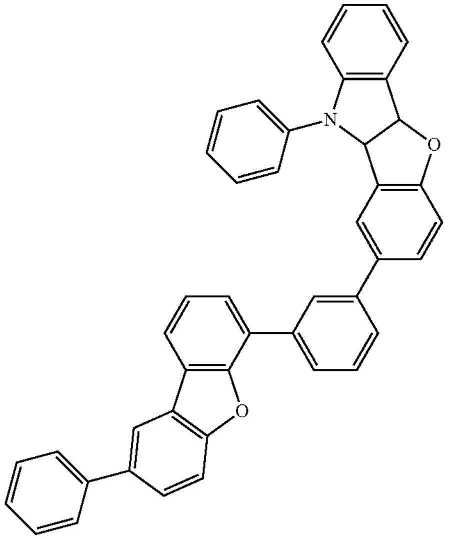
364
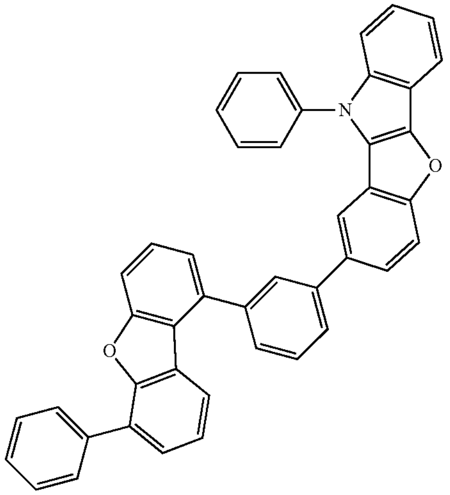
365
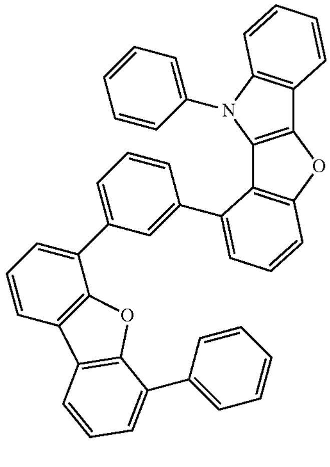
-continued
366
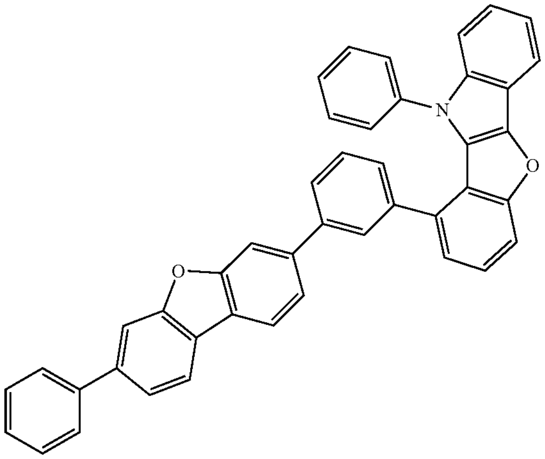
367
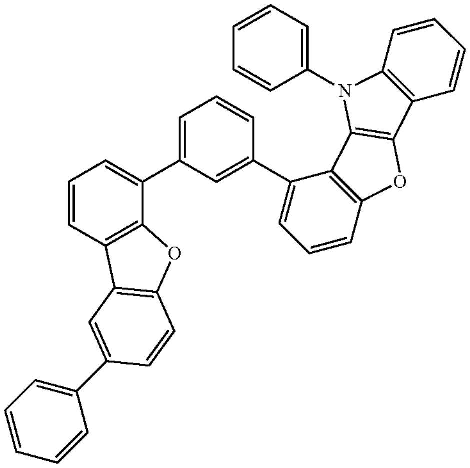
368
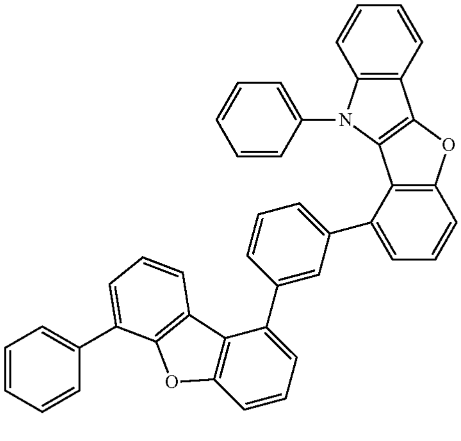

-continued
369
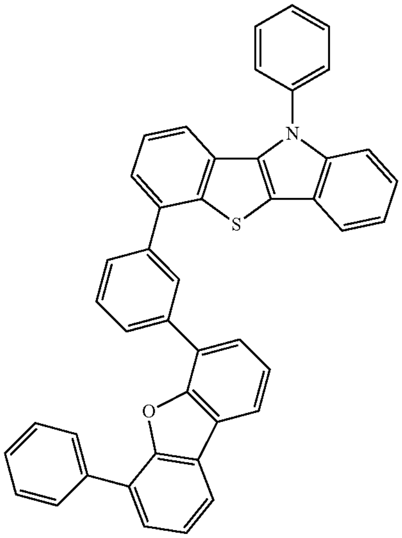
370
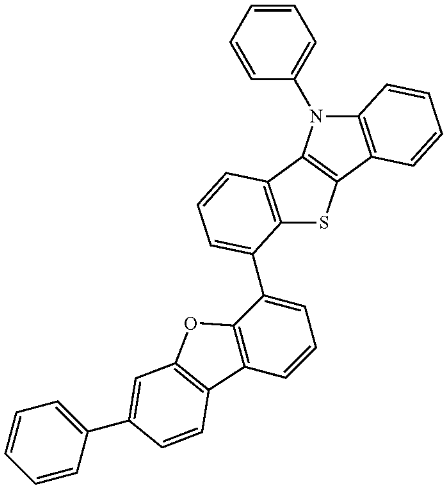
371
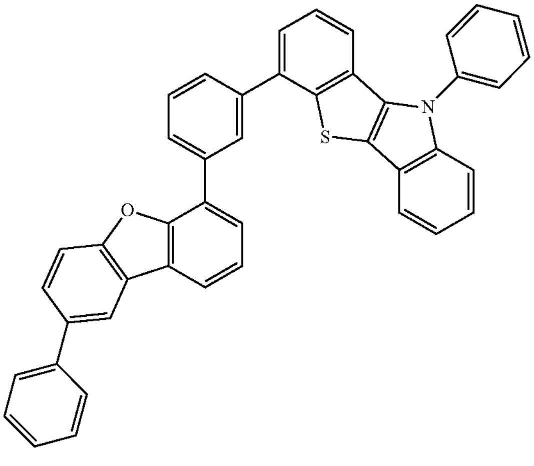
-continued
372
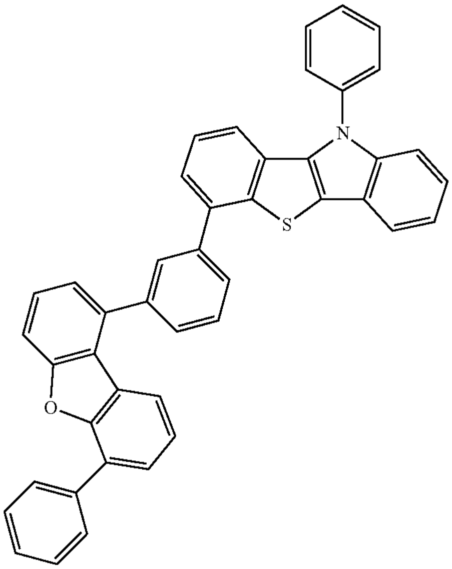
373
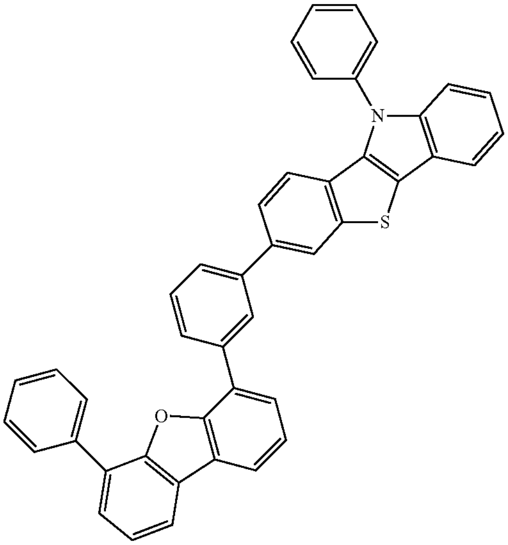
374
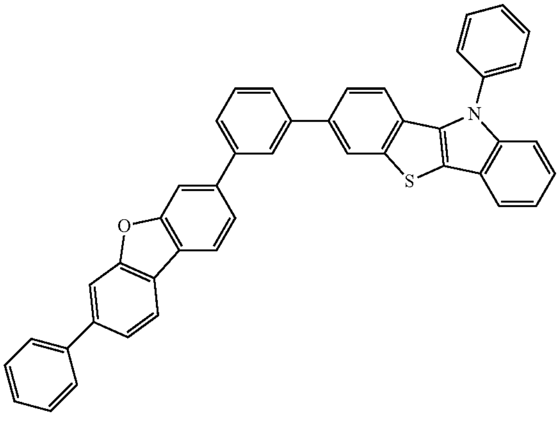

-continued
375
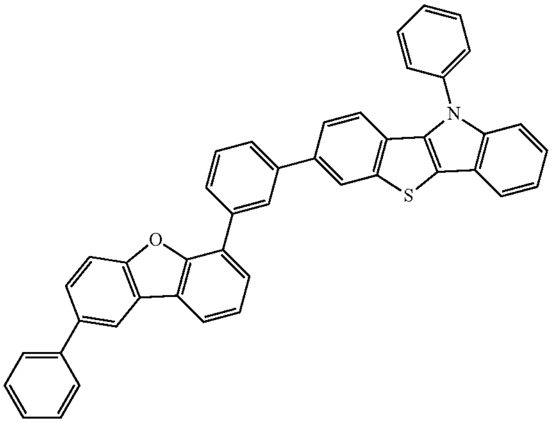
376
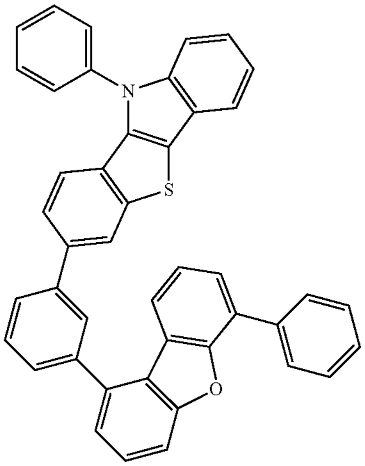
377
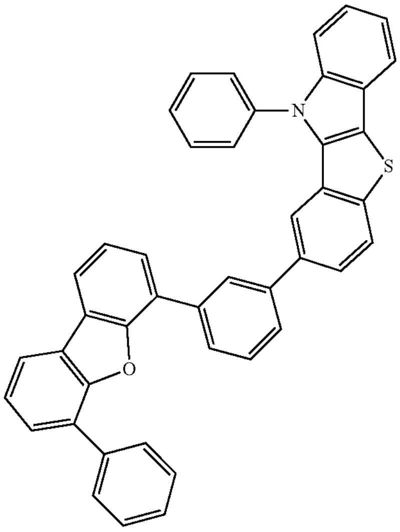
-continued
378
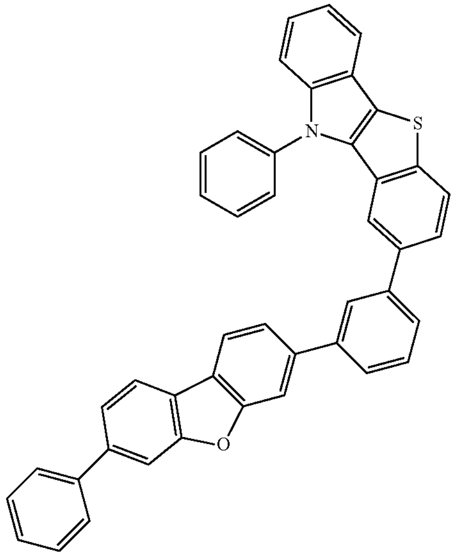
379
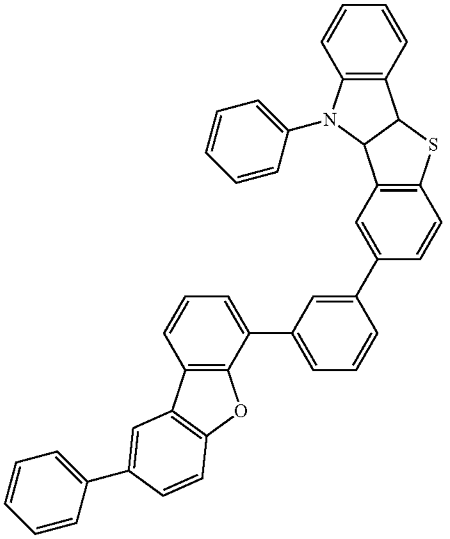
380
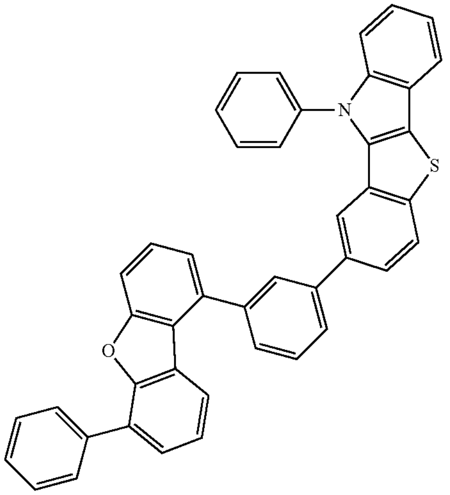

-continued
381
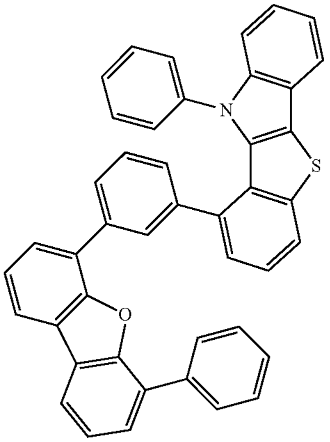
382
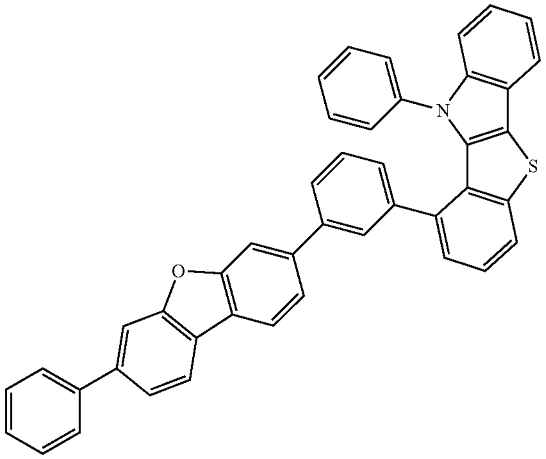
383
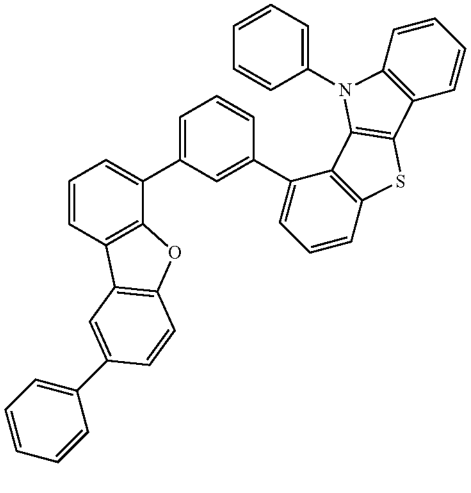
-continued
384
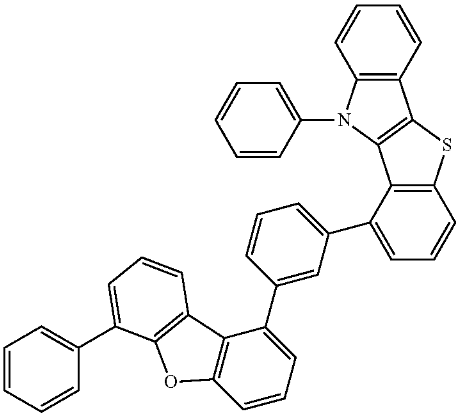
385
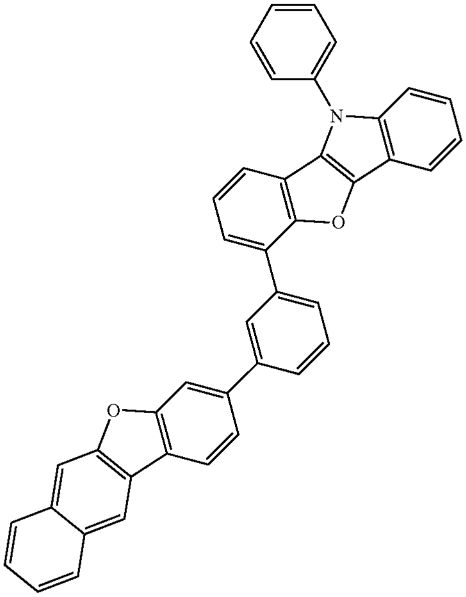
386
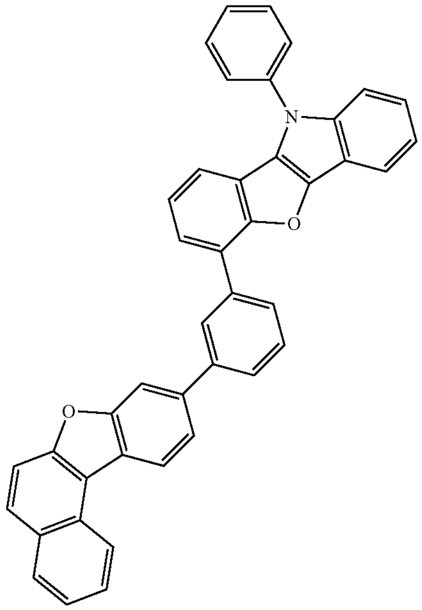

-continued
387
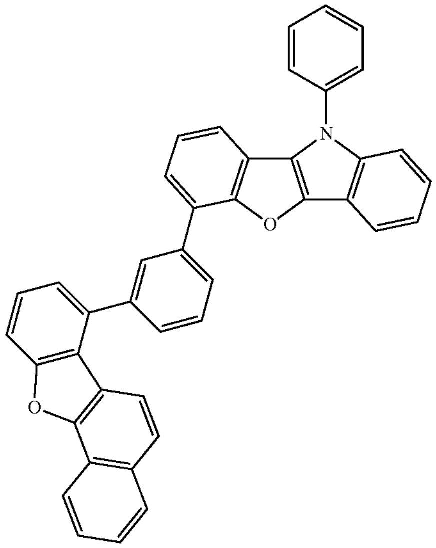
388
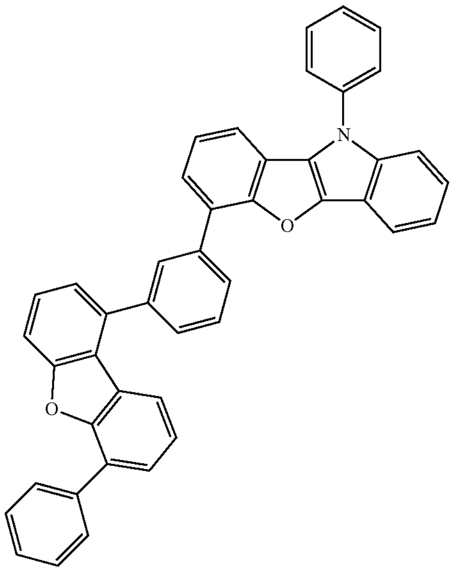
-continued
389
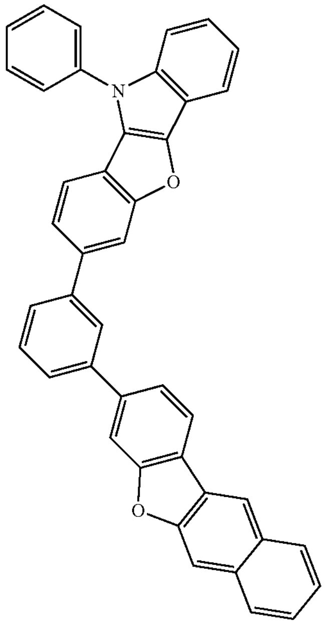
390
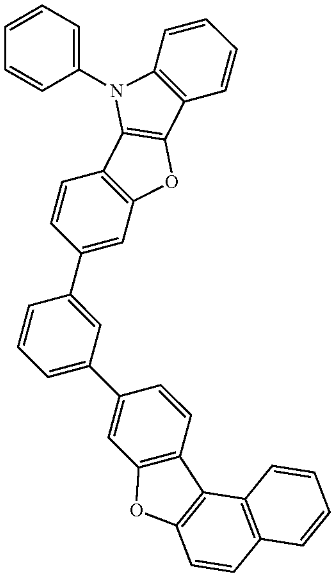
391
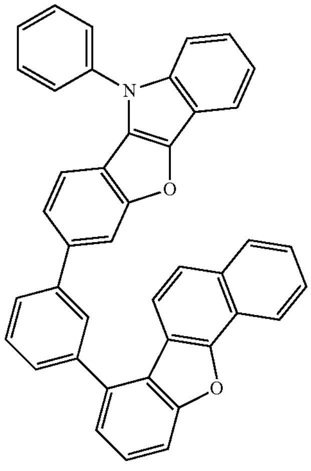

-continued
392
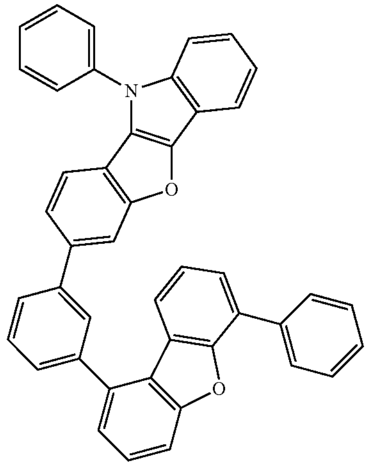
393
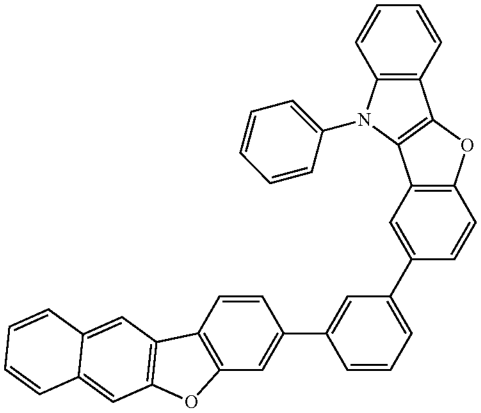
394
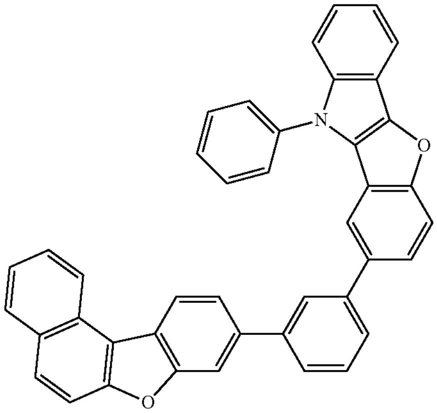
-continued
395
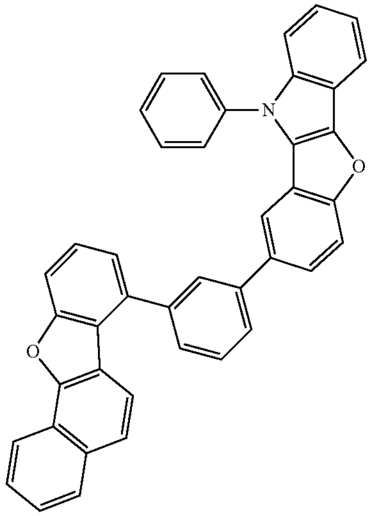
396
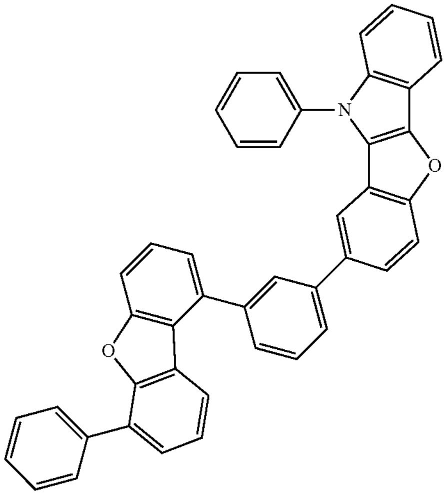
397
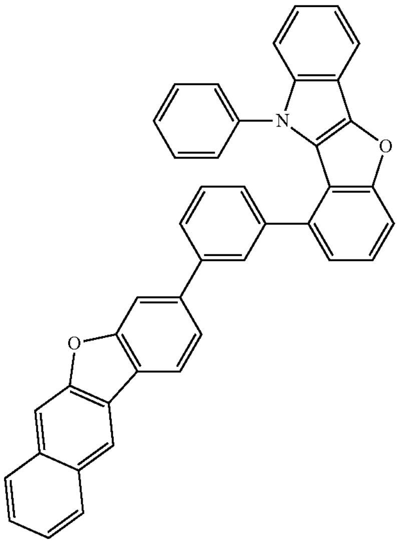

-continued
398
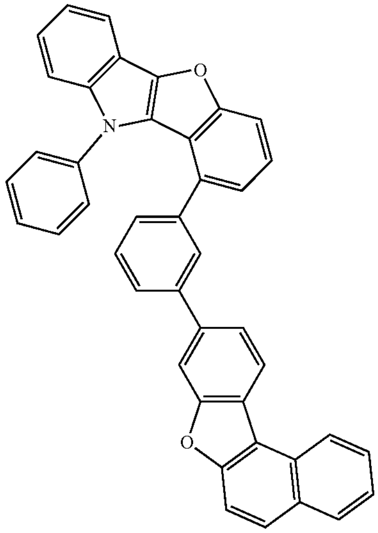
399
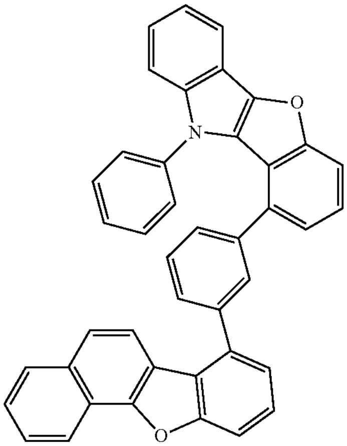
400
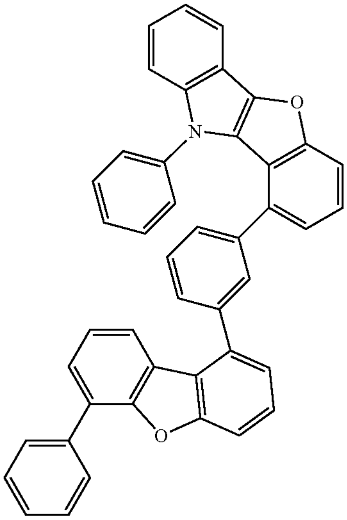
-continued
401
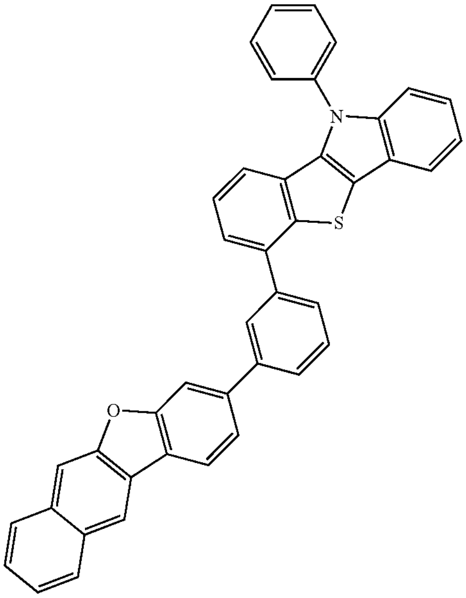
402
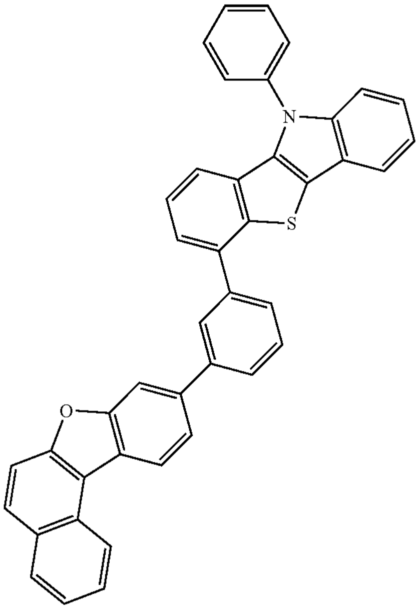

-continued
403
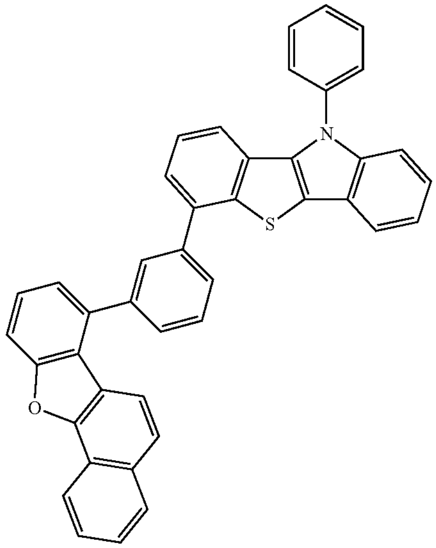
404
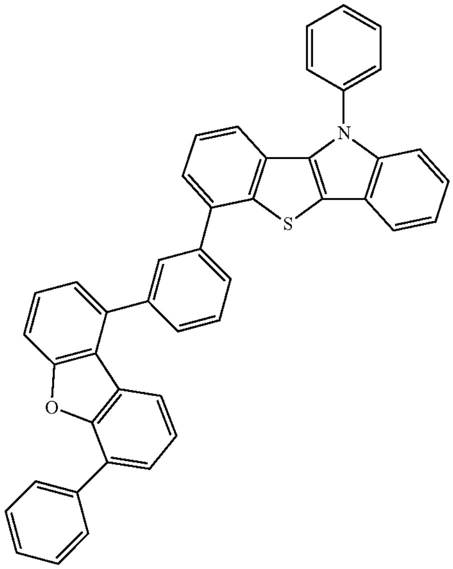
-continued
405
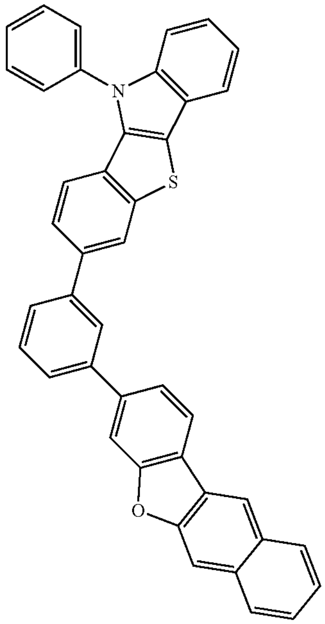
406
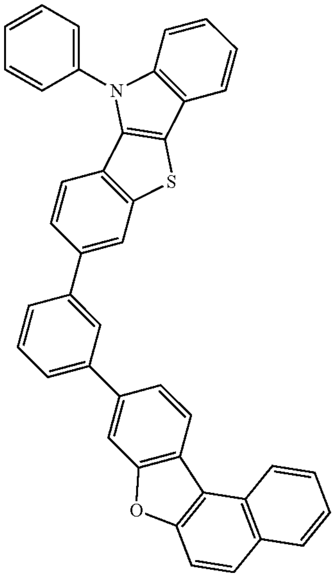
407
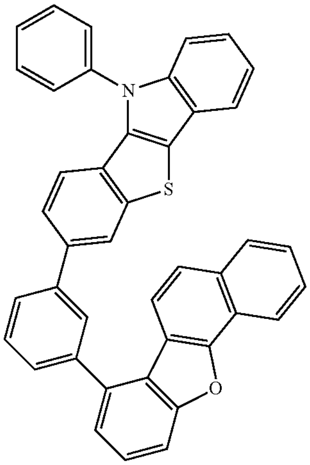

408
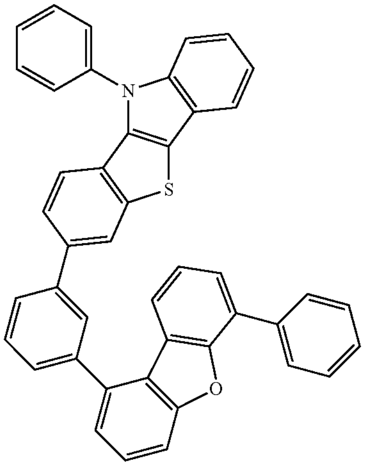
409
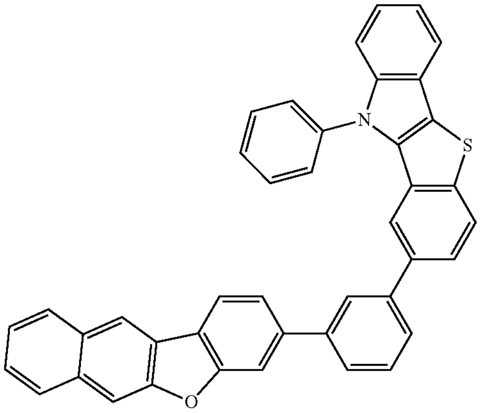
410
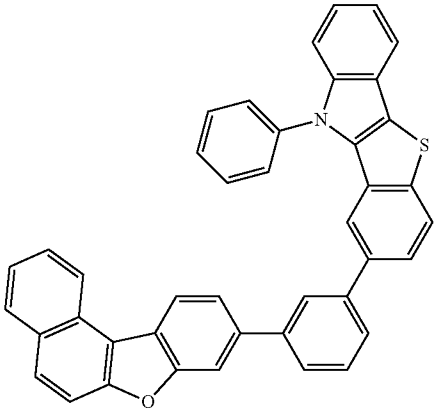
411
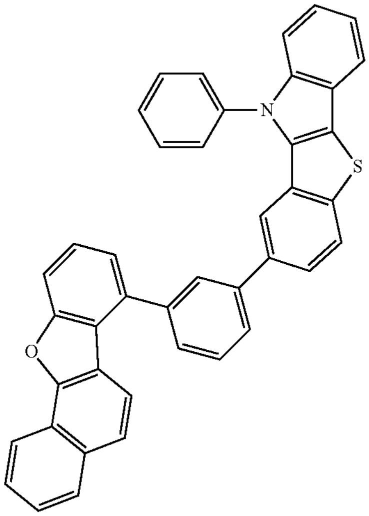
412
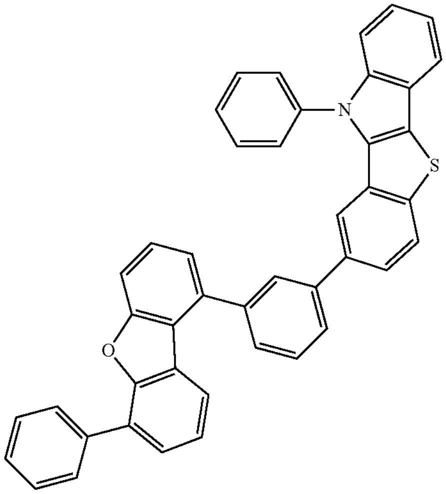
413
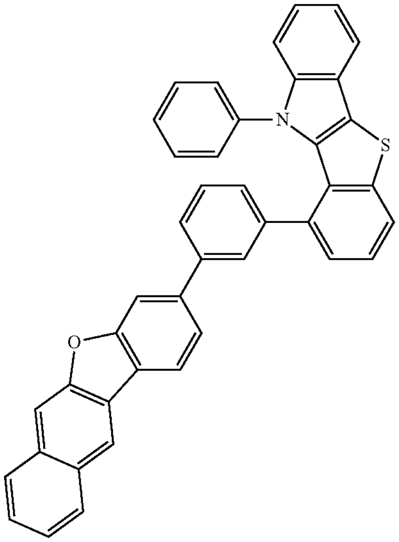

-continued
414
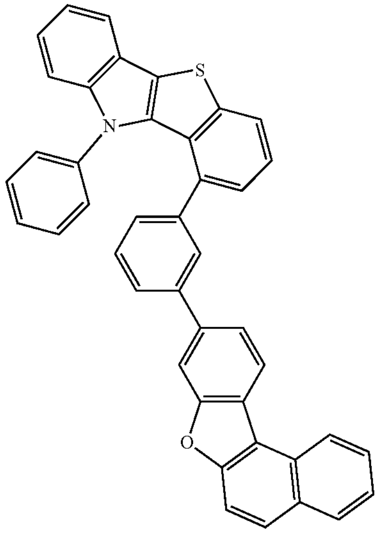
415
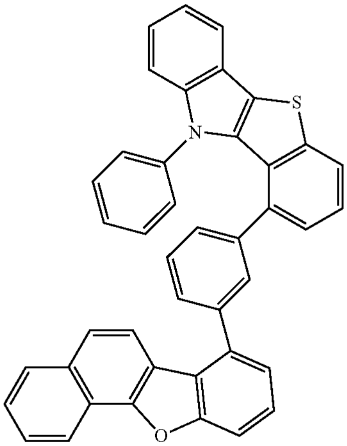
416
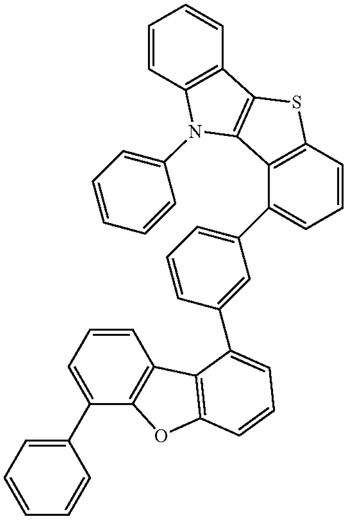
-continued
417
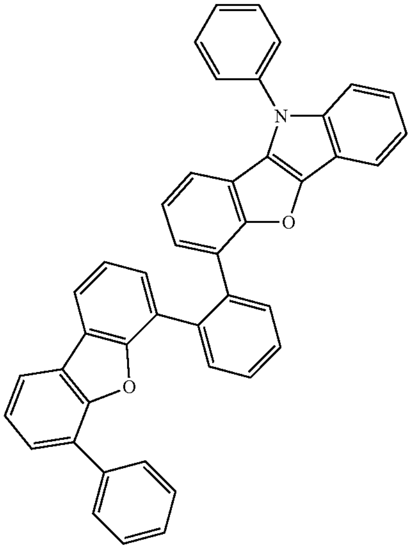
418
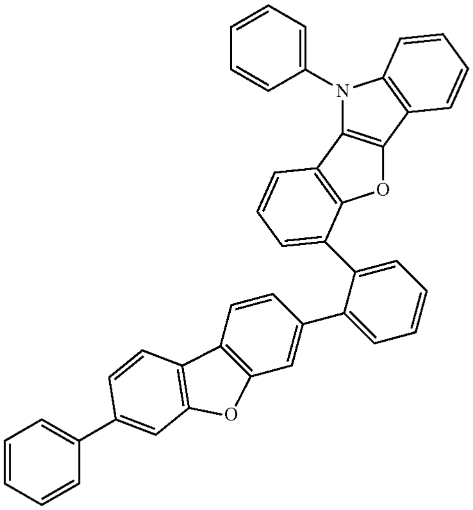
419
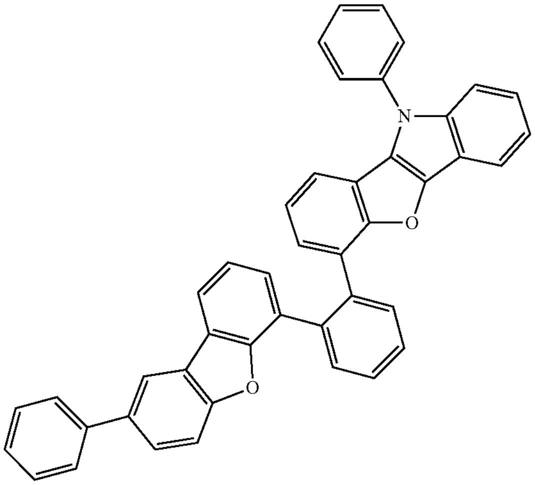

-continued
420
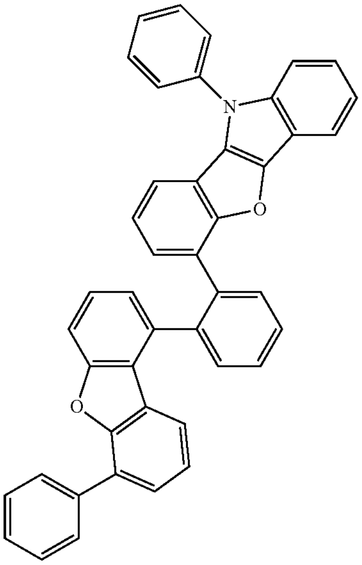
421
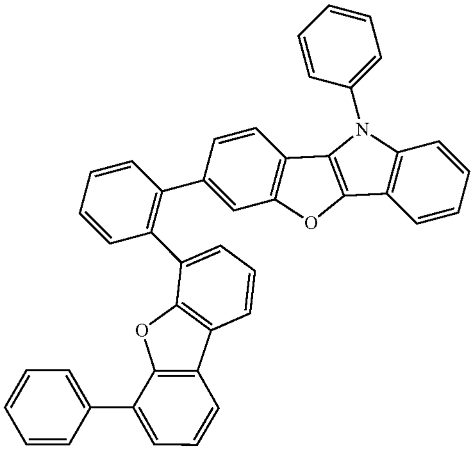
422
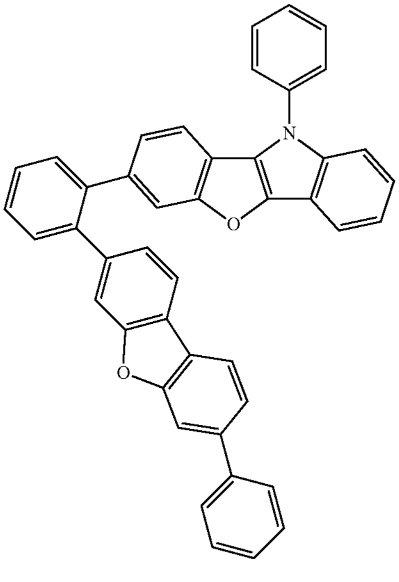
-continued
423
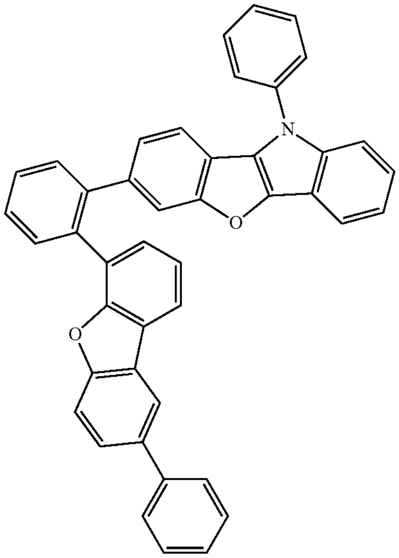
424
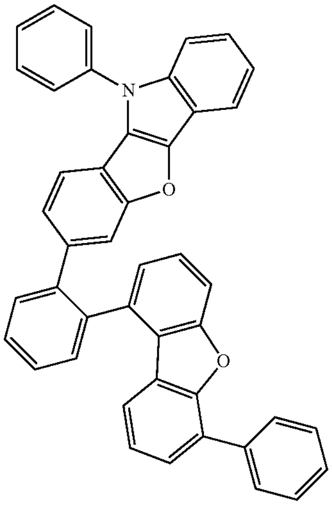
425
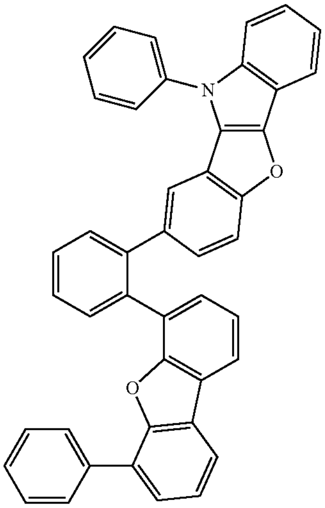

-continued
426
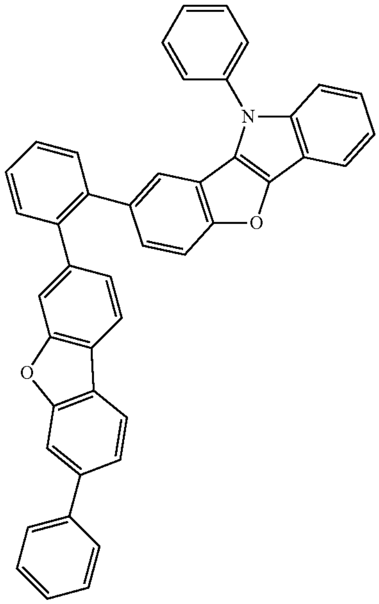
427
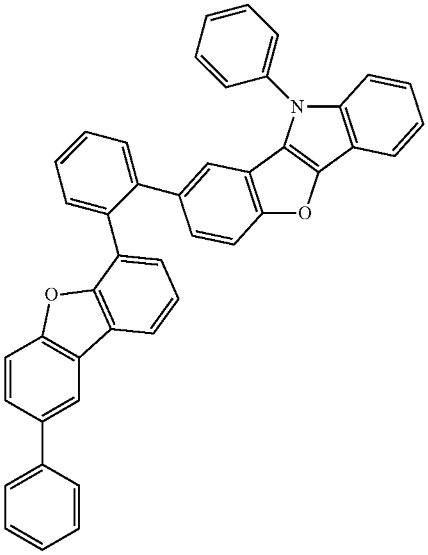
428
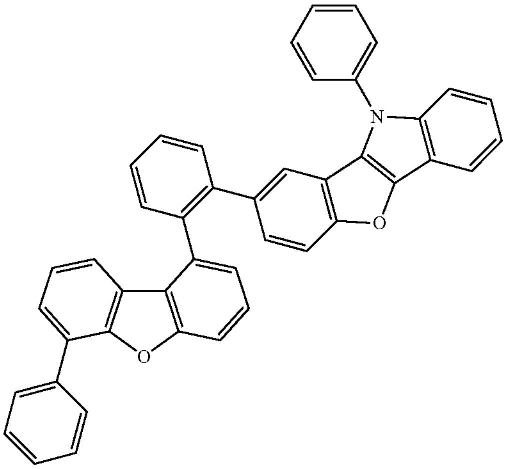
-continued
429
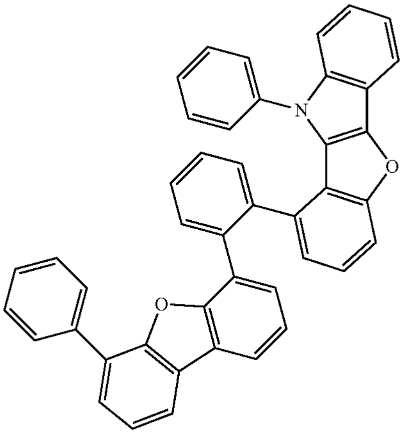
430
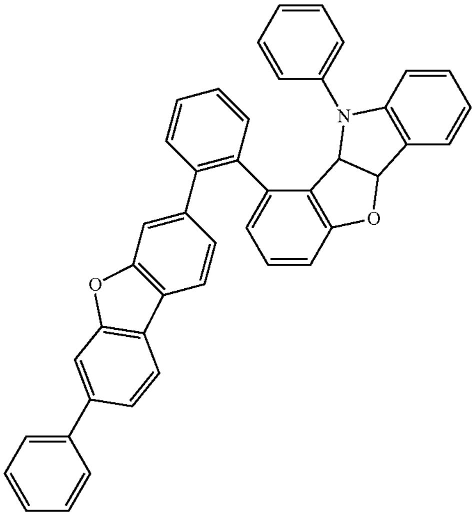
431
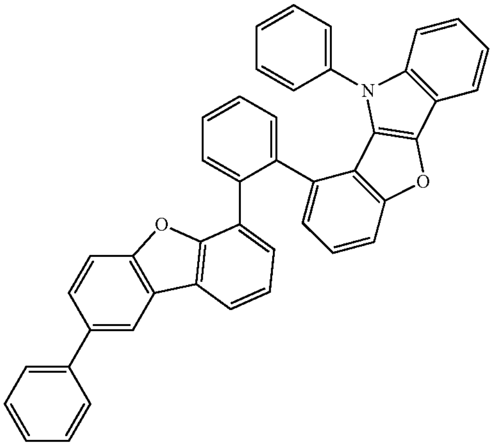

-continued
432
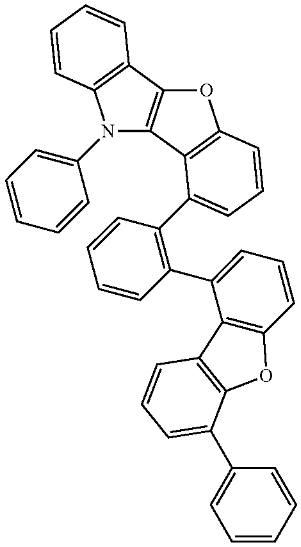
433
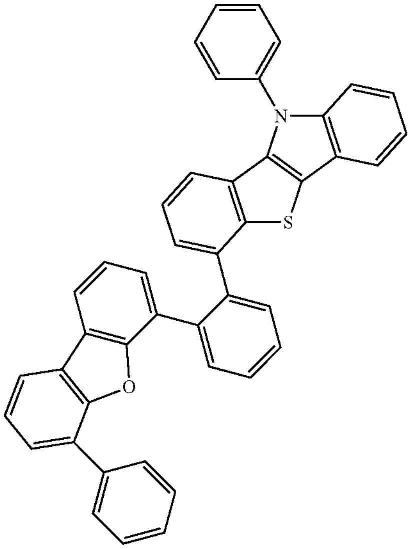
434
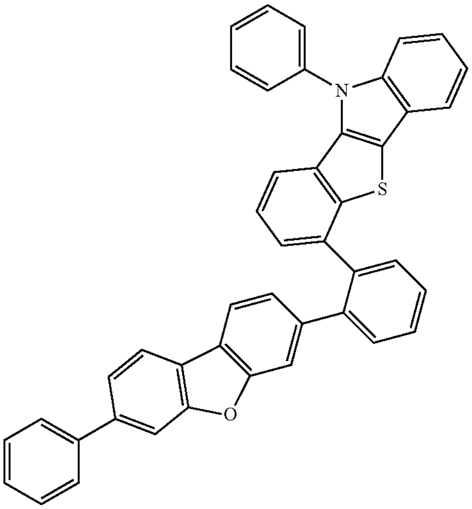
-continued
435
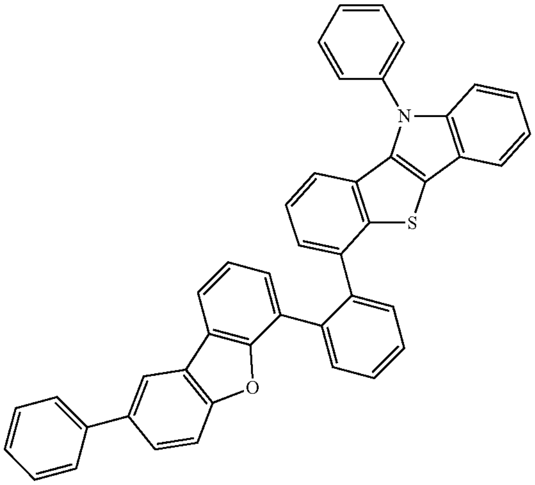
436
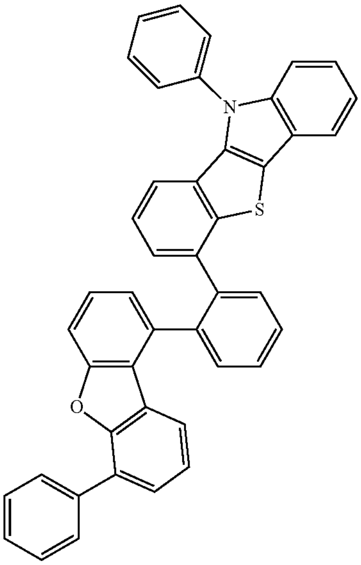
437
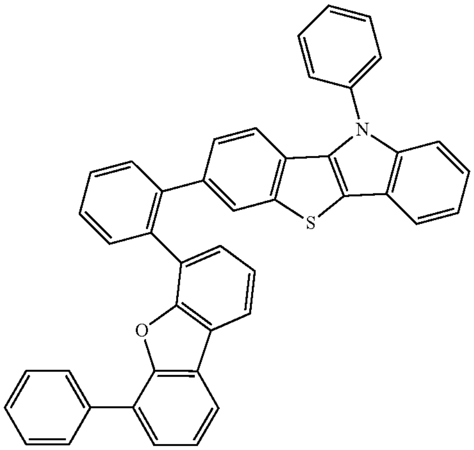

-continued
438
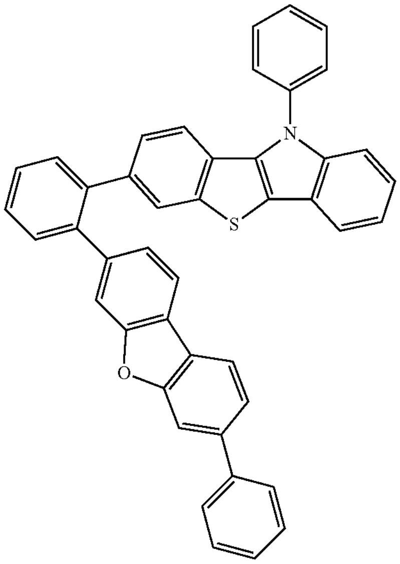
439
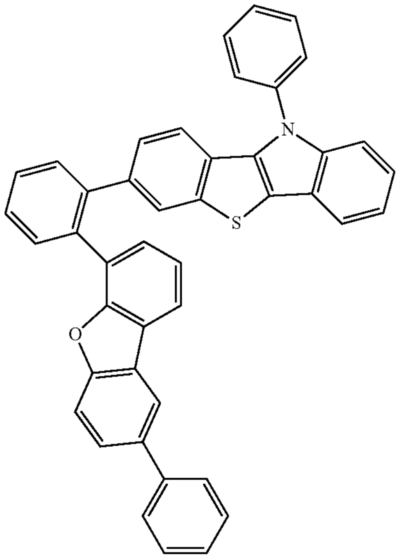
440
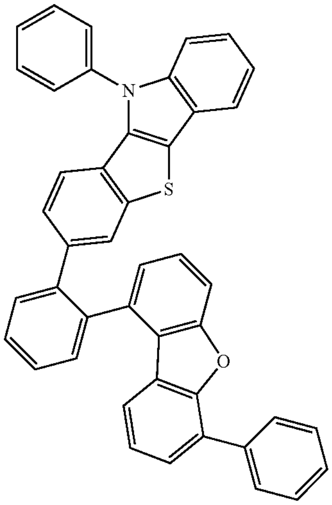
-continued
441
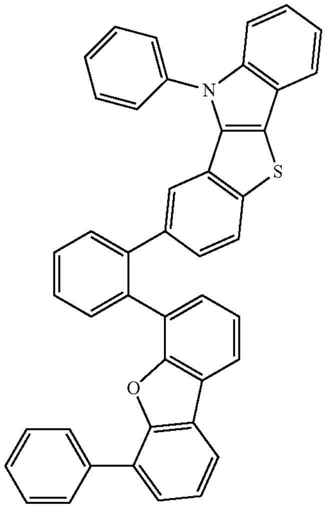
442
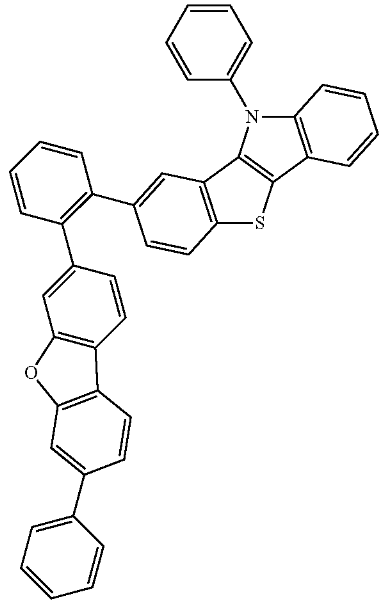
443
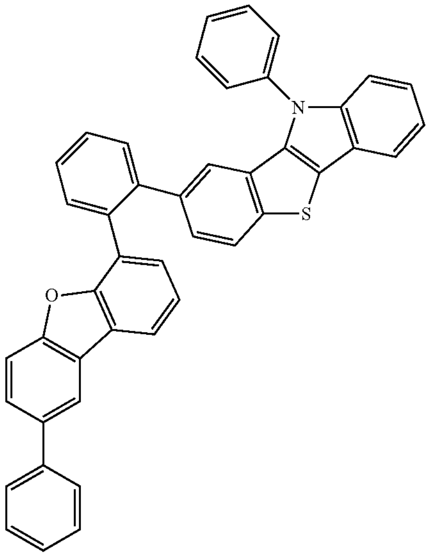

444
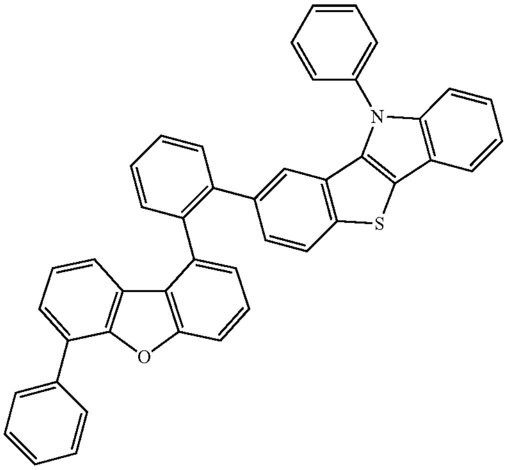
445
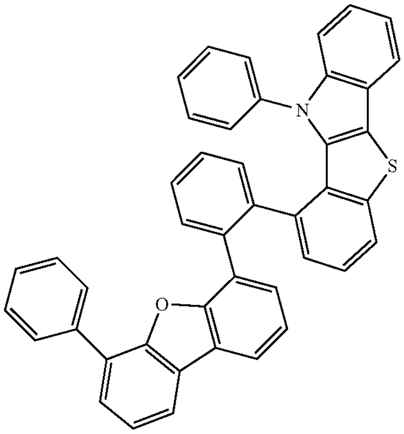
446
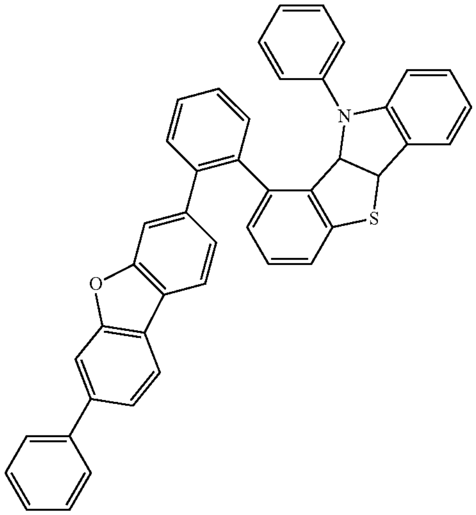
447
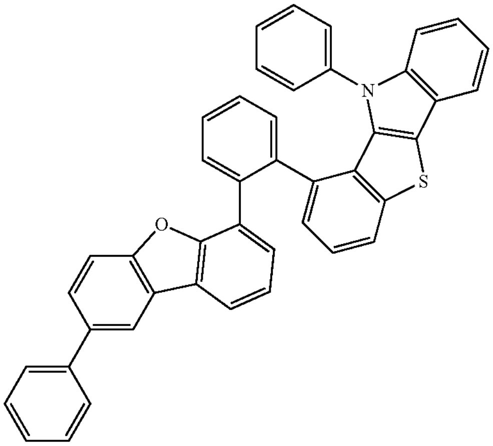
448
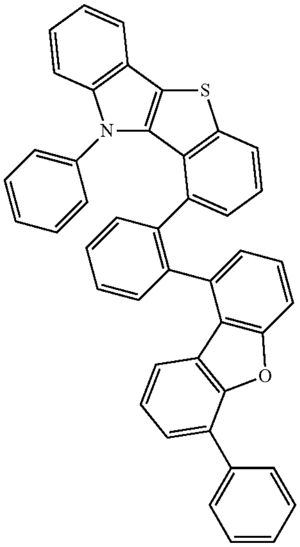
449
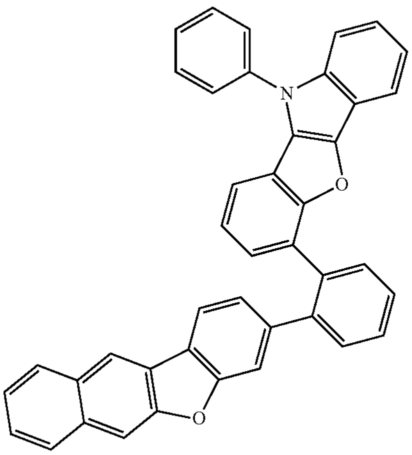

-continued
450
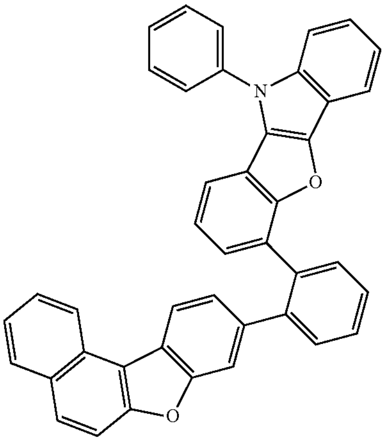
451
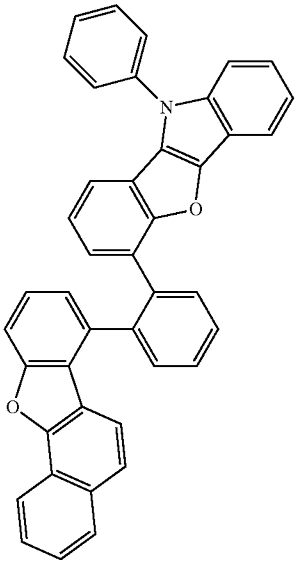
452
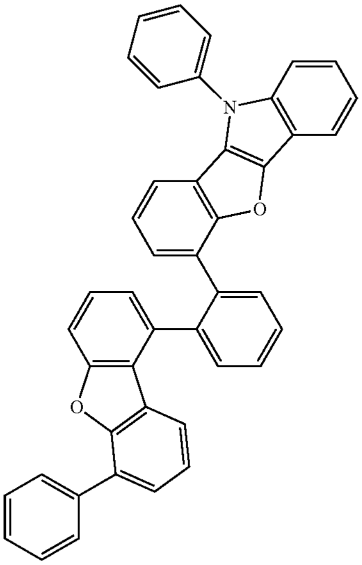
-continued
453
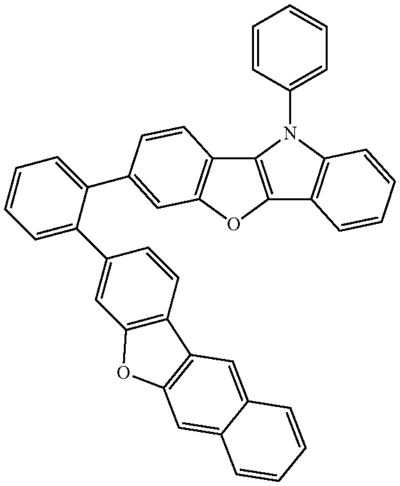
454
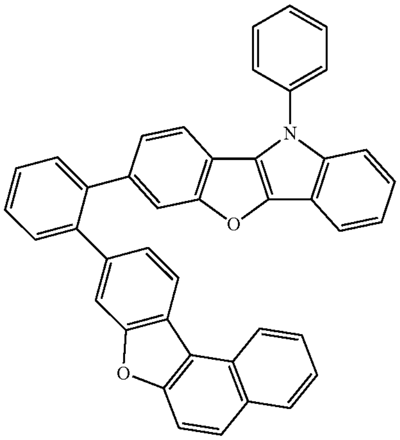
455
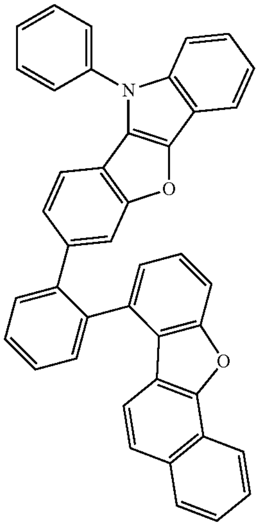

-continued
456
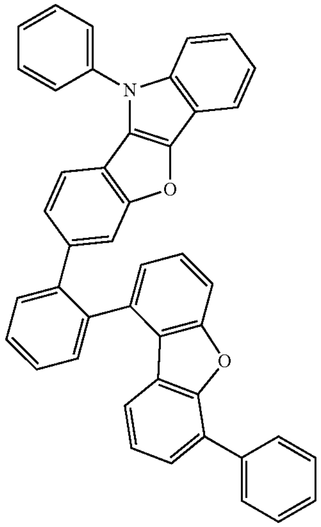
457
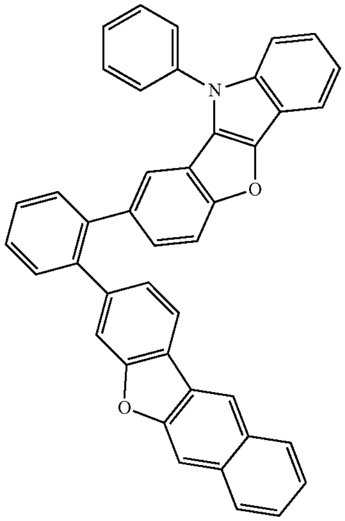
458
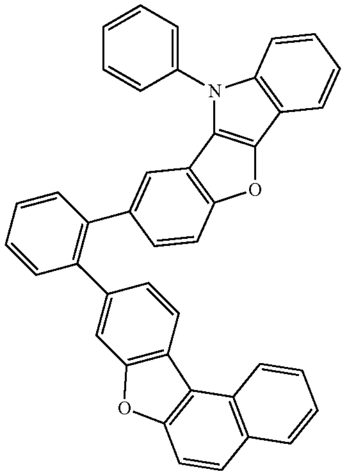
-continued
459
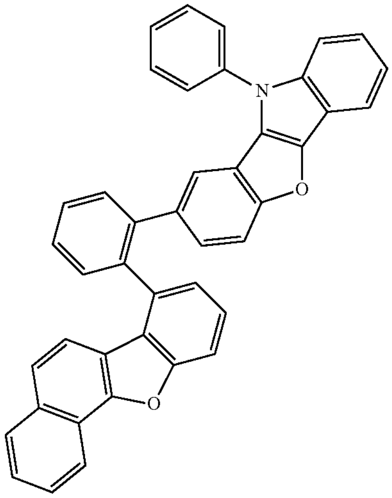
460
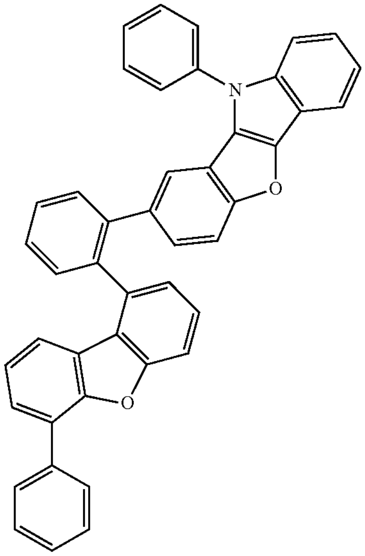
461
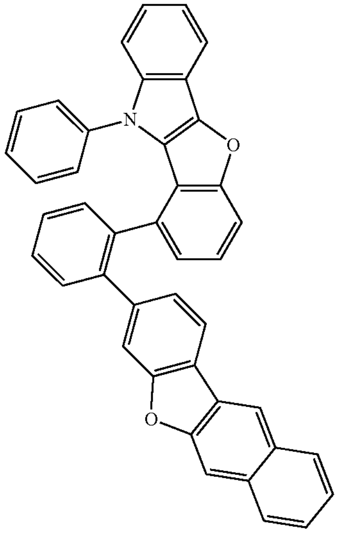

-continued
462
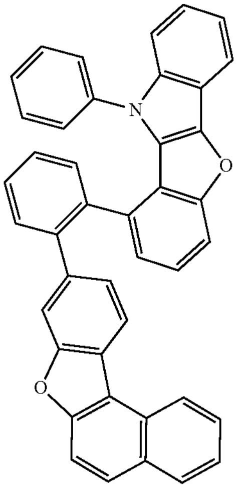
463
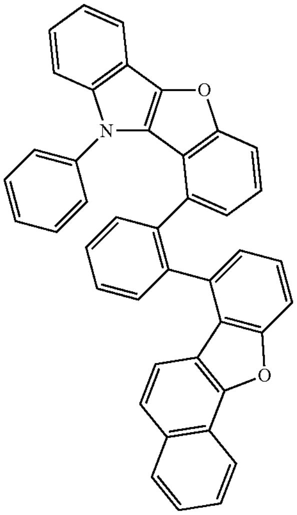
464
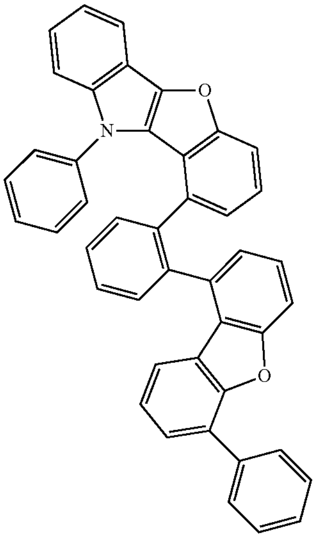
-continued
465
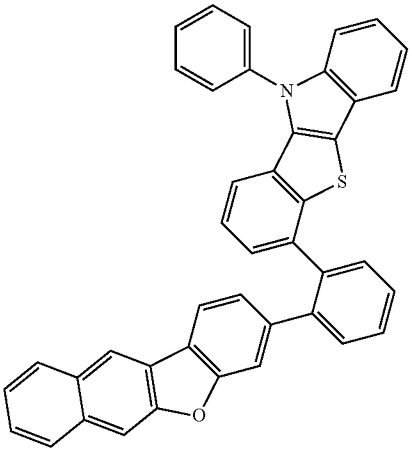
466
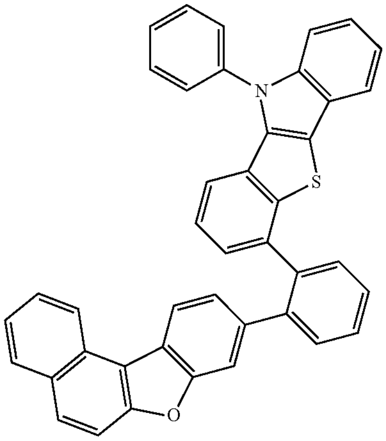
467
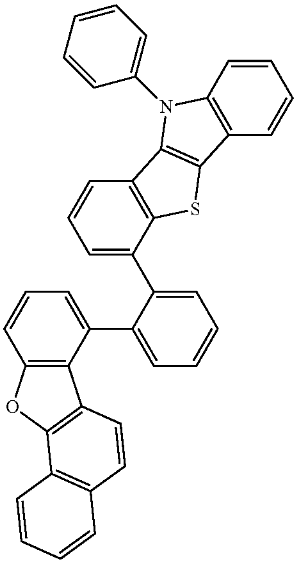

-continued
468
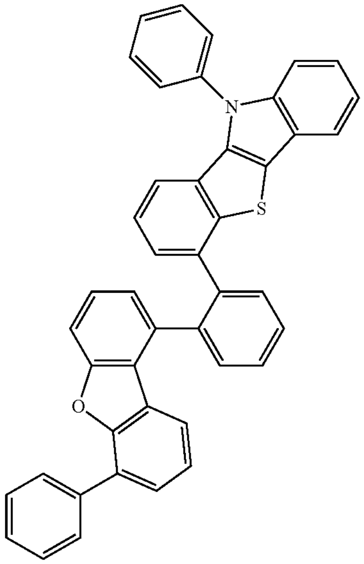
469
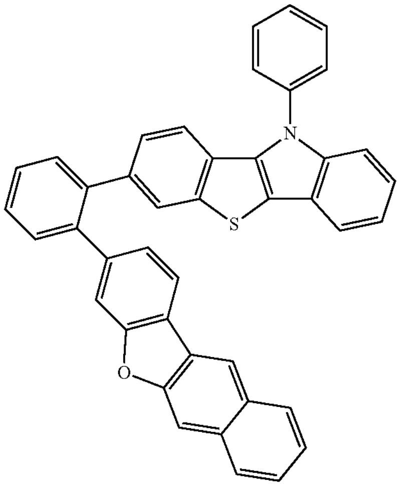
470
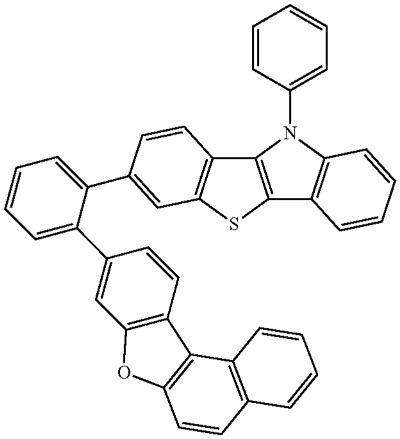
-continued
471
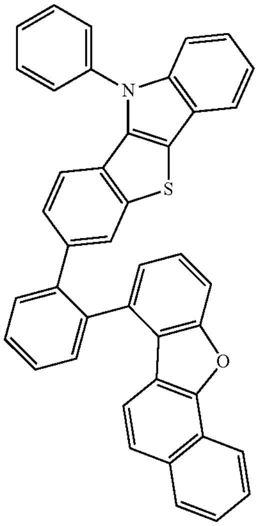
472
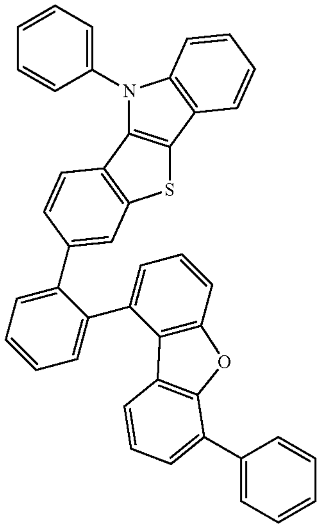
473
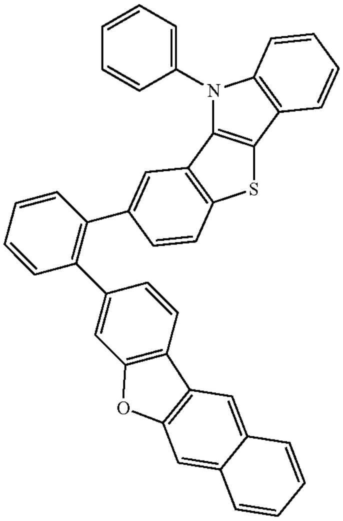

-continued
474
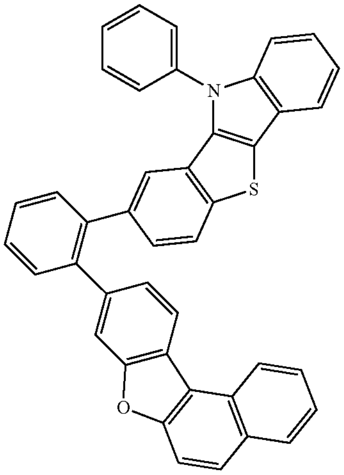
475
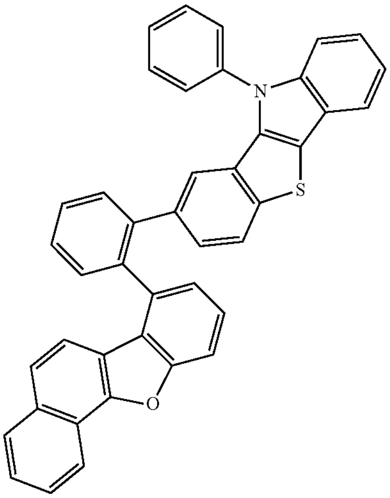
476
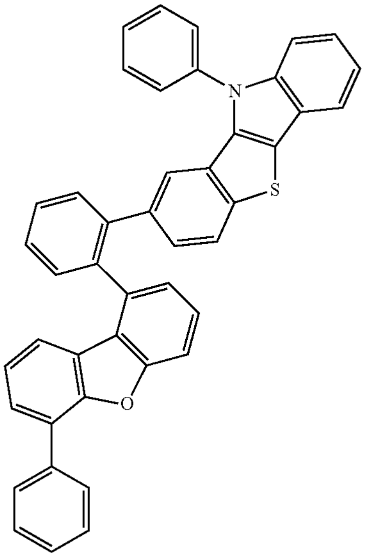
-continued
477
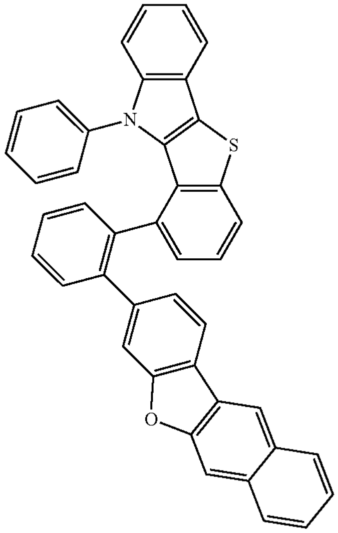
478
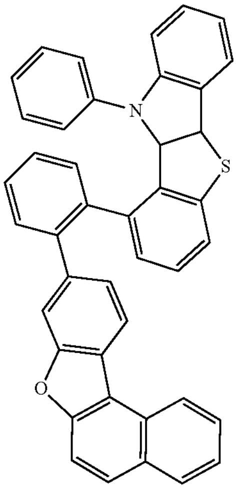
479
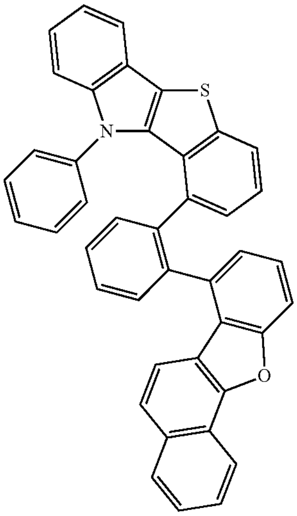

-continued
480
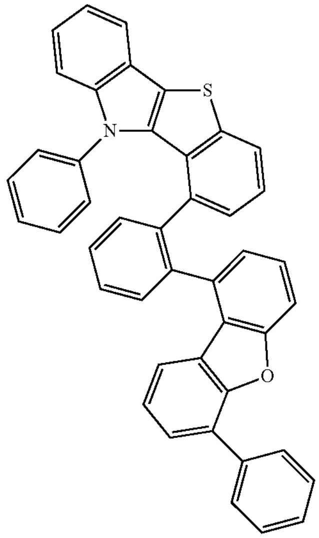
481
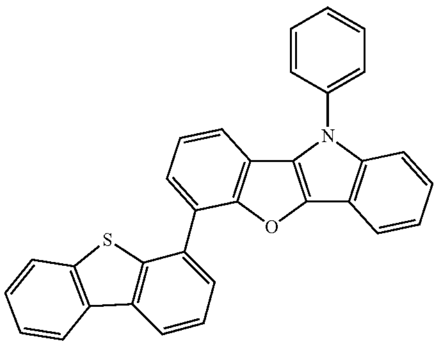
482
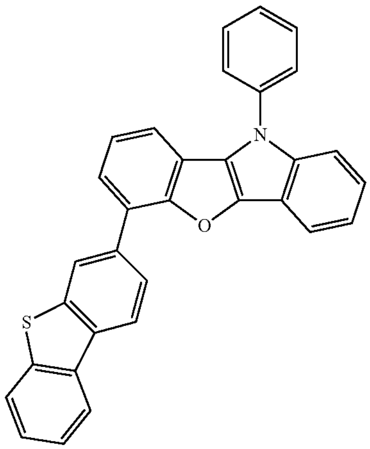
-continued
483
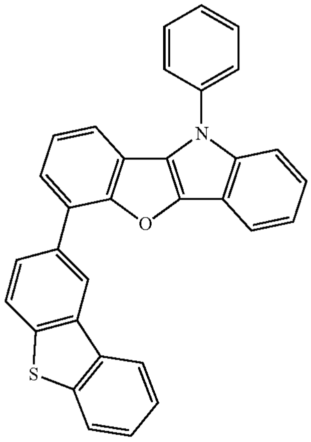
484
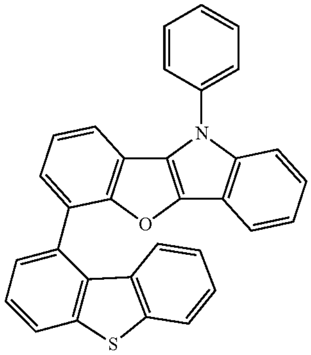
485
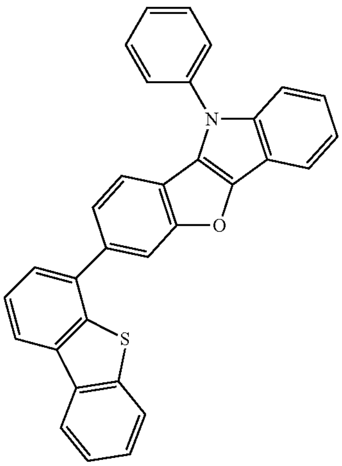

-continued
486
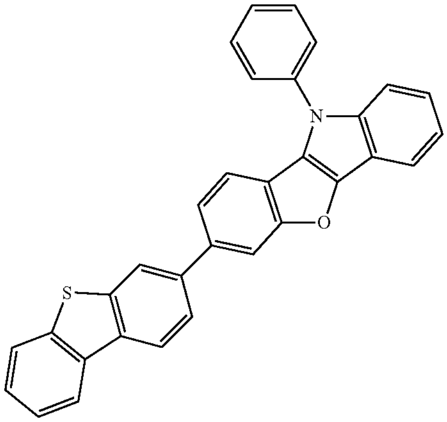
487
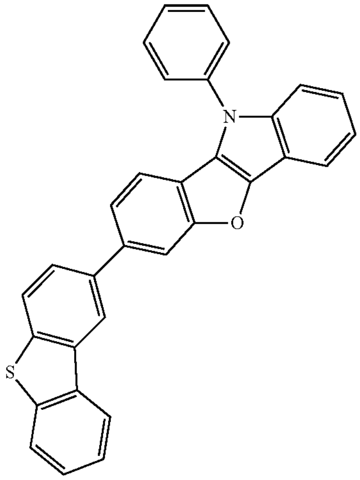
488
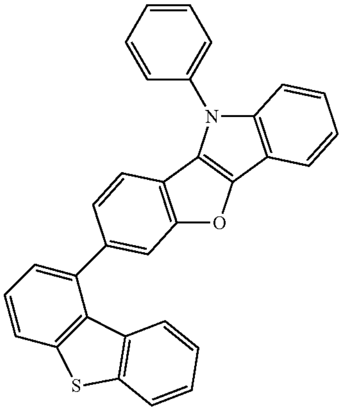
489
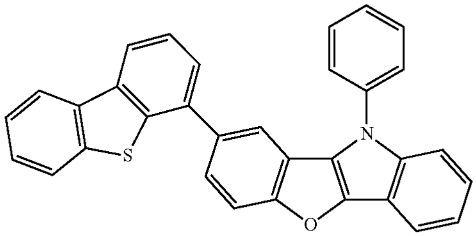
-continued
490
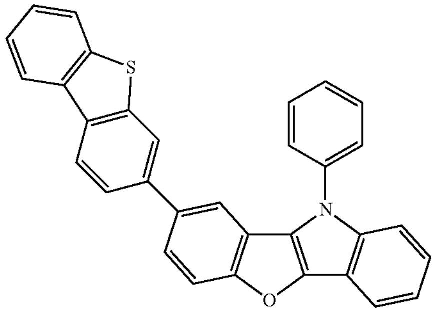
491
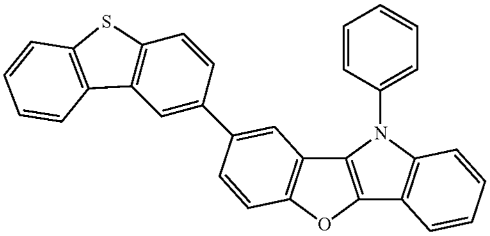
492
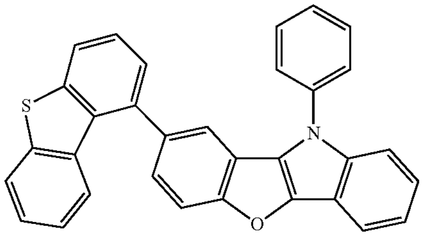
493
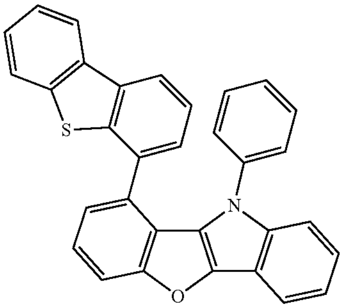
494
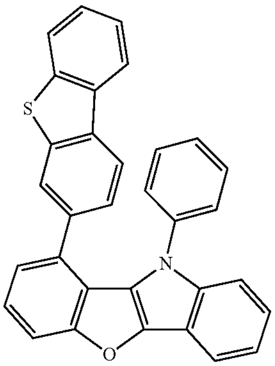

-continued
495
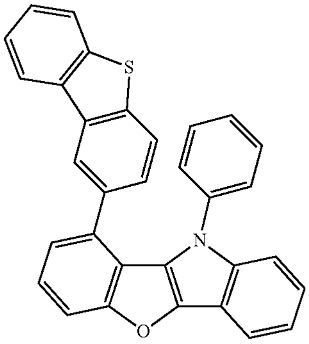
496
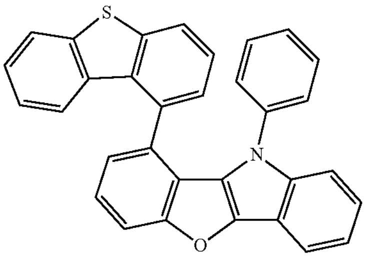
497
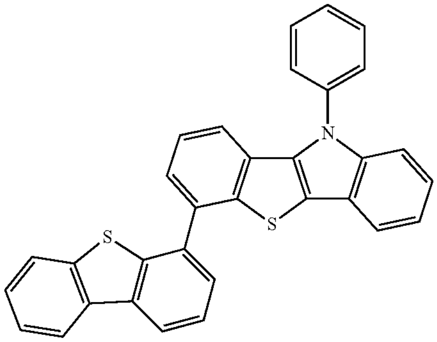
498
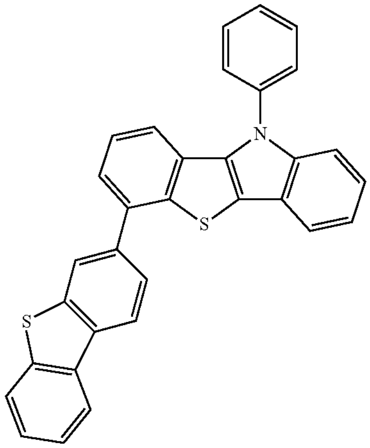
-continued
499
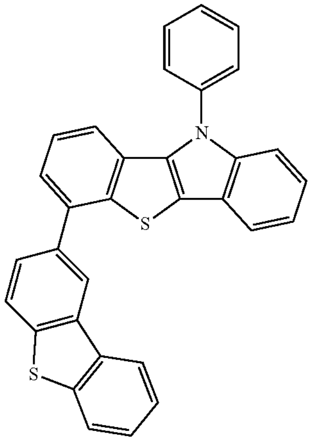
500
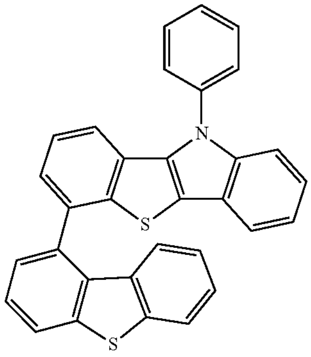
501
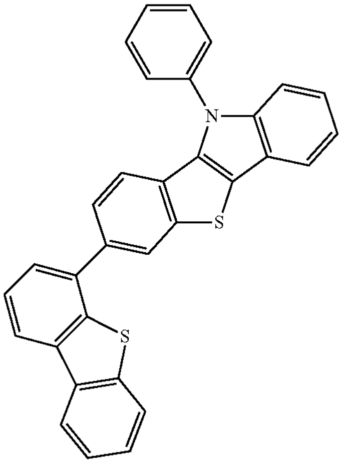

-continued
502
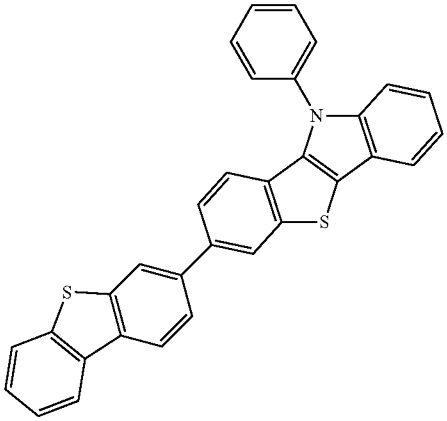
503
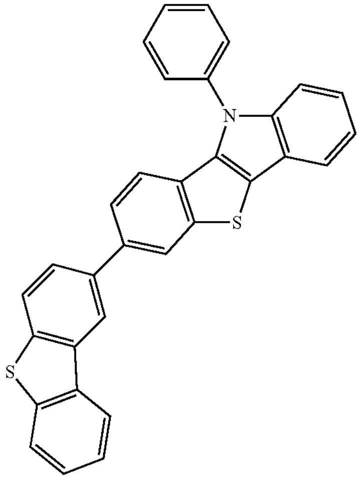
504
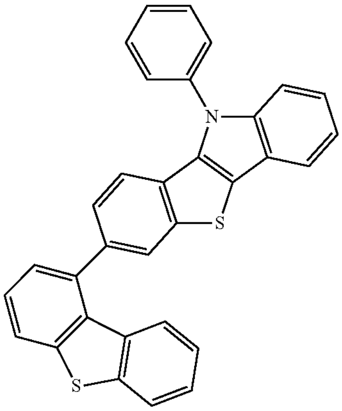
505
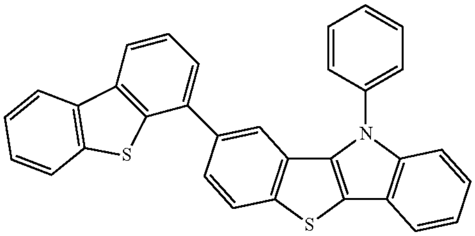
-continued
506
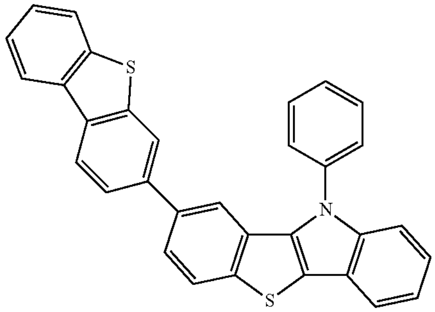
507
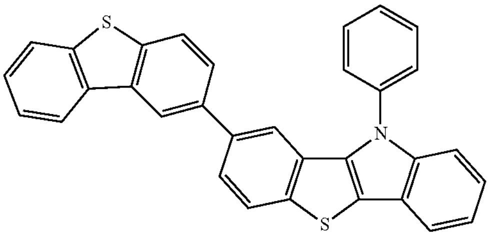
508
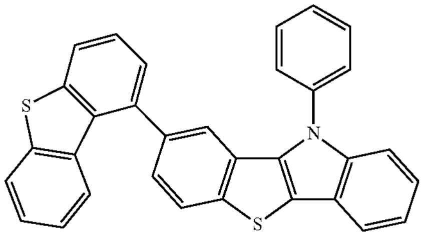
509
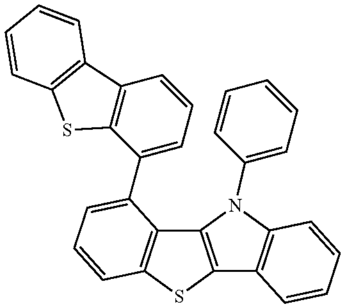
510
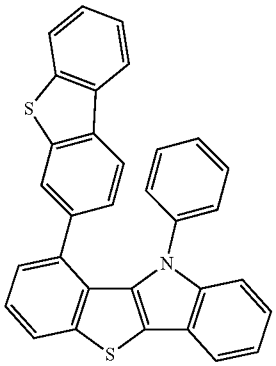

-continued
511
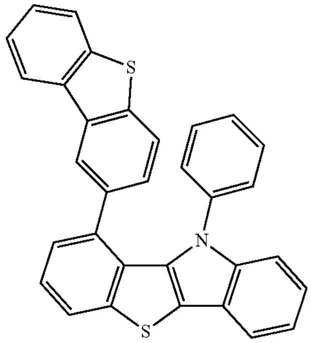
512
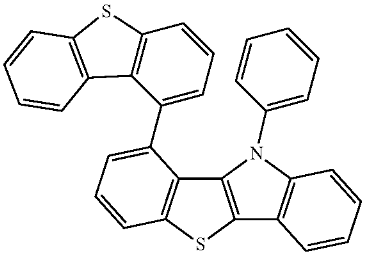
513
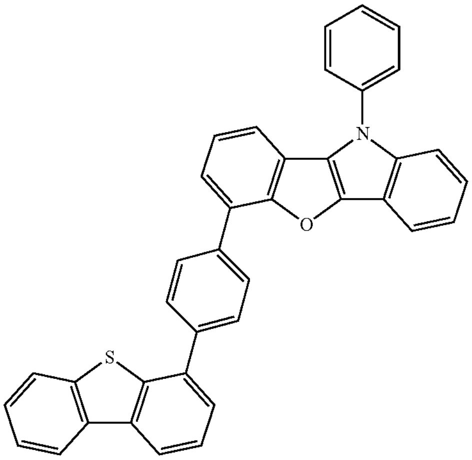
514
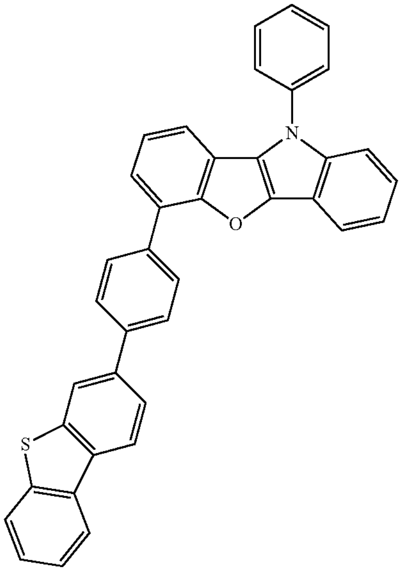
-continued
515
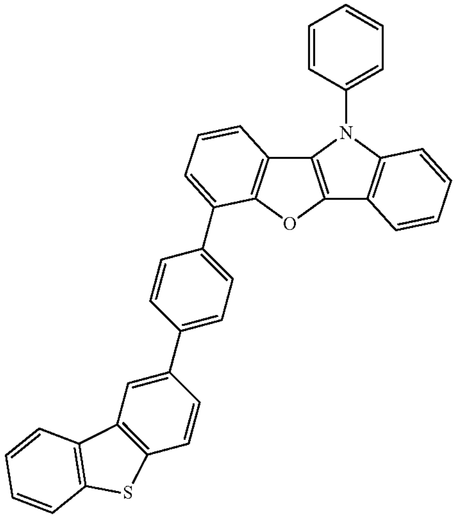
516
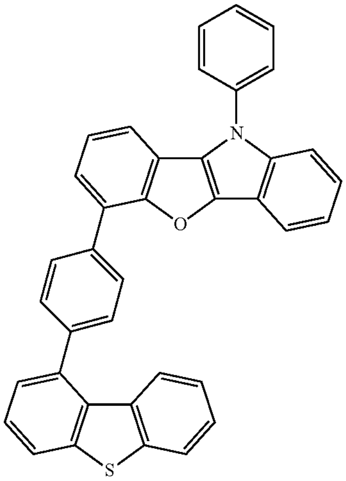
517
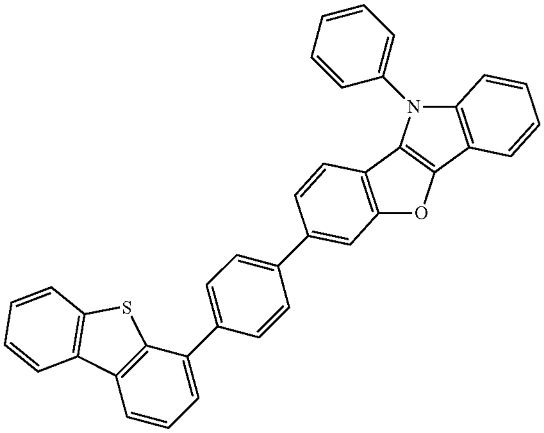

-continued
518
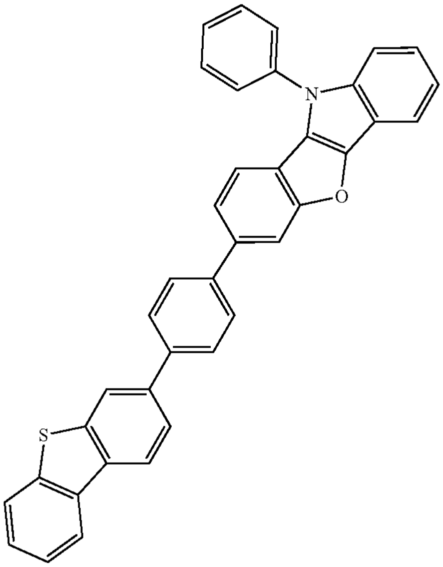
519
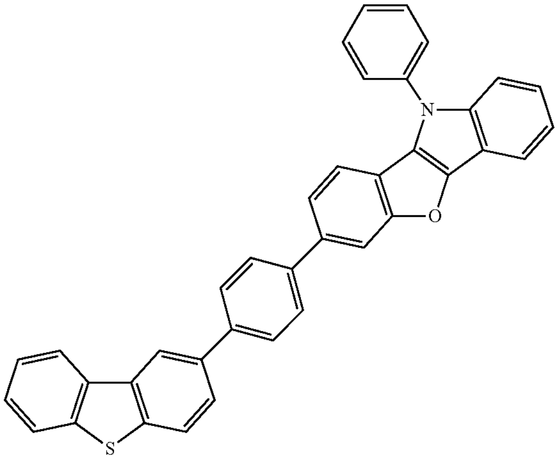
520
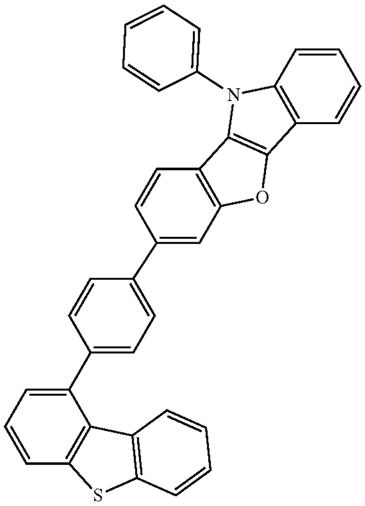
-continued
521
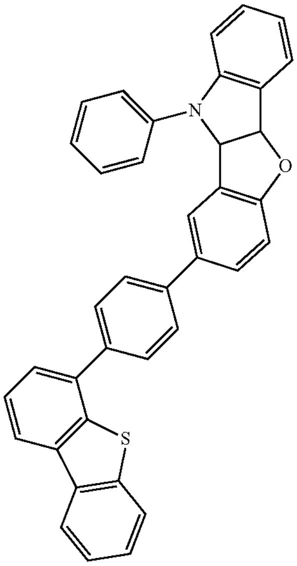
522
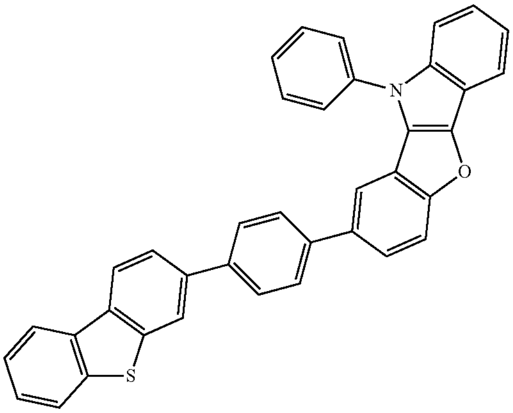
523
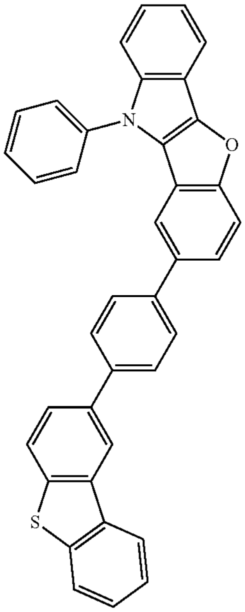

-continued
524
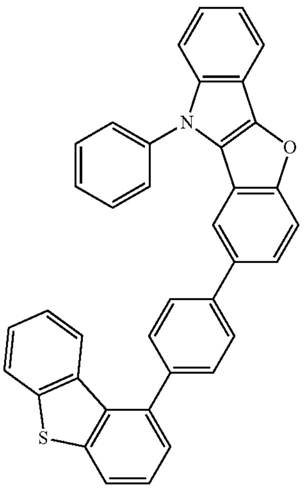
525
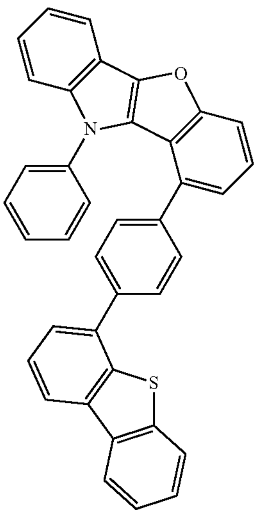
526
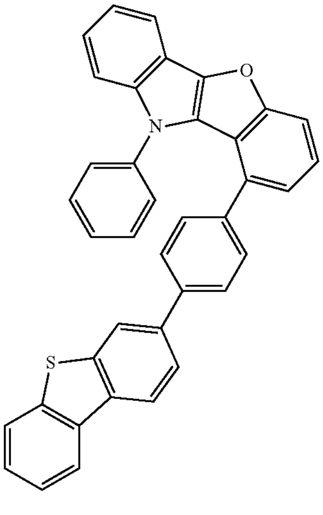
-continued
527
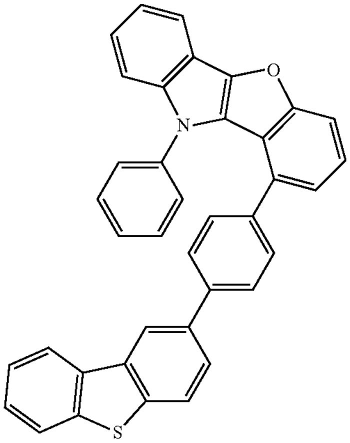
528
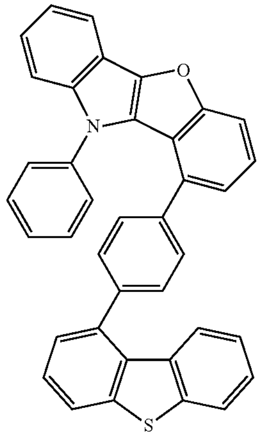
529
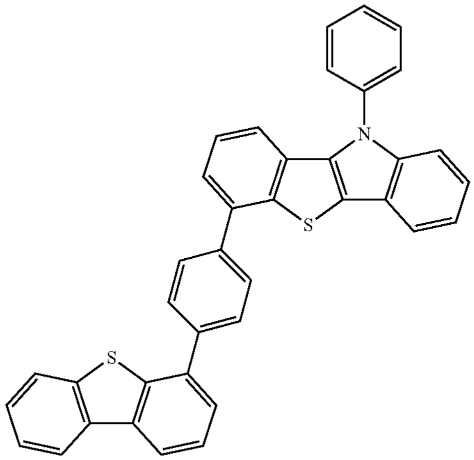

-continued
530
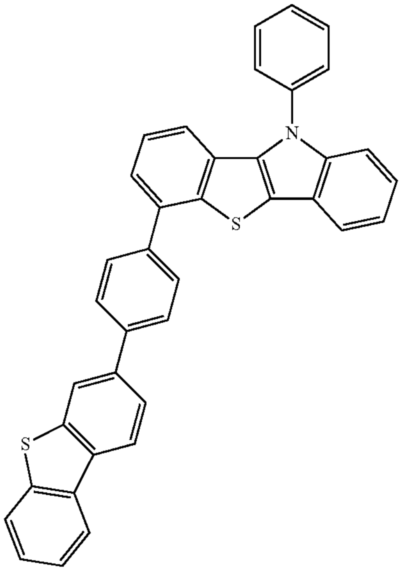
531
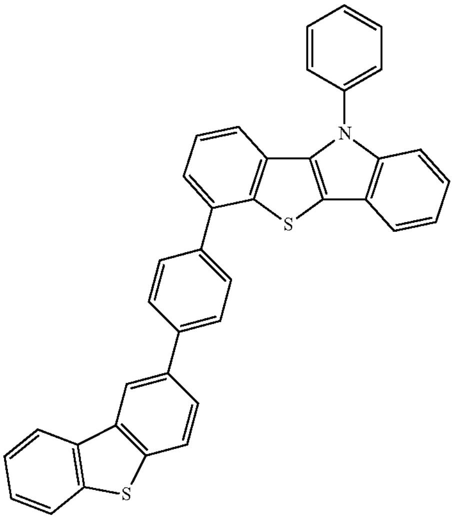
532
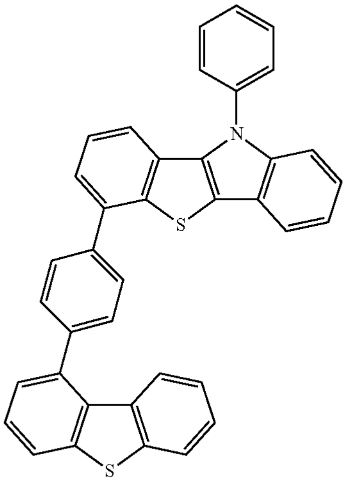
-continued
533
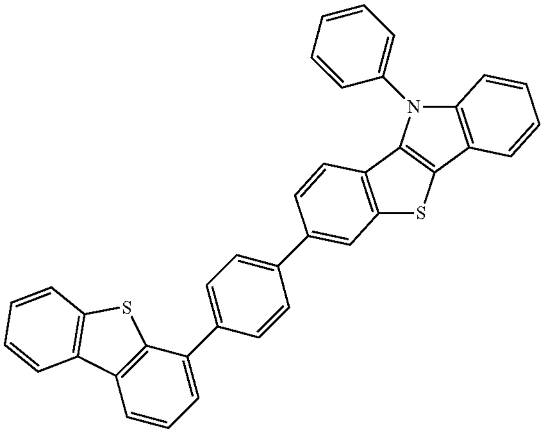
534
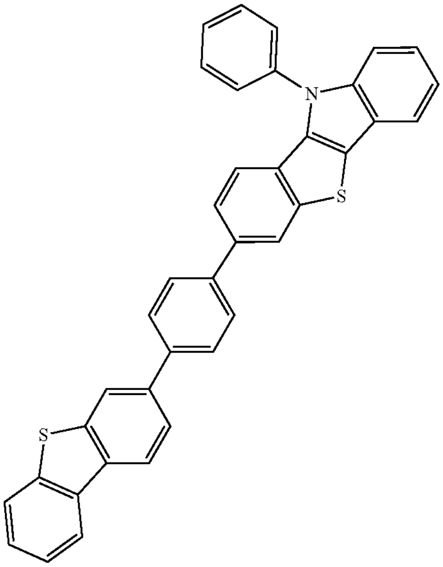
535
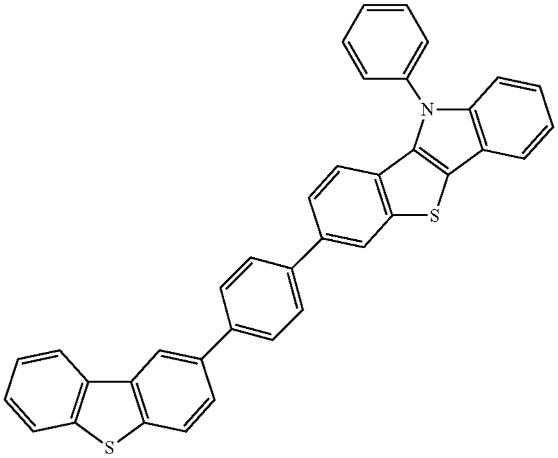

-continued
536
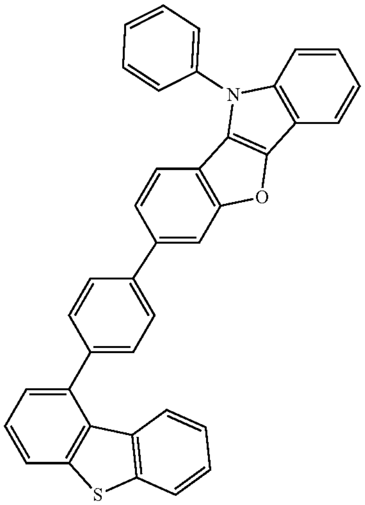
537
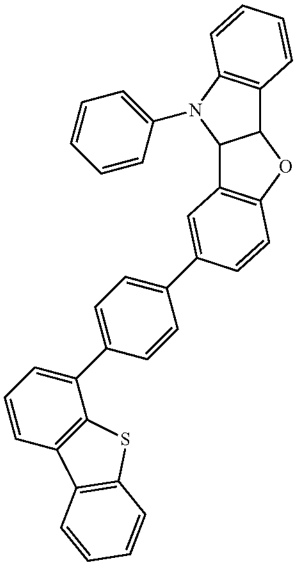
538
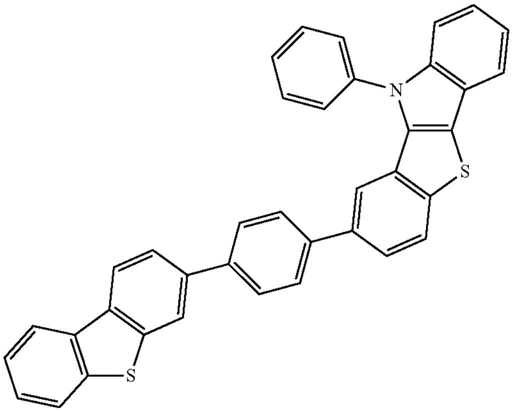
-continued
539
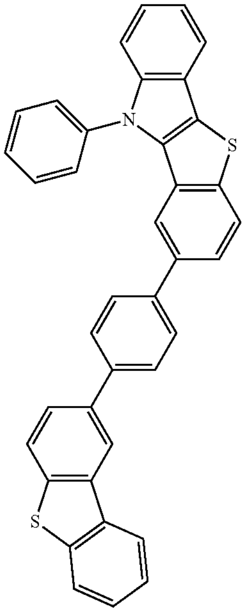
540
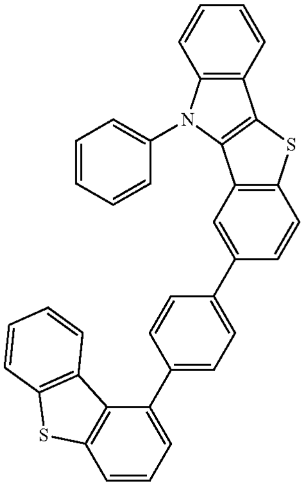
541
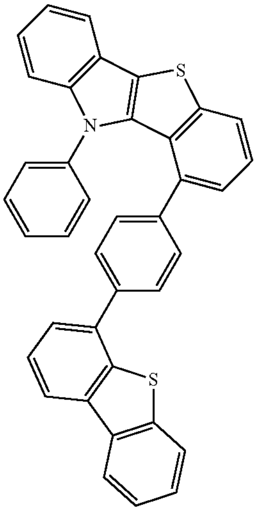

-continued
542
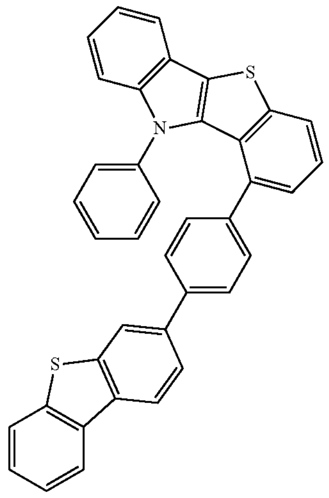
543
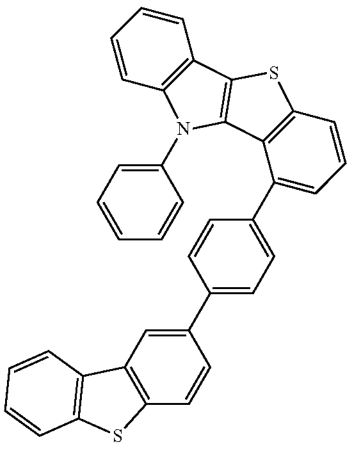
544
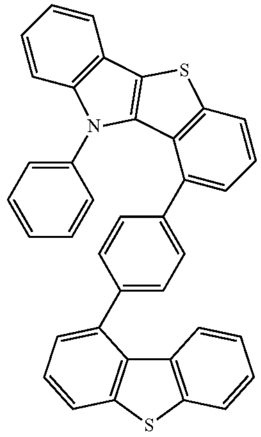
-continued
545
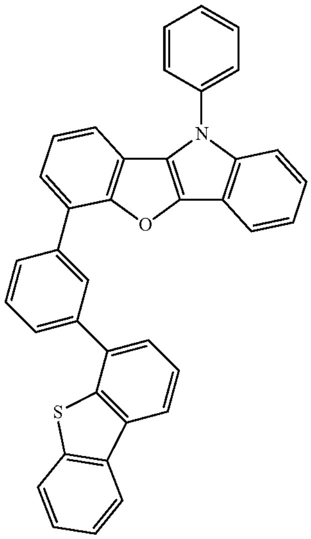
546
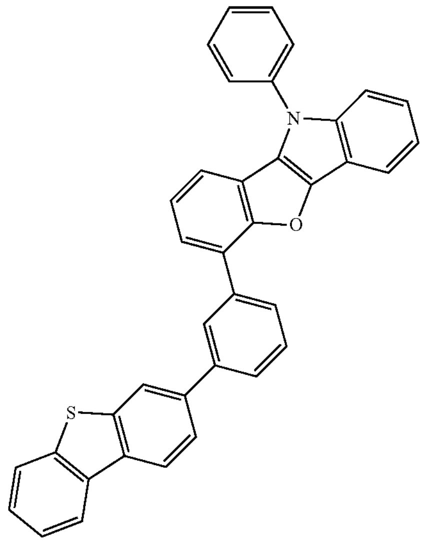
547
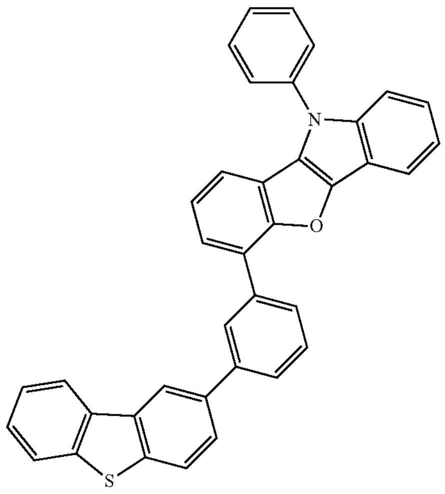

-continued
548
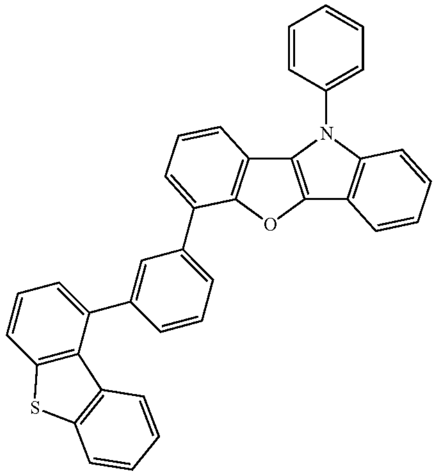
549
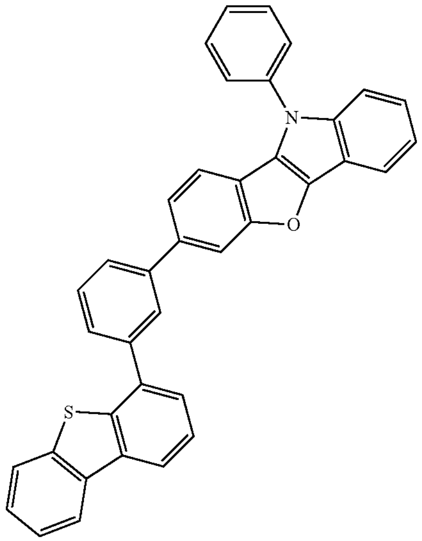
550
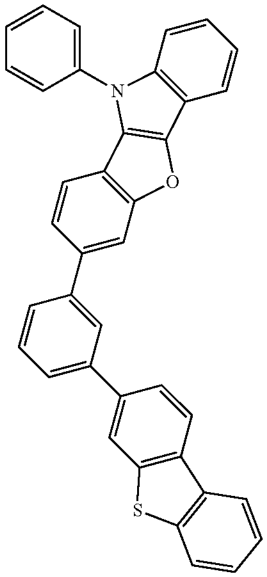
-continued
551
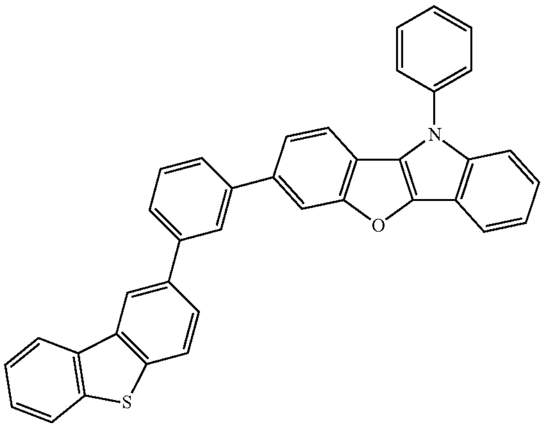
552
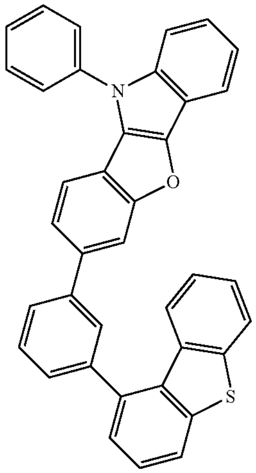
553
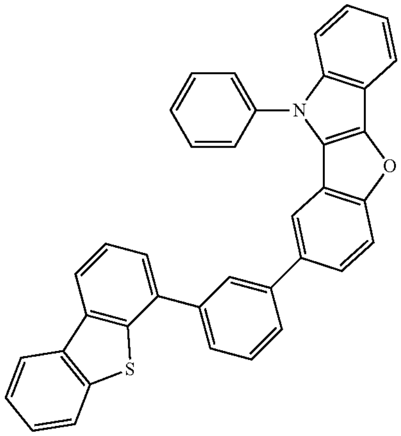

-continued
554
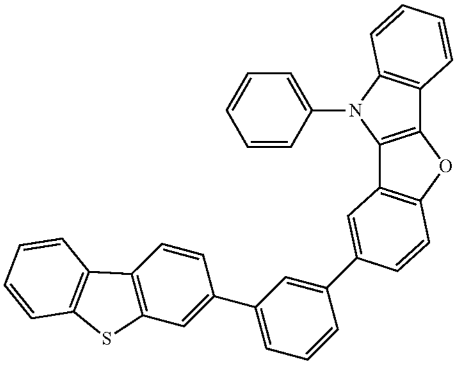
555
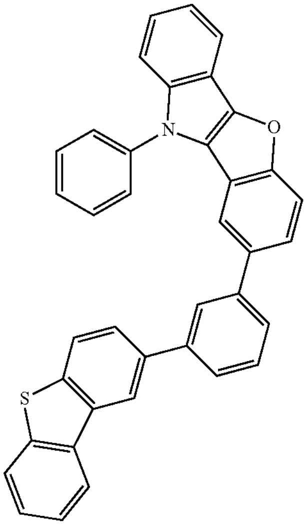
556
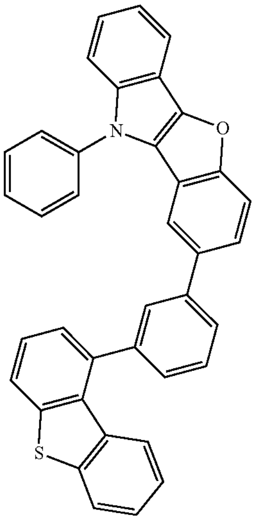
-continued
557
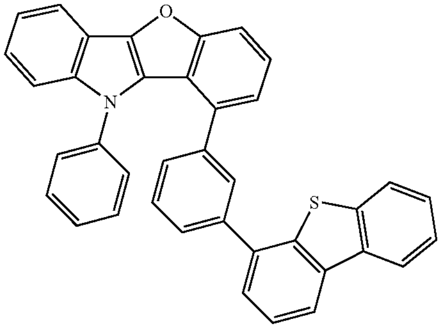
558
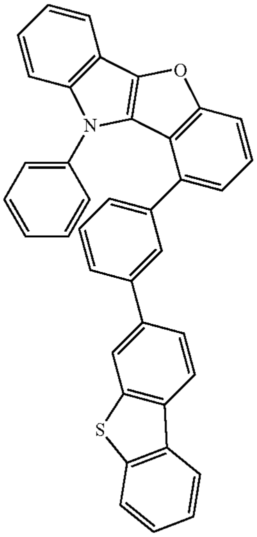
559
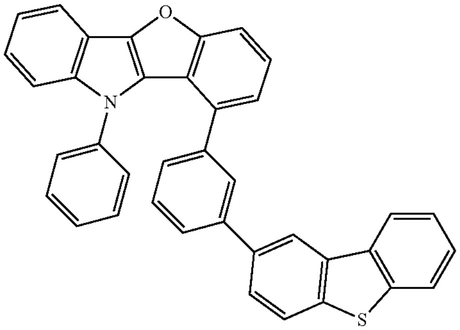
560
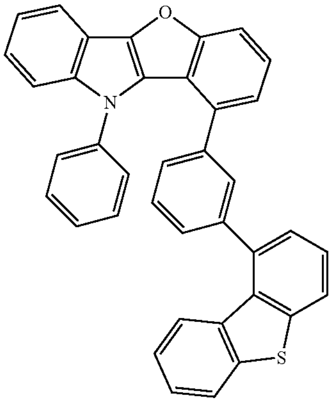

-continued
561
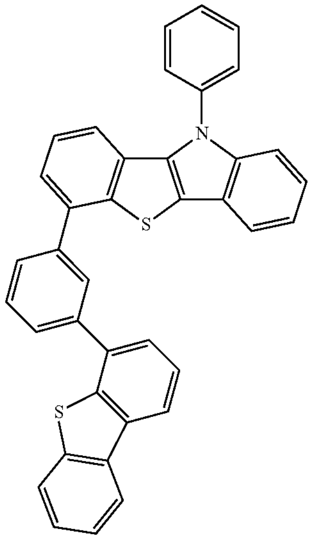
562
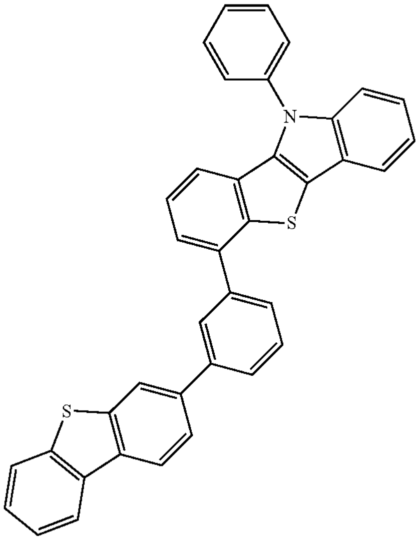
563
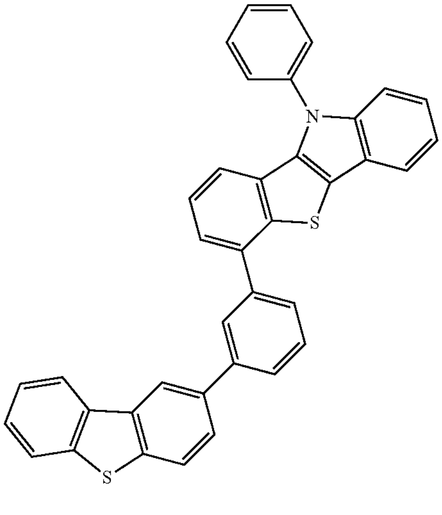
-continued
564
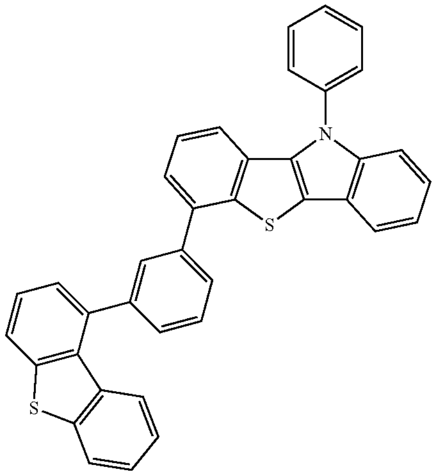
565
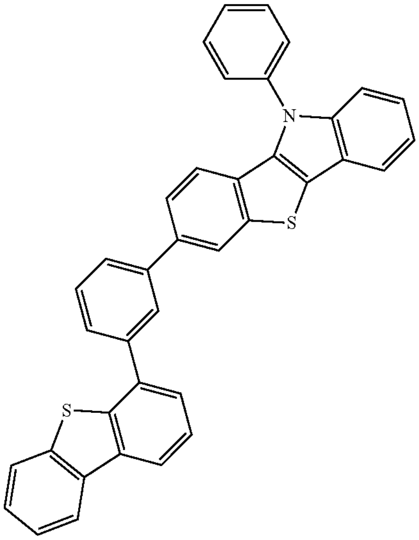
566
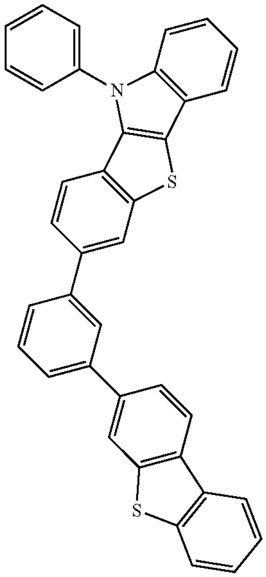

-continued
567
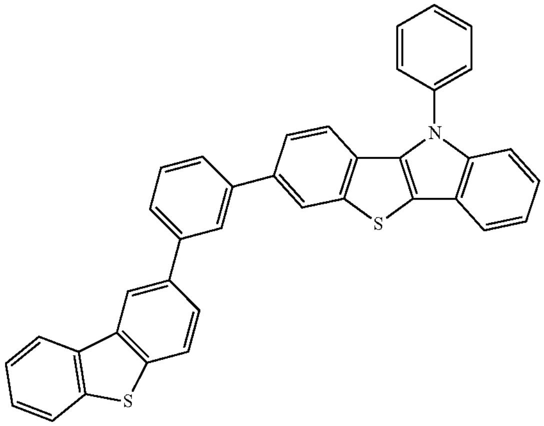
568
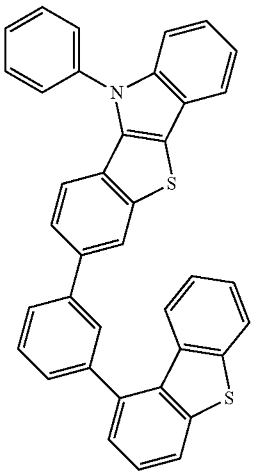
569
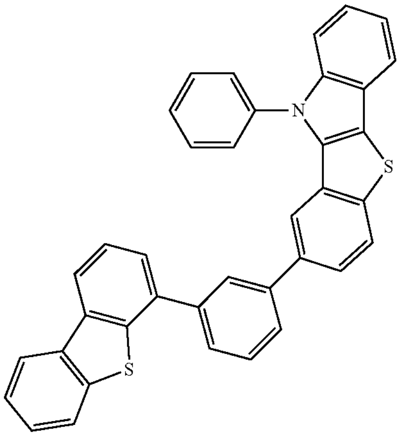
-continued
570
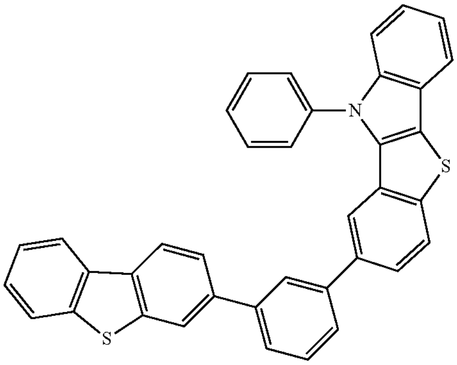
571
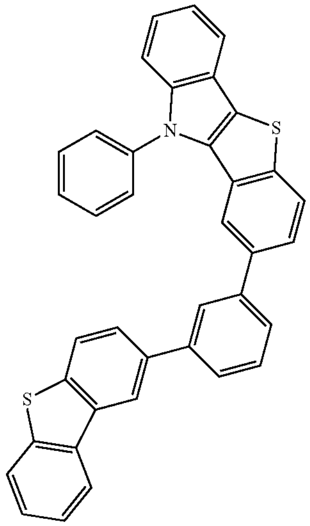
572
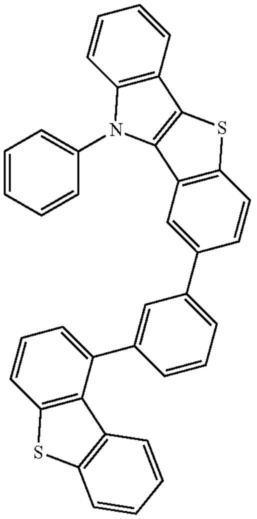

-continued
573
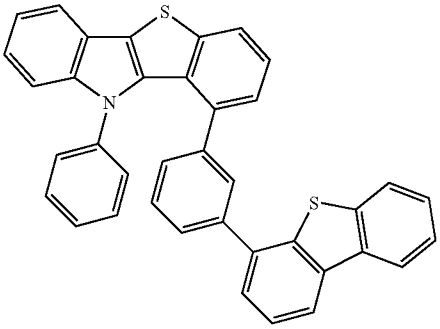
574
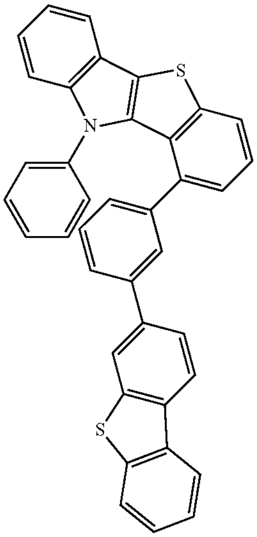
575
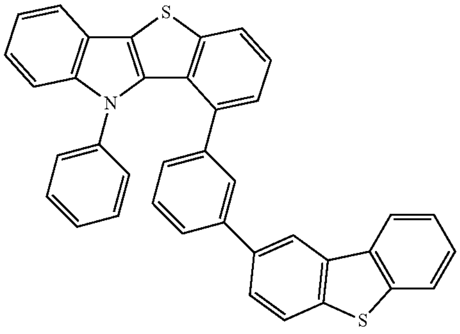
576
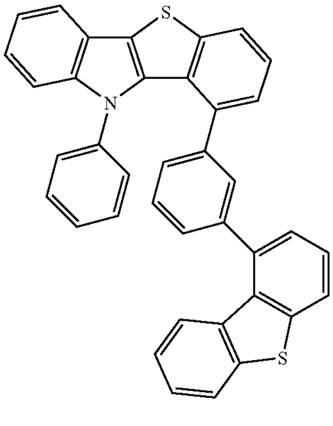
577
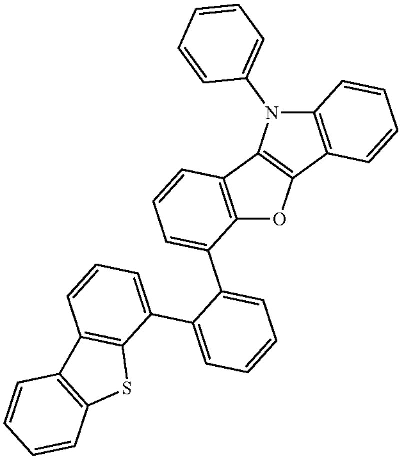
578
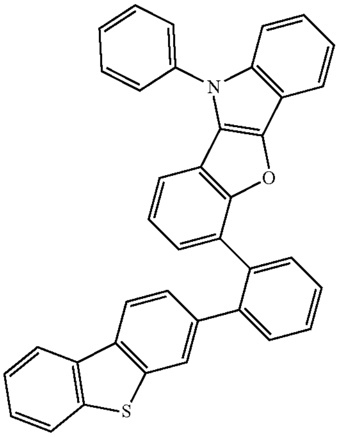
579
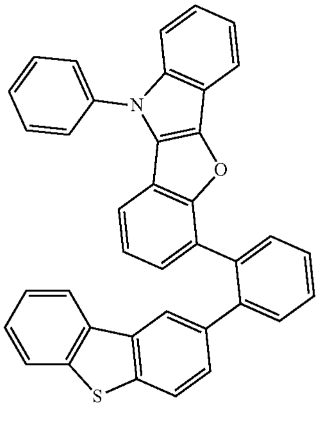

-continued
580
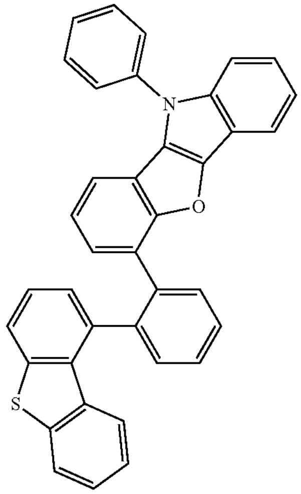
581
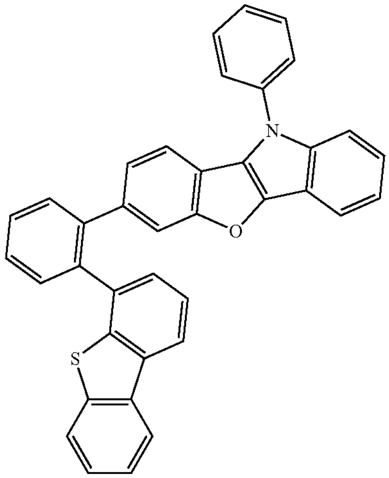
582
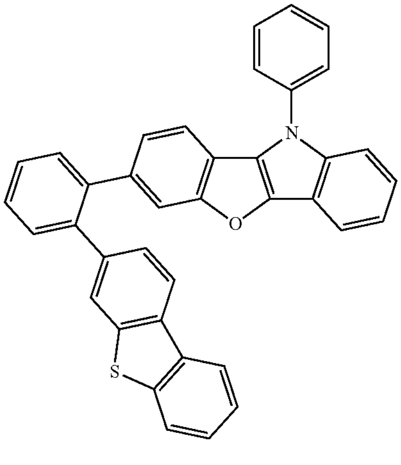
-continued
583
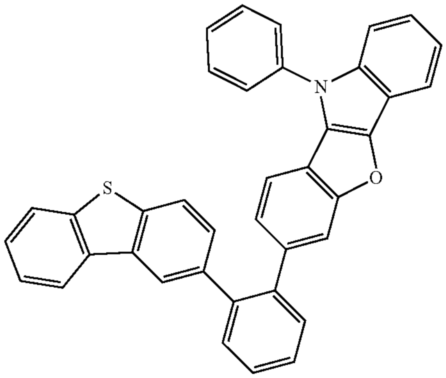
584
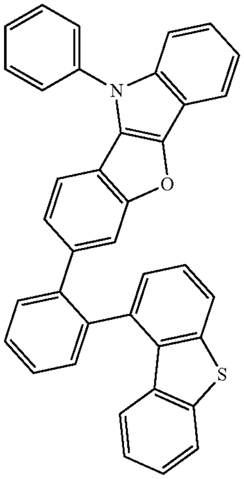
585
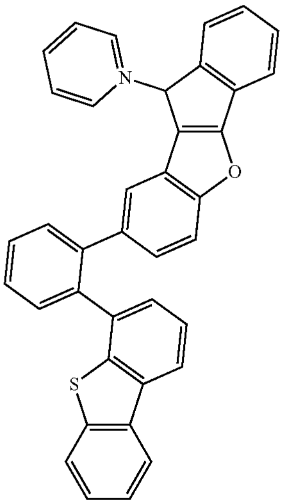

-continued
586
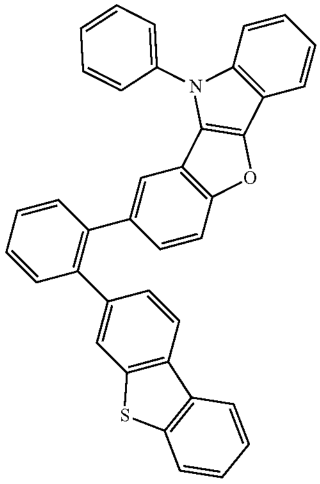
587
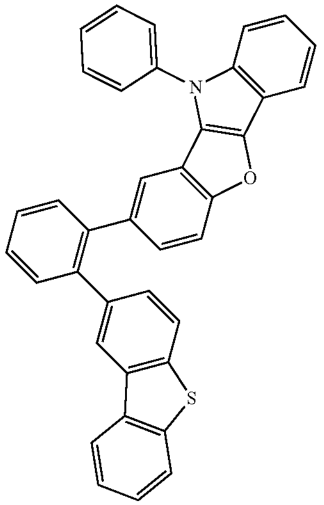
588
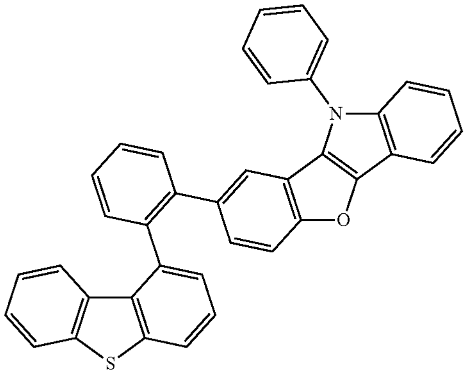
-continued
589
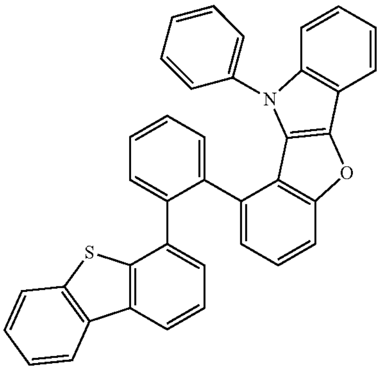
590
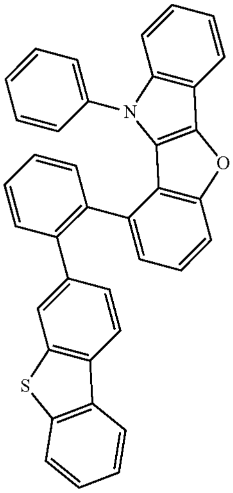
591
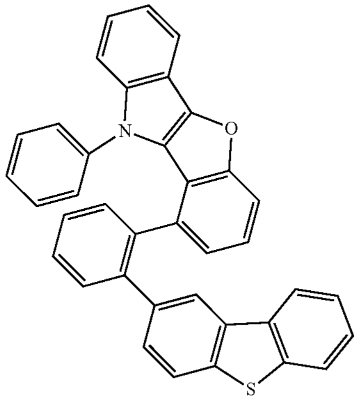

-continued
592
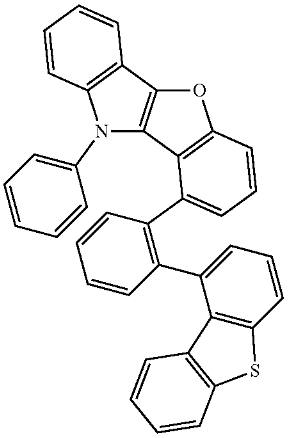
593
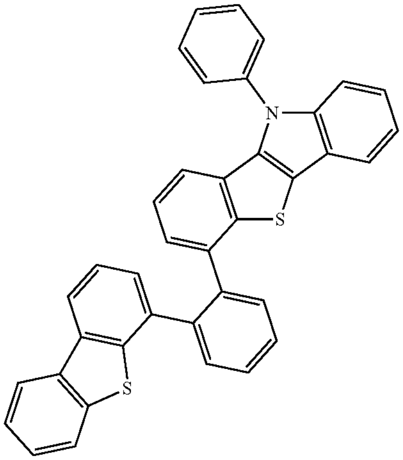
594
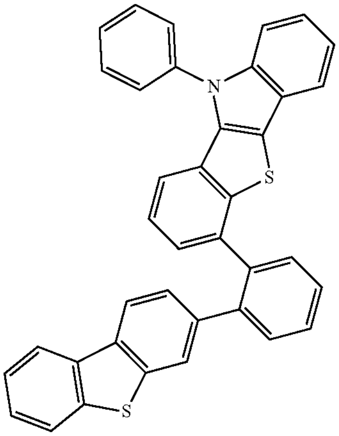
-continued
595
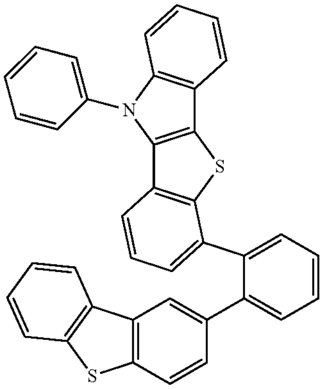
596
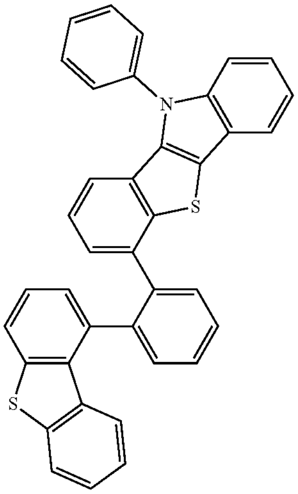
597
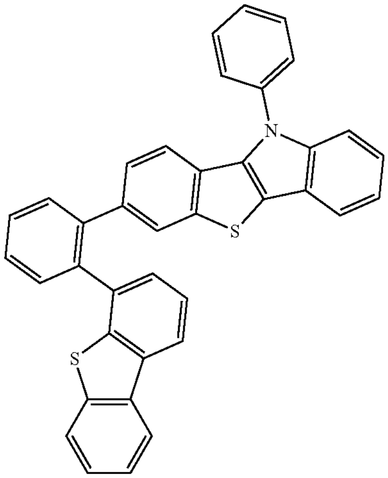

-continued
598
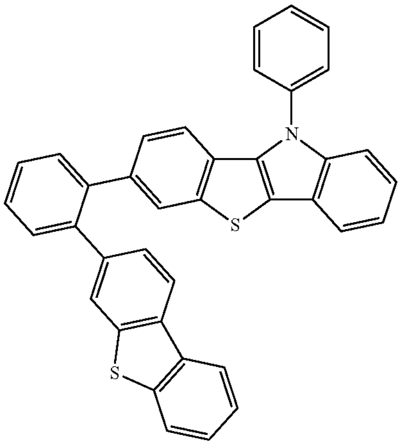
599
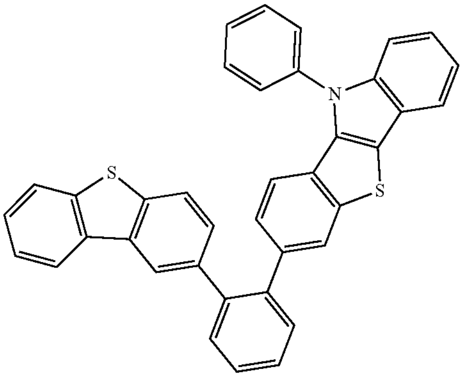
600
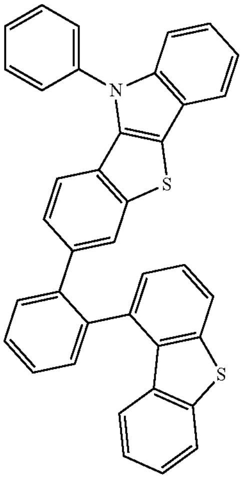
-continued
601
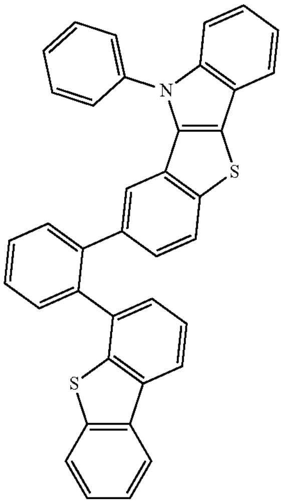
602
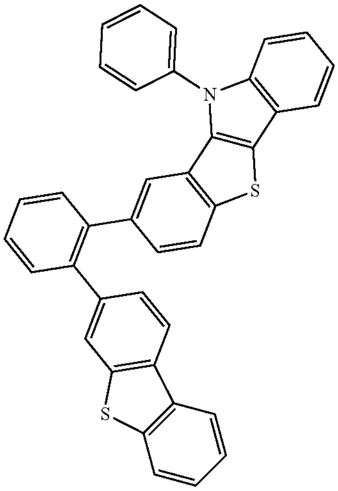
603
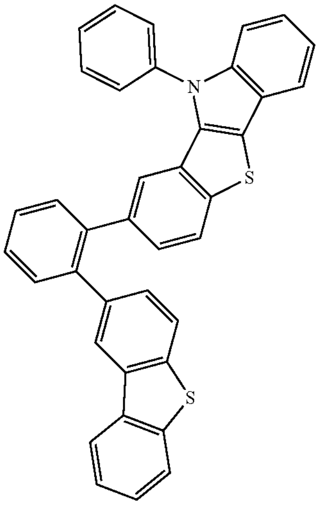

-continued
604
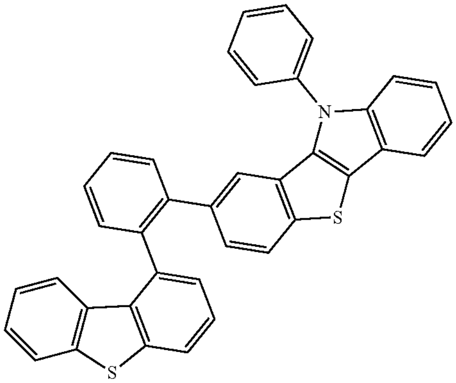
605
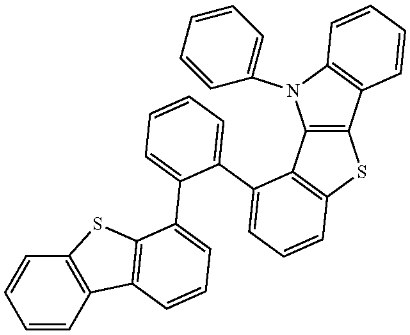
606
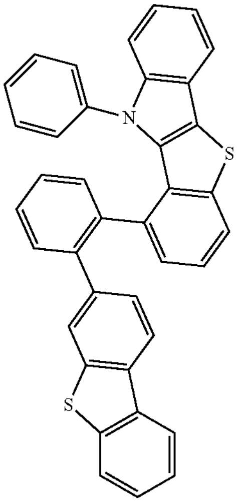
607
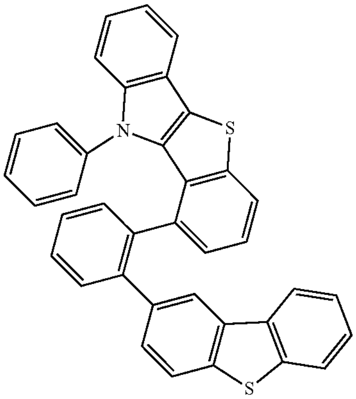
-continued
608
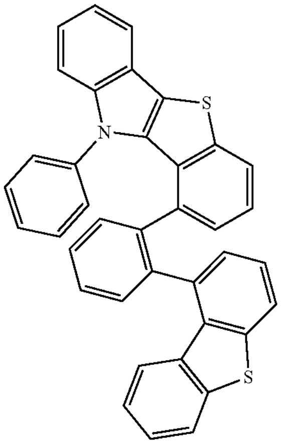
609
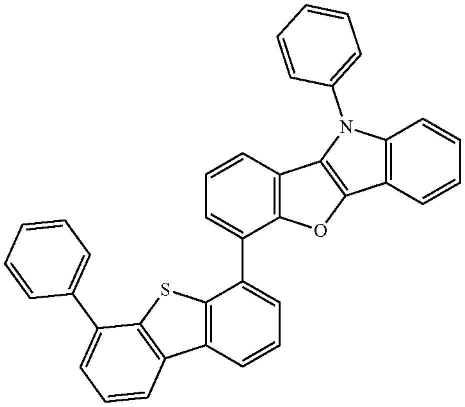
610
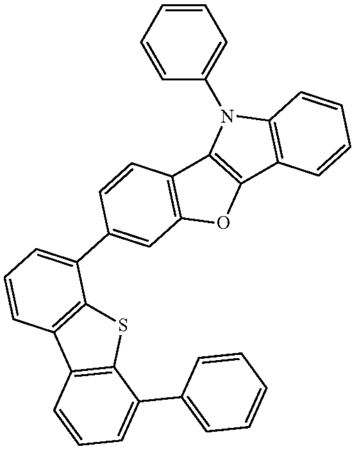

-continued
611
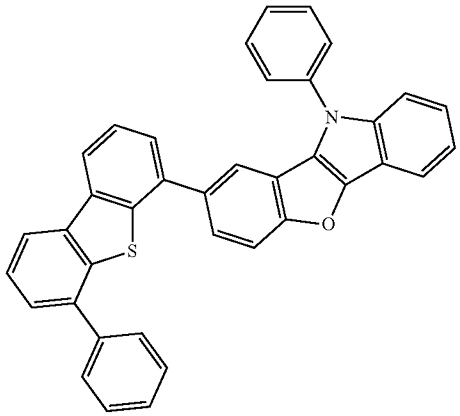
612
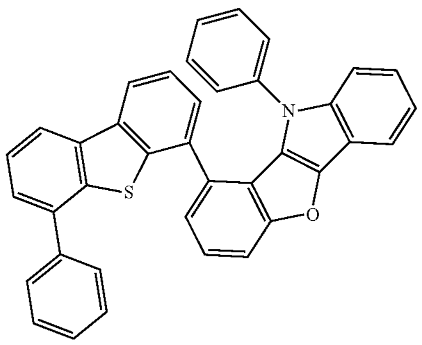
613
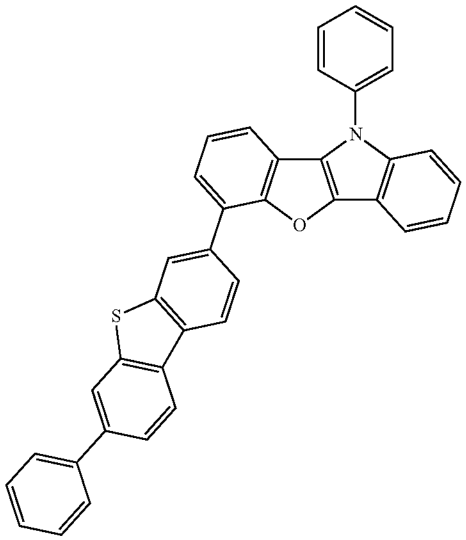
-continued
614
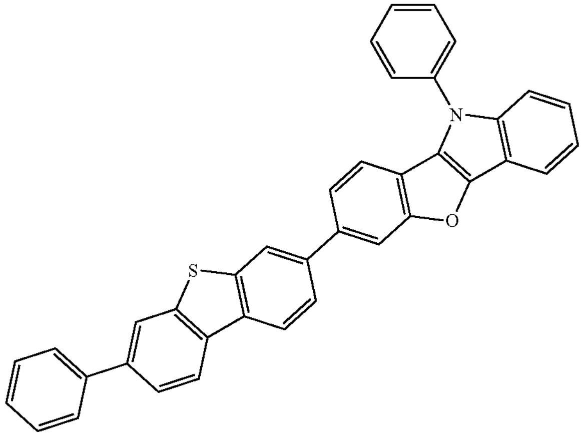
615
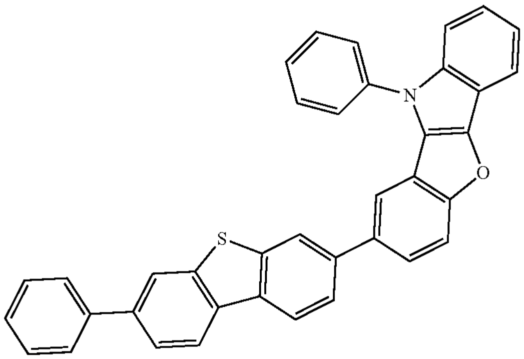
616
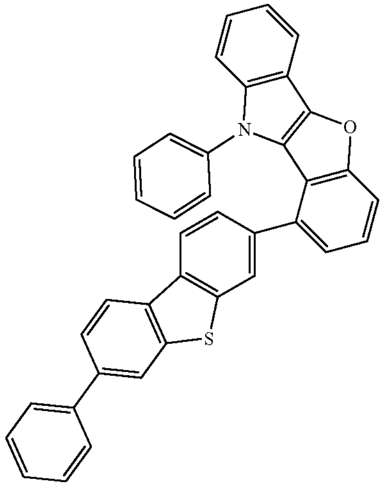

-continued
617
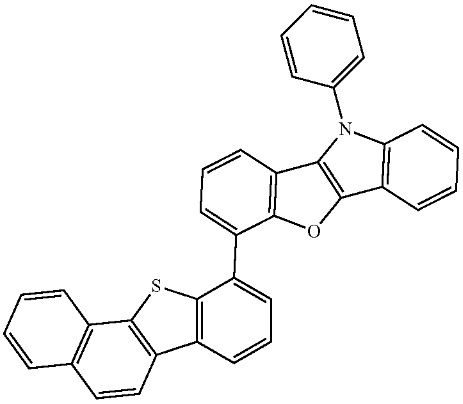
618
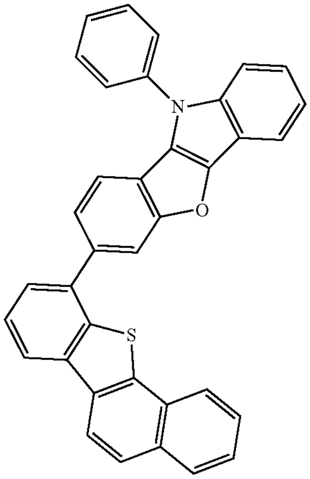
619
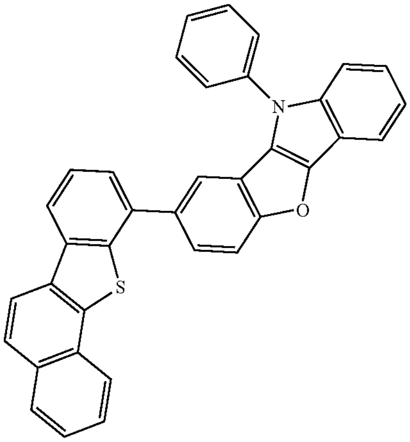
-continued
620
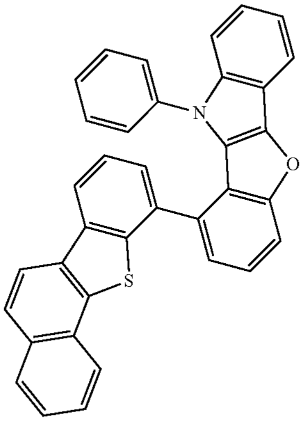
621
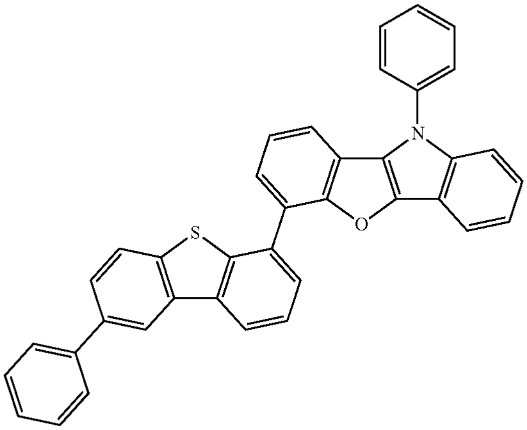
622
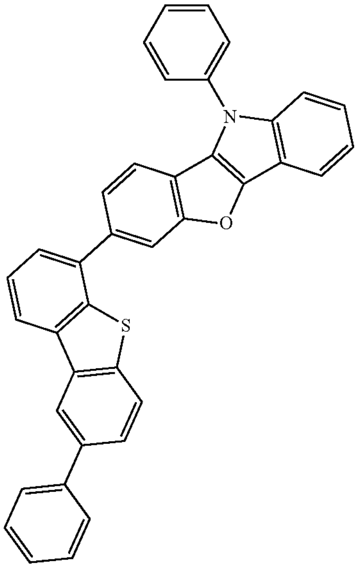

623
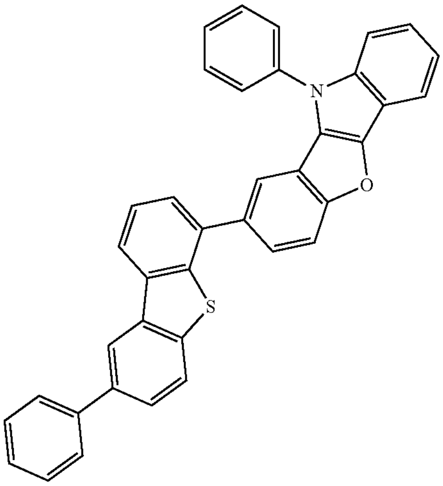
624
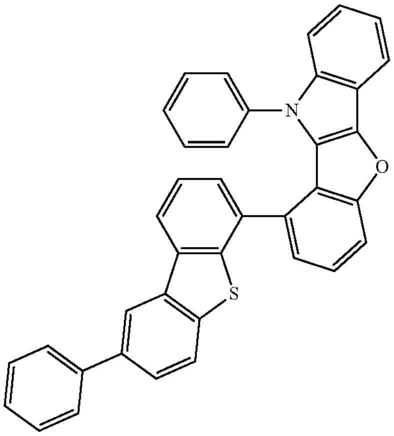
625
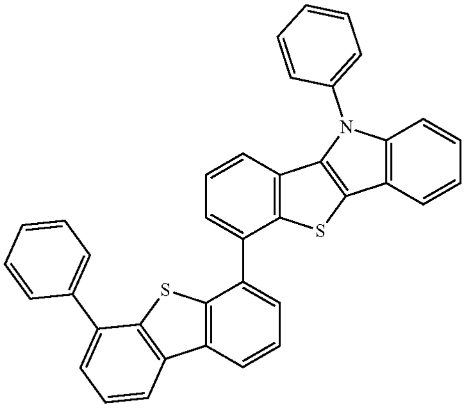
626
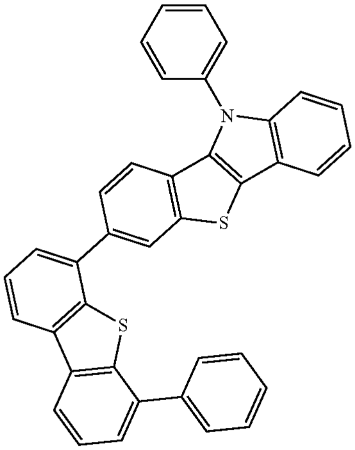
627
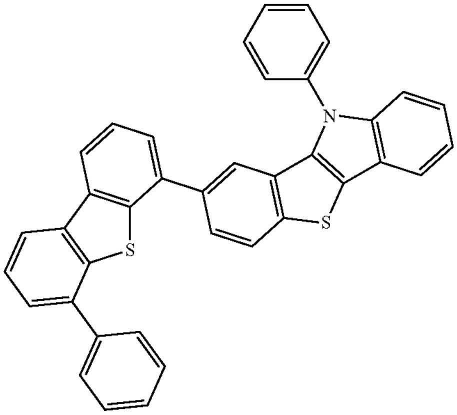
628
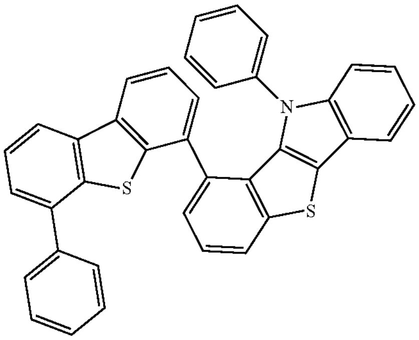

-continued
629
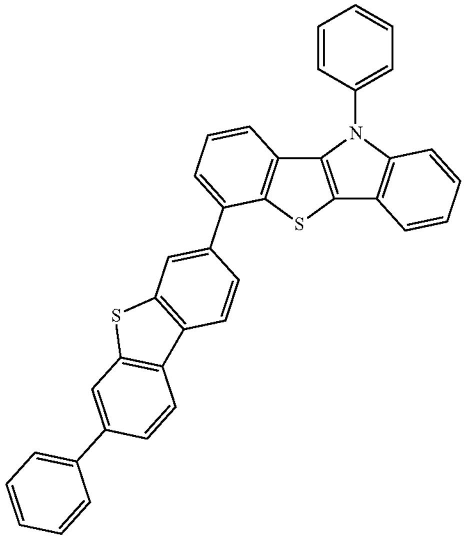
630
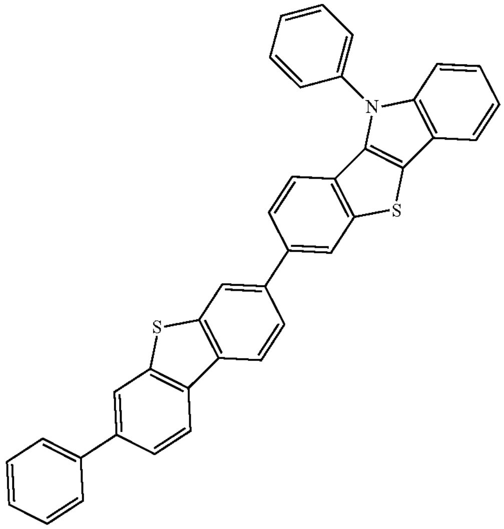
631
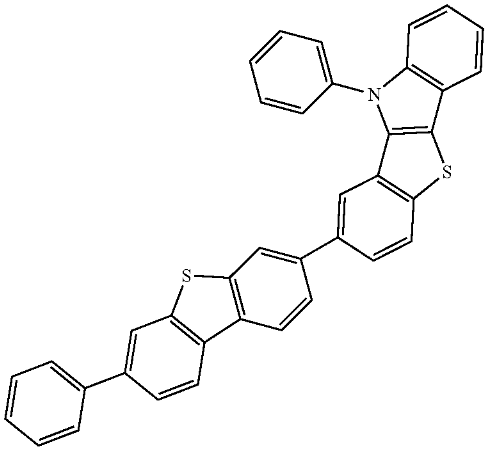
-continued
632
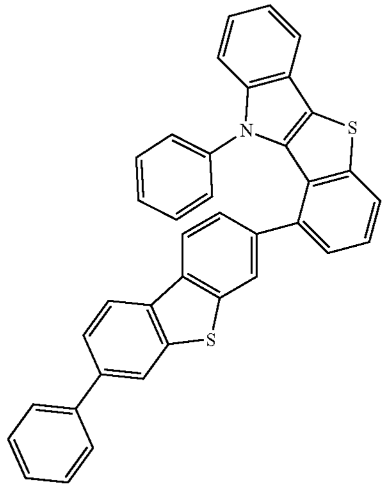
633
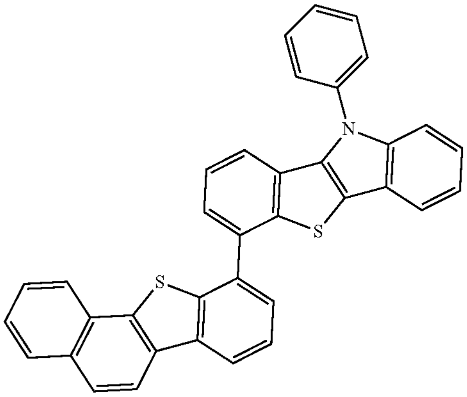
634
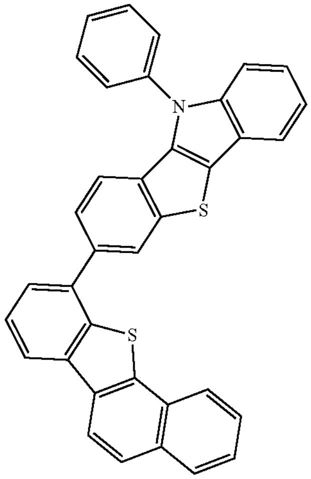

635
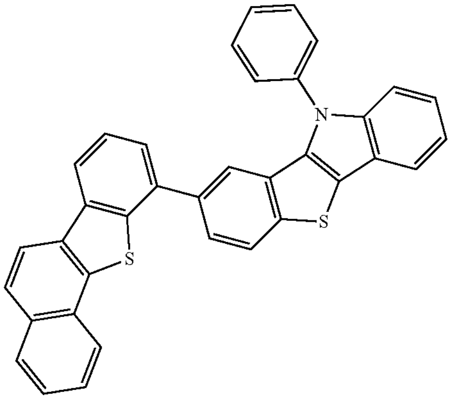
636
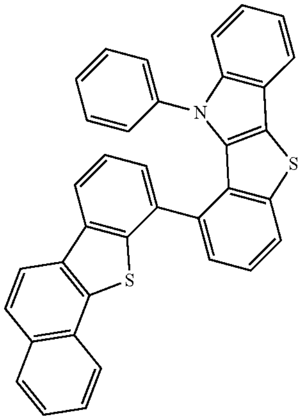
637
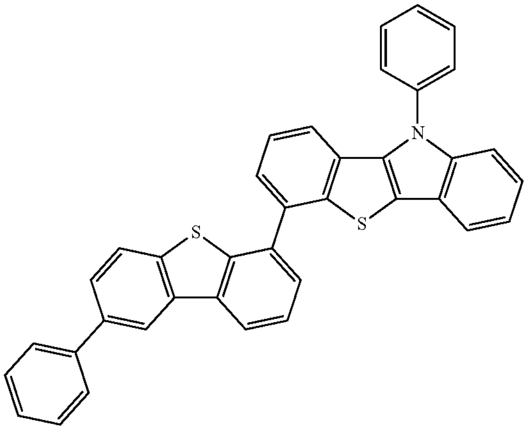
638
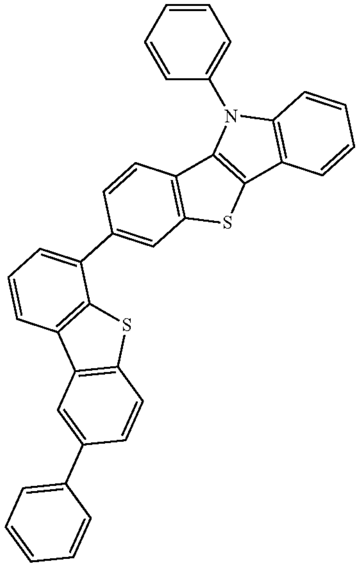
639
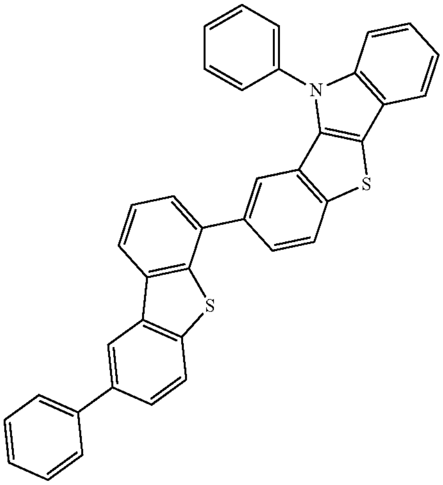
640
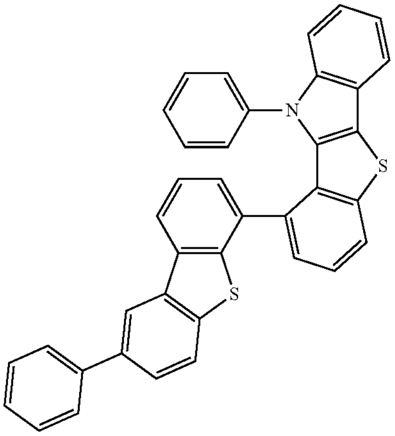

-continued
641
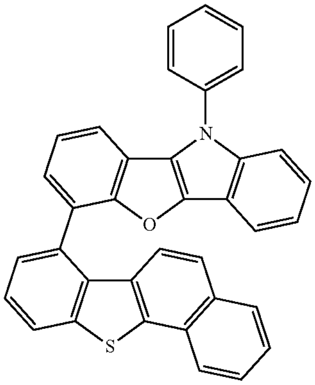
642
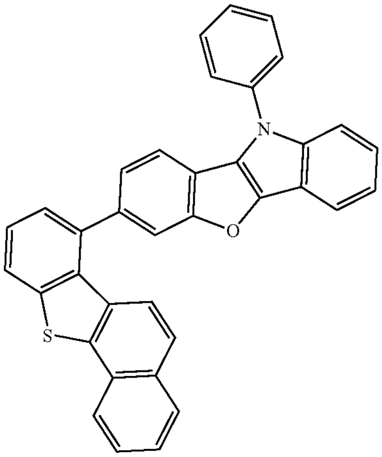
643
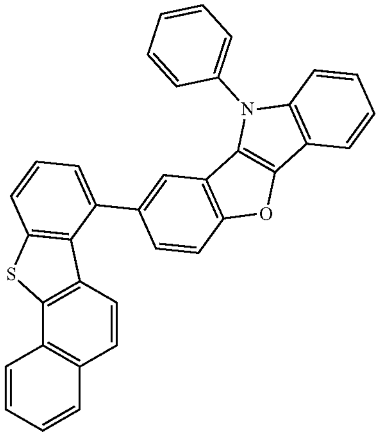
644
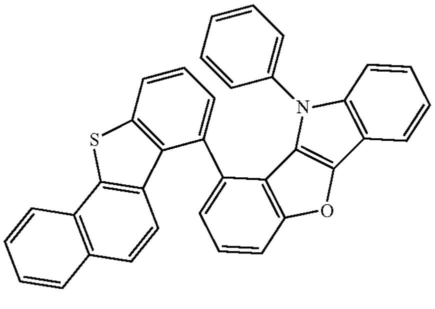
-continued
645
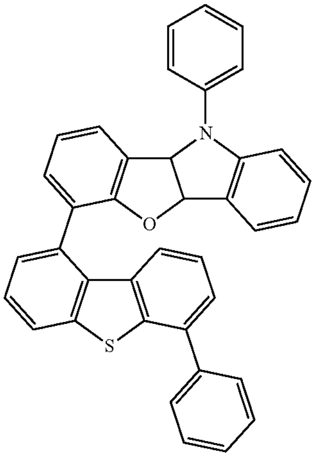
646
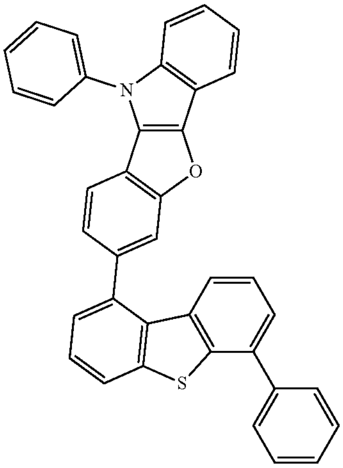
647
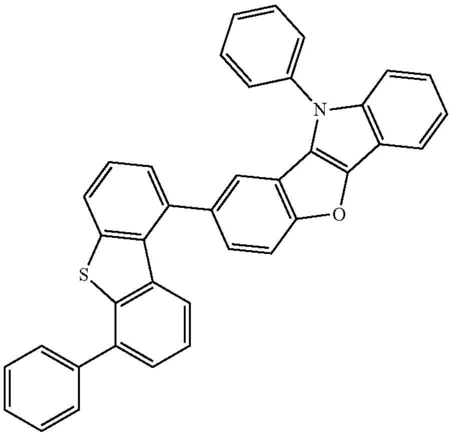

-continued
648
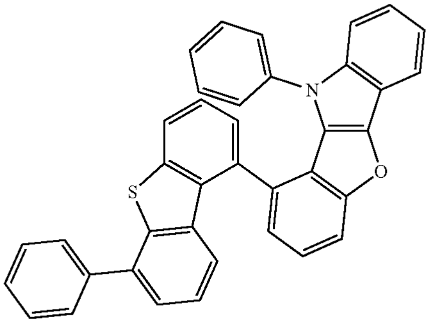
649
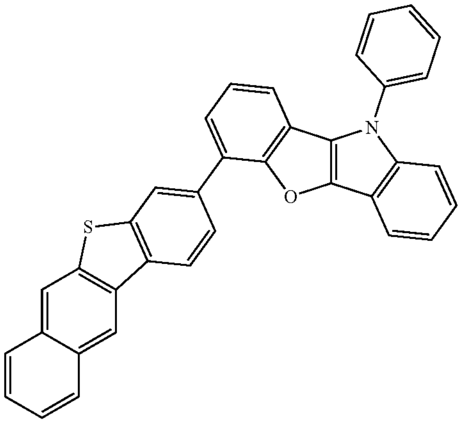
650
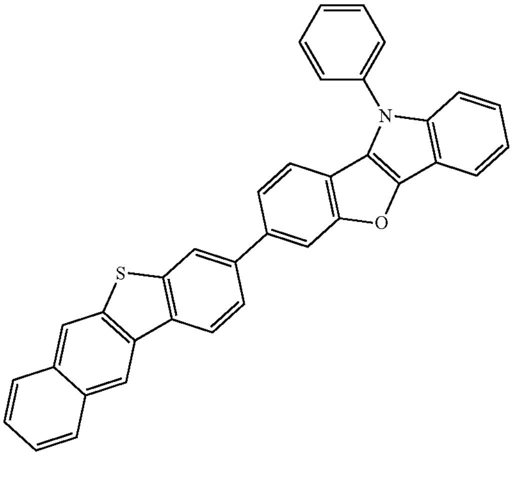
-continued
651
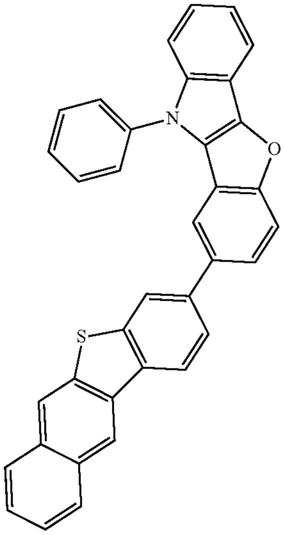
652
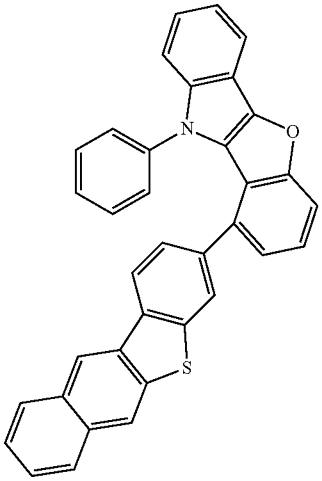
653
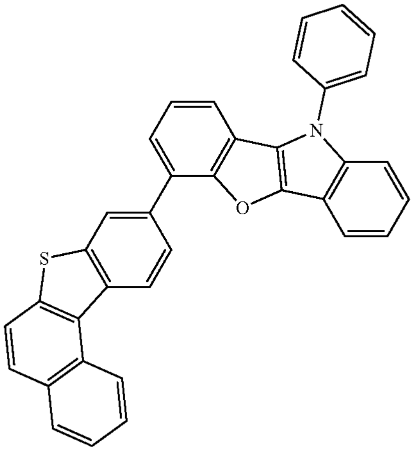

-continued
654
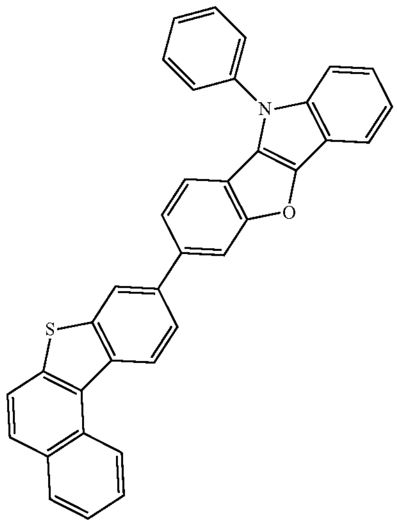
655
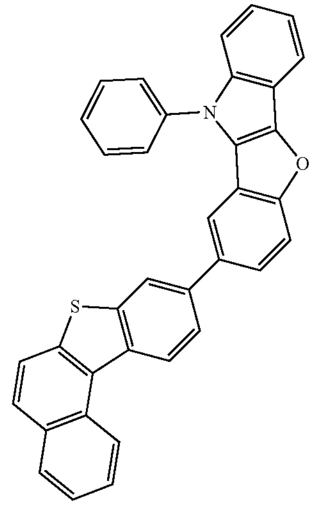
656
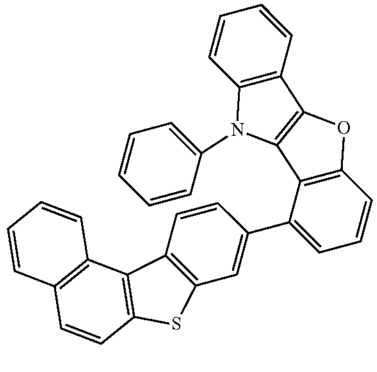
-continued
657
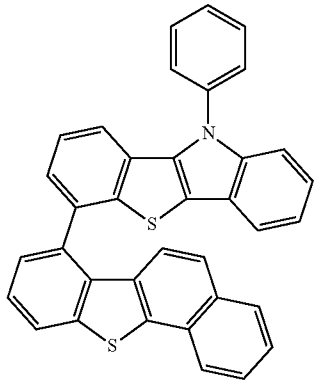
658
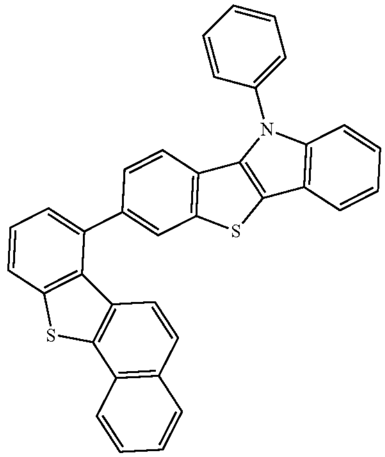
659
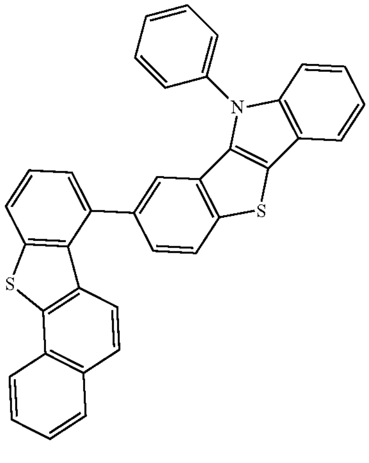
660
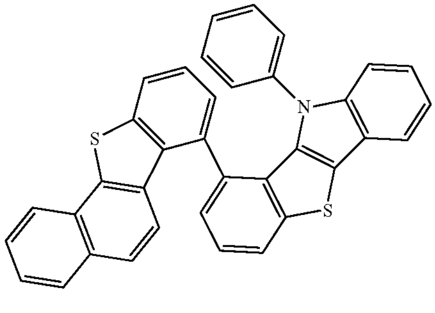

-continued
661
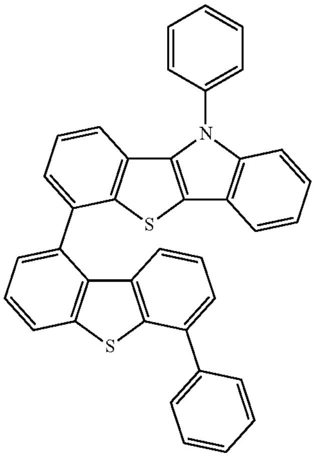
662
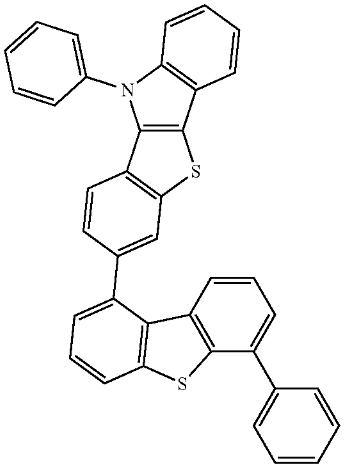
663
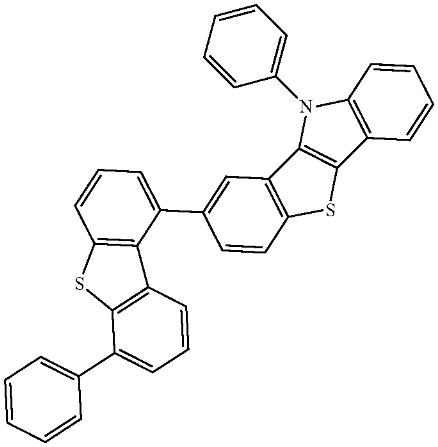
-continued
664
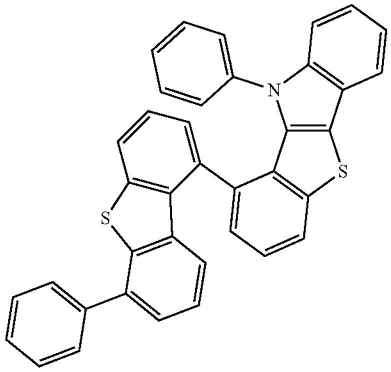
665
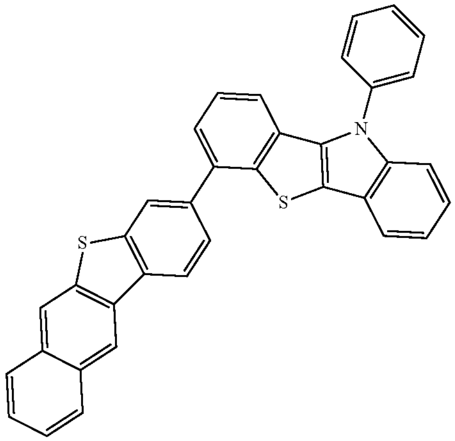
666
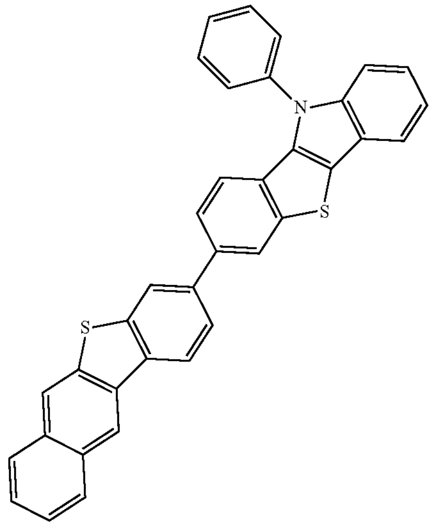

-continued
667
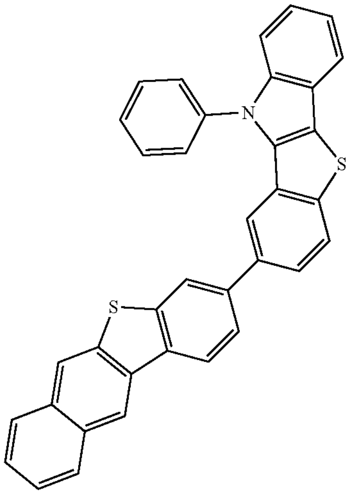
668
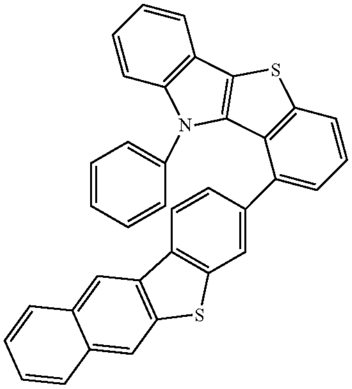
669
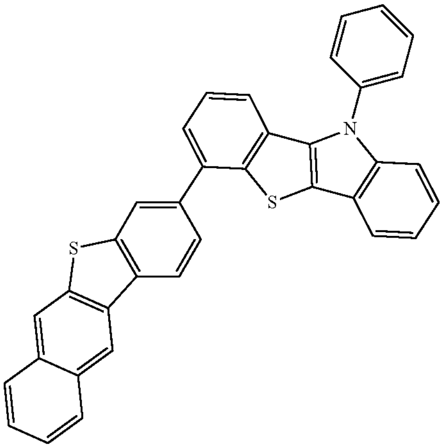
-continued
670
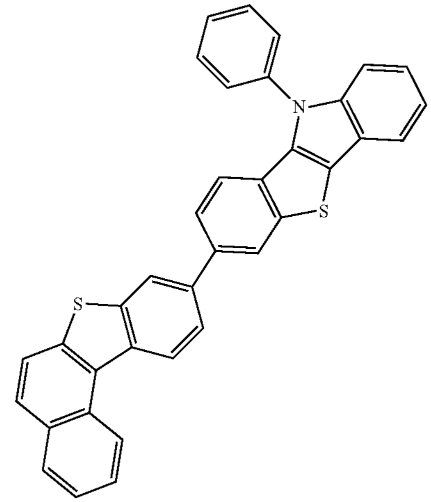
671
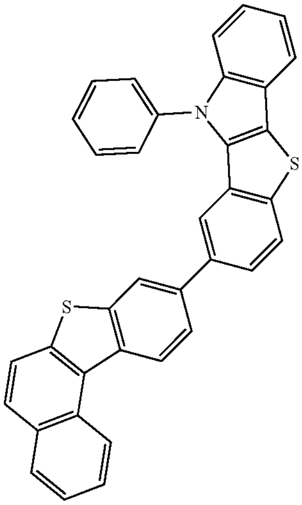
672
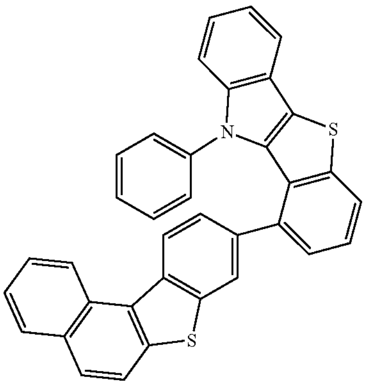

-continued
673
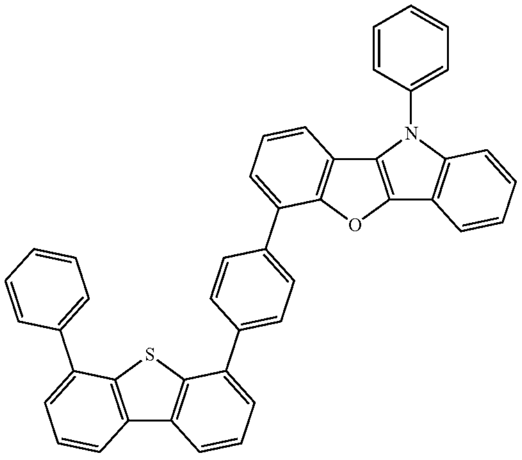
674
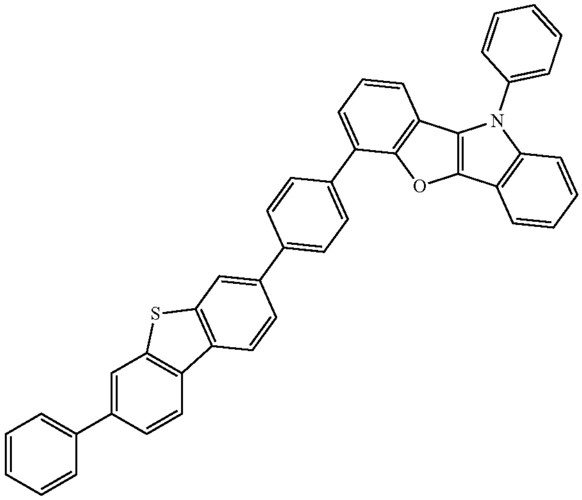
675
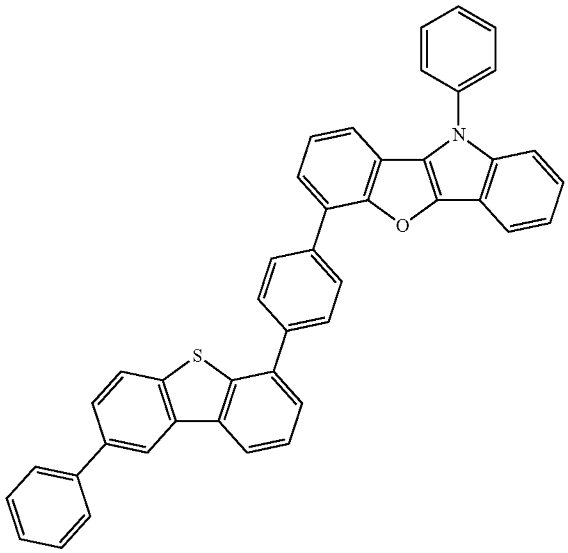
-continued
676
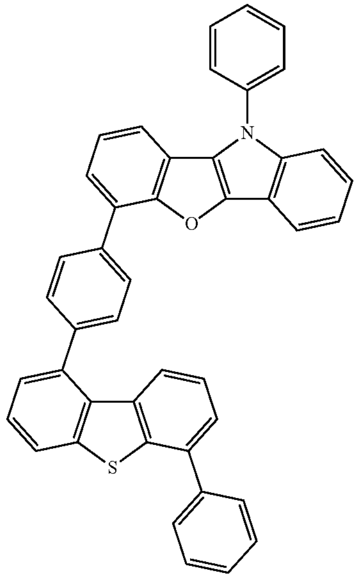
677
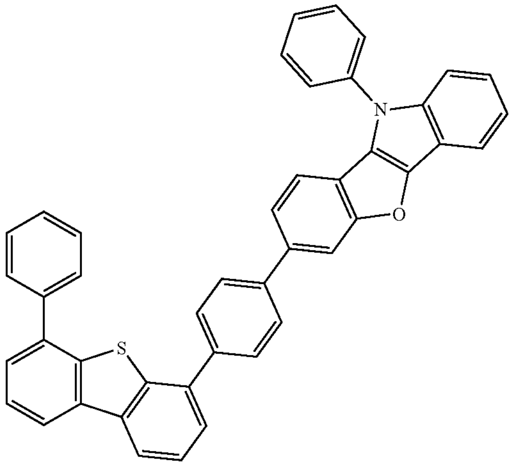
678
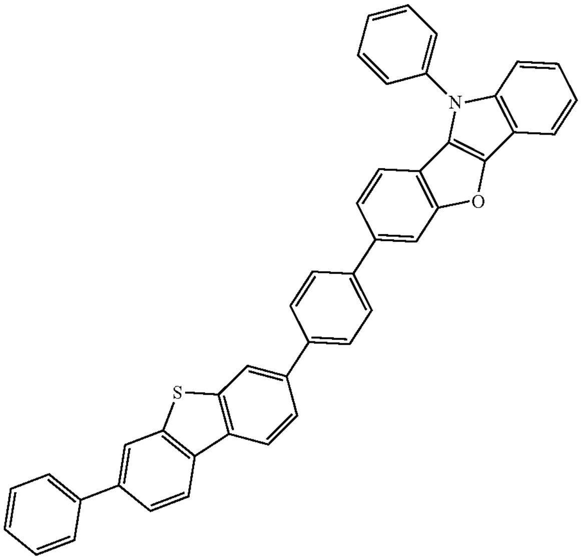

-continued
679
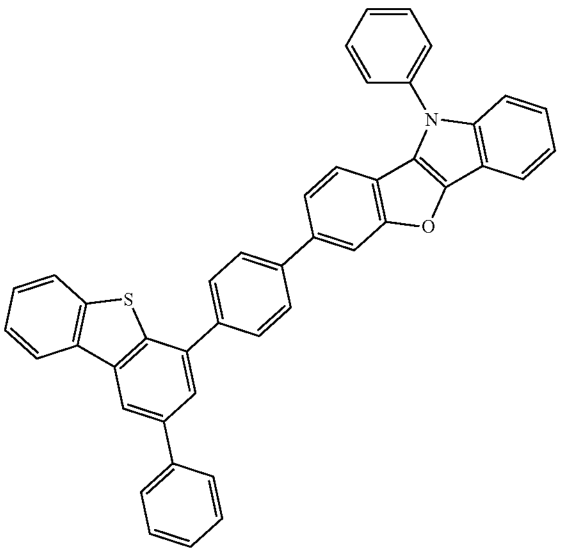
680
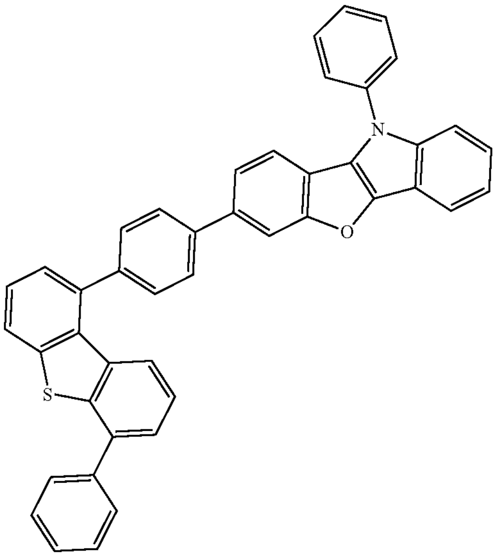
681
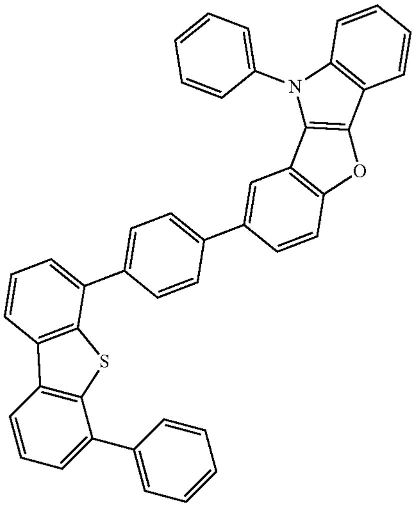
-continued
682
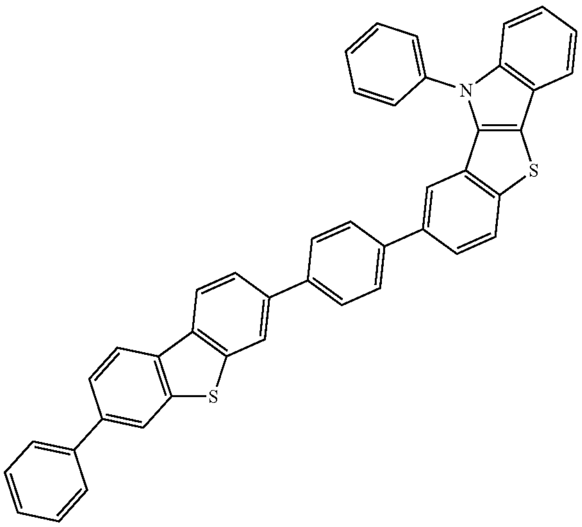
683
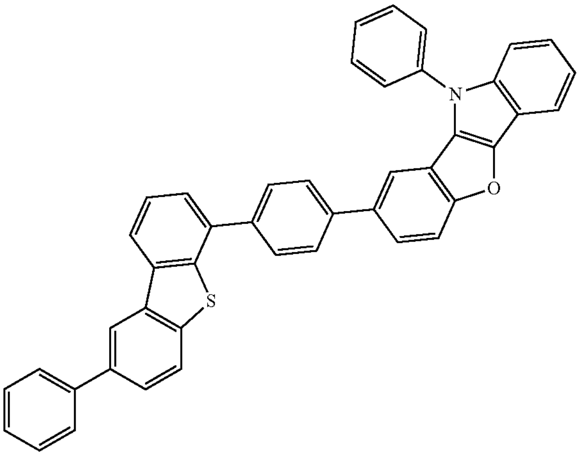
684
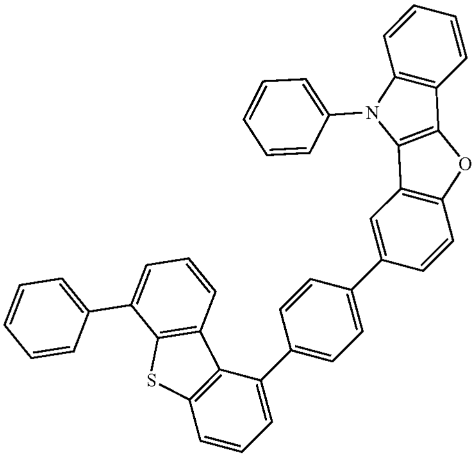

-continued
685
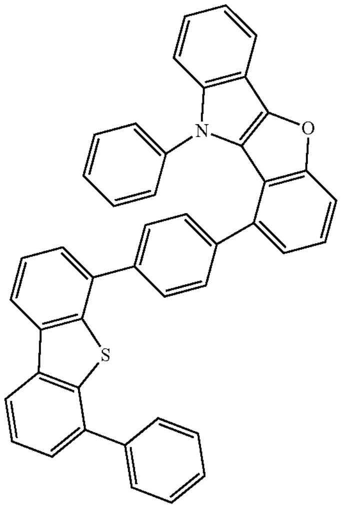
686
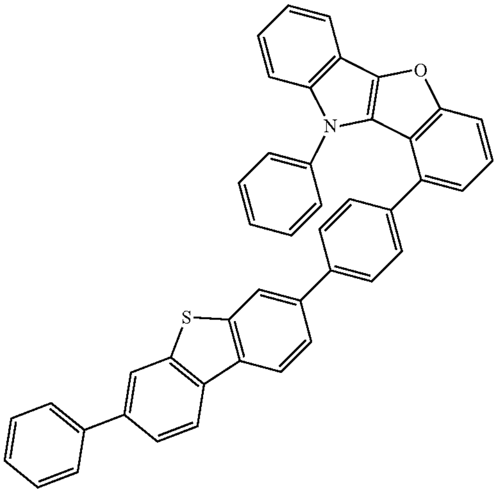
687
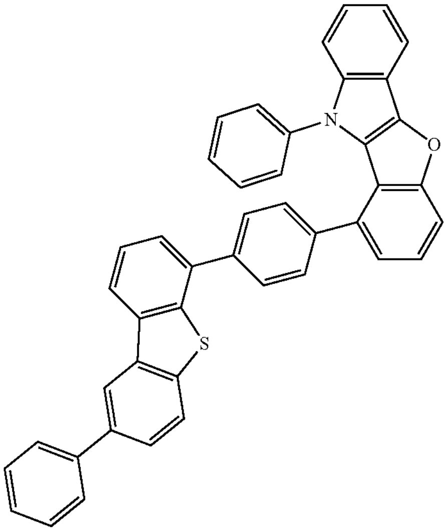
-continued
688
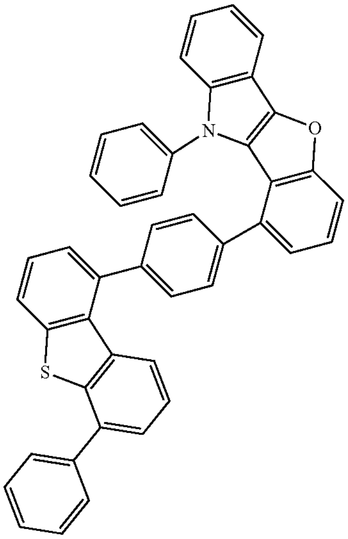
689
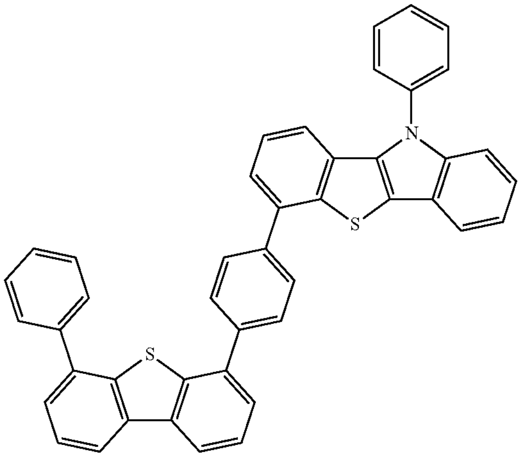
690
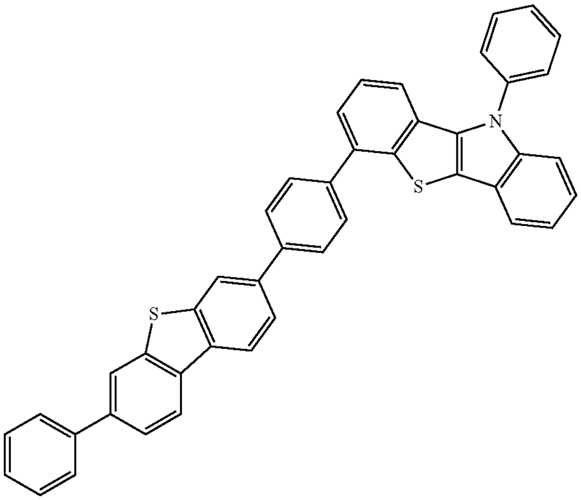

-continued
691
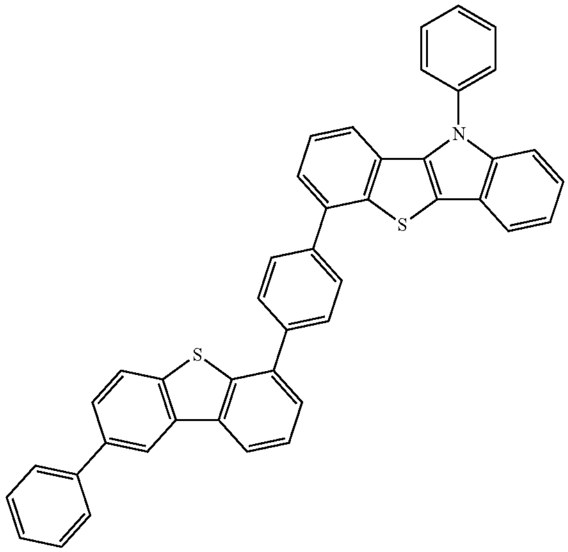
692
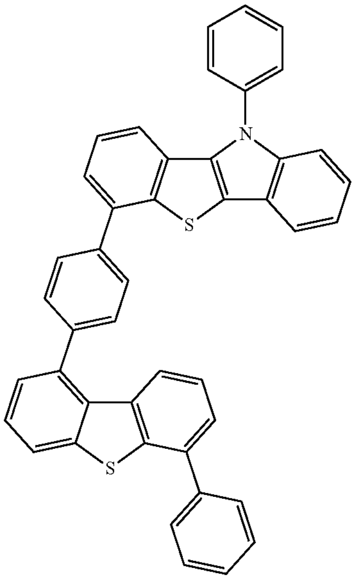
693
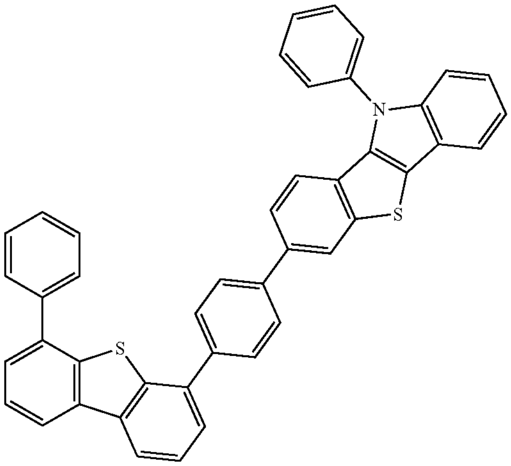
-continued
694
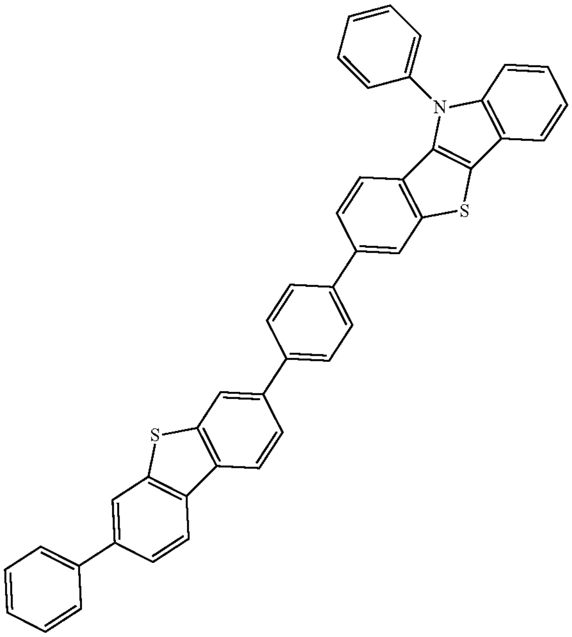
695
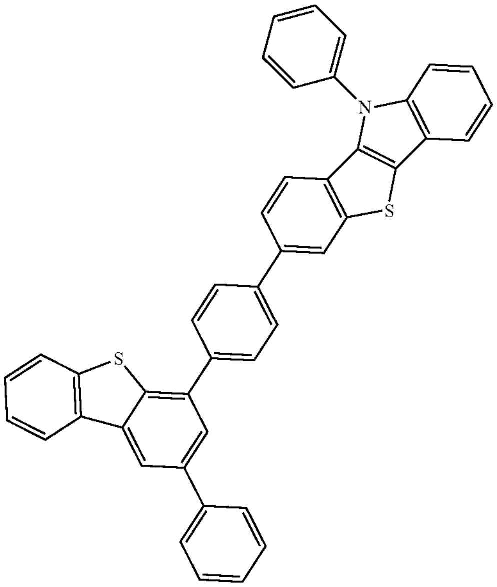

-continued
696
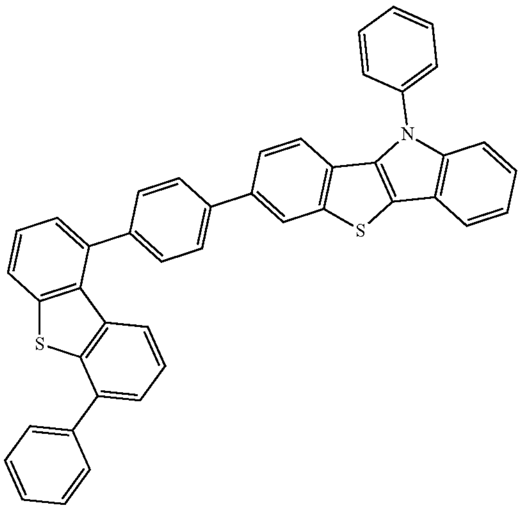
697
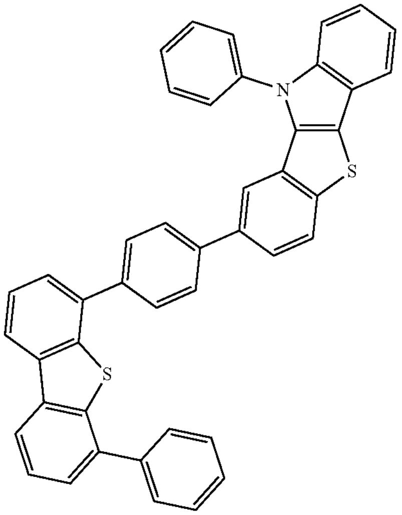
698
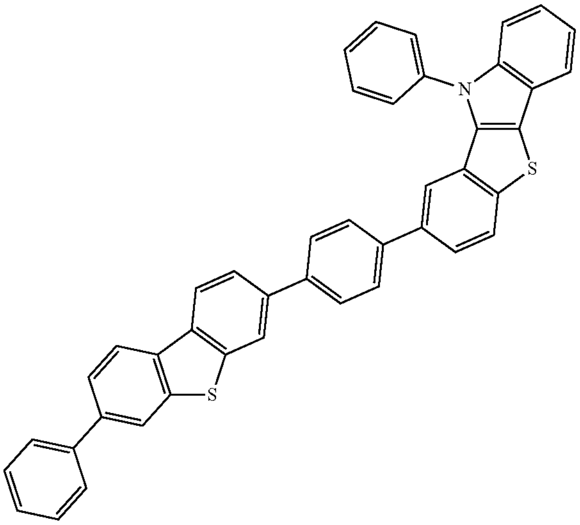
-continued
699
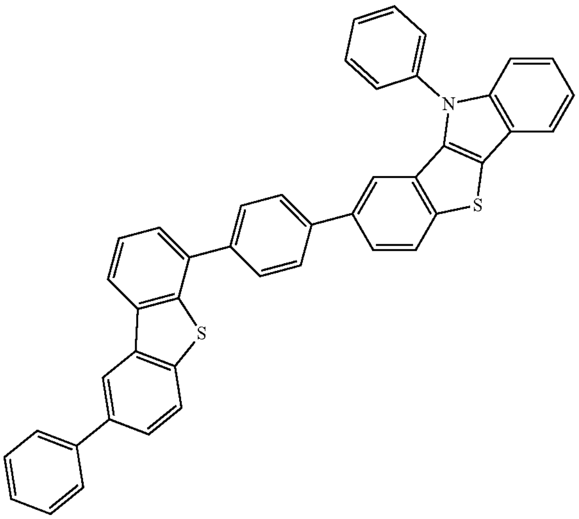
700
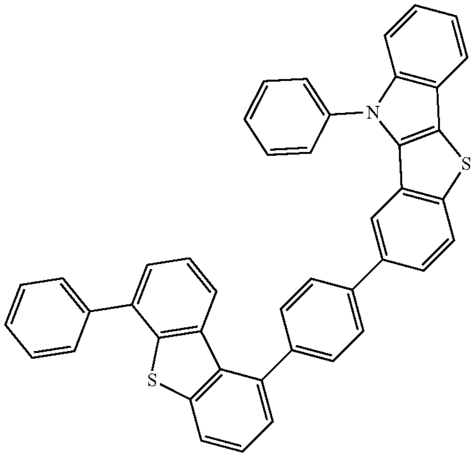
701
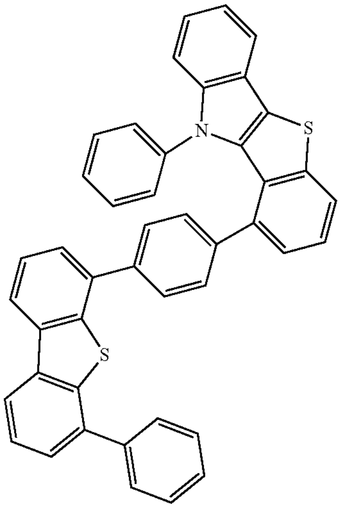

-continued
702
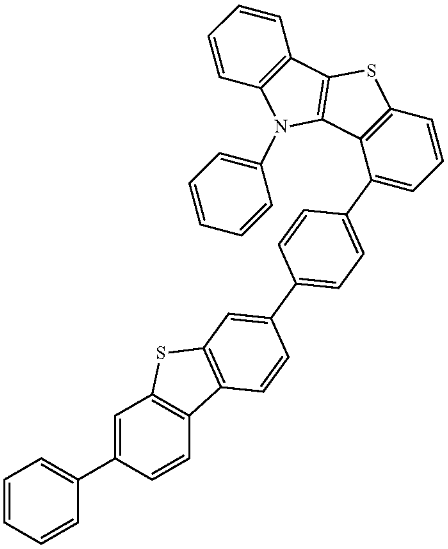
703
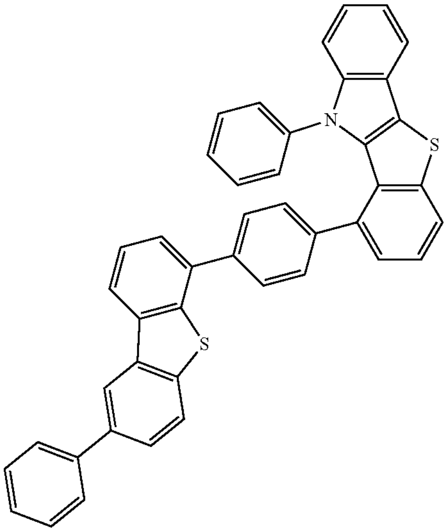
704
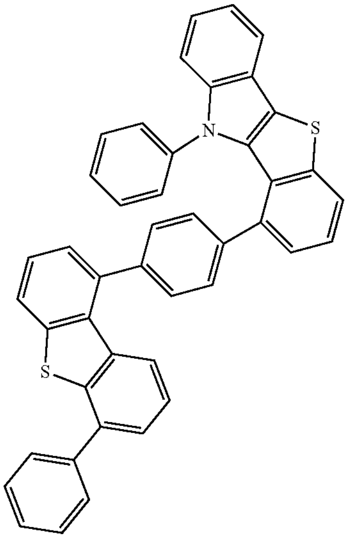
-continued
705
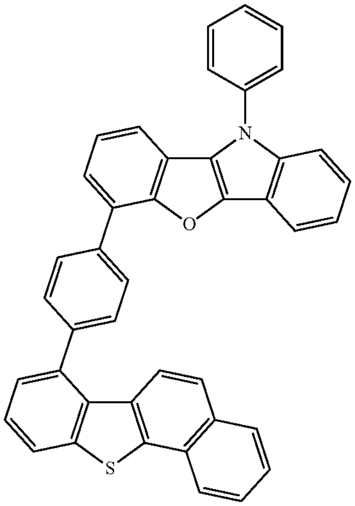
706
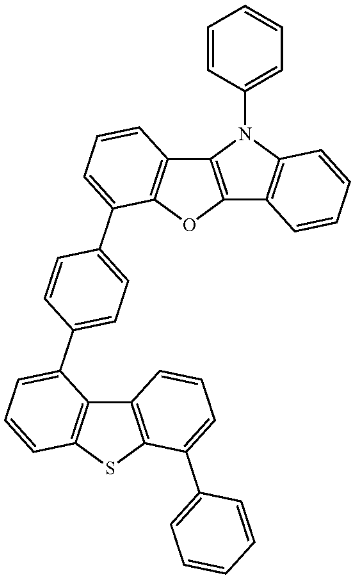

-continued
707
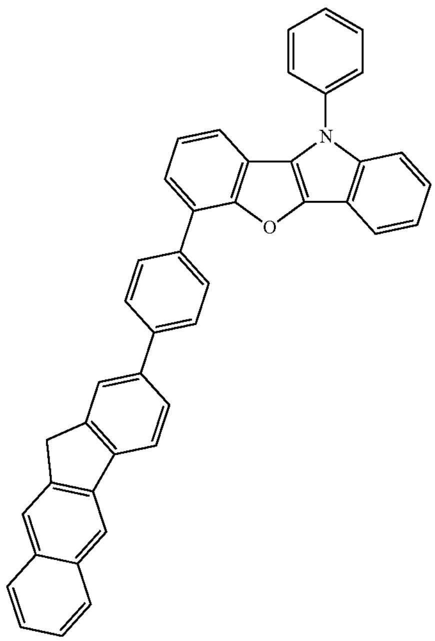
708
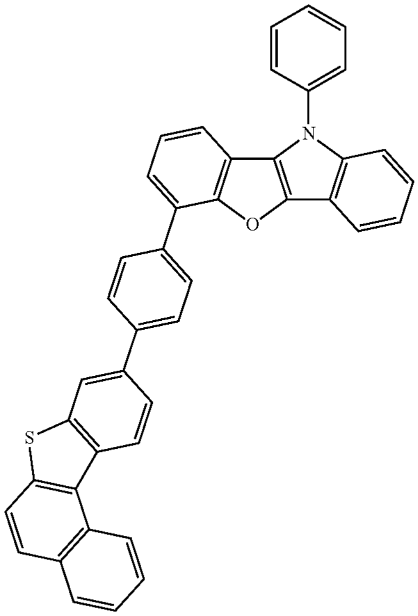
-continued
709
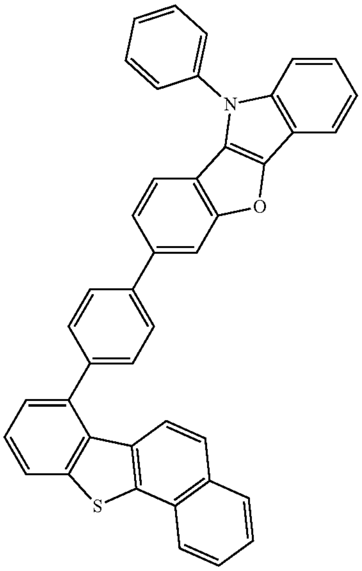
710
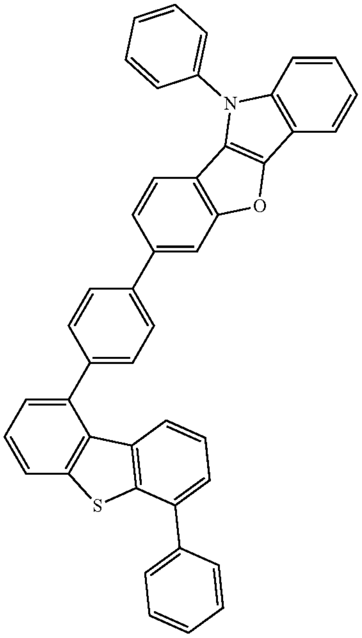

-continued
711
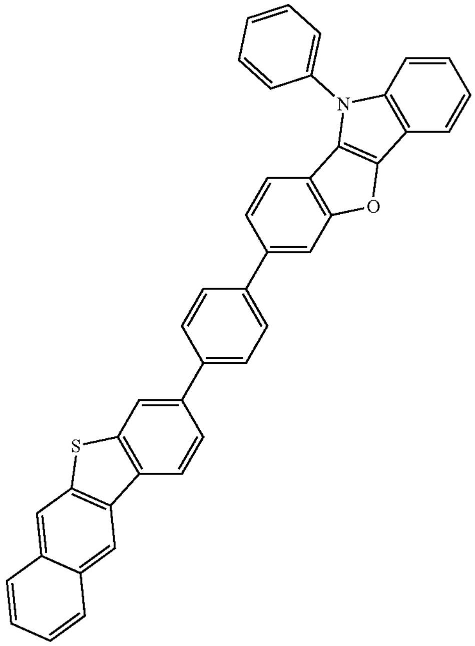
712
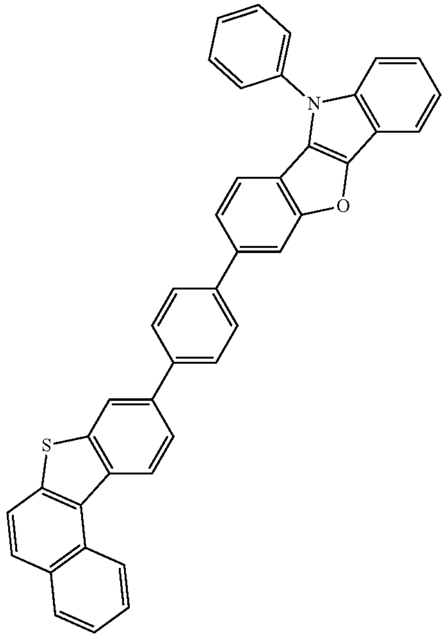
-continued
713
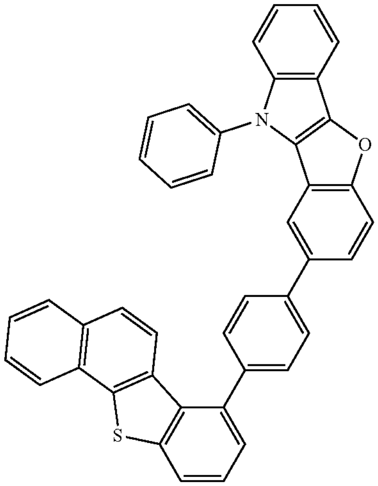
714
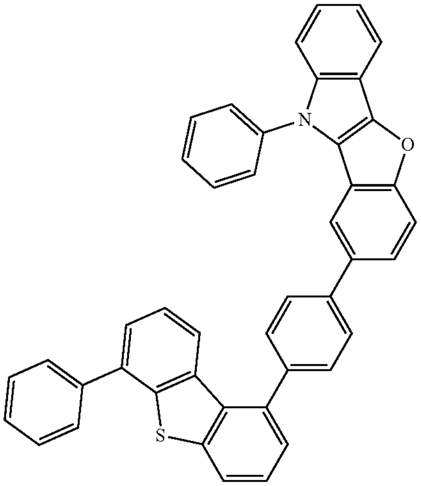
715
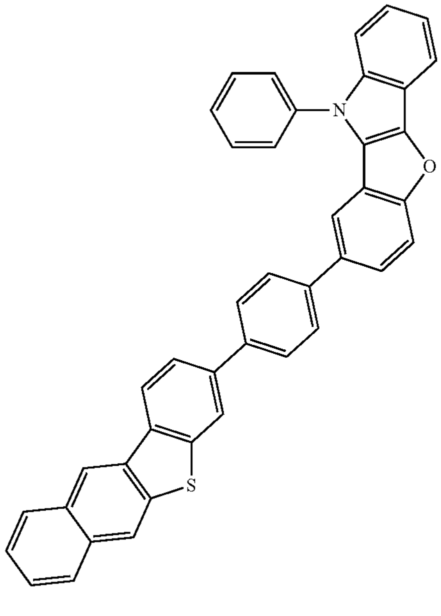

-continued
716
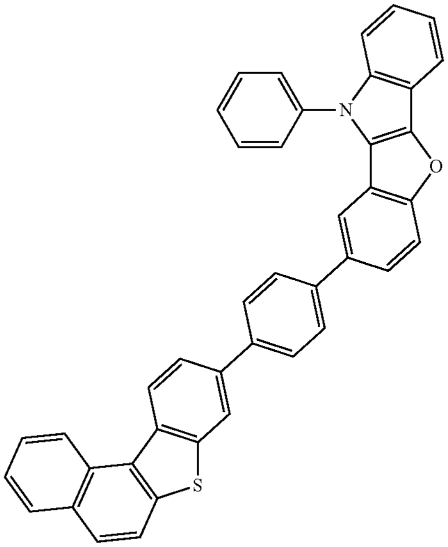
717
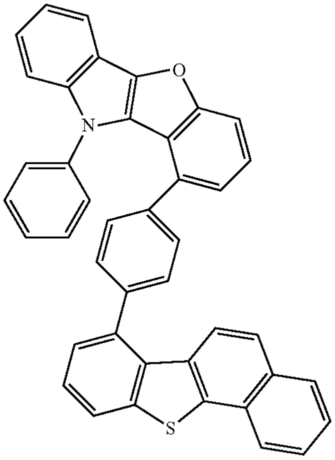
718
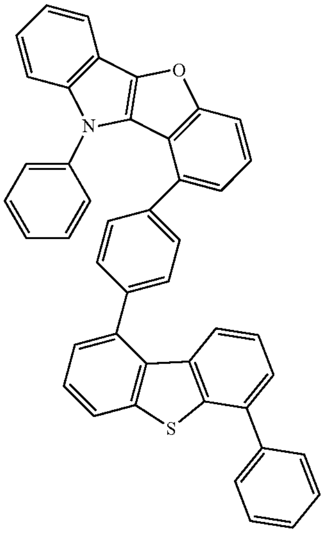
-continued
719
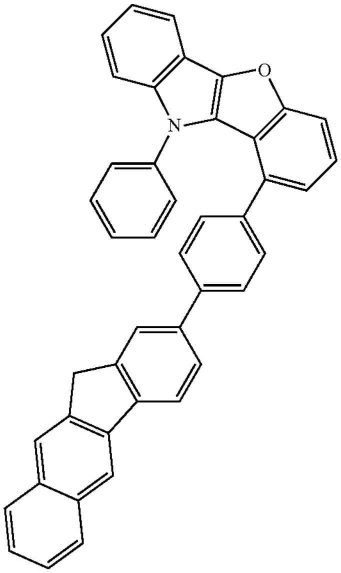
720
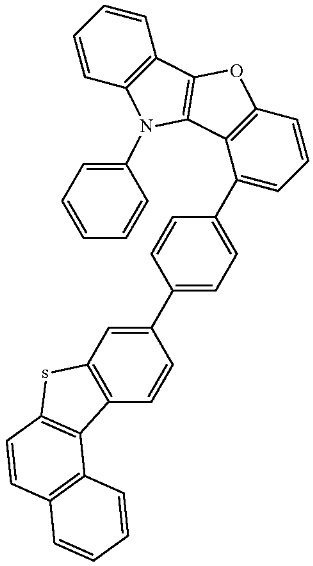
721
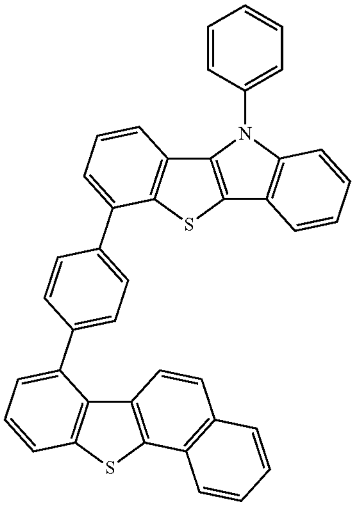

-continued
722
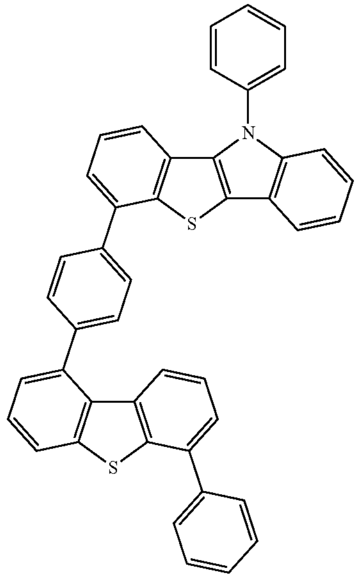
723
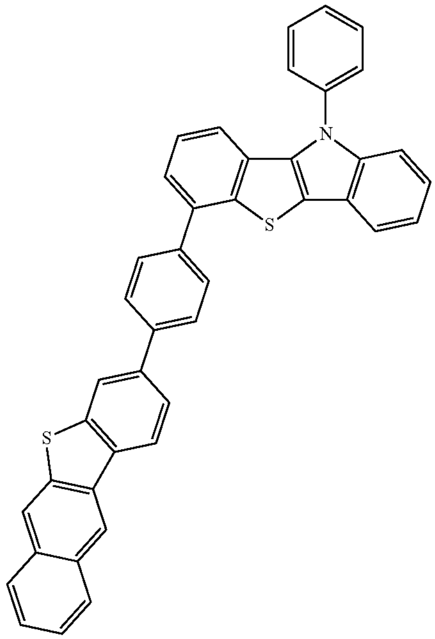
-continued
724
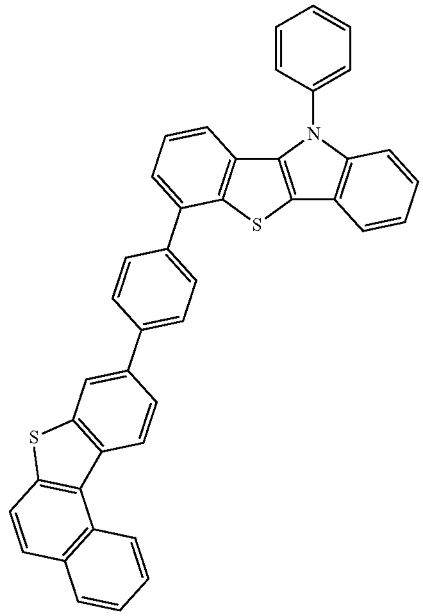
725
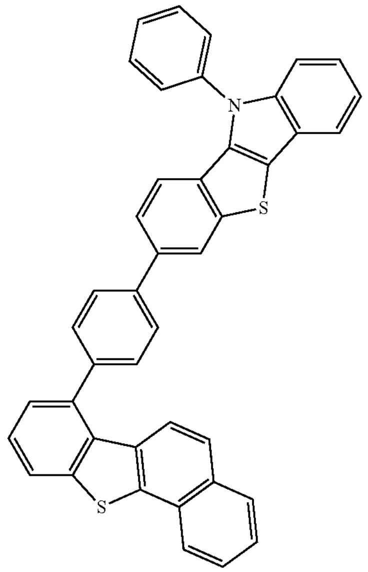

-continued
726
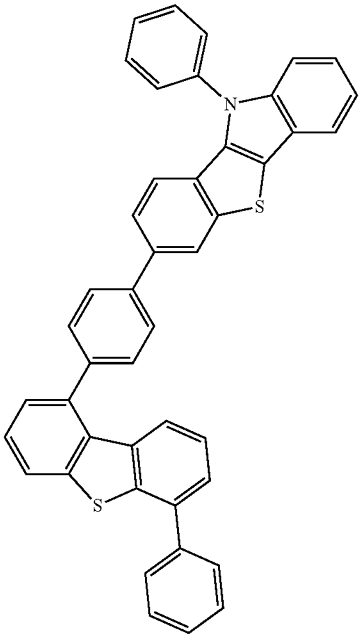
727
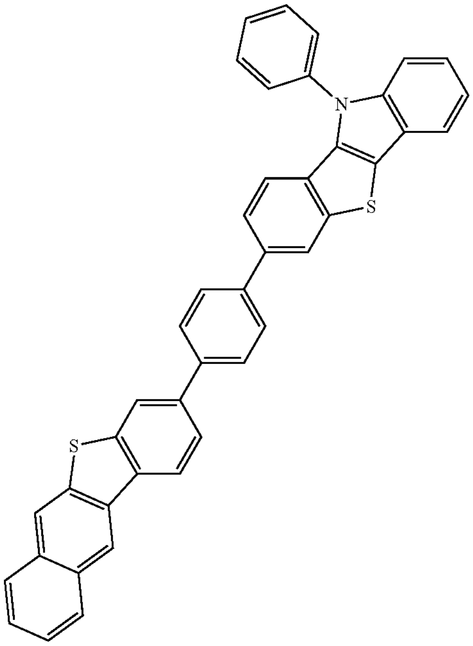
-continued
728
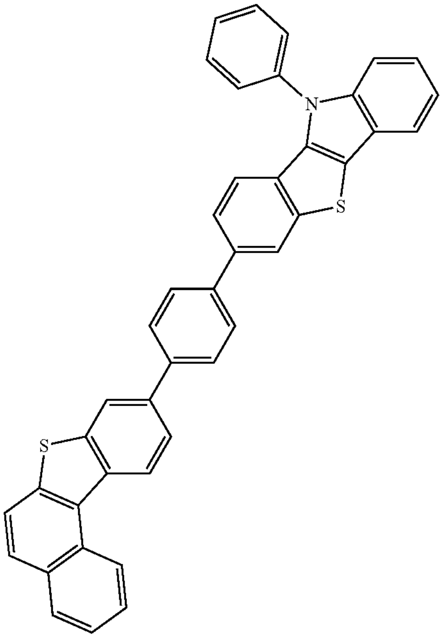
729
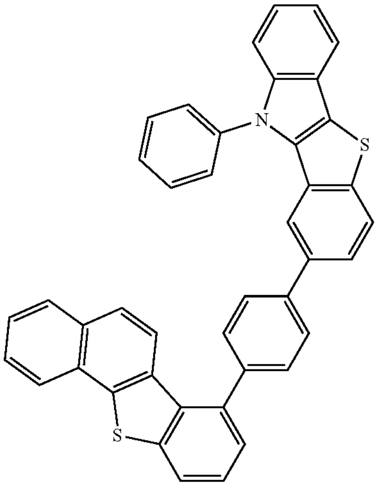
730
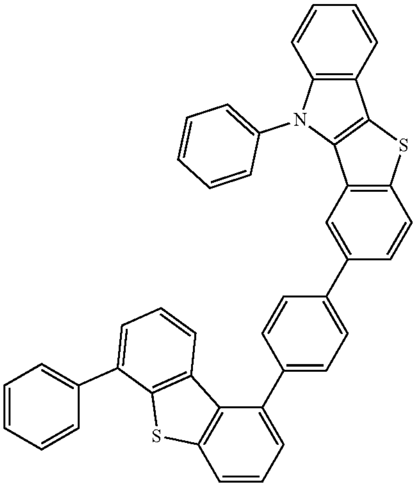

-continued
731
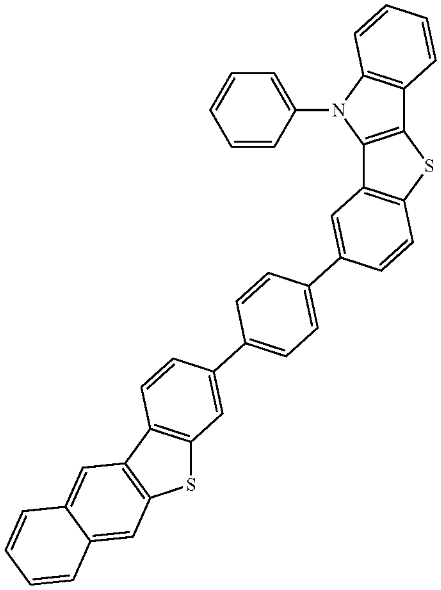
732
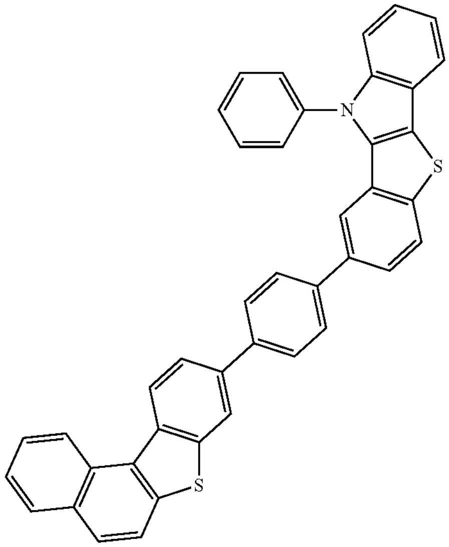
733
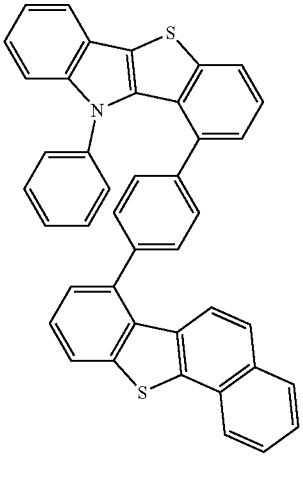
-continued
734
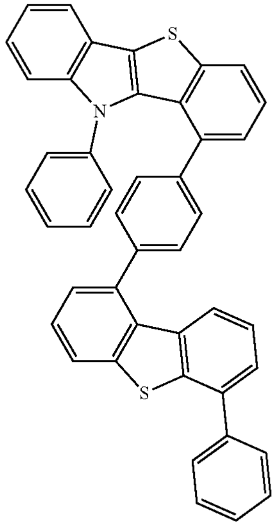
735
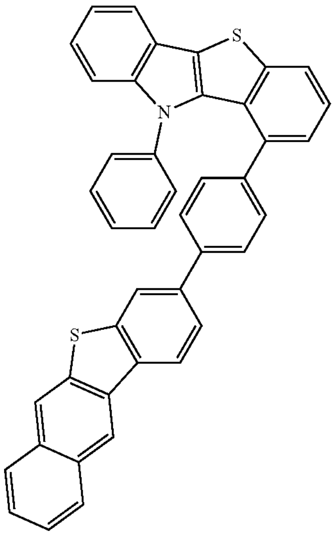
736
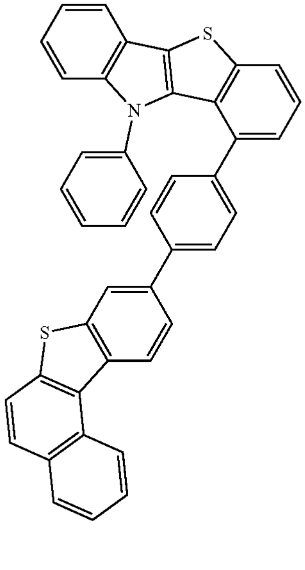

-continued
737
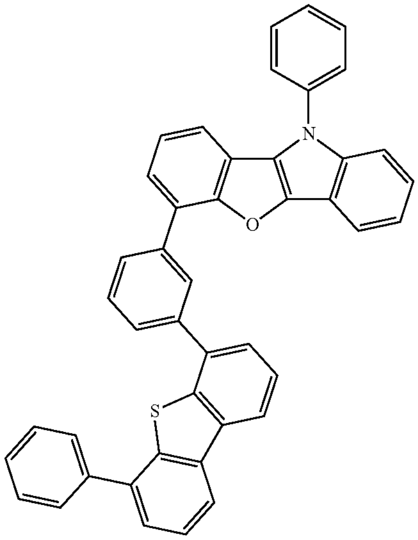
738
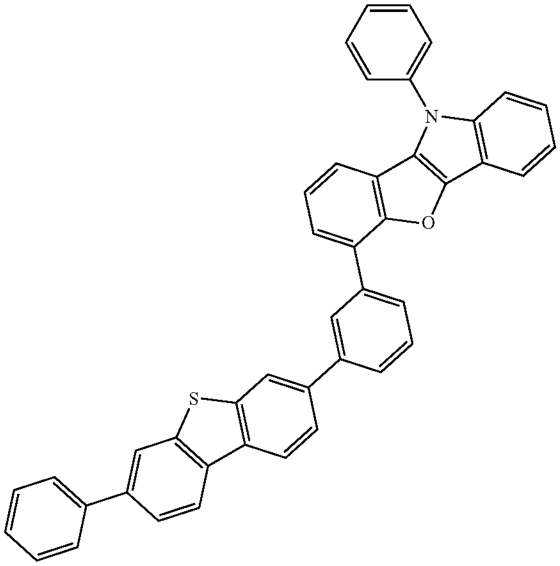
739
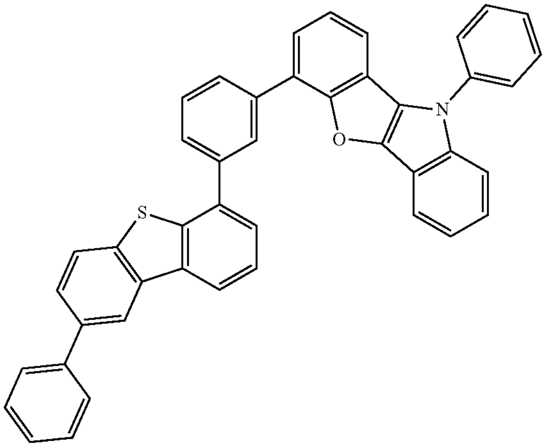
-continued
740
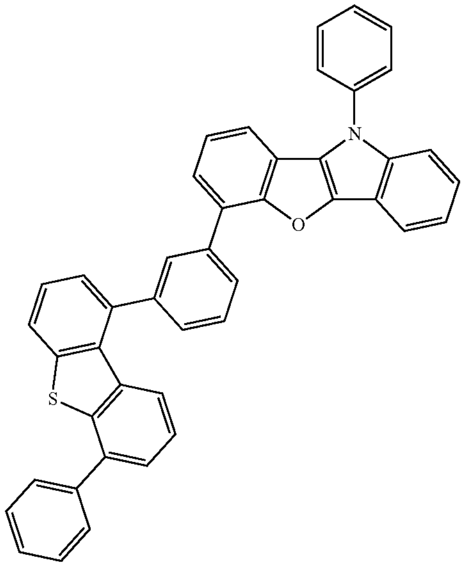
741
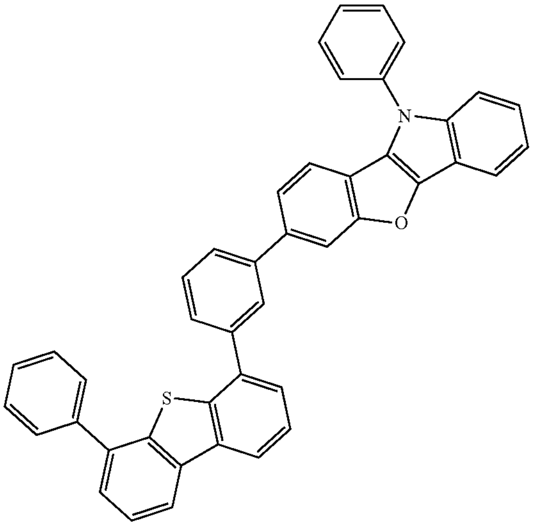

-continued
742
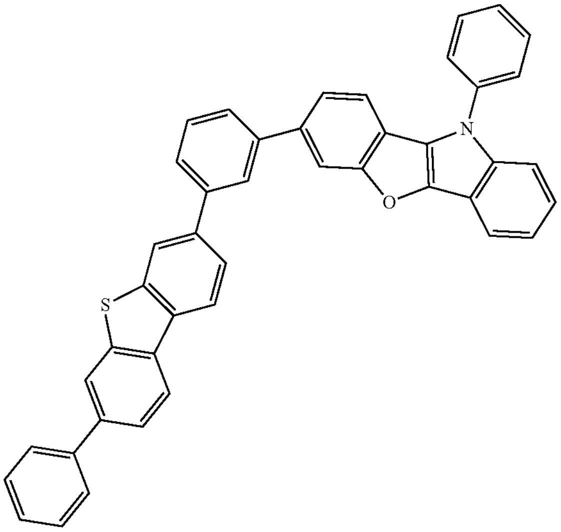
743
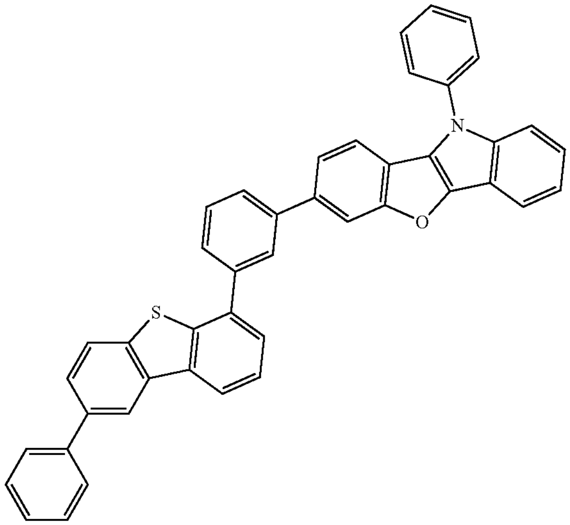
744
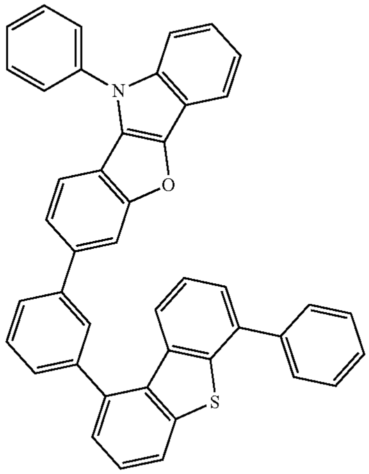
-continued
745
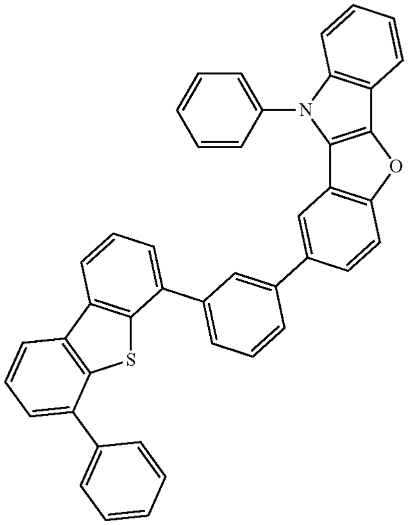
746
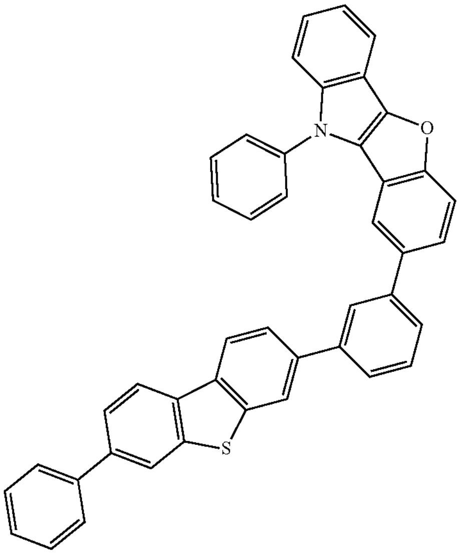
747
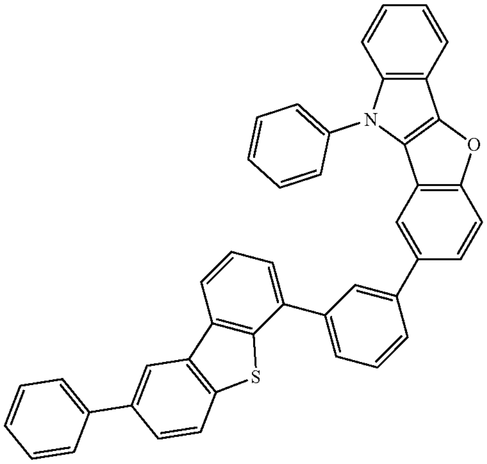

-continued
748
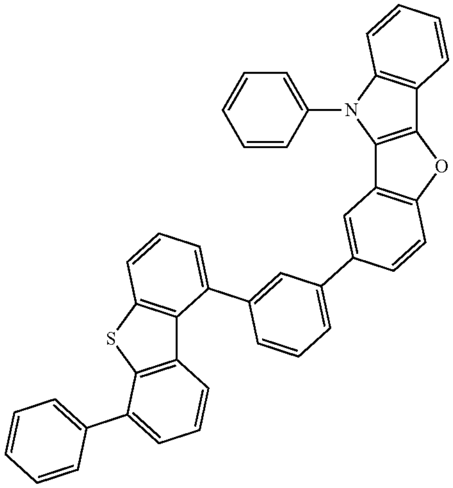
749
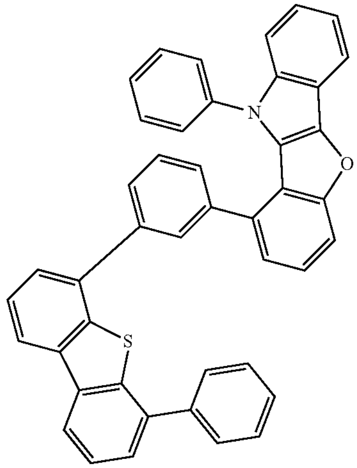
750
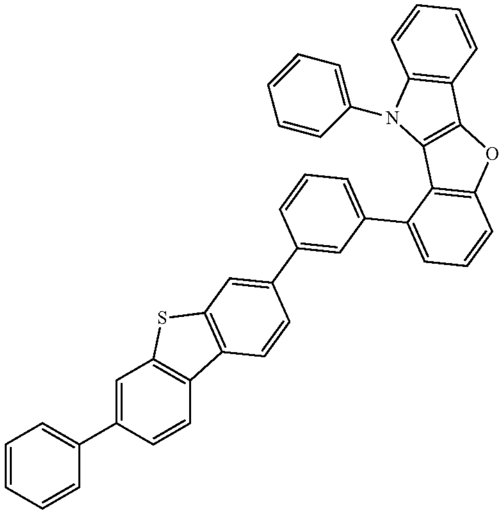
-continued
751
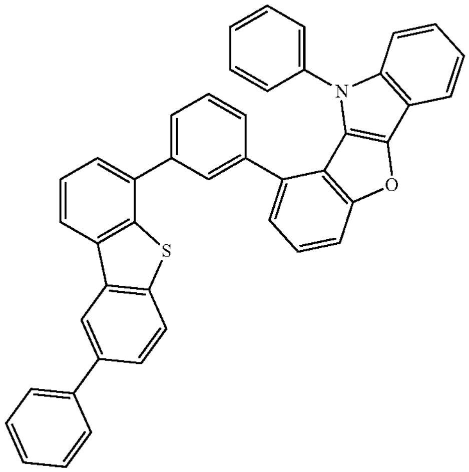
752
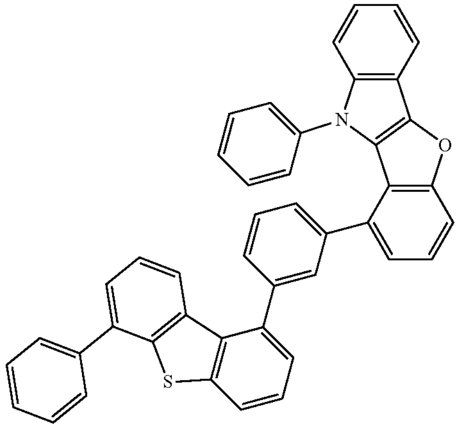
753
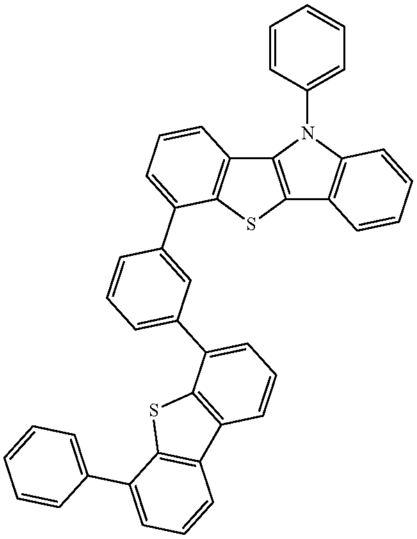

-continued
754
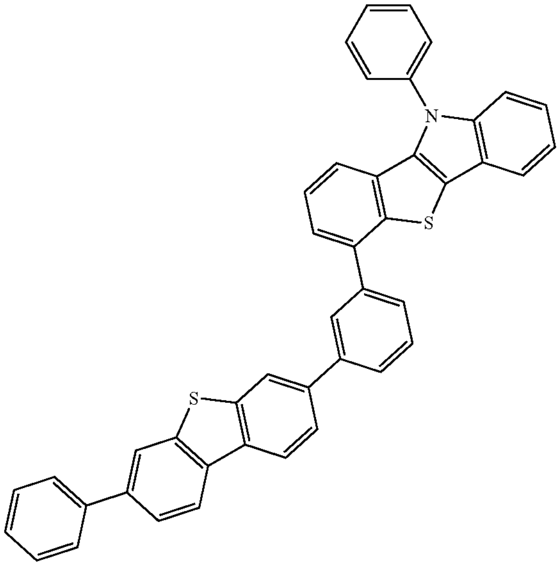
755
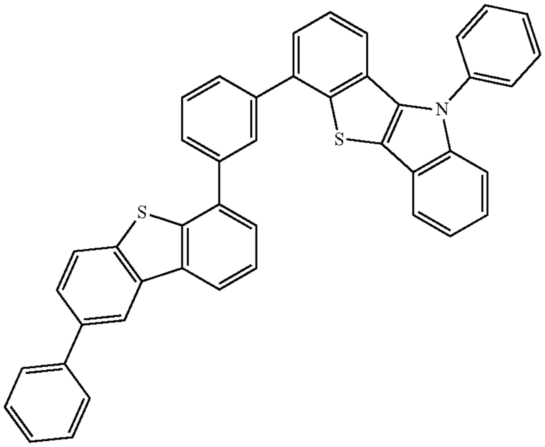
756
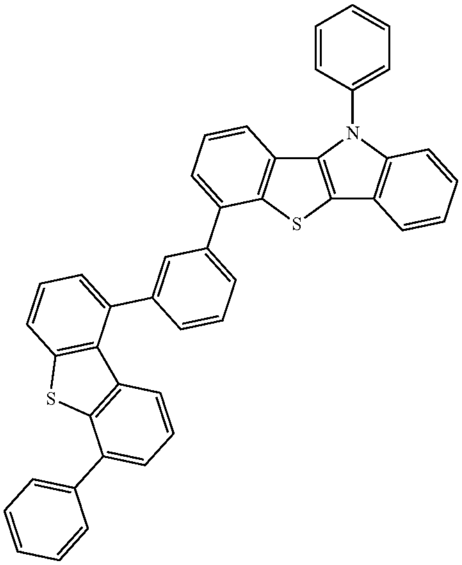
-continued
757
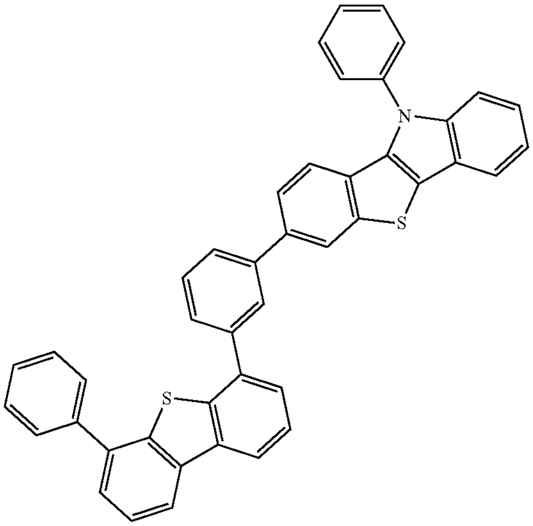
758
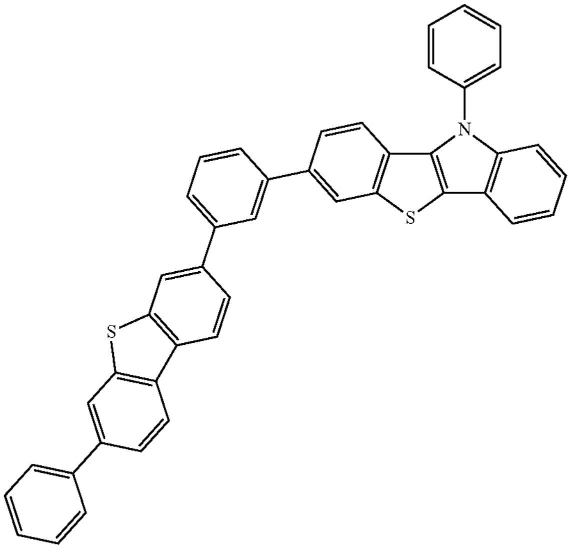

-continued
759
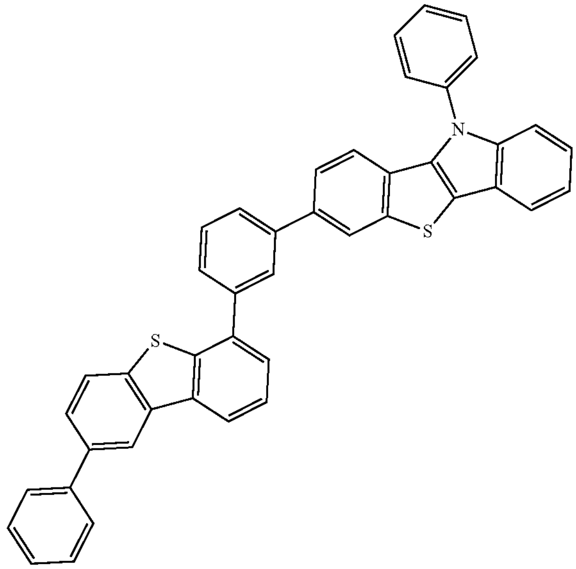
760
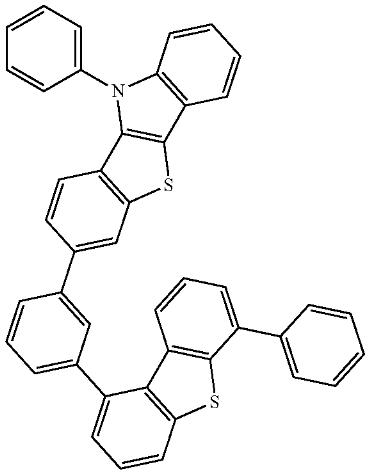
761
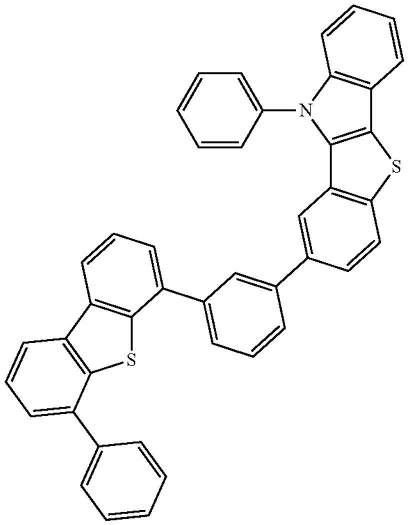
-continued
762
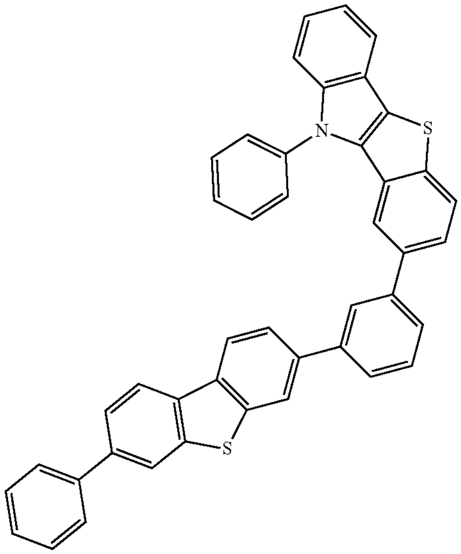
763
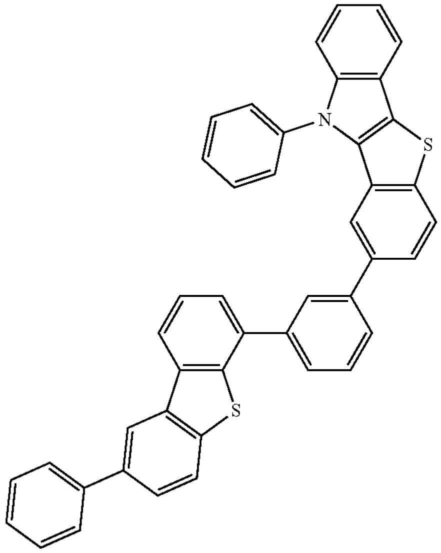
764
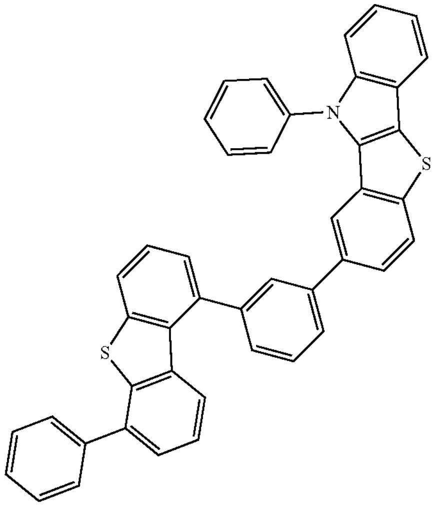

-continued
765
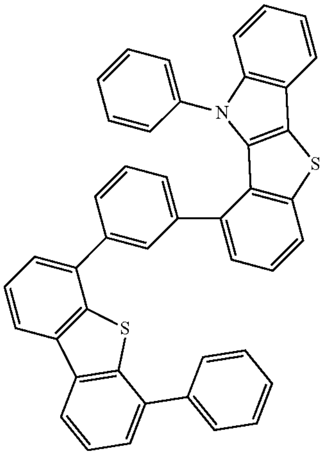
766
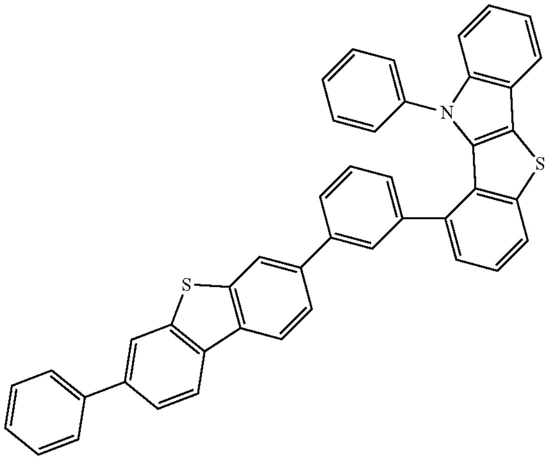
767
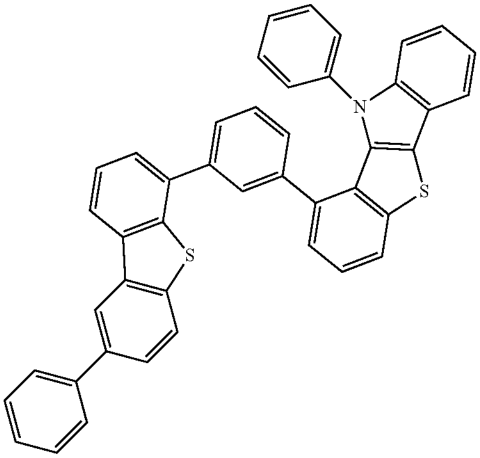
-continued
768
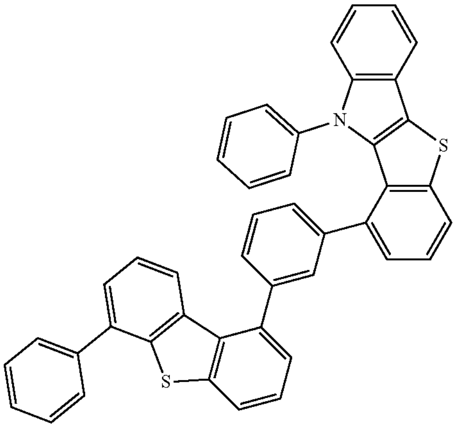
769
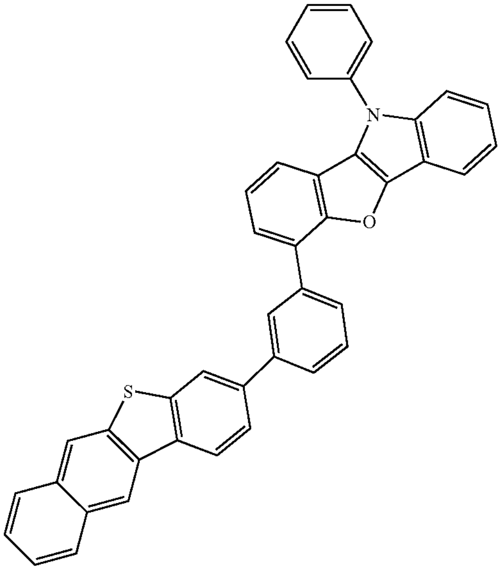

-continued
770
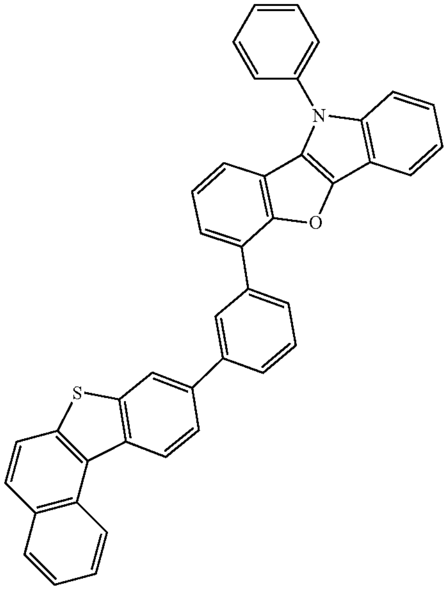
771
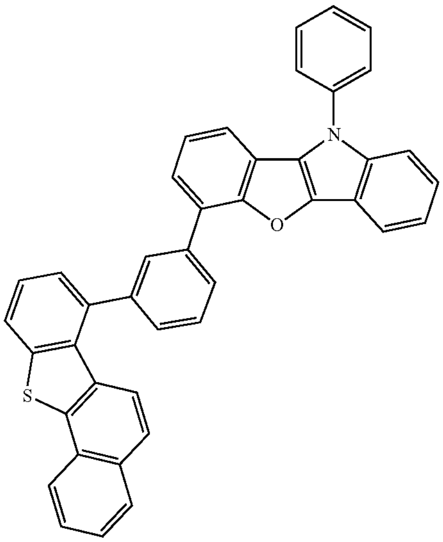
-continued
772
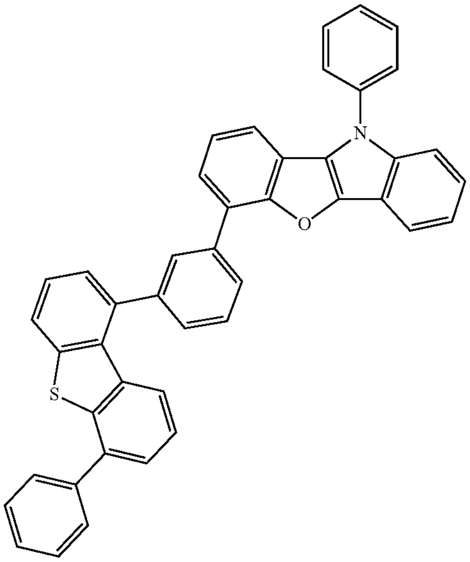
773
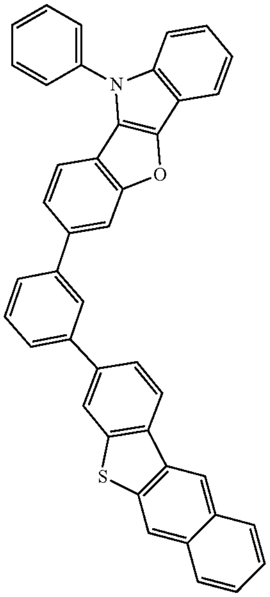

-continued
774
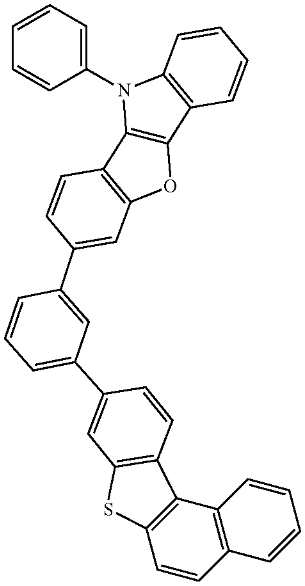
775
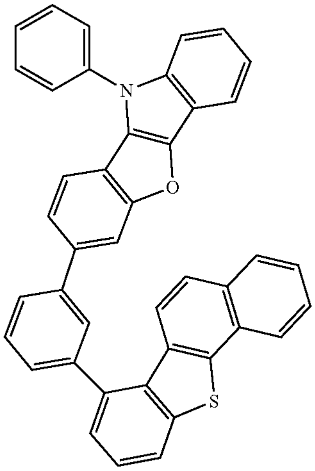
776
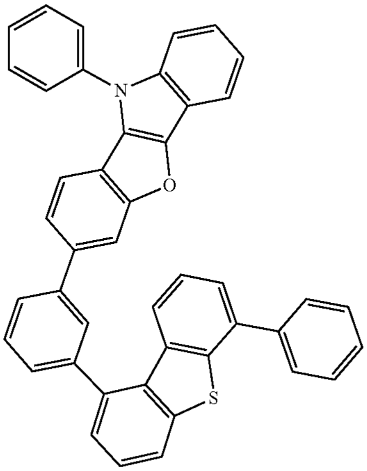
-continued
777
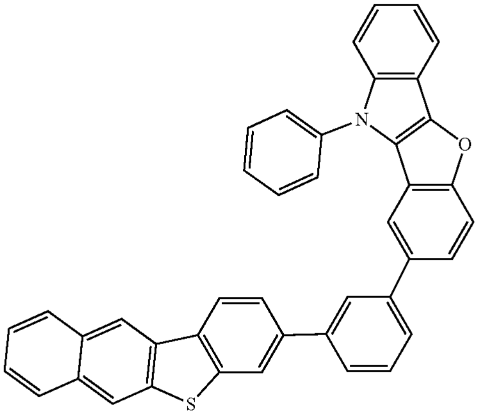
778
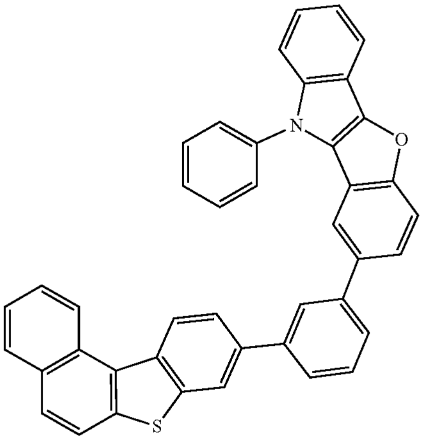
779
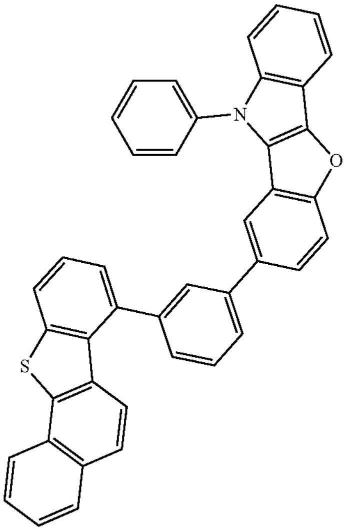

-continued
780
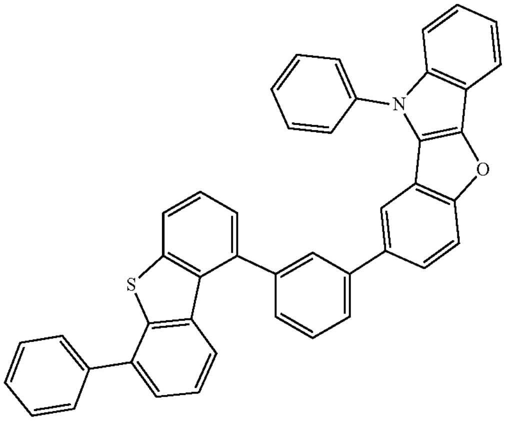
781
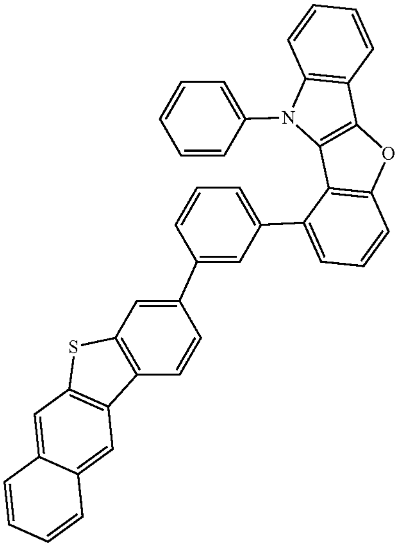
782
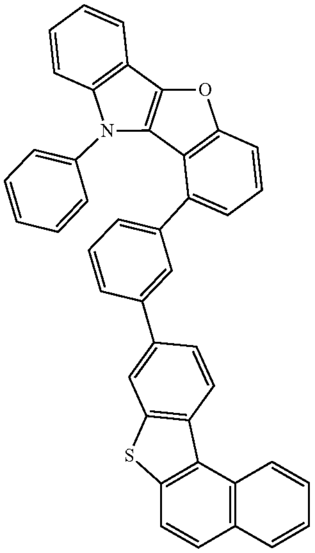
-continued
783
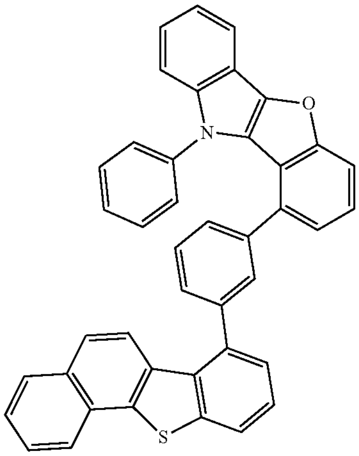
784
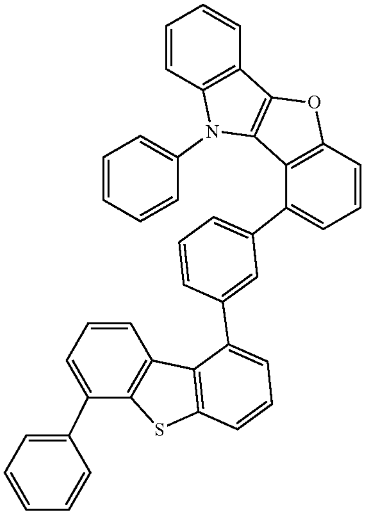
785
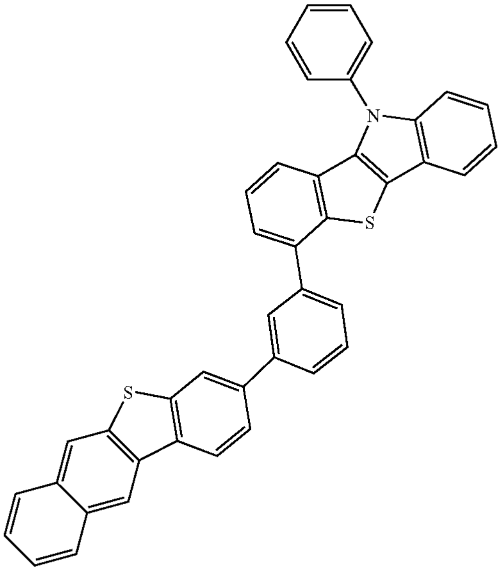

786
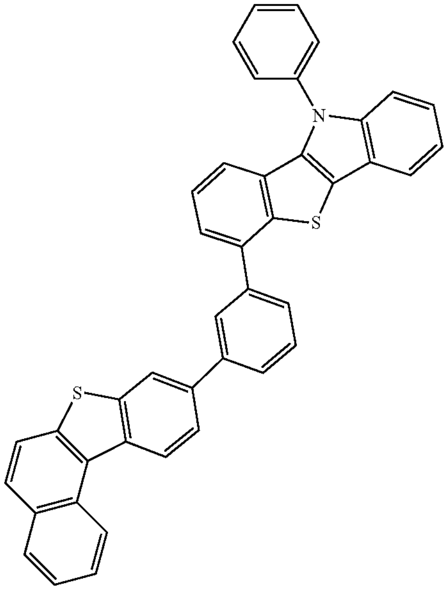
787
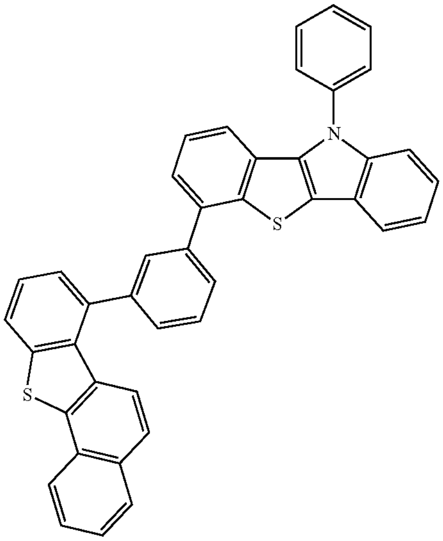
788
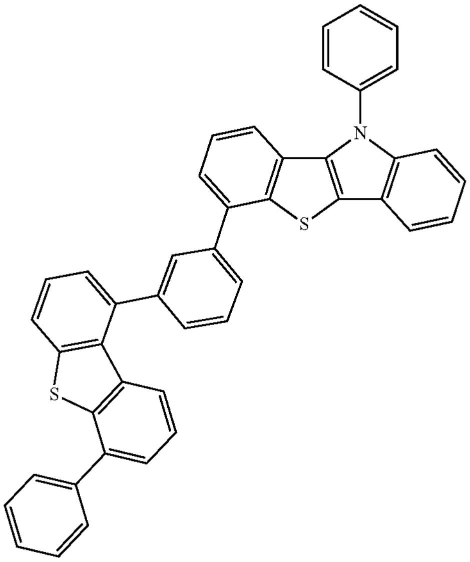
789
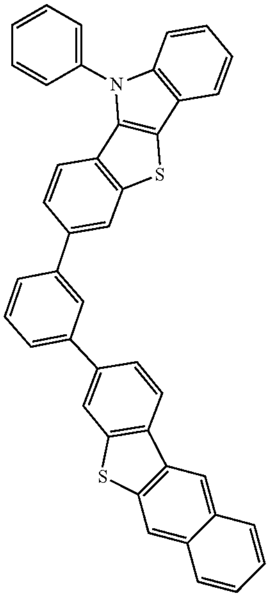

-continued
790
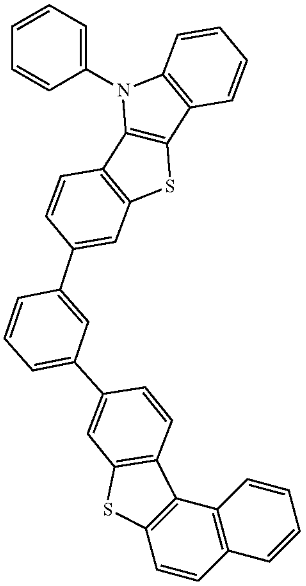
791
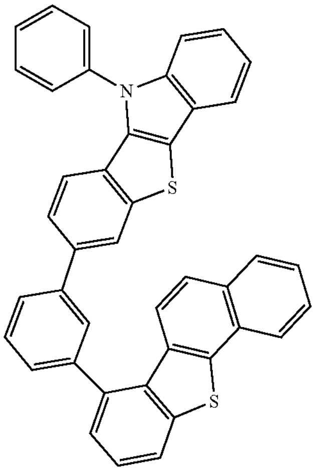
792
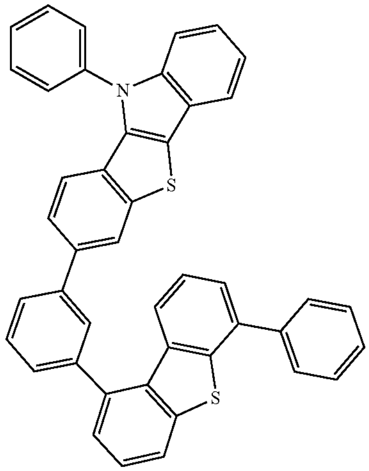
-continued
793
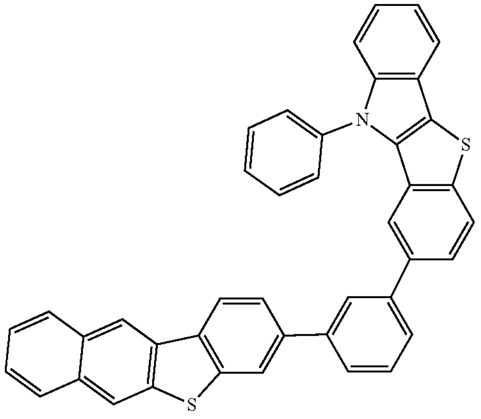
794
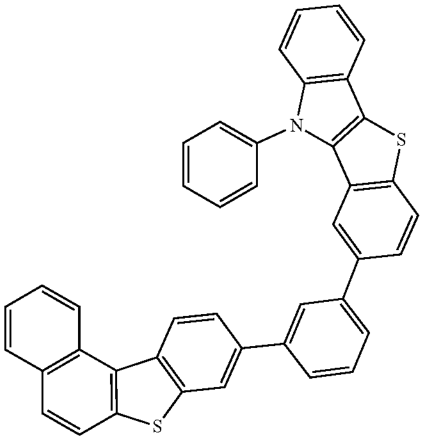
795
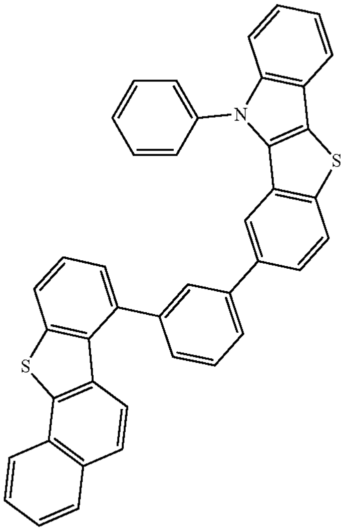

-continued
796
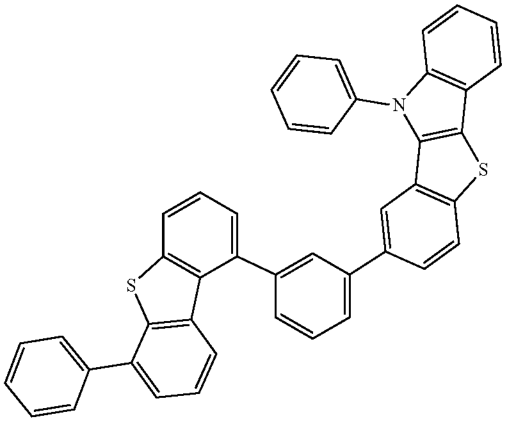
797
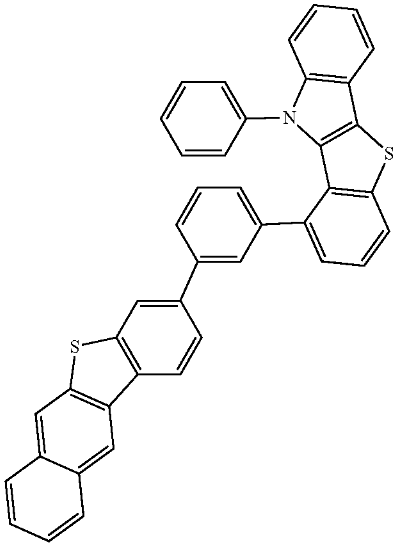
798
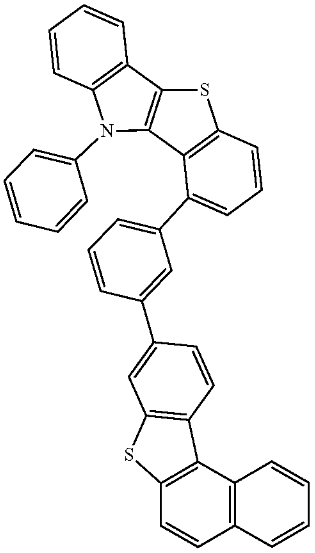
-continued
799
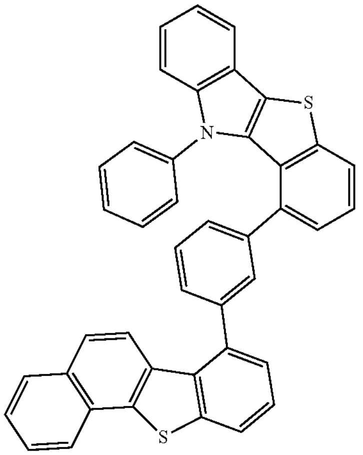
800
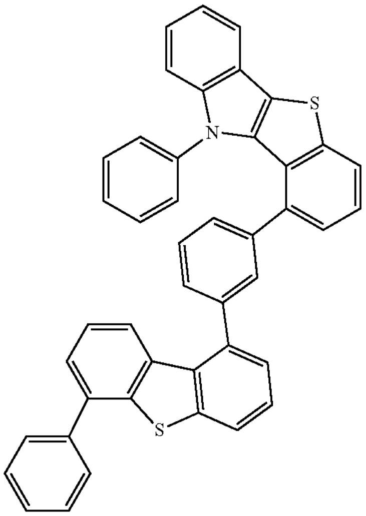
801
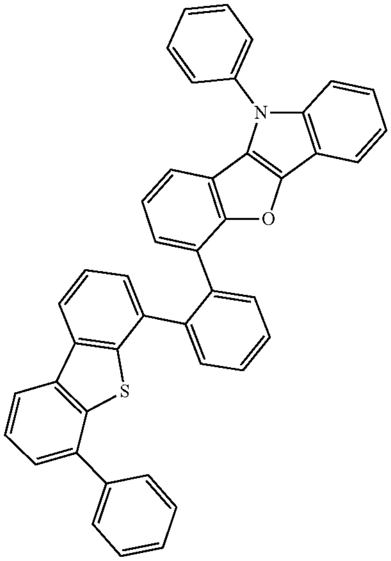

-continued
802
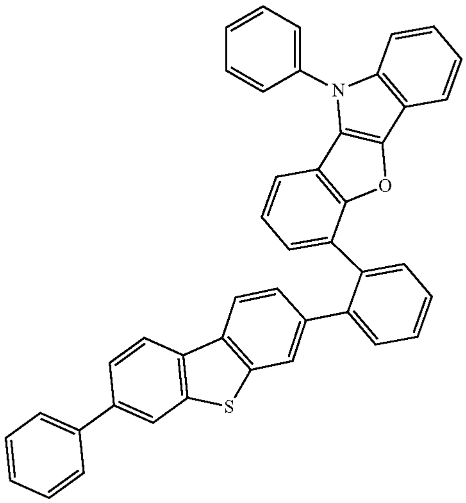
803
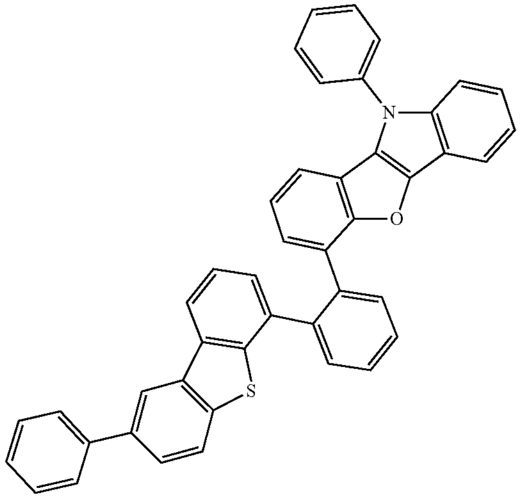
804
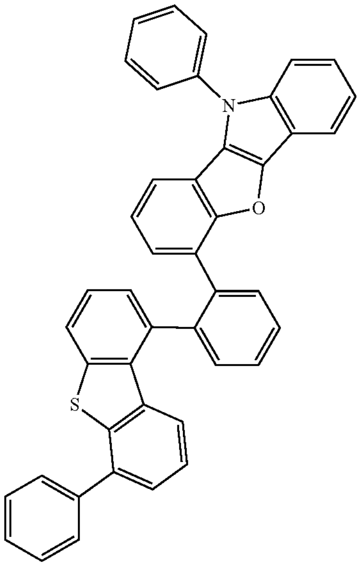
-continued
805
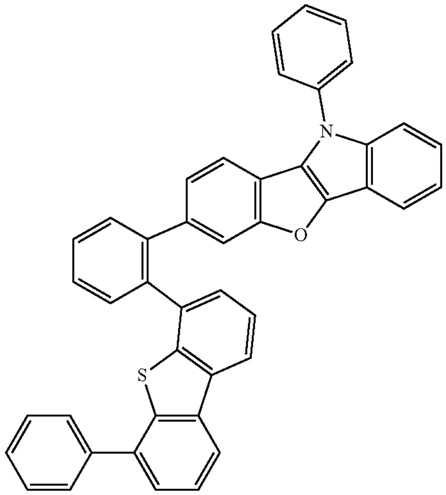
806
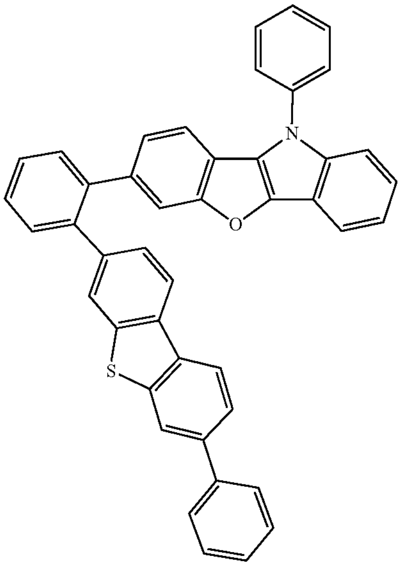
807
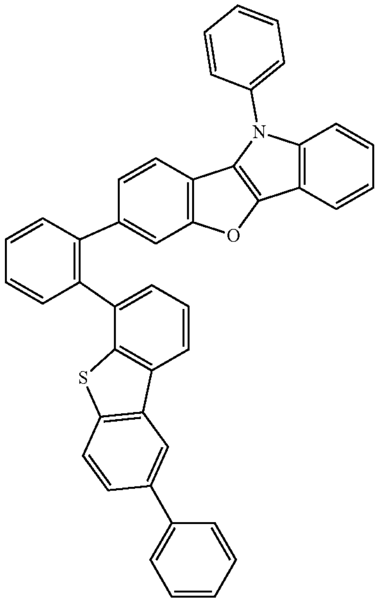

-continued
808
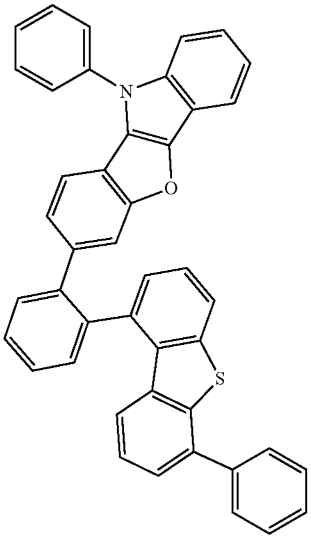
809
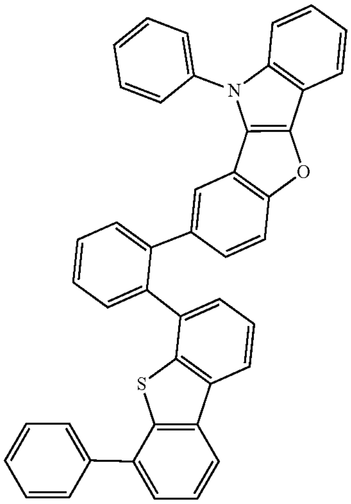
810
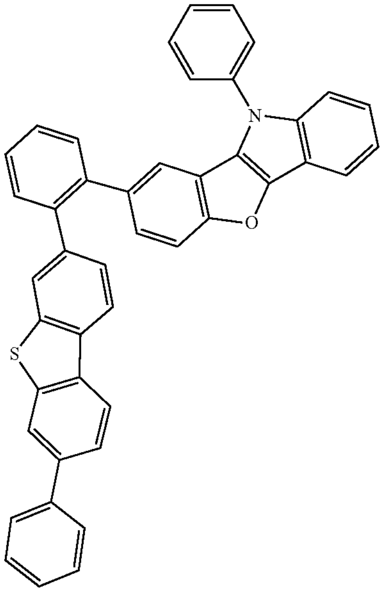
-continued
811
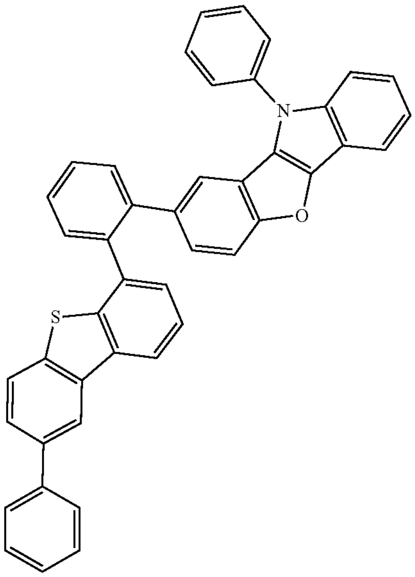
812
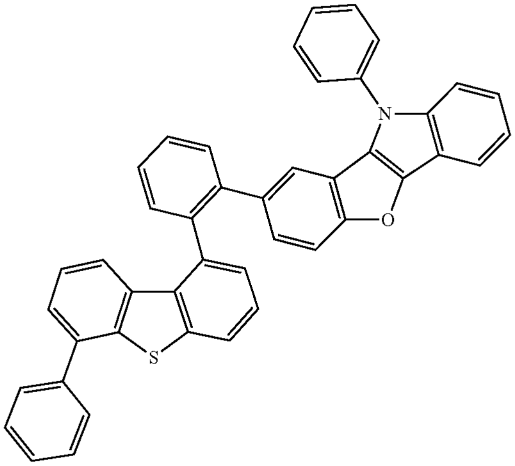
813
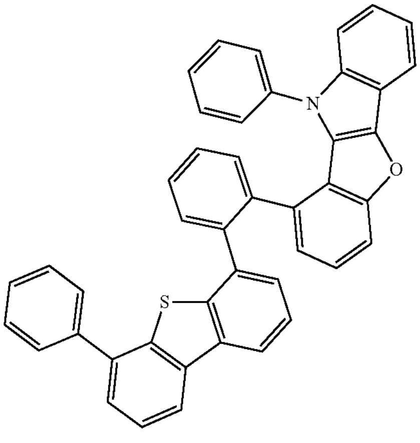

-continued
814
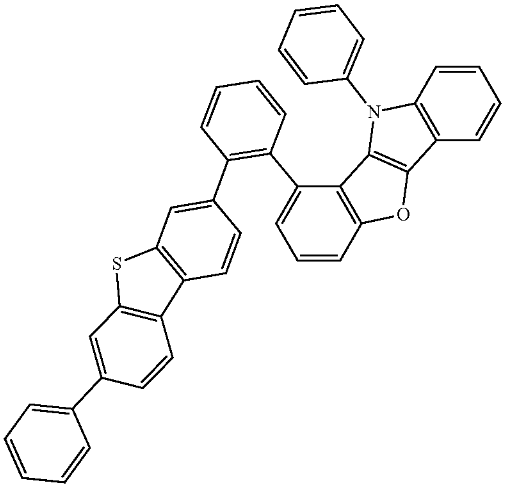
815
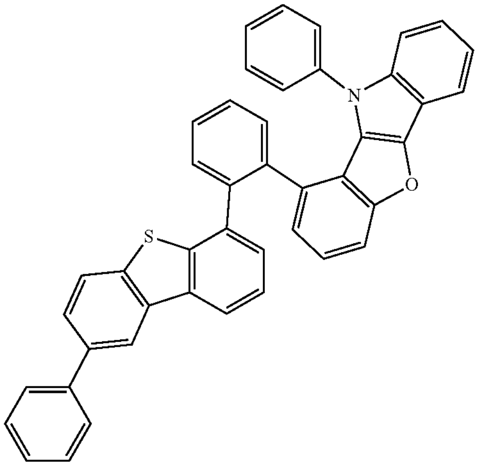
816
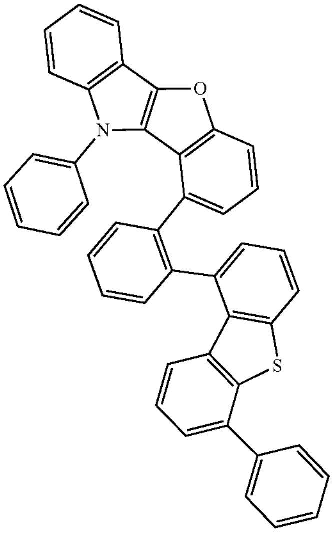
-continued
817
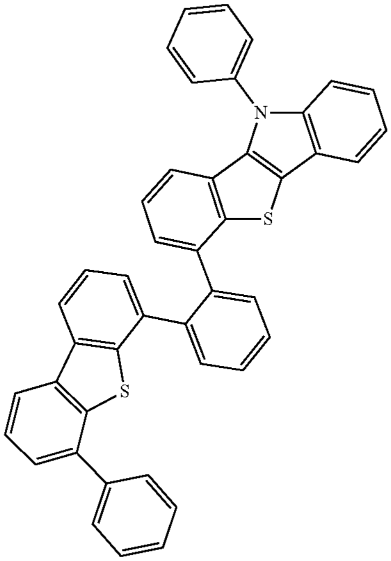
818
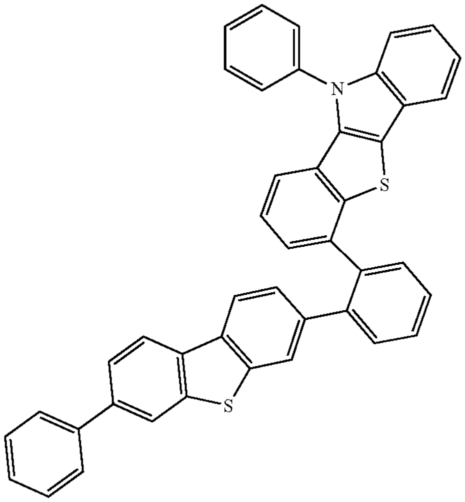
819
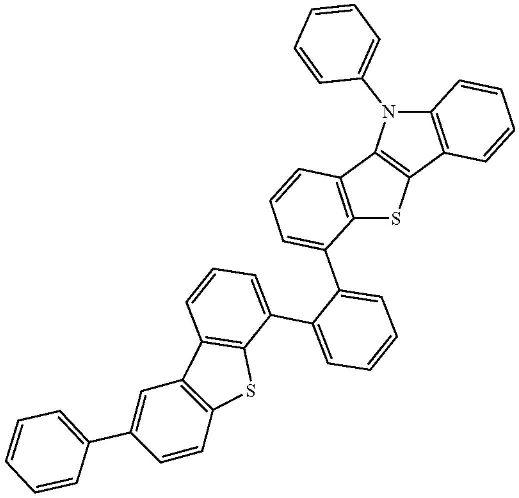

-continued
820
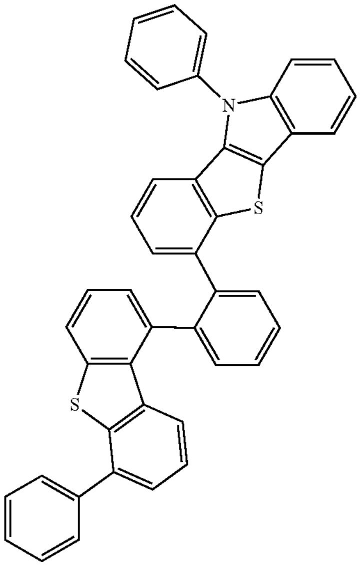
821
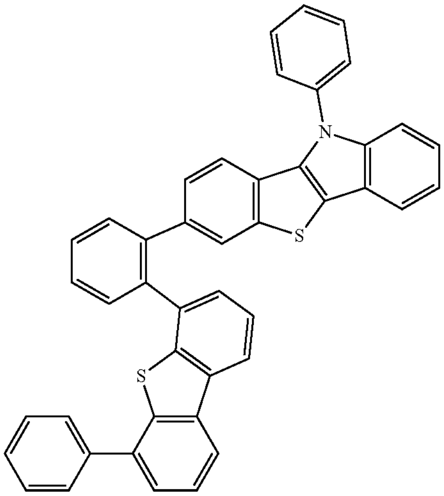
822
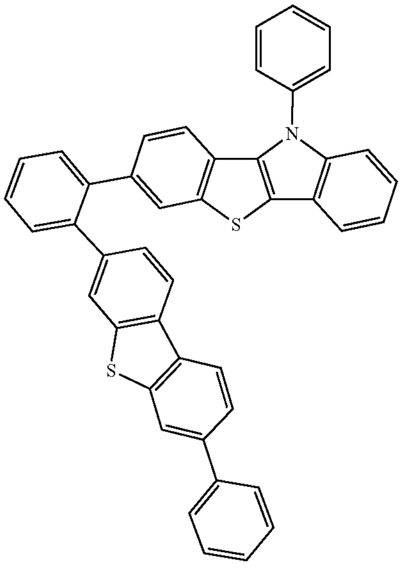
-continued
823
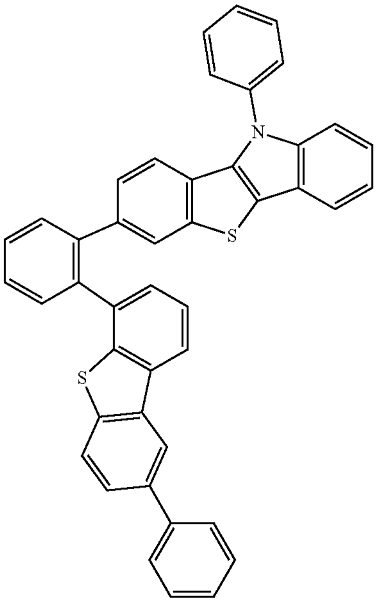
824
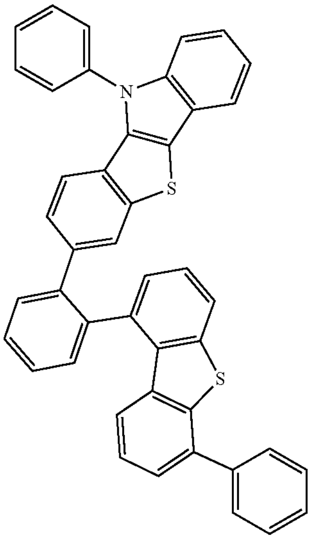
825
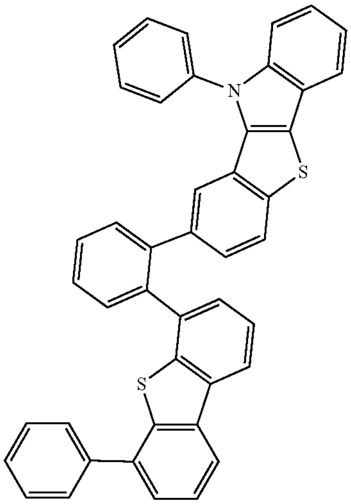

-continued
826
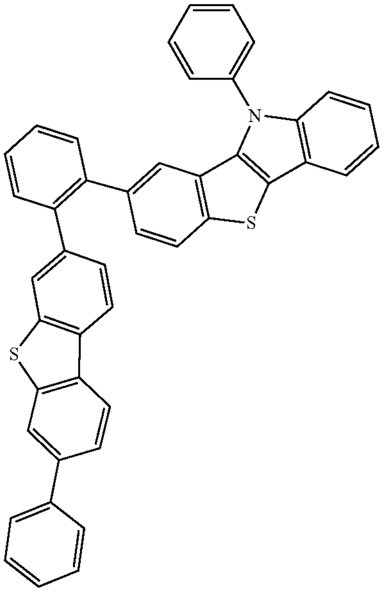
827
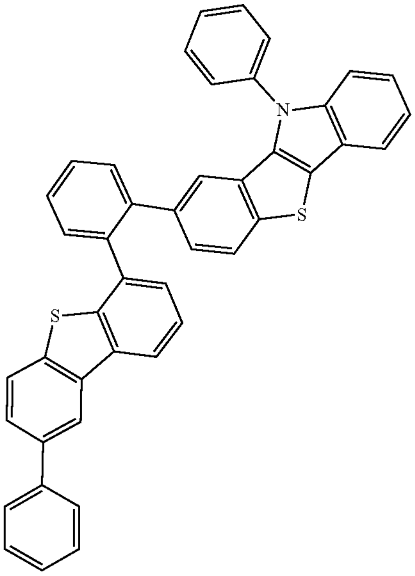
828
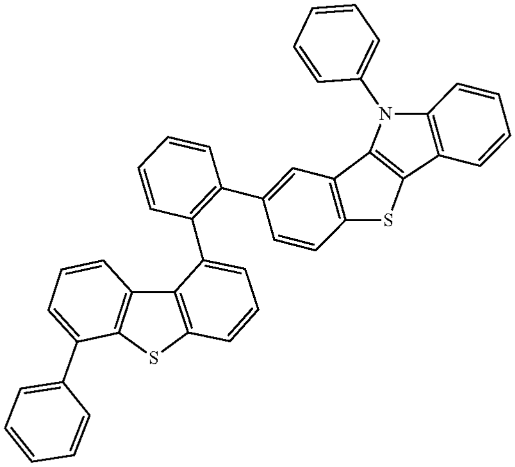
-continued
829
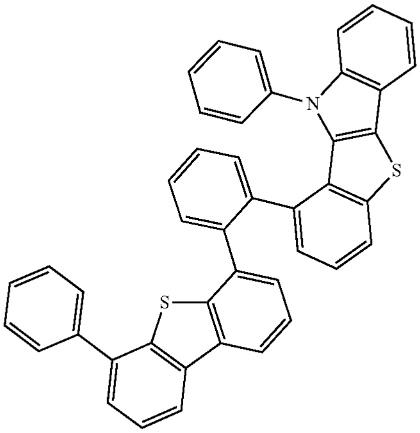
830
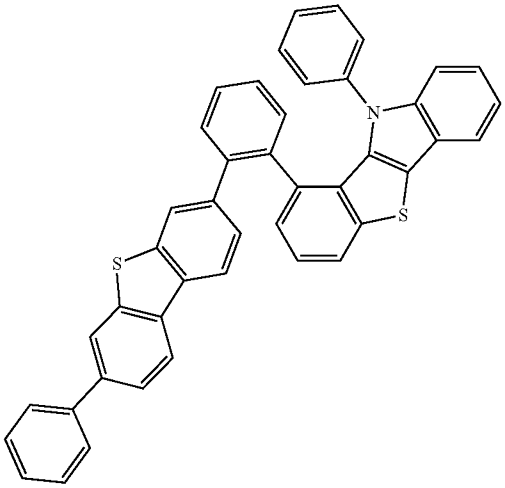
831
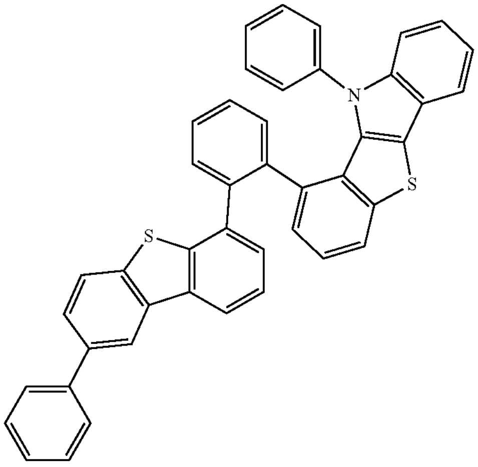

-continued
832
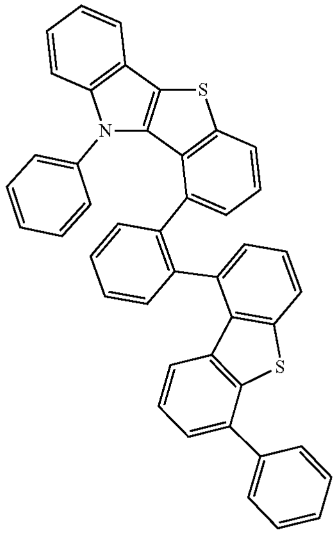
833
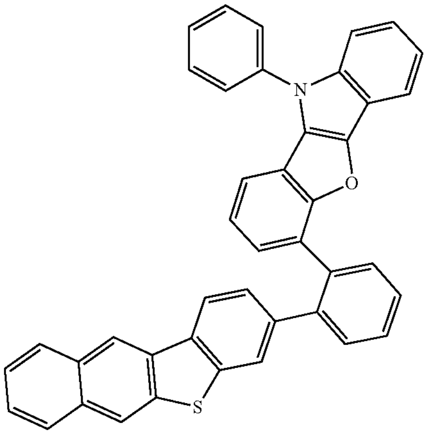
834
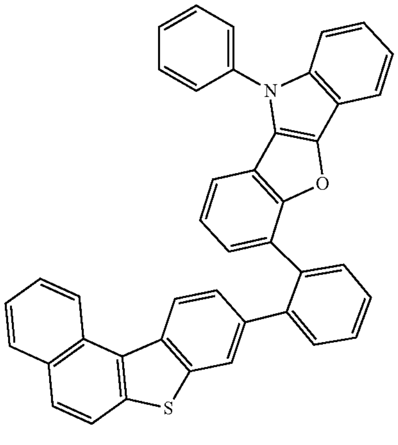
-continued
835
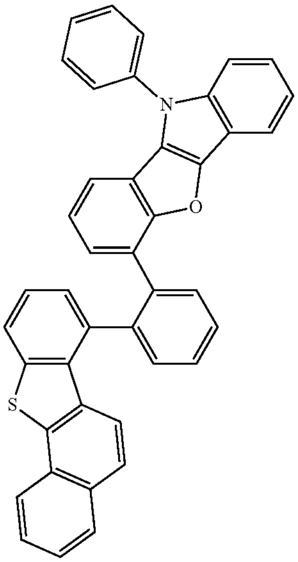
836
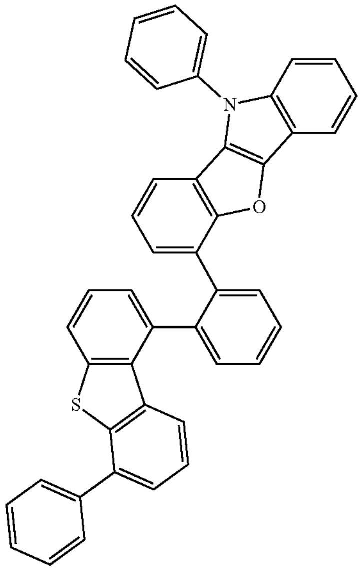
837
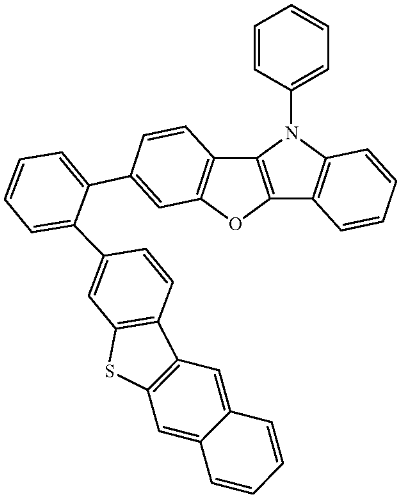

-continued
838
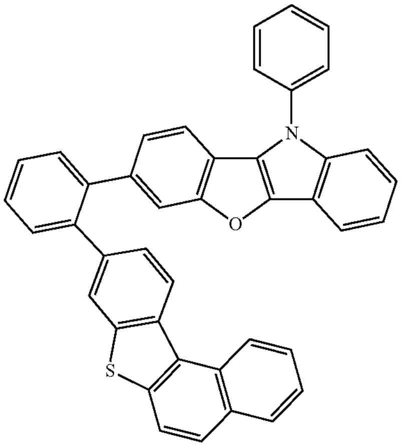
839
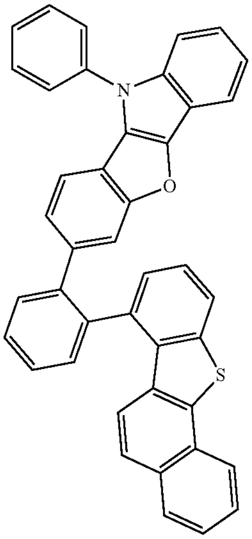
840
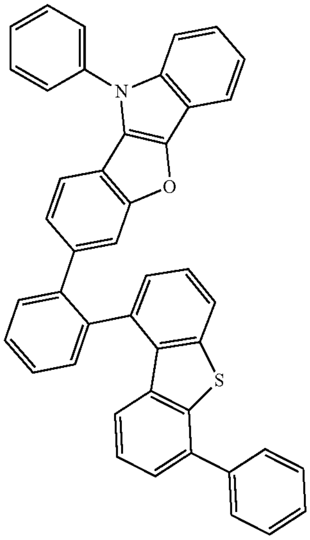
-continued
841
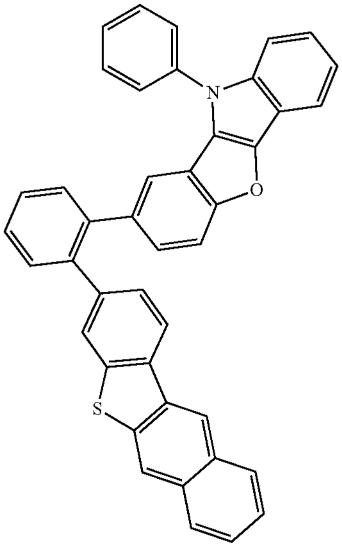
842
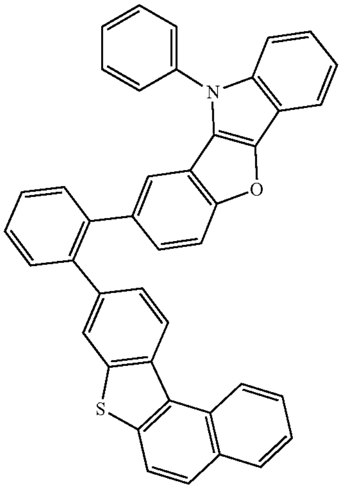
843
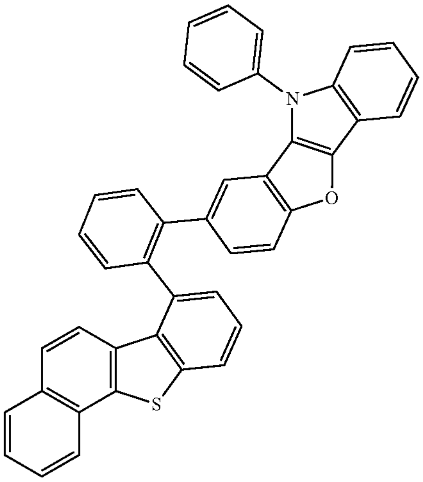

-continued
844
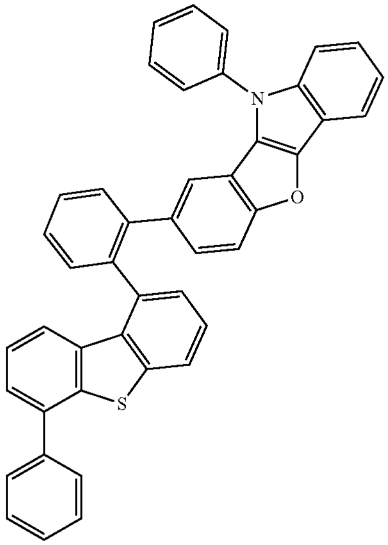
845
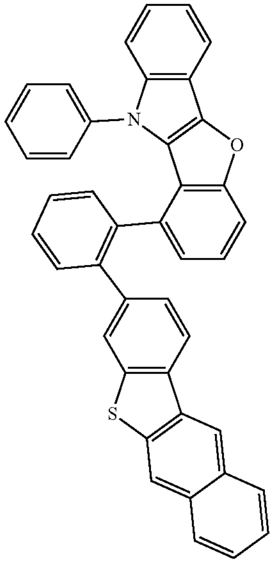
846
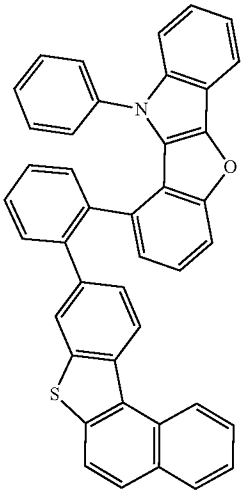
-continued
847
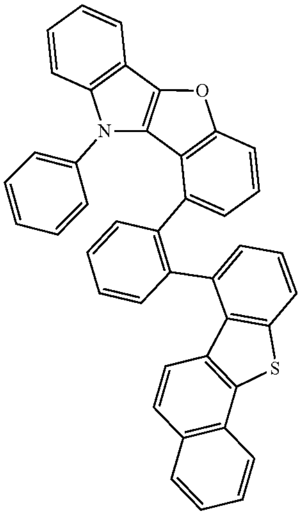
848
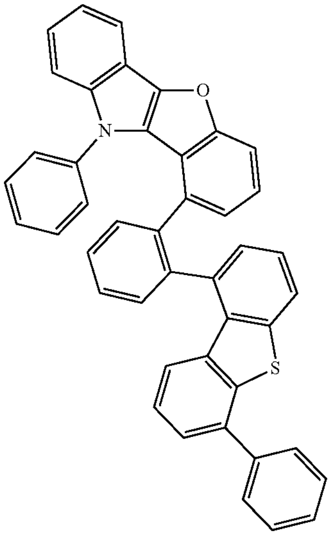
849
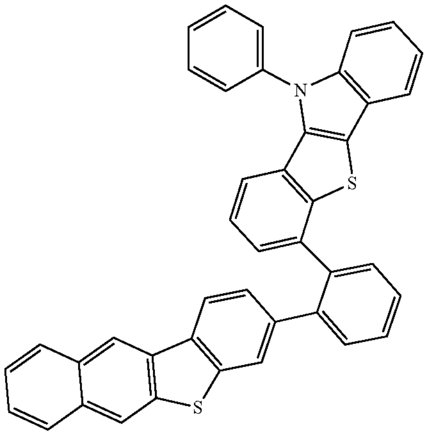

-continued
850
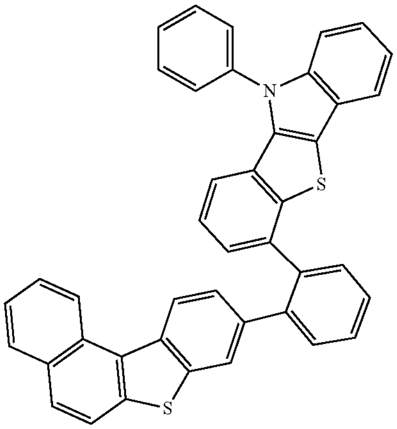
851
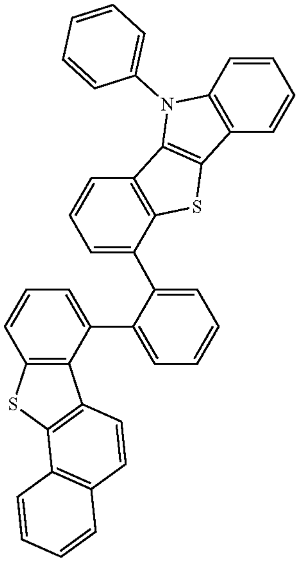
852
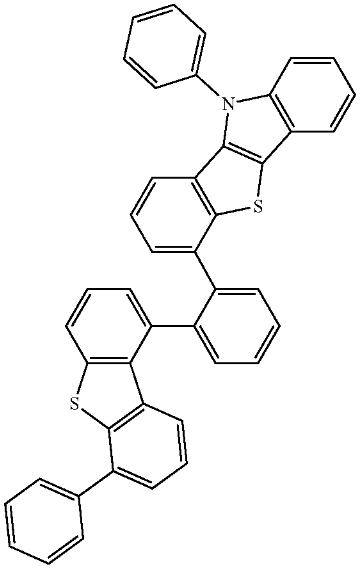
-continued
853
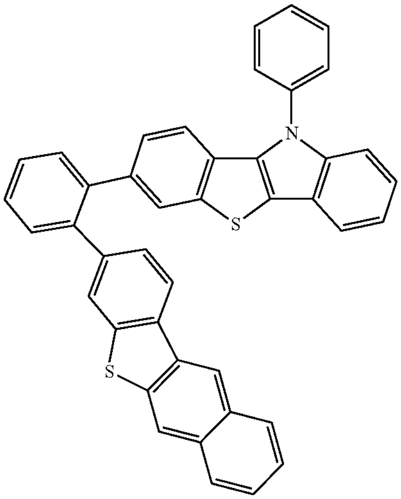
854
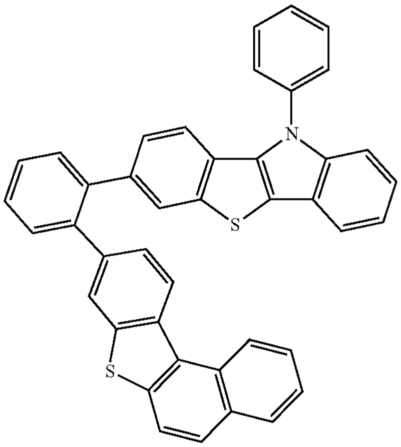
855
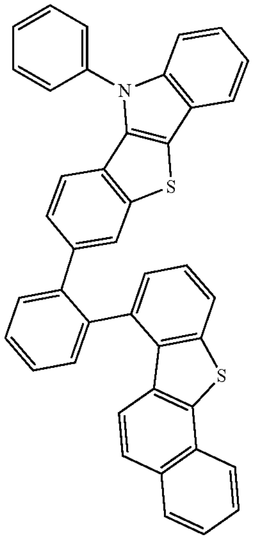

-continued
856
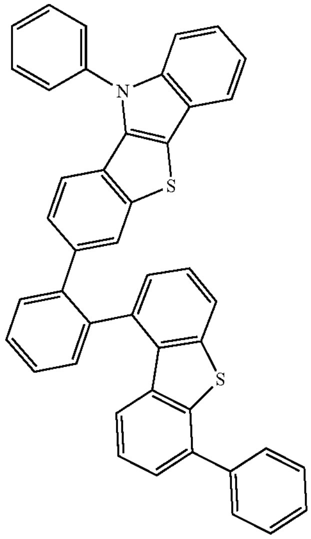
857
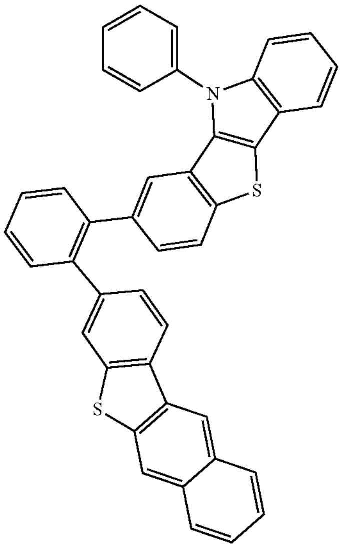
858
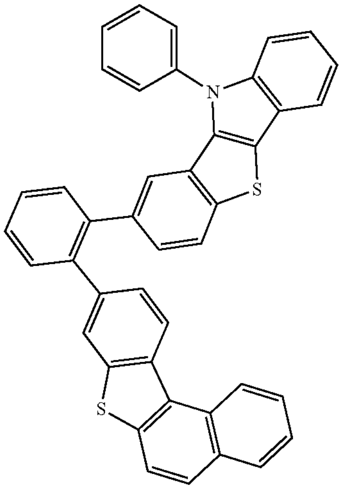
-continued
859
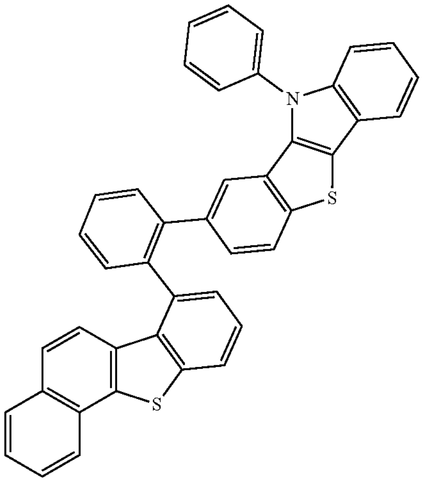
860
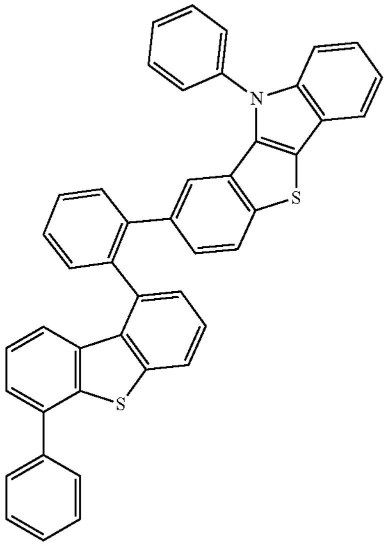
861
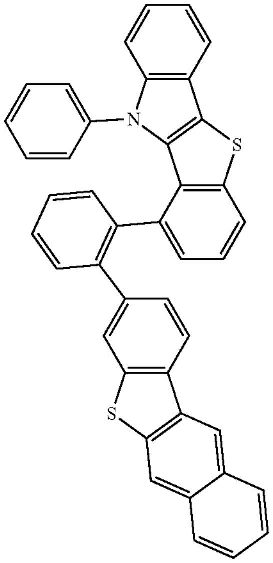

-continued
862
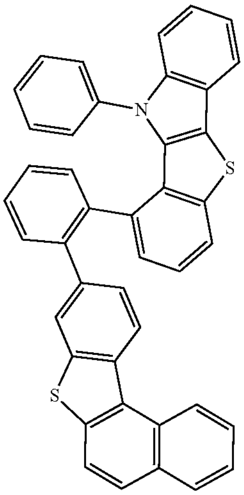
863
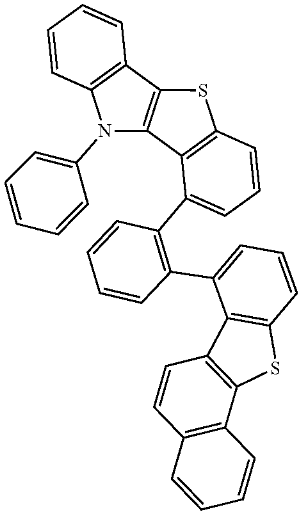
864
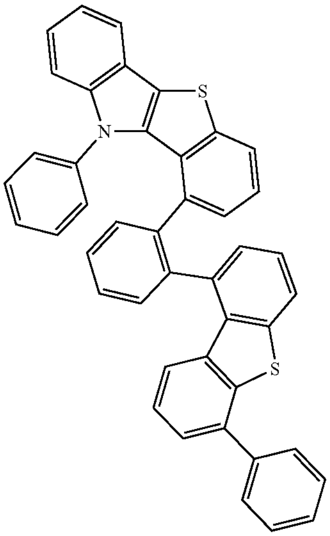
-continued
865
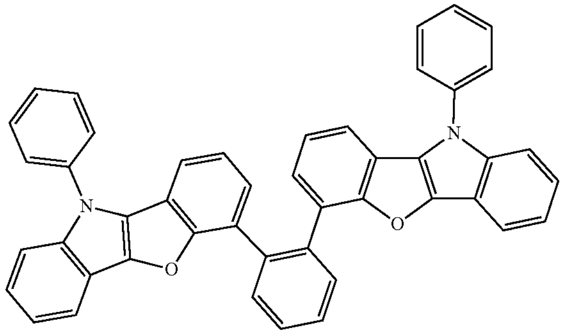
866
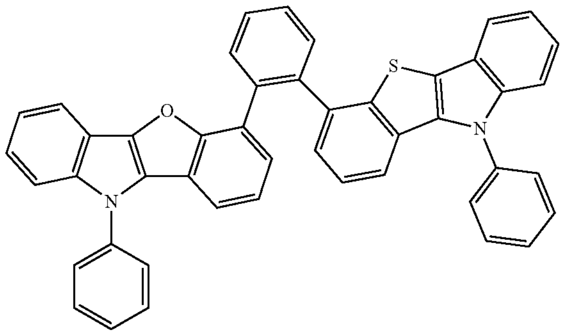
867
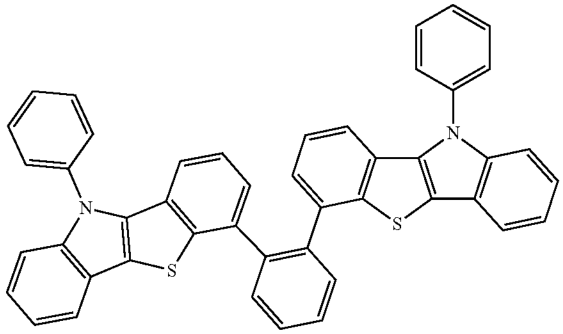
868
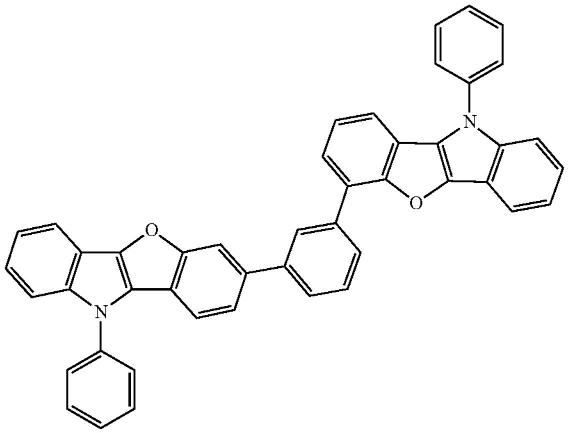

-continued
869
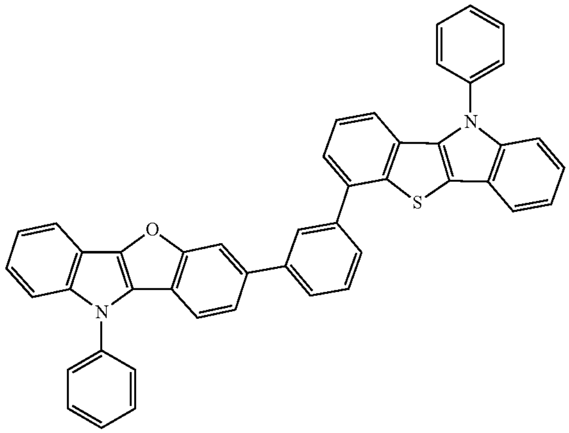
870
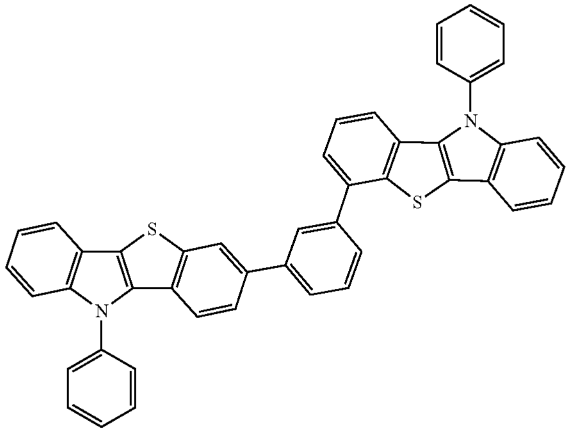
871
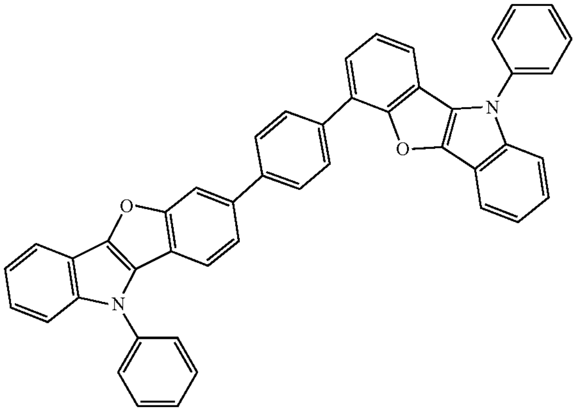
-continued
872
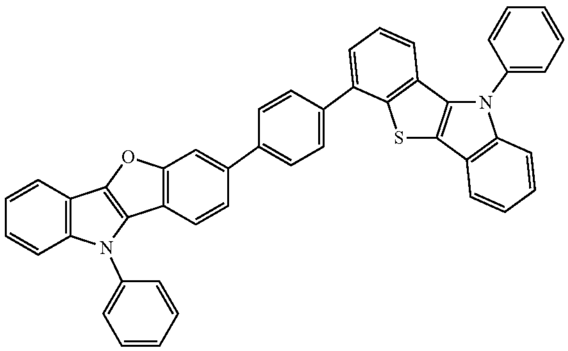
873
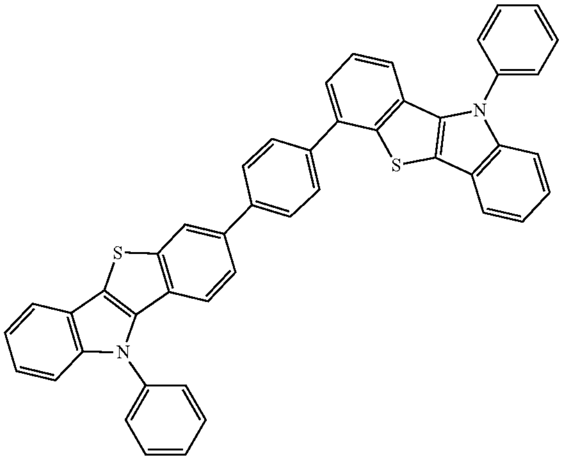
874
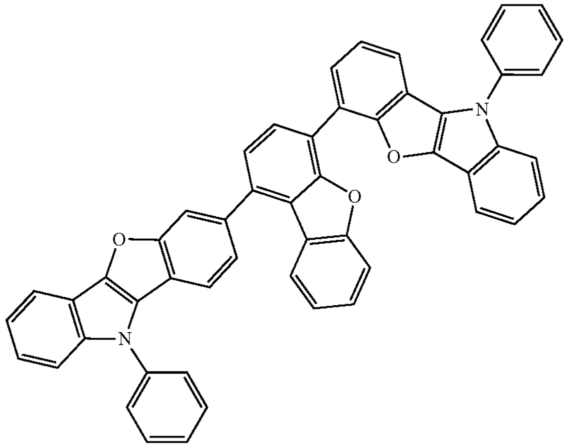

875
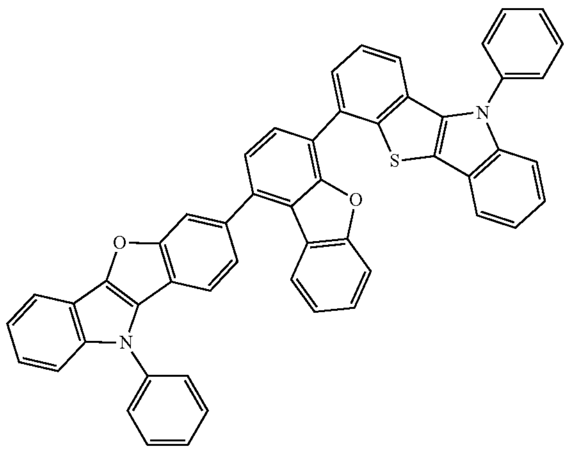
876
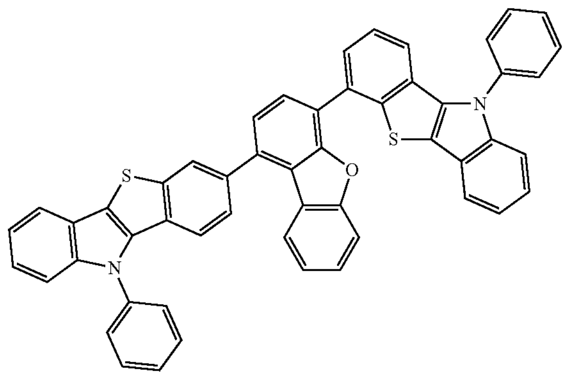
877
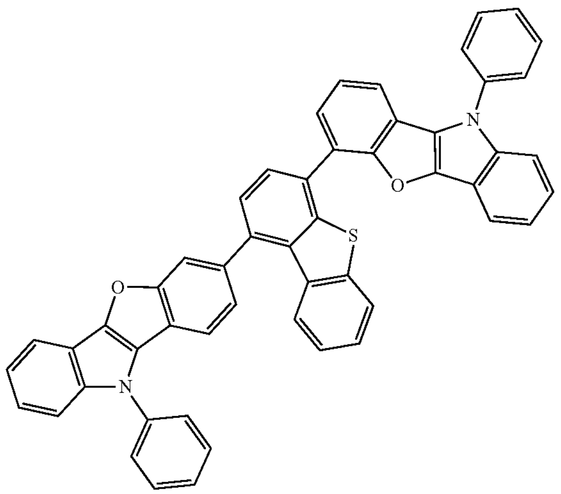
878
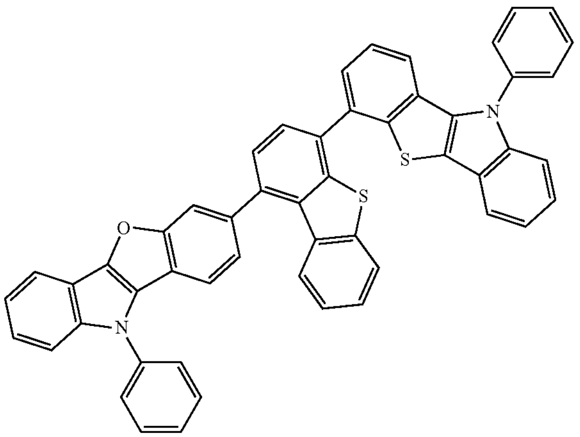
879
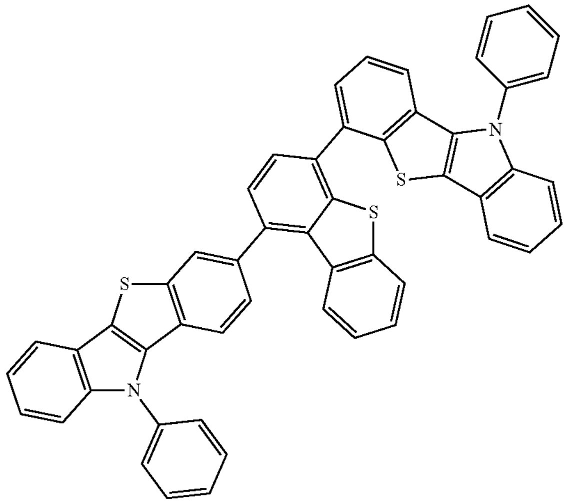
880
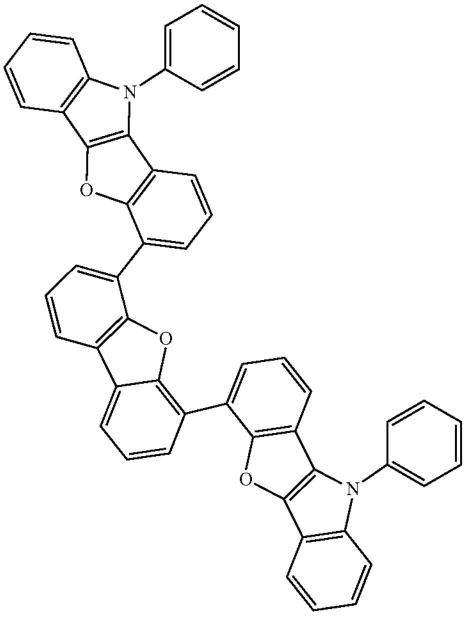

-continued
881
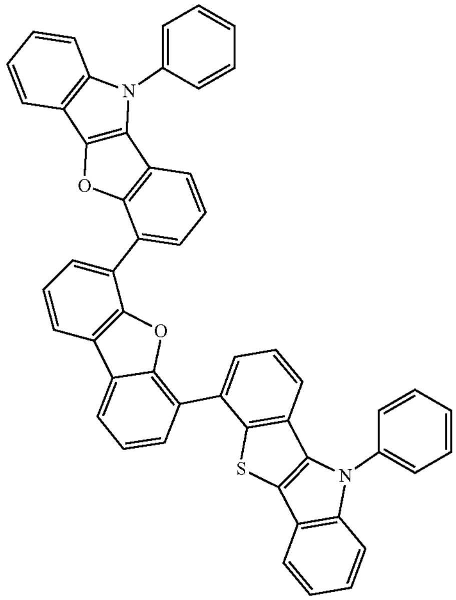
882
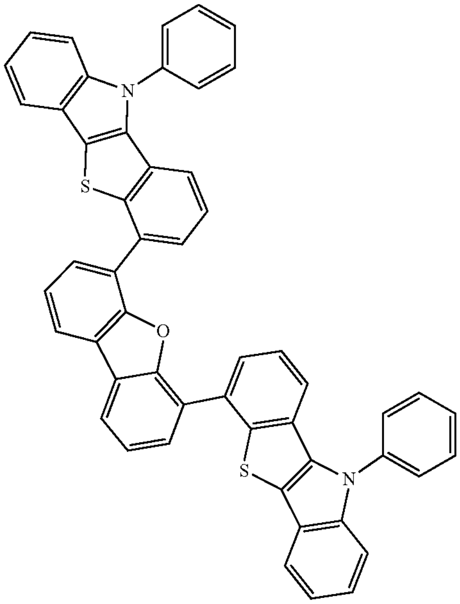
-continued
883
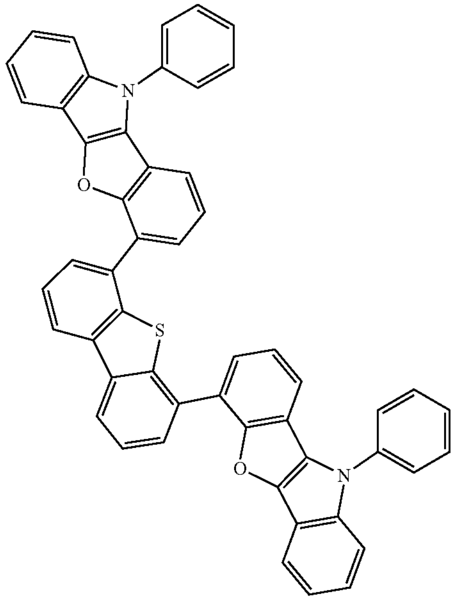
884
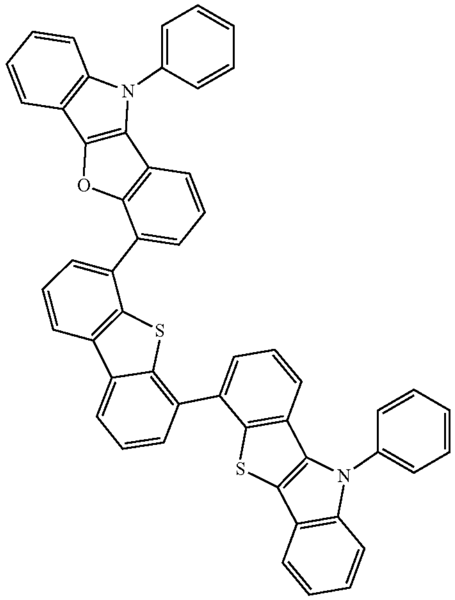

-continued
885
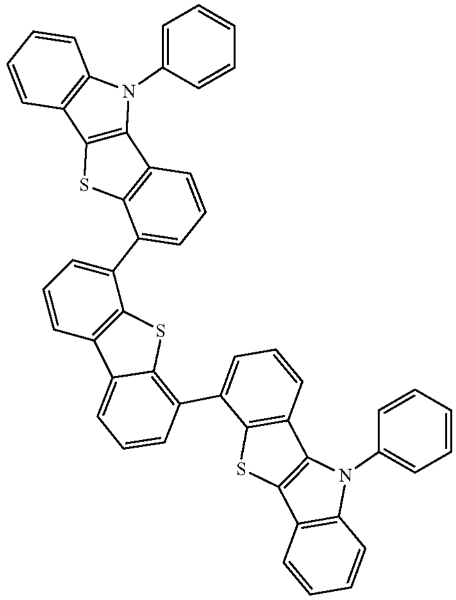
886
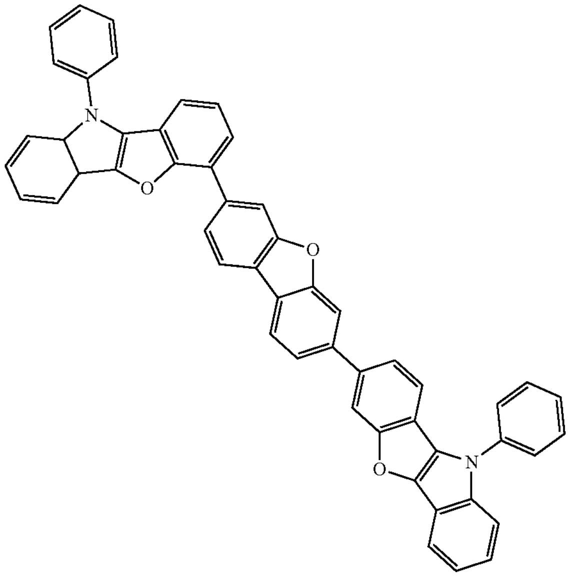
-continued
887
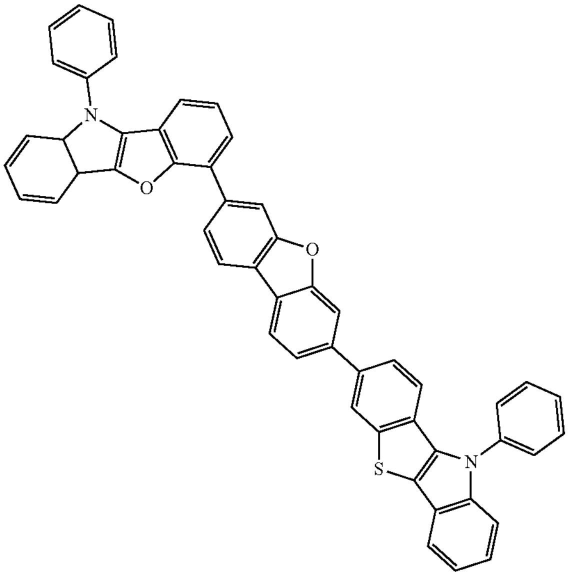
888
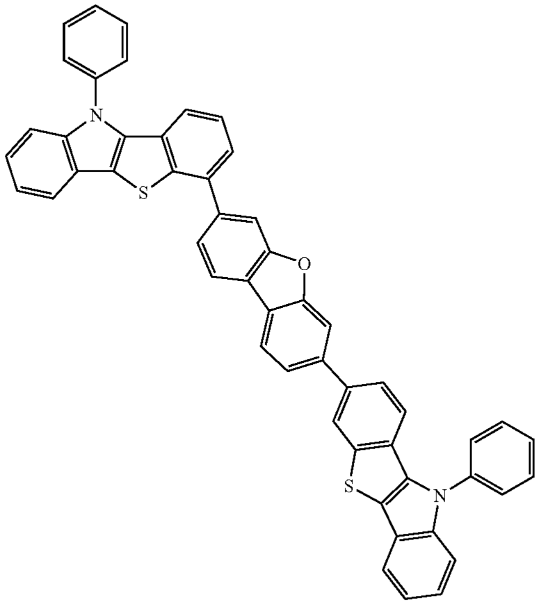

-continued
889
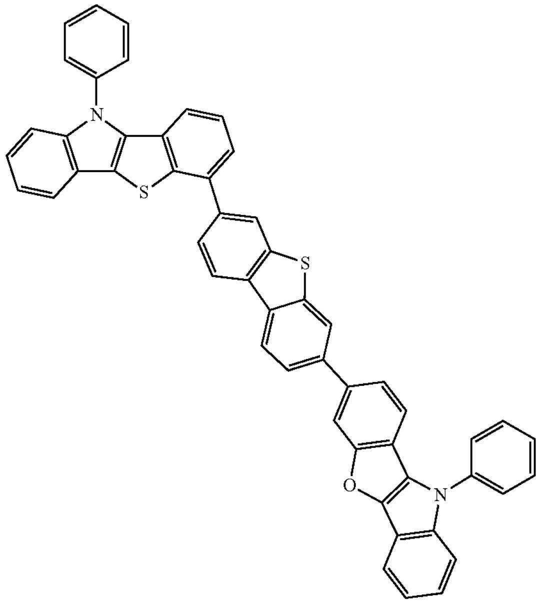
890
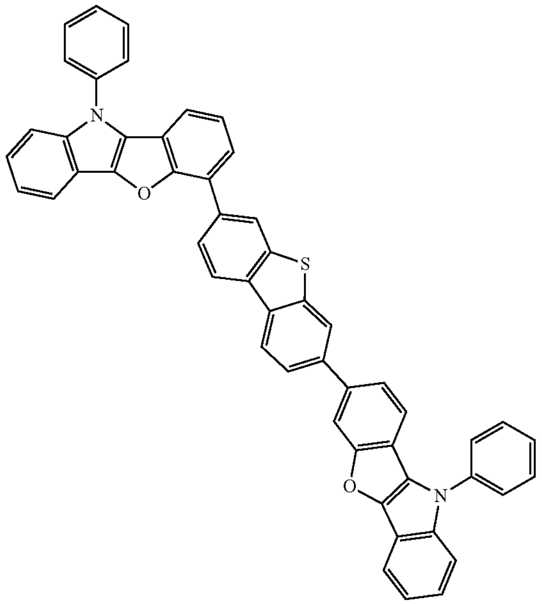
-continued
891
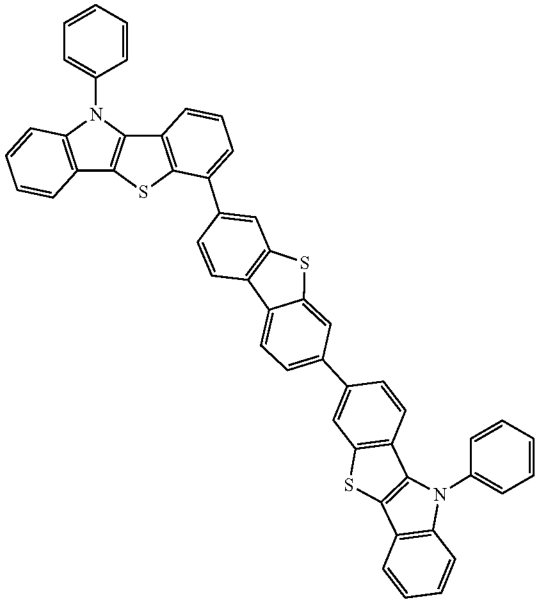
892
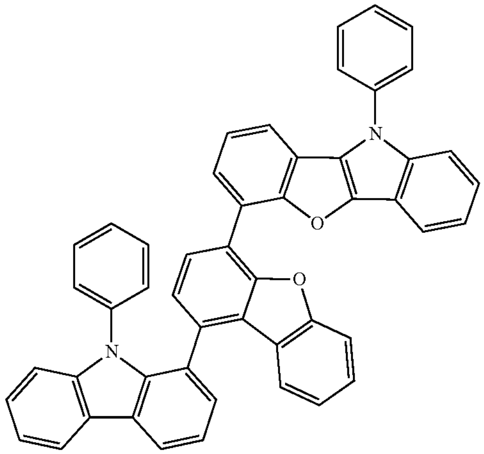
893
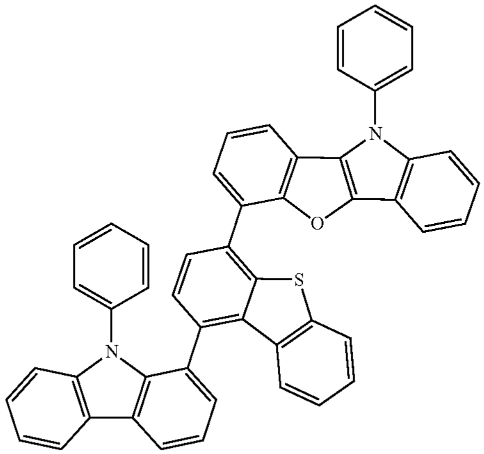

-continued
894
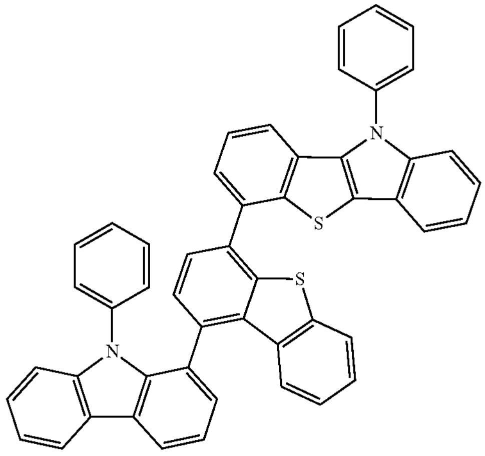
895
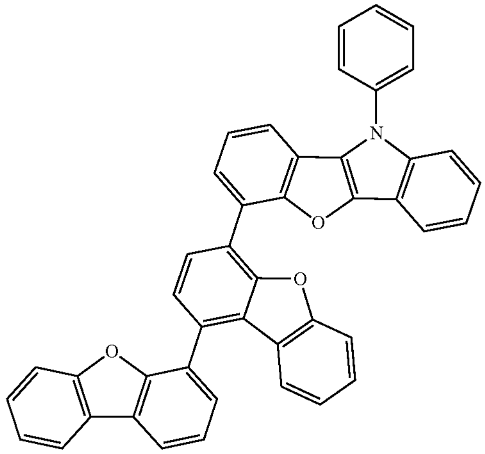
896
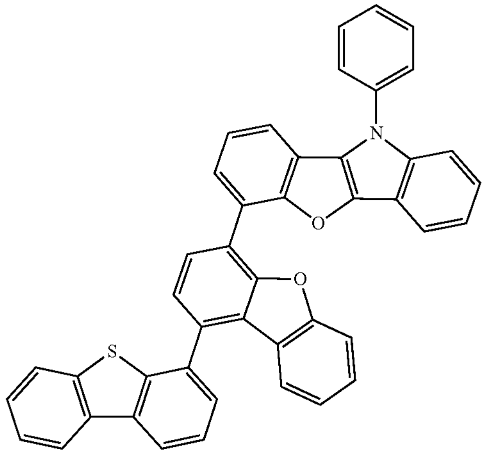
-continued
897
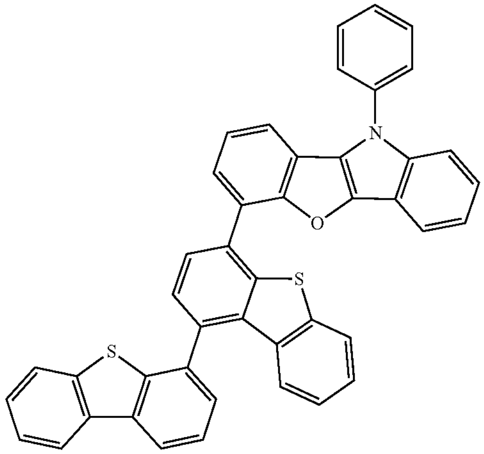
898
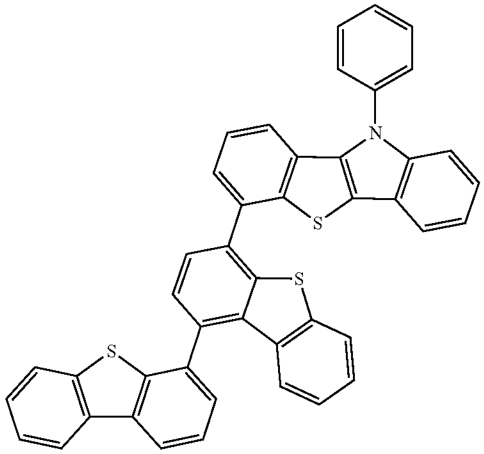
899
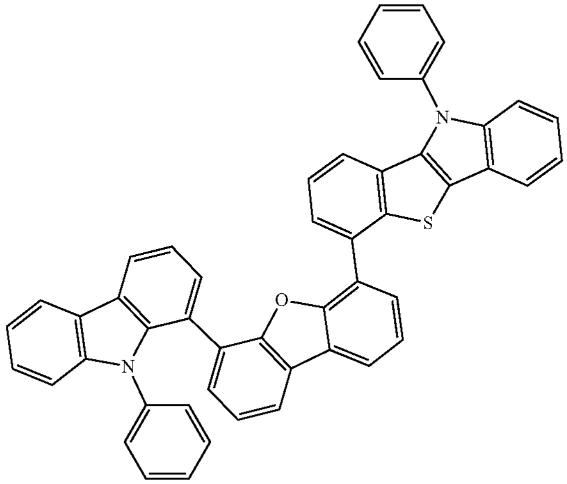

-continued
900
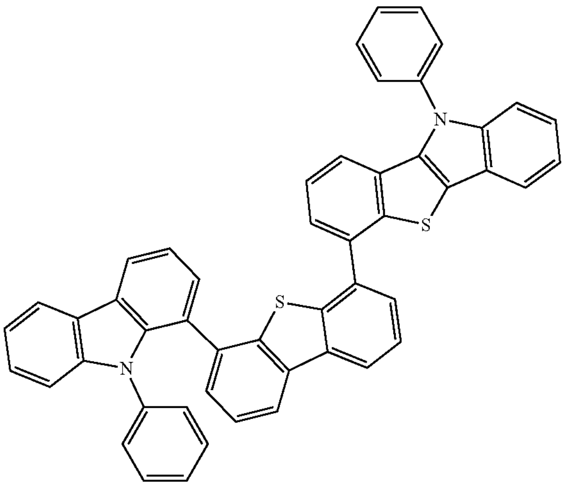
901
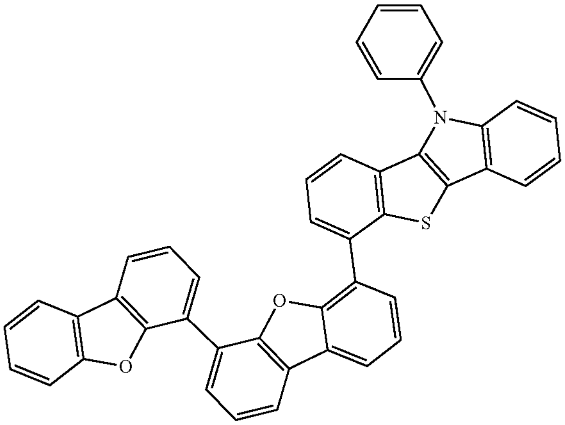
902
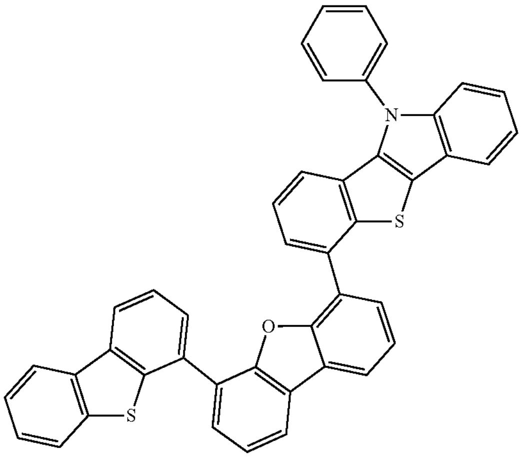
-continued
903
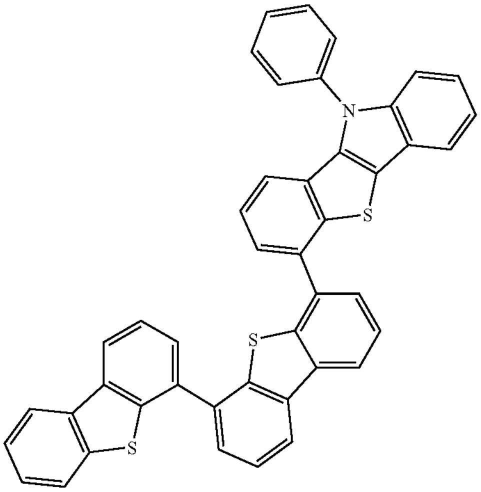
904
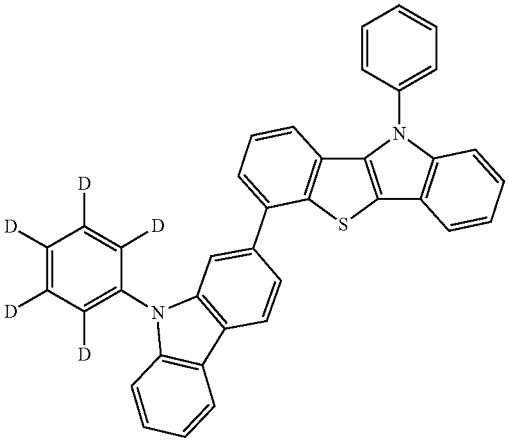
905
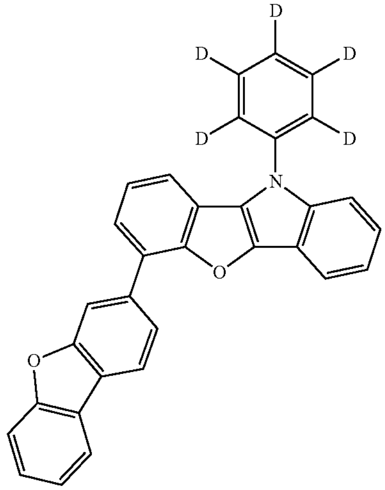

-continued

906

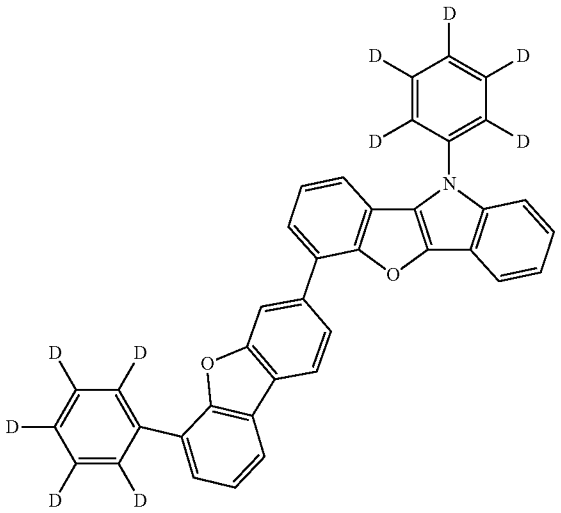

907

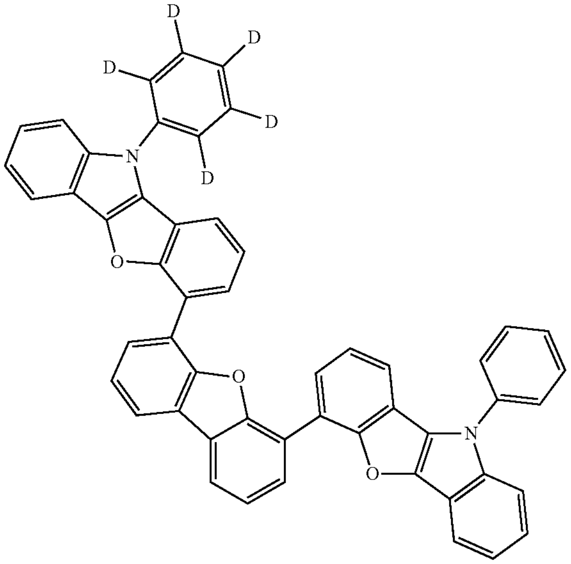

909

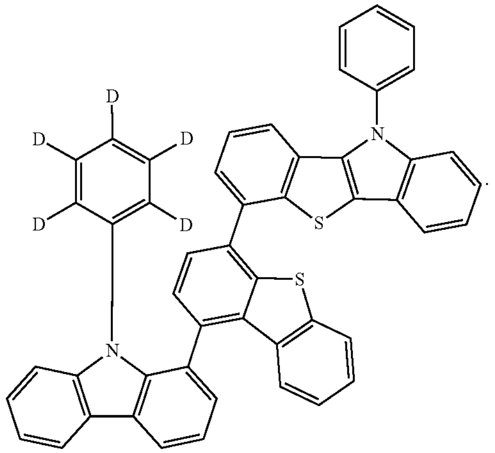

14. A polycyclic compound represented by Formula 1:

[Formula 1]

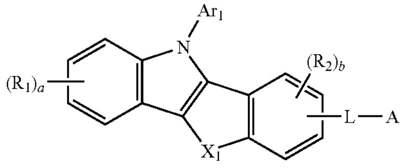

wherein in Formula 1, $X_1$ is O or S, $Ar_1$ is a substituted or unsubstituted aryl group having 6 to 30 ring-forming carbon atoms, or a substituted or unsubstituted heteroaryl group having 2 to 30 ring-forming carbon atoms, except that $Ar_1$ is not a heteroaryl group containing two or more nitrogen (N) atoms, $R_1$ is a hydrogen atom, a deuterium atom, a halogen atom, or a substituted or unsubstituted alkyl group having 1 to 20 carbon atoms, $R_2$ is a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or is bonded to an adjacent group to form a ring, a is an integer from 0 to 4, b is an integer from 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, except that L does not include a carbazole group, and A is a group represented by Formula 2-1 or Formula 2-2, except that L is not a direct linkage when A is a group represented by Formula 2-2:

[Formula 2-1]

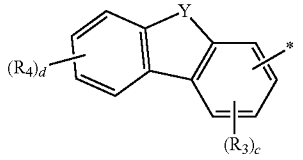

[Formula 2-2]

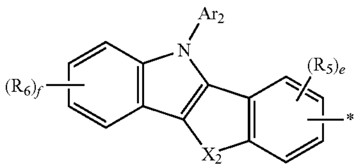

wherein in Formula 2-1 and Formula 2-2,

Y is $N(Ar_3)$, O, or S, $X_2$ is O or S, $Ar_2$ and $Ar_3$ are each independently a substituted or unsubstituted aryl group having 6 to 30 ring-forming carbon atoms, or a substituted or unsubstituted heteroaryl group having 2 to 30 ring-forming carbon atoms, except that $Ar_2$ and $Ar_3$ are each not a heteroaryl group containing two or more nitrogen (N) atoms, $R_3$ to $R_5$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, $R_6$ is a hydrogen atom, a deuterium atom, a halogen atom, or a substituted or unsubstituted alkyl group having 1 to 20 carbon atoms, c and e are each independently an integer from 0 to 3, d and f are each independently an integer from 0 to 4, and —* represents a binding site to a neighboring atom.

15. The polycyclic compound of claim 14, wherein the polycyclic compound represented by Formula 1 is represented by one of Formula 3-1 to Formula 3-3:

[Formula 3-1]

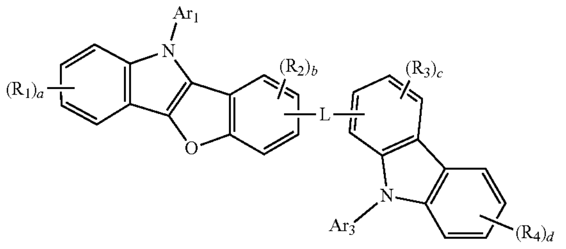

[Formula 3-2]

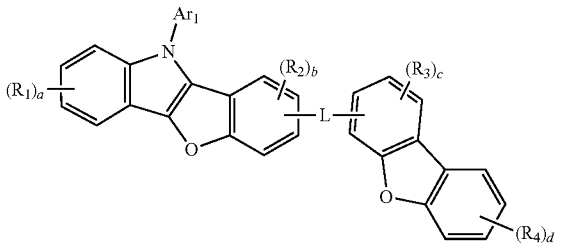

[Formula 3-3]

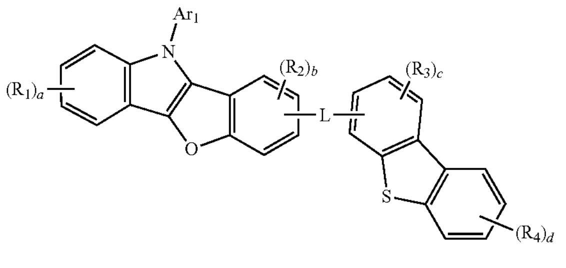

wherein in Formula 3-1 to Formula 3-3, $R_1$ to $R_4$, L, $Ar_1$, $Ar_3$, and a to d are the same as defined in connection with Formulas 1, and 2-1.

16. The polycyclic compound of claim 14, wherein the polycyclic compound represented by Formula 1 is represented by one of Formula 4-1 to Formula 4-3:

[Formula 4-1]

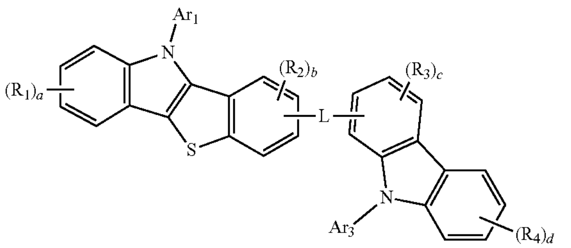

[Formula 4-2]

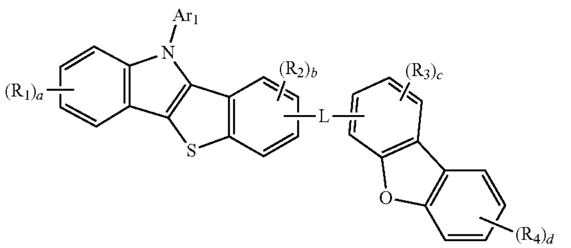

[Formula 4-3]

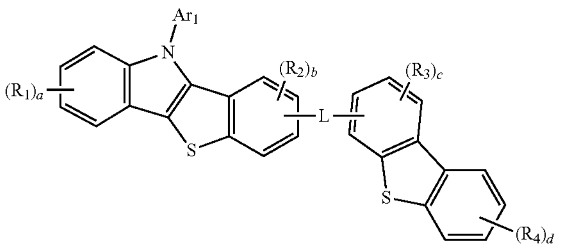

wherein in Formula 4-1 to Formula 4-3, $R_1$ to $R_4$, L, $Ar_1$, $Ar_3$, and a to d are the same as defined in connection with Formulas 1, and 2-1.

17. The polycyclic compound of claim 14, wherein the polycyclic compound represented by Formula 1 is represented by one of Formula 5-1 to Formula 5-3:

[Formula 5-1]

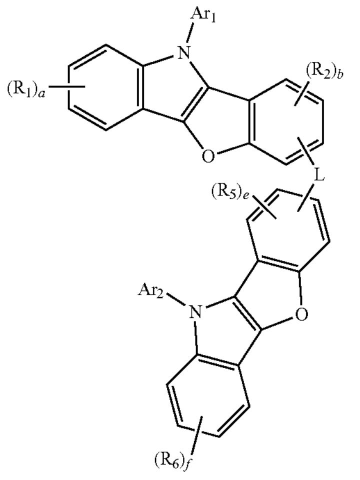

-continued

[Formula 5-2]

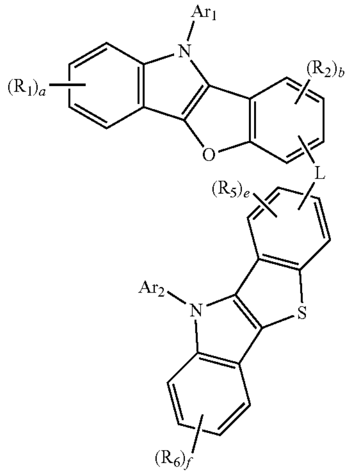

[Formula 5-3]

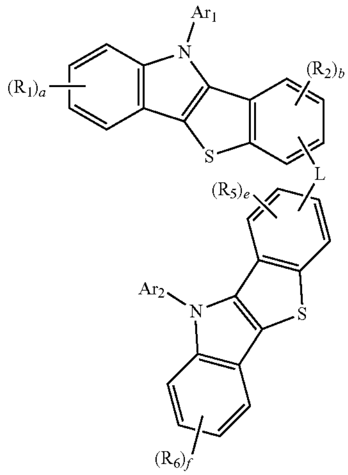

wherein in Formula 5-1 to Formula 5-3, $R_1$, $R_2$, $R_5$, $R_6$, L, $Ar_1$, $Ar_2$, a, b, e, and f are the same as defined in connection with Formulas 1, and 2-2.

18. The polycyclic compound of claim 14, wherein the polycyclic compound represented by Formula 1 is represented by Formula 6:

[Formula 6]

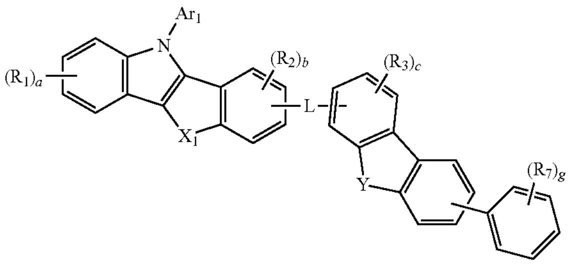

wherein in Formula 6, $R_7$ is a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and g is an integer from 0 to 5, and $R_1$ to $R_3$, L, $Ar_1$, Y, $X_1$, and a to c are the same as defined in connection with Formulas 1, and 2-2.

19. The polycyclic compound of claim 14, wherein the polycyclic compound represented by Formula 1 is represented by one of Formula 7-1 to Formula 7-3:

[Formula 7-1]

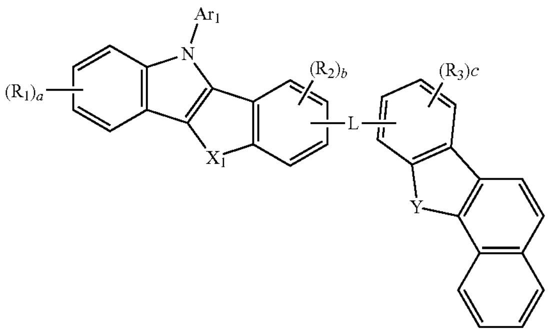

[Formula 7-2]

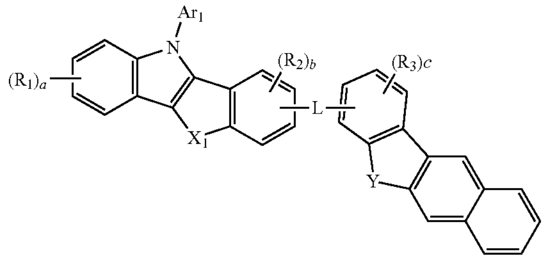

[Formula 7-3]

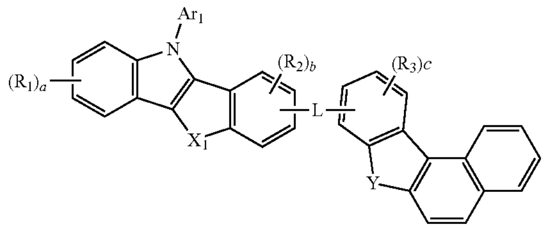

wherein in Formula 7-1 to Formula 7-3, $R_1$ to $R_3$, L, $Ar_1$, Y, $X_1$, and a to c are the same as defined in connection with Formulas 1, and 2-1.

20. The polycyclic compound of claim 14, wherein the polycyclic compound represented by Formula 1 is at least one selected from Compound Group 1:
[Compound Group 1]
1
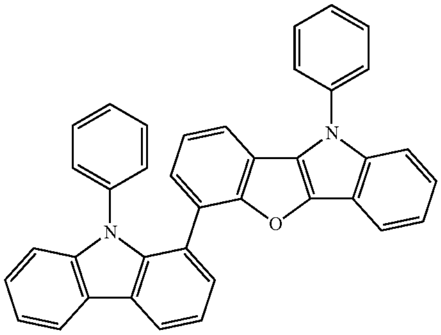
2
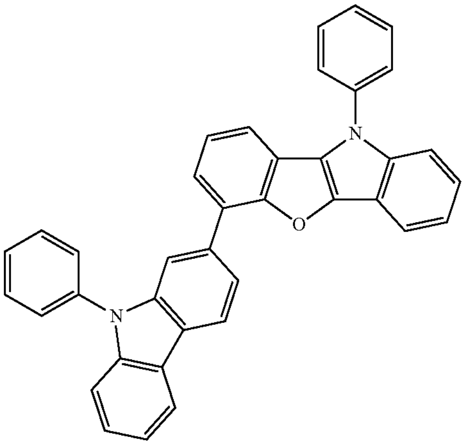
3
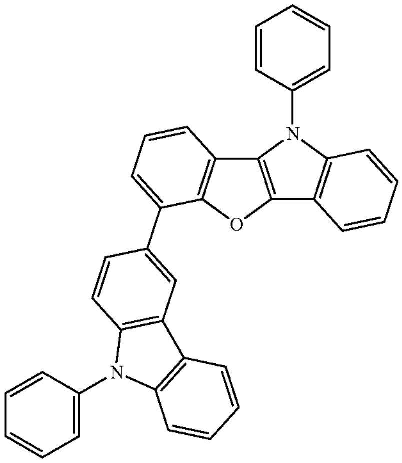
-continued
4
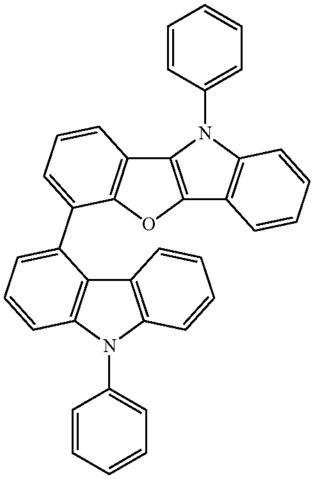
5
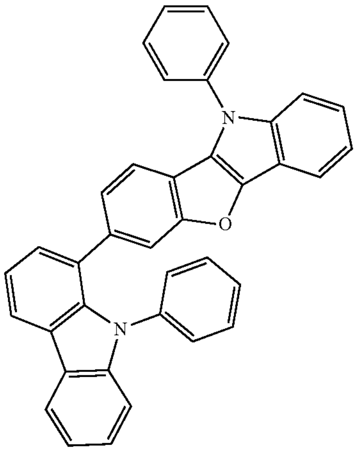
6
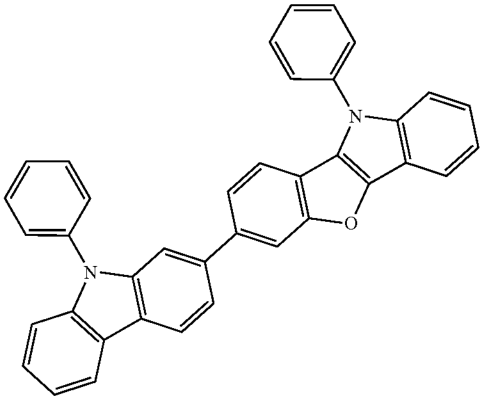

-continued
7
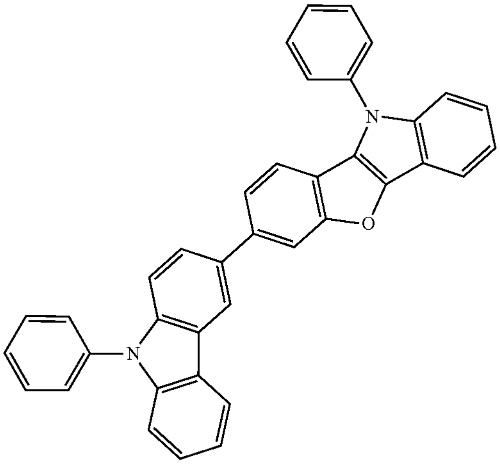
8
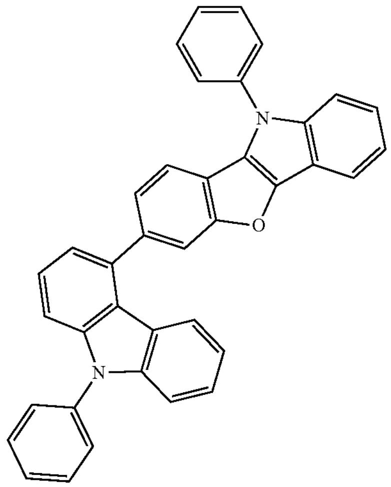
9
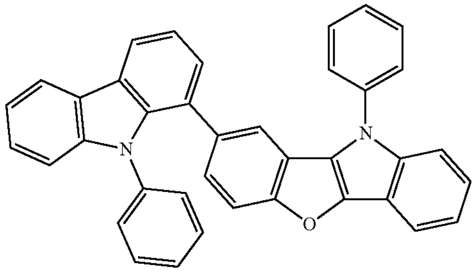
10
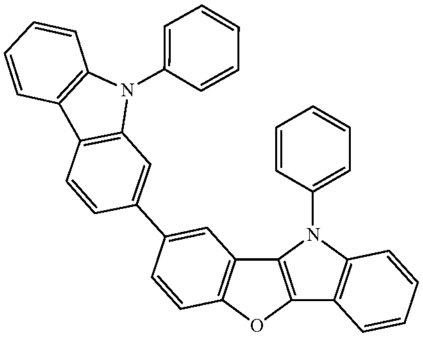
-continued
11
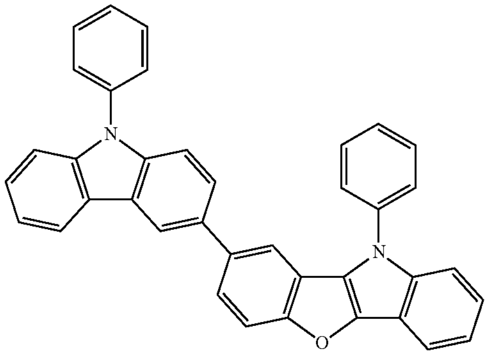
12
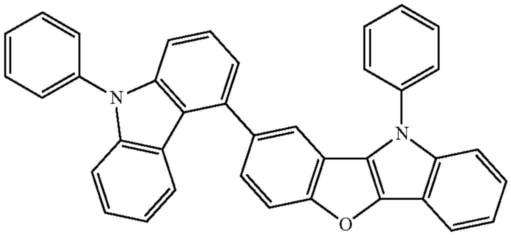
13
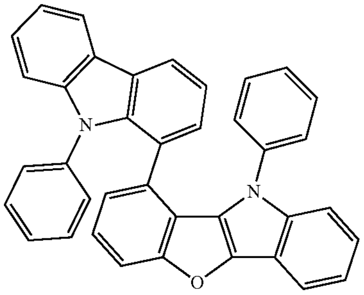
14
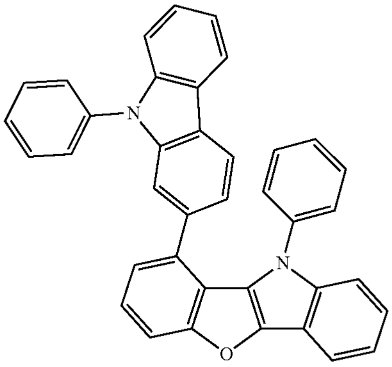

15
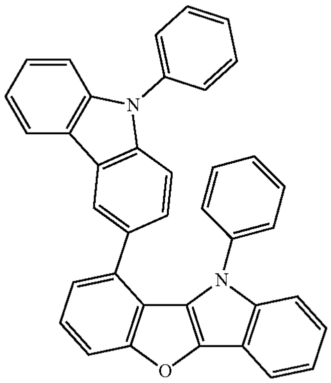
16
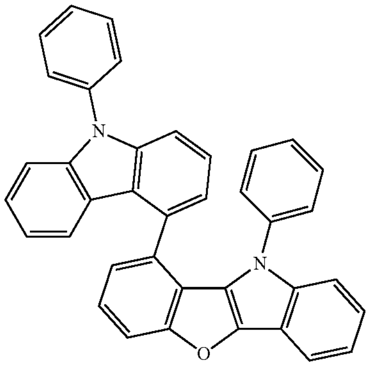
17
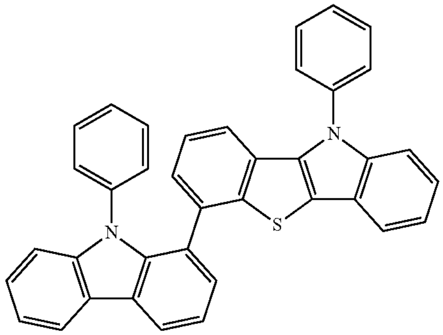
18
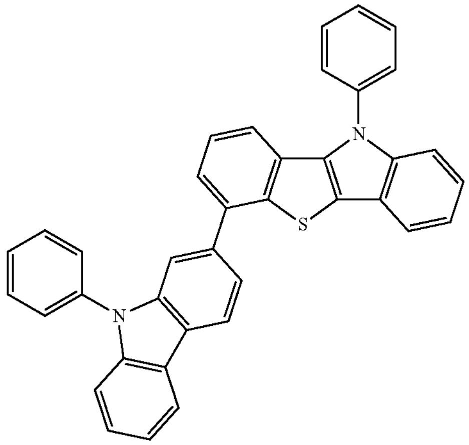
19
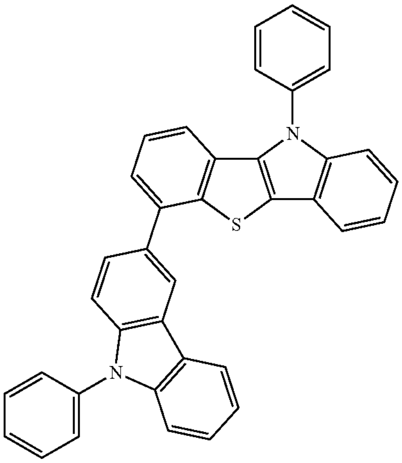
20
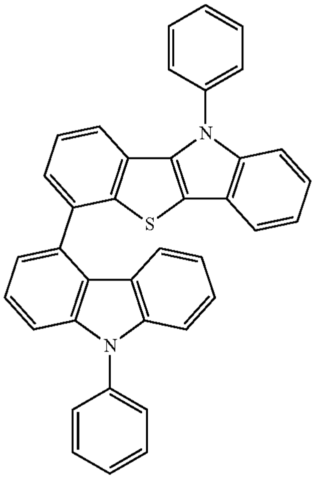
21
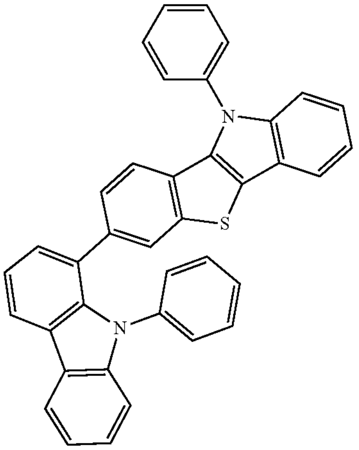

-continued
22
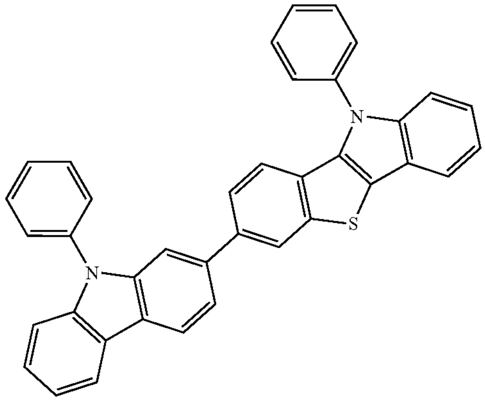
23
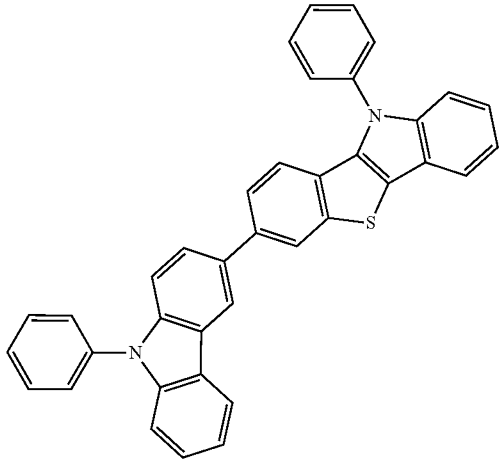
24
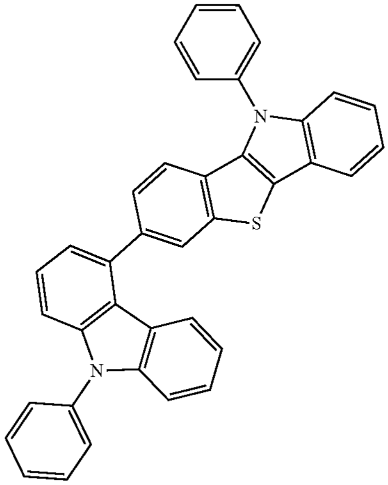
25
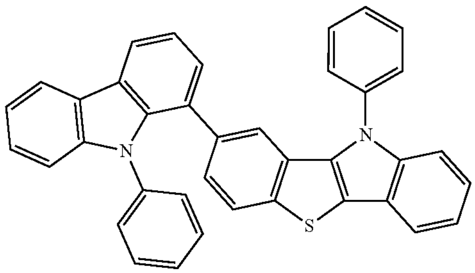
-continued
26
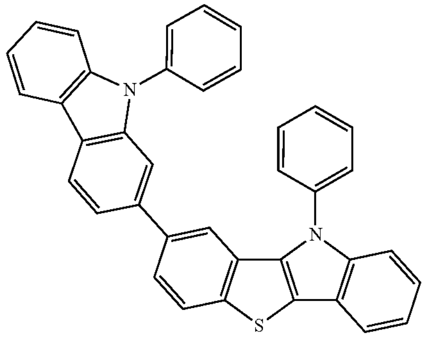
27
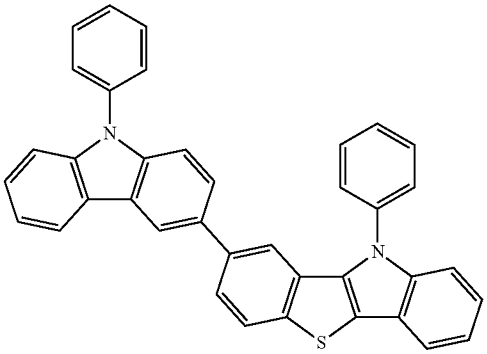
28
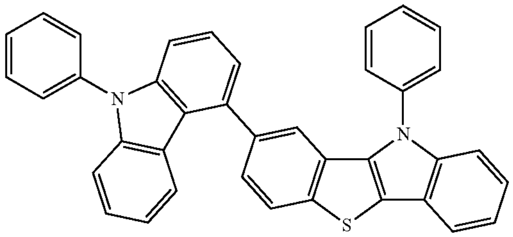
29
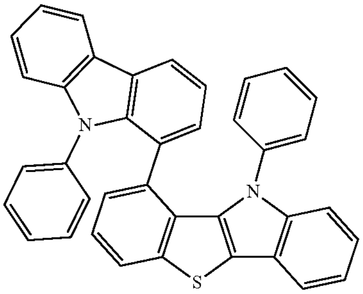
30
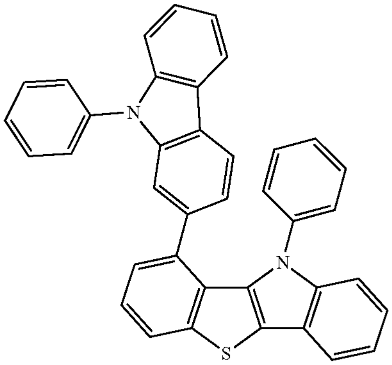

-continued
31
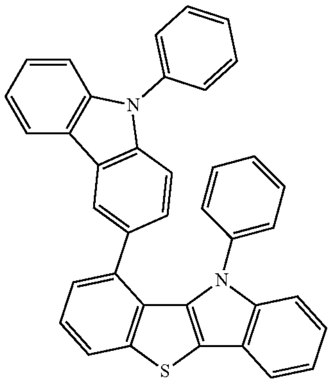
32
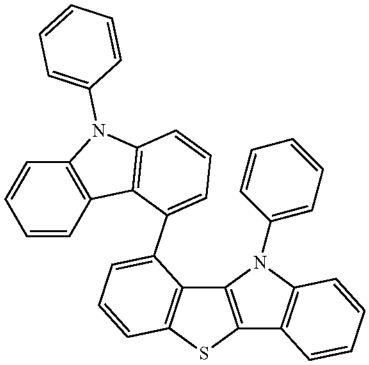
33
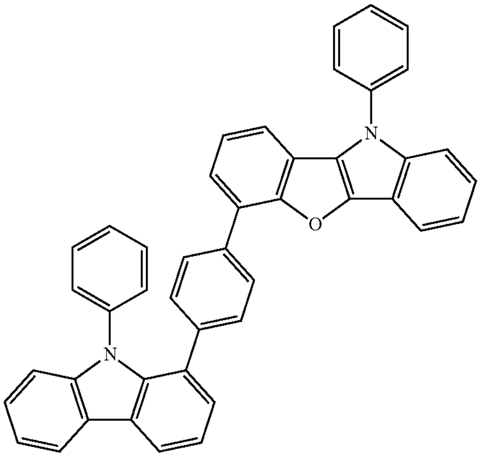
-continued
34
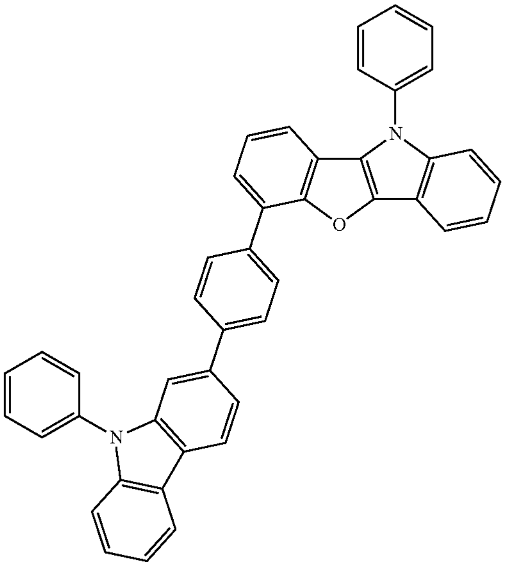
35
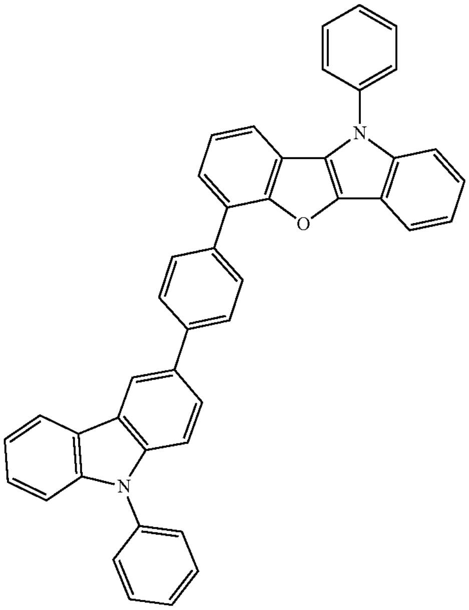

-continued
36
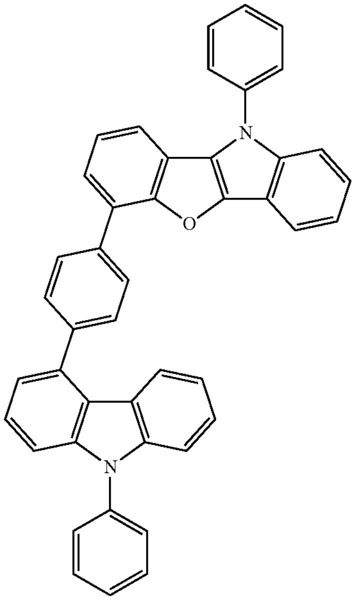
37
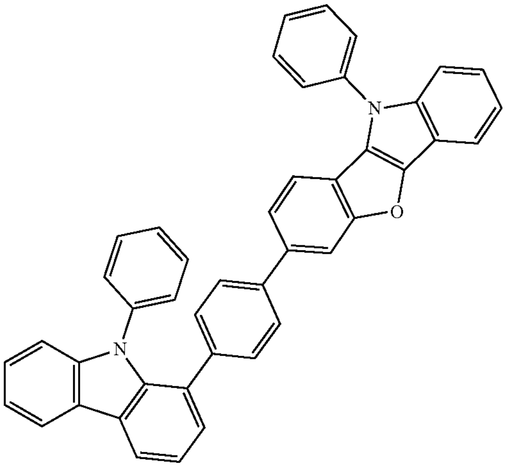
38
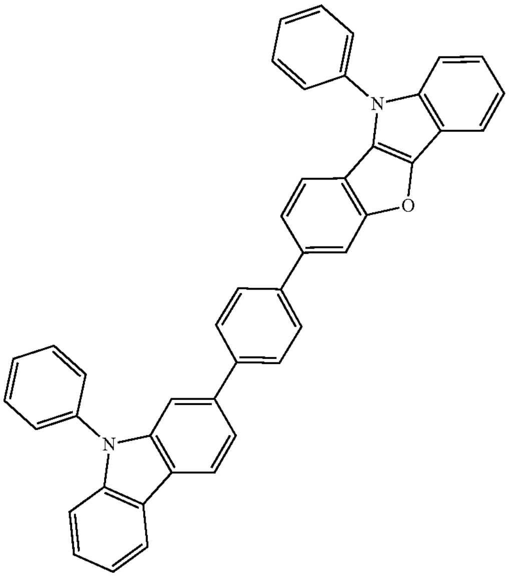
-continued
39
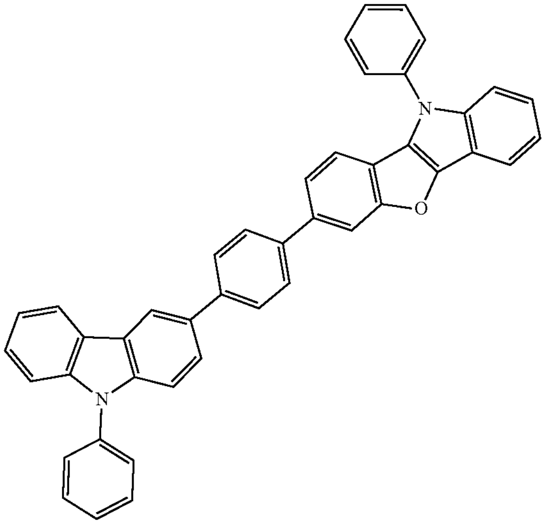
40
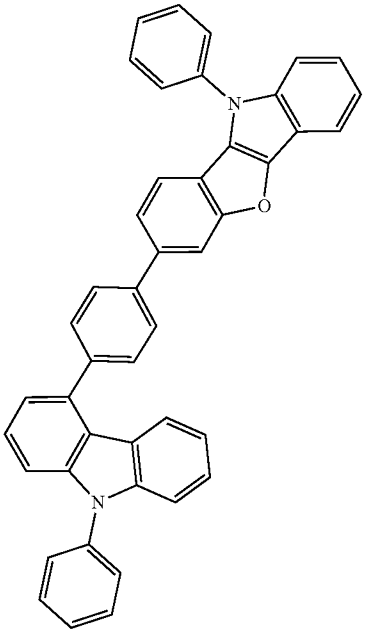

-continued
41
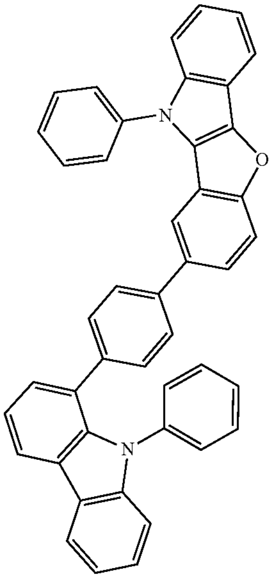
-continued
43
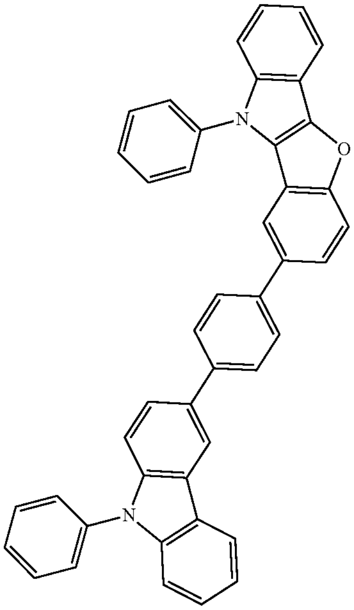
42
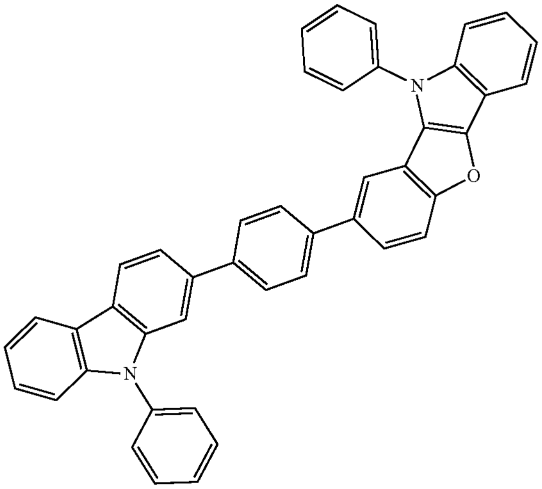
44
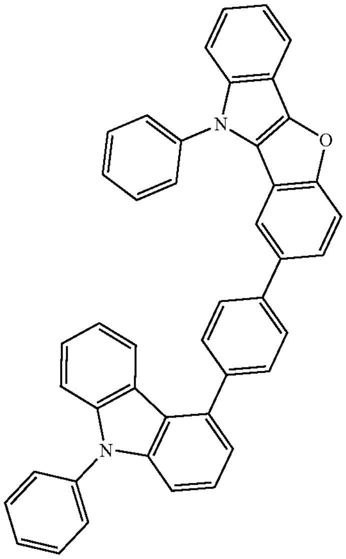

-continued
45
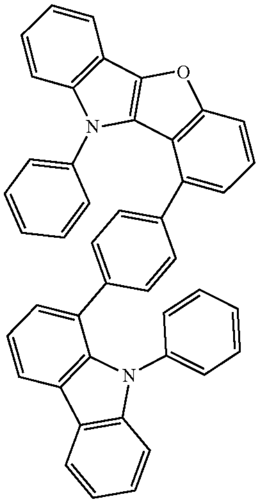
46
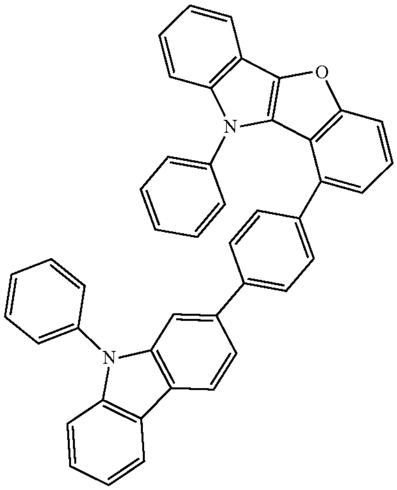
47
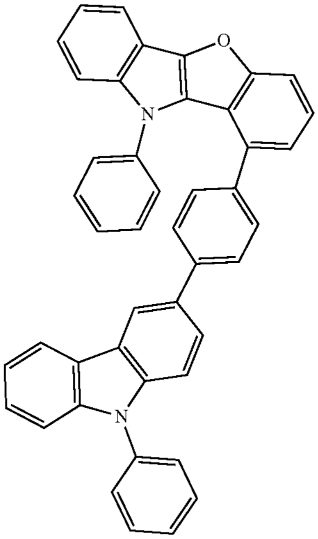
-continued
48
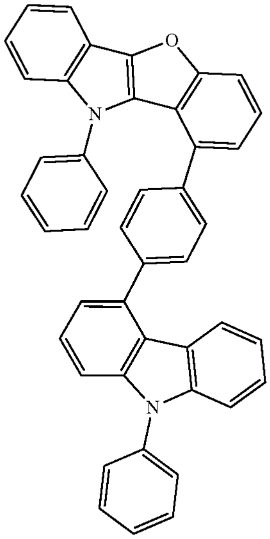
49
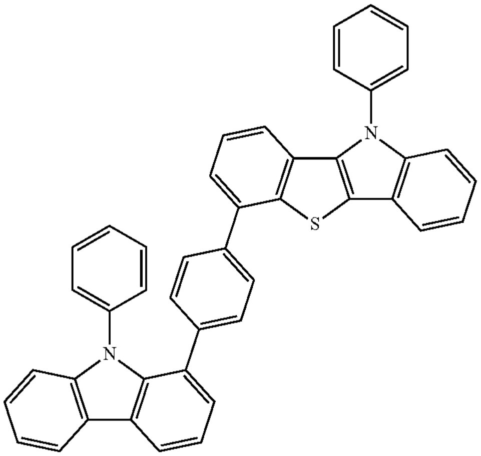
50
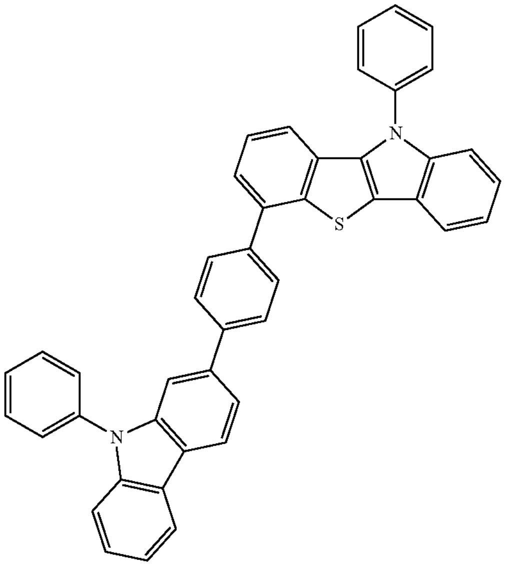

51
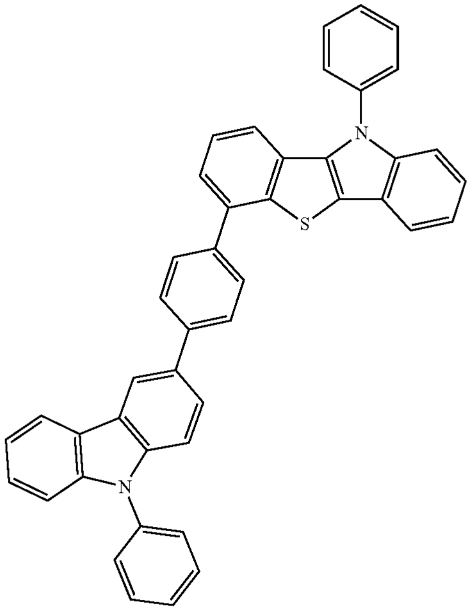
52
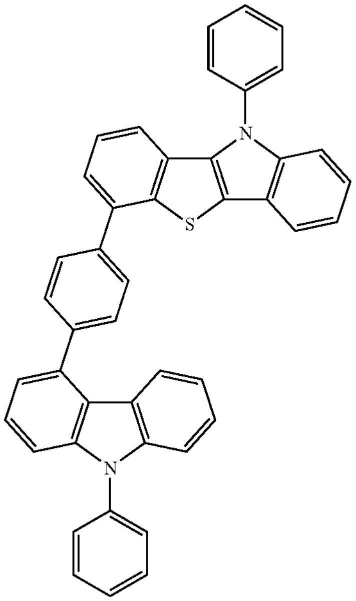
53
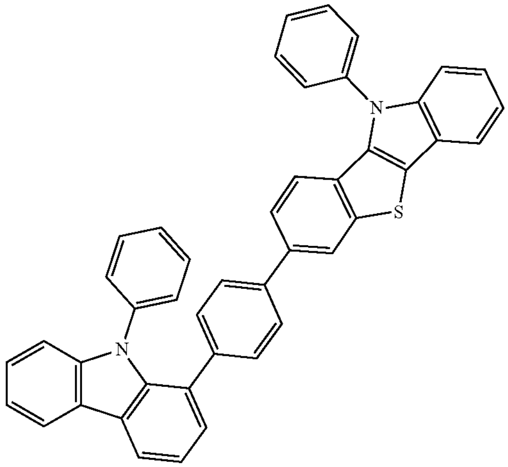
54
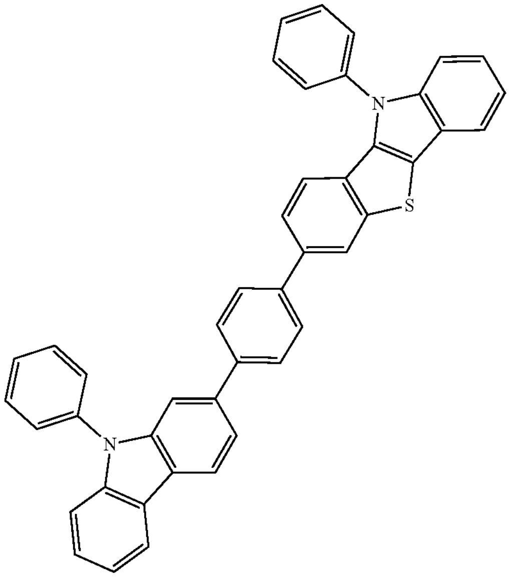
55
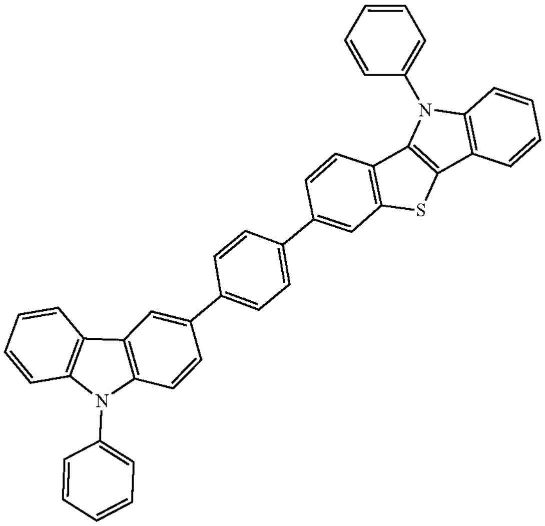

-continued
56
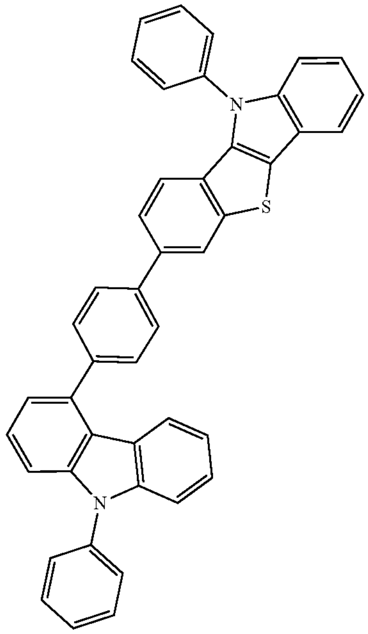
57
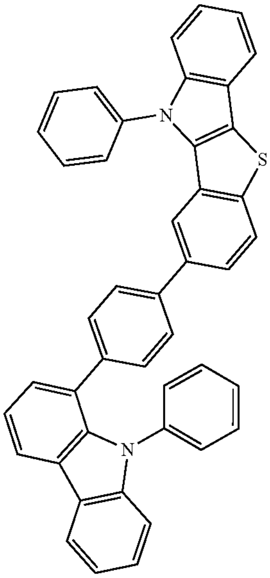
-continued
58
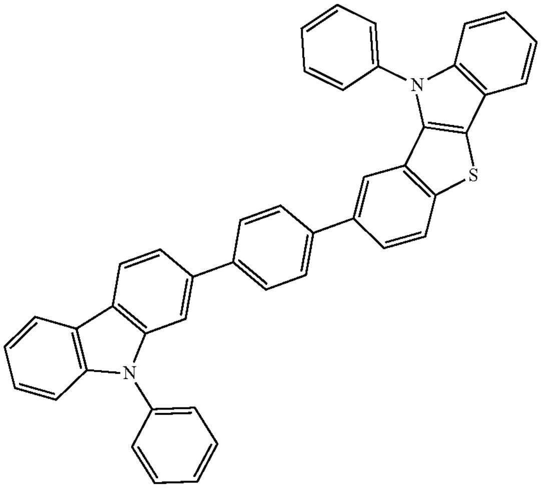
59
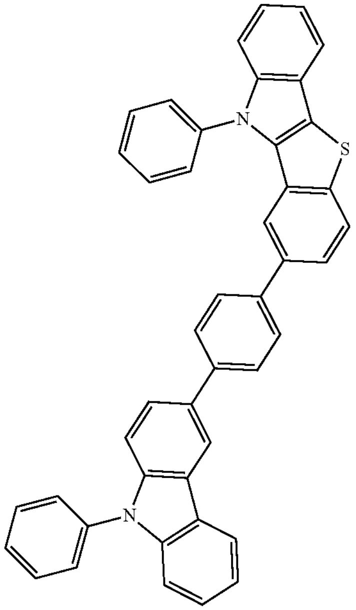

-continued
60
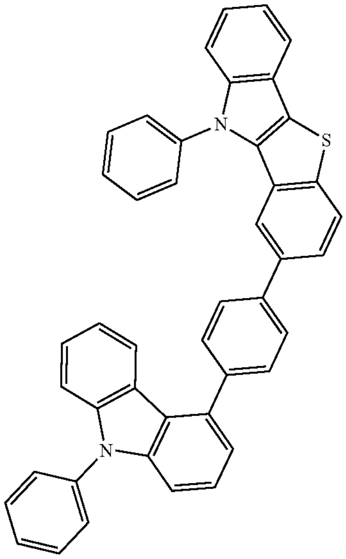
61
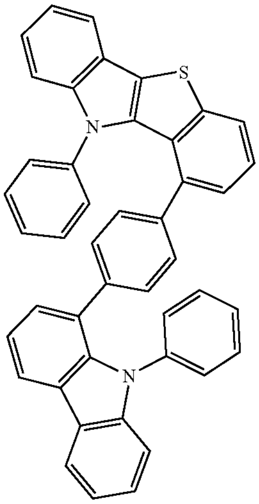
62
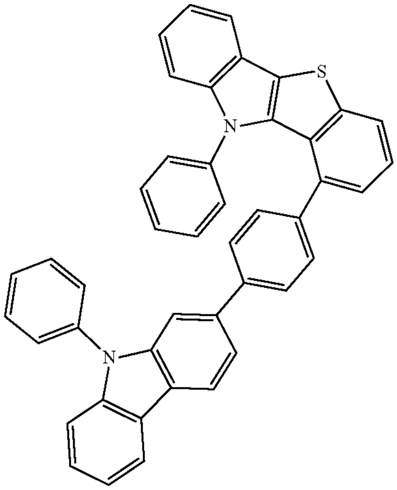
-continued
63
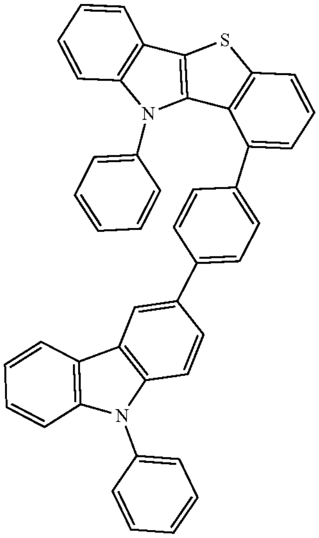
64
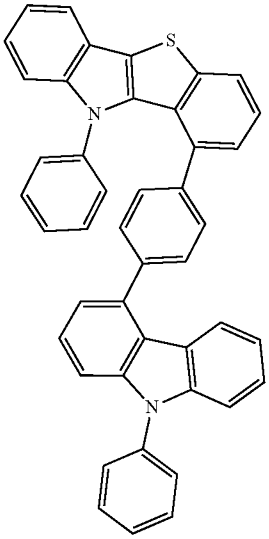
65
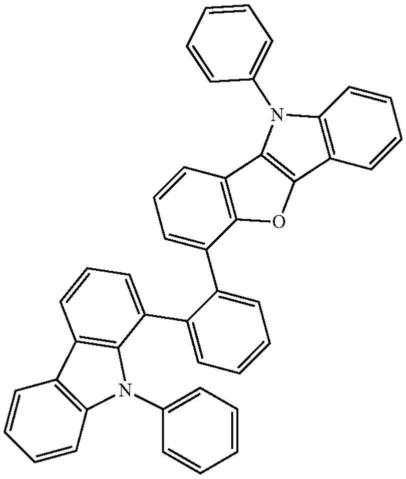

-continued
66
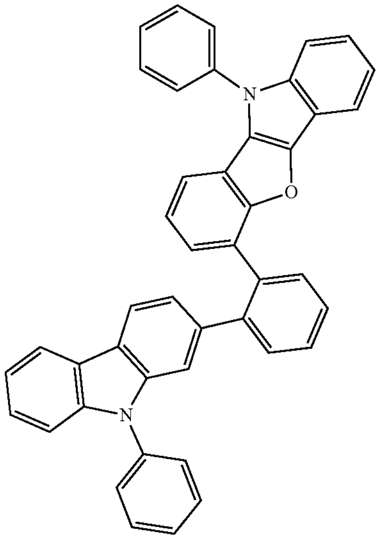
67
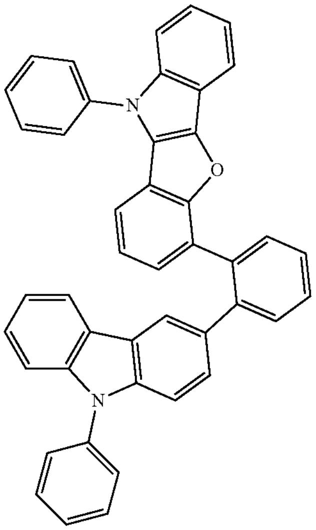
68
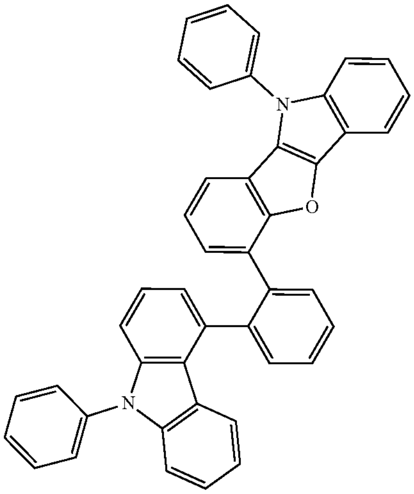
-continued
69
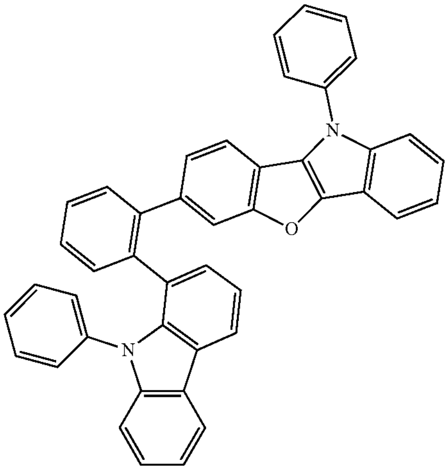
70
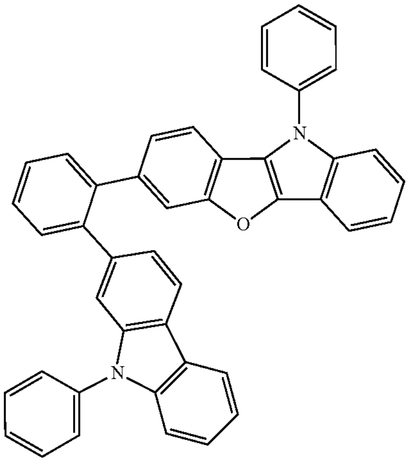
71
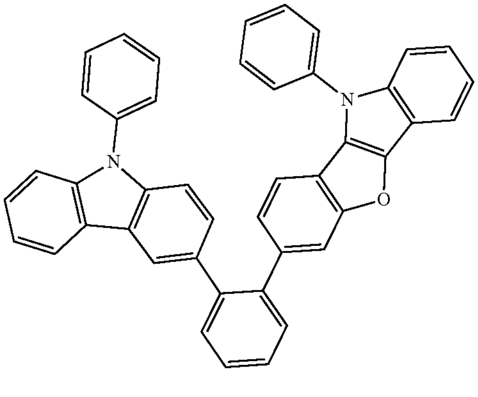

-continued
72
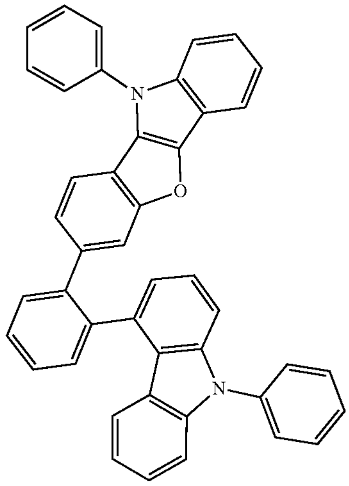
73
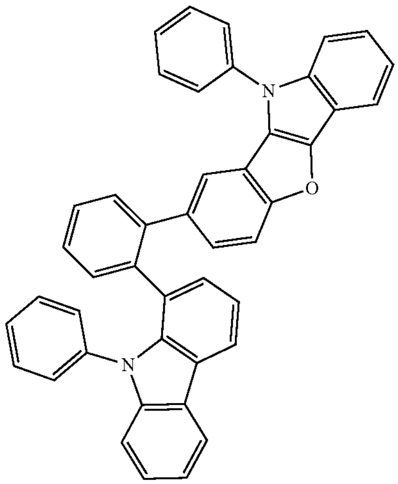
74
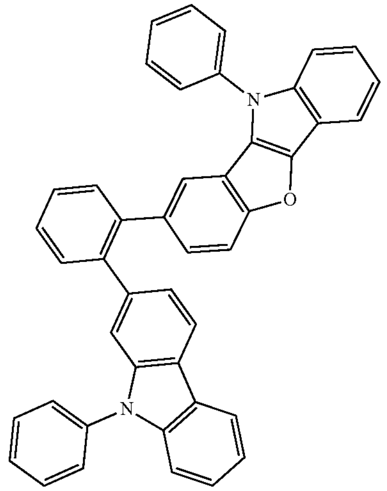
-continued
75
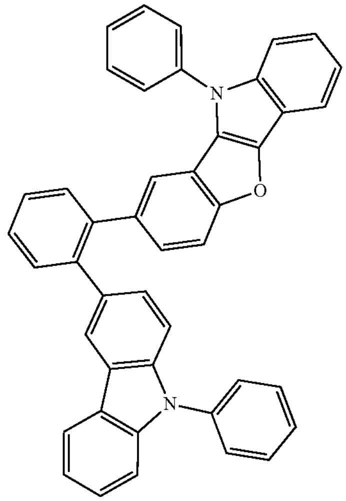
76
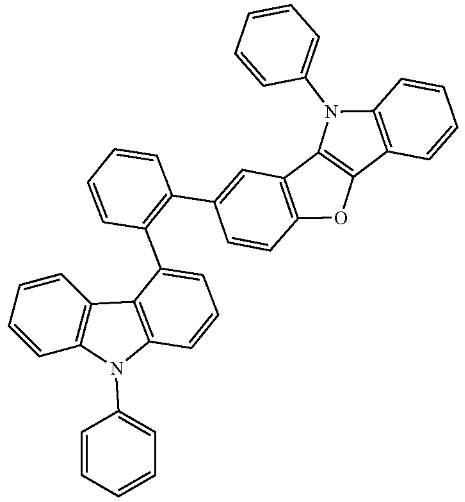
77
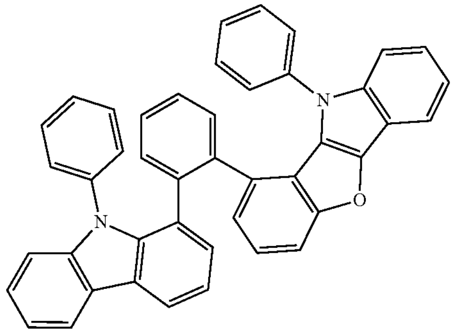

-continued
78
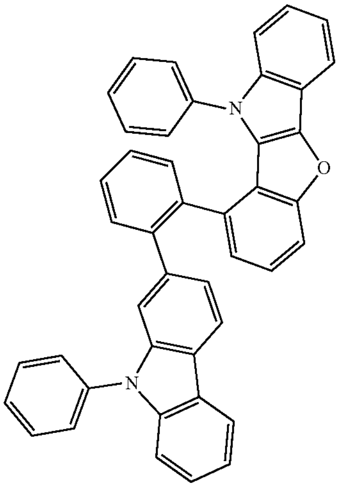
79
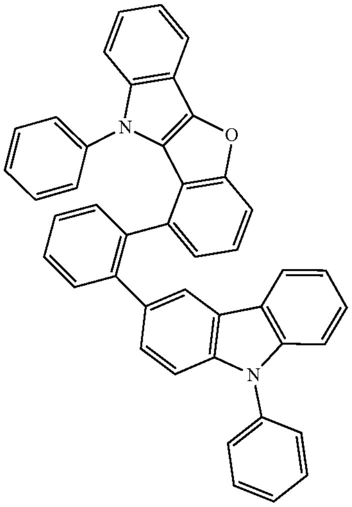
80
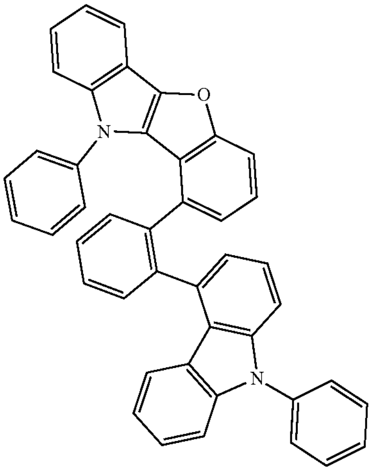
-continued
81
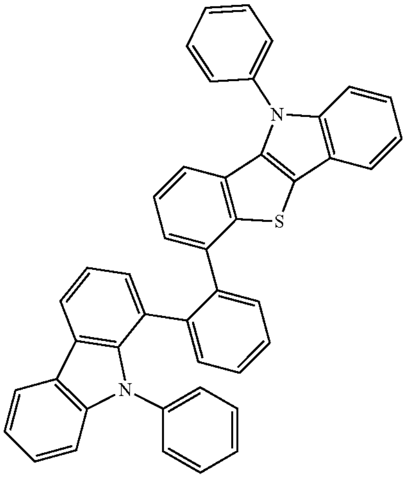
82
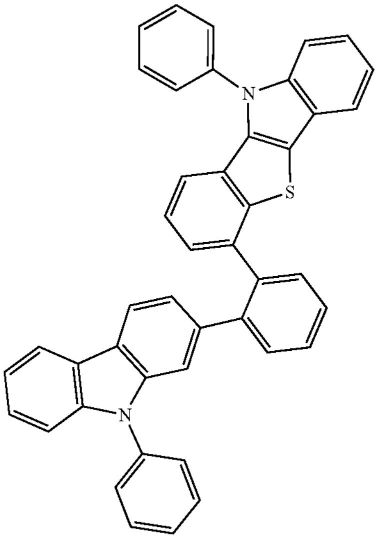
83
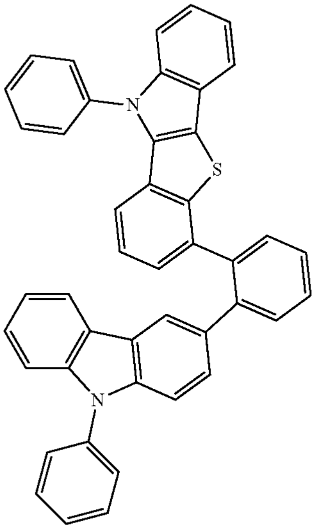

-continued
-continued
84
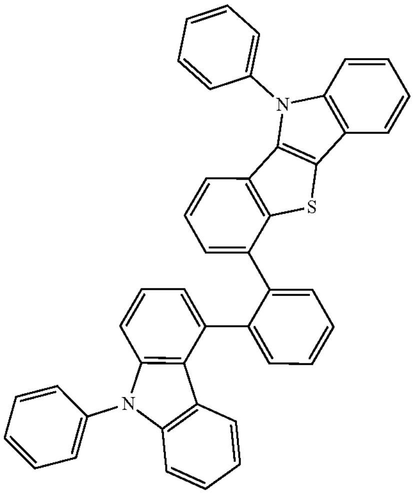
87
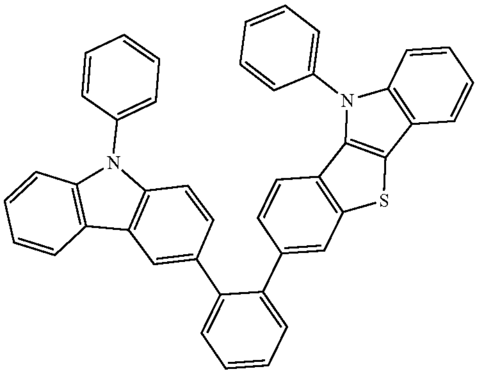
85
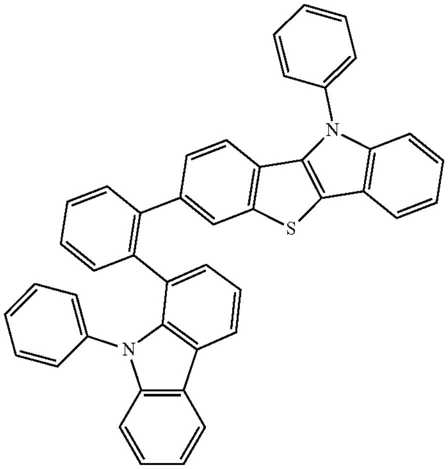
88
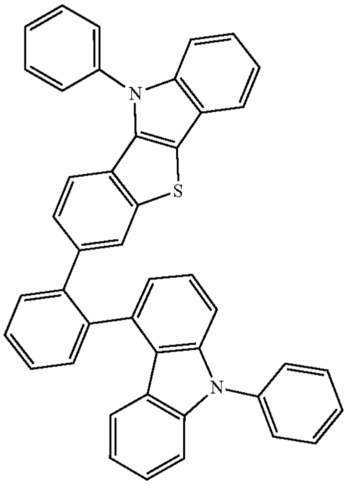
86
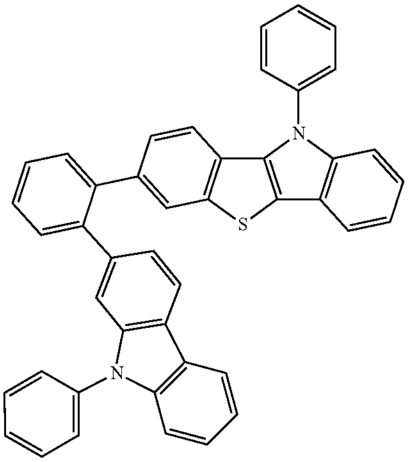
89
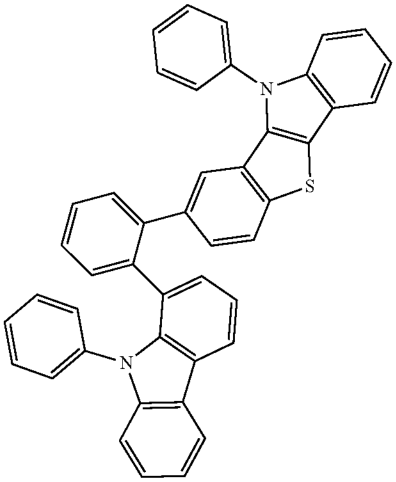

-continued
90
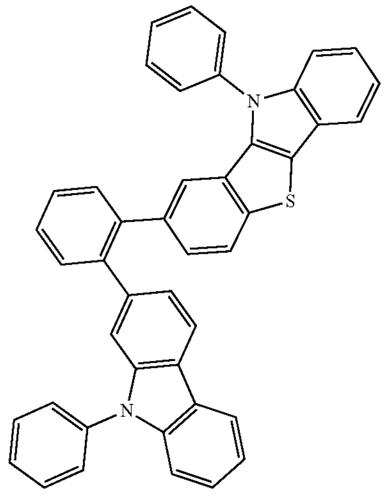
91
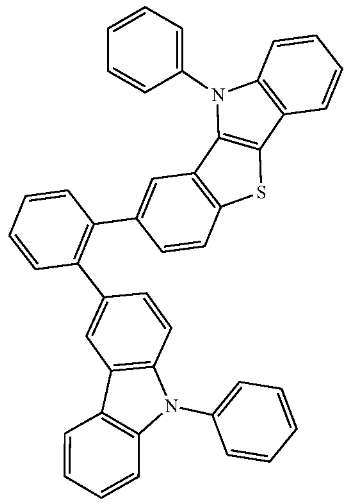
92
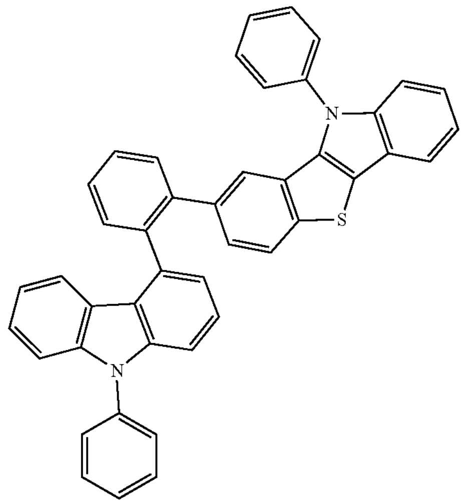
-continued
93
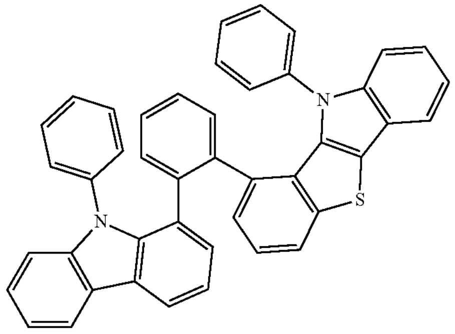
94
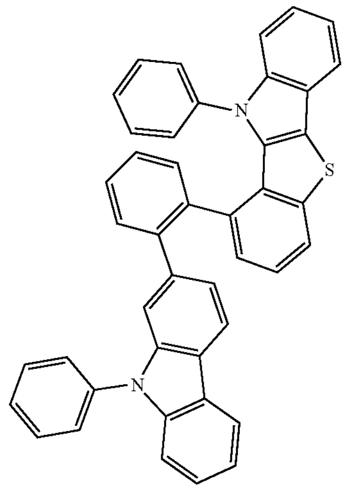
95
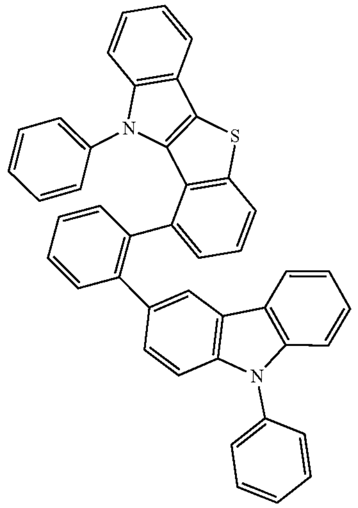

-continued
96
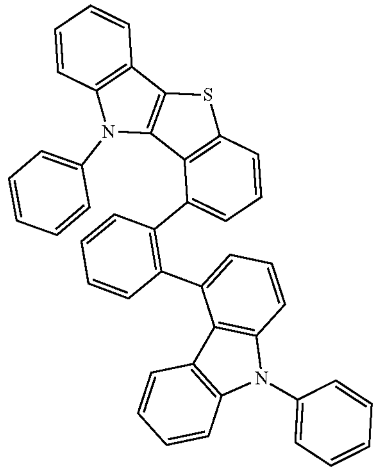
97
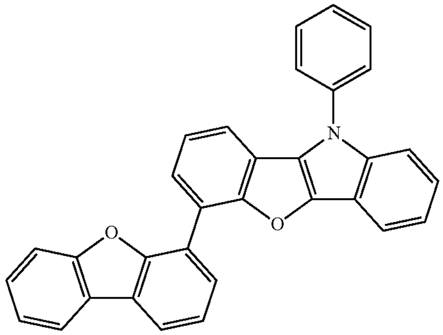
98
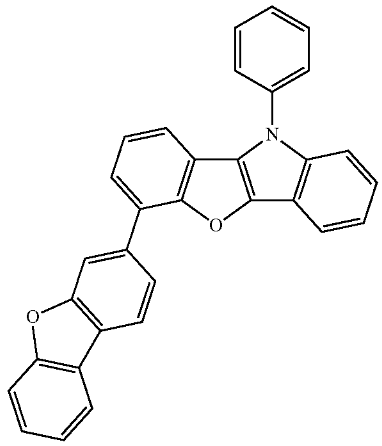
-continued
99
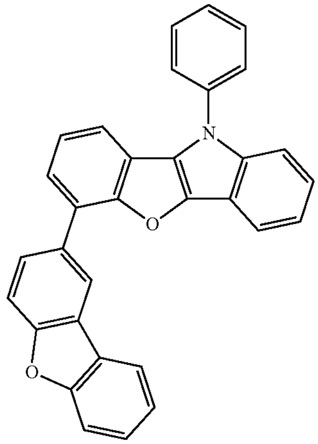
100
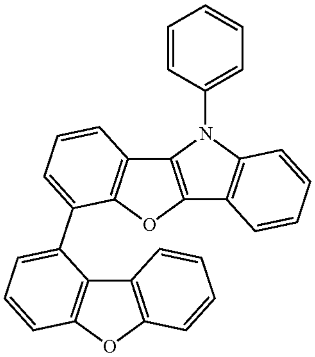
101
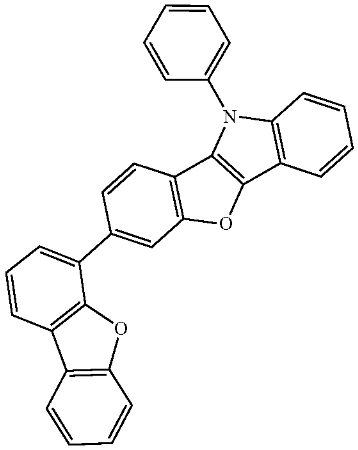

-continued
102
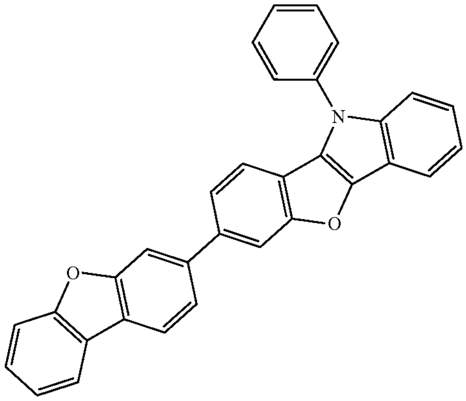
103
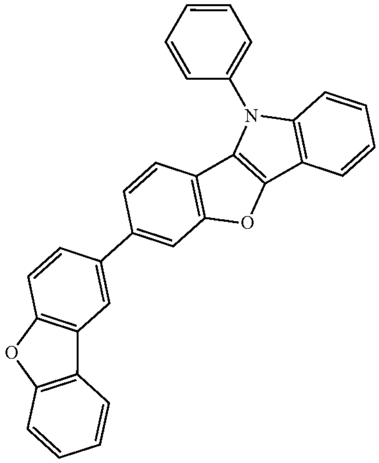
104
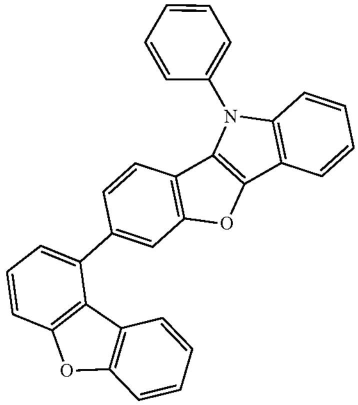
105
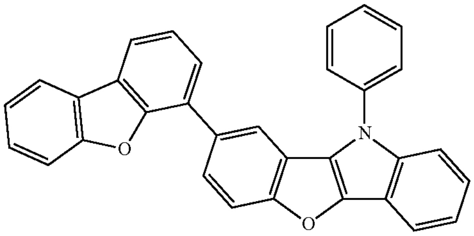
-continued
106
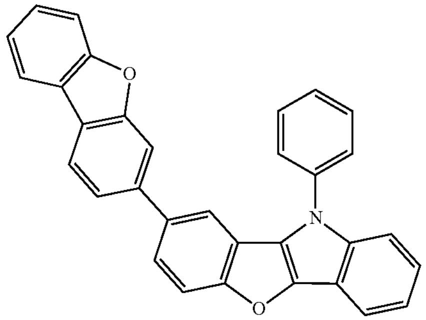
107
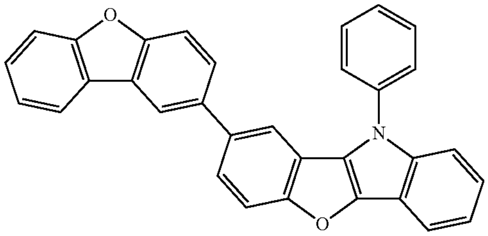
108
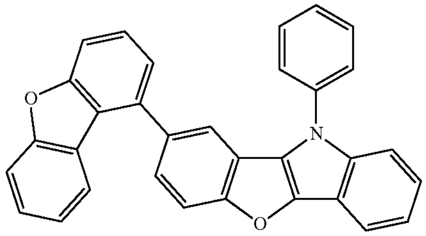
109
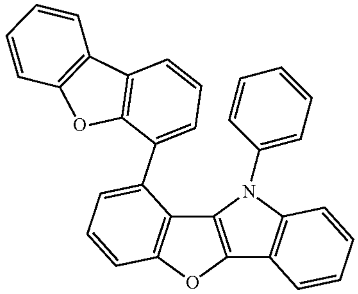
110
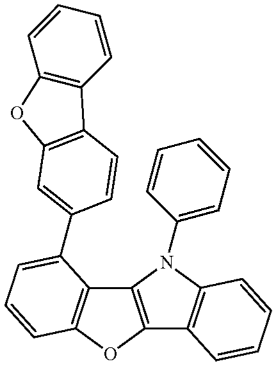

-continued
111
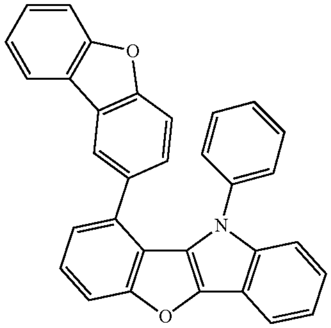
112
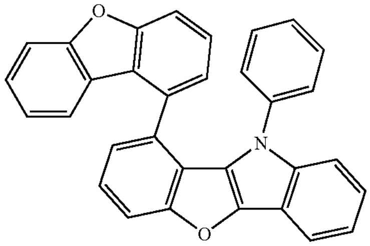
113
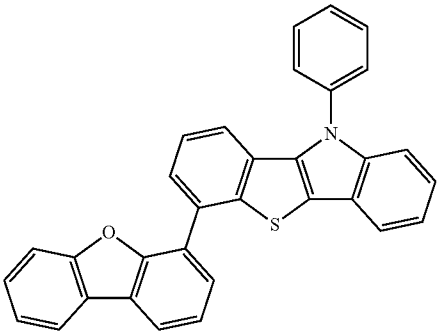
114
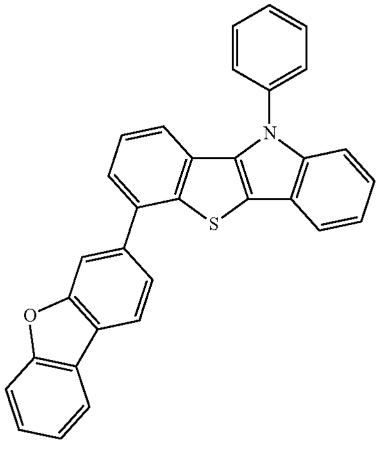
-continued
115
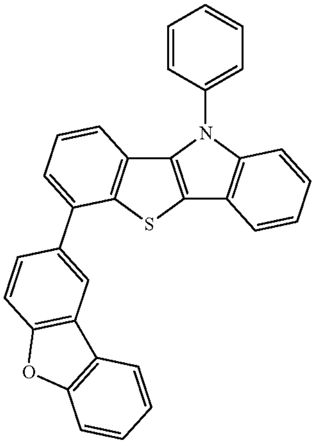
116
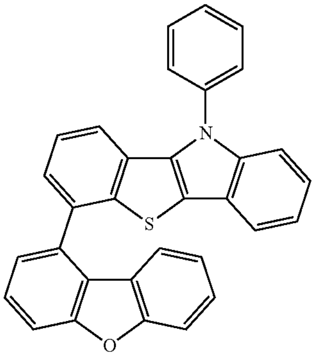
117
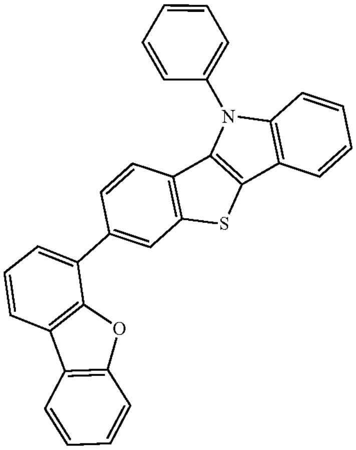

-continued
118
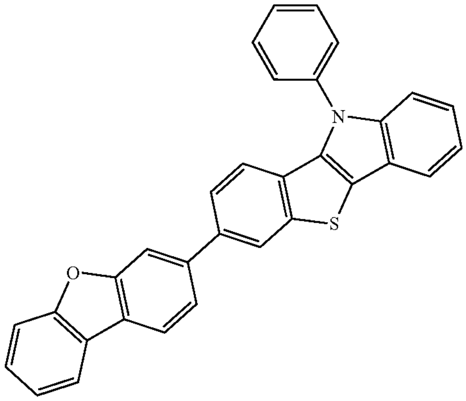
119
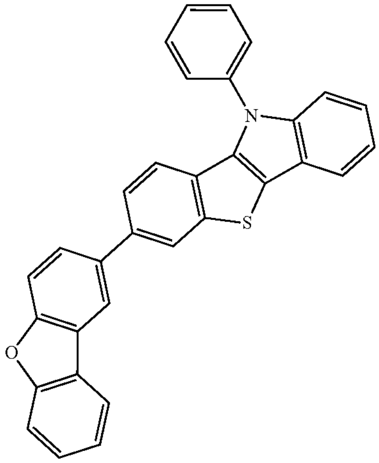
120
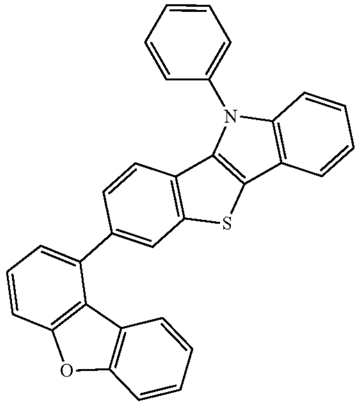
121
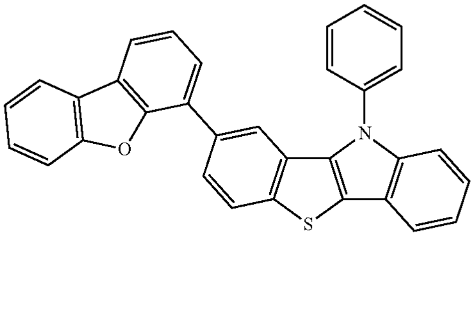
-continued
122
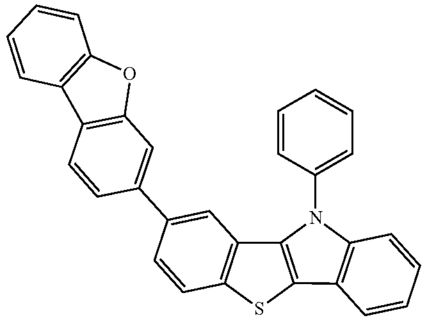
123
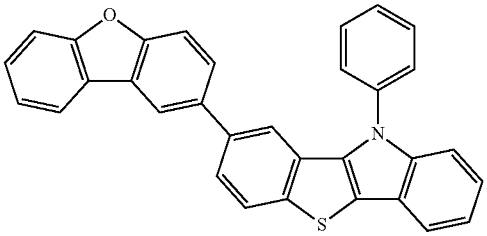
124
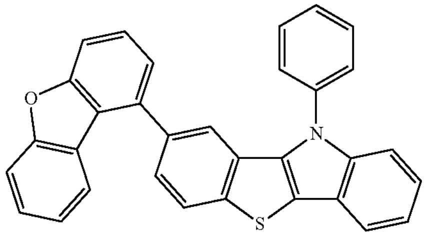
125
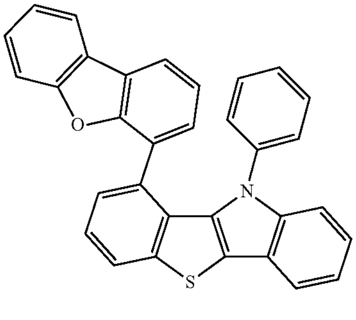
126
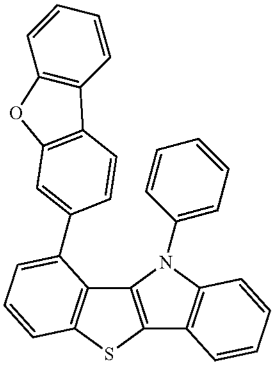

-continued
127
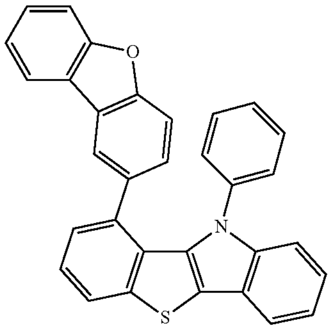
128
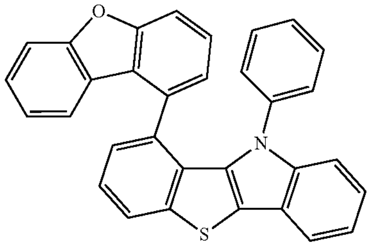
129
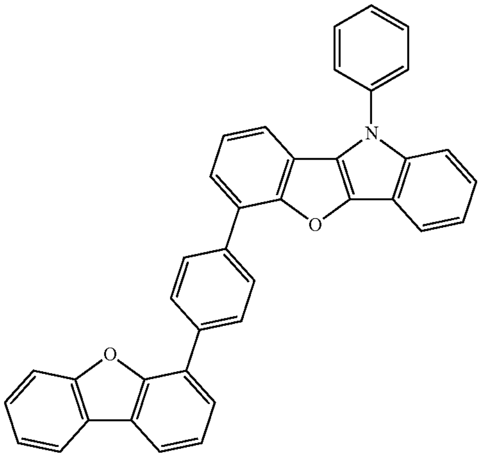
130
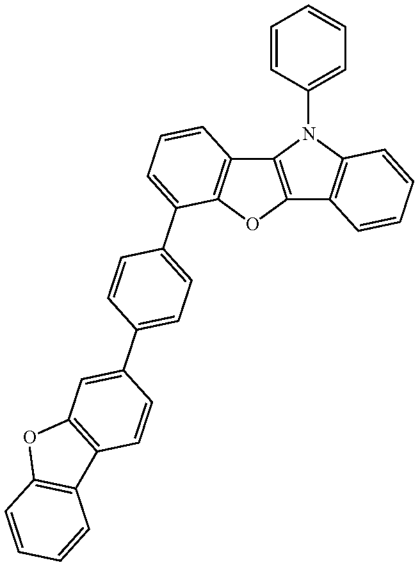
-continued
131
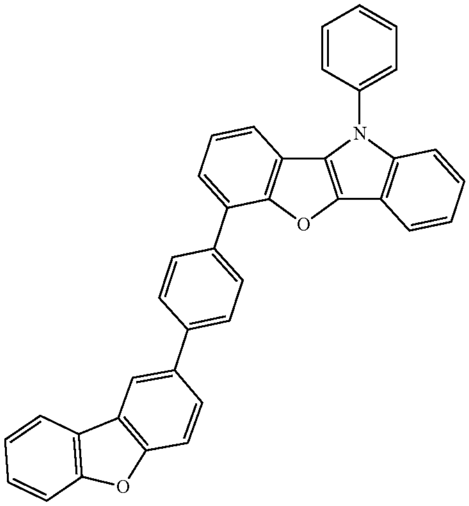
132
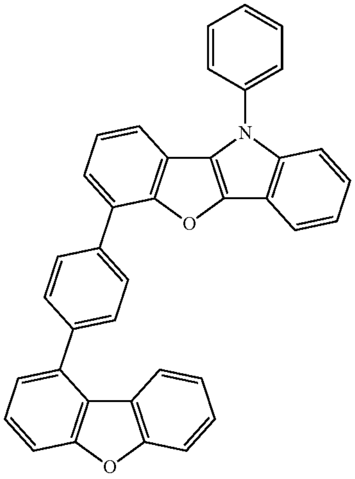
133
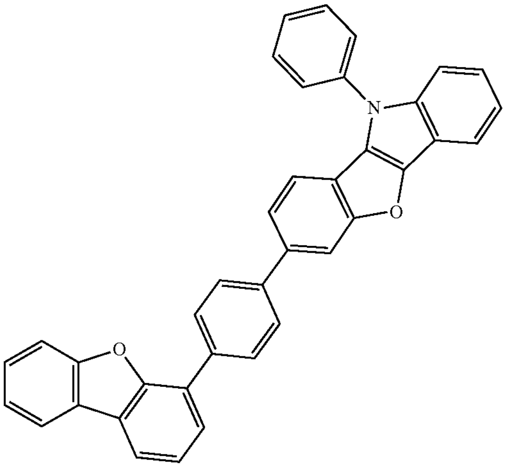

-continued
134
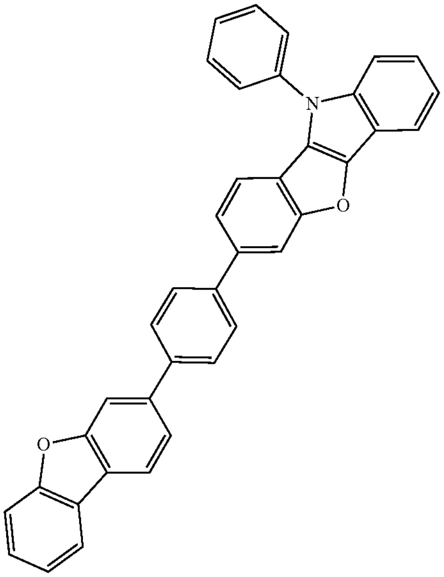
135
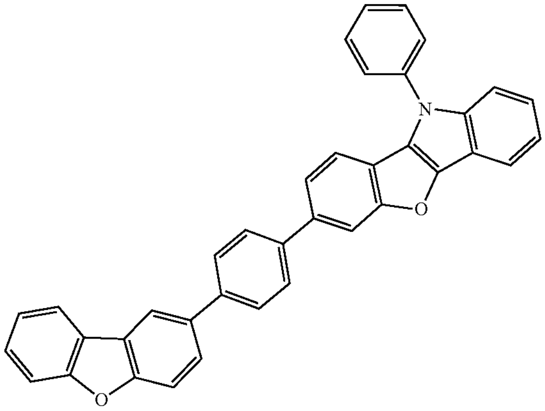
136
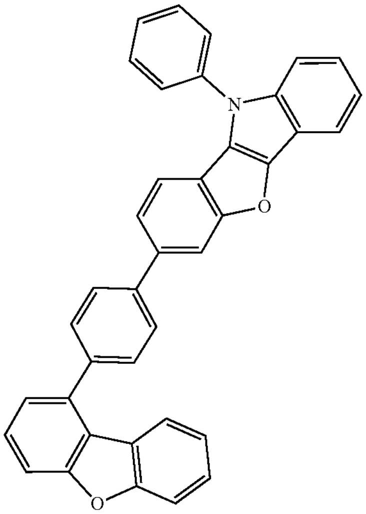
-continued
137
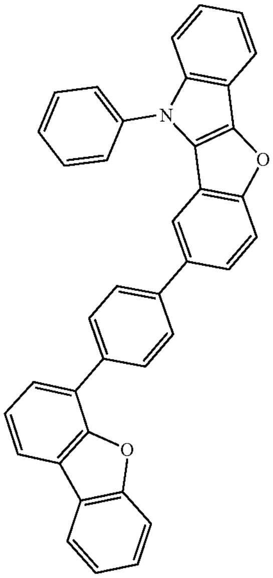
138
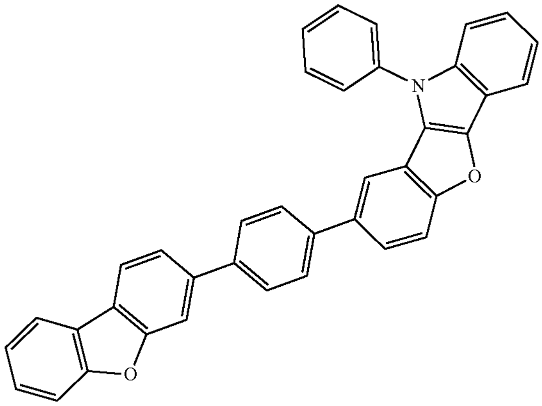
139
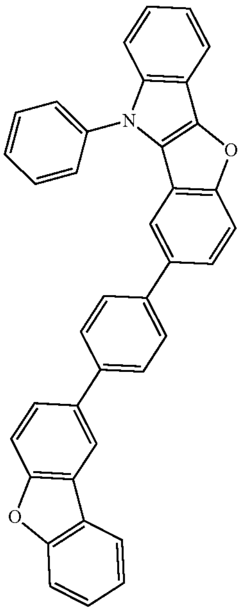

140
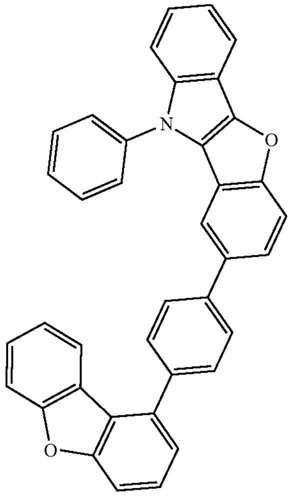
141
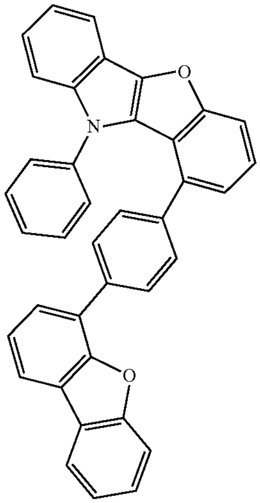
142
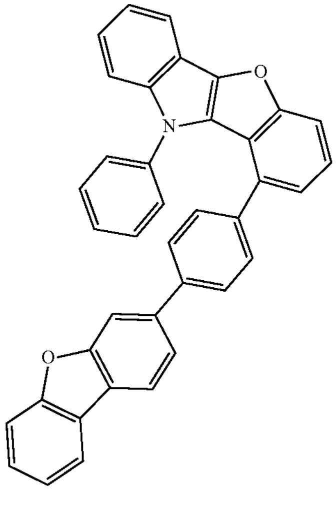
143
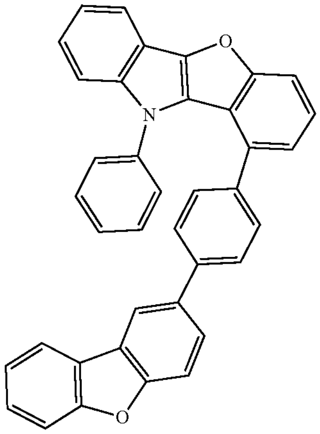
144
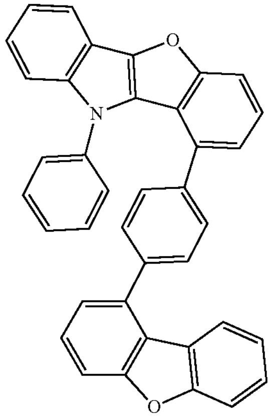
145
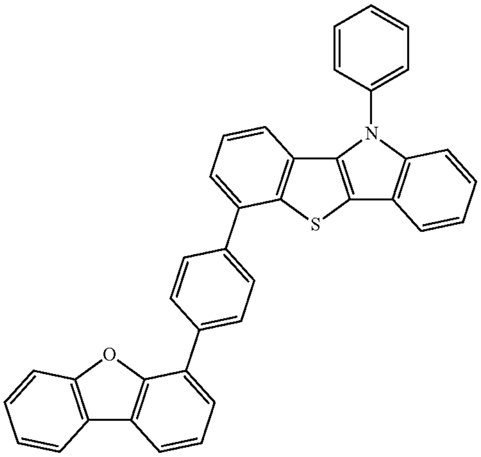

-continued
146
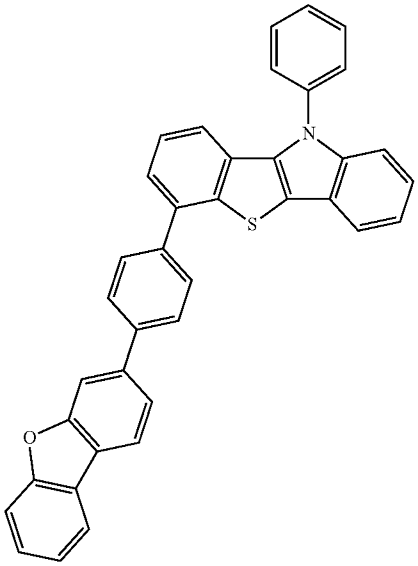
147
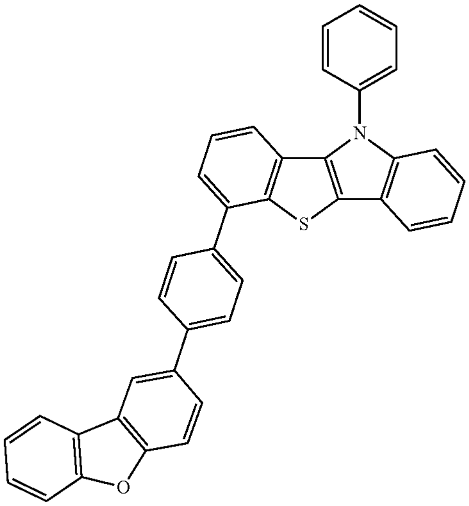
148
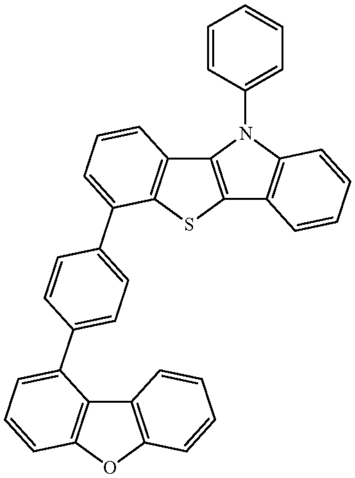
-continued
149
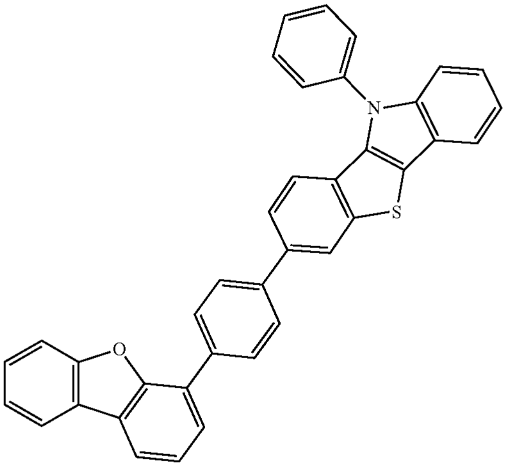
150
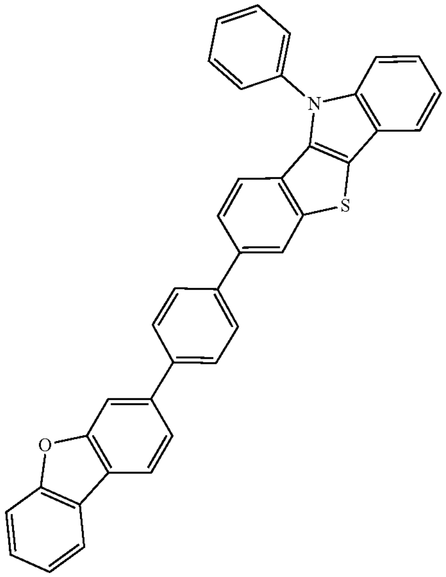
151
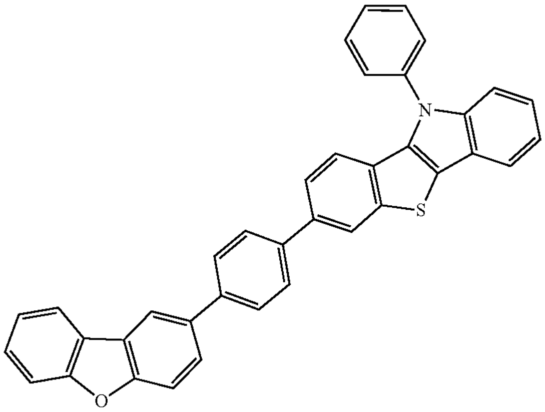

-continued
152
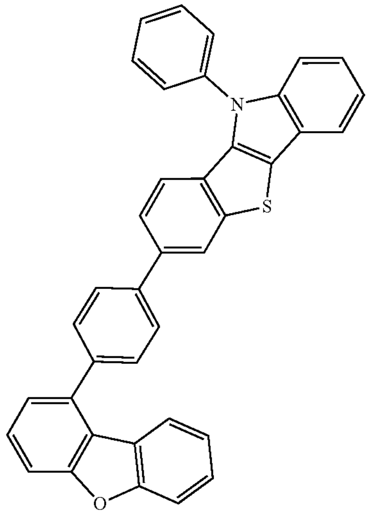
153
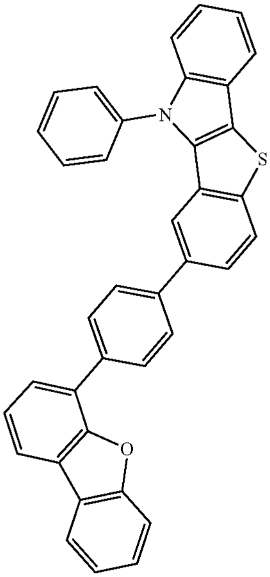
154
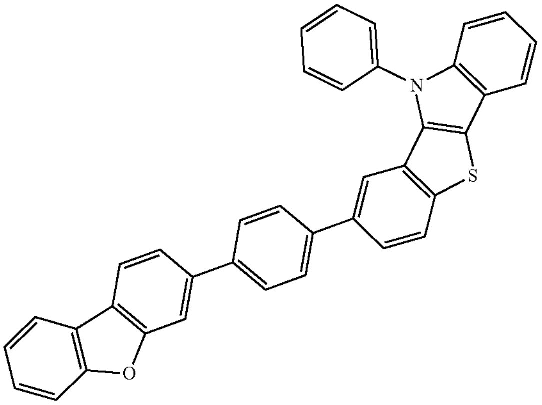
-continued
155
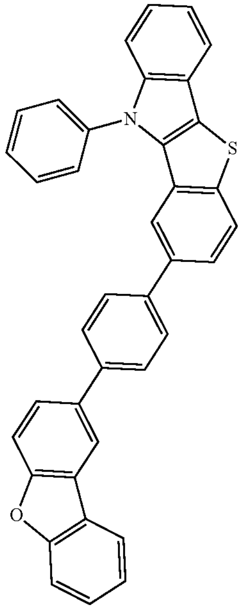
156
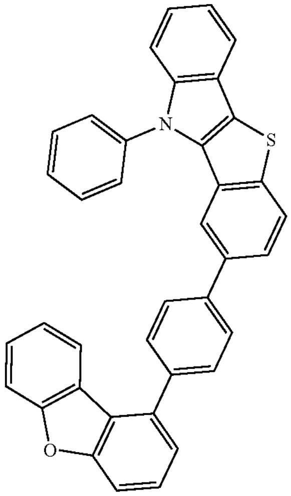
157
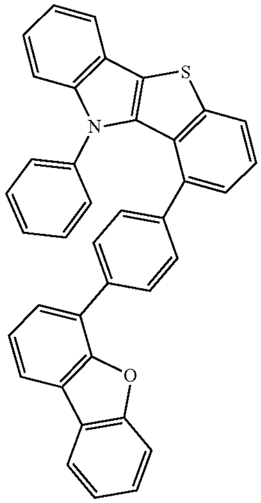

-continued
158
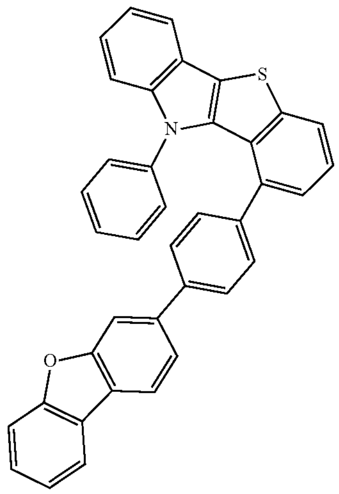
159
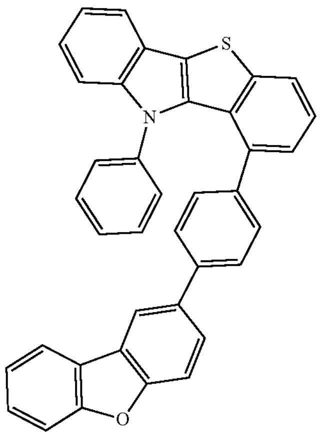
160
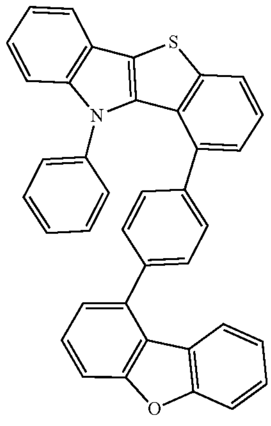
-continued
161
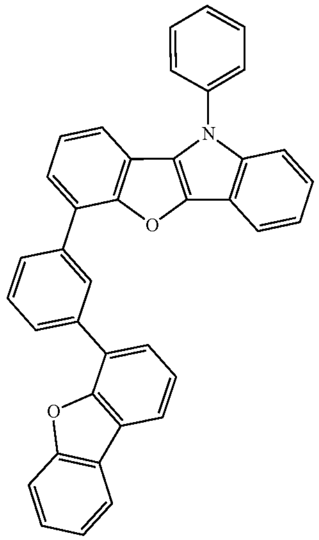
162
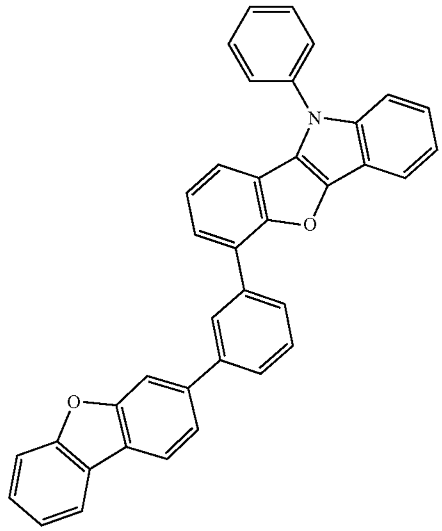
163
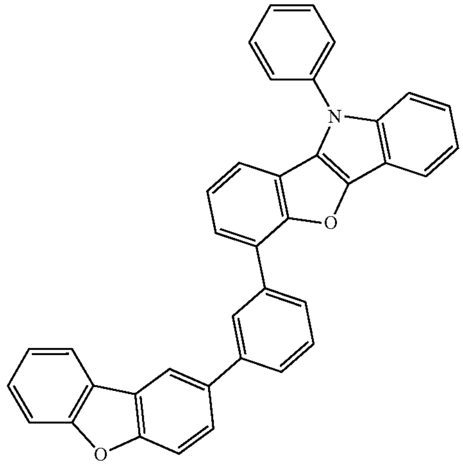

-continued
164
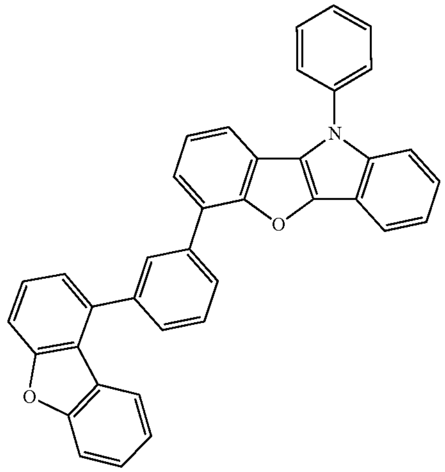
165
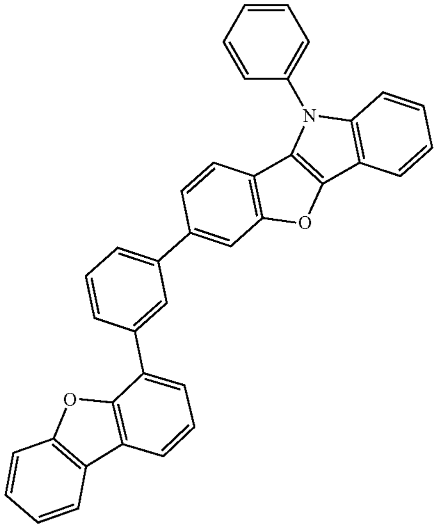
166
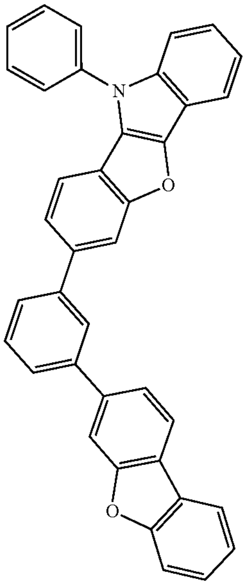
-continued
167
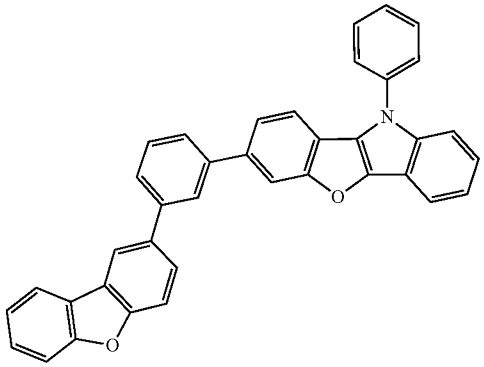
168
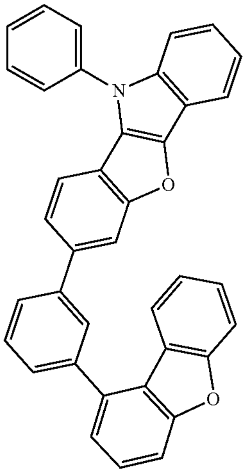
169
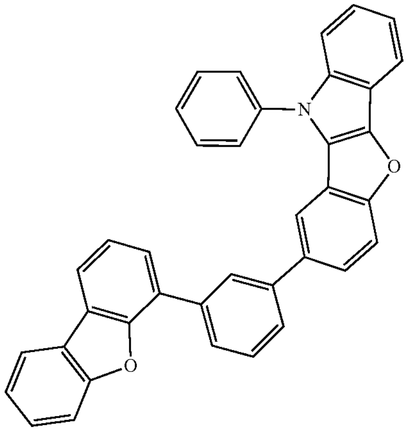

-continued
170
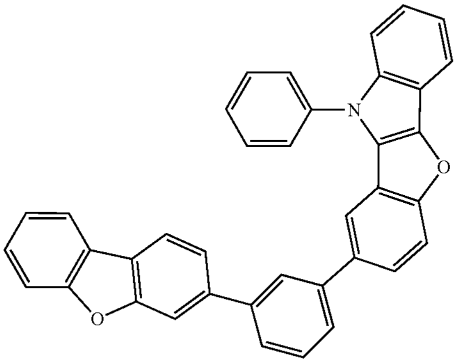
171
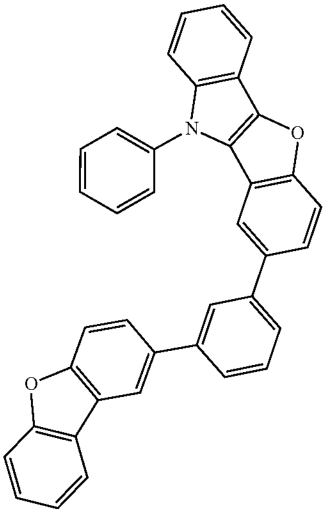
172
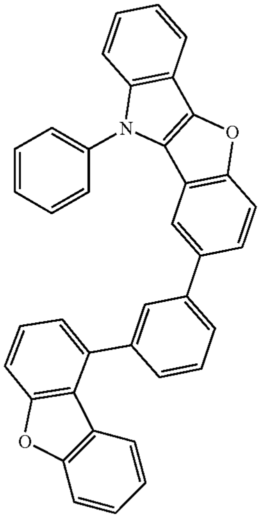
-continued
173
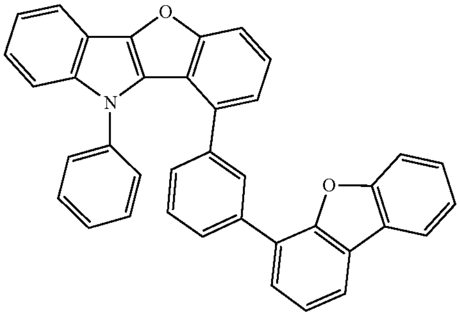
174
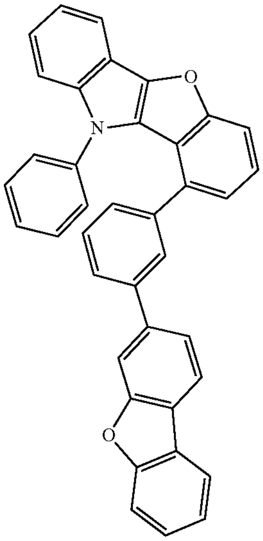
175
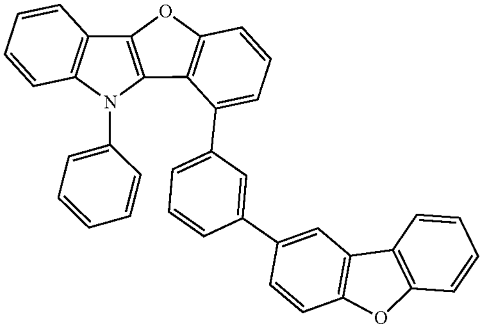
176
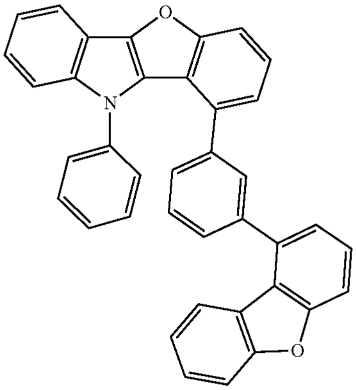

-continued
177
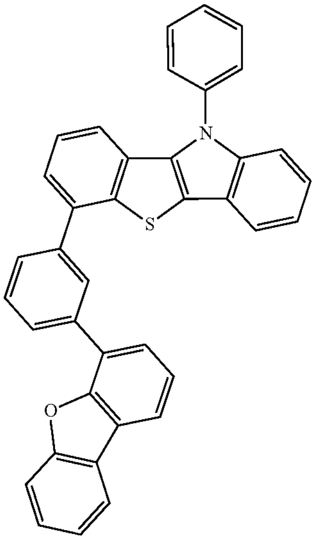
178
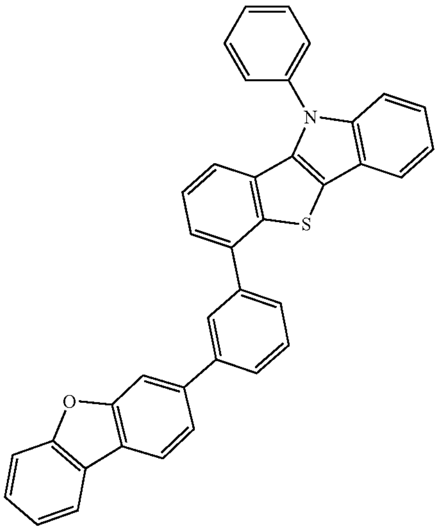
179
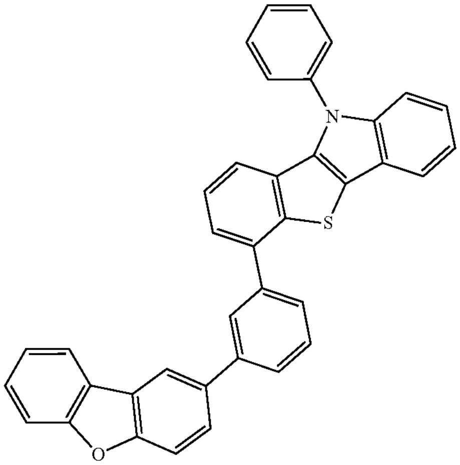
-continued
180
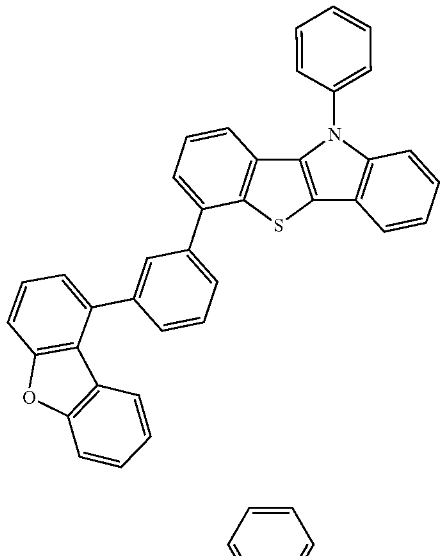
181
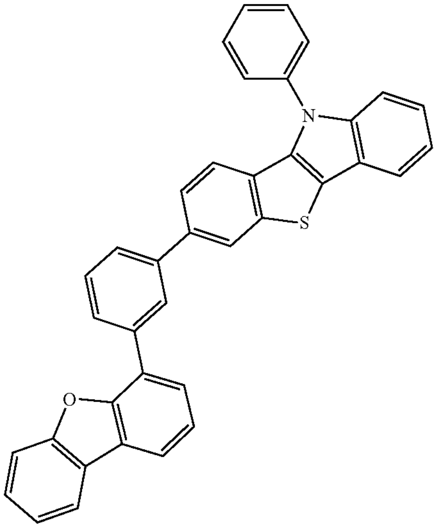
182
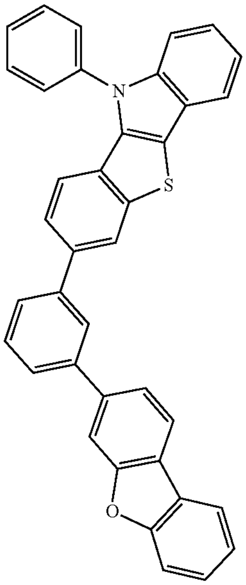

-continued
183
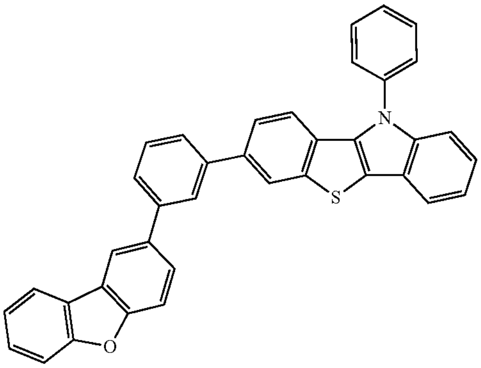
184
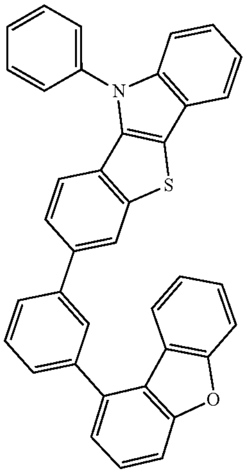
185
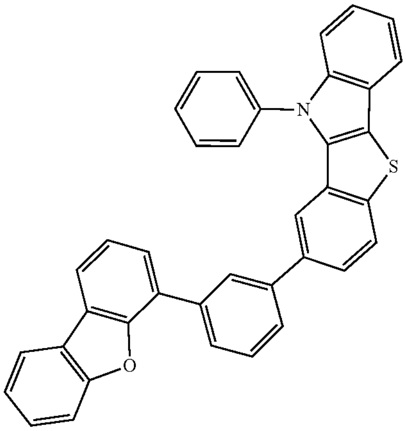
186
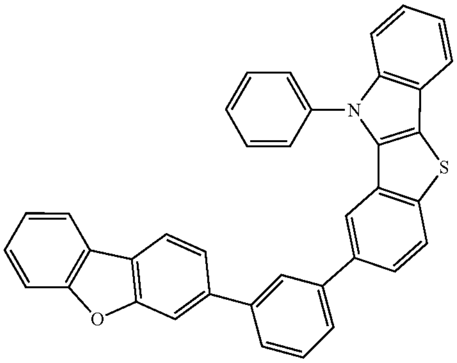
-continued
187
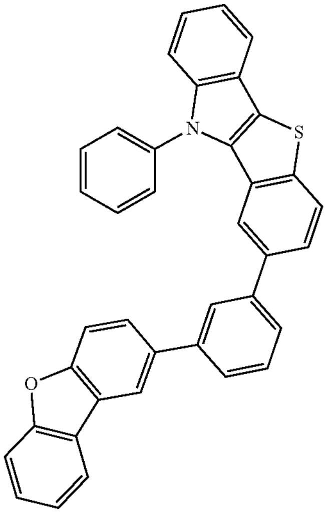
188
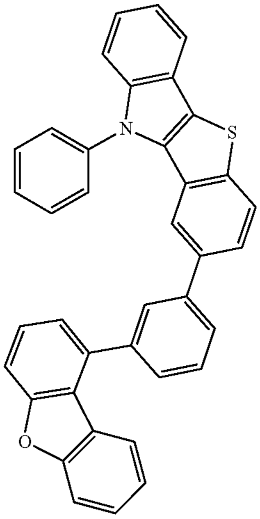
189
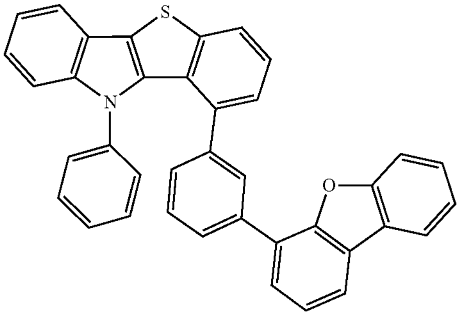

-continued
190
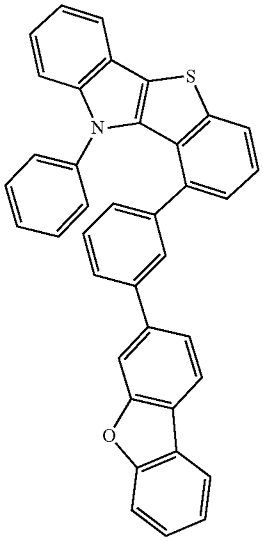
191
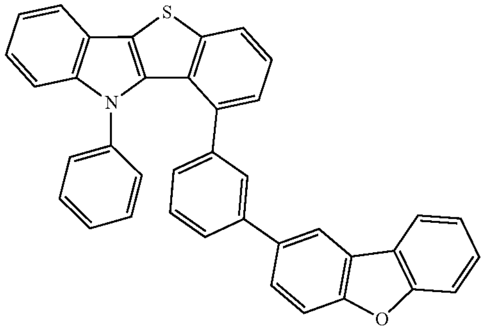
192
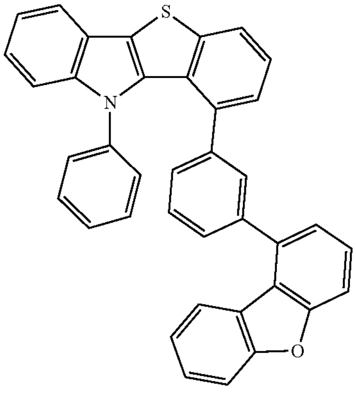
-continued
193
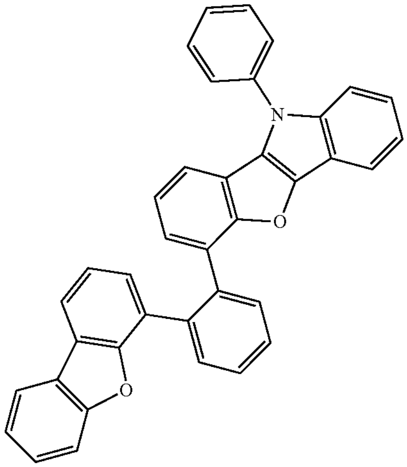
194
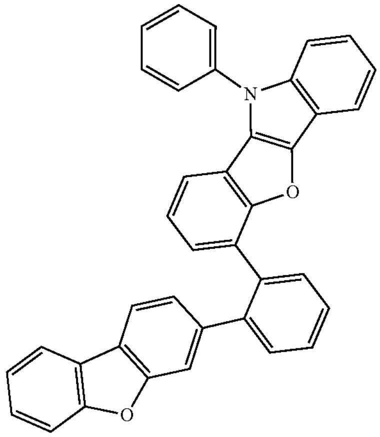
195
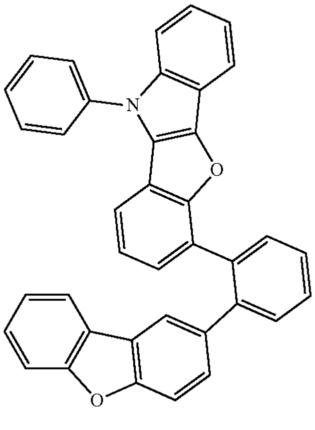

-continued
196
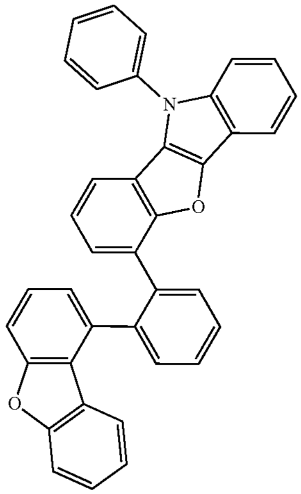
197
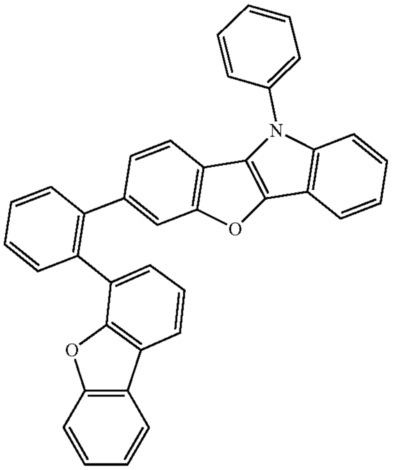
198
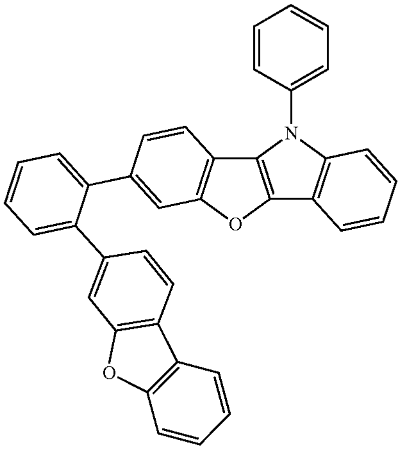
-continued
199
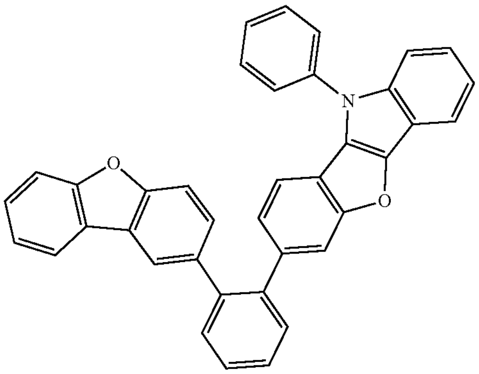
200
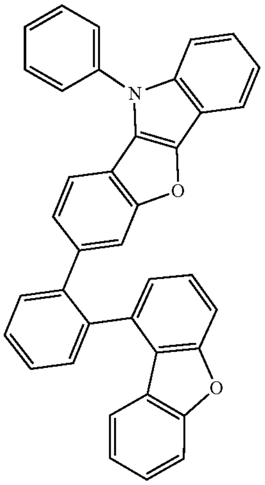
201
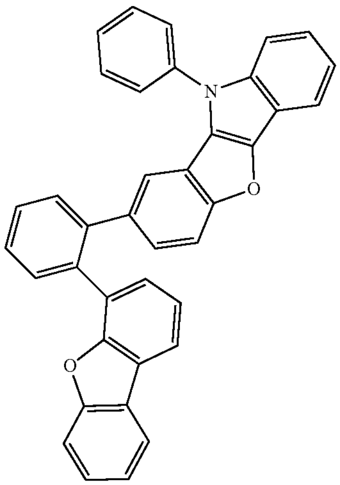

-continued
202
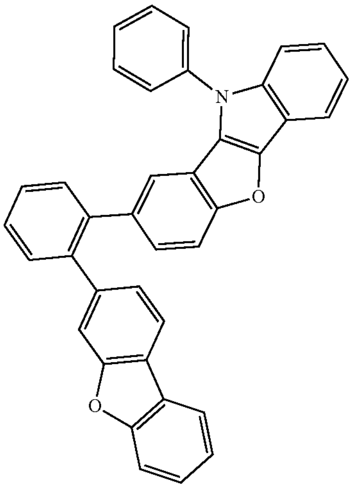
203
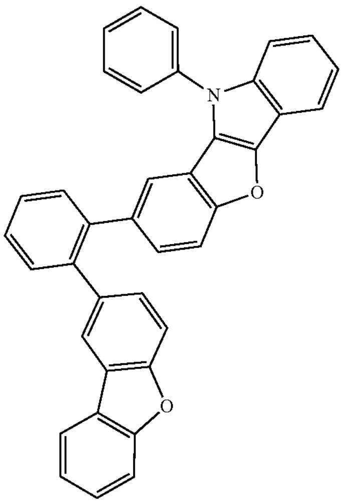
204
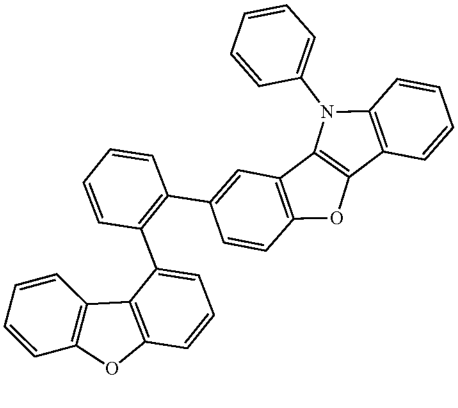
-continued
205
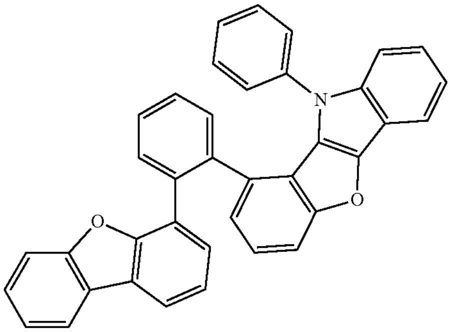
206
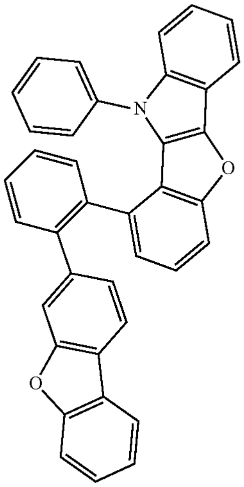
207
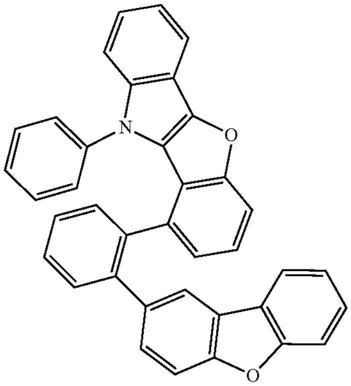

-continued
208
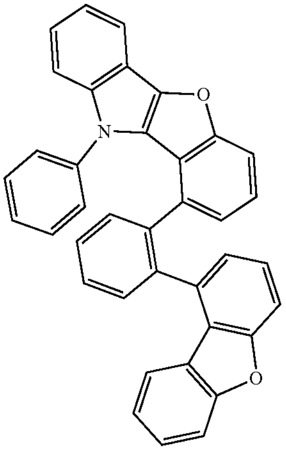
209
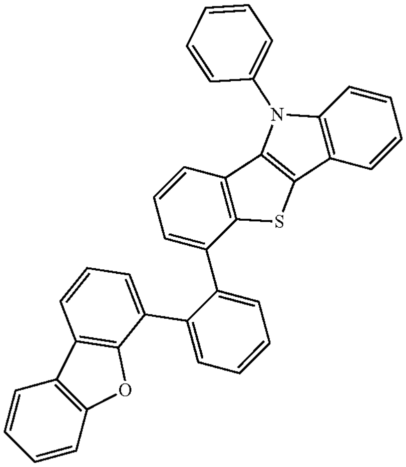
210
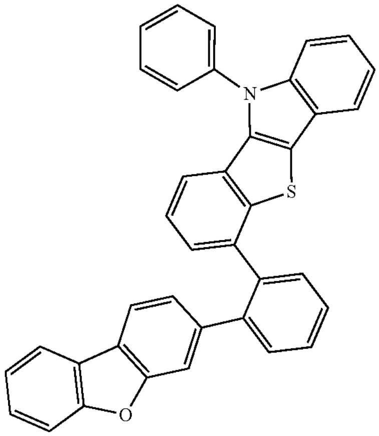
-continued
211
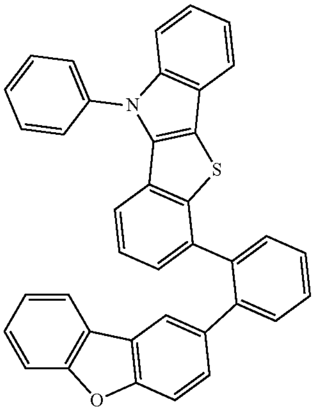
212
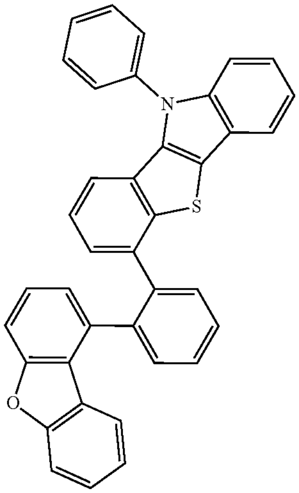
213
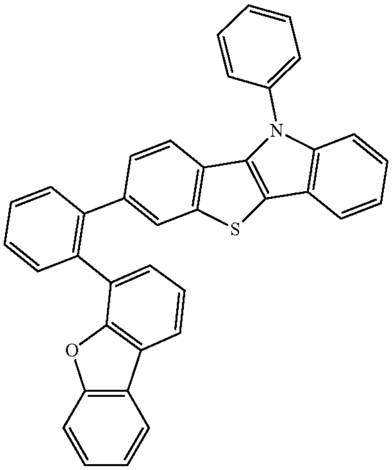

-continued
214
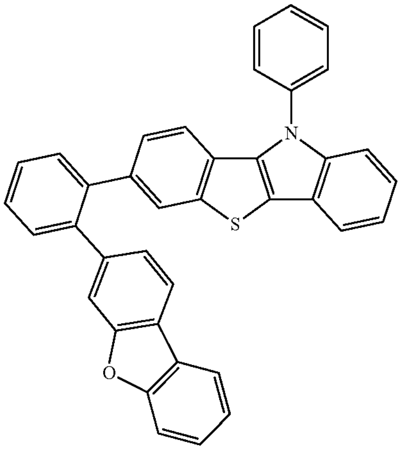
215
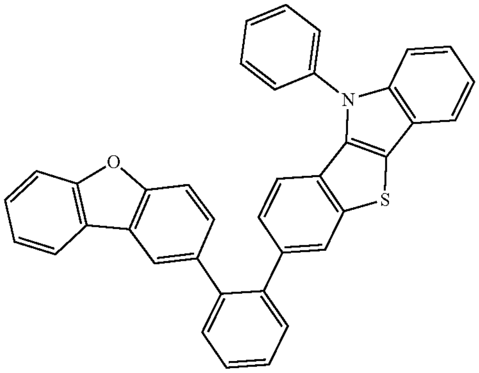
216
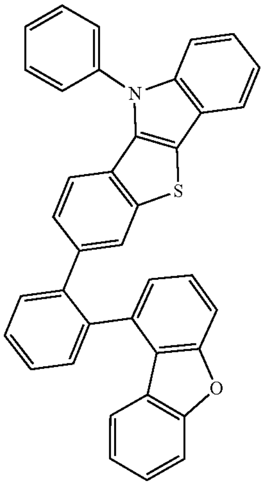
-continued
217
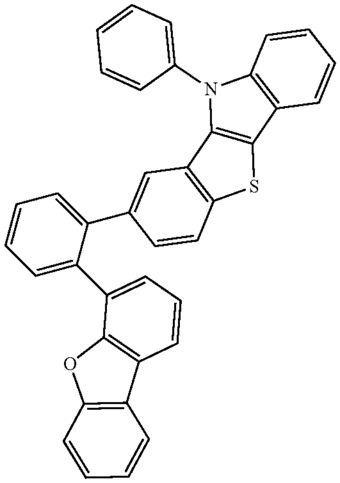
218
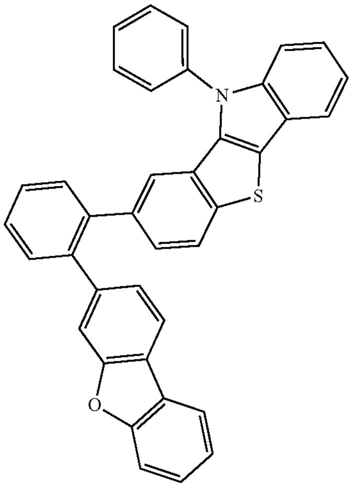
219
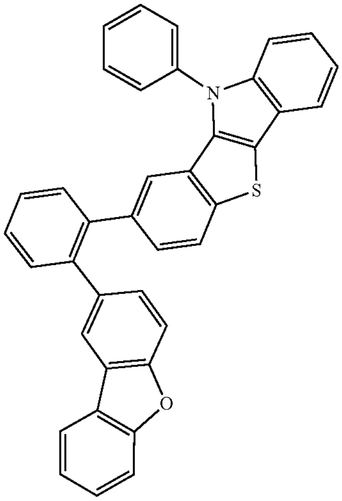

-continued
220
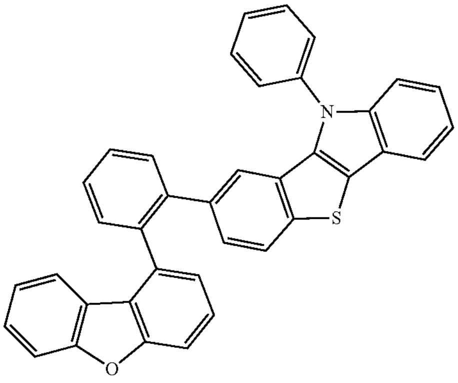
221
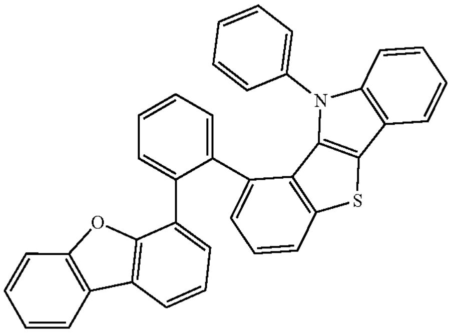
222
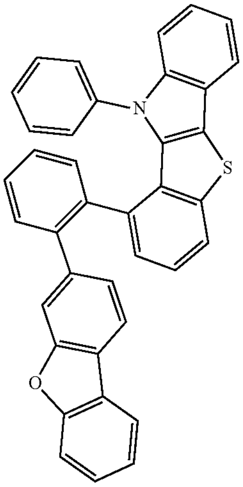
223
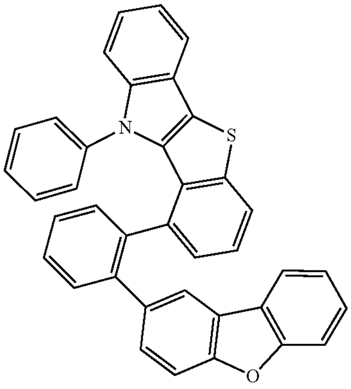
-continued
224
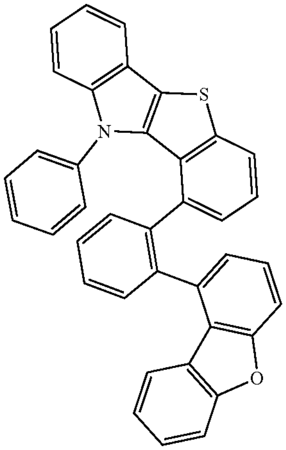
225
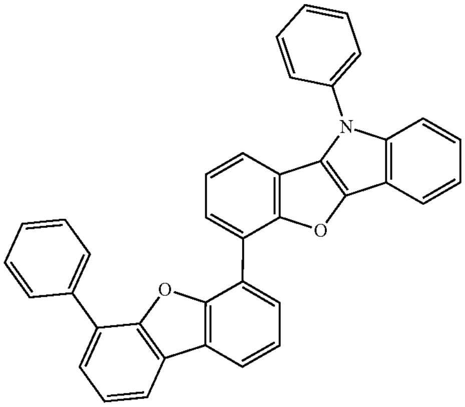
226
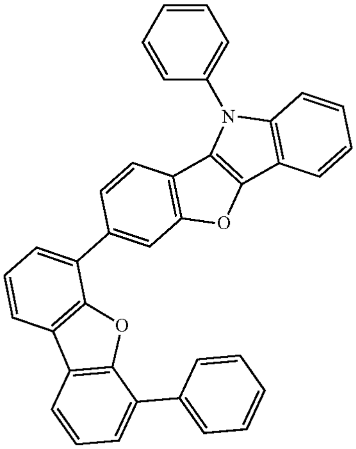

-continued
227
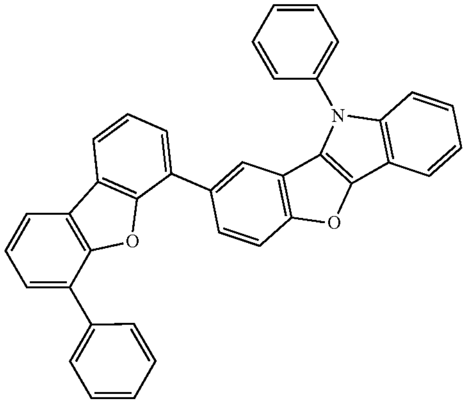
228
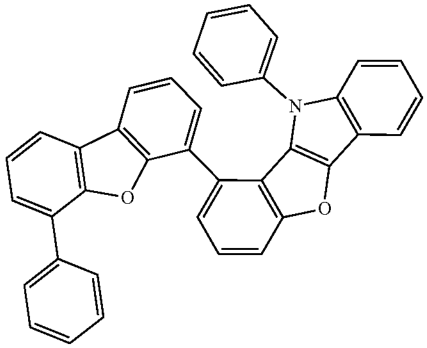
229
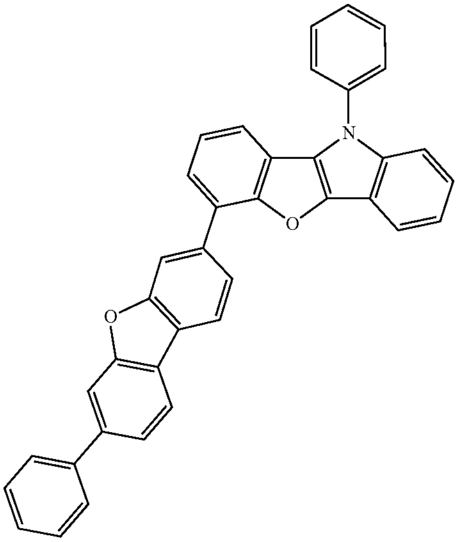
-continued
230
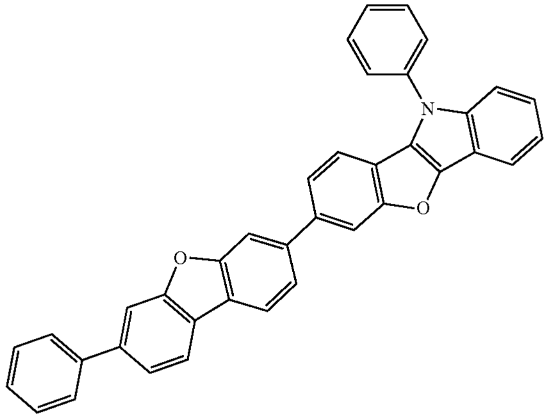
231
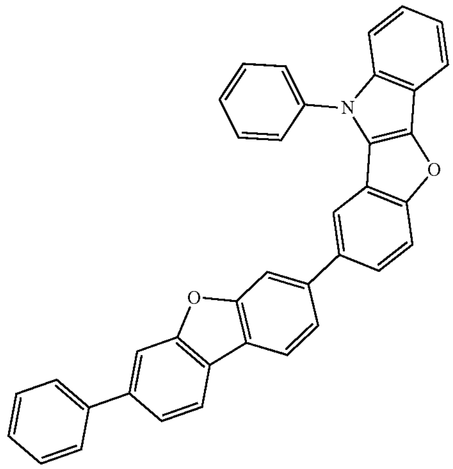
232
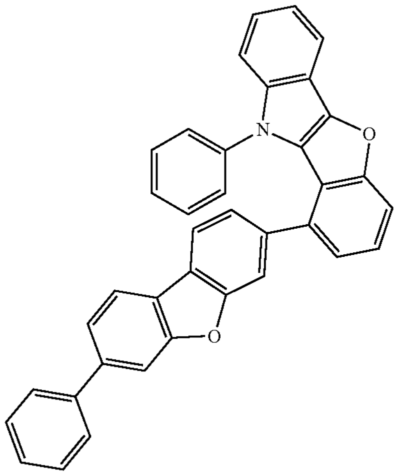

-continued
233
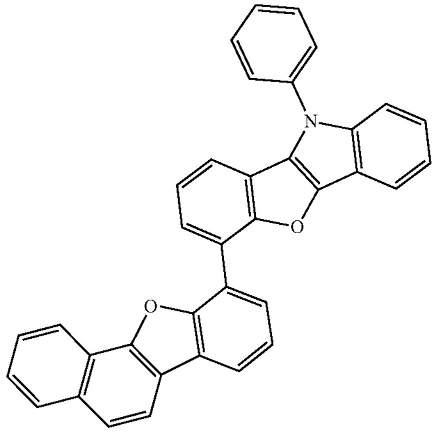
234
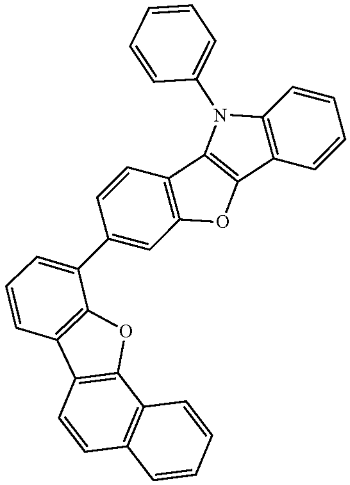
235
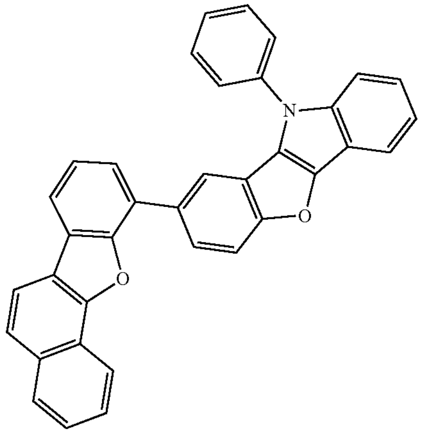
-continued
236
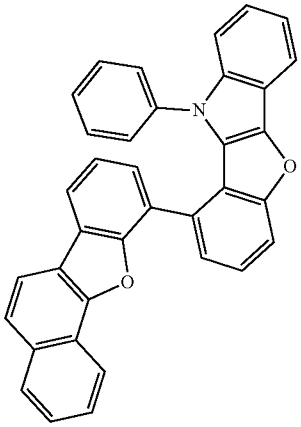
237
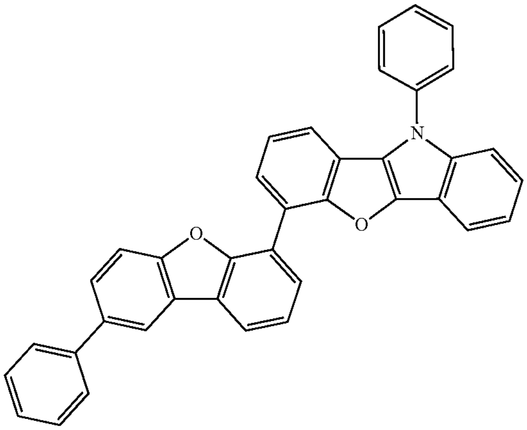
238
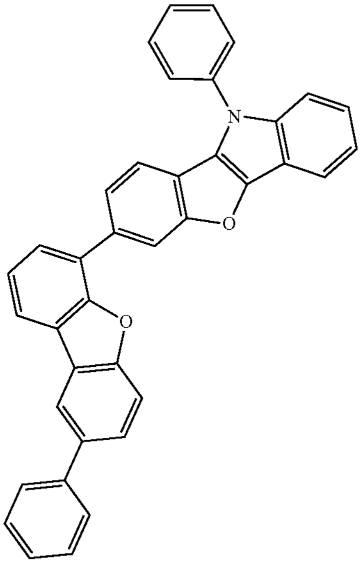

-continued
239
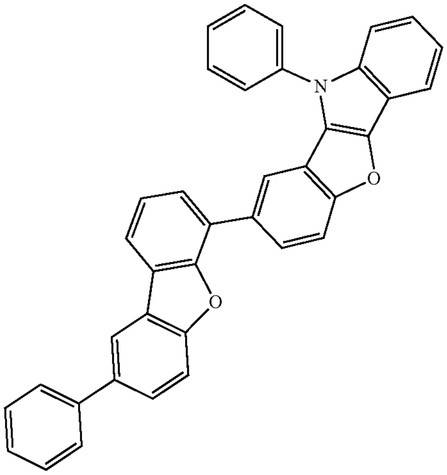
240
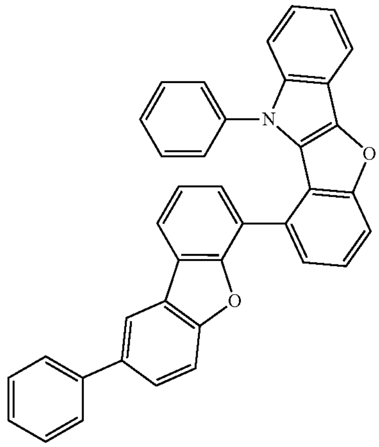
241
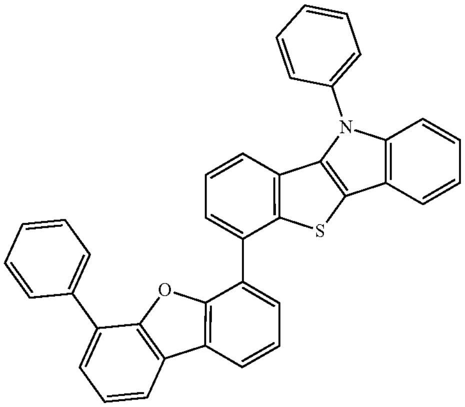
-continued
242
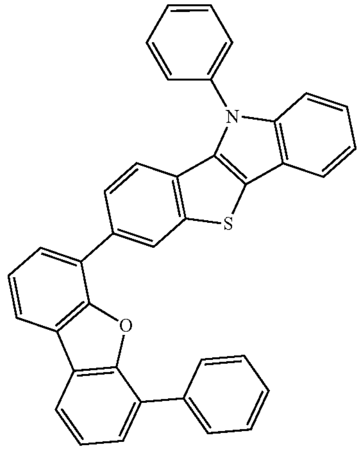
243
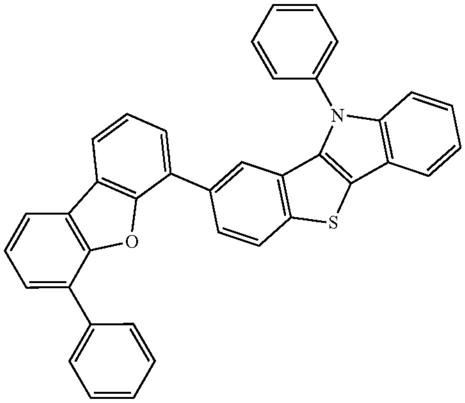
244
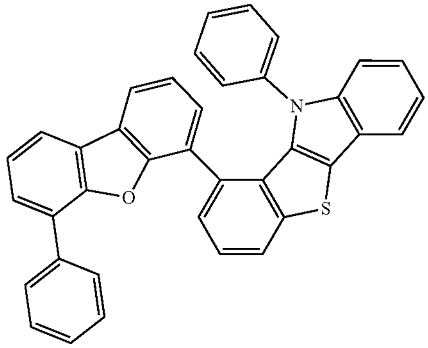

-continued
245
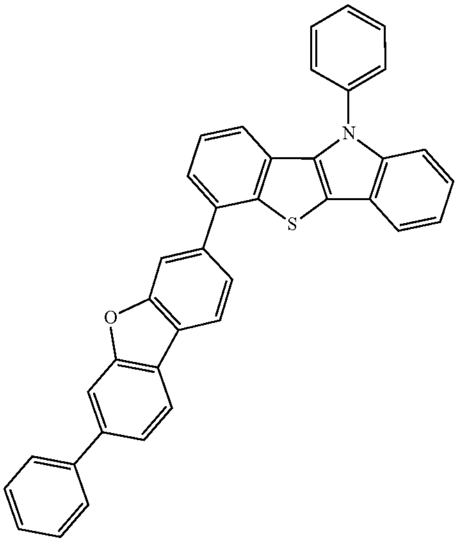
246
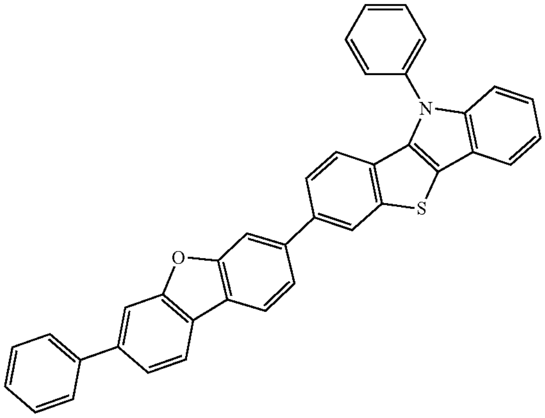
247
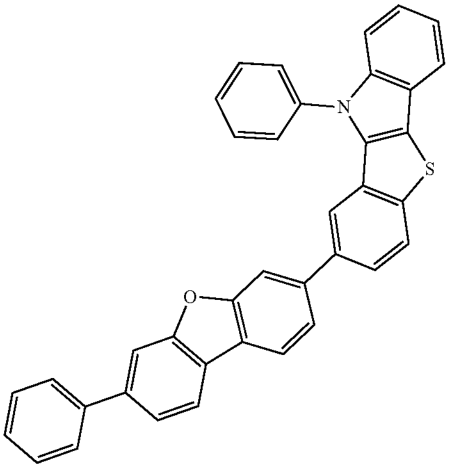
-continued
248
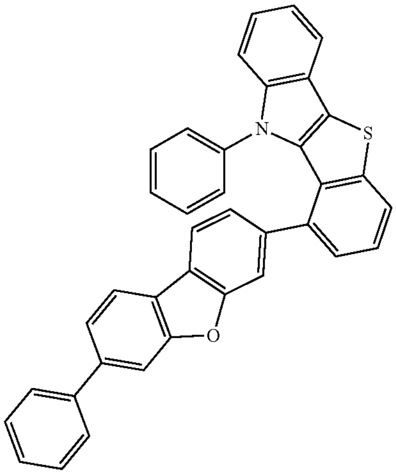
249
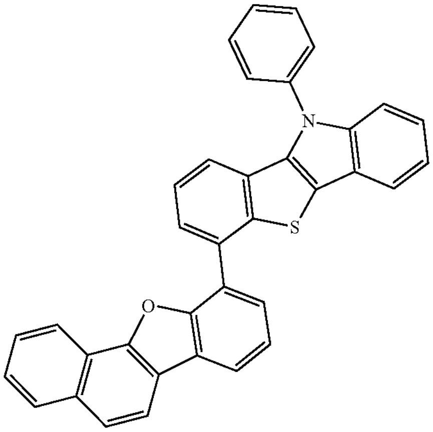
250
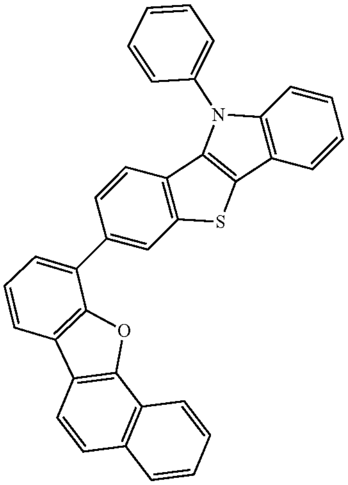

-continued
251
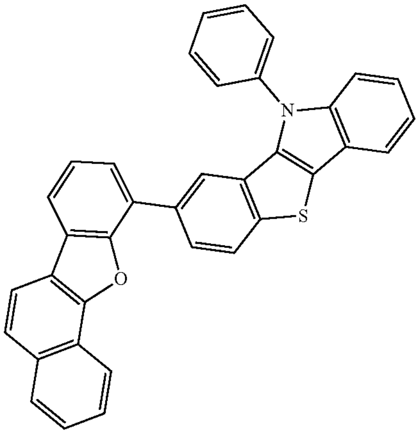
252
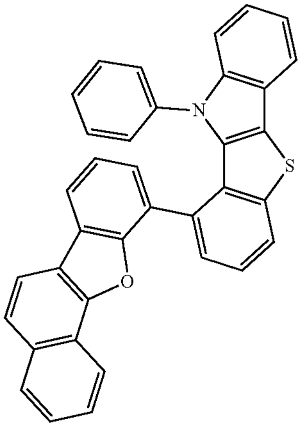
253
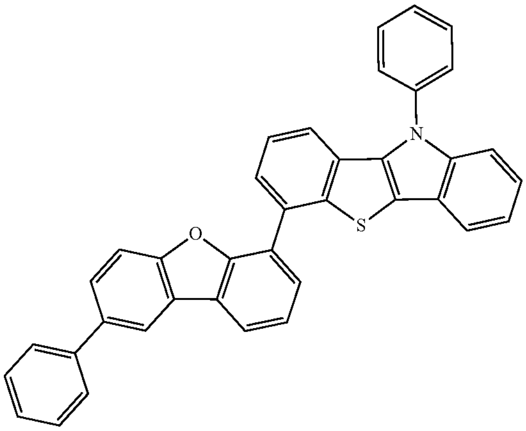
-continued
254
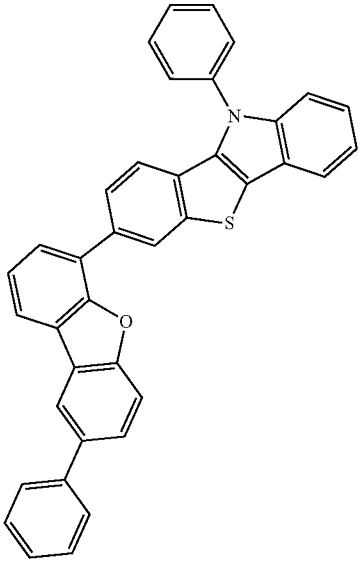
255
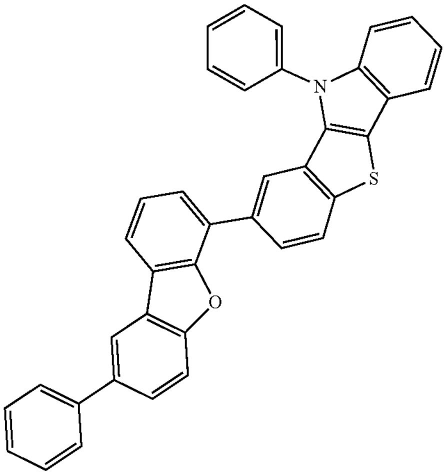
256
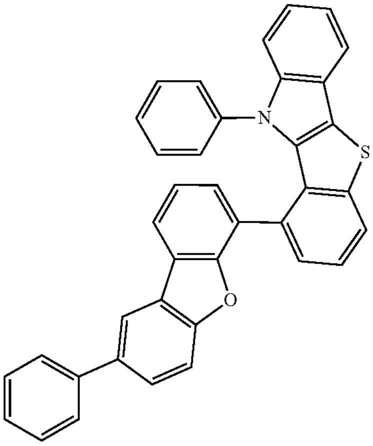

-continued
257
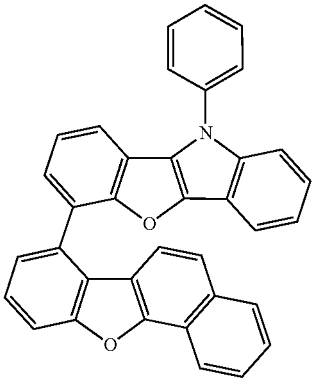
258
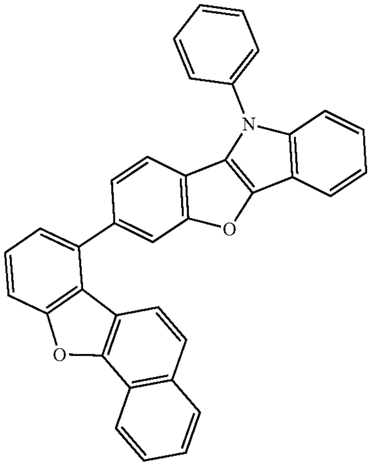
259
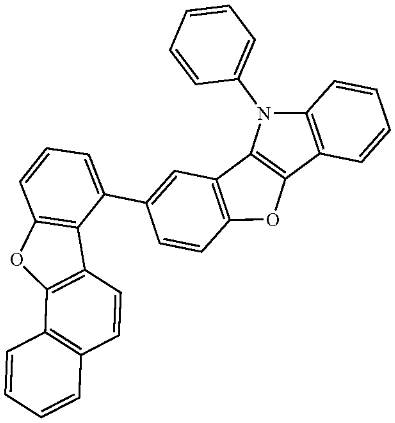
260
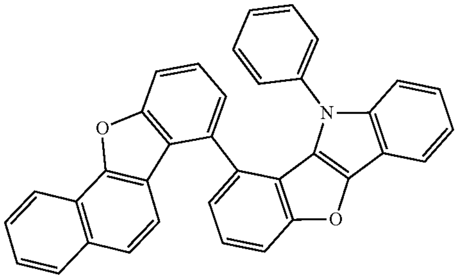
-continued
261
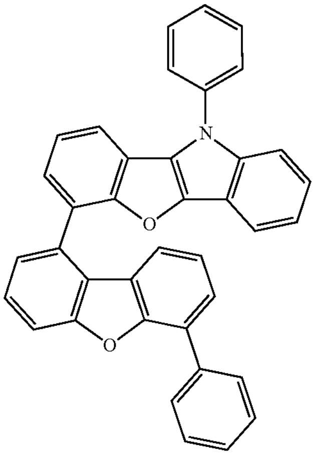
262
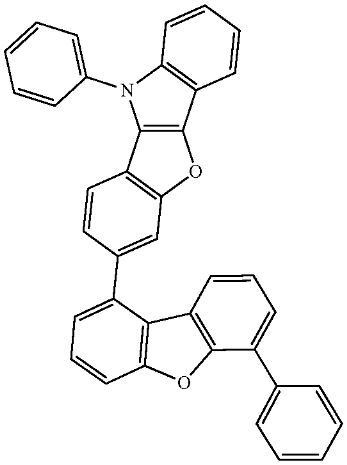
263
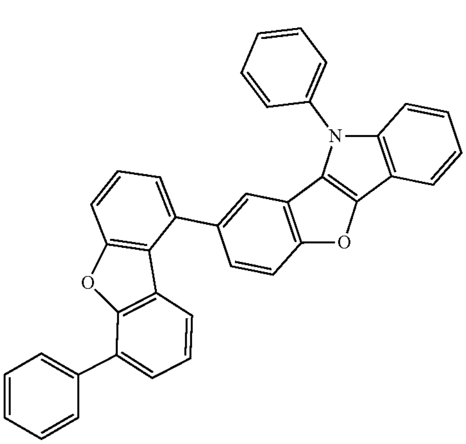

-continued
264
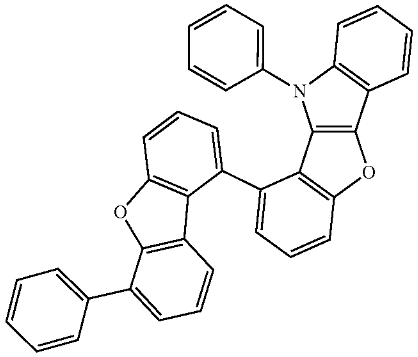
265
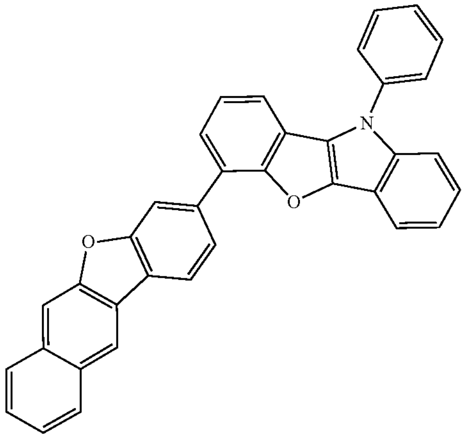
266
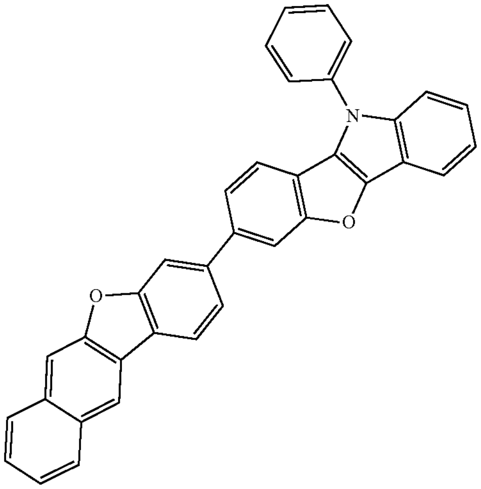
-continued
267
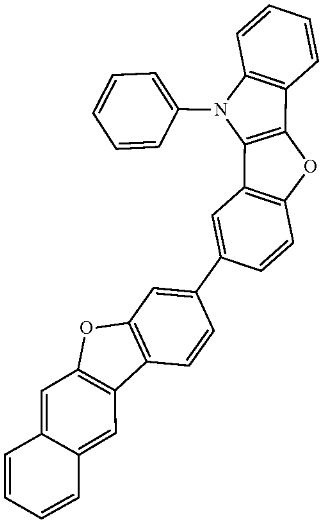
268
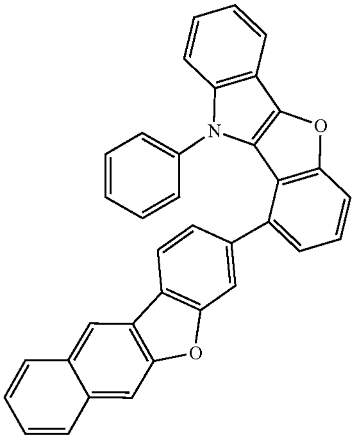
269
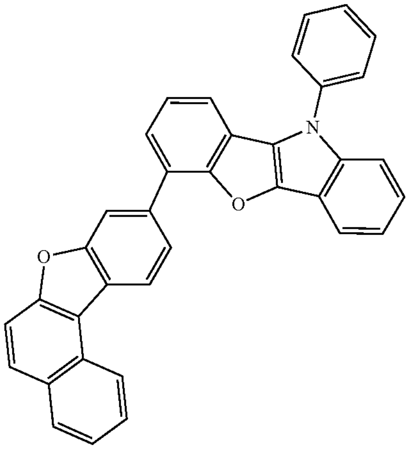

-continued
270
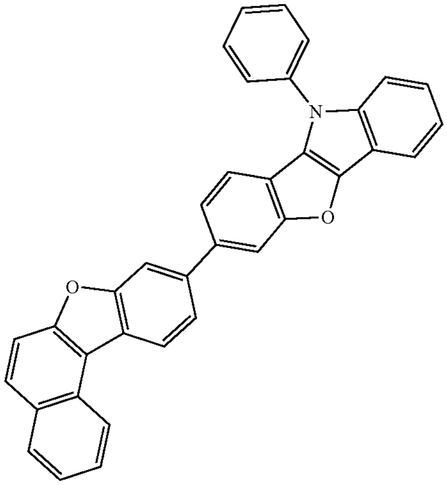
271
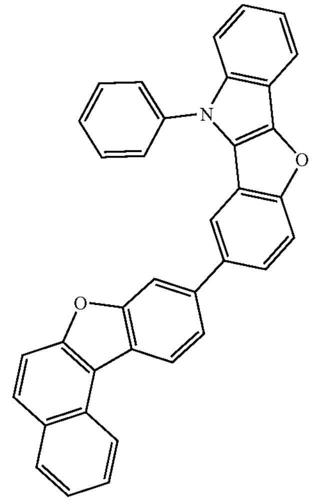
272
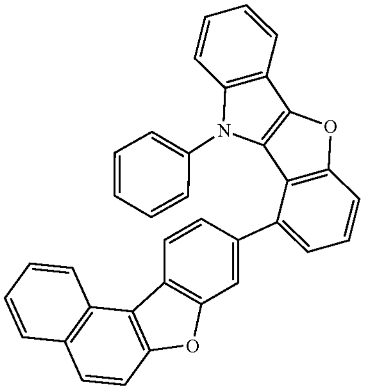
-continued
273
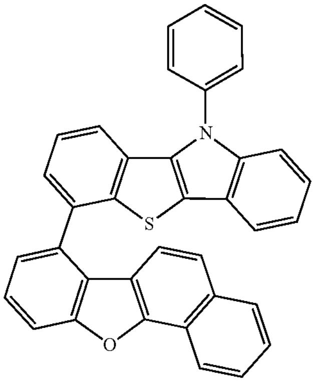
274
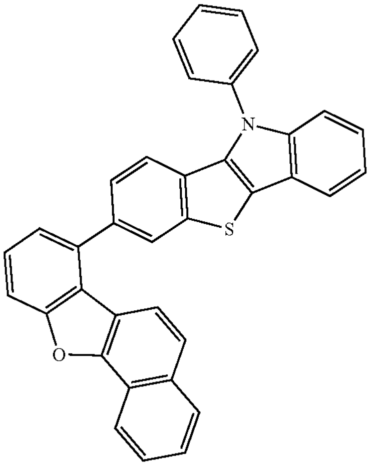
275
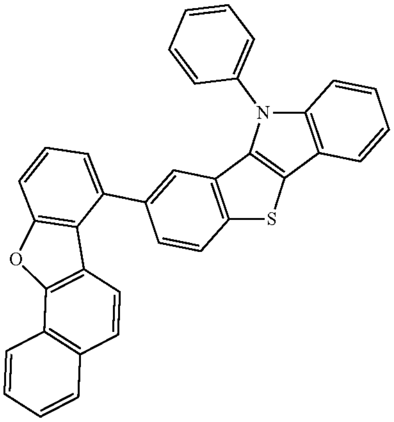
276
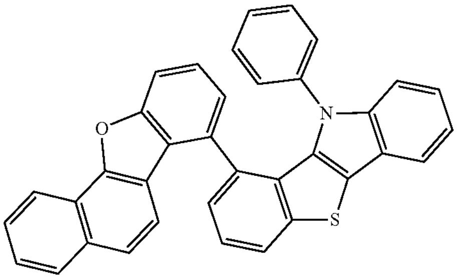

-continued
277
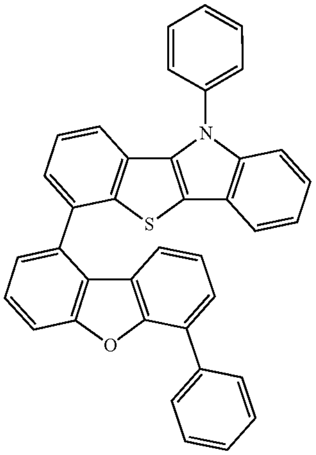
278
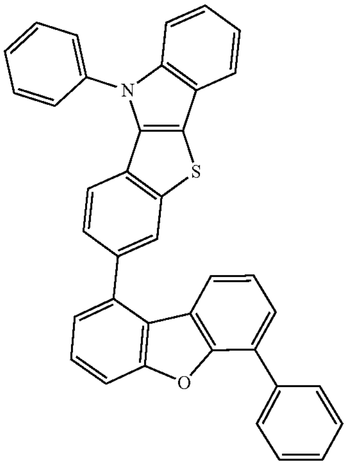
279
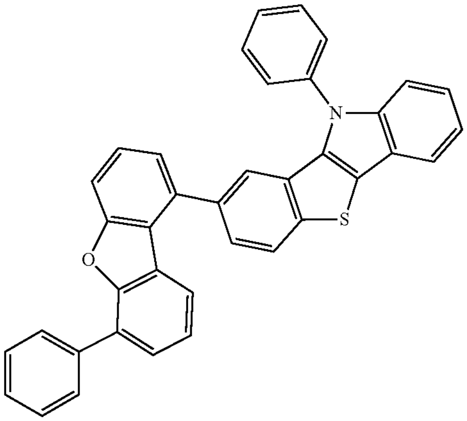
-continued
280
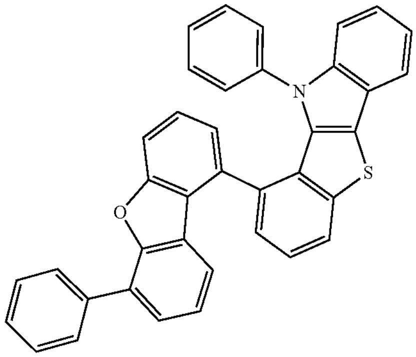
281
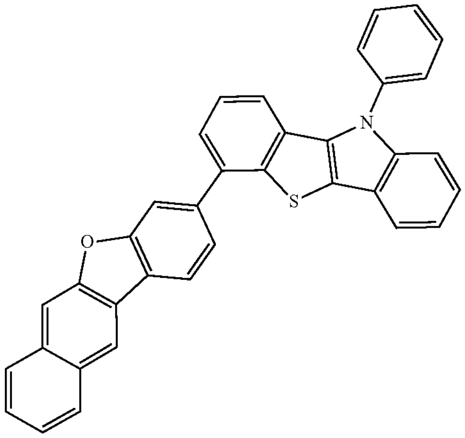
282
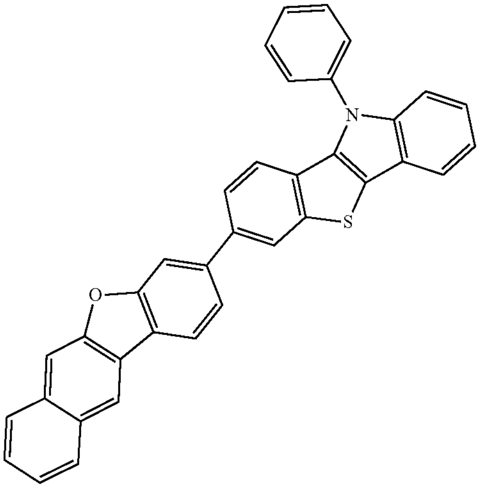

-continued
283
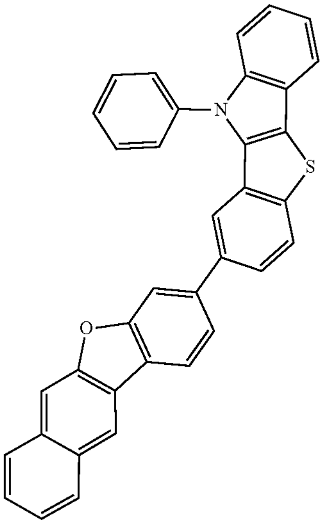
284
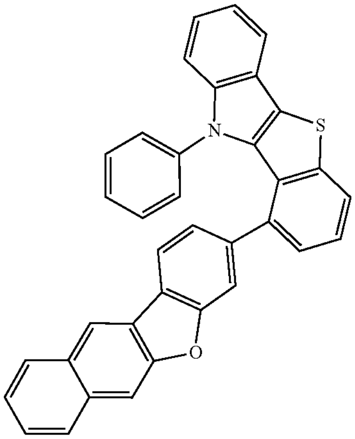
285
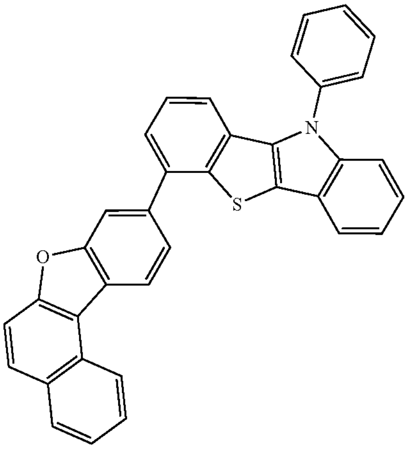
-continued
286
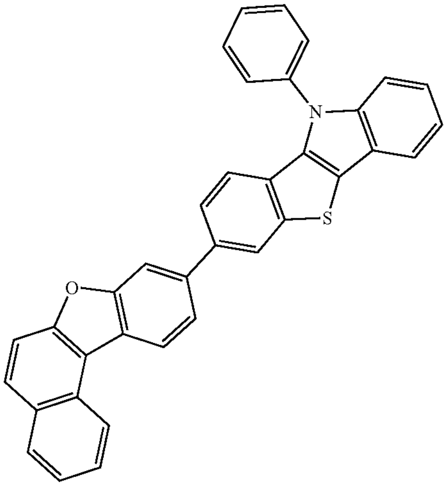
287
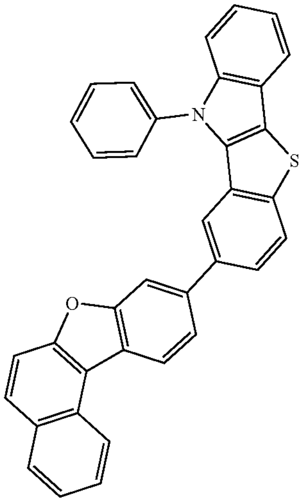
288
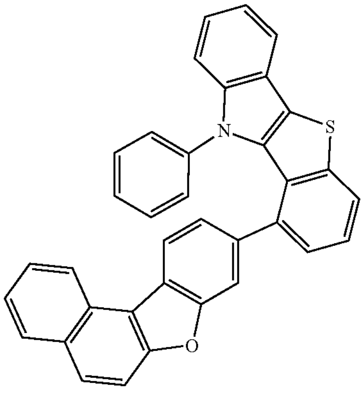

-continued
289
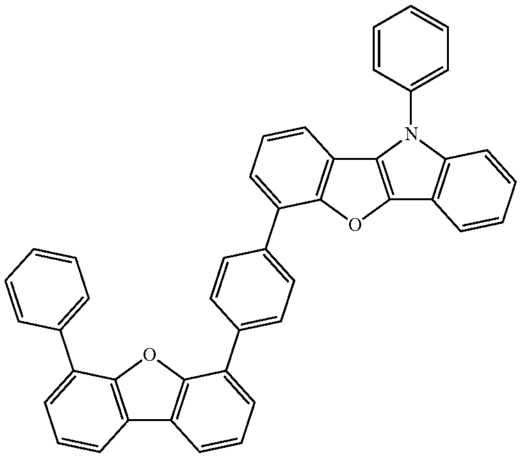
290
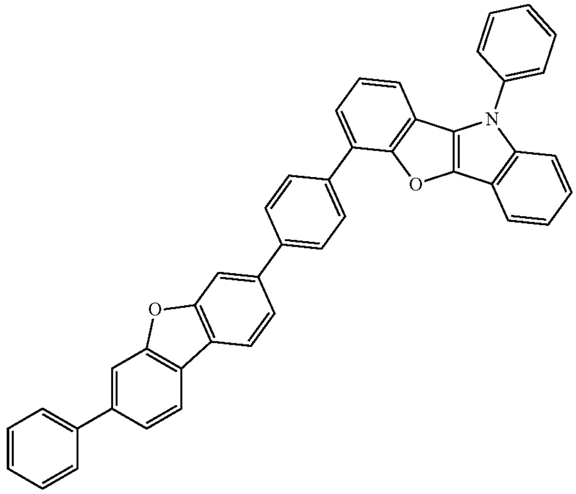
291
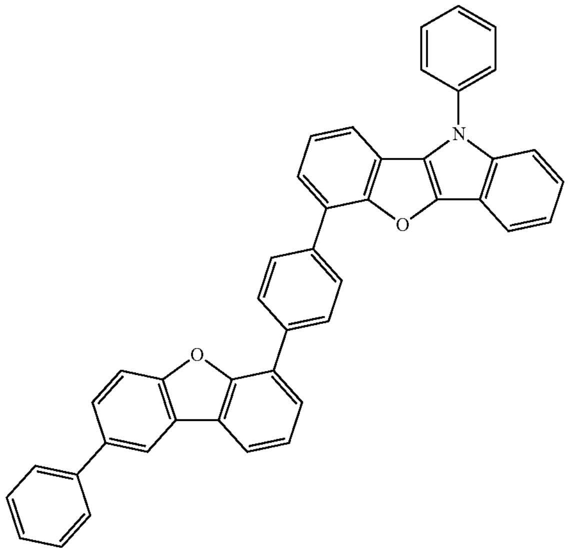
292
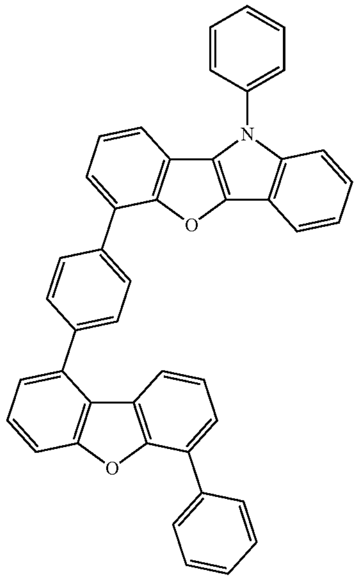
293
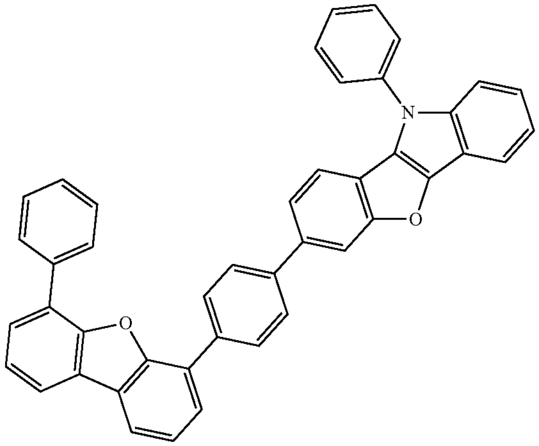
294
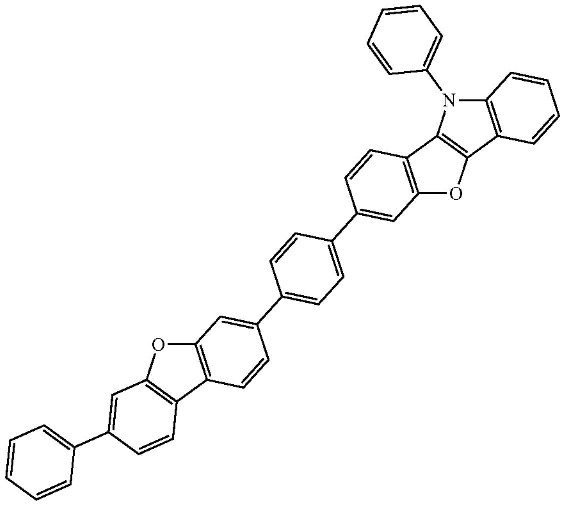

295
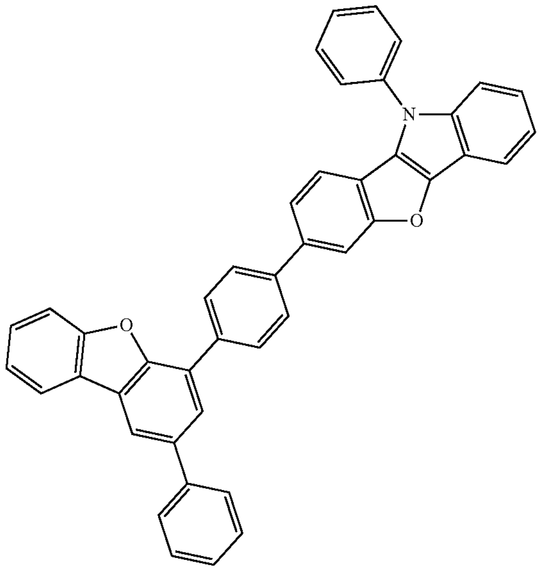
296
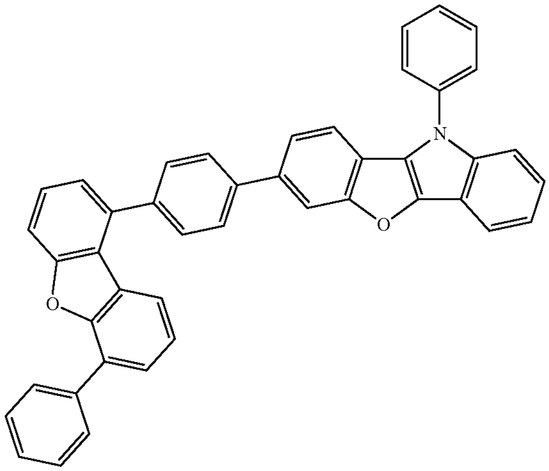
297
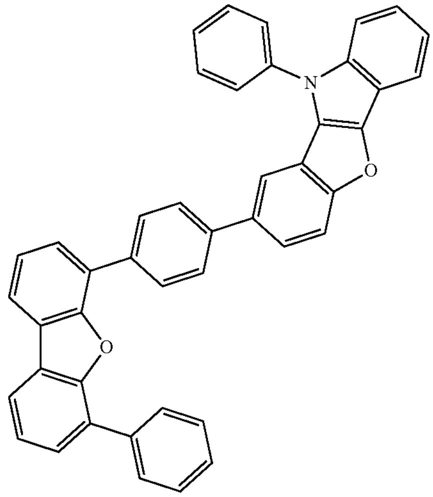
298
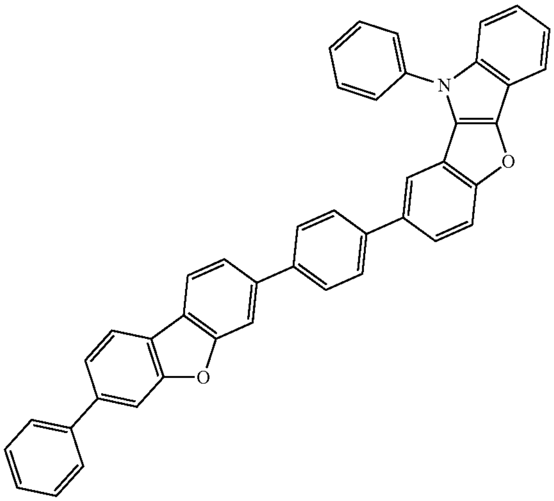
299
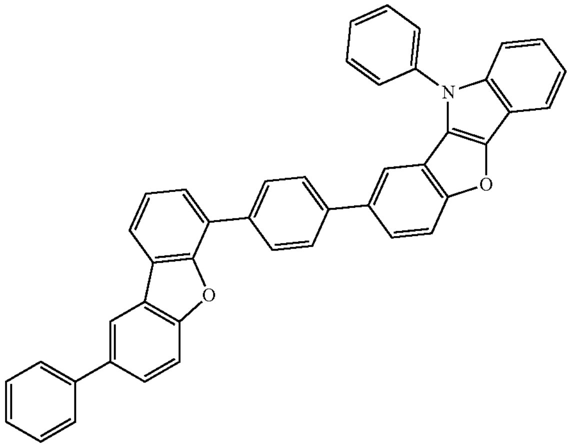
300
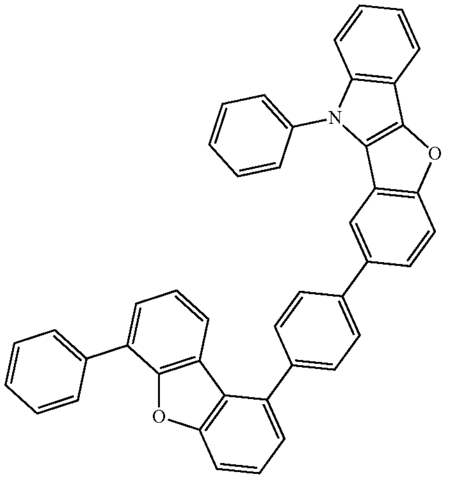

-continued
301
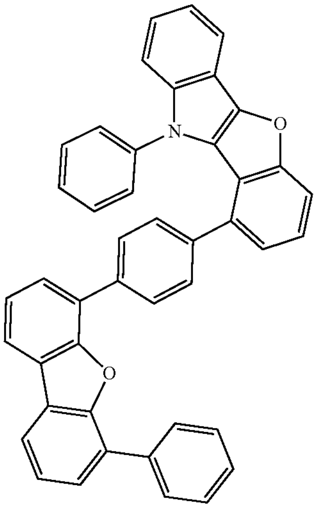
302
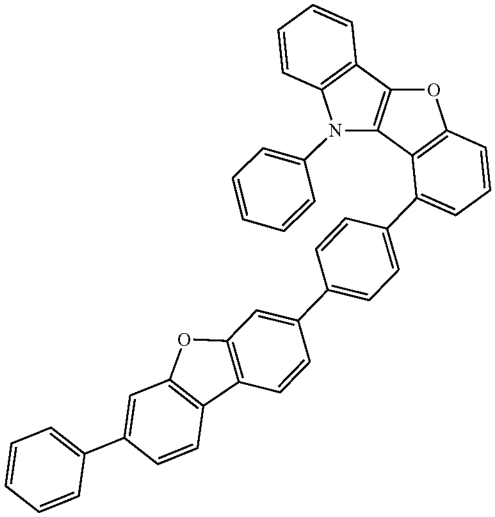
303
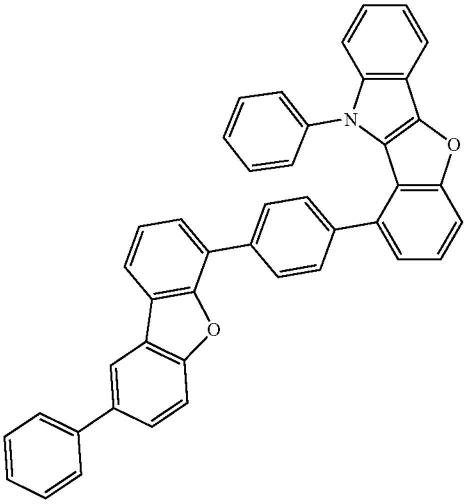
-continued
304
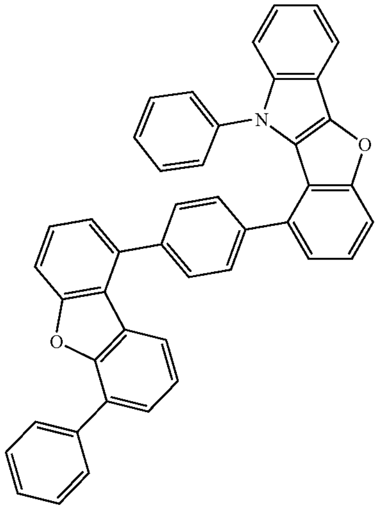
305
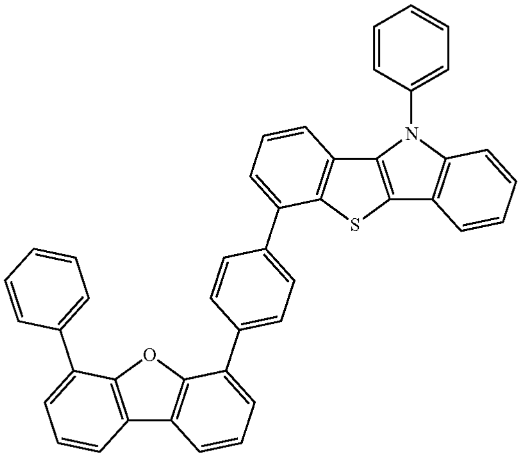
306
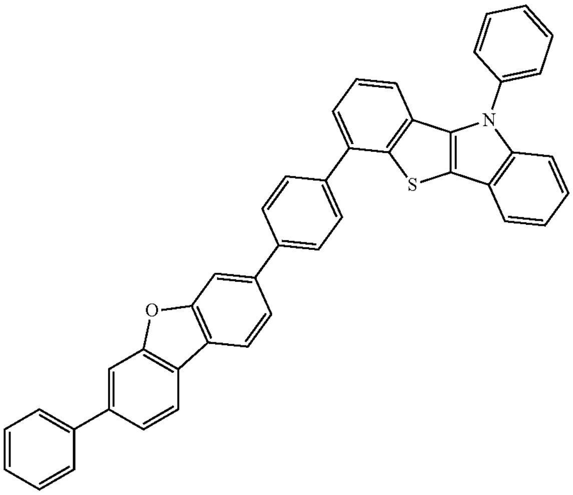

-continued
307
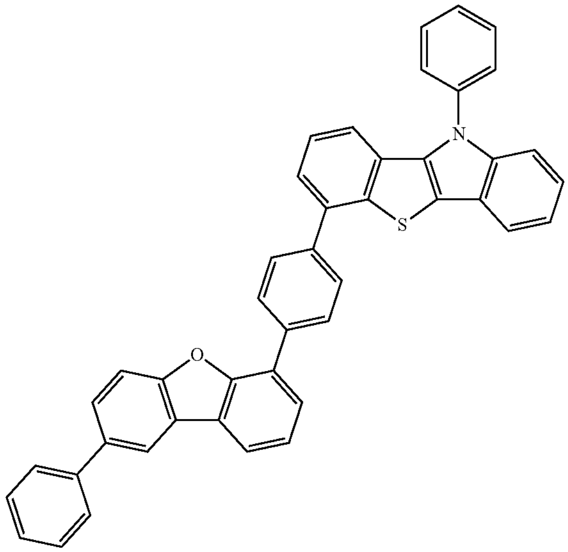
308
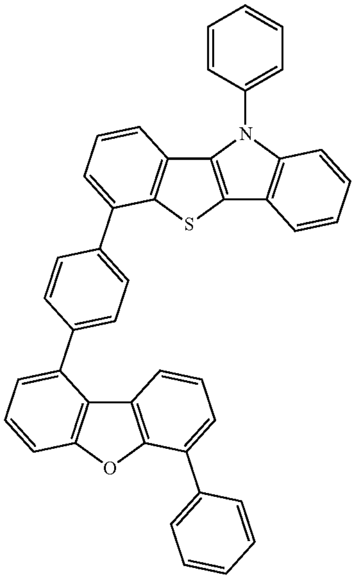
309
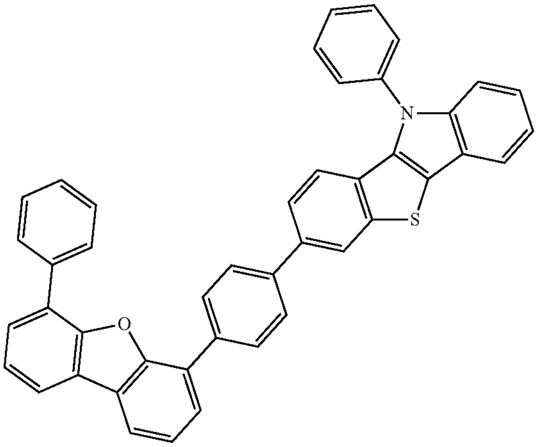
-continued
310
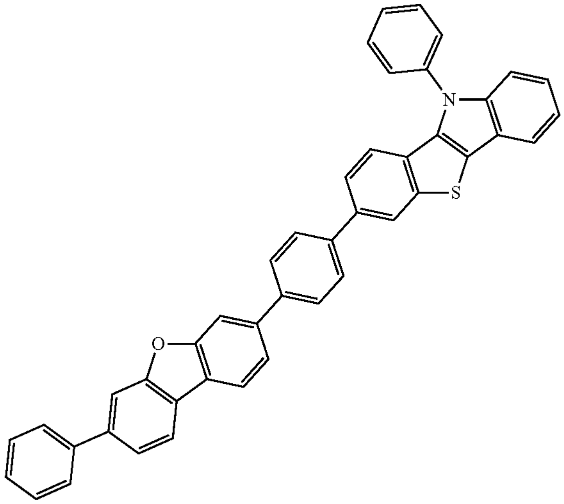
311
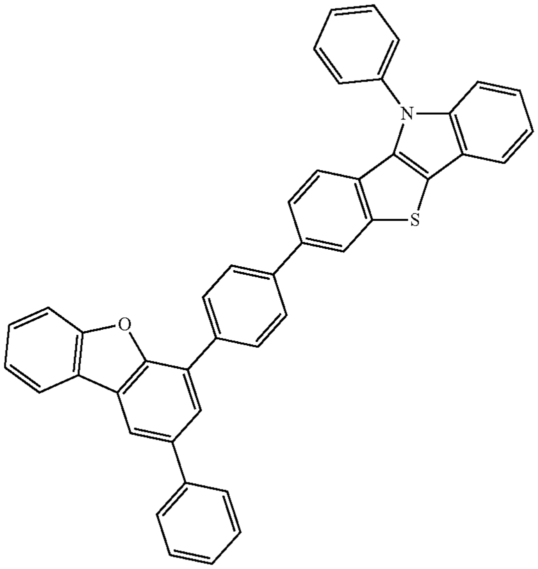
312
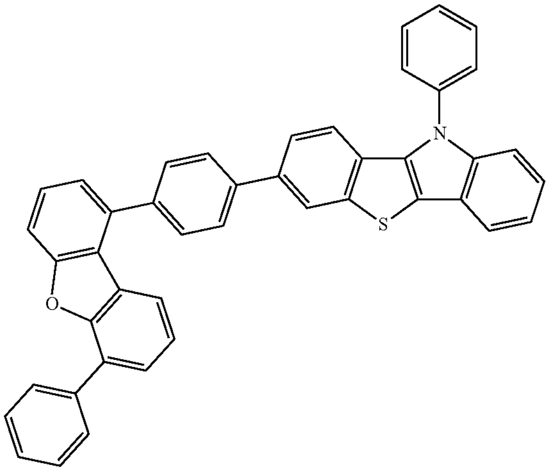

-continued
313
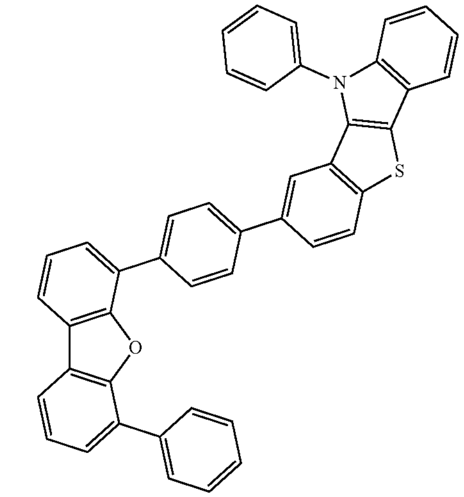
314
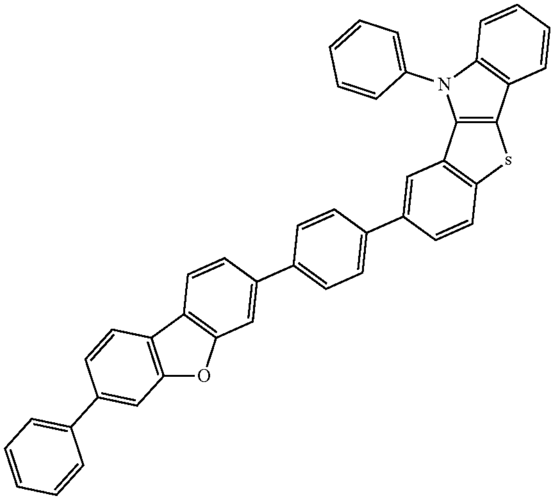
315
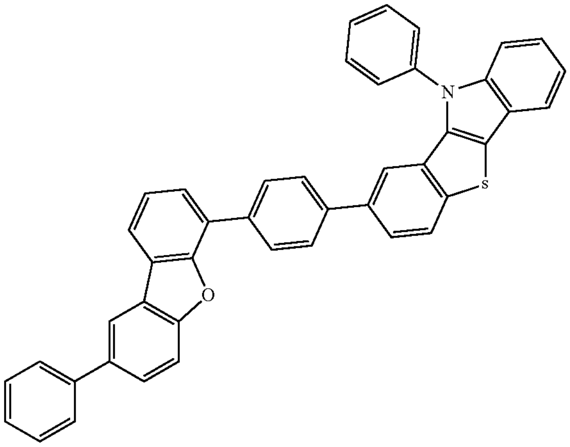
-continued
316
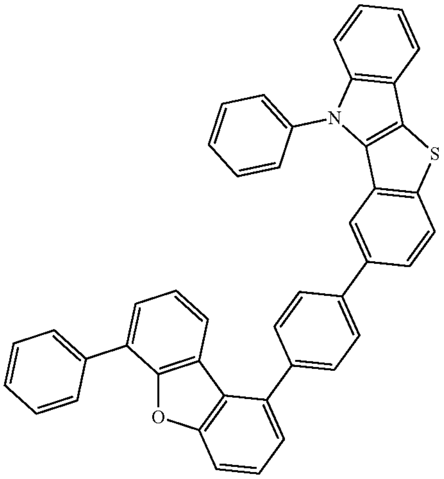
317
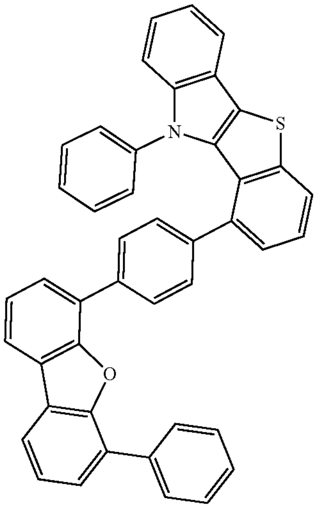
318
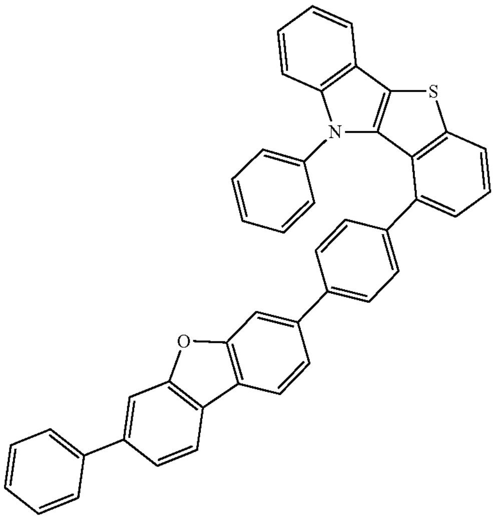

319
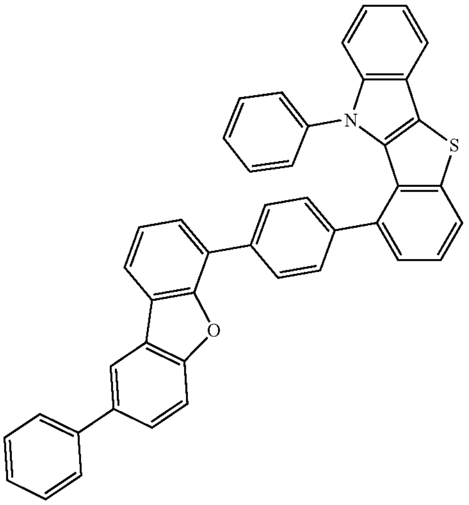
320
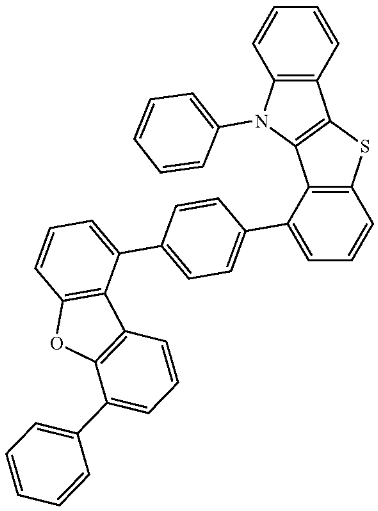
321
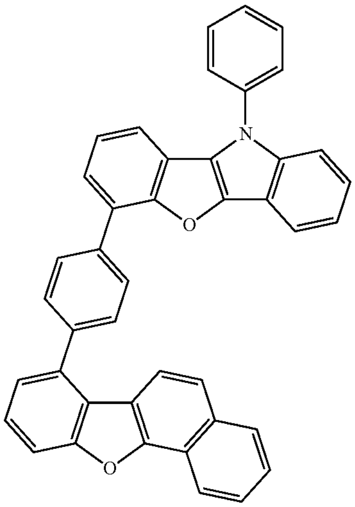
322
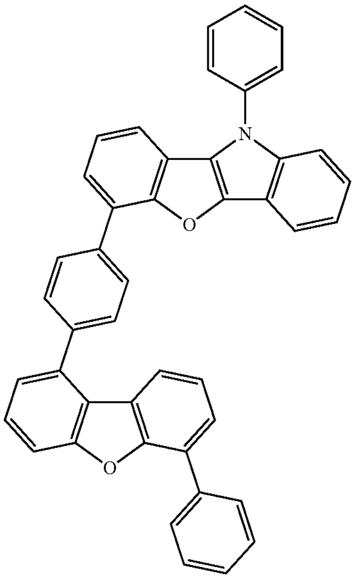
323
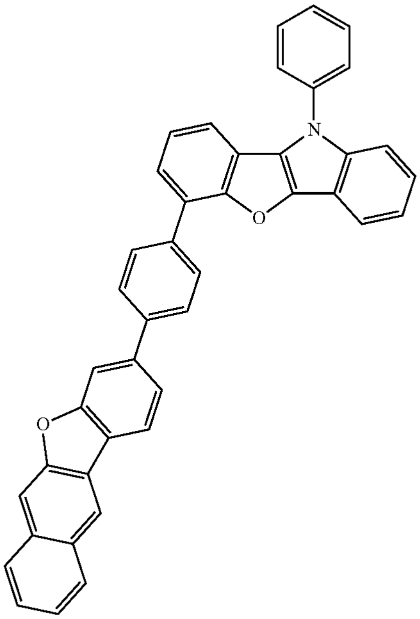

-continued
324
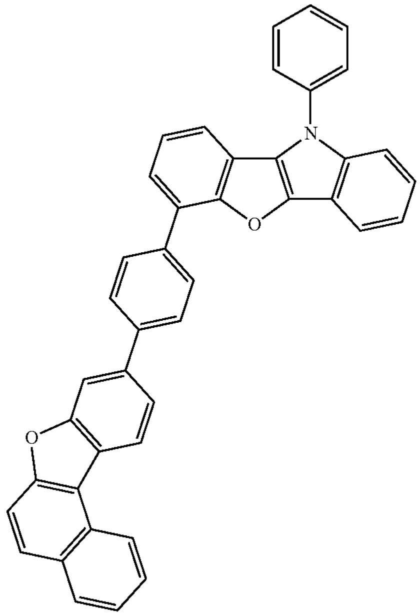
325
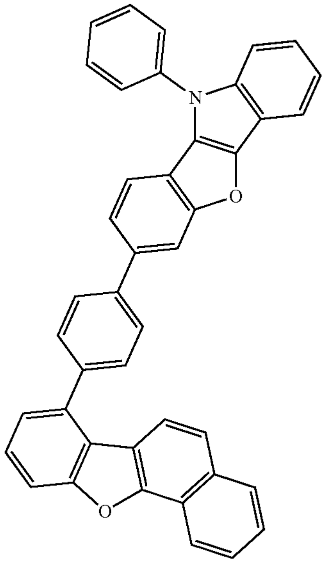
-continued
326
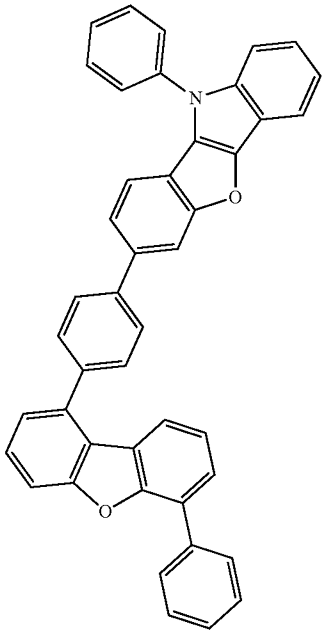
327
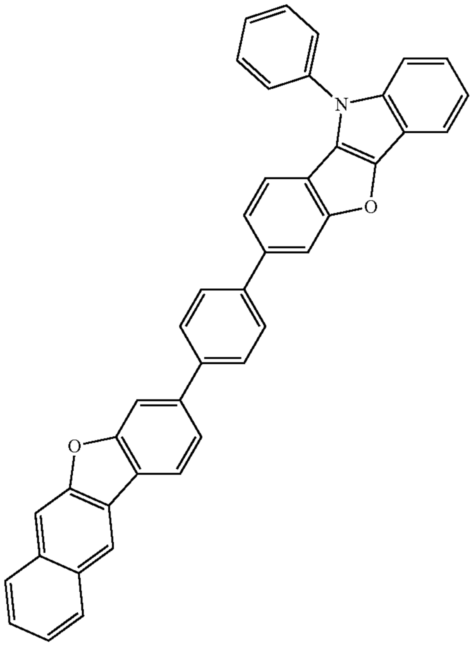

328
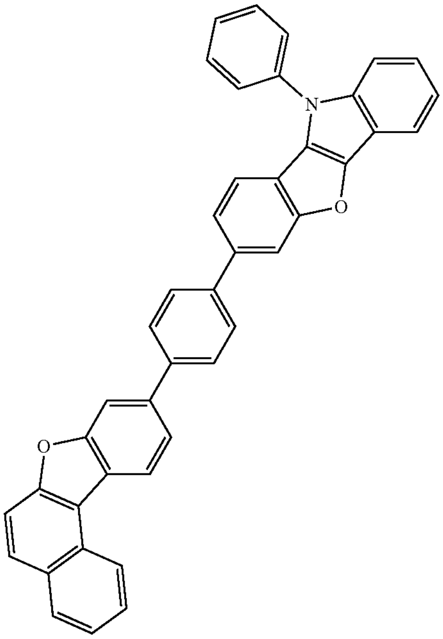
329
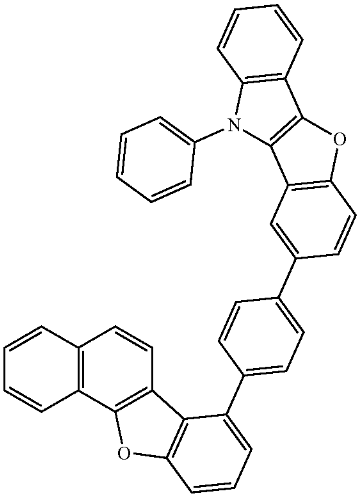
330
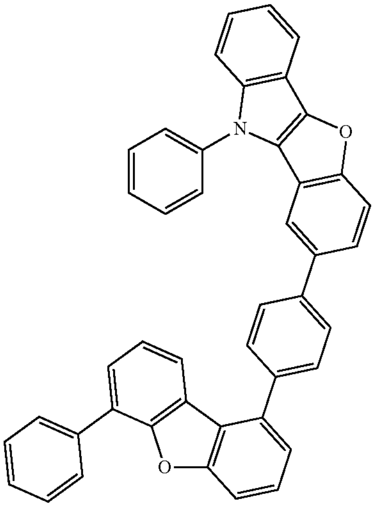
331
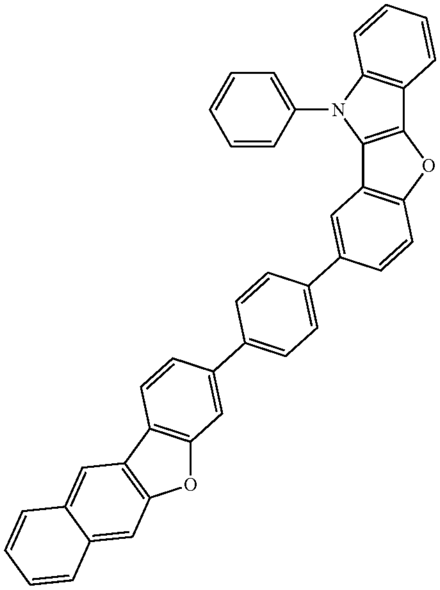
332
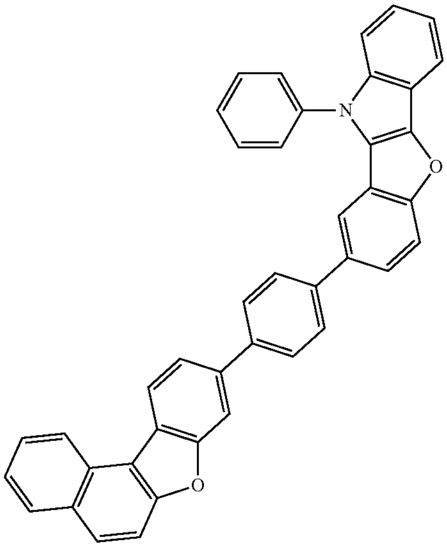
333
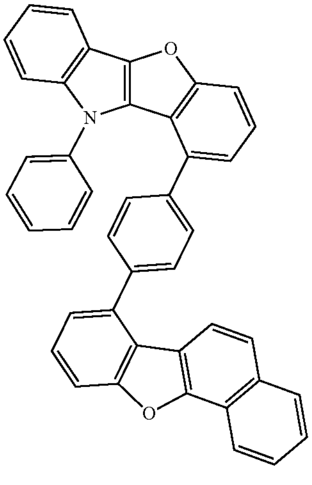

-continued
334
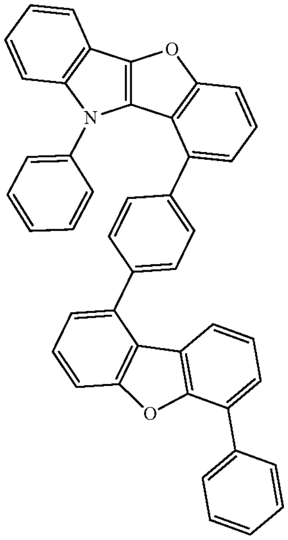
335
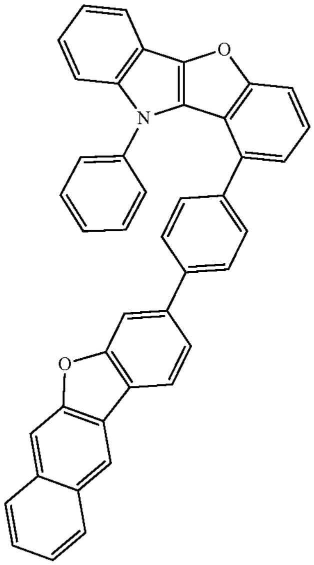
336
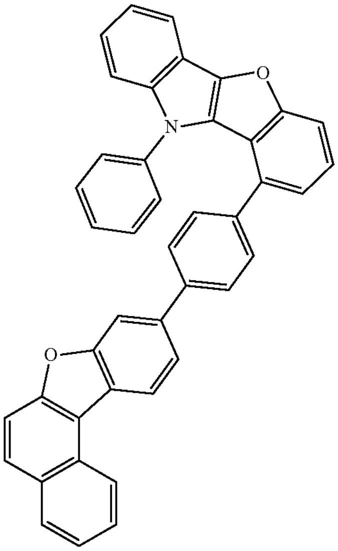
-continued
337
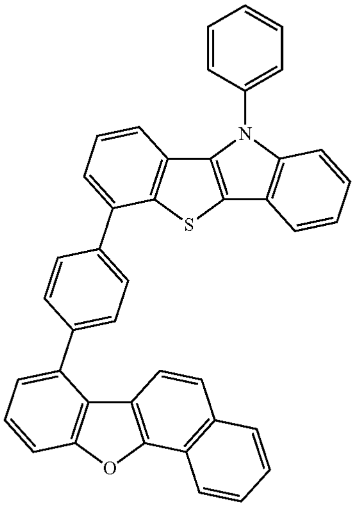
338
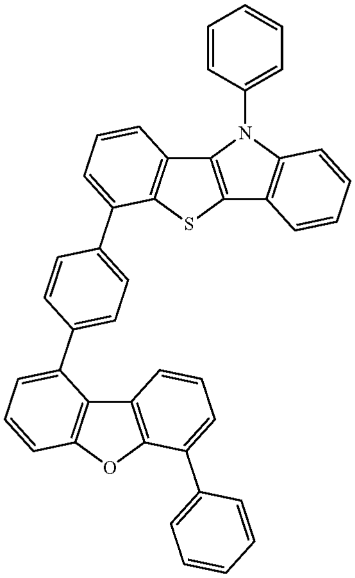

-continued
339
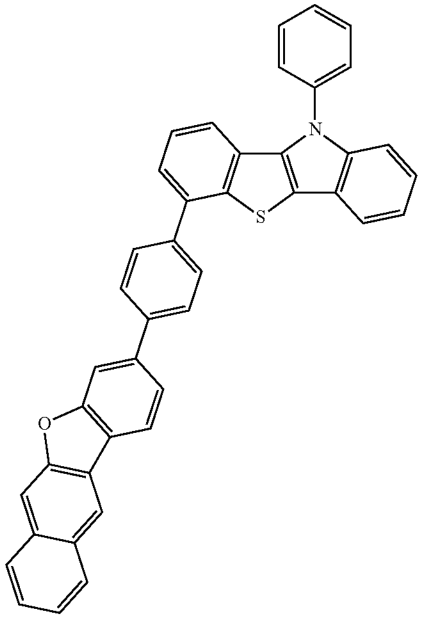
340
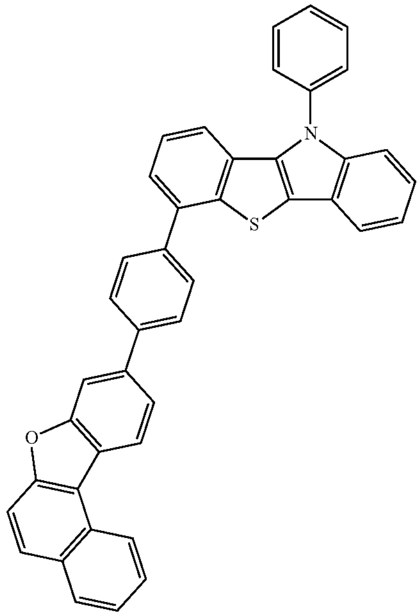
-continued
341
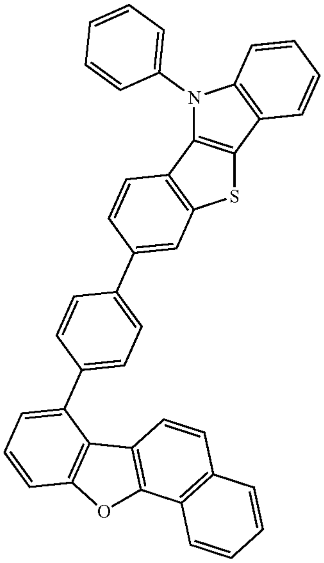
342
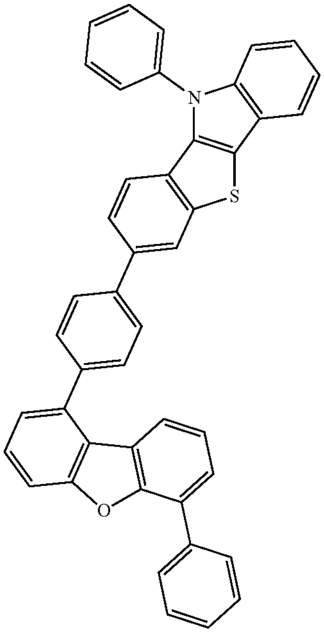

-continued
343
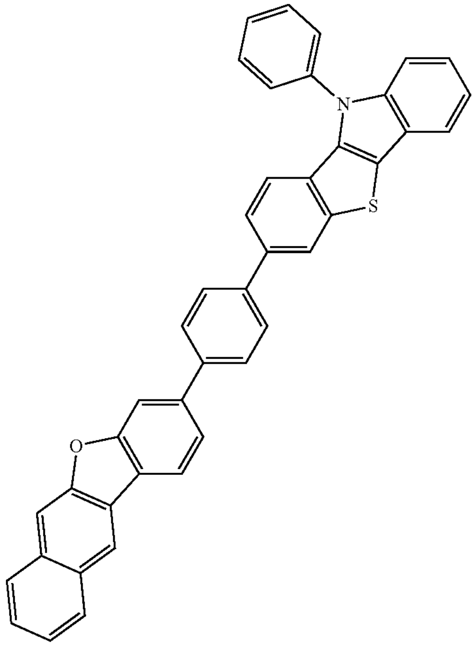
344
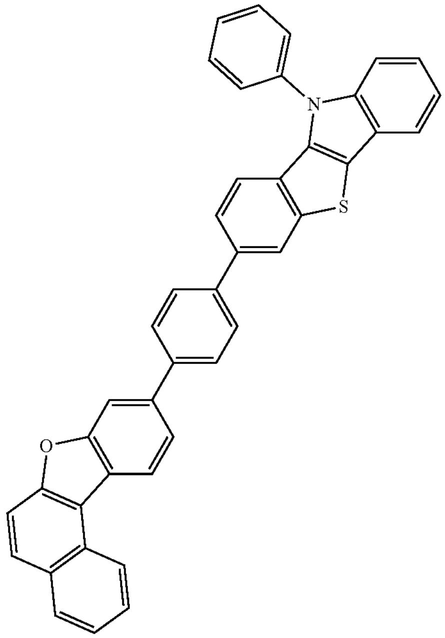
-continued
345
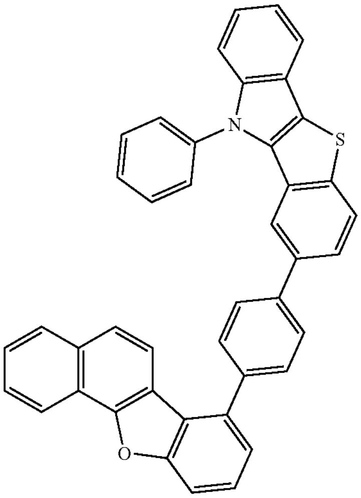
346
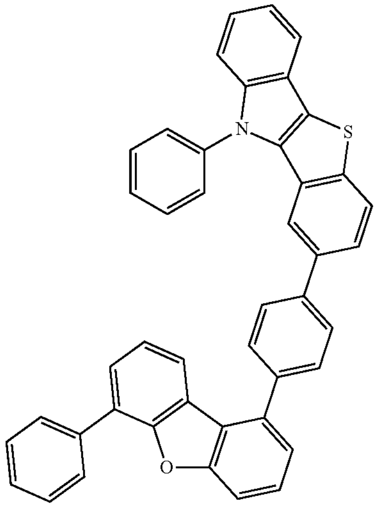
347
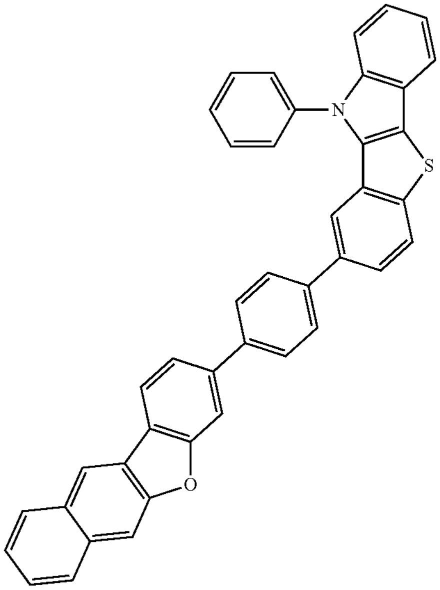

-continued
348
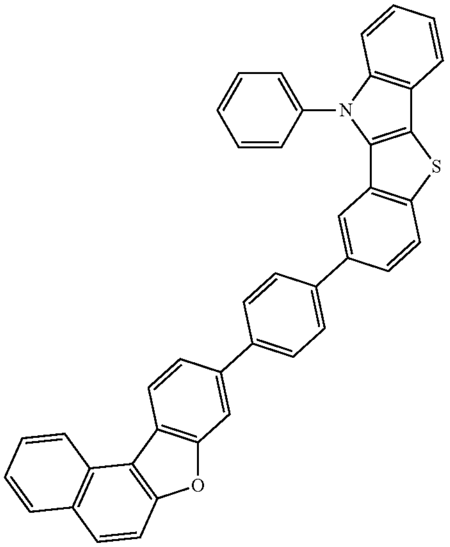
349
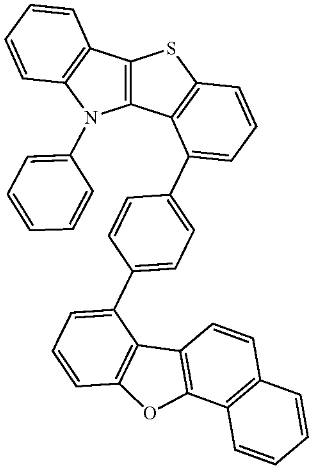
350
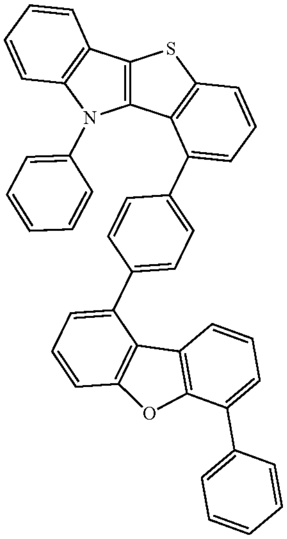
-continued
351
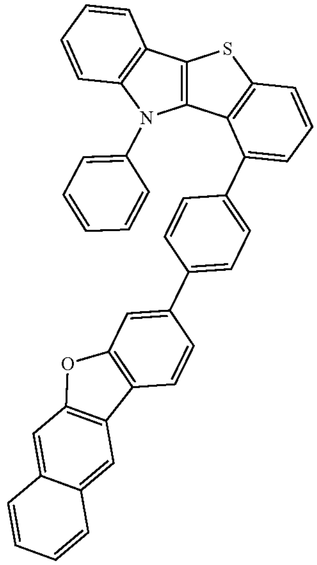
352
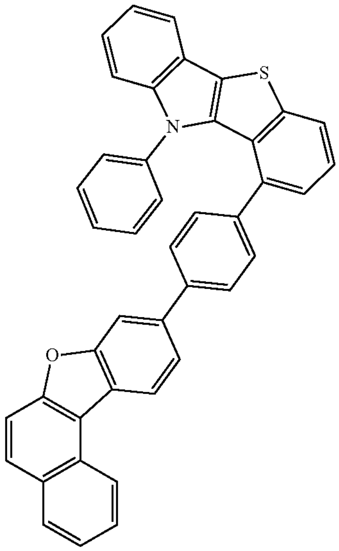
353
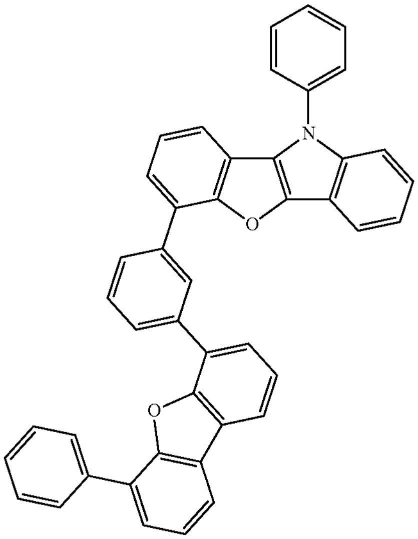

-continued
354
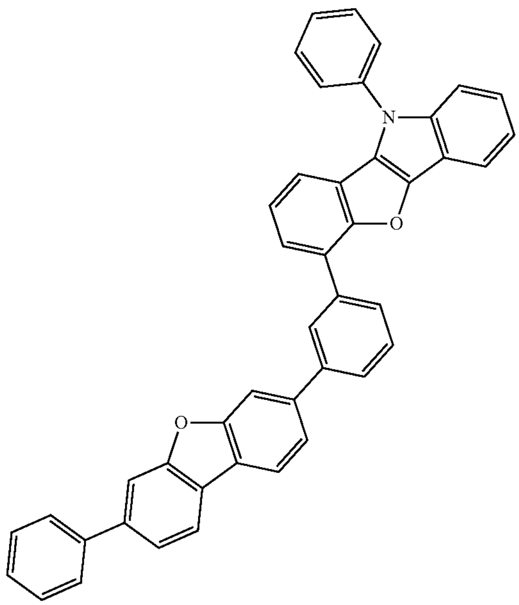
355
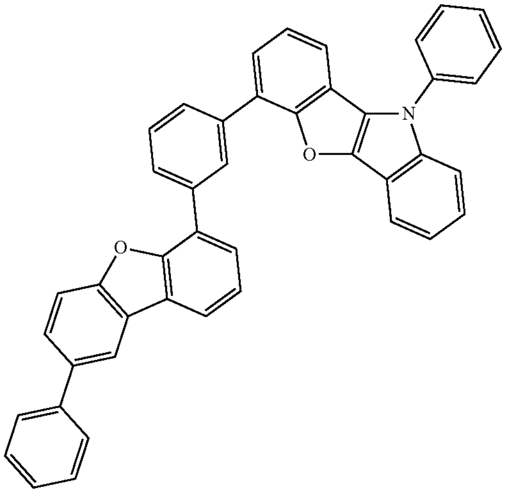
-continued
356
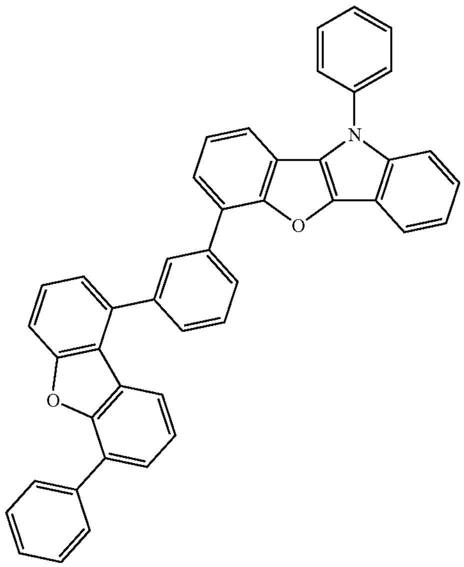
357
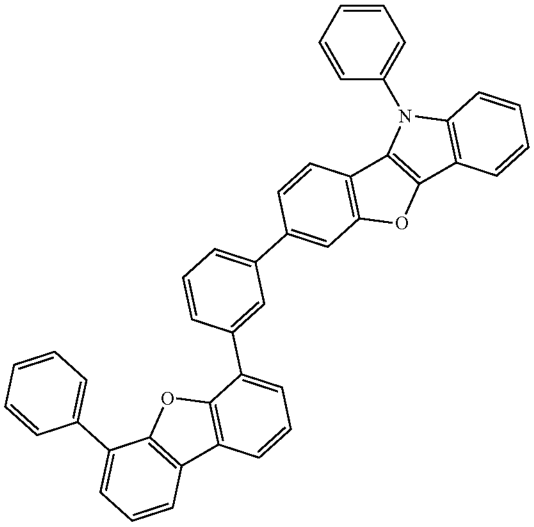
358
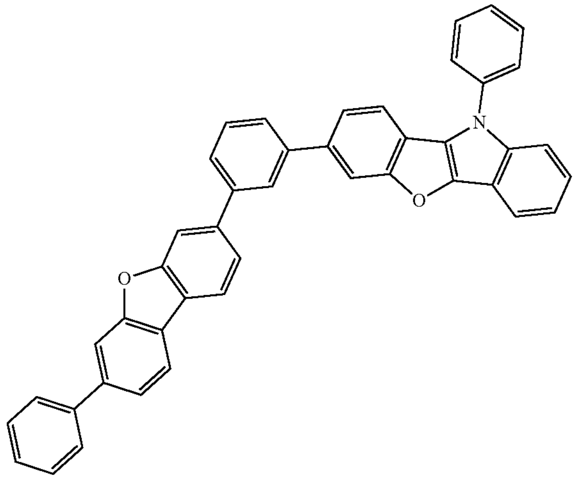

-continued
359
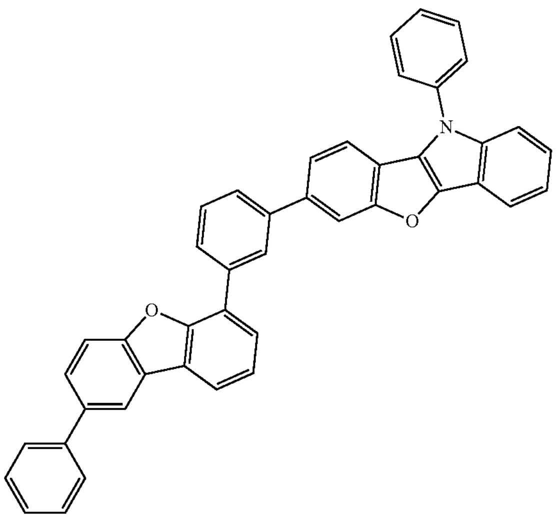
360
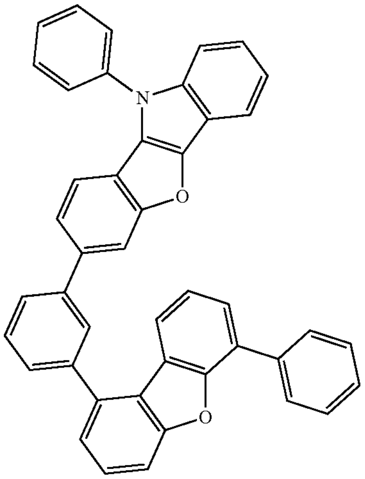
361
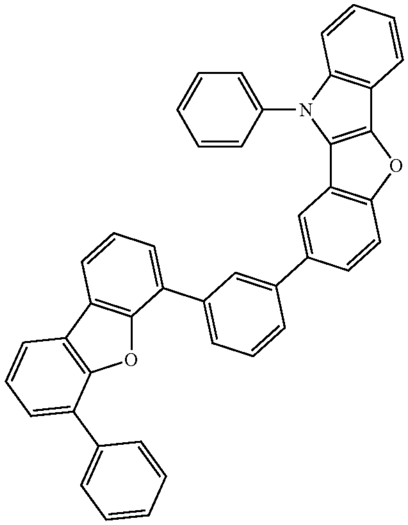
-continued
362
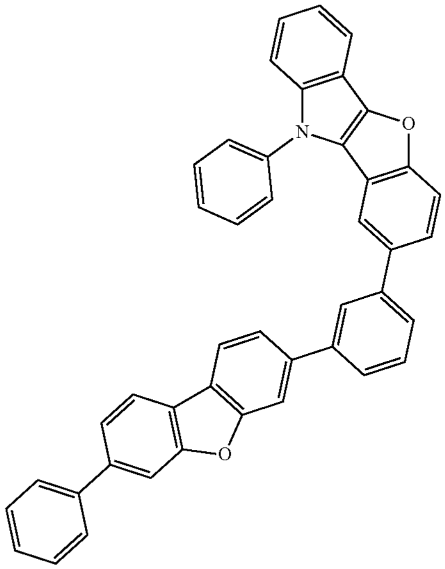
363
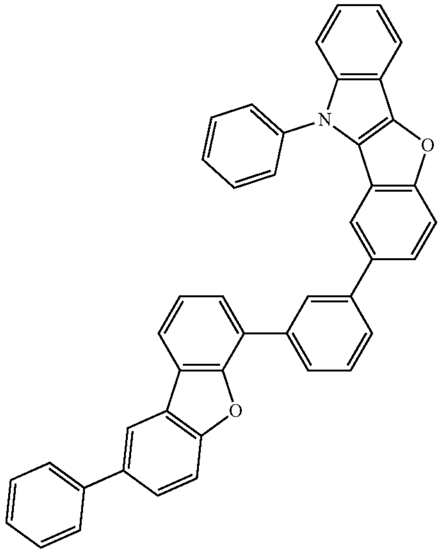
364
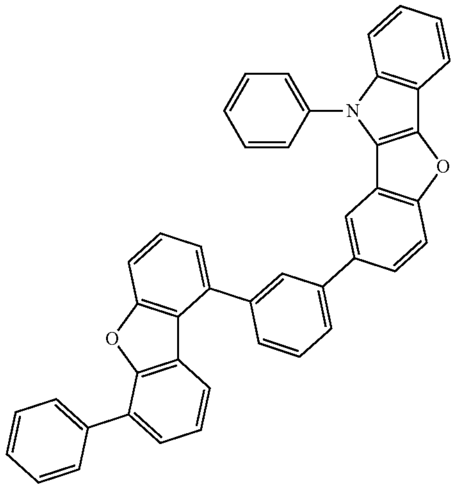

-continued
365
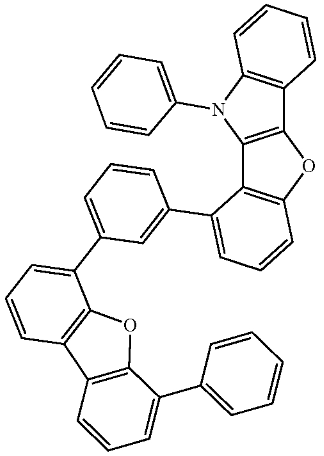
366
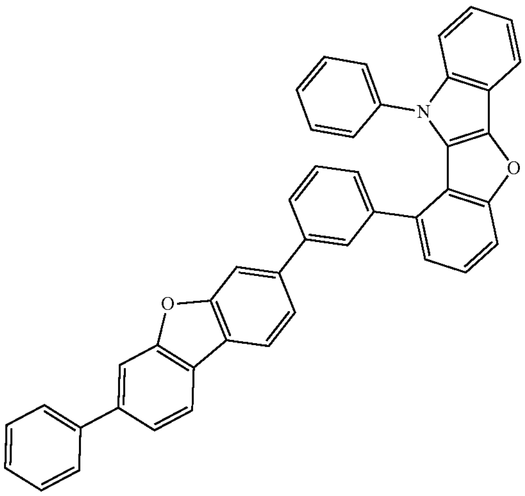
367
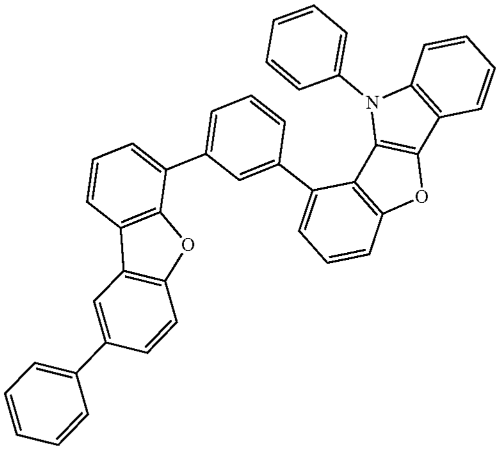
-continued
368
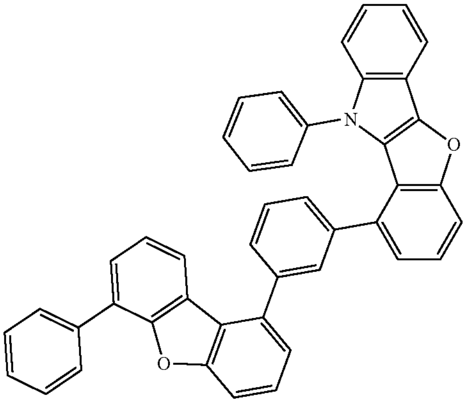
369
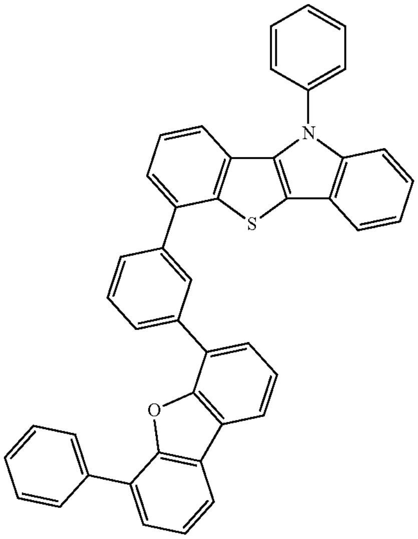
370
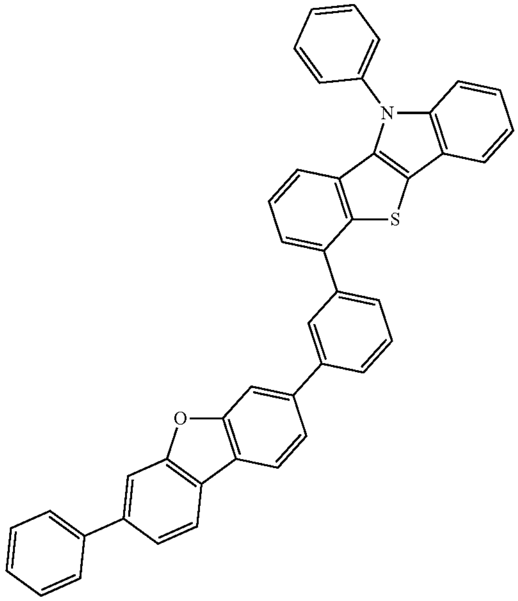

-continued
371
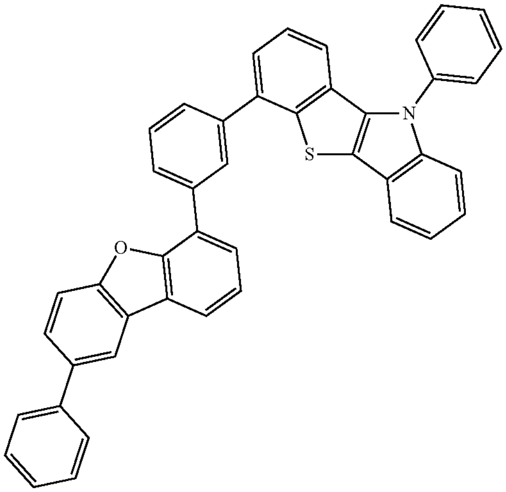
372
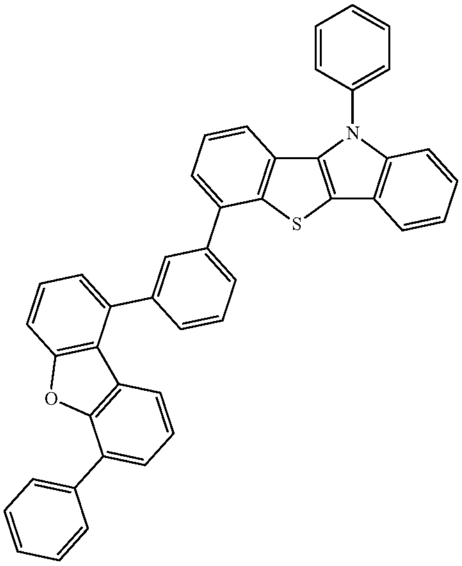
373
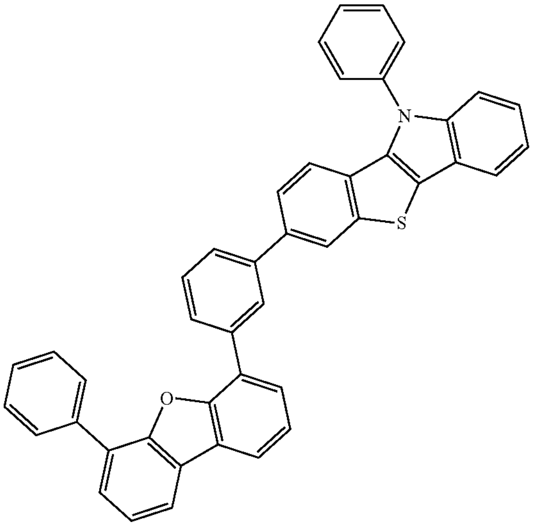
-continued
374
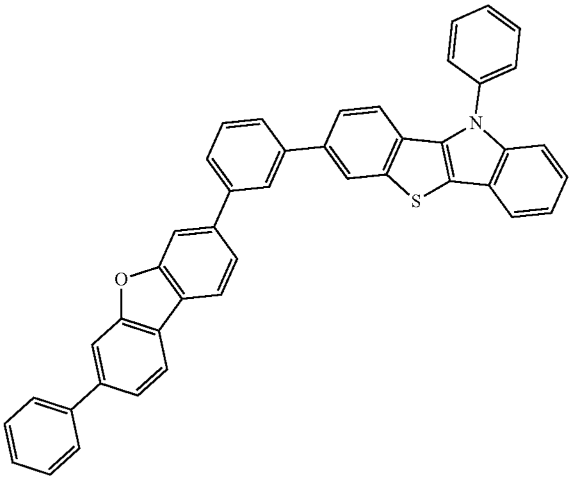
375
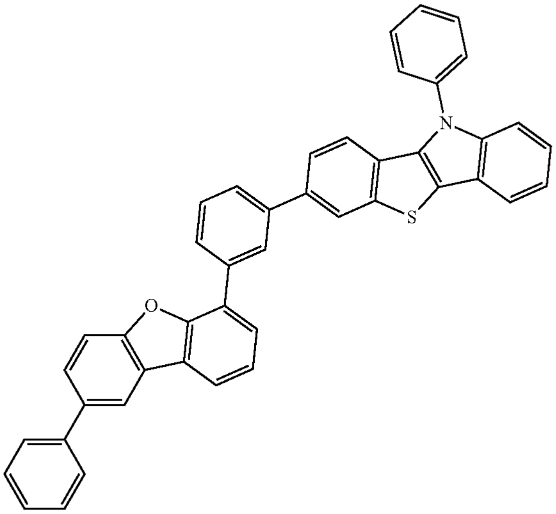
376
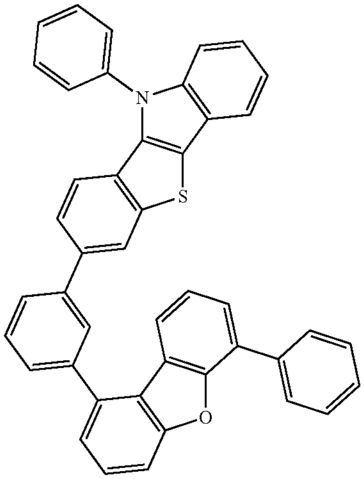

-continued
377
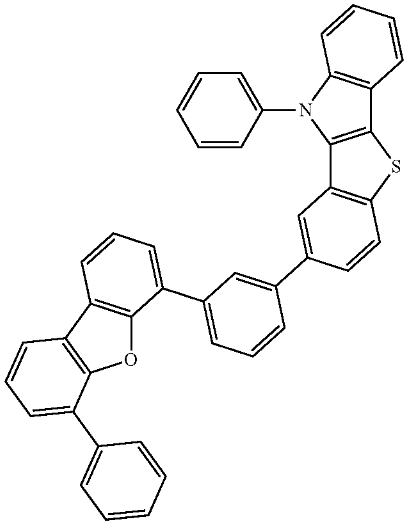
378
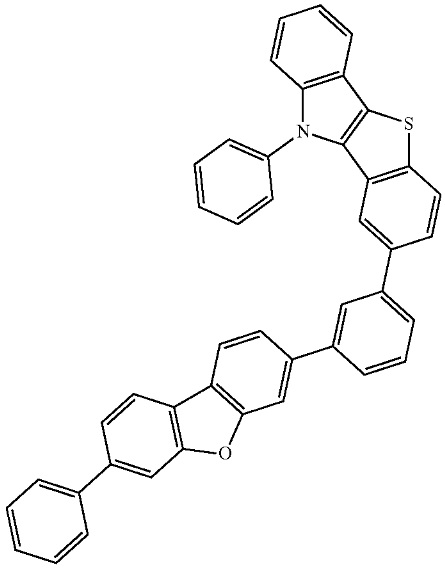
379
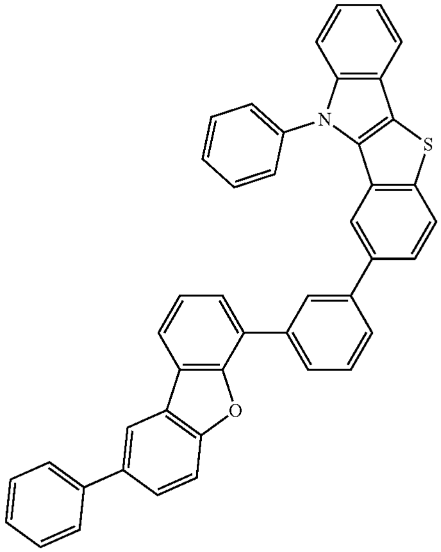
-continued
380
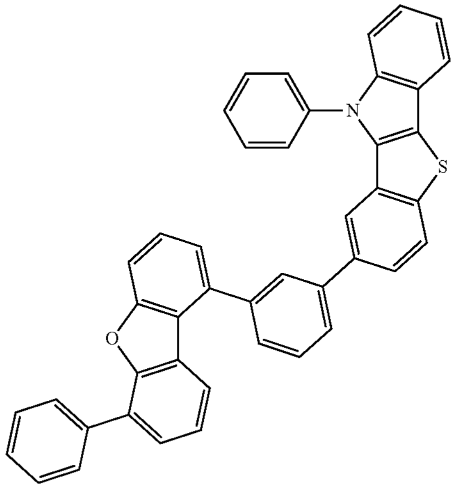
381
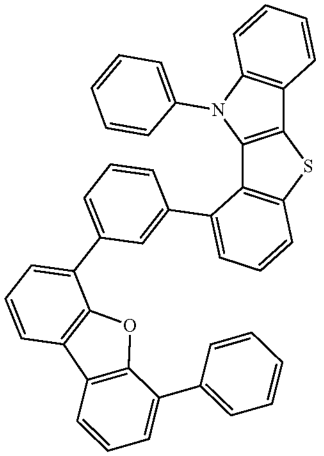
382
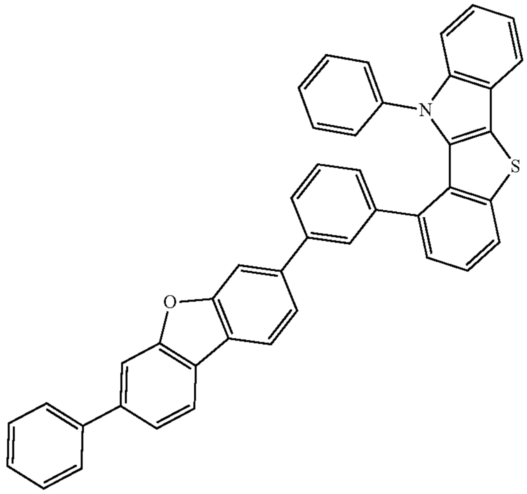

-continued
383
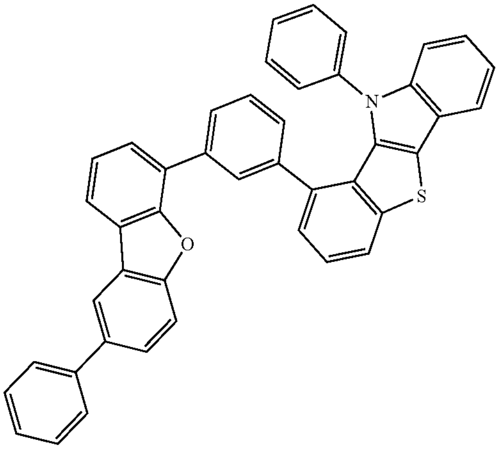
384
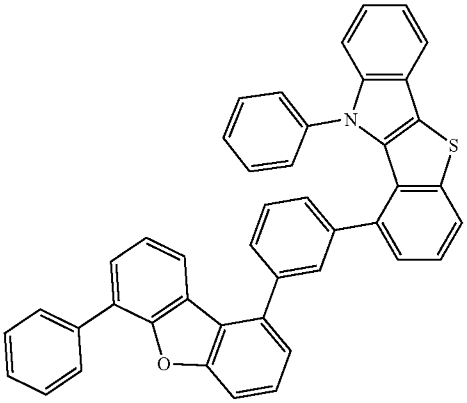
385
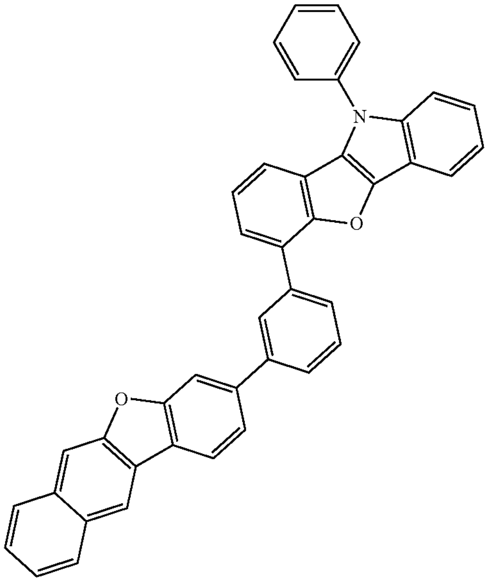
-continued
386
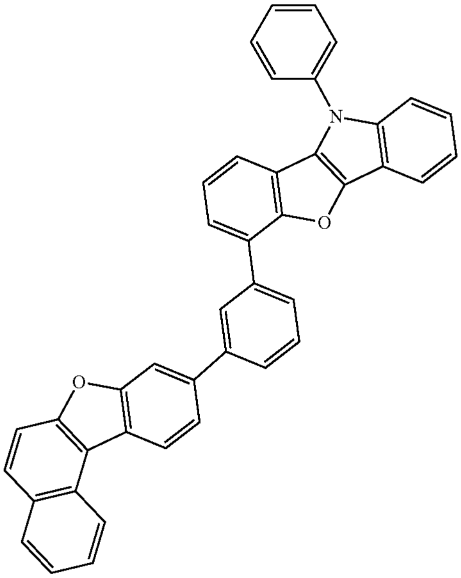
387
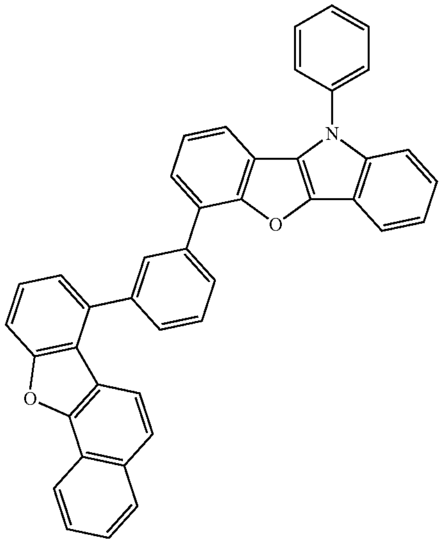

-continued
388
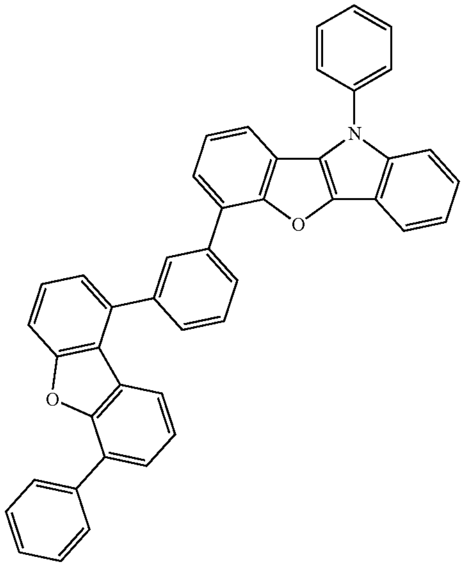
389
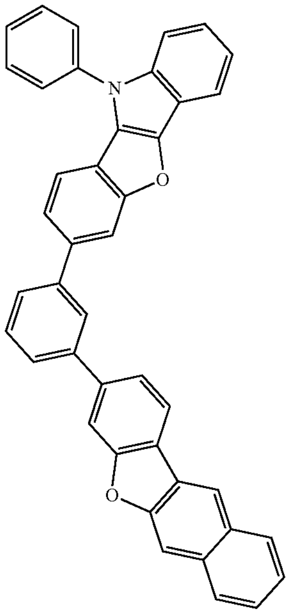
-continued
390
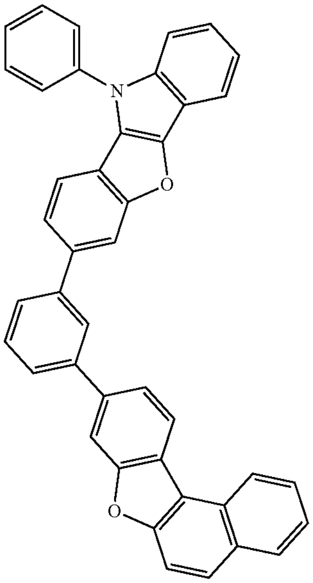
391
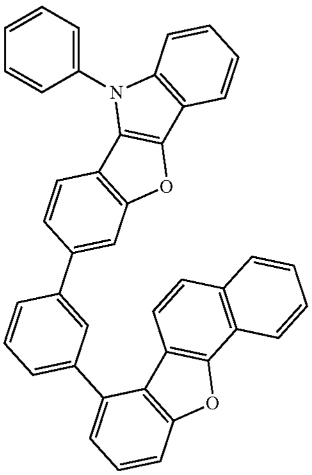
392
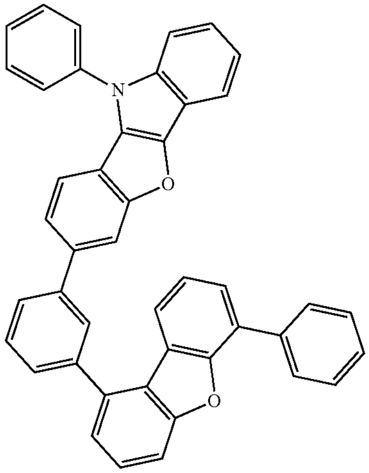

-continued
393
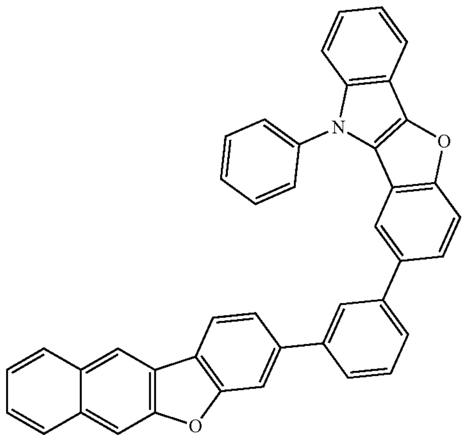
394
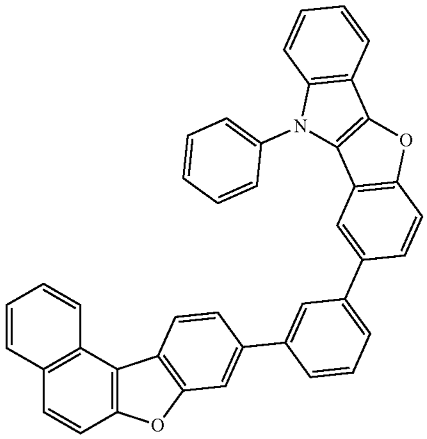
395
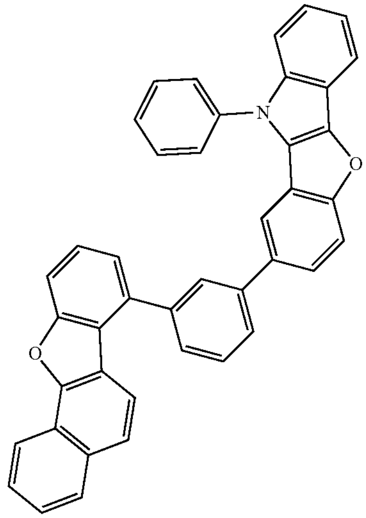
-continued
396
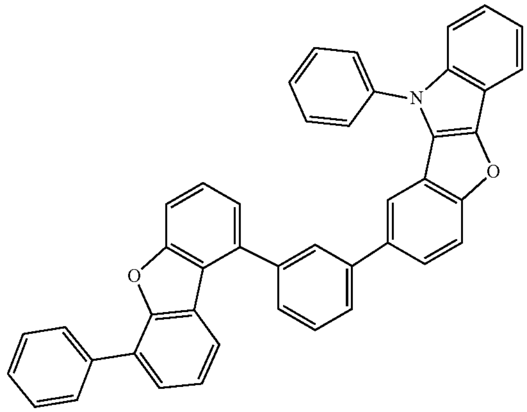
397
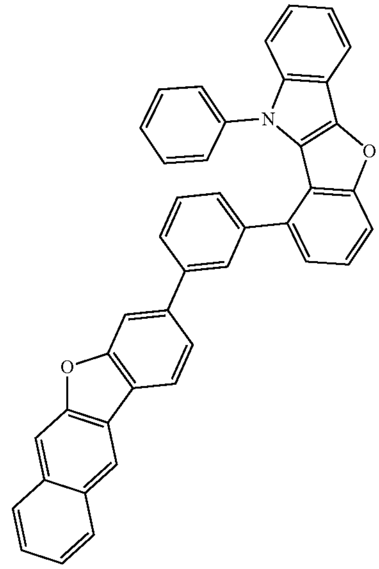
398
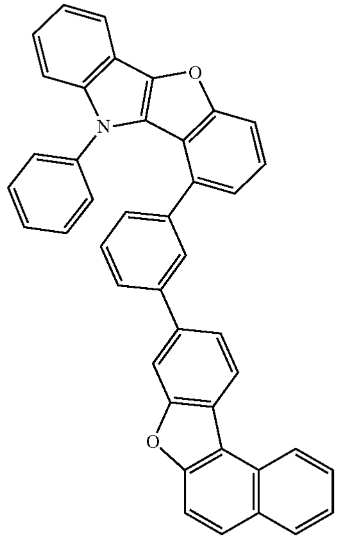

-continued
399
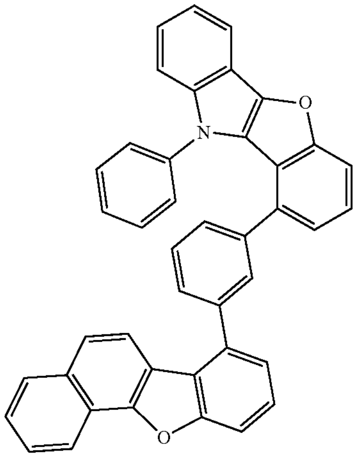
400
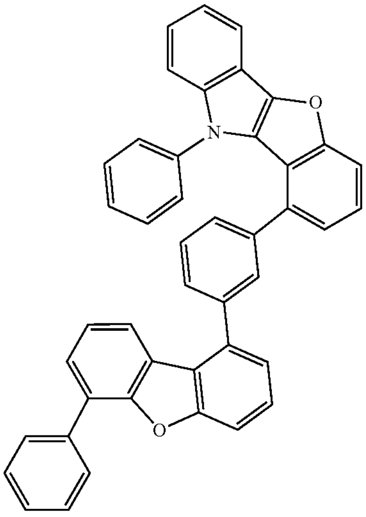
401
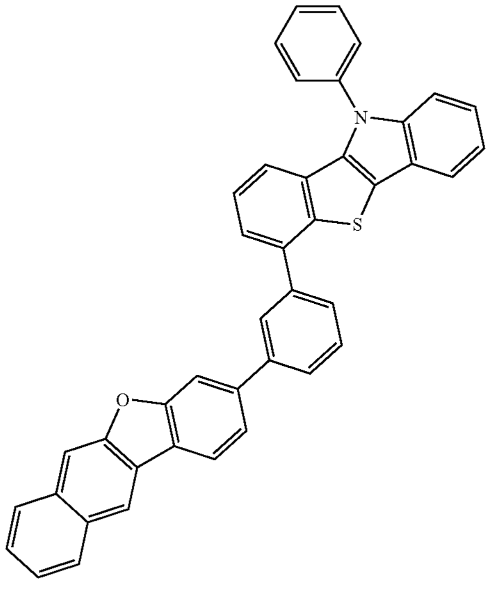
-continued
402
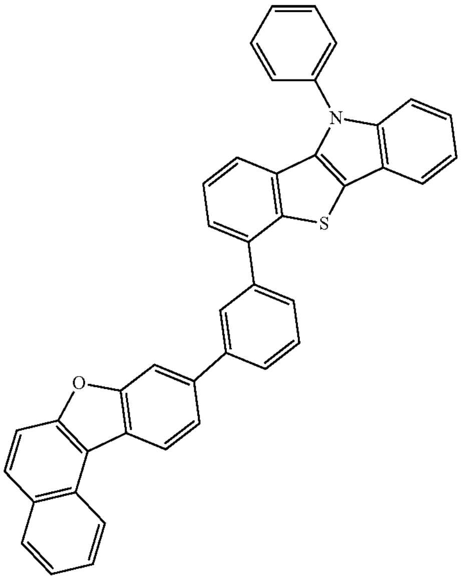
403
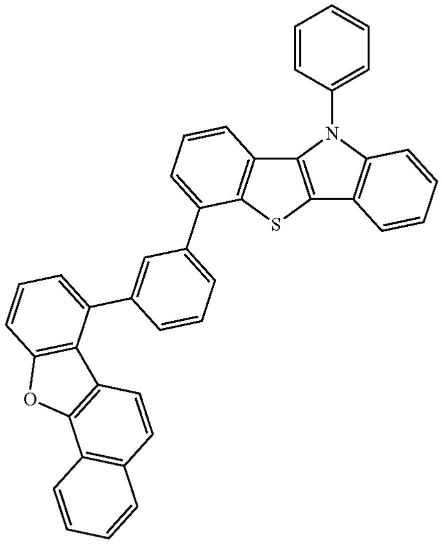

404
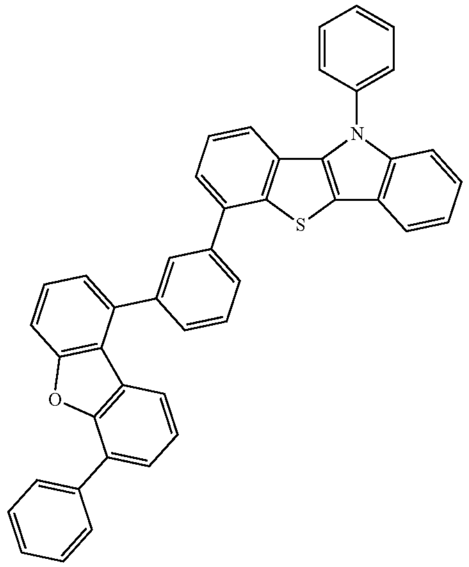
405
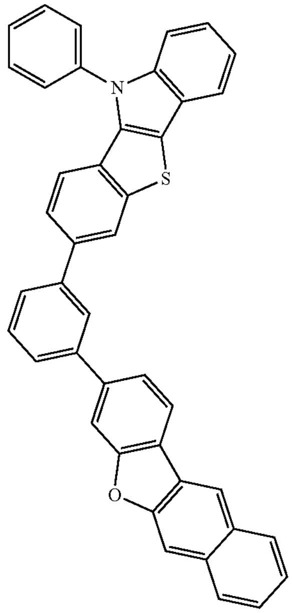
406
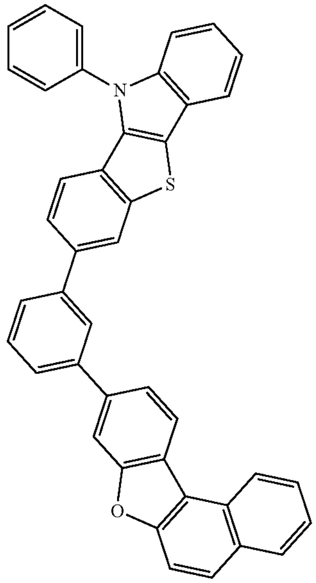
407
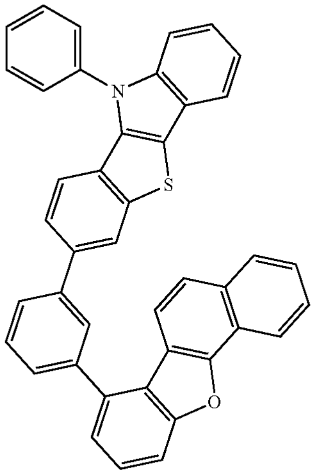
408
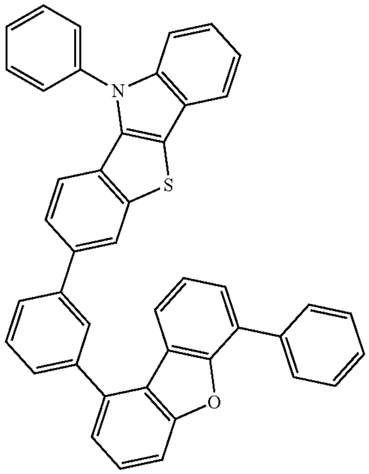

409
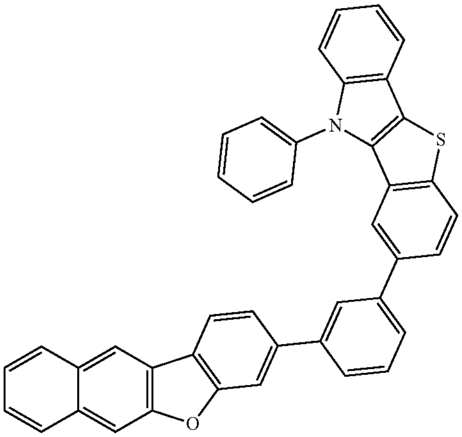
410
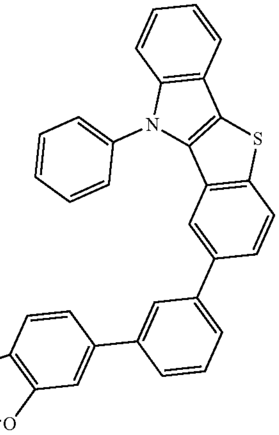
411
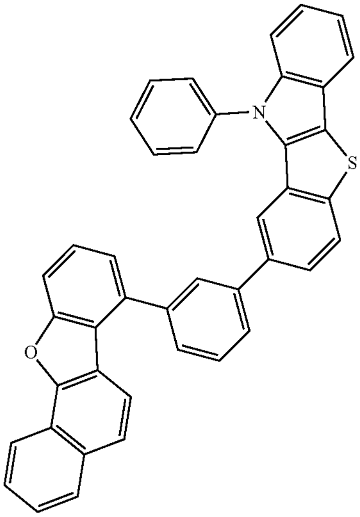
412
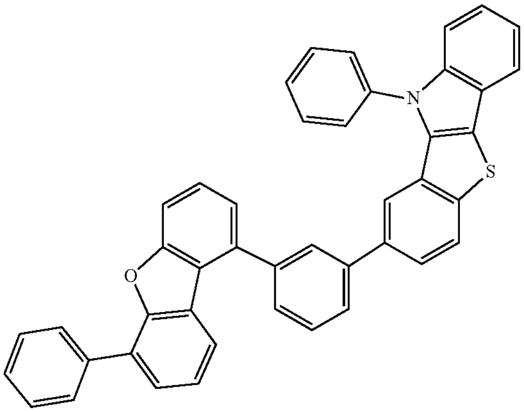
413
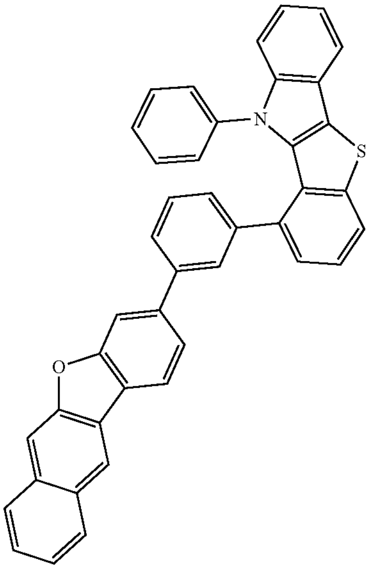
414
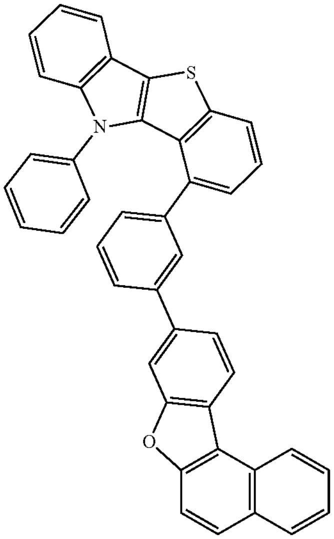

-continued
415
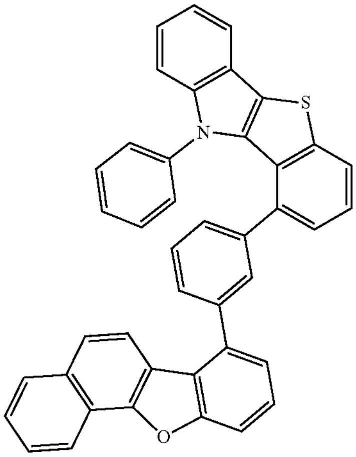
416
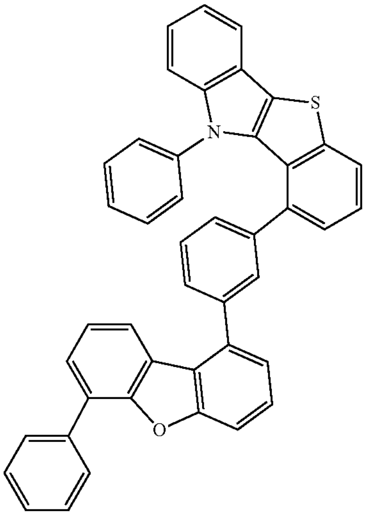
417
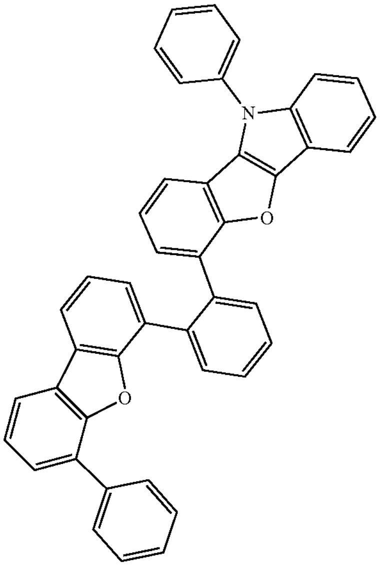
-continued
418
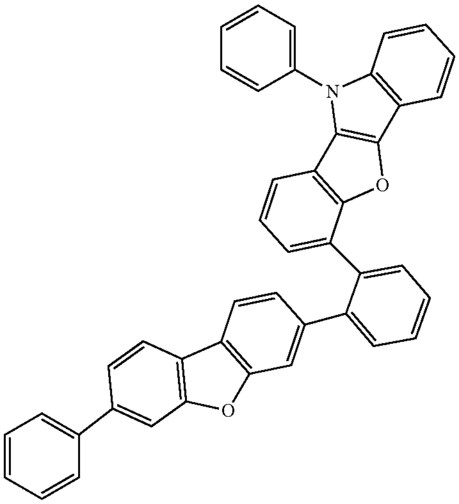
419
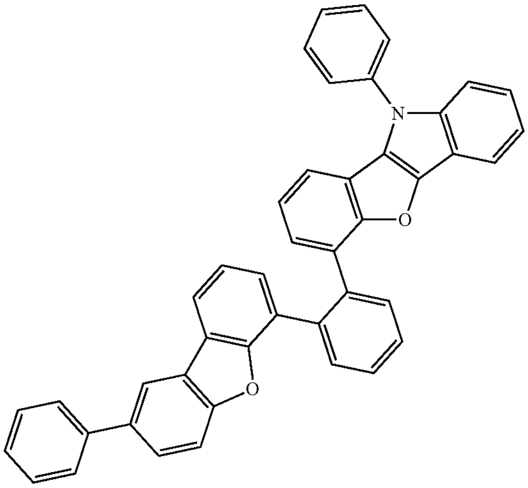
420
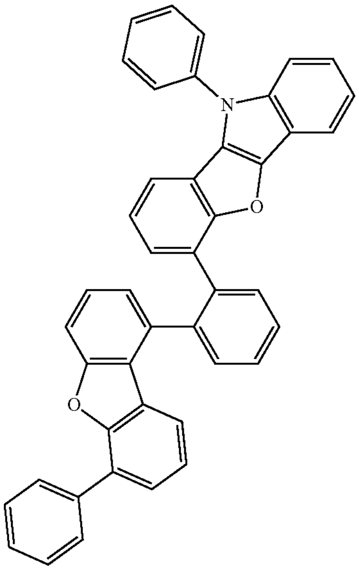

-continued
421
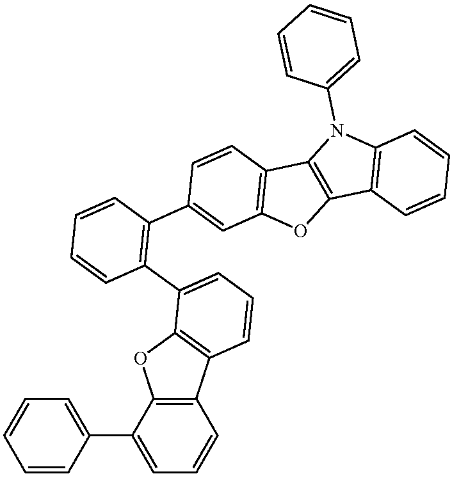
422
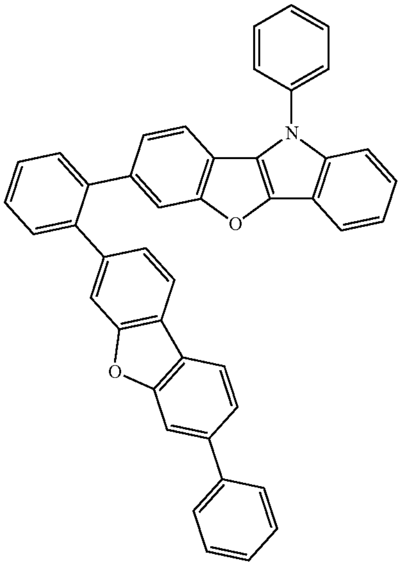
423
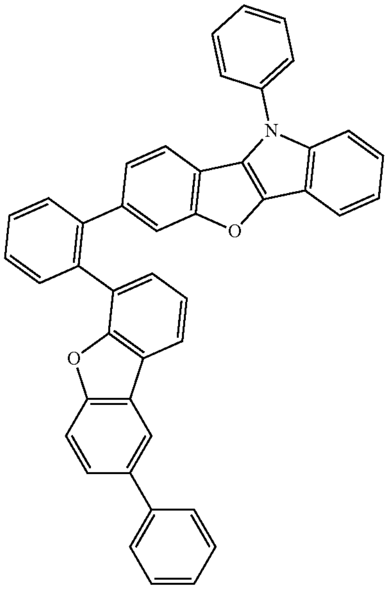
-continued
424
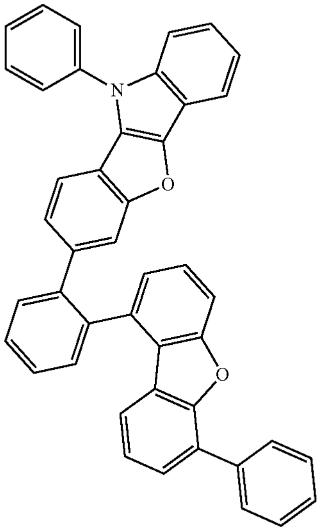
425
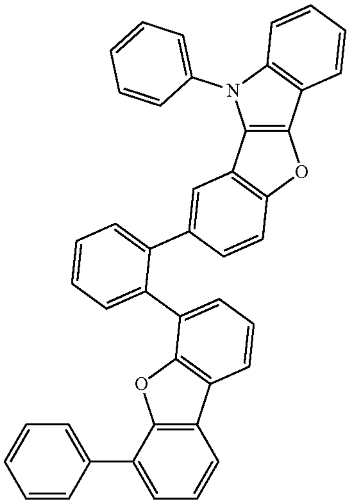
426
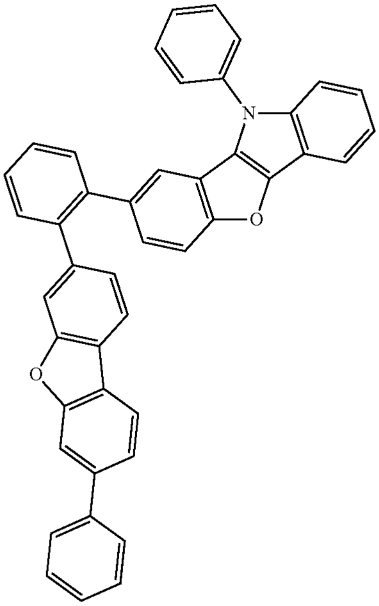

-continued
427
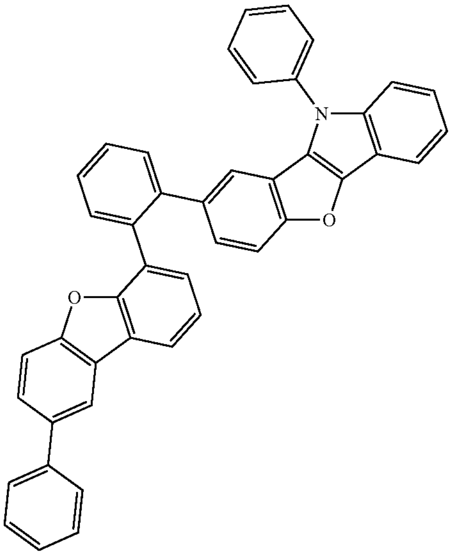
428
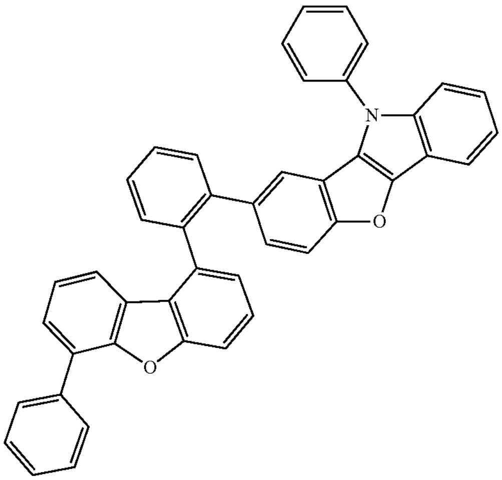
430
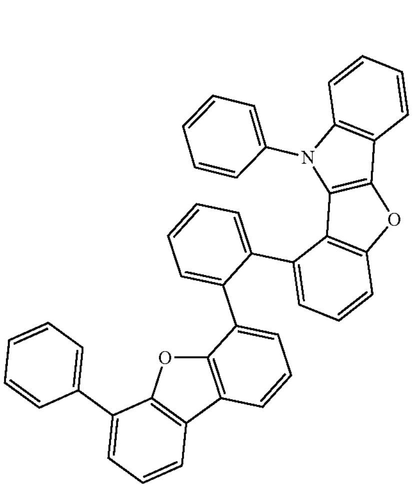
-continued
431
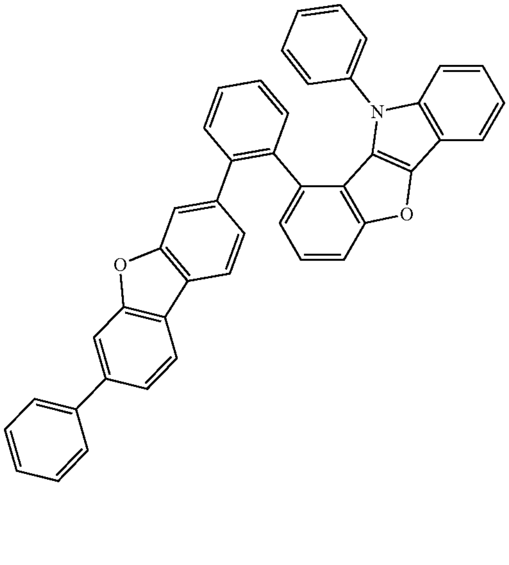
432
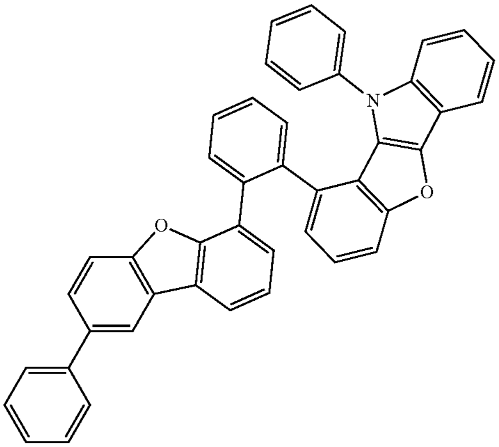
432
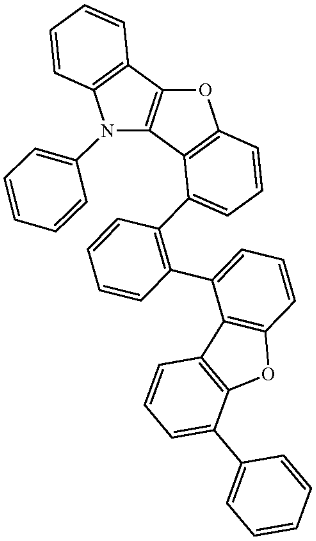

-continued
433
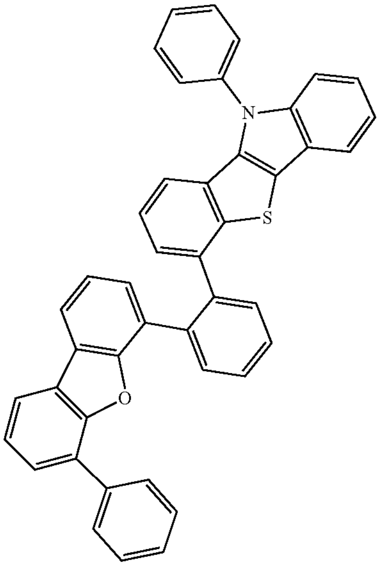
434
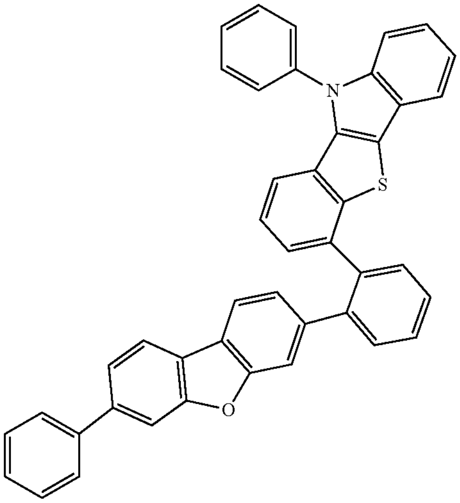
435
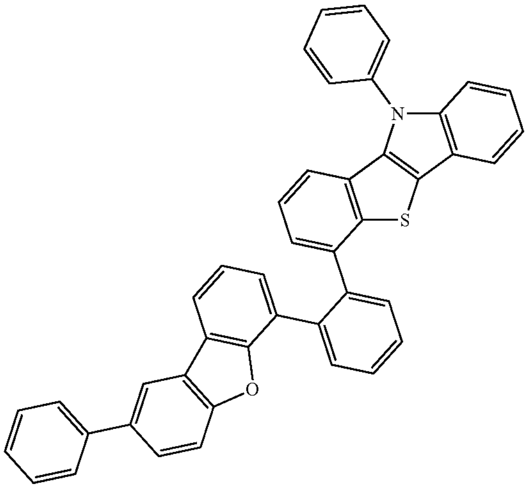
-continued
436
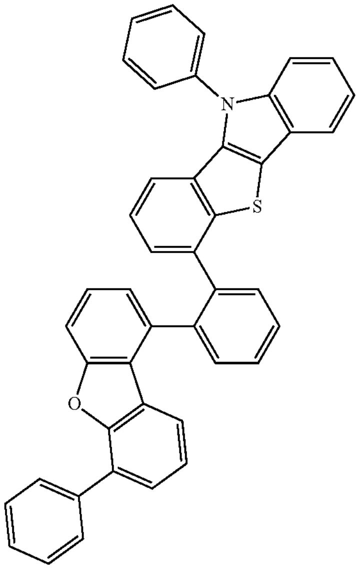
437
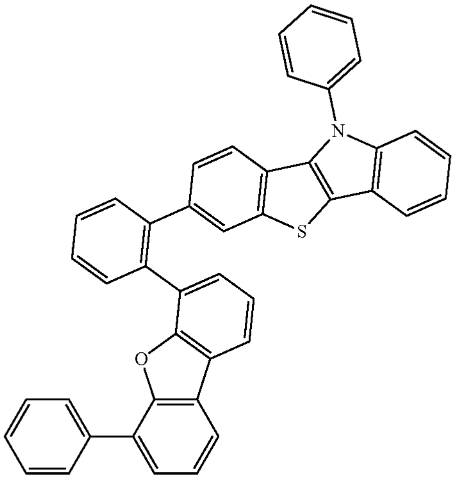
438
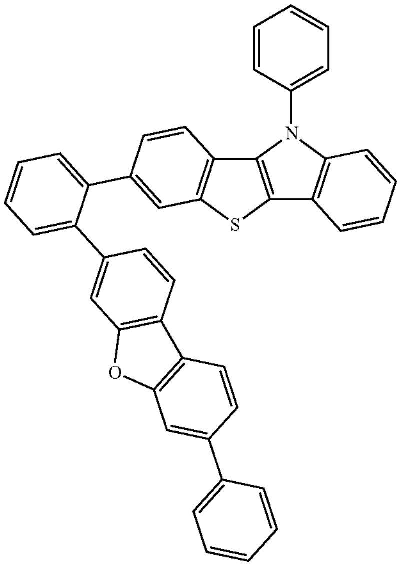

-continued
439
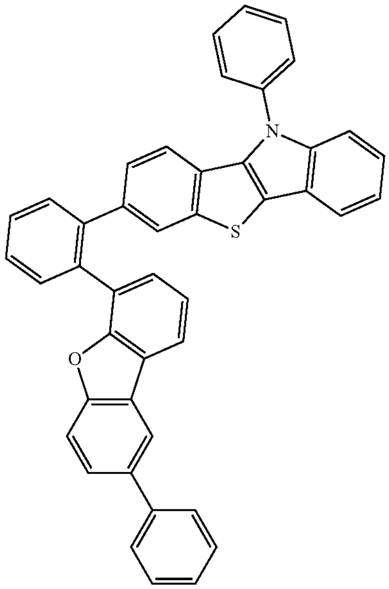
440
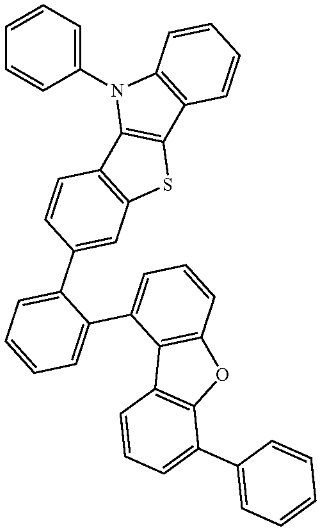
441
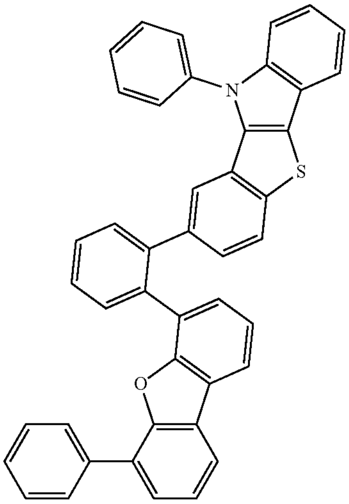
-continued
442
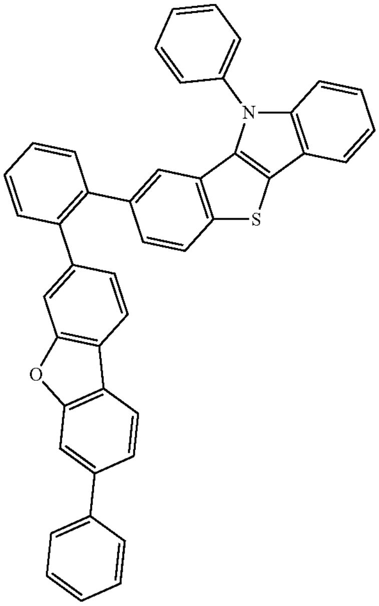
443
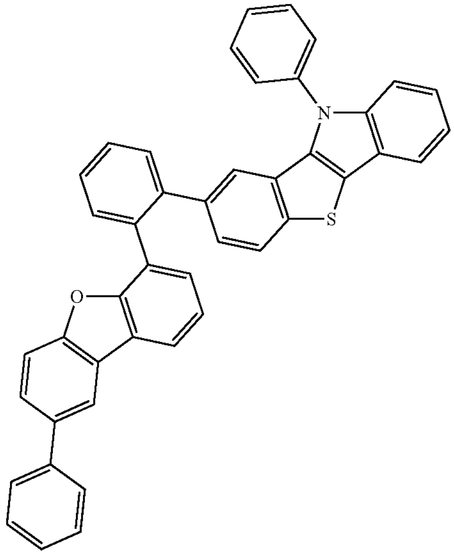
444
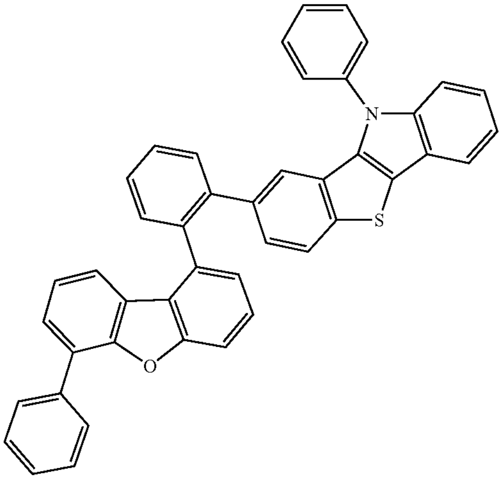

-continued
445
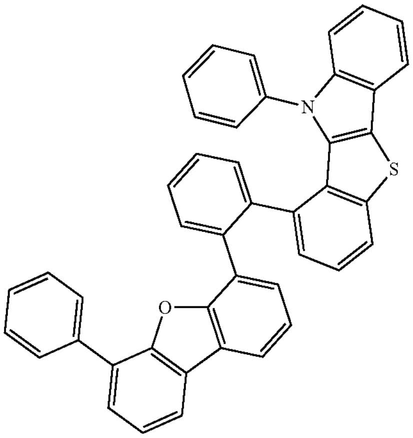
446
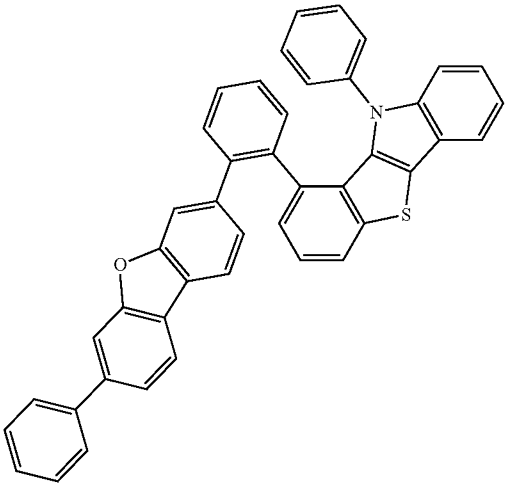
447
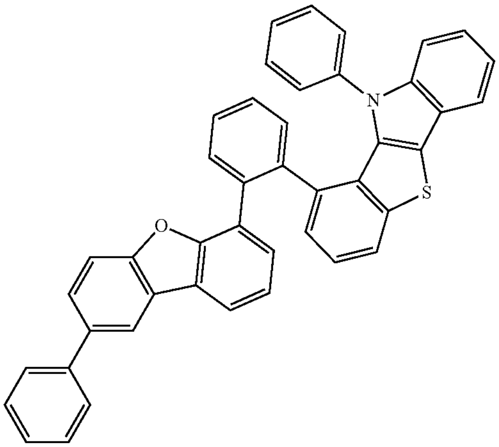
-continued
448
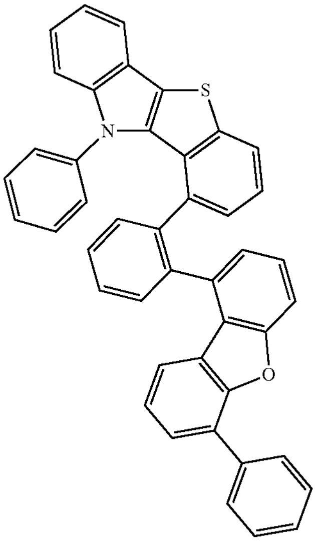
449
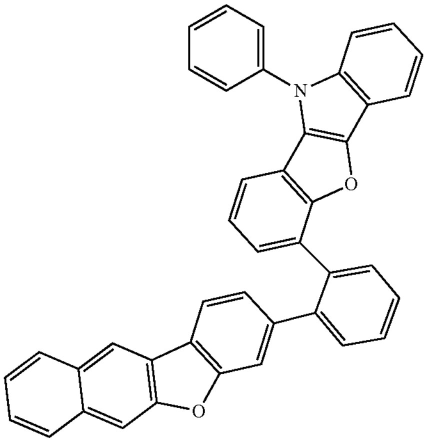
450
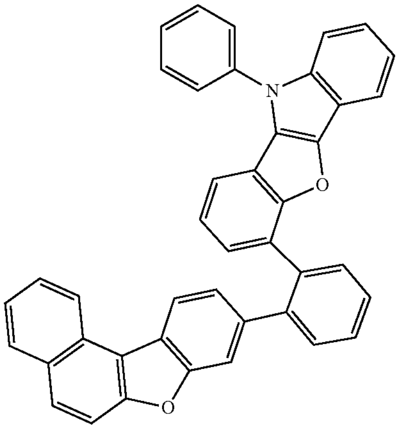

-continued
451
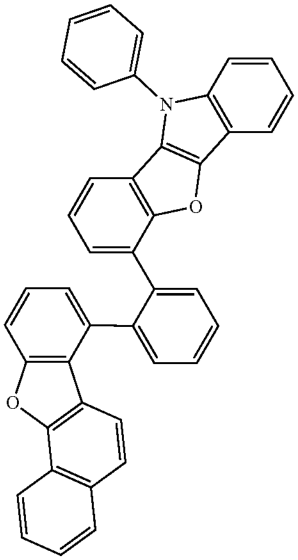
452
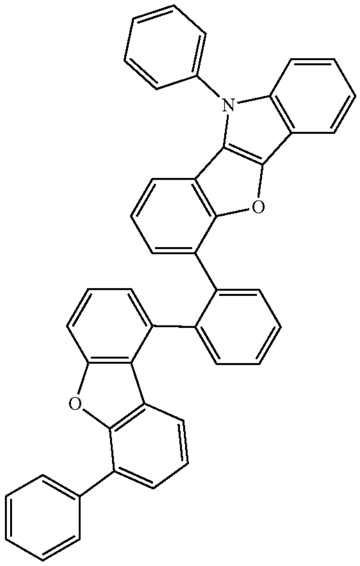
453
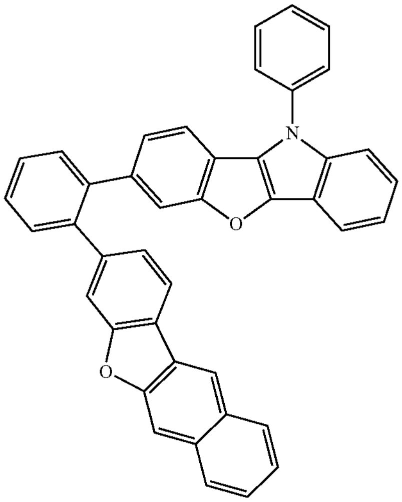
-continued
454
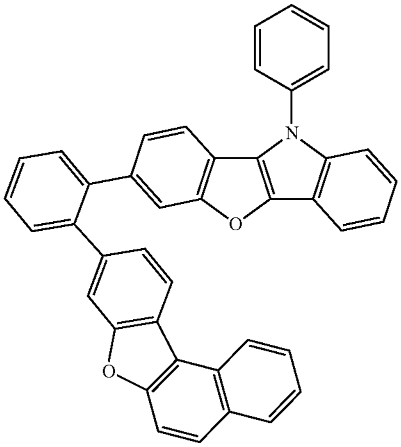
455
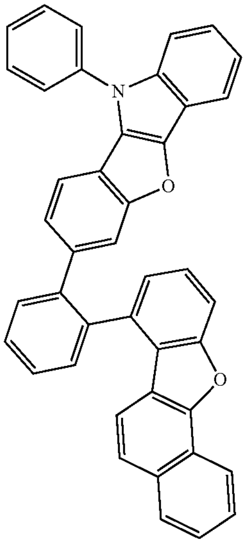
456
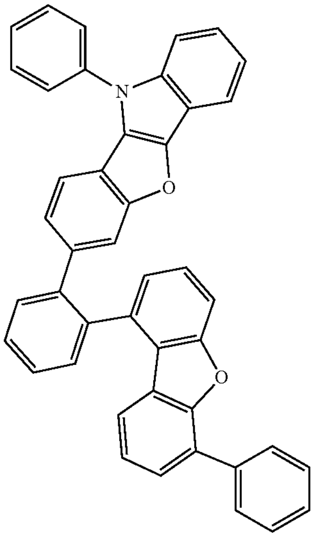

-continued
457
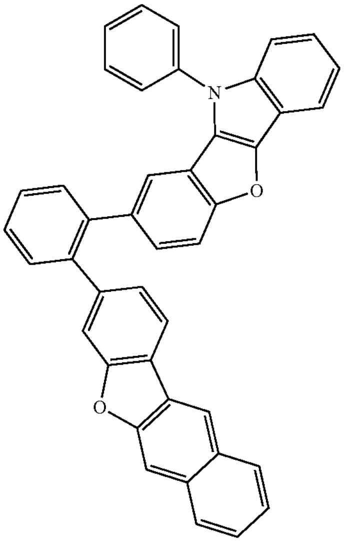
458
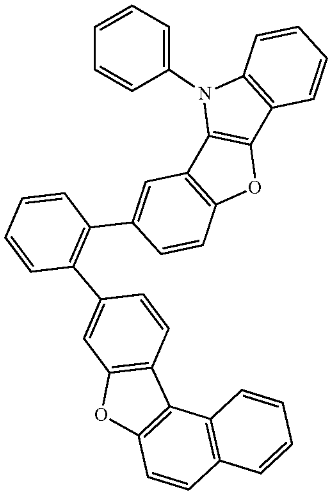
459
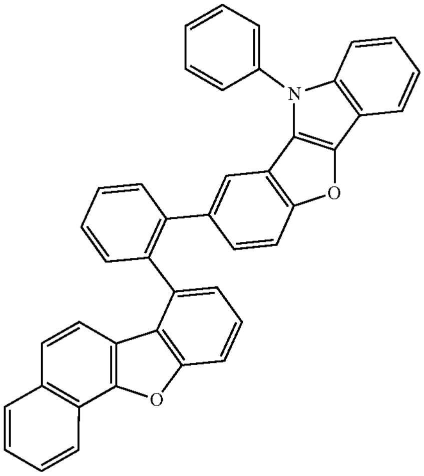
-continued
460
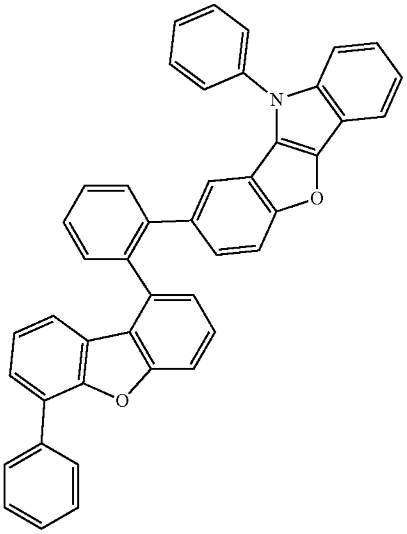
461
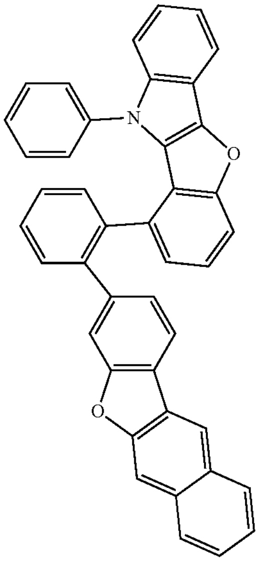
462
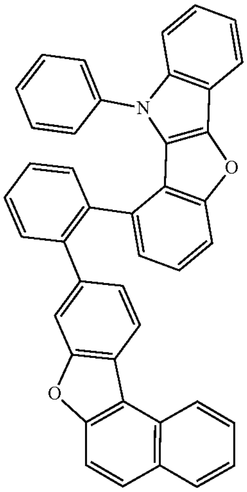

-continued
463
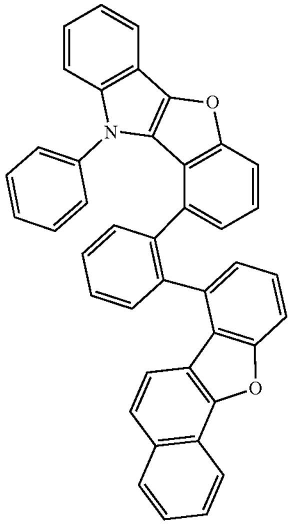
464
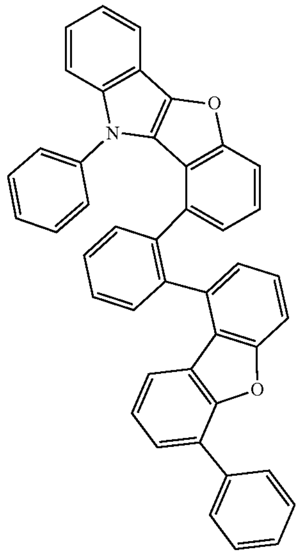
465
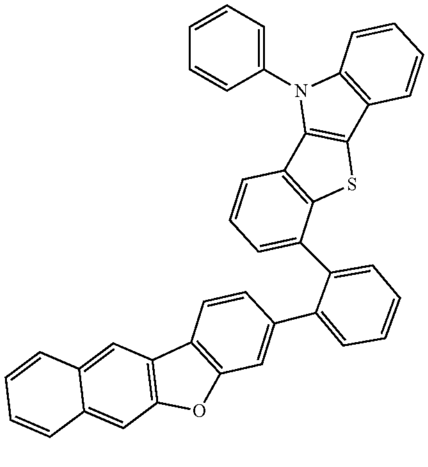
-continued
466
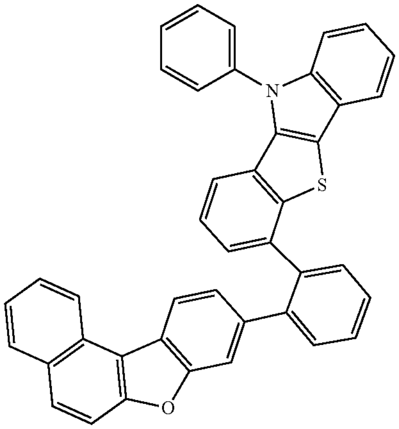
467
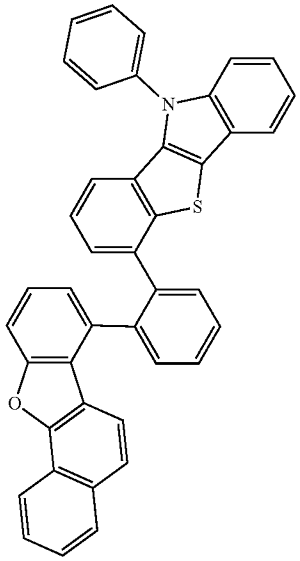
468
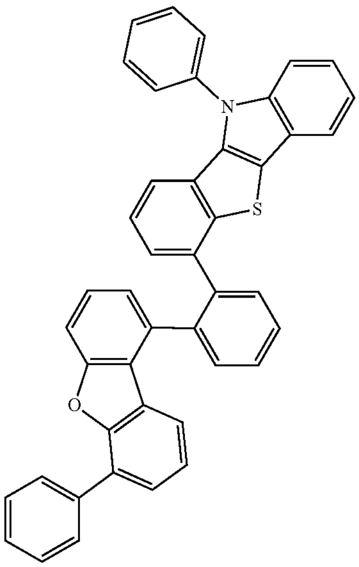

-continued
469
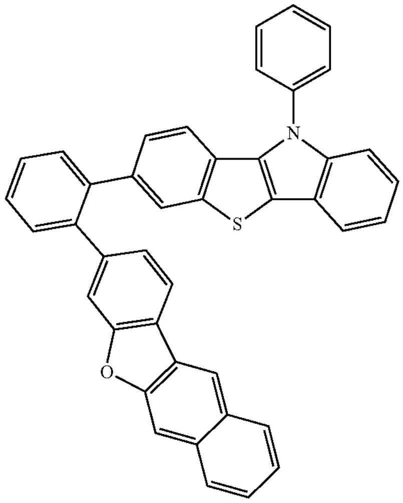
470
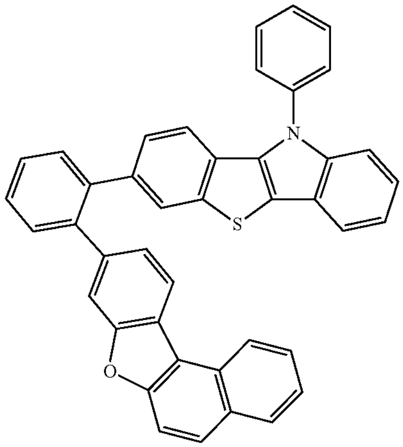
471
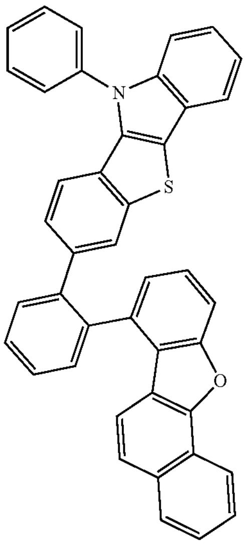
-continued
472
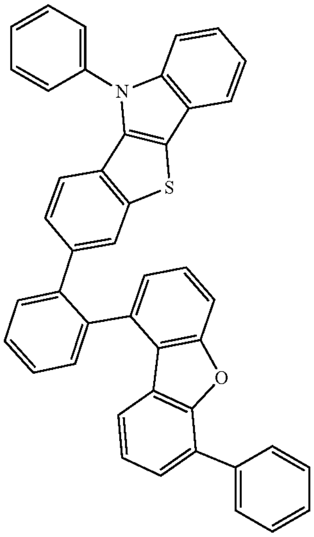
473
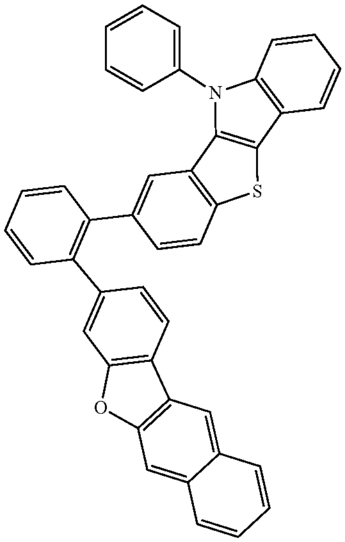
474
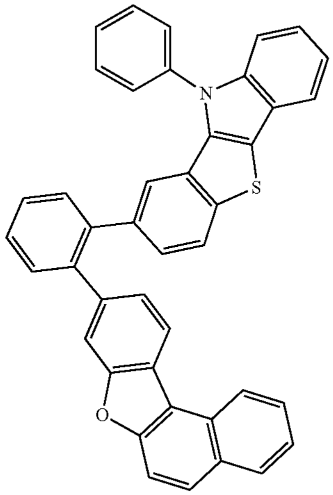

-continued
475
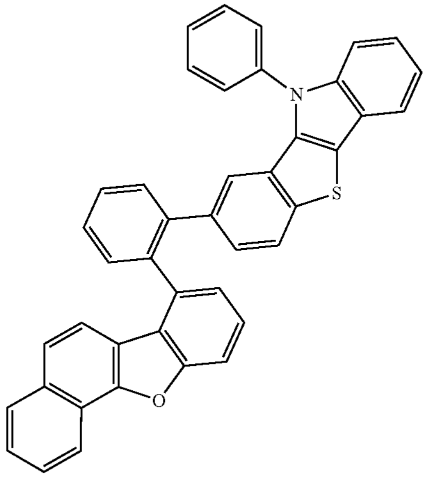
476
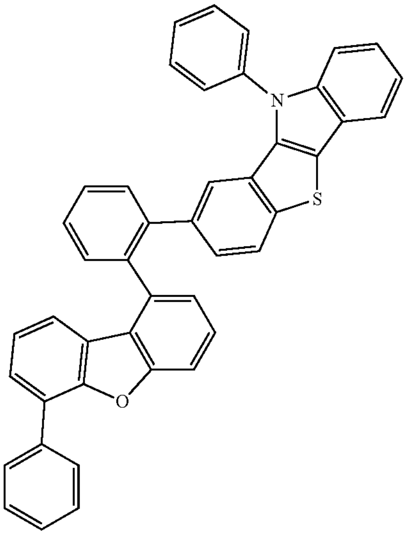
477
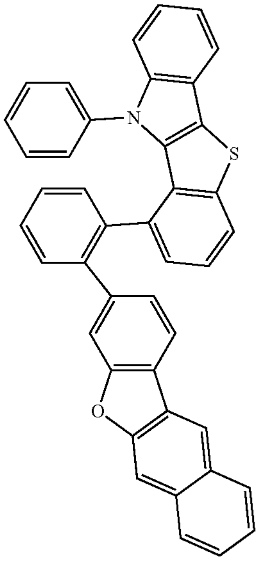
-continued
478
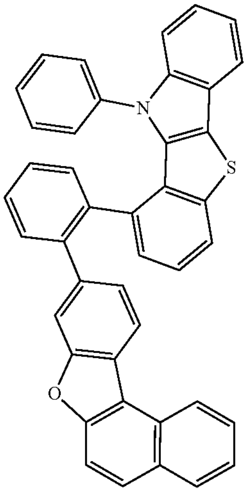
479
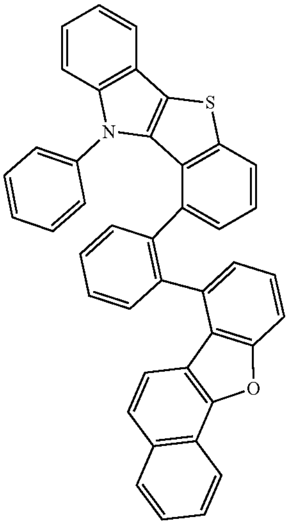
480
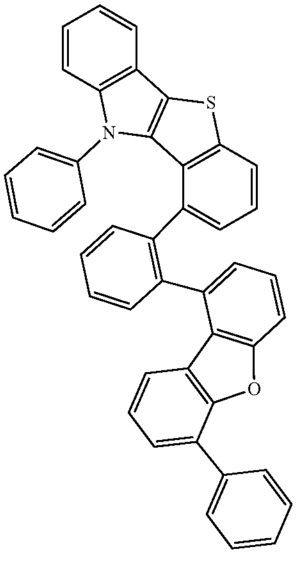

-continued
481
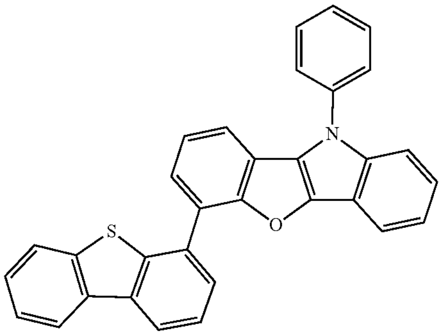
482
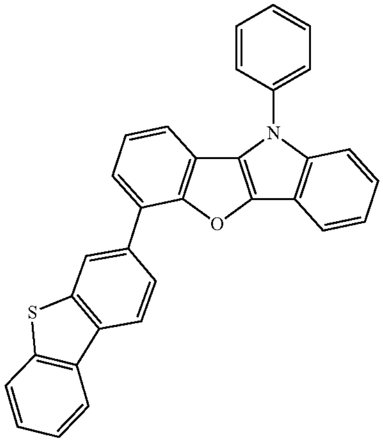
483
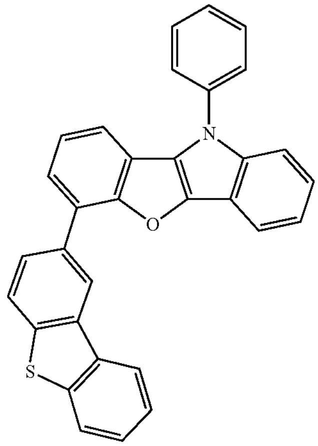
484
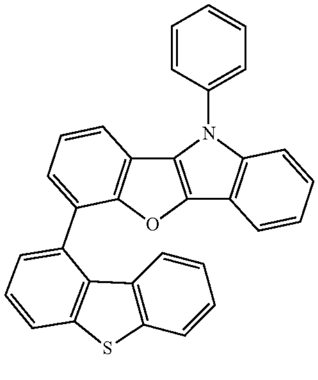
-continued
485
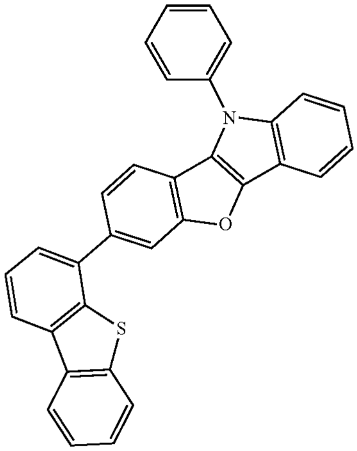
486
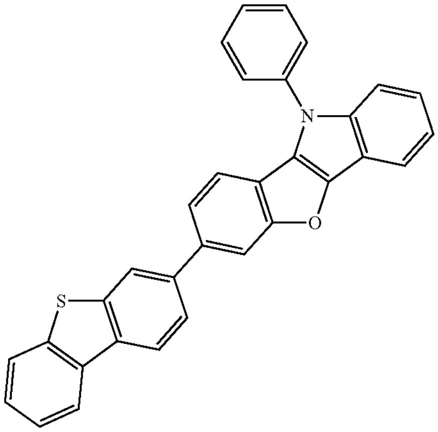
487
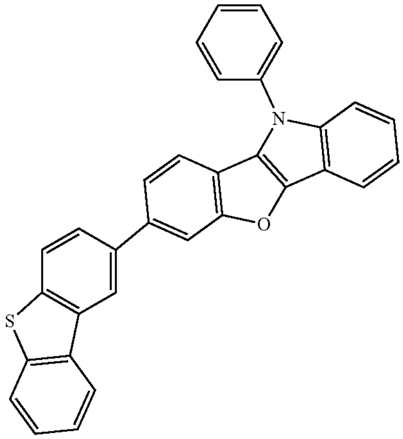

-continued
488
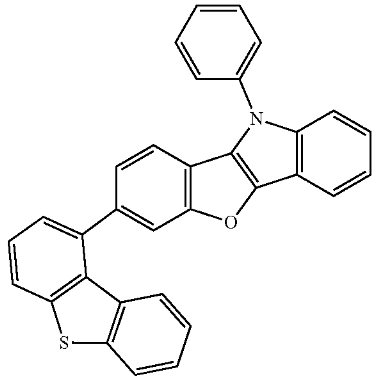
489
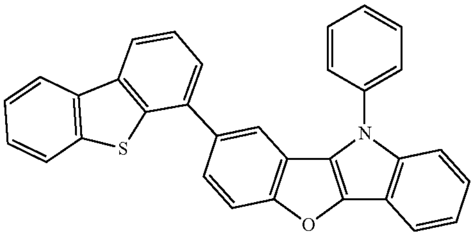
490
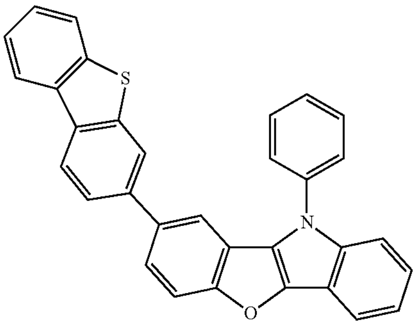
491
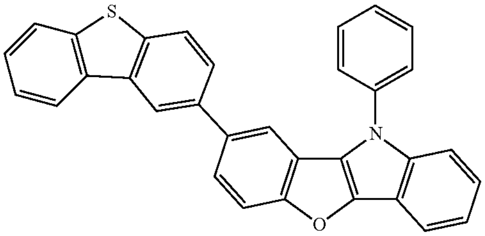
492
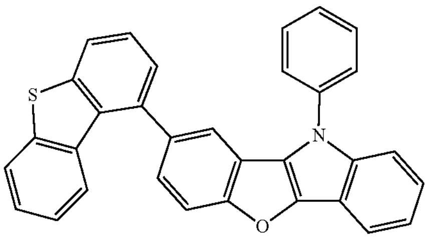
-continued
493
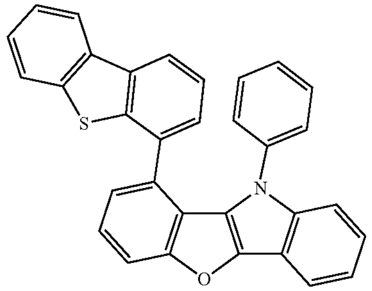
494
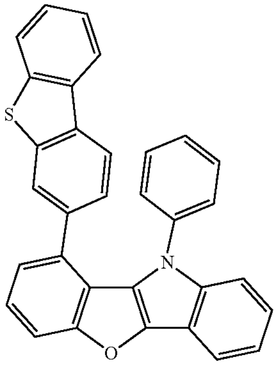
495
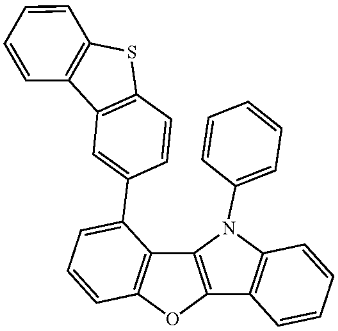
496
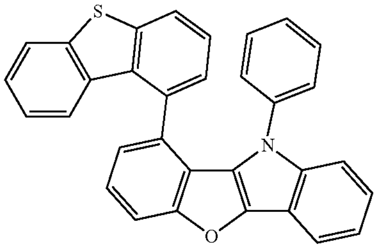
497
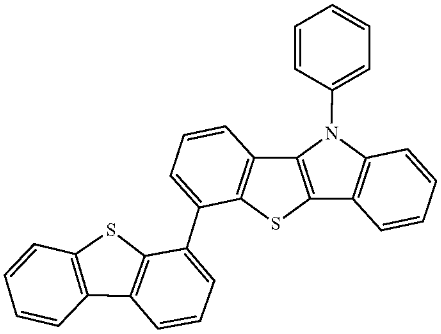

-continued
498
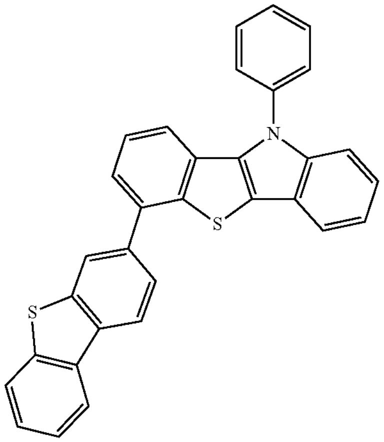
499
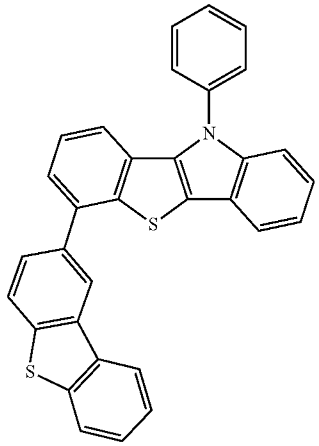
500
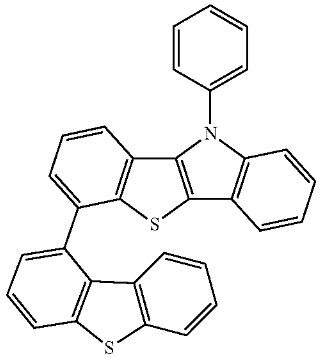
-continued
501
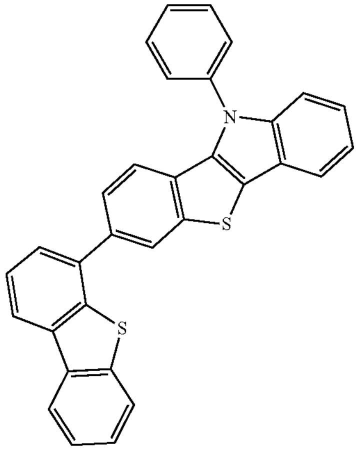
502
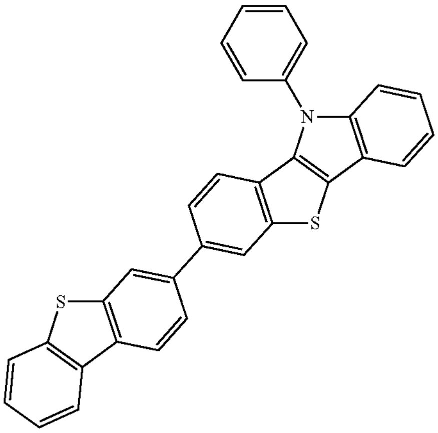
503
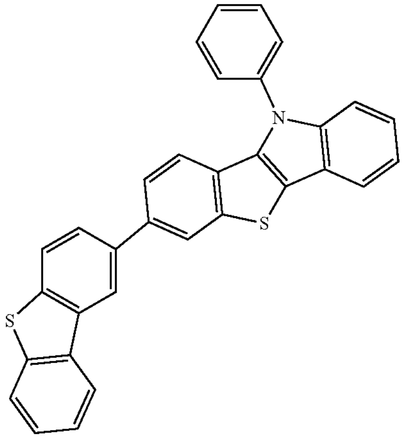

-continued
504
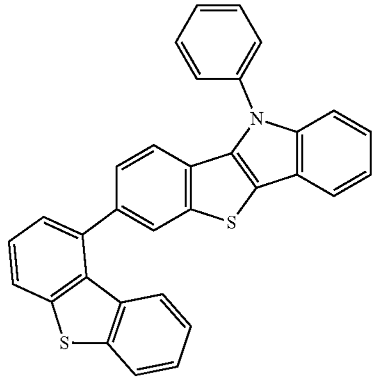
505
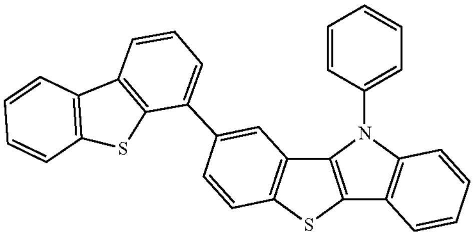
506
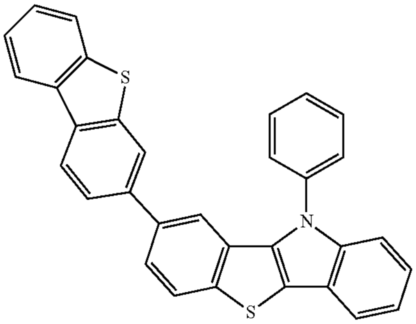
507
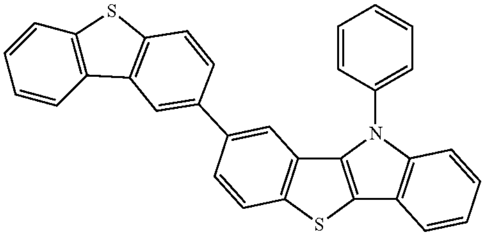
508
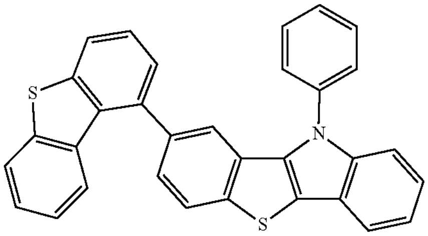
-continued
509
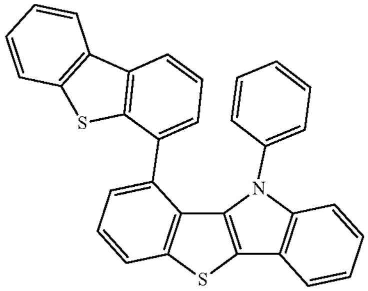
510
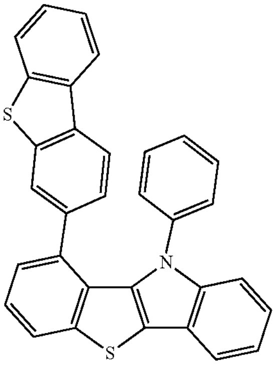
511
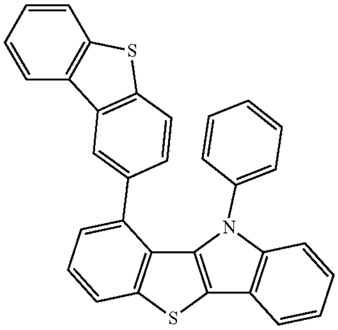
512
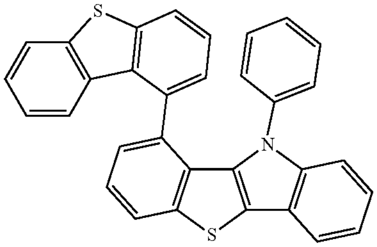

-continued
513
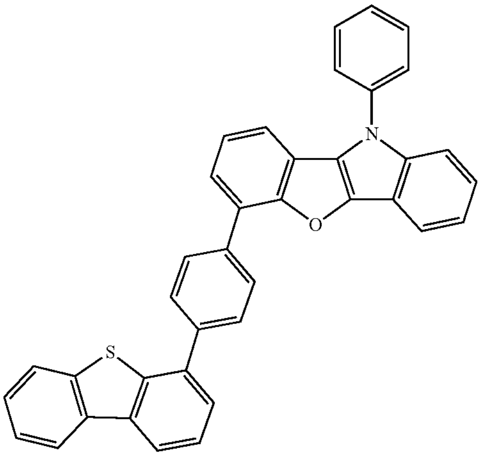
514
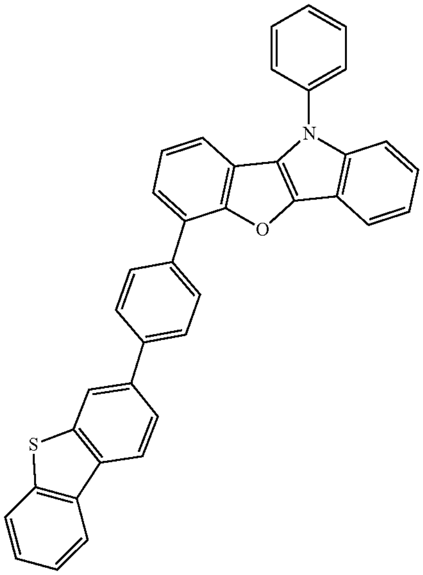
515
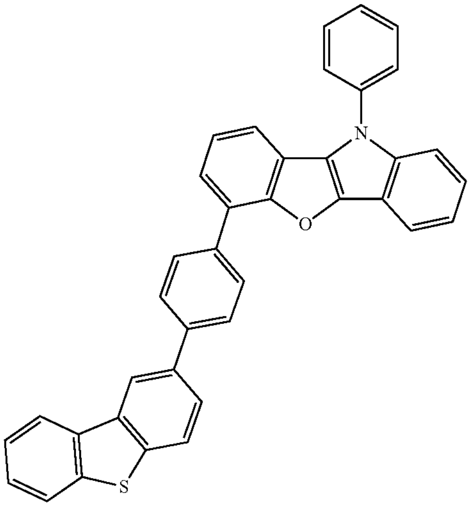
-continued
516
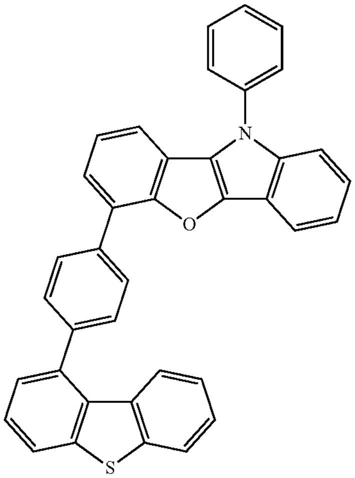
517
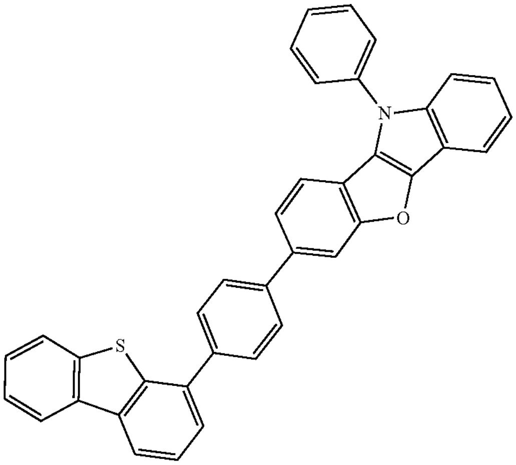
518
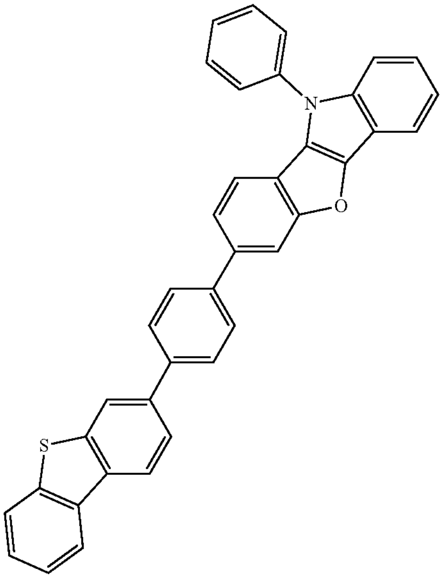

-continued
519
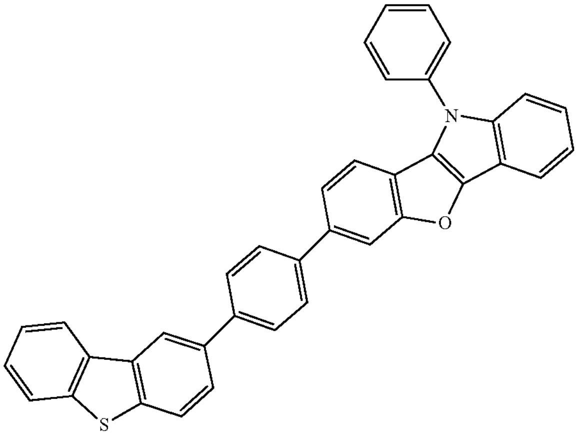
520
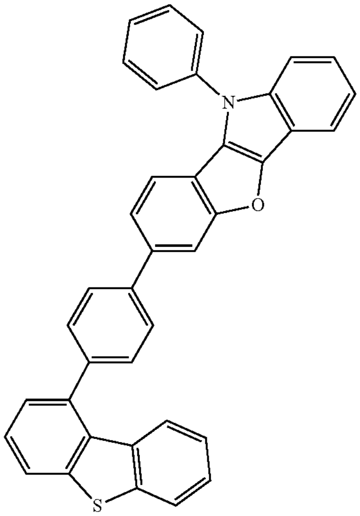
521
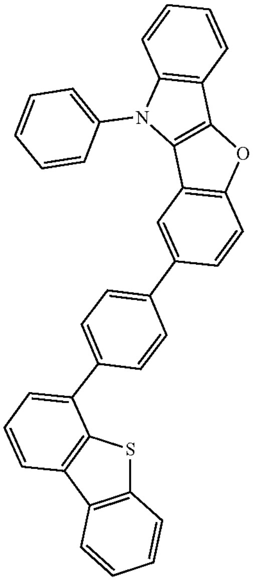
-continued
522
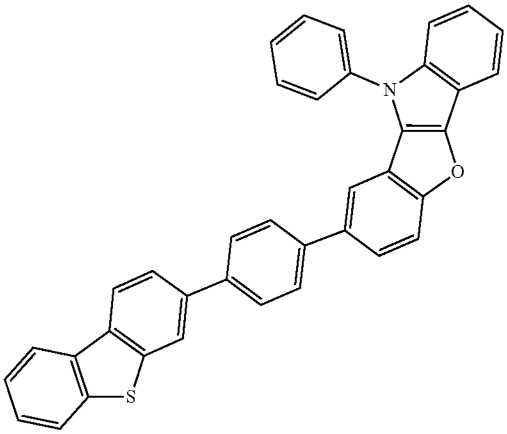
523
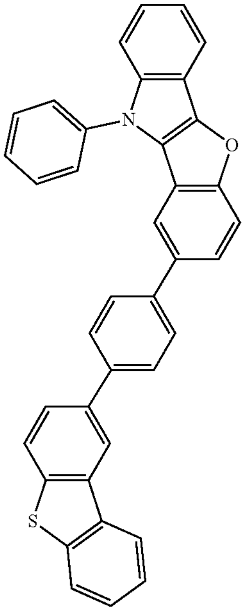
524
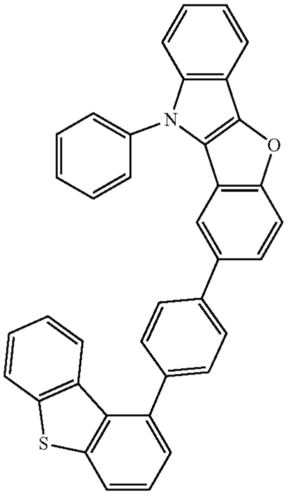

-continued
525
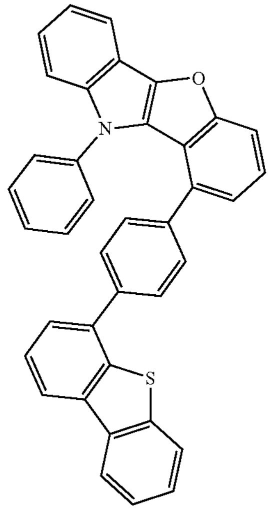
526
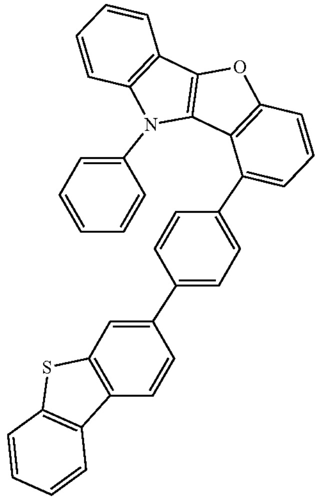
527
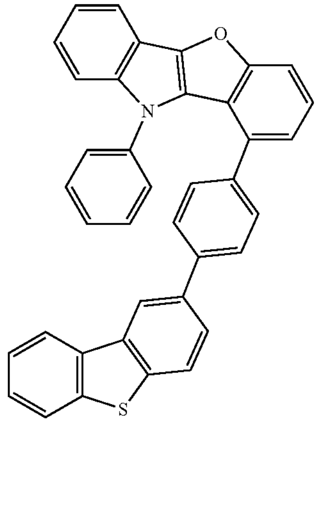
-continued
528
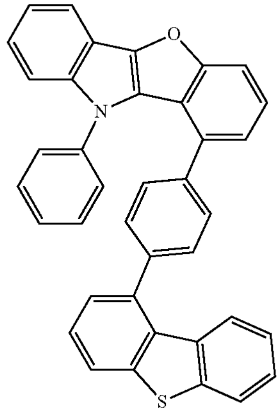
529
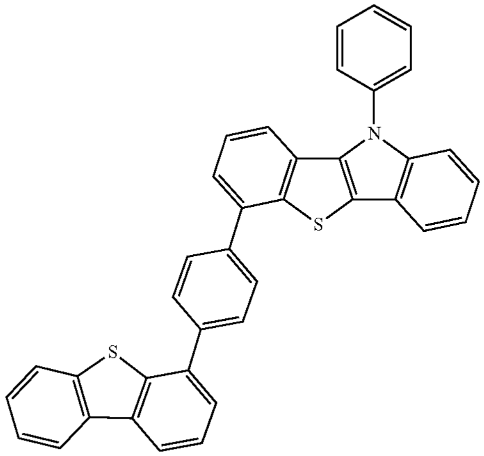
530
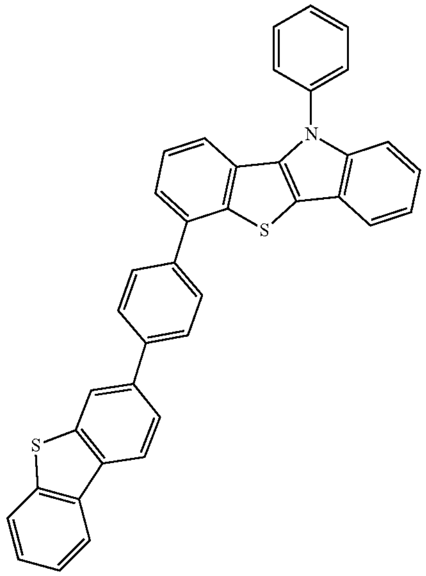

531
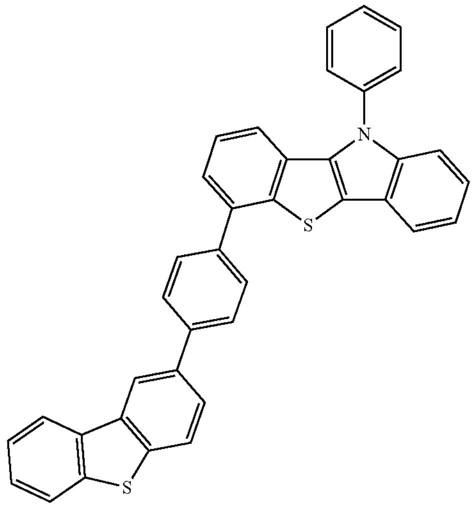
532
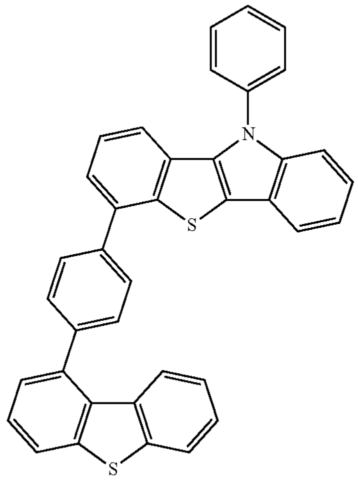
533
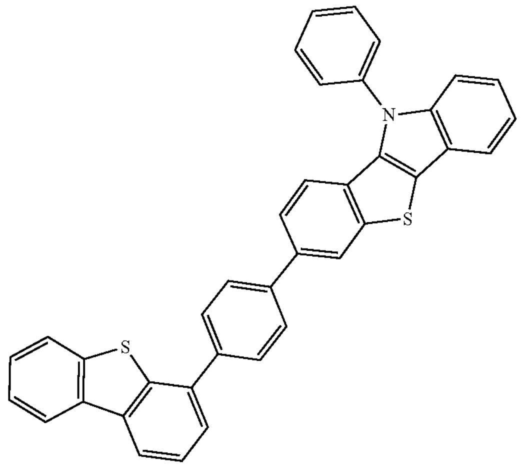
534
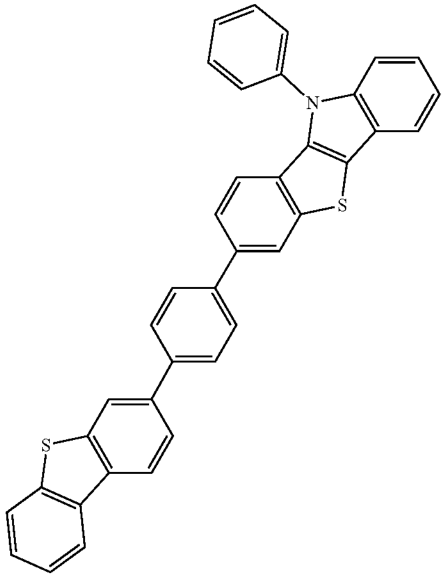
535
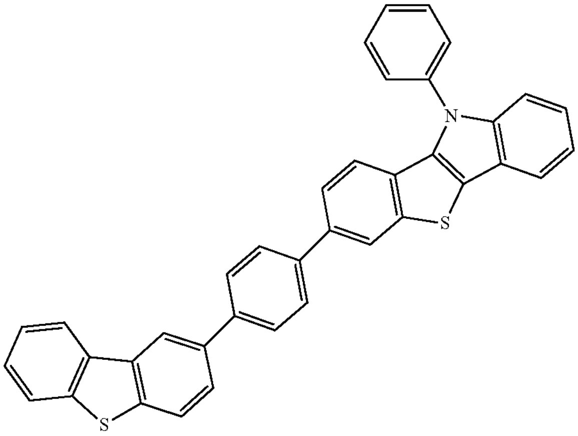
536
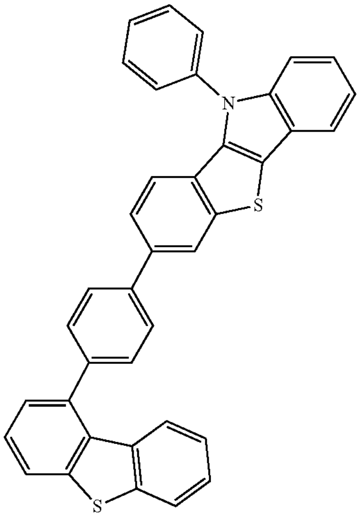

-continued
537
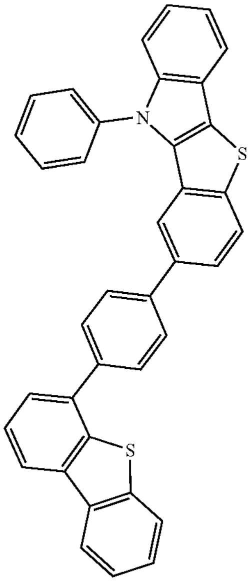
538
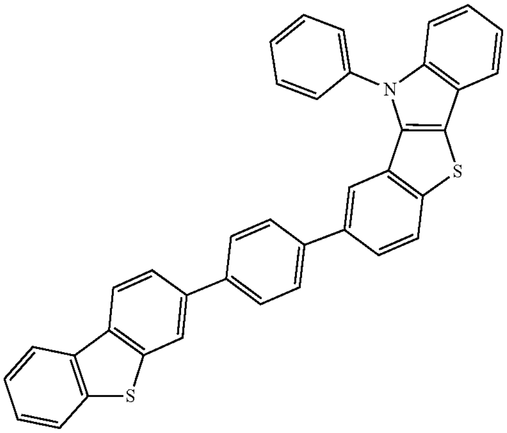
539
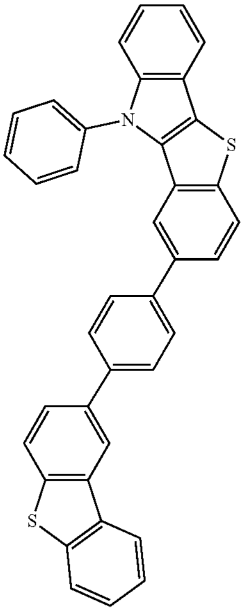
-continued
540
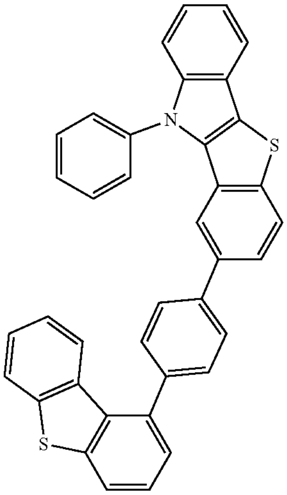
541
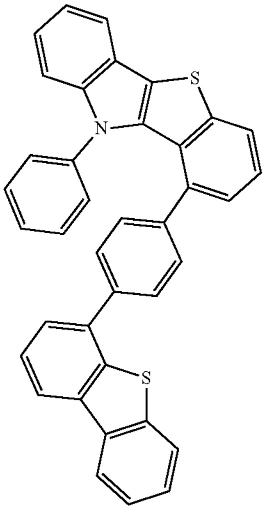
542
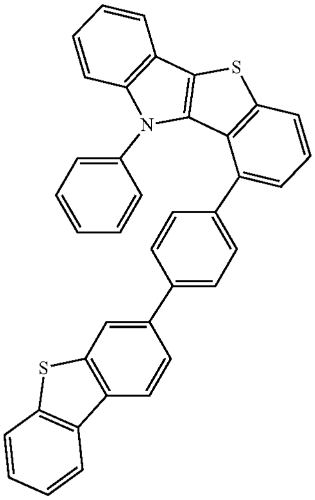

543
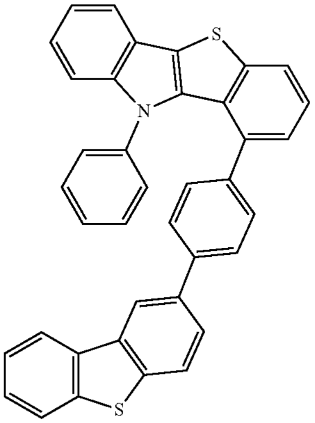
544
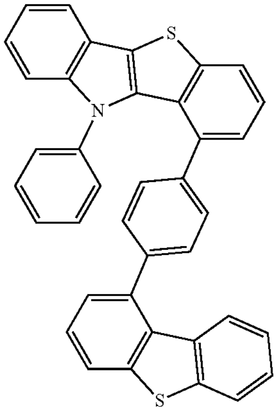
545
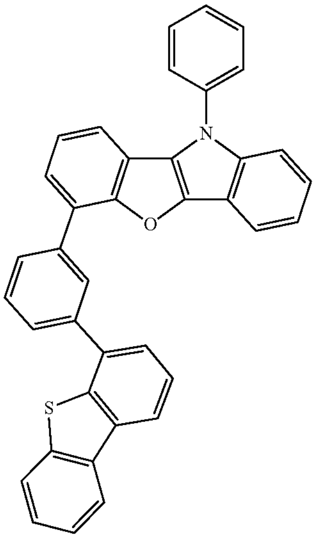
546
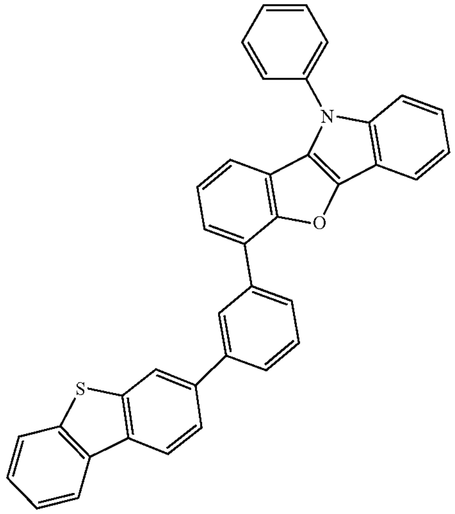
547
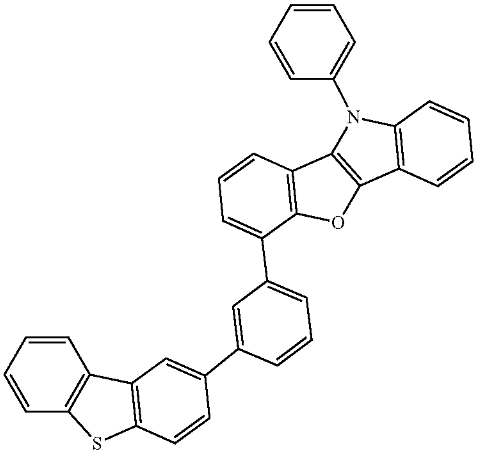
548
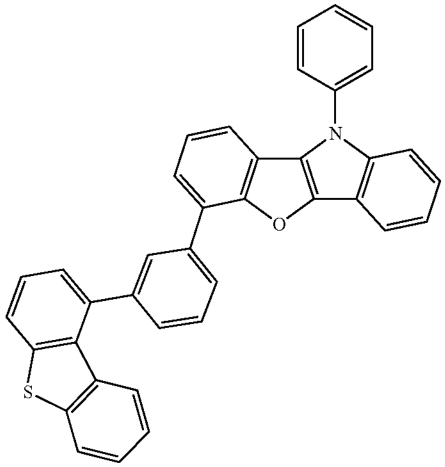

-continued
549
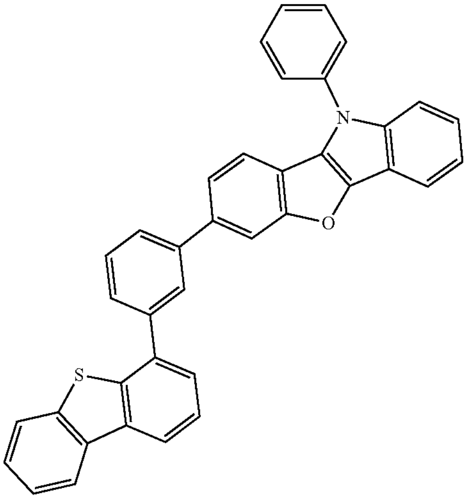
550
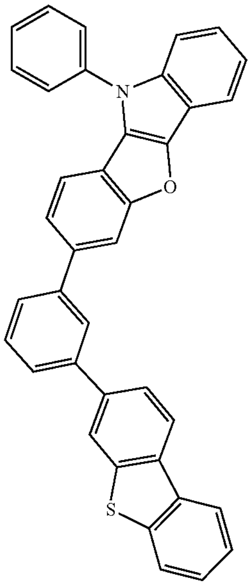
551
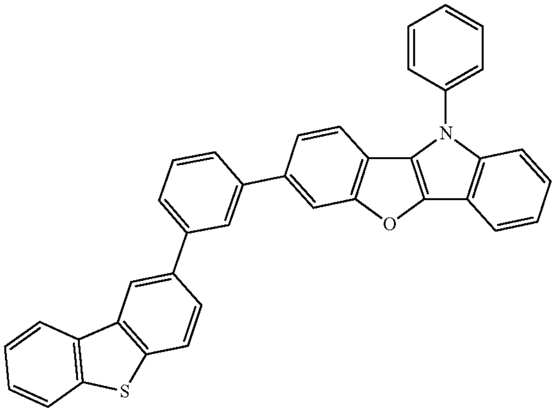
-continued
552
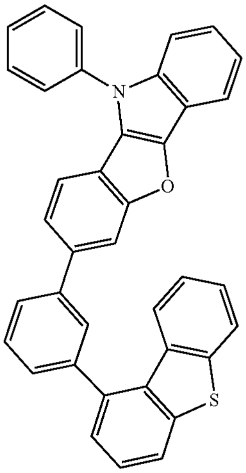
553
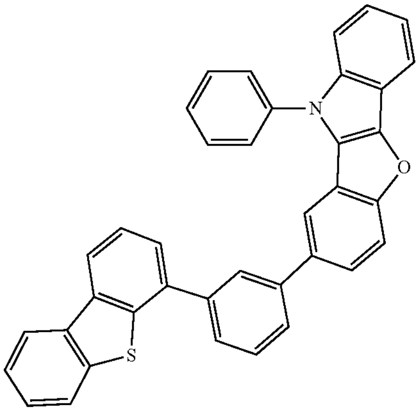
554
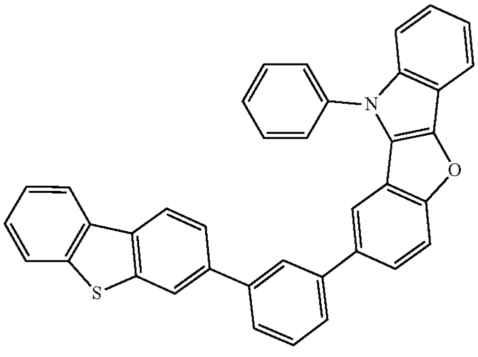

-continued
555
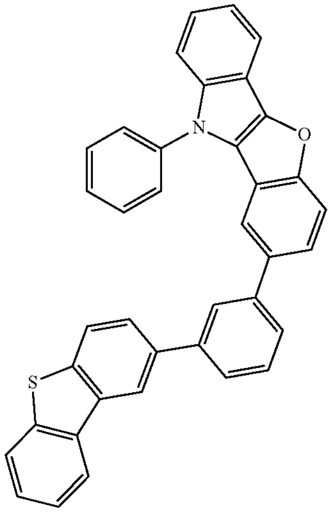
556
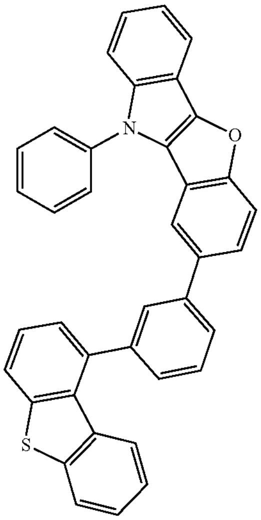
557
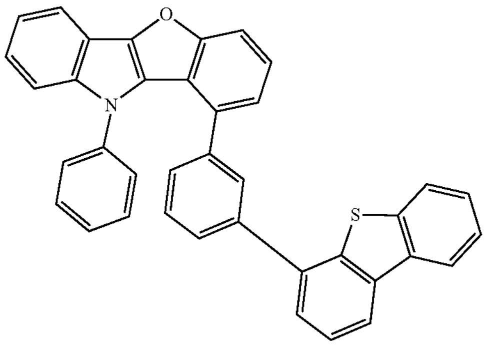
-continued
558
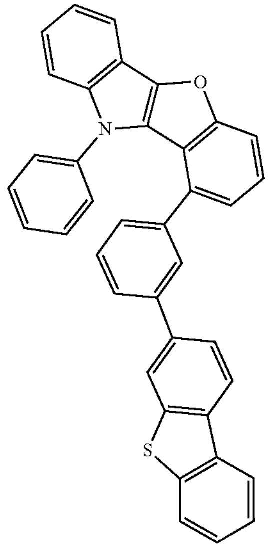
559
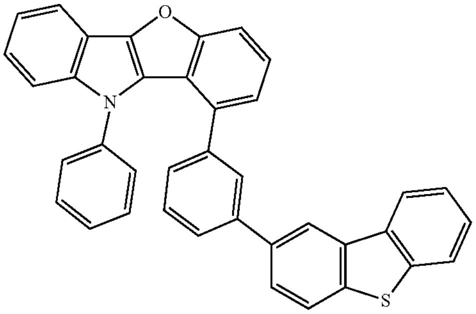
560
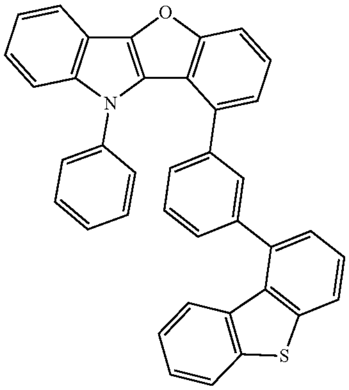

-continued
561
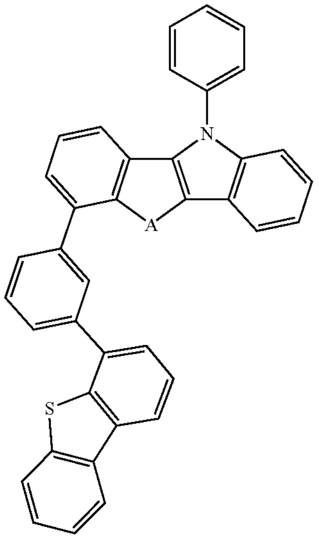
562
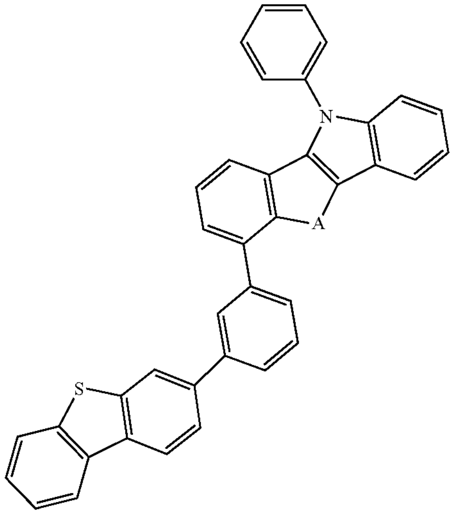
563
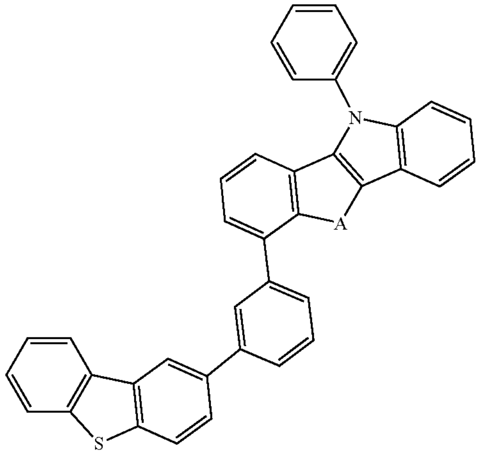
-continued
564
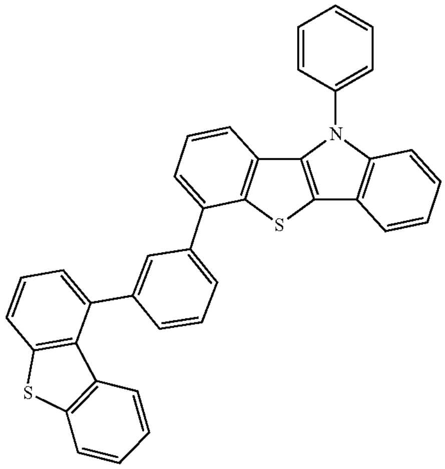
565
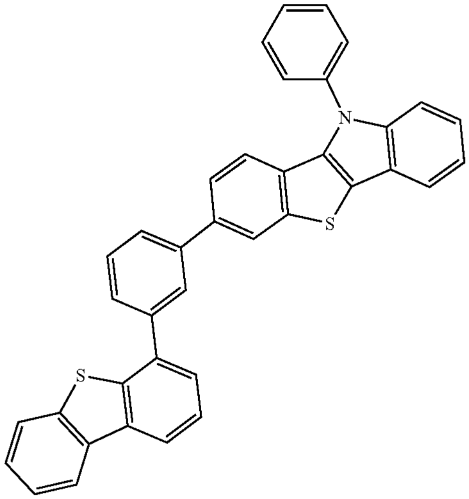
566
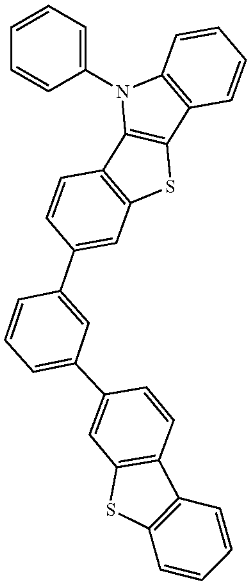

-continued
567
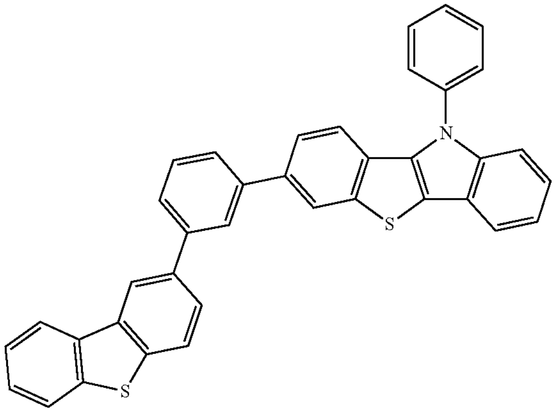
568
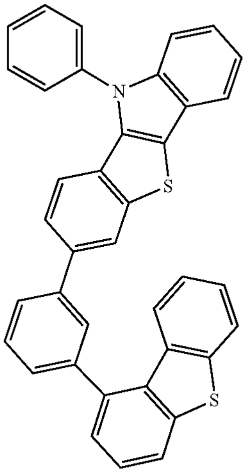
569
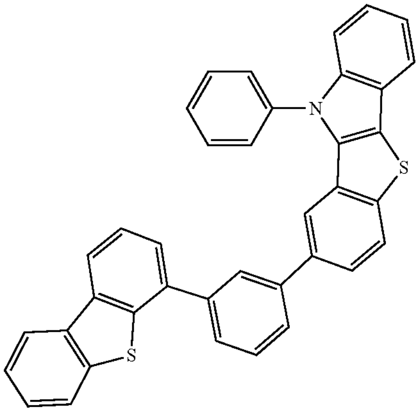
-continued
570
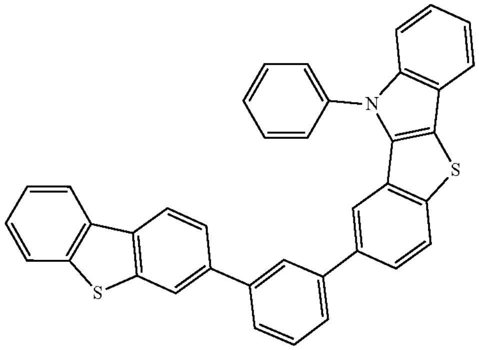
571
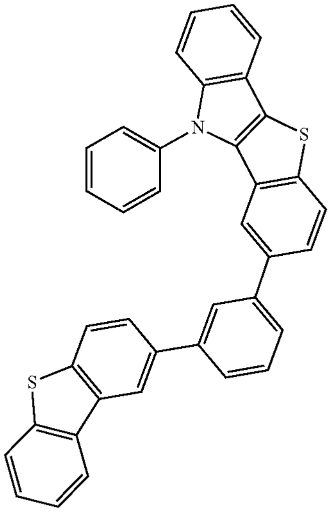
572
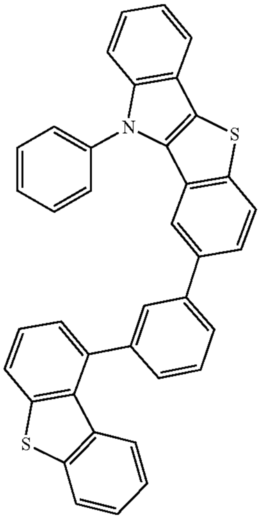

-continued
573
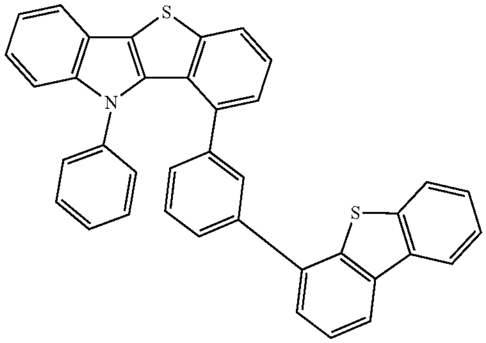
574
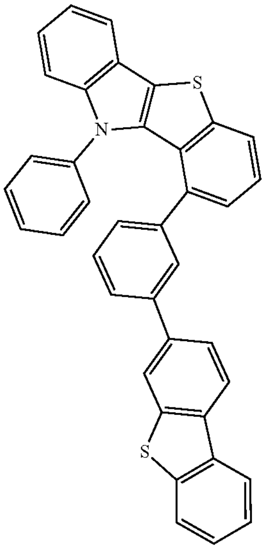
575
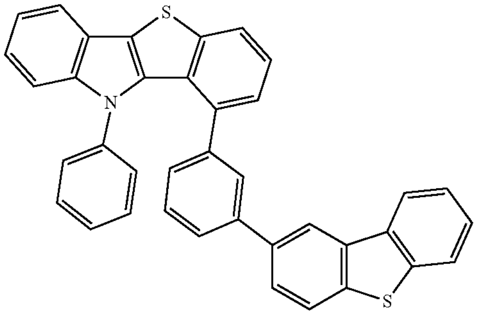
576
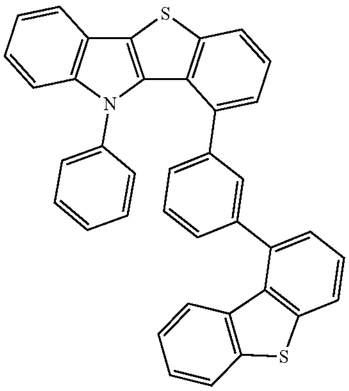
577
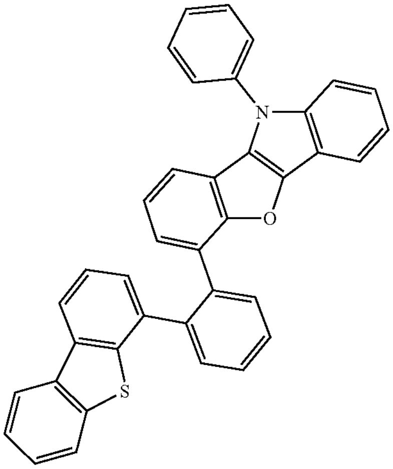
578
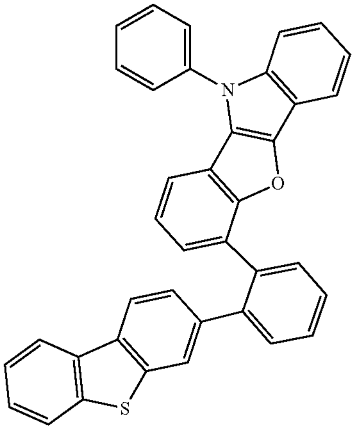
579
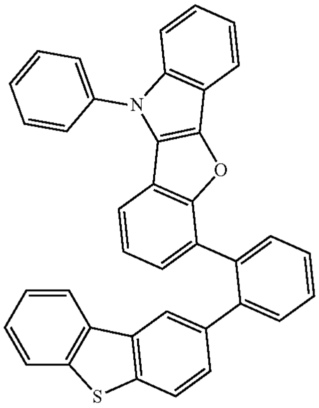

580
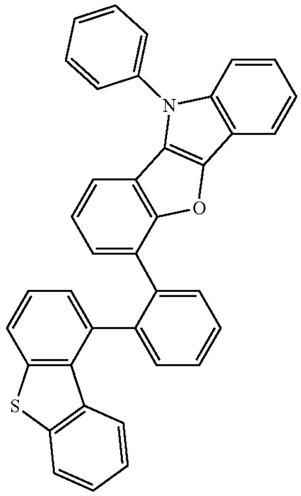
581
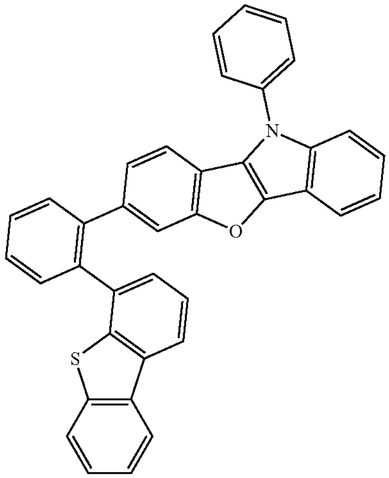
582
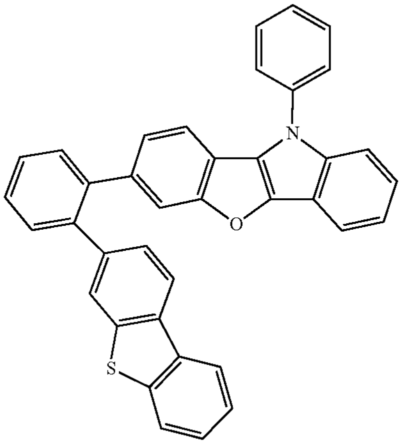
583
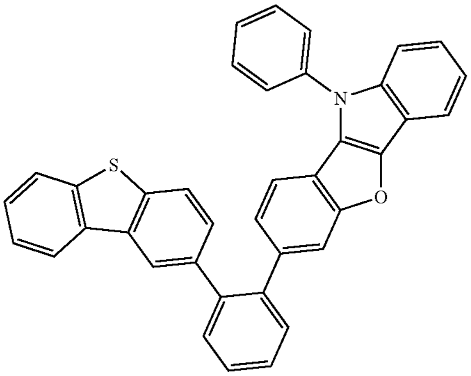
584
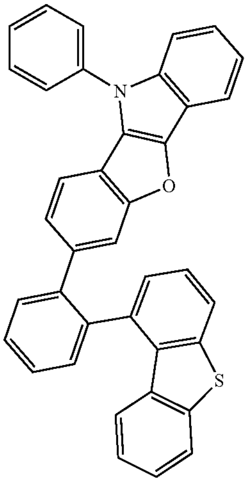
585
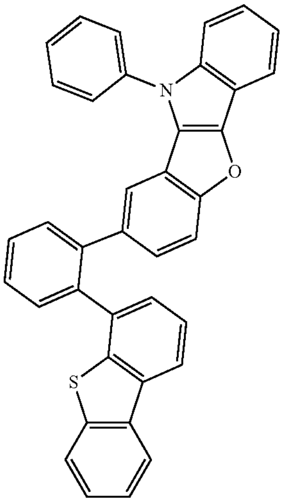

-continued
586
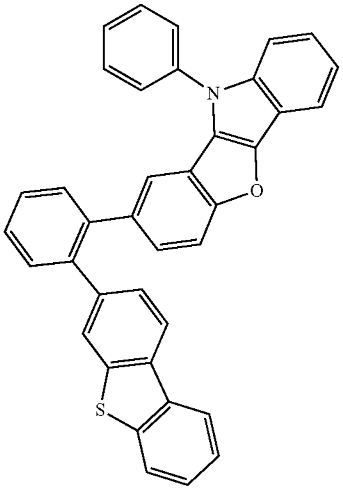
587
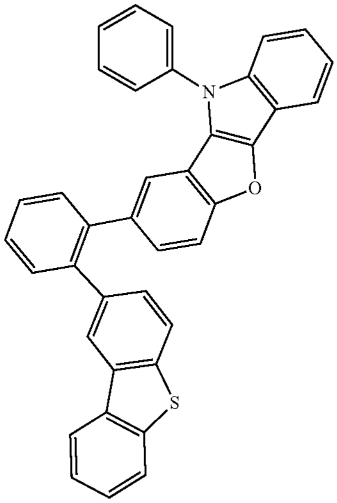
588
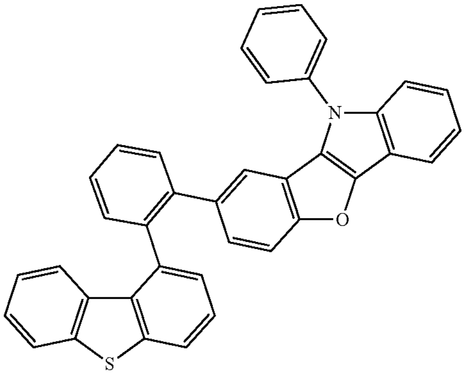
-continued
589
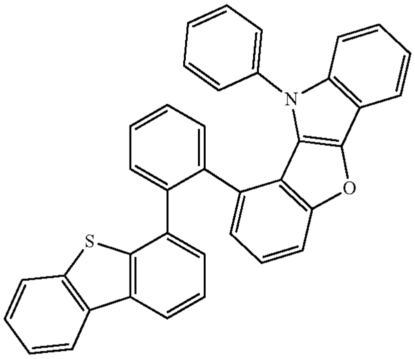
590
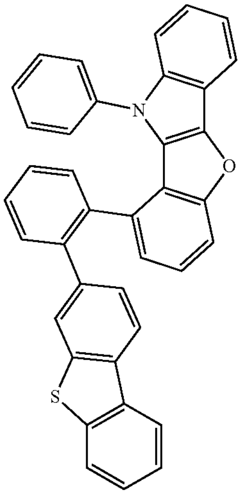
591
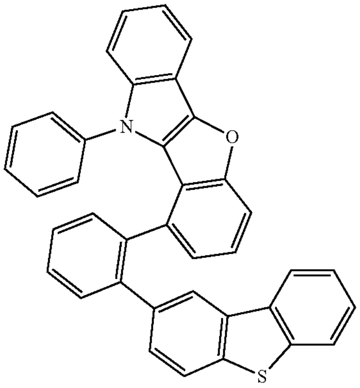

-continued
592
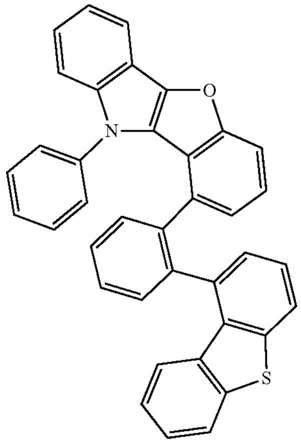
593
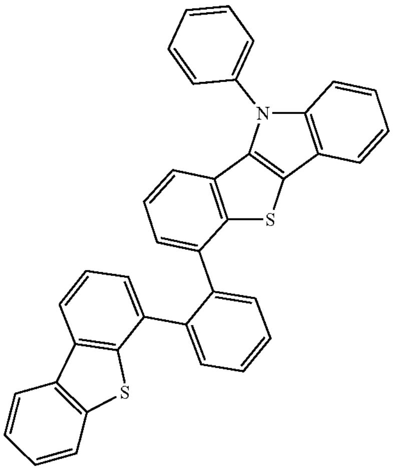
594
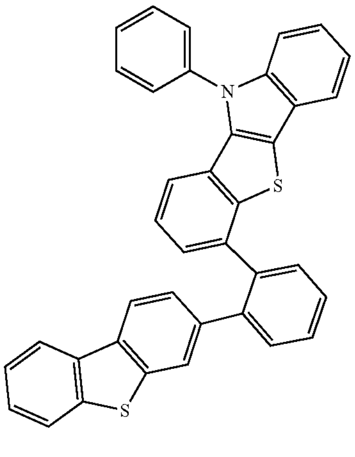
-continued
595
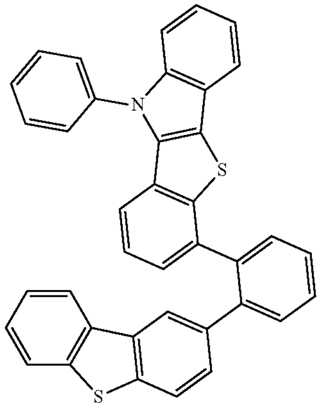
596
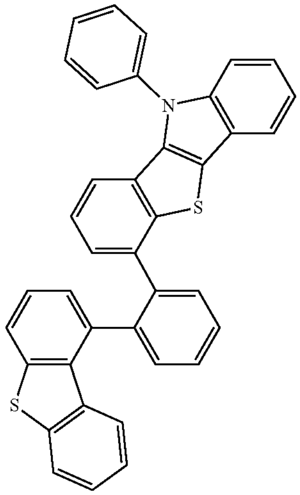
597
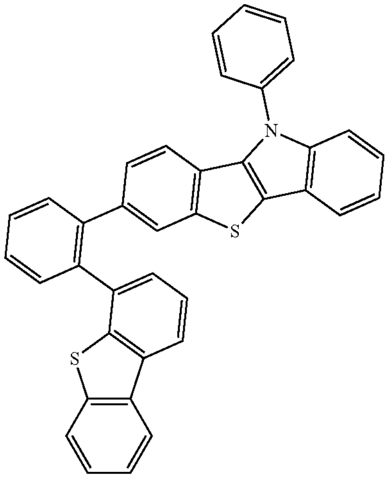

598
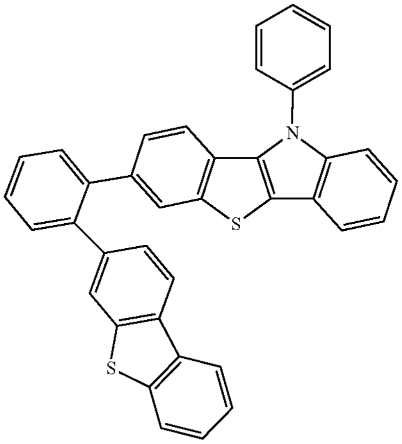
599
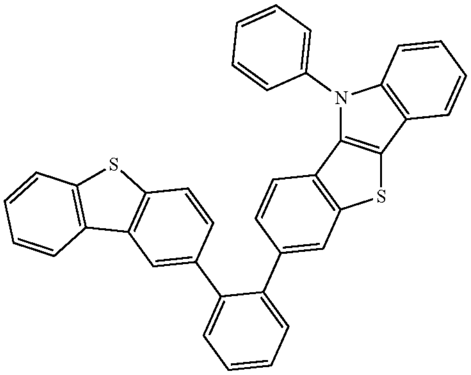
600
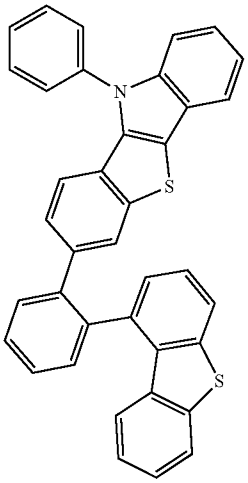
601
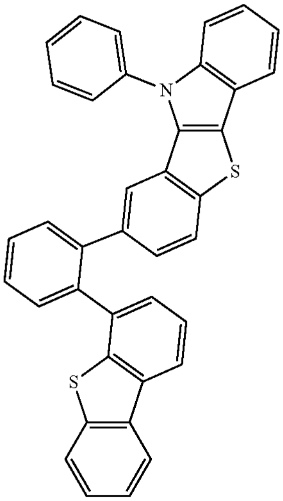
602
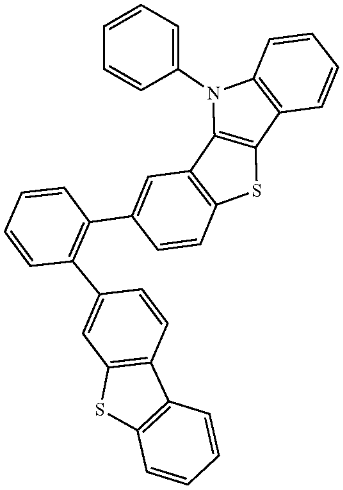
603
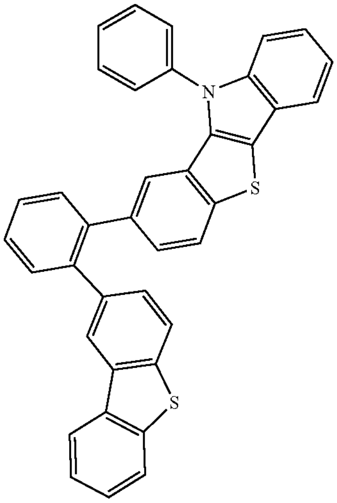

-continued
604
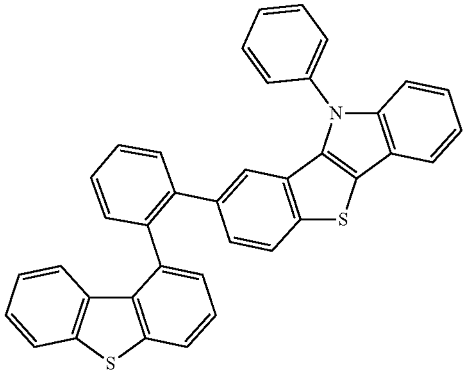
605
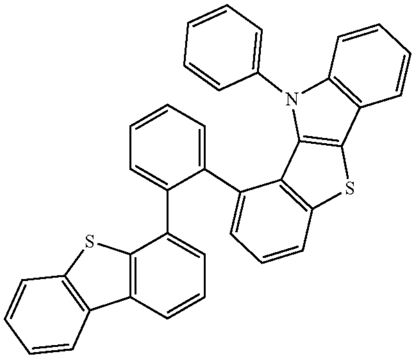
606
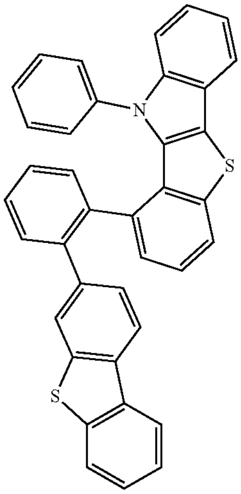
607
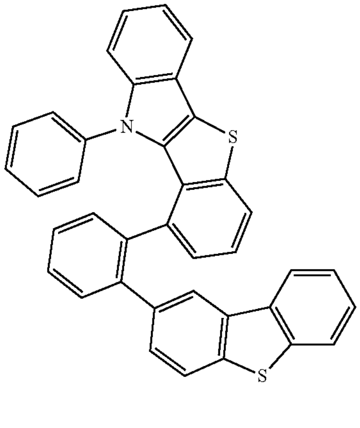
-continued
608
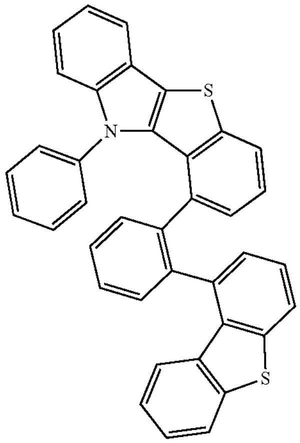
609
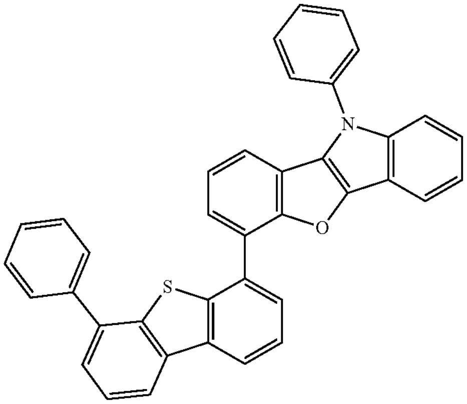
610
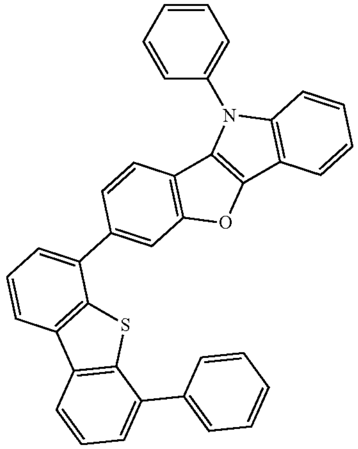

-continued
611
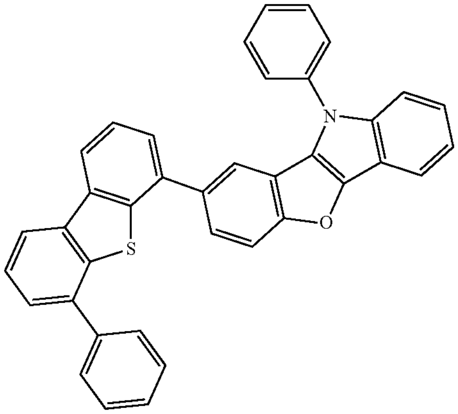
612
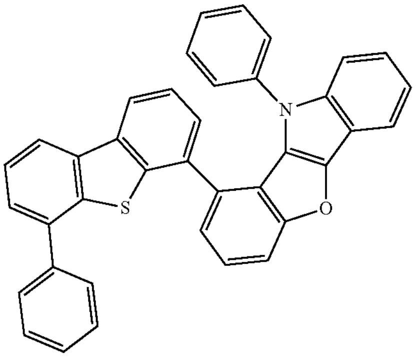
613
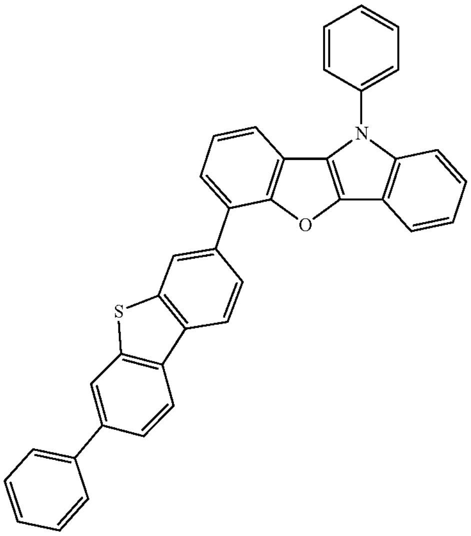
-continued
614
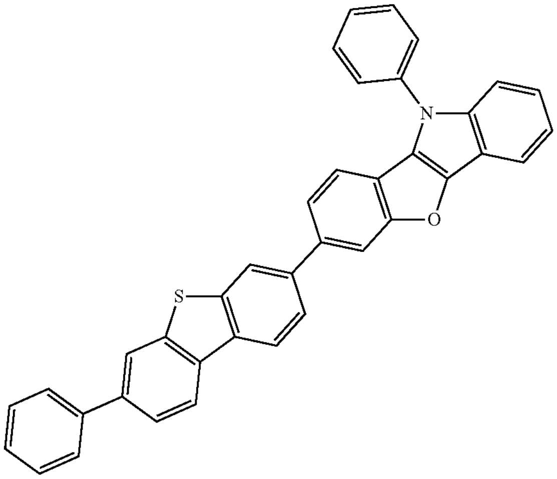
615
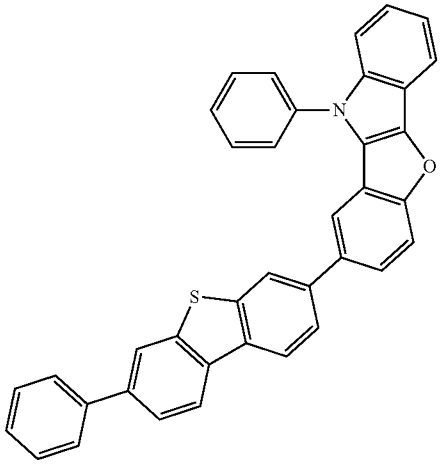
616
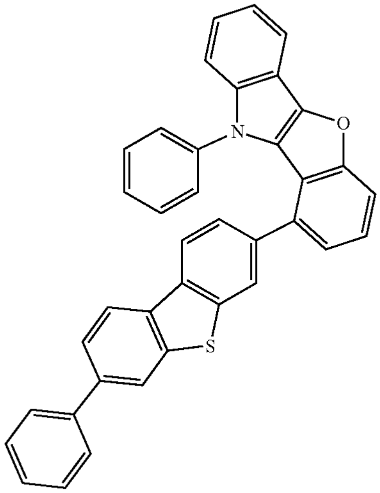

-continued
617
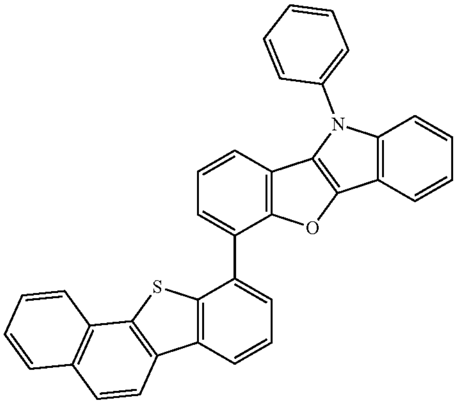
618
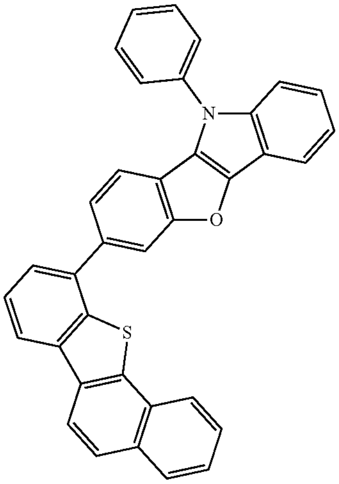
619
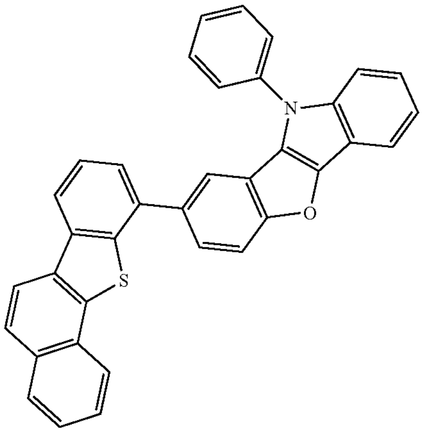
-continued
620
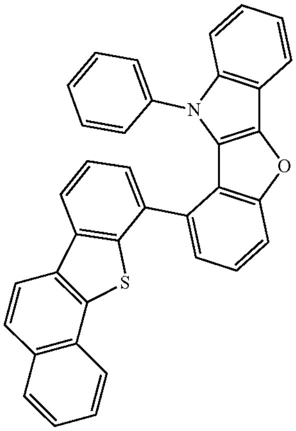
621
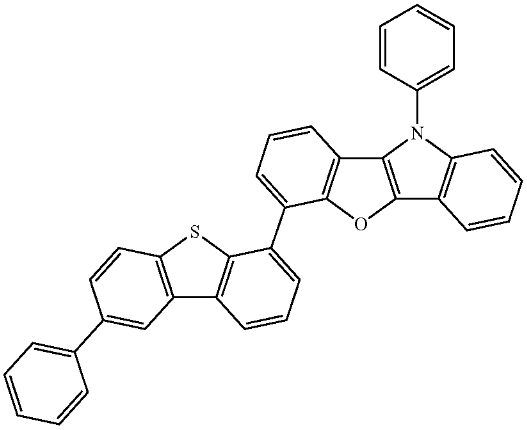
622
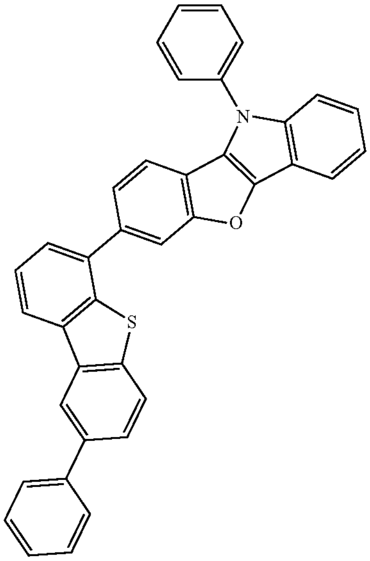

-continued
623
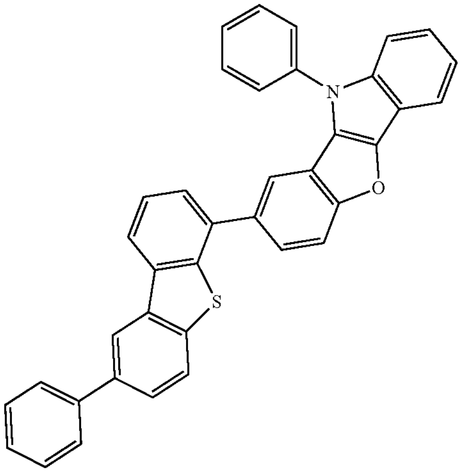
624
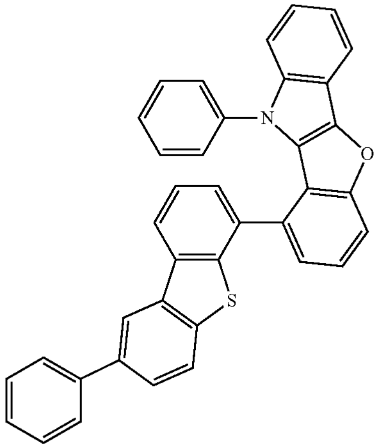
625
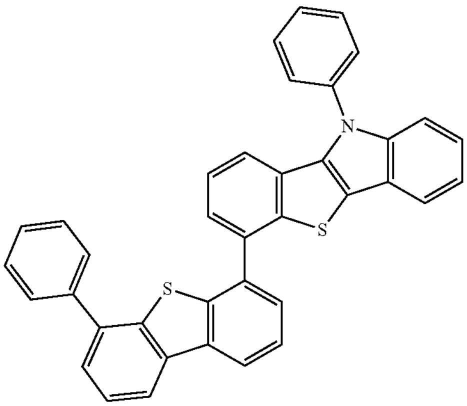
-continued
626
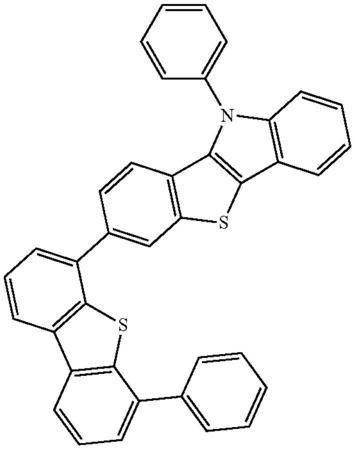
627
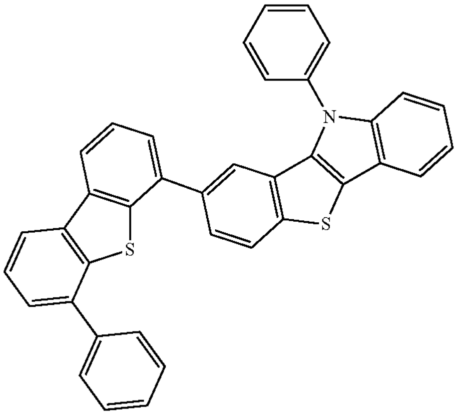
628
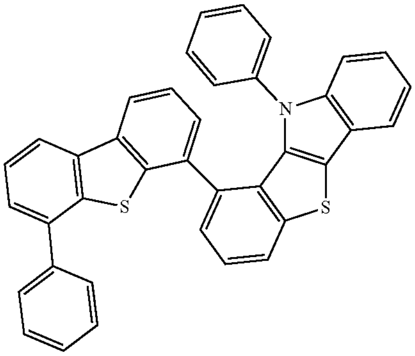

-continued
629
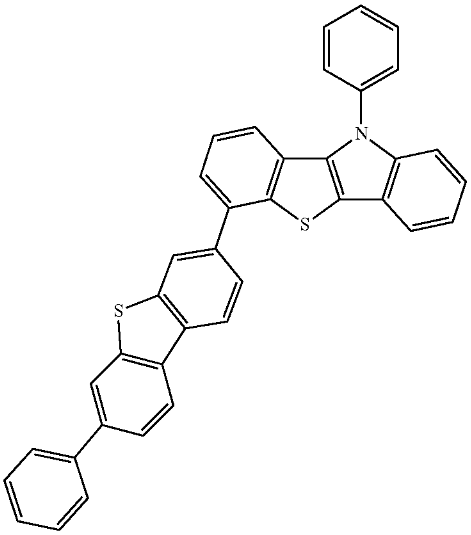
630
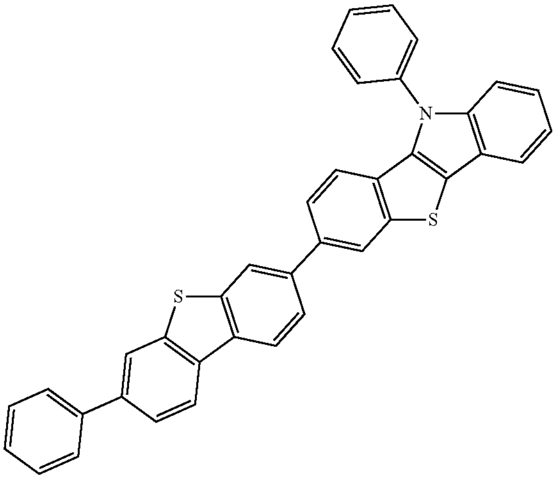
631
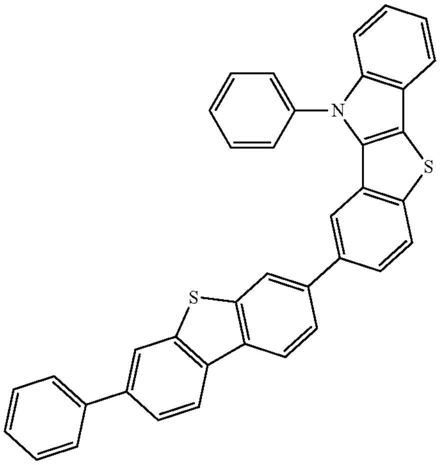
-continued
632
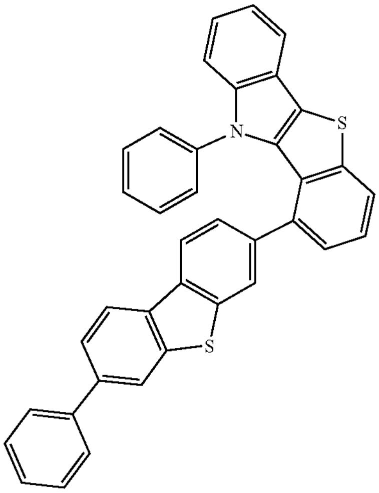
633
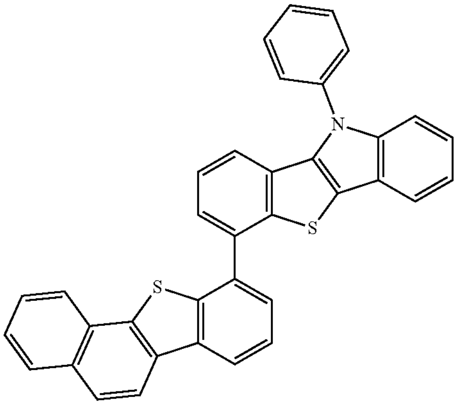
634
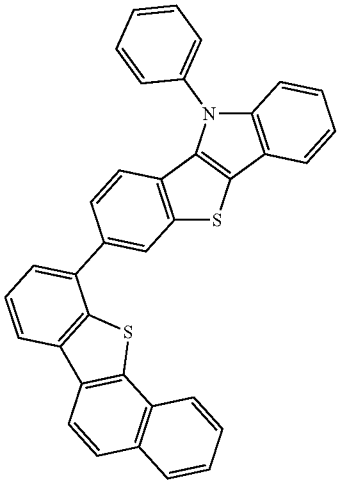

-continued
635
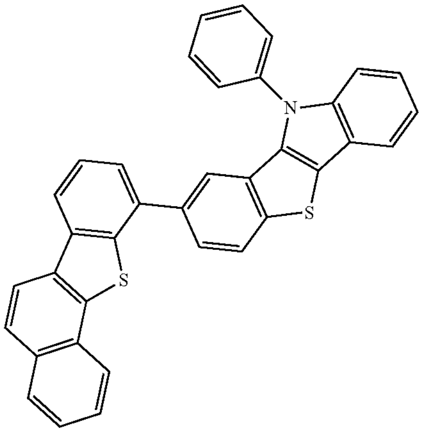
636
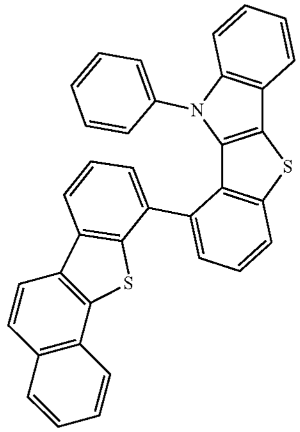
637
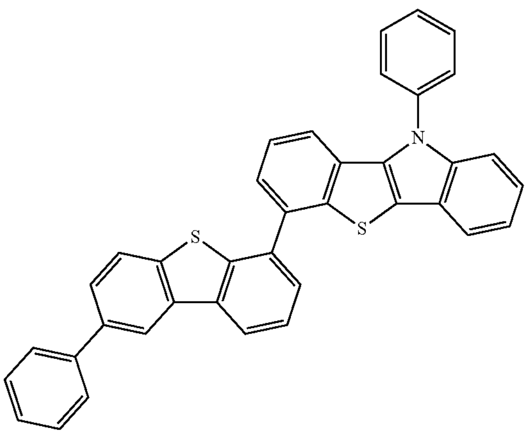
-continued
638
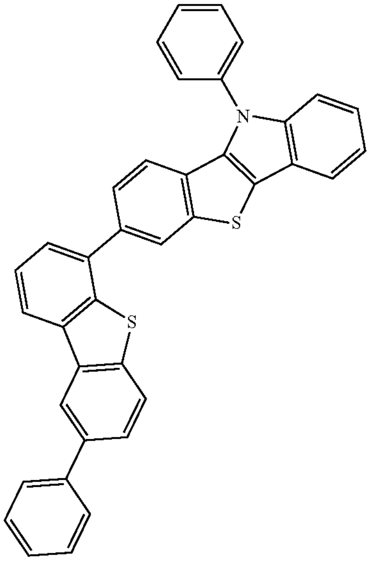
639
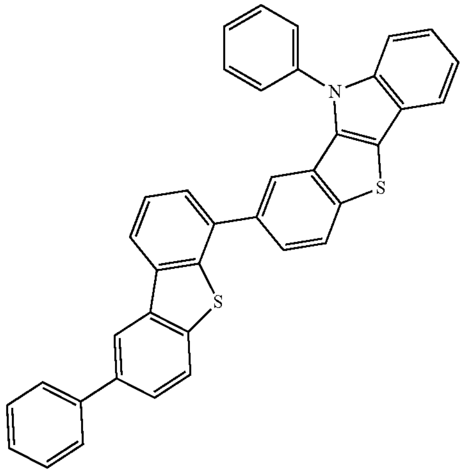
640
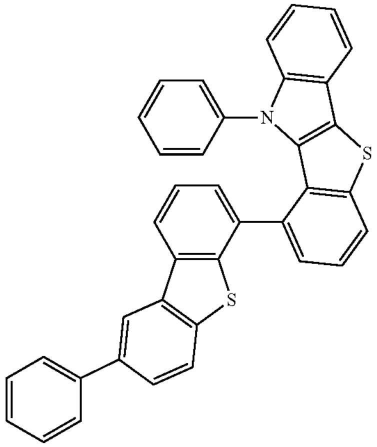

-continued
641
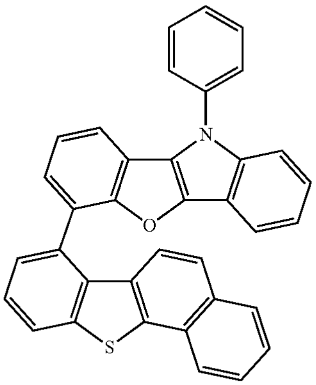
642
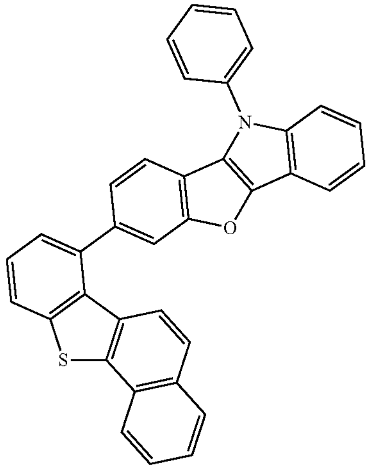
643
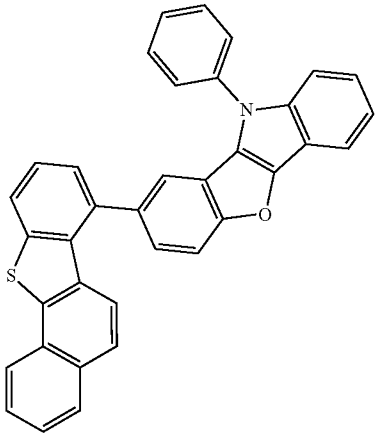
644
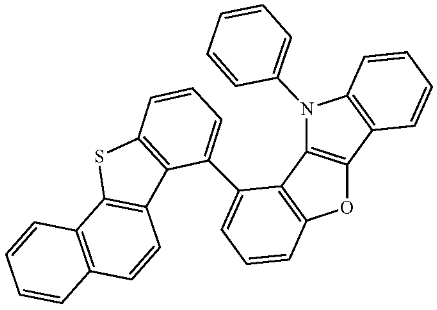
-continued
645
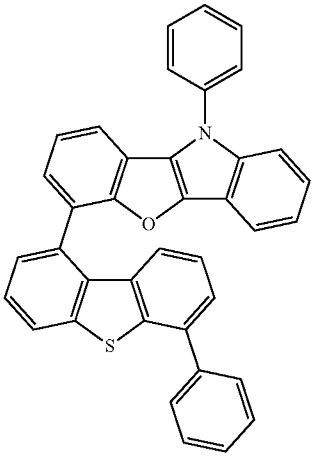
646
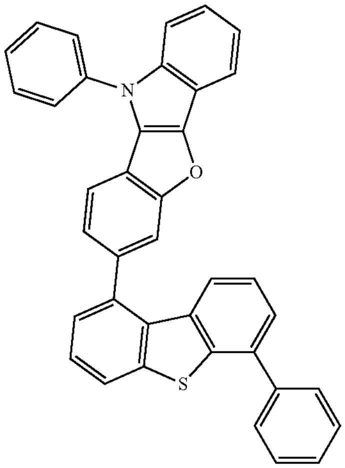
647
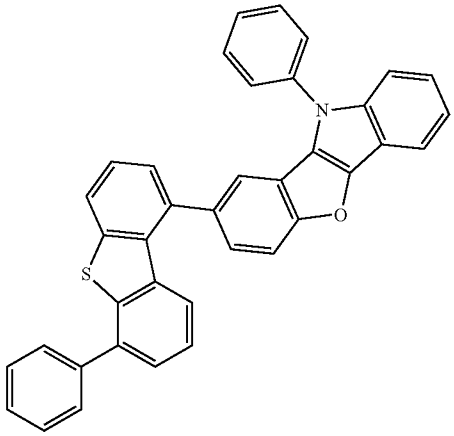

-continued
648
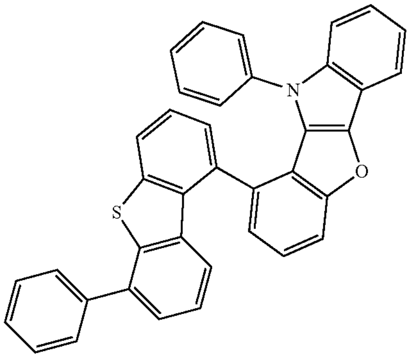
649
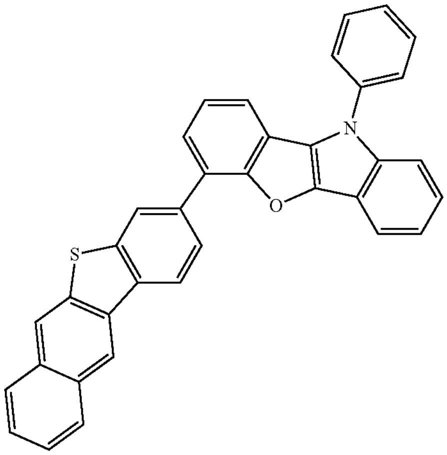
650
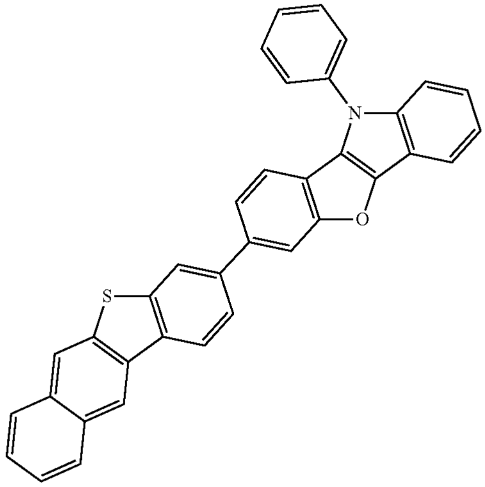
-continued
651
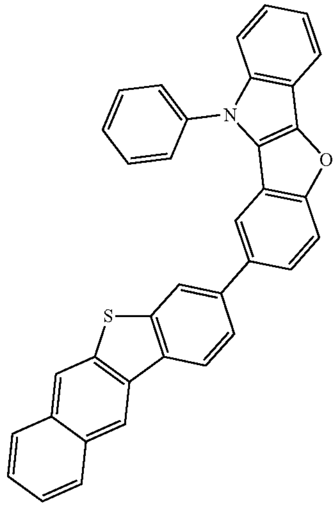
652
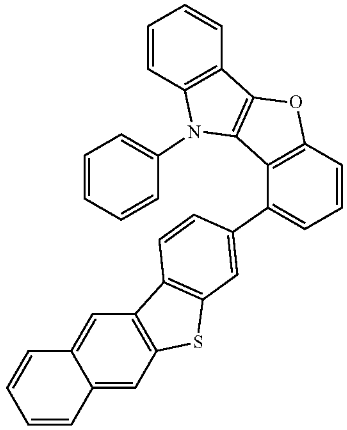
653
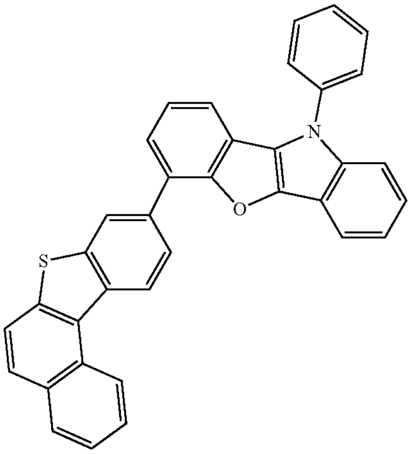

-continued
654
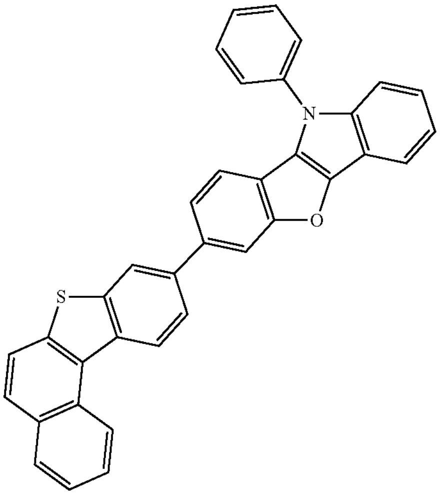
655
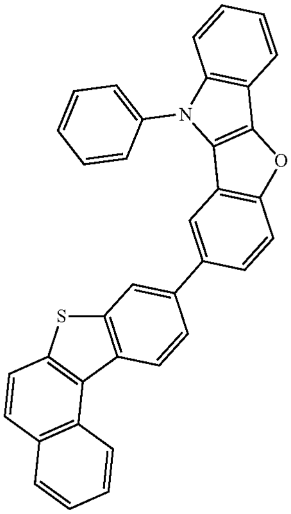
656
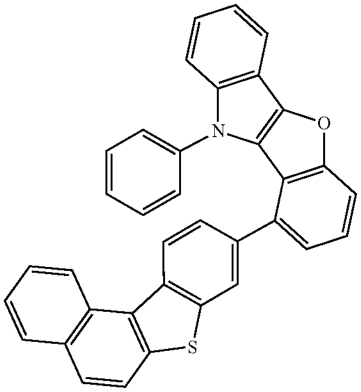
-continued
657
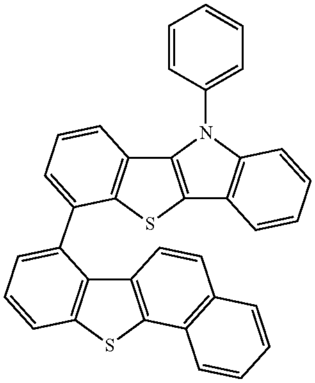
658
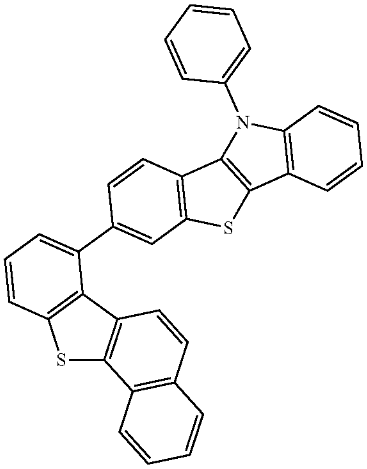
659
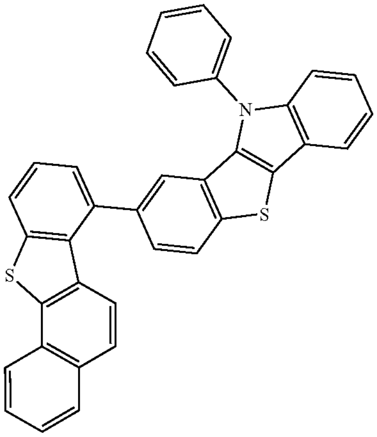
660
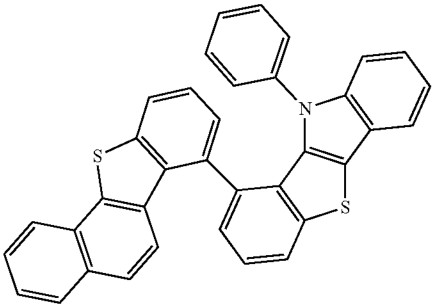

-continued
661
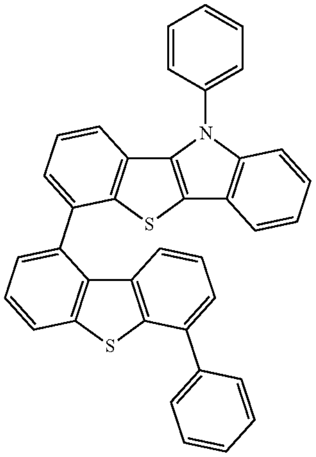
662
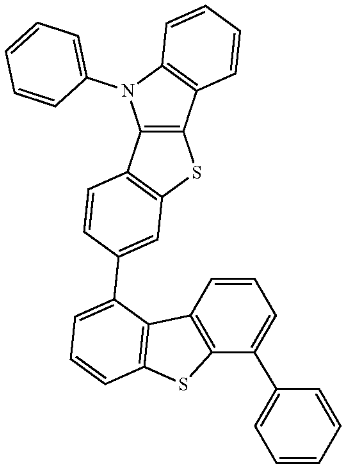
663
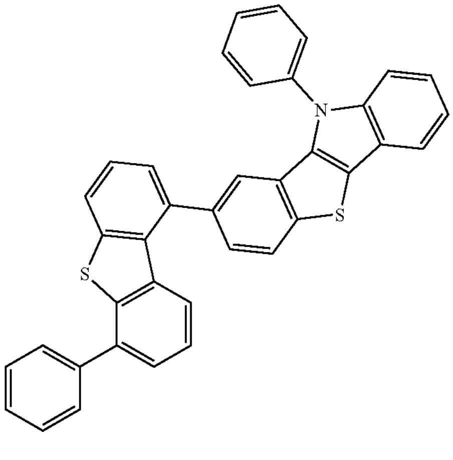
-continued
664
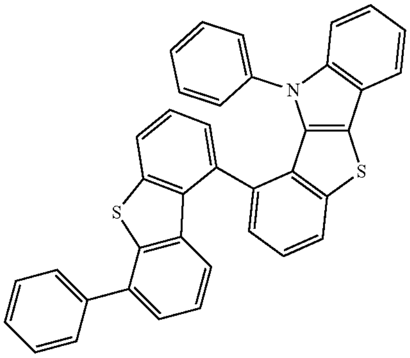
665
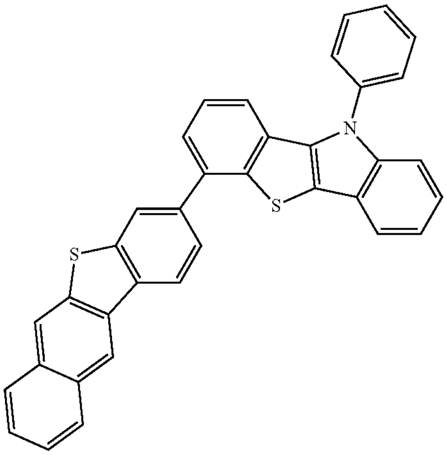
666
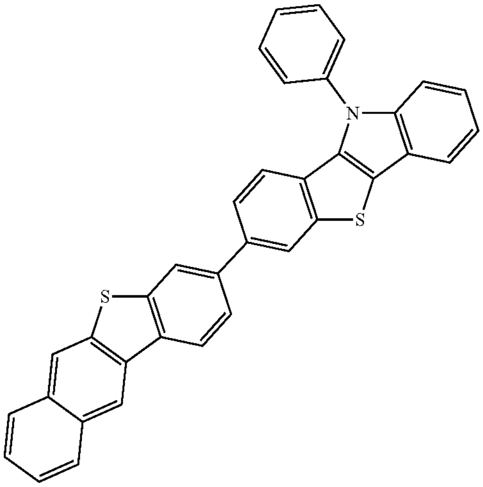

-continued
667
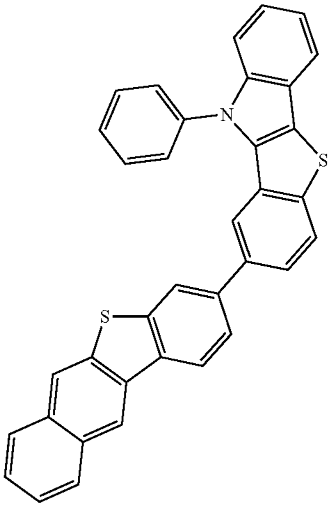
668
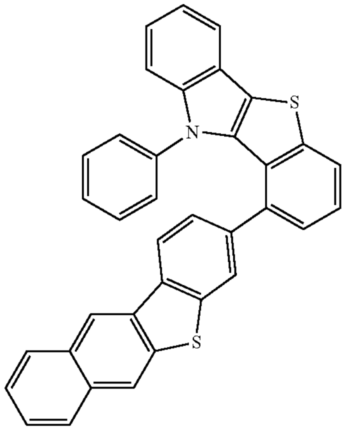
669
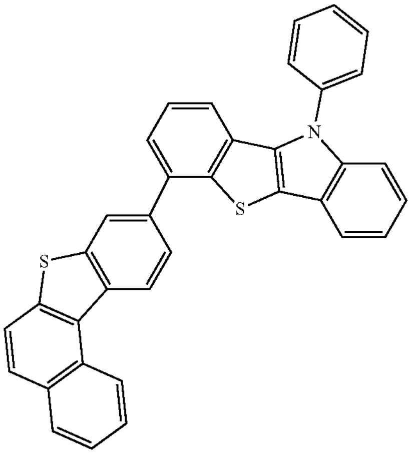
-continued
670
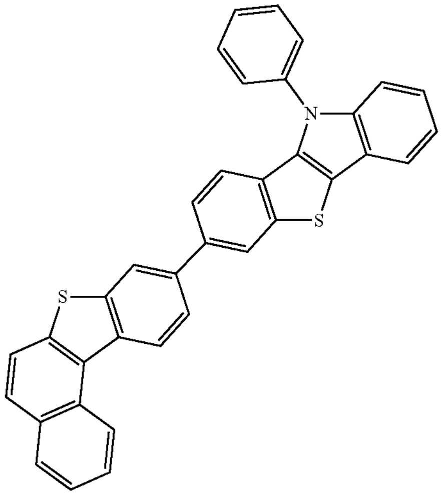
671
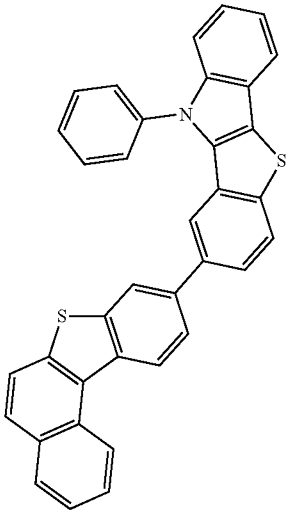
672
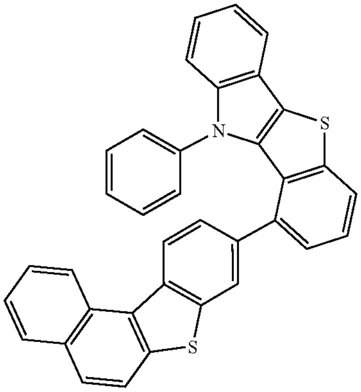

-continued
673
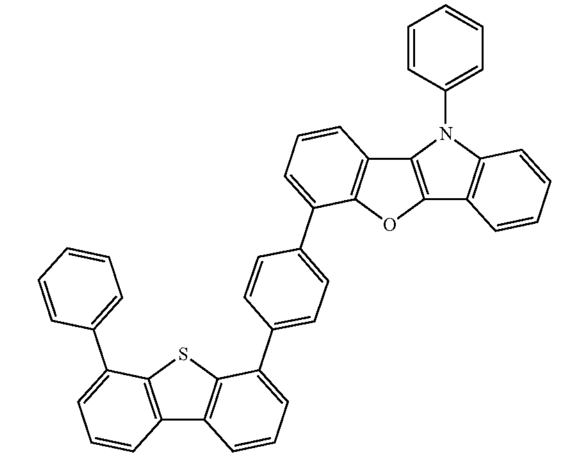
674
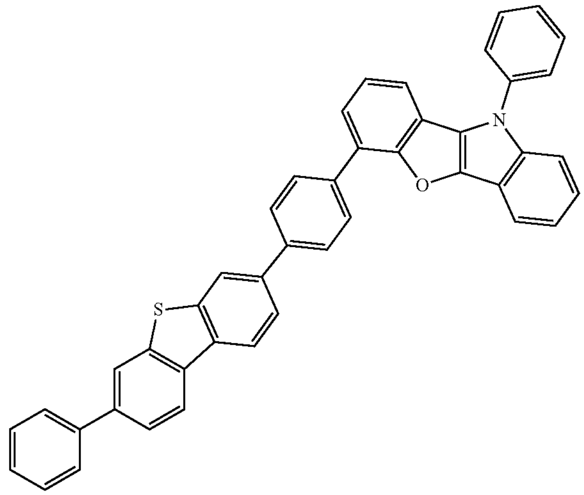
675
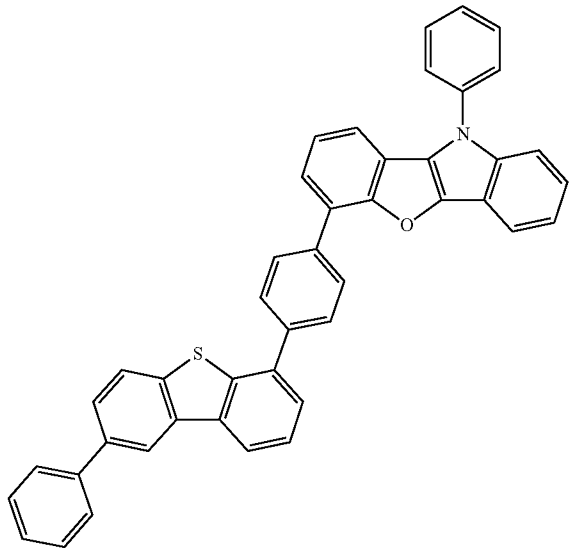
-continued
676
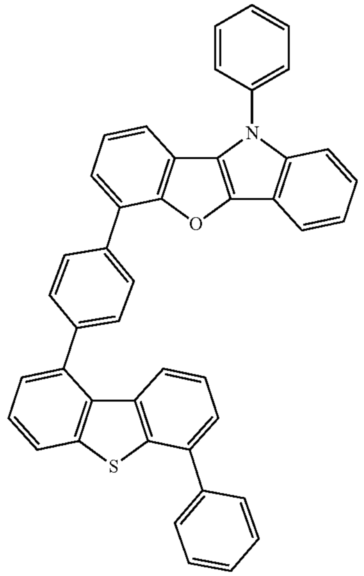
677
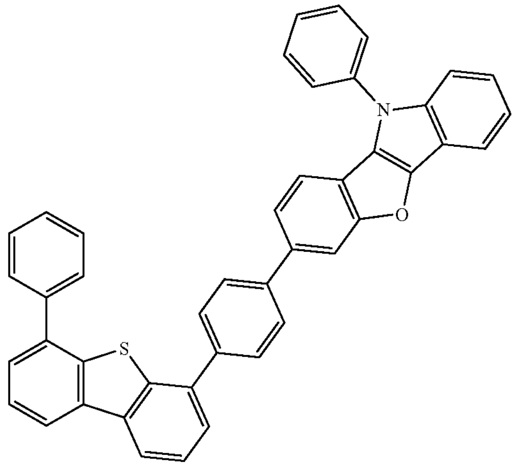
678
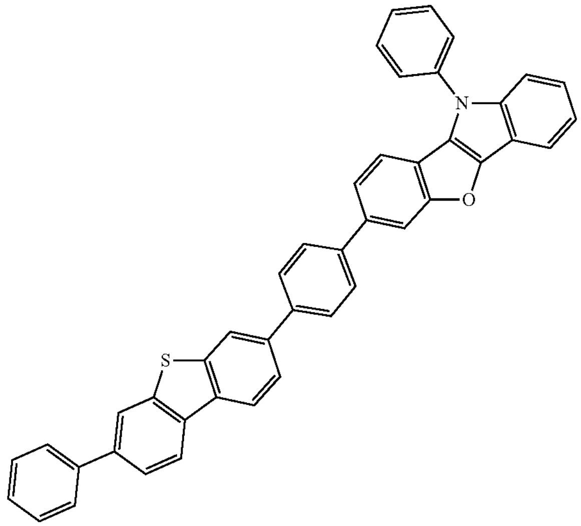

-continued
679
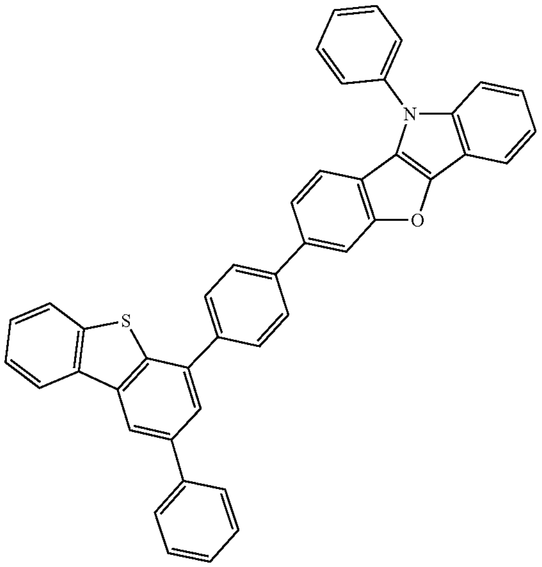
680
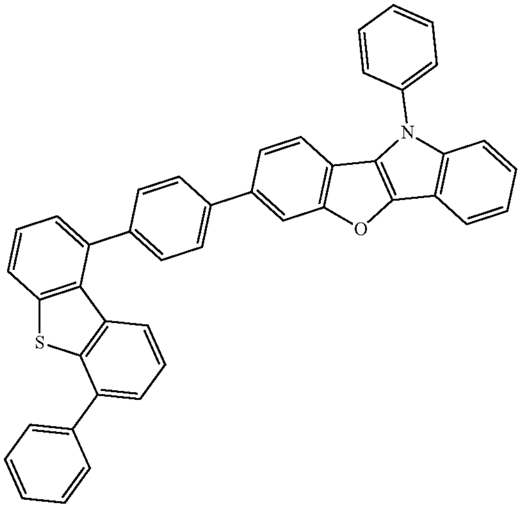
681
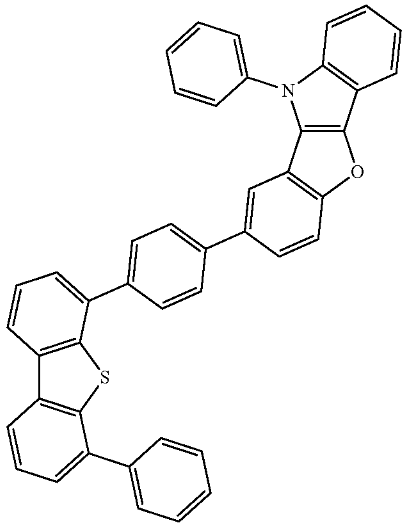
-continued
682
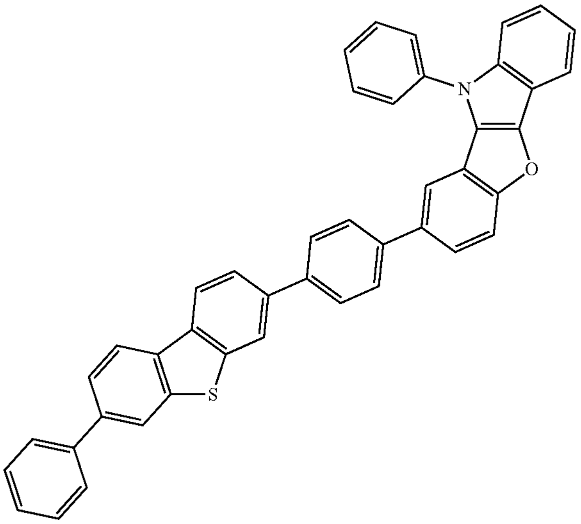
683
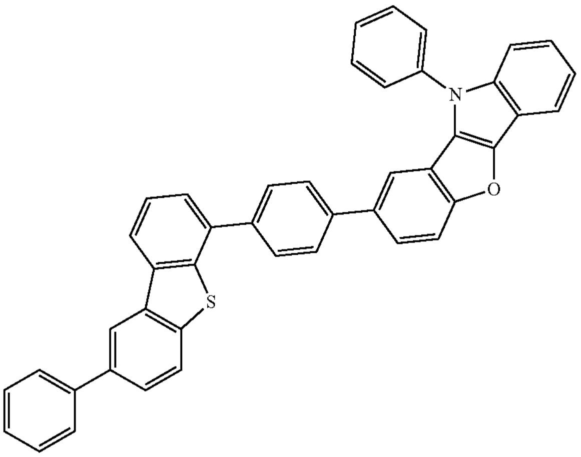
684
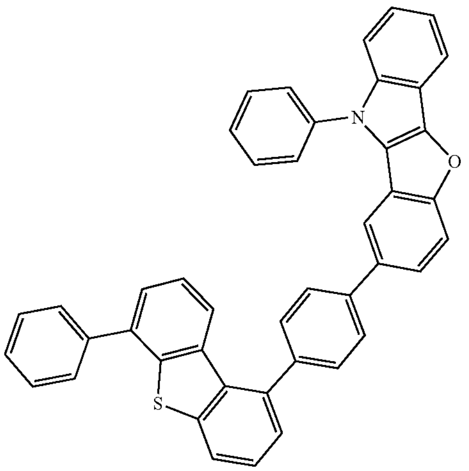

-continued
685
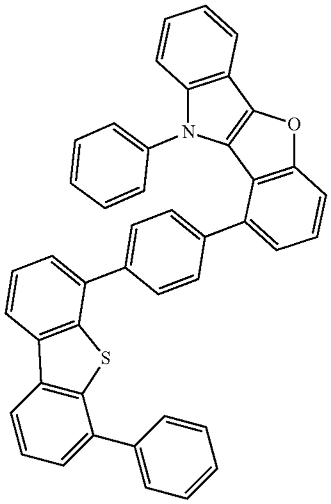
686
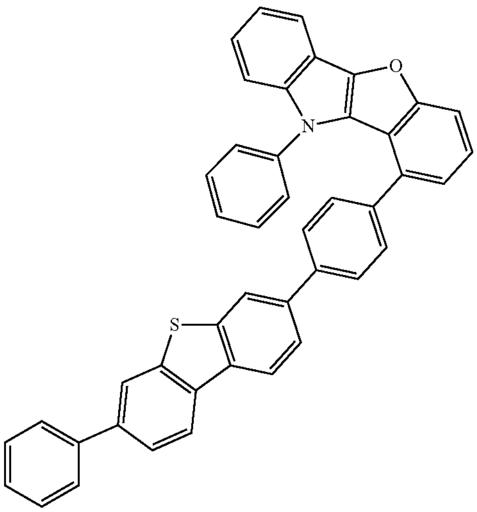
687
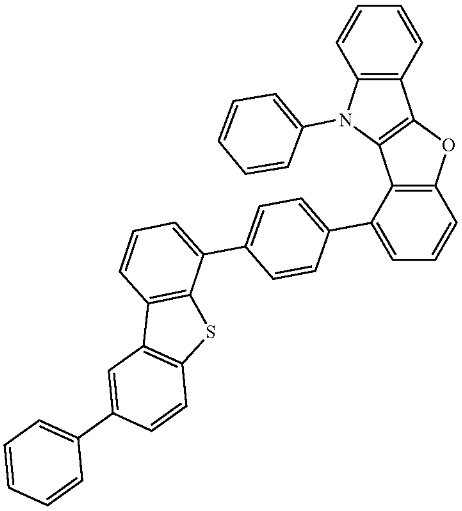
-continued
688
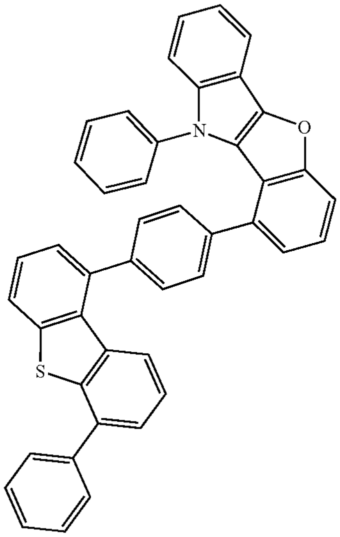
689
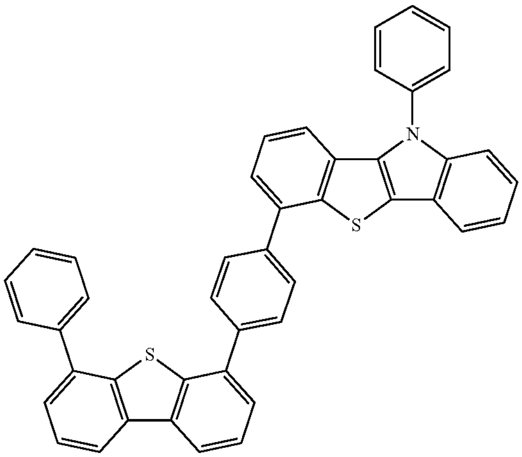
690
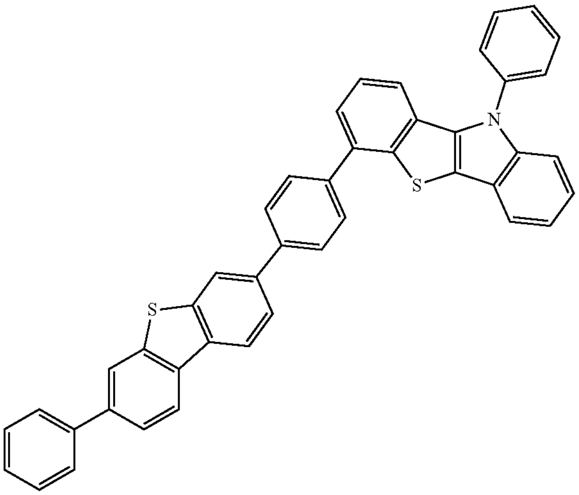

-continued
691
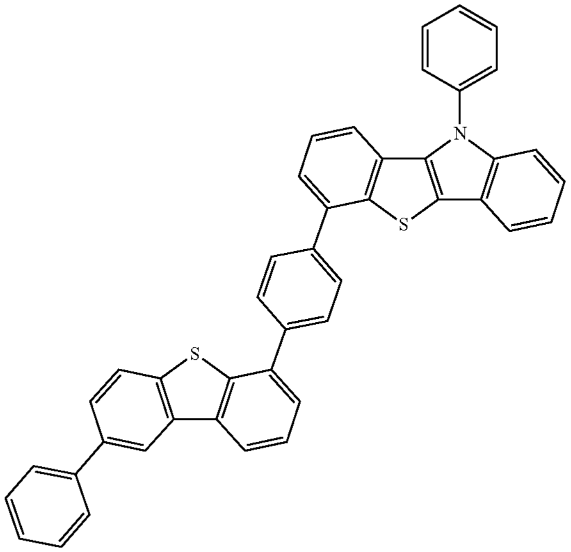
692
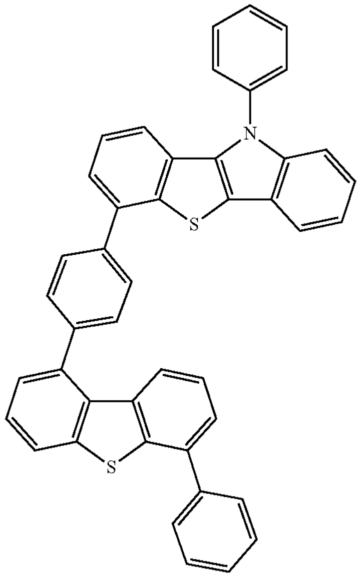
693
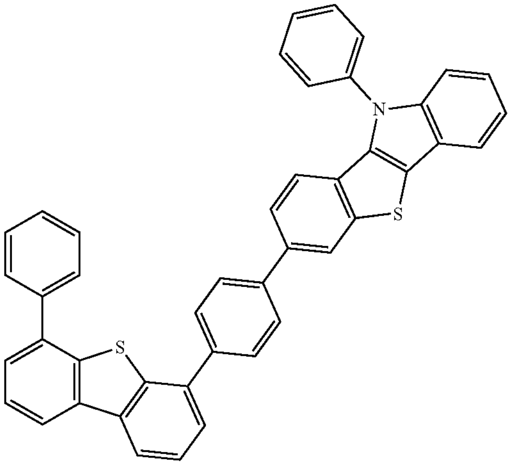
-continued
694
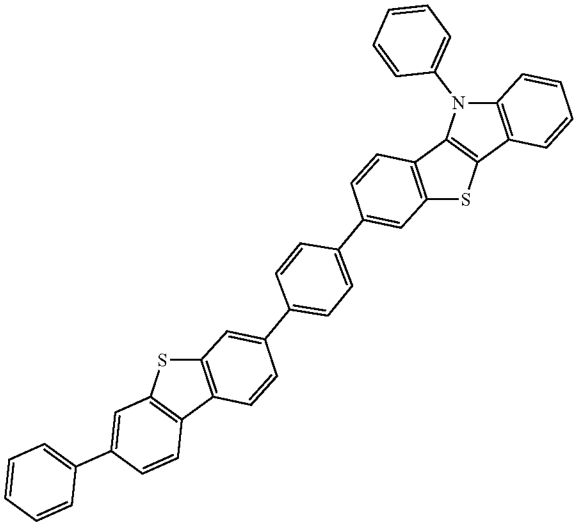
695
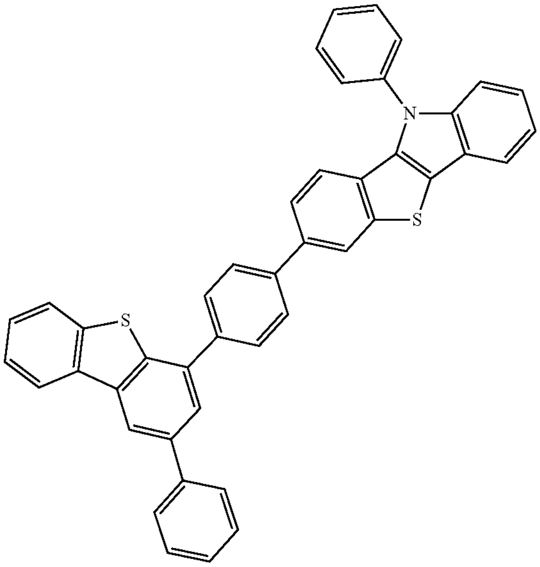
696
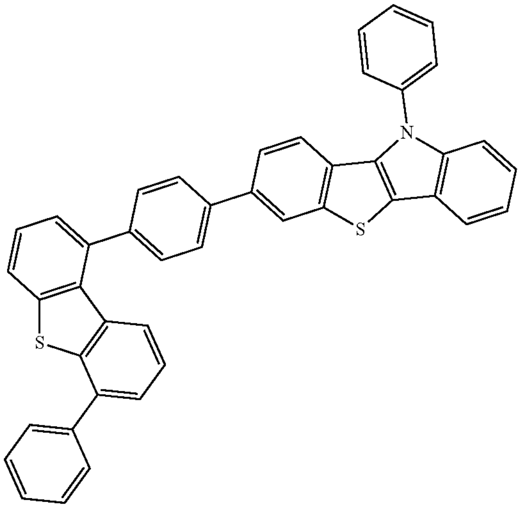

-continued
697
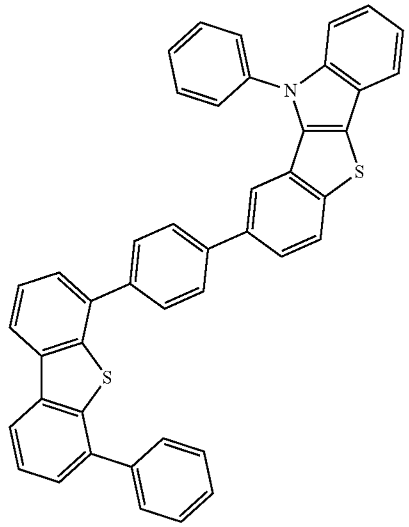
698
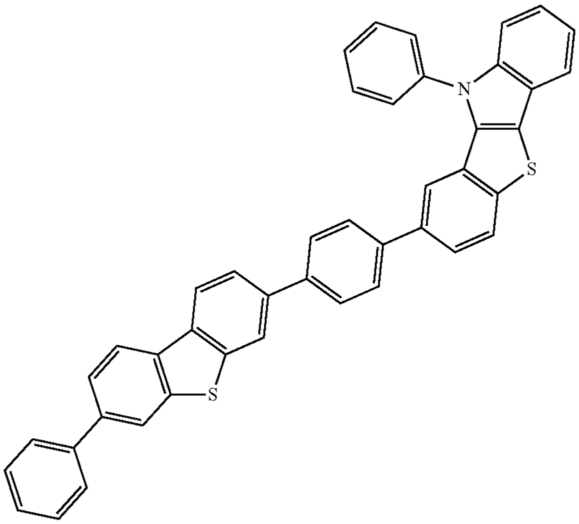
699
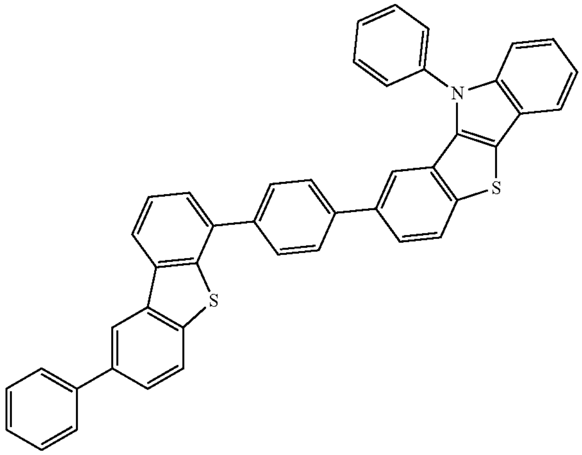
-continued
700
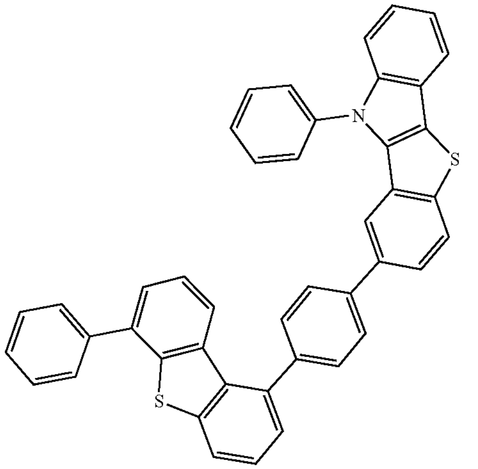
701
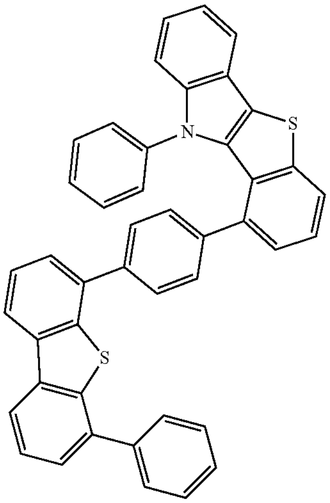
702
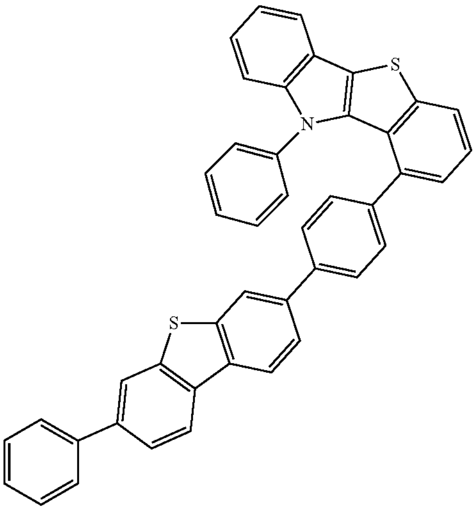

-continued
703
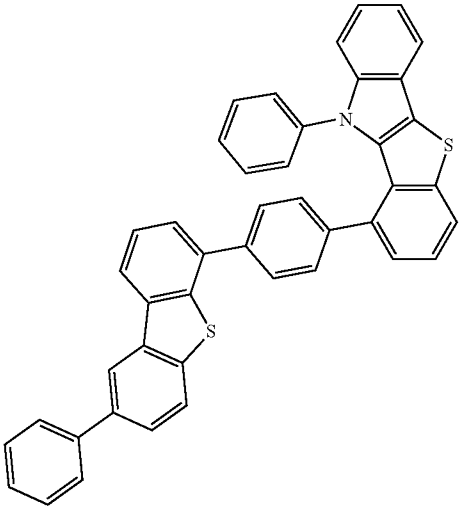
704
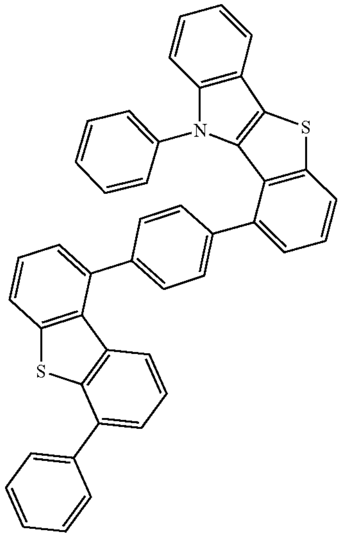
705
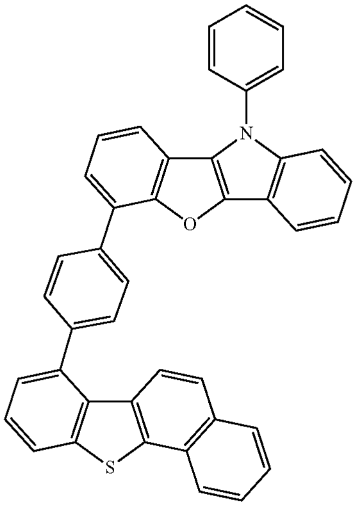
-continued
706
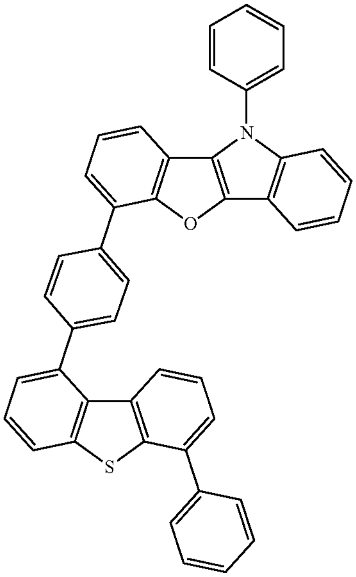
707
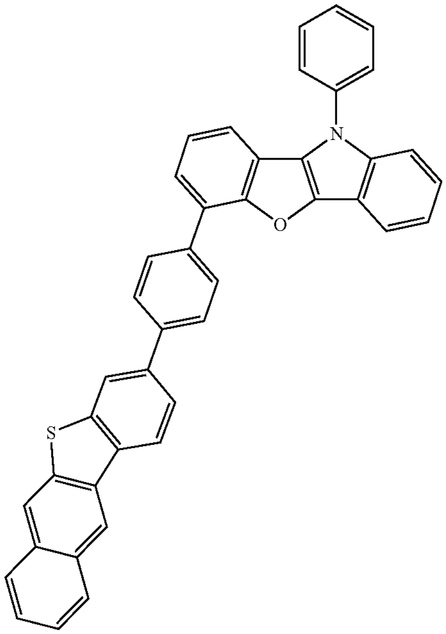

-continued
708
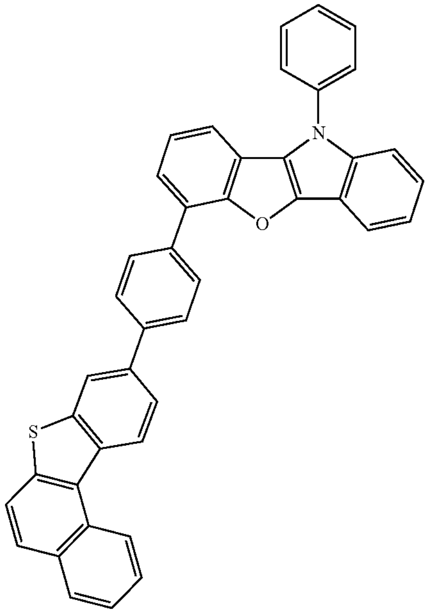
709
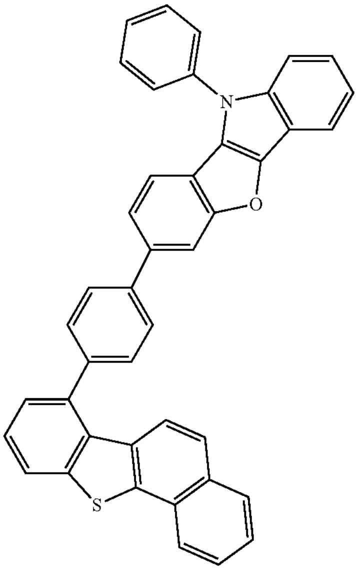
-continued
710
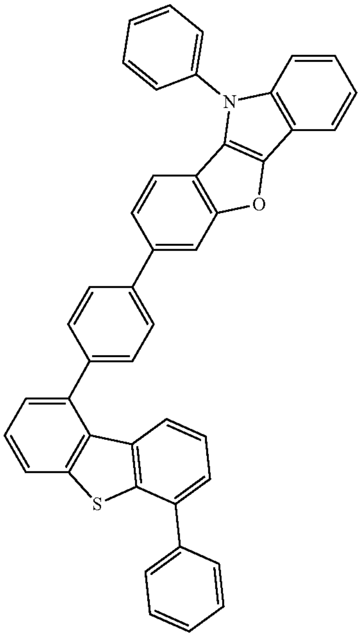
711
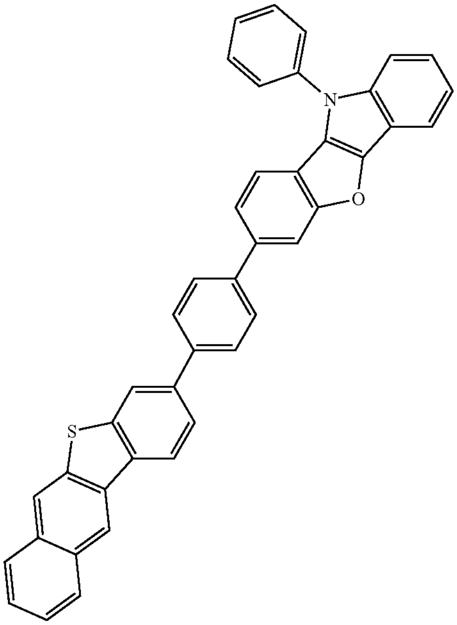

-continued
712
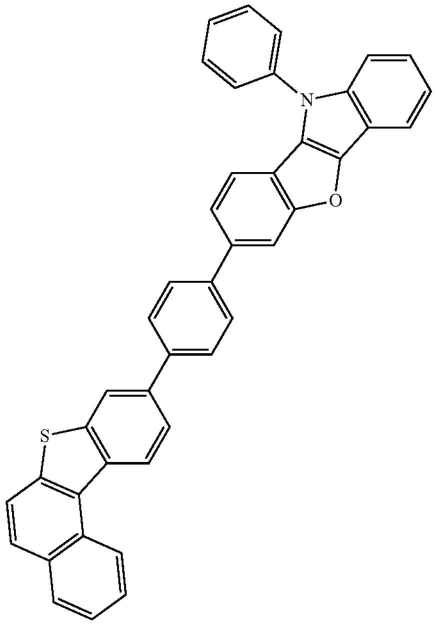
713
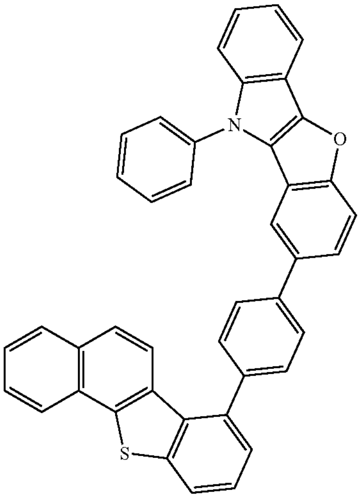
714
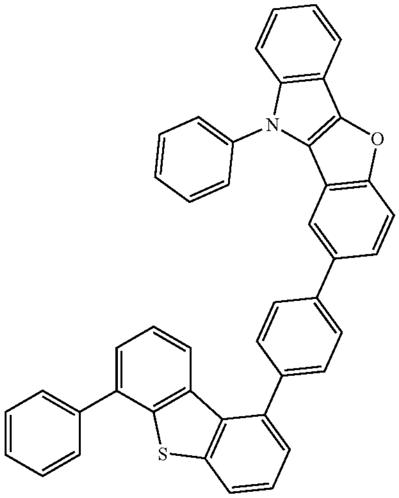
-continued
715
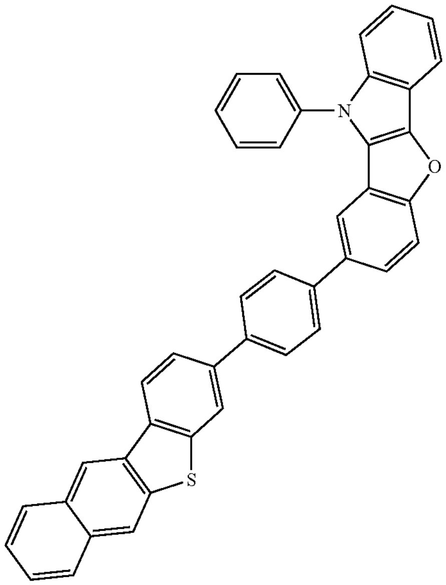
716
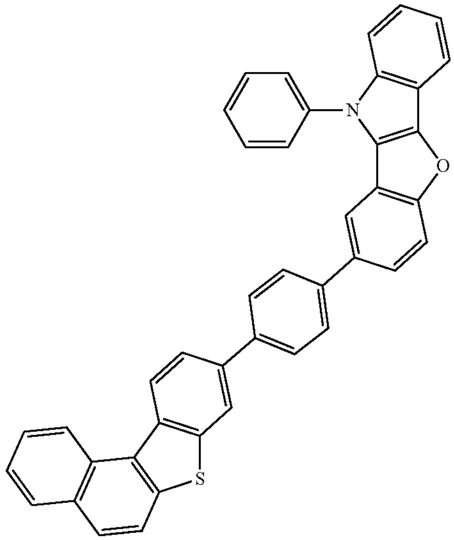
717
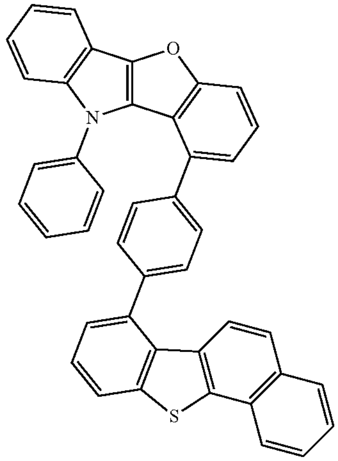

-continued
718
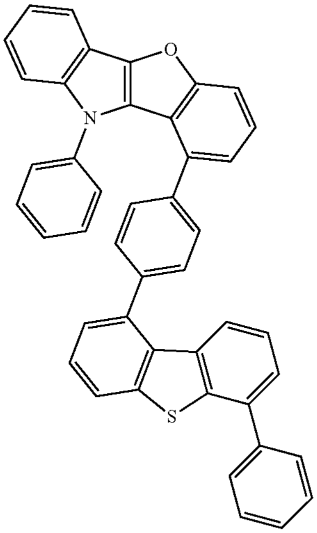
719
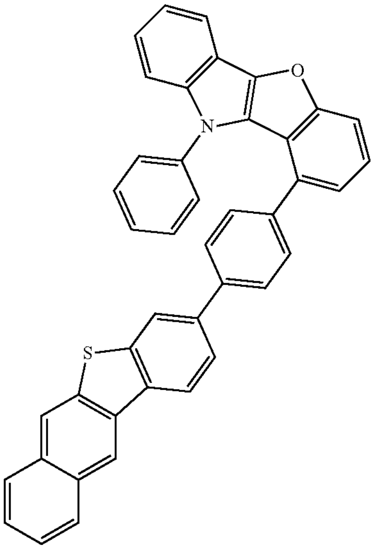
720
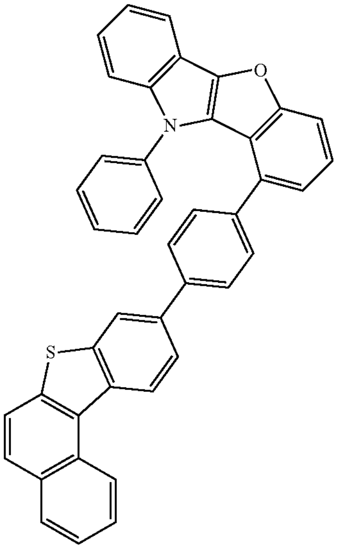
-continued
721
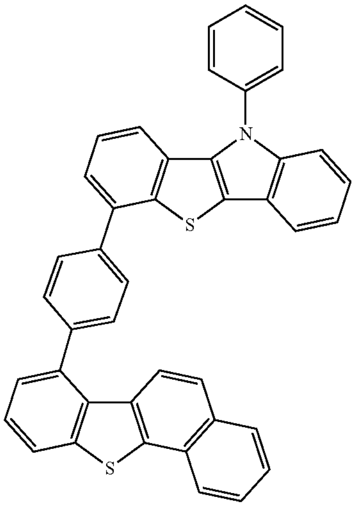
722
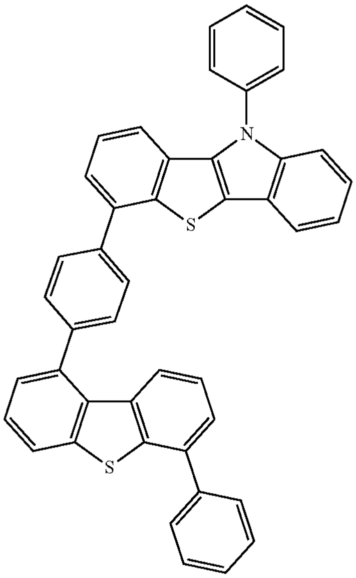

-continued
723
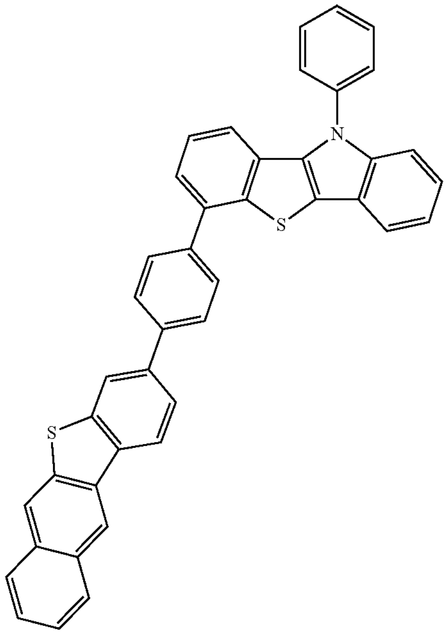
724
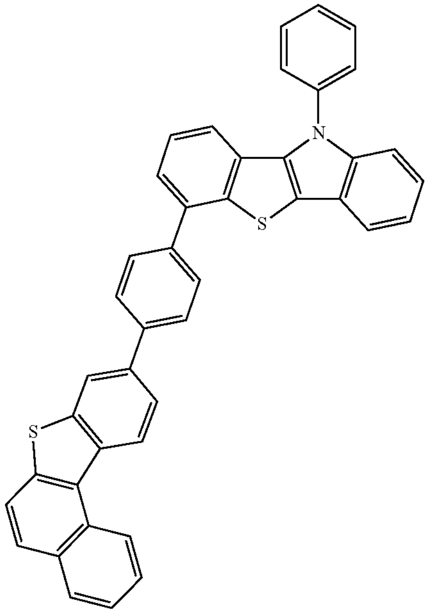
-continued
725
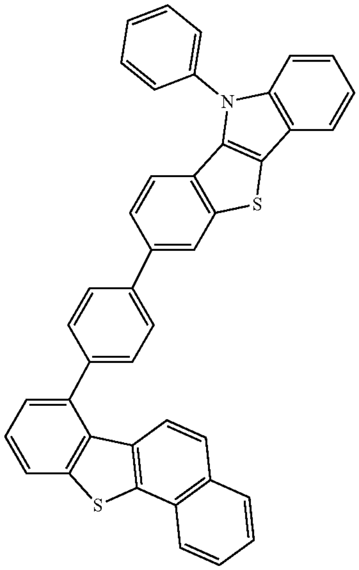
726
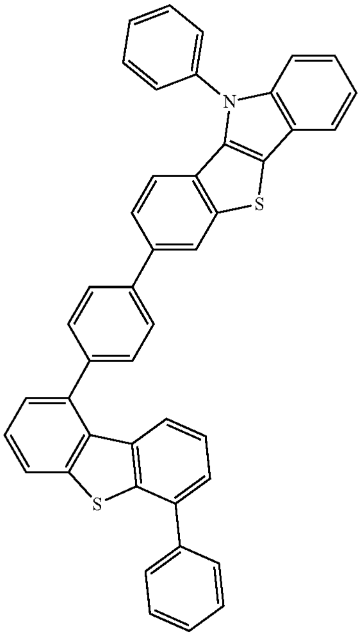

-continued
727
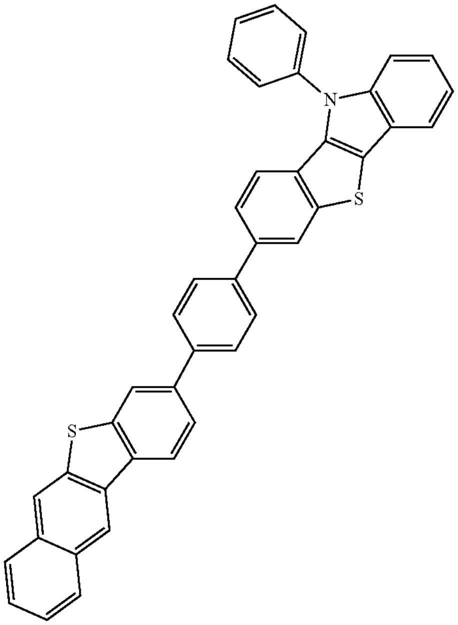
728
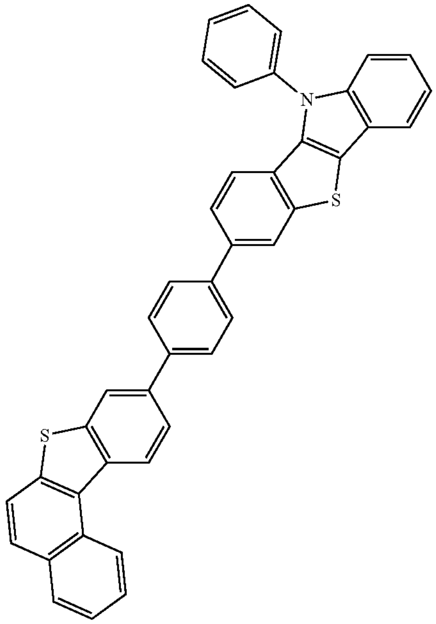
-continued
729
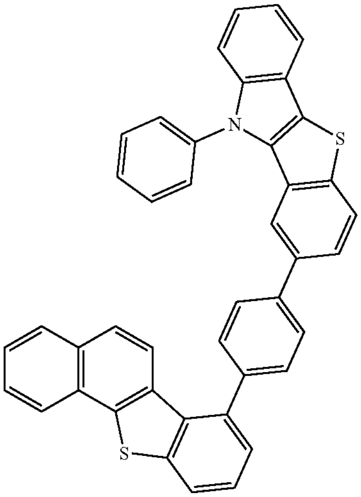
730
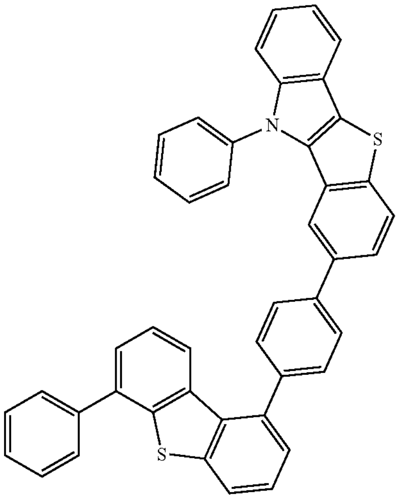
731
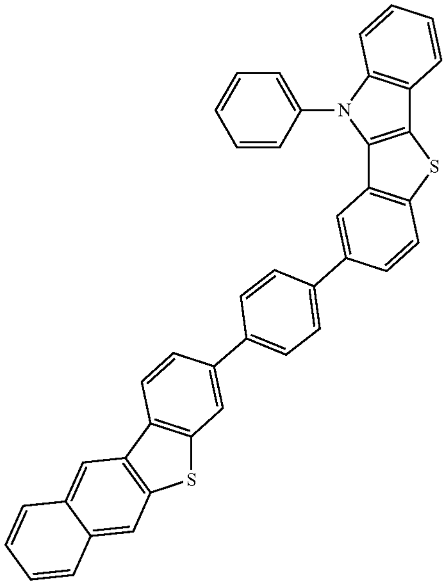

-continued
732
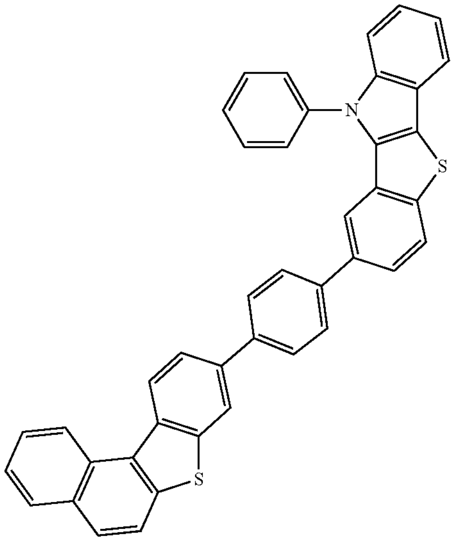
733
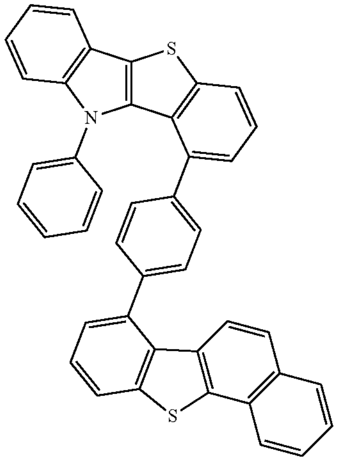
734
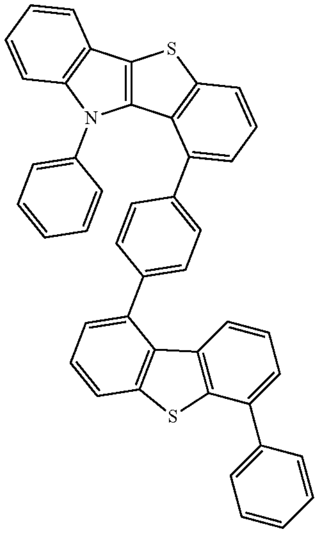
-continued
735
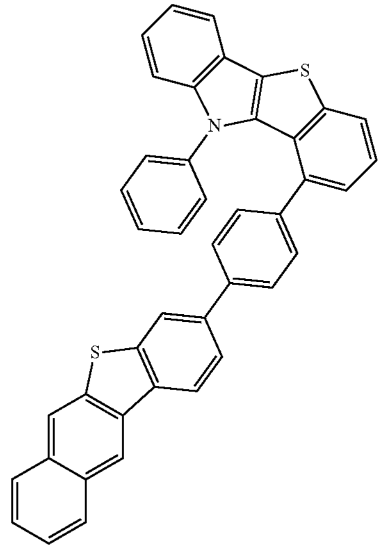
736
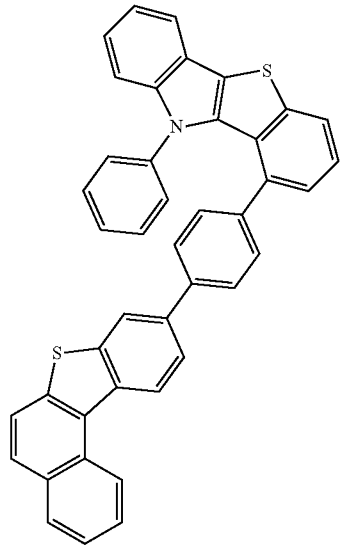
737
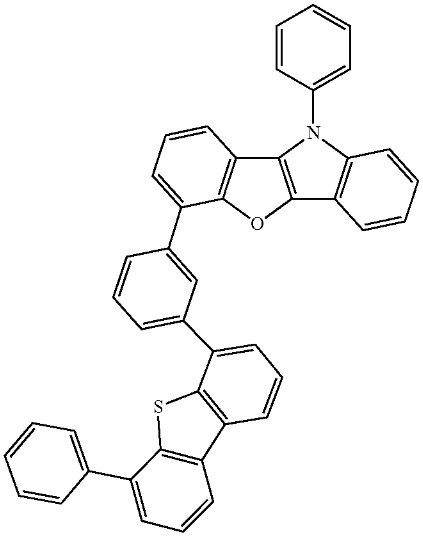

-continued
738
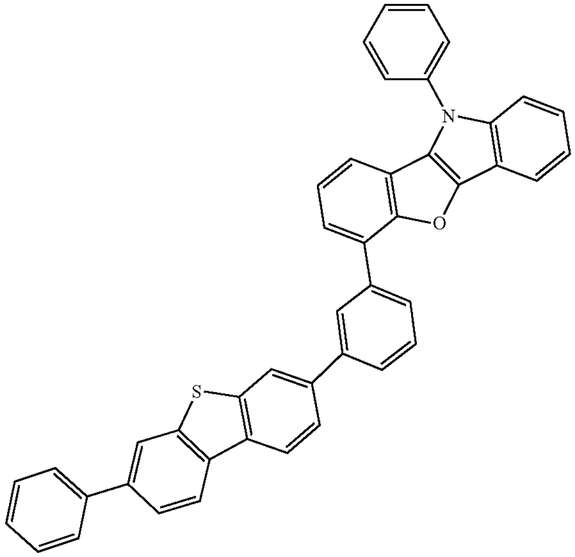
739
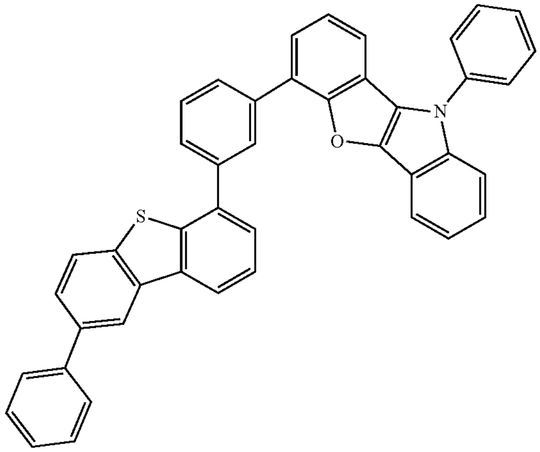
740
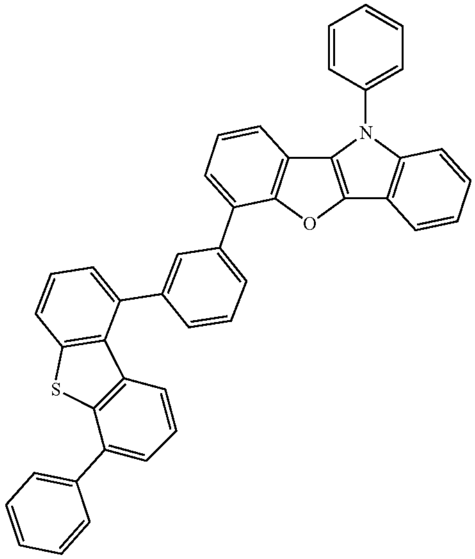
-continued
741
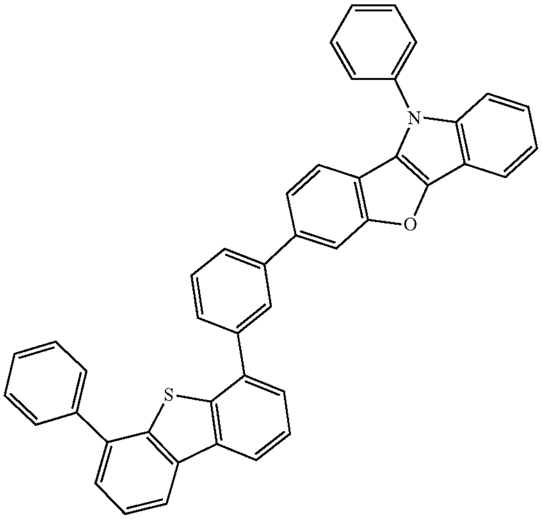
742
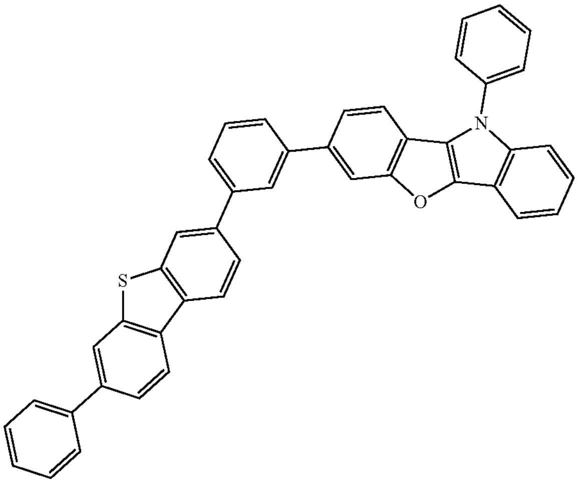
743
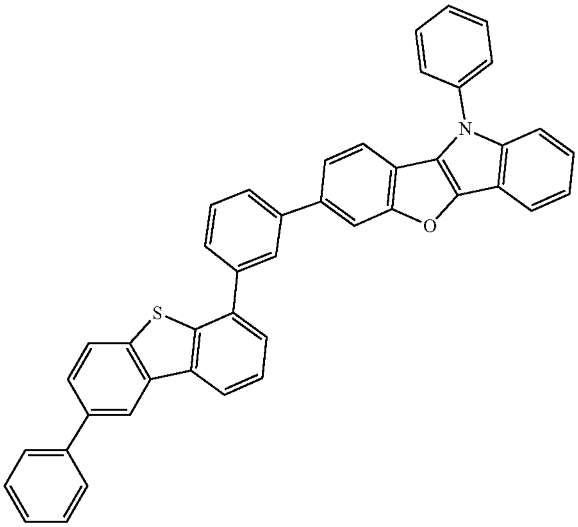

-continued
744
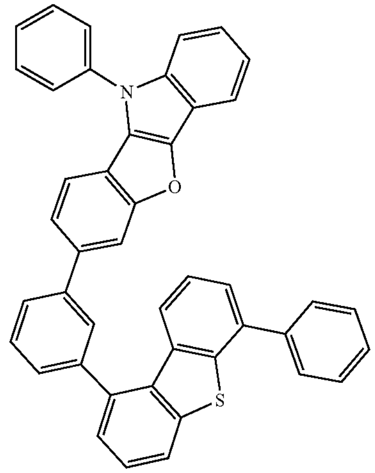
745
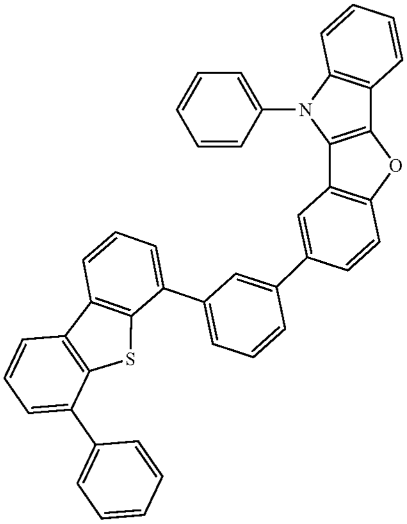
746
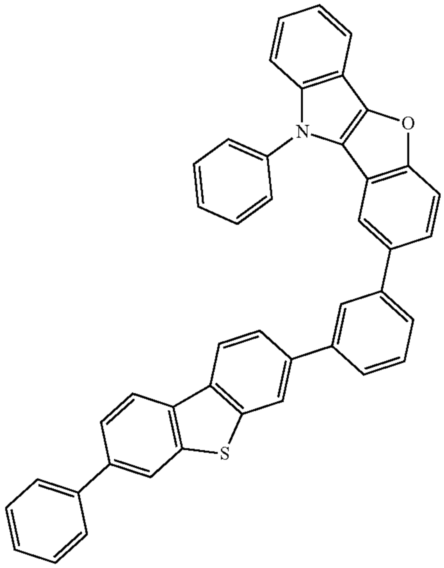
-continued
747
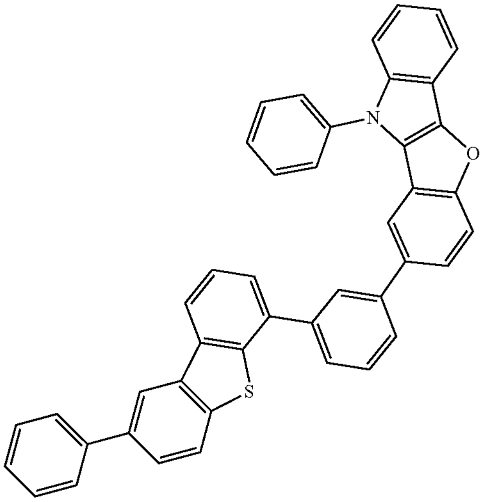
748
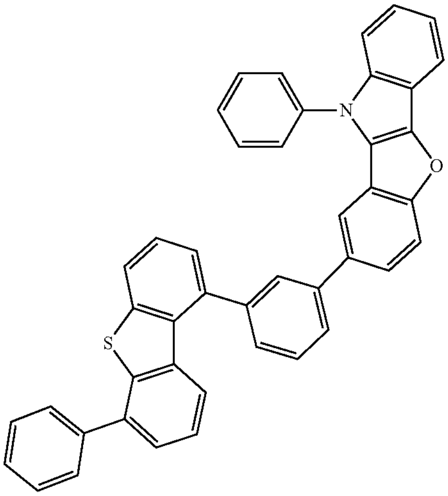
749
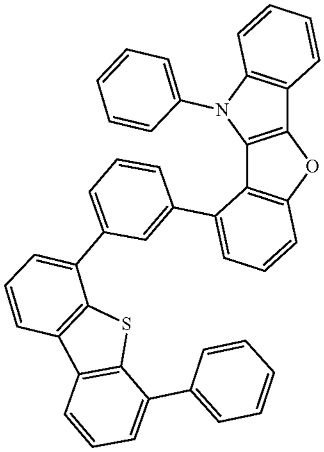

-continued
750
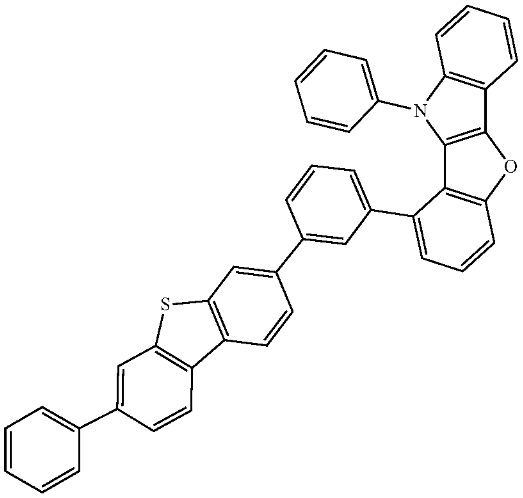
751
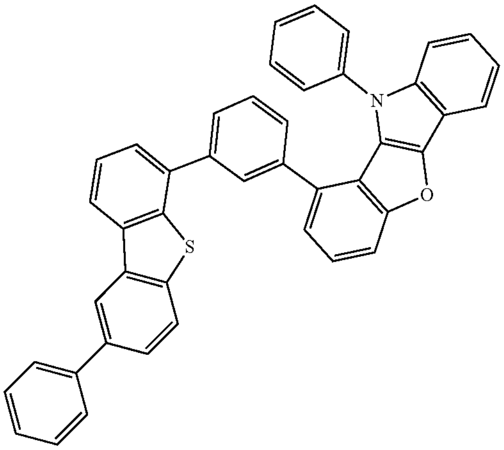
752
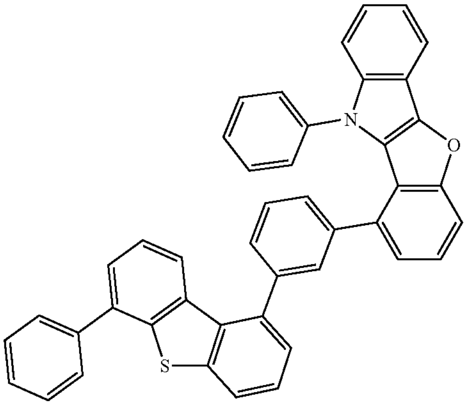
-continued
753
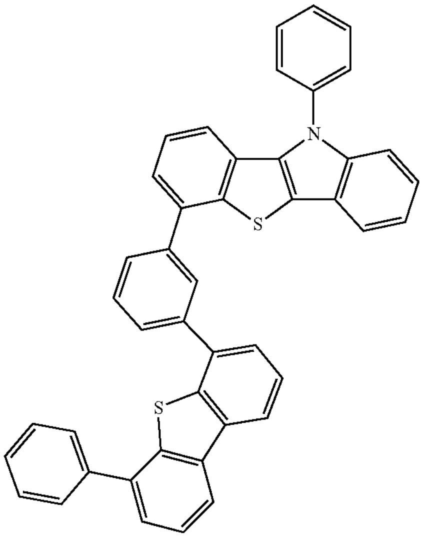
754
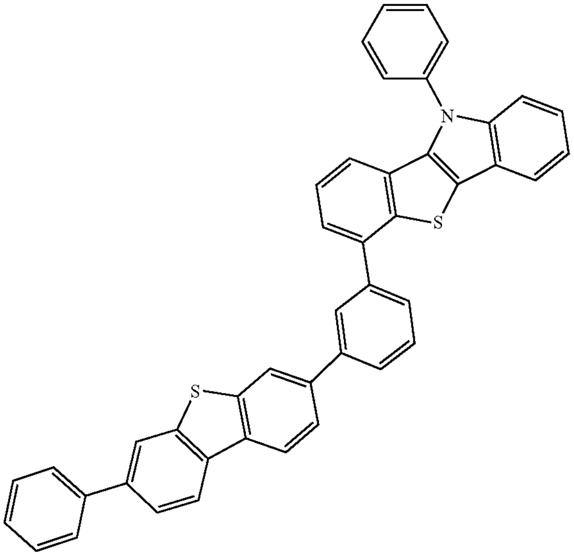
755
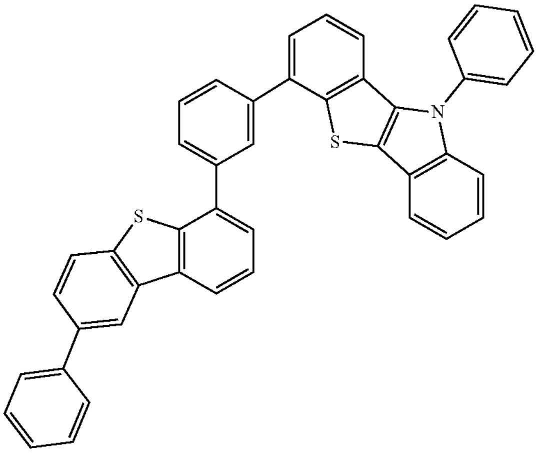

-continued
756
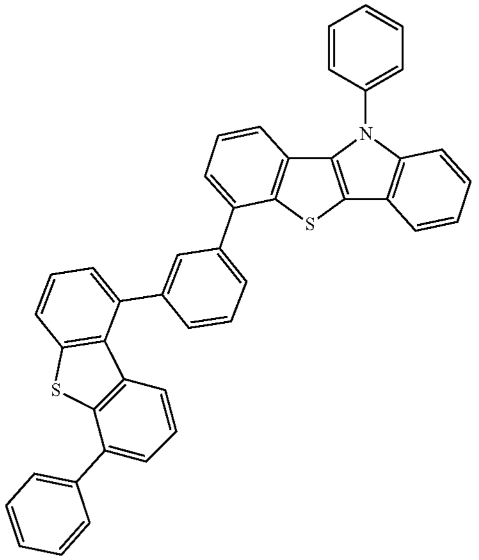
757
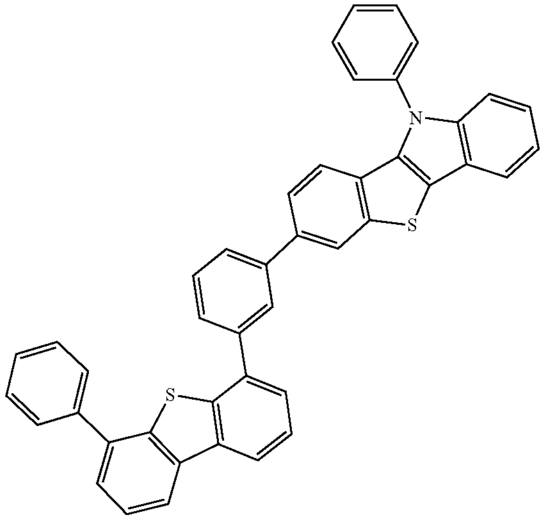
758
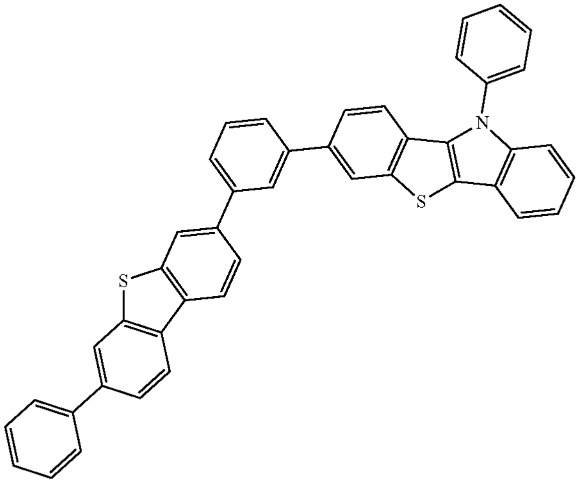
-continued
759
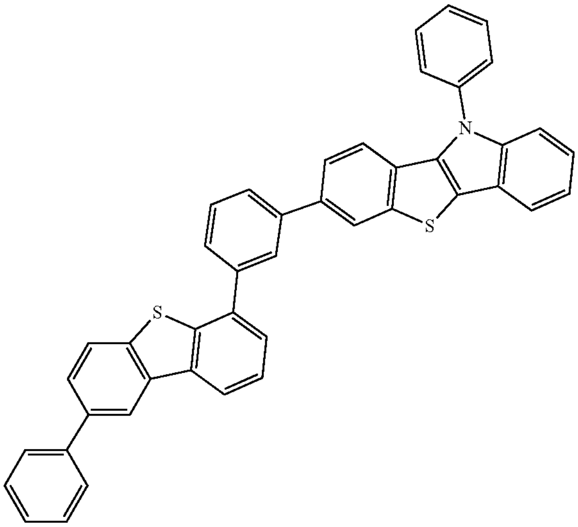
760
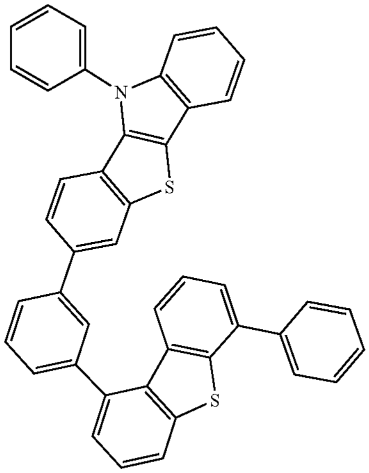
761
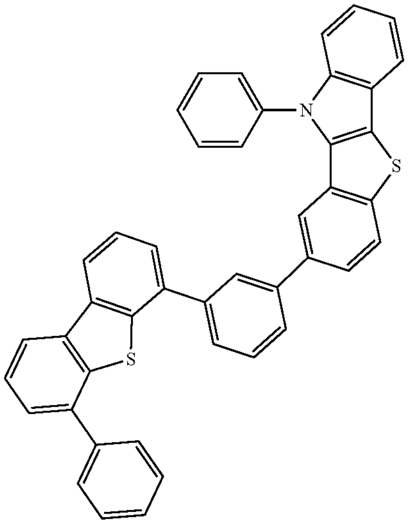

-continued
762
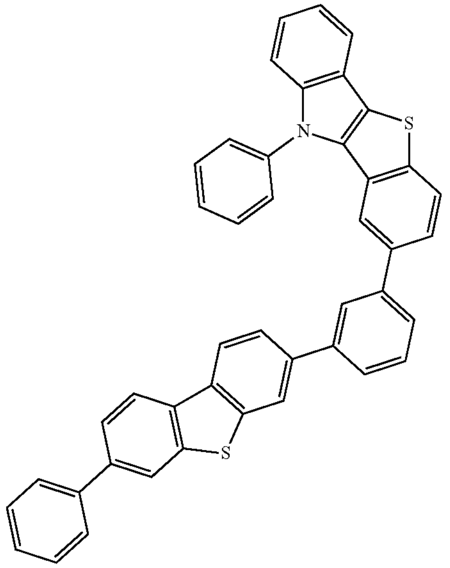
763
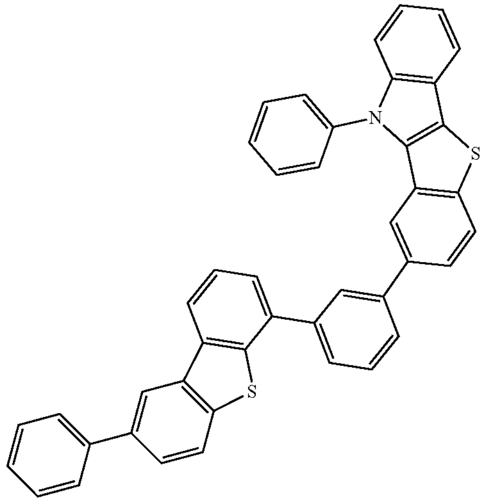
764
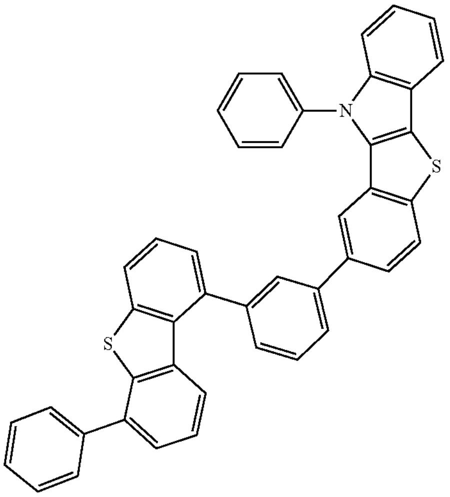
-continued
765
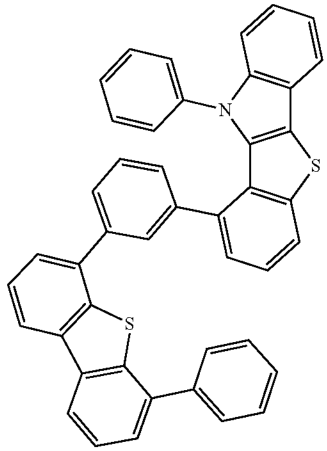
766
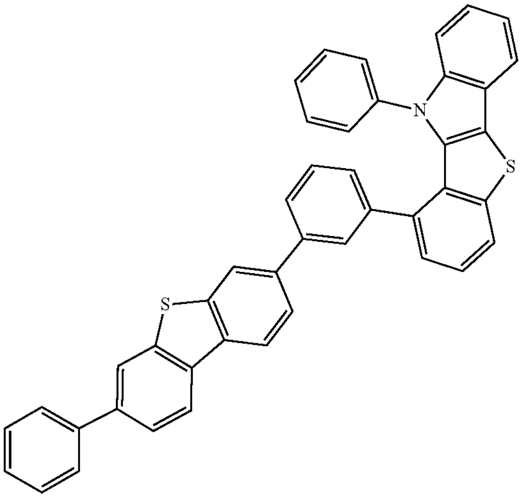
767
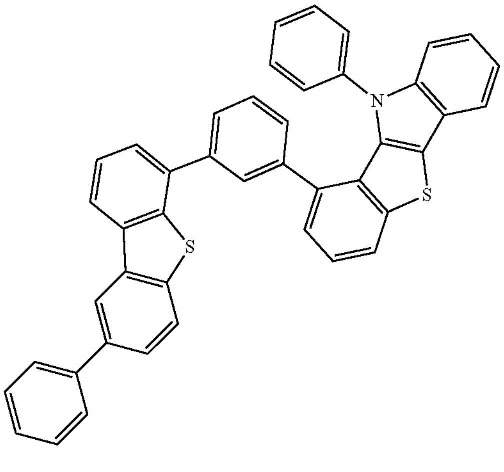

-continued
768
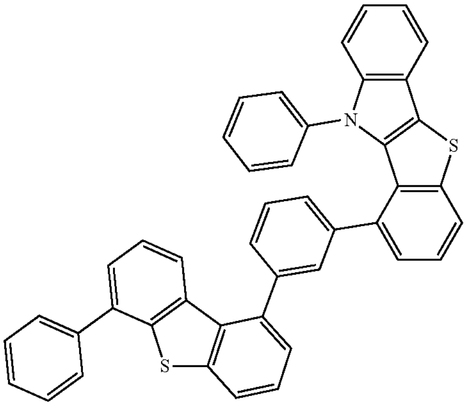
769
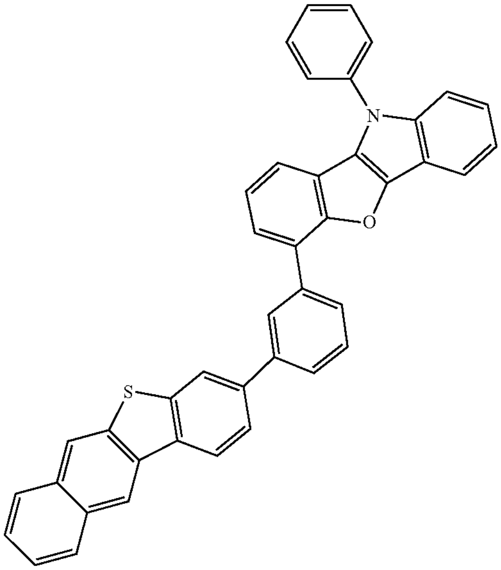
770
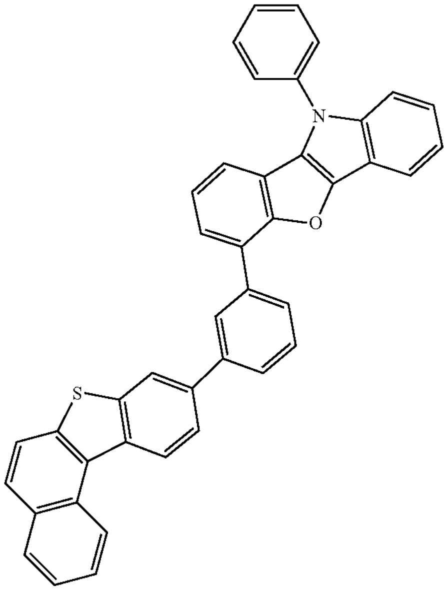
-continued
771
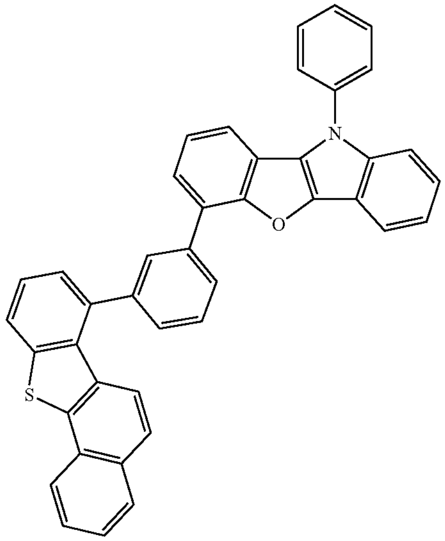
772
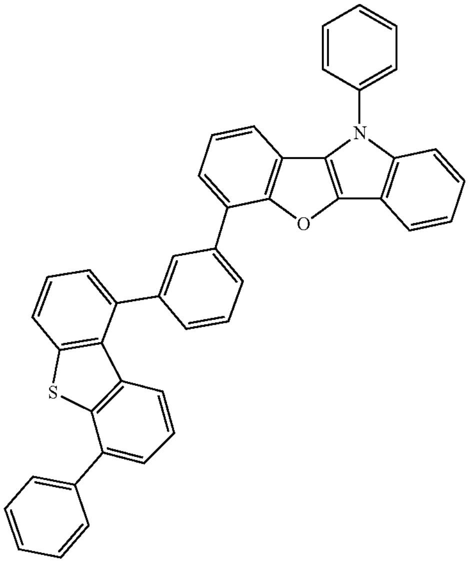

-continued
773
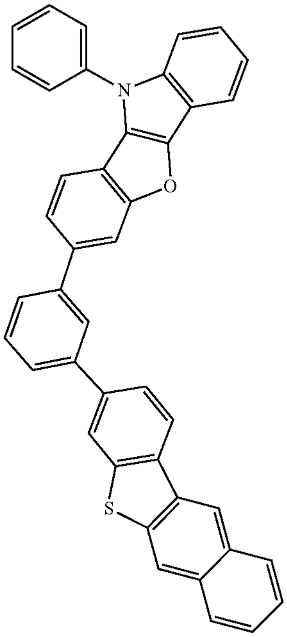
774
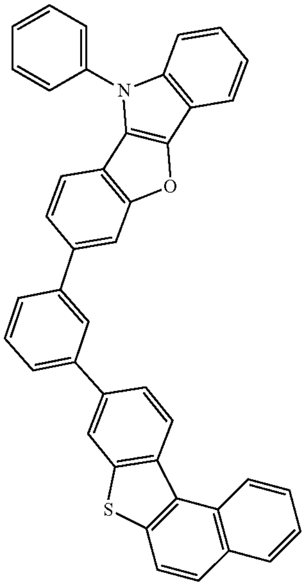
-continued
775
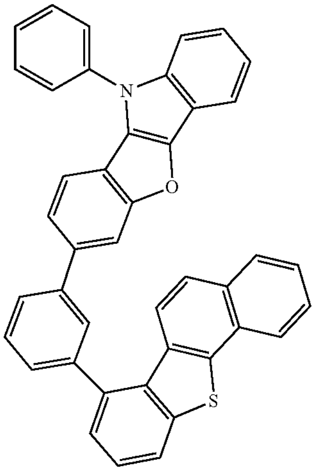
776
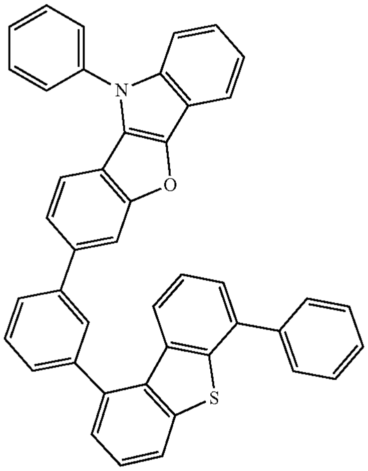
777
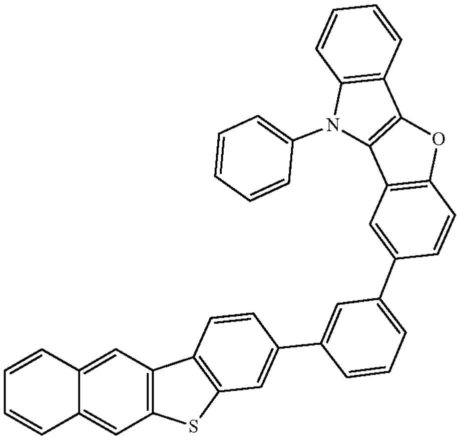

778
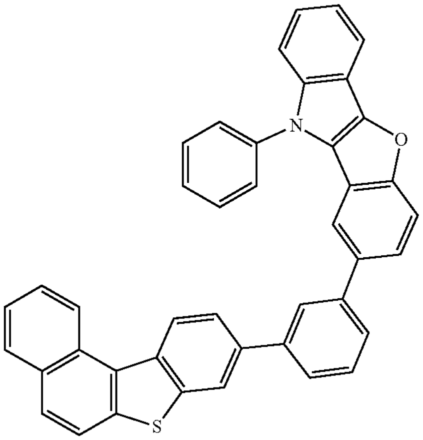
779
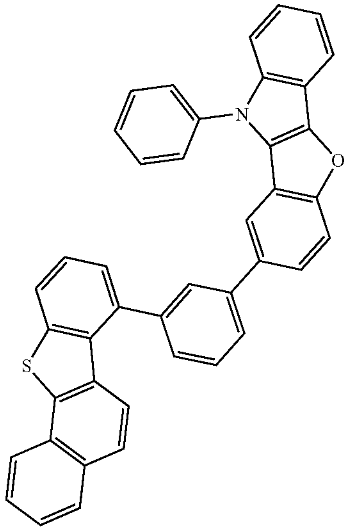
780
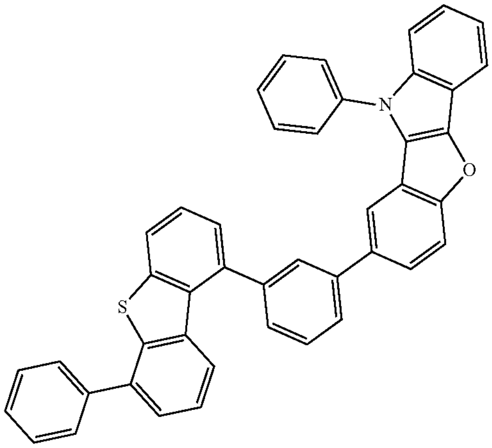
781
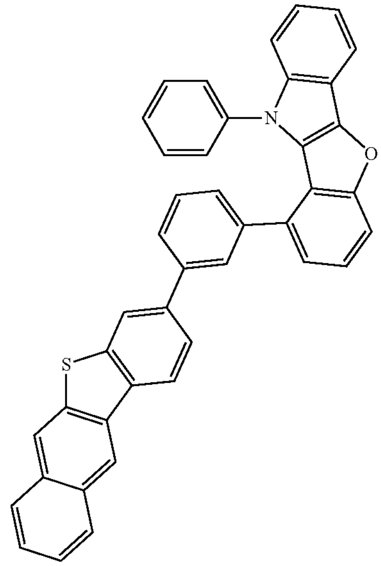
782
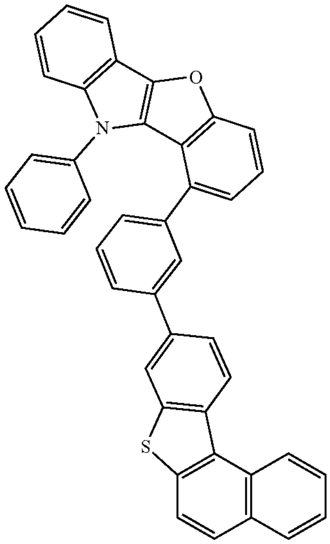
783
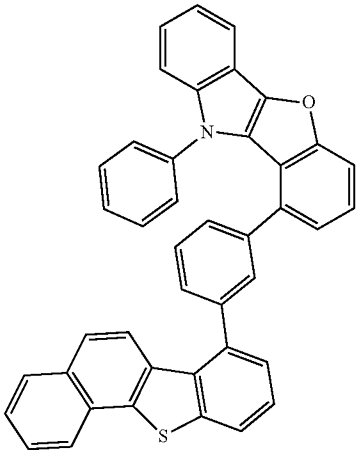

-continued
784
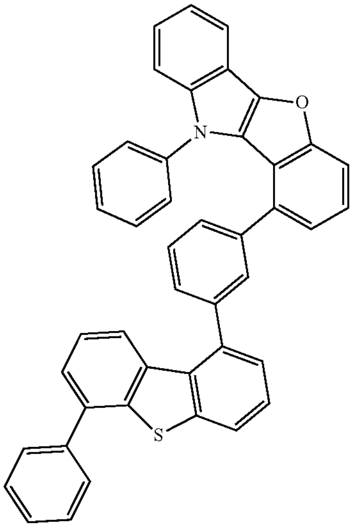
785
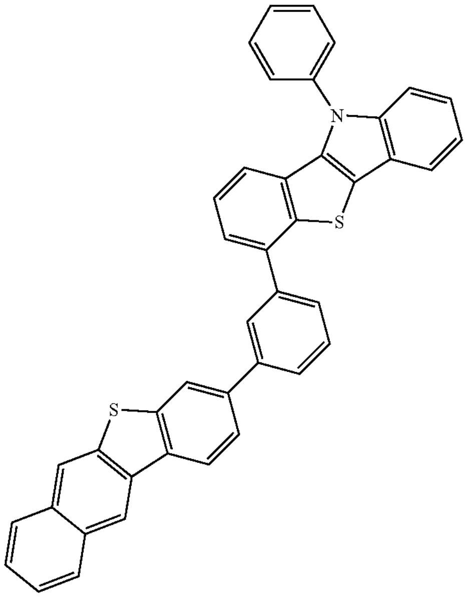
-continued
786
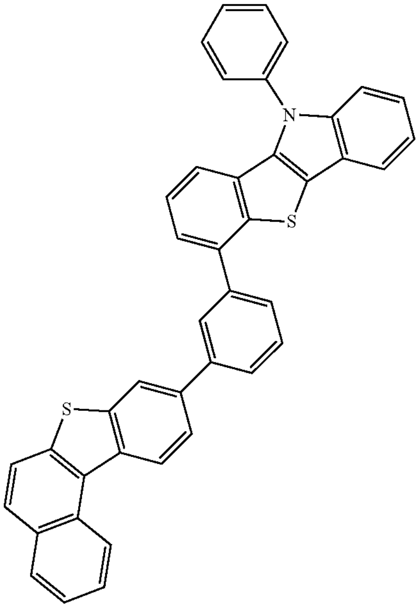
787
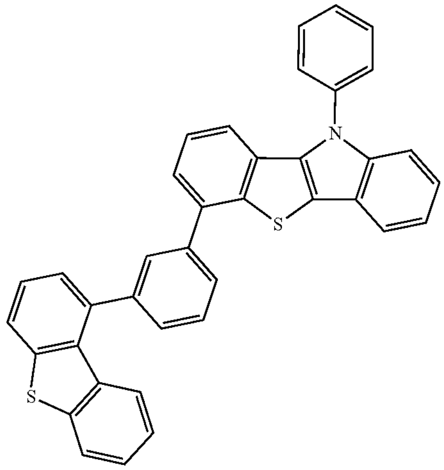
788
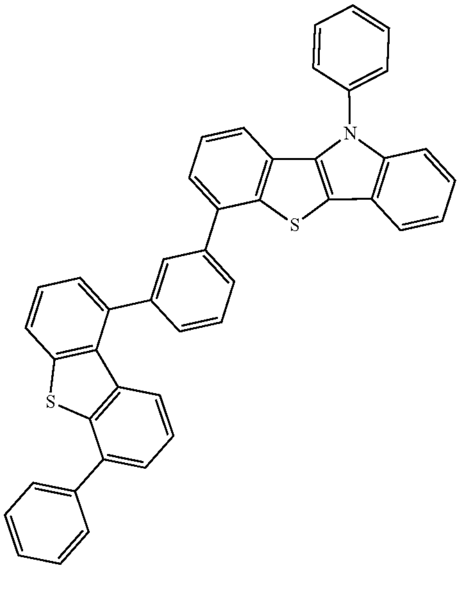

-continued
789
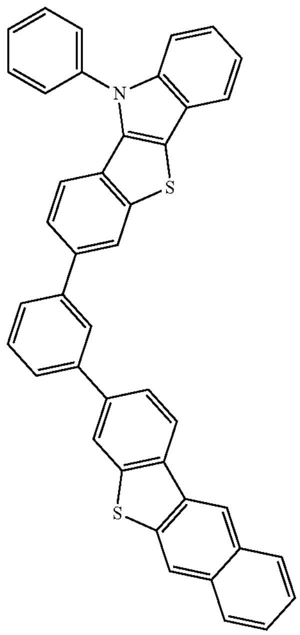
790
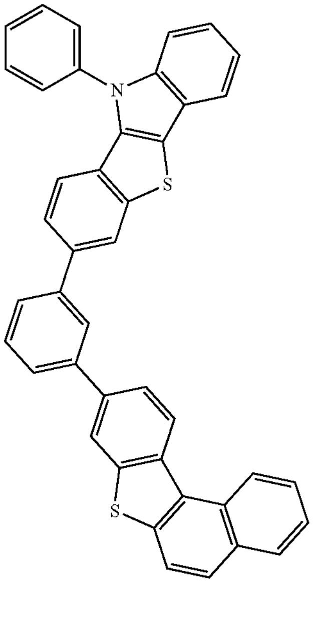
-continued
791
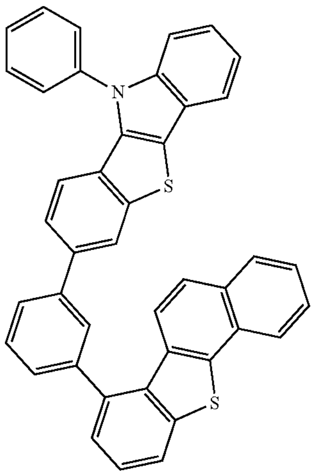
792
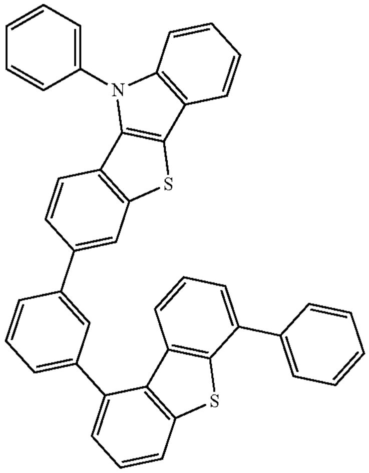
793
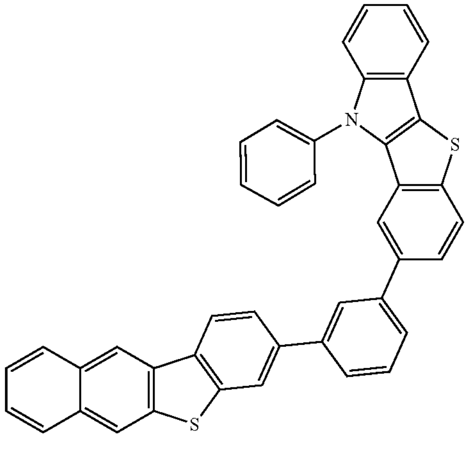

-continued
794
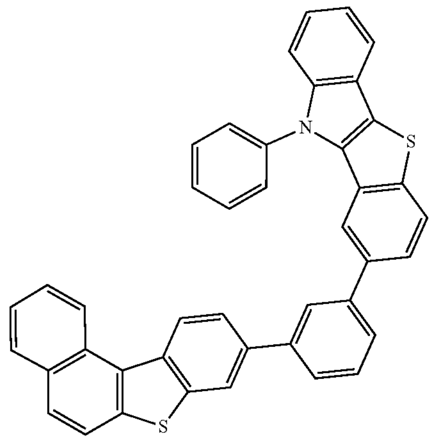
795
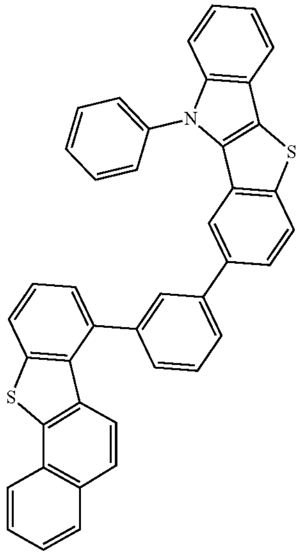
796
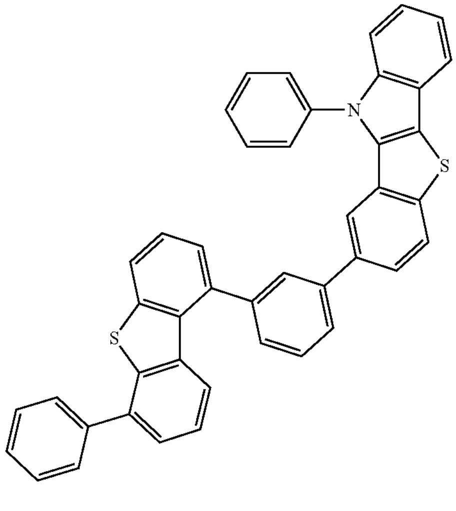
-continued
797
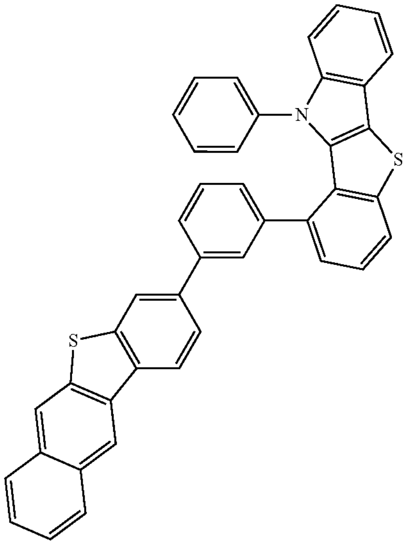
798
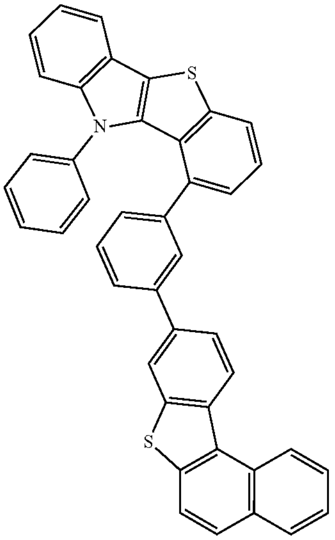
799
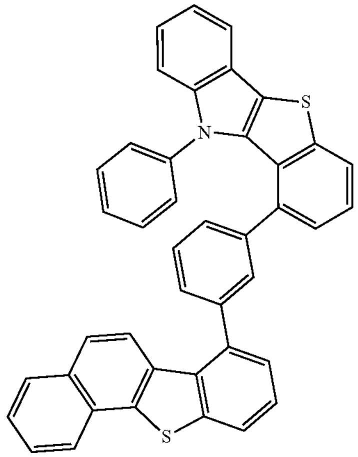

-continued
800
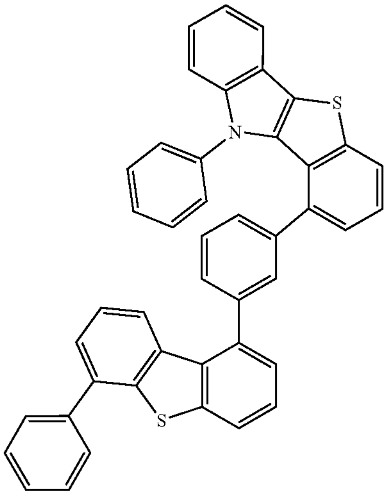
801
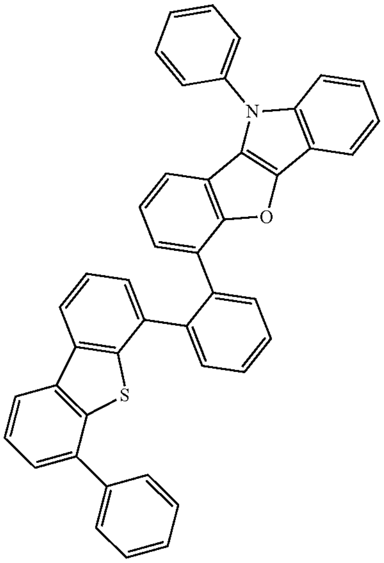
802
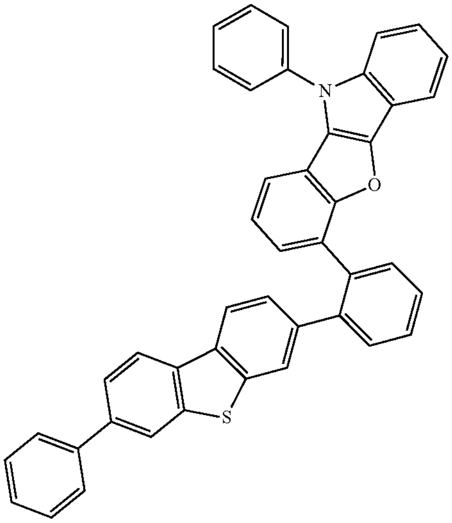
-continued
803
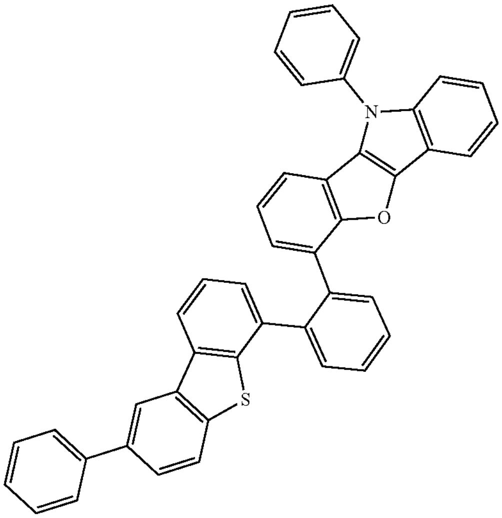
804
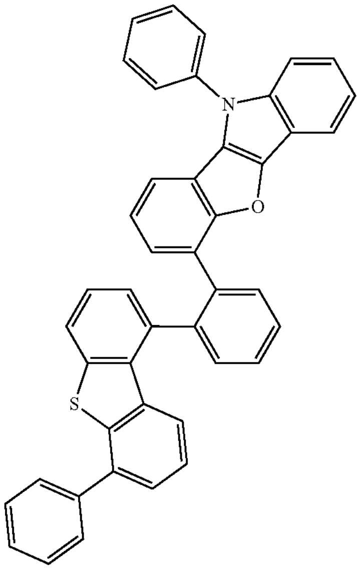
805
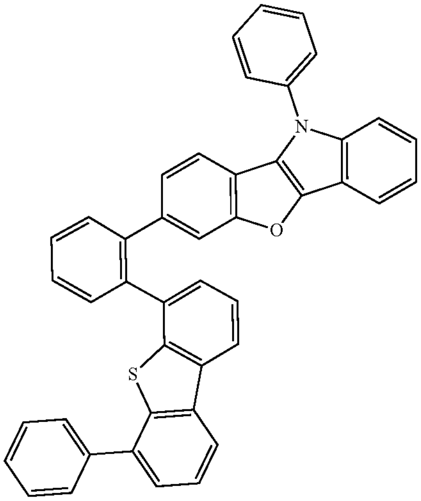

-continued
806
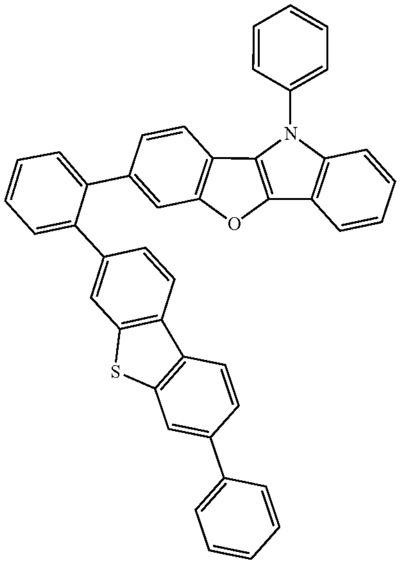
807
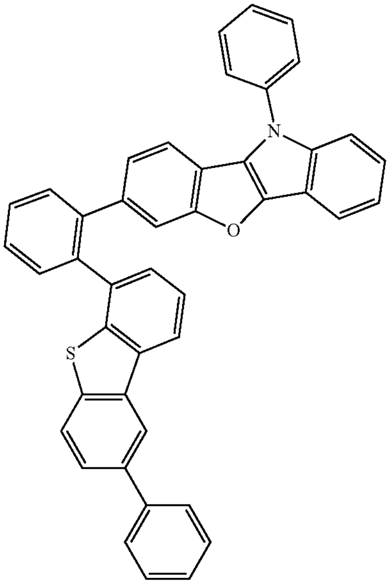
-continued
808
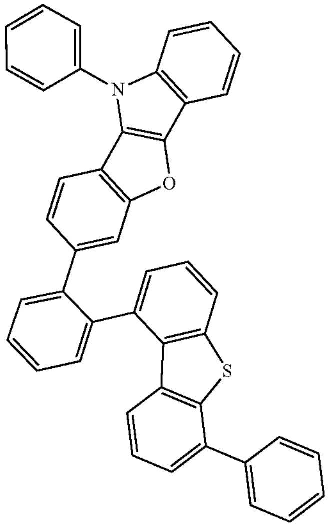
809
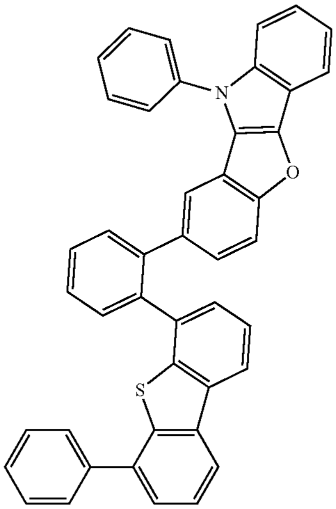
810
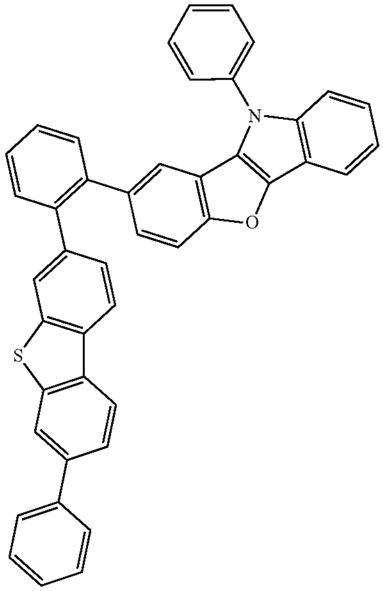

-continued
811
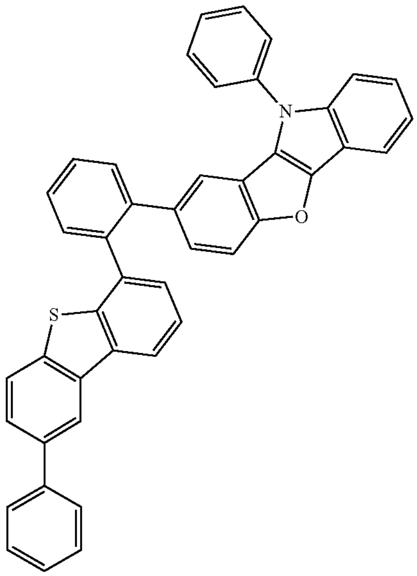
812
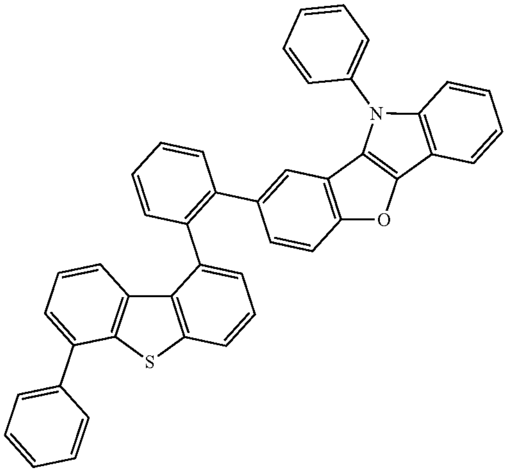
813
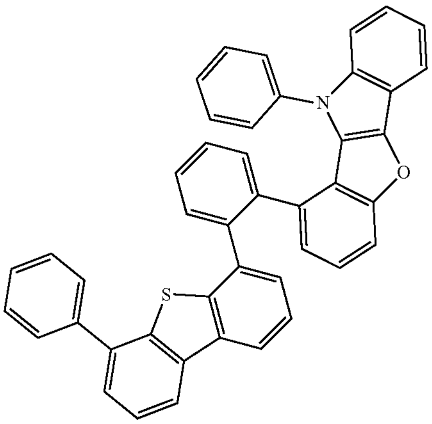
-continued
814
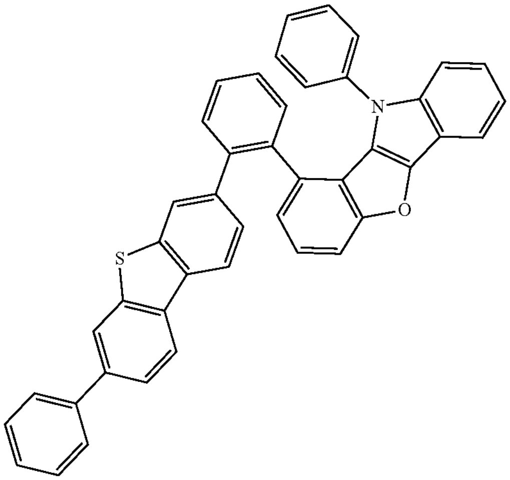
815
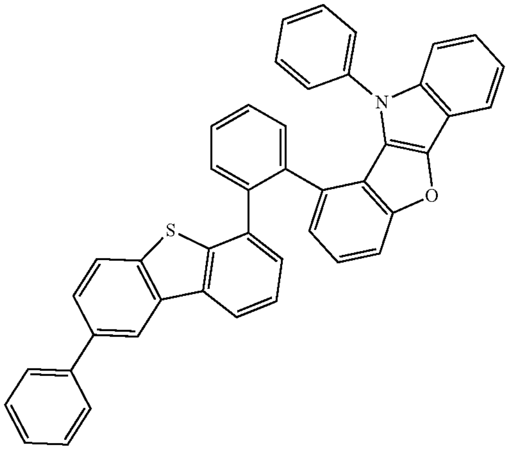
816
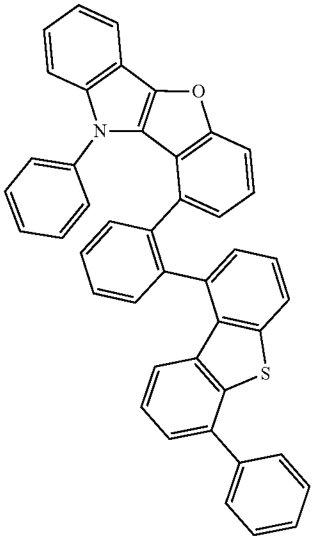

817
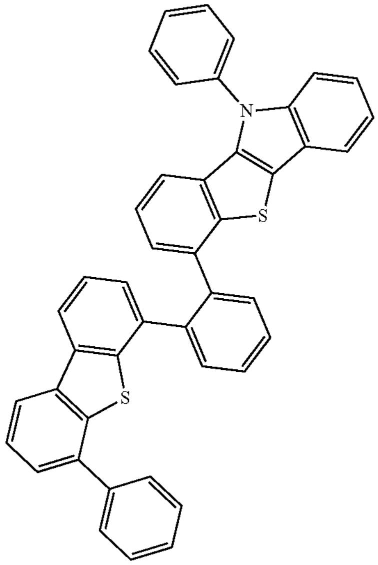
818
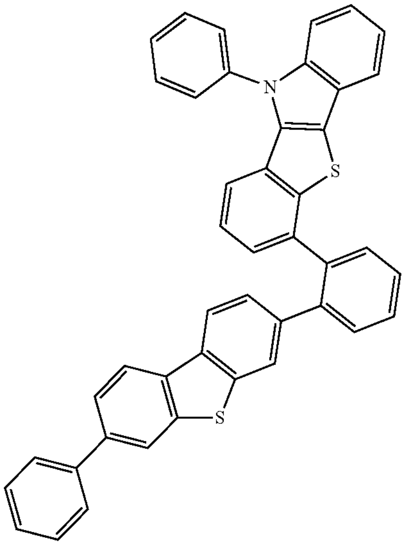
819
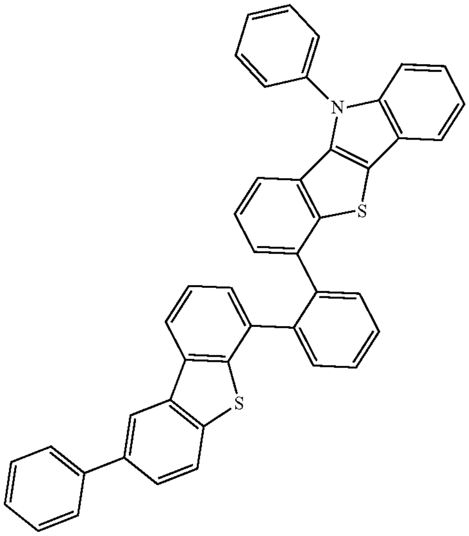
820
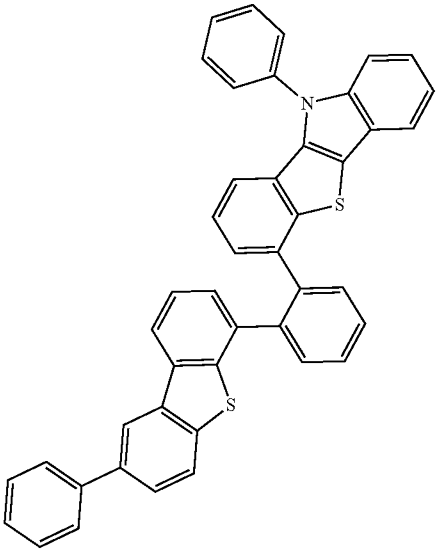
821
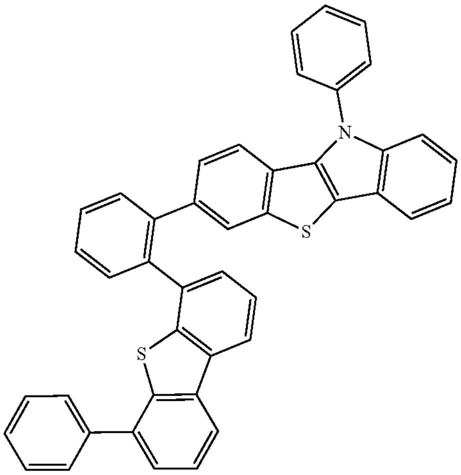
822
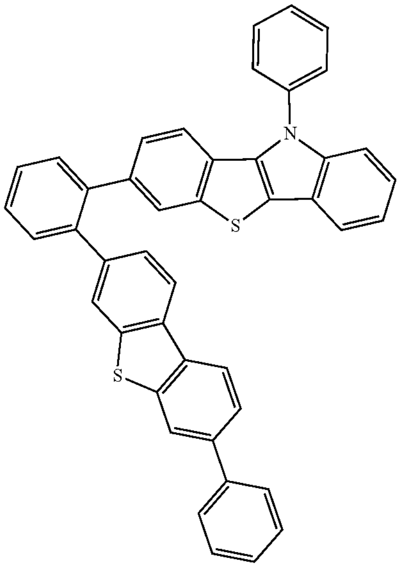

823
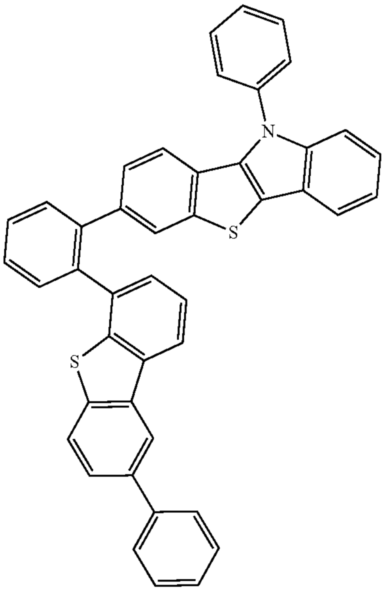
824
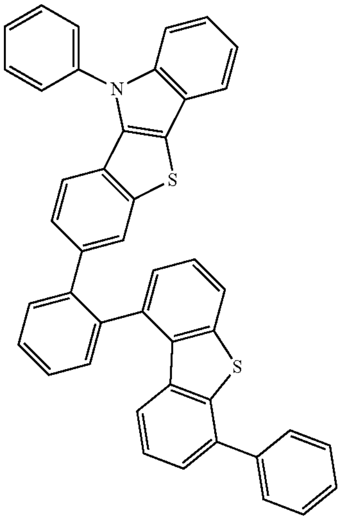
825
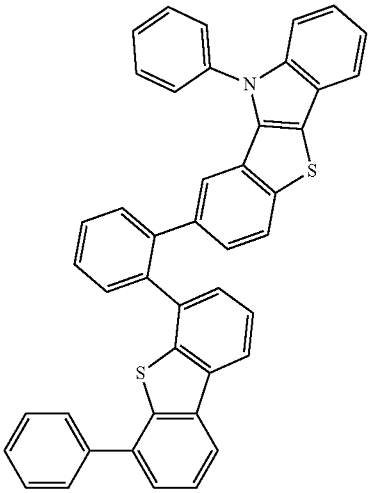
826
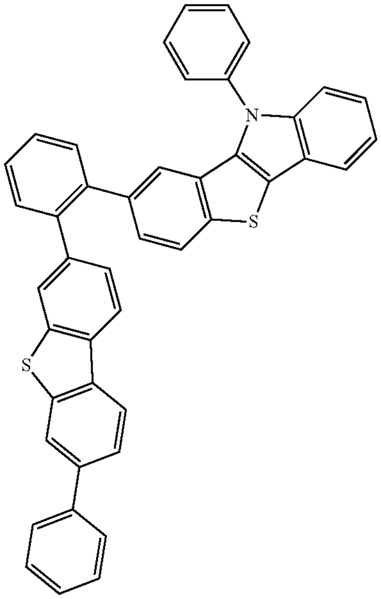
827
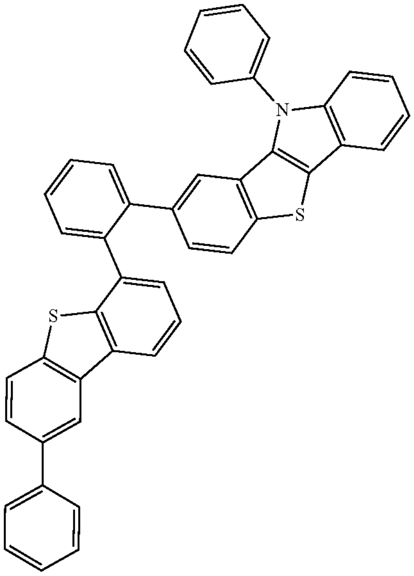
828
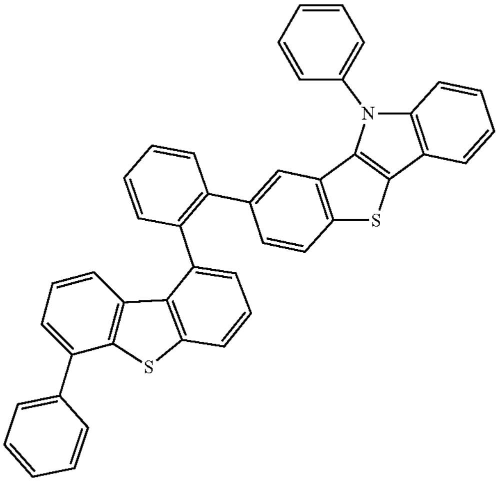

-continued
829
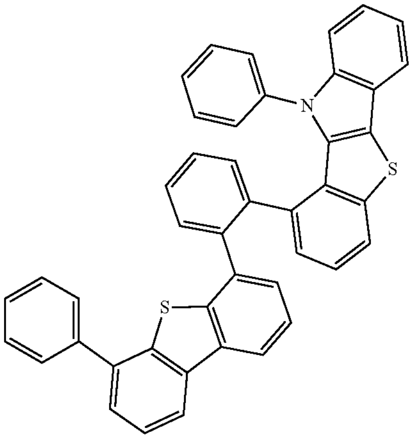
830
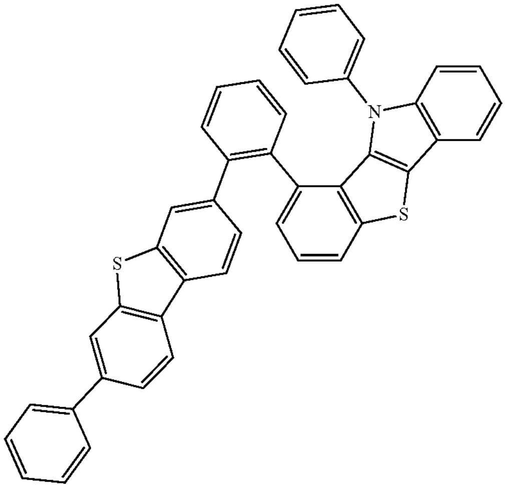
831
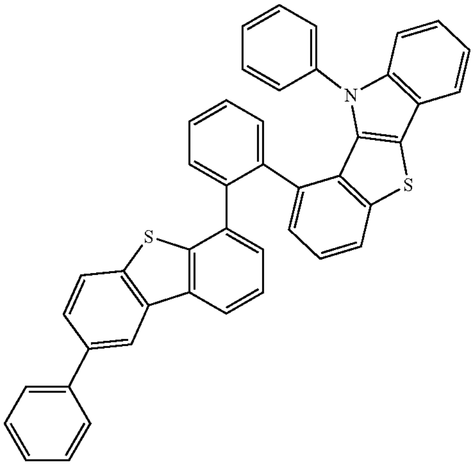
-continued
832
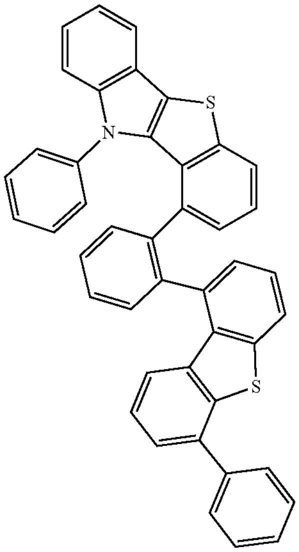
833
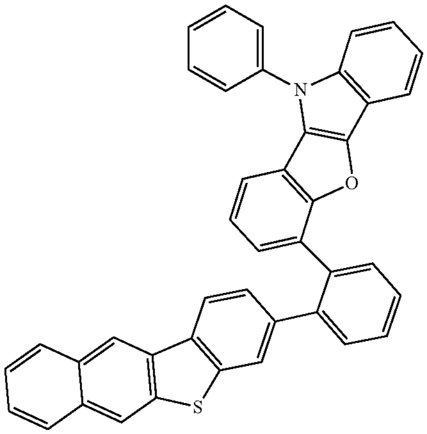
834
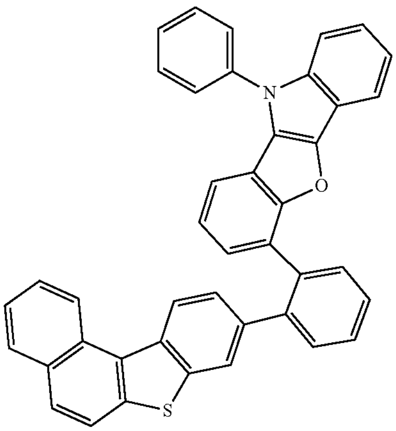

835
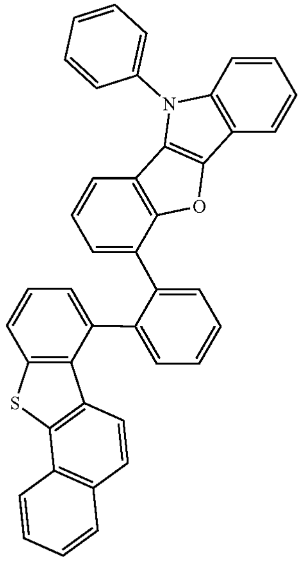
836
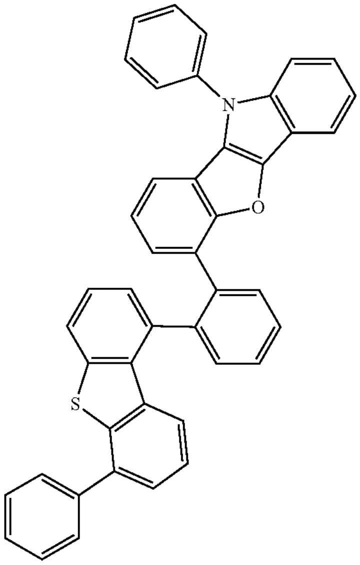
837
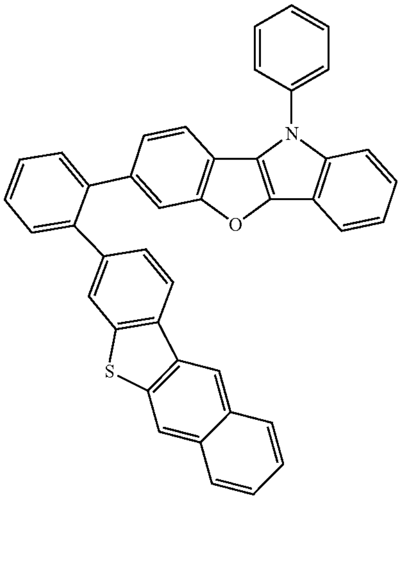
838
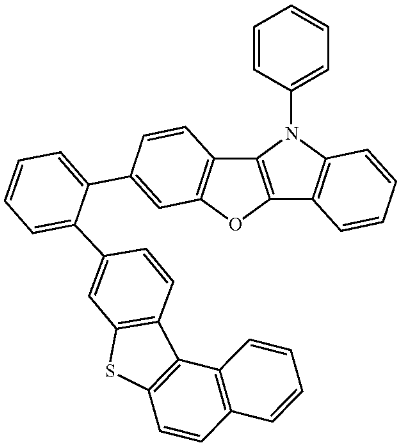
839
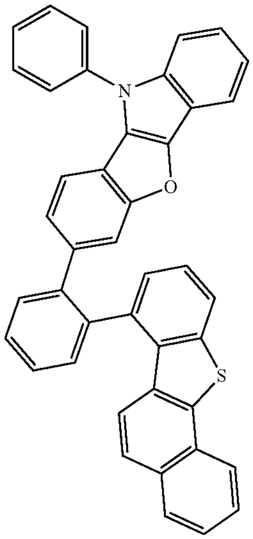
840
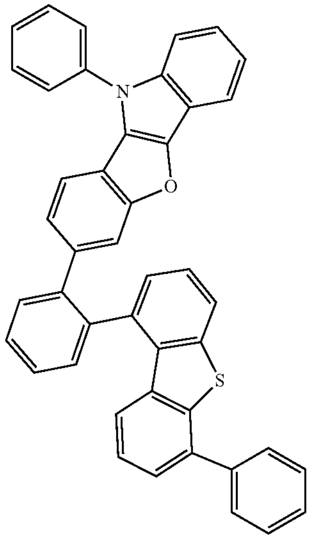

-continued
841
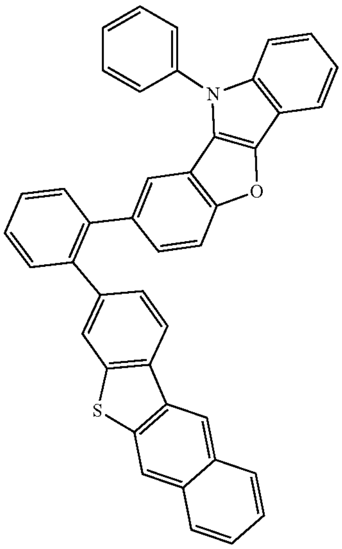
842
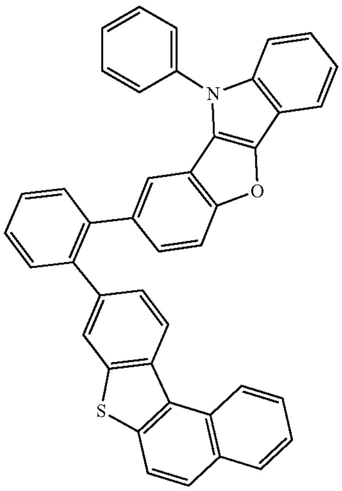
843
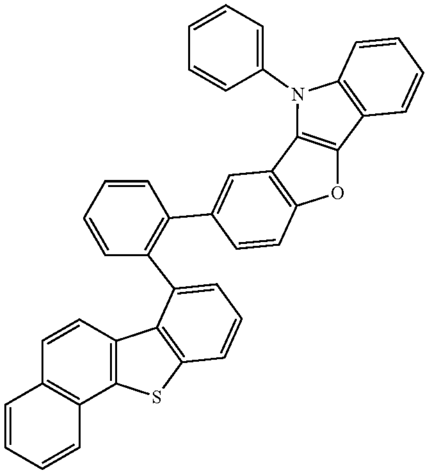
-continued
844
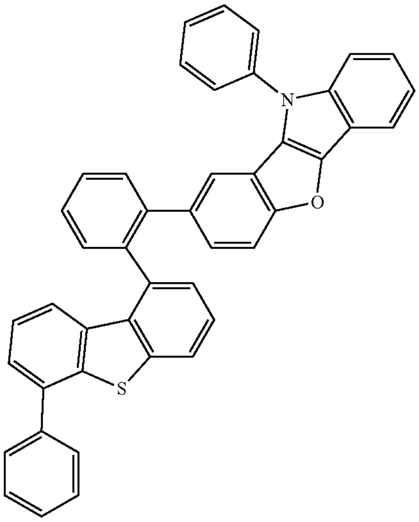
845
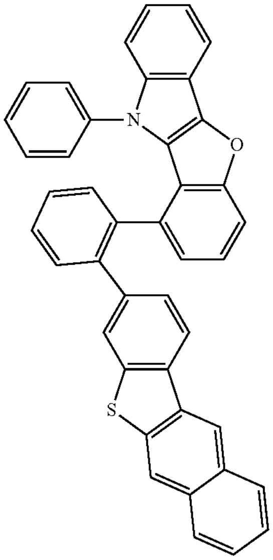
846
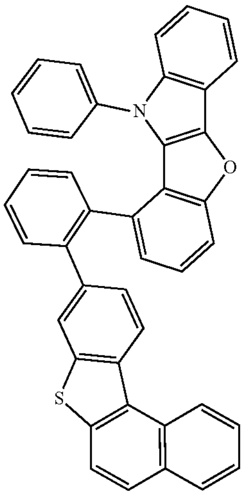

-continued
847
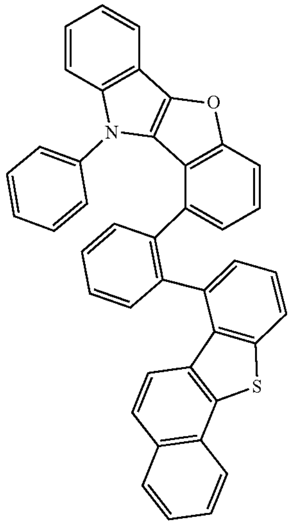
848
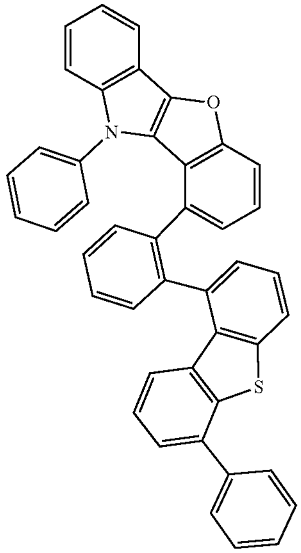
849
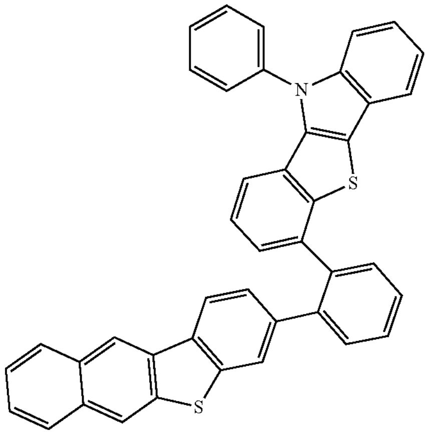
-continued
850
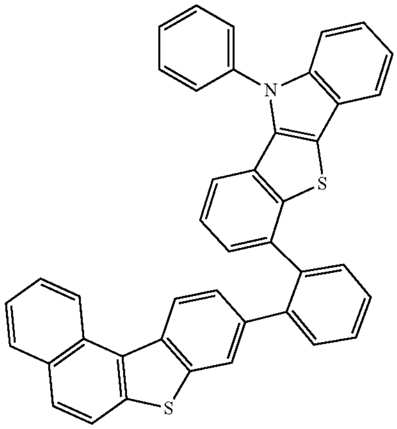
851
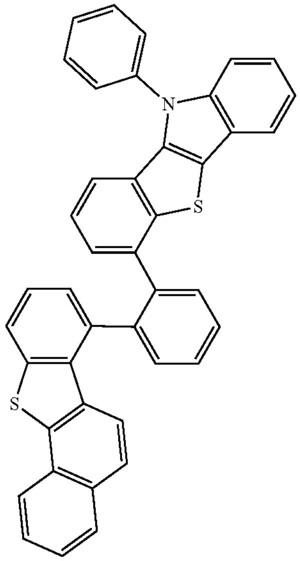
852
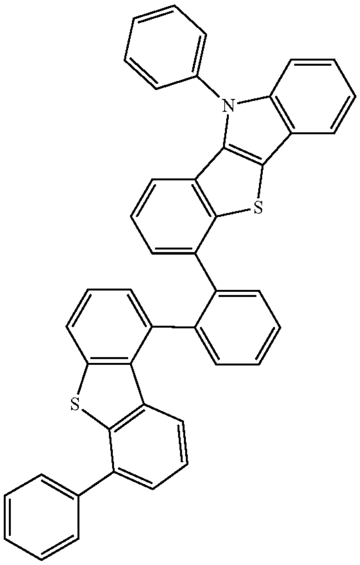

-continued
853
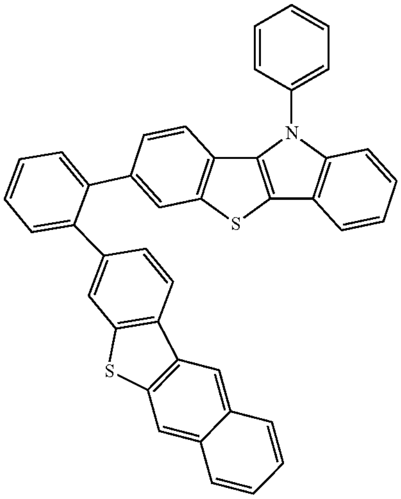
854
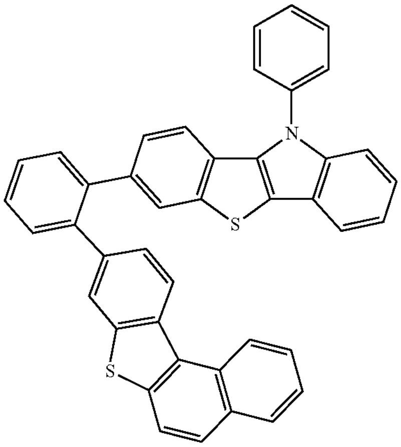
855
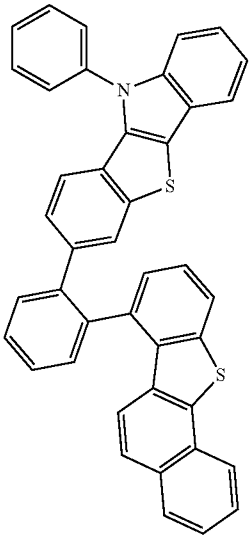
-continued
856
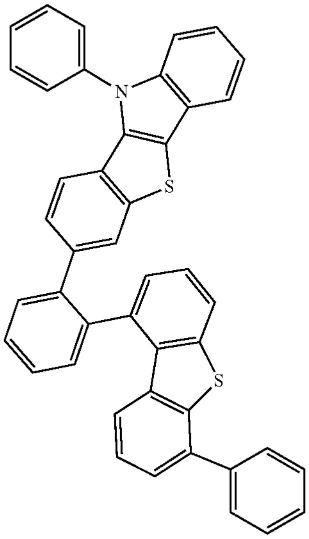
857
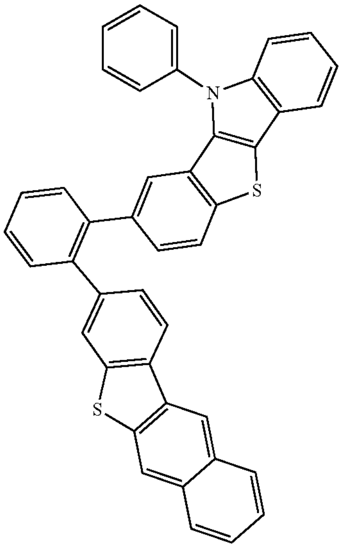
858
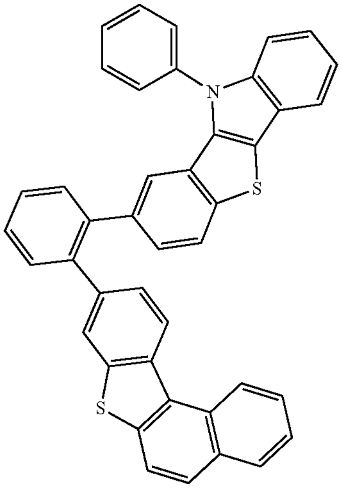

-continued
859
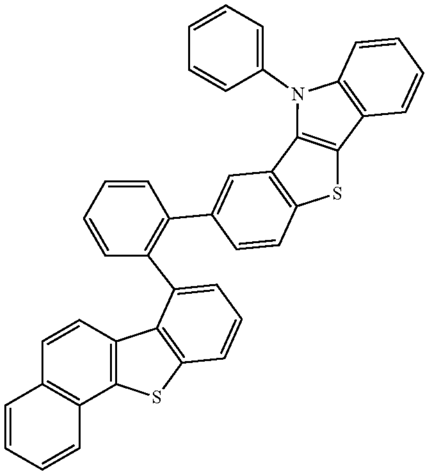
860
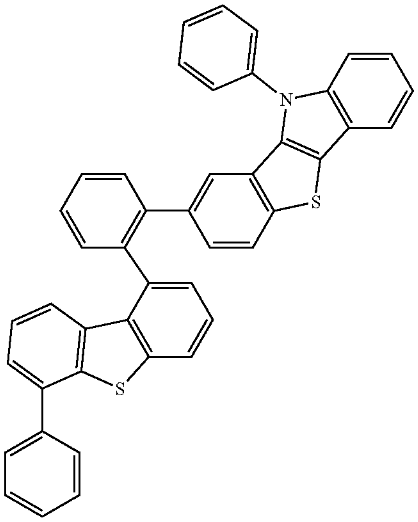
861
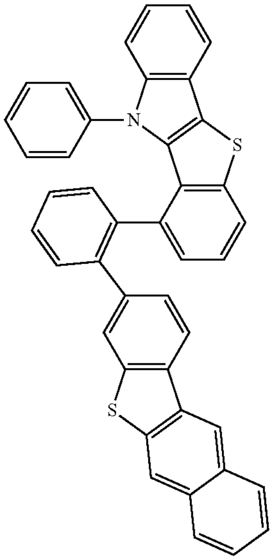
-continued
862
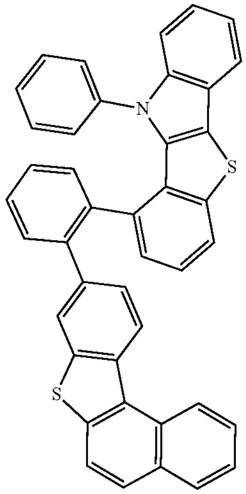
863
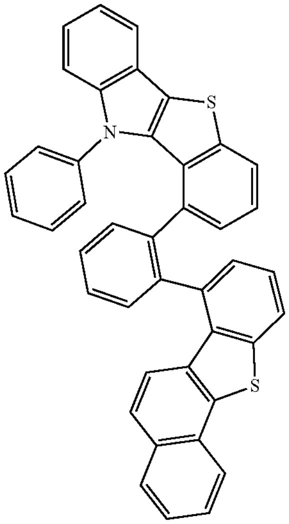
864
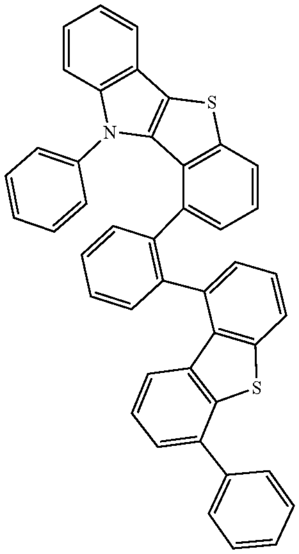

-continued
865
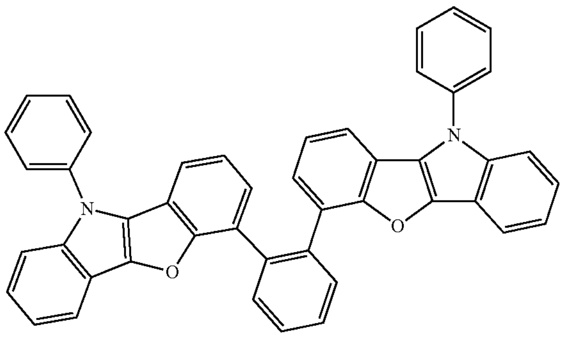
866
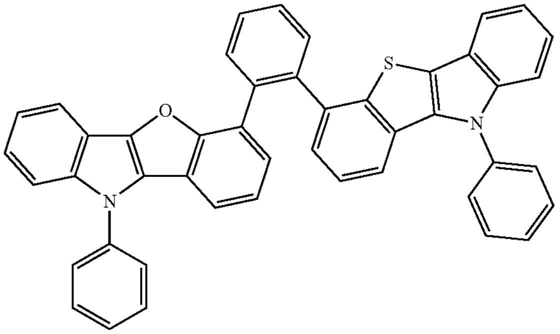
867
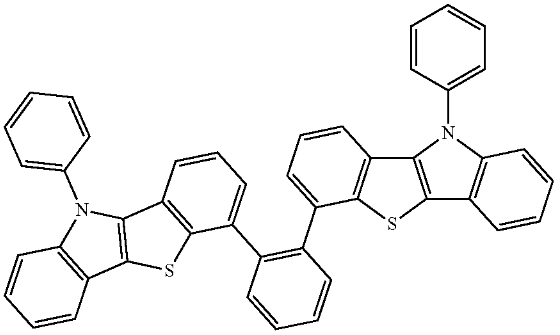
868
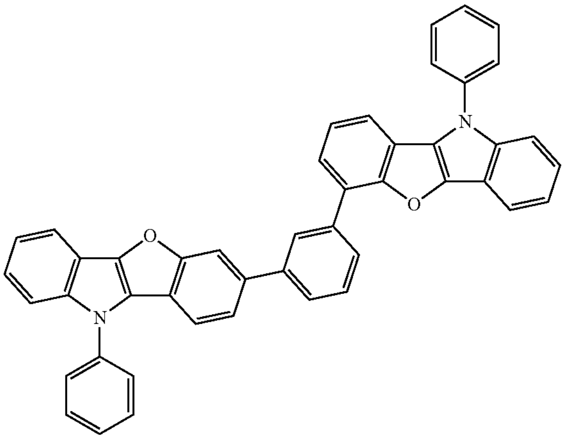
-continued
869
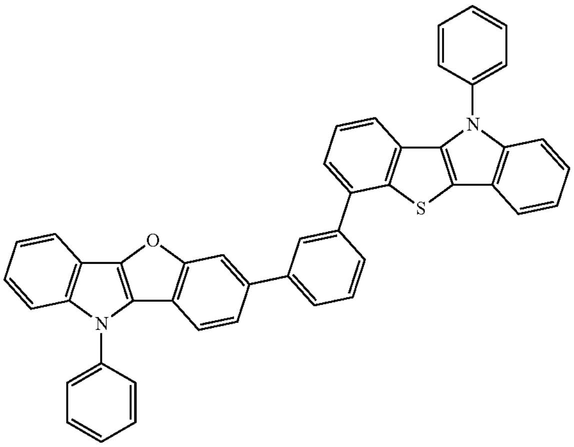
870
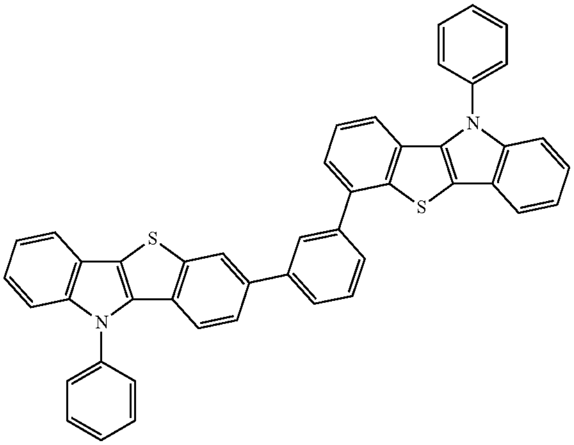
871
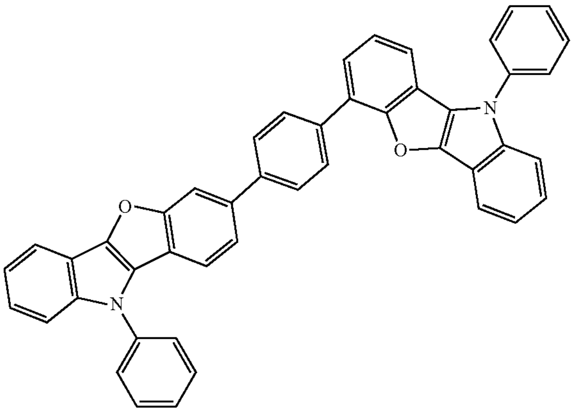

-continued
872
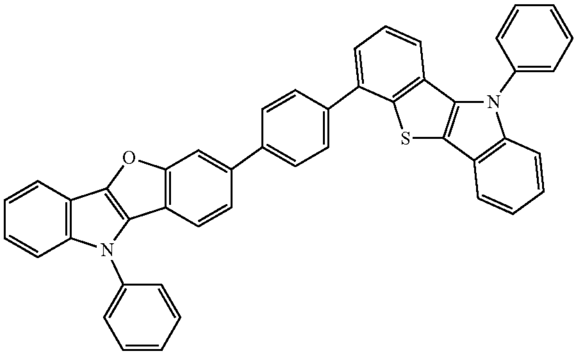
873
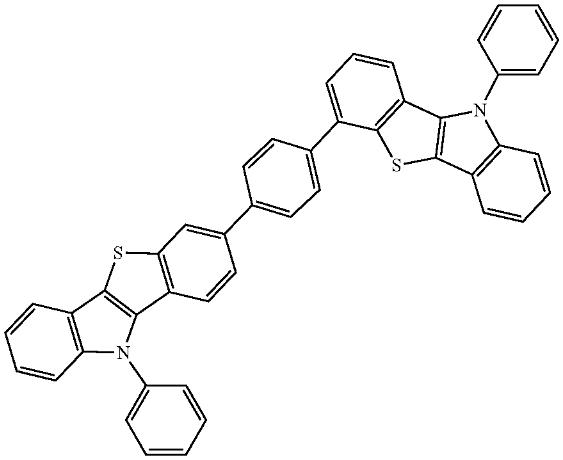
874
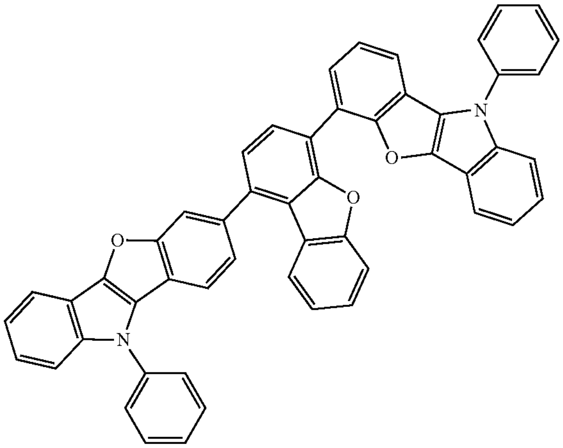
-continued
875
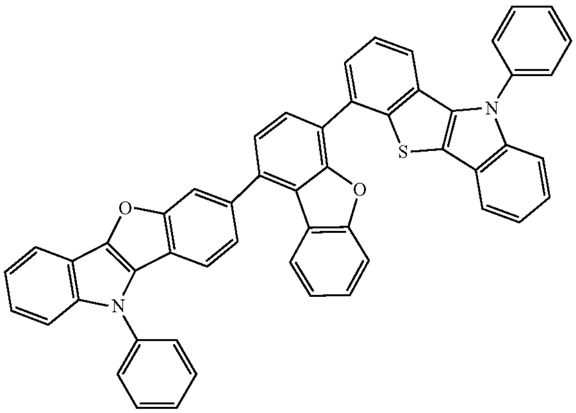
876
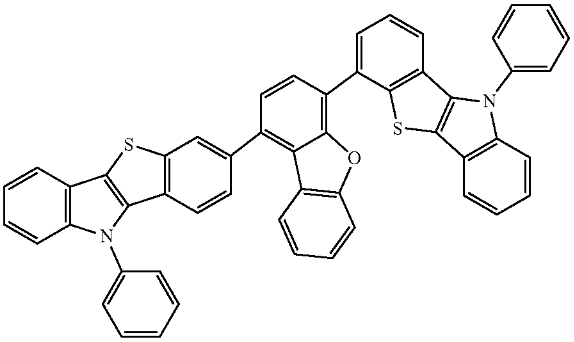
877
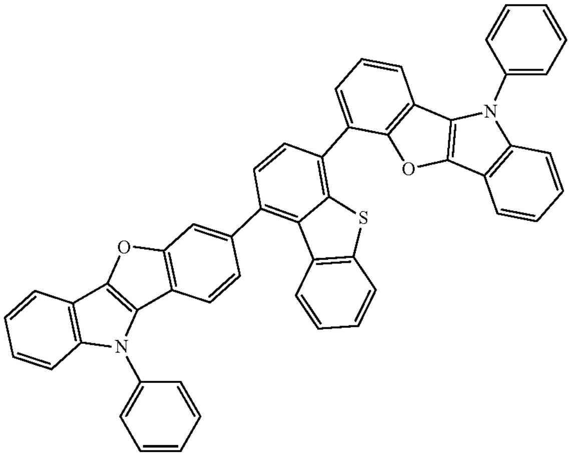

-continued
878
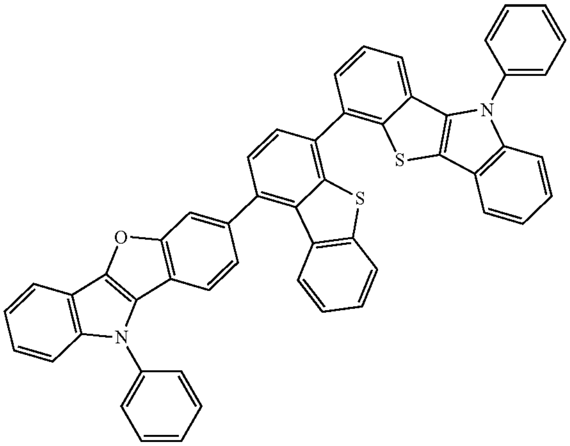
879
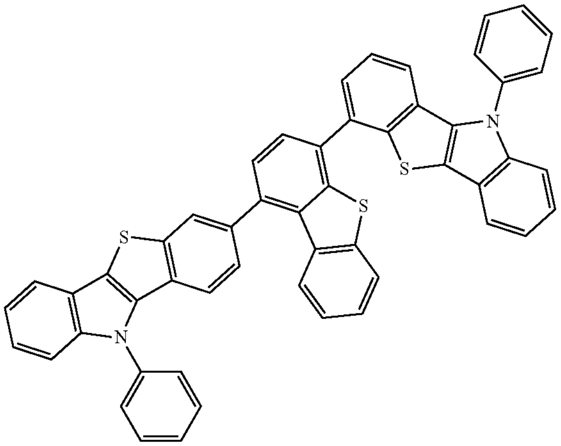
880
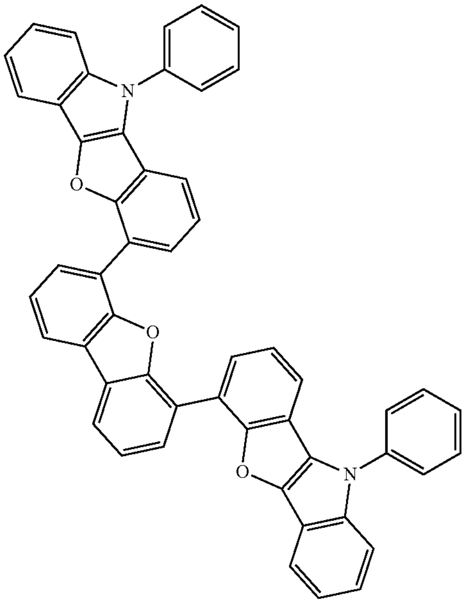
-continued
881
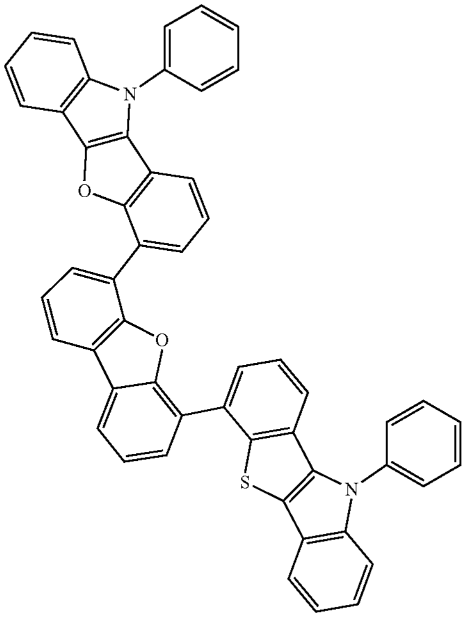
882
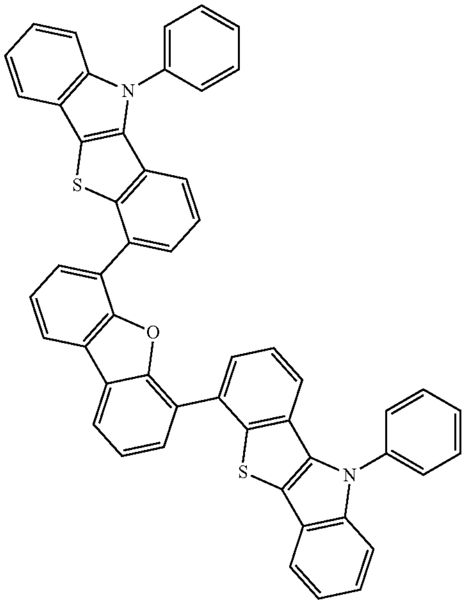

-continued
883
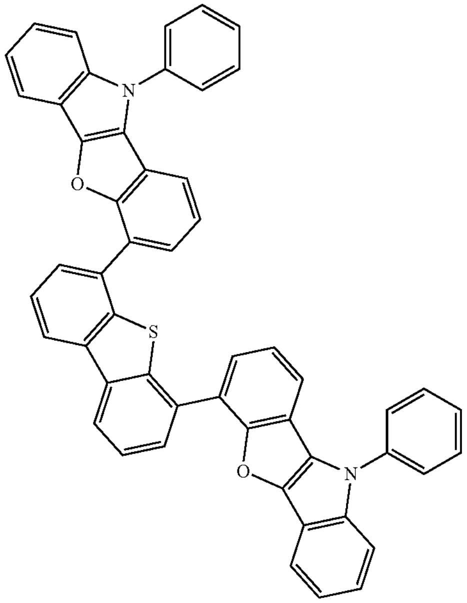
884
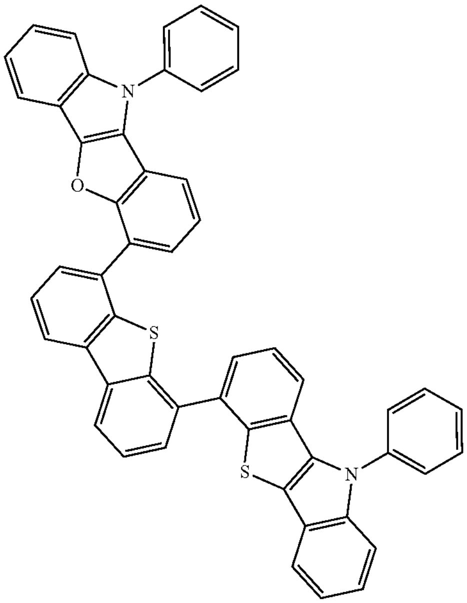
-continued
885
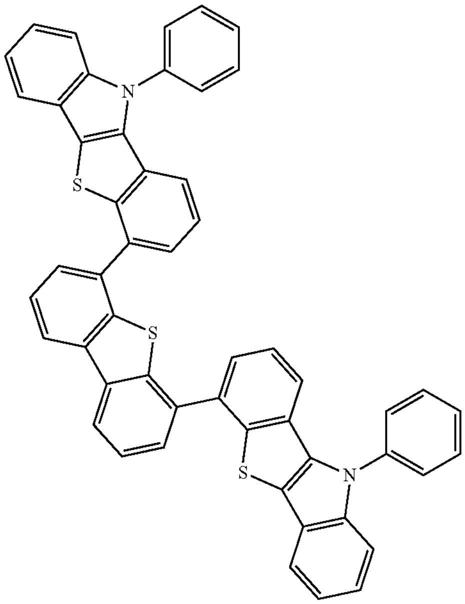
886
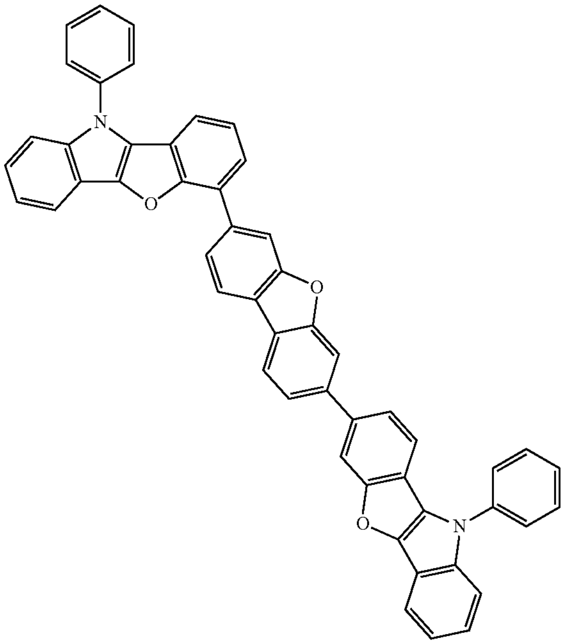

-continued
887
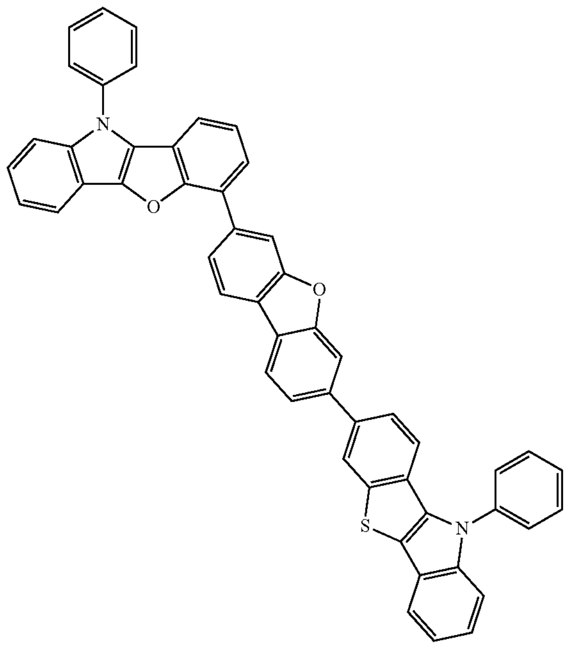
888
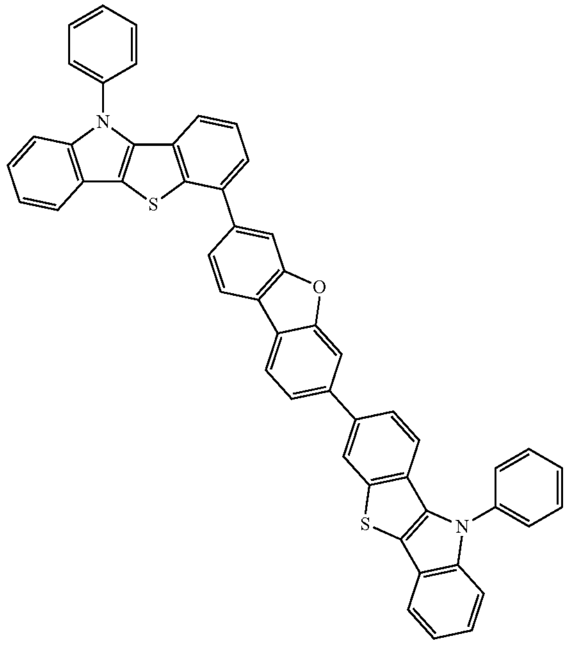
-continued
889
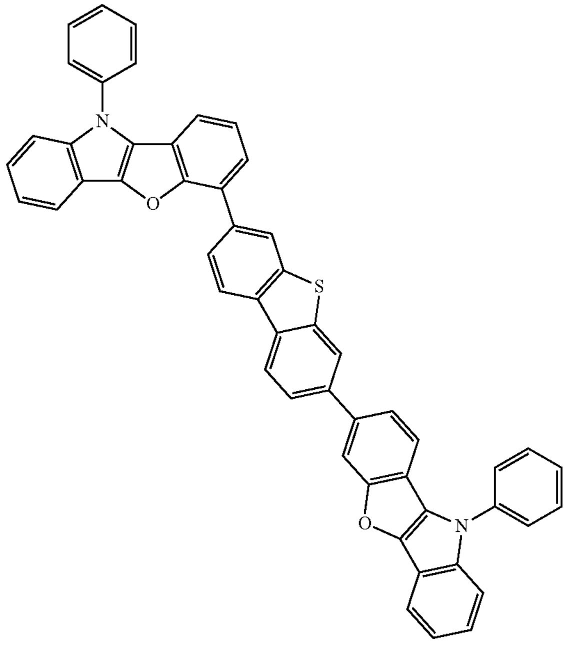
890
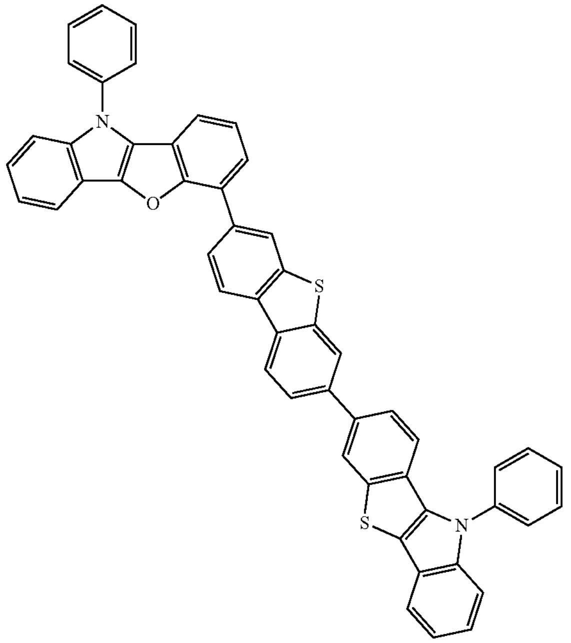

-continued
891
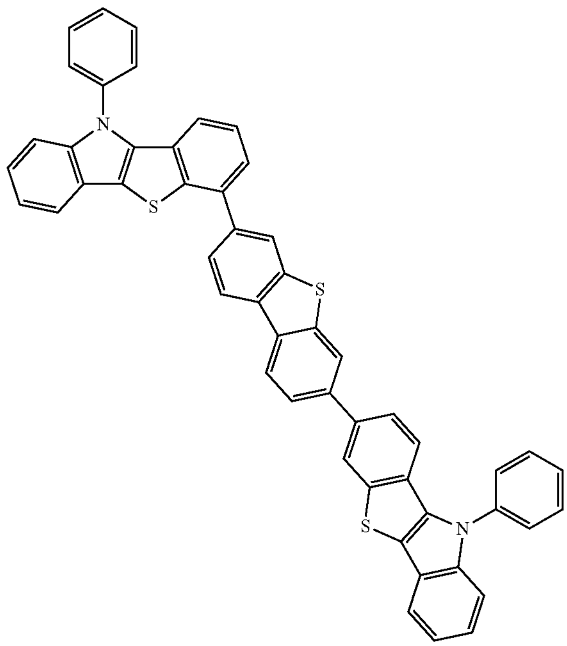
892
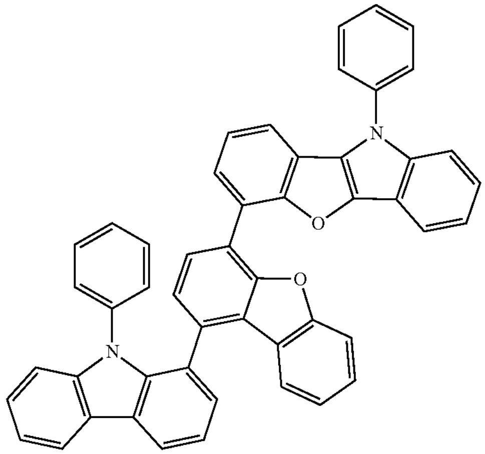
893
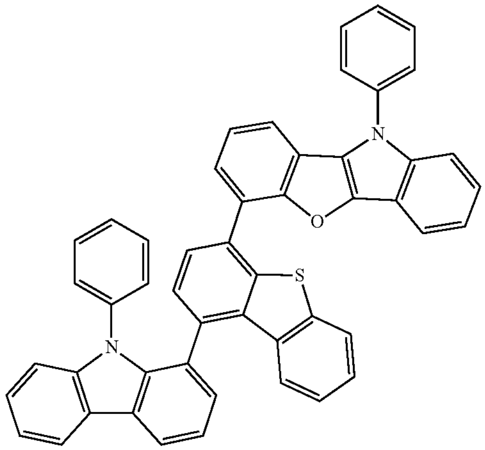
-continued
894
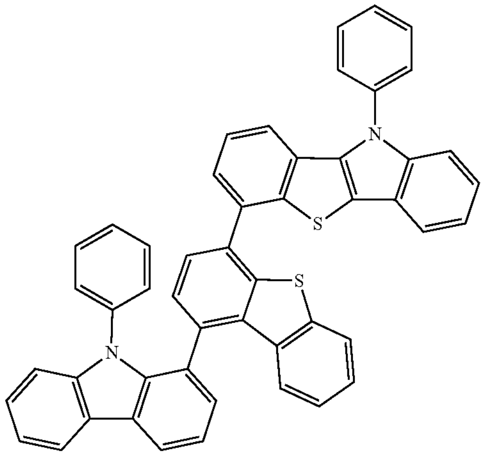
895
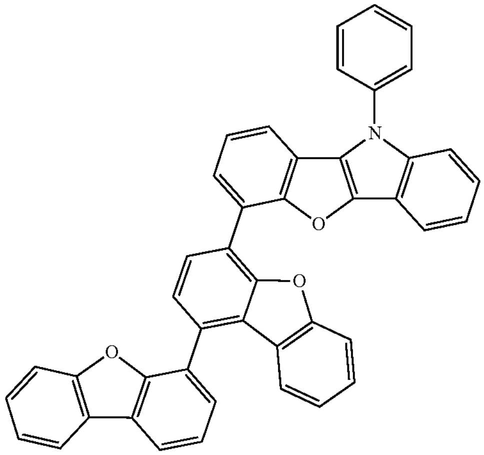
896
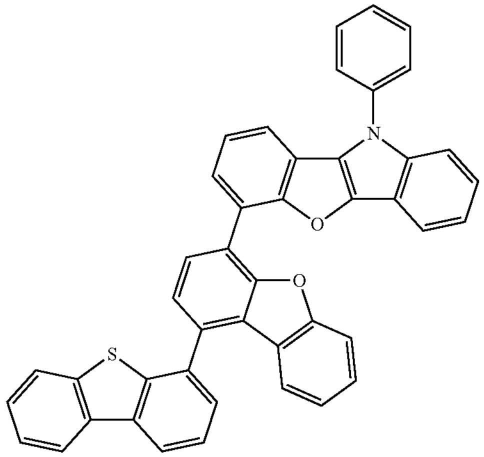

-continued
897
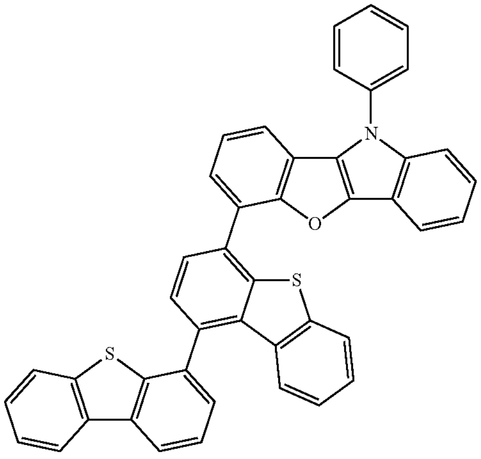
898
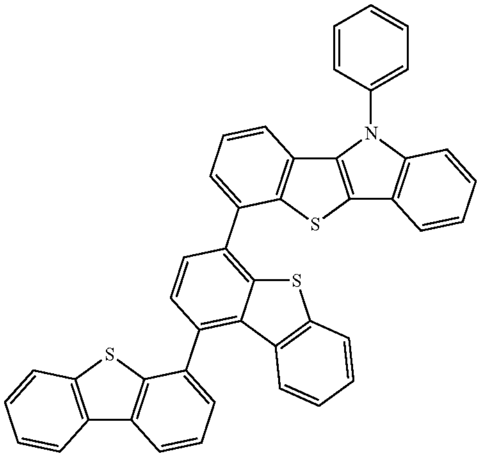
899
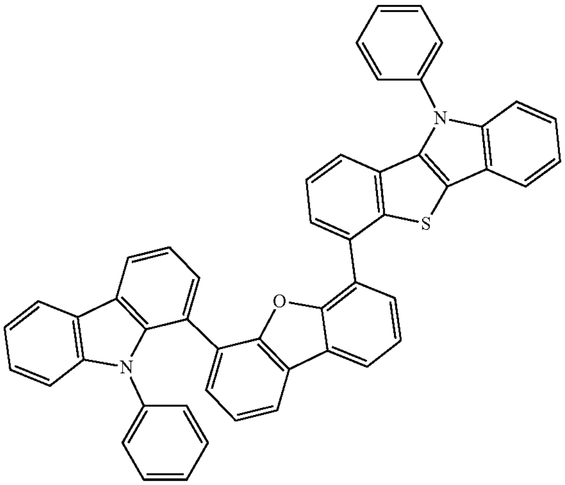
-continued
900
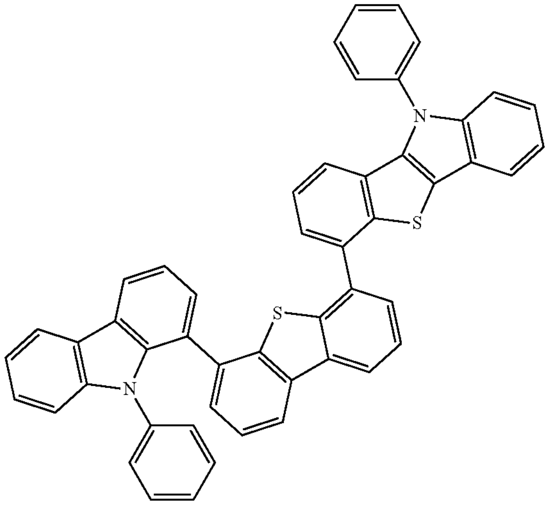
901
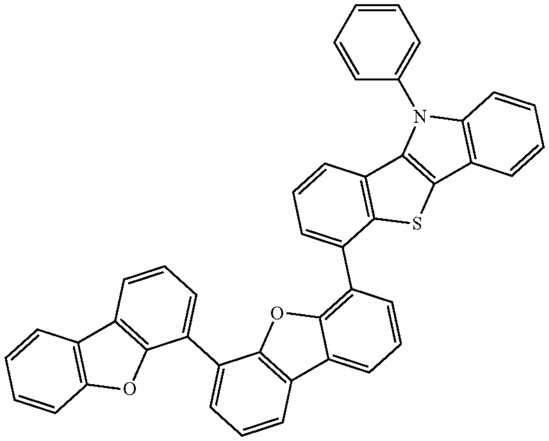
902
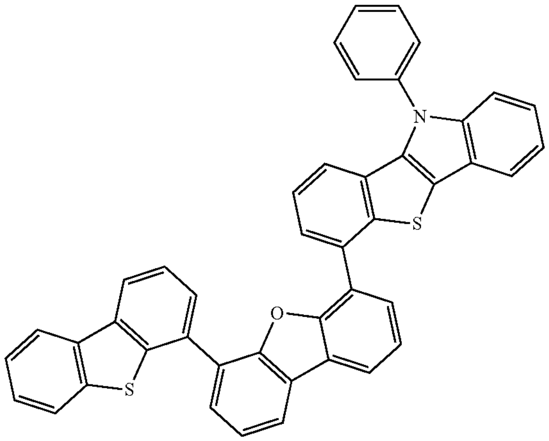

903
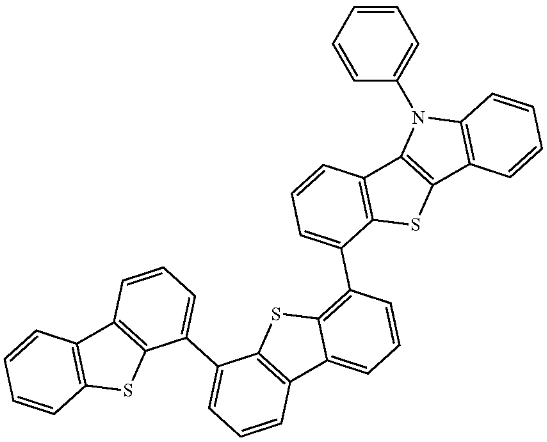
904
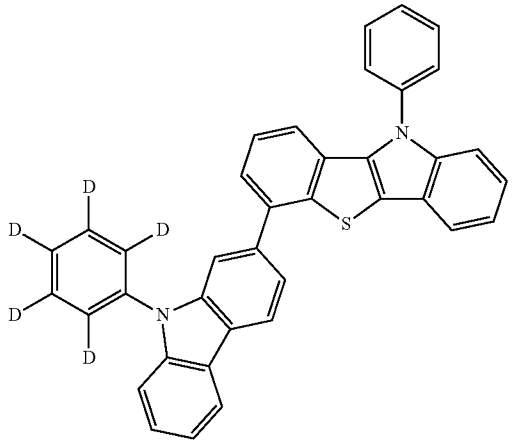
905
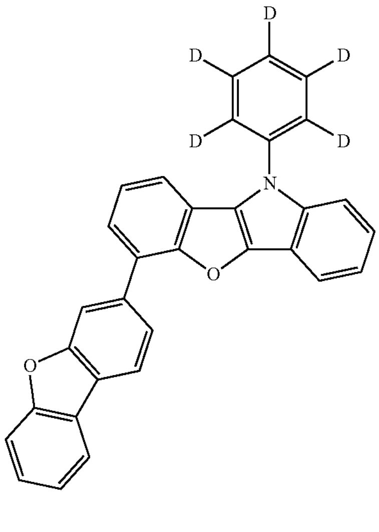
906
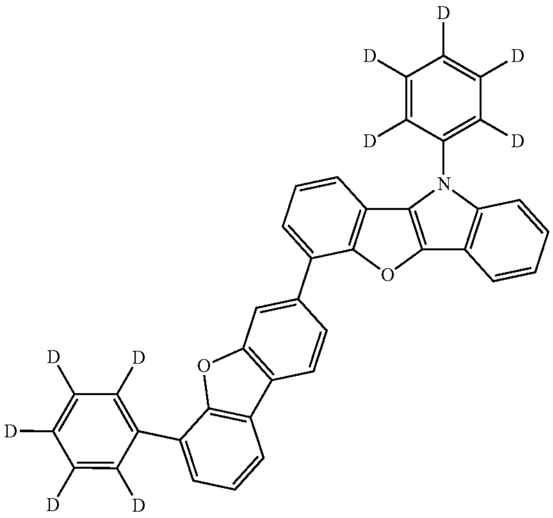
907
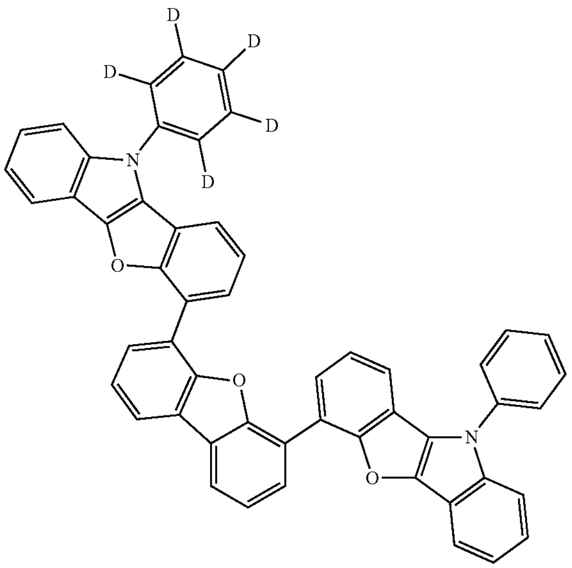
909
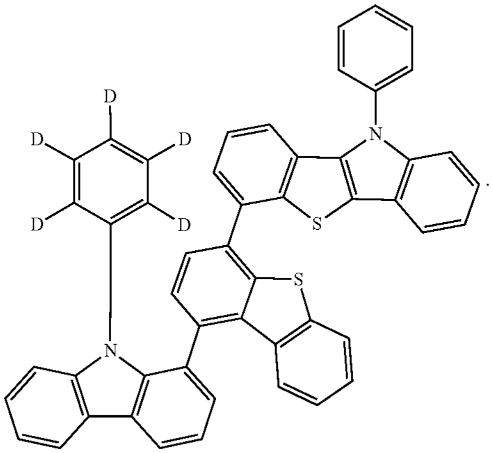
.
* * * * *